US012528984B2

(12) United States Patent
Tasaki et al.

(10) Patent No.: US 12,528,984 B2
(45) Date of Patent: Jan. 20, 2026

(54) ORGANIC ELECTROLUMINESCENT ELEMENT AND ELECTRONIC DEVICE

(71) Applicant: IDEMITSU KOSAN CO., LTD., Tokyo (JP)

(72) Inventors: Satomi Tasaki, Tokyo (JP); Kazuki Nishimura, Tokyo (JP); Yuki Nakano, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 987 days.

(21) Appl. No.: 17/642,219

(22) PCT Filed: Sep. 11, 2020

(86) PCT No.: PCT/JP2020/034591
§ 371 (c)(1),
(2) Date: Mar. 10, 2022

(87) PCT Pub. No.: WO2021/049651
PCT Pub. Date: Mar. 18, 2021

(65) Prior Publication Data

US 2023/0088213 A1 Mar. 23, 2023

(30) Foreign Application Priority Data

Sep. 13, 2019 (JP) ................................ 2019-167636
Nov. 26, 2019 (JP) ................................ 2019-213374
(Continued)

(51) Int. Cl.
*H01L 51/50* (2006.01)
*C07C 15/20* (2006.01)
(Continued)

(52) U.S. Cl.
CPC .............. *C09K 11/06* (2013.01); *C07C 15/20* (2013.01); *C07C 15/28* (2013.01); *C07C 15/30* (2013.01);
(Continued)

(58) Field of Classification Search
None
See application file for complete search history.

(56) References Cited

U.S. PATENT DOCUMENTS 11,094,886 B2 8/2021 Tasaki et al.
2006/0043858 A1 3/2006 Ikeda et al.
(Continued)

FOREIGN PATENT DOCUMENTS

CN 103827065 A 5/2014
CN 106565705 A 4/2017
(Continued)

OTHER PUBLICATIONS

International Preliminary Report on Patentability issued in corresponding International Patent Application No. PCT/JP2020/034595 dated Mar. 15, 2022.
(Continued)

*Primary Examiner* — Gregory D Clark
(74) *Attorney, Agent, or Firm* — Foley & Lardner LLP

(57) ABSTRACT

An organic electroluminescence device includes an anode, a cathode, a first emitting layer, and a second emitting layer provided between the first emitting layer and the cathode, in which the first emitting layer contains a first compound represented by a formula (101) below as a first host material, the second emitting layer contains a second compound represented by a formula (2) below as a second host material, and the first emitting layer is in direct contact with the second emitting layer.
(Continued)

(101)

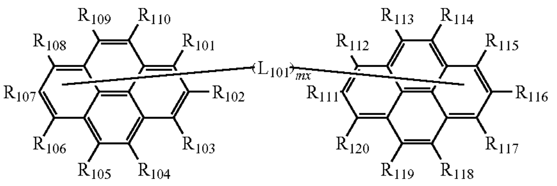

(2)

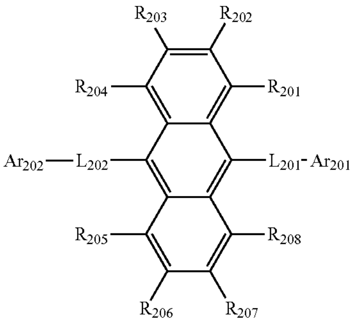

34 Claims, 1 Drawing Sheet

(30) Foreign Application Priority Data

Dec. 27, 2019 (JP) ................................ 2019-239596
Feb. 14, 2020 (JP) ................................ 2020-023551

(51) Int. Cl.

| | |
|---|---|
| ***C07C 15/28*** | (2006.01) |
| ***C07C 15/30*** | (2006.01) |
| ***C07C 15/38*** | (2006.01) |
| ***C07C 211/54*** | (2006.01) |
| ***C07D 307/91*** | (2006.01) |
| ***C07D 309/34*** | (2006.01) |
| ***C07D 333/76*** | (2006.01) |
| ***C07D 407/10*** | (2006.01) |
| ***C07D 409/04*** | (2006.01) |
| ***C07D 471/06*** | (2006.01) |
| ***C07D 487/06*** | (2006.01) |
| ***C07D 487/16*** | (2006.01) |
| ***C07D 487/22*** | (2006.01) |
| ***C07D 491/16*** | (2006.01) |
| ***C07D 491/22*** | (2006.01) |
| ***C07D 493/04*** | (2006.01) |
| ***C07D 495/04*** | (2006.01) |
| ***C07D 495/22*** | (2006.01) |
| ***C07F 5/02*** | (2006.01) |
| ***C07F 7/08*** | (2006.01) |
| ***C09K 11/06*** | (2006.01) |
| ***H10K 85/40*** | (2023.01) |
| ***H10K 85/60*** | (2023.01) |

(52) U.S. Cl.

CPC ............ *C07C 15/38* (2013.01); *C07C 211/54* (2013.01); *C07D 307/91* (2013.01); *C07D 309/34* (2013.01); *C07D 333/76* (2013.01); *C07D 407/10* (2013.01); *C07D 409/04* (2013.01); *C07D 471/06* (2013.01); *C07D 487/06* (2013.01); *C07D 487/16* (2013.01); *C07D 487/22* (2013.01); *C07D 491/16* (2013.01); *C07D 491/22* (2013.01); *C07D 493/04* (2013.01); *C07D 495/04* (2013.01); *C07D 495/22* (2013.01); *C07F 5/027* (2013.01); *C07F 7/0812* (2013.01); *C07F 7/0816* (2013.01); *H10K 85/40* (2023.02); *H10K 85/615* (2023.02); *H10K 85/622* (2023.02); *H10K 85/623* (2023.02); *H10K 85/624* (2023.02); *H10K 85/631* (2023.02); *H10K 85/633* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01)

(56) References Cited

U.S. PATENT DOCUMENTS

| | | | | |
|---|---|---|---|---|
| 2006/0154107 | A1 | 7/2006 | Kubota et al. | |
| 2007/0013296 | A1 | 1/2007 | Kubota et al. | |
| 2008/0012475 | A1 | 1/2008 | Oyamada et al. | |
| 2008/0193796 | A1 | 8/2008 | Arakane et al. | |
| 2009/0066227 | A1 * | 3/2009 | Okinaka .............. | H10K 85/633 313/504 |
| 2009/0200919 | A1 | 8/2009 | Kamatani et al. | |
| 2009/0278446 | A1 | 11/2009 | Igawa et al. | |
| 2010/0295444 | A1 | 11/2010 | Kuma et al. | |
| 2010/0301318 | A1 | 12/2010 | Kuma et al. | |
| 2010/0308718 | A1 | 12/2010 | Kubota et al. | |
| 2011/0034744 | A1 | 2/2011 | Ikeda et al. | |
| 2011/0037057 | A1 | 2/2011 | Lecloux et al. | |
| 2011/0095273 | A1 | 4/2011 | Meng et al. | |
| 2011/0108810 | A1 | 5/2011 | Kishino | |
| 2011/0133632 | A1 | 6/2011 | Lecloux et al. | |
| 2011/0285274 | A1 | 11/2011 | Hamada et al. | |
| 2012/0168736 | A1 | 7/2012 | Doi et al. | |
| 2012/0168739 | A1 | 7/2012 | Kamatani et al. | |
| 2012/0187826 | A1 | 7/2012 | Kawamura et al. | |
| 2012/0235561 | A1 | 9/2012 | Ikeda et al. | |
| 2013/0001542 | A1 | 1/2013 | Okajima et al. | |
| 2013/0048969 | A1 | 2/2013 | Sudo | |
| 2013/0270539 | A1 | 10/2013 | Kuma et al. | |
| 2013/0299814 | A1 | 11/2013 | Miyashita et al. | |
| 2014/0031787 | A1 | 1/2014 | Burnes et al. | |
| 2014/0183463 | A1 | 7/2014 | Lee et al. | |
| 2014/0183500 | A1 | 7/2014 | Ikeda et al. | |
| 2014/0225968 | A1 | 8/2014 | Kamatani et al. | |
| 2014/0231787 | A1 | 8/2014 | Ishige et al. | |
| 2014/0291653 | A1 | 10/2014 | Ikeda et al. | |
| 2015/0069344 | A1 | 3/2015 | Kim et al. | |
| 2015/0287949 | A1 | 10/2015 | Okamoto et al. | |
| 2016/0329494 | A1 | 11/2016 | Jun et al. | |
| 2016/0351818 | A1 | 12/2016 | Kim et al. | |
| 2017/0069864 | A1 | 3/2017 | Lee et al. | |
| 2017/0110667 | A1 | 4/2017 | Nishimura et al. | |
| 2017/0125687 | A1 | 5/2017 | Ikeda et al. | |
| 2017/0324043 | A1 | 11/2017 | Ikeda et al. | |
| 2017/0338432 | A1 | 11/2017 | Adamovich et al. | |
| 2017/0342318 | A1 | 11/2017 | Kim et al. | |
| 2018/0190726 | A1 | 7/2018 | Kim | |
| 2018/0261791 | A1 | 9/2018 | Yoo et al. | |
| 2019/0280209 | A1 | 9/2019 | Fujita | |
| 2019/0305227 | A1 | 10/2019 | Yoon et al. | |
| 2020/0095180 | A1 | 3/2020 | Nishide et al. | |
| 2020/0161558 | A1 | 5/2020 | Takaya et al. | |

FOREIGN PATENT DOCUMENTS

| | | | |
|---|---|---|---|
| CN | 108218663 | A | 6/2018 |
| CN | 109369598 | A | 2/2019 |
| JP | 2006-140235 | A | 6/2006 |
| JP | 2006-176494 | A | 7/2006 |
| JP | 2007-227152 | A | 9/2007 |
| JP | 2007-302650 | A | 11/2007 |
| JP | 2009-016693 | A | 1/2009 |
| JP | 2010-161356 | A | 7/2010 |

(56) References Cited

FOREIGN PATENT DOCUMENTS

| | | | |
|---|---|---|---|
| JP | 2011-103189 | A | 5/2011 |
| JP | 2011-173973 | A | 9/2011 |
| JP | 2011-241383 | A | 12/2011 |
| JP | 2012-064453 | A | 3/2012 |
| JP | 2012-158542 | A | 8/2012 |
| JP | 2013-051158 | A | 3/2013 |
| JP | 2013-067586 | A | 4/2013 |
| JP | 2013-513690 | A | 4/2013 |
| JP | 2013-528927 | A | 7/2013 |
| JP | 2013-157552 | A | 8/2013 |
| JP | 2014-022205 | A | 2/2014 |
| JP | 2015-041775 | A | 3/2015 |
| JP | 2017-123352 | A | 7/2017 |
| JP | 2018-125504 | A | 8/2018 |
| JP | 2019-161218 | A | 9/2019 |
| JP | 2019-186521 | A | 10/2019 |
| JP | 2020-033329 | A | 3/2020 |
| JP | 2020-045324 | A | 3/2020 |
| KR | 10-0967355 | B1 | 7/2010 |
| KR | 2011-0034981 | A | 4/2011 |
| KR | 2011-0049554 | A | 5/2011 |
| KR | 2012-0091144 | A | 8/2012 |
| KR | 2014-0058291 | A | 5/2014 |
| KR | 2014-0058292 | A | 5/2014 |
| KR | 2018-0077887 | A | 7/2018 |
| WO | WO-2004/018587 | A1 | 3/2004 |
| WO | WO-2005/115950 | A1 | 12/2005 |
| WO | WO-2007/007553 | A1 | 1/2007 |
| WO | WO-2008/062773 | A1 | 5/2008 |
| WO | WO-2010/134350 | A1 | 11/2010 |
| WO | WO-2011/077691 | A1 | 6/2011 |
| WO | WO-2014/104144 | A1 | 7/2014 |
| WO | WO-2019/124550 | A1 | 6/2019 |
| WO | WO-2020/080417 | A1 | 4/2020 |

OTHER PUBLICATIONS

International Preliminary Report on Patentability issued in corresponding International Patent Application No. PCT/JP2020/034596 dated Mar. 15, 2022.

International Preliminary Report on Patentability issued in corresponding International Patent Application No. PCT/JP2020/034599 dated Mar. 15, 2022.

International Preliminary Report on Patentability issued in corresponding International Patent Application No. PCT/JP2020/034604 dated Mar. 15, 2022.

International Preliminary Report on Patentability issued in corresponding International Patent Application No. PCT/JP2020/034605 dated Mar. 15, 2022.

International Preliminary Report on Patentability issued in corresponding International Patent Application No. PCT/JP2020/034606 dated Mar. 15, 2022.

International Preliminary Report on Patentability, "Written Opinion," issued in connection with International Patent Application No. PCT/JP2020/044062, dated May 17, 2022, English translation (7 pages).

International Preliminary Report on Patentability, "Written Opinion," issued in connection with International Patent Application No. PCT/JP2021/009835, dated Oct. 13, 2022, English translation (7 pages).

International Search Report dated Oct. 20, 2020 for corresponding International Patent Application No. PCT/JP2020/034591.

Yang et al., "Stable and efficient blue fluorescent organic light-emitting diode by blade coating with or without electron-transport layer," Organic Electronics, vol. 51, 2017. pp. 6-15.

International Searching Authority, "International Search Report," issued in connection with International Patent Application No. PCT/JP2020/034591, dated Oct. 20, 2020.

International Searching Authority, "Written Opinion," issued in connection with International Patent Application No. PCT/JP2020/034591, dated Oct. 20, 2020.

International Preliminary Report on Patentability issued in corresponding International Patent Application No. PCT/JP2020/034591 dated Mar. 15, 2022.

Office Action issued in corresponding Chinese Patent Application No. 202080063067.3 dated Jan. 18, 2025.

* cited by examiner

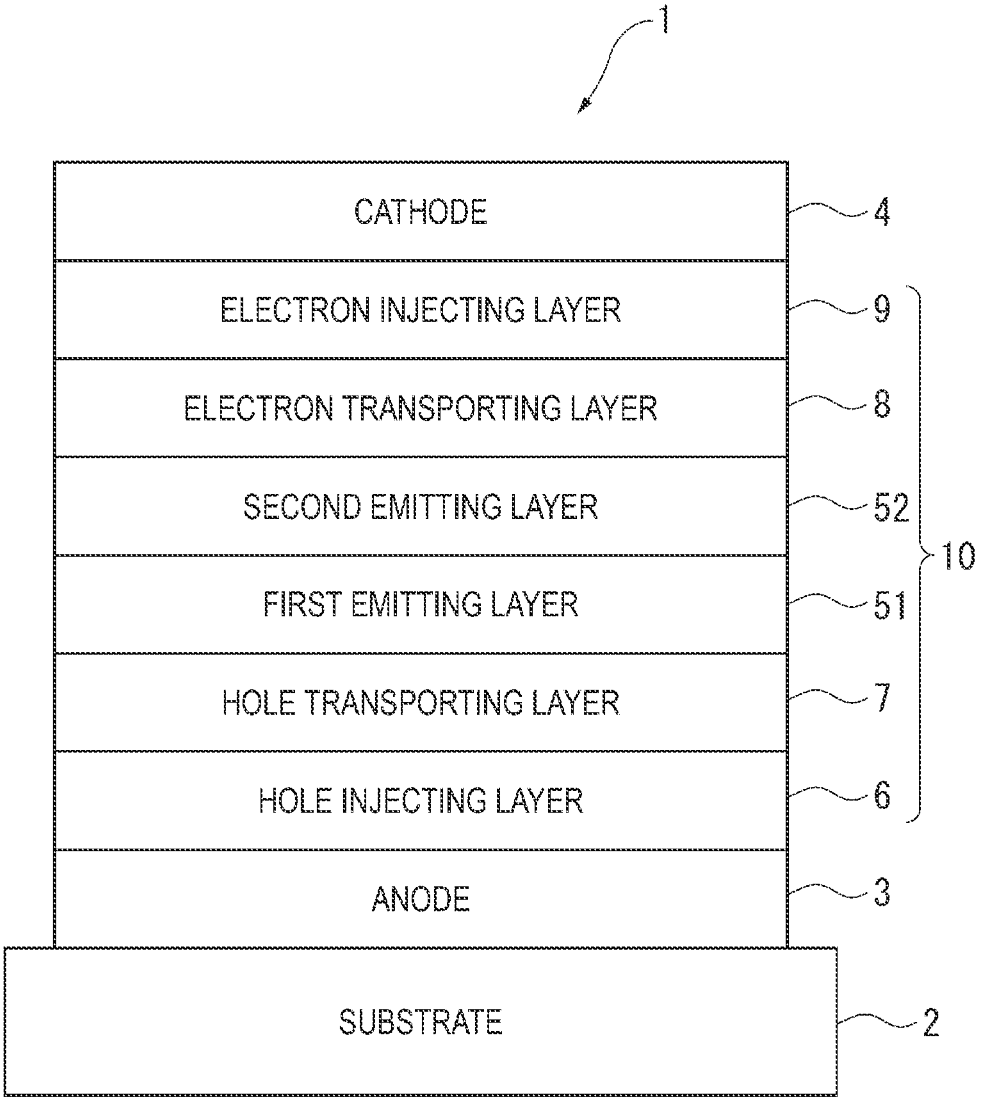
1
CATHODE
4
ELECTRON INJECTING LAYER
9
ELECTRON TRANSPORTING LAYER
8
SECOND EMITTING LAYER
52
FIRST EMITTING LAYER
51
HOLE TRANSPORTING LAYER
7
HOLE INJECTING LAYER
6
ANODE
3
10
SUBSTRATE
2

ORGANIC ELECTROLUMINESCENT ELEMENT AND ELECTRONIC DEVICE

CROSS-REFERENCE TO RELATED APPLICATIONS

The present application claims priority under 37 U.S.C. § 371 to International Patent Application No. PCT/JP2020/034591, filed Sep. 11, 2020, which claims priority to and the benefit of Japanese Patent Application Nos. 2019-167636, filed on Sep. 13, 2019, 2019-213374, filed on Nov. 26, 2019, 2019-239596, filed on Dec. 27, 2019, and 2020-023551, filed on Feb. 14, 2020. The contents of these applications are hereby incorporated by reference in their entireties.

TECHNICAL FIELD

The present invention relates to an organic electroluminescence device and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected electrons and holes are recombined in the emitting layer to form excitons. Specifically, according to the electron spin statistics theory, singlet excitons and triplet excitons are generated at a ratio of 25%:75%.

Various studies have been made for compounds to be used for the organic EL device in order to enhance the performance of the organic EL device (e.g., see Patent Literatures 1 to 6). The performance of the organic EL device is evaluable in terms of, for instance, luminance, emission wavelength, chromaticity, emission efficiency, drive voltage, and lifetime.

CITATION LIST

Patent Literature(s)

Patent Literature 1: JP 2013-157552 A
Patent Literature 2: International Publication No. WO2004/018587
Patent Literature 3: International Publication No. WO2005/115950
Patent Literature 4: International Publication No. WO2011/077691
Patent Literature 5: JP 2018-125504 A
Patent Literature 6: US Patent Application Publication No. 2019/280209

SUMMARY OF THE INVENTION

Problems to be Solved by the Invention

An object of the invention is to provide an organic electroluminescence device with enhanced performance. Another object of the invention is to provide an organic electroluminescence device with enhanced luminous efficiency and an electronic device including the organic electroluminescence device.

Means for Solving the Problems

Provided according to an aspect of the invention is an organic electroluminescence device including an anode, a cathode, a first emitting layer provided between the anode and the cathode, and a second emitting layer provided between the first emitting layer and the cathode, the first emitting layer containing a first host material in a form of a first compound containing at least one group represented by a formula (11) below, the first compound being represented by a formula (1) below, the second emitting layer containing a second host material in a form of a second compound represented by a formula (2) below, the first emitting layer and the second emitting layer being in direct contact with each other.

[Formula 1]

(1)

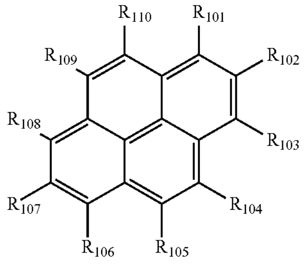

(11)

$$*-\!\!\left(L_{101}\right)_{mx}\!\!-Ar_{101}$$

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5; and when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 2]

(2)

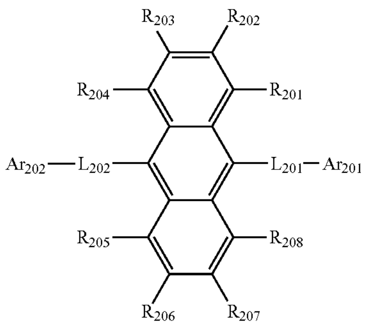

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms;

$Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the first compound represented by the formula (1) and the second compound represented by the formula (2): $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

Provided according to another aspect of the invention is an organic electroluminescence device including an anode, a cathode, a first emitting layer provided between the anode and the cathode, and a second emitting layer provided between the first emitting layer and the cathode, the first emitting layer containing a first host material in a form of a first compound represented by a formula (101) below, the second emitting layer containing the second host material in a form of the second compound represented by the formula (2), the first emitting layer and the second emitting layer being in direct contact with each other.

[Formula 3]

(101)

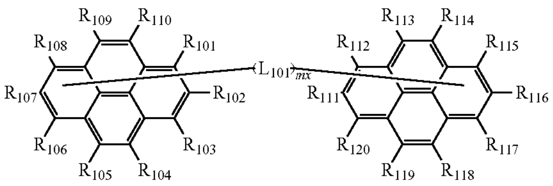

In the formula (101):

$R_{101}$ to $R_{110}$, and $R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 24 ring carbon atoms, or a substituted or unsubstituted divalent heterocyclic group having 5 to 24 ring atoms;

mx is 1, 2, 3, 4, or 5; and when two or more $L_{101}$ are present, the two or more $L_{101}$ are mutually the same or different.

According to still another aspect of the invention, an electronic device including the organic electroluminescence device according to the above aspect of the invention is provided.

According to the above aspect of the invention, an organic electroluminescence device with enhanced performance can be provided. In addition, according to the above aspect of the invention, an organic electroluminescence device with enhanced luminous efficiency can be provided. According to the above aspect of the invention, an electronic device installed with the organic electroluminescence device can be provided.

BRIEF DESCRIPTION OF DRAWING(S)

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded with each other to form the ring. When the ring is substituted by a substituent(s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded with a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded with hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and does not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituent Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B) (Herein, an unsubstituted aryl group refers to an "unsubstituted aryl group" in a "substituted or unsubstituted aryl group", and a substituted aryl group refers to a "substituted aryl group" in a "substituted or unsubstituted aryl group.") A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, a perylenyl group, and a monovalent aryl group derived by removing one hydrogen atom from cyclic structures represented by formulae (TEMP-1) to (TEMP-15) below.

[Formula 4]

(TEMP-1)

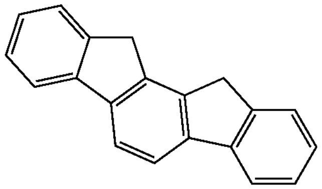

(TEMP-2)

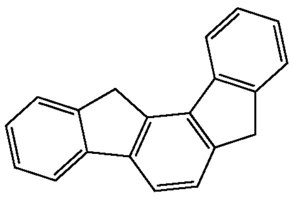

-continued (TEMP-3)

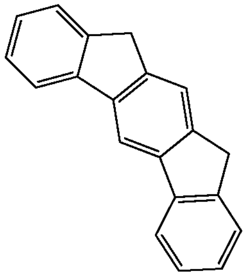

(TEMP-4)

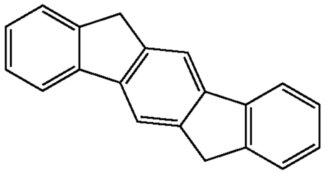

(TEMP-5)

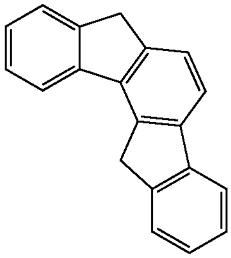

(TEMP-6)

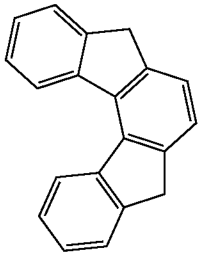

(TEMP-7)

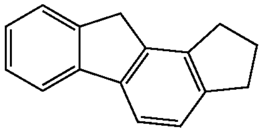

(TEMP-8)

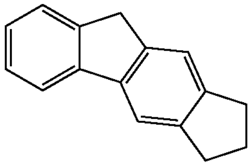

(TEMP-9)

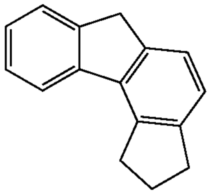

-continued

[Formula 5]

(TEMP-10)

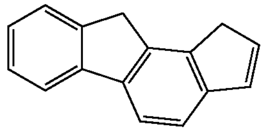

(TEMP-11)

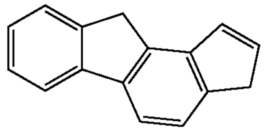

(TEMP-12)

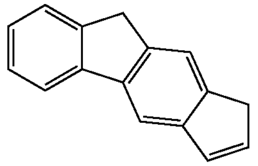

(TEMP-13)

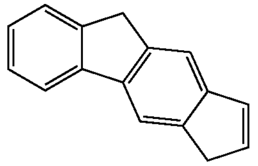

(TEMP-14)

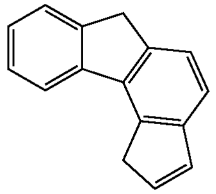

(TEMP-15)

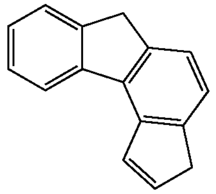

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B) (Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of "unsubstituted heterocyclic group" and "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, a dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing a Hydrogen Atom from Cyclic Structures Represented by Formulae (TEMP-16) to (TEMP-33) Below (Specific Example Group G2A4):

[Formula 6]

(TEMP-16)

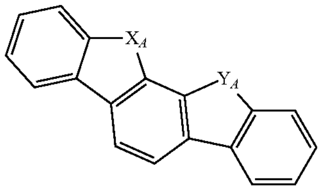

(TEMP-17)

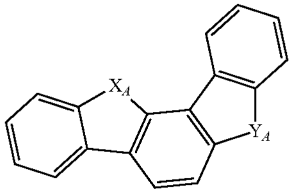

(TEMP-18)

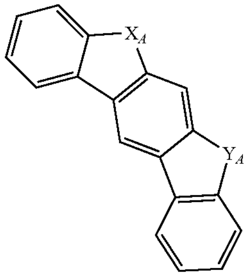

-continued (TEMP-19)

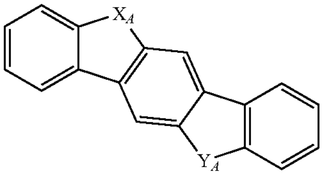

(TEMP-20)

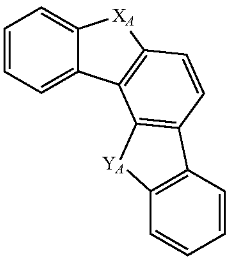

(TEMP-21)

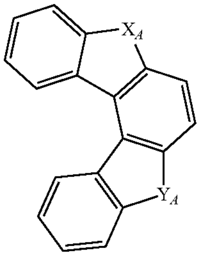

(TEMP-22)

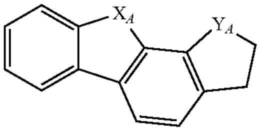

(TEMP-23)

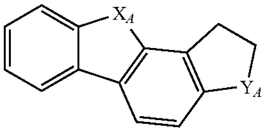

(TEMP-24)

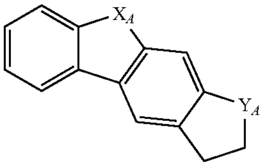

[Formula 7]

(TEMP-25)

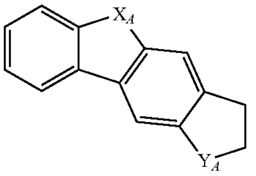

(TEMP-26)

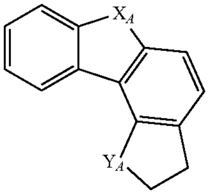

-continued (TEMP-27)

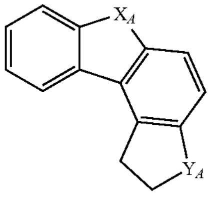

(TEMP-28)

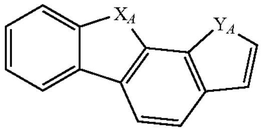

(TEMP-29)

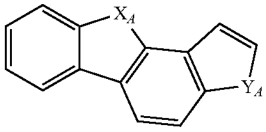

(TEMP-30)

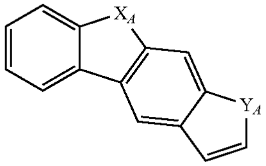

(TEMP-31)

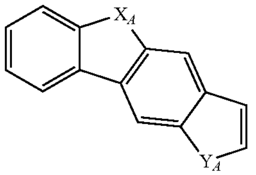

(TEMP-32)

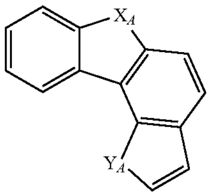

(TEMP-33)

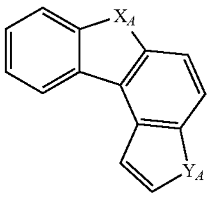

In the formulae (TEMP-16) to (TEMP-33), $X_A$ and $Y_A$ are each independently an oxygen atom, a sulfur atom, NH or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9,9'-[9H]fluorene].

Groups Derived by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of XA or YA in a form of NH, and a hydrogen atom of one of XA and YA in a form of a methylene group (CH2).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B below). (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group.") A simply termed "alkynyl group" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A): Ethynyl Group

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B) (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl group" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):

4-methylcyclohexyl group.

Group Represented by $—Si(R_{901})(R_{902})(R_{903})$

Specific examples (specific example group G7) of the group represented herein by $—Si(R_{901})(R_{902})(R_{903})$ include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —Si(G1)(G1)(G1) are mutually the same or different;

a plurality of G2 in —Si(G1)(G2)(G2) are mutually the same or different;

a plurality of G1 in —Si(G1)(G1)(G2) are mutually the same or different;

a plurality of G2 in —Si(G2)(G2)(G2) are mutually the same or different;

a plurality of G3 in —Si(G3)(G3)(G3) are mutually the same or different; and a plurality of G6 in —Si(G6)(G6)(G6) are mutually the same or different.

Group Represented by $—O—(R_{904})$

Specific examples (specific example group G8) of a group represented by $—O—(R_{904})$ herein include: —O(G1); —O(G2); —O(G3); and —O(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6), where:

G1 represents a “substituted or unsubstituted aryl group” in the specific example group G1;

G2 represents a “substituted or unsubstituted heterocyclic group” in the specific example group G2;

G3 represents a “substituted or unsubstituted alkyl group” in the specific example group G3; and G6 represents a “substituted or unsubstituted cycloalkyl group” in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6), where:

G1 represents a “substituted or unsubstituted aryl group” in the specific example group G1;

G2 represents a “substituted or unsubstituted heterocyclic group” in the specific example group G2;

G3 represents a “substituted or unsubstituted alkyl group” in the specific example group G3;

G6 represents a “substituted or unsubstituted cycloalkyl group” in the specific example group G6;

a plurality of G1 in —N(G1)(G1) are mutually the same or different;

a plurality of G2 in —N(G2)(G2) are mutually the same or different;

a plurality of G3 in —N(G3)(G3) are mutually the same or different; and a plurality of G6 in —N(G6)(G6) are mutually the same or different.

Halogen Atom

Specific examples (specific example group G11) of “halogen atom” mentioned herein include a fluorine atom, chlorine atom, bromine atom, and iodine atom.

Substituted or Unsubstituted Fluoroalkyl Group

The “substituted or unsubstituted fluoroalkyl group” mentioned herein refers to a group derived by substituting at least one hydrogen atom bonded to at least one of carbon atoms forming an alkyl group in the “substituted or unsubstituted alkyl group” with a fluorine atom, and also includes a group (perfluoro group) derived by substituting all of hydrogen atoms bonded to carbon atoms forming the alkyl group in the “substituted or unsubstituted alkyl group” with fluorine atoms. An “unsubstituted fluoroalkyl group” has, unless otherwise specified herein, 1 to 50, preferably 1 to 30, more preferably 1 to 18 carbon atoms. The “substituted fluoroalkyl group” refers to a group derived by substituting at least one hydrogen atom in a “fluoroalkyl group” with a substituent. It should be noted that the examples of the “substituted fluoroalkyl group” mentioned herein include a group derived by further substituting at least one hydrogen atom bonded to a carbon atom of an alkyl chain of a “substituted fluoroalkyl group” with a substituent, and a group derived by further substituting at least one hydrogen atom of a substituent of the “substituted fluoroalkyl group” with a substituent. Specific examples of the “substituted fluoroalkyl group” include a group derived by substituting at least one hydrogen atom of the “alkyl group” (specific example group G3) with a fluorine atom.

Substituted or Unsubstituted Haloalkyl Group

The “substituted or unsubstituted haloalkyl group” mentioned herein refers to a group derived by substituting at least one hydrogen atom bonded to carbon atoms forming the alkyl group in the “substituted or unsubstituted alkyl group” with a halogen atom, and also includes a group derived by substituting all hydrogen atoms bonded to carbon atoms forming the alkyl group in the “substituted or unsubstituted alkyl group” with halogen atoms. An “unsubstituted haloalkyl group” has, unless otherwise specified herein, 1 to 50, preferably 1 to 30, more preferably 1 to 18 carbon atoms. The “substituted haloalkyl group” refers to a group derived by substituting at least one hydrogen atom in a “haloalkyl group” with a substituent. It should be noted that the examples of the “substituted haloalkyl group” mentioned herein include a group derived by further substituting at least one hydrogen atom bonded to a carbon atom of an alkyl chain of a “substituted haloalkyl group” with a substituent, and a group derived by further substituting at least one hydrogen atom of a substituent of the “substituted haloalkyl group” with a substituent. Specific examples of the “substituted haloalkyl group” include a group derived by substituting at least one hydrogen atom of the “alkyl group” (specific example group G3) with a halogen atom. The haloalkyl group is sometimes referred to as a halogenated alkyl group.

Substituted or Unsubstituted Alkoxy Group

Specific examples of a “substituted or unsubstituted alkoxy group” mentioned herein include a group represented by —O(G3), G3 being the “substituted or unsubstituted alkyl group” in the specific example group G3. An “unsubstituted alkoxy group” has, unless otherwise specified herein, 1 to 50, preferably 1 to 30, more preferably 1 to 18 carbon atoms.

Substituted or Unsubstituted Alkylthio Group

Specific examples of a “substituted or unsubstituted alkylthio group” mentioned herein include a group represented by —S(G3), G3 being the “substituted or unsubstituted alkyl group” in the specific example group G3. An “unsubstituted alkylthio group” has, unless otherwise specified herein, 1 to 50, preferably 1 to 30, more preferably 1 to 18 carbon atoms.

Substituted or Unsubstituted Aryloxy Group

Specific examples of a “substituted or unsubstituted aryloxy group” mentioned herein include a group represented by —O(G1), G1 being the “substituted or unsubstituted aryl group” in the specific example group G1. An “unsubstituted aryloxy group” has, unless otherwise specified herein, 6 to 50, preferably 6 to 30, more preferably 6 to 18 ring carbon atoms.

Substituted or Unsubstituted Arylthio Group

Specific examples of a “substituted or unsubstituted arylthio group” mentioned herein include a group represented by —S(G1), G1 being the “substituted or unsubstituted aryl group” in the specific example group G1. An “unsubstituted arylthio group” has, unless otherwise specified herein, 6 to 50, preferably 6 to 30, more preferably 6 to 18 ring carbon atoms.

Substituted or Unsubstituted Trialkylsilyl Group

Specific examples of a “trialkylsilyl group” mentioned herein include a group represented by —Si(G3)(G3)(G3), G3 being the “substituted or unsubstituted alkyl group” in the specific example group G3. The plurality of G3 in —Si(G3)(G3)(G3) are mutually the same or different. Each of the alkyl groups in the “trialkylsilyl group” has, unless otherwise specified herein, 1 to 50, preferably 1 to 20, more preferably 1 to 6 carbon atoms.

Substituted or Unsubstituted Aralkyl Group

Specific examples of a “substituted or unsubstituted aralkyl group” mentioned herein include a group represented by (G3)-(G1), G3 being the “substituted or unsubstituted alkyl group” in the specific example group G3, G1 being the “substituted or unsubstituted aryl group” in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 8]

(TEMP-Cz1)

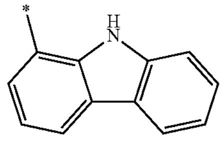

(TEMP-Cz2)

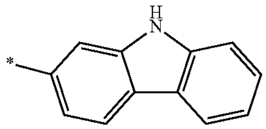

-continued (TEMP-Cz3)

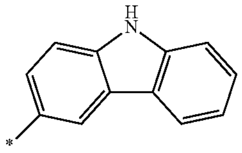

(TEMP-Cz4)

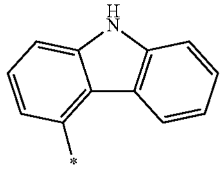

(TEMP-Cz5)

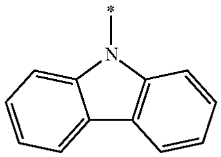

The (9-phenyl)carbazolyl group mentioned herein is, unless otherwise specified herein, specifically a group represented by one of formulae below.

[Formula 9]

(TEMP-Cz6)

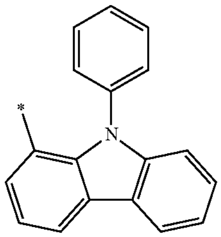

(TEMP-Cz7)

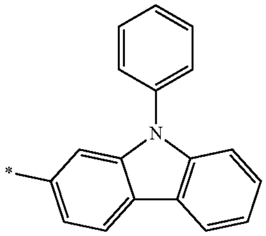

(TEMP-Cz8)

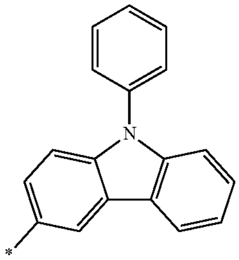

-continued (TEMP-Cz9)

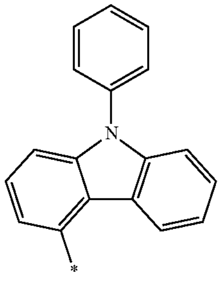

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 10]

(TEMP-34)

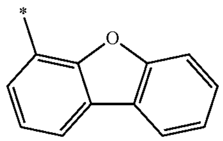

(TEMP-35)

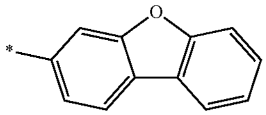

(TEMP-36)

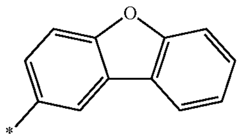

(TEMP-37)

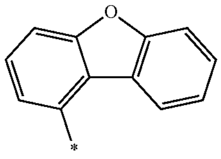

(TEMP-38)

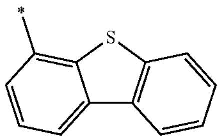

(TEMP-39)

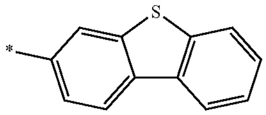

(TEMP-40)

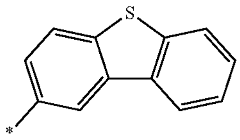

-continued (TEMP-41)

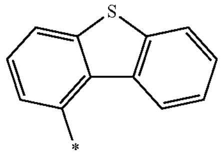

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The “substituted or unsubstituted arylene group” mentioned herein is, unless otherwise specified herein, a divalent group derived by removing one hydrogen atom on an aryl ring of the “substituted or unsubstituted aryl group.” Specific examples of the “substituted or unsubstituted arylene group” (specific example group G12) include a divalent group derived by removing one hydrogen atom on an aryl ring of the “substituted or unsubstituted aryl group” in the specific example group G1.

Substituted or Unsubstituted Divalent Heterocyclic Group

The “substituted or unsubstituted divalent heterocyclic group” mentioned herein is, unless otherwise specified herein, a divalent group derived by removing one hydrogen atom on a heterocycle of the “substituted or unsubstituted heterocyclic group.” Specific examples of the “substituted or unsubstituted divalent heterocyclic group” (specific example group G13) include a divalent group derived by removing one hydrogen atom on a heterocyclic ring of the “substituted or unsubstituted heterocyclic group” in the specific example group G2.

Substituted or Unsubstituted Alkylene Group

The “substituted or unsubstituted alkylene group” mentioned herein is, unless otherwise specified herein, a divalent group derived by removing one hydrogen atom on an alkyl chain of the “substituted or unsubstituted alkyl group.” Specific examples of the “substituted or unsubstituted alkylene group” (specific example group G14) include a divalent group derived by removing one hydrogen atom on an alkyl chain of the “substituted or unsubstituted alkyl group” in the specific example group G3.

The substituted or unsubstituted arylene group mentioned herein is, unless otherwise specified herein, preferably any one of groups represented by formulae (TEMP-42) to (TEMP-68) below.

[Formula 11]

(TEMP-42)

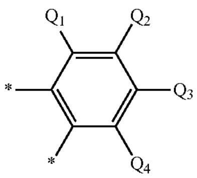

-continued
(TEMP-43)
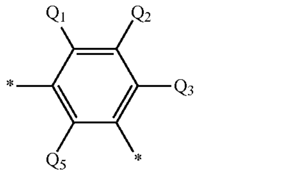
(TEMP-44)
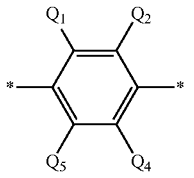
(TEMP-45)
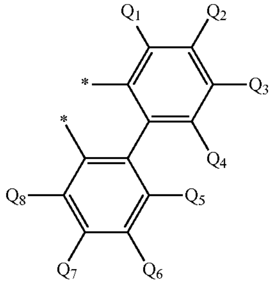
(TEMP-46)
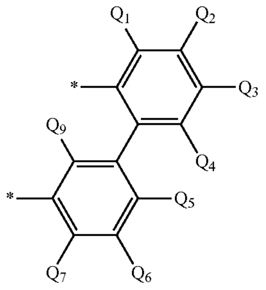
(TEMP-47)
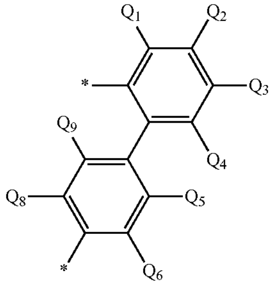
[Formula 12]
(TEMP-48)
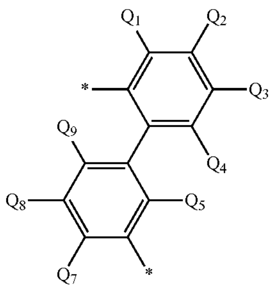
-continued
(TEMP-49)
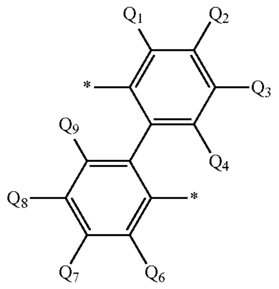
(TEMP-50)
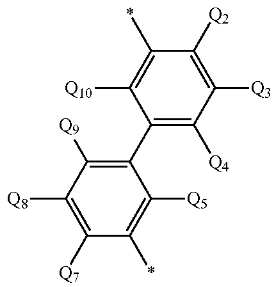
(TEMP-51)
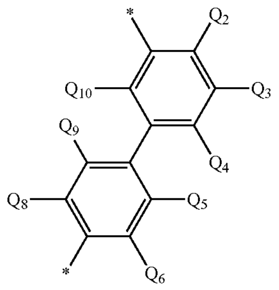
(TEMP-52)
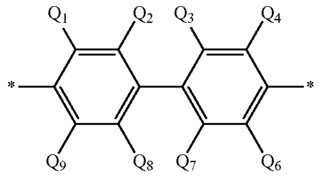
In the formulae (TEMP-42) to (TEMP-52), $Q_1$ to $Q_{10}$ each independently are a hydrogen atom or a substituent.
In the formulae (TEMP-42) to (TEMP-52), * represents a bonding position.
[Formula 13]
(TEMP-53)
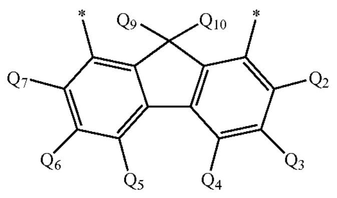

-continued
(TEMP-54)
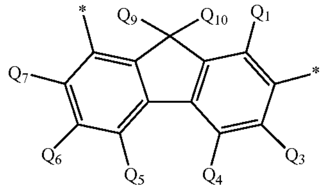
(TEMP-55)
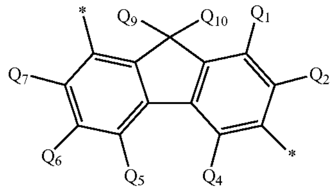
(TEMP-56)
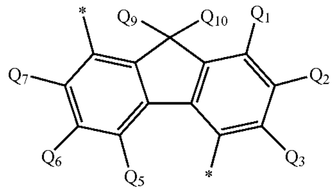
(TEMP-57)
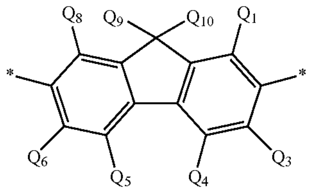
(TEMP-58)
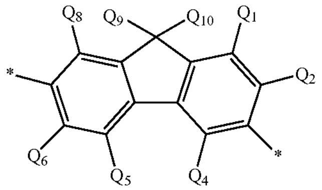
(TEMP-59)
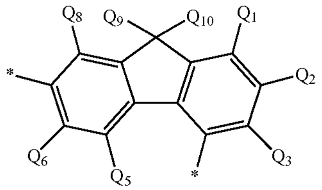
(TEMP-60)
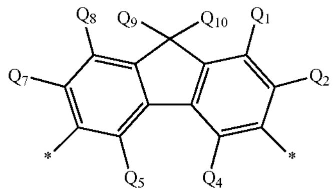
(TEMP-61)
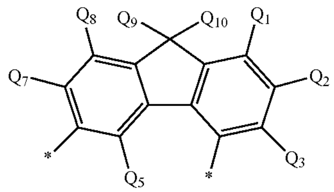
-continued
(TEMP-62)
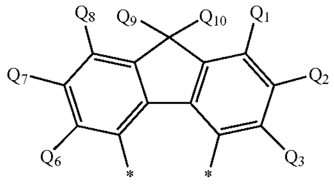
In the formulae (TEMP-53) to (TEMP-62), $Q_1$ to $Q_{10}$ each independently are a hydrogen atom or a substituent.
In the formulae, $Q_9$ and $Q_{10}$ may be mutually bonded through a single bond to form a ring.
In the formulae (TEMP-53) to (TEMP-62), * represents a bonding position.
[Formula 14]
(TEMP-63)
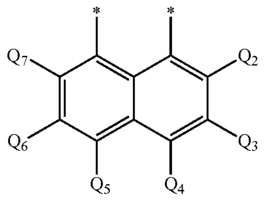
(TEMP-64)
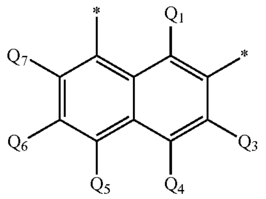
(TEMP-65)
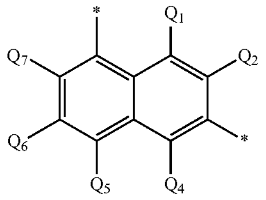
(TEMP-66)
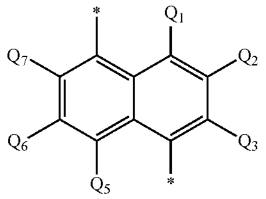
(TEMP-67)
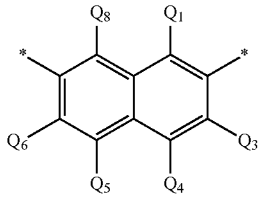

-continued (TEMP-68)

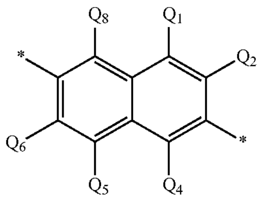

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 15]

(TEMP-69)

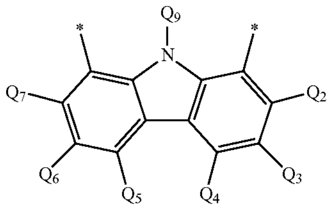

(TEMP-70)

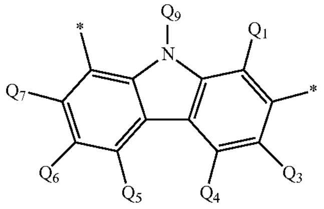

(TEMP-71)

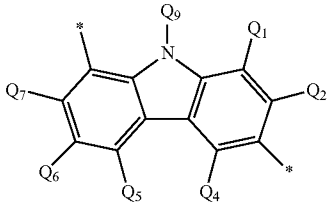

(TEMP-72)

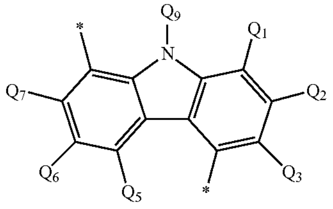

(TEMP-73)

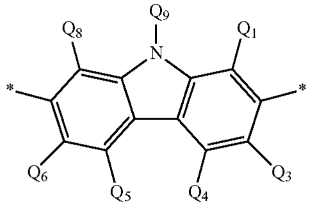

-continued (TEMP-74)

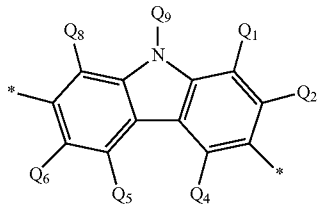

[Formula 16]

(TEMP-75)

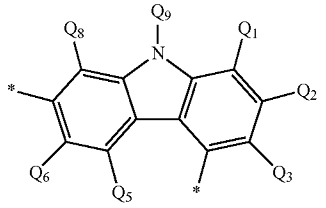

(TEMP-76)

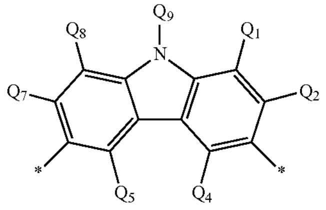

(TEMP-77)

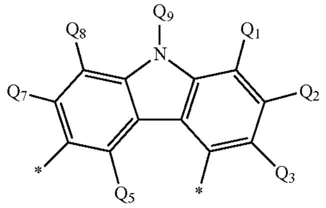

(TEMP-78)

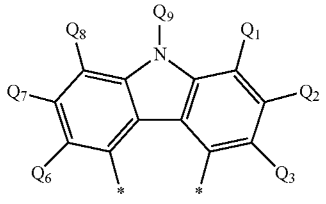

(TEMP-79)

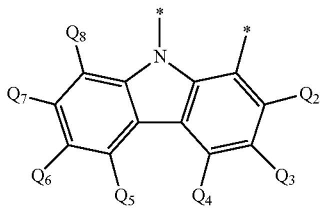

(TEMP-80)

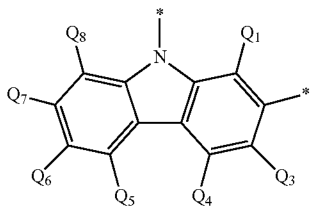

-continued
[Formula 17]
(TEMP-81)
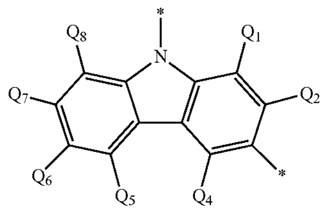
(TEMP-82)
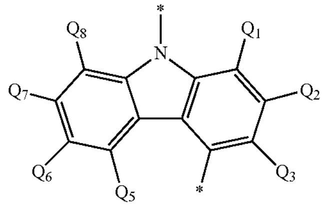
In the formulae (TEMP-69) to (TEMP-82), $Q_1$ to $Q_9$ each independently are a hydrogen atom or a substituent.
[Formula 18]
(TEMP-83)
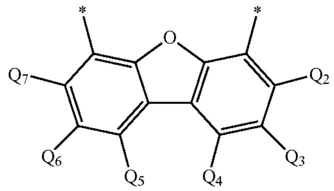
(TEMP-84)
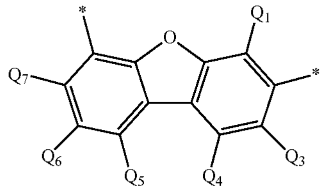
(TEMP-85)
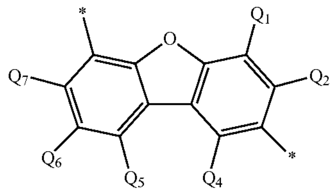
(TEMP-86)
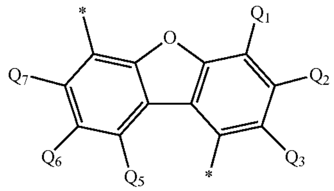
-continued
(TEMP-87)
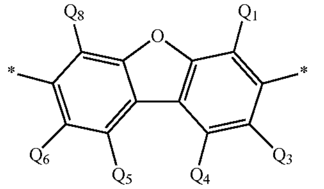
(TEMP-88)
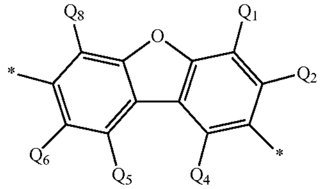
[Formula 19]
(TEMP-89)
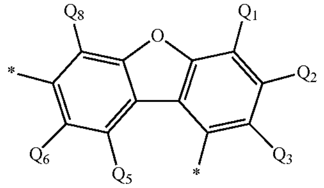
(TEMP-90)
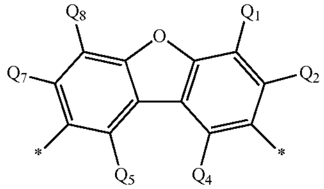
(TEMP-91)
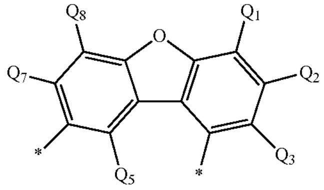
(TEMP-92)
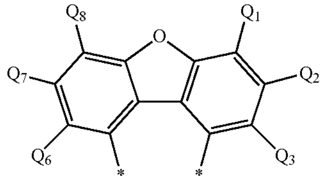
[Formula 20]
(TEMP-93)
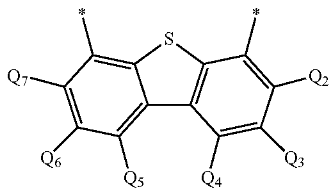

-continued (TEMP-94)

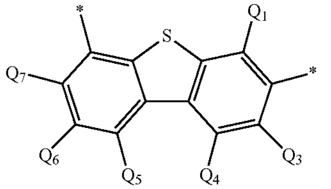

(TEMP-95)

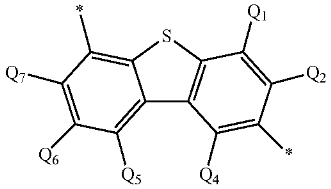

(TEMP-96)

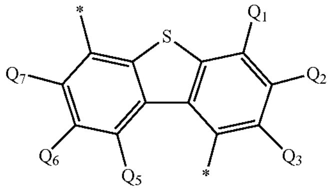

(TEMP-97)

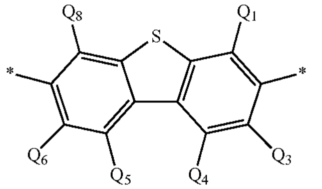

(TEMP-98)

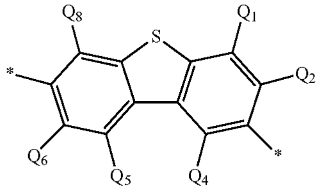

[Formula 21]

(TEMP-99)

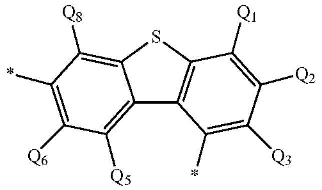

(TEMP-100)

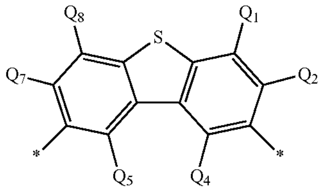

(TEMP-101)

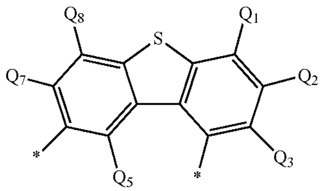

-continued (TEMP-102)

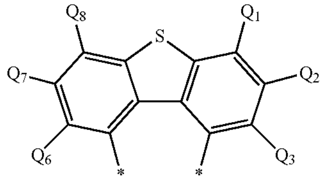

In the formulae (TEMP-83) to (TEMP-102), $Q_1$ to $Q_8$ each independently are a hydrogen atom or a substituent.

The substituent mentioned herein has been described above.

Instance of "Bonded to Form a Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 22]

(TEMP-103)

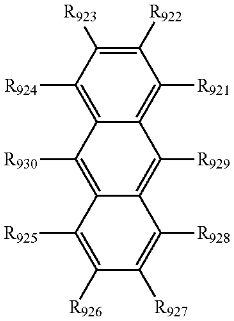

For instance, when "at least one combination of adjacent two or more of" $R_{921}$ to $R_{930}$ "are mutually bonded to form a ring," the combination of adjacent ones of $R_{921}$ to $R_{930}$ (i.e. the combination at issue) is a combination of $R_{921}$ and a combination of $R_{922}$, $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 23]

(TEMP-104)

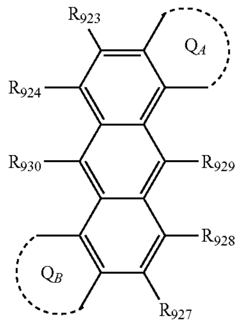

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$, $R_{923}$ are mutually bonded to form a ring Qc, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring Qc share $R_{922}$.

[Formula 24]

(TEMP-105)

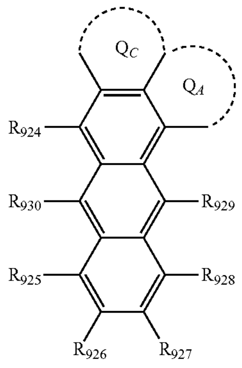

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring Qc formed in the formula (TEMP-105) are each a "fused ring." The ring $Q_A$ and the ring Qc in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded with $R_{921}$, a carbon atom of the anthracene skeleton bonded with $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded with $R_{921}$, a carbon atom of the anthracene skeleton bonded with $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance "bonded to form a ring").

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms; $R_{901}$ to $R_{907}$ each independently are a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted saturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represents a range whose lower limit is the value (AA) recited before "to" and whose upper limit is the value (BB) recited after "to."

First Exemplary Embodiment

Organic Electroluminescence Device

An organic electroluminescence device according to a first exemplary embodiment includes an anode, a cathode, a first emitting layer disposed between the anode and the cathode, and a second emitting layer disposed between the first emitting layer and the cathode. The first emitting layer contains a first host material in a form of a first compound including at least one group represented by a formula (11) below, the first compound being represented by a formula (1) below. The second emitting layer contains a second host material in a form of a second compound represented by a formula (2) below. In the organic EL device according to the exemplary embodiment, the first emitting layer and the second emitting layer are in direct contact with each other.

The organic electroluminescence device according to the exemplary embodiment includes the anode, the first emitting layer, the second emitting layer, and the cathode in this order.

Herein, a layer arrangement in which the first emitting layer and the second emitting layer are in direct contact with each other can include one of embodiments (LS1), (LS2) and (LS3) below.

(LS1) An embodiment in which a region containing both the first compound and the second compound is generated in a process of vapor-depositing the compound of the first emitting layer and vapor-depositing the compound of the second emitting layer, and is present on the interface between the first emitting layer and the second emitting layer.

(LS2) An embodiment in which in a case of containing an emitting compound in the first emitting layer and the second emitting layer, a region containing all of the first compound, the second compound and the emitting compound is generated in a process of vapor-depositing the compound of the first emitting layer and vapor-depositing the compound of the second emitting layer, and is present on the interface between the first emitting layer and the second emitting layer.

(LS3) An embodiment in which in a case of containing an emitting compound in the first emitting layer and the second emitting layer, a region containing the emitting compound, a region containing the first compound or a region containing the second compound is generated in a process of vapor-depositing the compound of the first emitting layer and vapor-depositing the compound of the second emitting layer, and is present on the interface between the first emitting layer and the second emitting layer.

Herein, the "host material" refers to, for instance, a material that accounts for "50 mass % or more of the layer." Accordingly, for instance, the first emitting layer contains 50 mass % or more of the first compound represented by the formula (1) below with respect to a total mass of the first emitting layer. The second emitting layer contains 50 mass % or more of the second compound represented by the formula (2) below with respect to a total mass of the second emitting layer.

Emission Wavelength of Organic EL Device

It is preferable that the organic electroluminescence device according to the exemplary embodiment emits, when being driven, light having a main peak wavelength in a range from 430 nm to 480 nm.

The main peak wavelength of the light emitted when the organic EL device is driven is measured as follows. Voltage is applied on the organic EL devices such that a current density becomes 10 mA/cm$^2$, where spectral radiance spectrum is measured by a spectroradiometer CS-2000 (manufactured by Konica Minolta, Inc.). A peak wavelength of an emission spectrum, at which the luminous intensity of the resultant spectral radiance spectrum is at the maximum, is measured and defined as the main peak wavelength (unit: nm).

The organic EL device according to the exemplary embodiment may include one or more organic layer in addition to the first emitting layer and the second emitting layer. Examples of the organic layer include at least one layer selected from the group consisting of a hole injecting layer, a hole transporting layer, an emitting layer, an electron injecting layer, an electron transporting layer, a hole blocking layer, and an electron blocking layer.

In the organic EL device according to the exemplary embodiment, the organic layer may consist of the first emitting layer and the second emitting layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

Hole Transporting Layer

The organic EL device according to the exemplary embodiment preferably includes a hole transporting layer between the anode and the first emitting layer.

The organic EL device according to the exemplary embodiment preferably includes an electron transporting layer between the cathode and the second emitting layer.

The FIGURE schematically shows an exemplary structure of the organic EL device of the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, a first emitting layer 51, a second emitting layer 52, an electron transporting layer 8, and an electron injecting layer 9, these layers being layered in this order from the anode 3.

First Compound

In the organic EL device according to the exemplary embodiment, the first compound is a compound represented by the formula (1) below.

[Formula 25]

(1)

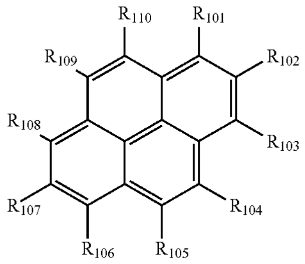

(11)

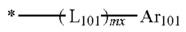

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

In the first compound according to the exemplary embodiment: $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, the group represented by the formula (11) is also preferably a group represented by a formula (111) below.

[Formula 26]

(111)

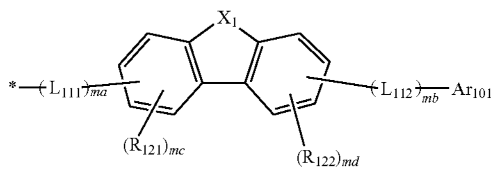

In the formula (111):

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$Ar_{101}$ represents the same as $Ar_{101}$ in the formula (11);

$R_{121}$, $R_{122}$, $R_{123}$, $R_{124}$, and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —C(═O)$R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

Among positions *1 to *8 of carbon atoms in a cyclic structure represented by a formula (111a) below in the group represented by the formula (111), $L_{111}$ is bonded to one of the positions *1 to *4, $R_{121}$ is bonded to each of three positions of the rest of *1 to *4, $L_{112}$ is bonded to one of the positions *5 to *8, and $R_{122}$ is bonded to each of three positions of the rest of *5 to *8.

[Formula 27]

(111a)

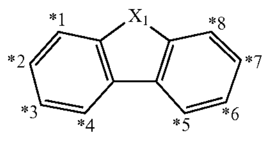

For instance, in the group represented by the formula (111), when $L_{111}$ is bonded to a carbon atom at the position *2 in the cyclic structure represented by the formula (111a) and $L_{112}$ is bonded to a carbon atom at the position *7 in the cyclic structure represented by the formula (111a), the group represented by the formula (111) is represented by a formula (111b) below.

[Formula 28]

(111b)

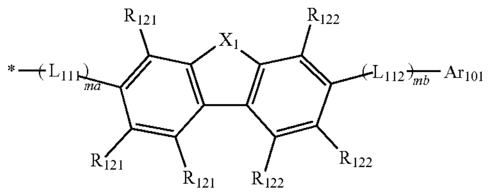

In the formula (111b):

$X_1$, $L_{111}$, $L_{112}$, ma, mb, $Ar_{101}$, $R_{121}$, $R_{122}$, $R_{123}$, $R_{124}$, and $R_{125}$ each independently represent the same as X1, $L_{111}$, $L_{112}$, ma, mb, $Ar_{101}$, $R_{121}$, $R_{122}$, $R_{123}$, $R_{124}$, and $R_{125}$ in the formula (111);

a plurality of $R_{121}$ are mutually the same or different; and a plurality of $R_{122}$ are mutually the same or different.

In the organic EL device according to the exemplary embodiment, the group represented by the formula (111) is preferably a group represented by the formula (111b).

In the organic EL device according to the exemplary embodiment, it is preferable that: ma is 0, 1, or 2; and mb is 0, 1, or 2.

In the organic EL device according to the exemplary embodiment, it is preferable that: ma is 0 or 1; and mb is 0 or 1.

In the organic EL device according to the exemplary embodiment, $Ar_{101}$ is preferably a substituted or unsubstituted aryl group having 6 to 50 ring carbon atoms.

In the organic EL device according to the exemplary embodiment, $Ar_{101}$ is preferably a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, $Ar_{101}$ is also preferably a group represented by a formula (12), (13) or (14) below.

[Formula 29]

(12)

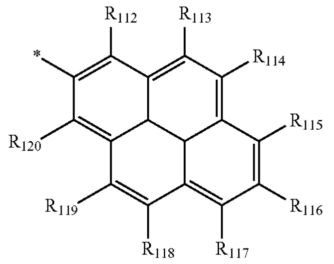

(13)

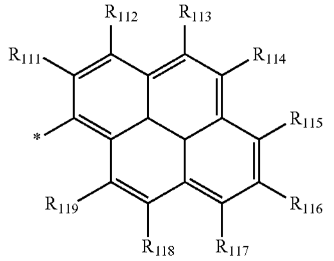

(14)

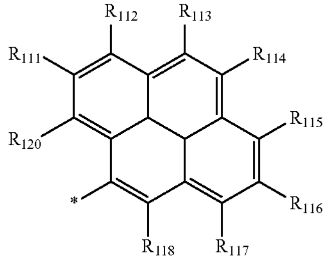

In the formulae (12), (13), and (14):

$R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{124}$, a group represented by —COO$R_{125}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formulae (12), (13) and (14) represents a bonding position to $L_{101}$ in the formula (11), or a bonding position to $L_{112}$ in the formula (111) or (111b).

In the organic EL device according to the exemplary embodiment, the first compound is preferably represented by a formula (101) below.

[Formula 30]

(101)

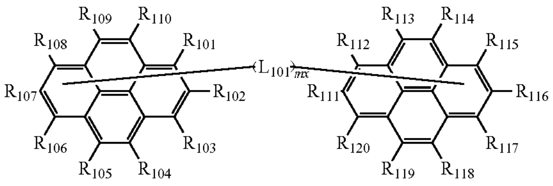

In the formula (101):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

In the first compound represented by the formula (101), it is preferable that: $R_{101}$ to $R_{110}$, and $R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 24 ring carbon atoms, or a substituted or unsubstituted divalent heterocyclic group having 5 to 24 ring atoms;

mx is 1, 2, 3, 4, or 5; and when two or more $L_{101}$ are present, the two or more $L_{101}$ are mutually the same or different.

In the first compound represented by the formula (101), it is also preferable that: $R_{101}$ to $R_{110}$, and $R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a divalent group derived by removing one hydrogen atom from an aryl ring of a substituted or unsubstituted phenyl group, a substituted or unsubstituted 1-naphthyl group or a substituted or unsubstituted 2-naphthyl group;

mx is 1, 2, or 3; and when two or more $L_{101}$ are present, the two or more $L_{101}$ are mutually the same or different.

In the organic EL device according to the exemplary embodiment, the first compound is preferably represented by a formula (1010), (1011), (1012), (1013), (1014), or (1015) below.

[Formula 31]

(1010)

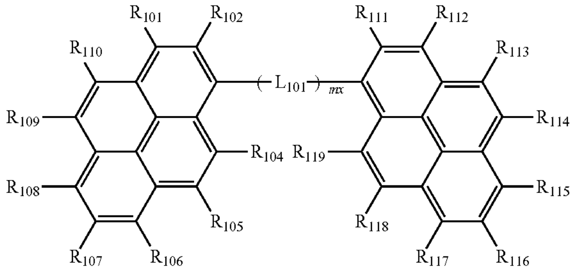

[Formula 32]

(1011)

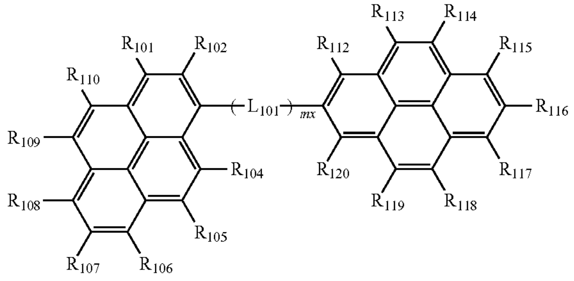

-continued

[Formula 33]

(1012)

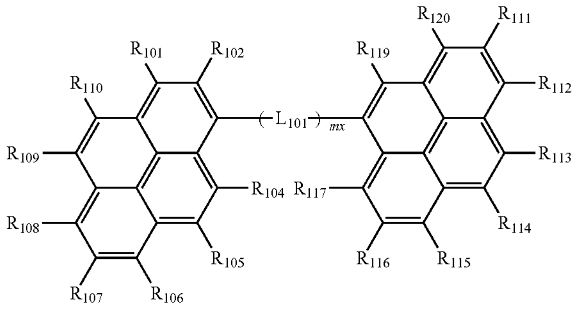

[Formula 34]

(1013)

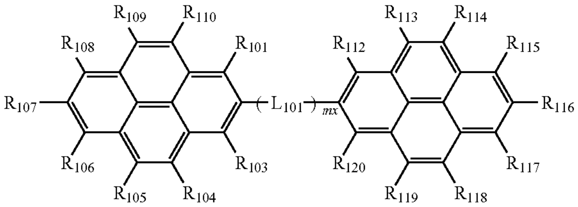

[Formula 35]

(1014)

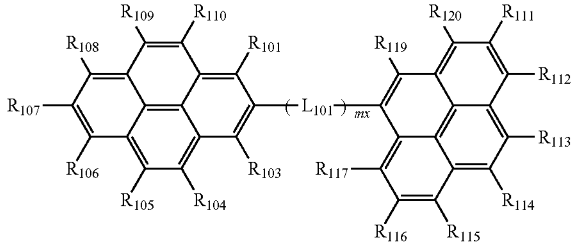

[Formula 36]

(1015)

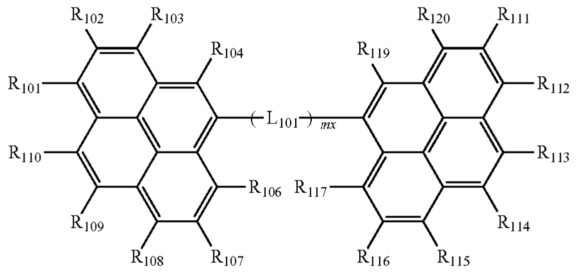

In the formulae (1010) to (1015):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

The compound represented by the formula (1010) corresponds to a compound, in which $R_{103}$ represents a bonding position to $L_{101}$ and $R_{120}$ represents a bonding position to $L_{101}$.

The compound represented by the formula (1011) corresponds to a compound, in which $R_{103}$ represents a bonding position to $L_{101}$ and $R_{111}$ represents a bonding position to $L_{101}$.

The compound represented by the formula (1012) corresponds to a compound, in which $R_{103}$ represents a bonding position to $L_{101}$ and $R_{111}$ represents a bonding position to $L_{101}$.

The compound represented by the formula (1013) corresponds to a compound, in which $R_{102}$ represents a bonding position to $L_{101}$ and $R_{111}$ represents a bonding position to $L_{101}$.

The compound represented by the formula (1014) corresponds to a compound, in which $R_{102}$ represents a bonding position to $L_{101}$ and $R_{111}$ represents a bonding position to $L_{101}$.

The compound represented by the formula (1015) corresponds to a compound, in which $R_{105}$ represents a bonding position to $L_{101}$ and $R_{111}$ represents a bonding position to $L_{101}$.

In the organic EL device according to the exemplary embodiment, the first compound is preferably represented by the formula (1010).

In the organic EL device according to the exemplary embodiment, $R_{101}$ to $R_{110}$ not being a bonding position to $L_{101}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{101}$ to $R_{110}$ not being a bonding position to $L_{101}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being a bonding position to $L_{101}$ are each preferably a hydrogen atom.

In the organic EL device according to the exemplary embodiment, $R_{111}$ to $R_{120}$ not being a bonding position to $L_{101}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{111}$ to $R_{120}$ not being a bonding position to $L_{101}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{111}$ to $R_{120}$ not being a bonding position to $L_{101}$ are each preferably a hydrogen atom.

In the organic EL device according to the exemplary embodiment, a group represented by a formula (11X) below in the first compound also preferably has a total of 21 or less carbon atoms, and also preferably has a total of 13 or less carbon atoms.

[Formula 37]

$$*-(L_{101})_{mx}-* \quad (11X)$$

In the formula (11X): $L_{101}$ and mx each represent the same as $L_{101}$ and mx in the formula (1010); and * represents a bonding position.

Since the total number of carbon atoms of the group represented by the formula (11X) is 21 or less, a decrease in luminous efficiency can be inhibited, for instance, even when increasing a vapor deposition rate of the first compound used for forming the first emitting layer or heating the first compound for a long time in mass production of organic electroluminescence devices, as compared with a compound, such as a compound R—BH2 described below, that contains a linking group having many ring carbon atoms (i.e., having a large molecular weight) and provided between two pyrene rings. A compound usable for film formation is, when forming an organic layer such as an emitting layer at a high speed or when heating the compound for a long time, placed under an environment where thermal decomposition is likely to occur. It is thus presumed that the compound that contains a linking group having many ring carbon atoms (i.e., having a large molecular weight) and provided between two pyrene rings is prone to thermal decomposition in high speed film formation or heating for a long time, resulting in a likely decrease in performance (decrease in luminous efficiency) of an organic EL device.

In the organic EL device according to the exemplary embodiment, the total number of carbon atoms contained in $R_{101}$ to $R_{110}$ and $R_{111}$ to $R_{120}$ not being a bonding position to $L_{101}$ is also preferably 21 or less.

In the organic EL device according to the exemplary embodiment, the total number of carbon atoms contained in $R_{101}$ to $R_{110}$ and $R_{111}$ to $R_{120}$ not being a bonding position to $L_{101}$ and in the group represented by the formula (11X) is also preferably 21 or less, and also preferably 13 or less.

In the organic EL device according to the exemplary embodiment, $L_{101}$ is preferably a single bond, or a substituted or unsubstituted arylene group having 6 to 50 ring carbon atoms.

In the organic EL device according to the exemplary embodiment, it is also preferable that $L_{101}$ is a single bond, a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that $L_{101}$ is a single bond, or a substituted or unsubstituted arylene group having 6 to 18 ring carbon atoms.

In the organic EL device according to the exemplary embodiment, it is also preferable that $L_{101}$ is a substituted or unsubstituted arylene group having 6 to 18 ring carbon atoms.

In the organic EL device according to the exemplary embodiment, it is also preferable that $L_{101}$ is a single bond, a substituted or unsubstituted arylene group having 6 to 13 ring carbon atoms, or a substituted or unsubstituted divalent heterocyclic group having 5 to 13 ring atoms.

In the organic EL device according to the exemplary embodiment, it is also preferable that $L_{101}$ is a single bond, or a substituted or unsubstituted arylene group having 6 to 13 ring carbon atoms.

In the organic EL device according to the exemplary embodiment, it is also preferable that $L_{101}$ is a substituted or unsubstituted arylene group having 6 to 13 ring carbon atoms.

In the formulae (1010) to (1015), it is also preferable that $L_{101}$ is a divalent group derived by removing one hydrogen atom from an aryl ring of a substituted or unsubstituted phenyl group, a substituted or unsubstituted 1-naphthyl group or a substituted or unsubstituted 2-naphthyl group, and mx is 1, 2, or 3.

$L_{101}$ is also preferably a substituted or unsubstituted arylene group selected from the group consisting of groups represented by formulae (TEMP-42) to (TEMP-52), and (TEMP-63) to (TEMP-68) below.

[Formula 38]

(TEMP-42)

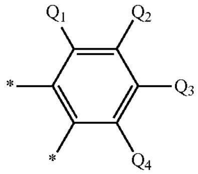

(TEMP-43)

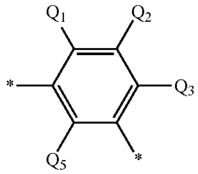

(TEMP-44)

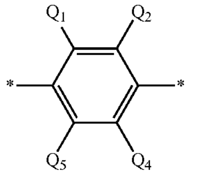

(TEMP-45)

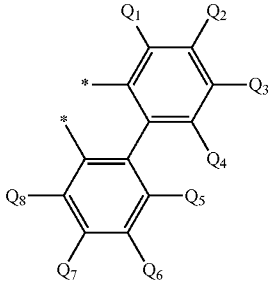

-continued (TEMP-46)

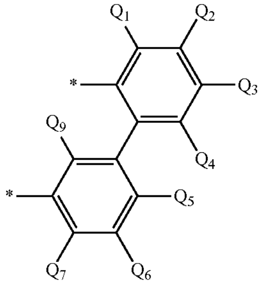

(TEMP-47)

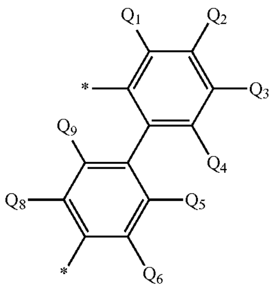

[Formula 39]

(TEMP-48)

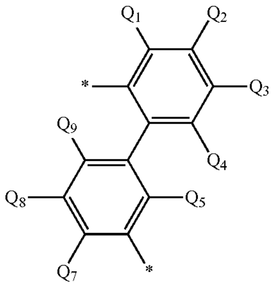

(TEMP-49)

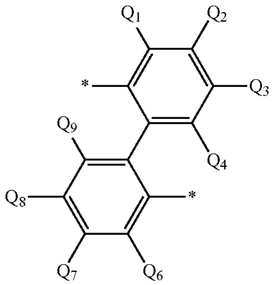

(TEMP-50)

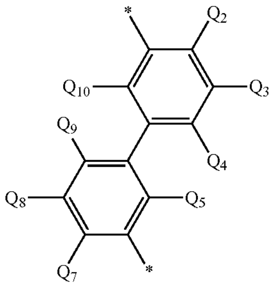

-continued (TEMP-51)

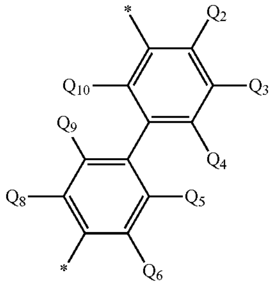

(TEMP-52)

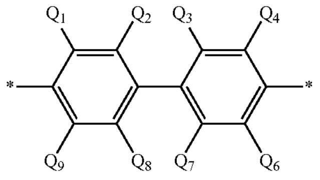

[Formula 40]

(TEMP-63)

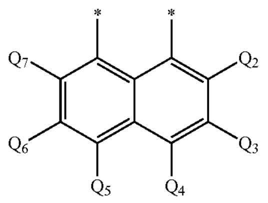

(TEMP-64)

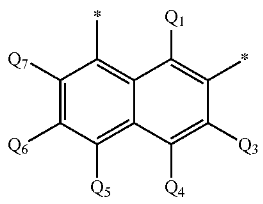

(TEMP-65)

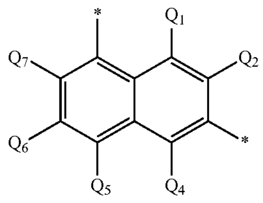

(TEMP-66)

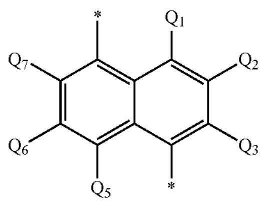

(TEMP-67)

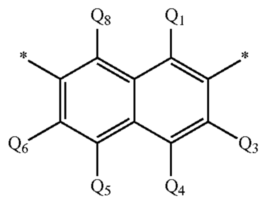

-continued (TEMP-68)

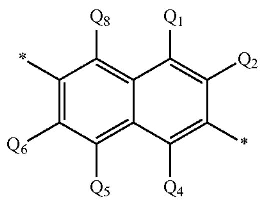

In the formulae (TEMP-42) to (TEMP-52) and (TEMP-63) to (TEMP-68), $Q_1$ to $Q_{10}$ are each independently a hydrogen atom or a substituent, $Q_1$ to $Q_{10}$ as a substituent are each independently an unsubstituted phenyl group, an unsubstituted 1-naphthyl group or an unsubstituted 2-naphthyl group, and * represents a bonding position.

$L_{101}$ is also preferably a divalent group represented by a formula (112) below.

[Formula 41]

(112)

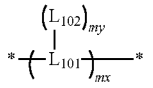

In the formula (112):

$L_{101}$ is a divalent group derived by removing one hydrogen atom from an aryl ring of a substituted or unsubstituted phenyl group, a substituted or unsubstituted 1-naphthyl group or a substituted or unsubstituted 2-naphthyl group;

$L_{102}$ is an unsubstituted phenyl group, an unsubstituted 1-naphthyl group, or an unsubstituted 2-naphthyl group;

mx is 1, 2, or 3;

my is 0, 1, or 2;

mx+my is 1, 2, or 3;

when two or more $L_{101}$ are present, the two or more $L_{101}$ are mutually the same or different;

when two or more $L_{102}$ are present, the two or more $L_{102}$ are mutually the same or different; and

* in the formula (112) represents a bonding position.

The group represented by $-(L_{101})_{mx}-$ is preferably a group represented by any one of formulae (113) to (122) below.

[Formula 42]

(113)

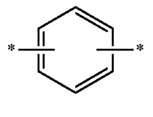

(114)

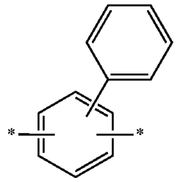

(115)

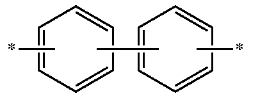

-continued (116)

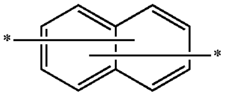

(117)

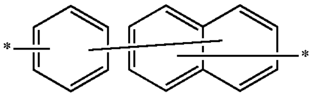

[Formula 43]

(118)

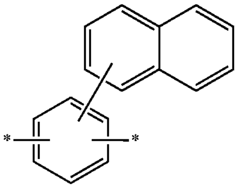

(119)

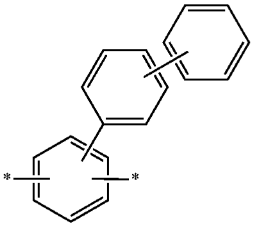

(120)

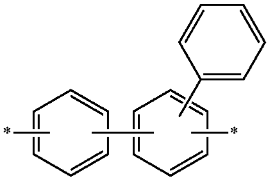

(121)

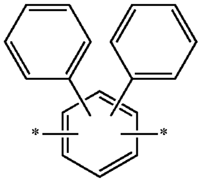

(122)

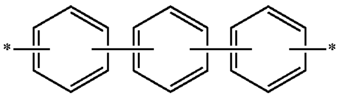

* in the formulae (113) to (122) represents a bonding position.

In the organic EL device according to the exemplary embodiment, the number of carbon atoms forming an aromatic hydrocarbon ring in a group represented by the formula (11X) is also preferably 6 to 13, also preferably 6 to 10, and also preferably 6.

In the organic EL device according to the exemplary embodiment, the group represented by the formula (11X) also preferably does not contain a fused ring.

The group represented by the formula (11X) is also preferably a group selected from the group consisting of groups represented by formulae (1110) to (1119) below.

[Formula 44]

(1110)

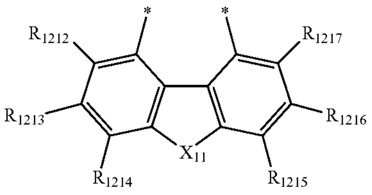

(1111)

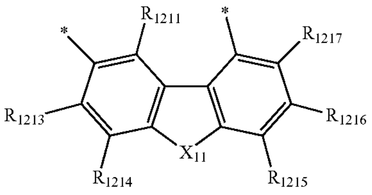

(1112)

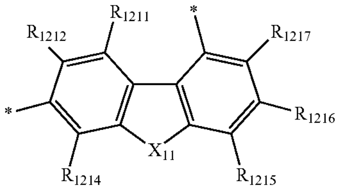

(1113)

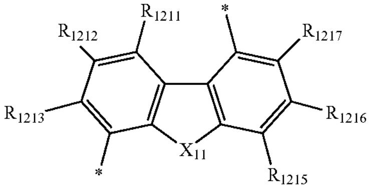

[Formula 45]

(1114)

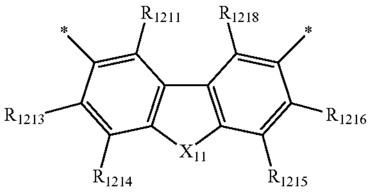

(1115)

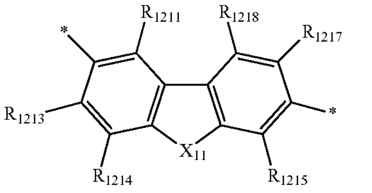

(1116)

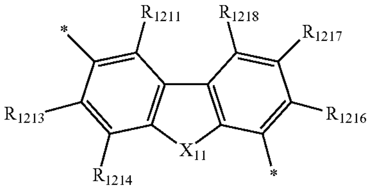

(1117)

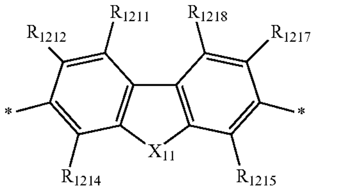

-continued (1118)

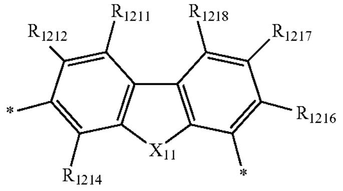

(1119)

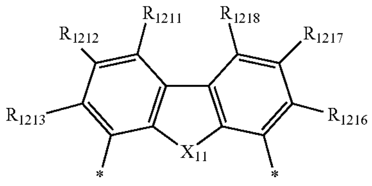

In the formulae (1110) to (1119):

$X_{11}$ is $CR_{1223}R_{1224}$, an oxygen atom, a sulfur atom, or $NR_{1225}$;

$R_{1211}$ to $R_{1218}$, $R_{1223}$, $R_{1224}$ and $R_{1225}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —C(=O)$R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position.

$X_{11}$ is preferably $CR_{1223}R_{1224}$, an oxygen atom, or a sulfur atom.

$X_{11}$ is preferably an oxygen atom, or a sulfur atom.

$R_{1211}$ to $R_{1218}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

$R_{1211}$ to $R_{1218}$ are preferably each independently a hydrogen atom, or a substituted or unsubstituted alkyl group having 1 to 50 carbon atoms.

$R_{1211}$ to $R_{1218}$ are each preferably a hydrogen atom.

$R_{1223}$, $R_{1224}$ and $R_{1225}$ are preferably each independently a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

The group represented by the formula (11X) is also preferably a group selected from the group consisting of groups represented by formulae (1130) to (1135) below.

[Formula 46]

(1130)

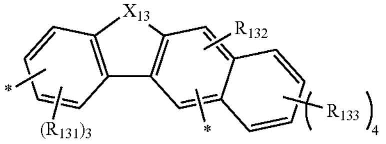

(1131)

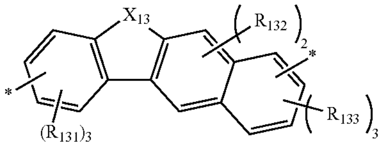

(1132)

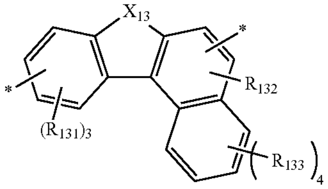

(1133)

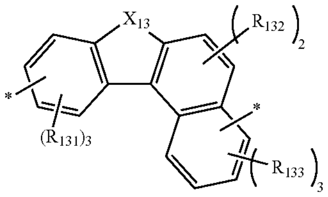

(1134)

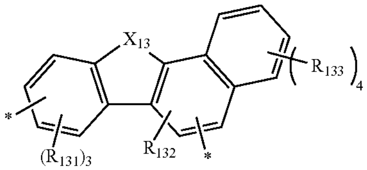

(1135)

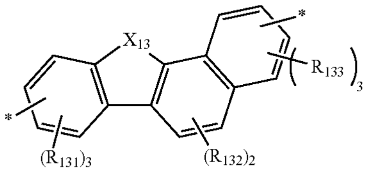

In the formulae (1130) to (1135):

$X_{13}$ is $CR_{134}R_{135}$, an oxygen atom, a sulfur atom, or $NR_{136}$;

$R_{131}$, $R_{132}$, $R_{133}$, $R_{134}$, $R_{135}$ and $R_{136}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —C(=O)$R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position.

$X_{13}$ is preferably an oxygen atom, or a sulfur atom.

$R_{131}$ to $R_{133}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

$R_{131}$ to $R_{133}$ are preferably each independently a hydrogen atom, or a substituted or unsubstituted alkyl group having 1 to 50 carbon atoms.

$R_{131}$ to $R_{133}$ are each preferably a hydrogen atom.

$R_{134}$, $R_{135}$ and $R_{136}$ are preferably each independently a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, mx is also preferably 1, 2, or 3.

In the organic EL device according to the exemplary embodiment, mx is also preferably 1 or 2.

In the organic EL device according to the exemplary embodiment, it is also preferable that: mx is 1, 2, or 3; and $L_{101}$ is a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that: mx is 1 or 2; and $L_{101}$ is a substituted or unsubstituted arylene group having 6 to 18 ring carbon atoms, or a substituted or unsubstituted divalent heterocyclic group having 5 to 18 ring atoms.

In the organic EL device according to the exemplary embodiment, it is also preferable that: mx is 1 or 2; and $L_{101}$ is a substituted or unsubstituted arylene group having 6 to 18 ring carbon atoms.

In the organic EL device according to the exemplary embodiment, the first compound is preferably represented by a formula (102) below.

[Formula 47]

(102)

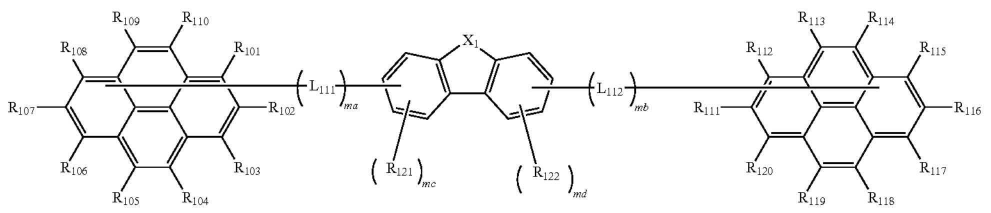

In the formula (102):

$R_{101}$ to $R_{120}$ each independently represent the same as $R_{101}$ to $R_{120}$ in the formula (101);

one of $R_{101}$ to $R_{110}$ represents a bonding position to $L_{111}$, and one of $R_{111}$ to $R_{120}$ represents a bonding position to $L_{112}$;

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$R_{121}$, $R_{122}$, $R_{123}$, $R_{124}$, and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

In the compound represented by the formula (102), it is preferable that: ma is 0, 1, or 2; and mb is 0, 1, or 2.

In the compound represented by the formula (102), it is preferable that: ma is 0 or 1; and mb is 0 or 1.

In the compound represented by the formula (102), it is preferable that $L_{111}$ and $L_{112}$ are each independently a single bond, a substituted or unsubstituted arylene group having 6 to 24 ring carbon atoms, or a substituted or unsubstituted divalent heterocyclic group having 5 to 24 ring atoms.

In the compound represented by the formula (102), ma is 1, 2, or 3; mb is 1, 2, or 3; and ma+mb is 2, 3, or 4.

In the compound represented by the formula (102), it is preferable that: ma is 1 or 2; and mb is 1 or 2.

In the compound represented by the formula (102), it is preferable that: ma is 1; and mb is 1.

In the formula (102), it is also preferable that: ma is 0; mb is 1; and $L_{112}$ is a substituted or unsubstituted phenylene group.

In the formula (102), it is also preferable that: ma is 0; mb is 1; $L_{112}$ is a substituted or unsubstituted phenylene group; X1 is $CR_{123}R_{124}$; and $R_{123}$ and $R_{124}$ are each independently a substituted or unsubstituted alkyl group having 1 to 6 carbon atoms.

In the organic EL device according to the exemplary embodiment, the first compound is also preferably represented by a formula (103) below.

[Formula 48]

(103)

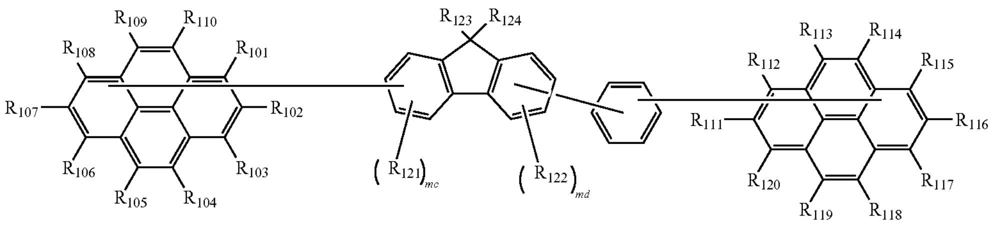

In the formula (103):

$R_{101}$ to $R_{120}$ each independently represent the same as $R_{101}$ to $R_{120}$ in the formula (101);

$R_{123}$ and $R_{124}$ are each independently a substituted or unsubstituted alkyl group having 1 to 6 carbon atoms;

mc is 3;

three $R_{121}$ are mutually the same or different;

md is 3; and three $R_{122}$ are mutually the same or different.

In the organic EL device according to the exemplary embodiment, the first compound is also preferably represented by a formula (104) below.

[Formula 49]

(104)

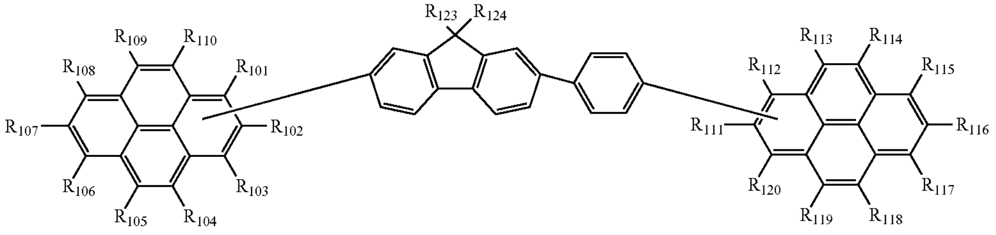

In the formula (104):

$R_{101}$ to $R_{120}$ each independently represent the same as $R_{101}$ to $R_{120}$ in the formula (101); and $R_{123}$ and $R_{124}$ are each independently a substituted or unsubstituted alkyl group having 1 to 6 carbon atoms.

In the organic EL device according to the exemplary embodiment, $R_{101}$ to $R_{110}$ not being a bonding position to $L_{111}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{101}$ to $R_{110}$ not being a bonding position to $L_{111}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being a bonding position to $L_{111}$ are each preferably a hydrogen atom.

In the organic EL device according to the exemplary embodiment, $R_{111}$ to $R_{120}$ not being a bonding position to $L_{112}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{111}$ to $R_{120}$ not being a bonding position to $L_{112}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{111}$ to $R_{120}$ not being a bonding position to $L_{112}$ are each preferably a hydrogen atom.

In the organic EL device according to the exemplary embodiment, it is preferable that two or more of $R_{101}$ to $R_{110}$ are groups represented by the formula (11).

In the organic EL device according to the exemplary embodiment, it is preferable that: two or more of $R_{101}$ to $R_{110}$ are groups represented by the formula (11); and $Ar_{101}$ is a substituted or unsubstituted aryl group having 6 to 50 ring carbon atoms.

In the organic EL device according to the exemplary embodiment, it is preferable that: $Ar_{101}$ is not a substituted or unsubstituted pyrenyl group;

$L_{101}$ is not a substituted or unsubstituted pyrenylene group; and the substituted or unsubstituted aryl group having 6 to 50 ring carbon atoms for $R_{101}$ to $R_{110}$ not being the group represented by the formula (11) is not a substituted or unsubstituted pyrenyl group.

In the organic EL device according to the exemplary embodiment, $R_{101}$ to $R_{110}$ not being the group represented by the formula (11) are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{101}$ to $R_{110}$ not being the group represented by the formula (11) are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the group represented by the formula (11) are each preferably a hydrogen atom.

In the first compound and the second compound, the groups specified to be "substituted or unsubstituted" are each preferably an "unsubstituted" group.

In the organic EL device according to the exemplary embodiment, for instance, two of $R_{101}$ to $R_{110}$ in the first compound represented by the formula (1) are groups represented by the formula (11).

In the organic EL device according to the exemplary embodiment, for instance, three of $R_{101}$ to $R_{110}$ in the first compound represented by the formula (1) are groups represented by the formula (11).

In the organic EL device according to the exemplary embodiment, for instance, four of $R_{101}$ to $R_{110}$ in the first compound represented by the formula (1) are groups represented by the formula (11).

In the organic EL device according to the exemplary embodiment, for instance, one of $R_{101}$ to $R_{110}$ in the first compound represented by the formula (1) is a group represented by the formula (11) and mx is 1 or more.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted aryl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group including a nitrogen atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group including a sulfur atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted furyl group, oxazolyl group, isoxazolyl group, oxadiazolyl group, xanthenyl group, benzofuranyl group, isobenzofuranyl group, dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is at least one group selected from the group consisting of unsubstituted furyl group, oxazolyl group, isoxazolyl group, oxadiazolyl group, xanthenyl group, benzofuranyl group, isobenzofuranyl group, a dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted dibenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is an unsubstituted dibenzofuranyl group.

In the organic EL device according to the exemplary embodiment, for instance, mx in the first compound represented by the formula (101) is 2 or more.

In the organic EL device according to the exemplary embodiment, for instance, mx in the first compound represented by the formula (101) is 1 or more, and $L_{101}$ is an arylene group having 6 to 24 ring carbon atoms or a divalent heterocyclic group having 5 to 24 ring atoms.

In the organic EL device according to the exemplary embodiment, for instance, mx in the first compound represented by the formula (101) is 1 or more, and $L_{101}$ is an arylene group having 6 to 18 ring carbon atoms or a divalent heterocyclic group having 5 to 18 ring atoms.

Method of Manufacturing First Compound

The first compound can be manufactured by a known method. The first compound can also be manufactured based on a known method through a known alternative reaction using a known material(s) tailored for the target compound.

Specific Examples of First Compound

Specific examples of the first compound include the following compounds. It should however be noted that the invention is not limited by the specific examples of the first compound.

[Formula 50]

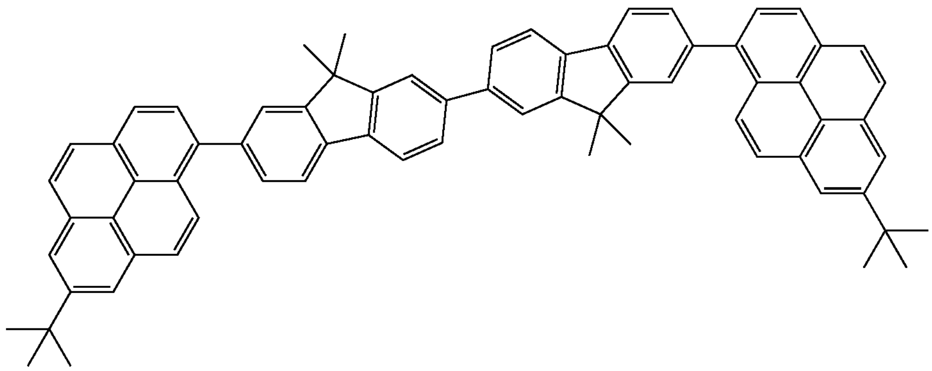

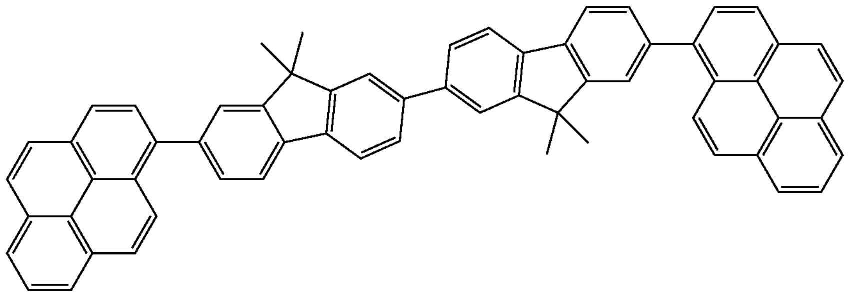

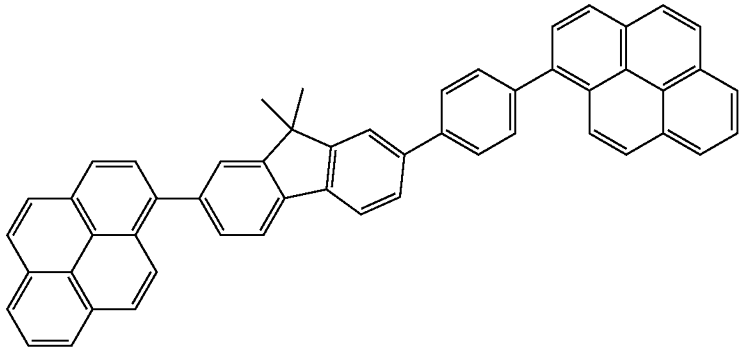

-continued
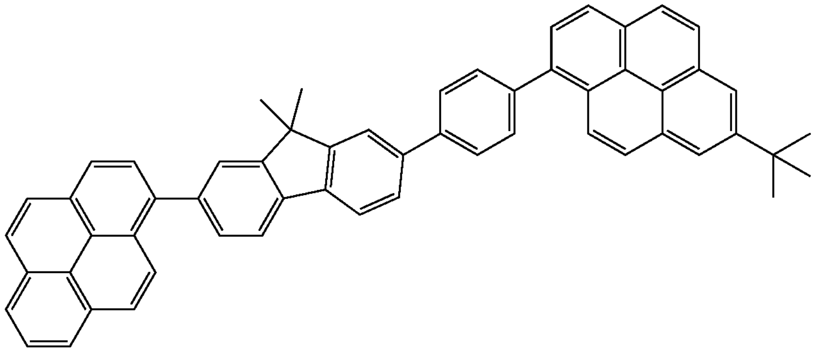
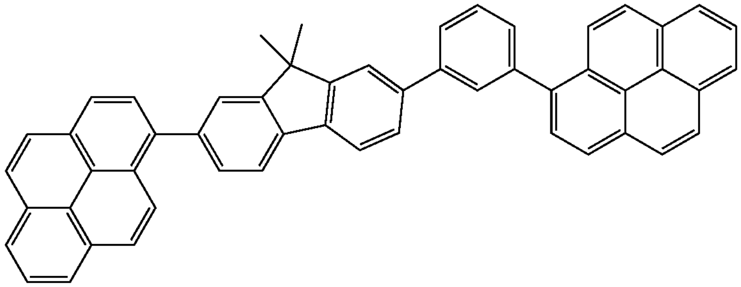
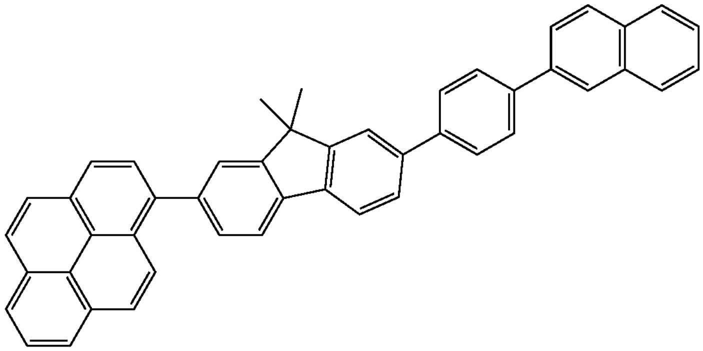
[Formula 51]
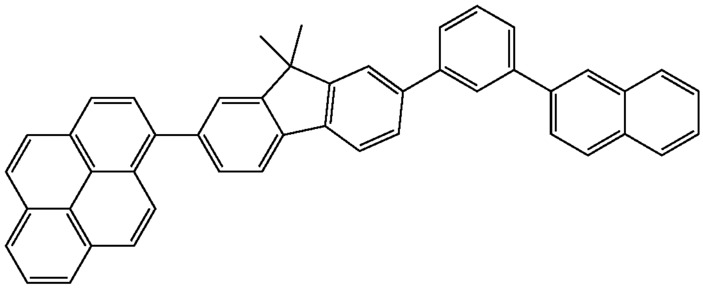
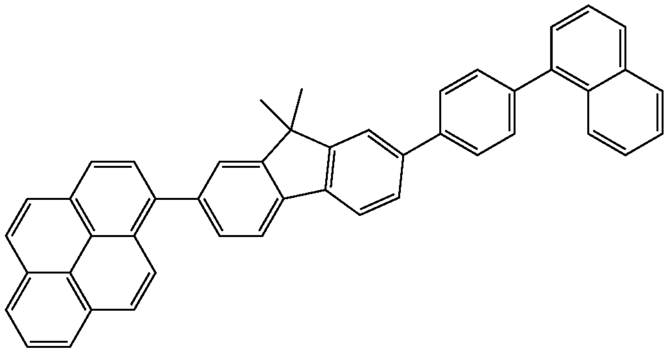

-continued
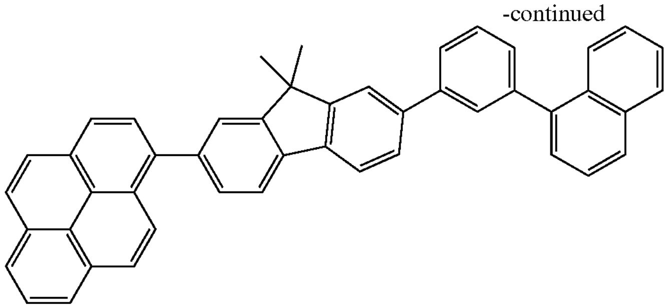
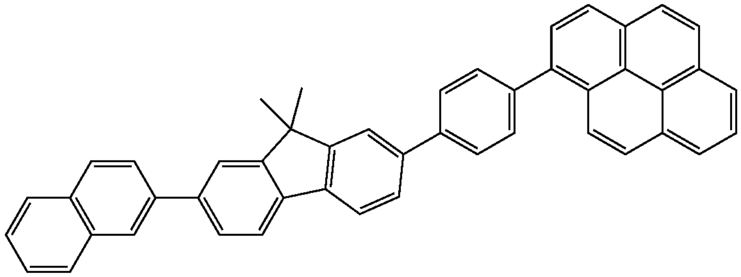
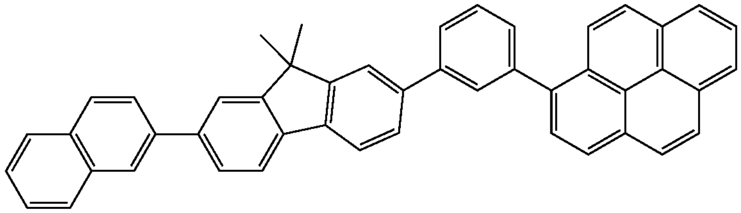
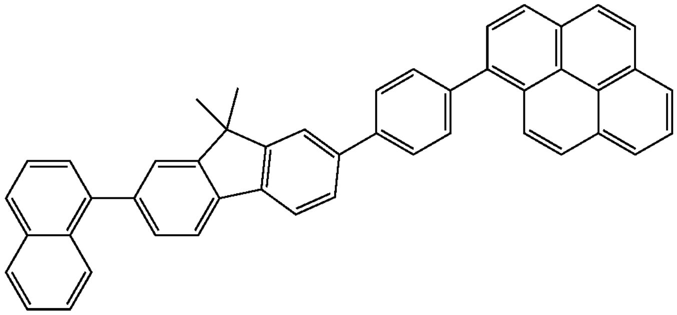
[Formula 52]
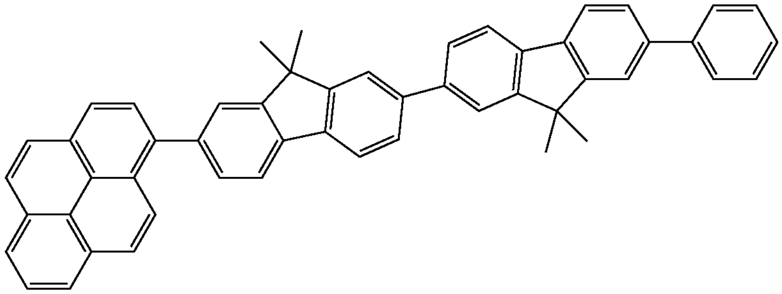
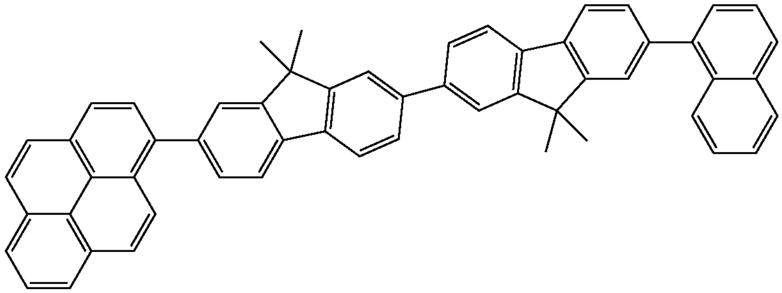

-continued
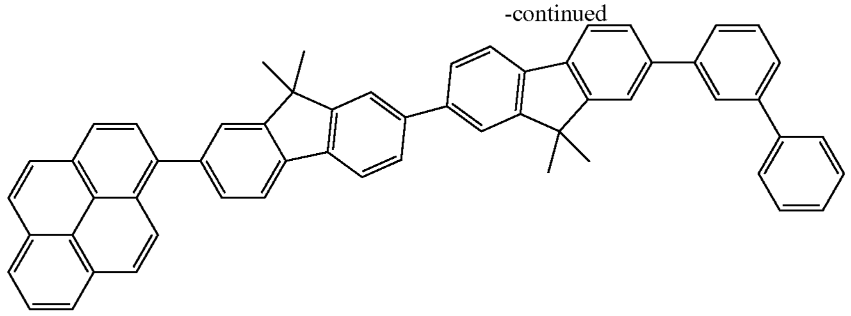
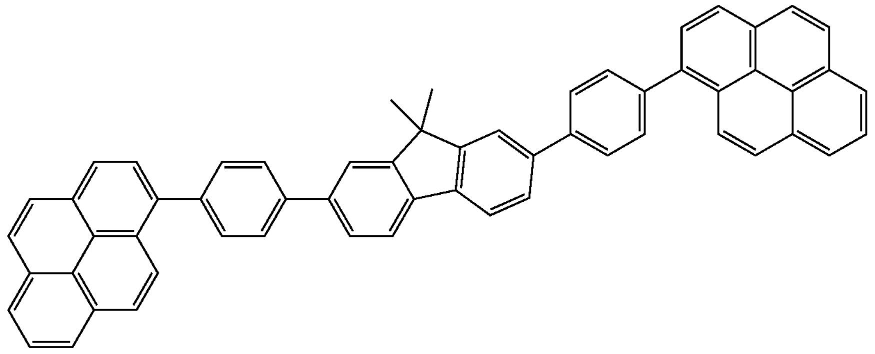
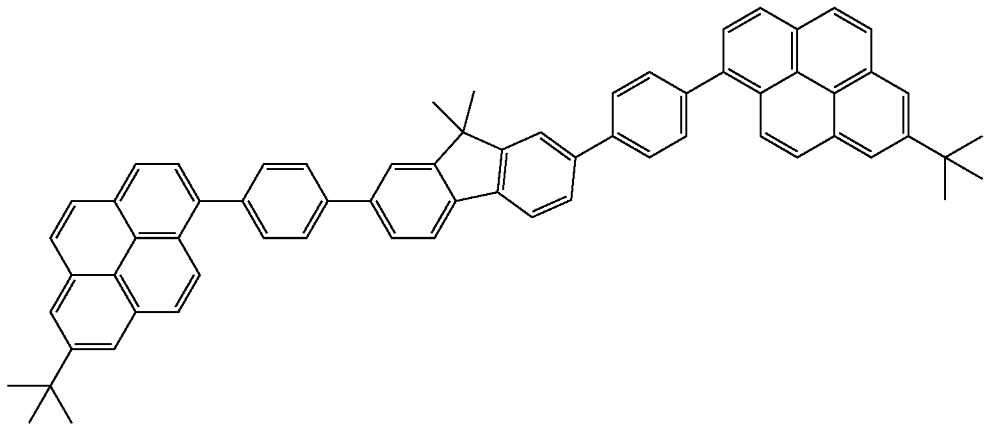
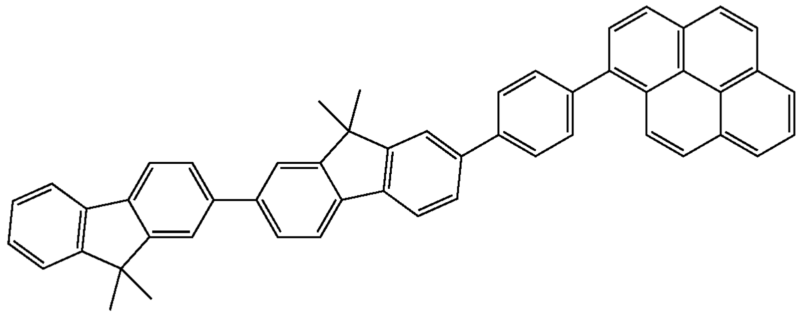

-continued
[Formula 53]
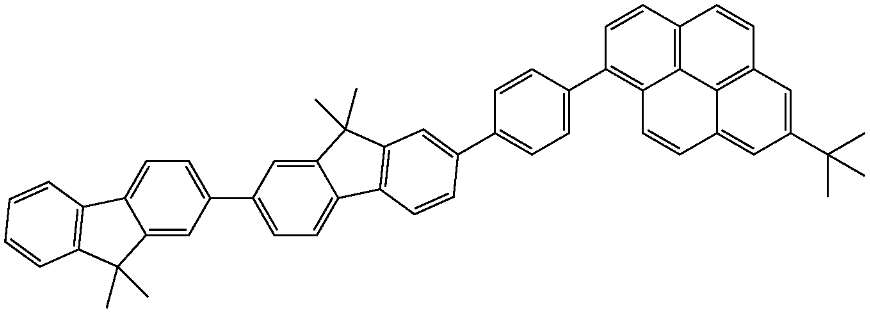
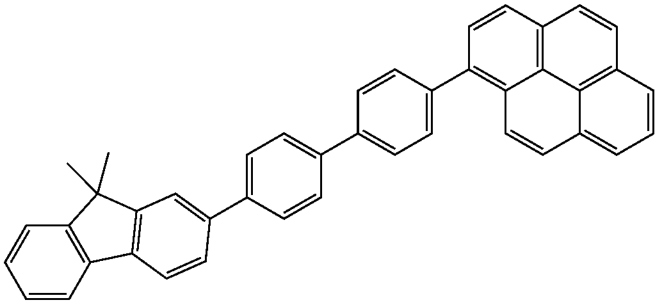
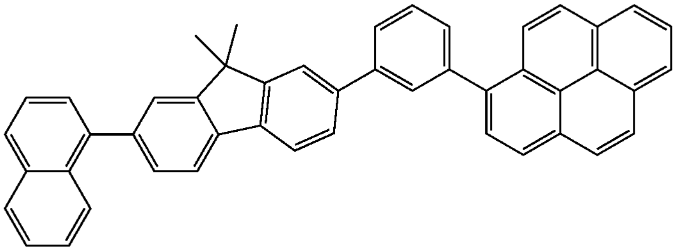
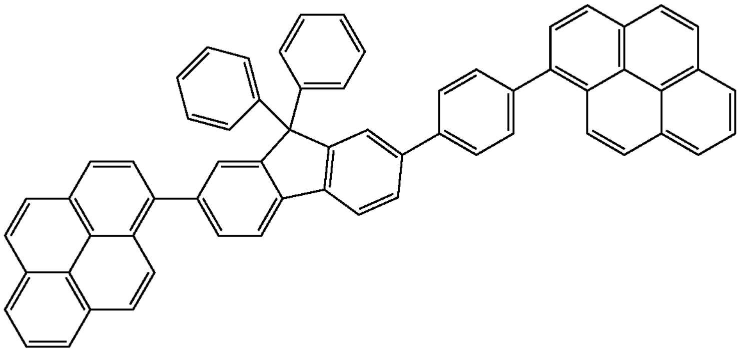
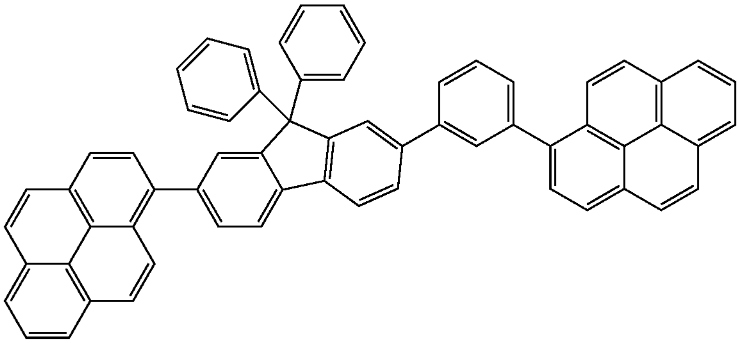

-continued
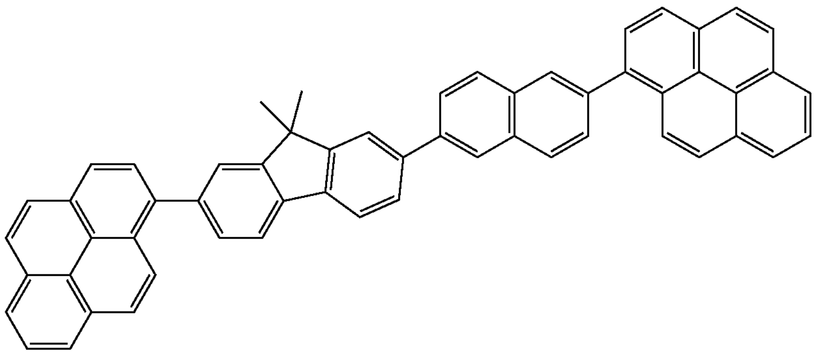
[Formula 54]
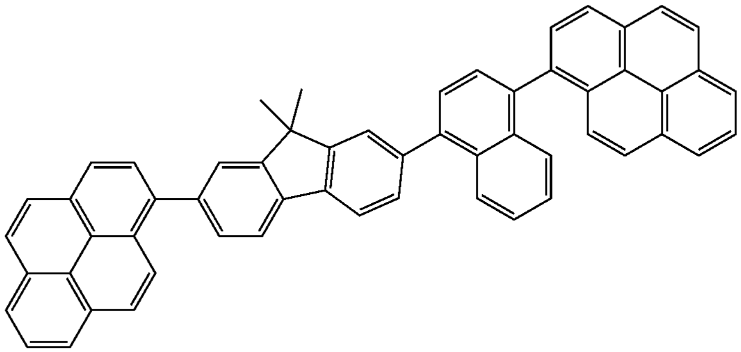
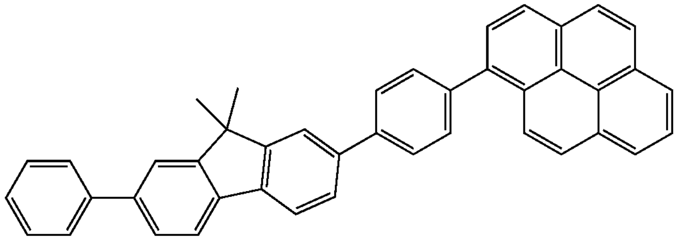
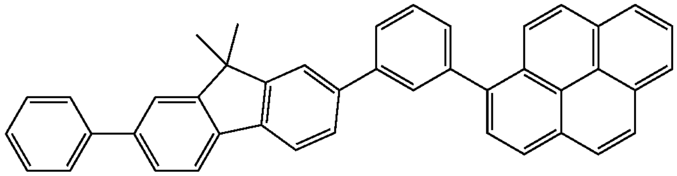
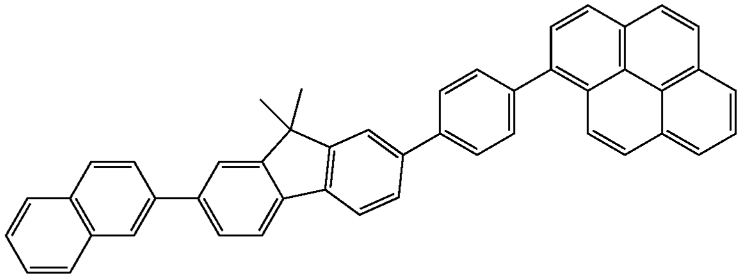
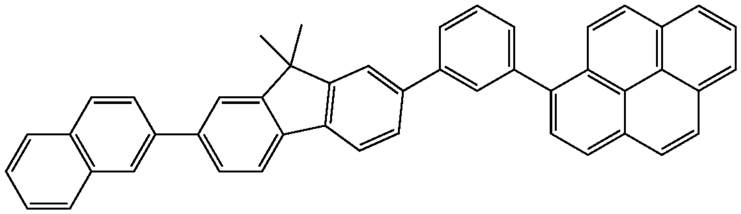

-continued
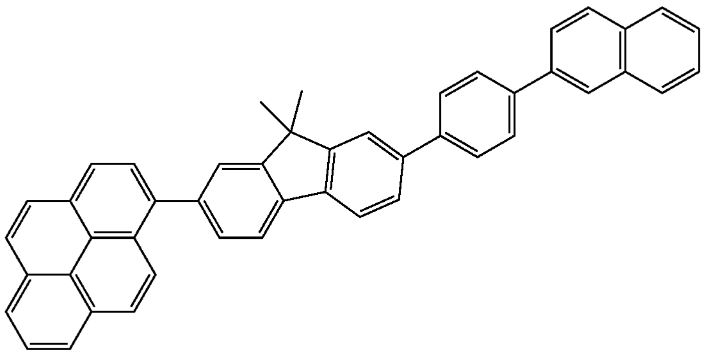
[Formula 55]
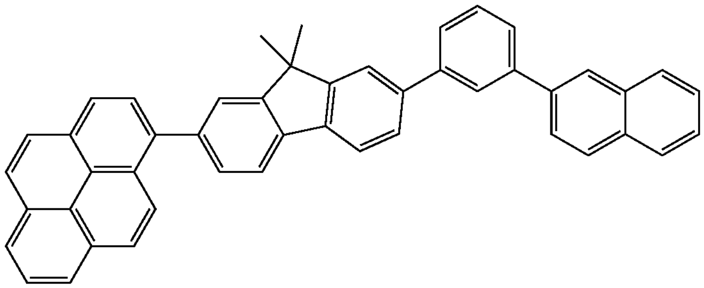
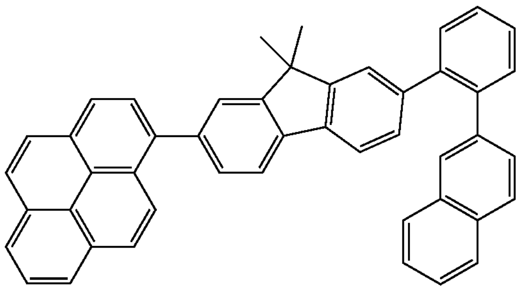
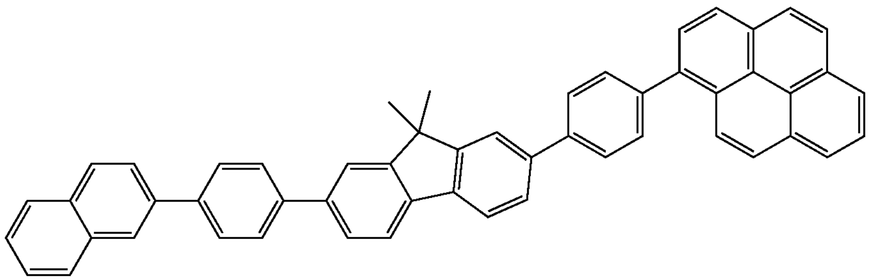
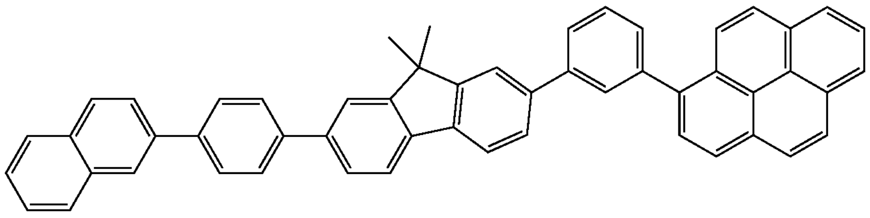

-continued
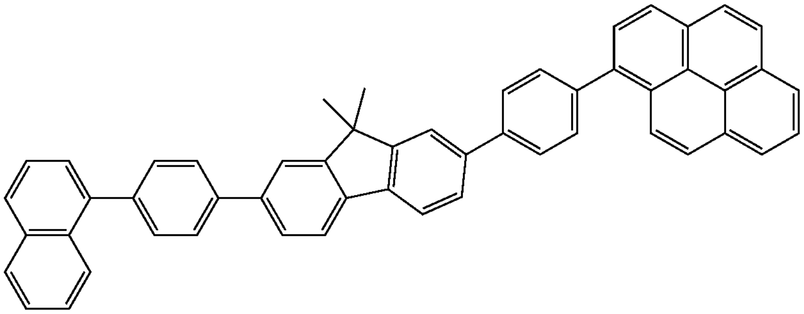
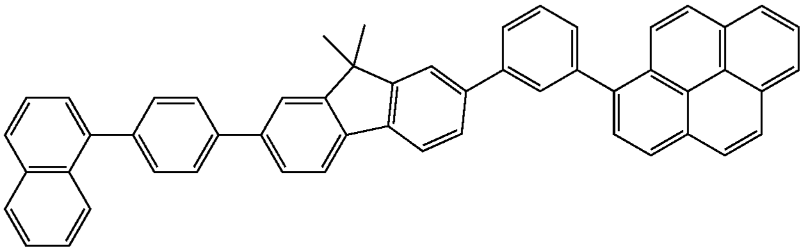
[Formula 56]
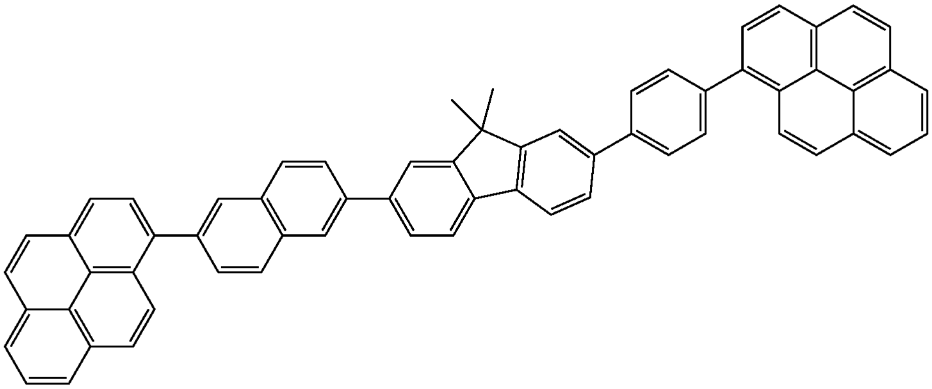
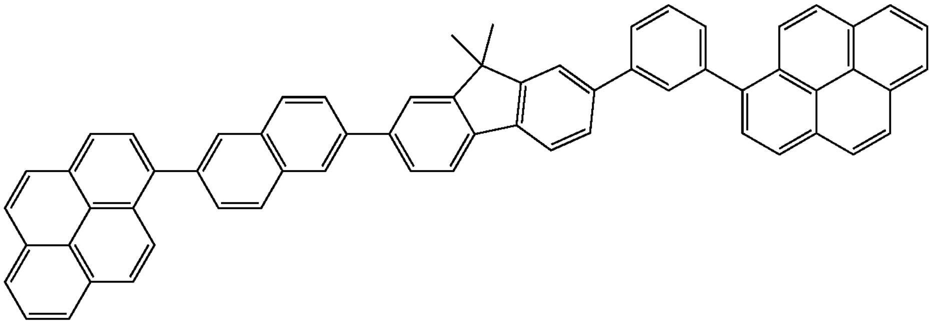
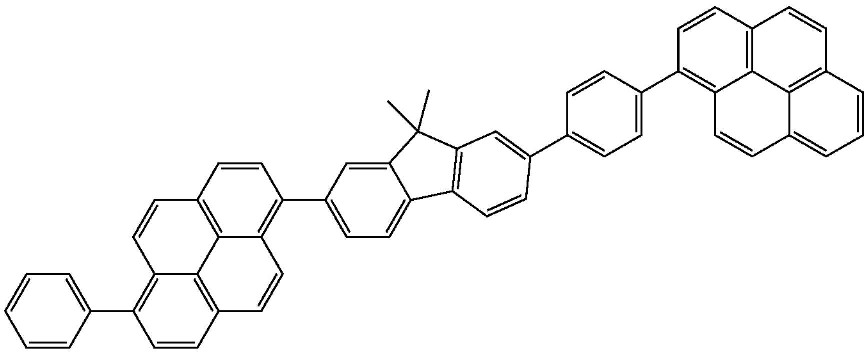

-continued
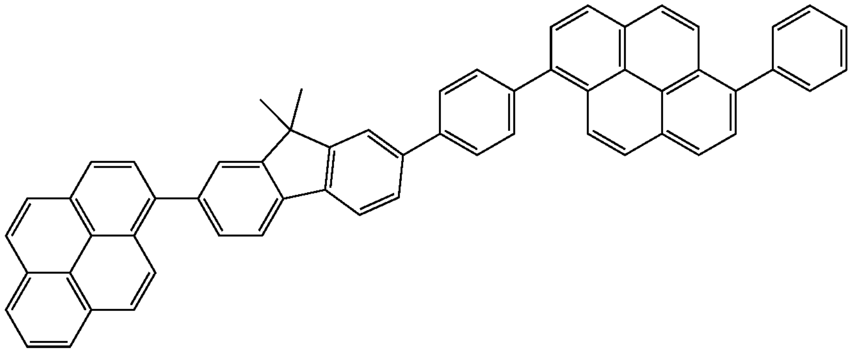
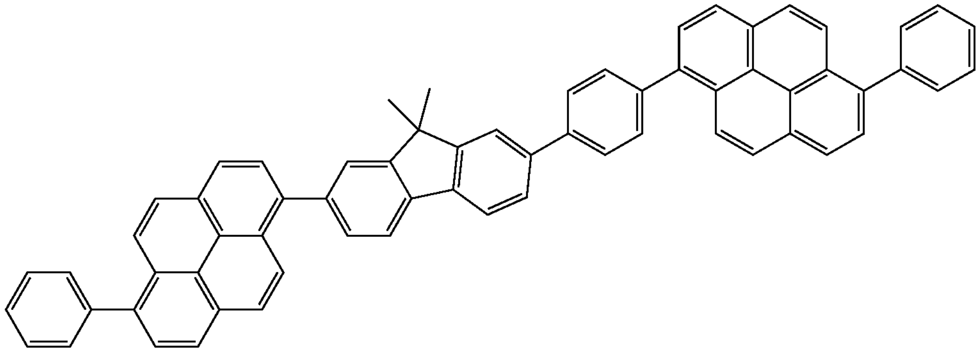
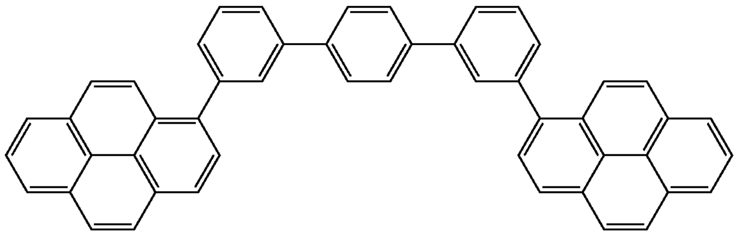
[Formula 57]
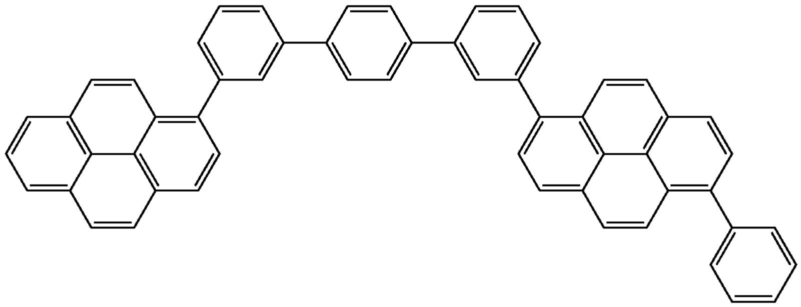
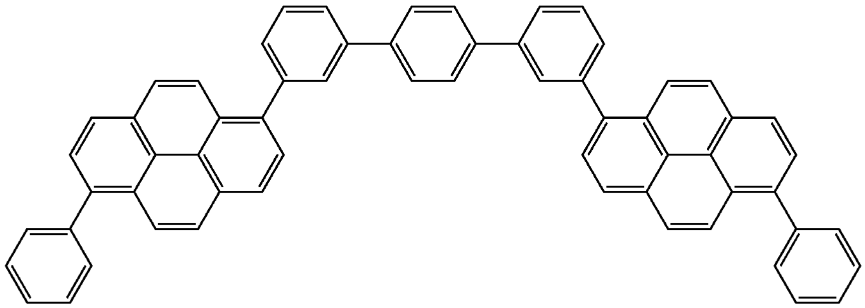

-continued
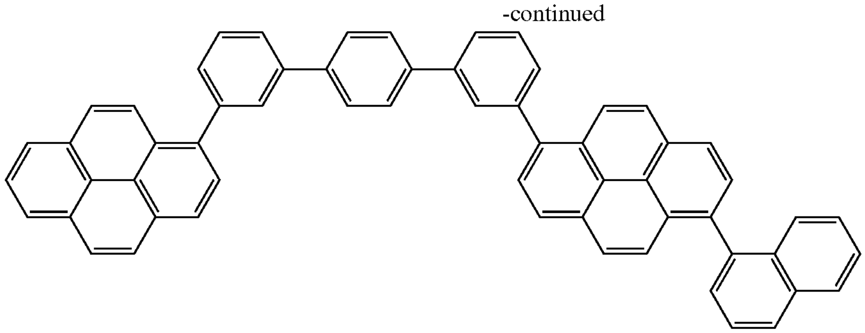
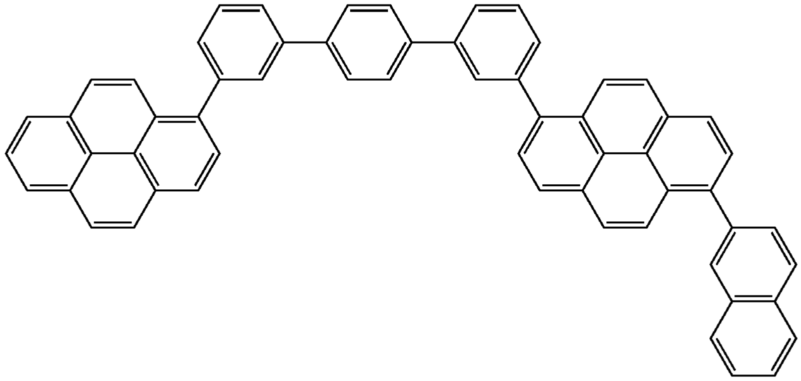
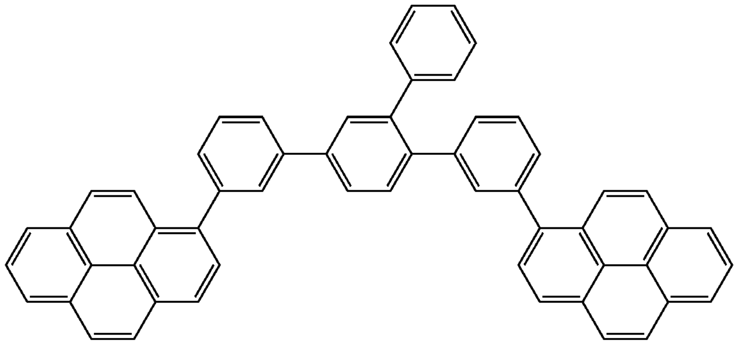
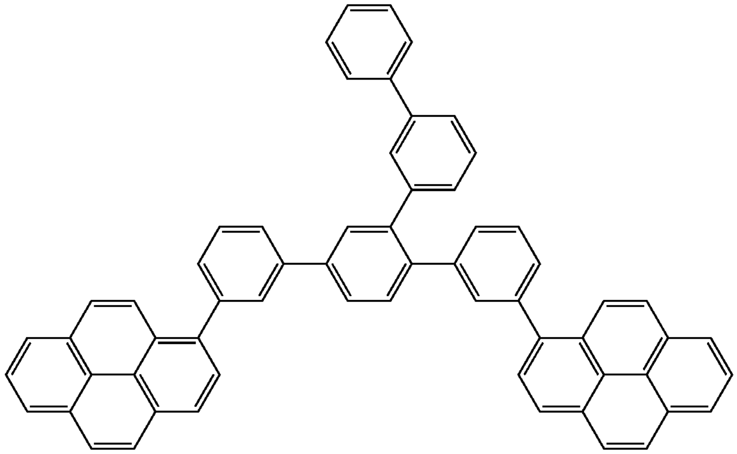

-continued
[Formula 58]
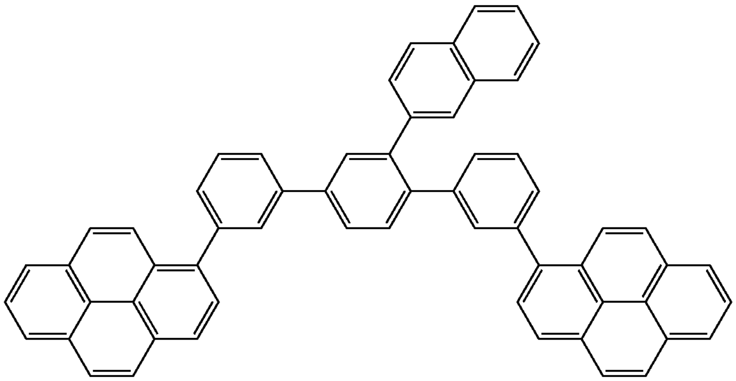
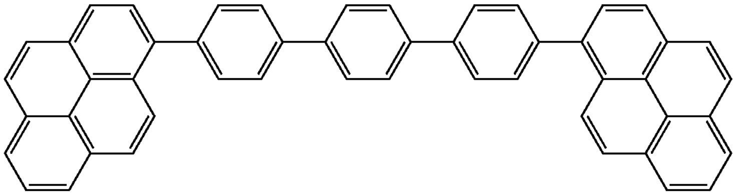
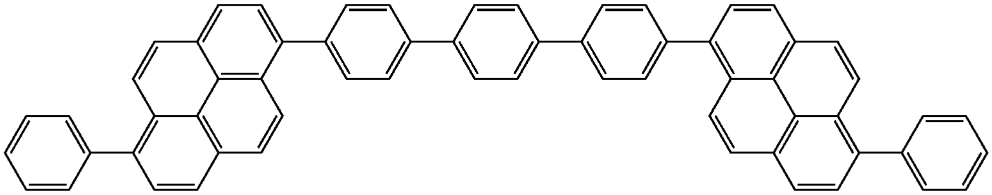
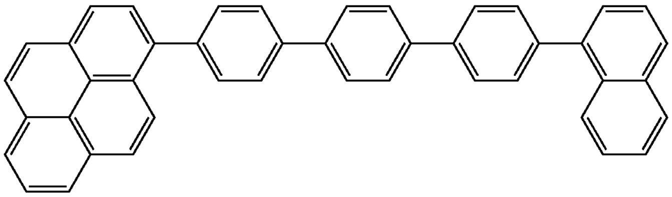
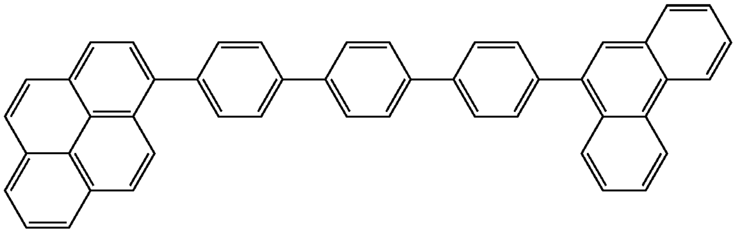
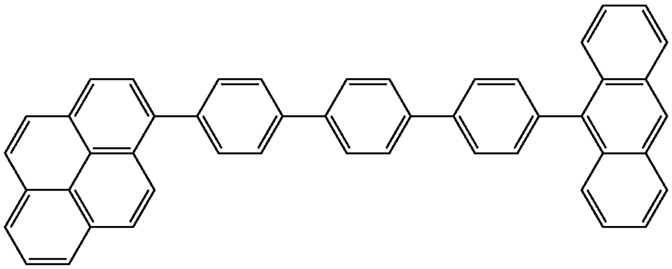

-continued
[Formula 59]
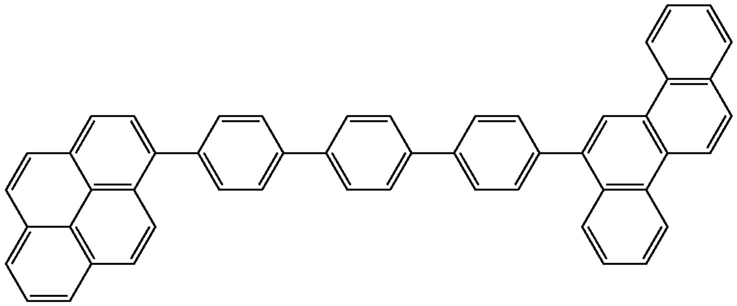
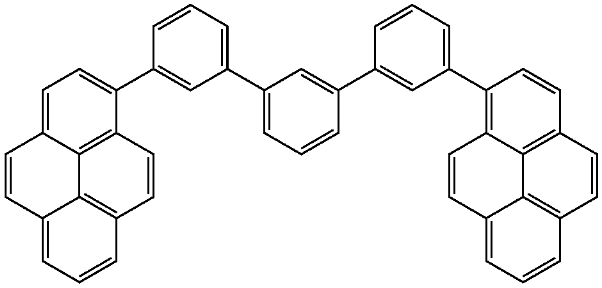
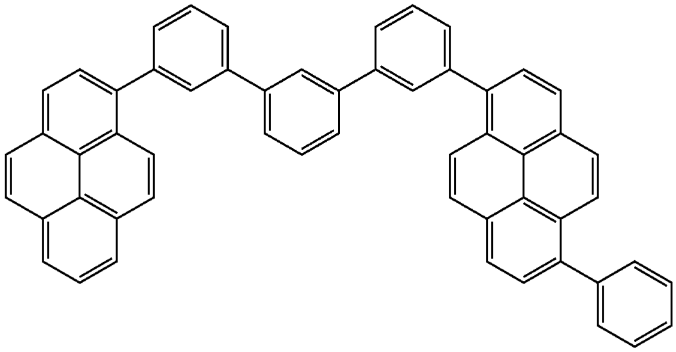
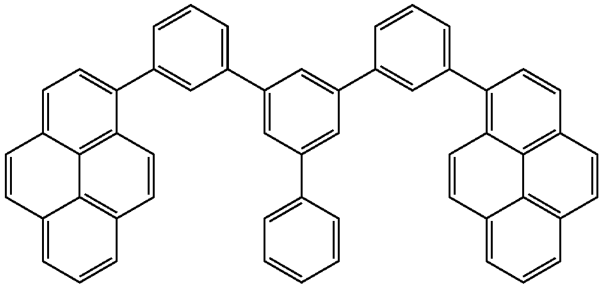
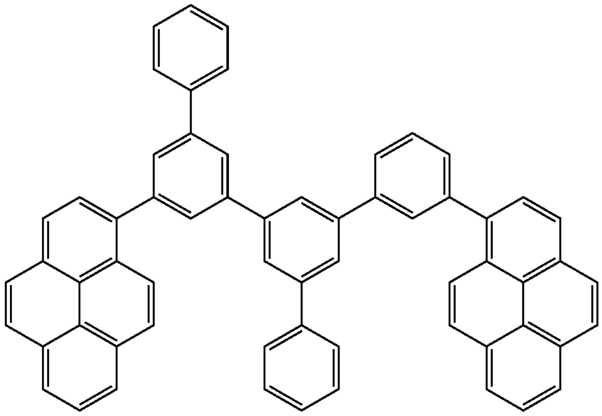

-continued
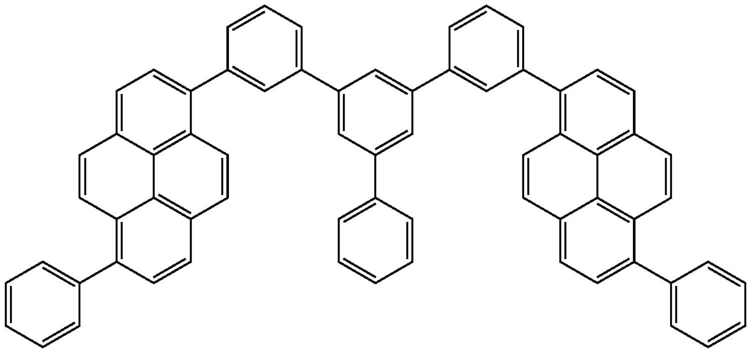
[Formula 60]
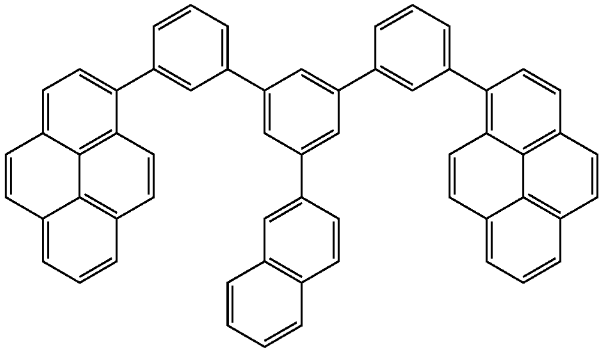
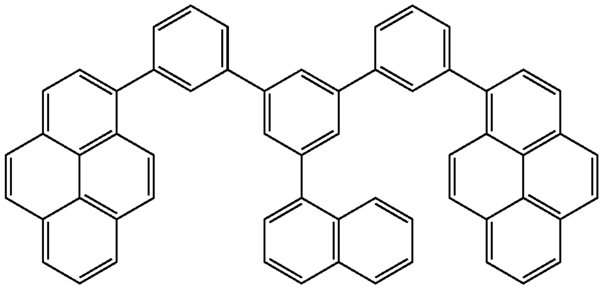
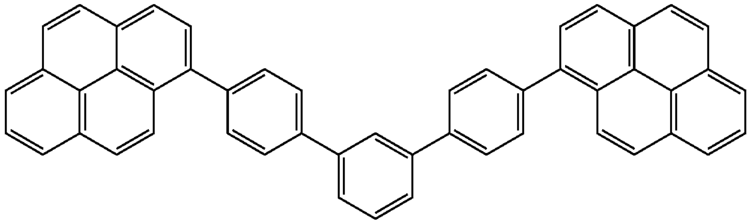
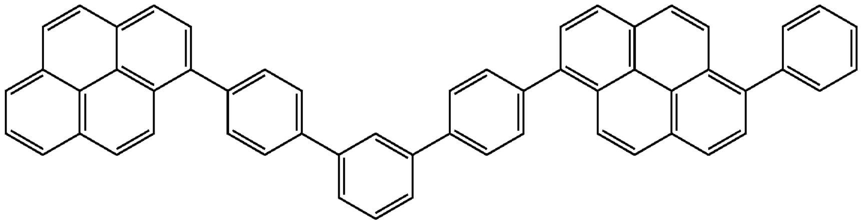
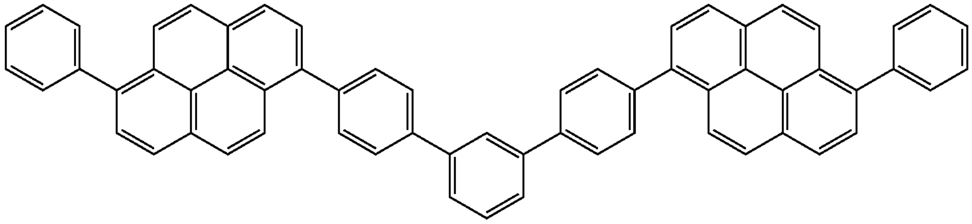

-continued
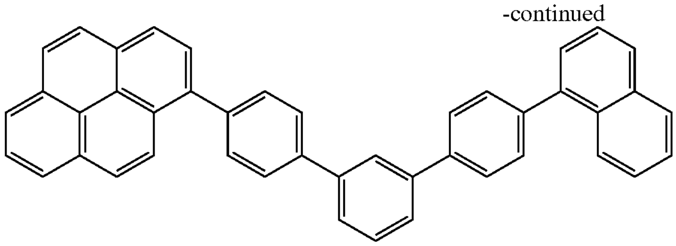
[Formula 61]
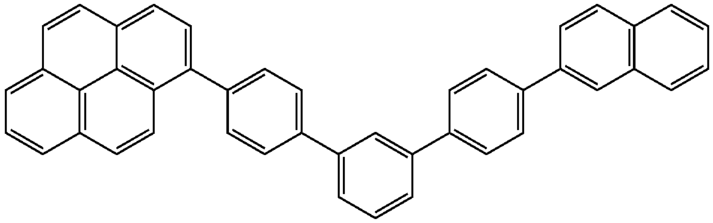
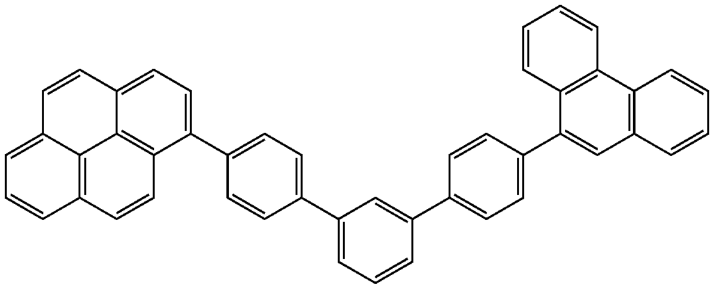
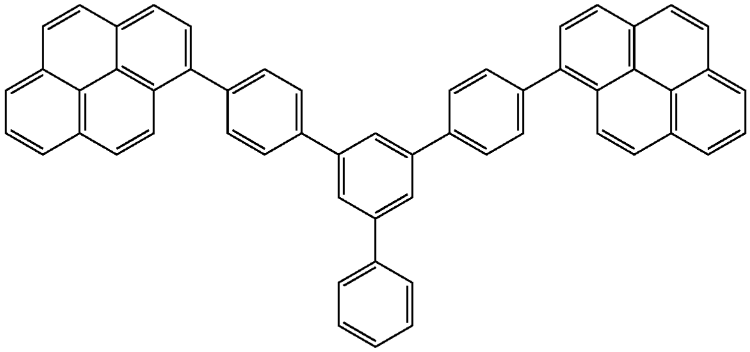
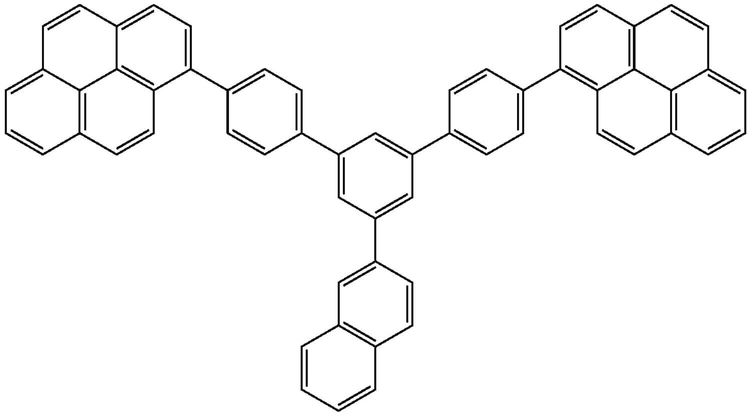

-continued
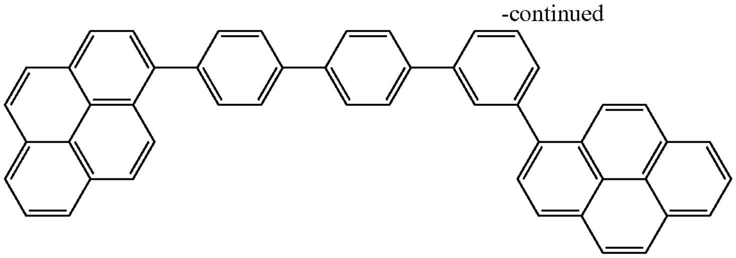
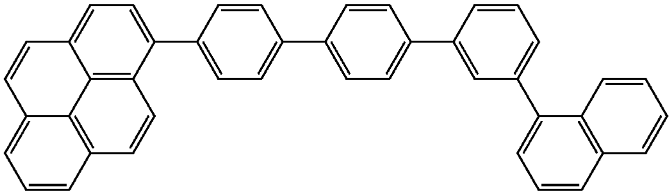
[Formula 62]
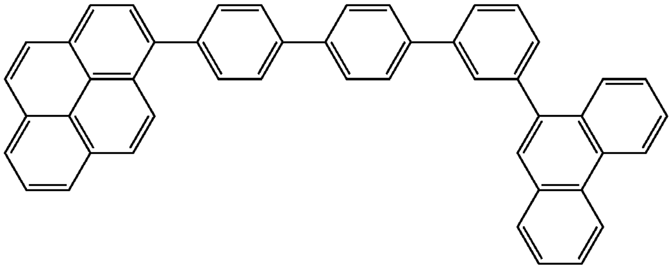
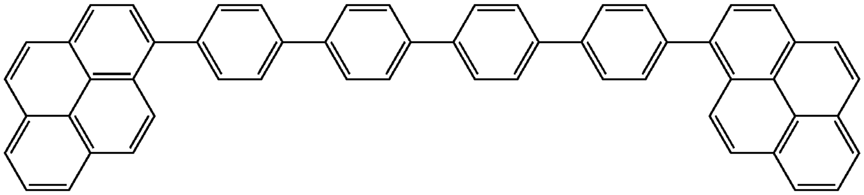
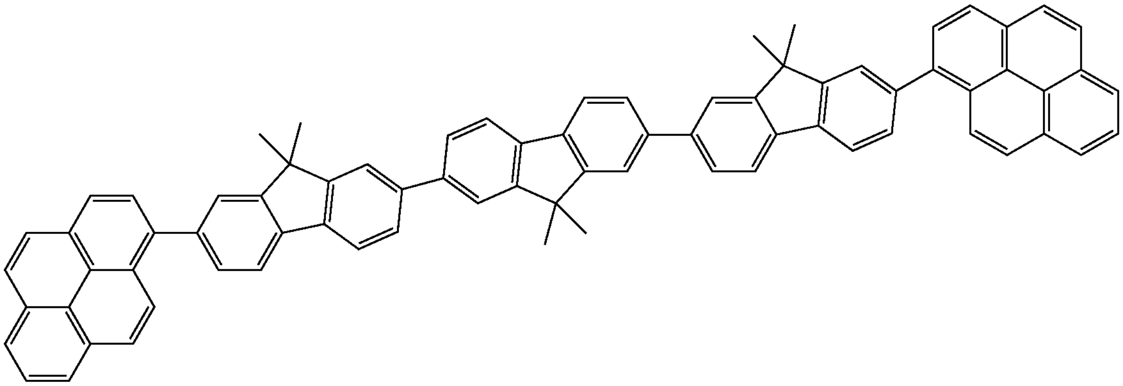

-continued
[Formula 63]
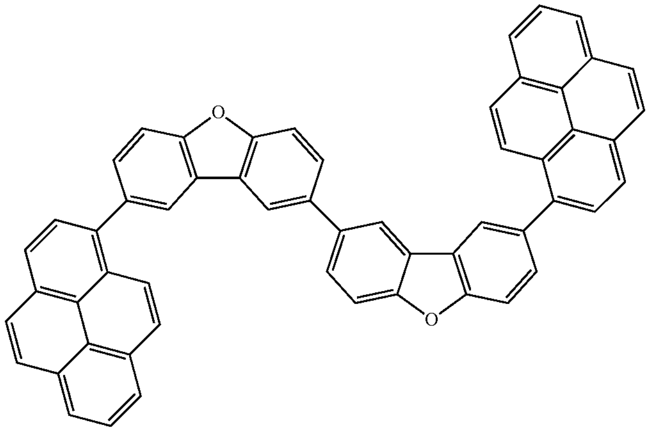
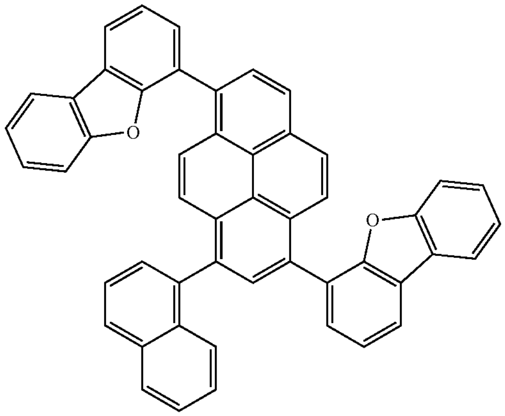
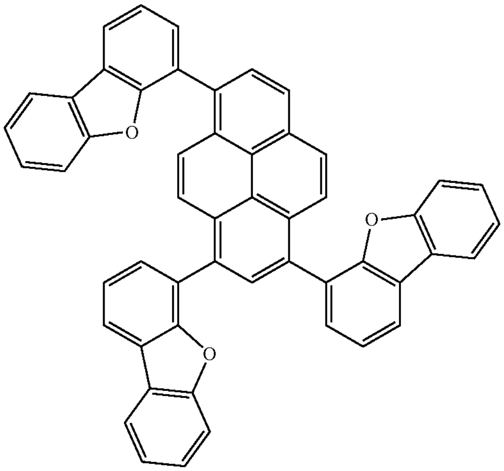
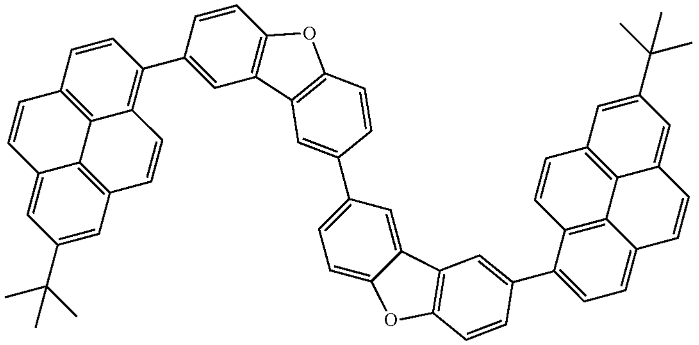
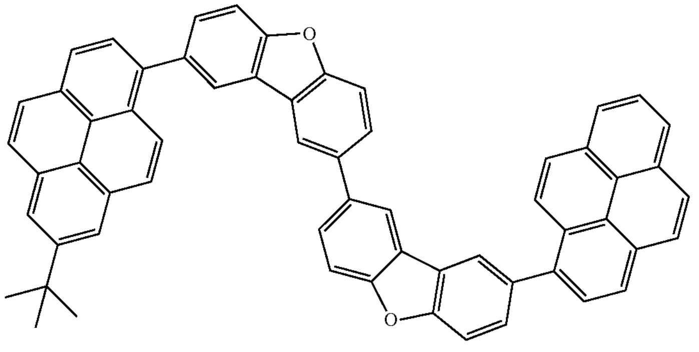

-continued
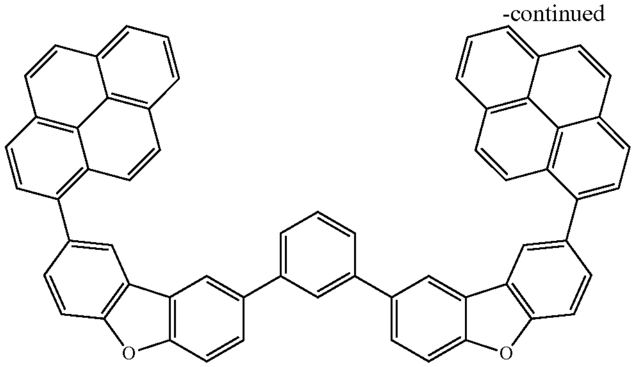
[Formula 64]
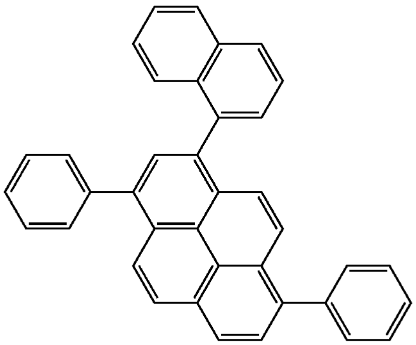
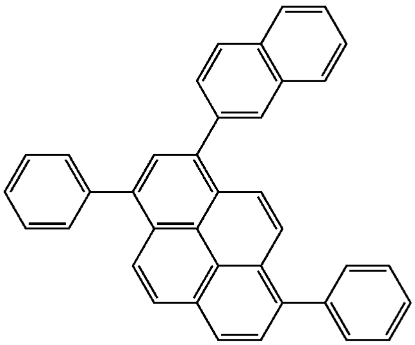
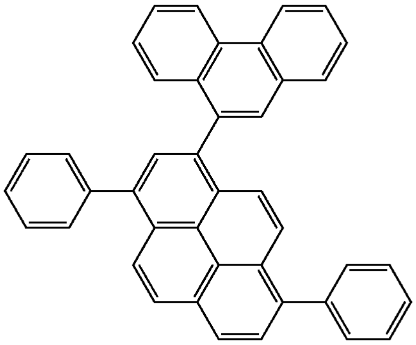
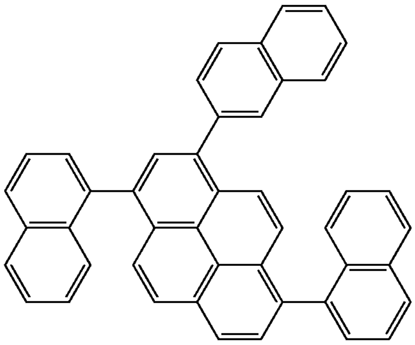
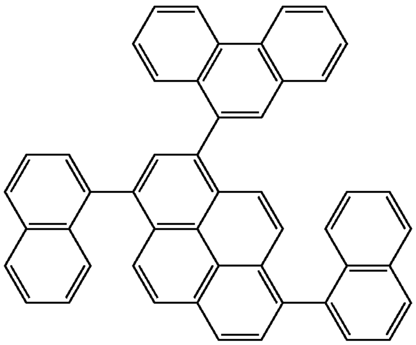
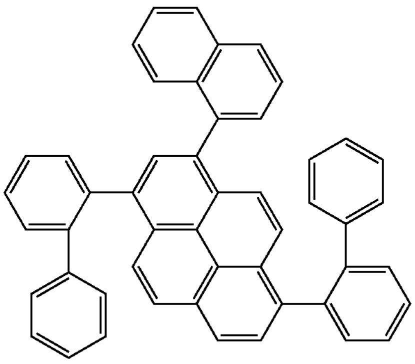

-continued
[Formula 65]
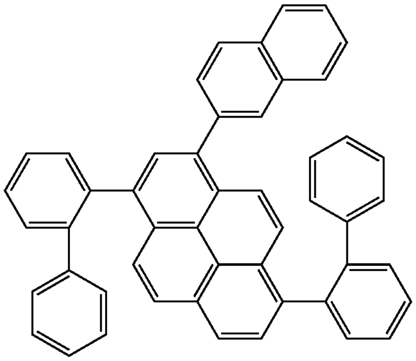
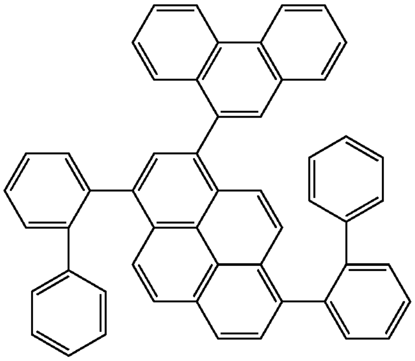
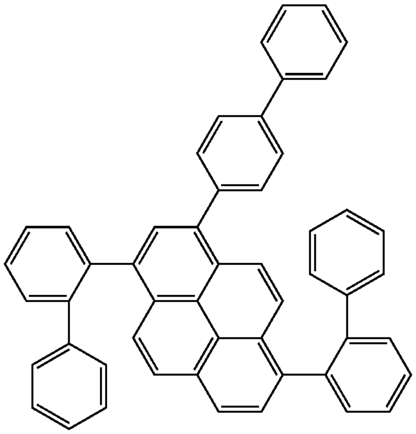
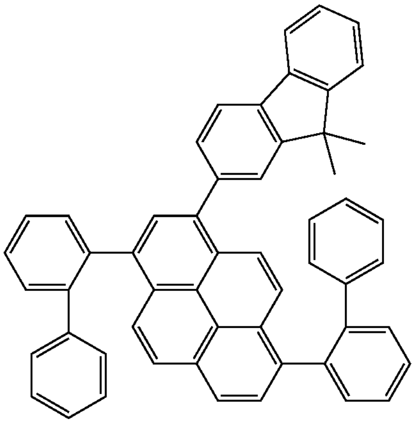
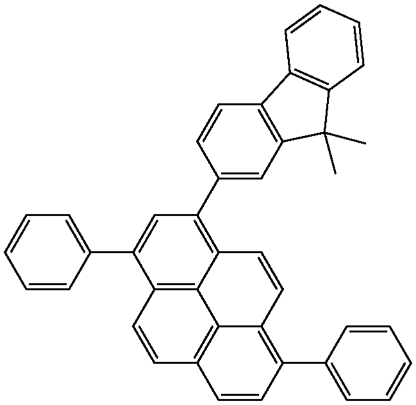
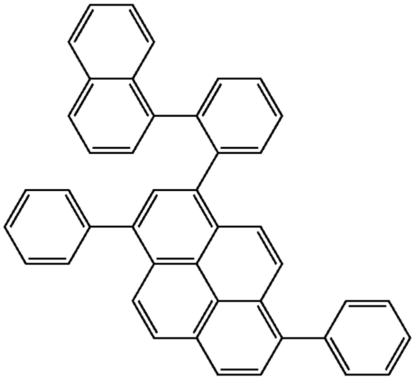
[Formula 66]
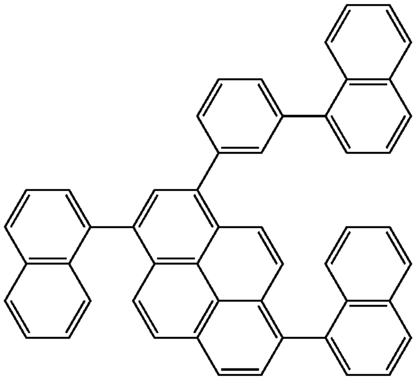
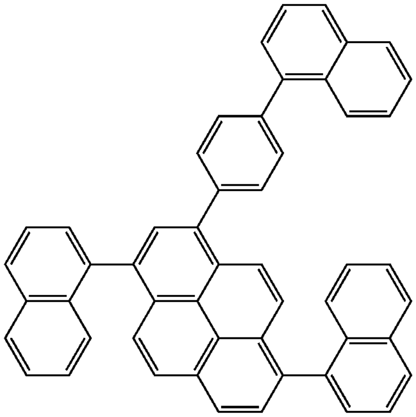

-continued
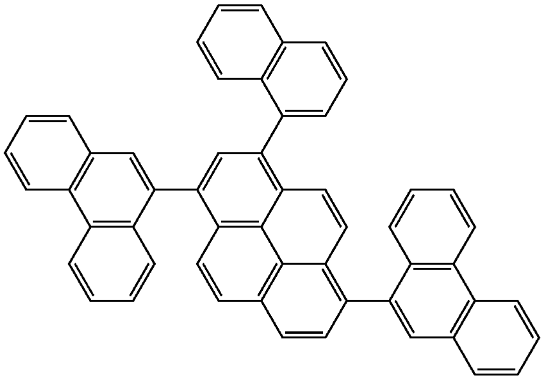
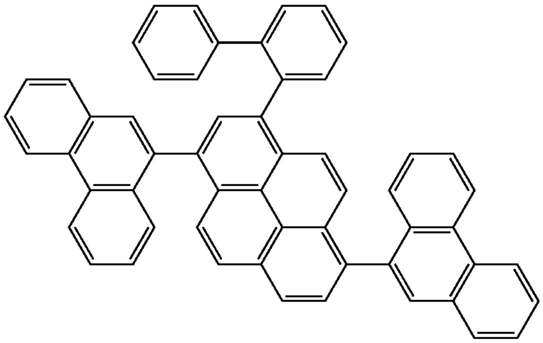
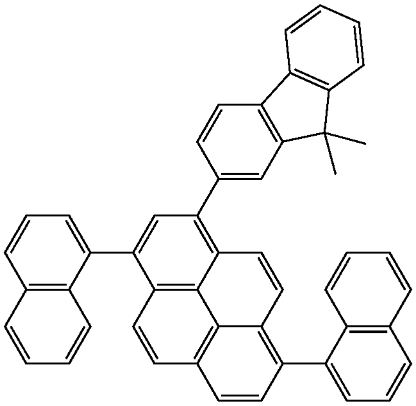
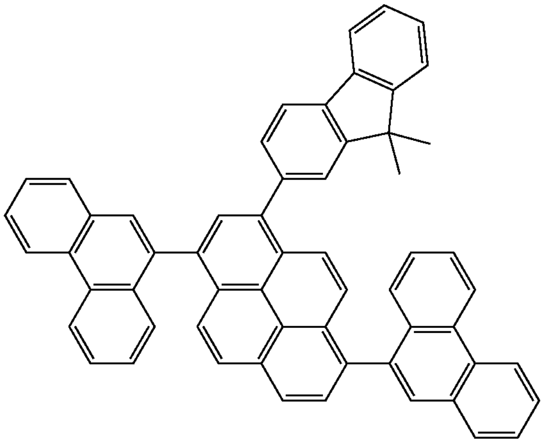
[Formula 67]
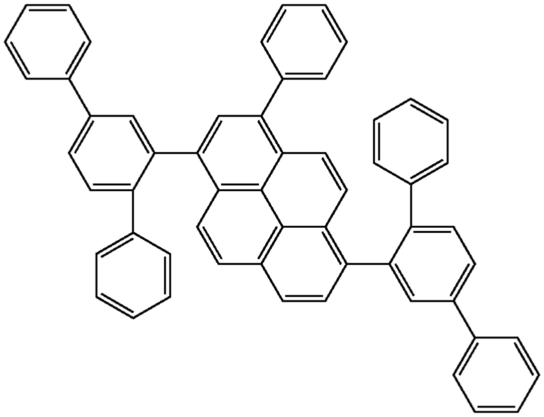
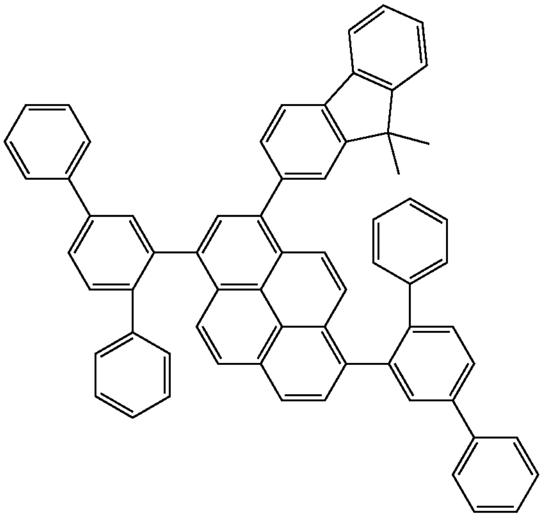

-continued
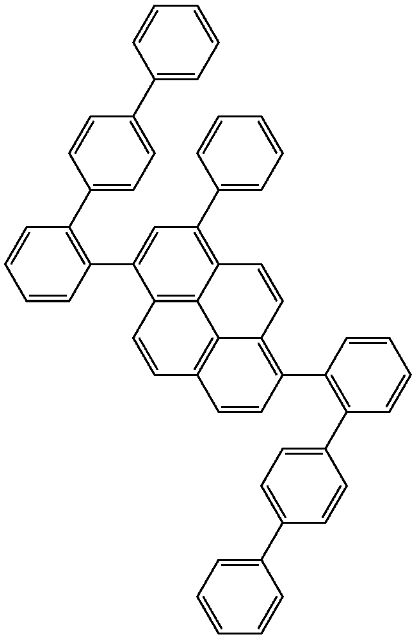
[Formula 68]
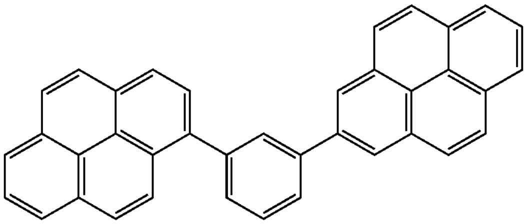
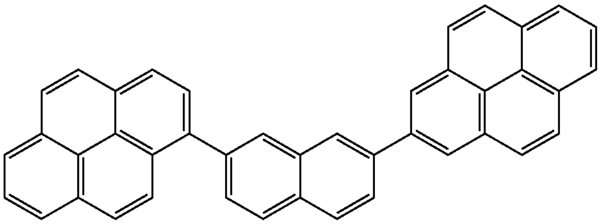
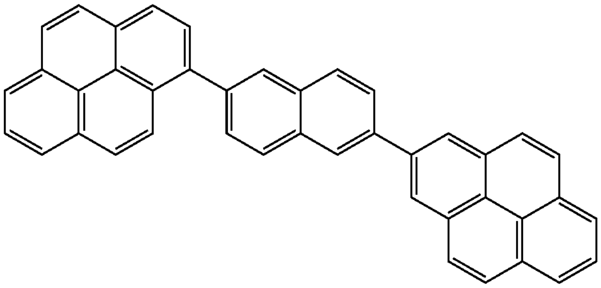
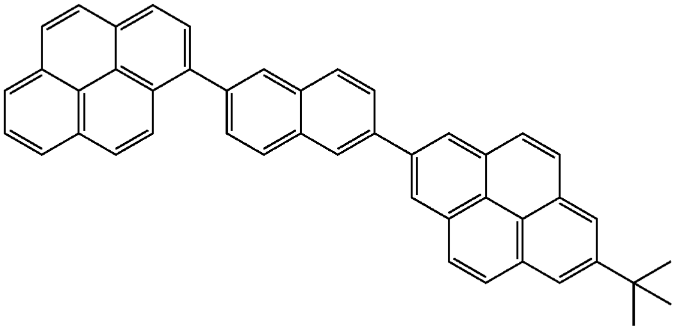

-continued
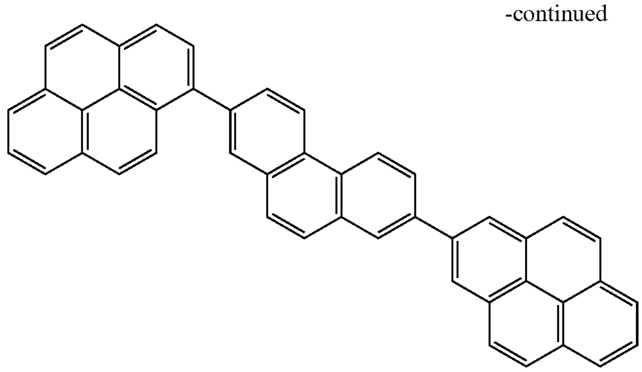
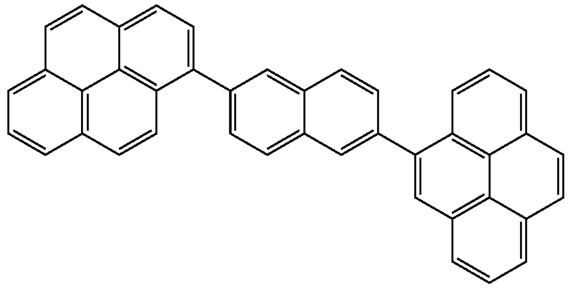
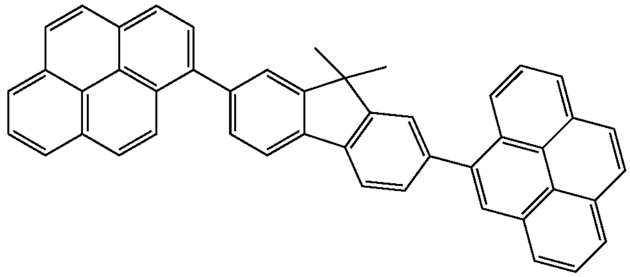
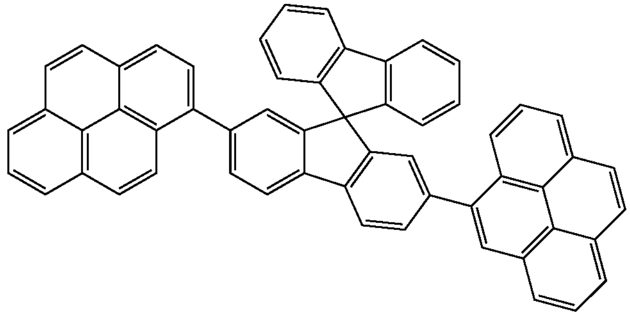
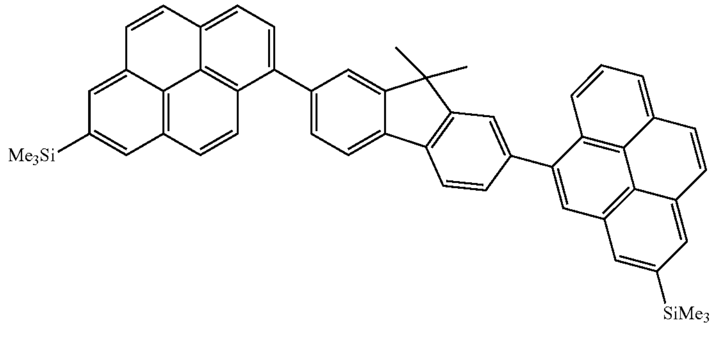

-continued
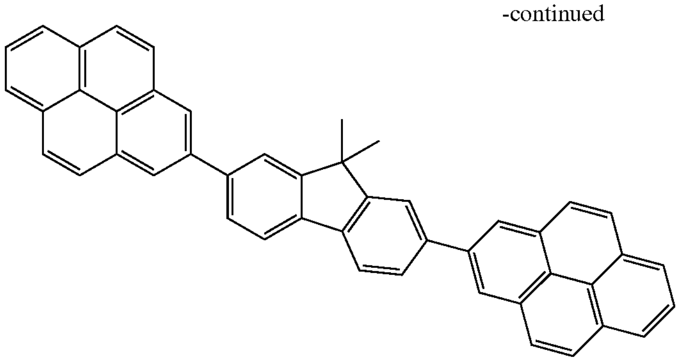
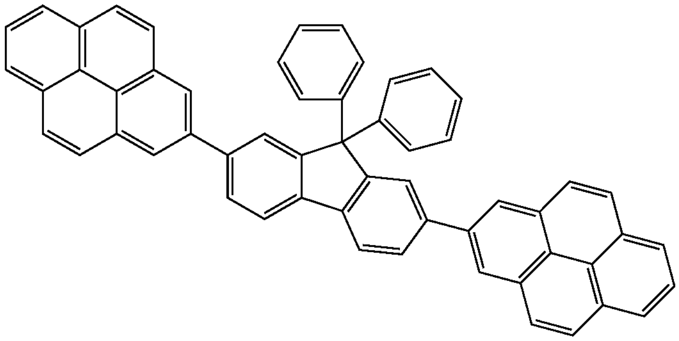
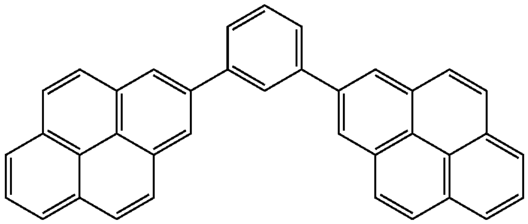
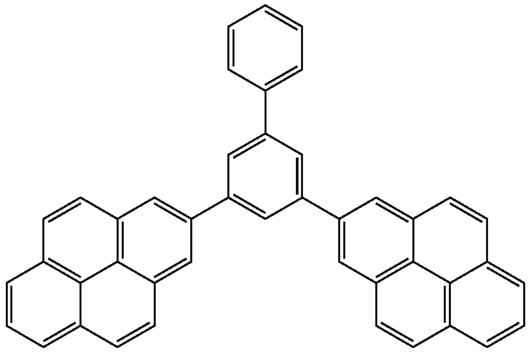
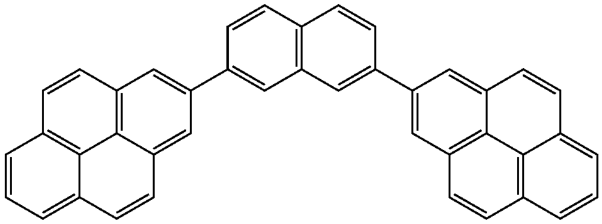
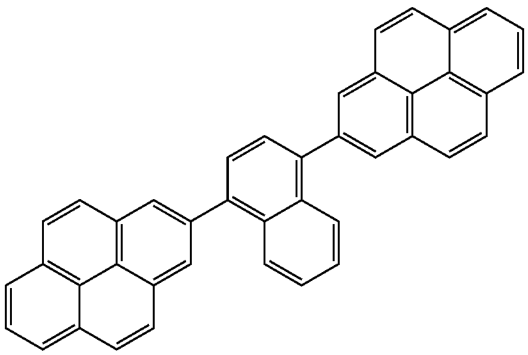
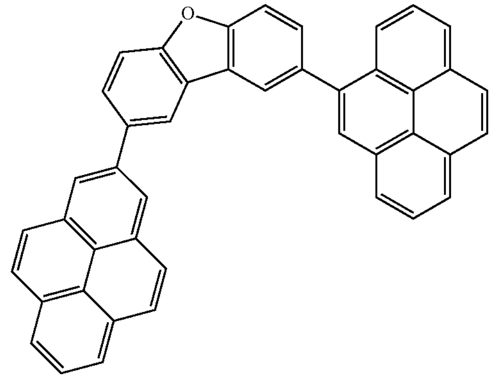

-continued
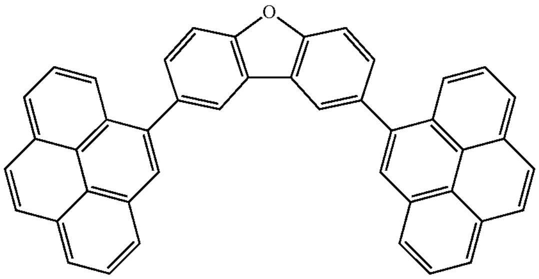
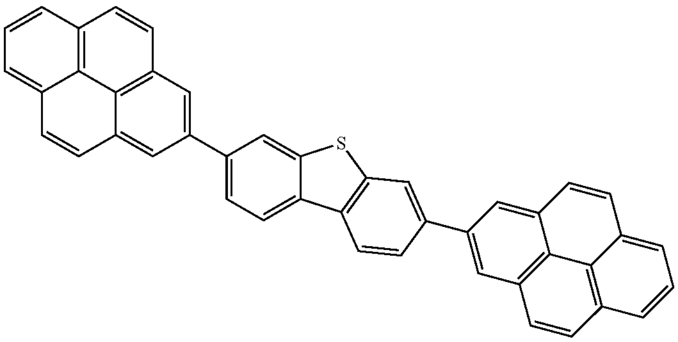
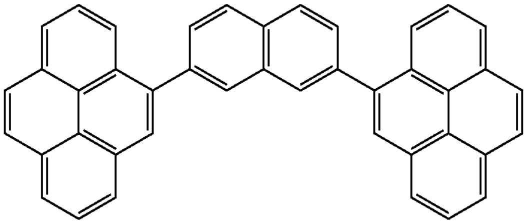
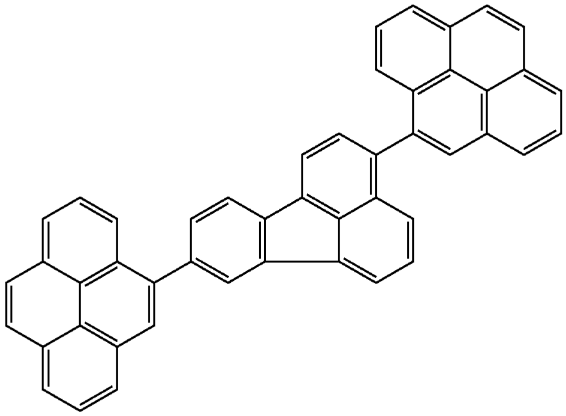
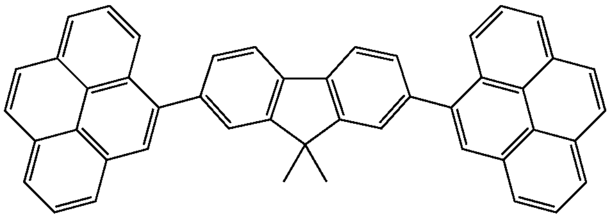
[Formula 69]
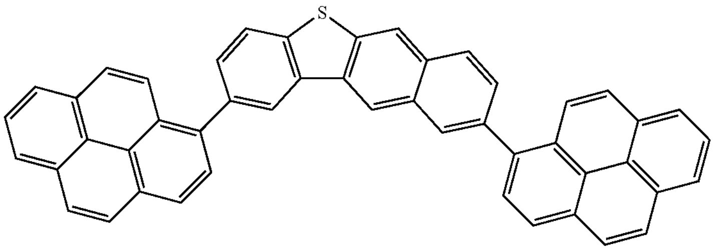

-continued
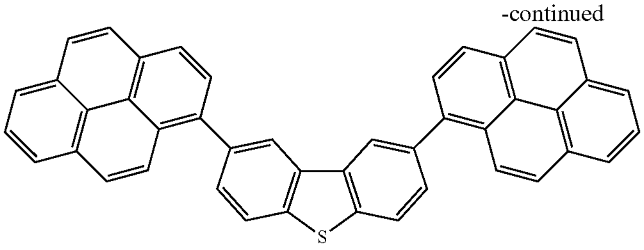
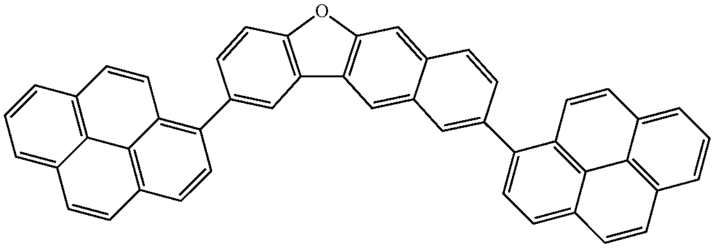
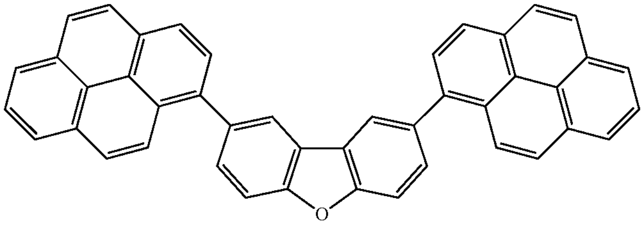
[Formula 70]
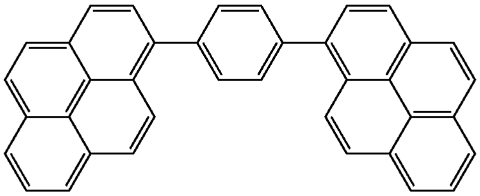
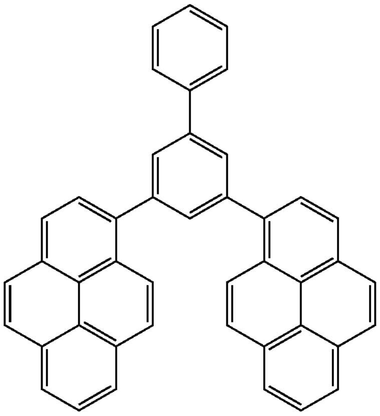
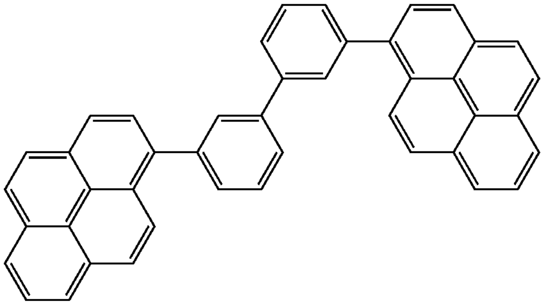
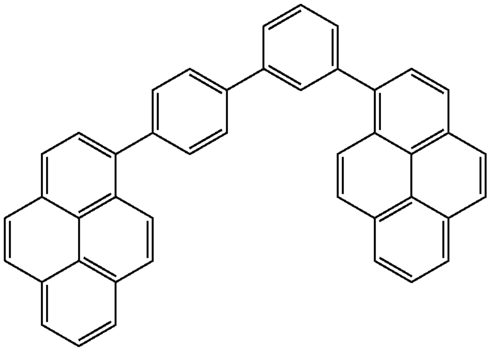

-continued
[Formula 71]
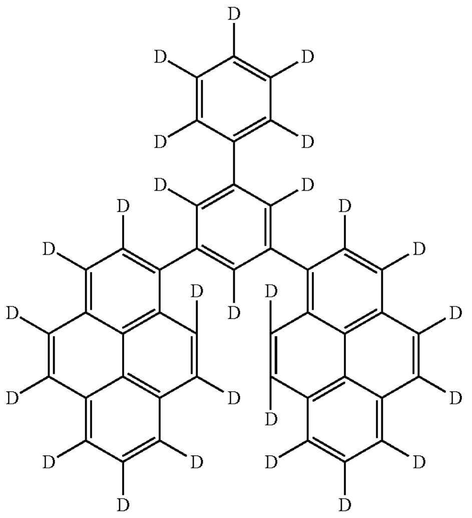
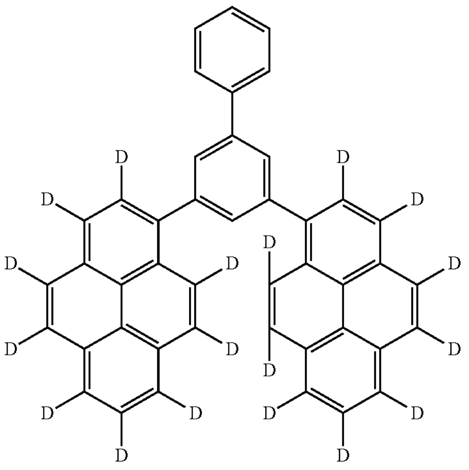
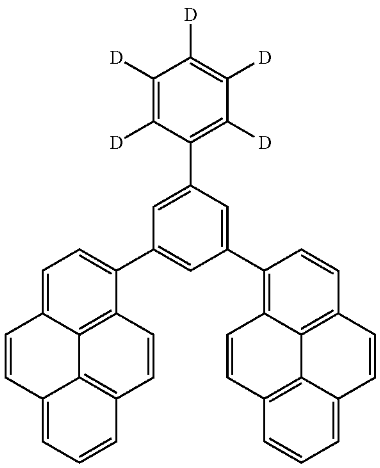 [SMILES: [2H]c1c([2H])c([2H])c(-c2cc(-c3ccc4ccc5cccc6ccc3c4c56)cc(-c3ccc4ccc5cccc6ccc3c4c56)c2)c([2H])c1[2H]]
The first compound is also preferably one of compounds represented by formulae (PY-1) to (PY-12) below.
[Formula 72]
(PY-1)
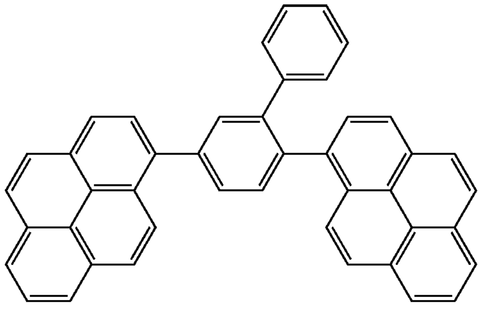
-continued
(PY-2)
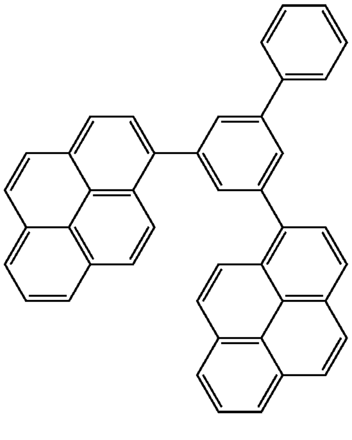

-continued
(PY-3)
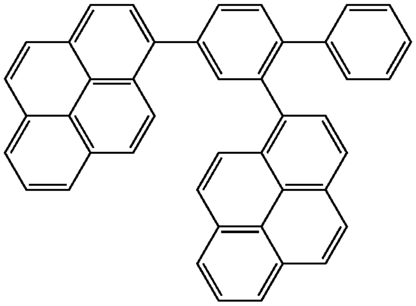
(PY-4)
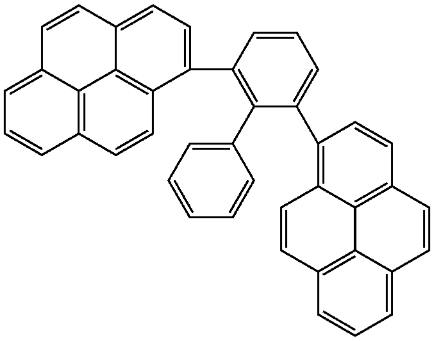
(PY-5)
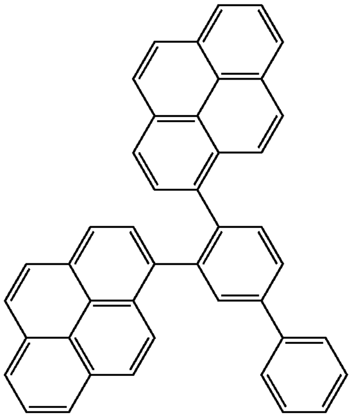
(PY-6)
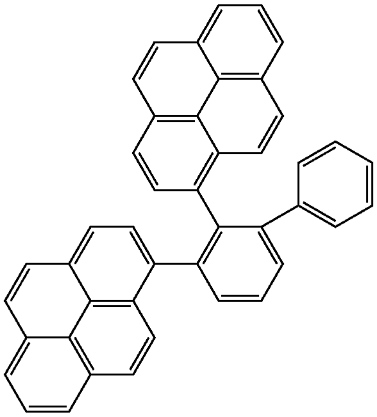
-continued
[Formula 73]
(PY-7)
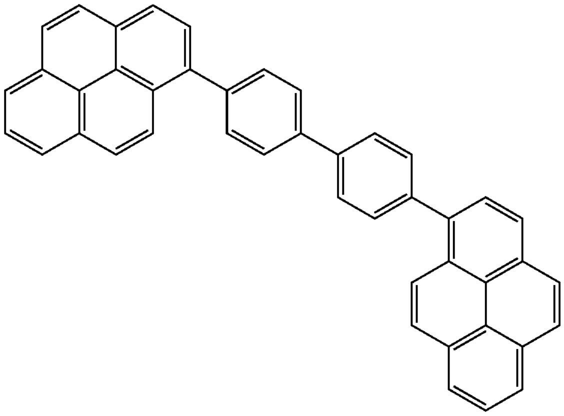
(PY-8)
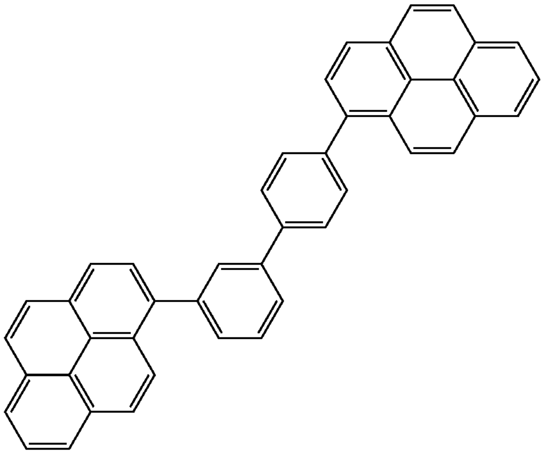
(PY-9)
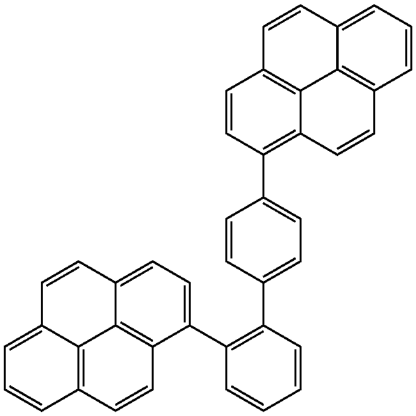

-continued (PY-10)

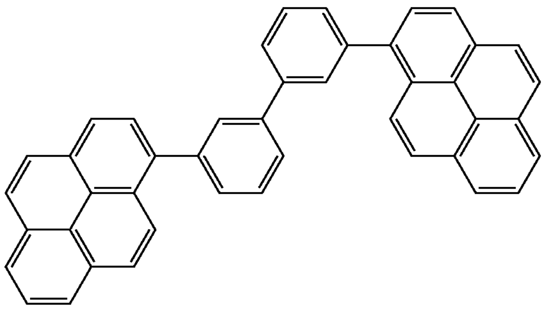

(PY-11)

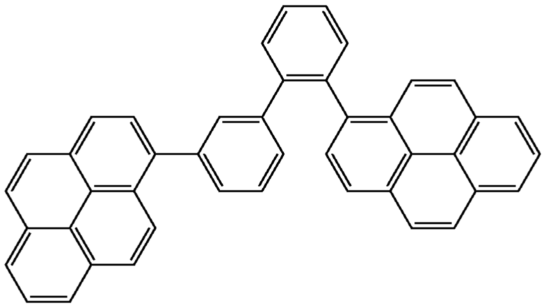

(PY-12)

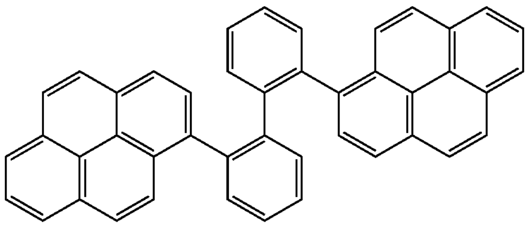

Second Compound

In the organic EL device according to the exemplary embodiment, the second compound is a compound represented by the formula (2).

[Formula 74]

(2)

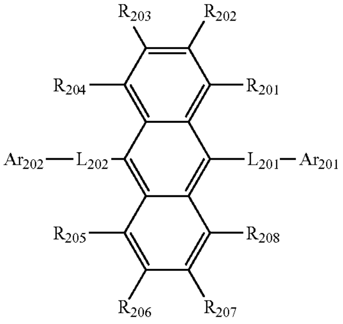

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the second compound according to the exemplary embodiment: $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, it is preferable that: $R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, or a nitro group; $L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that: $L_{201}$ and $L_{202}$ are each independently a single bond, or a substituted or unsubstituted arylene group having 6 to 50 ring carbon atoms; and $Ar_{201}$ and $Ar_{202}$ are each independently a substituted or unsubstituted aryl group having 6 to 50 ring carbon atoms.

In the organic EL device according to the exemplary embodiment, $Ar_{201}$ and $Ar_{202}$ are preferably each independently a phenyl group, a naphthyl group, a phenanthryl group, a biphenyl group, a terphenyl group, a diphenylfluorenyl group, a dimethylfluorenyl group, a benzodiphenylfluorenyl group, a benzodimethylfluorenyl group, a dibenzofuranyl group, a dibenzothienyl group, a naphthobenzofuranyl group, or a naphthobenzothienyl group.

In the organic EL device according to the exemplary embodiment, the second compound represented by the formula (2) is preferably a compound represented by a formula (201), (202), (203), (204), (205), (206), (207), (208) or (209) below.

[Formula 75]

(201)

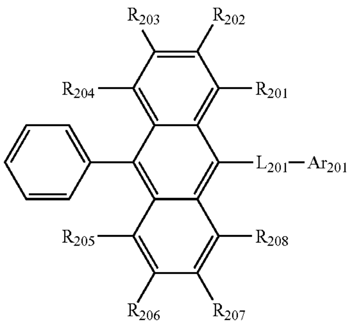

[Formula 76]

(202)

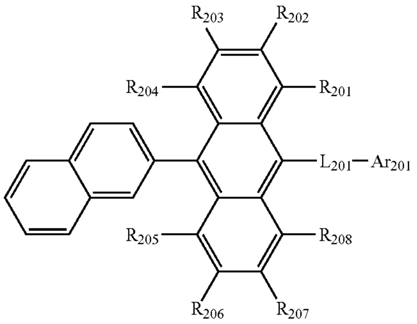

-continued

[Formula 77]

(203)

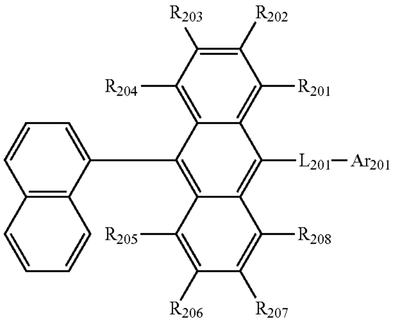

[Formula 78]

(204)

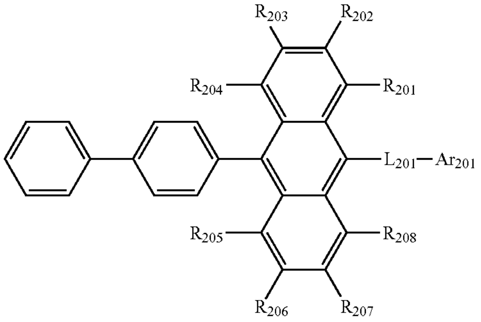

[Formula 79]

(205)

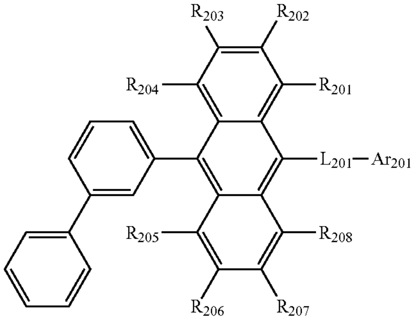

[Formula 80]

(206)

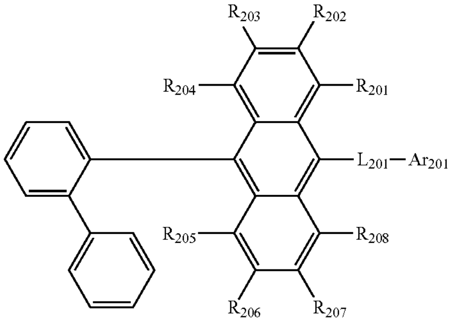

-continued
[Formula 81]
(207)
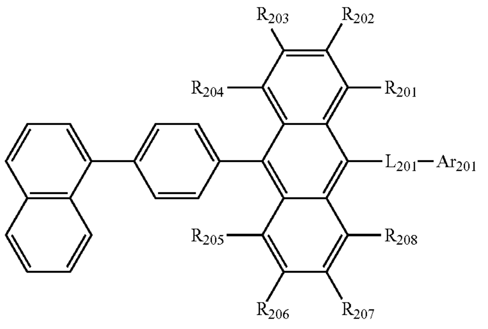
[Formula 82]
(208)
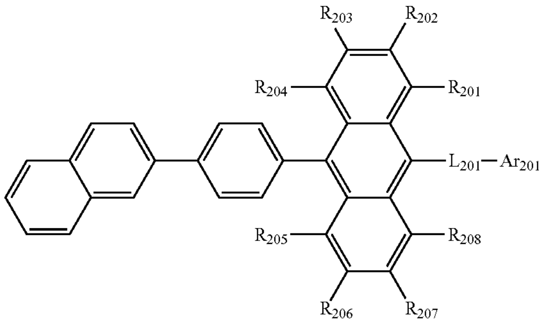
[Formula 83]
(209)
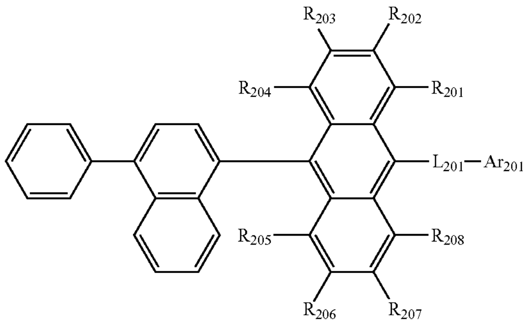
In the formulae (201) to (209):
$L_{201}$ and $Ar_{201}$ represent the same as $L_{201}$ and $Ar_{201}$ in the formula (2); and
$R_{201}$ to $R_{208}$ each independently represent the same as $R_{201}$ to $R_{208}$ in the formula (2).
The second compound represented by the formula (2) is also preferably a compound represented by a formula (221), (222), (223), (224), (225), (226), (227), (228) or (229) below.
[Formula 84]
(221)
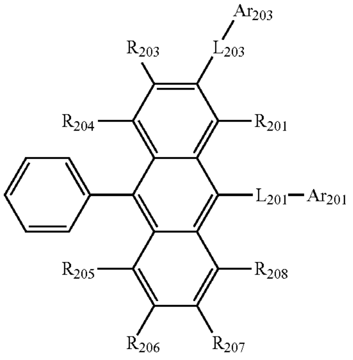
[Formula 85]
(222)
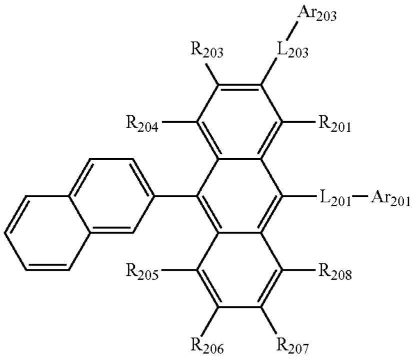
[Formula 86]
(223)
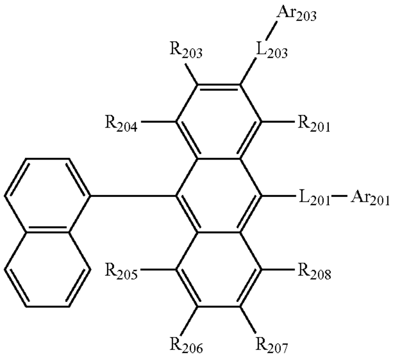
[Formula 87]
(224)
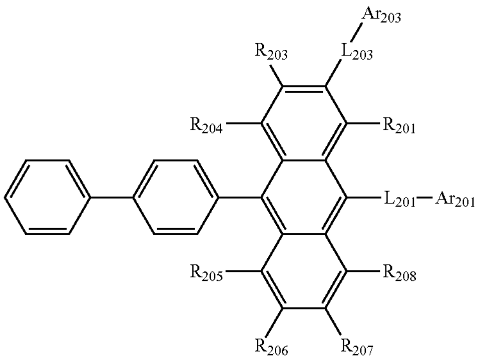

-continued

[Formula 88]

(225)

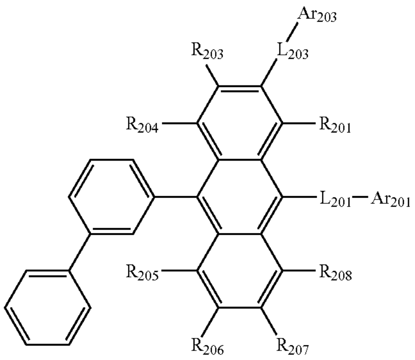

[Formula 89]

(226)

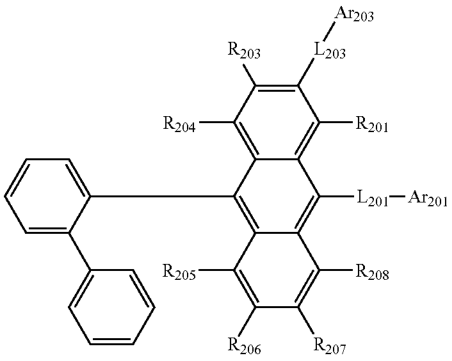

[Formula 90]

(227)

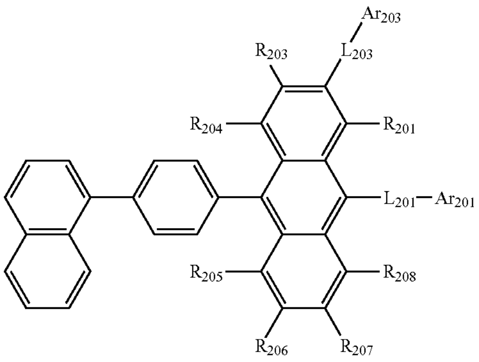

[Formula 91]

(228)

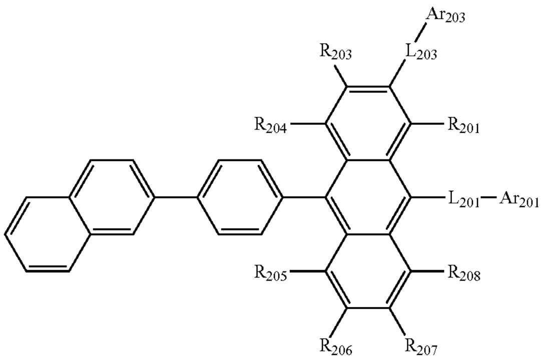

-continued

[Formula 92]

(229)

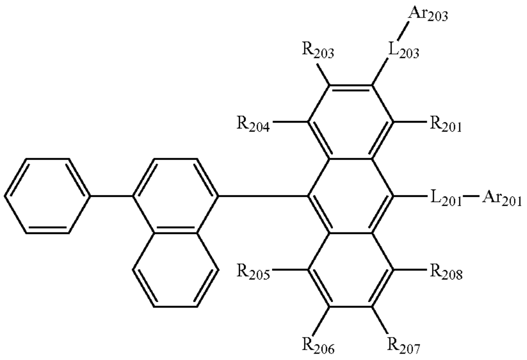

In the formulae (221), (222), (223), (224), (225), (226), (227), (228), and (229):

$R_{201}$ and $R_{203}$ to $R_{208}$ each independently represent the same as $R_{201}$ and $R_{203}$ to $R_{208}$ in the formula (2);

$L_{201}$ and $Ar_{201}$ each represent the same as $L_{201}$ and $Ar_{201}$ in the formula (2);

$L_{203}$ represents the same as $L_{201}$ in the formula (2);

$L_{203}$ and $L_{20}R$ are mutually the same or different;

$Ar_{203}$ represents the same as $Ar_{201}$ in the formula (2); and $Ar_{203}$ and $Ar_{201}$ are mutually the same or different.

The second compound represented by the formula (2) is also preferably a compound represented by a formula (241), (242), (243), (244), (245), (246), (247), (248) or (249) below.

[Formula 93]

(241)

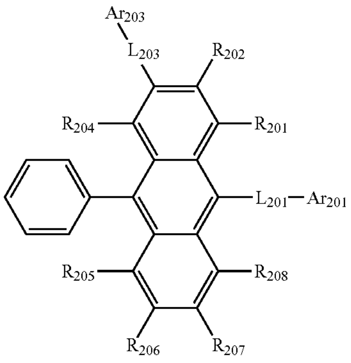

[Formula 94]

(242)

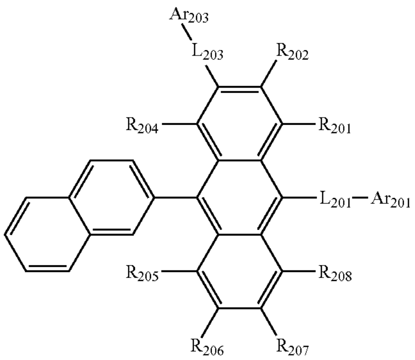

-continued

[Formula 95]

(243)

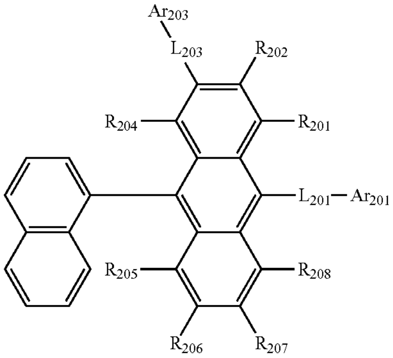

[Formula 96]

(244)

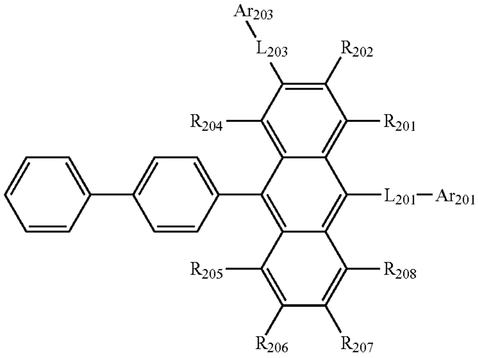

[Formula 97]

(245)

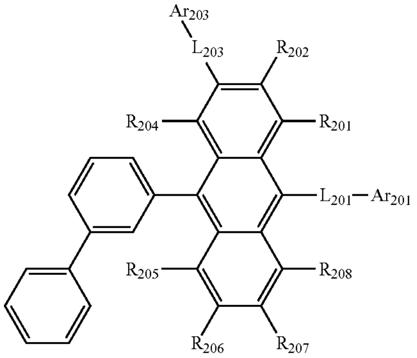

[Formula 98]

(246)

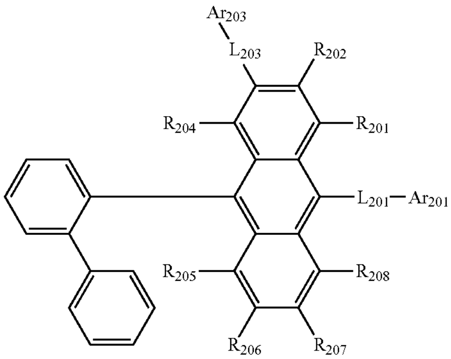

-continued

[Formula 99]

(247)

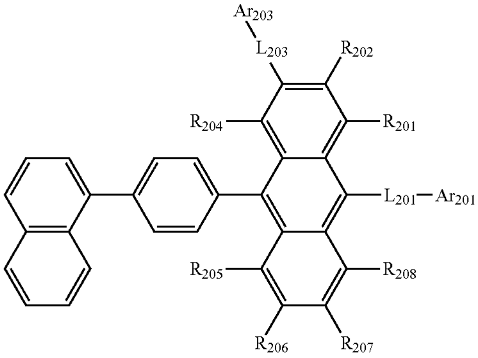

[Formula 100]

(248)

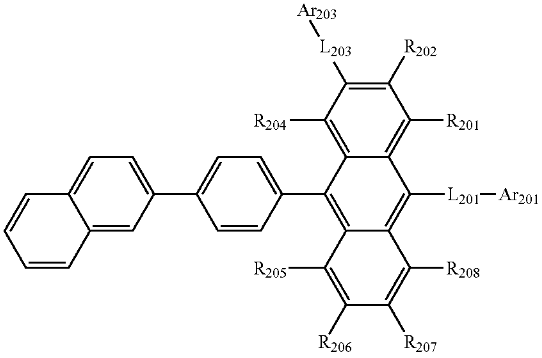

[Formula 101]

(249)

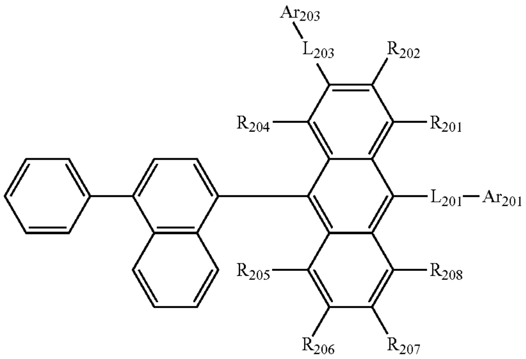

In the formulae (241), (242), (243), (244), (245), (246), (247), (248), and (249):

$R_{201}$, $R_{202}$, and $R_{204}$ to $R_{208}$ each independently represent the same as $R_{201}$, $R_{202}$, and $R_{204}$ to $R_{208}$ in the formula (2);

$L_{203}$ represents the same as $L_{201}$ in the formula (2);

$L_{203}$ and $L_{201}$ are mutually the same or different;

$Ar_2O_3$ represents the same as $Ar_{201}$ in the formula (2); and $Ar_2O_3$ and $Ar_{201}$ are mutually the same or different.

$R_{201}$ to $R_{208}$ in the second compound represented by the formula (2) are preferably each independently a hydrogen atom, a substituted or unsubstituted alkyl group having 1 to 50 carbon atoms, a substituted or unsubstituted cycloalkyl group having 3 to 50 ring carbon atoms, or a group represented by —Si($R_{901}$)($R_{902}$)($R_{903}$).

It is preferable that: $L_{101}$ is a single bond, or an unsubstituted arylene group having 6 to 22 ring carbon atoms; and $Ar_{101}$ is a substituted or unsubstituted aryl group having 6 to 22 ring carbon atoms.

In the organic EL device according to the exemplary embodiment, $R_{201}$ to $R_{208}$ that are substituents on an anthracene skeleton in the second compound represented by the formula (2) are preferably hydrogen atoms in terms of preventing inhibition of intermolecular interaction to inhibit a decrease in electron mobility. However, $R_{201}$ to $R_{208}$ may be a substituted or unsubstituted aryl group having 6 to 50 ring carbon atoms or a substituted or unsubstituted heterocyclic group having 5 to 50 ring atoms.

Assuming that $R_{201}$ to $R_{208}$ each are a bulky substituent such as an alkyl group and a cycloalkyl group, intermolecular interaction may be inhibited to decrease the electron mobility of the second compound relative to that of the first compound, so that a relationship of μH2>μH1 shown by a numerical formula below (Numerical Formula 3) may not be satisfied. When the second compound is used in the second emitting layer, it can be expected that satisfying the relationship of μH2>μH1 inhibits a decrease in a recombination ability between holes and electrons in the first emitting layer and a decrease in a luminous efficiency. It should be noted that substituents, namely, a haloalkyl group, alkenyl group, alkynyl group, group represented by —$Si(R_{901})(R_{902})(R_{903})$, group represented by —O—($R_{904}$), group represented by —S—($R_{905}$), group represented by —$N(R_{906})(R_{907})$, aralkyl group, group represented by —C(═O)$R_{801}$, group represented by —$COOR_{802}$, halogen atom, cyano group, and nitro group are likely to be bulky, and an alkyl group and cycloalkyl group are likely to be further bulky.

In the second compound represented by the formula (2), $R_{201}$ to $R_{208}$, which are the substituents on the anthracene skeleton, are each preferably not a bulky substituent and preferably not an alkyl group and cycloalkyl group. More preferably, $R_{201}$ to $R_{208}$ are not an alkyl group, cycloalkyl group, haloalkyl group, alkenyl group, alkynyl group, group represented by —$Si(R_{901})(R_{902})(R_{903})$, group represented by —O—($R_{904}$), group represented by —S—($R_{905}$), group represented by —$N(R_{906})(R_{907})$, aralkyl group, group represented by —C(═O)$R_{801}$, group represented by —$COOR_{802}$, halogen atom, cyano group, and nitro group.

In the organic EL device according to the exemplary embodiment, $R_{201}$ to $R_{208}$ in the second compound represented by the formula (2) are also preferably each independently a hydrogen atom, a substituted or unsubstituted alkyl group having 1 to 50 carbon atoms, a substituted or unsubstituted cycloalkyl group having 3 to 50 ring carbon atoms, or a group represented by —$Si(R_{901})(R_{902})(R_{903})$.

In the organic EL device according to the exemplary embodiment, $R_{201}$ to $R_{208}$ in the second compound represented by the formula (2) are each preferably a hydrogen atom.

In the second compound, examples of the substituent for a "substituted or unsubstituted group" on $R_{201}$ to $R_{208}$ also preferably do not include the above-described substituent that is likely to be bulky, especially a substituted or unsubstituted alkyl group and a substituted or unsubstituted cycloalkyl group. Since examples of the substituent for a "substituted or unsubstituted" group on $R_{201}$ to $R_{208}$ do not include a substituted or unsubstituted alkyl group and a substituted or unsubstituted cycloalkyl group, inhibition of intermolecular interaction to be caused by presence of a bulky substituent such as an alkyl group and a cycloalkyl group can be prevented, thereby preventing a decrease in the electron mobility. Moreover, when the second compound described above is used in the second emitting layer, a decrease in a recombination ability between holes and electrons in the first emitting layer and a decrease in the luminous efficiency can be inhibited.

It is more preferable that $R_{201}$ to $R_{208}$, which are the substituents on the anthracene skeleton, are not bulky substituents, and $R_{201}$ to $R_{208}$ as substituents are unsubstituted. Assuming that $R_{201}$ to $R_{208}$, which are the substituents on the anthracene skeleton, are not bulky substituents and substituents are bonded to $R_{201}$ to $R_{208}$ which are the not-bulky substituents, the substituents bonded to $R_{201}$ to $R_{208}$ are preferably not the bulky substituents; the substituents bonded to $R_{201}$ to $R_{208}$ serving as substituents are preferably not an alkyl group and cycloalkyl group, more preferably not an alkyl group, cycloalkyl group, haloalkyl group, alkenyl group, alkynyl group, group represented by —$Si(R_{901})(R_{902})(R_{903})$, group represented by —O—($R_{904}$), group represented by —S—($R_{905}$), group represented by —$N(R_{906})(R_{907})$, aralkyl group, group represented by —C(═O)$R_{801}$, group represented by —$COOR_{802}$, halogen atom, cyano group, and nitro group.

In the second compound, the groups specified to be "substituted or unsubstituted" are each preferably an "unsubstituted" group.

In the organic EL device according to the exemplary embodiment, for instance, $Ar_{201}$ in the second compound represented by the formula (2) is a substituted or unsubstituted dibenzofuranyl group.

In the organic EL device according to the exemplary embodiment, for instance, $Ar_{201}$ in the second compound represented by the formula (2) is an unsubstituted dibenzofuranyl group.

In the organic EL device according to the exemplary embodiment, for instance, at least one hydrogen atom is included in the second compound represented by the formula (2), the hydrogen atom including at least one deuterium atom.

In the organic EL device according to the exemplary embodiment, for instance, $L_{201}$ in the second compound represented by the formula (2) is one of TEMP-63 to TEMP-68.

[Formula 102]

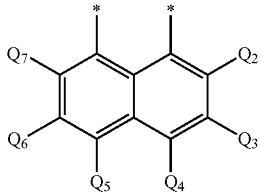

(TEMP-63)

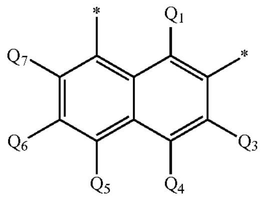

(TEMP-64)

-continued (TEMP-65)

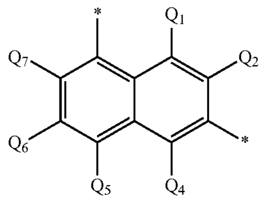

(TEMP-66)

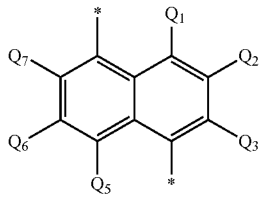

(TEMP-67)

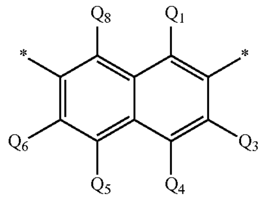

(TEMP-68)

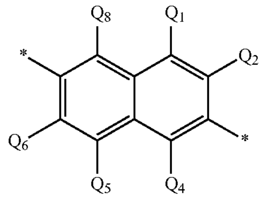

In the organic EL device according to the exemplary embodiment, for instance, $Ar_{201}$ in the second compound represented by the formula (2) is at least one group selected from the group consisting of substituted or unsubstituted anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluoranthenyl group, benzofluoranthenyl group, and perylenyl group.

In the organic EL device according to the exemplary embodiment, for instance, $Ar_{201}$ in the second compound represented by the formula (2) is a substituted or unsubstituted fluorenyl group.

In the organic EL device according to the exemplary embodiment, for instance, $Ar_{201}$ in the second compound represented by the formula (2) is a substituted or unsubstituted xanthenyl group.

In the organic EL device according to the exemplary embodiment, for instance, $Ar_{201}$ in the second compound represented by the formula (2) is a benzoxanthenyl group.

Method of Manufacturing Second Compound

The second compound can be manufactured by a known method. The second compound can also be manufactured based on a known method through a known alternative reaction using a known material(s) tailored for the target compound.

Specific Examples of Second Compound

Specific examples of the second compound include the following compounds. It should however be noted that the invention is not limited by the specific examples of the second compound.

[Formula 103]

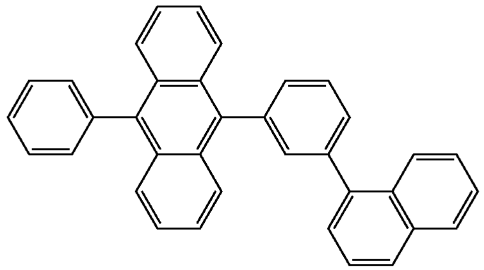

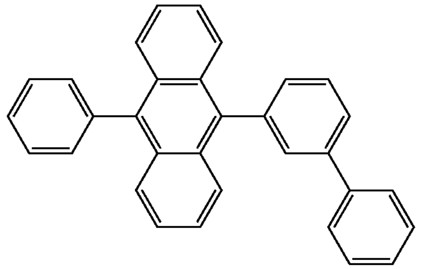

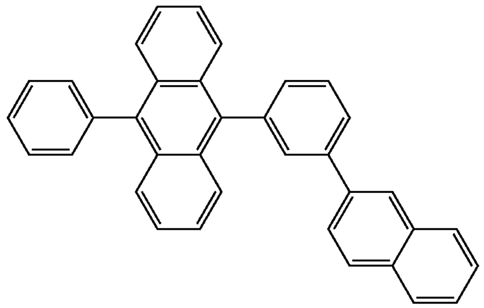

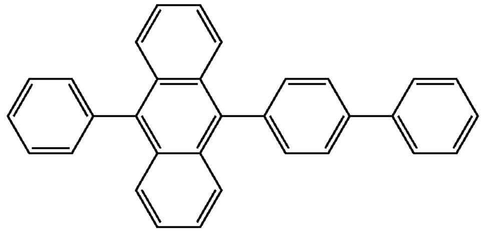

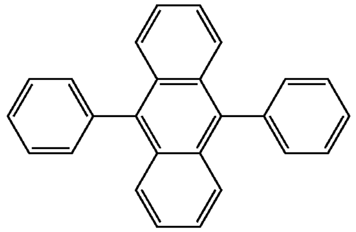

-continued
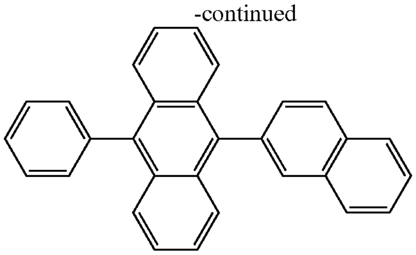
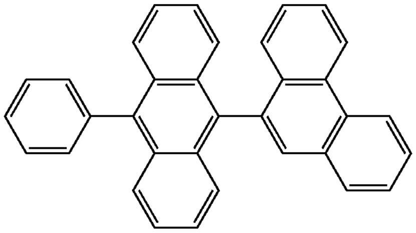
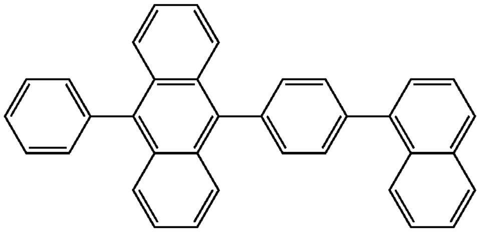
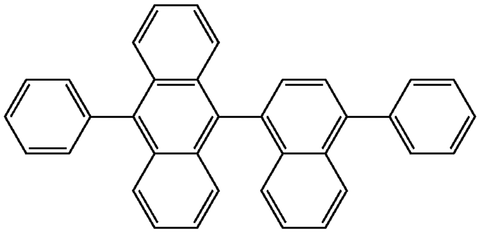
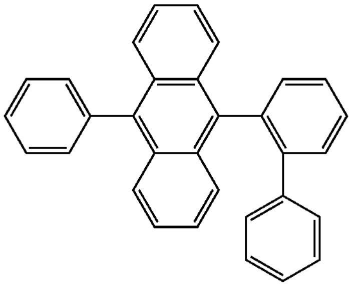
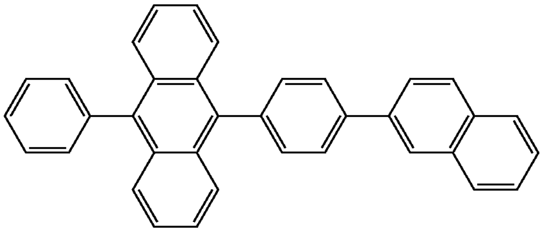
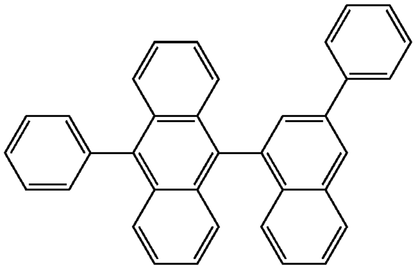
-continued
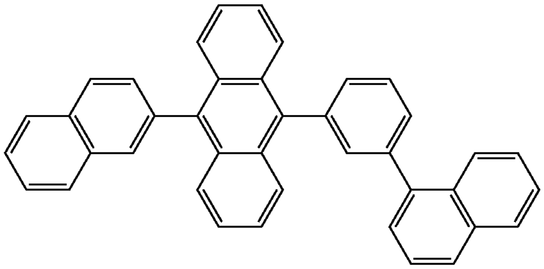
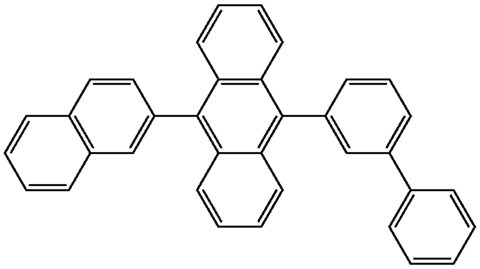
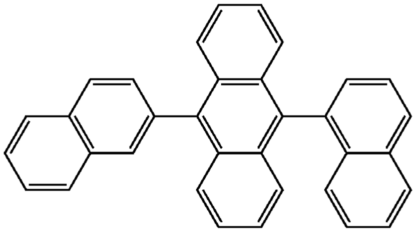
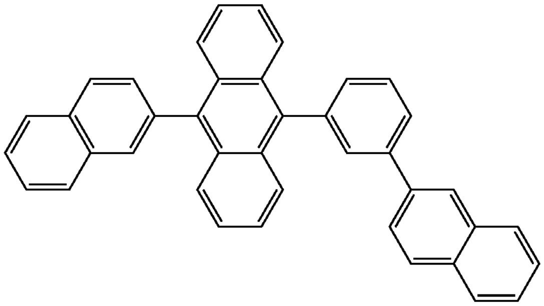
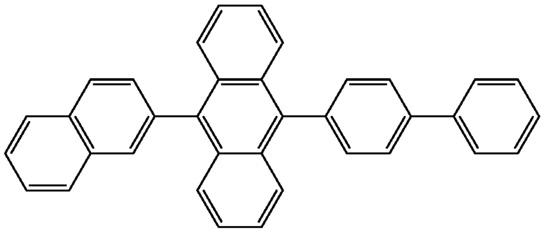
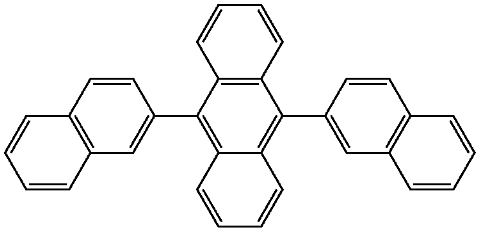

-continued
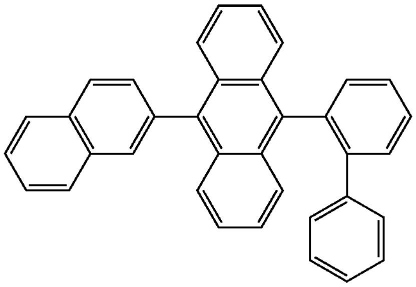
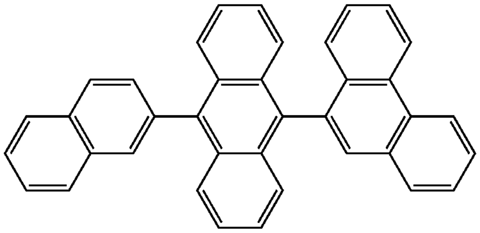
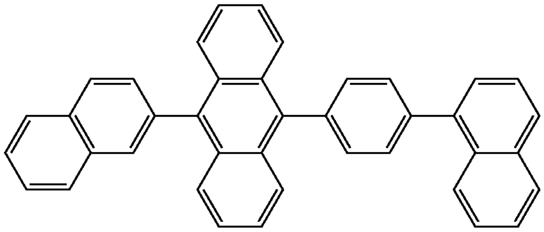
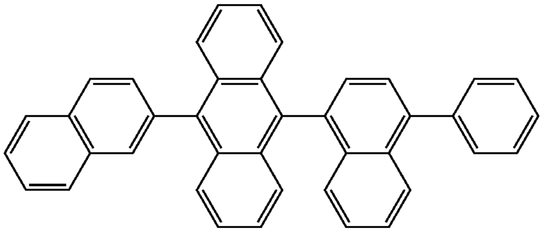
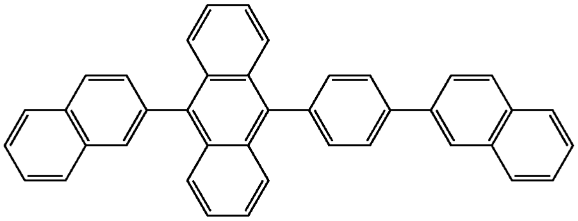
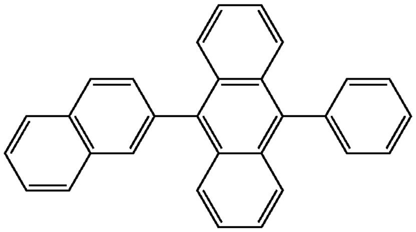
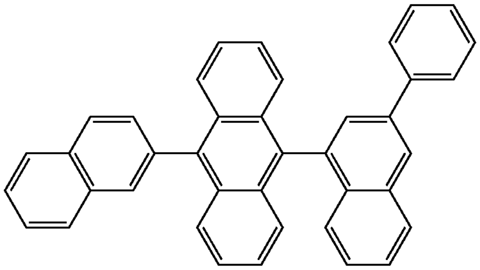
-continued
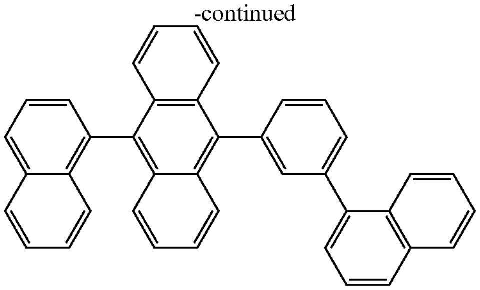
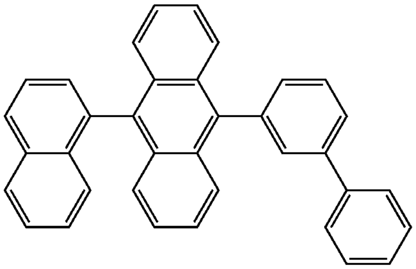
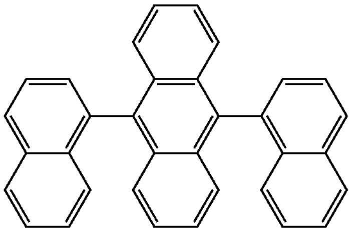
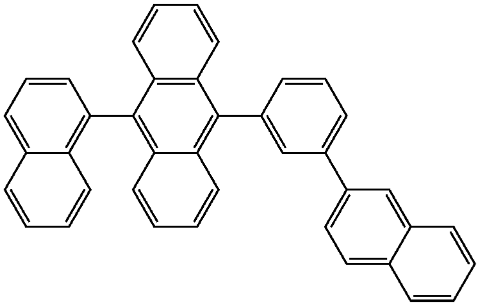
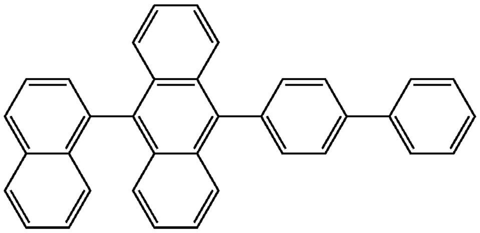
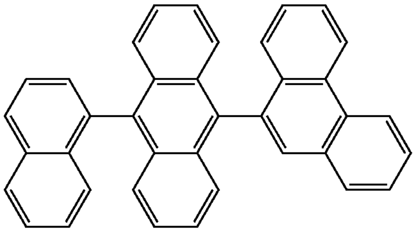

-continued
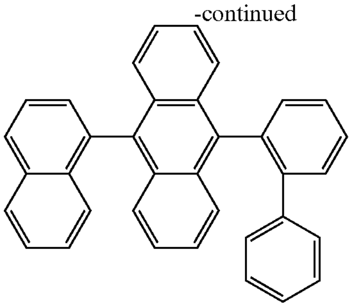
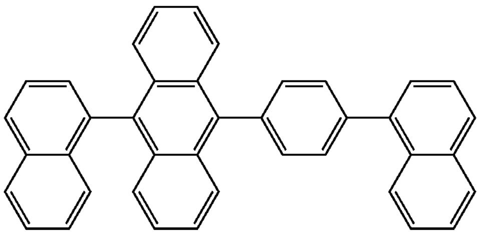
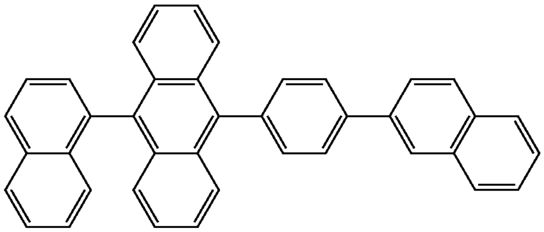
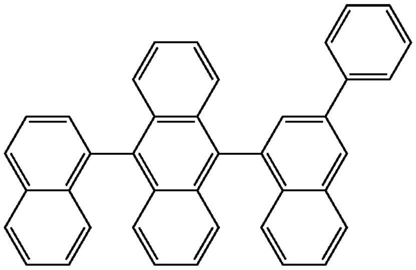
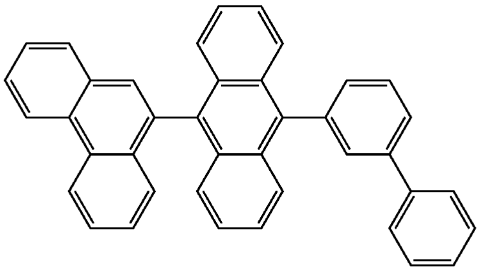
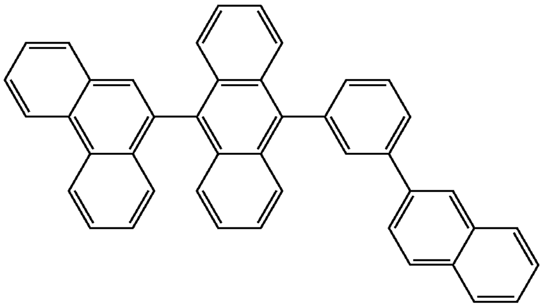
-continued
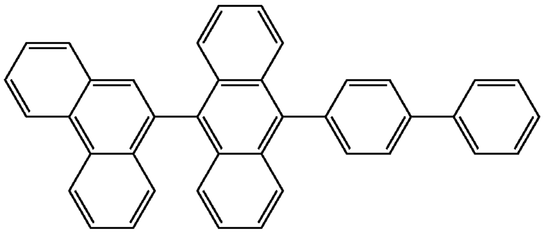
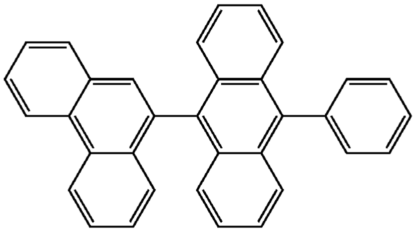
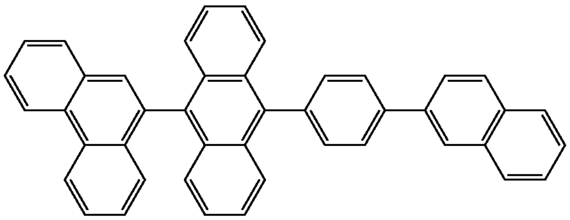
[Formula 104]
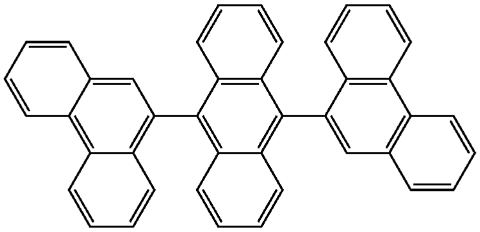
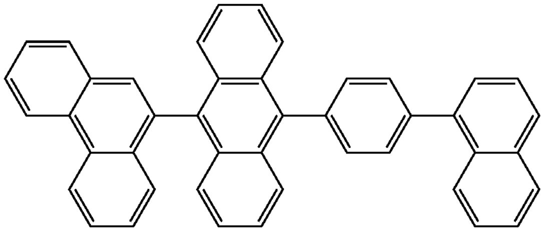
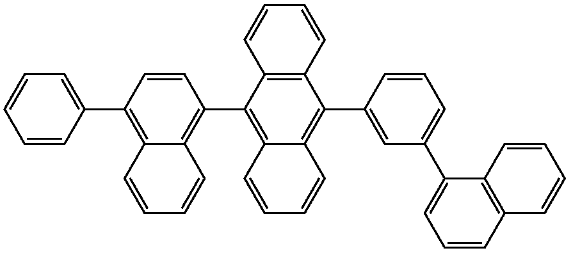
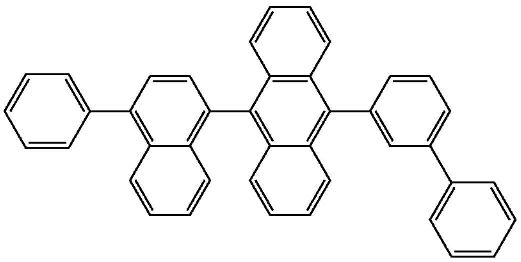

-continued
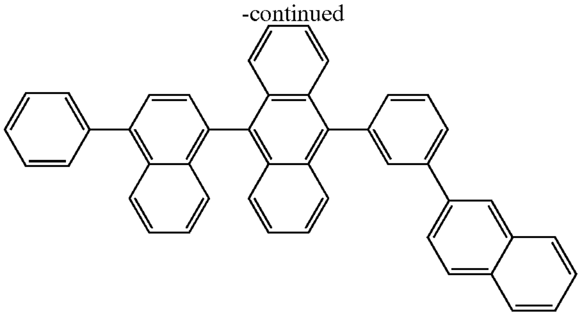
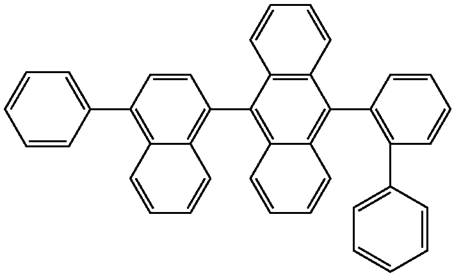
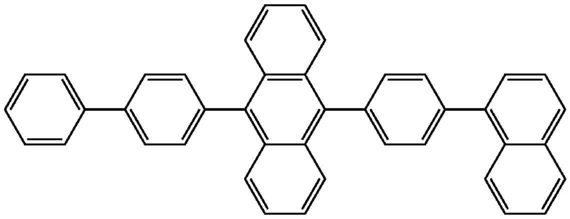
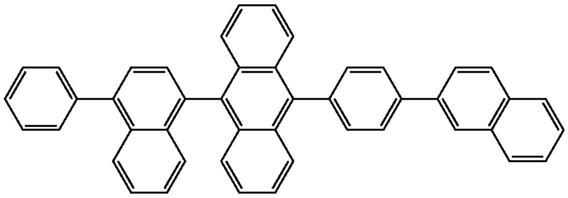
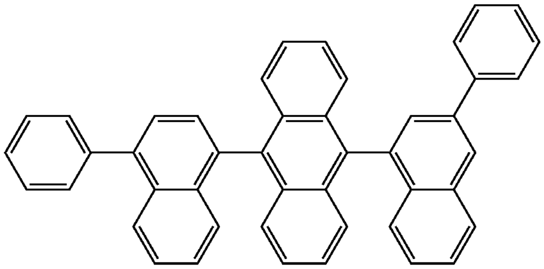
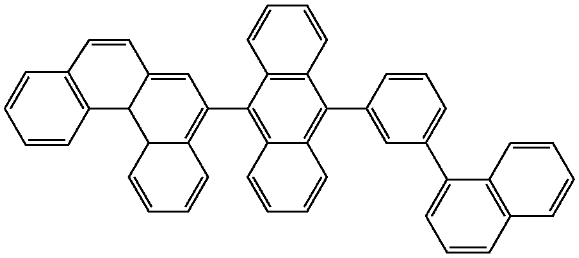
-continued
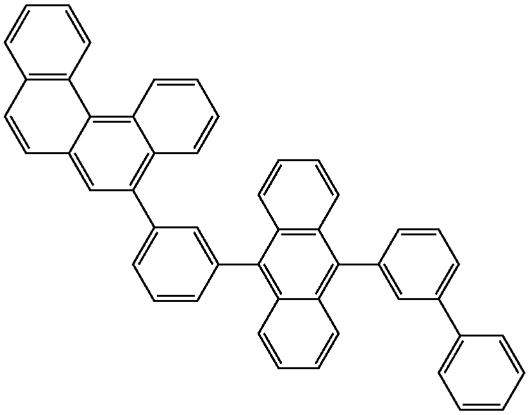
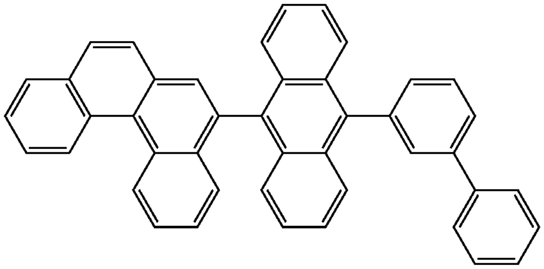
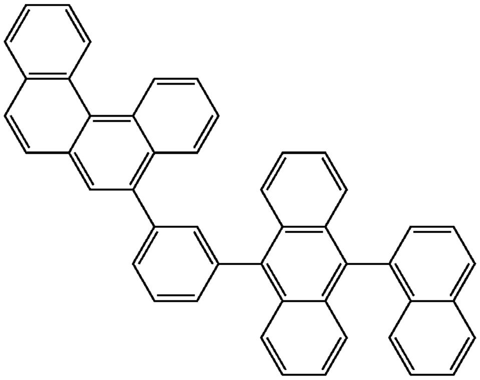
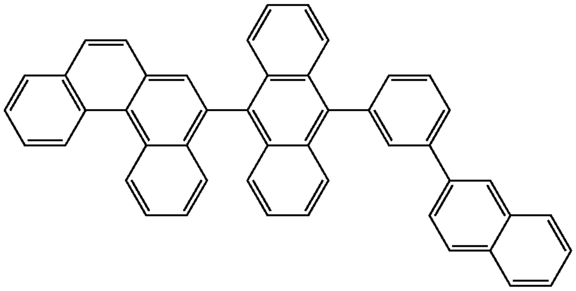
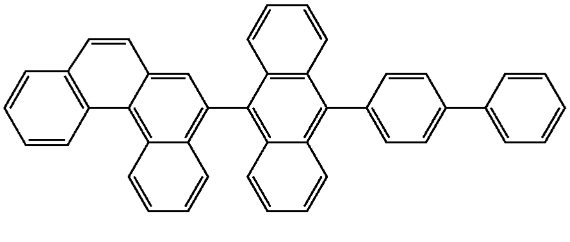

-continued
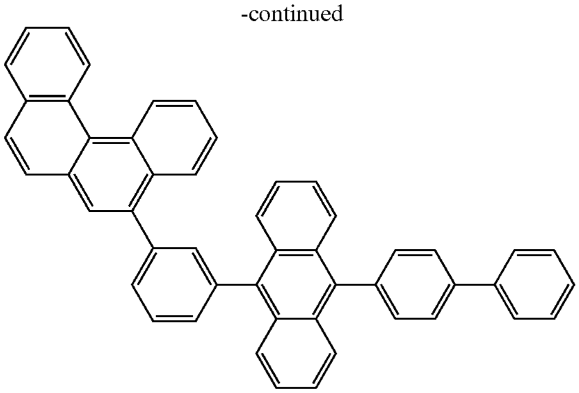
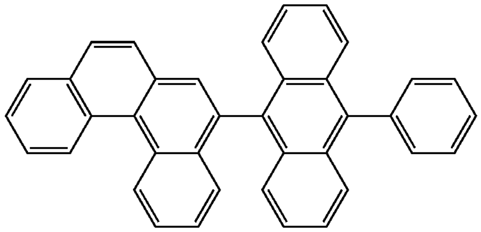
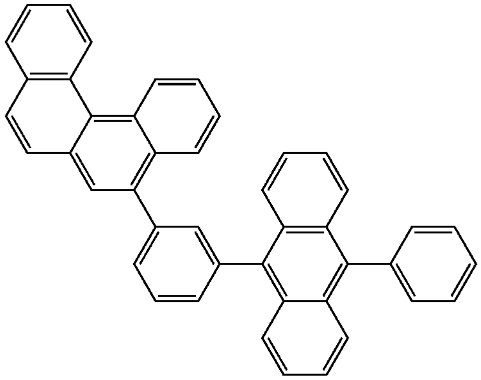
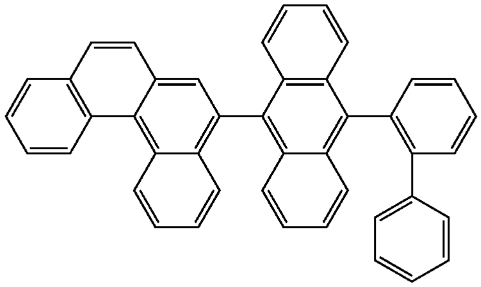
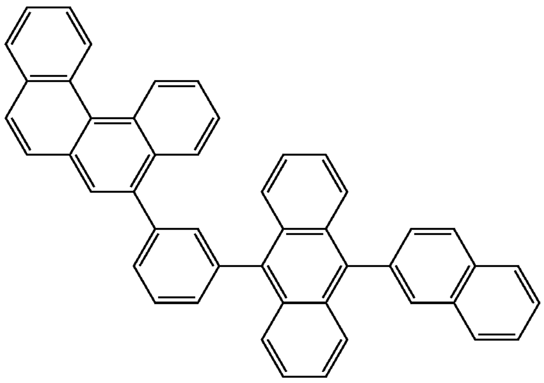
-continued
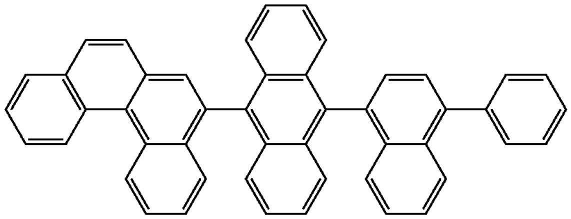
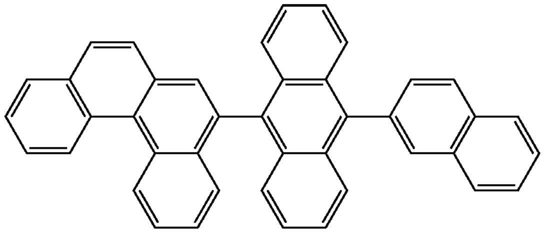
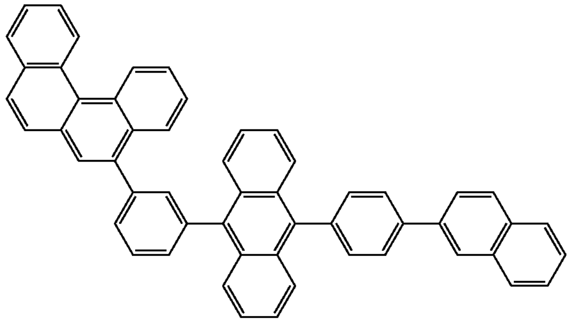
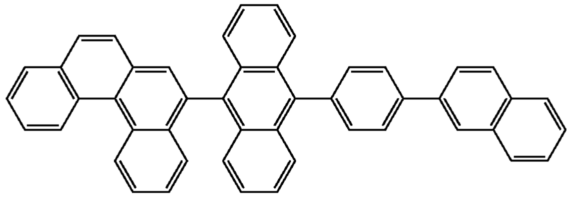
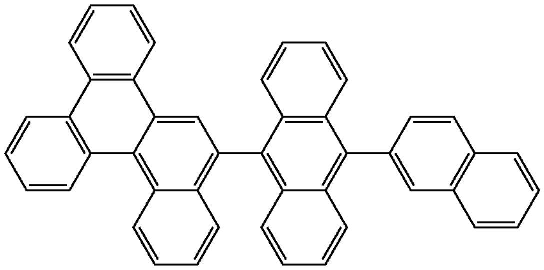
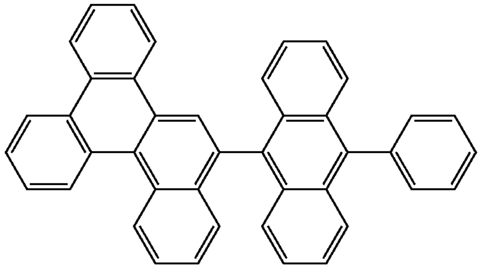

-continued
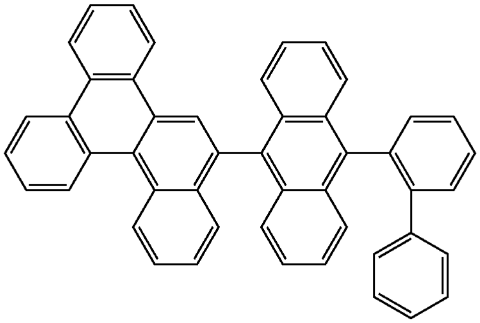
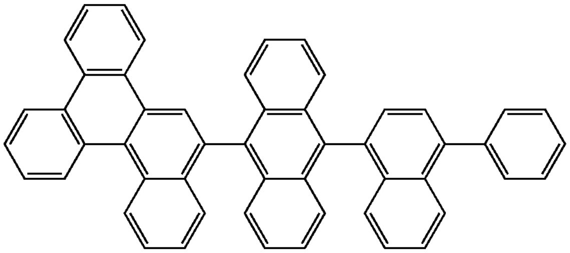
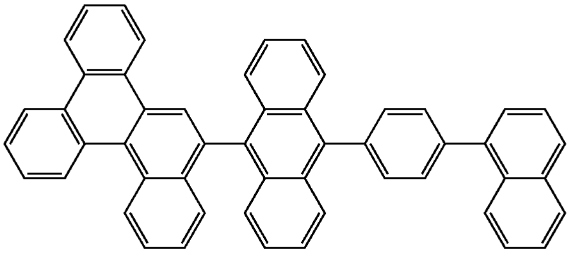
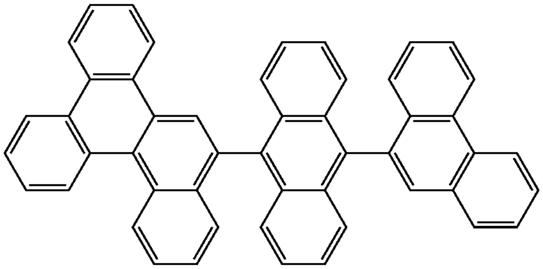
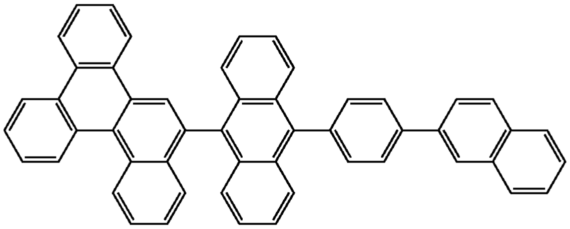
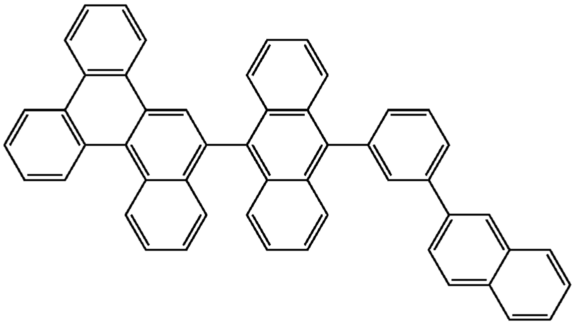
-continued
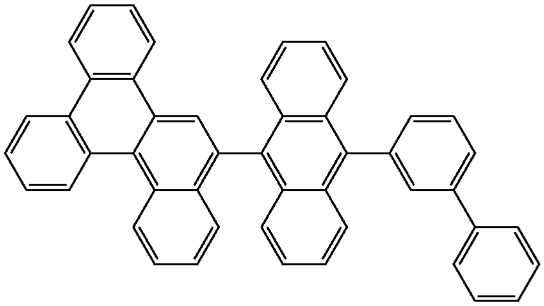
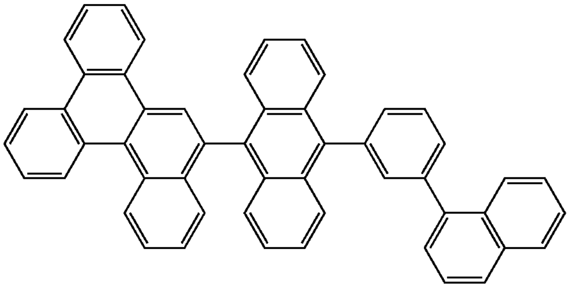
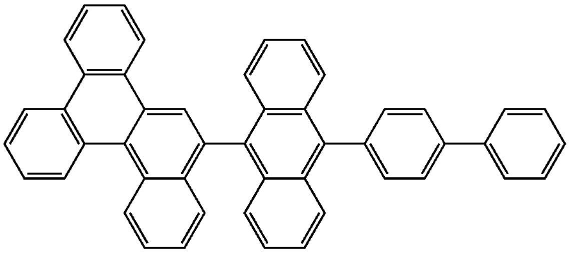
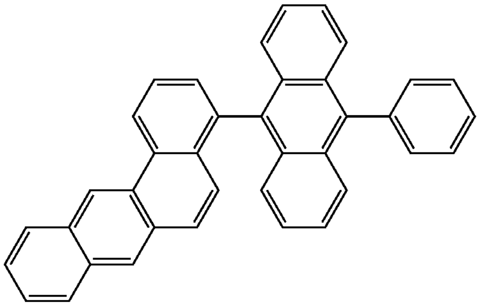
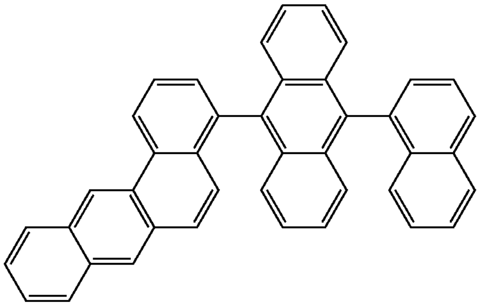

-continued
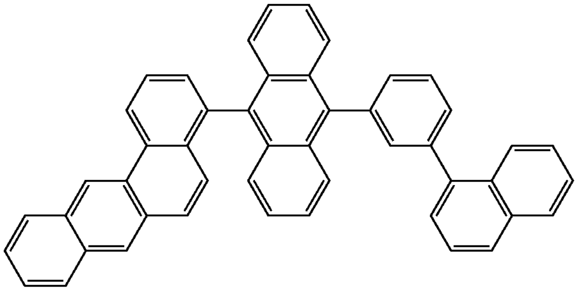
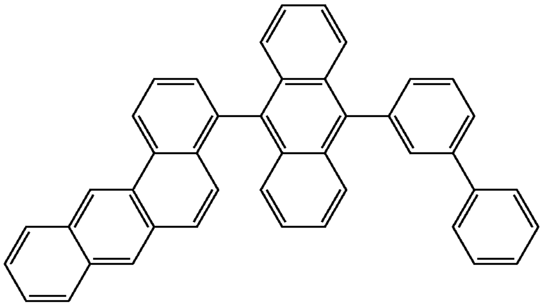
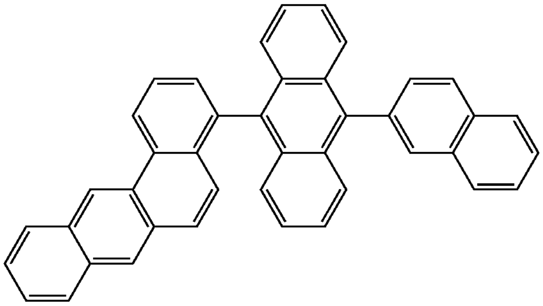
[Formula 105]
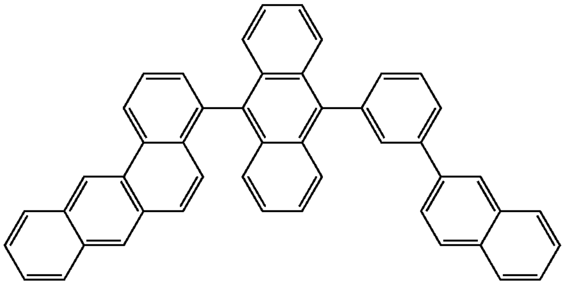
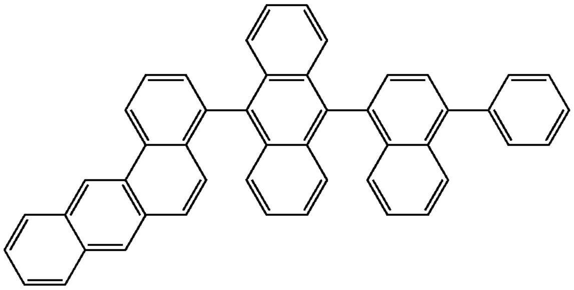
-continued
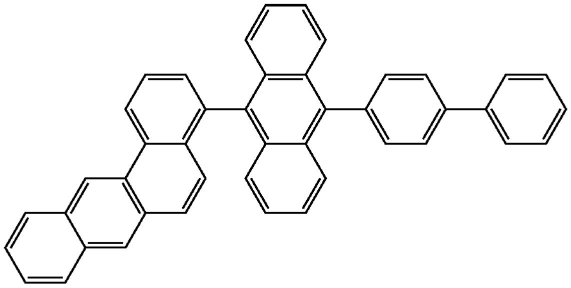
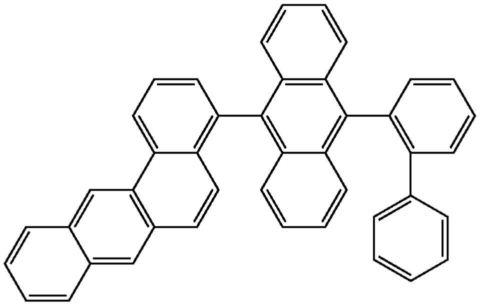
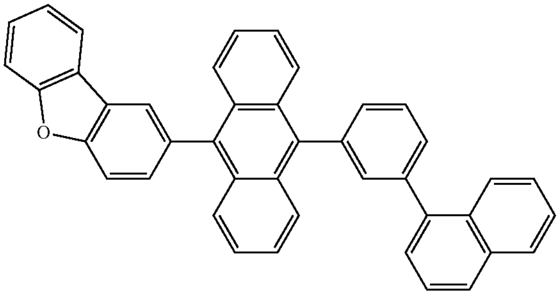
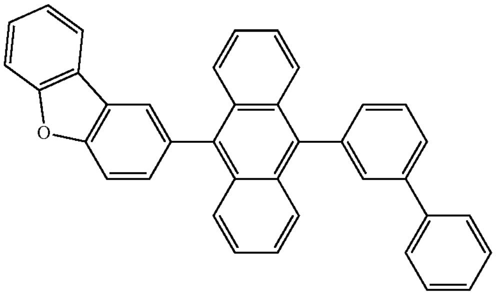
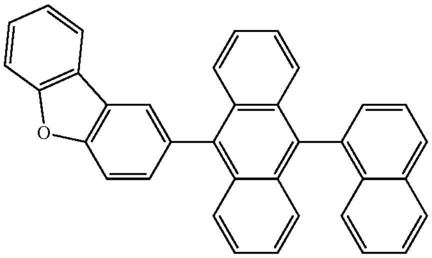

-continued
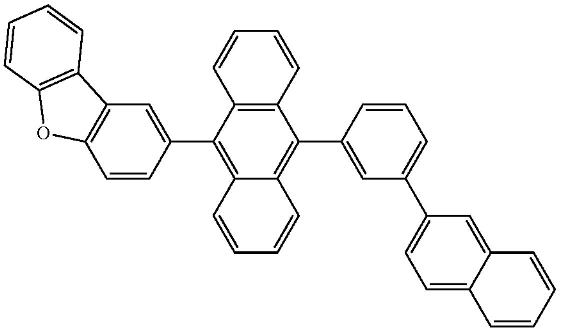
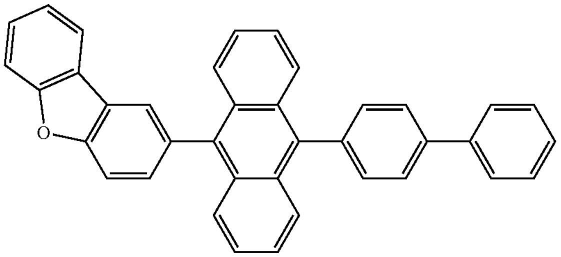
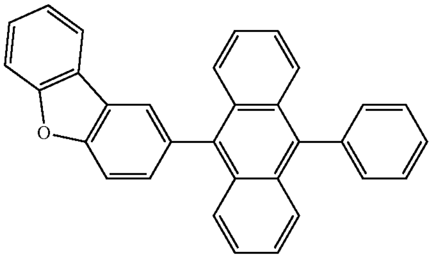
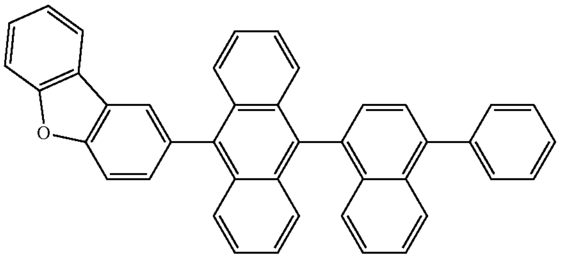
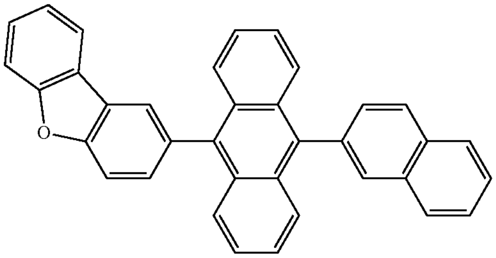
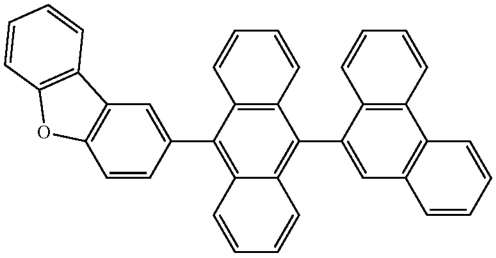
-continued
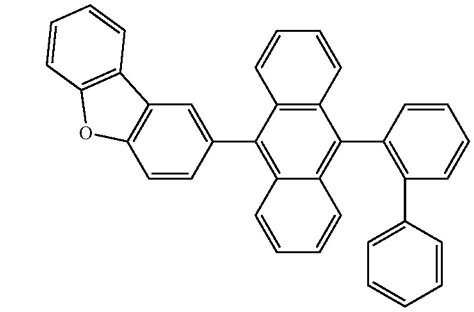
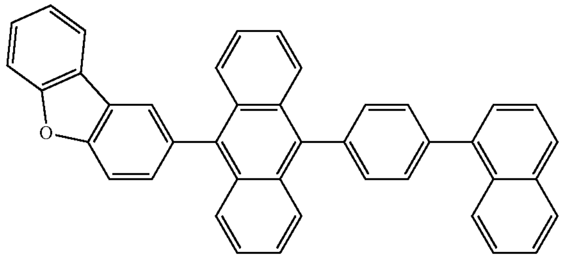
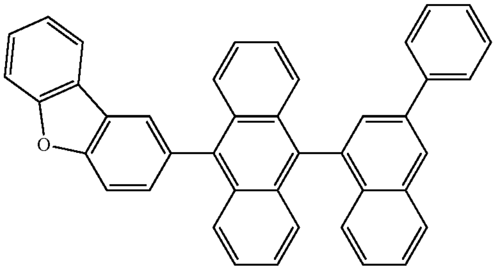
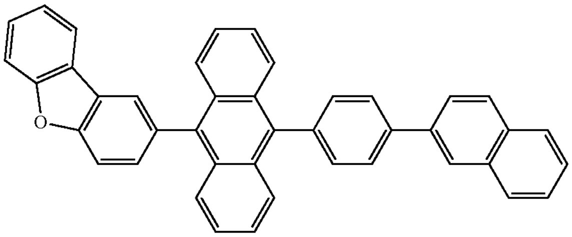
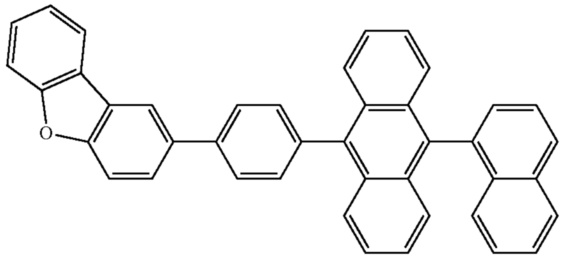
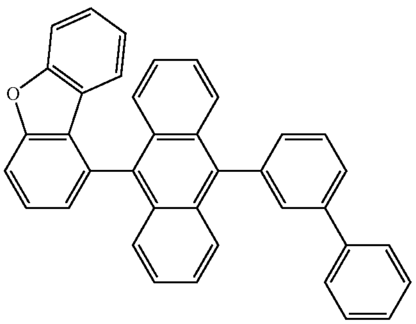

-continued
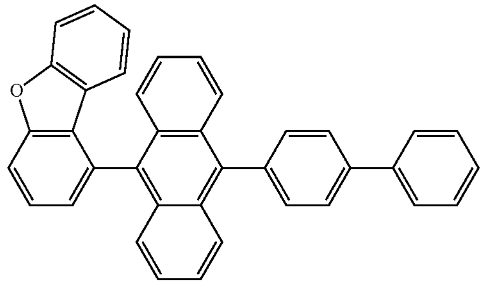
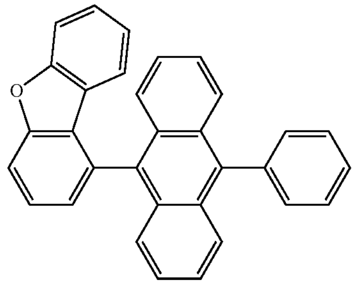
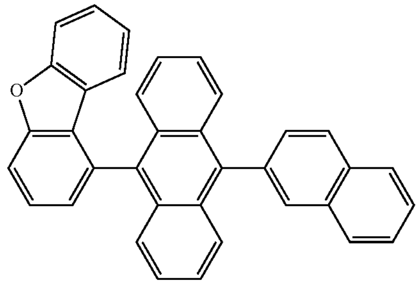
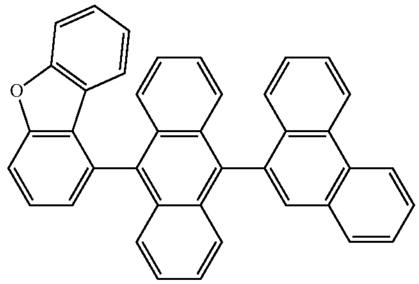
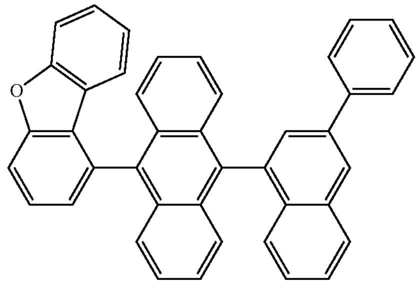
-continued
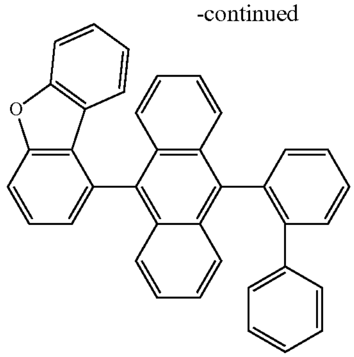
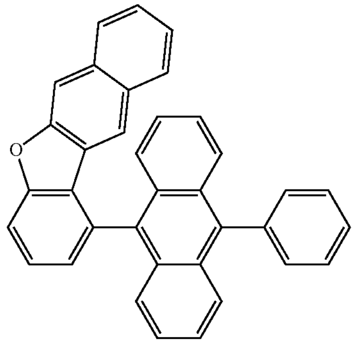
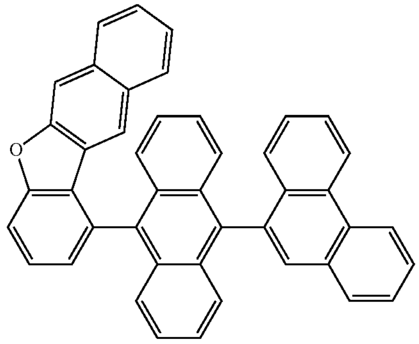
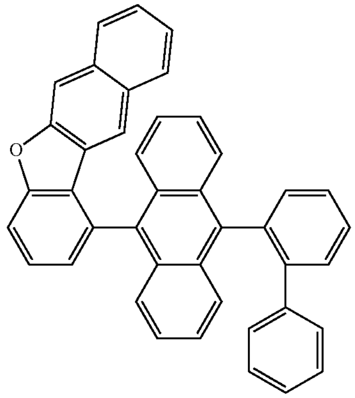

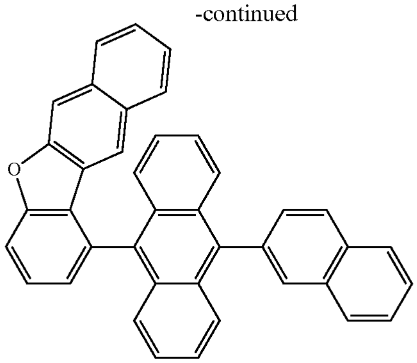
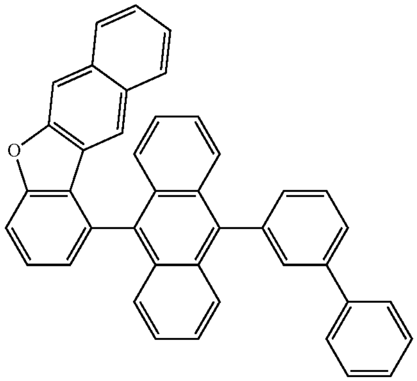
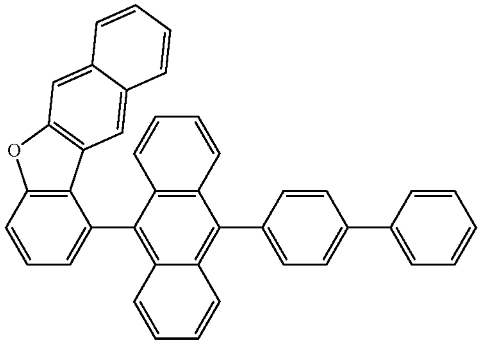
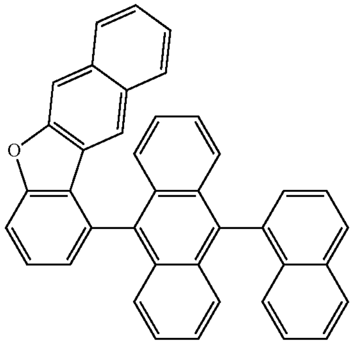
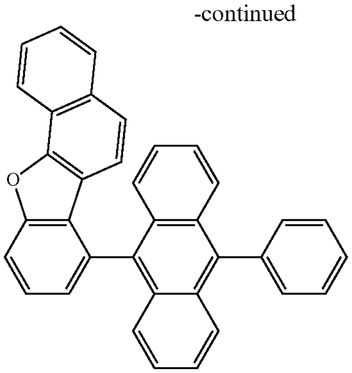
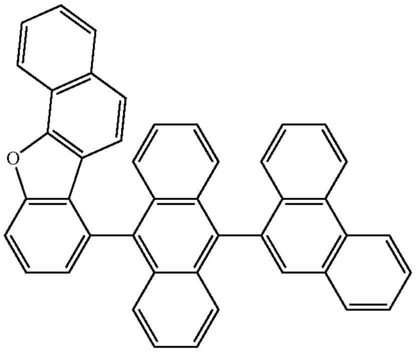
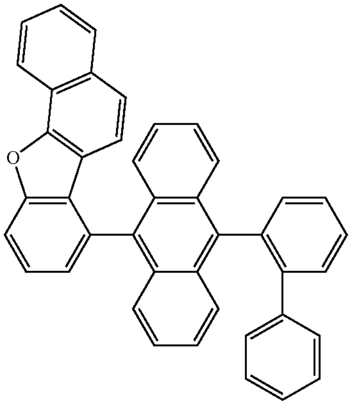
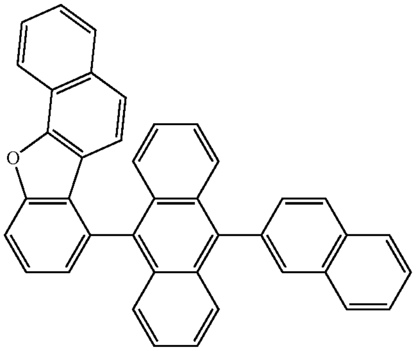

-continued
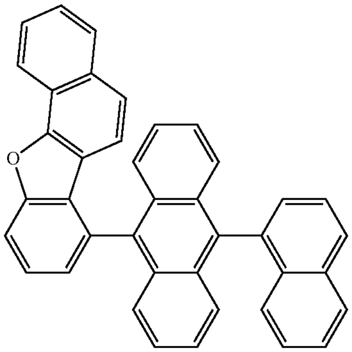
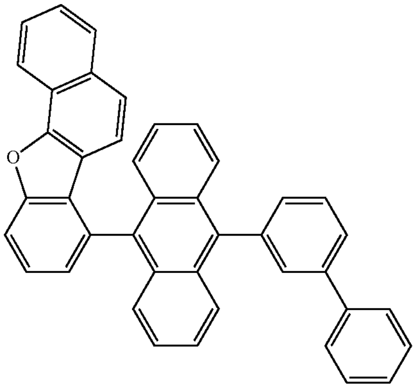
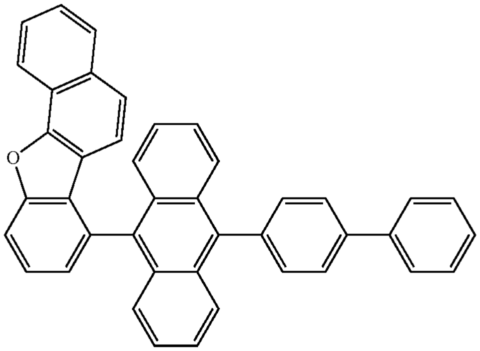
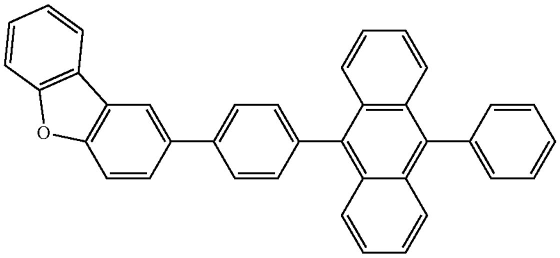
[Formula 106]
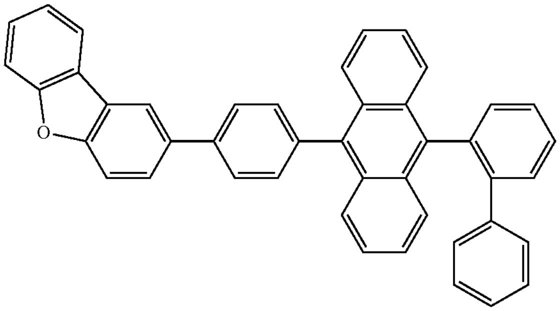
-continued
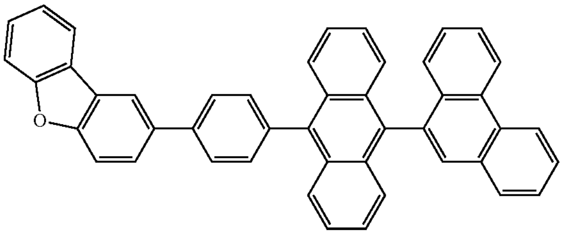
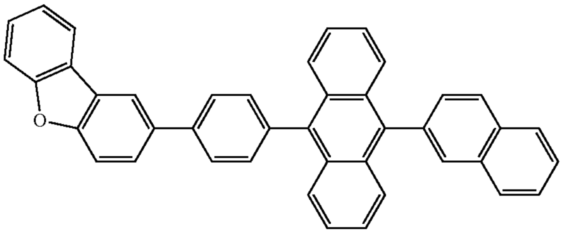
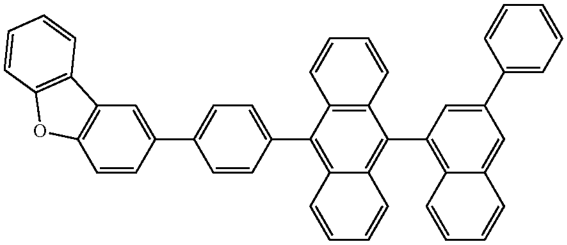
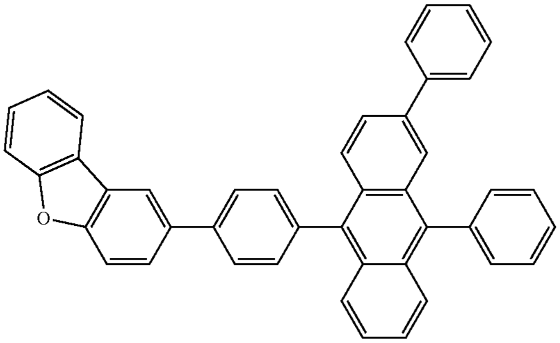
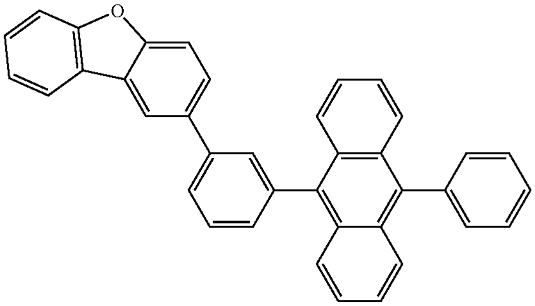
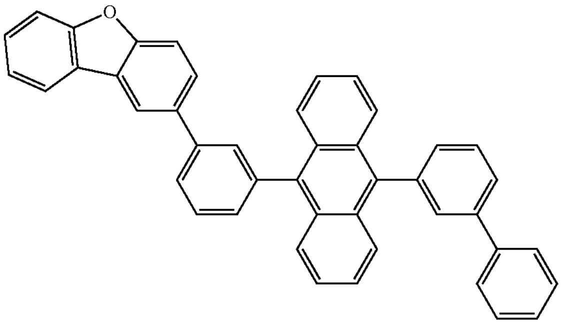

-continued
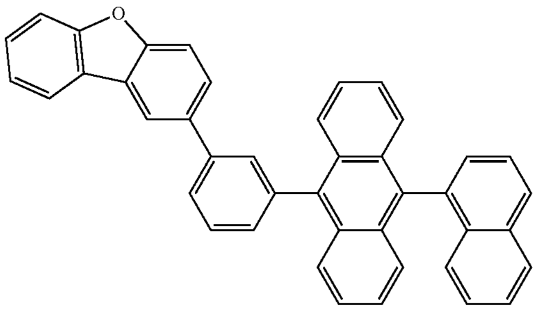
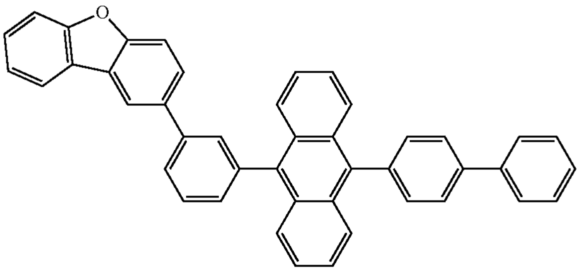
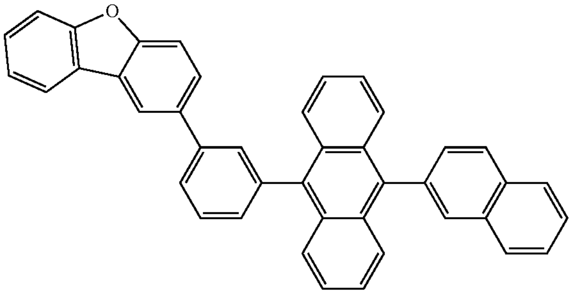
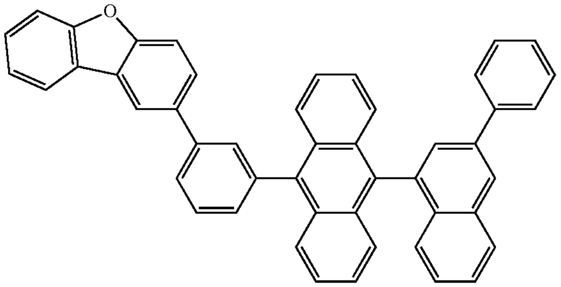
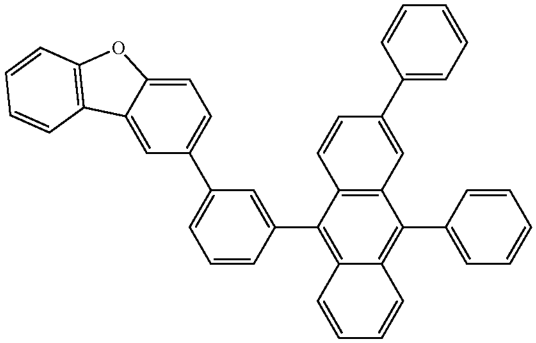
-continued
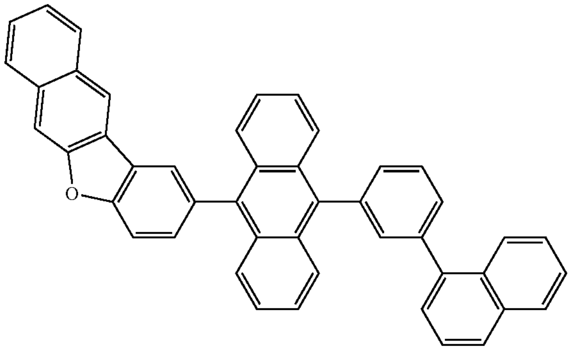
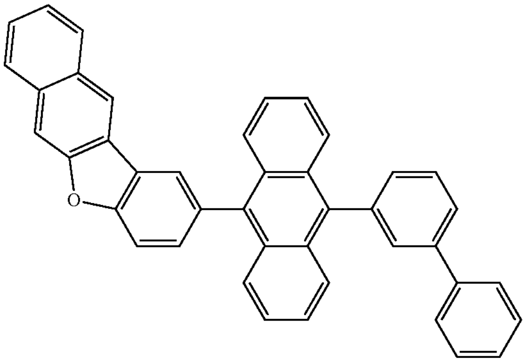
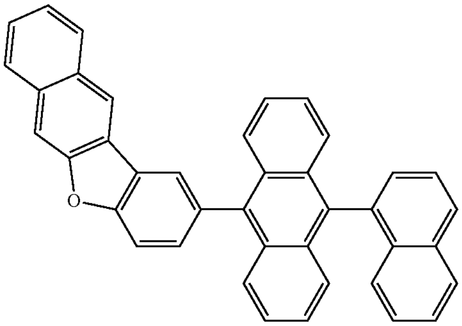
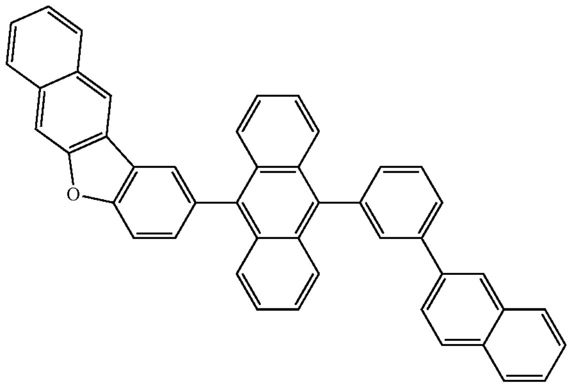

-continued
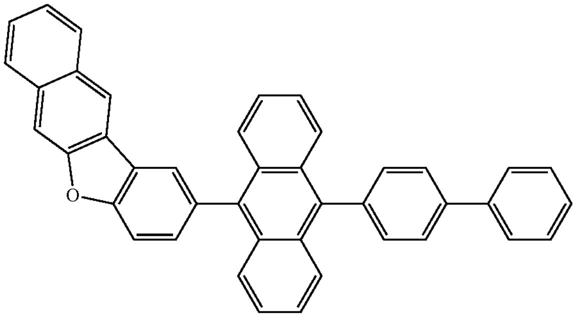
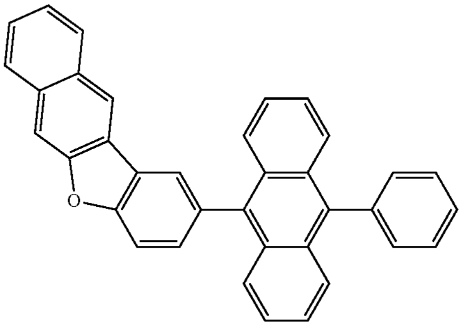
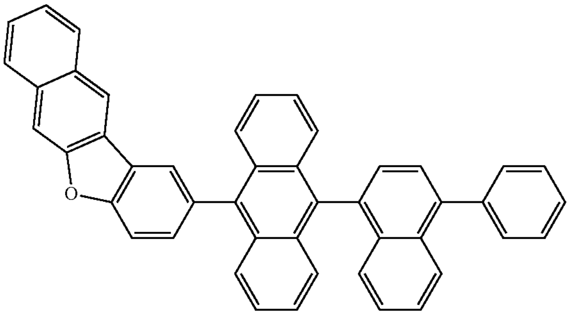
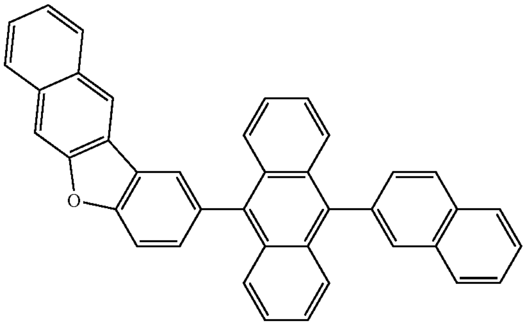
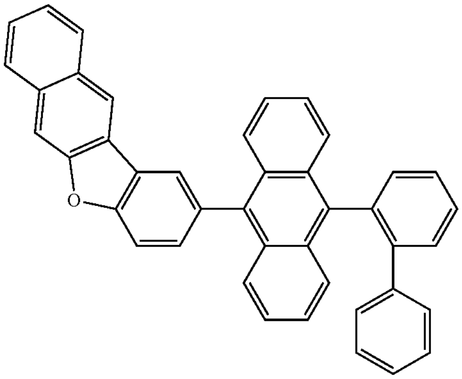
-continued
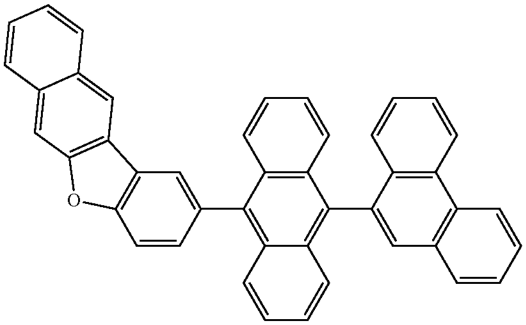
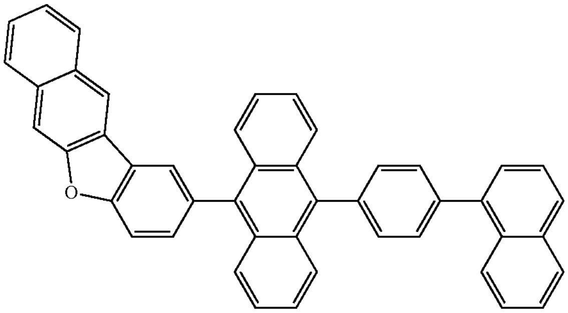
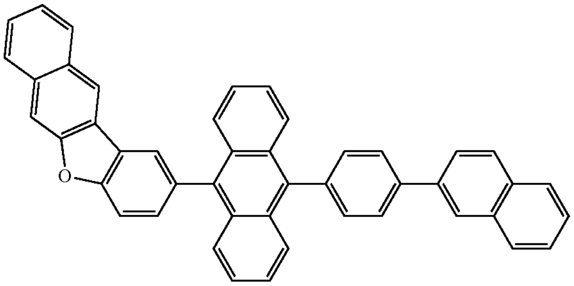
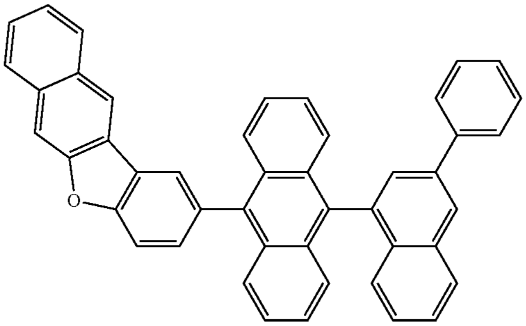
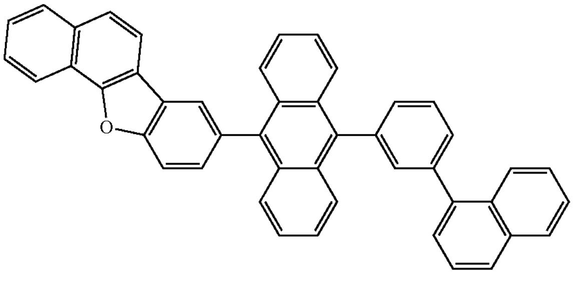

-continued
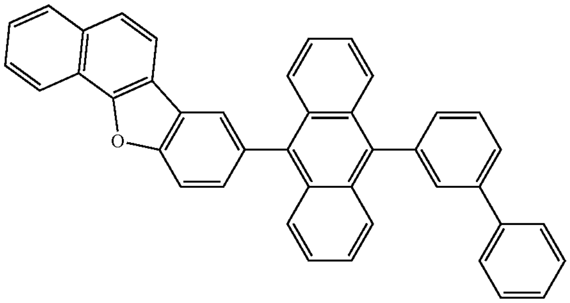
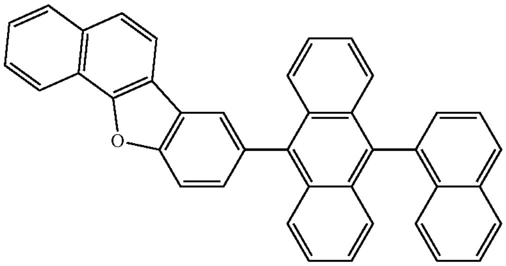
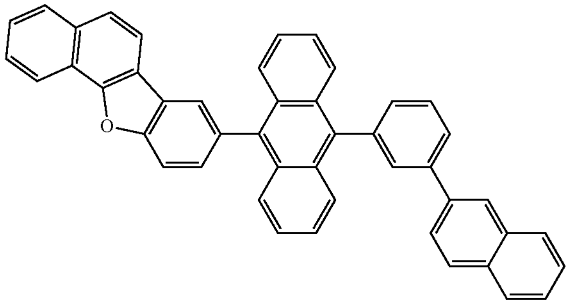
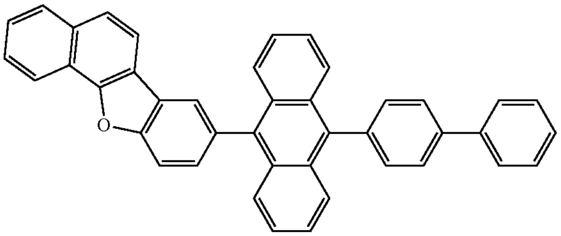
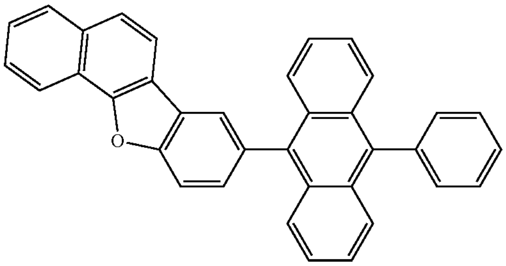
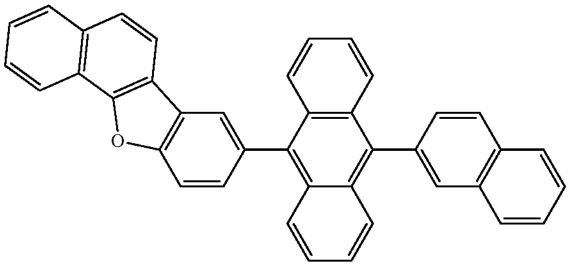
-continued
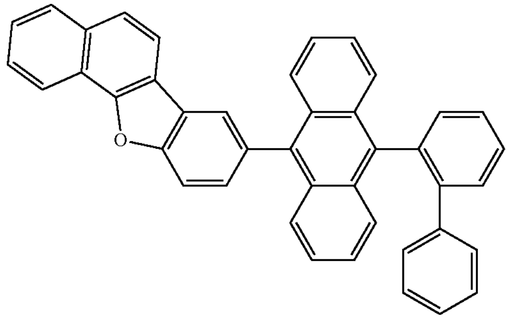
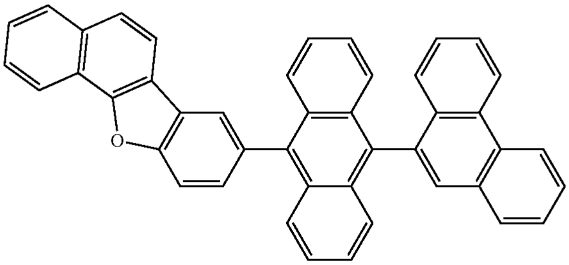
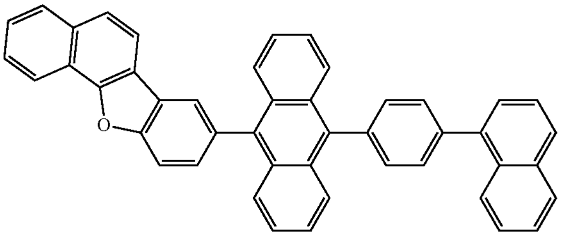
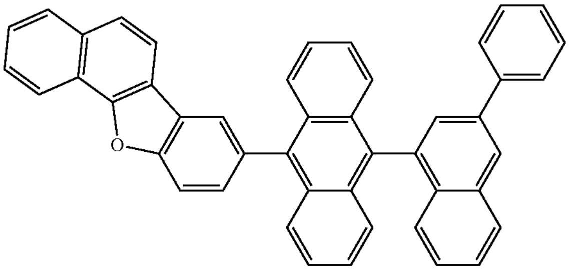
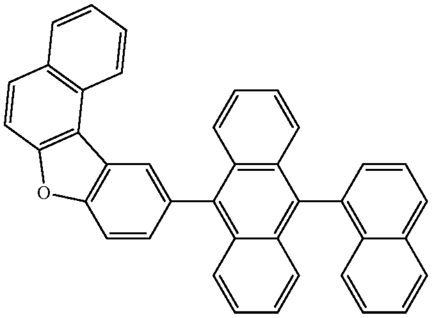

-continued
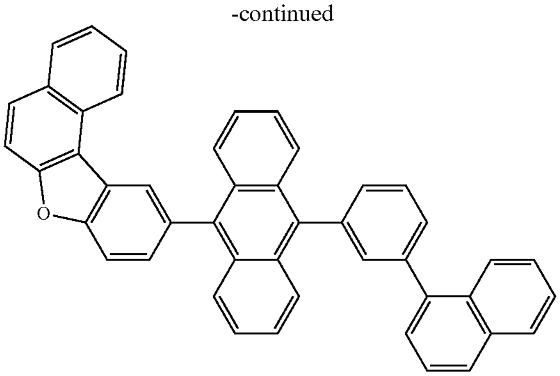
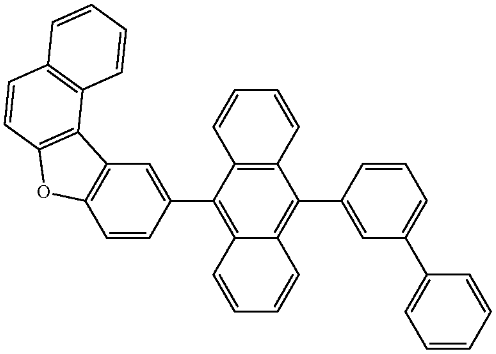
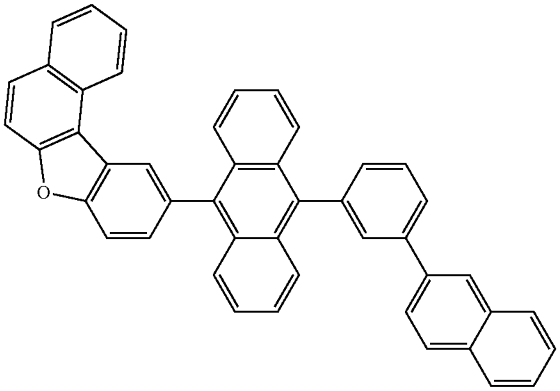
[Formula 107]
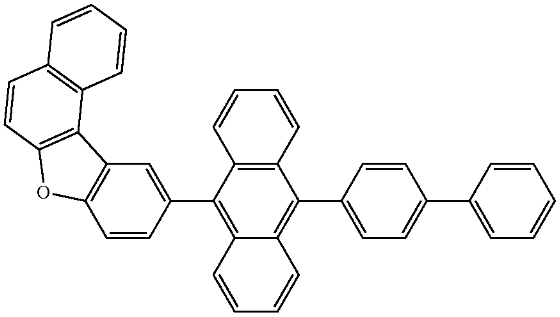
-continued
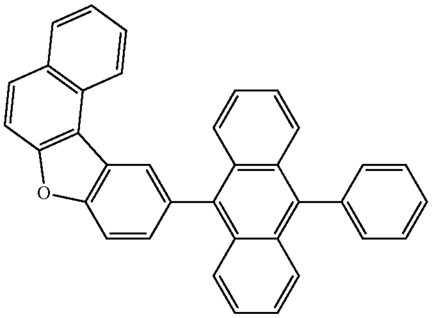
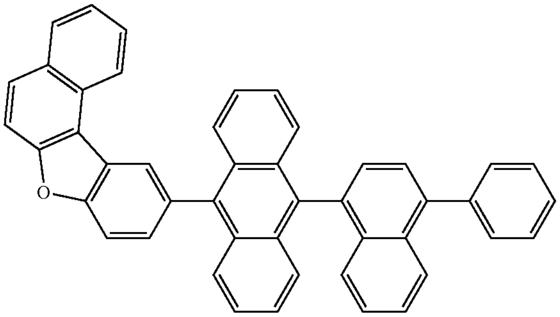
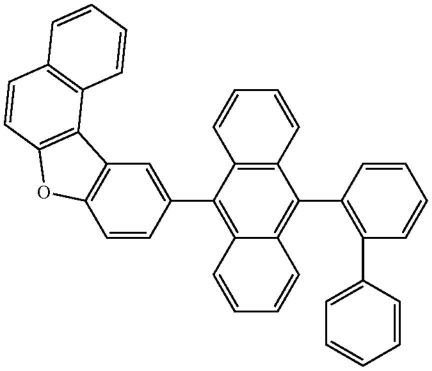
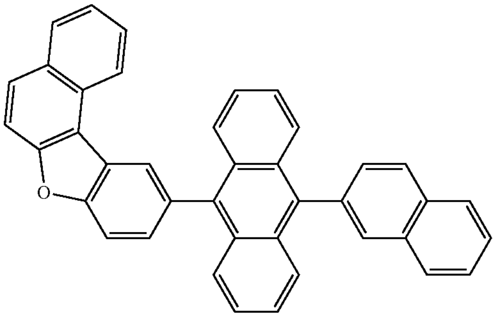
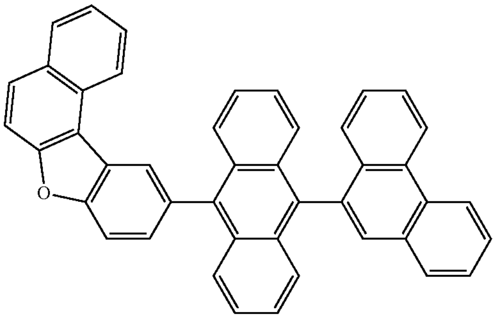

-continued
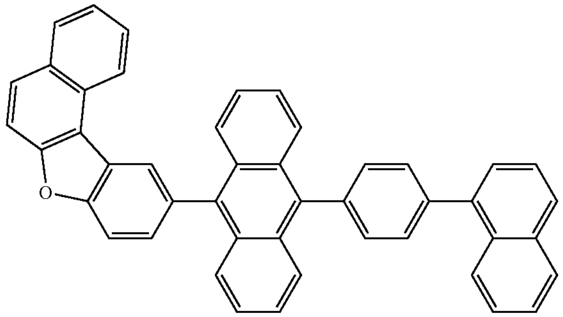
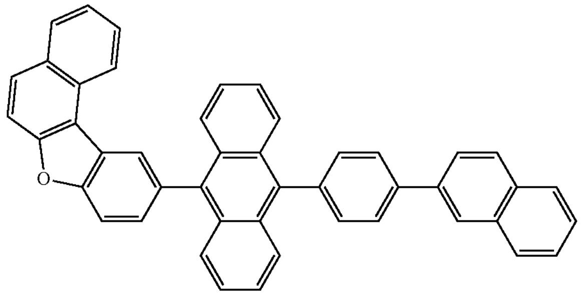
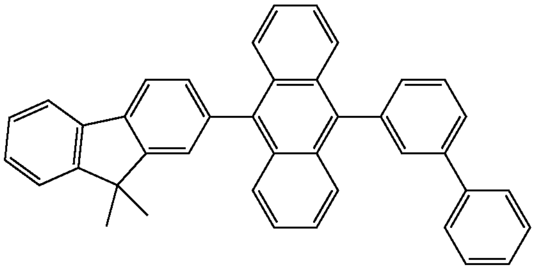
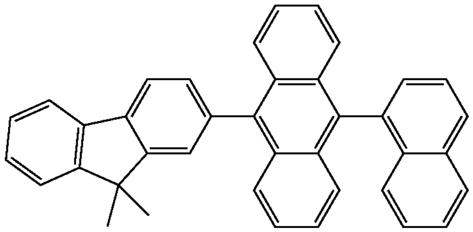
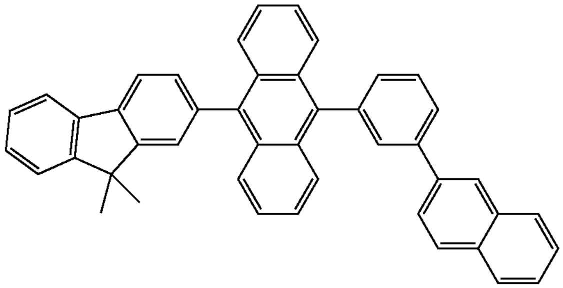
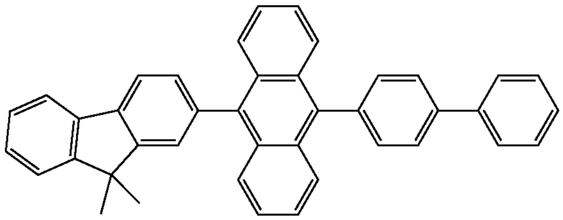
-continued
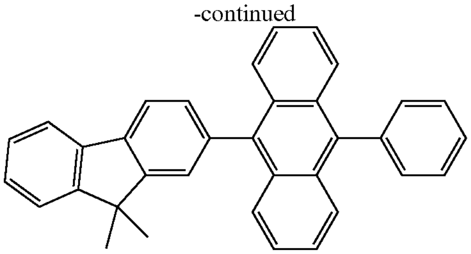
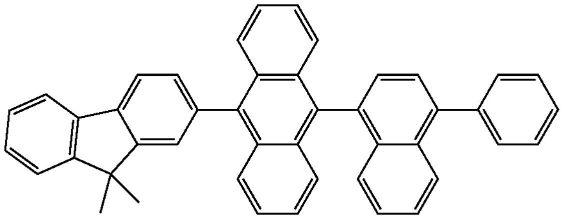
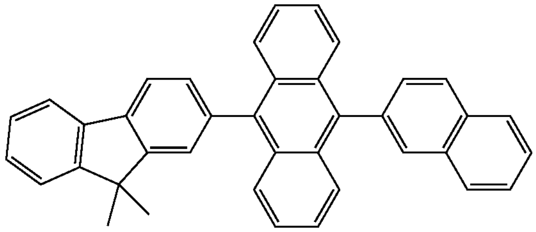
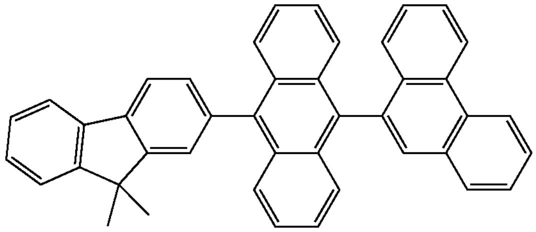
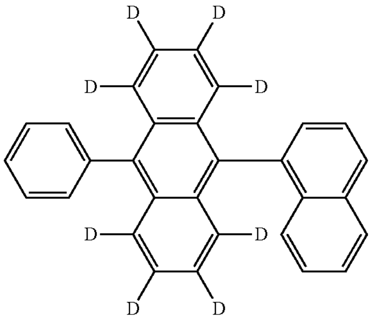
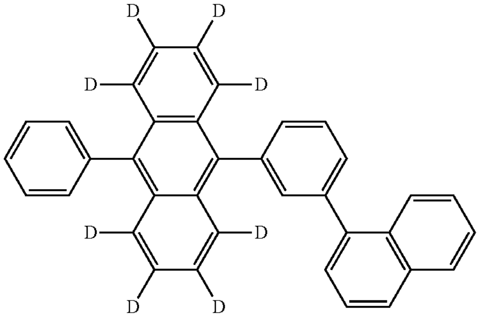

-continued
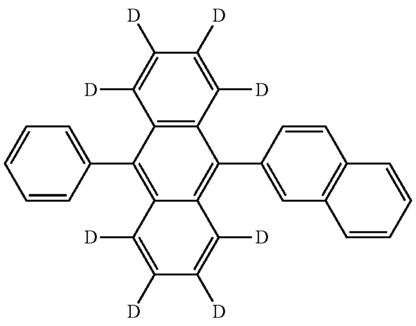
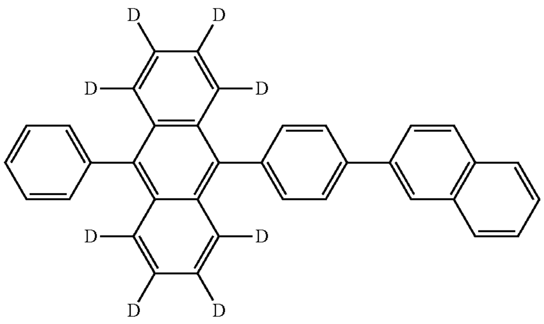
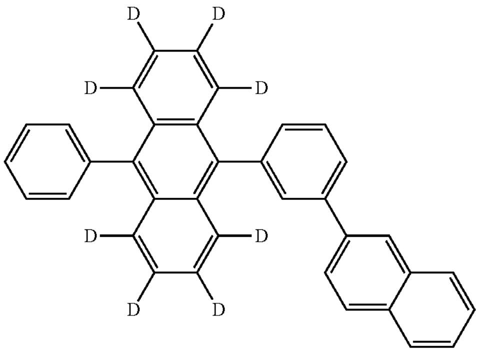
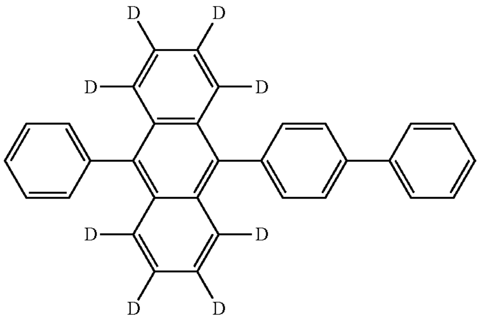
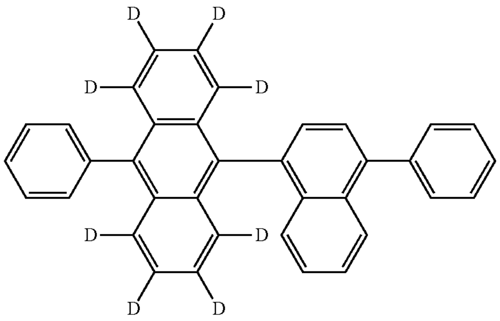
-continued
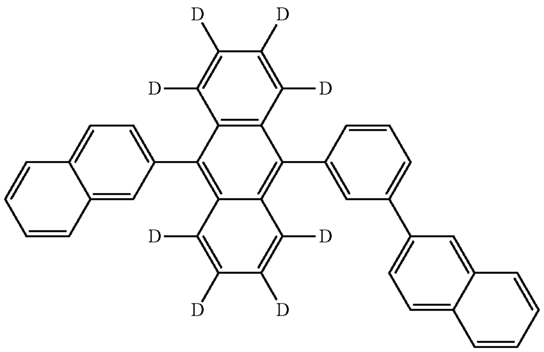
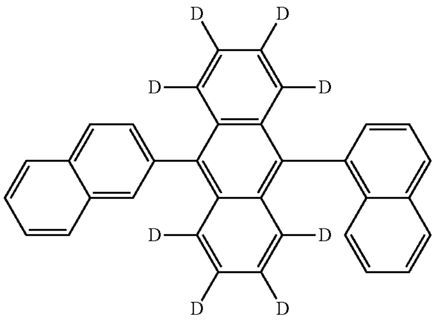
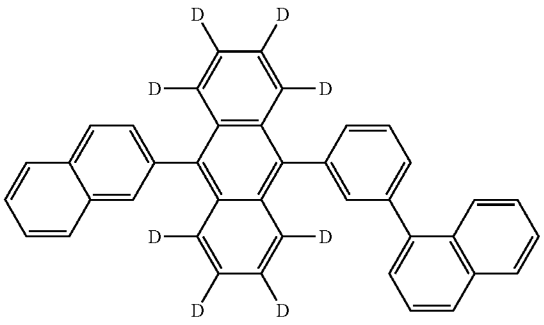
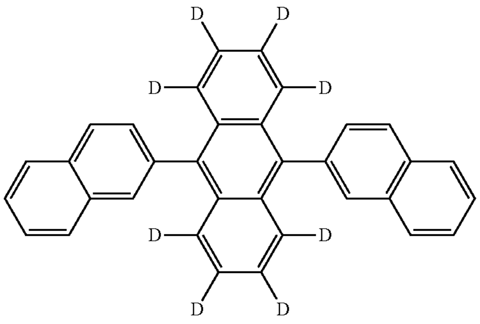
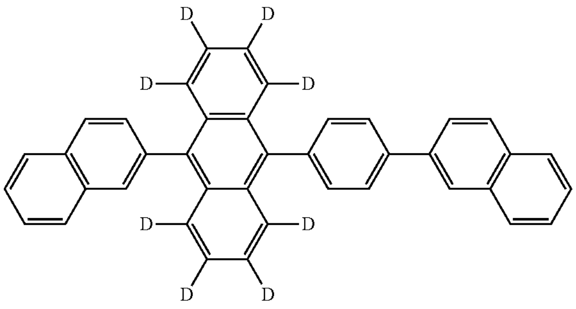

-continued
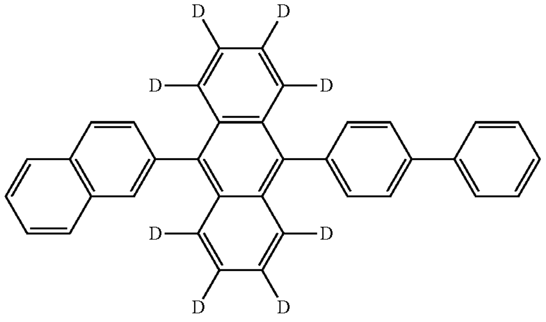
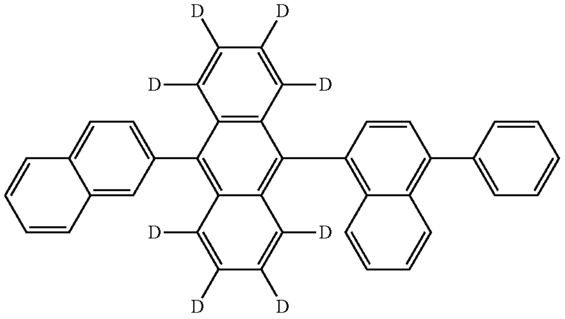
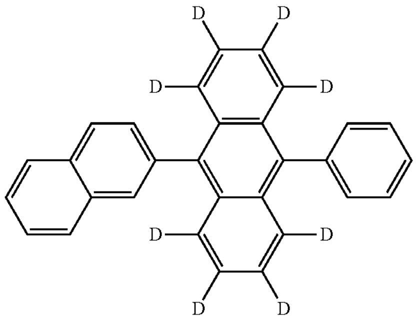
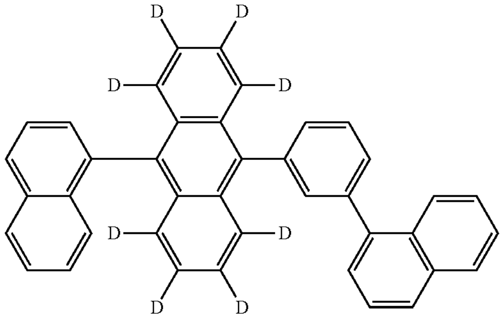
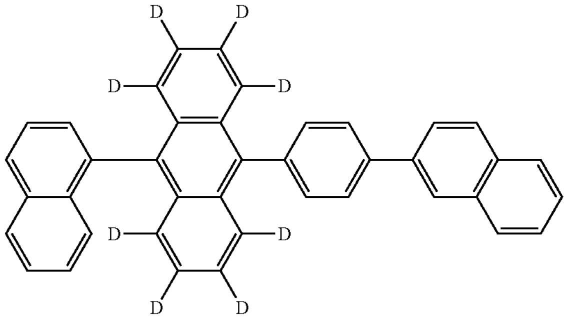
-continued
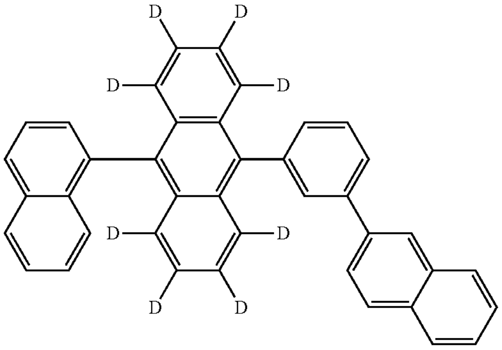
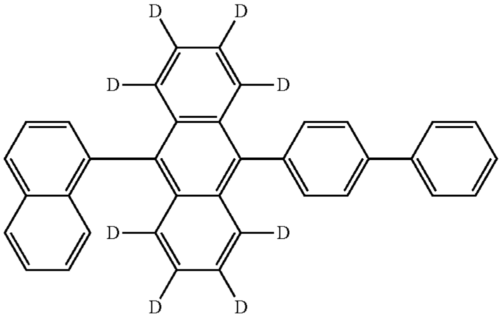
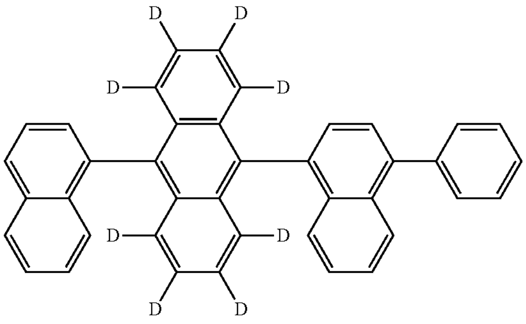
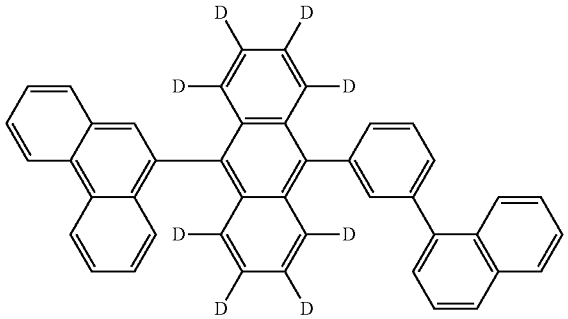
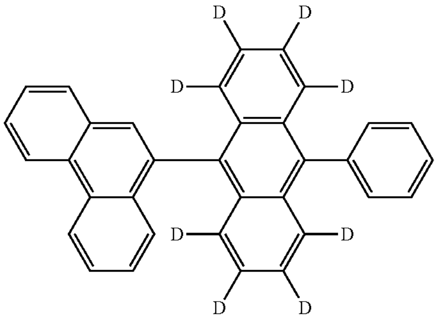

-continued
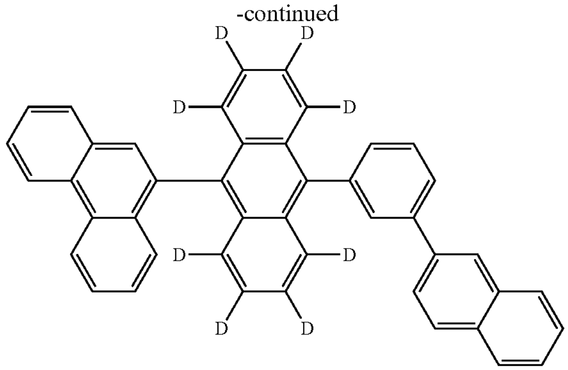
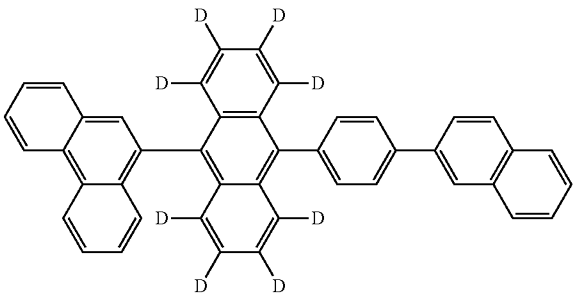
[Formula 108]
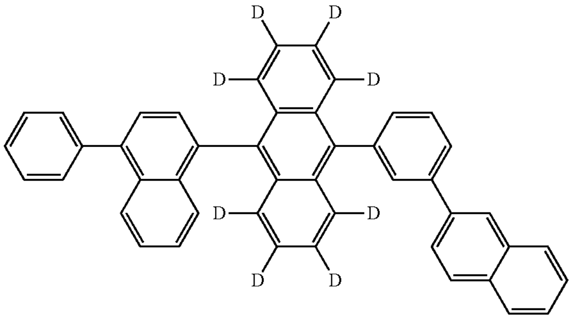
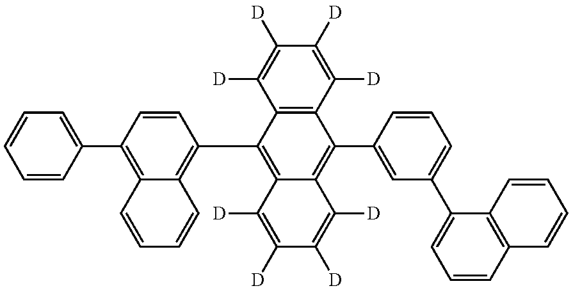
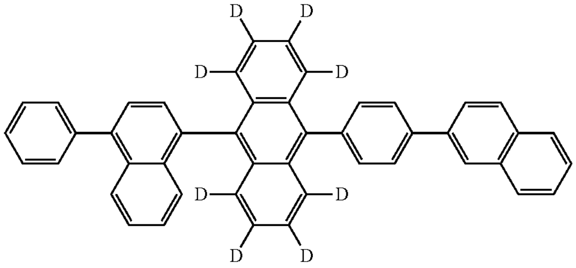
-continued
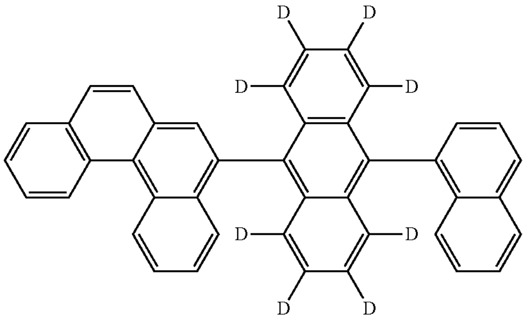
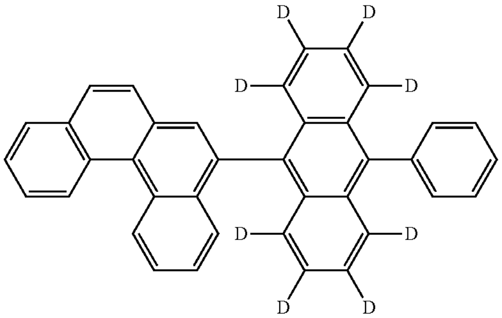
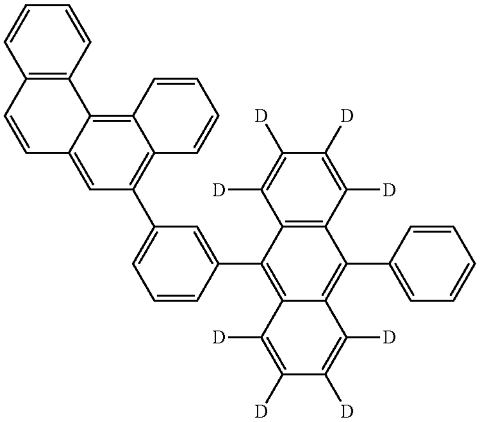
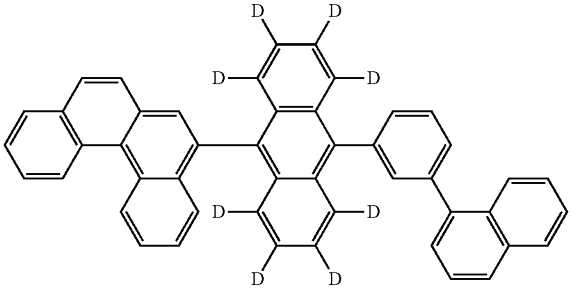

-continued
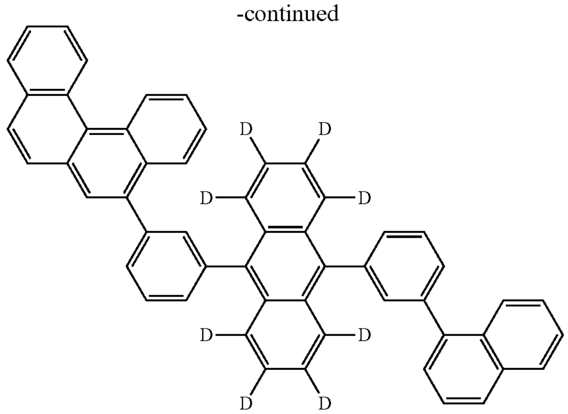
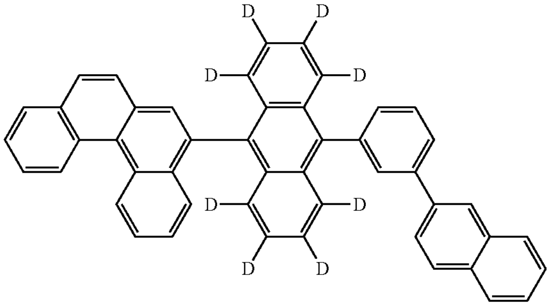
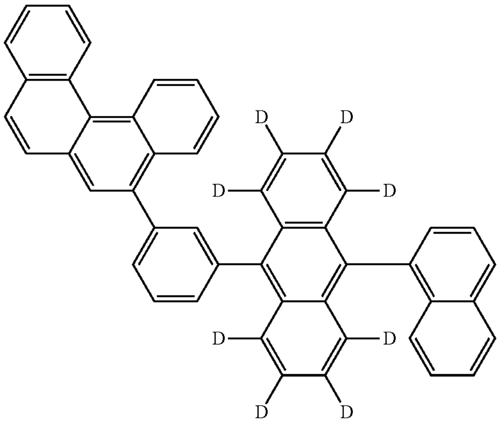
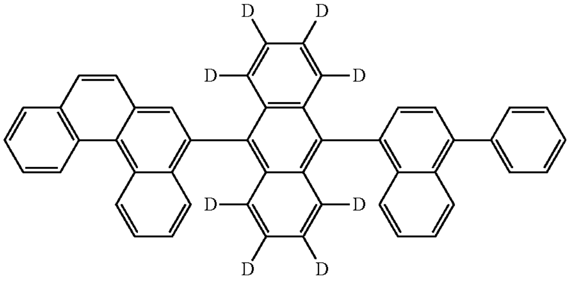
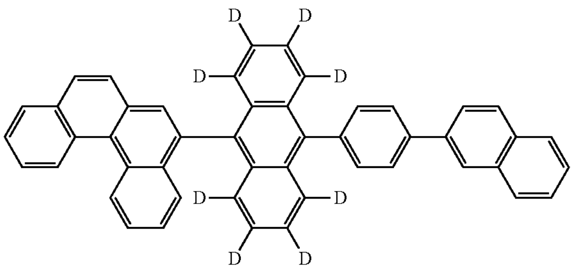
-continued
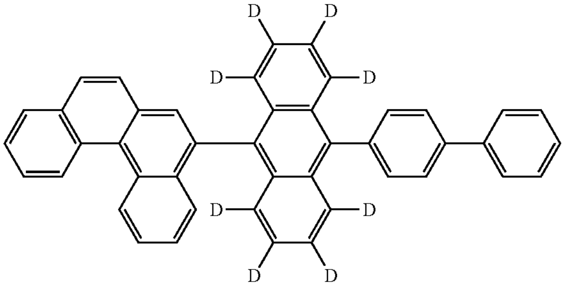
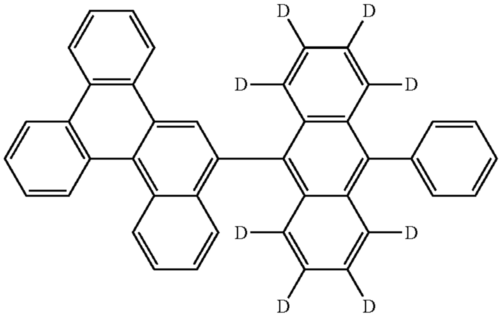
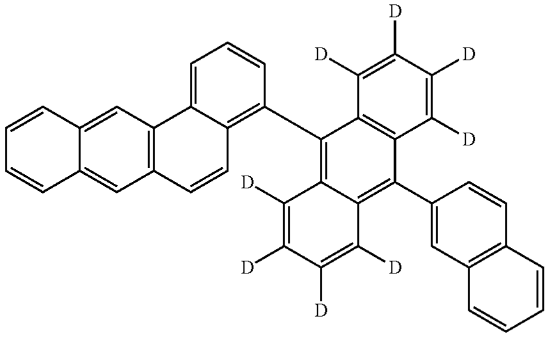
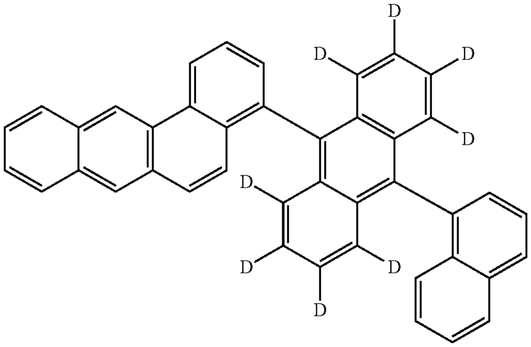
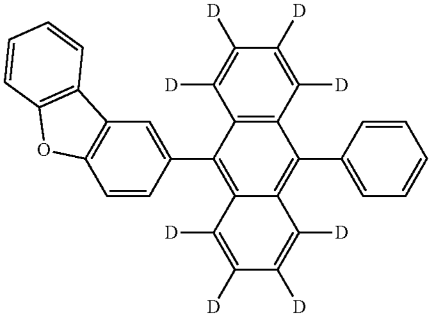

-continued
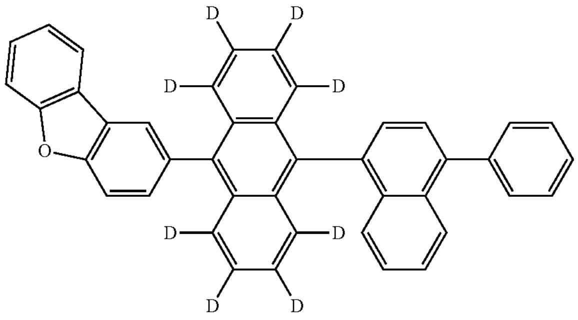
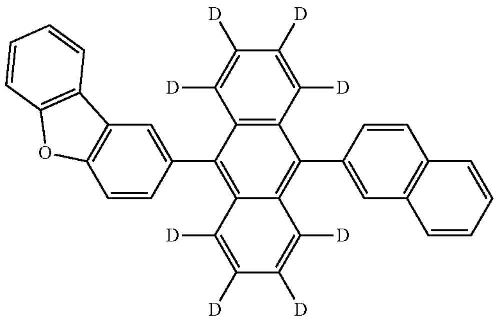
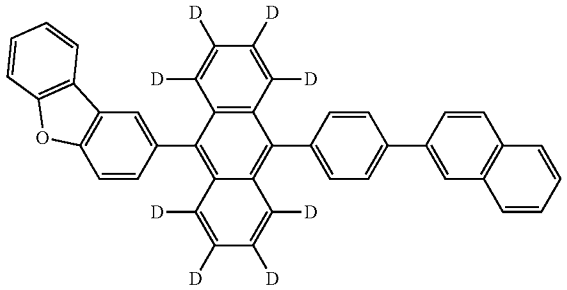
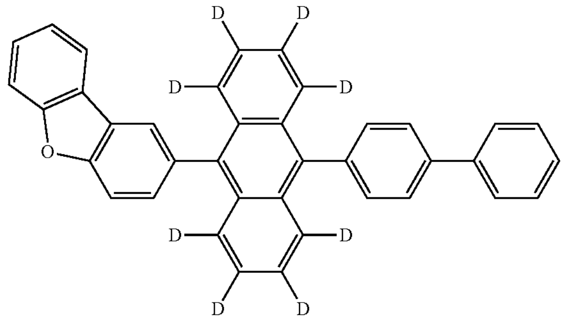
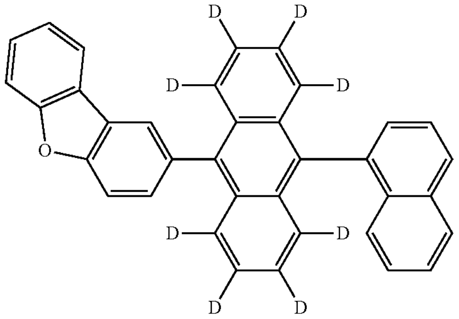
-continued
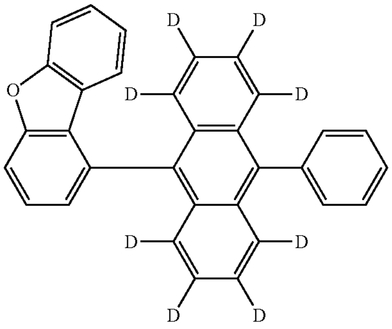
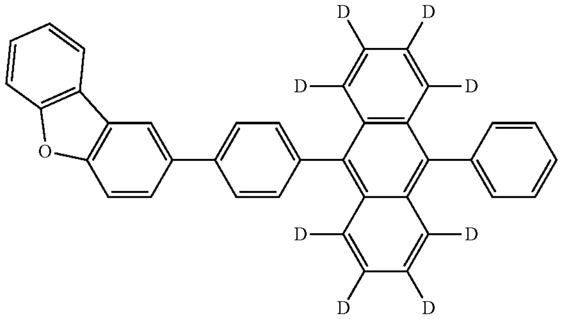
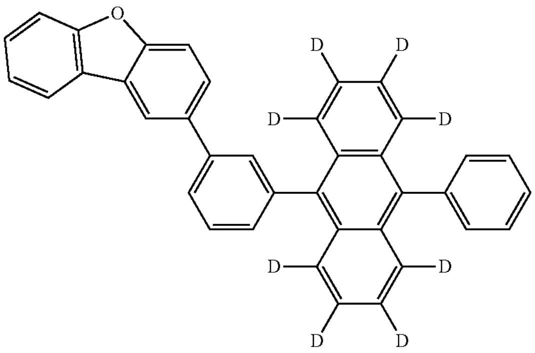
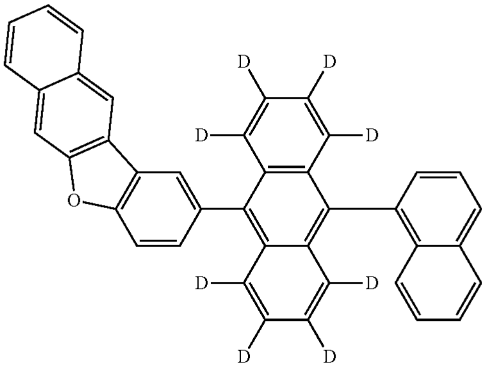
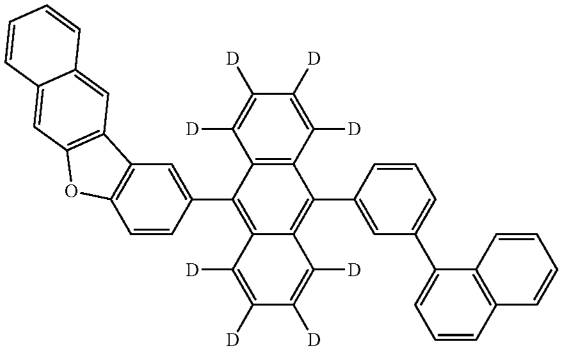

-continued
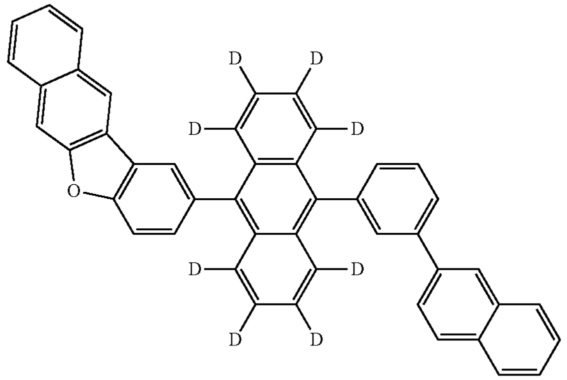
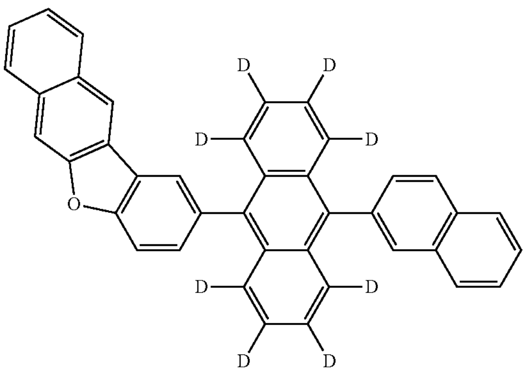
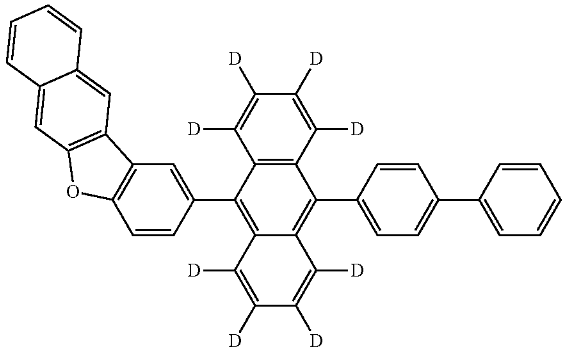
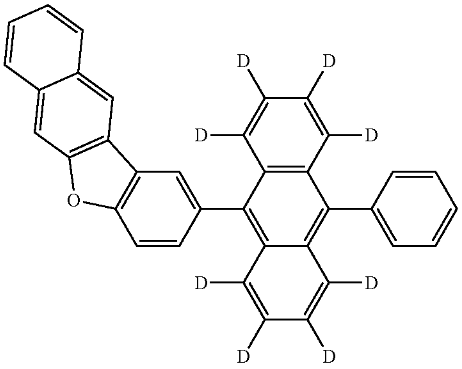
-continued
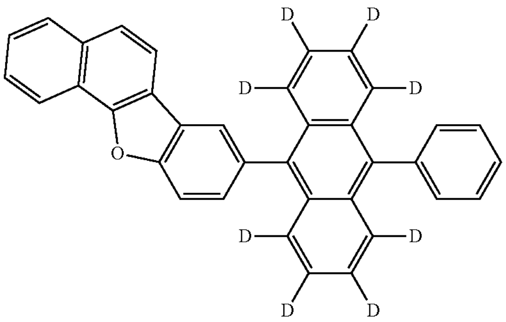
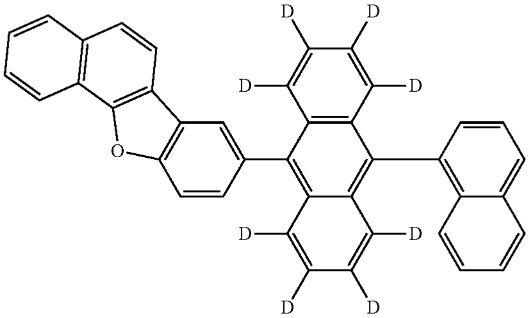
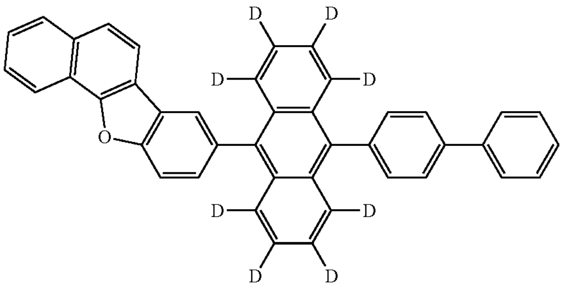
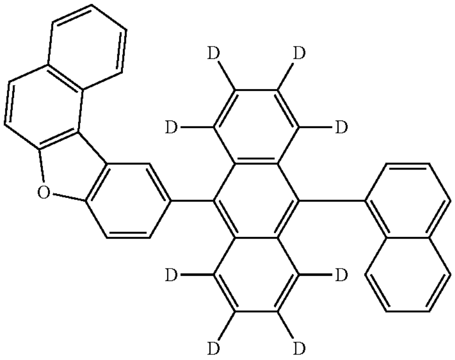
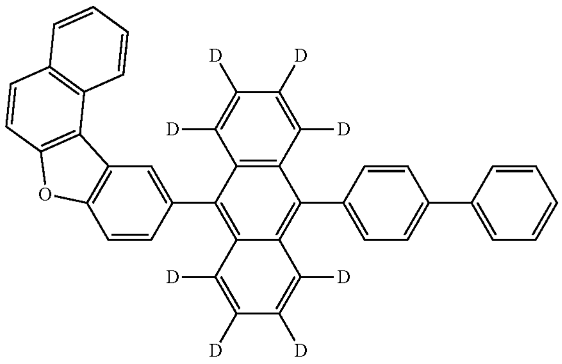

-continued
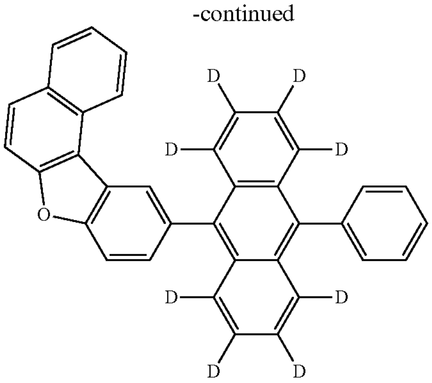
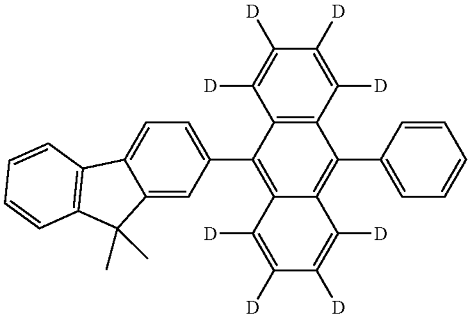
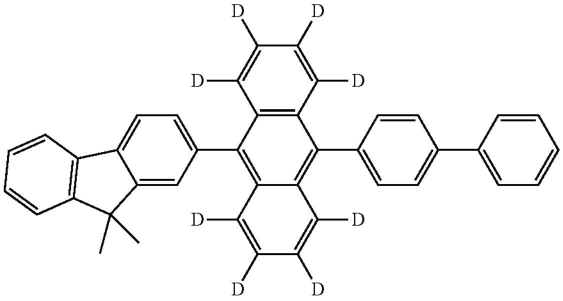
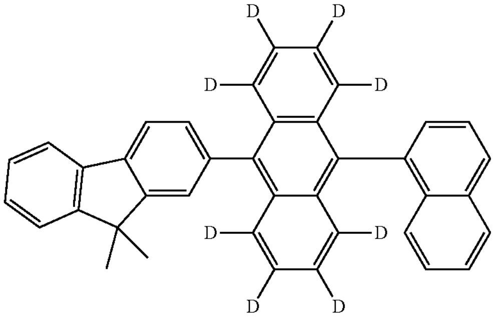
[Formula 109]
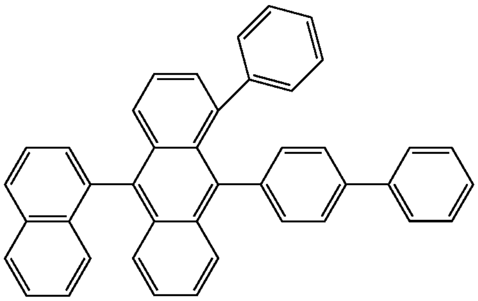
-continued
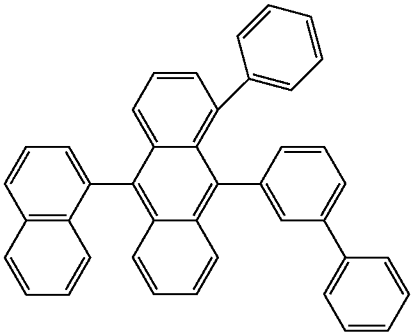
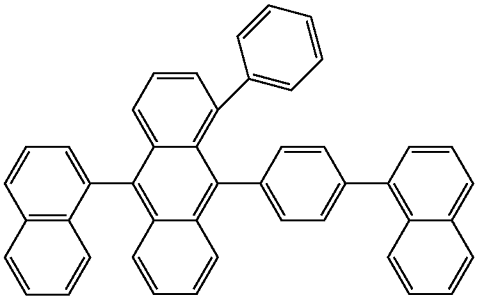
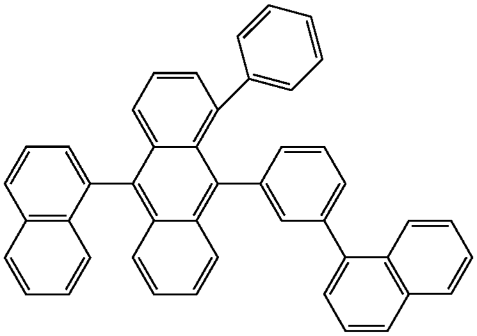
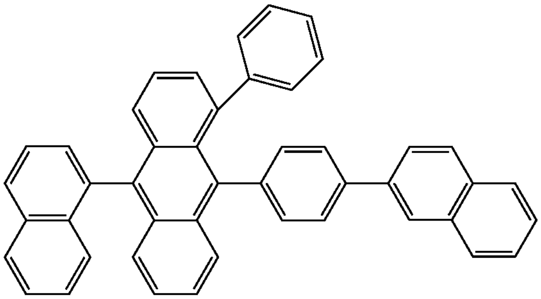
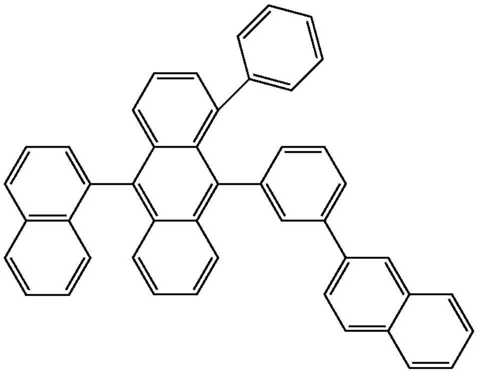

-continued
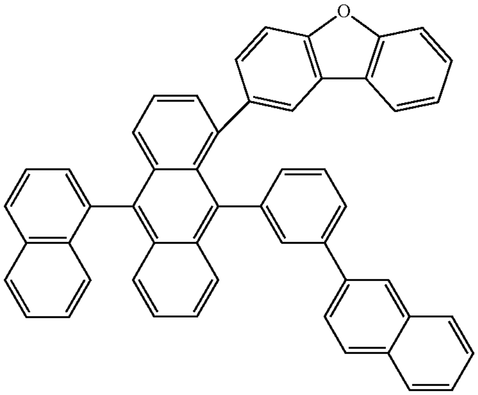
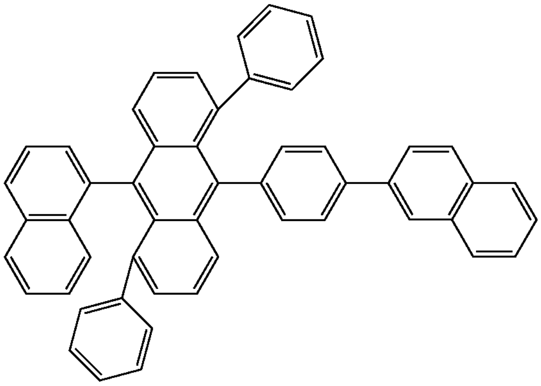
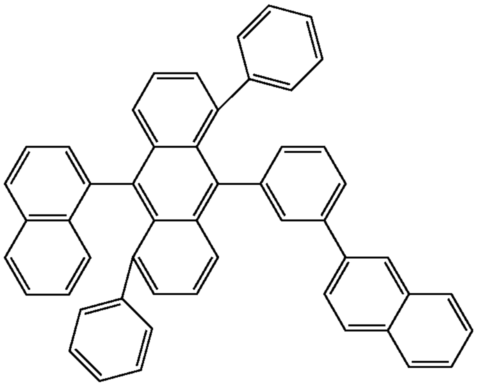
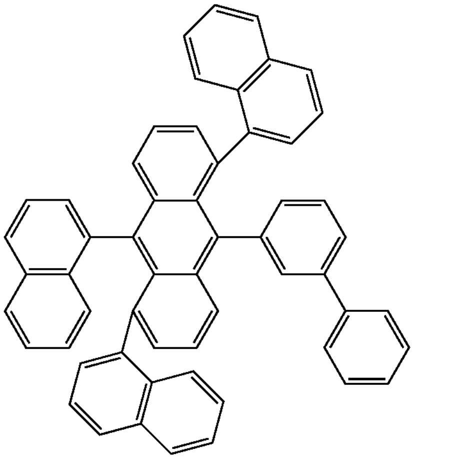
-continued
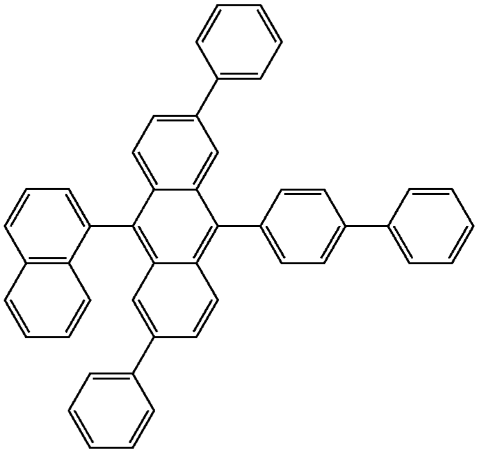
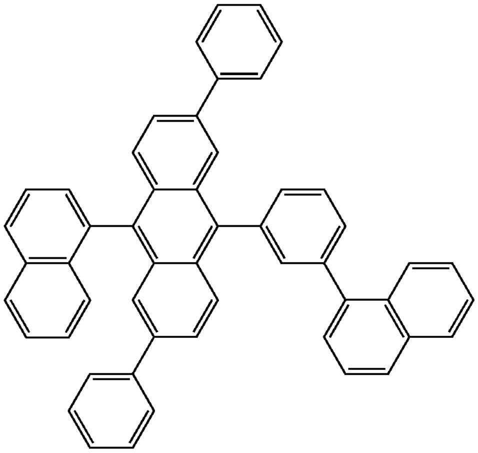
[Formula 110]
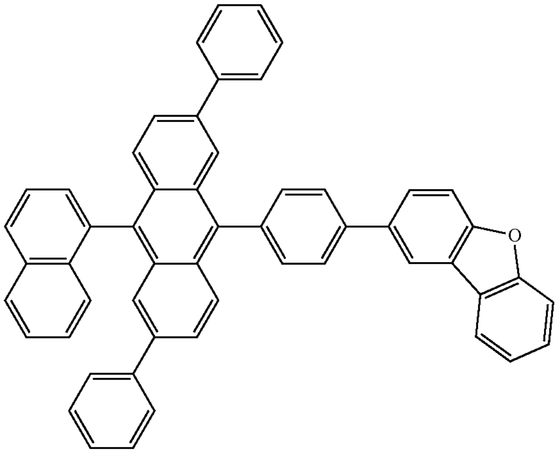

-continued
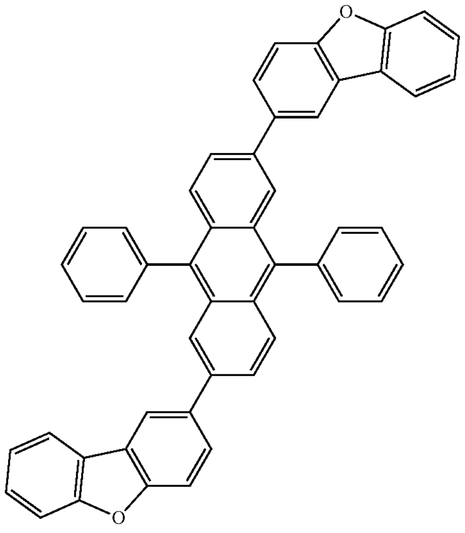
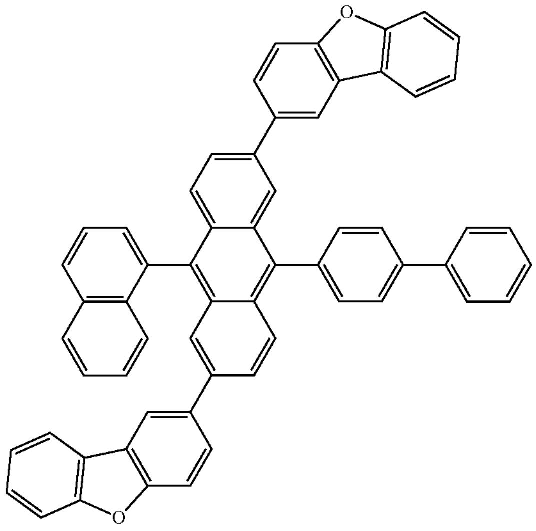
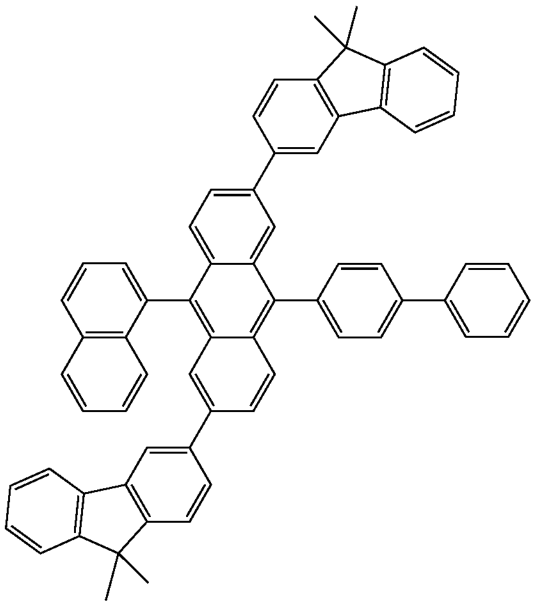
-continued
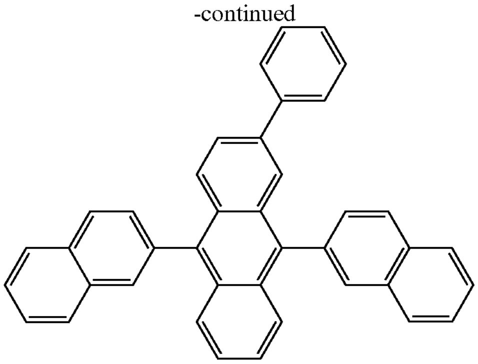
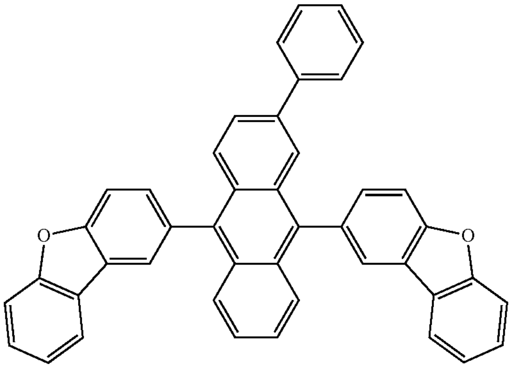
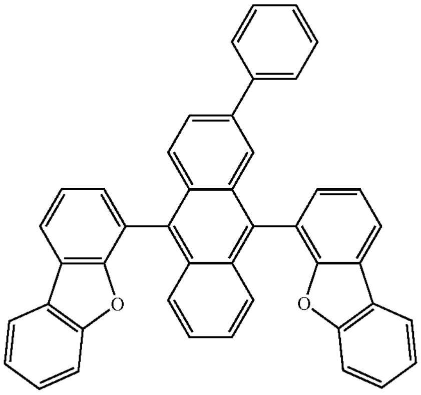
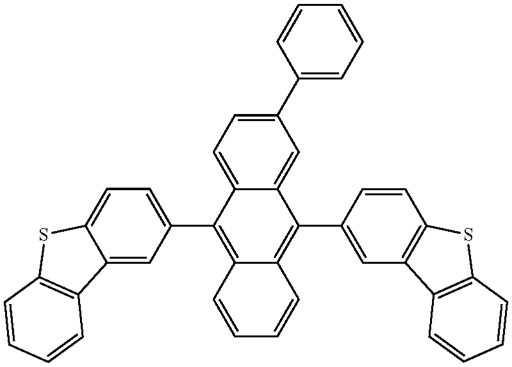

-continued
[Formula 111]
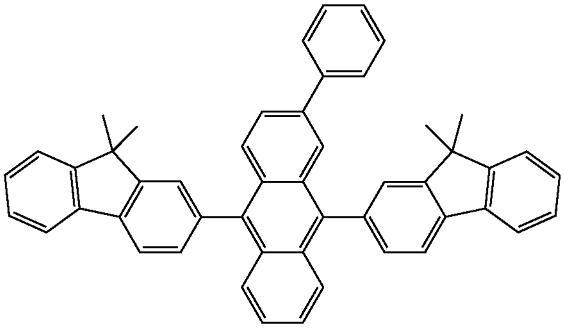
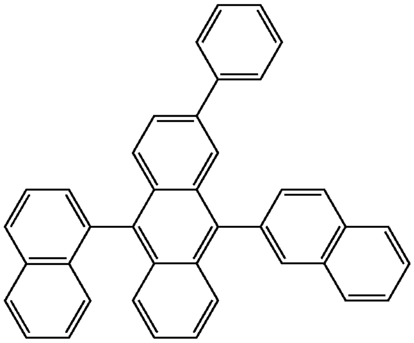
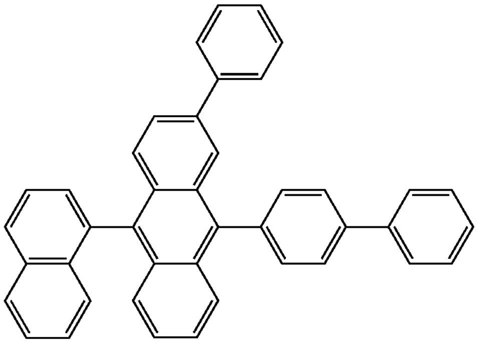
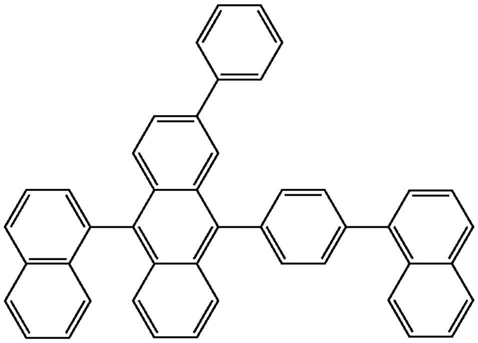
-continued
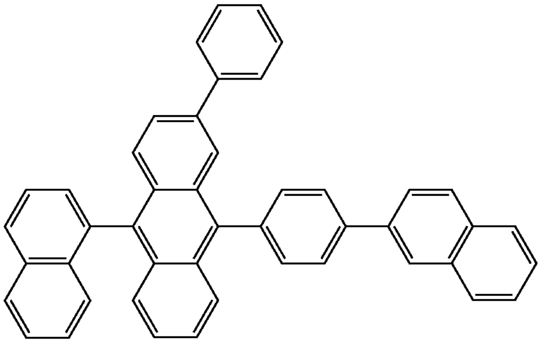
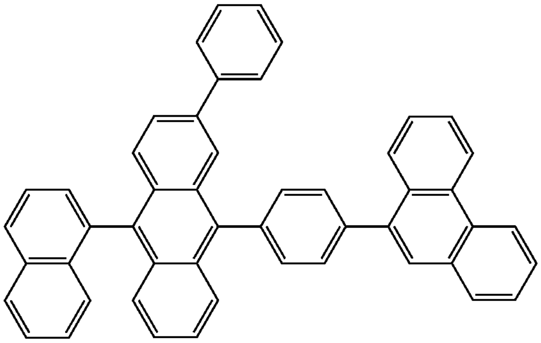
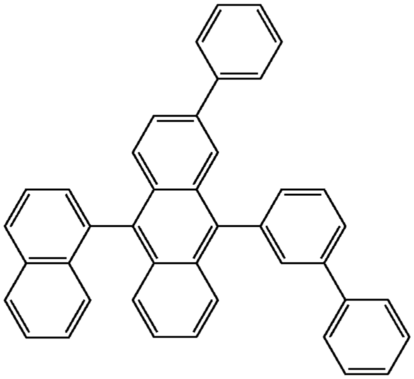
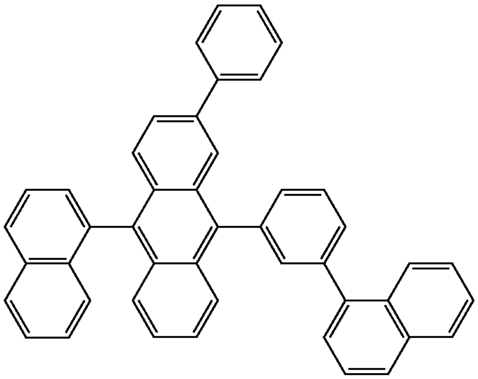

-continued
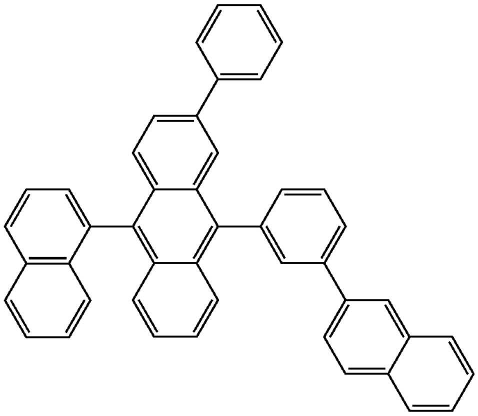
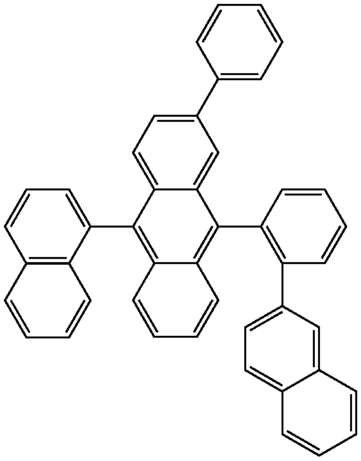
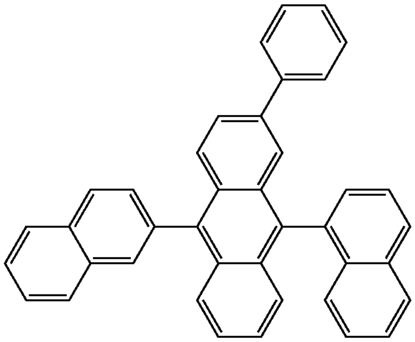
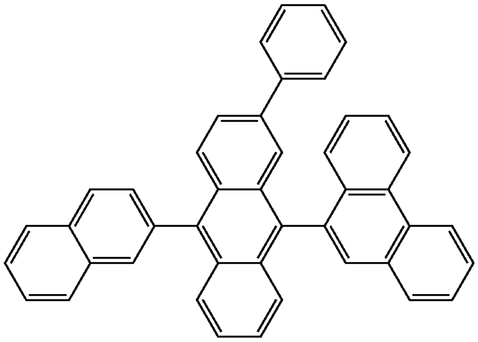
-continued
[Formula 112]
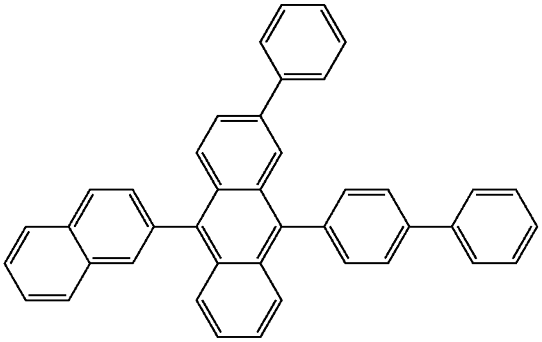
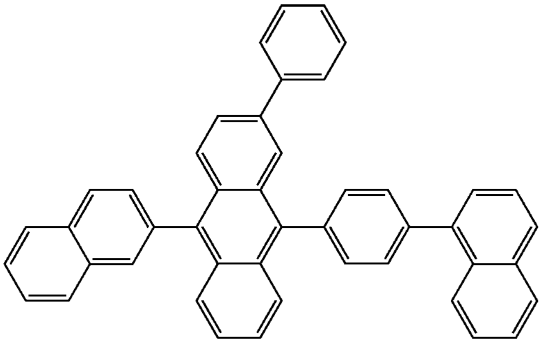
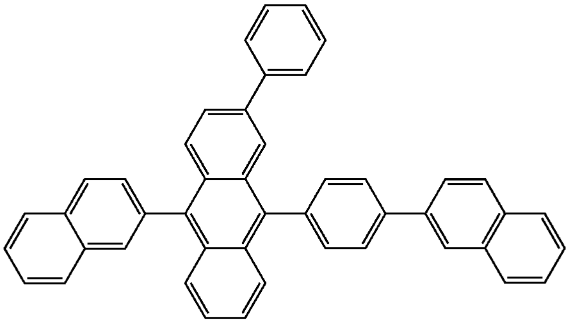
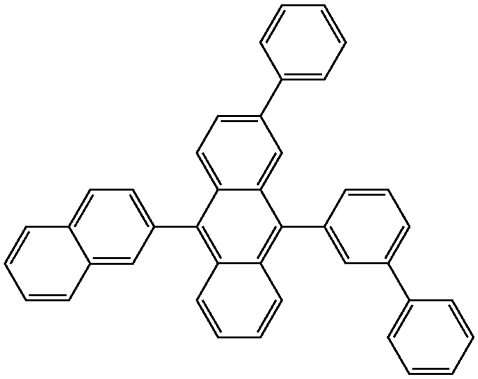

-continued
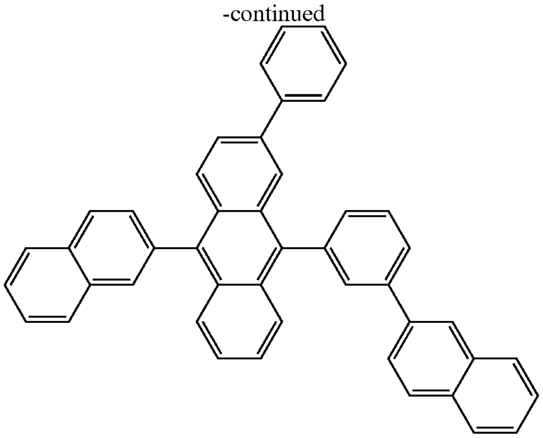
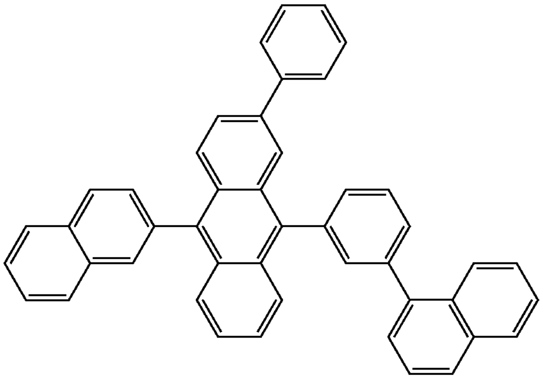
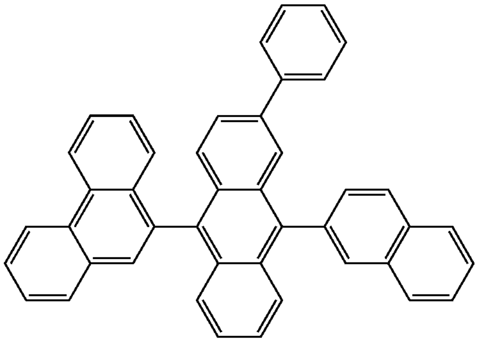
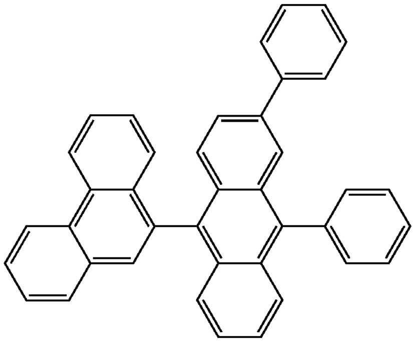
-continued
[Formula 113]
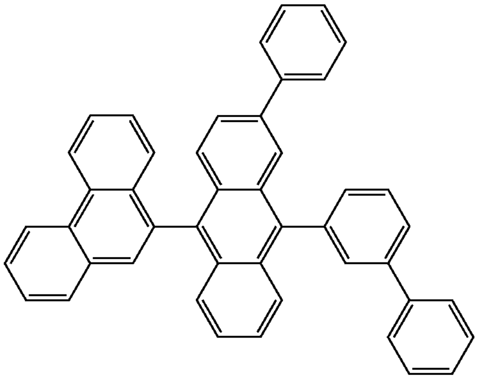
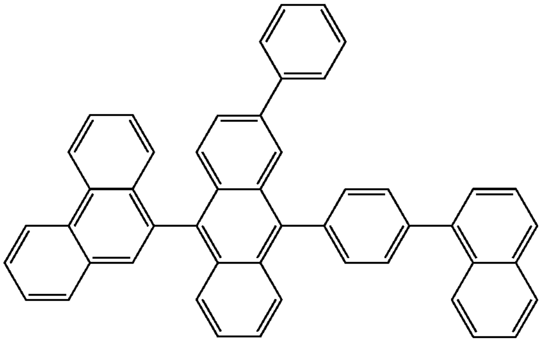
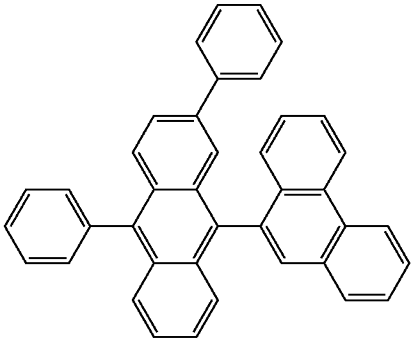
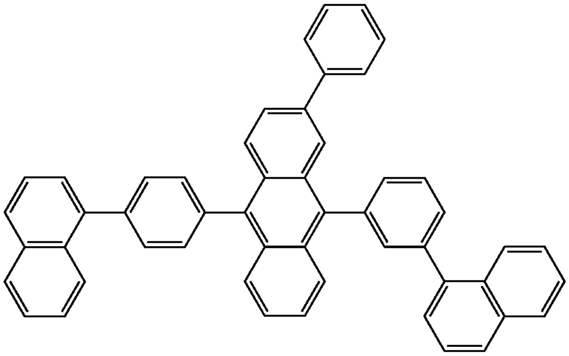

-continued
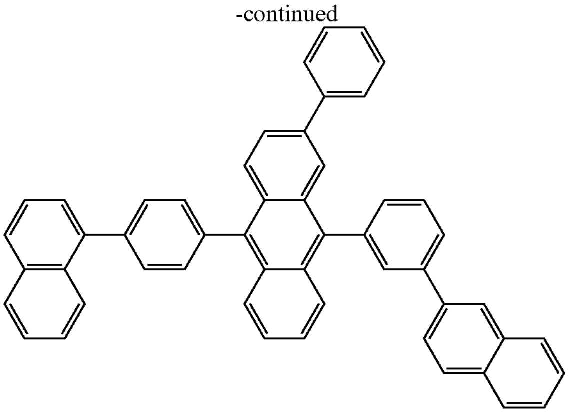
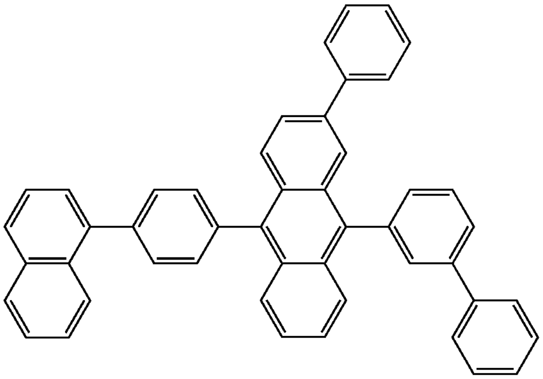
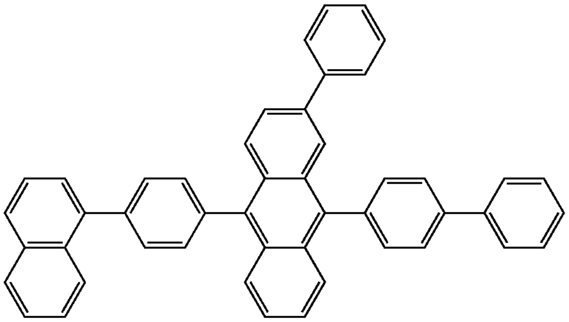
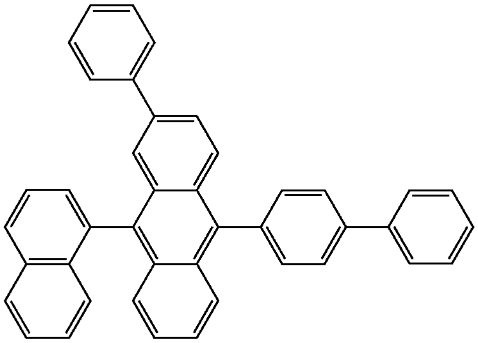
-continued
[Formula 114]
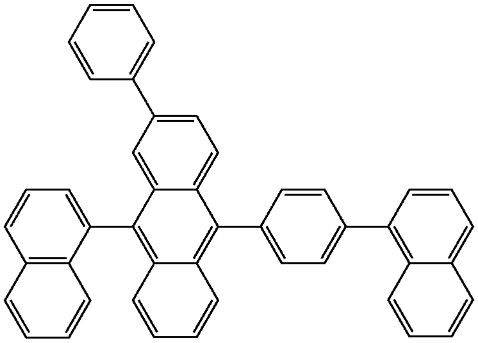
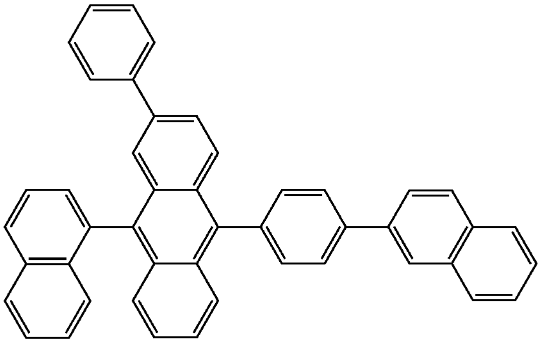
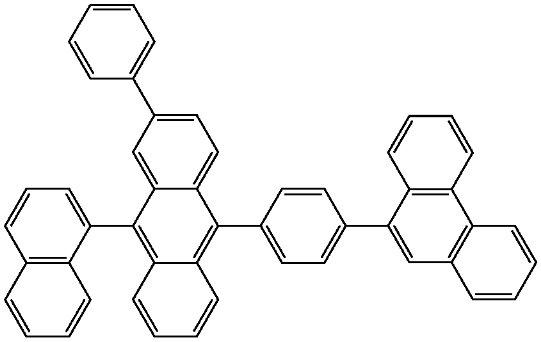
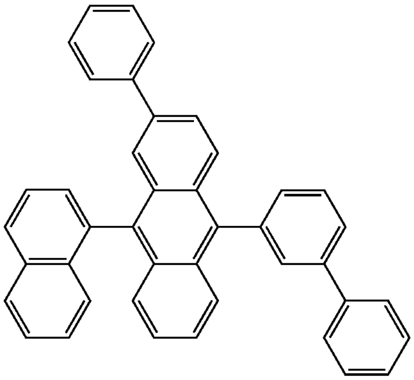

-continued
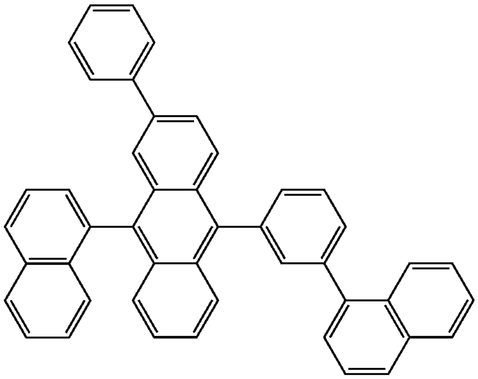
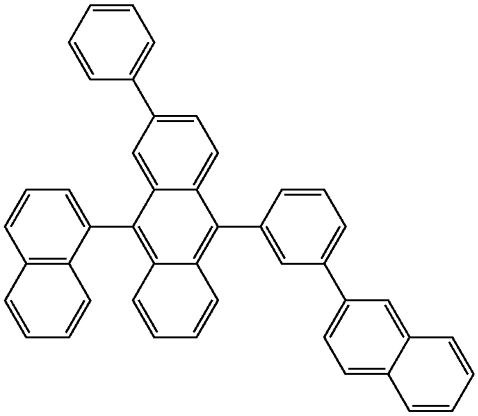
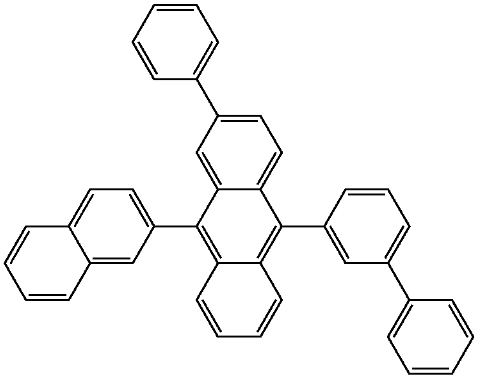
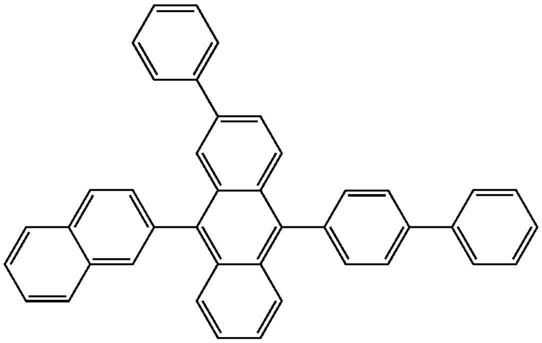
-continued
[Formula 115]
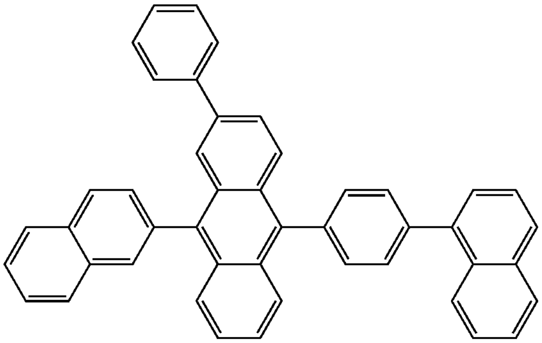
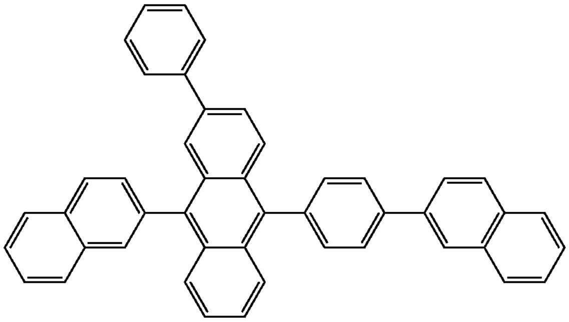
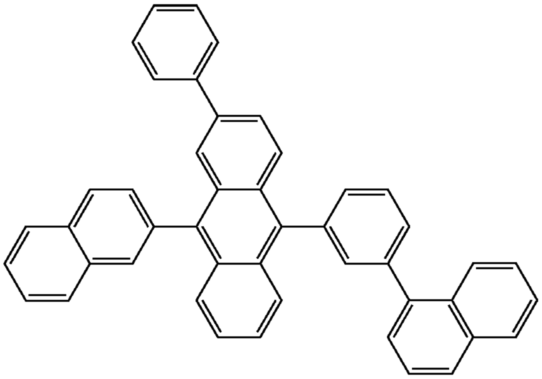
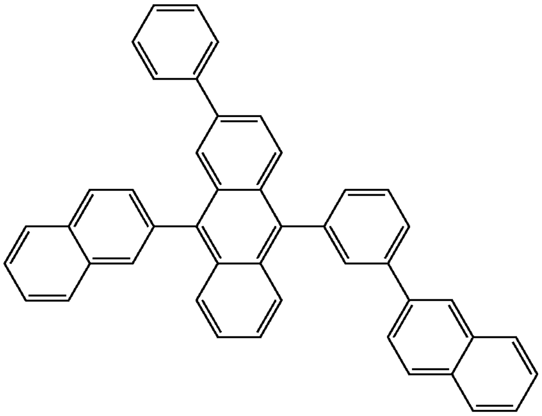

-continued
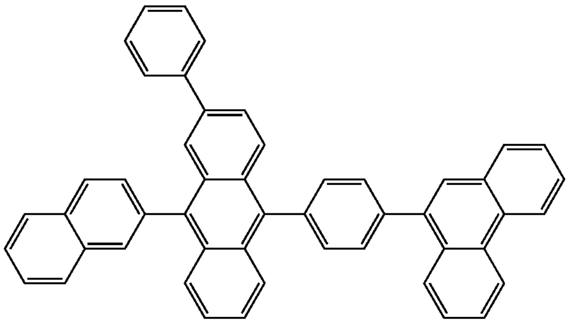
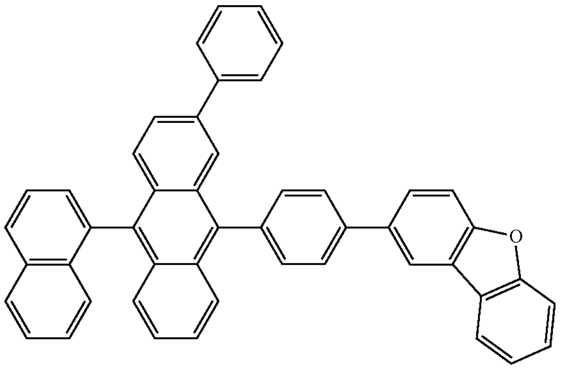
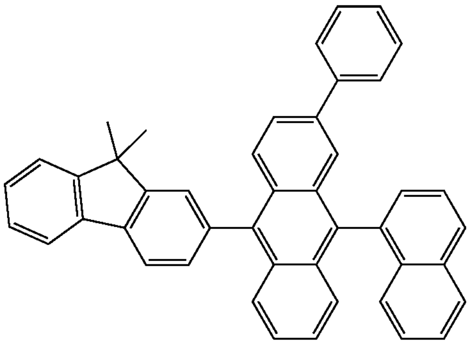
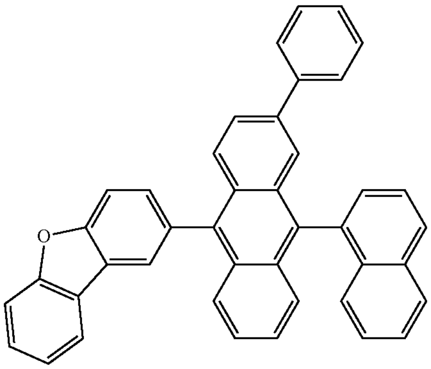
-continued
[Formula 116]
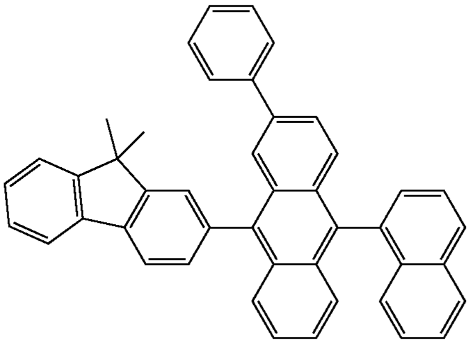
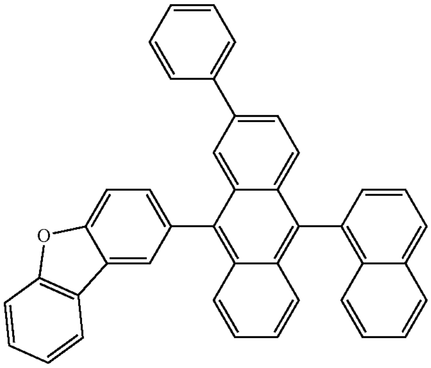
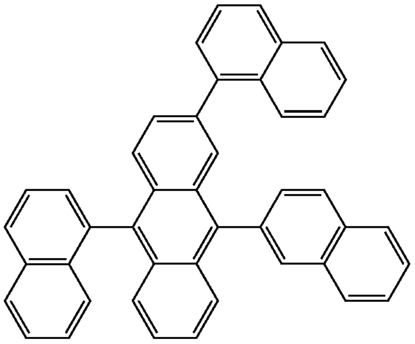
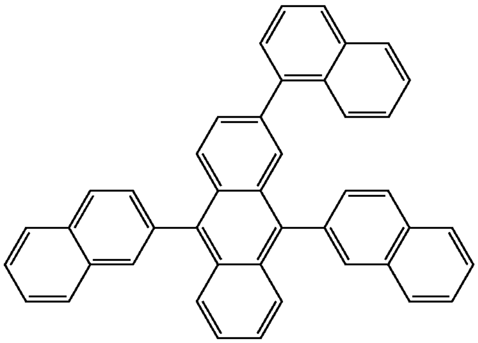

-continued
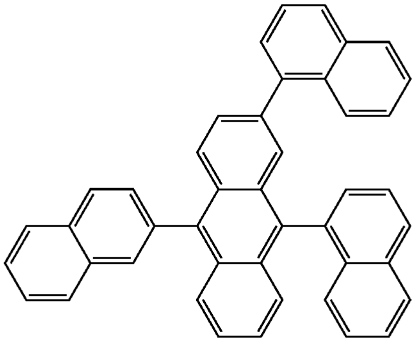
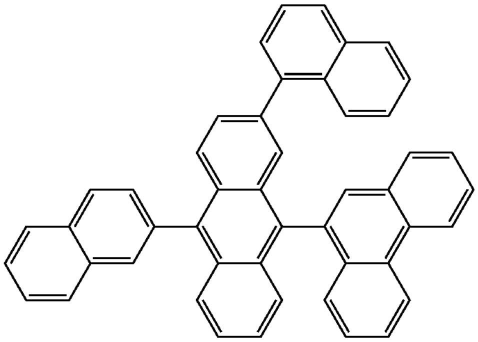
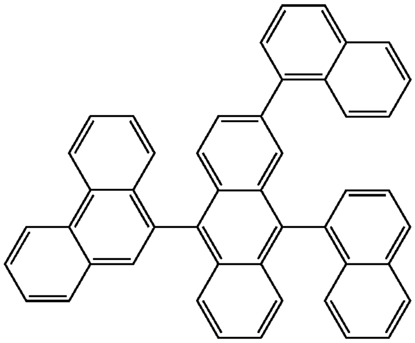
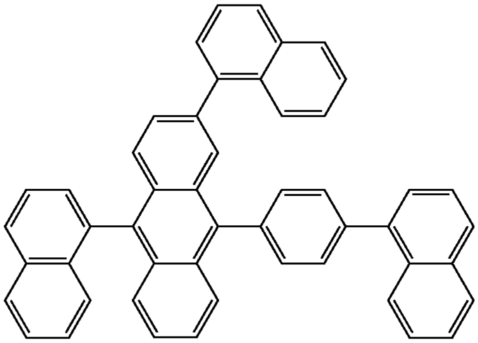
-continued
[Formula 117]
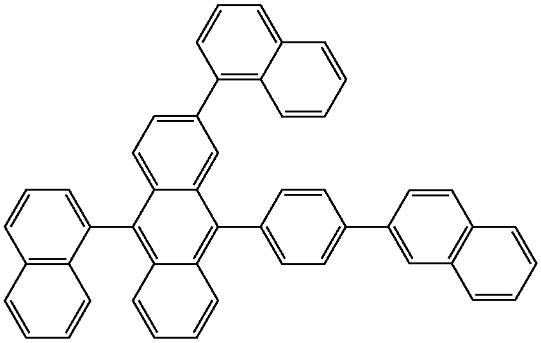
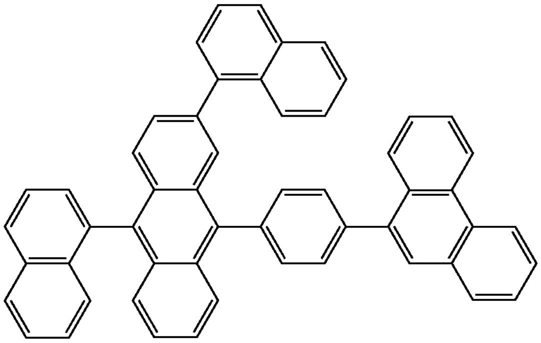
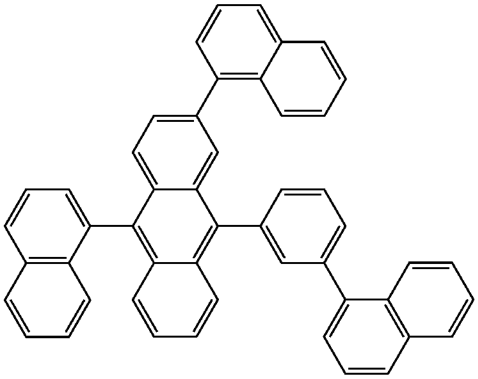
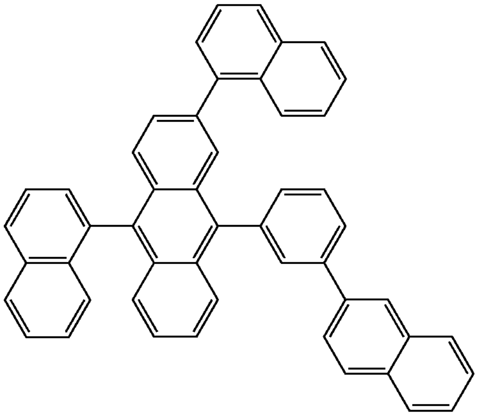

-continued
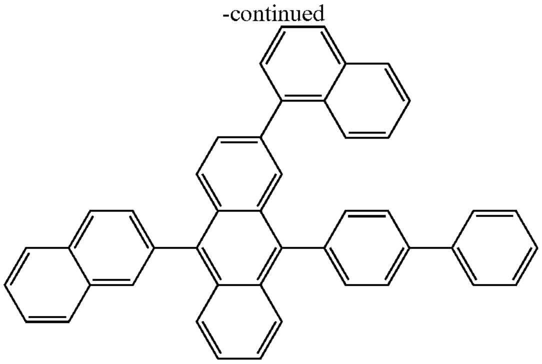
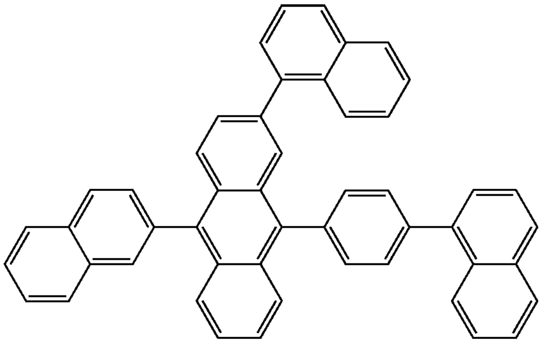
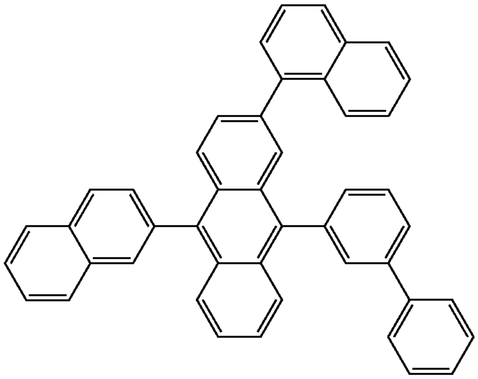
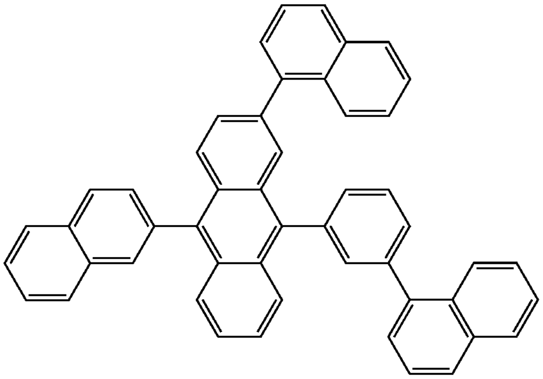
-continued
[Formula 118]
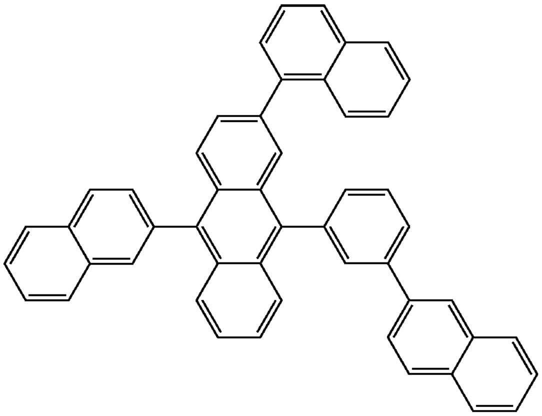
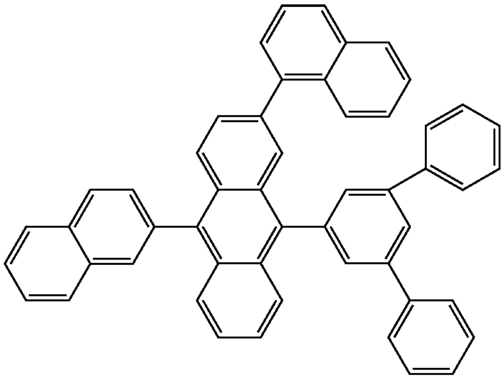
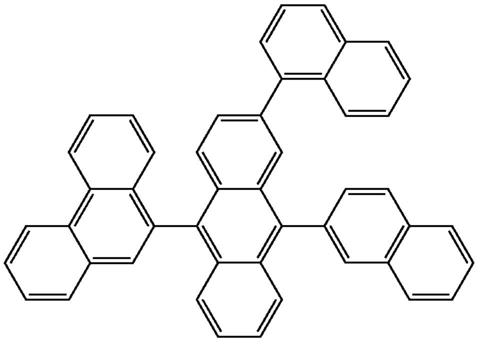
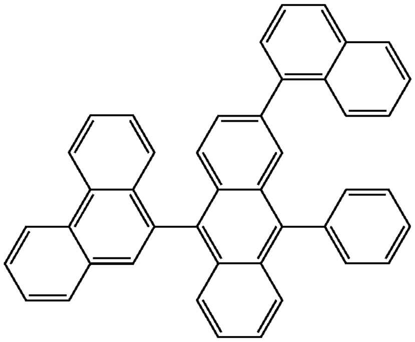

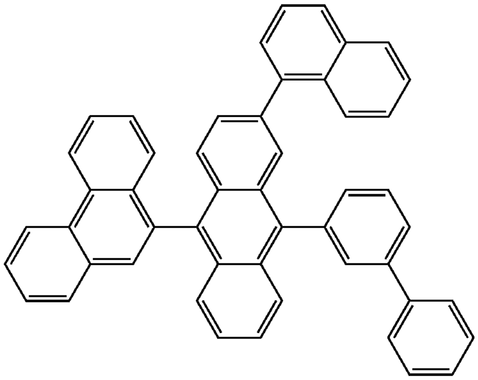
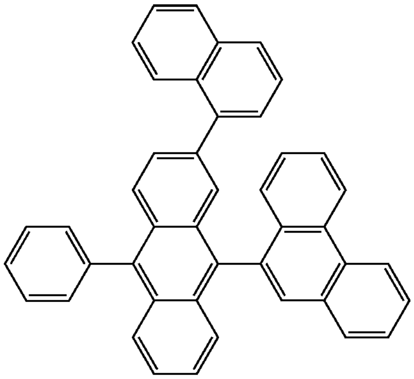
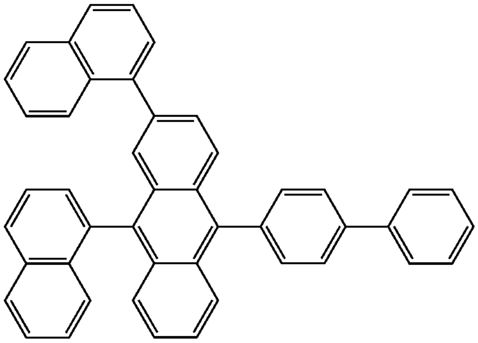
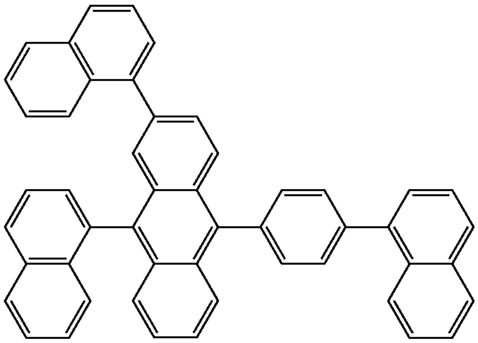
[Formula 119]
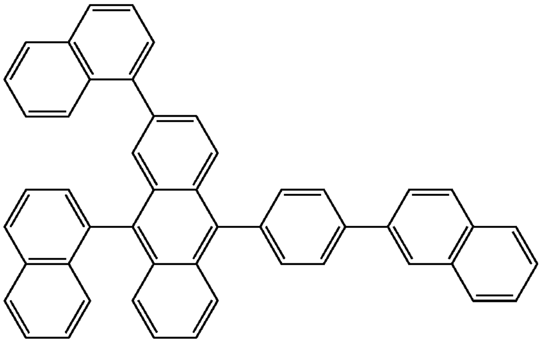
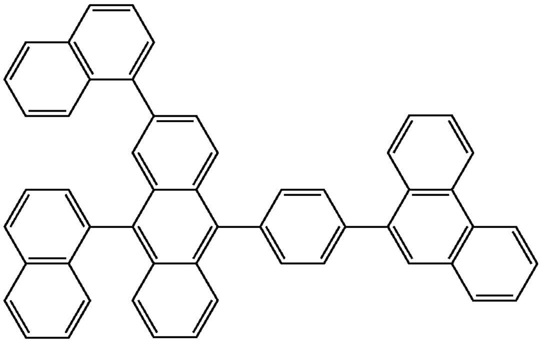
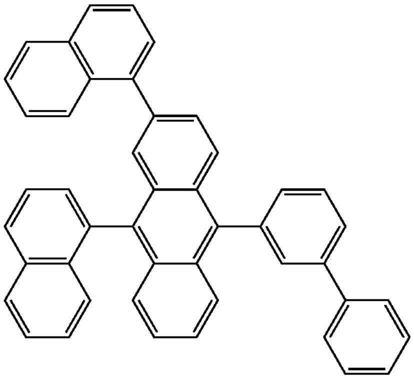
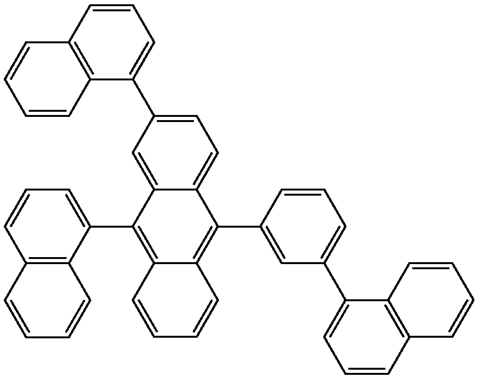

-continued
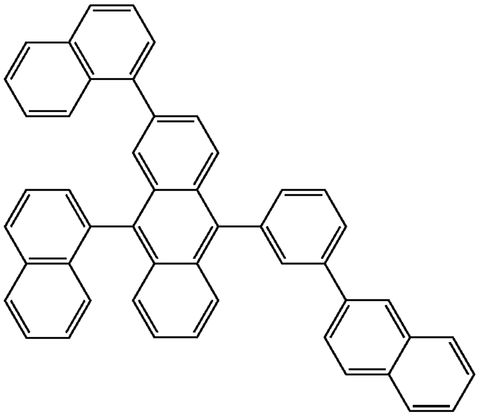
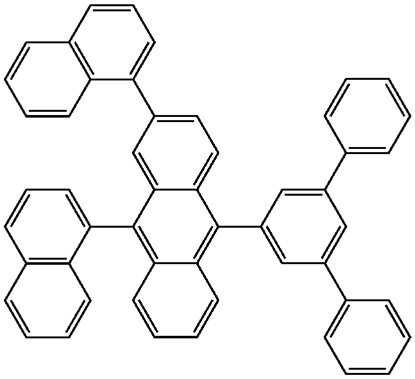
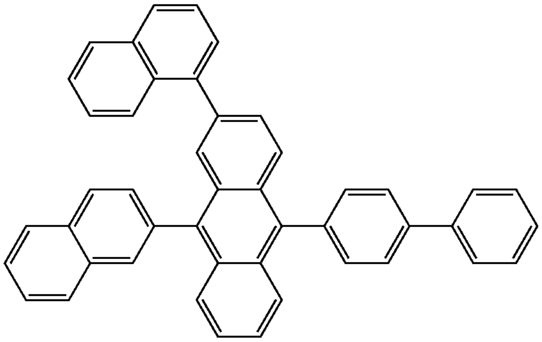
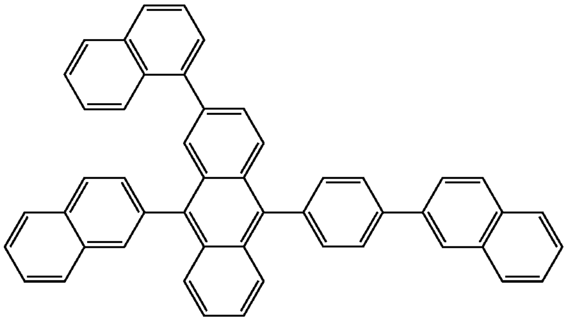
-continued
[Formula 120]
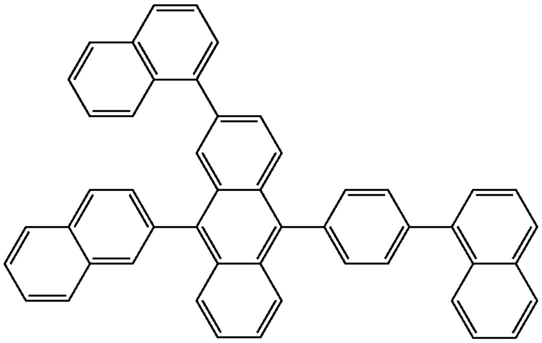
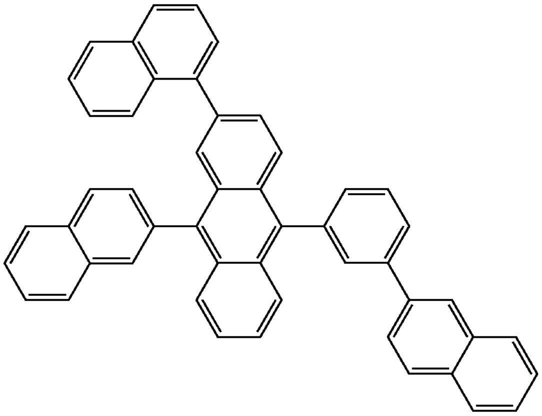
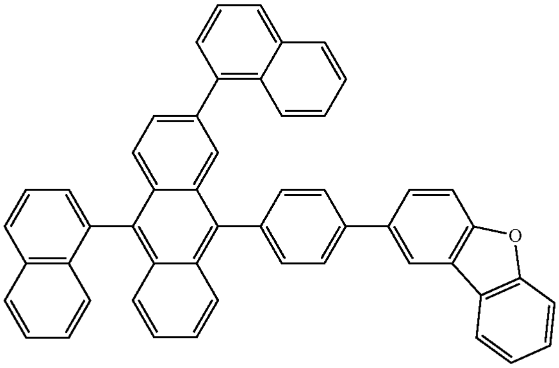
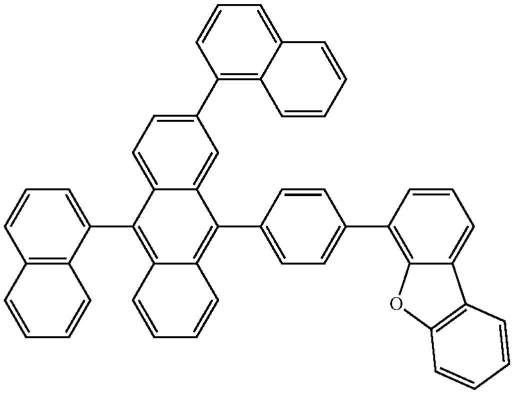

-continued
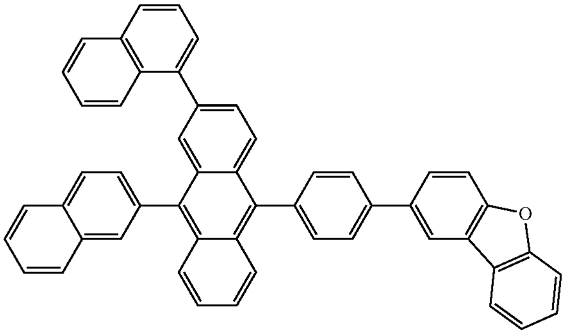
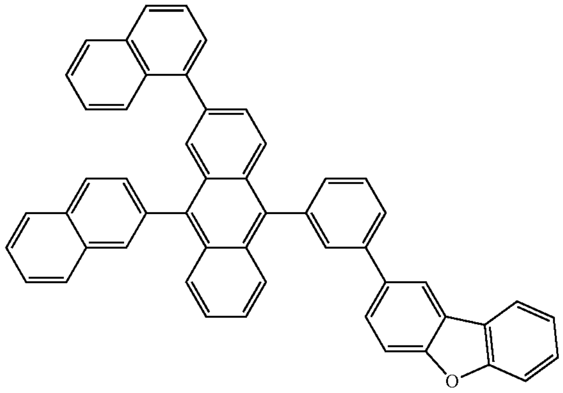
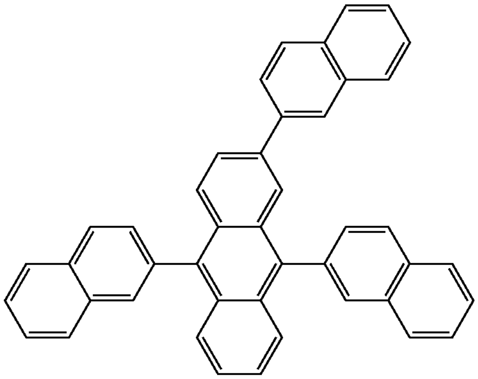
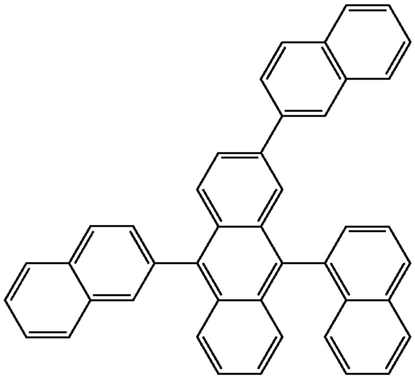
-continued
[Formula 121]
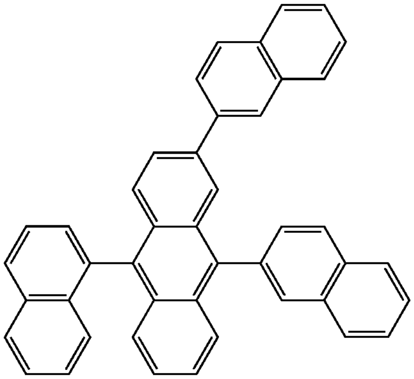
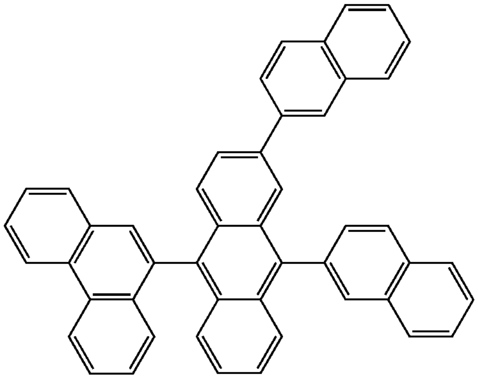
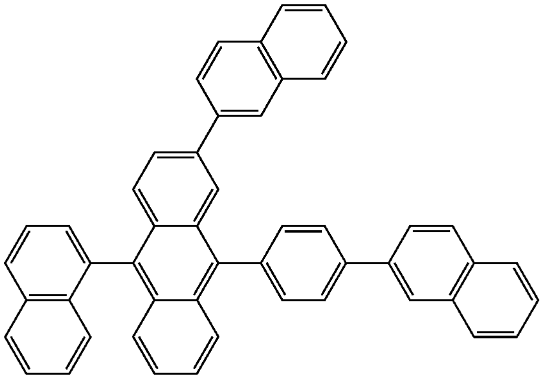
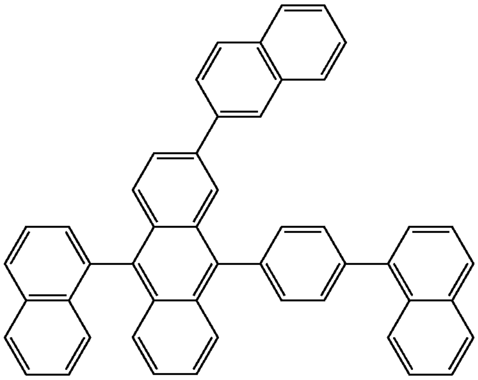

-continued
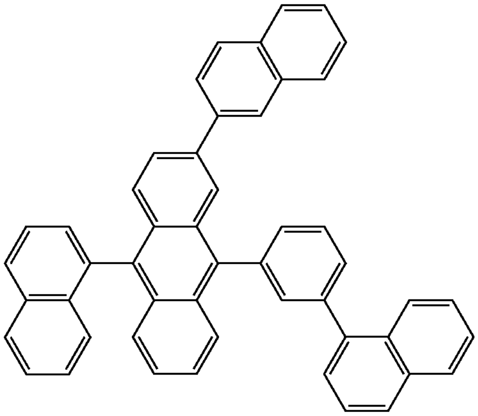
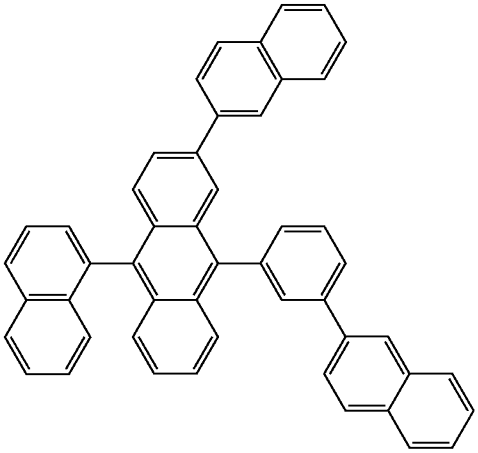
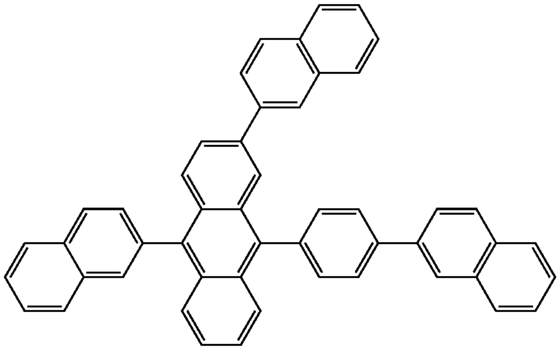
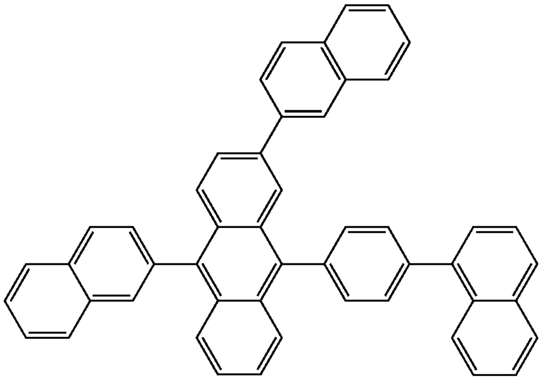
-continued
[Formula 122]
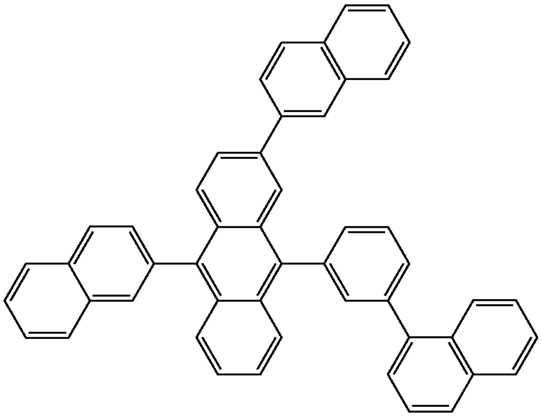
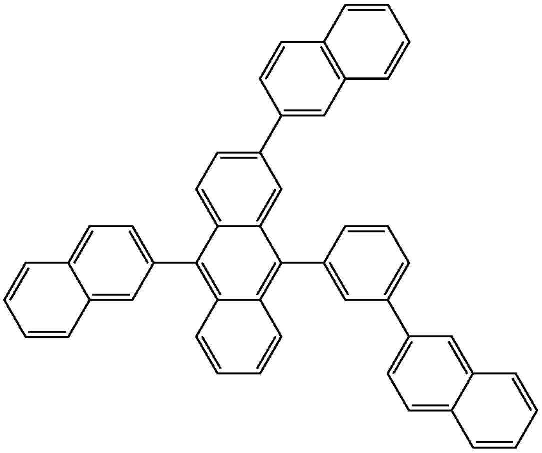
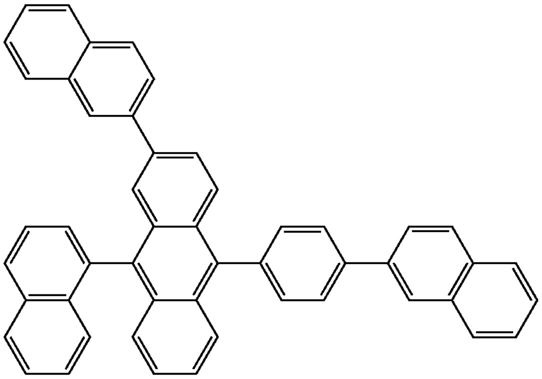
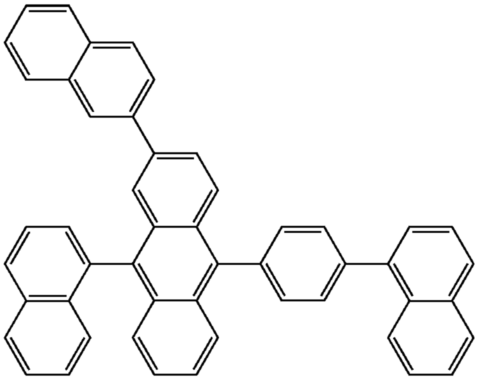

-continued
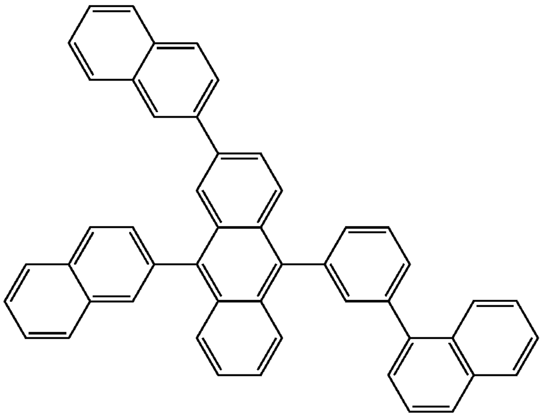
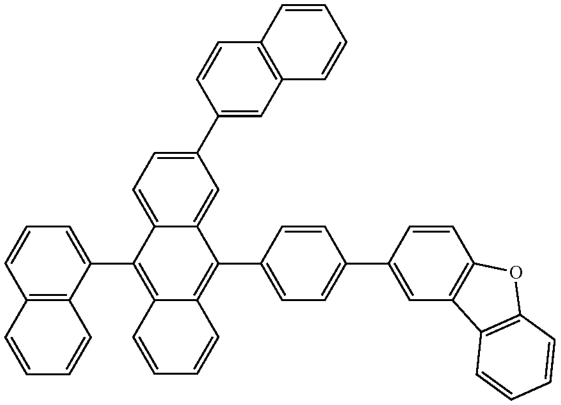
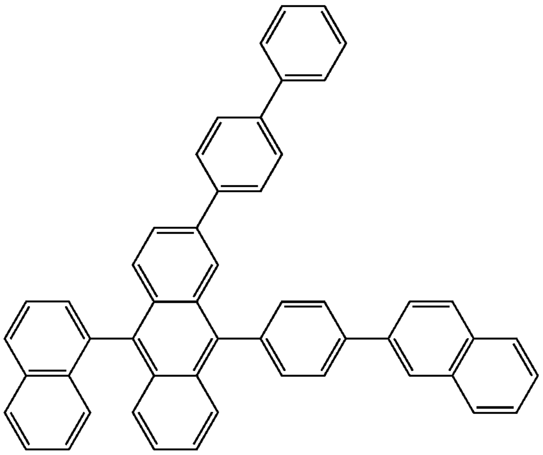
-continued
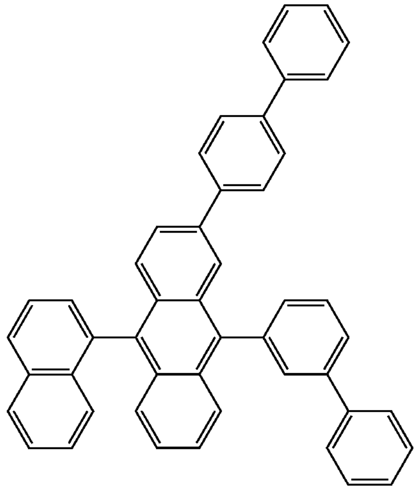
[Formula 123]
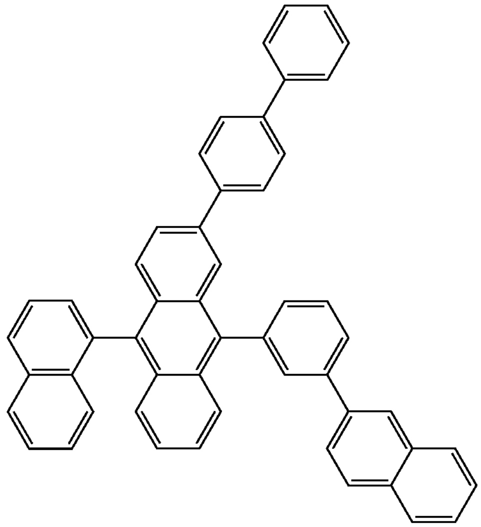
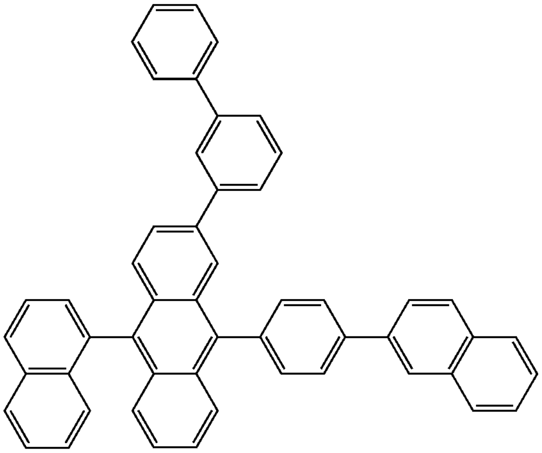

-continued
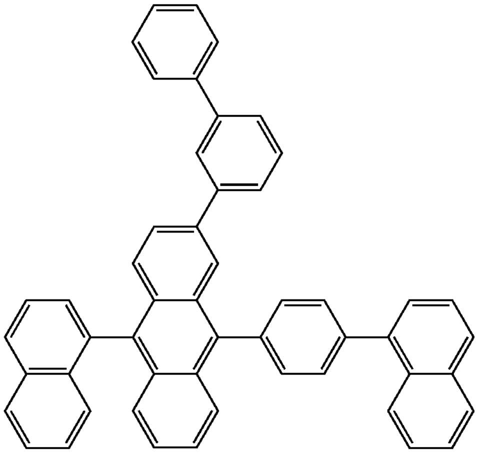
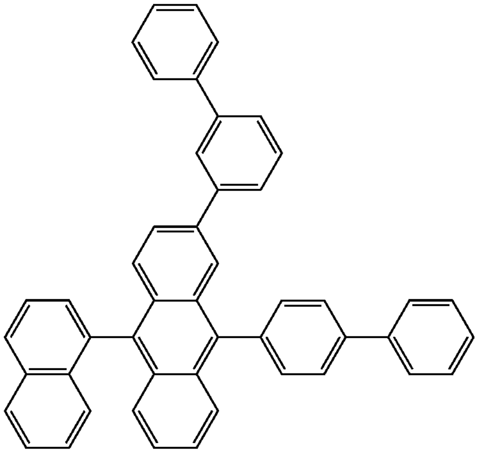
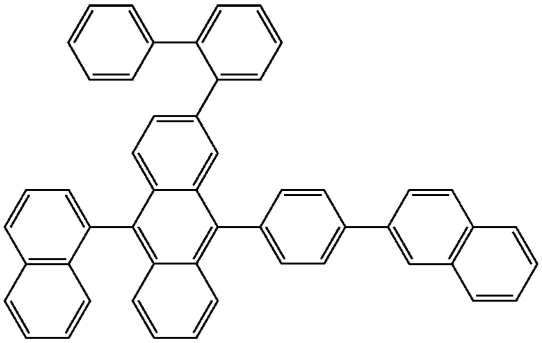
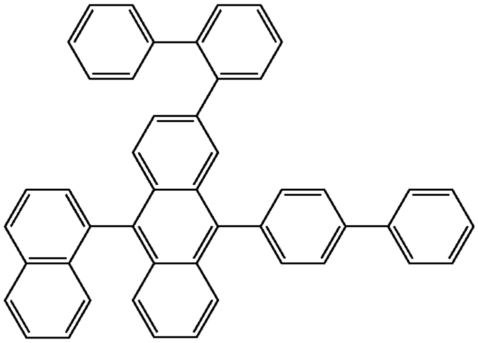
-continued
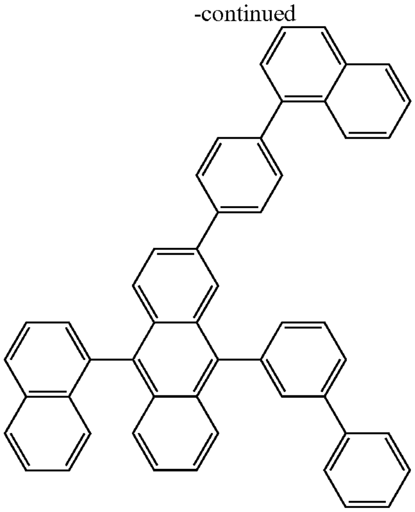
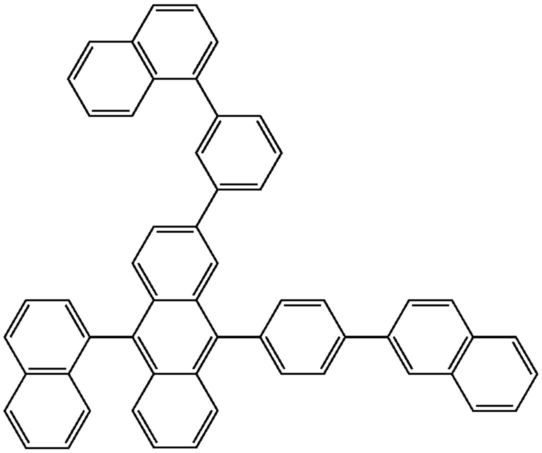
[Formula 124]
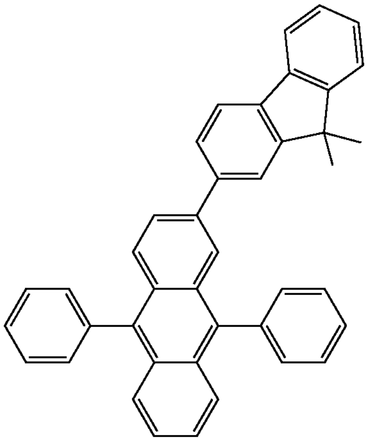

-continued
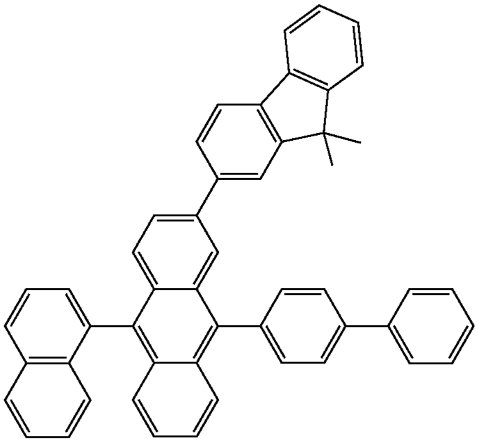
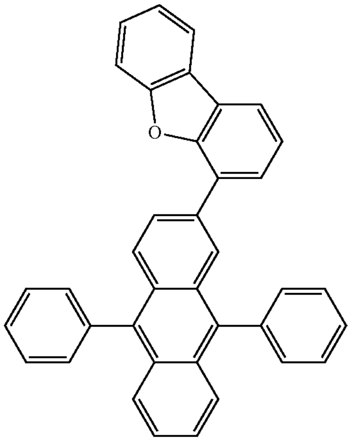
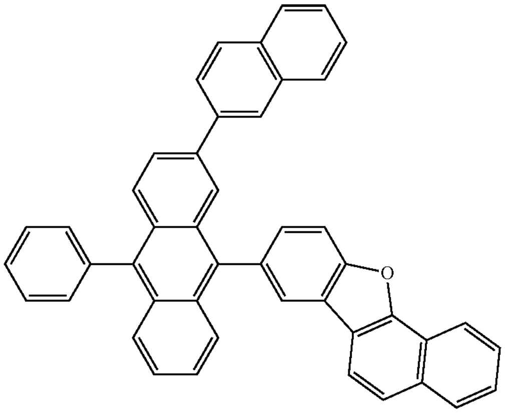
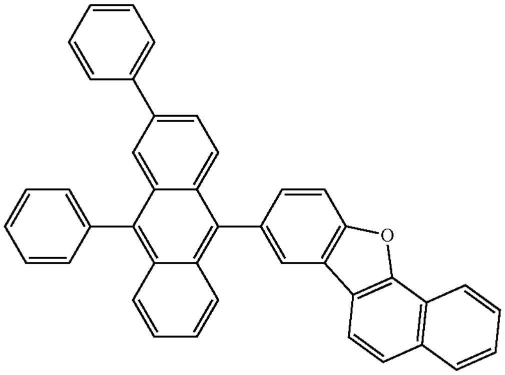
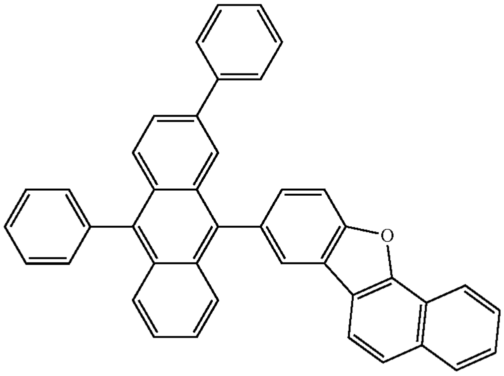
-continued
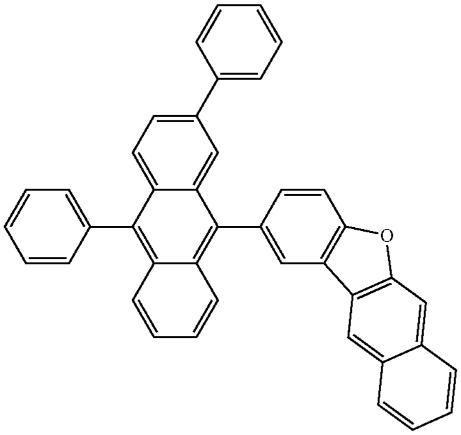
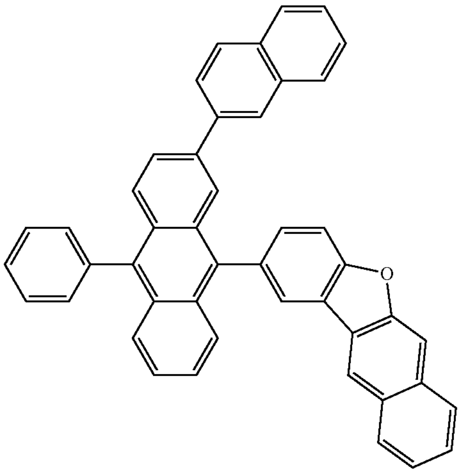

-continued
[Formula 125]
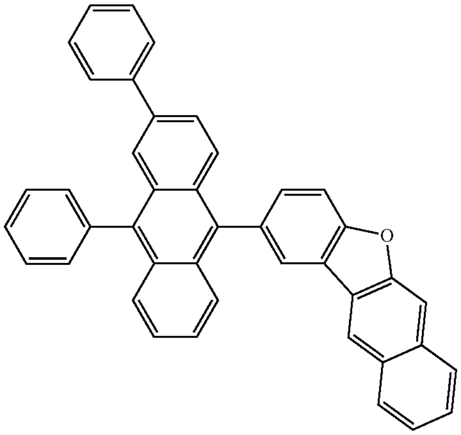
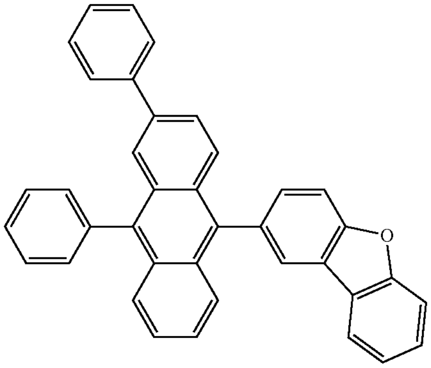
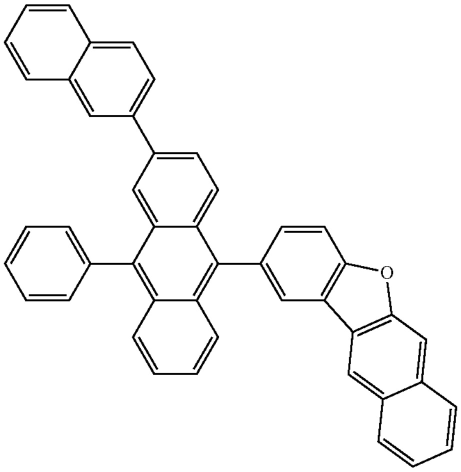
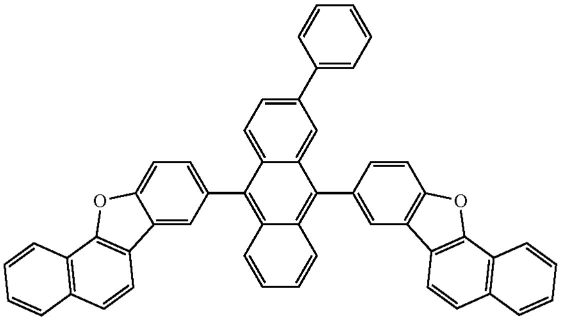
-continued
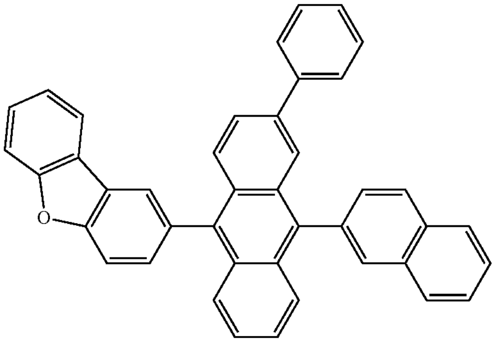
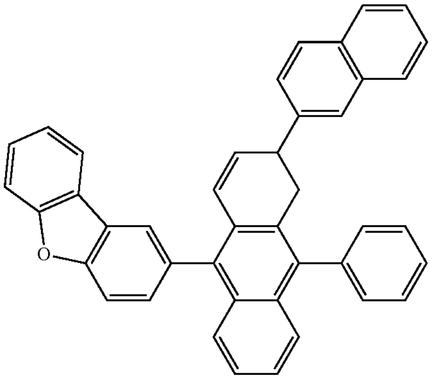
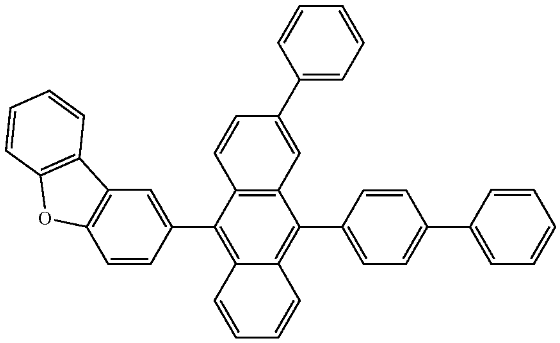
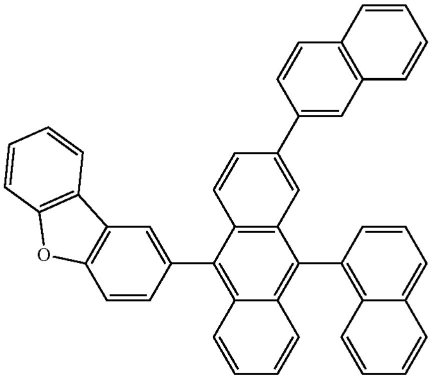

-continued
[Formula 126]
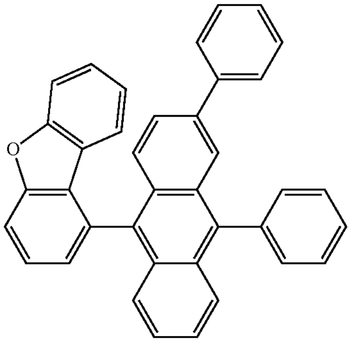
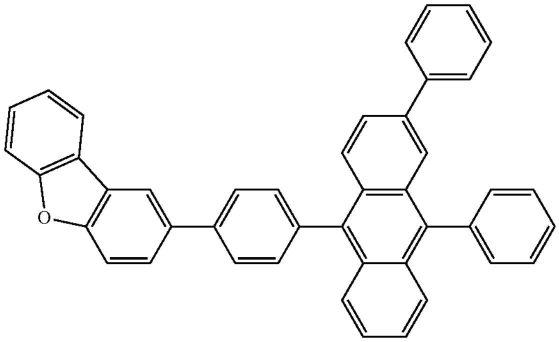
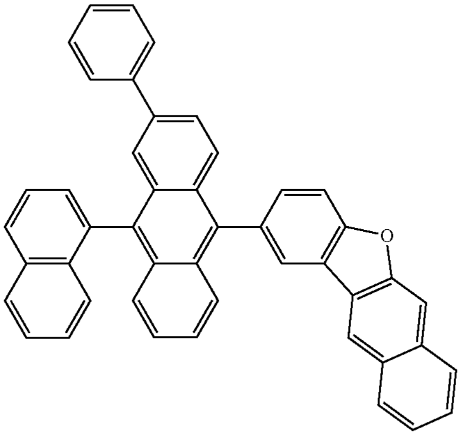
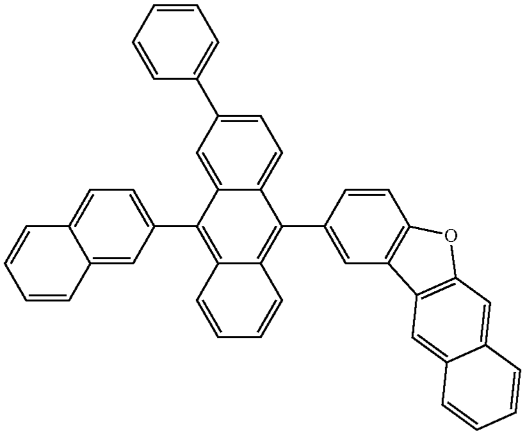
-continued
[Formula 127]
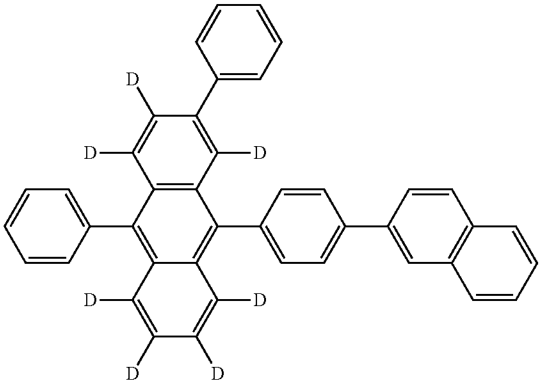
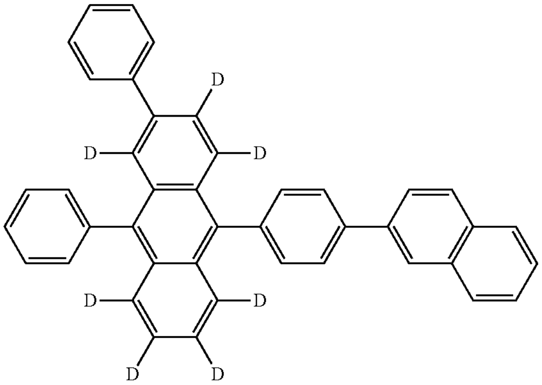
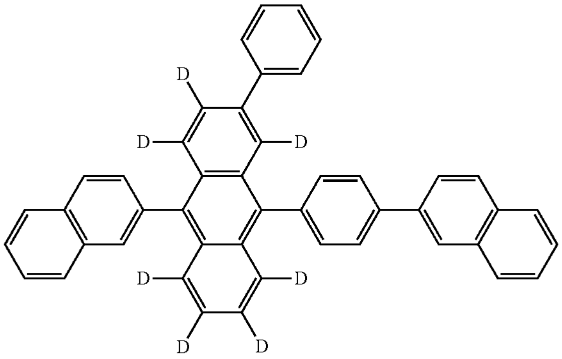
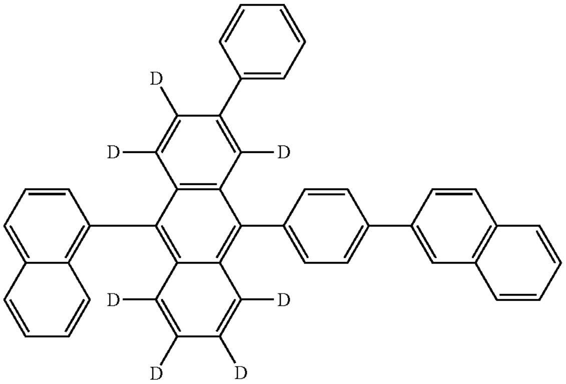

-continued
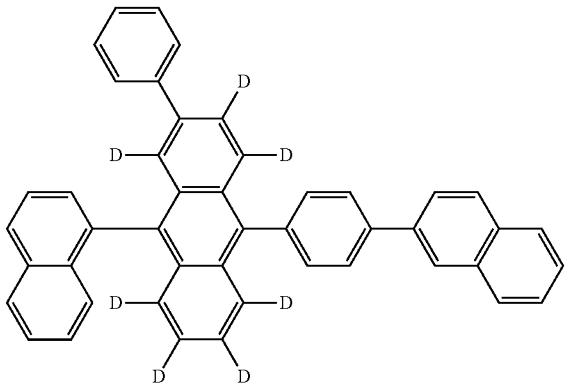
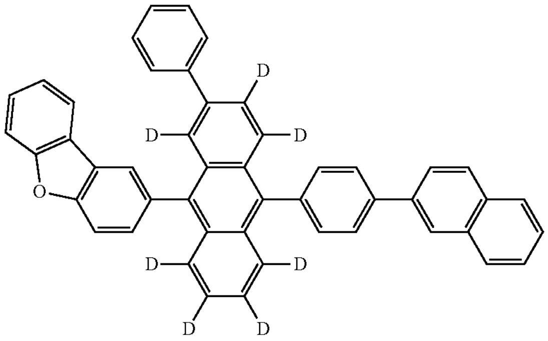
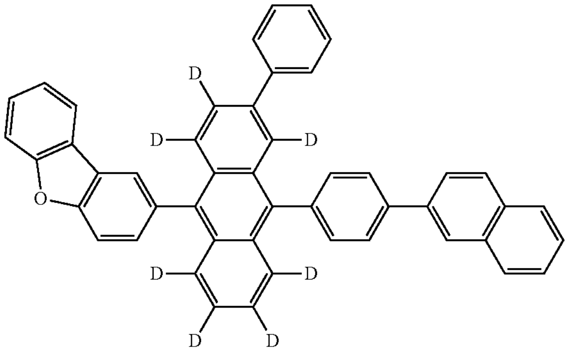
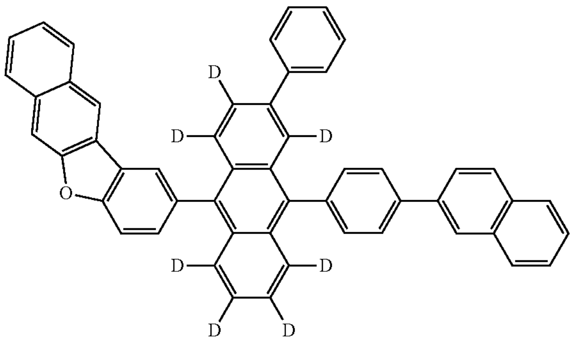
-continued
[Formula 128]
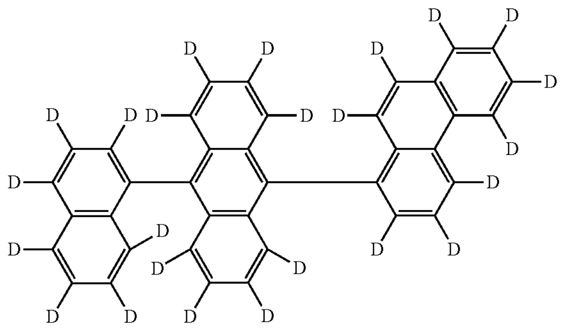
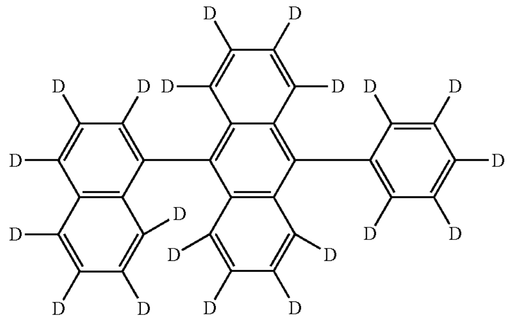
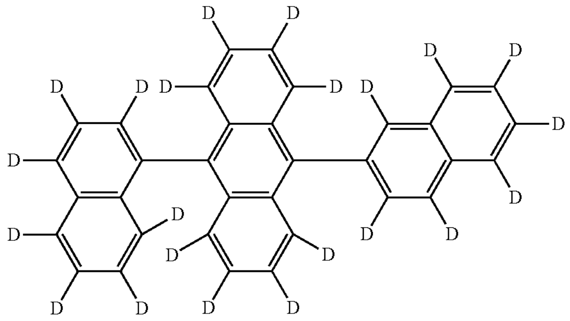
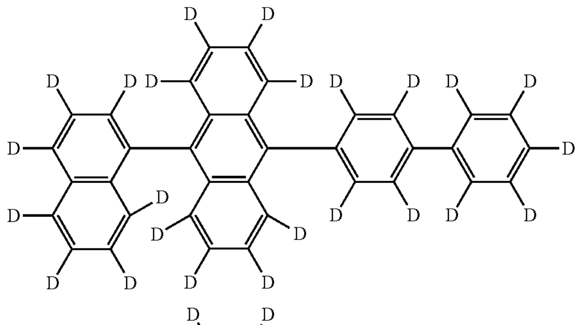
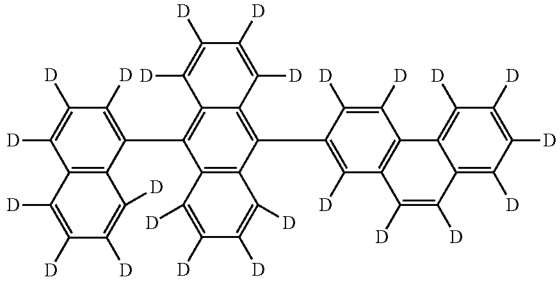

-continued
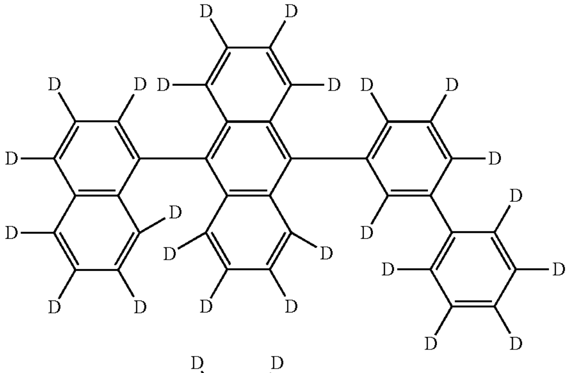
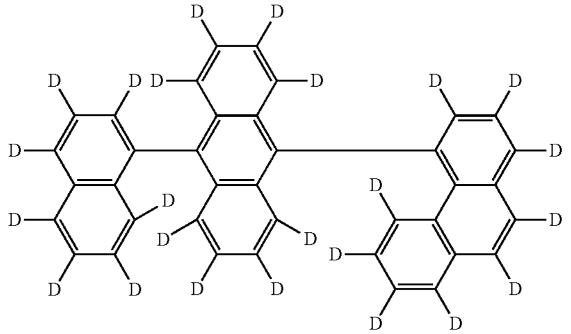
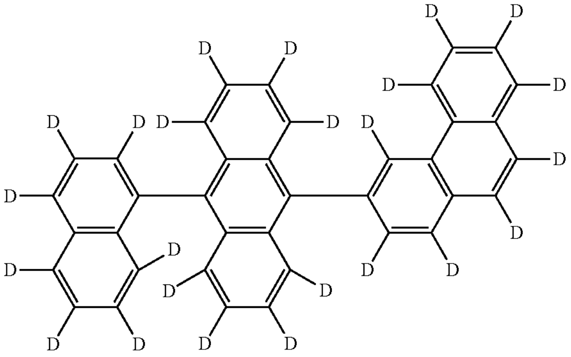
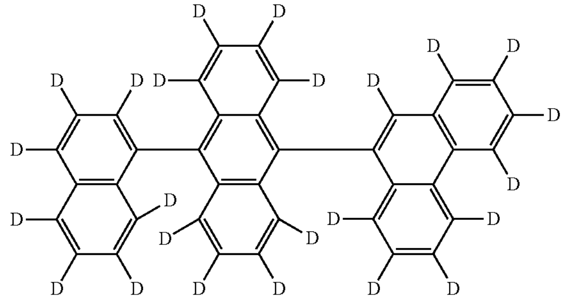
-continued
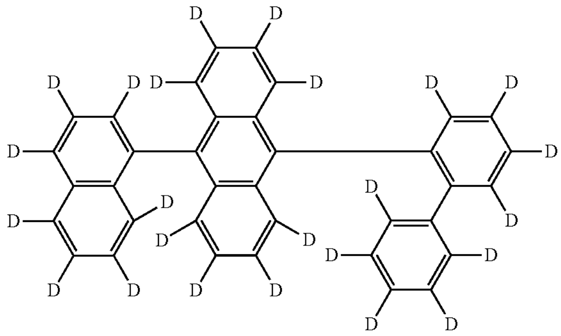
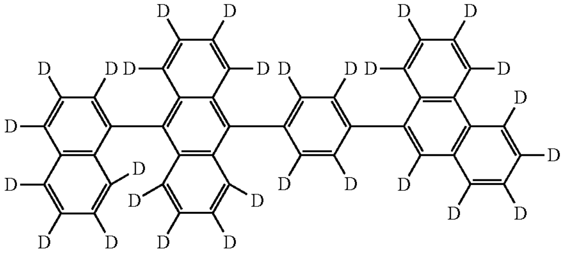
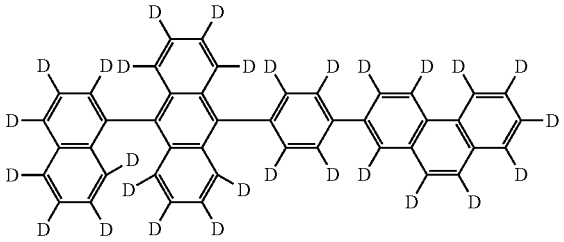
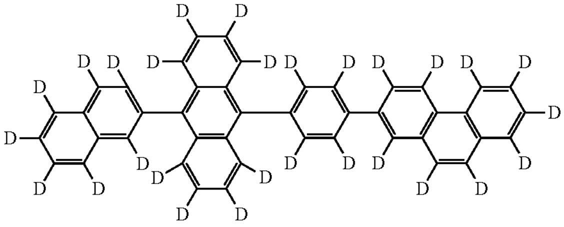

[Formula 129]
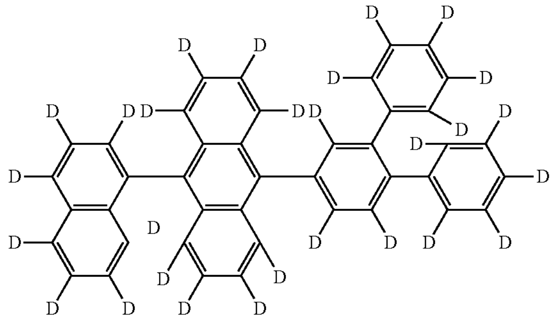
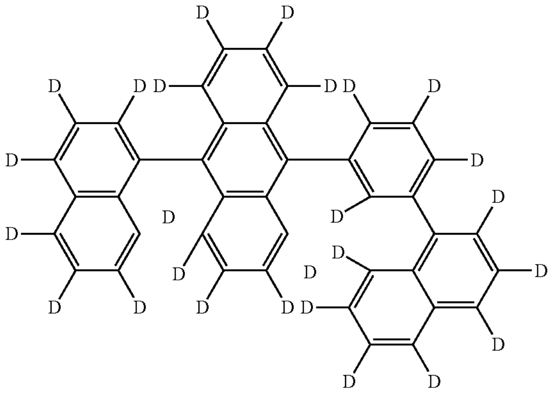
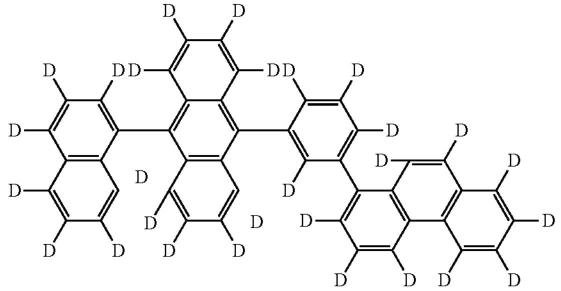
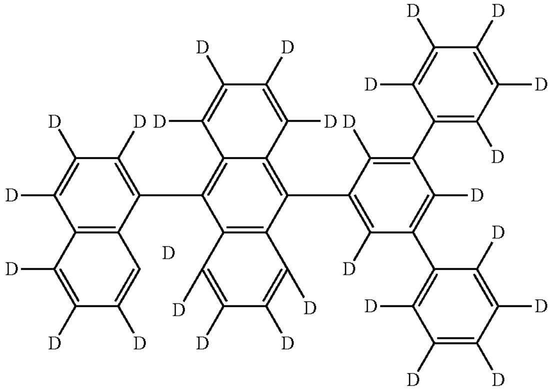
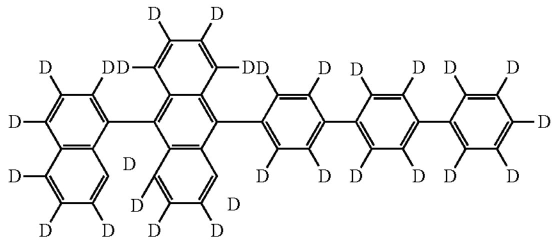
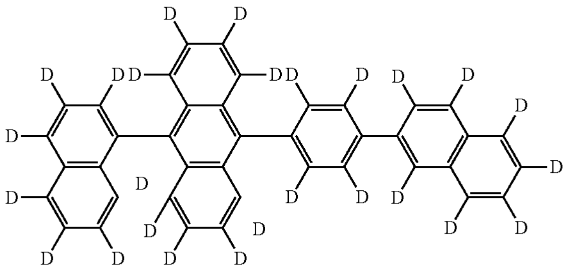
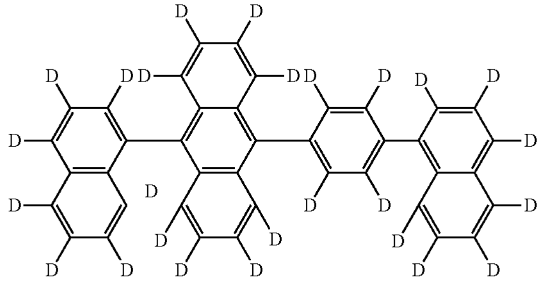
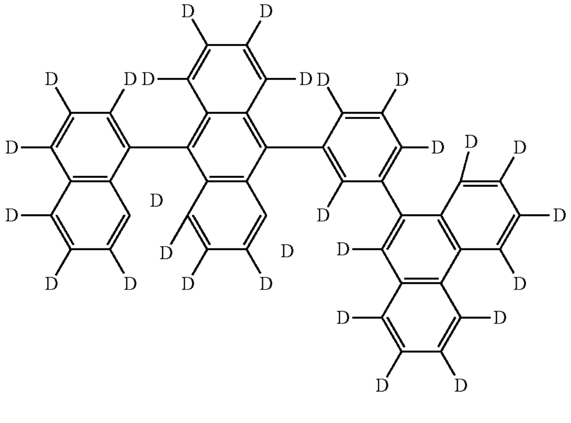

-continued
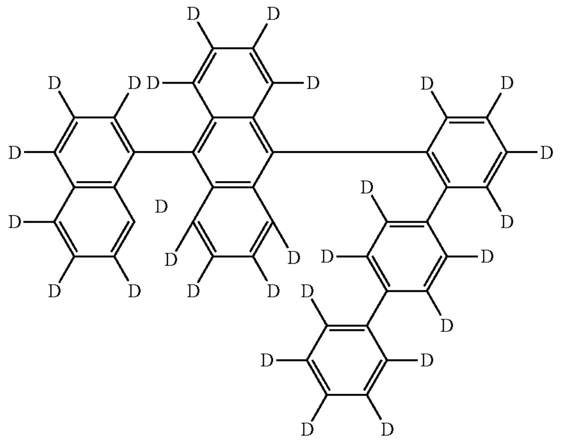
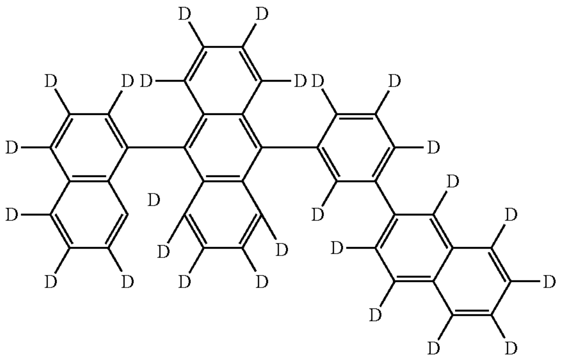
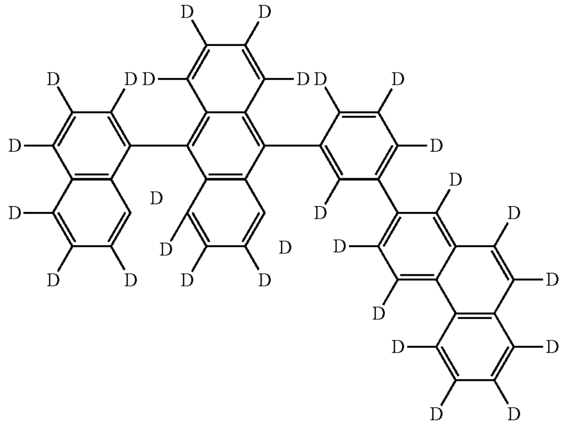
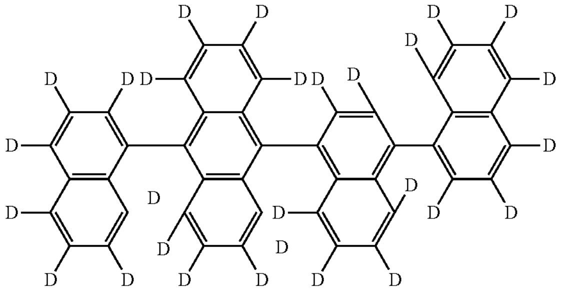
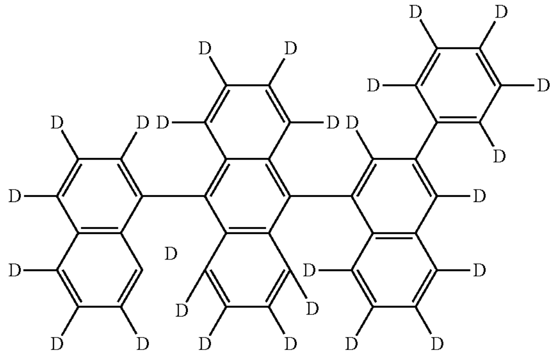
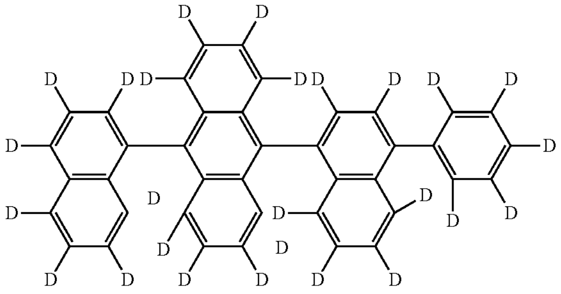
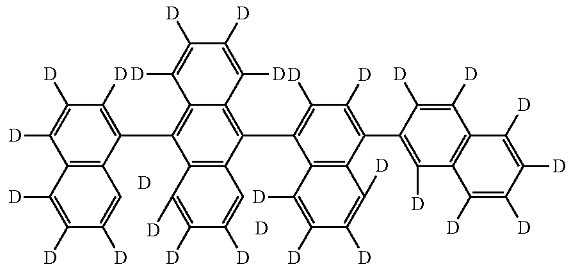
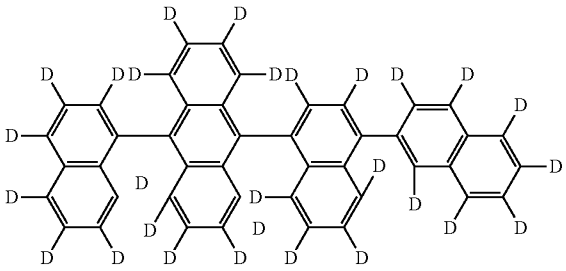

-continued
[Formula 130]
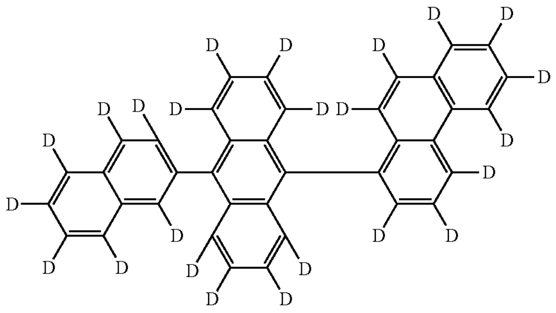
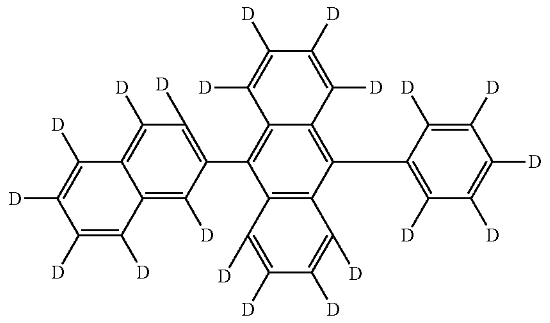
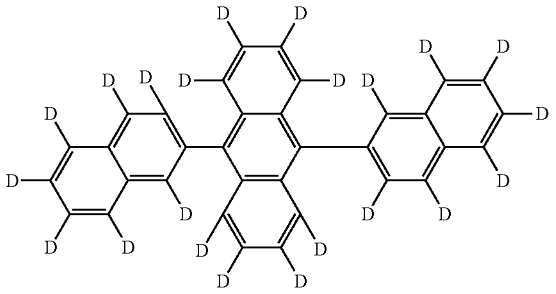
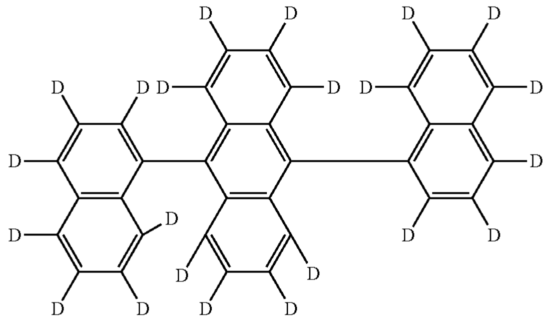
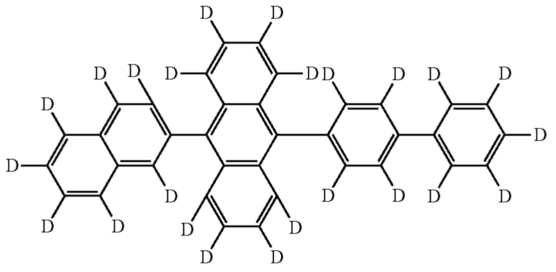
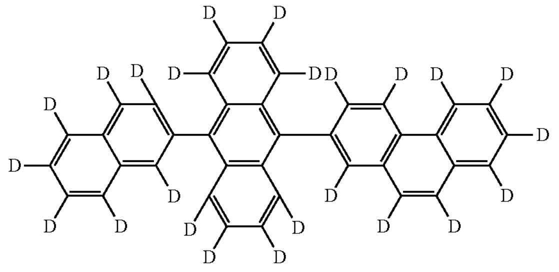
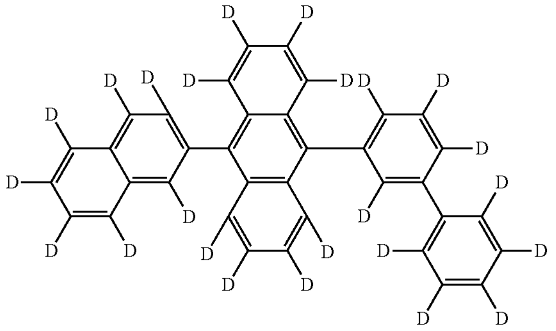
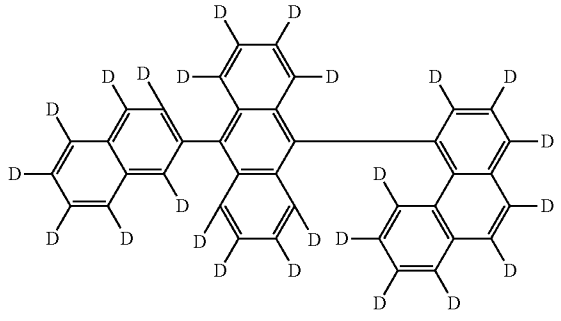
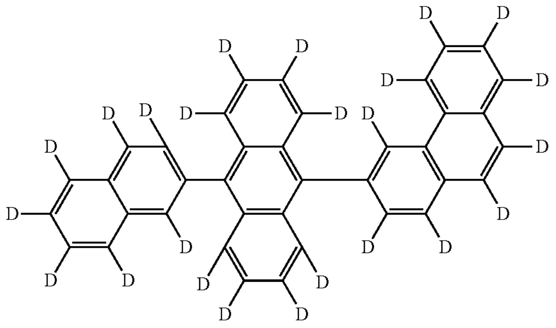
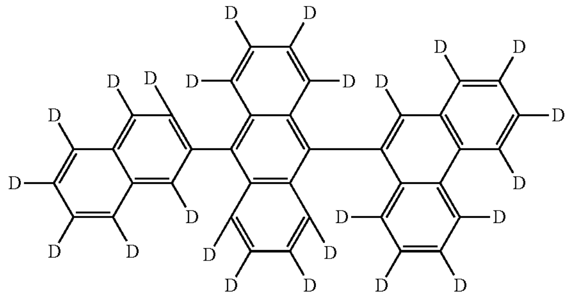

-continued
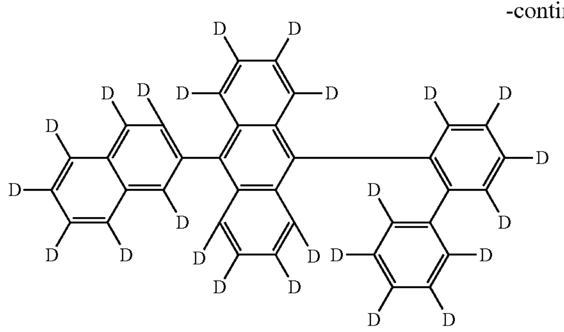
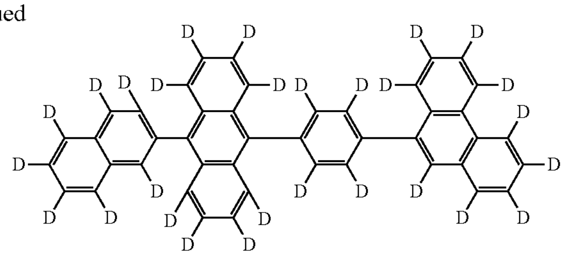
[Formula 131]
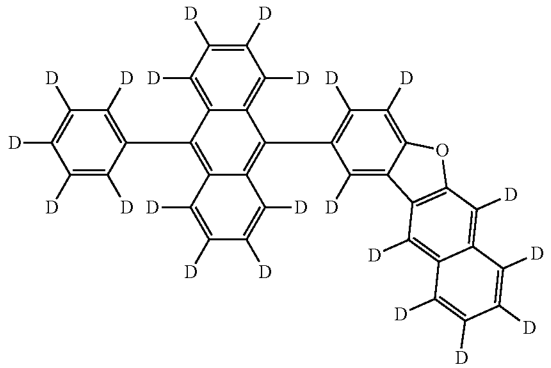
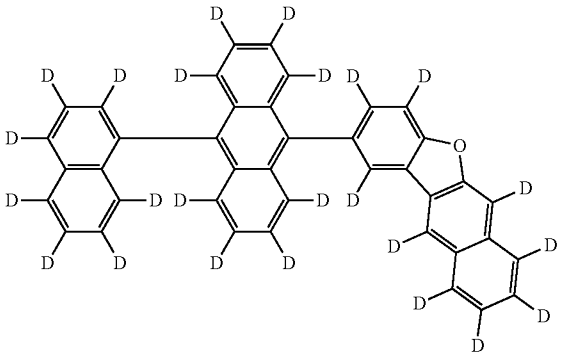
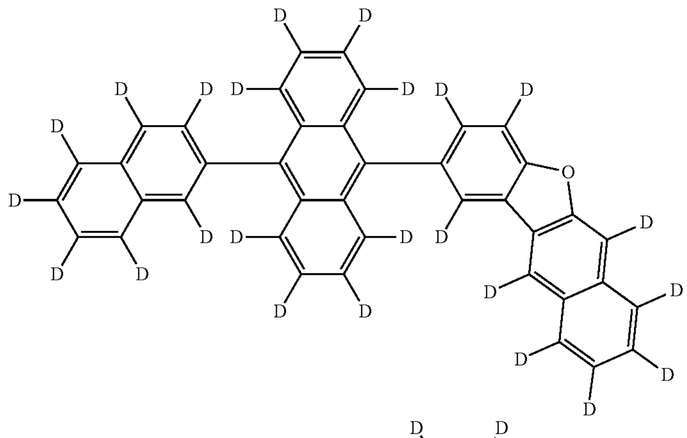
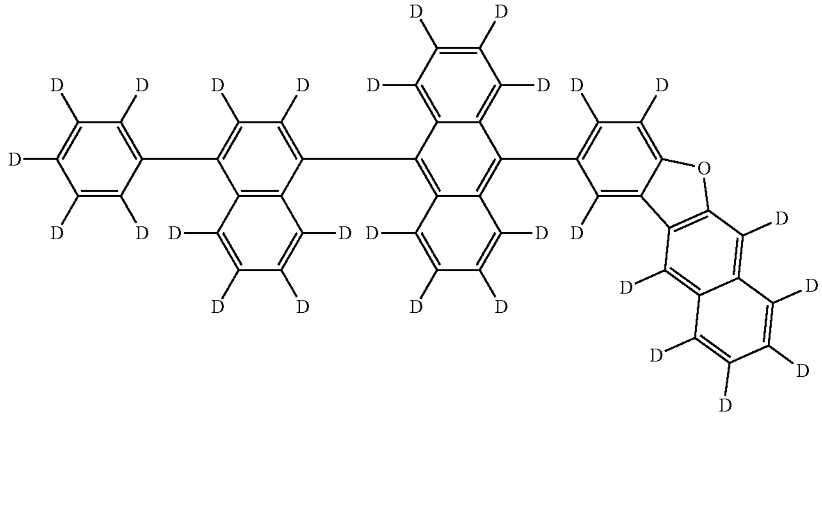

-continued
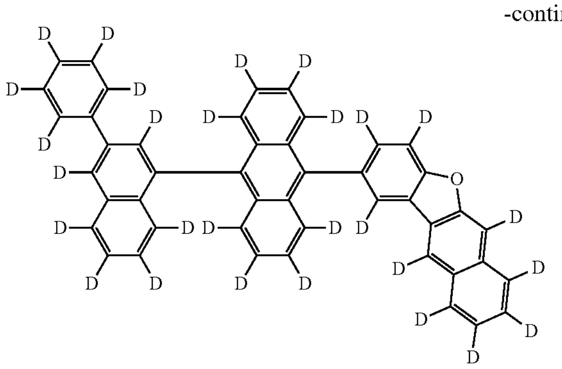
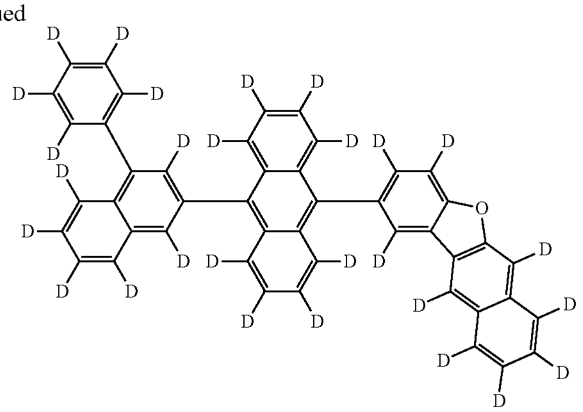
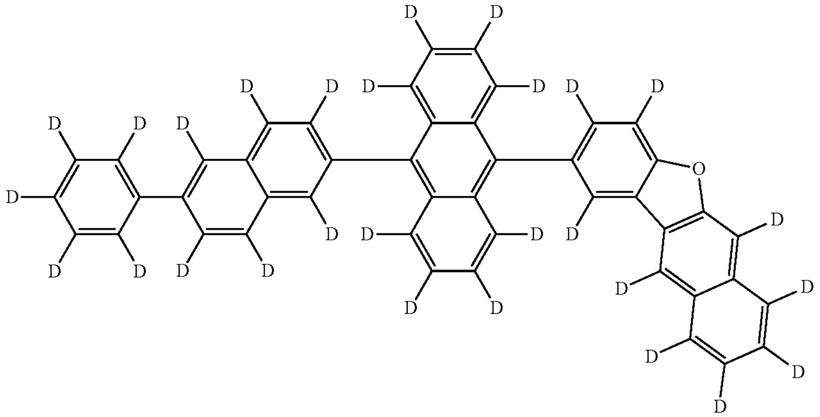
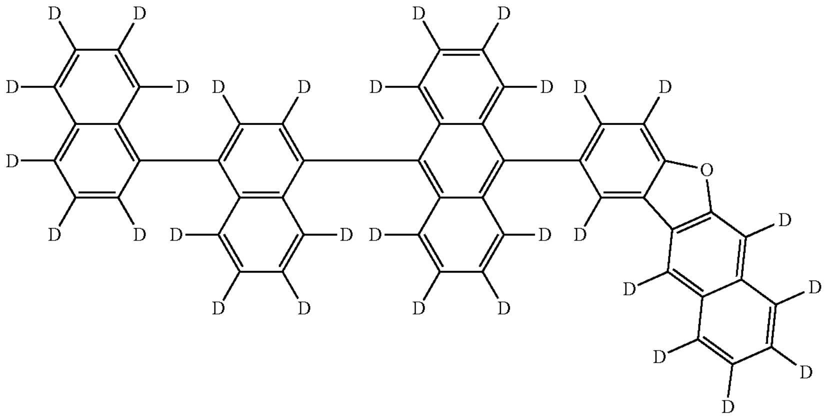
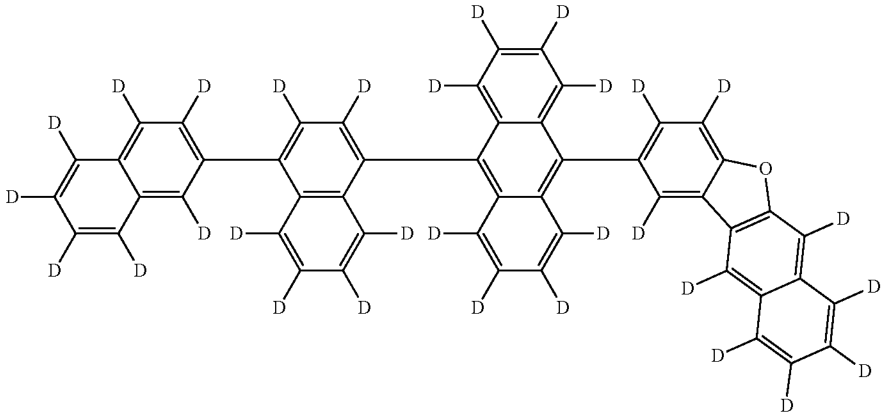

-continued
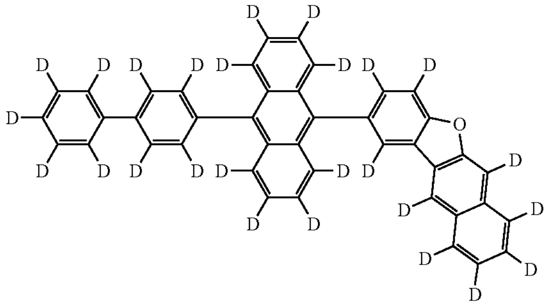
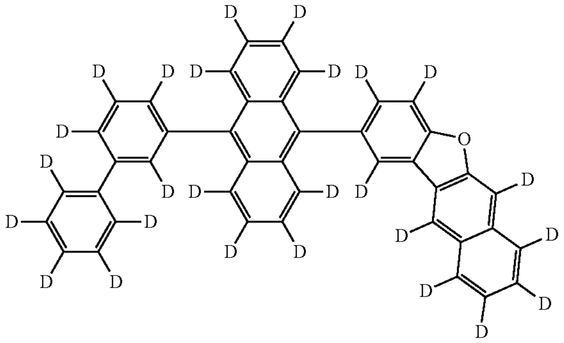
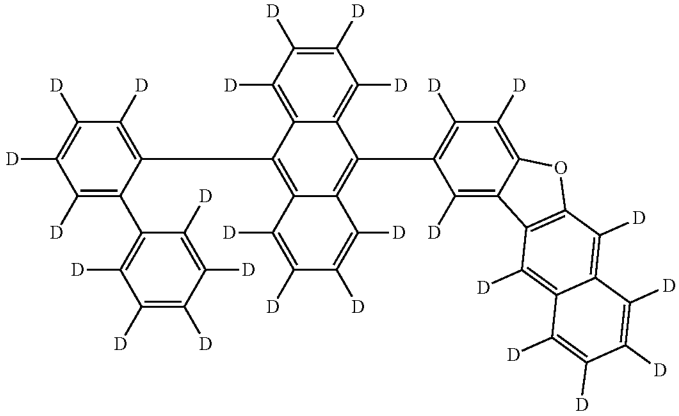
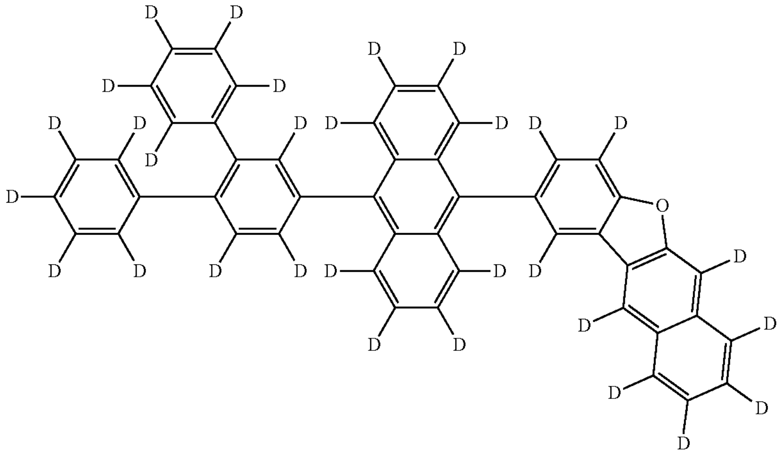
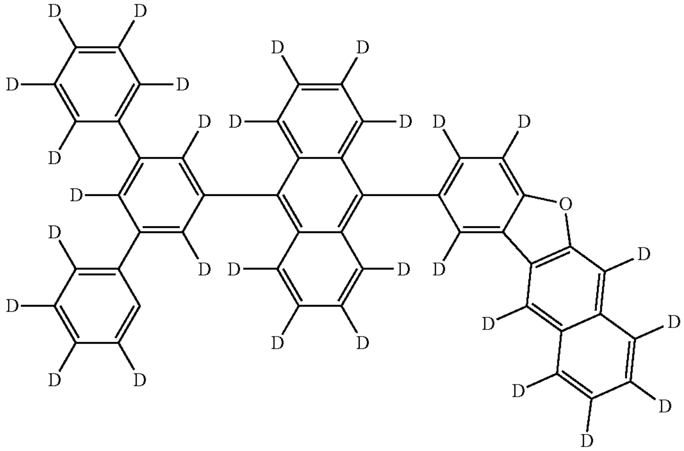

-continued
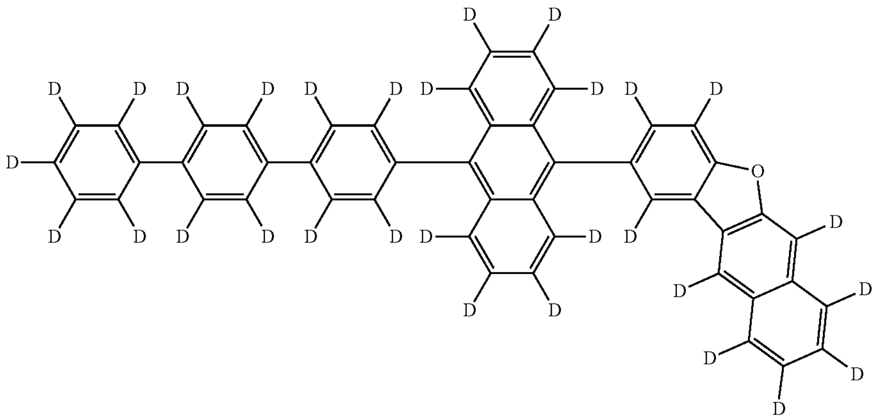
[Formula 132]
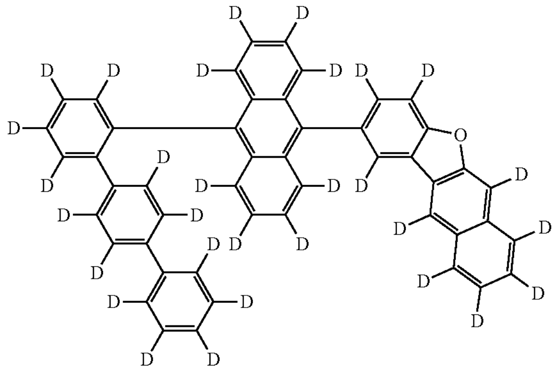
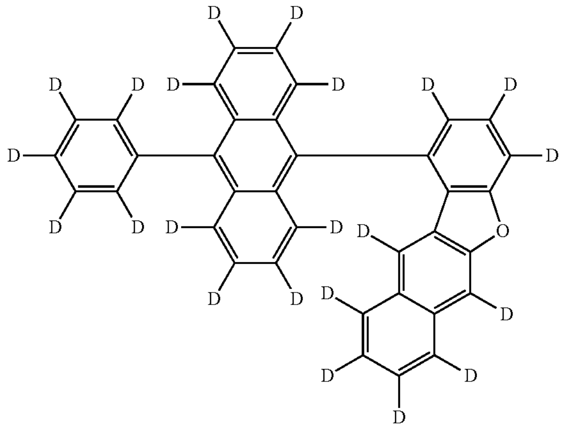
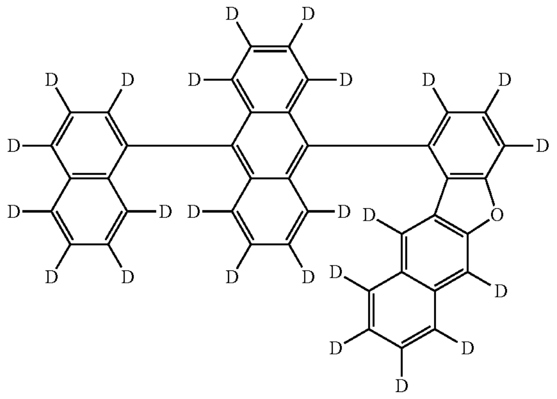
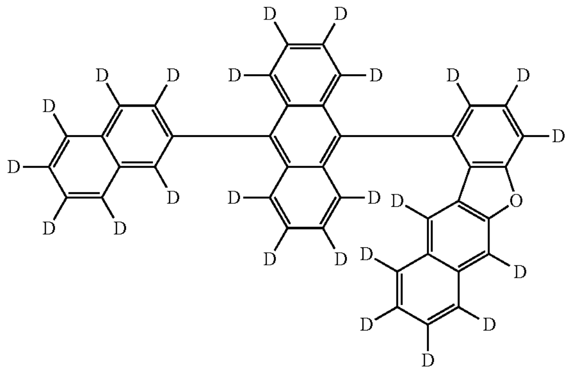
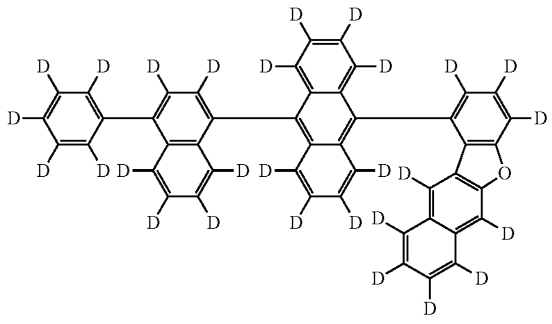
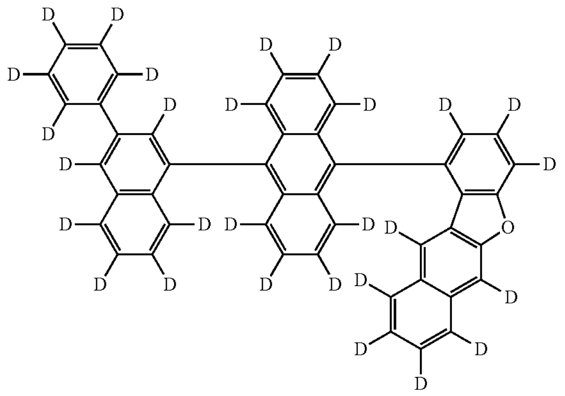

-continued
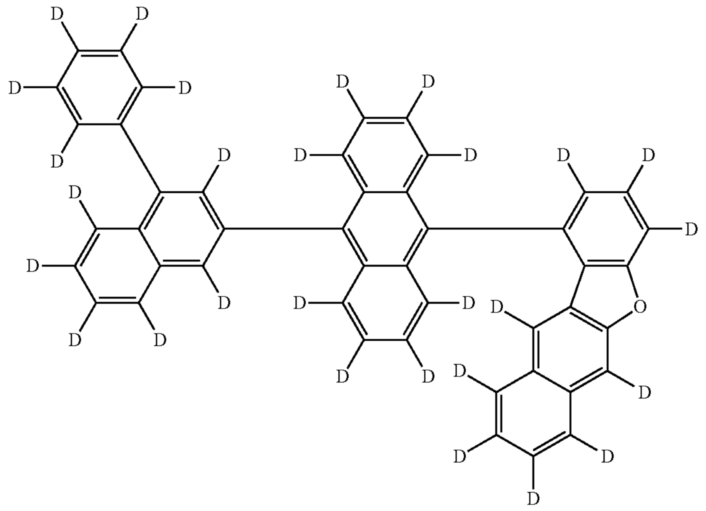
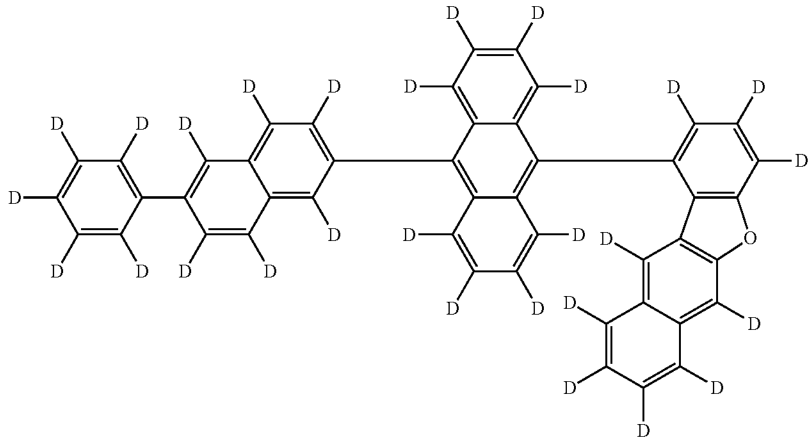
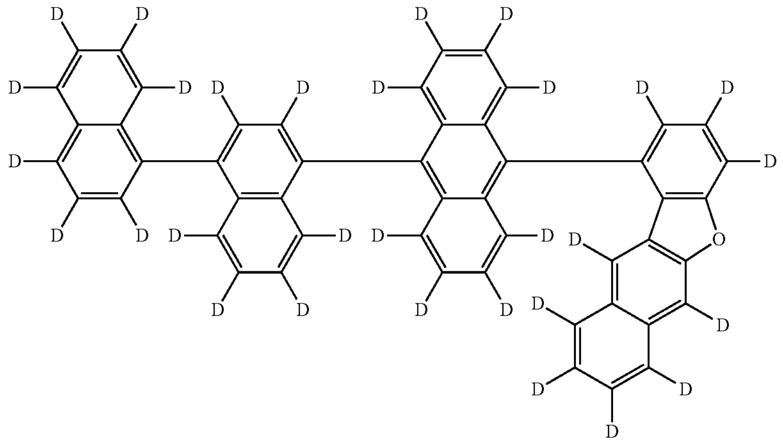

-continued
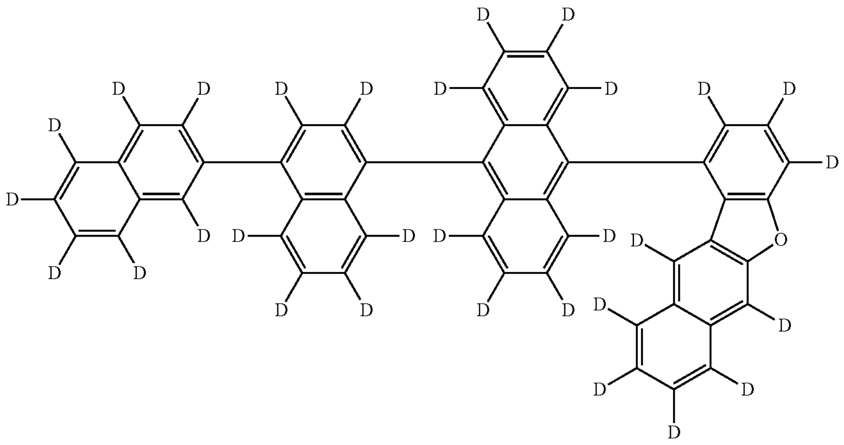
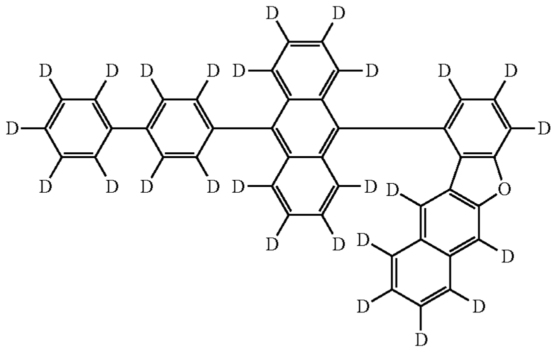
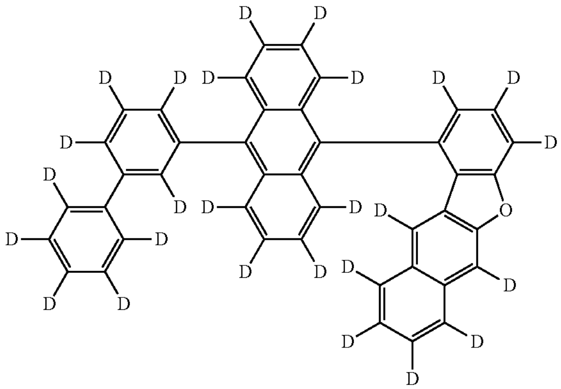
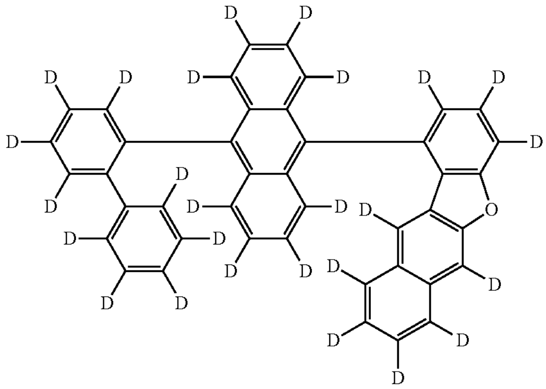
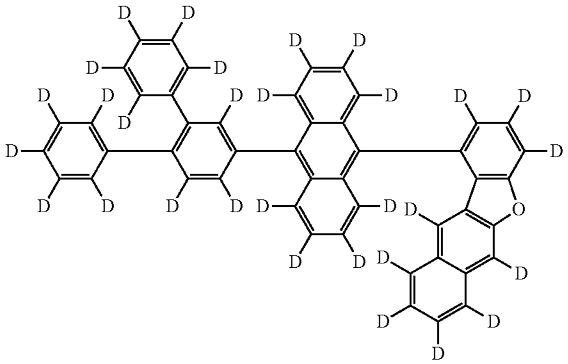
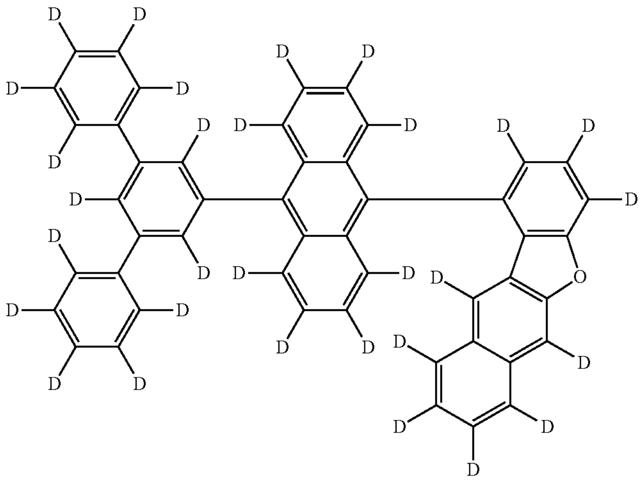

-continued
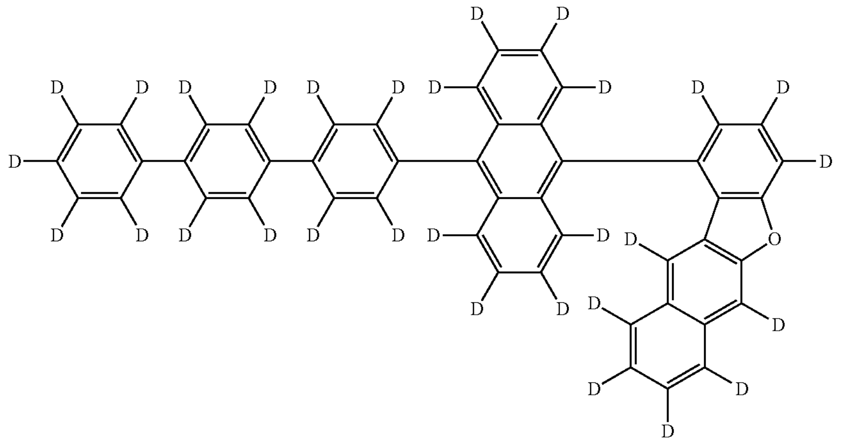
[Formula 133]
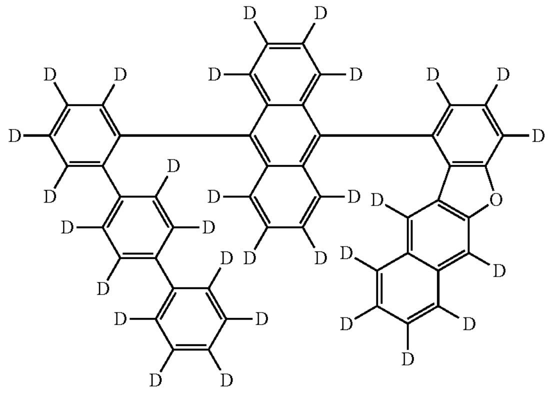
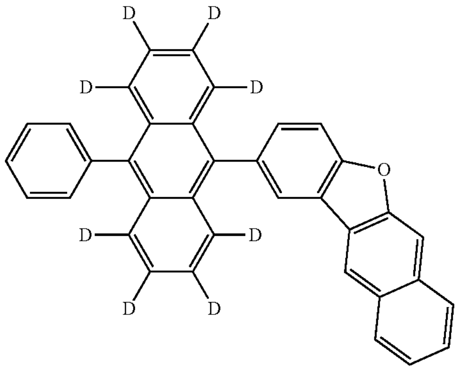
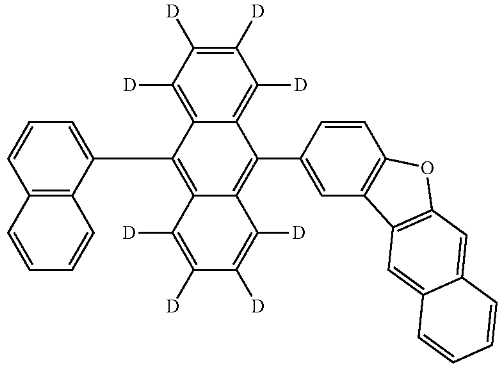
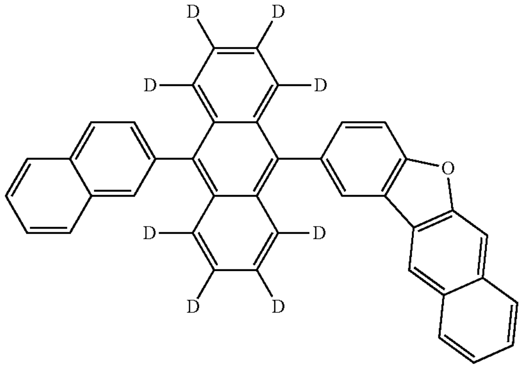
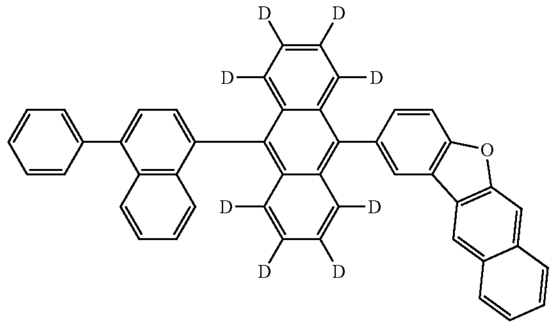
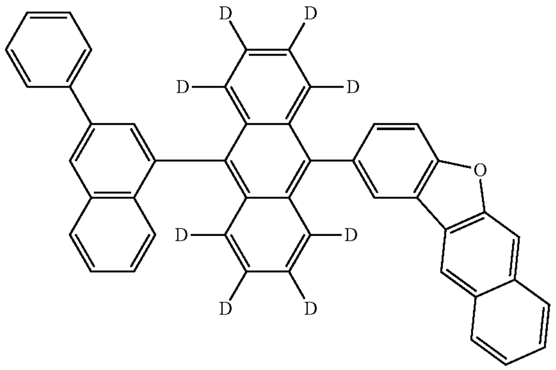

-continued
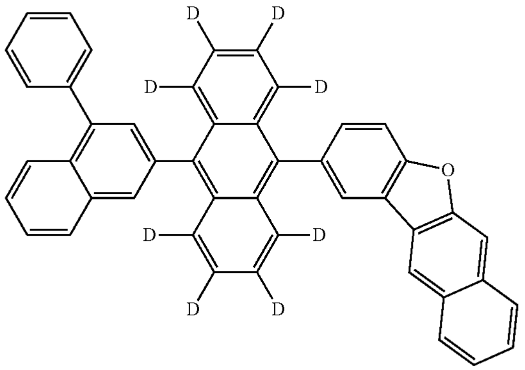
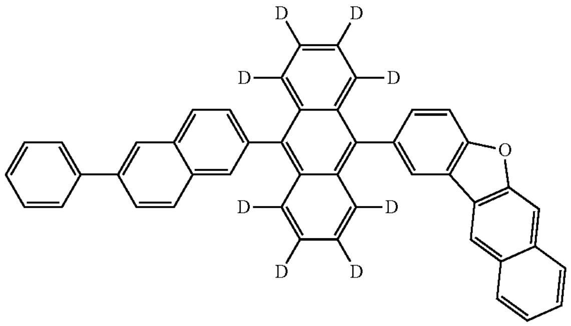
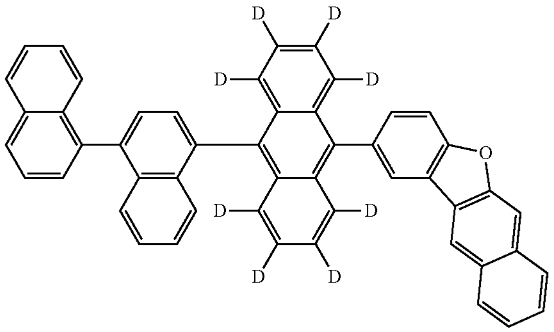
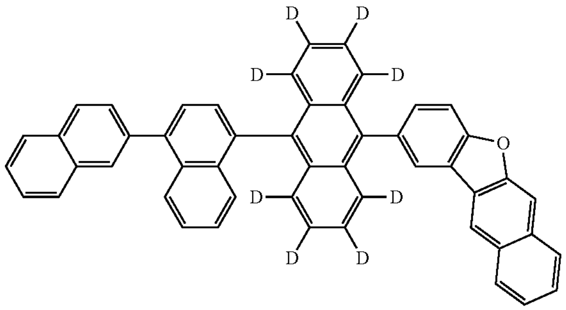
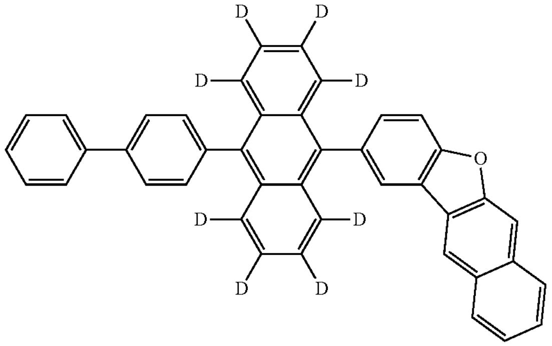
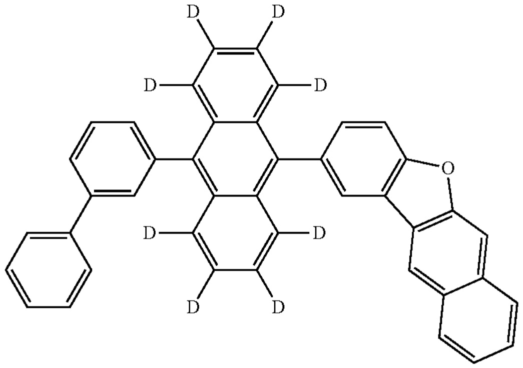
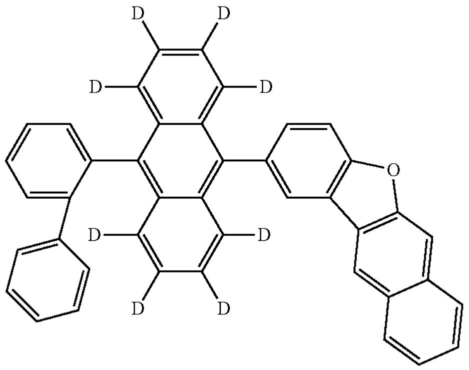
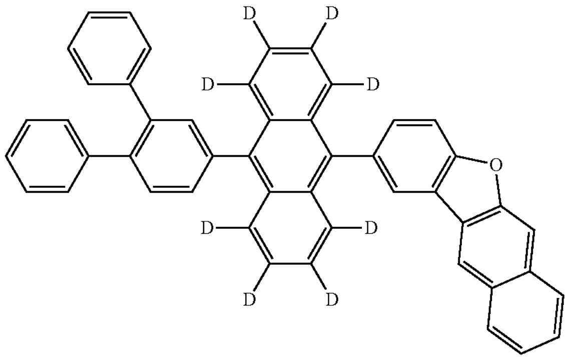

-continued
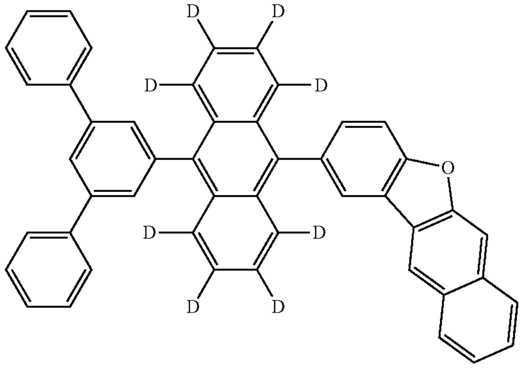
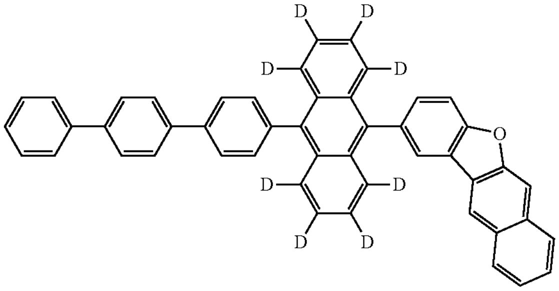
[Formula 134]
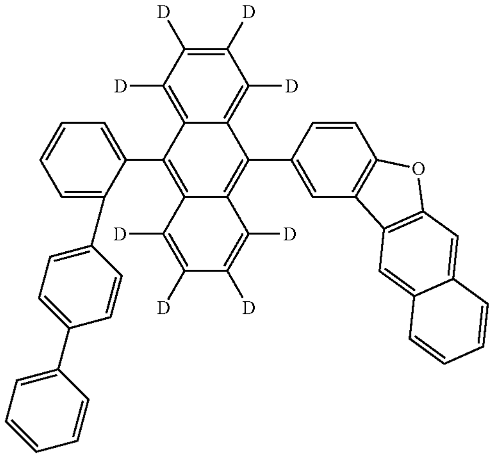
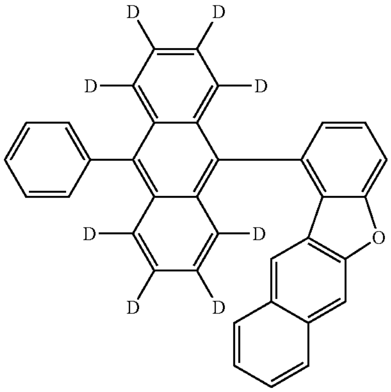
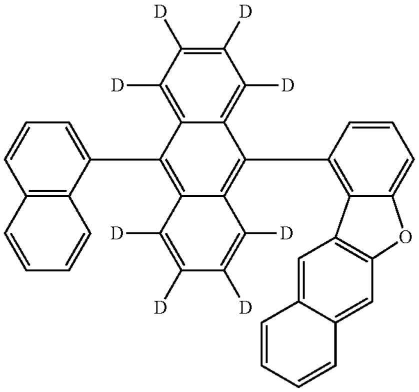
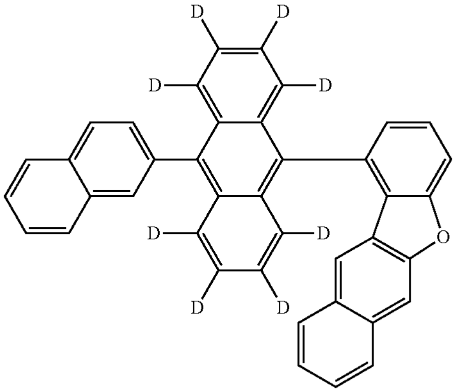
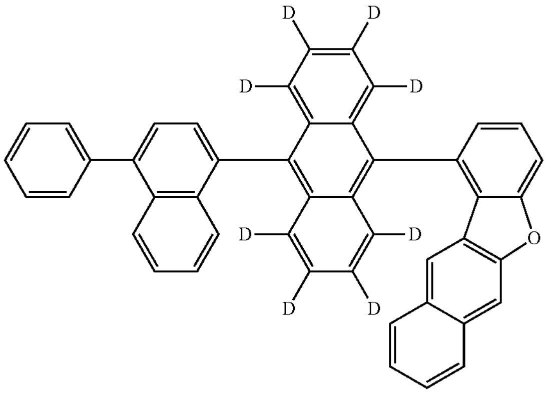
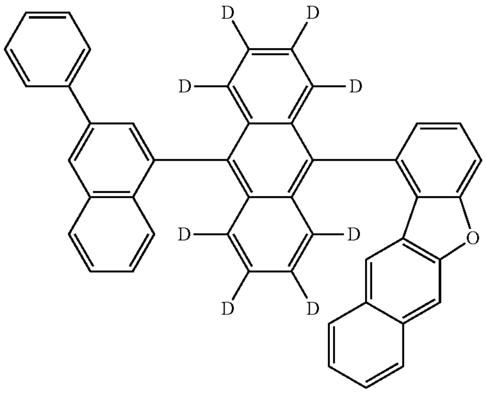

-continued
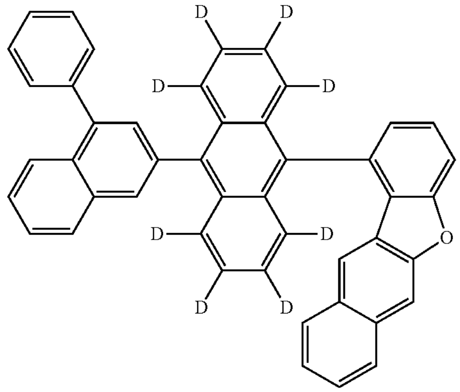
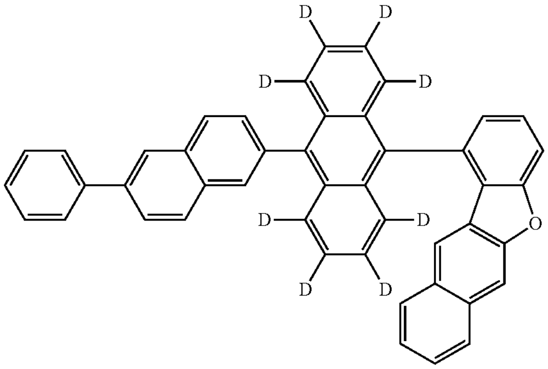
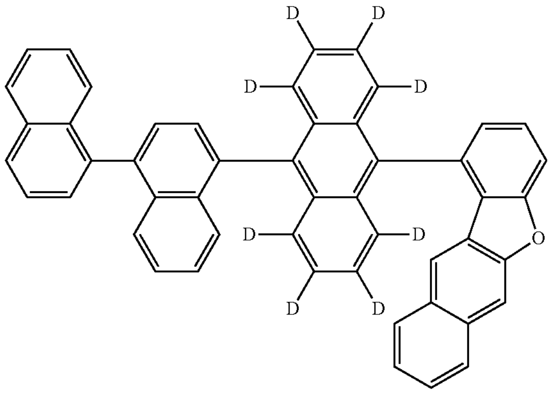
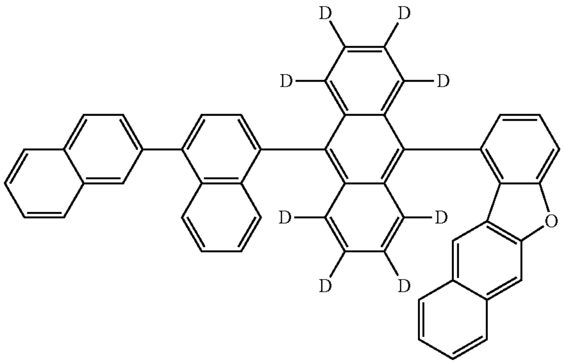
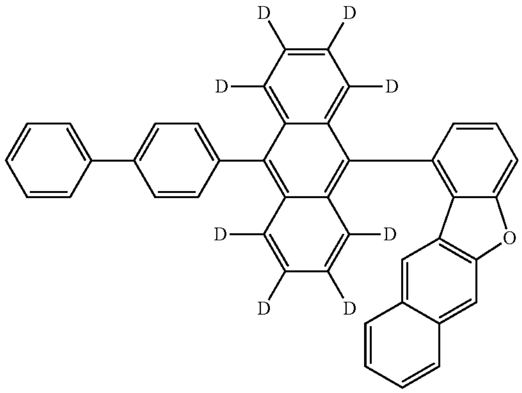
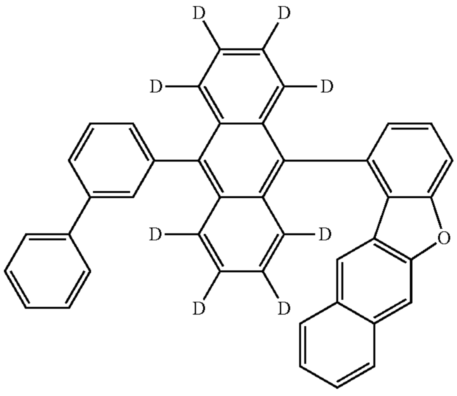
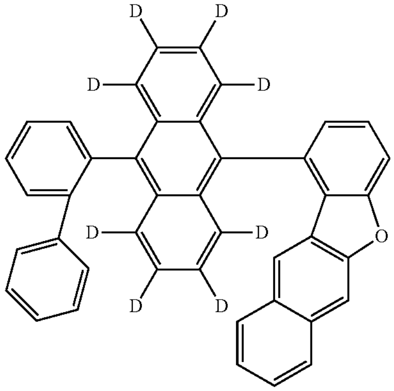
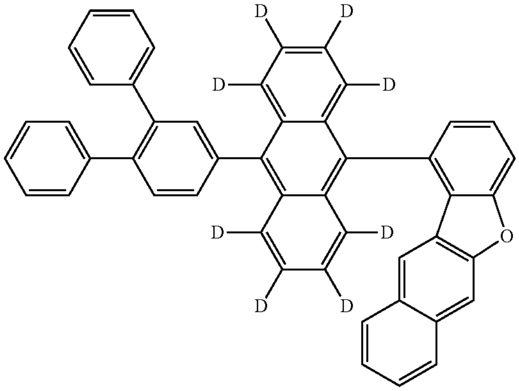

-continued
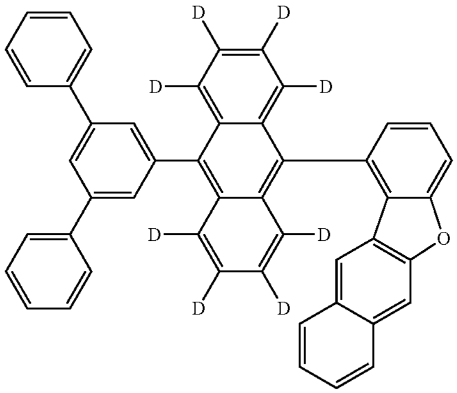
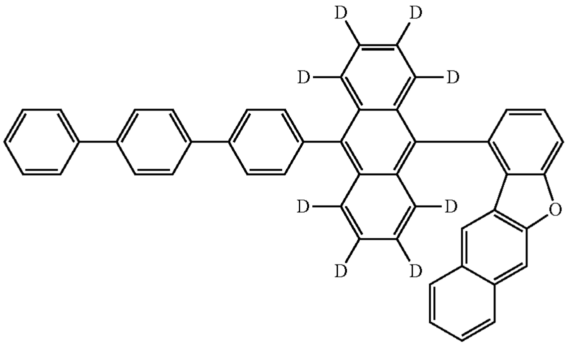
[Formula 135]
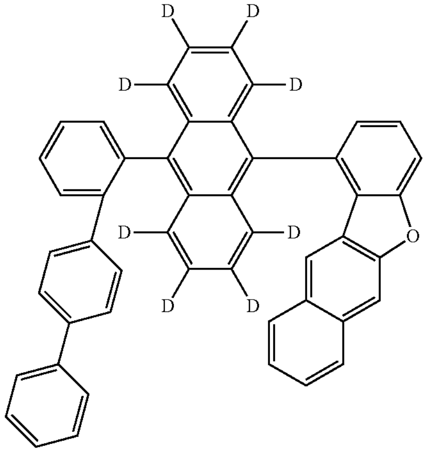
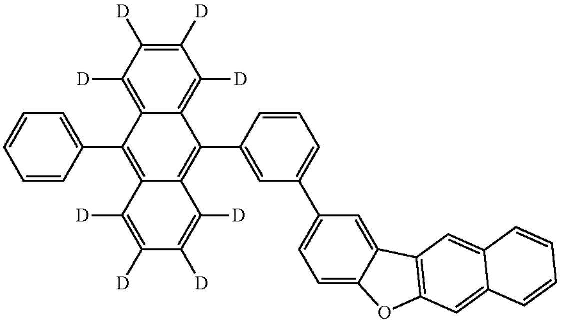
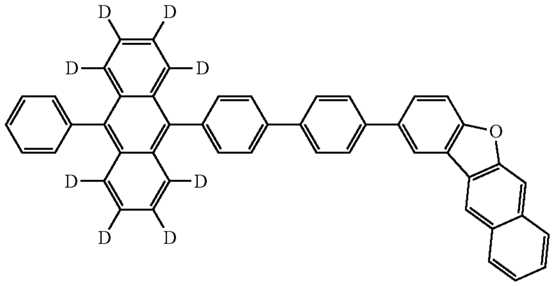
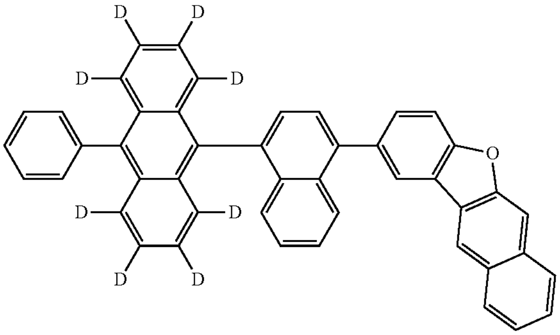
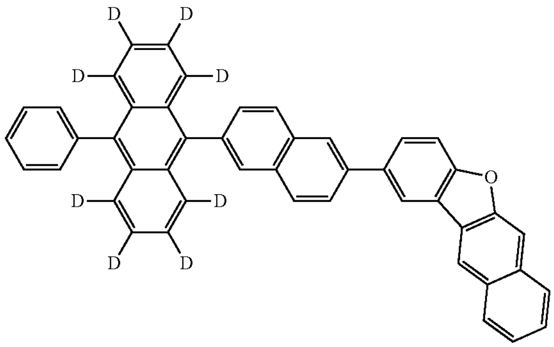
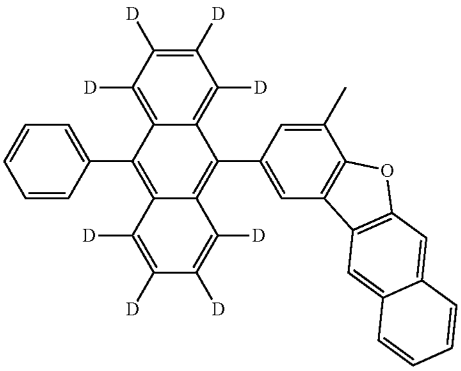

-continued
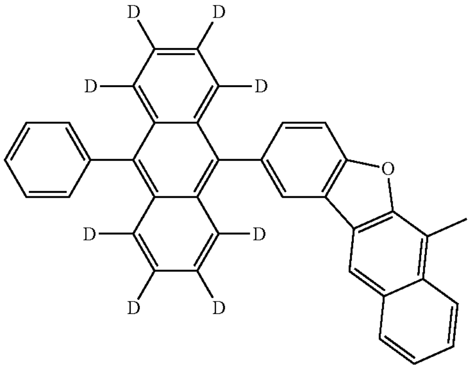
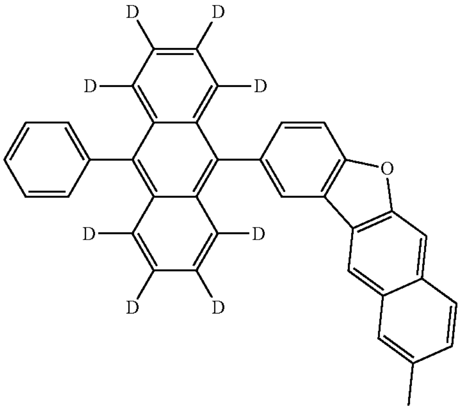
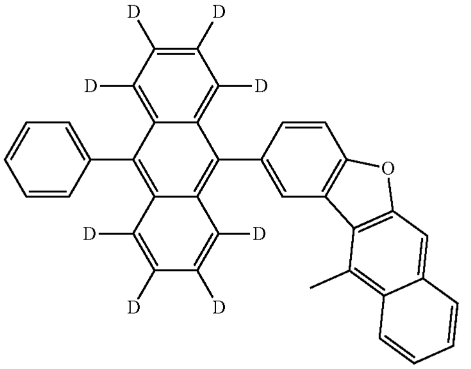
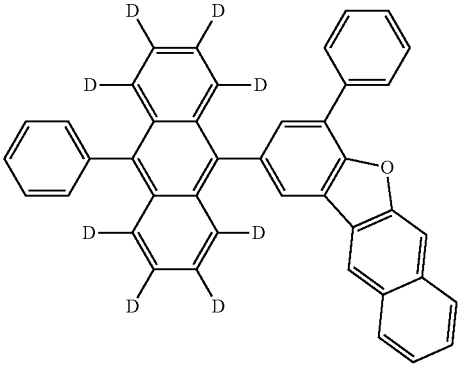
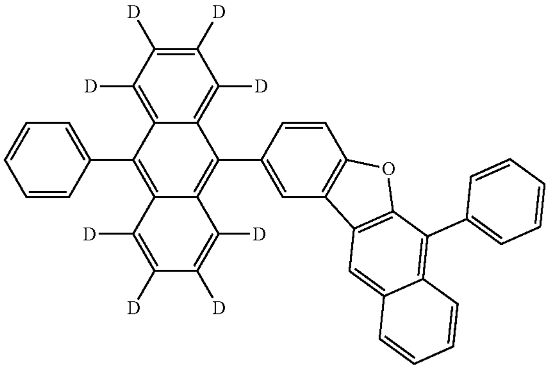
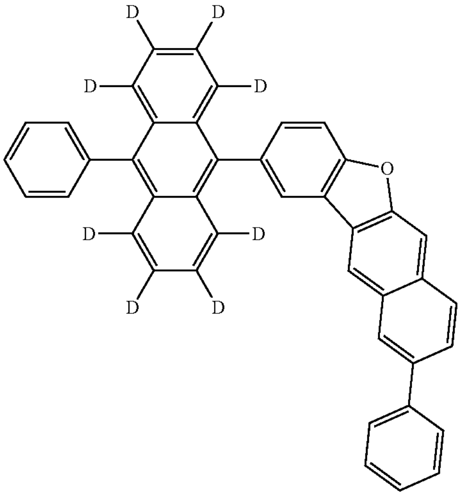
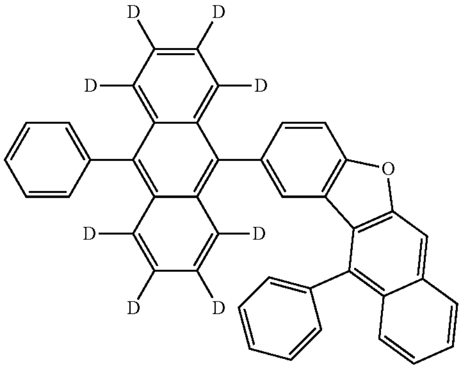

[Formula 137]
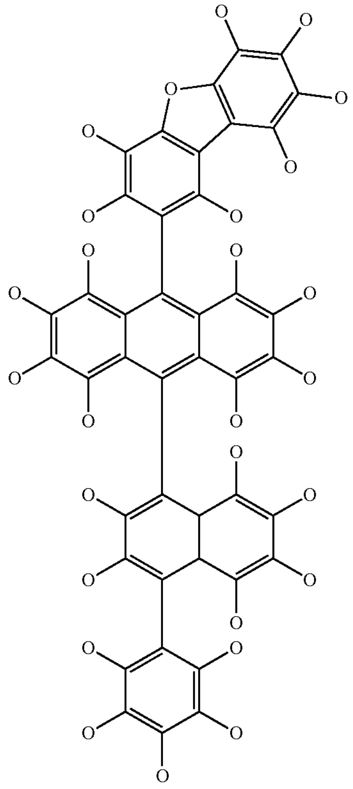
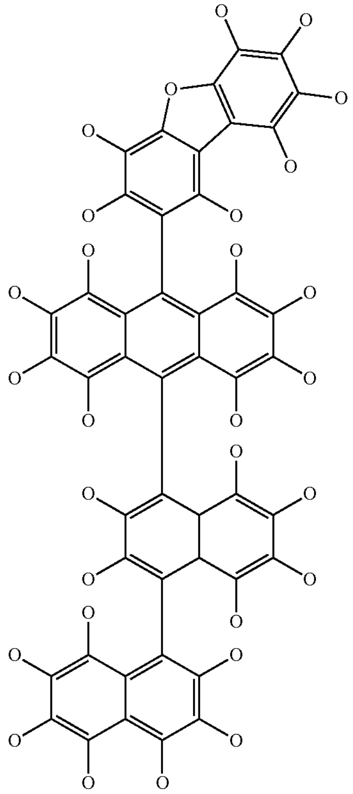
-continued
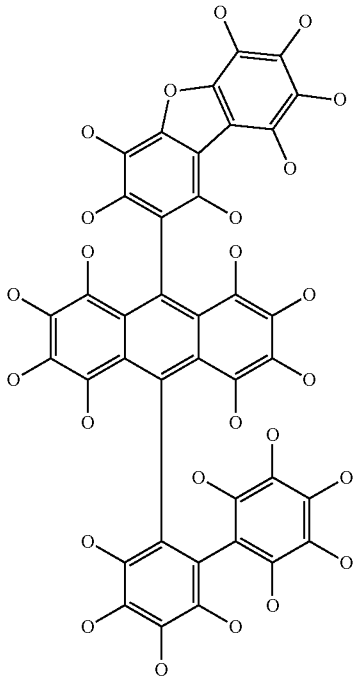
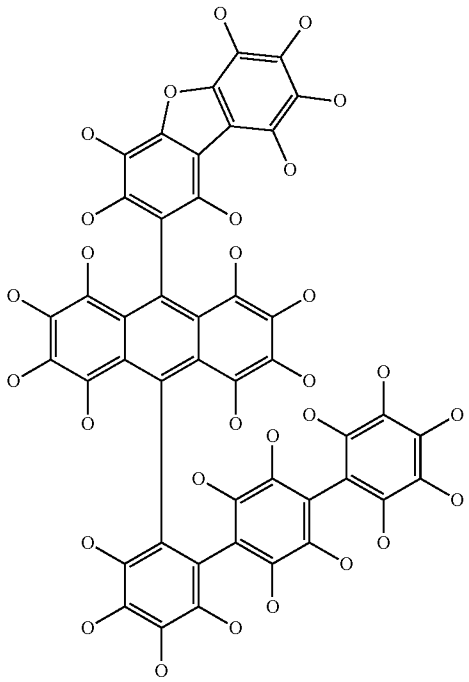

-continued
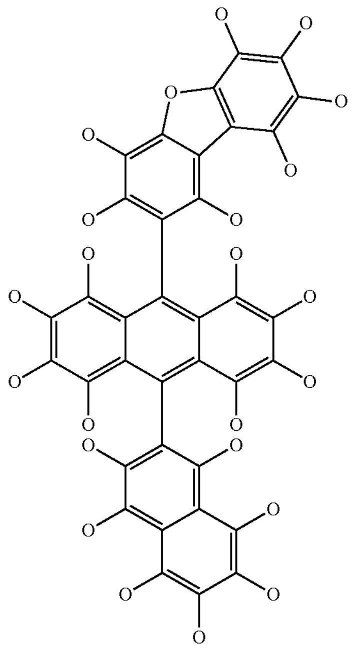
-continued
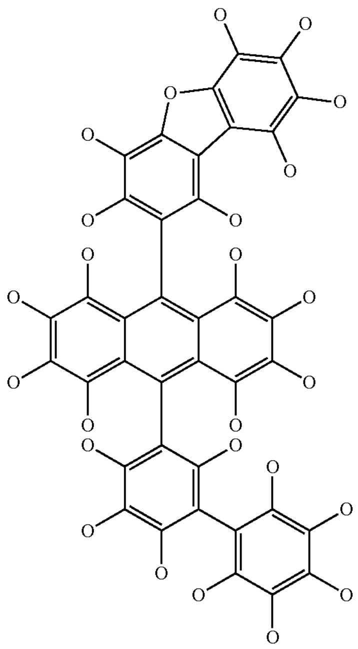
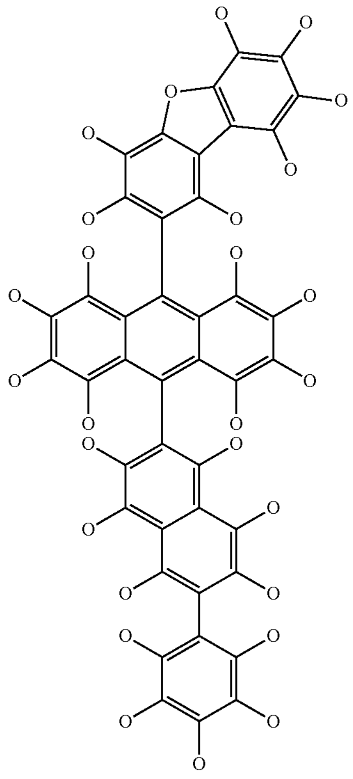
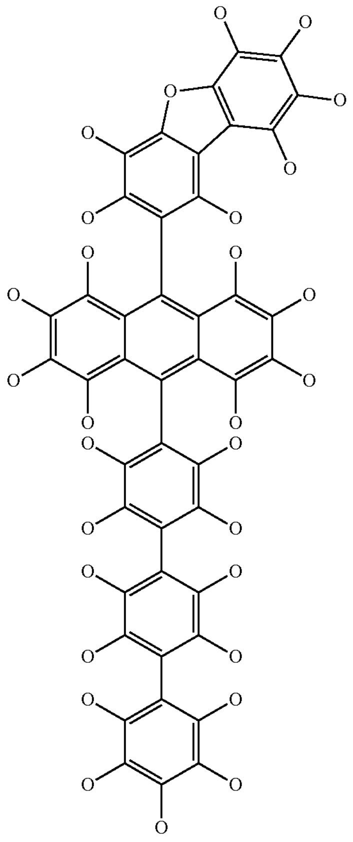

-continued
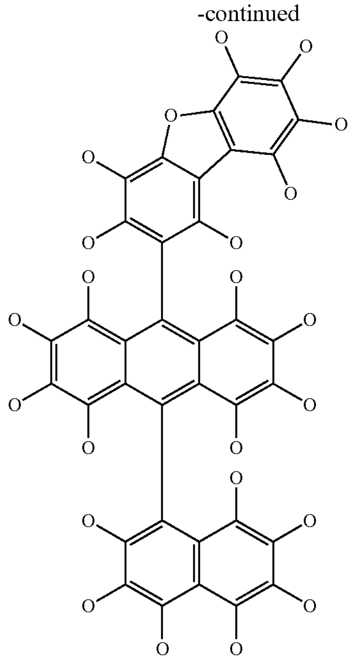
-continued
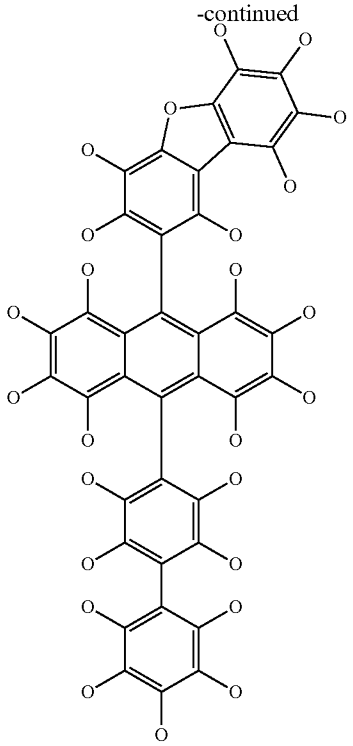
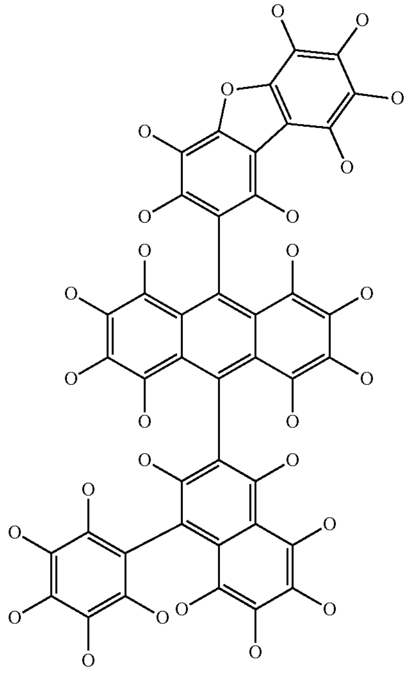
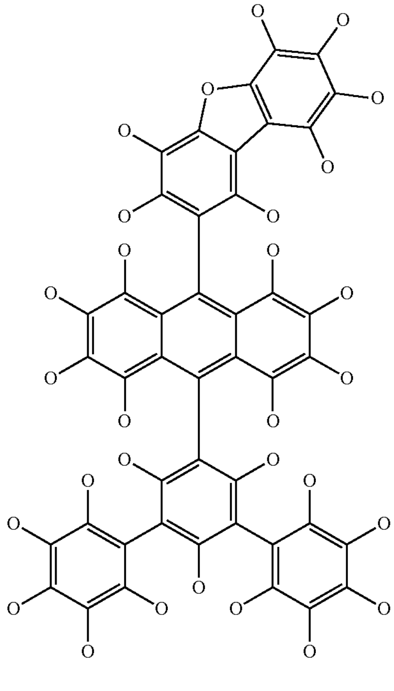

-continued
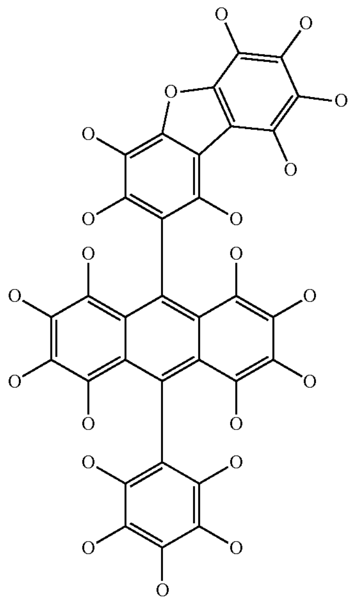
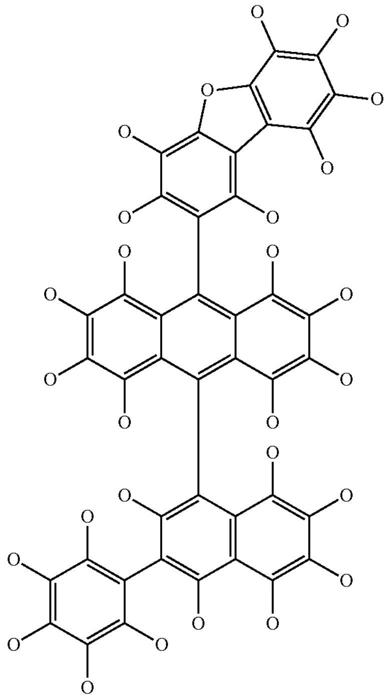
-continued
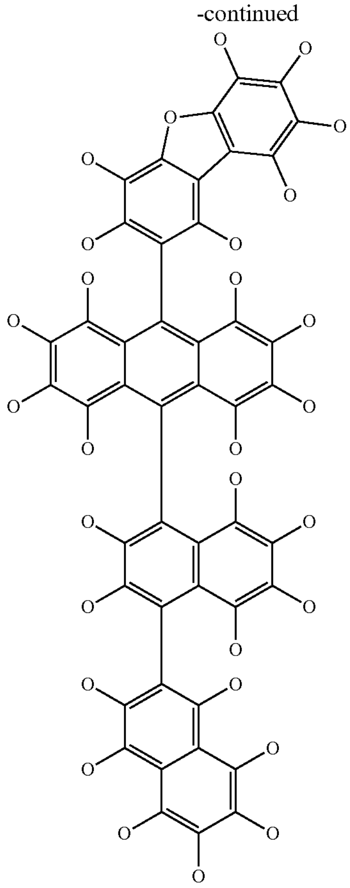
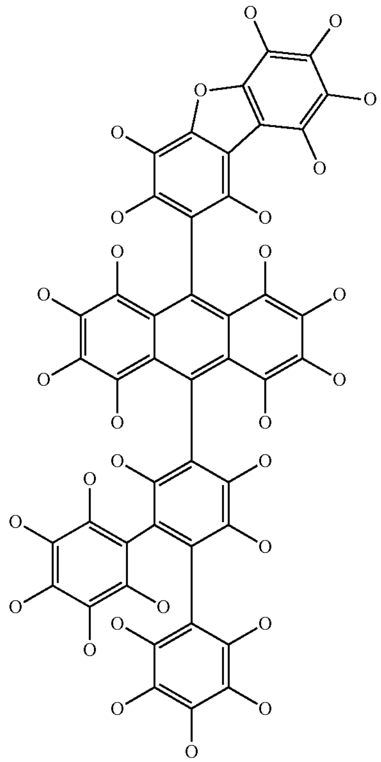

-continued
[Formula 138]
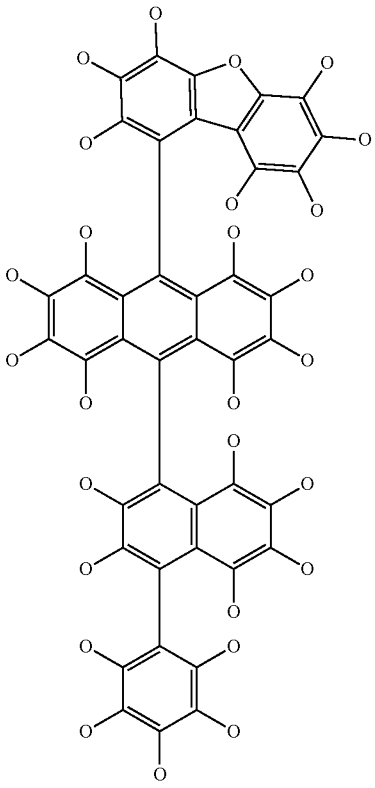
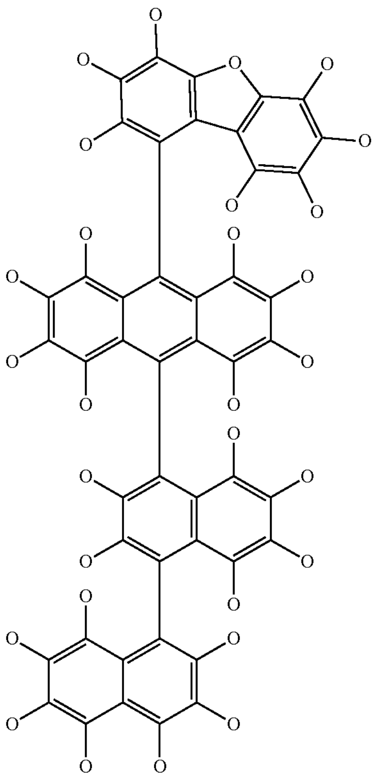
-continued
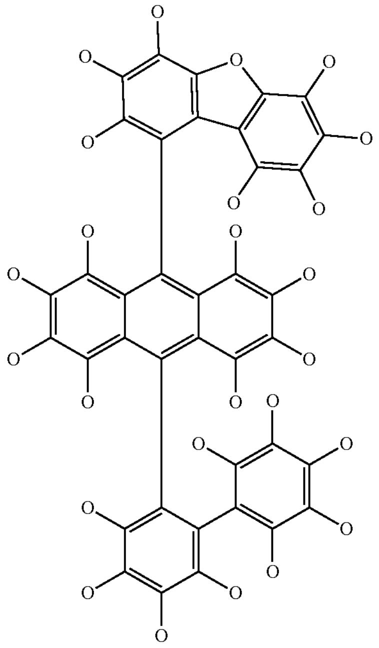
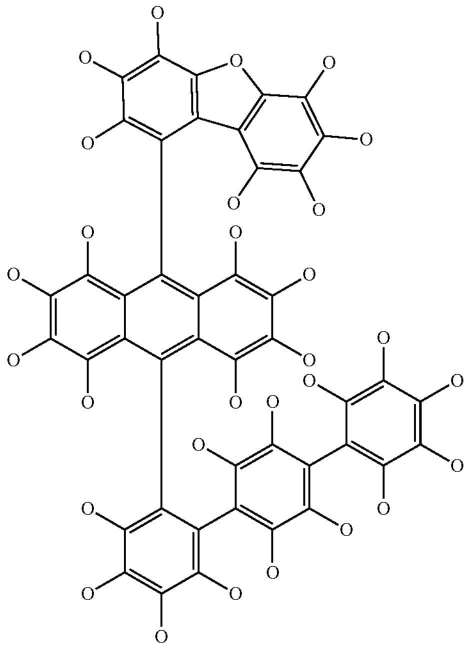

-continued
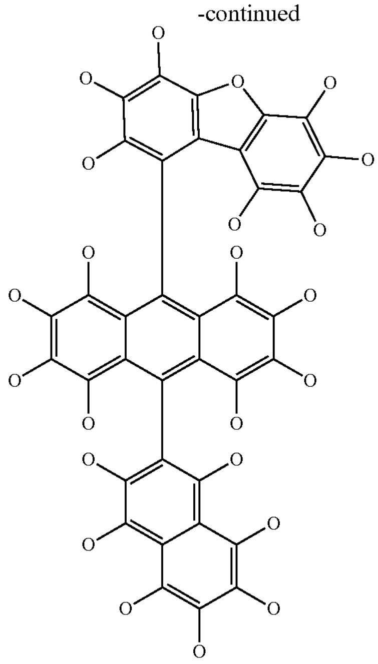
-continued
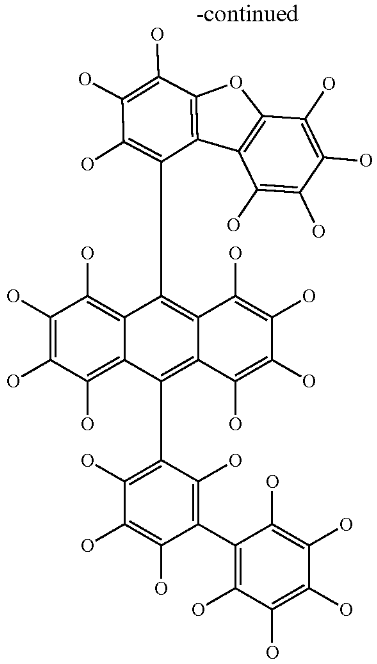
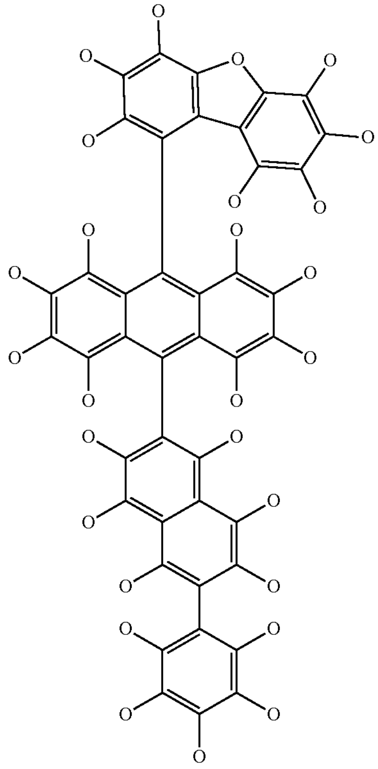
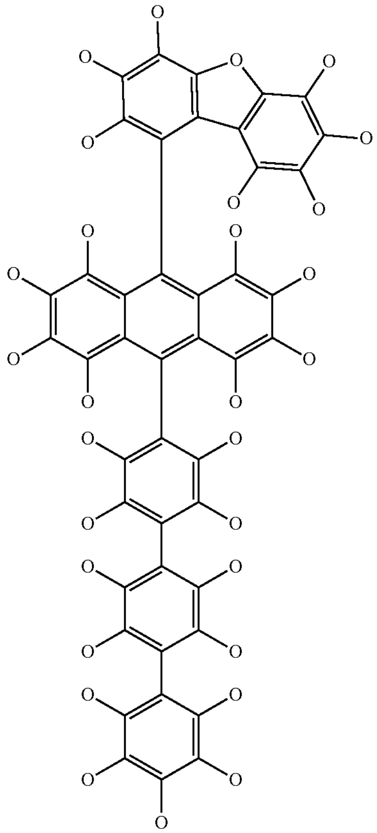

-continued
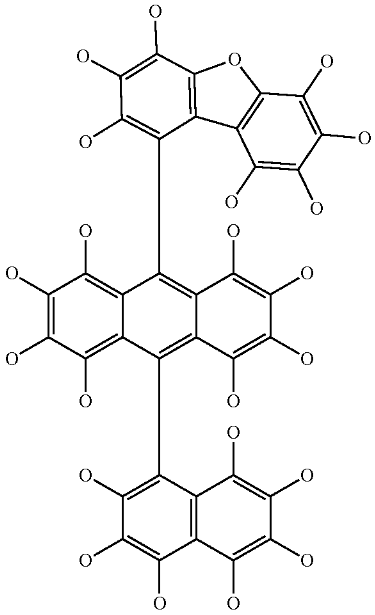
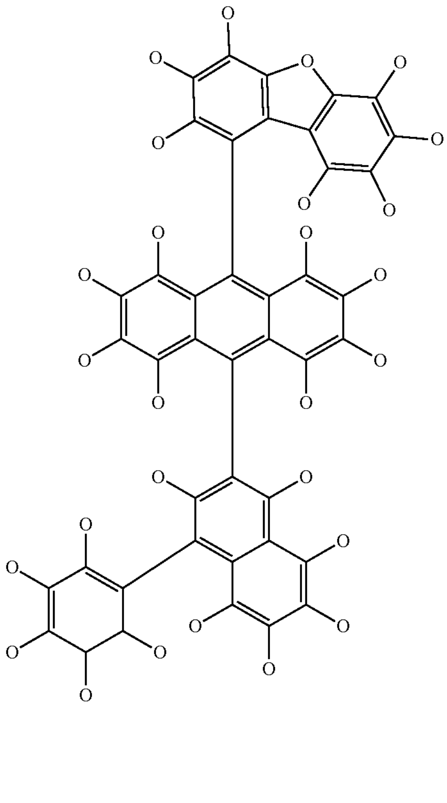
-continued
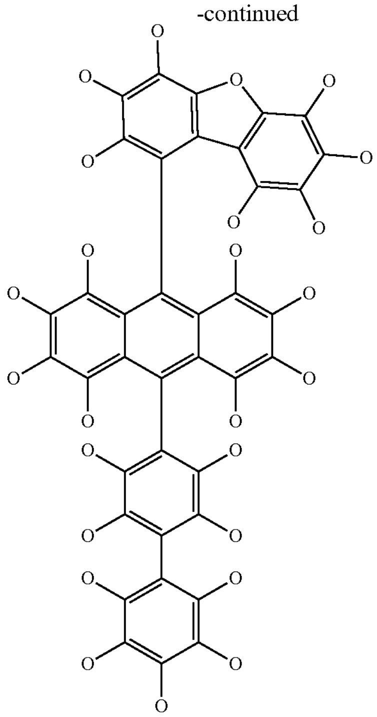
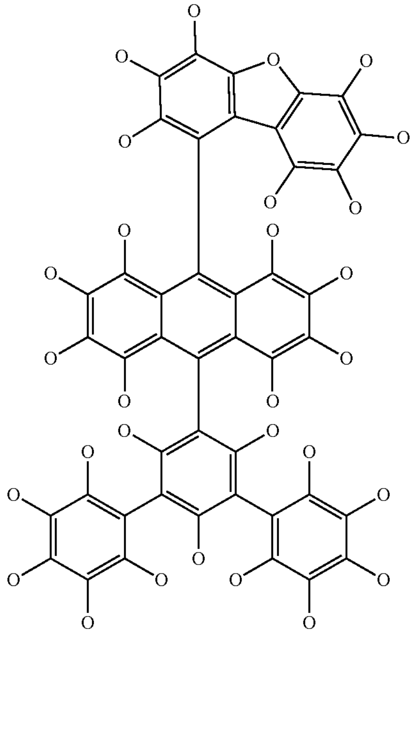

-continued
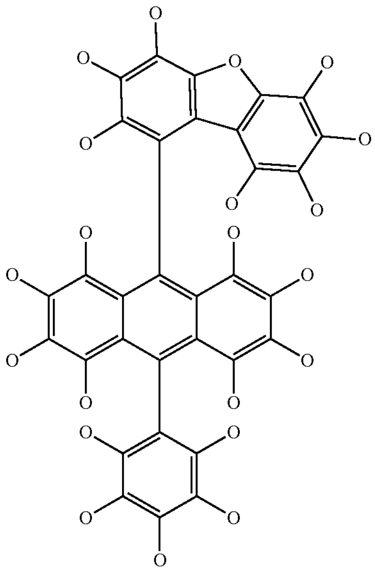
-continued
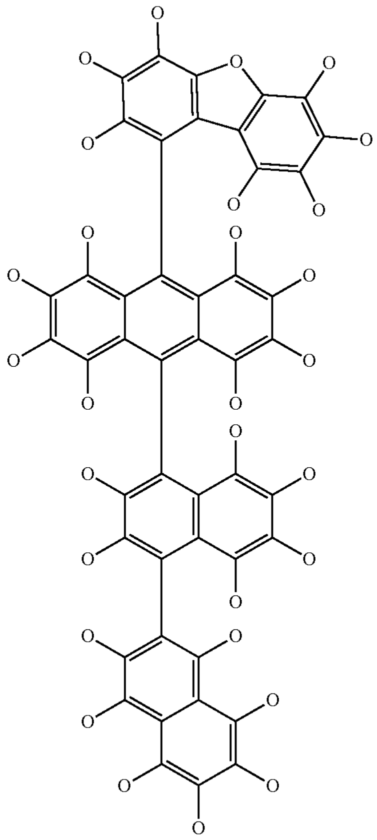
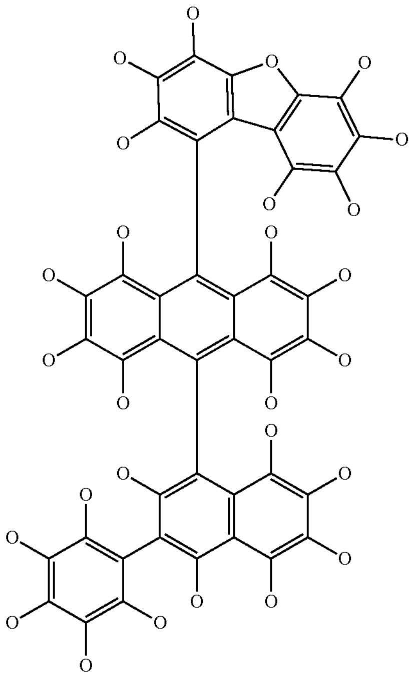
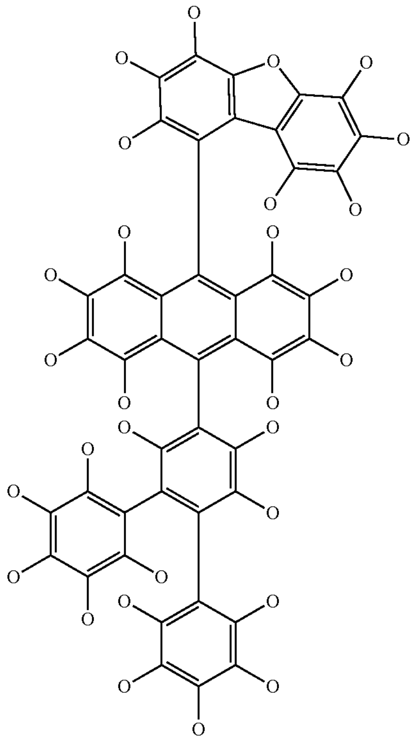

-continued
[Formula 139]
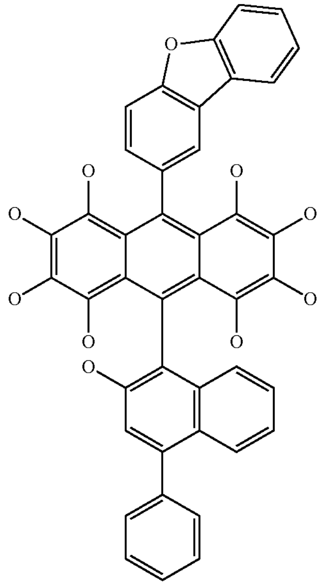
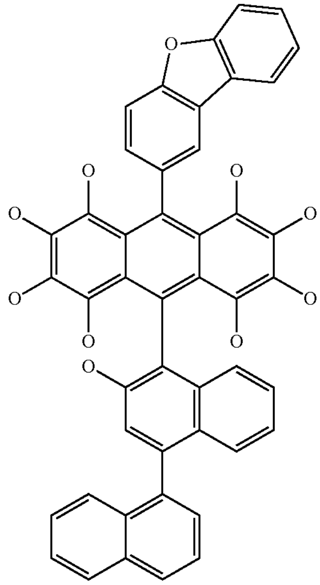
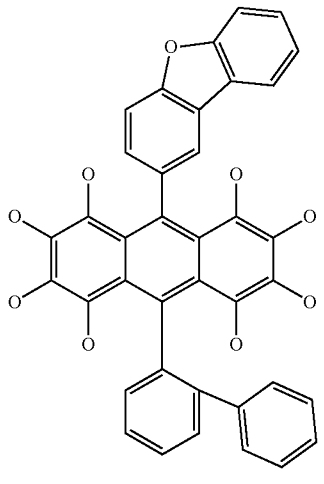
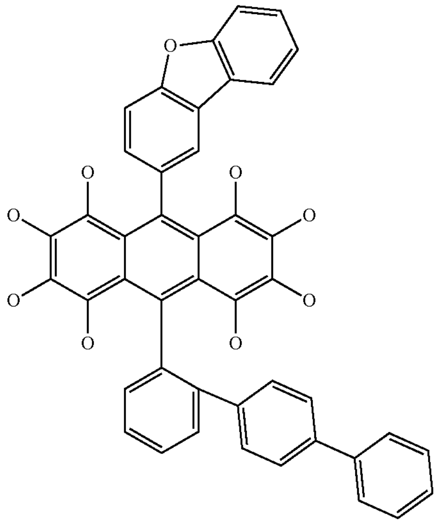
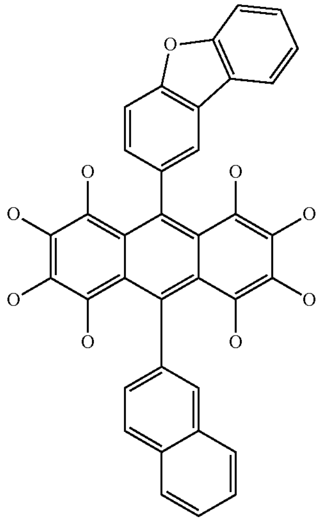
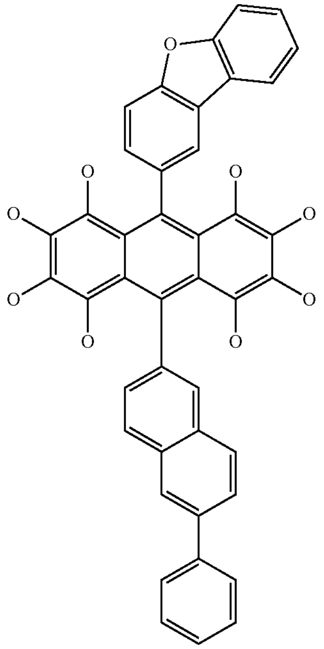
-continued -continued
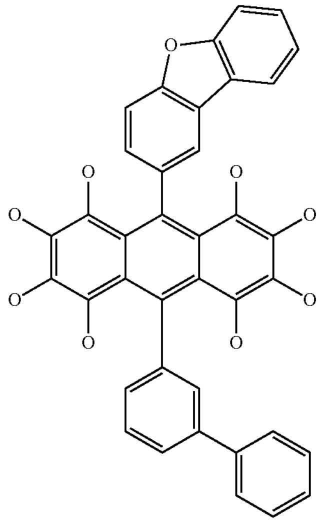
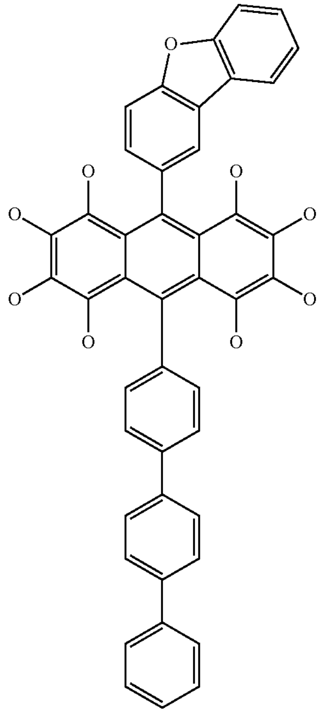
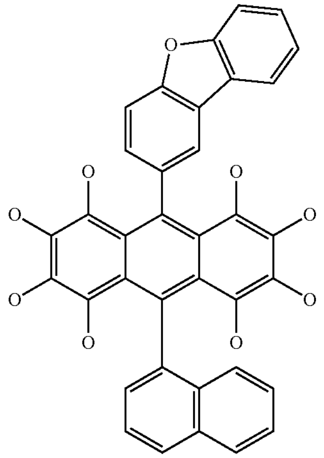
-continued
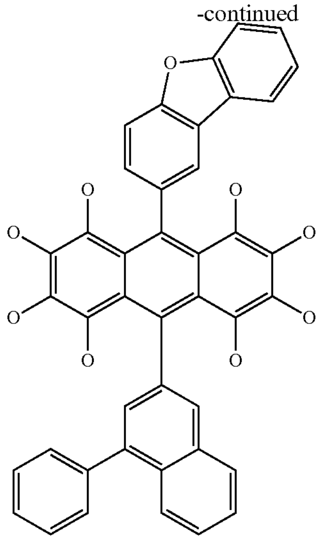
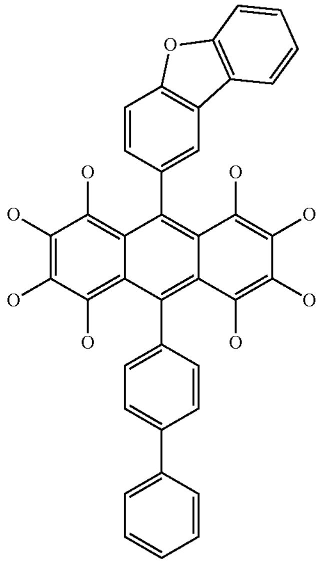
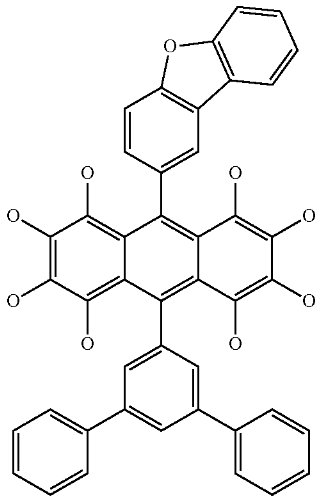

-continued
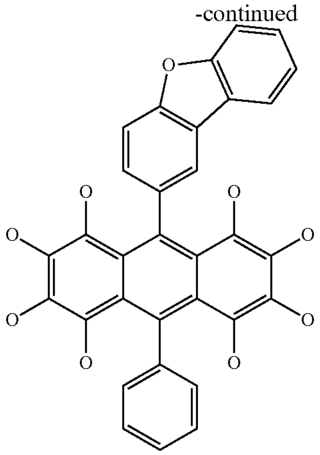
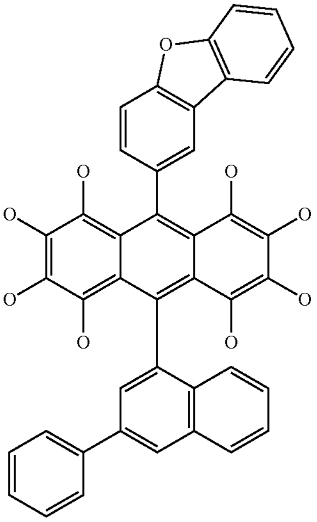
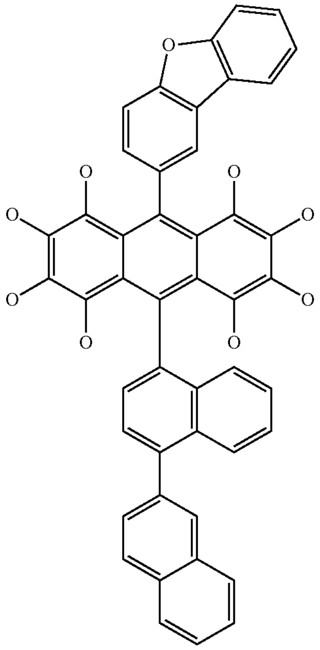
-continued
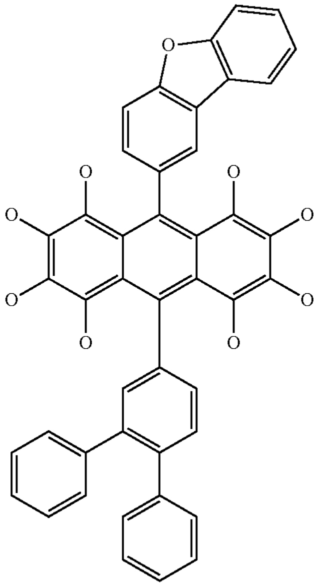
[Formula 140]
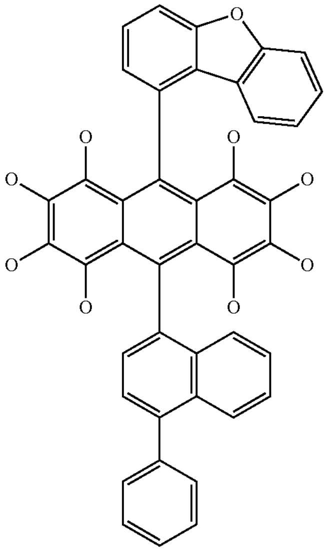
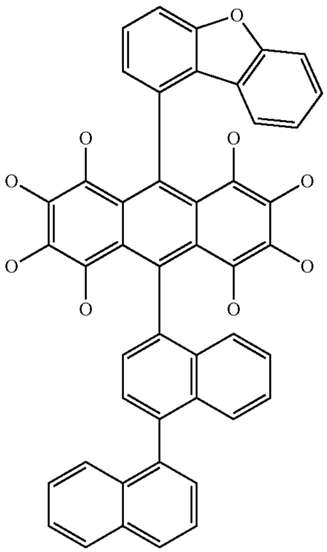

-continued
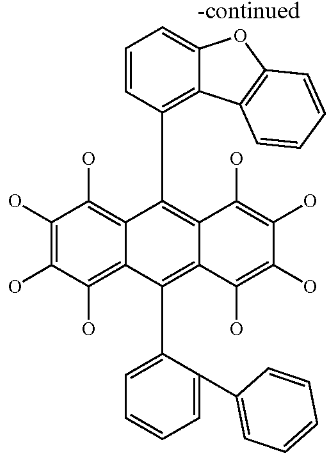
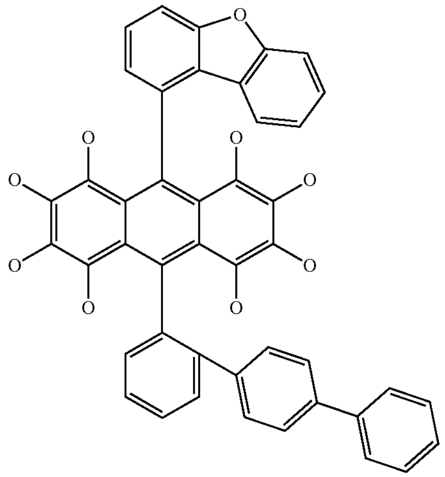
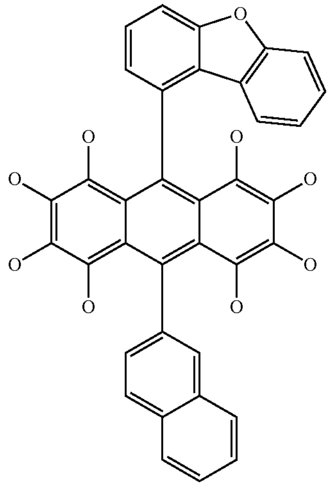
-continued
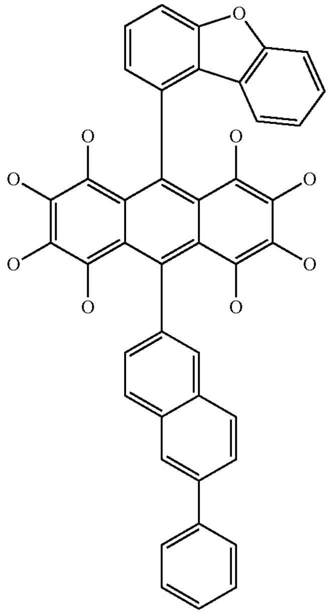
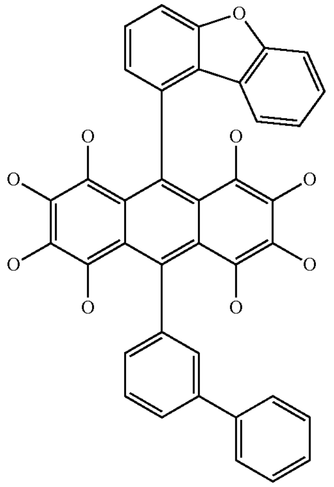

-continued
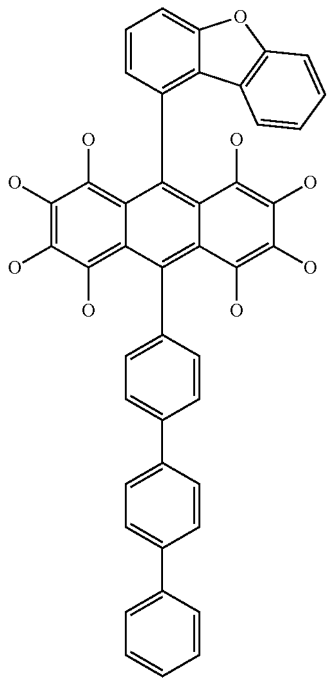
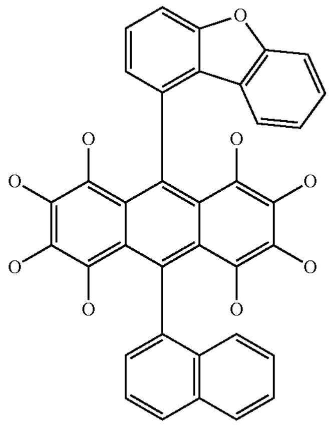
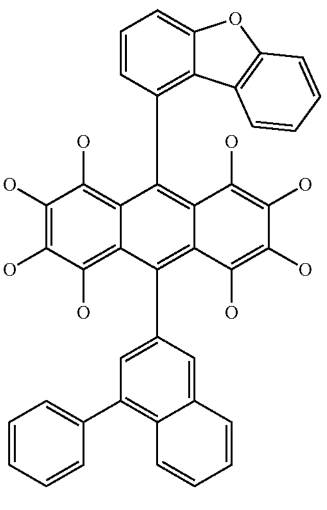
-continued
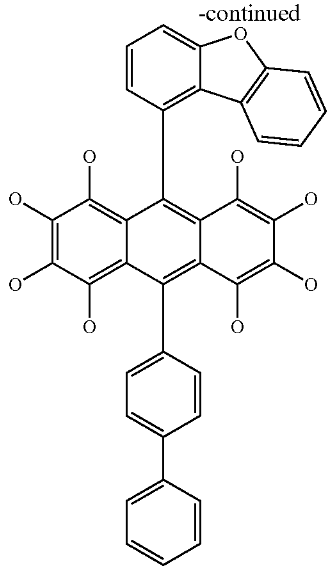
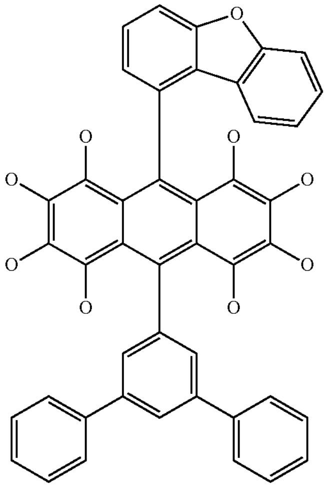
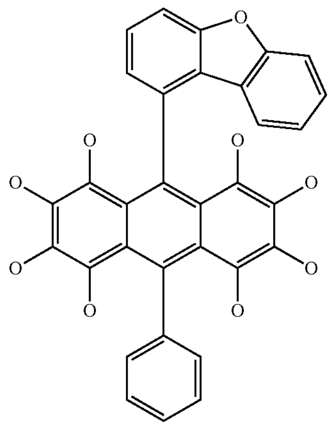

-continued
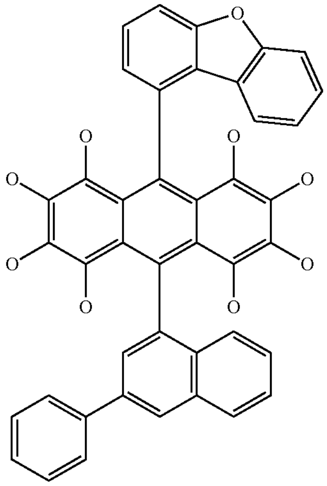
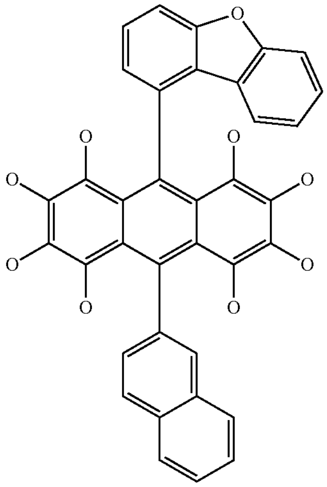
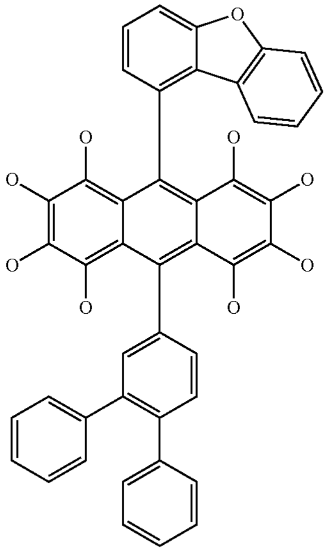
-continued
[Formula 141]
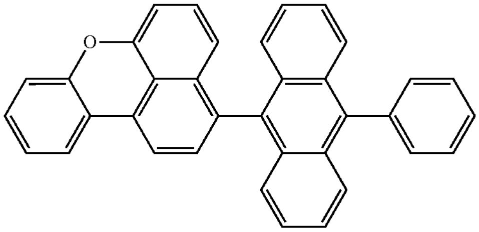
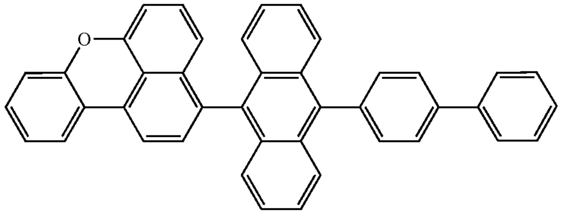
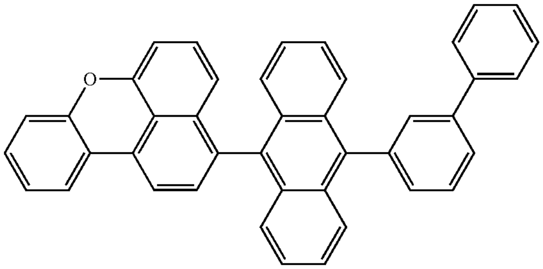
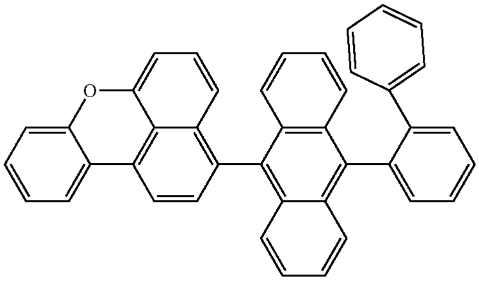
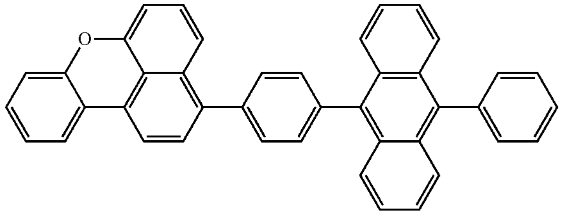
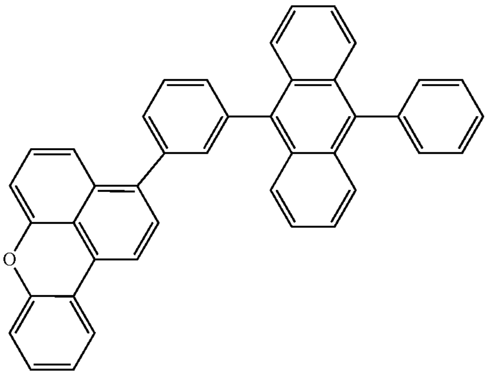

-continued
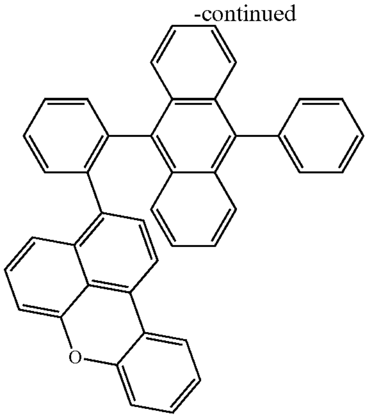
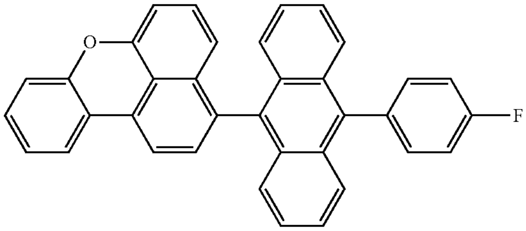
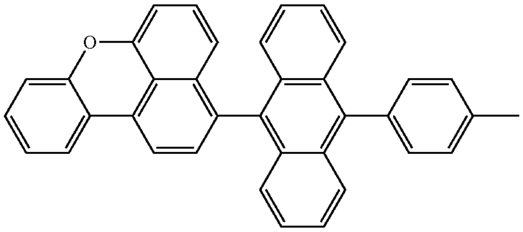
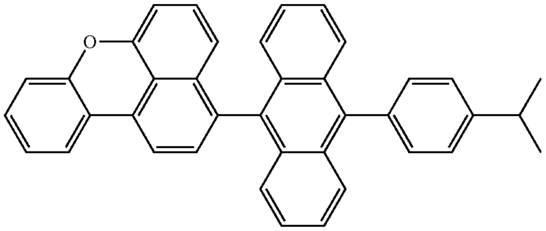
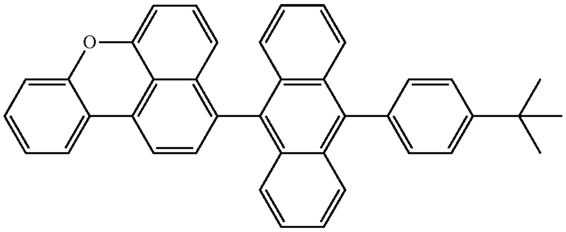
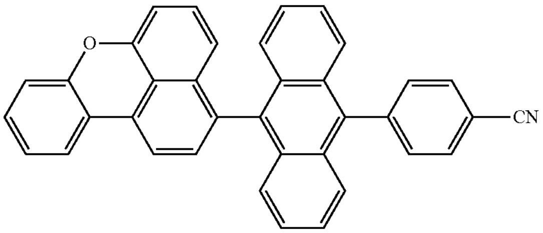
-continued
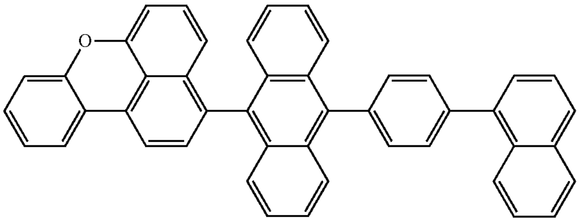
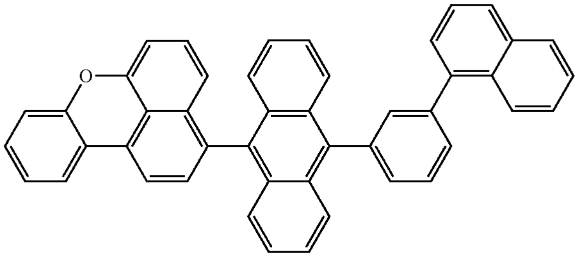
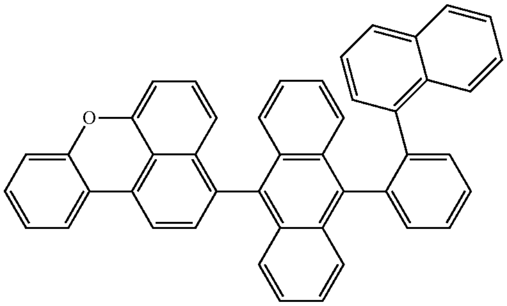
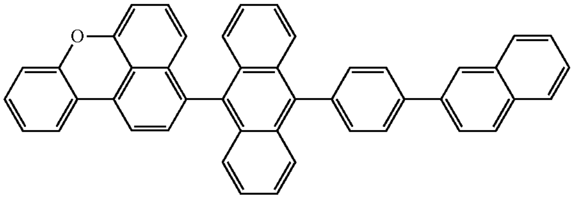
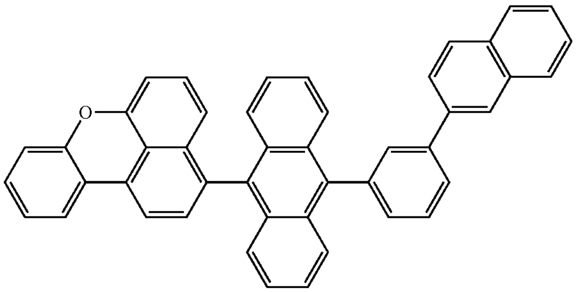
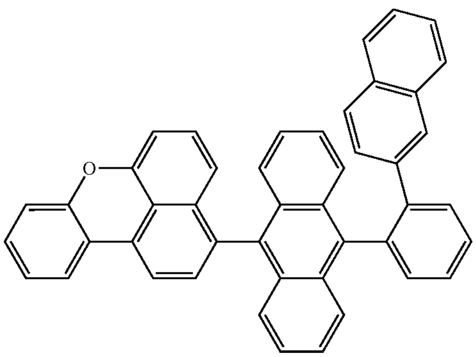

-continued
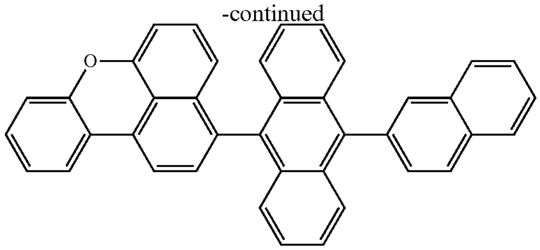
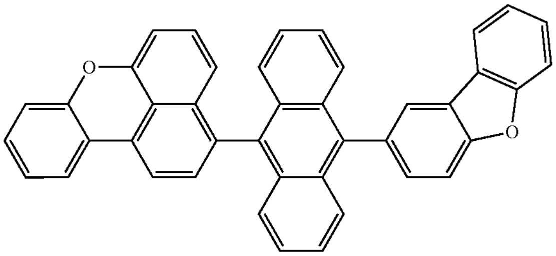
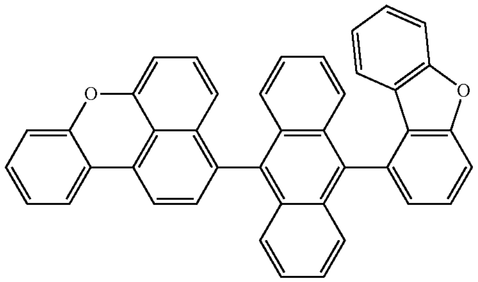
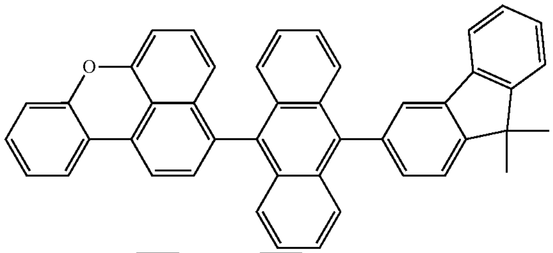
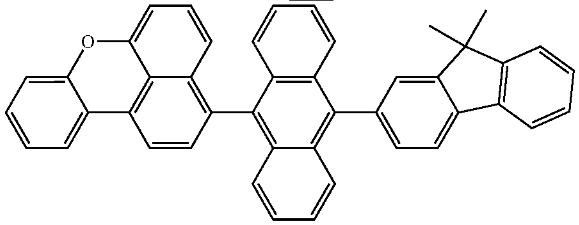
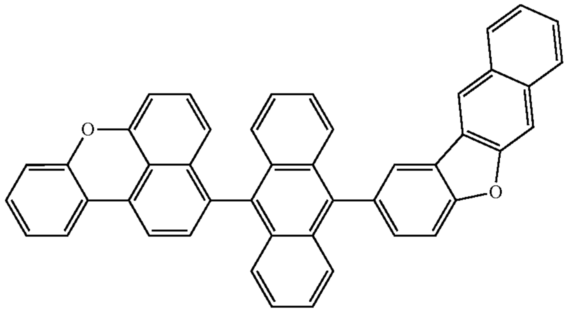
-continued
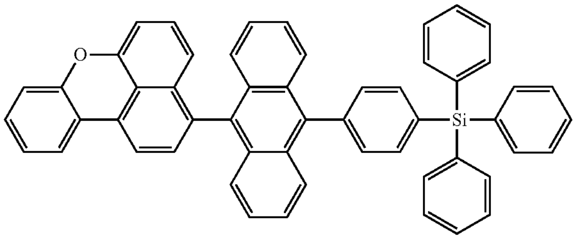
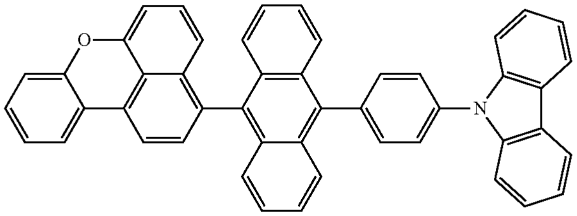
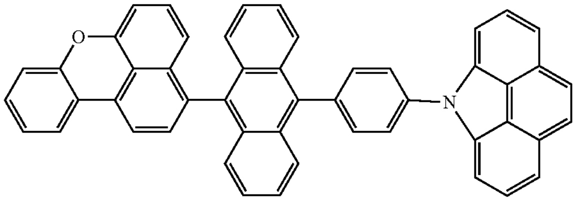
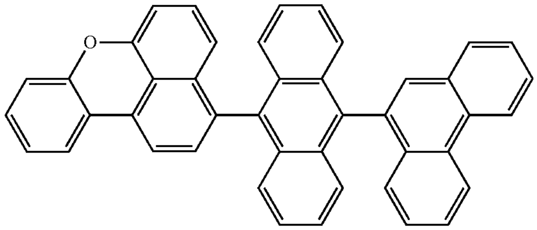
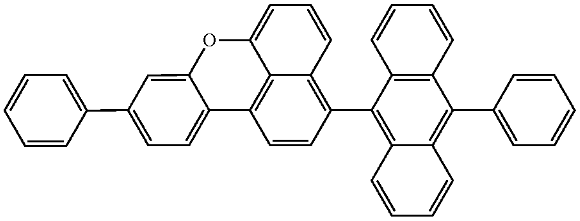
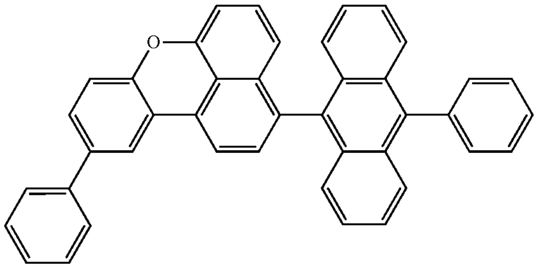
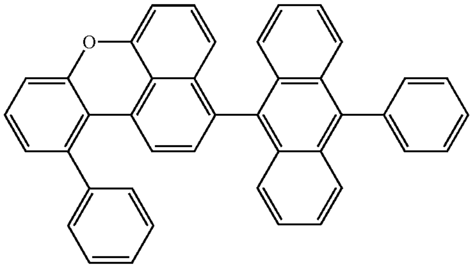

-continued
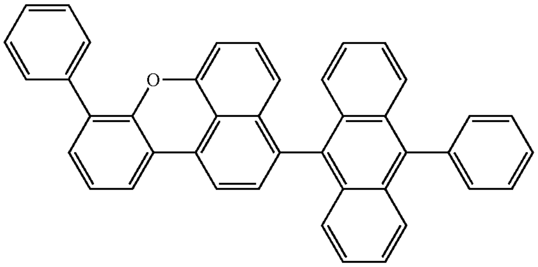
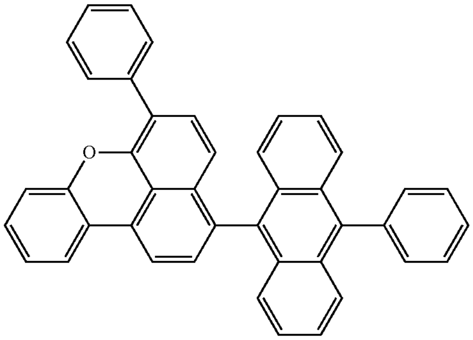
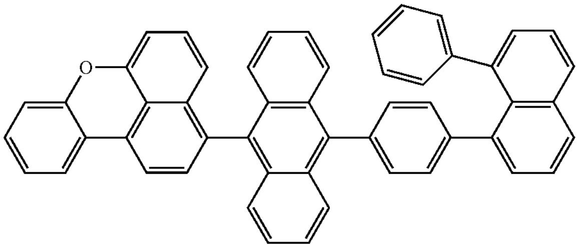
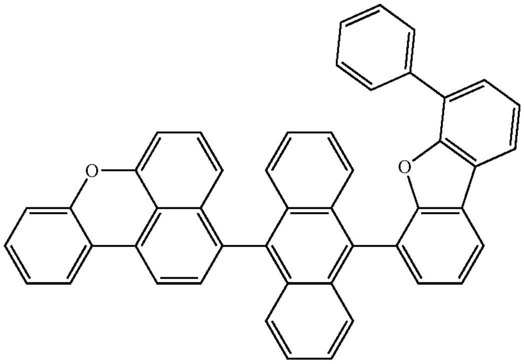
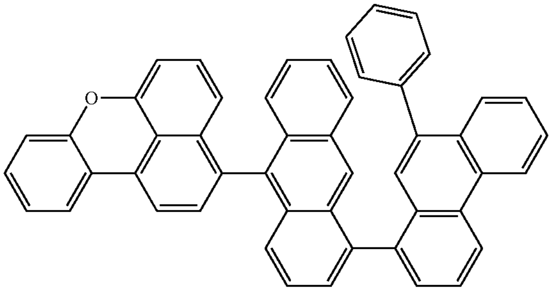
-continued
[Formula 142]
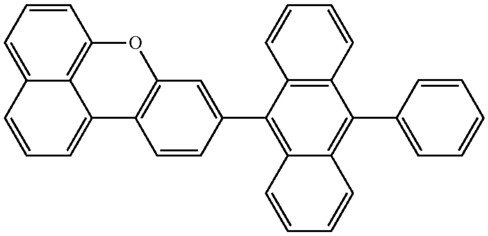
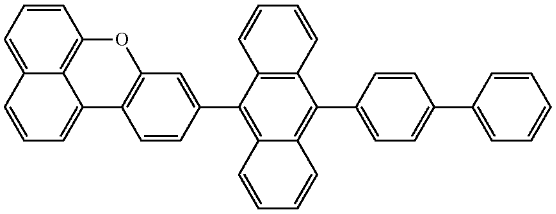
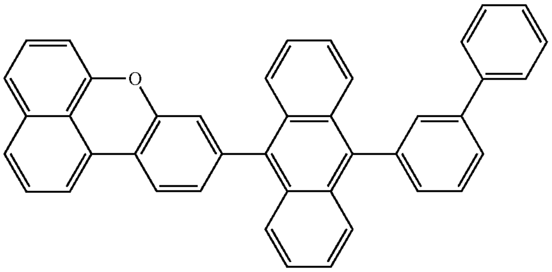
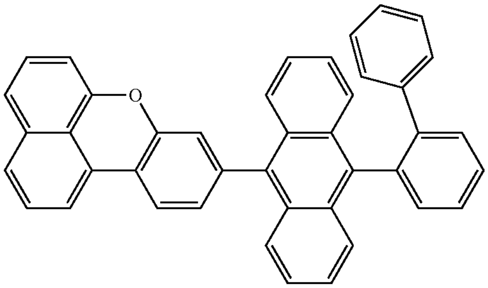
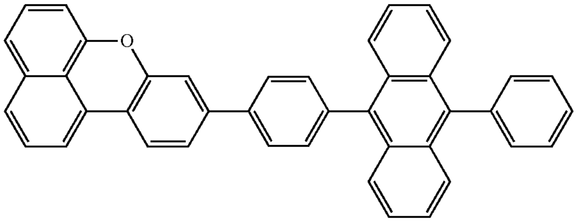
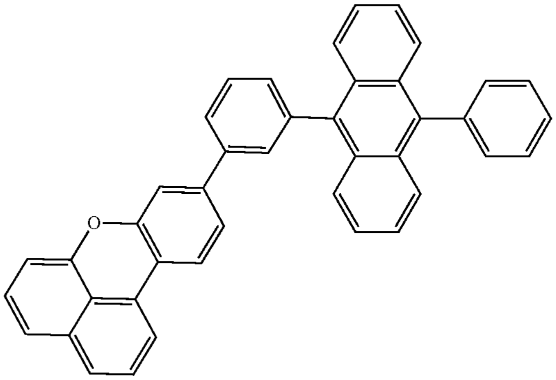

-continued
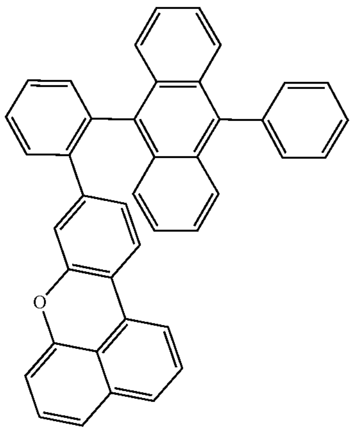
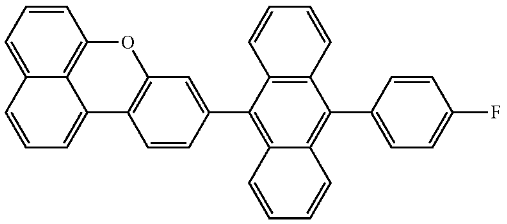
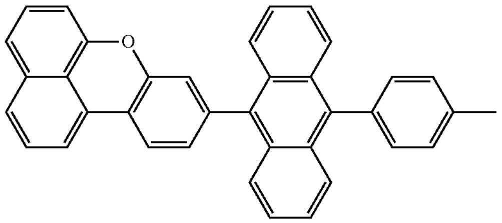
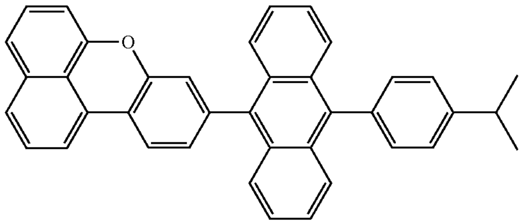
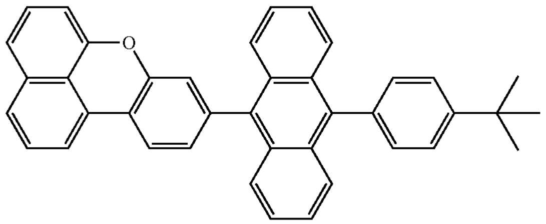
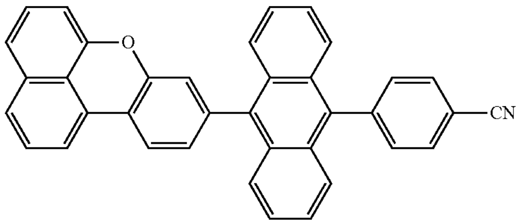
-continued
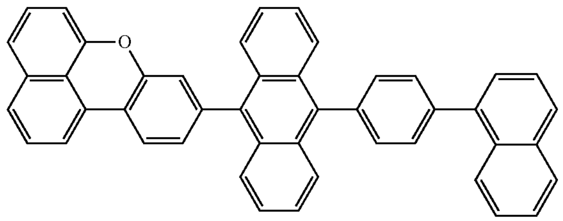
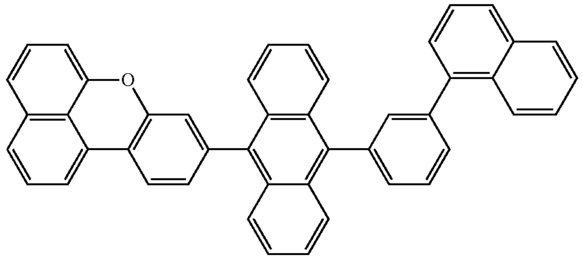
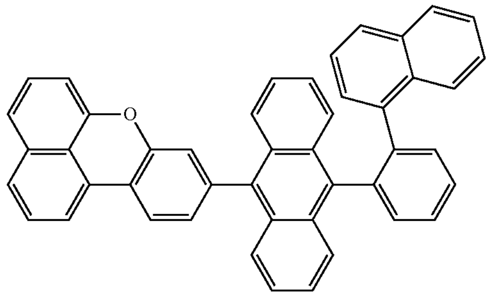
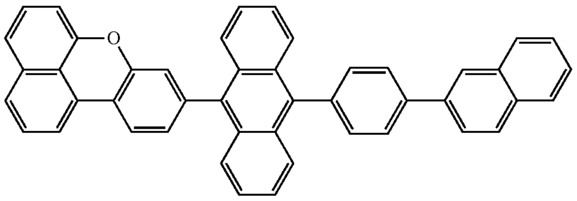
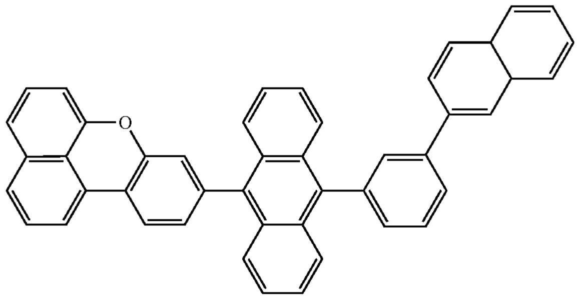
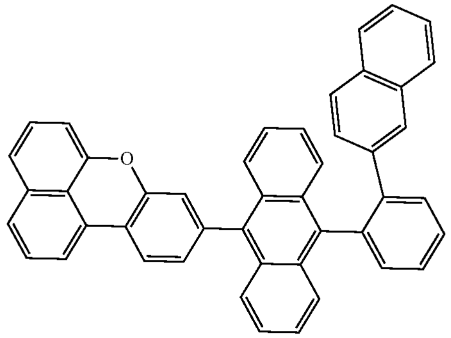

-continued
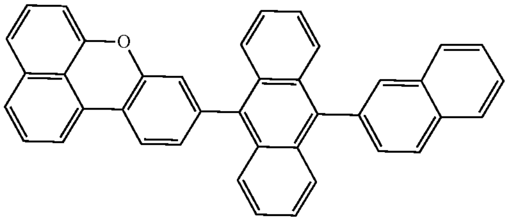
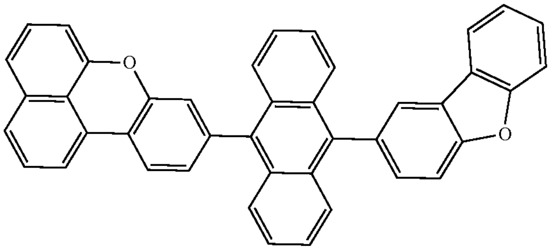
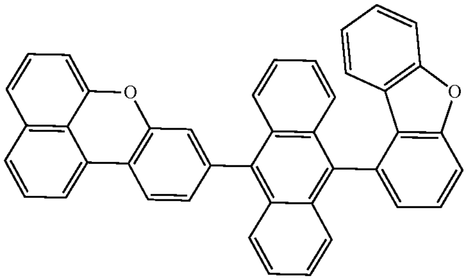
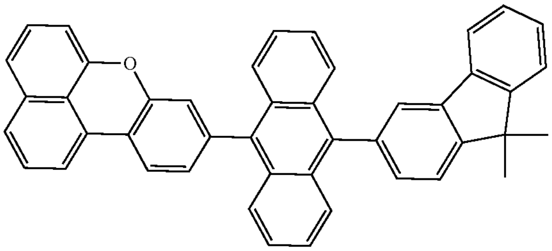
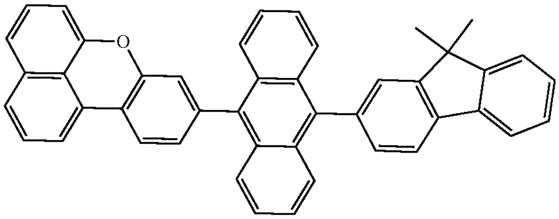
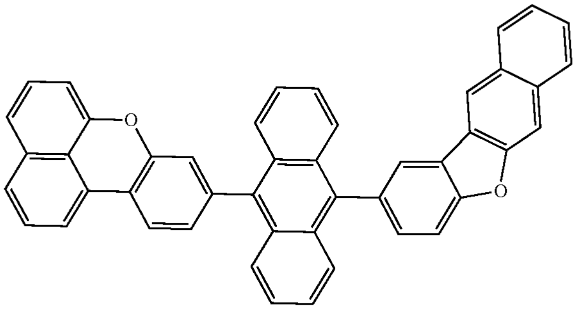
-continued
[Formula 143]
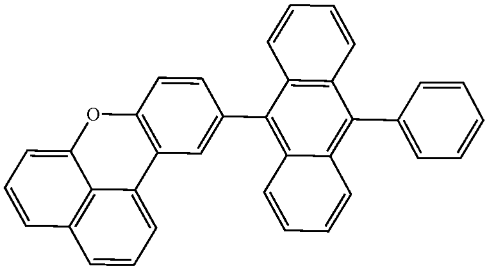
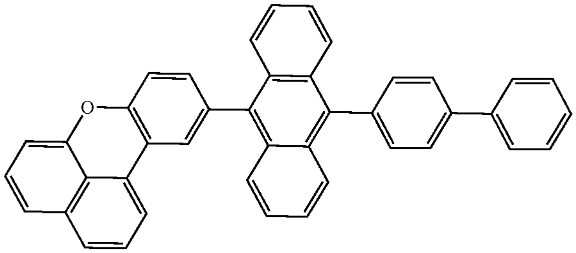
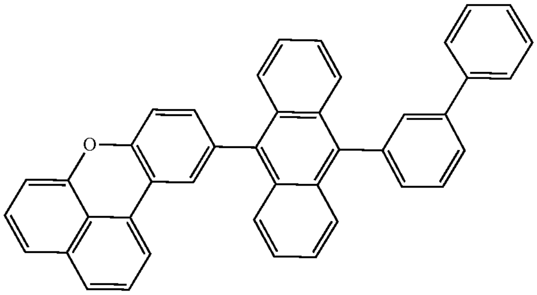
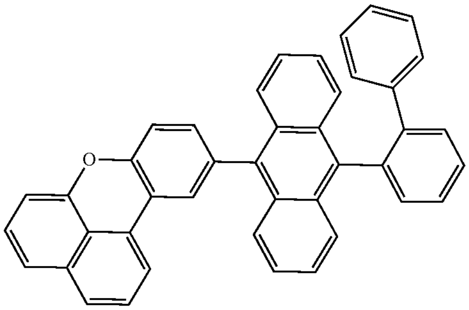
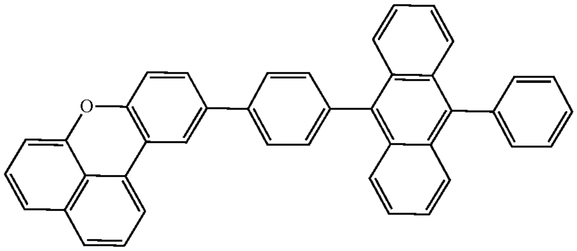

-continued
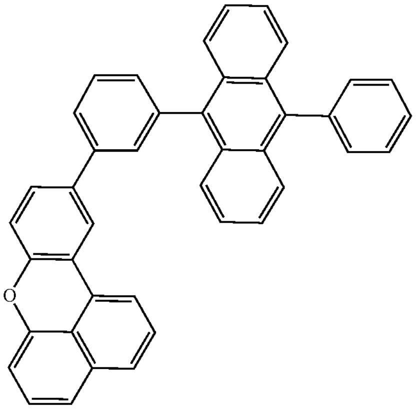
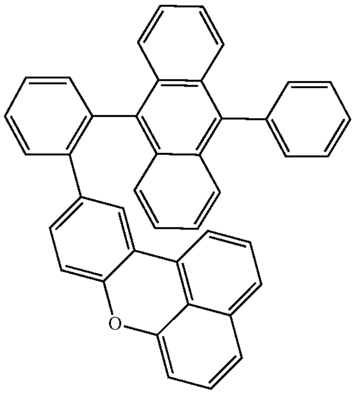
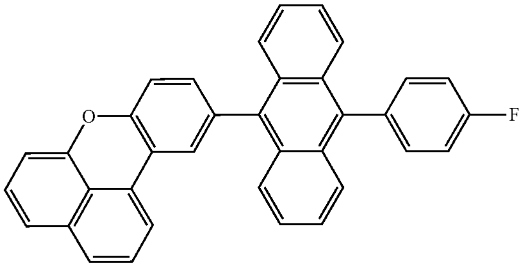
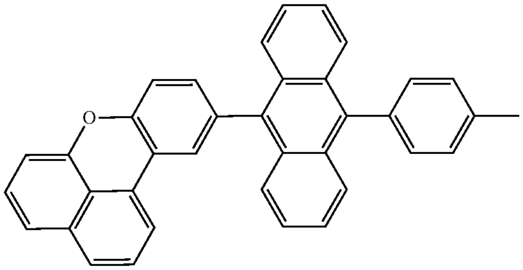
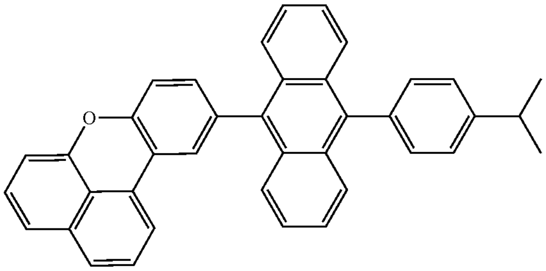
-continued
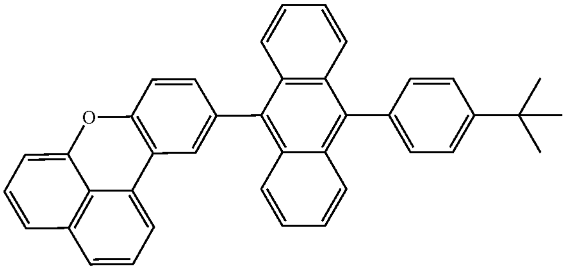
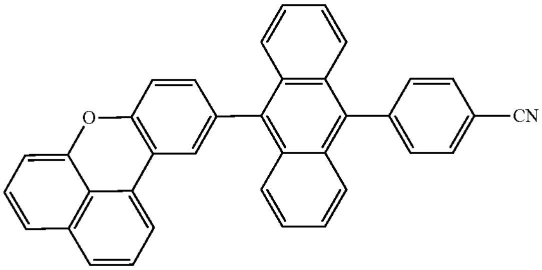
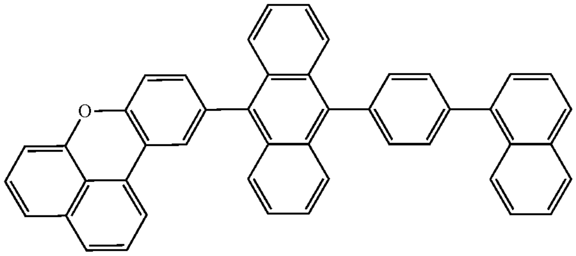
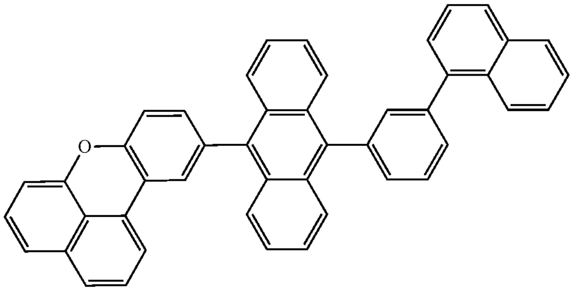
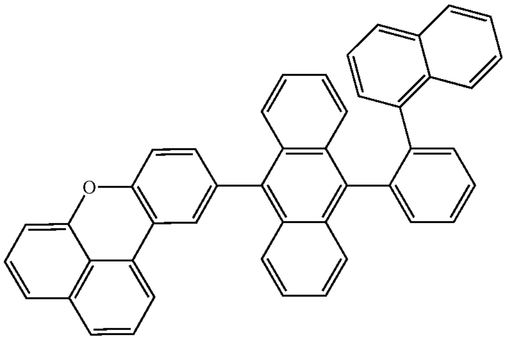
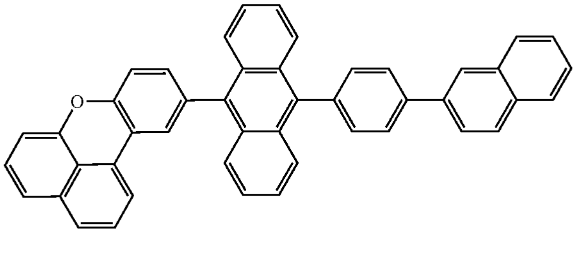

-continued
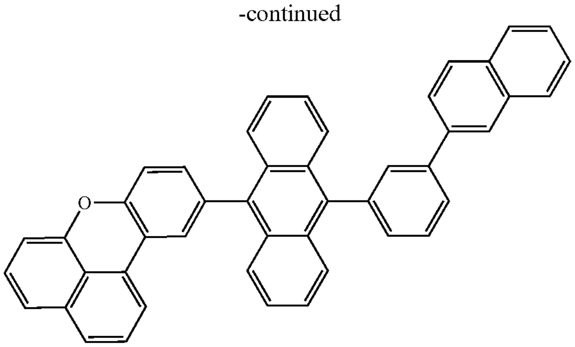
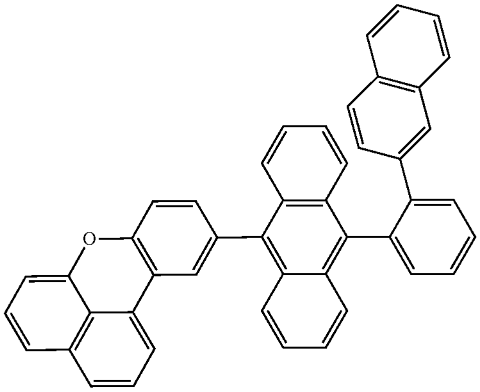
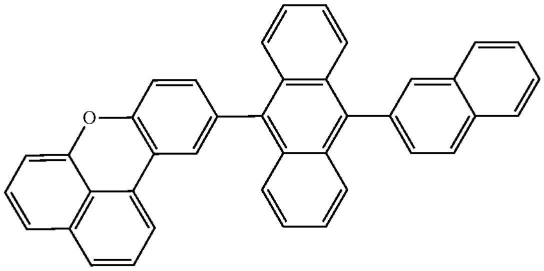
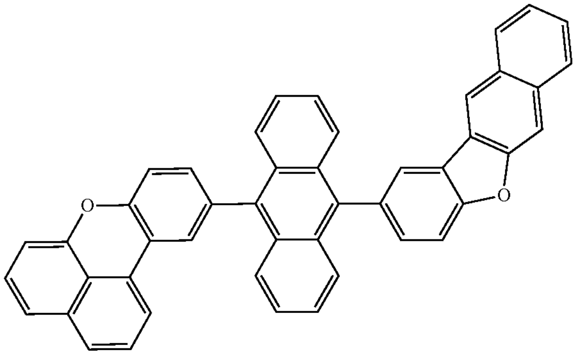
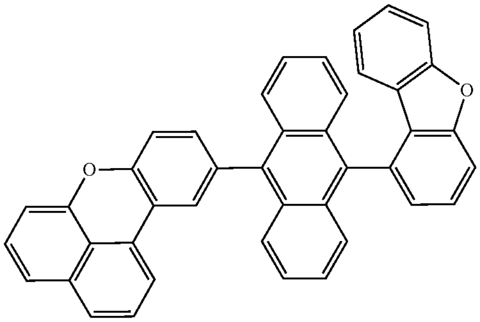
-continued
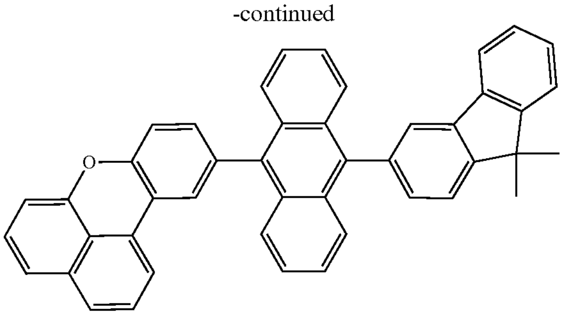
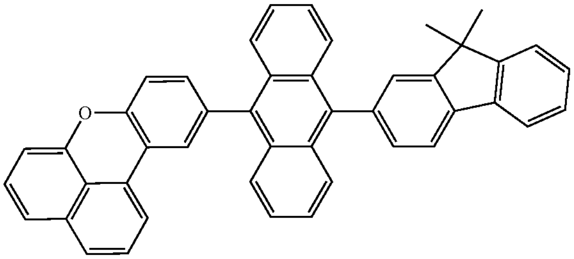
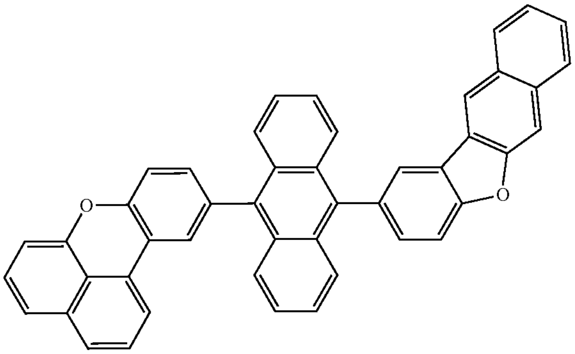
[Formula 144]
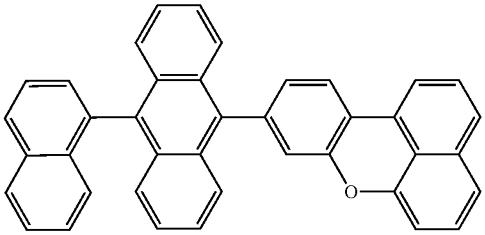
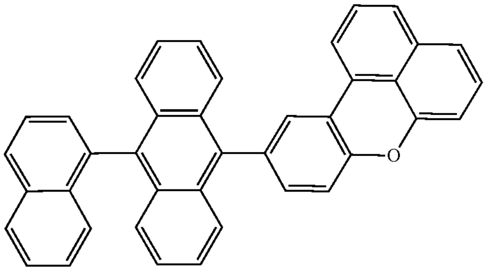
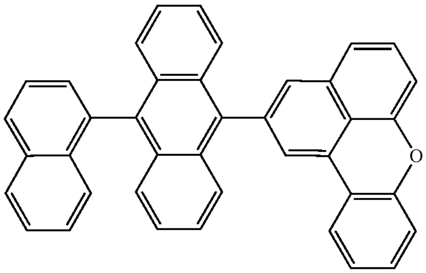

-continued
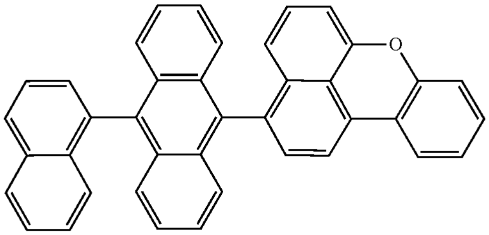
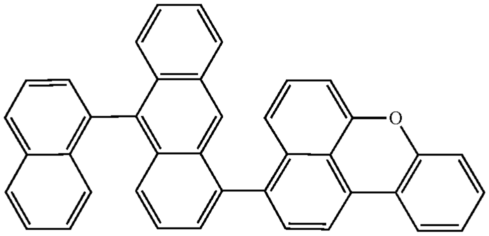
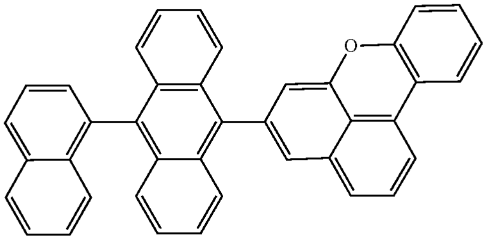
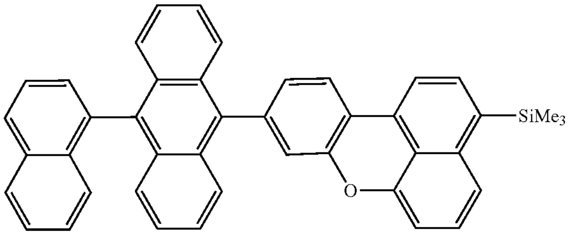
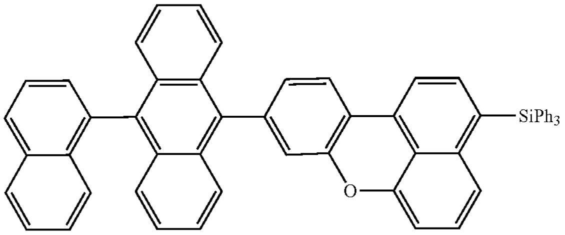
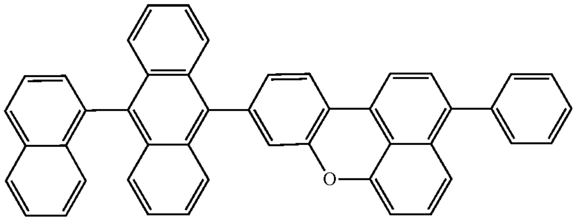
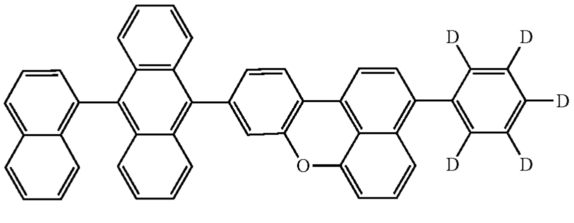
-continued
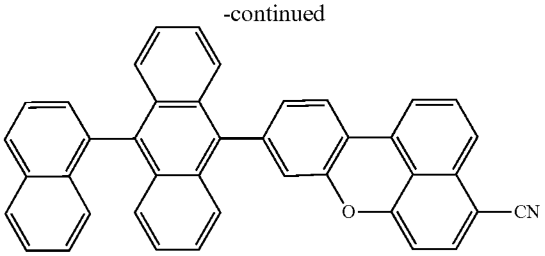
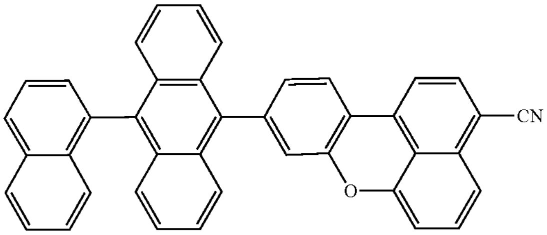
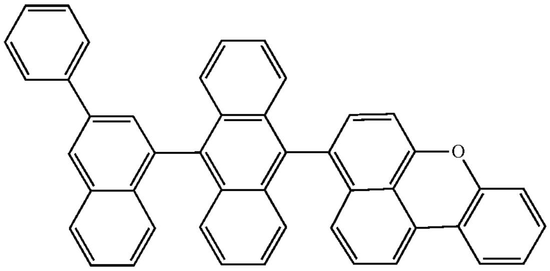
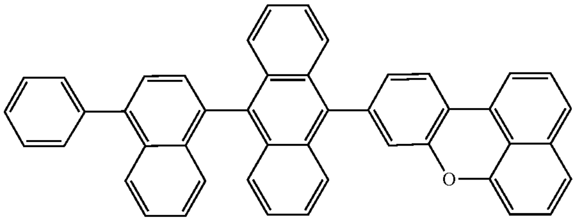
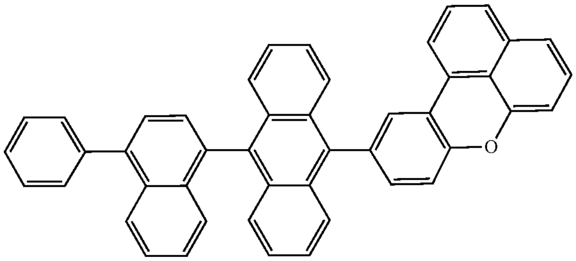
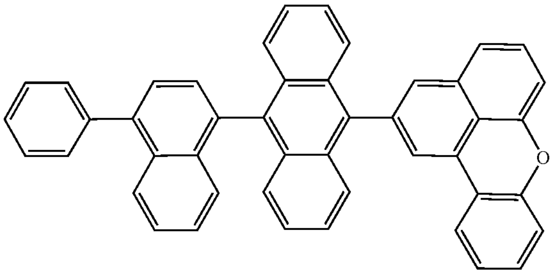
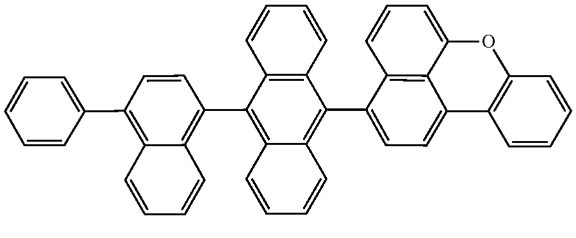

-continued
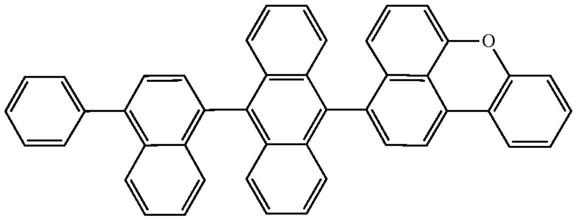
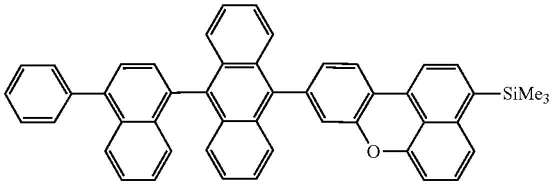
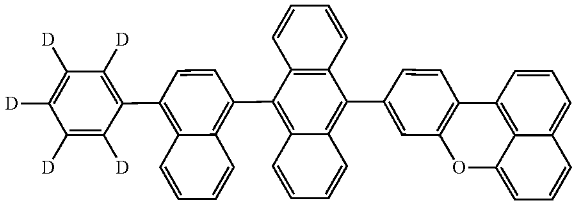
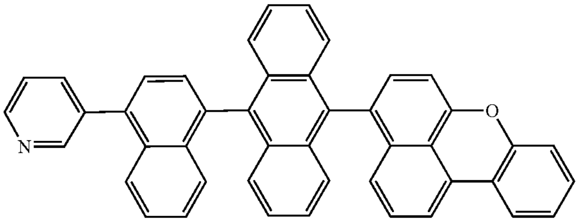
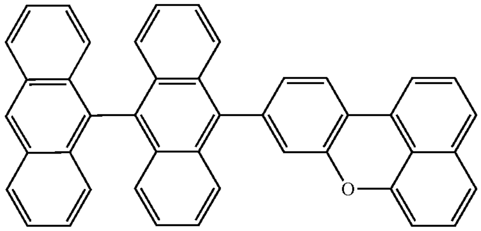
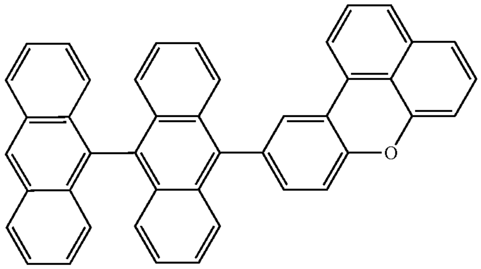
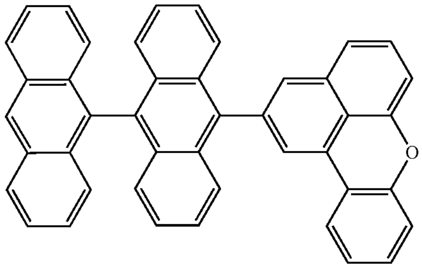
-continued
[Formula 145]
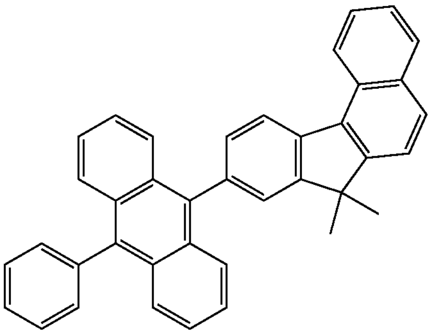
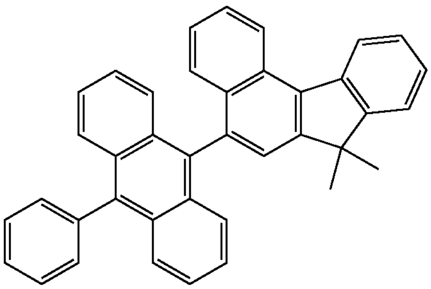
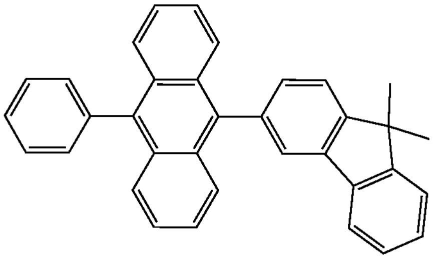
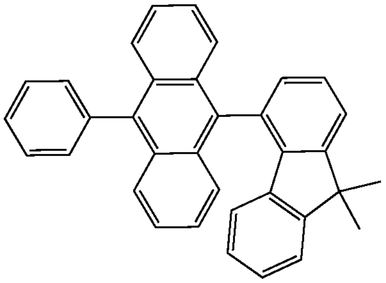
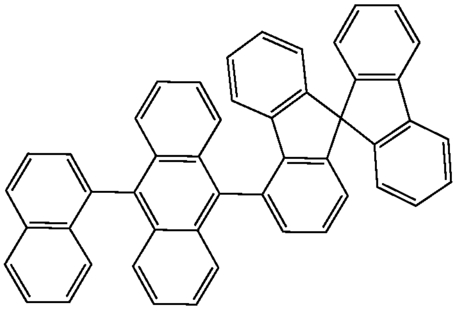

-continued

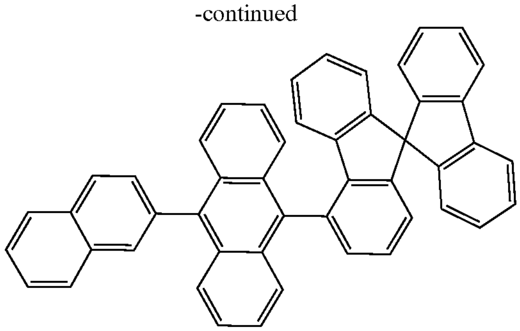

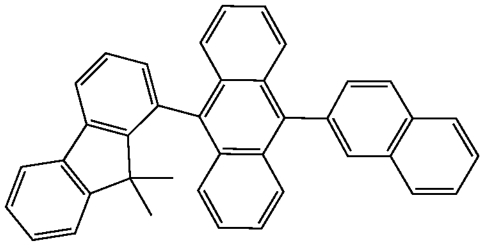

-continued

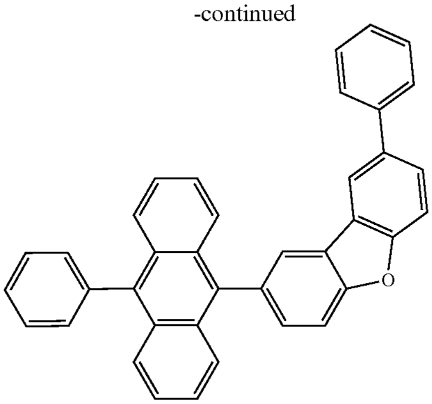

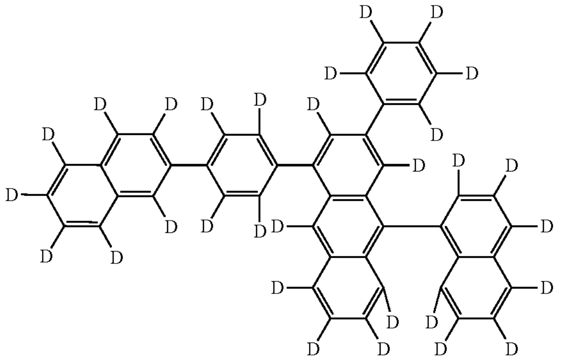 [SMILES: [2H]c1c([2H])c([2H])c(-c2c([2H])c(-c3c([2H])c([2H])c(-c4c([2H])c([2H])c5c([2H])c([2H])c([2H])c([2H])c5c4[2H])c([2H])c3[2H])c3c([2H])c4c([2H])c([2H])c([2H])c([2H])c4c(-c4c([2H])c([2H])c([2H])c5c([2H])c([2H])c([2H])c([2H])c45)c3c2[2H])c([2H])c1[2H]]

Examples of Combination of First Compound and Second Compound

In the organic EL device according to the exemplary embodiment, for instance, it is also preferable that the first emitting layer contains the first compound shown in combinations below and the second emitting layer contains the second compound shown in the combinations below. It should however be noted that the invention is not limited by the specific examples of these combinations.

Combination 1

The first compound is BH1 and the second compound is BH2-19.

[Formula 146]

BH1

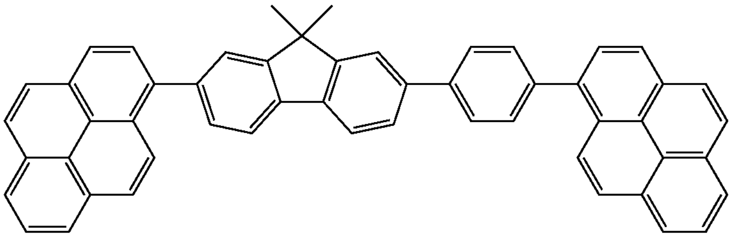

-continued
BH2-19
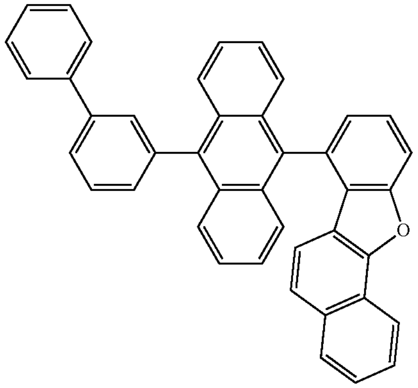
Combination 2
The first compound is BH1 and the second compound is BH2-7.
[Formula 147]
BH1
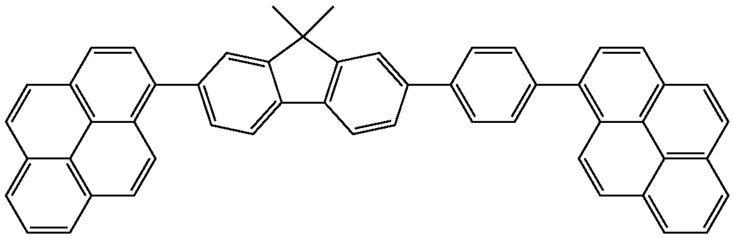
BH2-7
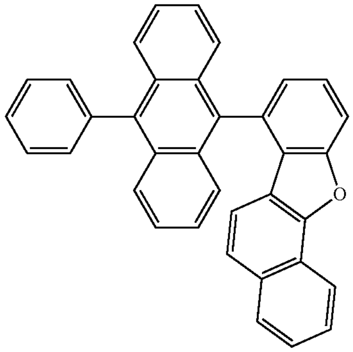

Combination 3
The first compound is BH1 and the second compound is BH2-20.
[Formula 148]
BH1
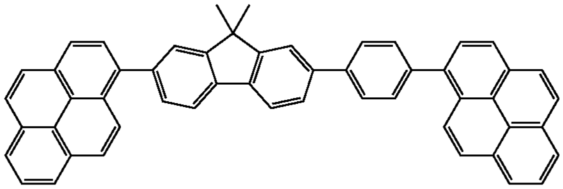
BH2-20
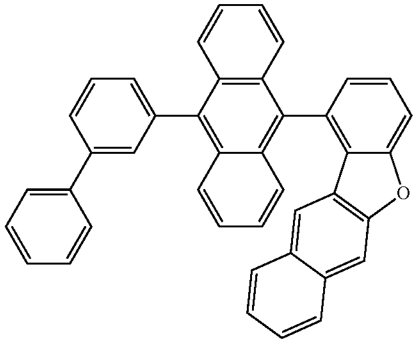
Combination 4
The first compound is BH1 and the second compound is BH2-31.
[Formula 149]
BH1
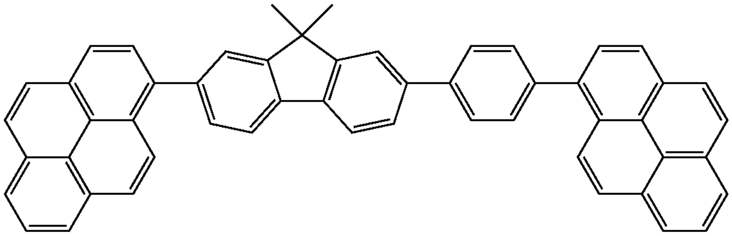
BH2-31
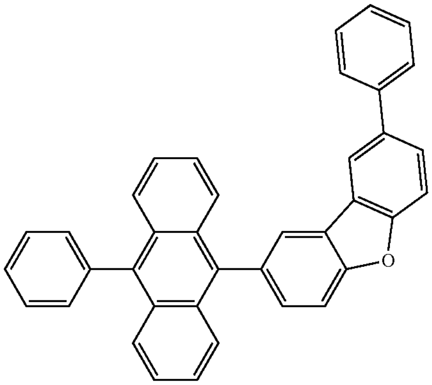

Combination 5
The first compound is BH1 and the second compound is BH2-32.
[Formula 150]
BH1
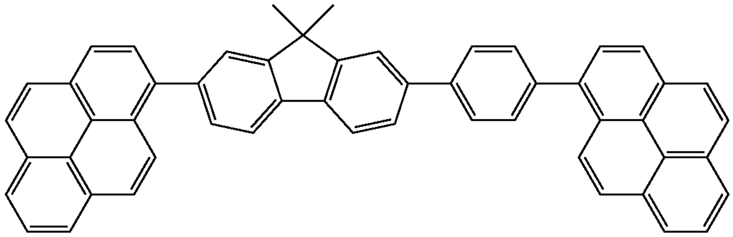
BH2-32
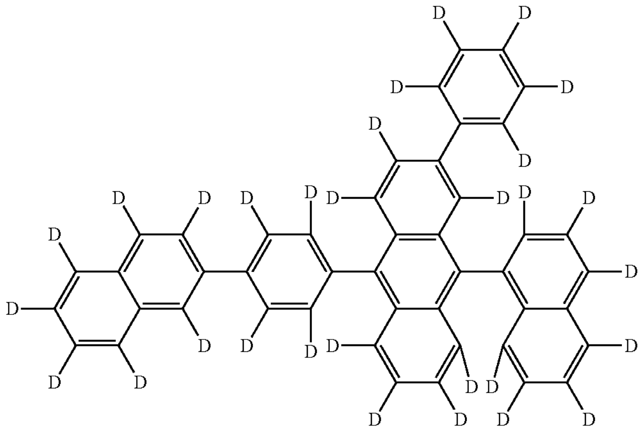
Combination 6
The first compound is BH1 and the second compound is BH2-33.
[Formula 151]
BH1
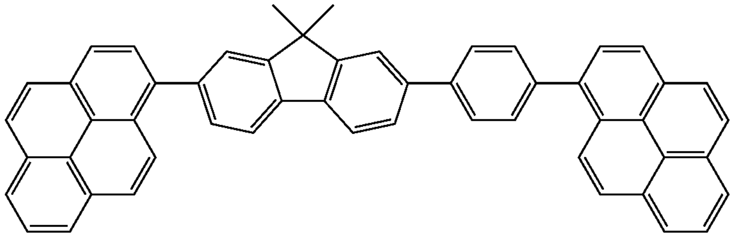
BH2-33
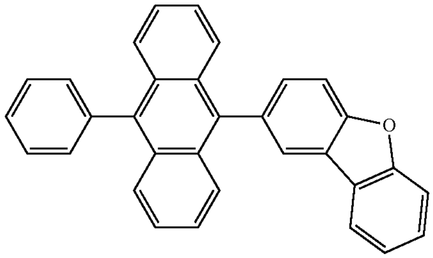

Combination 7
The first compound is BH1 and the second compound is BH2-5.
[Formula 152]
BH1
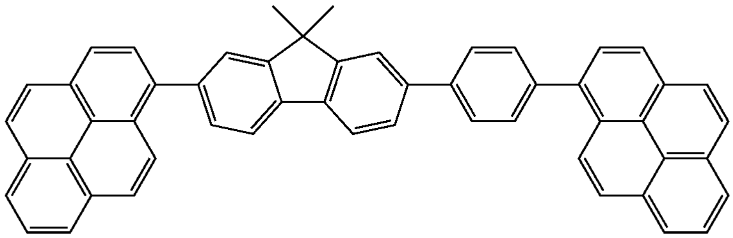
BH2-5
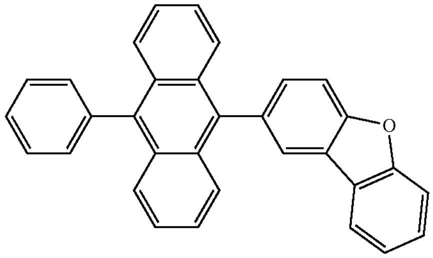
Combination 8
The first compound is BH1 and the second compound is BH2-8.
[Formula 153]
BH1
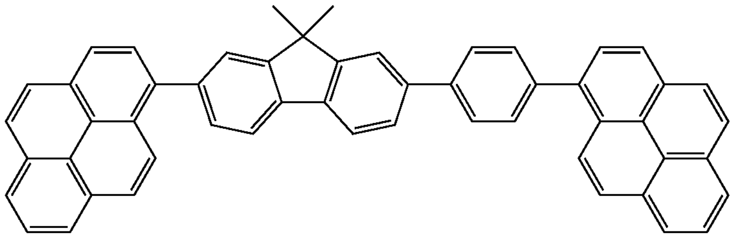
BH2-8
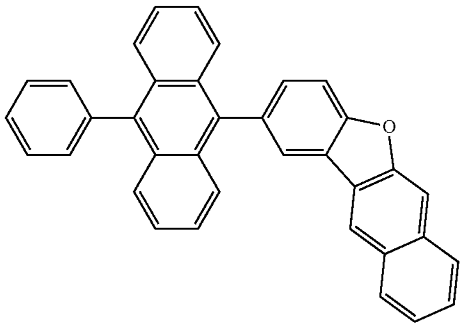

Combination 9
The first compound is BH1 and the second compound is BH2.
[Formula 154]
BH1
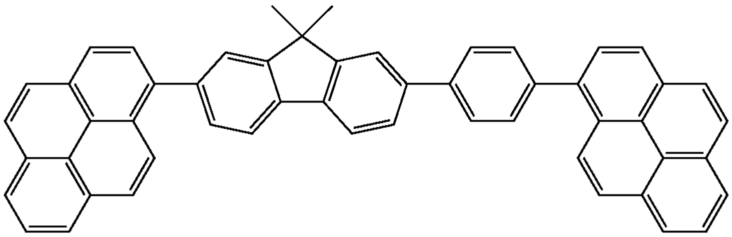
BH2
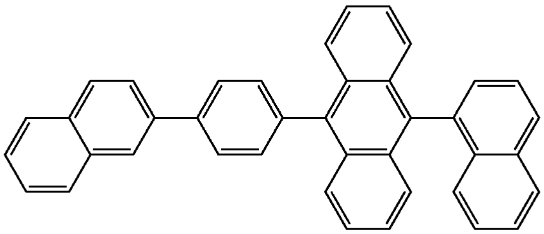
Combination 10
The first compound is BH1 and the second compound is BH2-30.
[Formula 155]
BH1
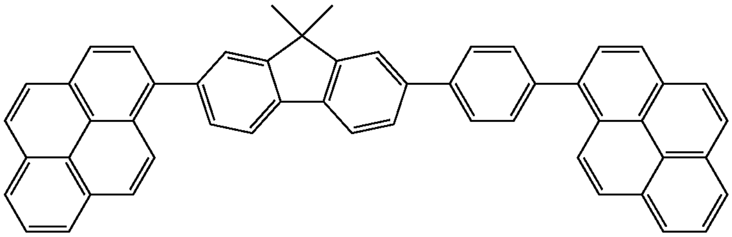
BH2-30
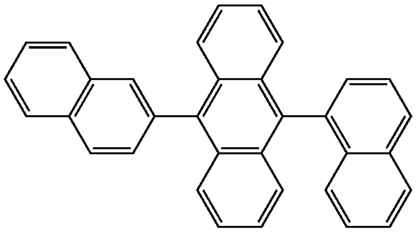

Combination 11
The first compound is BH1 and the second compound is BH2 and BH2-30.
[Formula 156]
BH1
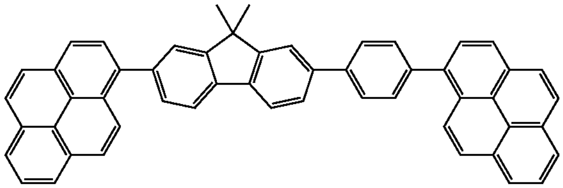
-continued
BH2
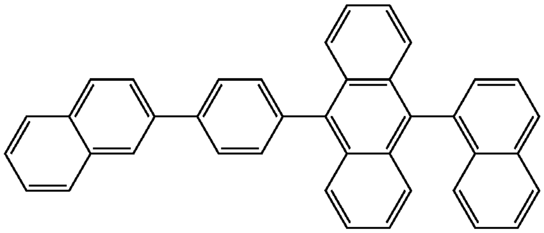
BH2-30
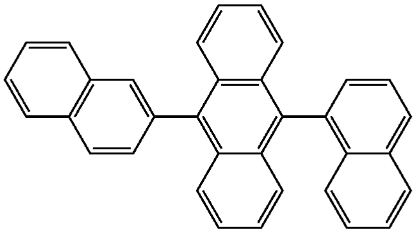
Combination 12
The first compound is BH1 and the second compound is BH2-9.
[Formula 157]
BH1
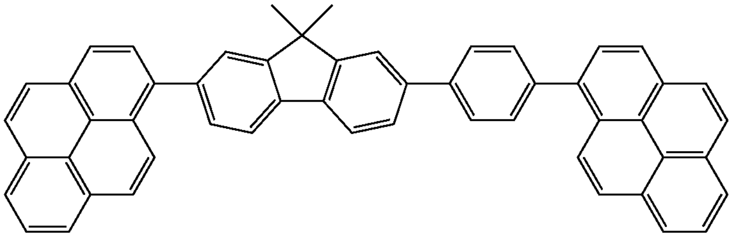
BH2-9
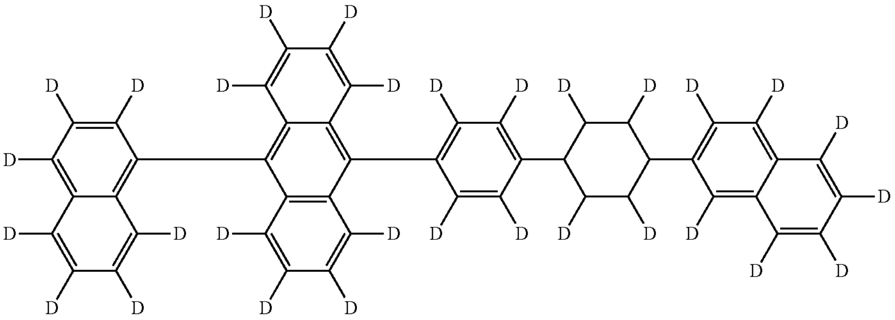

Combination 13
The first compound is BH1 and the second compound is BH2-3.
[Formula 158]
BH1
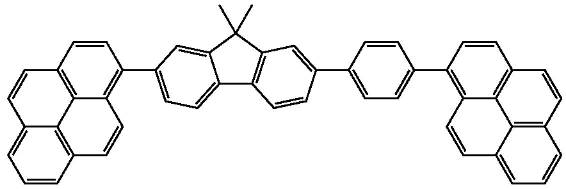
-continued
BH2-3
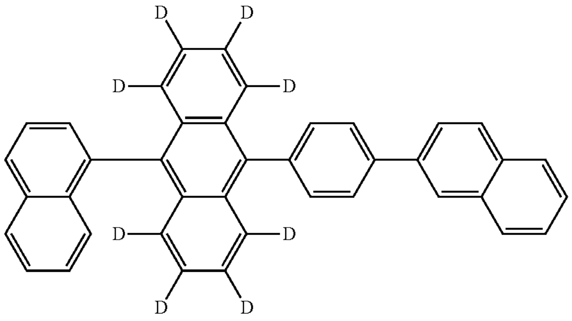
Combination 14
The first compound is BH1 and the second compound is BH2-34.
[Formula 159]
BH1
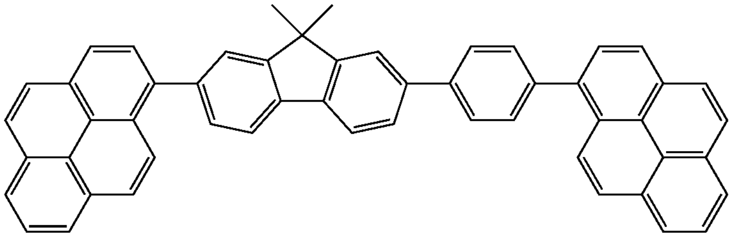
BH2-34
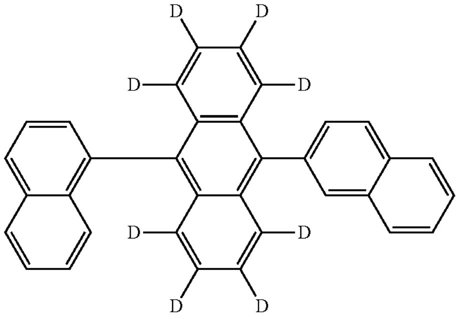

Combination 15
The first compound is BH1 and the second compound is BH2-35.
[Formula 160]
BH1
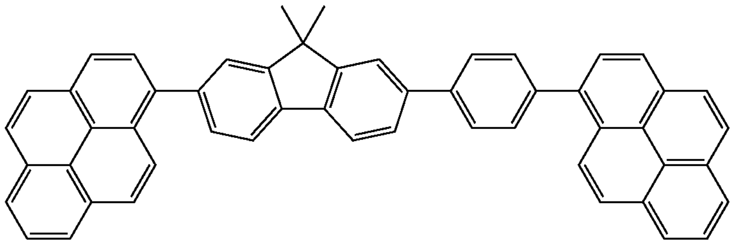
BH2-35
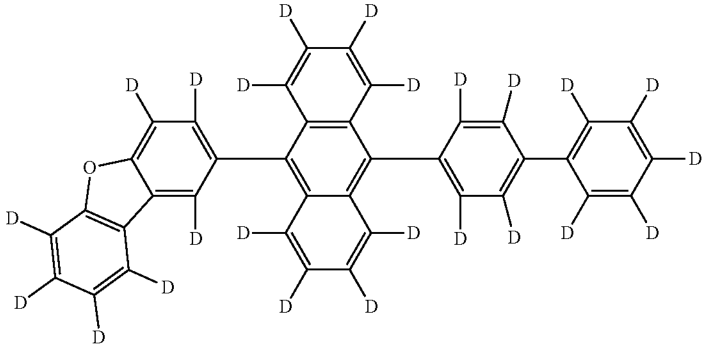
Combination 16
The first compound is BH1 and the second compound is BH2-36.
[Formula 161]
BH1
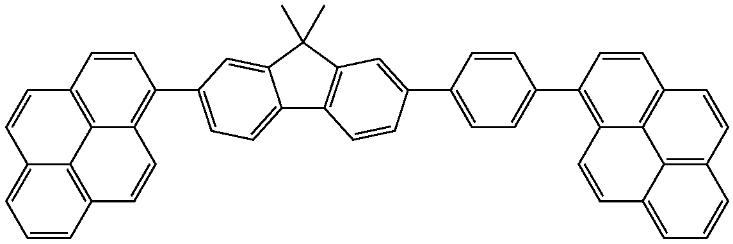
BH2-36
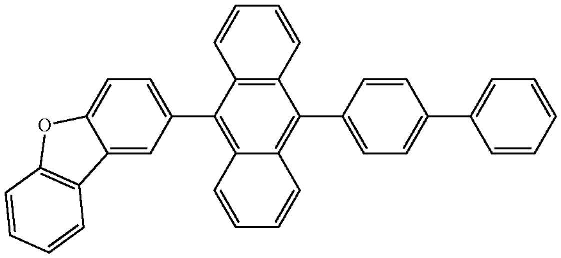

Combination 17
The first compound is BH1 and the second compound is BH2-37.
[Formula 162]
BH1
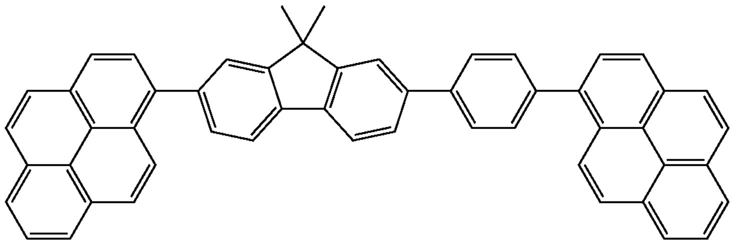
BH2-37
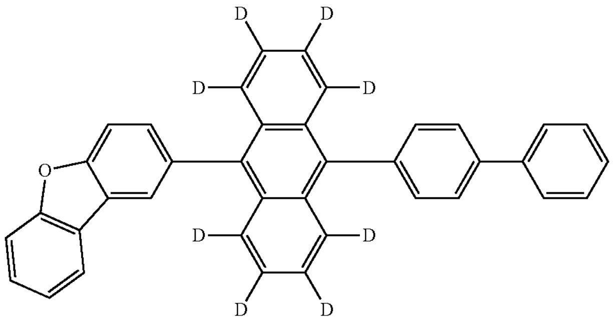
Combination 18
The first compound is BH1-84 and the second compound is BH2-19.
[Formula 163]
BH1-84
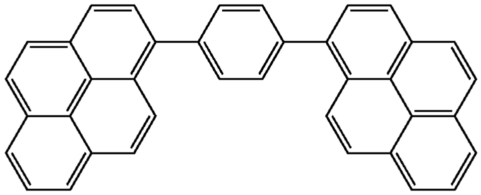
BH2-19
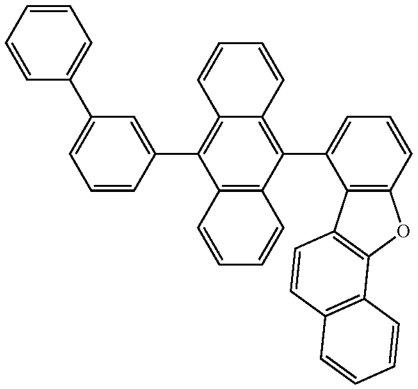
Combination 19
The first compound is BH1-84 and the second compound is BH2-7.
[Formula 164]
BH1-84
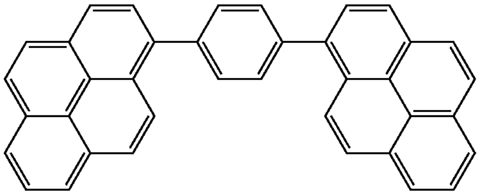
BH2-7
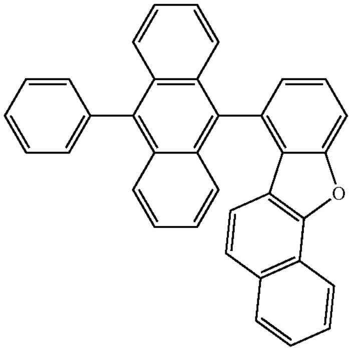

Combination 20
The first compound is BH1-84 and the second compound is BH2-20.
[Formula 165]
BH1-84
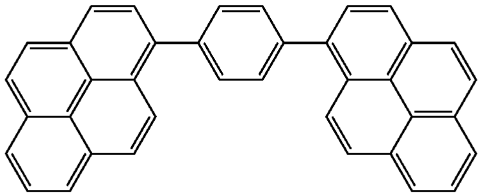
BH2-20
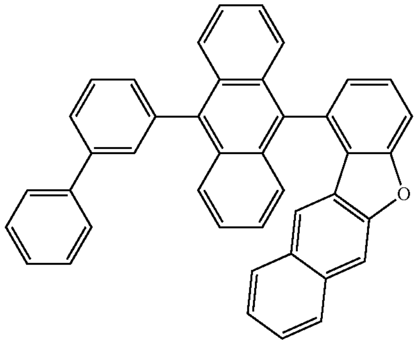
Combination 21
The first compound is BH1-84 and the second compound is BH2-31.
[Formula 166]
BH1-84
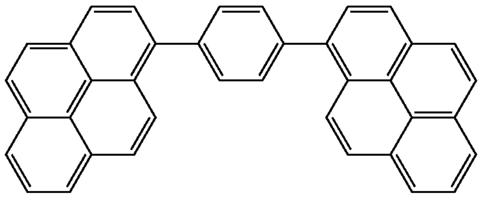
BH2-31
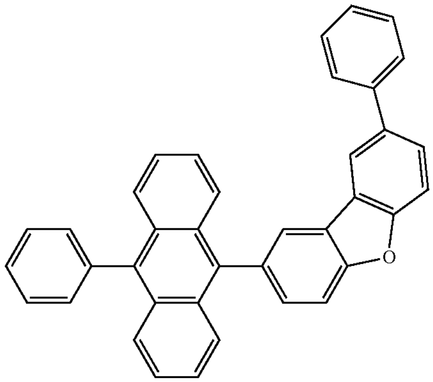
Combination 22
The first compound is BH1-84 and the second compound is BH2-32.
[Formula 167]
BH1-84
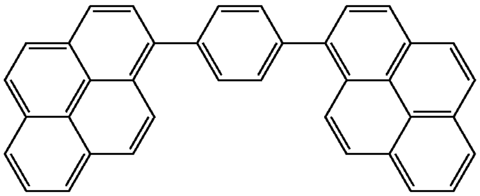
BH2-32
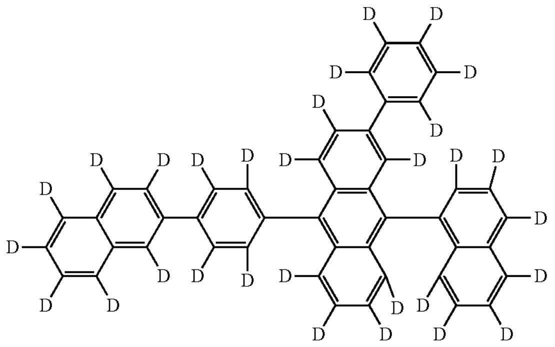
Combination 23
The first compound is BH1-84 and the second compound is BH2-33.
[Formula 168]
BH1-84
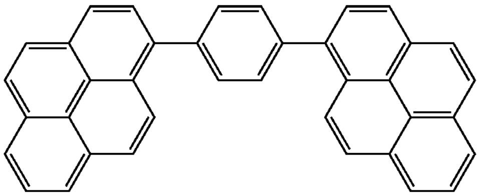
BH2-33
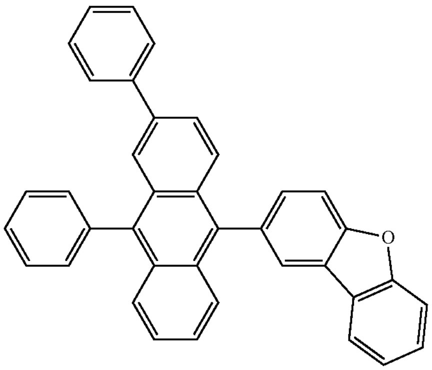

Combination 24

The first compound is BH1-84 and the second compound is BH2-5.

[Formula 169]

BH1-84

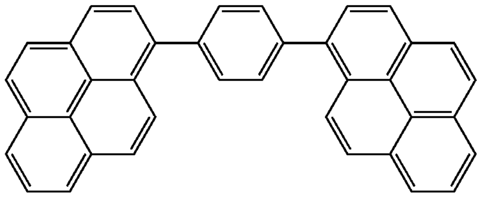

BH2-5

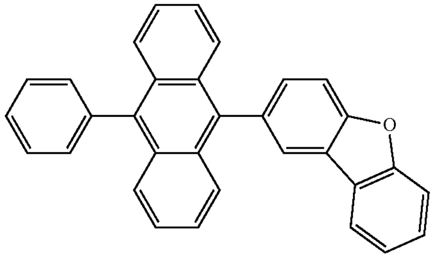

Combination 25

The first compound is BH1-84 and the second compound is BH2-8.

[Formula 170]

BH1-84

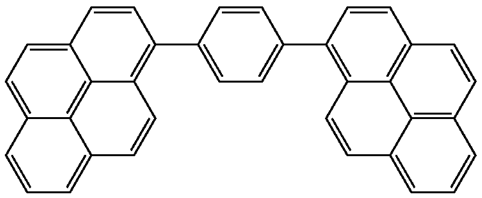

BH2-8

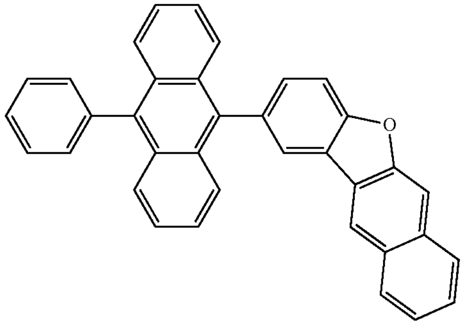

Combination 26

The first compound is BH1-84 and the second compound is BH2.

[Formula 171]

BH1-84

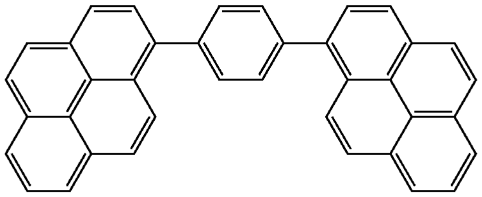

BH2

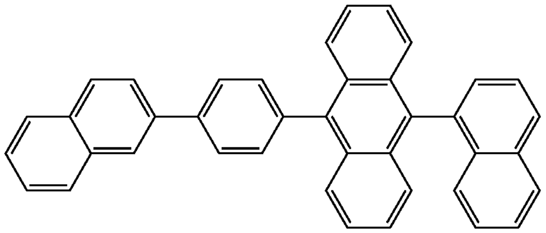

Combination 27

The first compound is BH1-84 and the second compound is BH2-30.

[Formula 172]

BH1-84

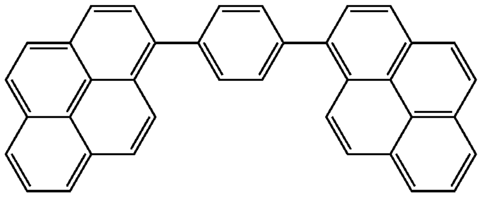

BH2-30

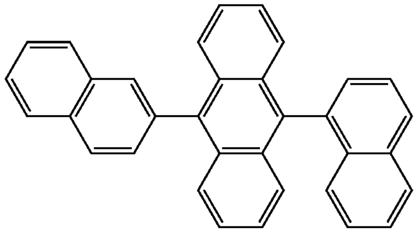

Combination 28

The first compound is BH1-84 and the second compound is BH2 and BH2-30.

[Formula 173]

BH1-84

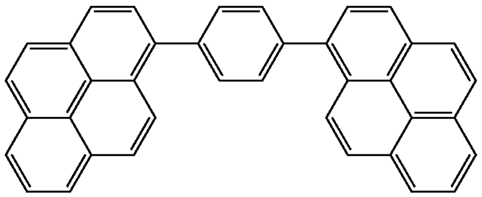

-continued
BH2
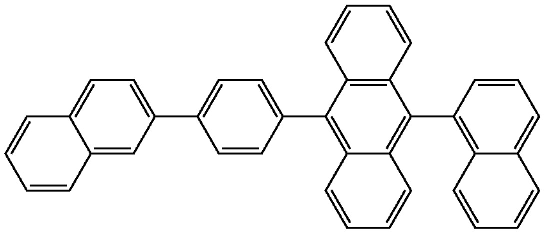
BH2-30
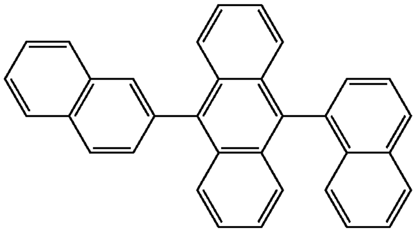
Combination 29
The first compound is BH1-84 and the second compound is BH2-9.
[Formula 174]
BH1-84
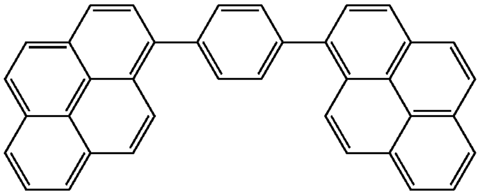
BH2-9
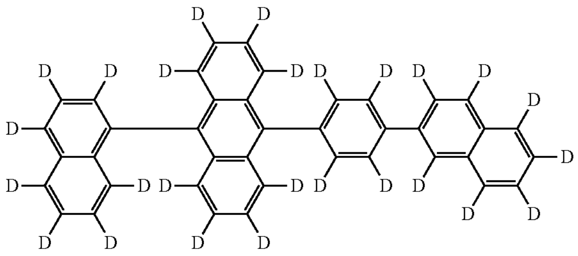
Combination 30
The first compound is BH1-84 and the second compound is BH2-3.
[Formula 175]
BH1-84
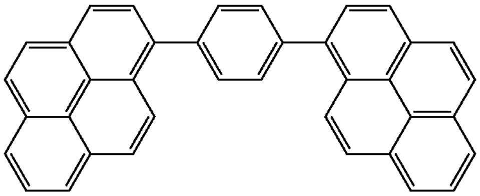
-continued
BH2-3
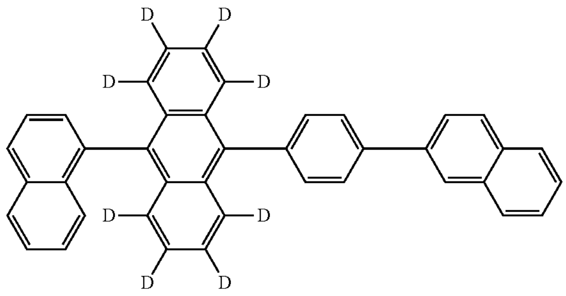
Combination 31
The first compound is BH1-84 and the second compound is BH2-34.
[Formula 176]
BH1-84
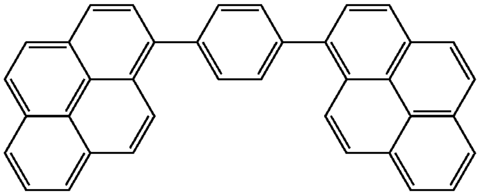
BH2-34
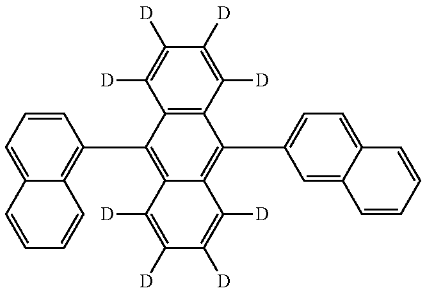
Combination 32
The first compound is BH1-84 and the second compound is BH2-35.
[Formula 177]
BH1-84
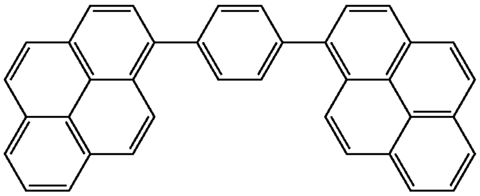

-continued
BH2-35
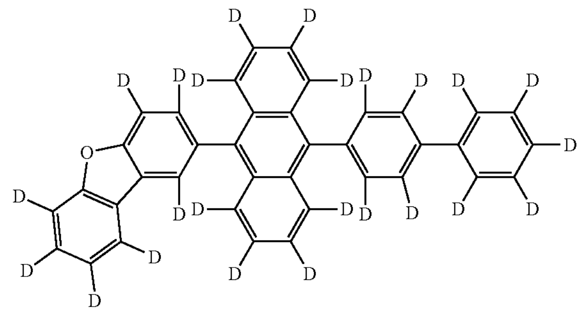
Combination 33
The first compound is BH1-84 and the second compound is BH2-36.
[Formula 178]
BH1-84
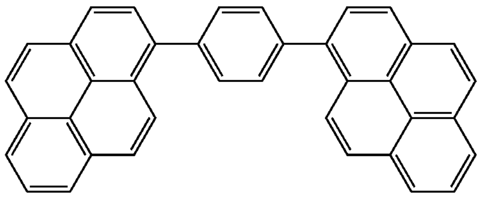
BH2-36
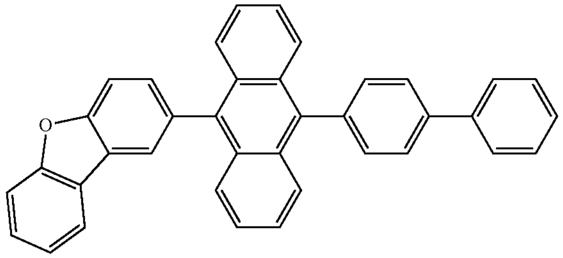
Combination 34
The first compound is BH1-84 and the second compound is BH2-37.
[Formula 179]
BH1-84
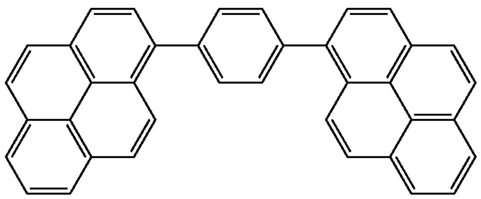
-continued
BH2-37
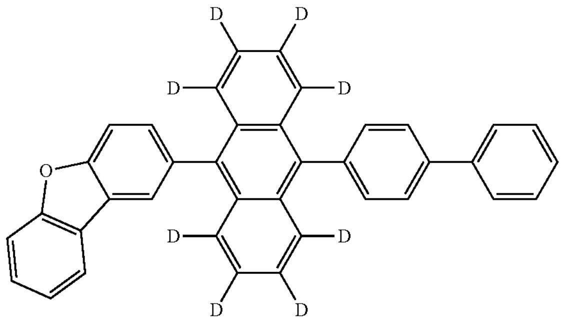
Combination 35
The first compound is BH1-85 and the second compound is BH2-19.
[Formula 180]
BH1-85
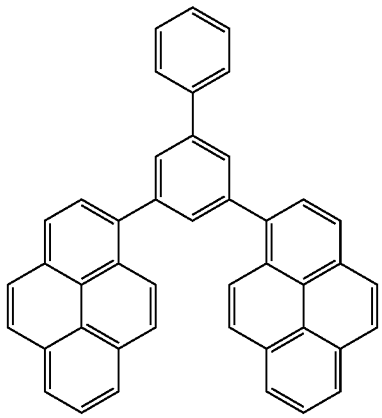
BH2-19
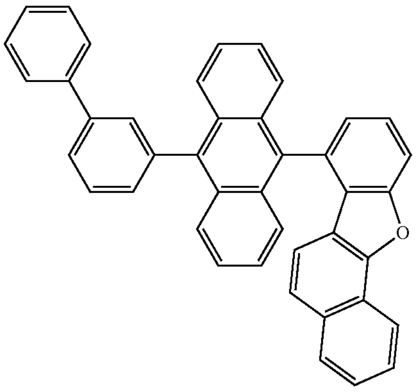

Combination 36
The first compound is BH1-85 and the second compound is BH2-7.
[Formula 181]
BH1-85
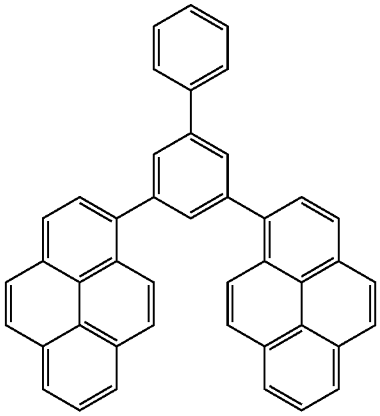
BH2-7
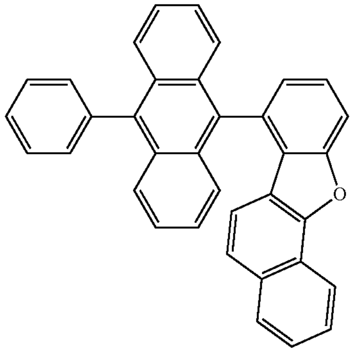
Combination 37
The first compound is BH1-85 and the second compound is BH2-20.
[Formula 182]
BH1-85
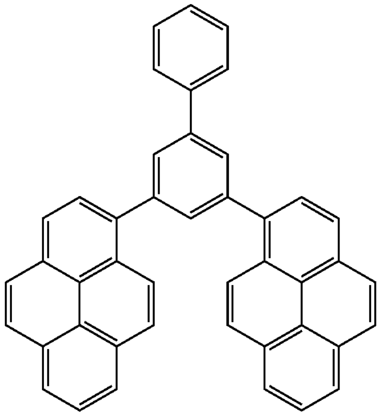
-continued
BH2-20
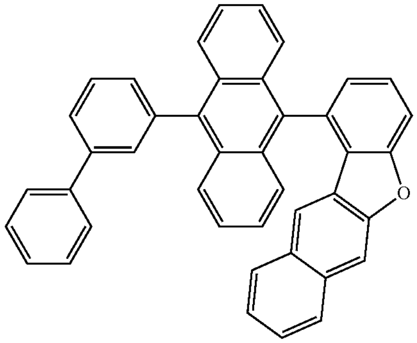
Combination 38
The first compound is BH1-85 and the second compound is BH2-31.
[Formula 183]
BH1-85
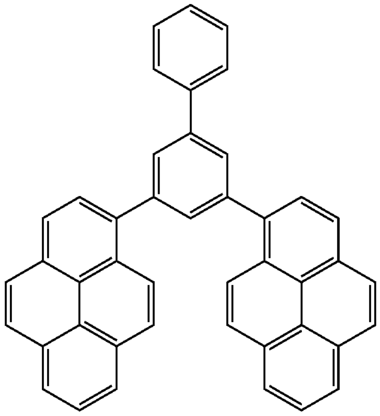
BH2-31
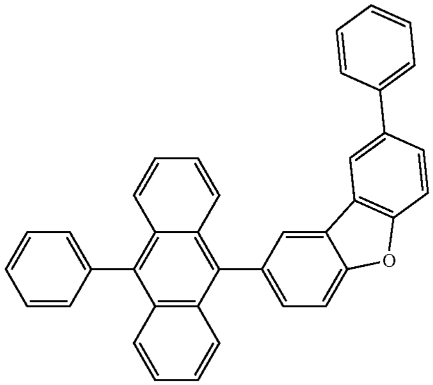

Combination 39
The first compound is BH1-85 and the second compound is BH2-32.
[Formula 184]
BH1-85
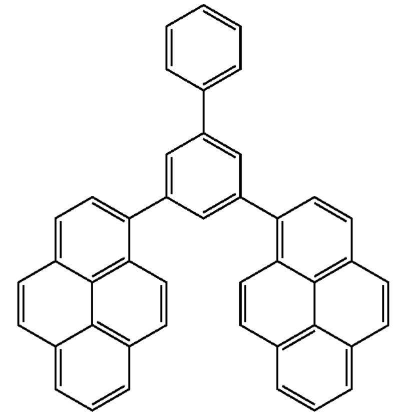
BH2-32
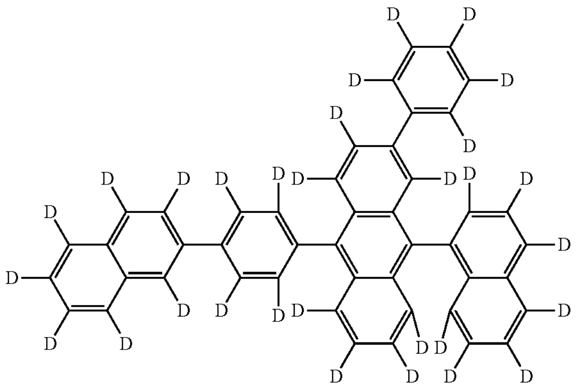
Combination 40
The first compound is BH1-85 and the second compound is BH2-33.
[Formula 185]
BH1-85
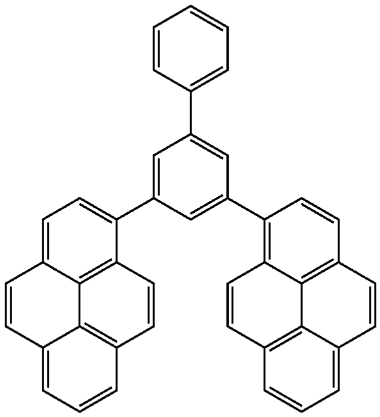
-continued
BH2-33
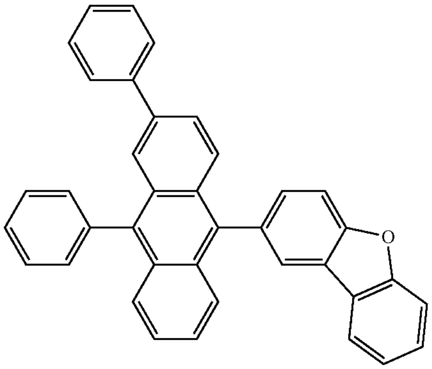
Combination 41
The first compound is BH1-85 and the second compound is BH2-5.
[Formula 186]
BH1-85
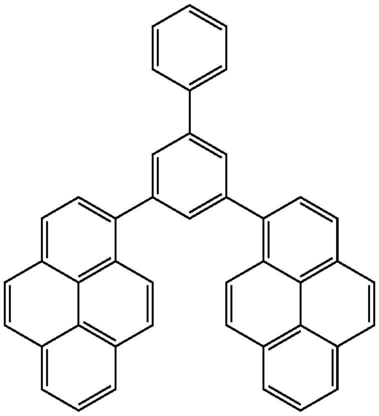
BH2-5
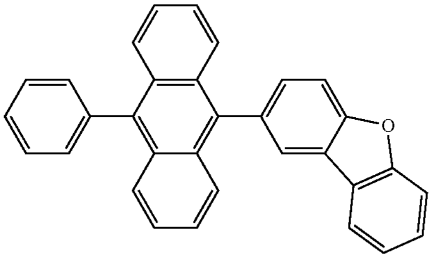

Combination 42
The first compound is BH1-85 and the second compound is BH2-8.
[Formula 187]
BH1-85
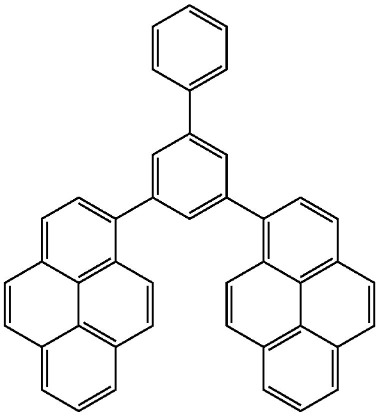
BH2-8
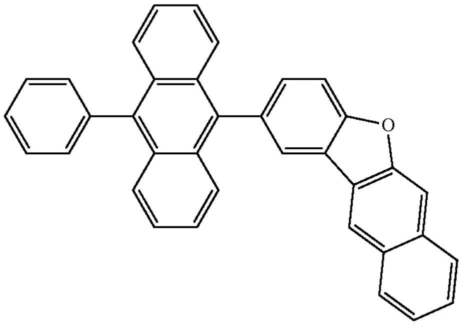
Combination 43
The first compound is BH1-85 and the second compound is BH2.
[Formula 188]
BH1-85
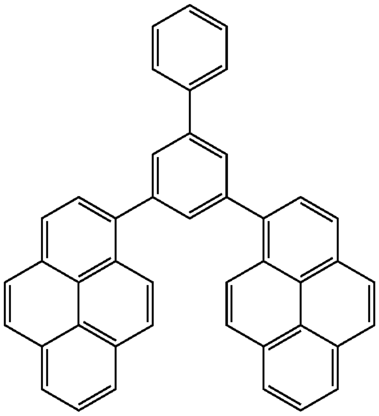
-continued
BH2
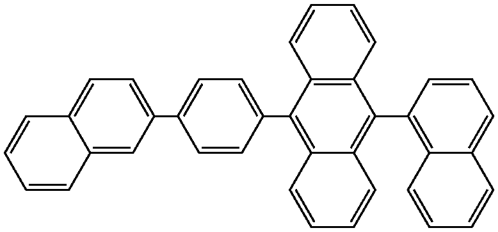
Combination 44
The first compound is BH1-85 and the second compound is BH2-30.
[Formula 189]
BH1-85
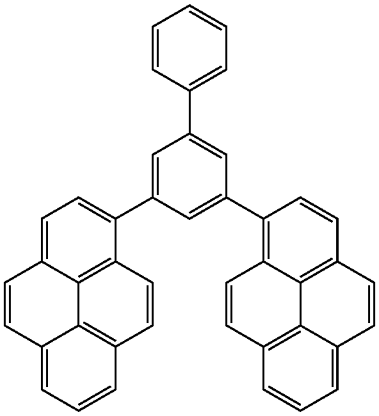
BH2-30
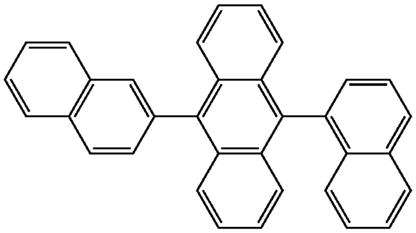

Combination 45
The first compound is BH1-85 and the second compound is BH2 and BH2-30.
[Formula 190]
BH1-85
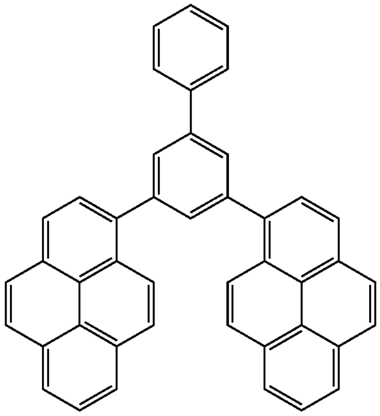
BH2
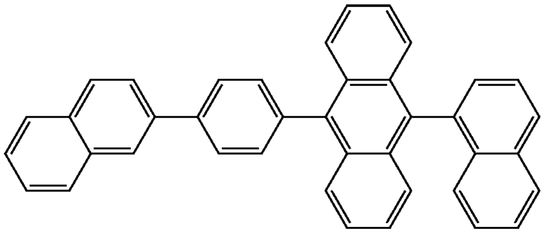
BH2-30
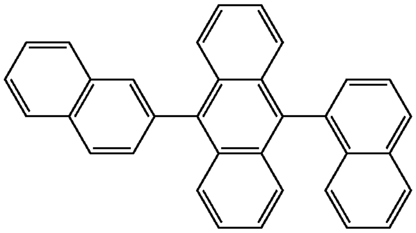
Combination 46
The first compound is BH1-85 and the second compound is BH2-9.
[Formula 191]
BH1-85
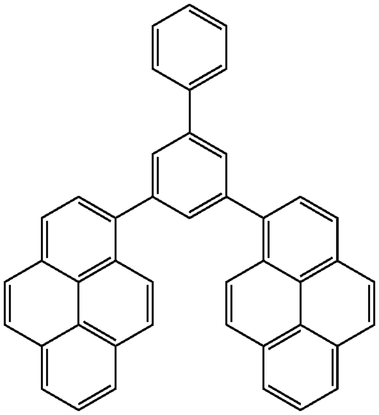
BH2-9
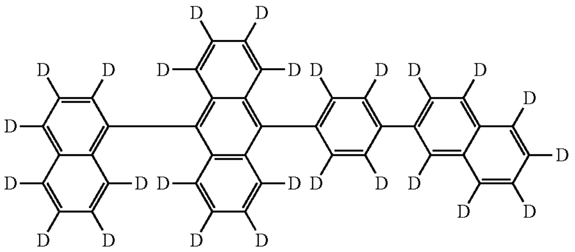
Combination 47
The first compound is BH1-85 and the second compound is BH2-3.
[Formula 192]
BH1-85
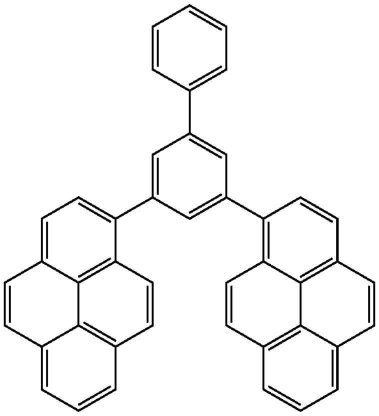

-continued
BH2-3
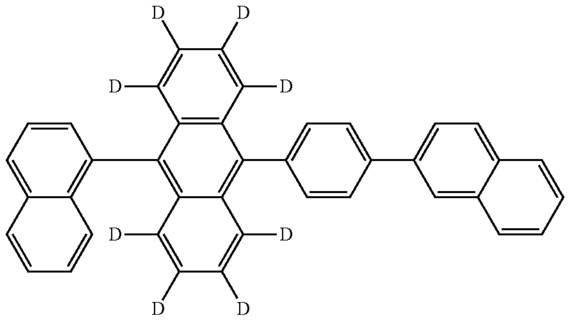
Combination 48
The first compound is BH1-85 and the second compound is BH2-34.
[Formula 193]
BH1-85
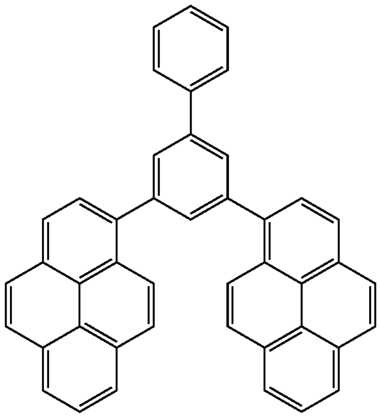
BH2-34
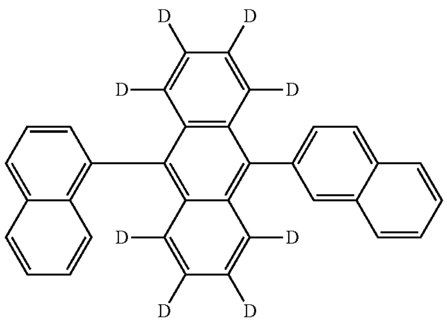
Combination 49
The first compound is BH1-85 and the second compound is BH2-35.
[Formula 194]
BH1-85
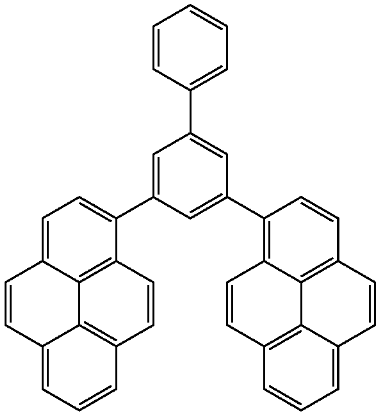
BH2-35
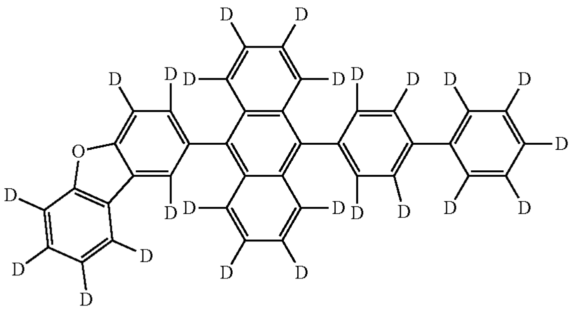
Combination 50
The first compound is BH1-85 and the second compound is BH2-36.
[Formula 195]
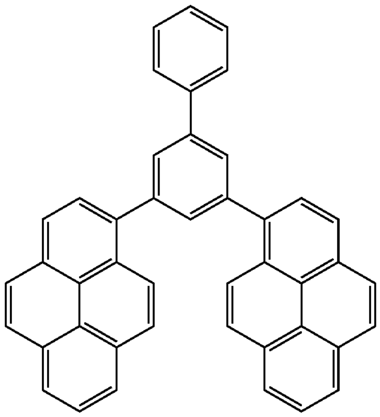
BH1-85

-continued
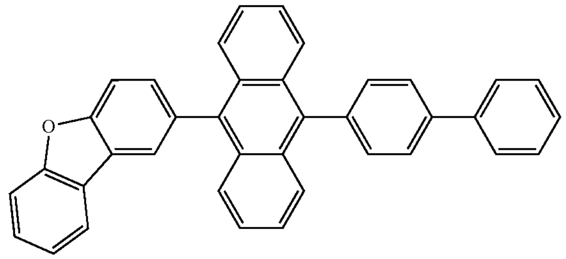
BH2-36
Combination 51
The first compound is BH1-85 and the second compound is BH2-37.
[Formula 196]
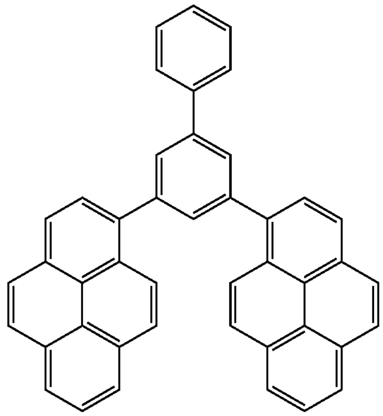
BH1-85
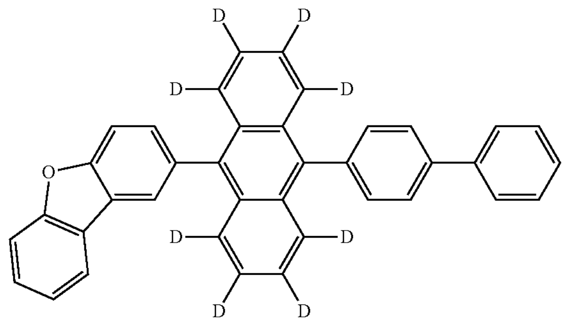
BH2-37
Combination 52
The first compound is BH1-86 and the second compound is BH2-19.
[Formula 197]
BH1-86
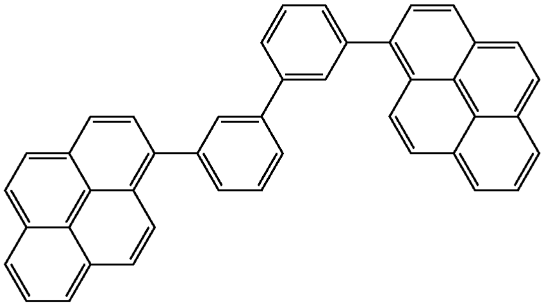
BH2-19
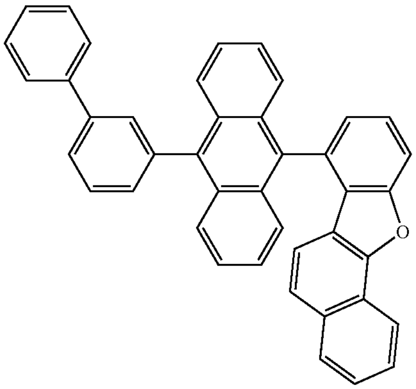
Combination 53
The first compound is BH1-86 and the second compound is BH2-7.
[Formula 198]
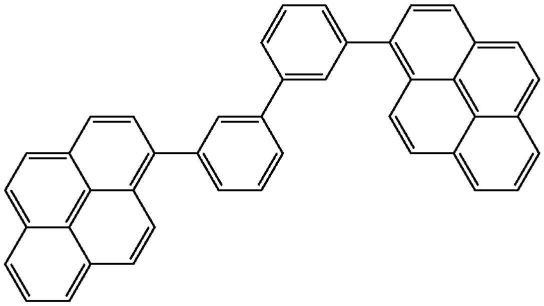
BH1-86

-continued
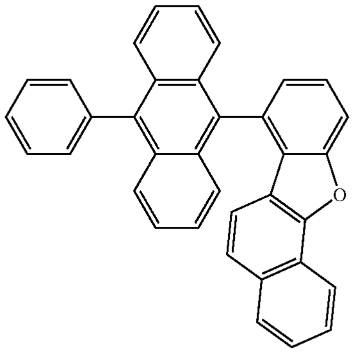
BH2-7
Combination 54
The first compound is BH1-86 and the second compound is BH2-20.
[Formula 199]
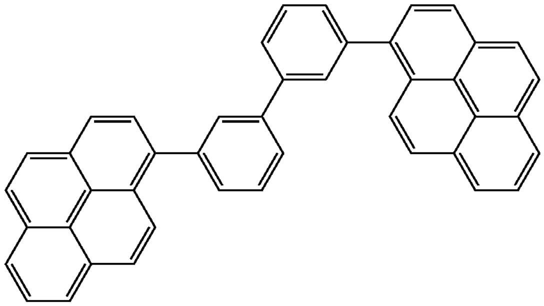
BH1-86
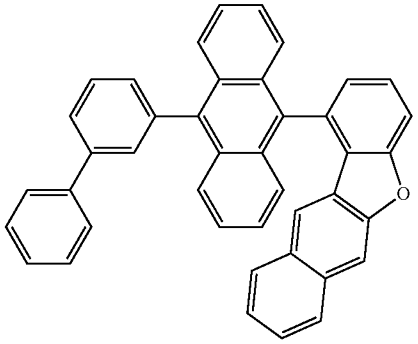
BH2-20
Combination 55
The first compound is BH1-86 and the second compound is BH2-31.
[Formula 200]
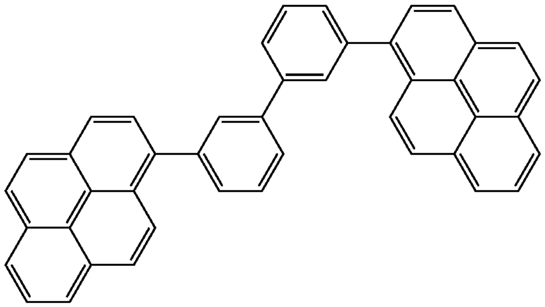
BH1-86
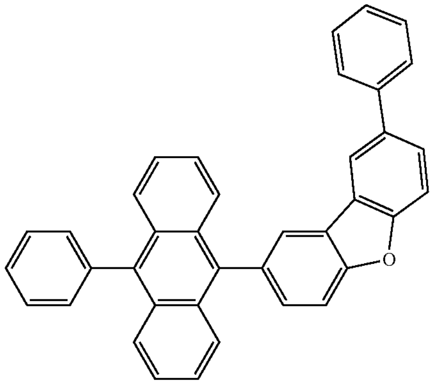
BH2-31
Combination 56
The first compound is BH1-86 and the second compound is BH2-32.
[Formula 201]
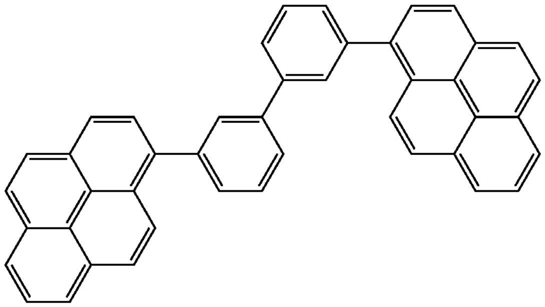
BH1-86

-continued
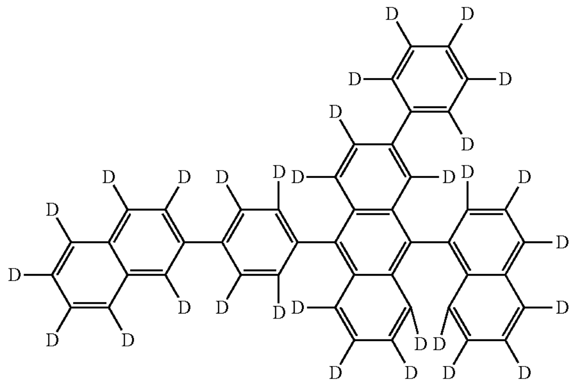
BH2-32
Combination 57
The first compound is BH1-86 and the second compound is BH2-33.
[Formula 202]
BH1-86
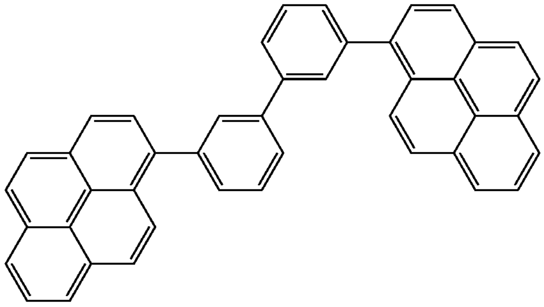
BH2-33
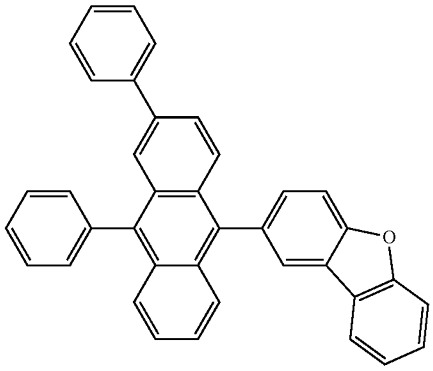
Combination 58
The first compound is BH1-86 and the second compound is BH2-5.
[Formula 203]
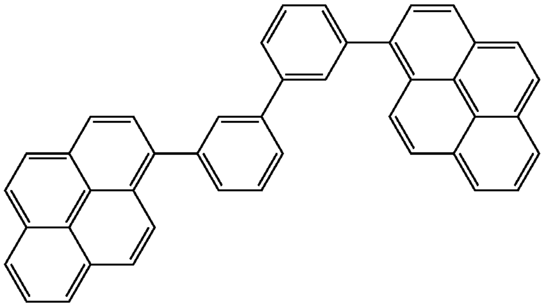
BH1-86
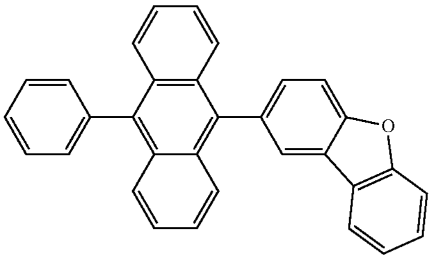
BH2-5
Combination 59
The first compound is BH1-86 and the second compound is BH2-8.
[Formula 204]
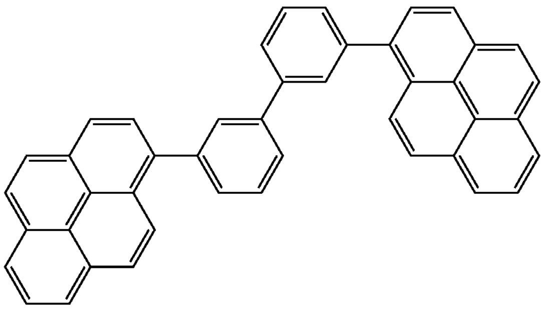
BH1-86

-continued
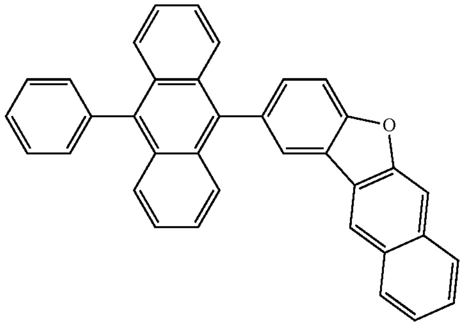
BH2-8
Combination 60
The first compound is BH1-86 and the second compound is BH2.
[Formula 205]
BH1-86
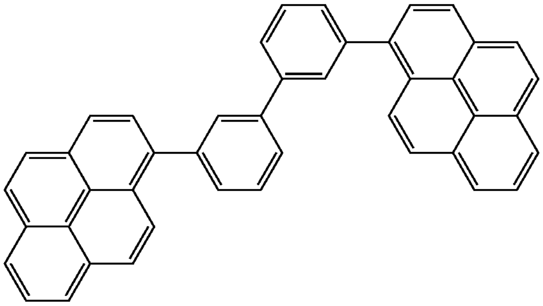
BH2
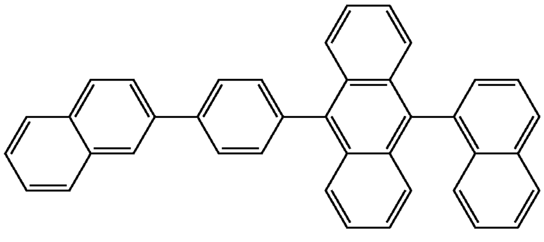
Combination 61
The first compound is BH1-86 and the second compound is BH2-30.
[Formula 206]
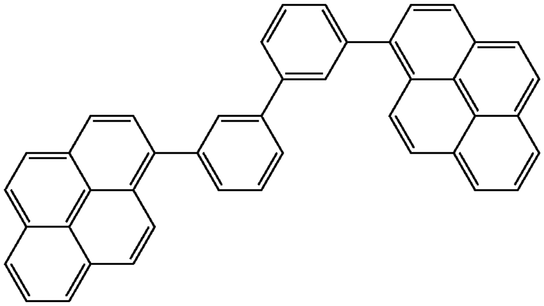
BH1-86
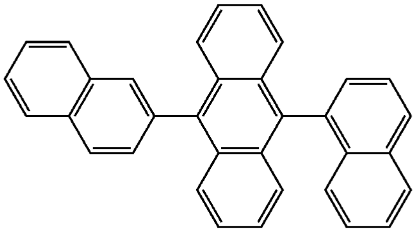
BH2-30
Combination 62
The first compound is BH1-86 and the second compound is BH2 and BH2-30.
[Formula 207]
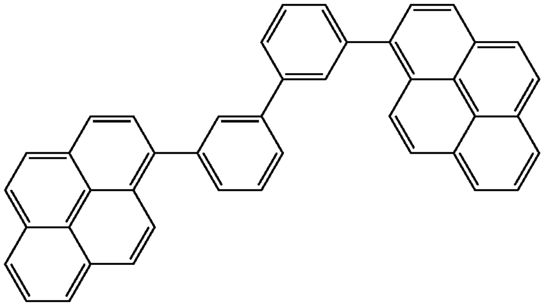
BH1-86
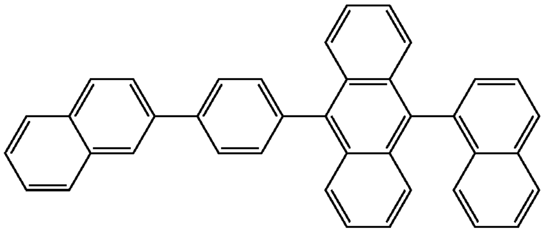
BH2

-continued
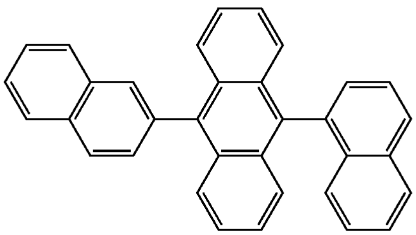
BH2-30
Combination 63
The first compound is BH1-86 and the second compound is BH2-9.
[Formula 208]
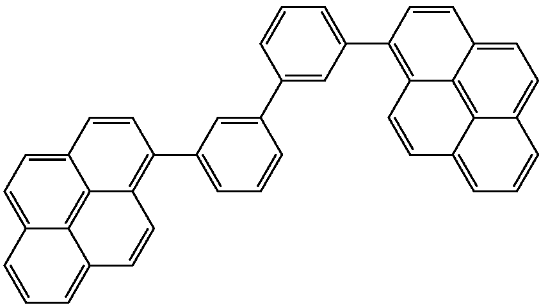
BH1-86
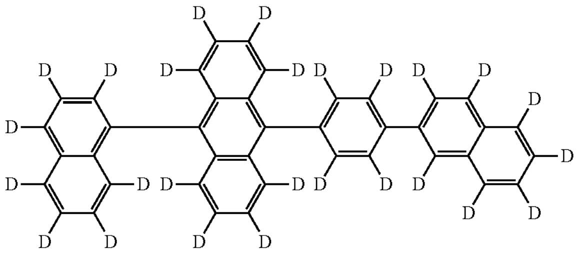
BH2-9
Combination 64
The first compound is BH1-86 and the second compound is BH2-3.
[Formula 209]
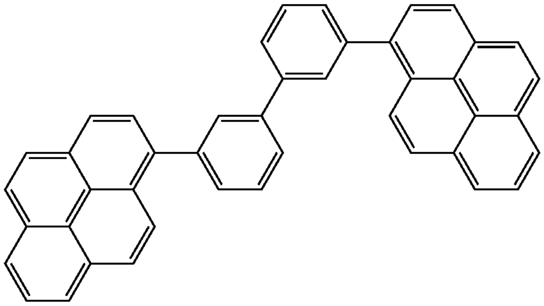
BH1-86
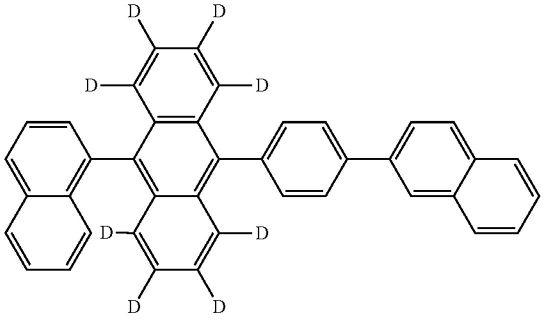
BH2-3
Combination 65
The first compound is BH1-86 and the second compound is BH2-34.
[Formula 210]
BH1-86
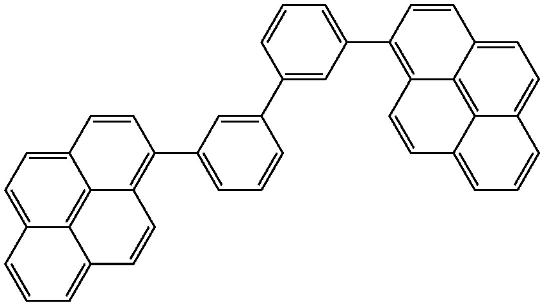

-continued
BH2-34
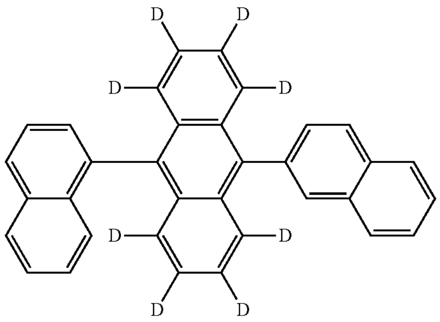
Combination 66
The first compound is BH1-86 and the second compound is BH2-35.
[Formula 211]
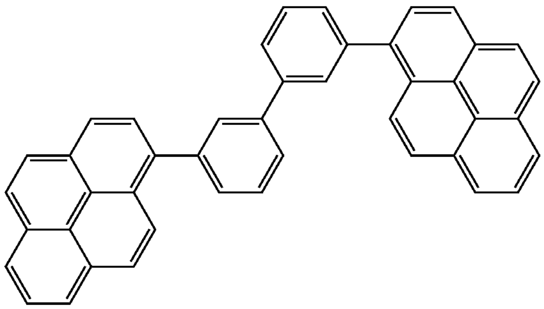
BH1-86
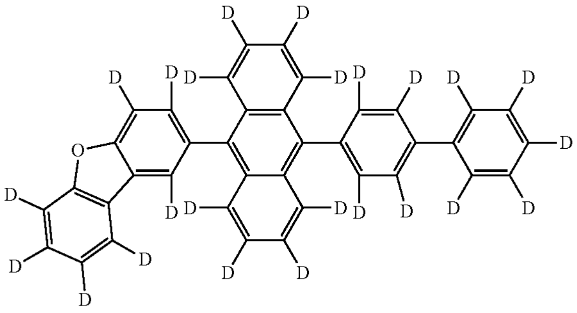
BH2-35
Combination 67
The first compound is BH1-86 and the second compound is BH2-36.
[Formula 212]
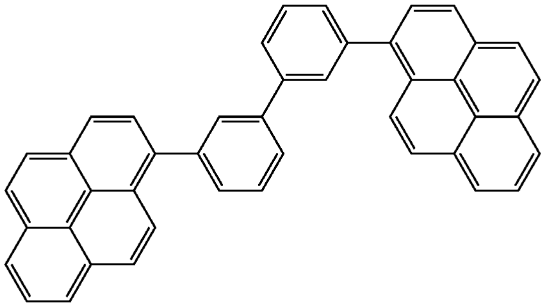
BH1-86
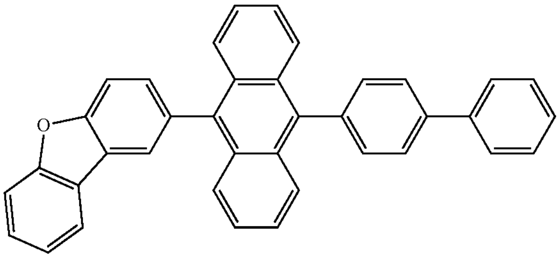
BH2-36
Combination 68
The first compound is BH1-86 and the second compound is BH2-37.
[Formula 213]
BH1-86
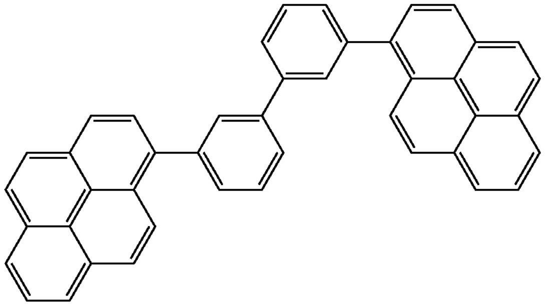

-continued
BH2-37
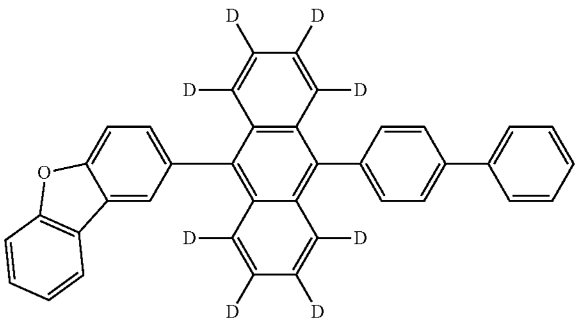
Combination 69
The first compound is BH1-87 and the second compound is BH2-19.
[Formula 214]
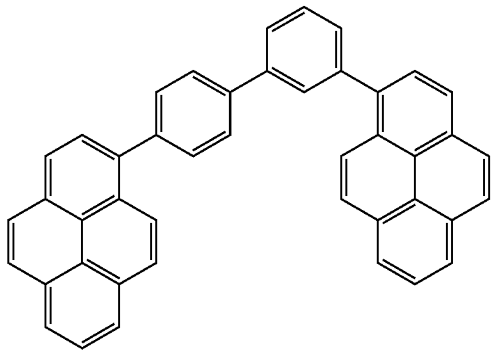
BH1-87
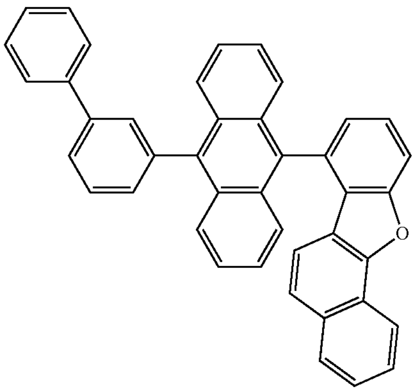
BH2-19
Combination 70
The first compound is BH1-87 and the second compound is BH2-7.
[Formula 215]
BH1-87
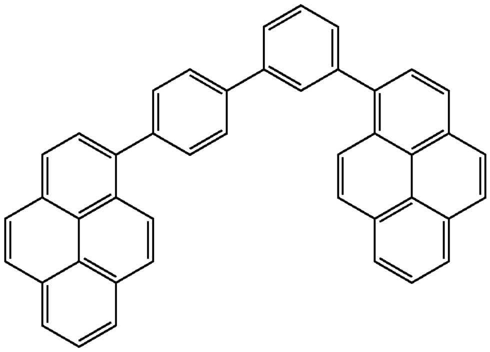
BH2-7
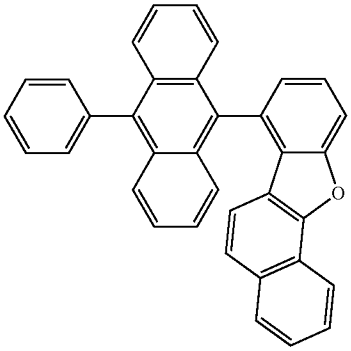
Combination 71
The first compound is BH1-87 and the second compound is BH2-20.
[Formula 216]
BH1-87
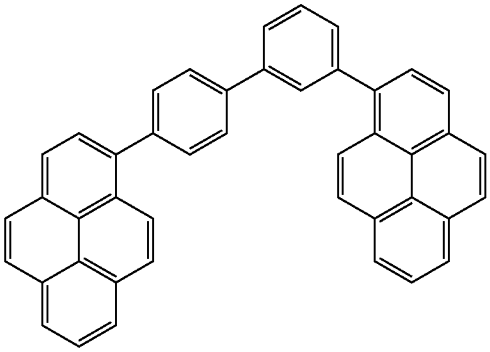

-continued
BH2-20
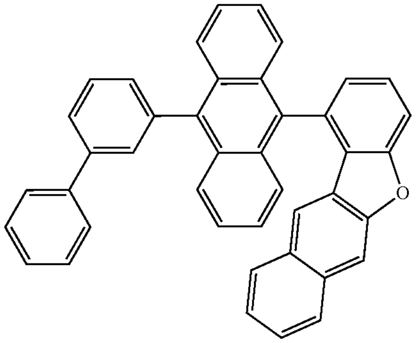
Combination 72
The first compound is BH1-87 and the second compound is BH2-31.
[Formula 217]
BH1-87
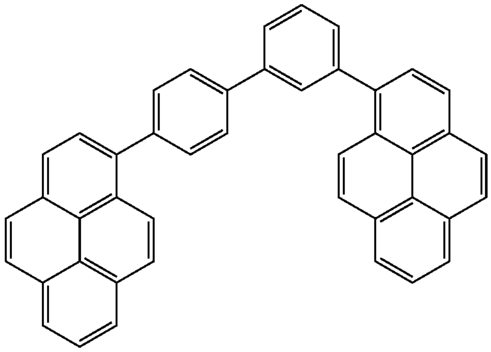
BH2-31
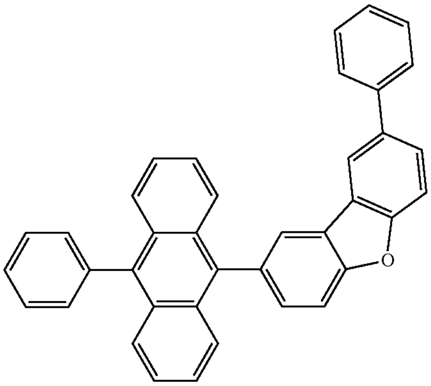
Combination 73
The first compound is BH1-87 and the second compound is BH2-32.
[Formula 218]
BH1-87
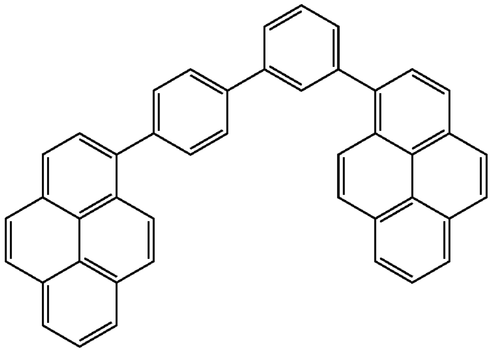
BH2-32
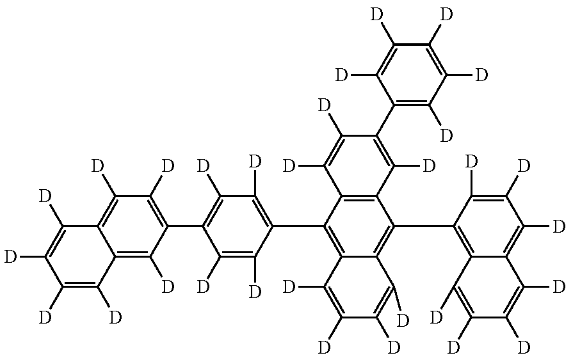
Combination 74
The first compound is BH1-87 and the second compound is BH2-33.
[Formula 219]
BH1-87
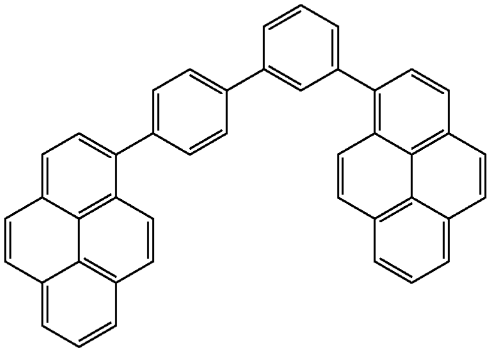

-continued
BH2-33
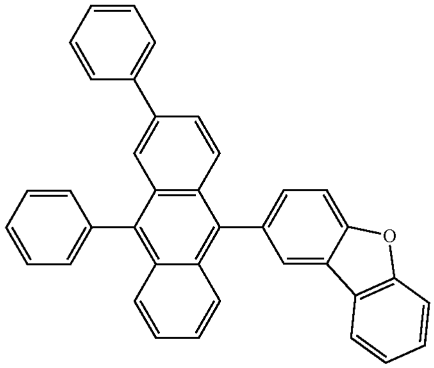
Combination 75
The first compound is BH1-87 and the second compound is BH2-5.
[Formula 220]
BH1-87
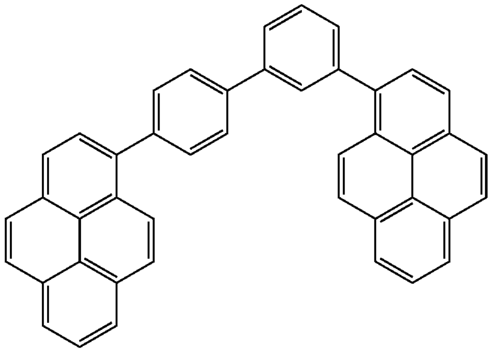
BH2-5
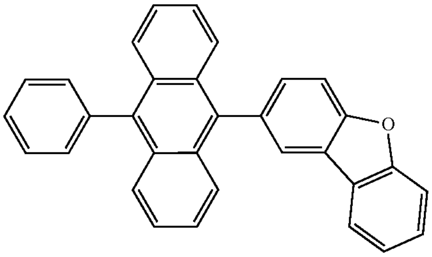
Combination 76
The first compound is BH1-87 and the second compound is BH2-8.
[Formula 221]
BH1-87
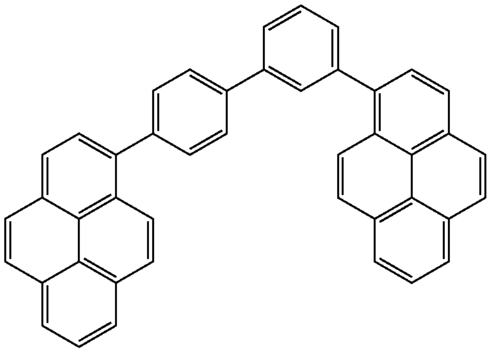
BH2-8
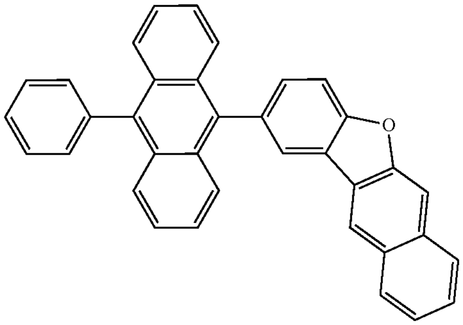
Combination 77
The first compound is BH1-87 and the second compound is BH2.
[Formula 222]
BH1-87
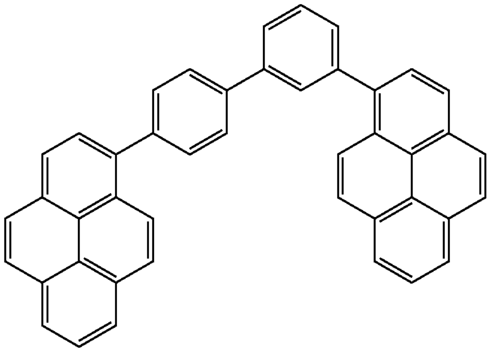

-continued
BH2
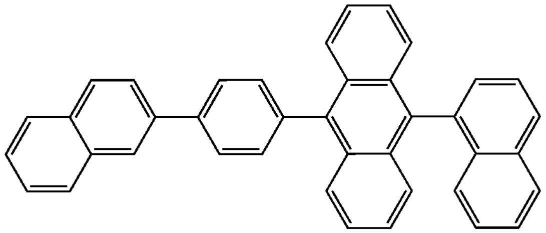
Combination 78
The first compound is BH1-87 and the second compound is BH2-30.
[Formula 223]
BH1-87
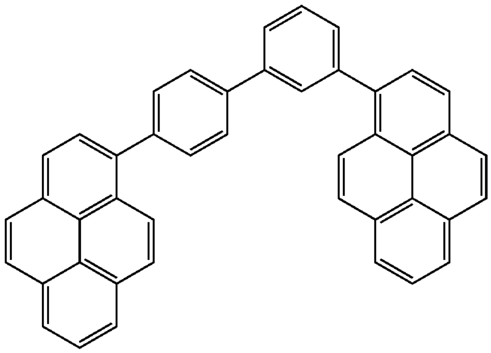
BH2-30
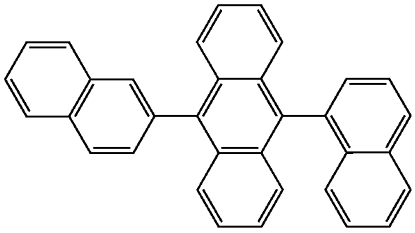
Combination 79
The first compound is BH1-87 and the second compound is BH2 and BH2-30.
[Formula 224]
BH1-87
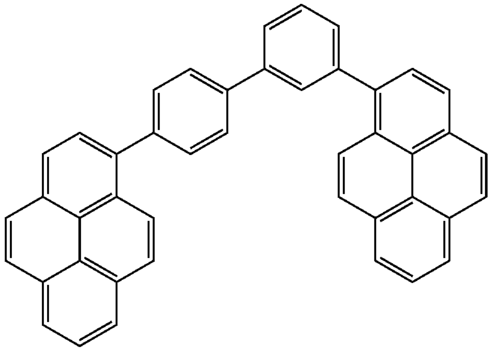
-continued
BH2
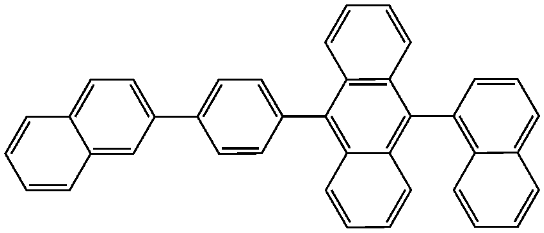
BH2-30
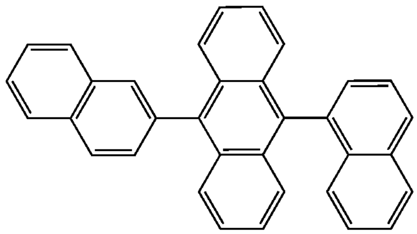
Combination 80
The first compound is BH1-87 and the second compound is BH2-9.
[Formula 225]
BH1-87
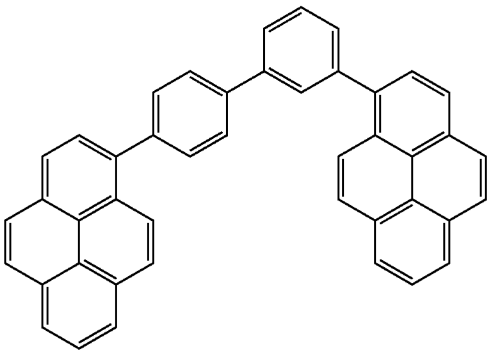
BH2-9
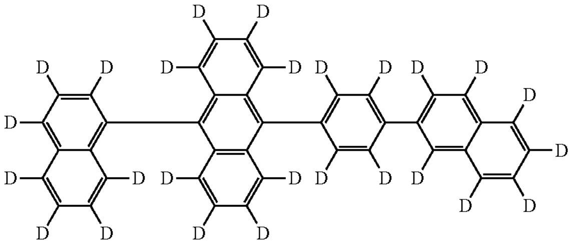

Combination 81
The first compound is BH1-87 and the second compound is BH2-3.
[Formula 226]
BH1-87
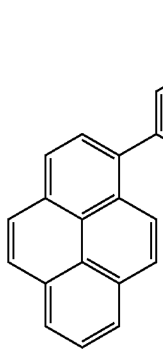
BH2-3
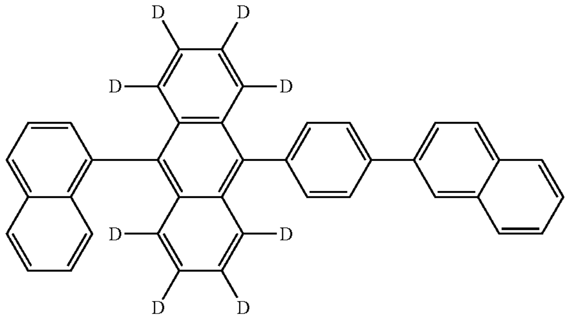
Combination 82
The first compound is BH1-87 and the second compound is BH2-34.
[Formula 227]
BH1-87
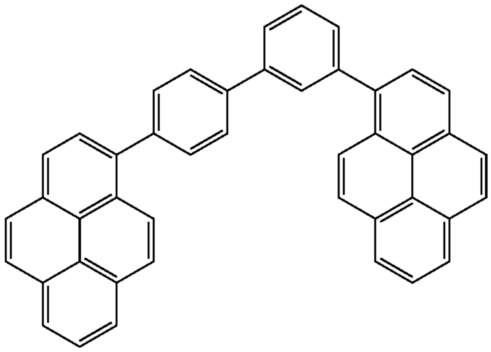
-continued
BH2-34
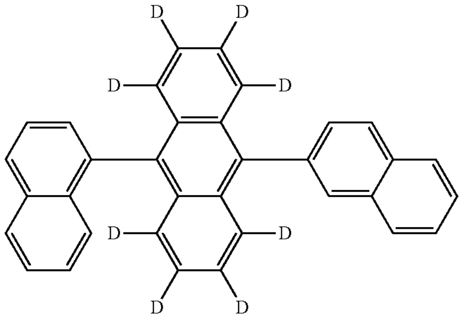
Combination 83
The first compound is BH1-87 and the second compound is BH2-35.
[Formula 228]
BH1-87
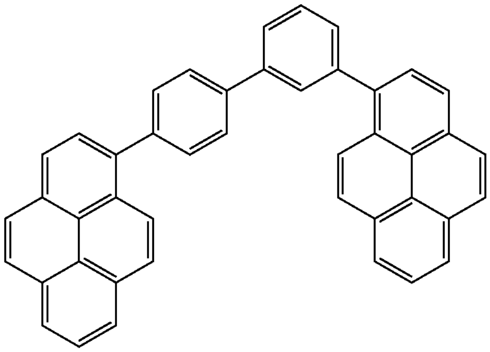
BH2-35
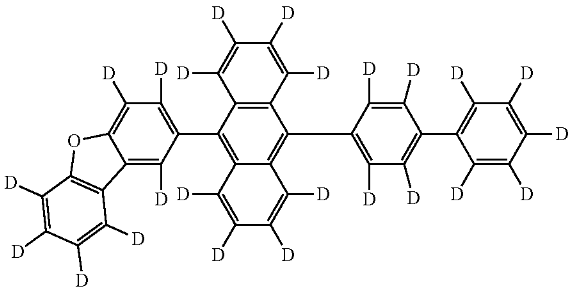

Combination 84
The first compound is BH1-87 and the second compound is BH2-36.
[Formula 229]
BH1-87
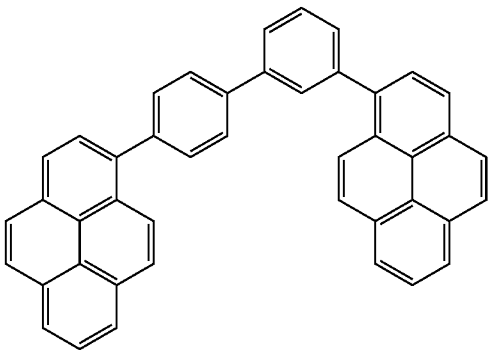
BH2-36
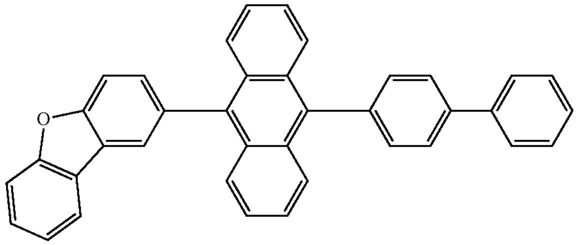
Combination 85
The first compound is BH1-87 and the second compound is BH2-37.
[Formula 230]
BH1-87
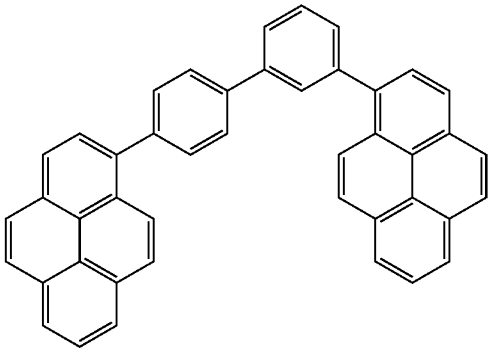
-continued
BH2-37
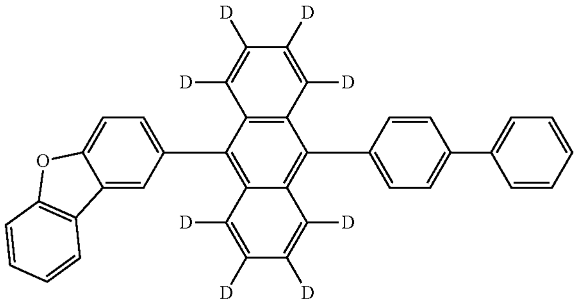
Combination 86
The first compound is BH1-88 and the second compound is BH2-19.
[Formula 231]
BH1-88
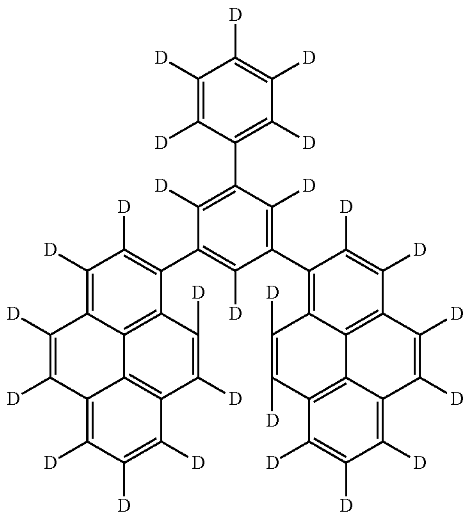
BH2-19
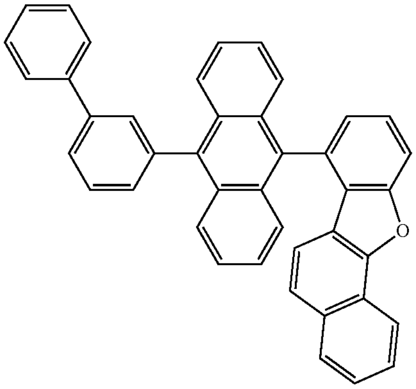

Combination 87
The first compound is BH1-88 and the second compound is BH2-7.
[Formula 232]
BH1-88
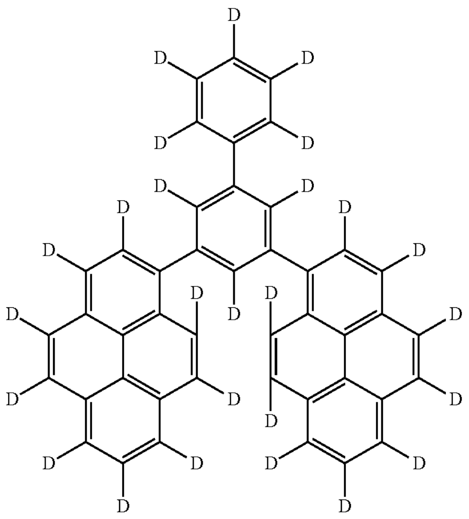
BH2-7
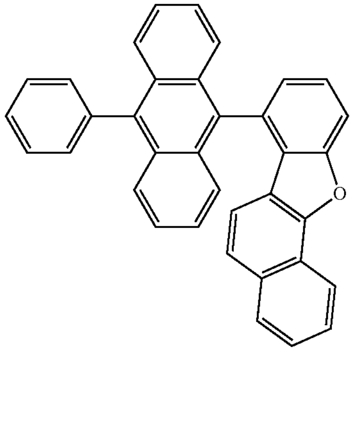
Combination 88
The first compound is BH1-88 and the second compound is BH2-20.
BH1-88
[Formula 233]
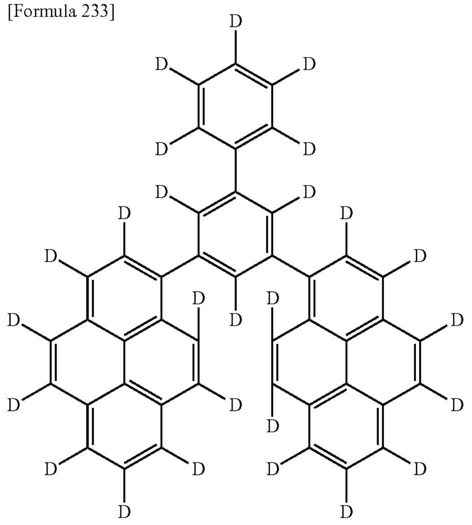
BH2-20
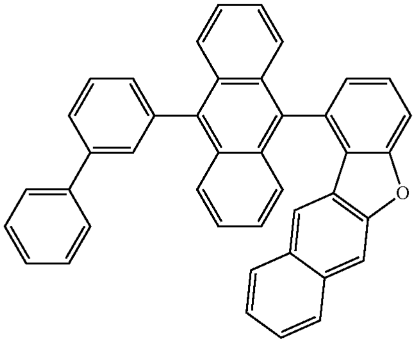
Combination 89
The first compound is BH1-88 and the second compound is BH2-31.
[Formula 234]
BH1-88
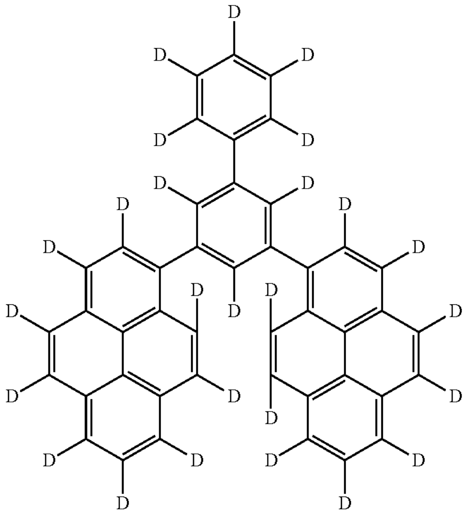

-continued
BH2-31
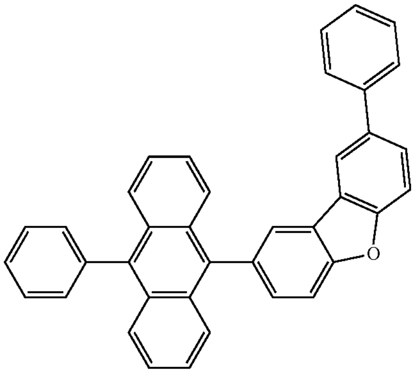
Combination 90
The first compound is BH1-88 and the second compound is BH2-32.
[Formula 235]
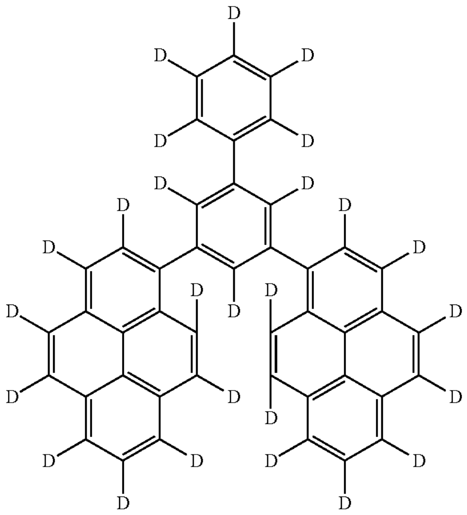
BH1-88
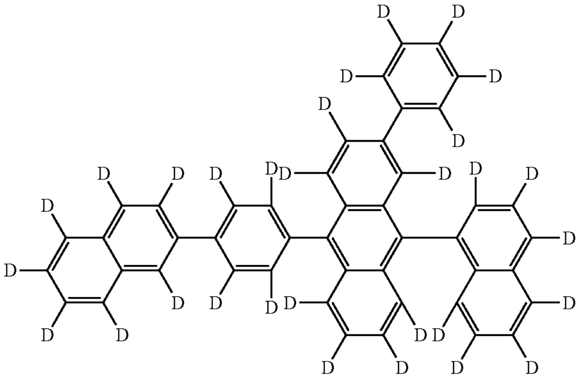
BH2-32
Combination 91
The first compound is BH1-88 and the second compound is BH2-33.
[Formula 236]
BH1-88
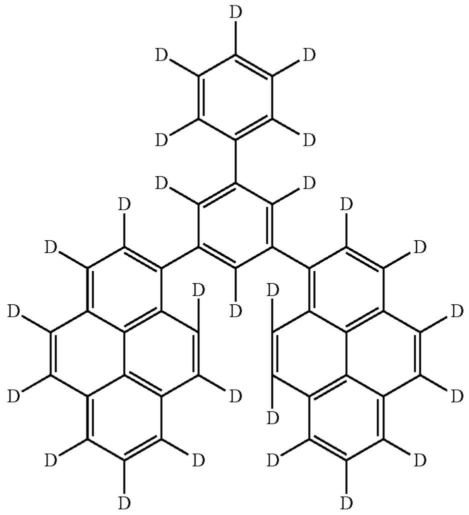
BH2-33
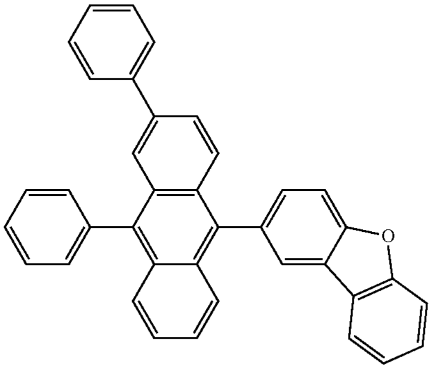

Combination 92
The first compound is BH1-88 and the second compound is BH2-5.
[Formula 237]
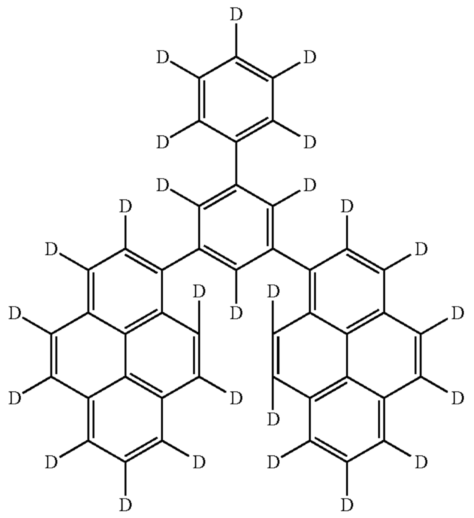
BH1-88
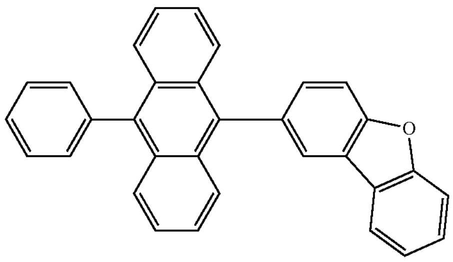
BH2-5
Combination 93
The first compound is BH1-88 and the second compound is BH2-8.
[Formula 238]
BH1-88
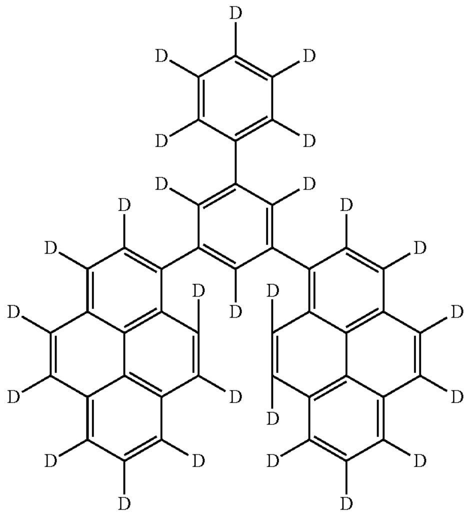
BH2-8
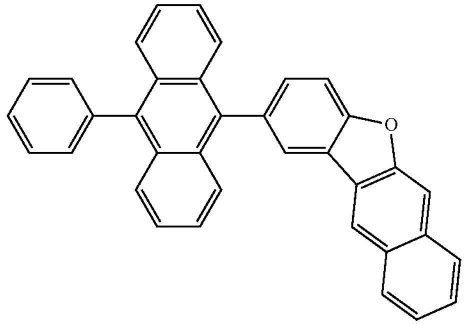
Combination 94
The first compound is BH1-88 and the second compound is BH2.
[Formula 239]
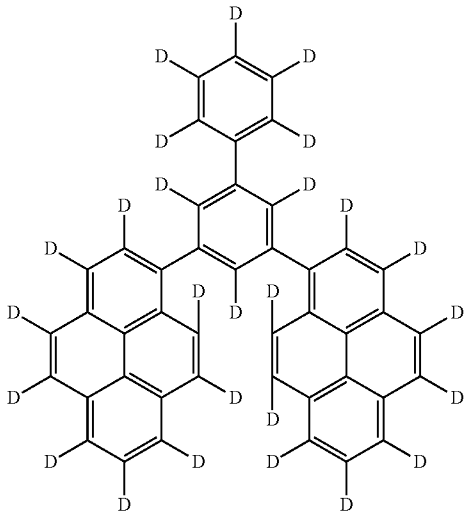
BH1-88

-continued
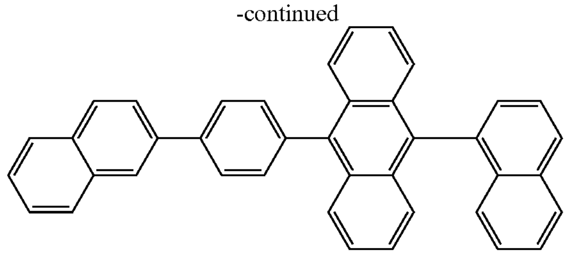
BH2
Combination 95
The first compound is BH1-88 and the second compound is BH2-30.
[Formula 240]
BH1-88
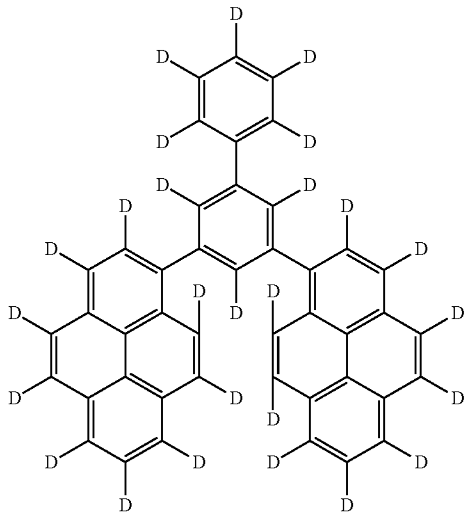
BH2-30
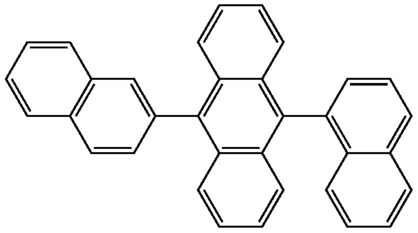
Combination 96
The first compound is BH1-88 and the second compound is BH2 and BH2-30.
[Formula 241]
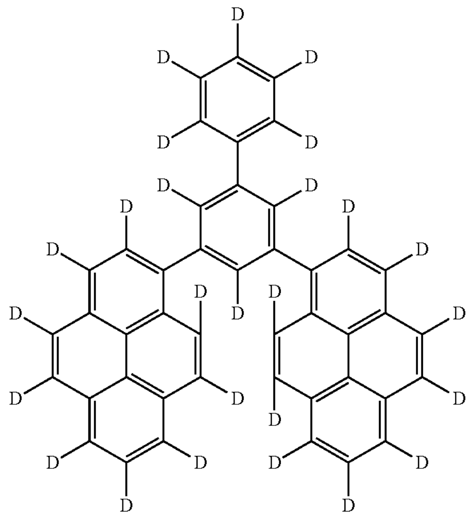
BH1-88
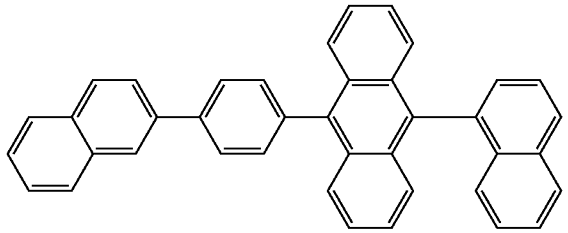
BH2
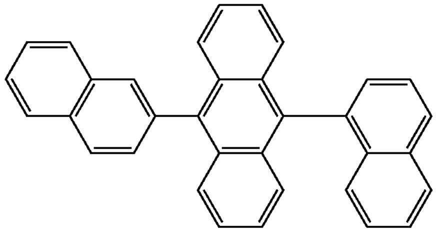
BH2-30

Combination 97
The first compound is BH1-88 and the second compound is BH2-9.
[Formula 242]
BH1-88
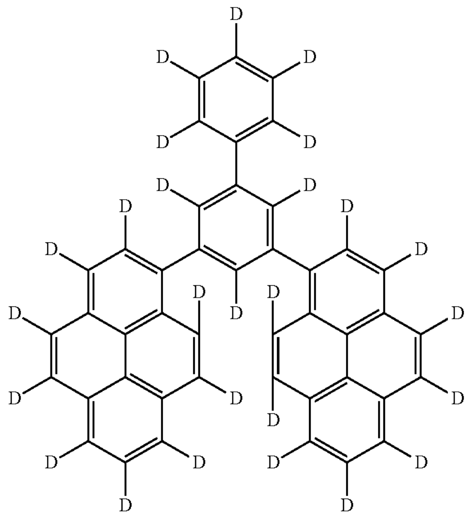
BH2-9
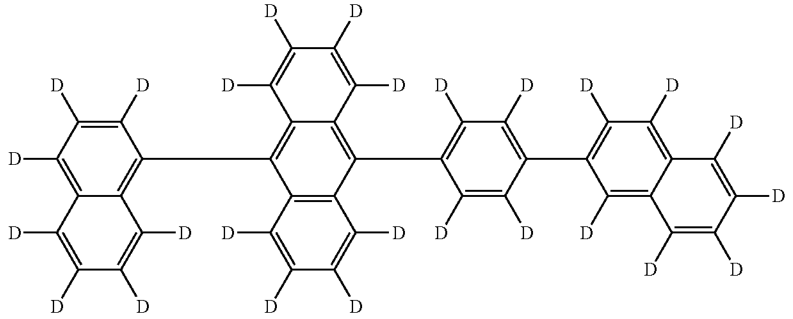

Combination 98
The first compound is BH1-88 and the second compound is BH2-3.
[Formula 243]
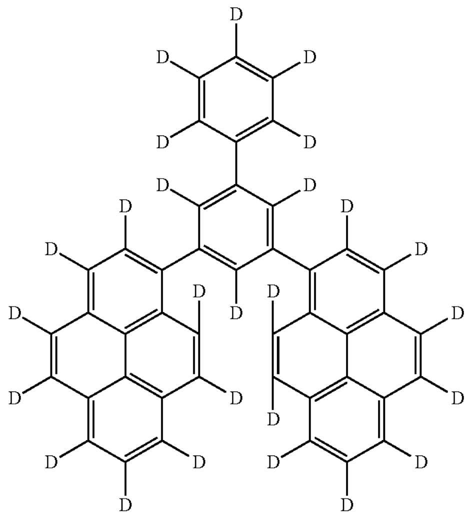
BH1-88
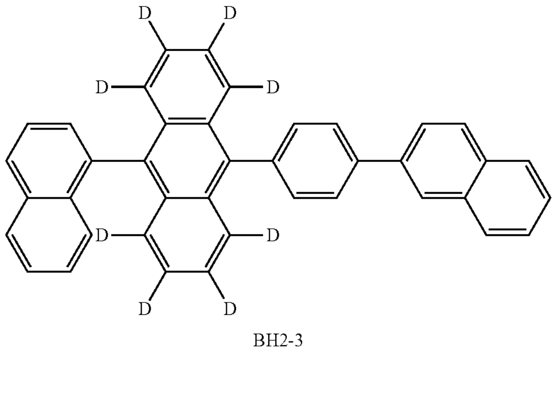
BH2-3
Combination 99
The first compound is BH1-88 and the second compound is BH2-34.
[Formula 244]
BH1-88
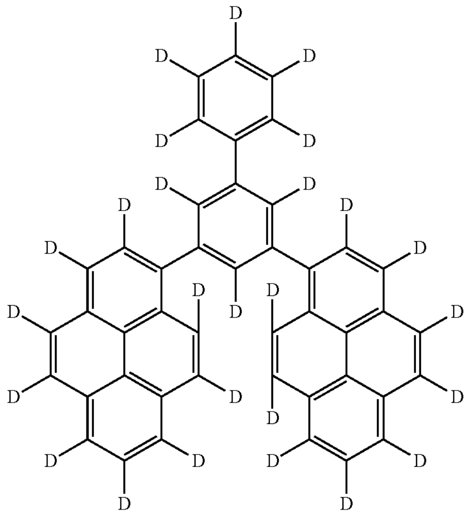
BH2-34
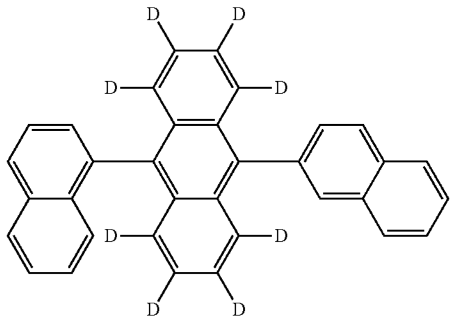
Combination 100
The first compound is BH1-88 and the second compound is BH2-35.
[Formula 245]
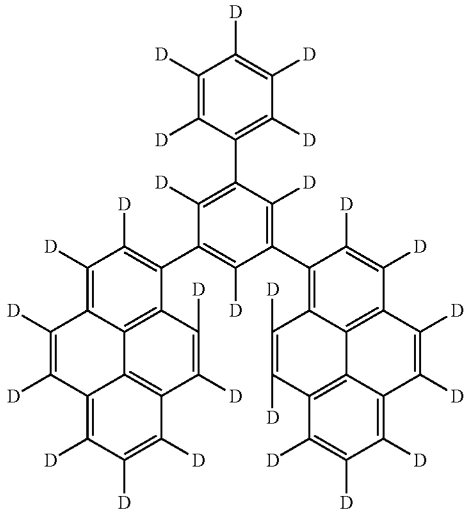
BH1-88

-continued
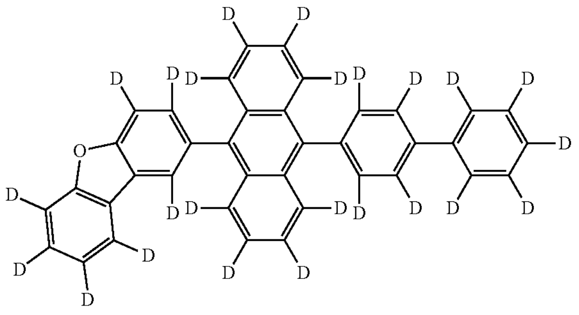
BH2-35
Combination 101
The first compound is BH1-88 and the second compound is BH2-36.
[Formula 246]
BH1-88
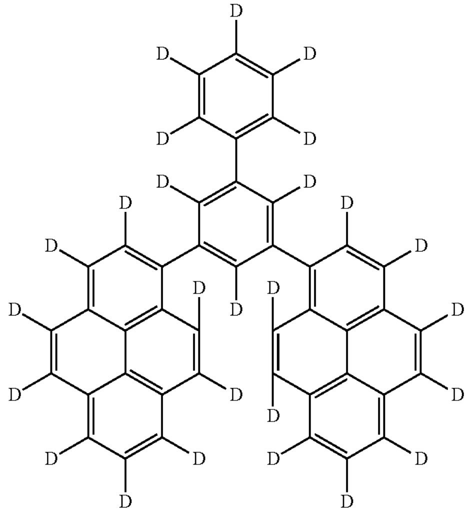
BH2-36
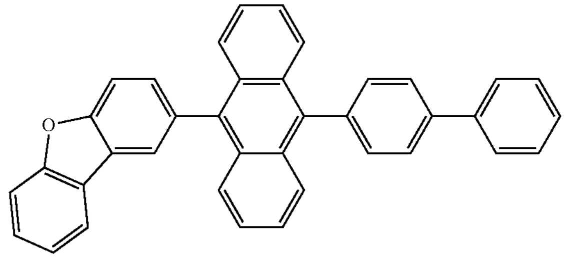
Combination 102
The first compound is BH1-88 and the second compound is BH2-37.
[Formula 247]
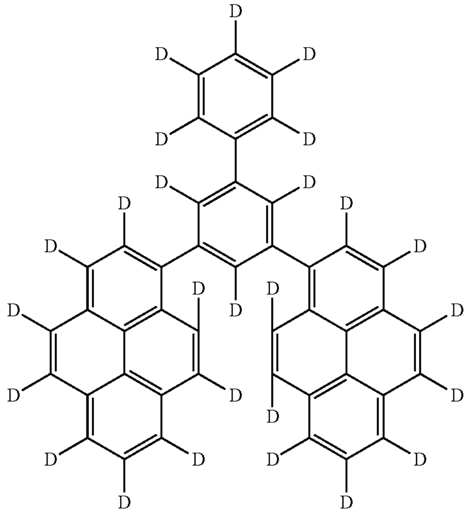
BH1-88
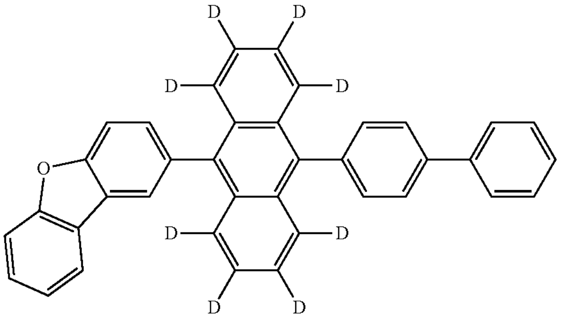
BH2-37
Combination 103
The first compound is BH1-89 and the second compound is BH2-19.
[Formula 248]
BH1-89
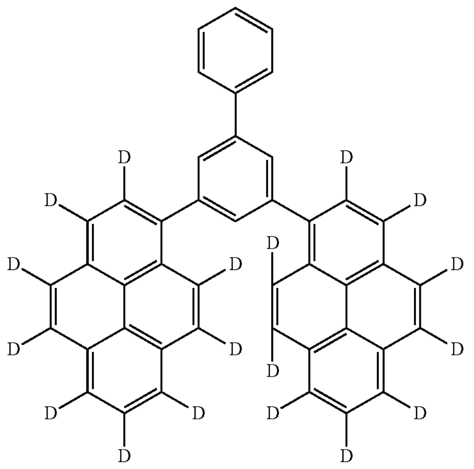

-continued
BH2-19
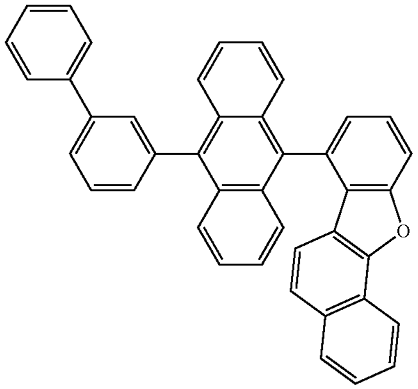
Combination 104
The first compound is BH1-89 and the second compound is BH2-7.
[Formula 249]
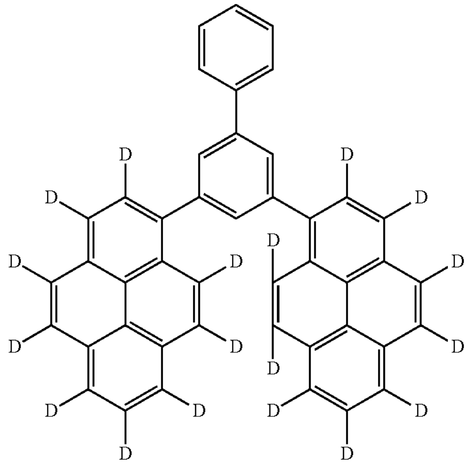
BH1-89
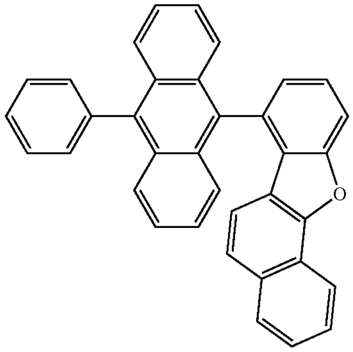
BH2-7
Combination 105
The first compound is BH1-89 and the second compound is BH2-20.
[Formula 250]
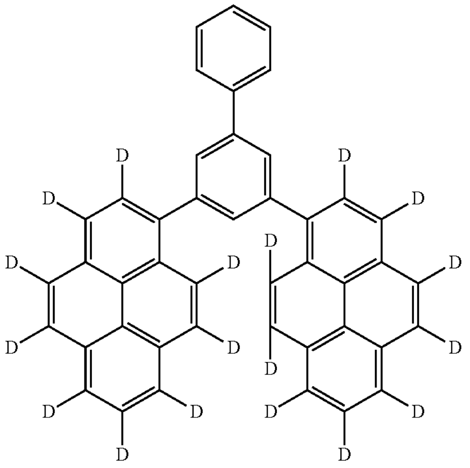
BH1-89
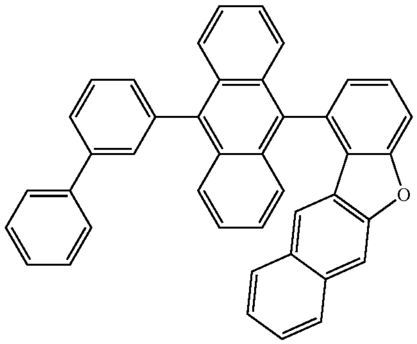
BH2-20
Combination 106
The first compound is BH1-89 and the second compound is BH2-31.
[Formula 251]
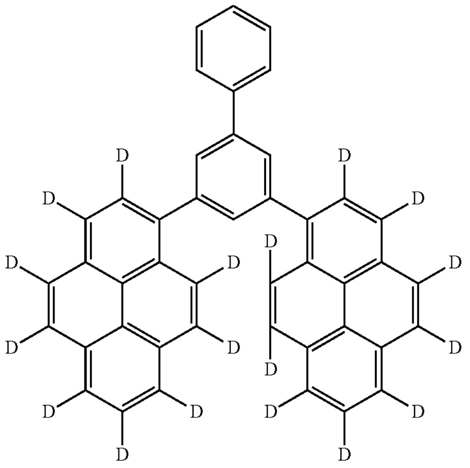
BH1-89

-continued
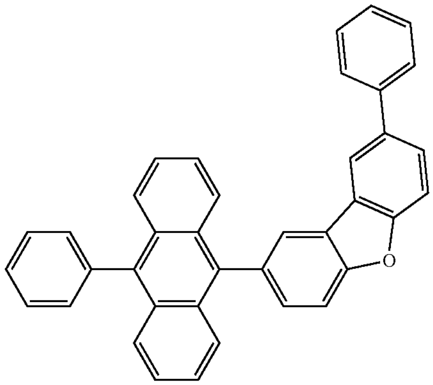
BH2-31
Combination 107
The first compound is BH1-89 and the second compound is BH2-32.
[Formula 252]
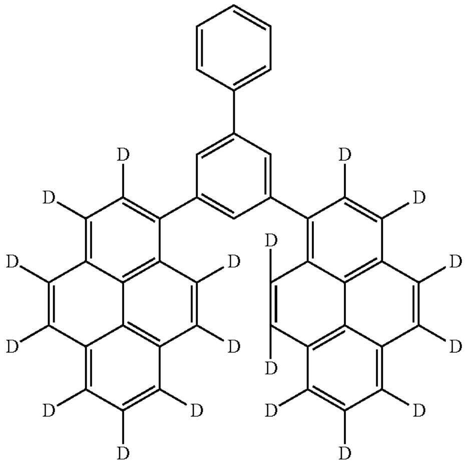
BH1-89
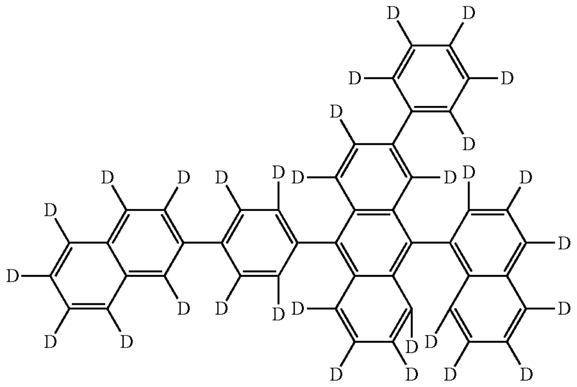
BH2-32
Combination 108
The first compound is BH1-89 and the second compound is BH2-33.
[Formula 253]
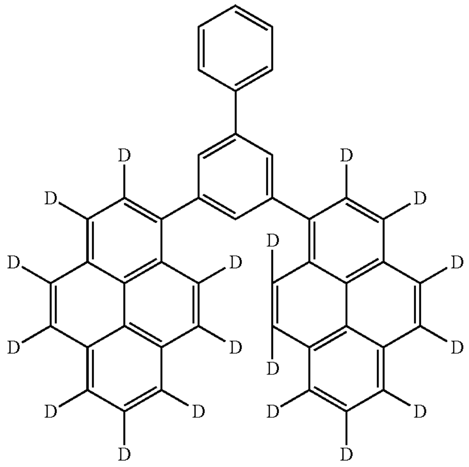
BH1-89
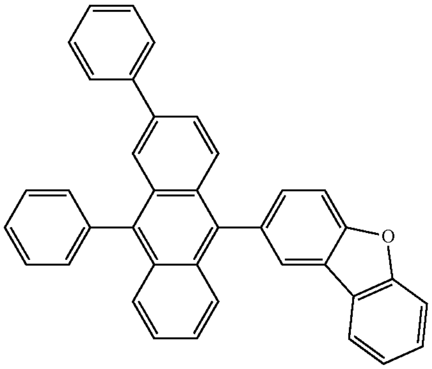
BH2-33
Combination 109
The first compound is BH1-89 and the second compound is BH2-5.
[Formula 254]
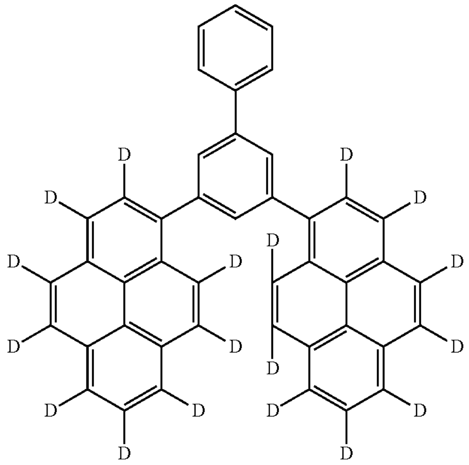
BH1-89

-continued
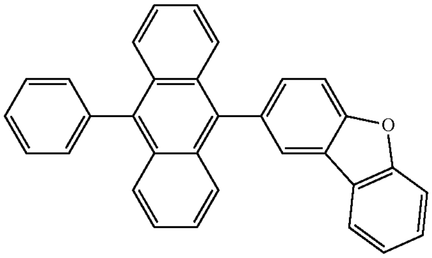
BH2-5
Combination 110
The first compound is BH1-89 and the second compound is BH2-8.
[Formula 255]
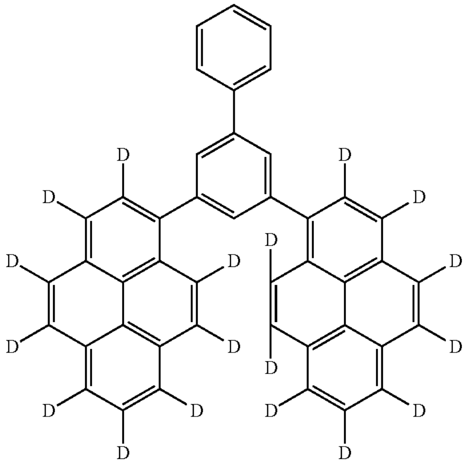
BH1-89
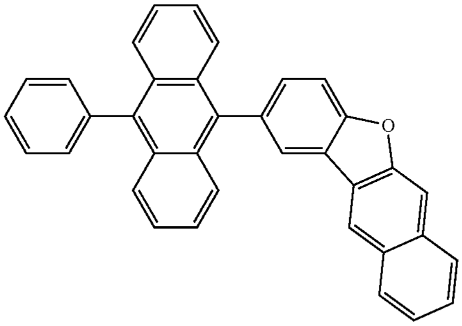
BH2-8
Combination 111
The first compound is BH1-89 and the second compound is BH2.
[Formula 256]
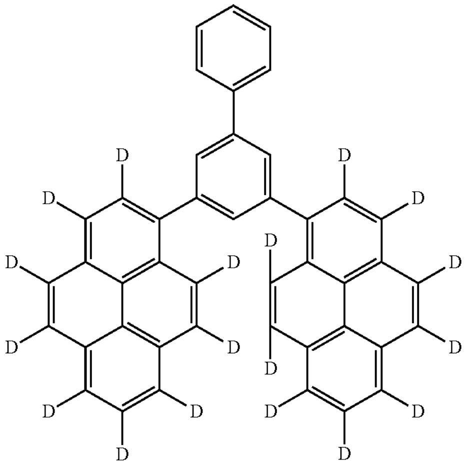
BH1-89
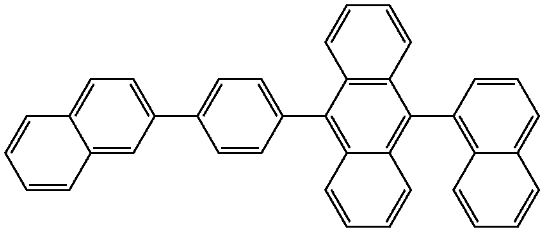
BH2
Combination 112
The first compound is BH1-89 and the second compound is BH2-30.
[Formula 257]
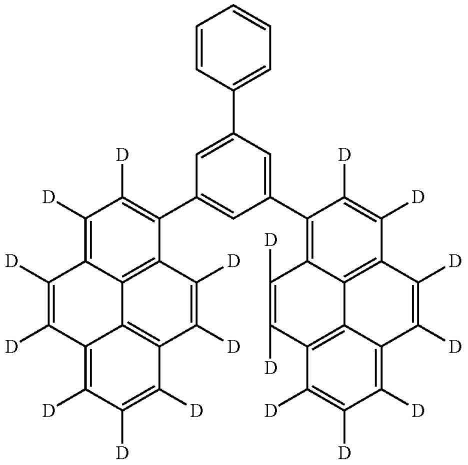
BH1-89

-continued
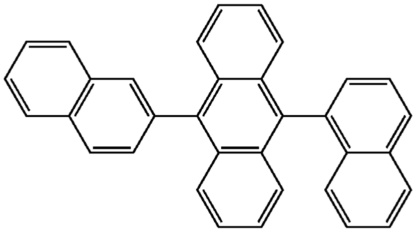
BH2-30
Combination 113
The first compound is BH1-89 and the second compound is BH2 and BH2-30.
[Formula 258]
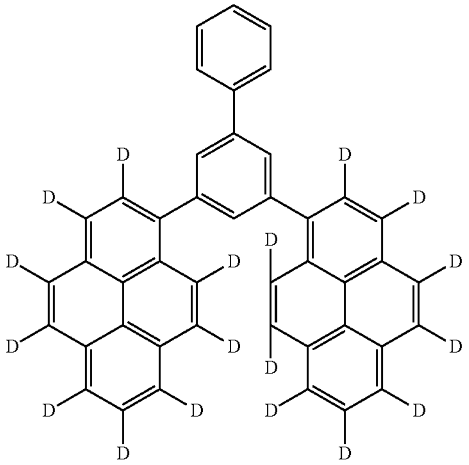
BH1-89
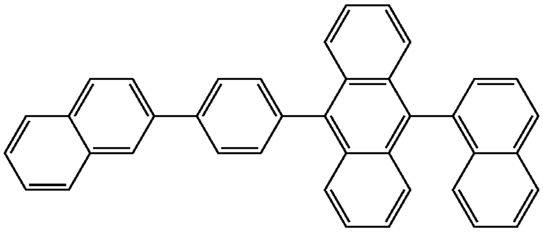
BH2
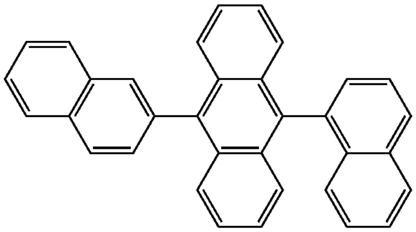
BH2-30
Combination 114
The first compound is BH1-89 and the second compound is BH2-9.
[Formula 259]
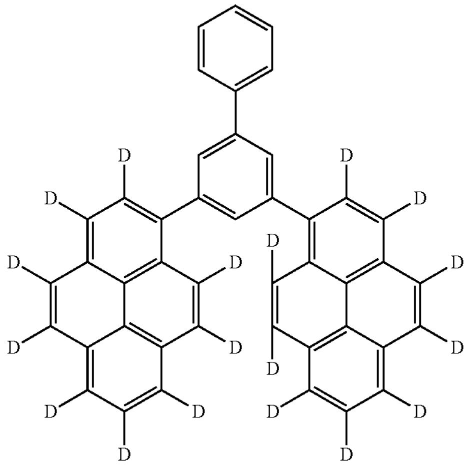
BH1-89
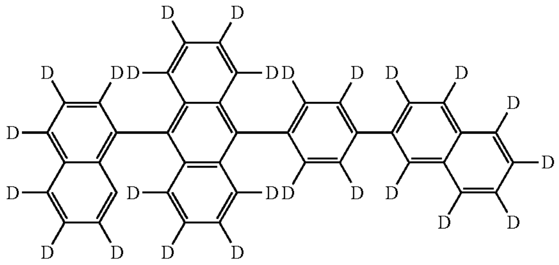
BH2-9
Combination 115
The first compound is BH1-89 and the second compound is BH2-3.
[Formula 260]
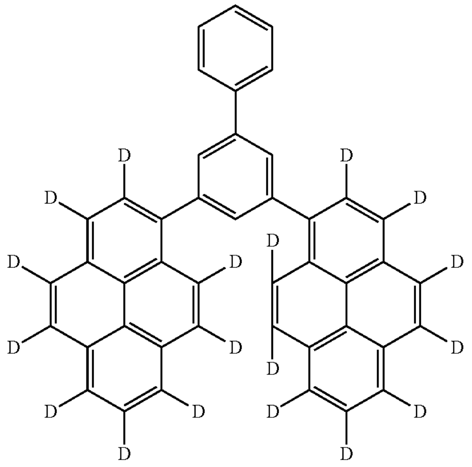
BH1-89

-continued
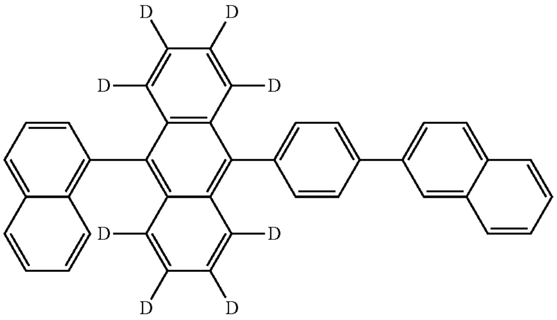
BH2-3
Combination 116
The first compound is BH1-89 and the second compound is BH2-34.
[Formula 261]
BH1-89
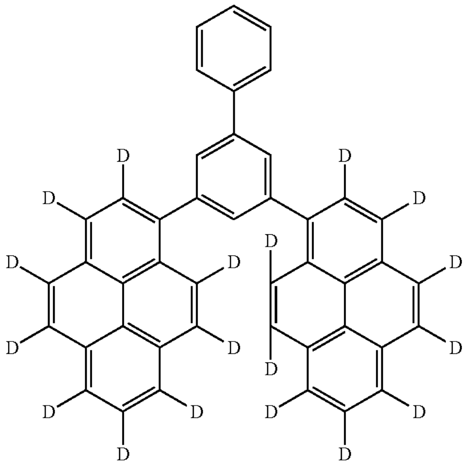
BH2-34
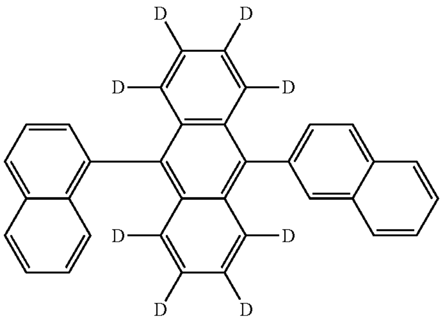
Combination 117
The first compound is BH1-89 and the second compound is BH2-35.
[Formula 262]
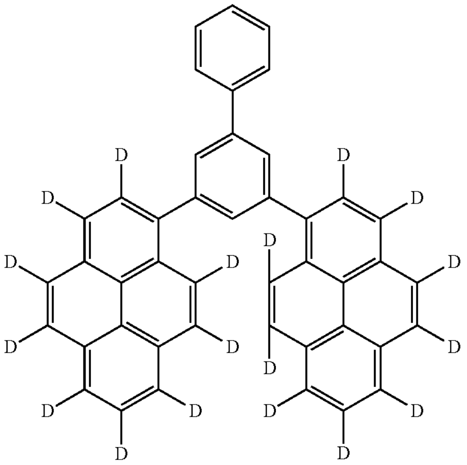
BH1-89
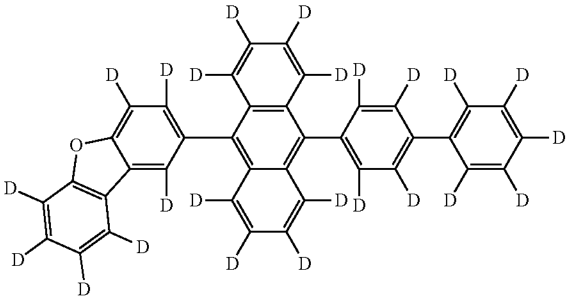
BH2-35
Combination 118
The first compound is BH1-89 and the second compound is BH2-36.
[Formula 263]
BH1-89
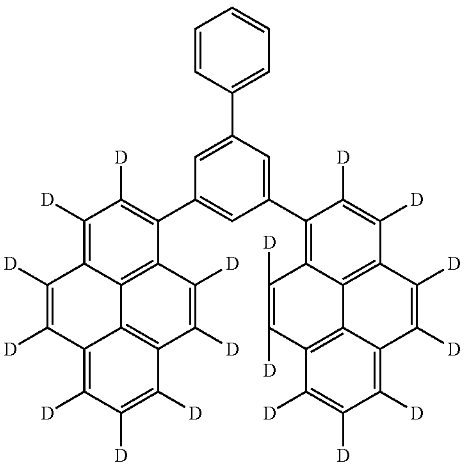

-continued
BH2-36
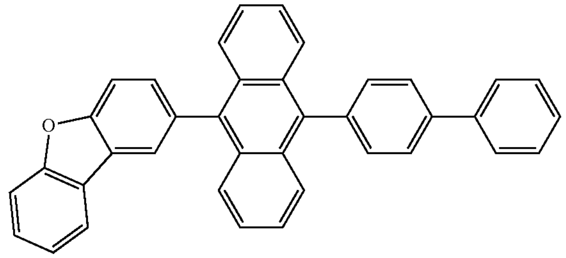
Combination 119
The first compound is BH1-89 and the second compound is BH2-37.
[Formula 264]
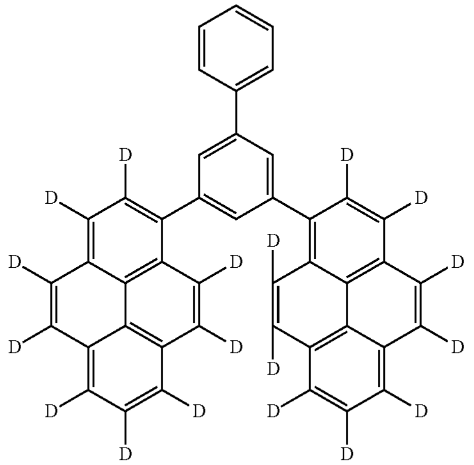
BH1-89
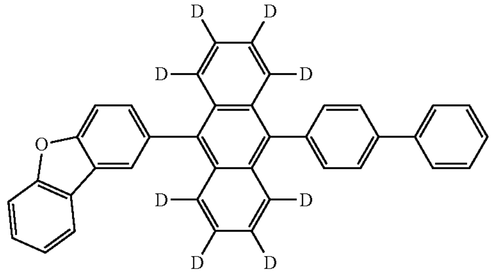
BH2-37
Combination 120
The first compound is BH1-90 and the second compound is BH2-19.
[Formula 265]
BH1-90
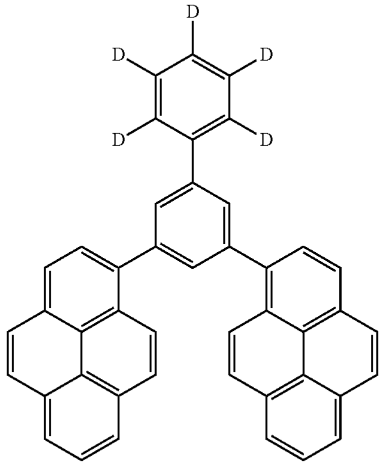
BH2-19
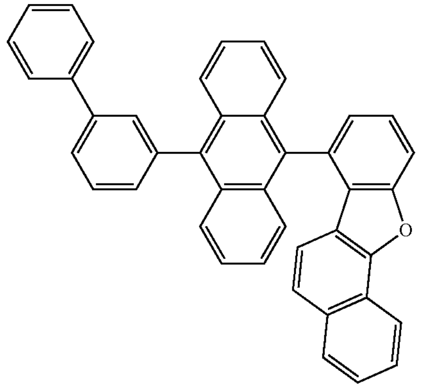
Combination 121
The first compound is BH1-90 and the second compound is BH2-7.
[Formula 266]
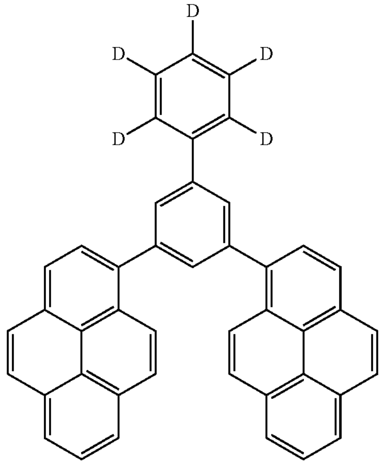
BH1-90

-continued
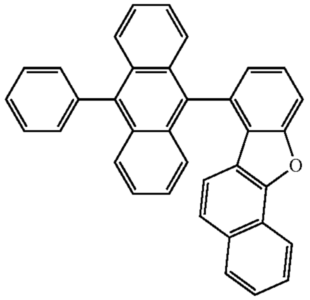
BH2-7
Combination 122
The first compound is BH1-90 and the second compound is BH2-20.
[Formula 267]
BH1-90
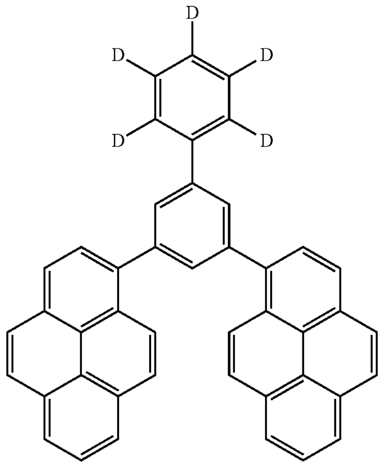
BH2-20
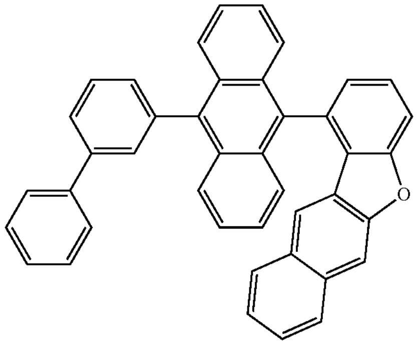
Combination 123
The first compound is BH1-90 and the second compound is BH2-31.
[Formula 268]
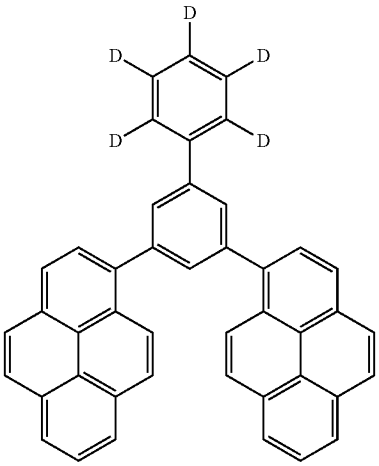
BH1-90
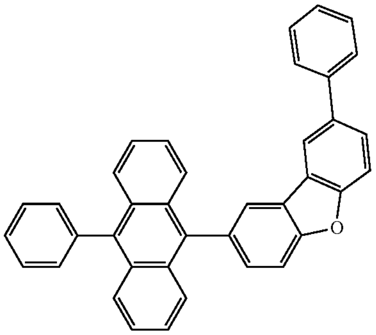
BH2-31
Combination 124
The first compound is BH1-90 and the second compound is BH2-32.
[Formula 269]
BH1-90
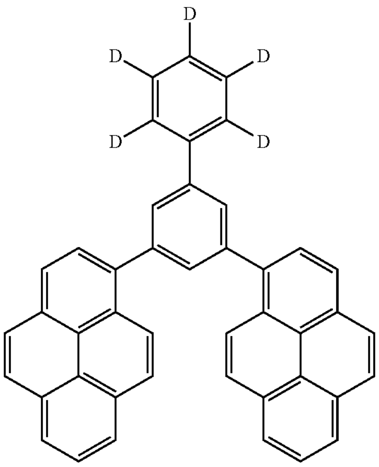

-continued
BH2-32
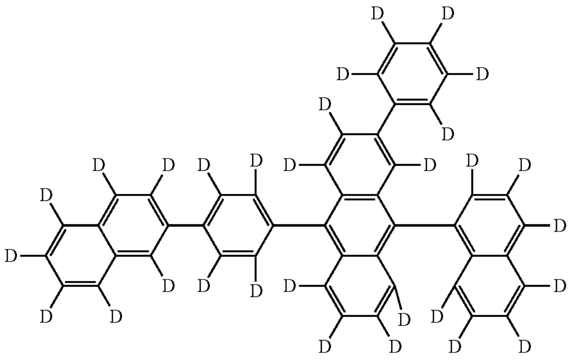
Combination 125
The first compound is BH1-90 and the second compound is BH2-33.
[Formula 270]
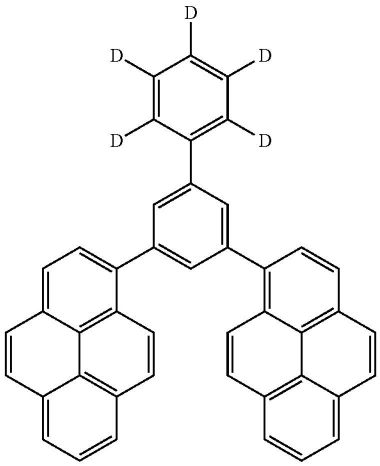
BH1-90
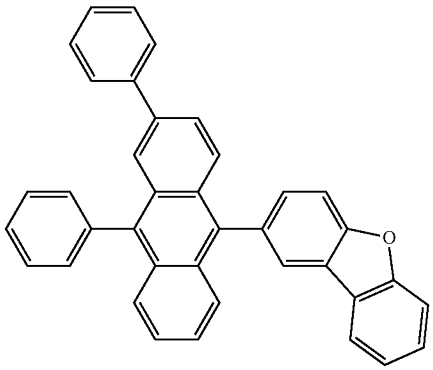
BH2-33
Combination 126
The first compound is BH1-90 and the second compound is BH2-5.
[Formula 271]
BH1-90
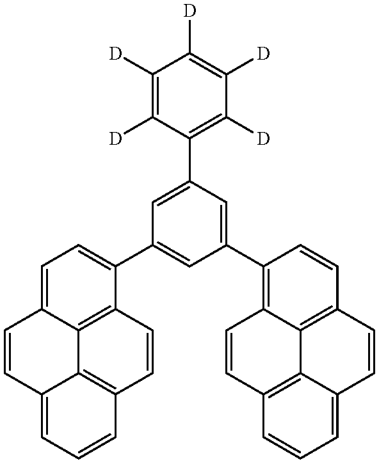
BH2-5
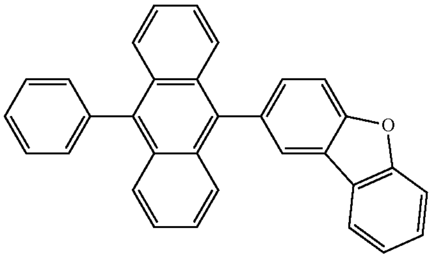
Combination 127
The first compound is BH1-90 and the second compound is BH2-8.
[Formula 272]
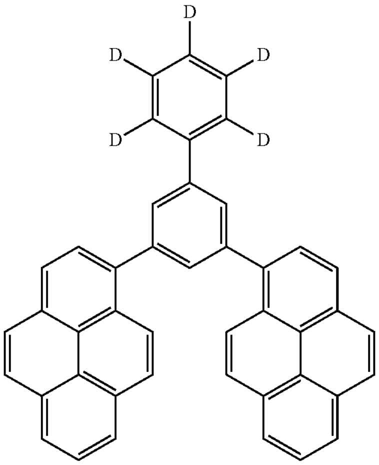
BH1-90

-continued
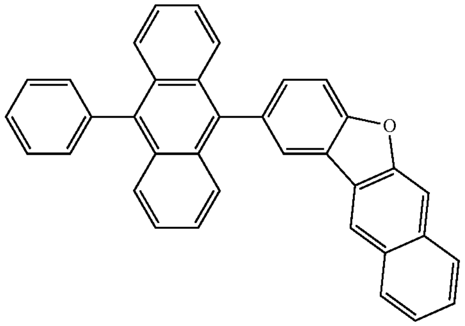
BH2-8
Combination 128
The first compound is BH1-90 and the second compound is BH2.
[Formula 273]
BH1-90
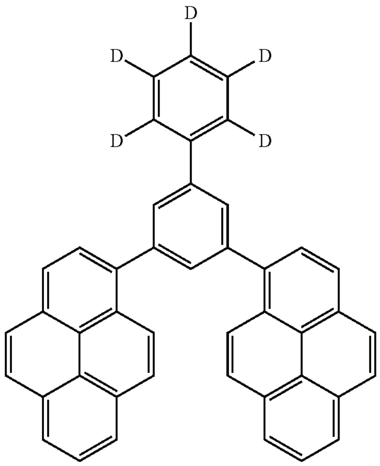
BH2
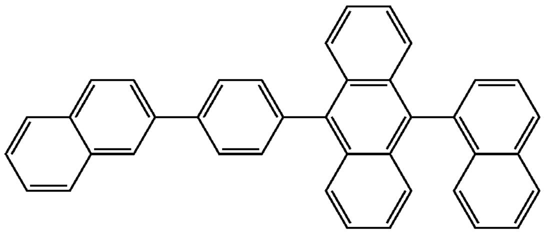
Combination 129
The first compound is BH1-90 and the second compound is BH2-30.
[Formula 274]
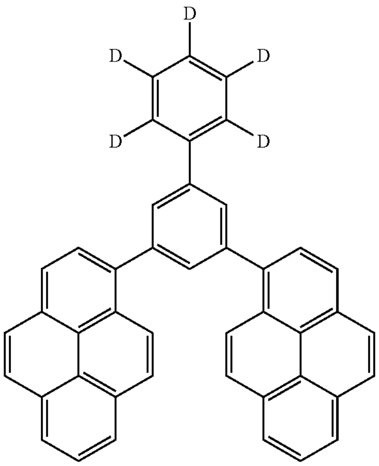
BH1-90
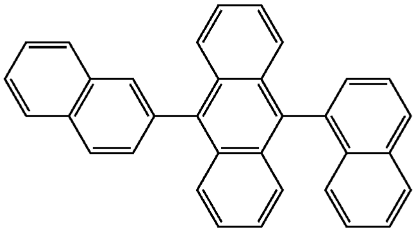
BH2-30
Combination 130
The first compound is BH1-90 and the second compound is BH2 and BH2-30.
[Formula 275]
BH1-90
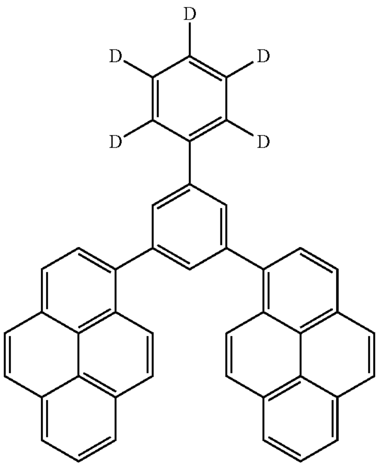

-continued
BH2
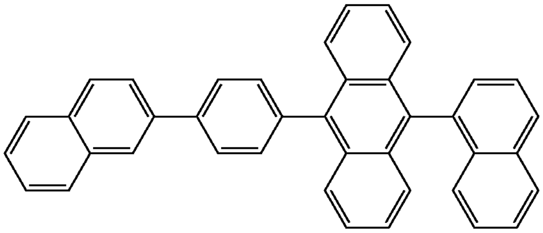
BH2-30
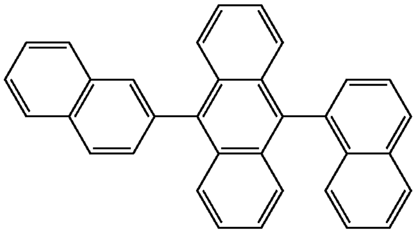
Combination 131
The first compound is BH1-90 and the second compound is BH2-9.
[Formula 276]
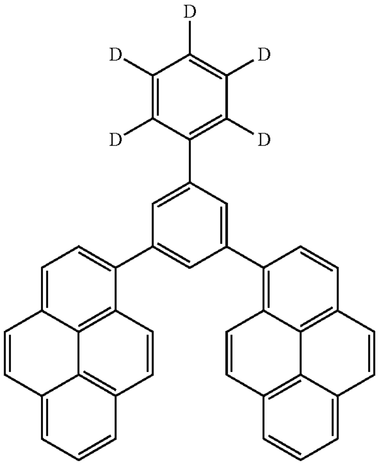
BH1-90
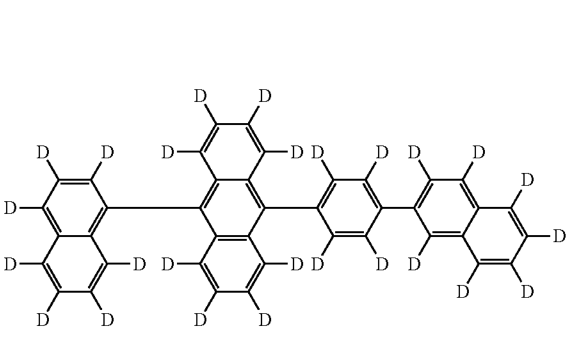
BH2-9
Combination 132
The first compound is BH1-90 and the second compound is BH2-3.
[Formula 277]
BH1-90
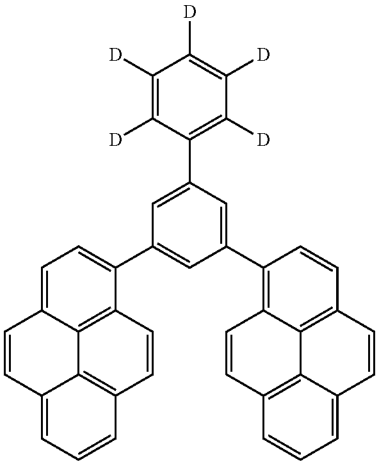
BH2-3
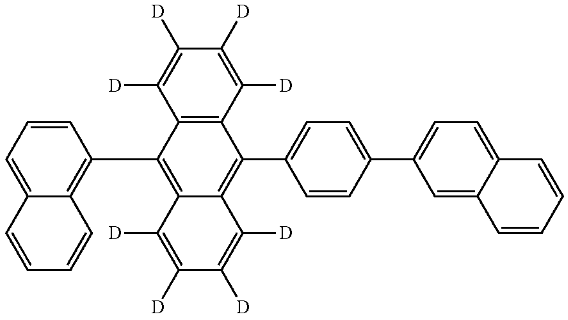
Combination 133
The first compound is BH1-90 and the second compound is BH2-34.
[Formula 278]
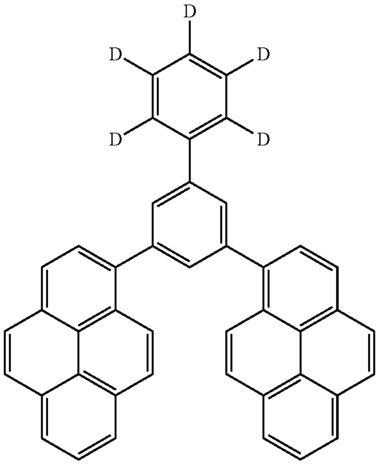
BH1-90

-continued
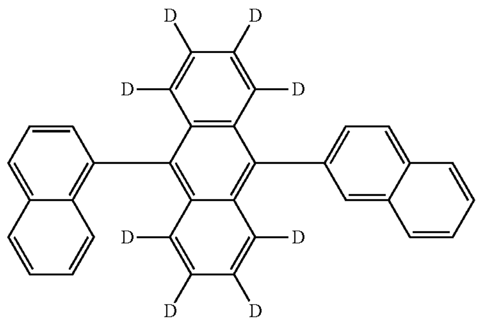
BH2-34
Combination 134
The first compound is BH1-90 and the second compound is BH2-35.
[Formula 279]
BH1-90
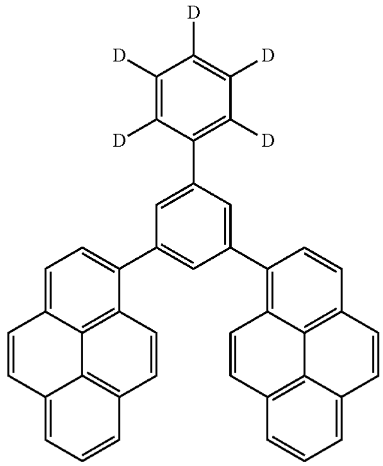
BH2-35
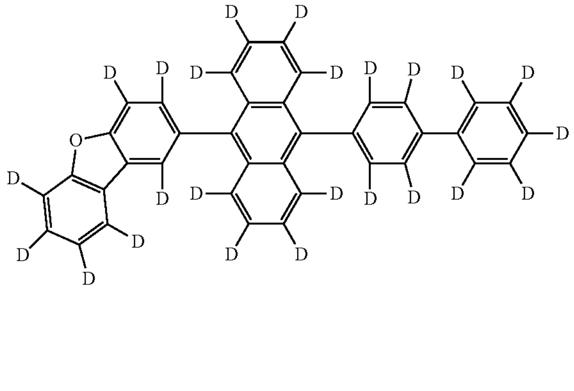
Combination 135
The first compound is BH1-90 and the second compound is BH2-36.
[Formula 280]
BH1-90
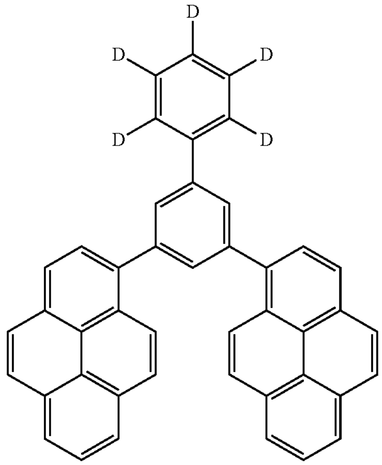
BH2-36
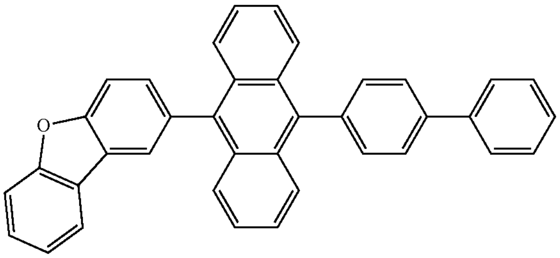
Combination 136
The first compound is BH1-90 and the second compound is BH2-37.
[Formula 281]
BH1-90
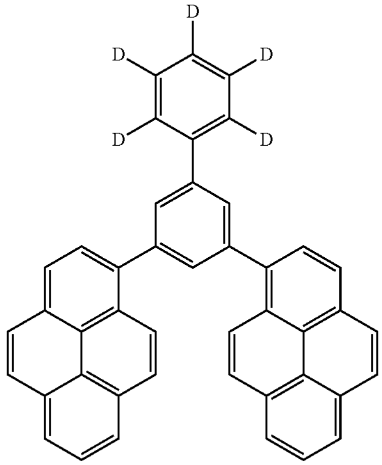

-continued

BH2-37

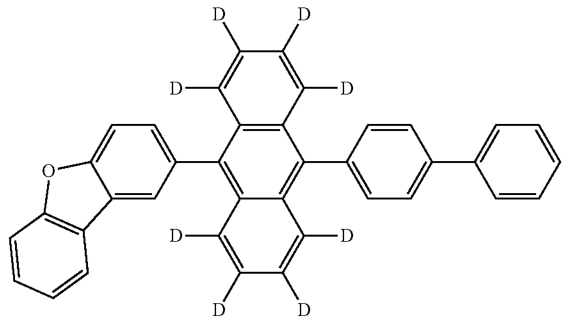

Third Compound and Fourth Compound

In the organic EL device according to the exemplary embodiment, the first emitting layer also preferably further contains a third compound that emits fluorescence.

In the organic EL device according to the exemplary embodiment, the second emitting layer also preferably further contains a fourth compound that emits fluorescence.

When the first emitting layer contains the third compound and the second emitting layer contains the fourth compound, the third compound and the fourth compound are mutually the same or different.

The third compound and the fourth compound are each independently at least one compound selected from the group consisting of a compound represented by a formula (3) below, a compound represented by a formula (4) below, a compound represented by a formula (5) below, a compound represented by a formula (6) below, a compound represented by a formula (7) below, a compound represented by a formula (8) below, a compound represented by a formula (9) below, and a compound represented by a formula (10) below.

Compound Represented by Formula (3)

The compound represented by the formula (3) will be described below.

[Formula 282]

(3)

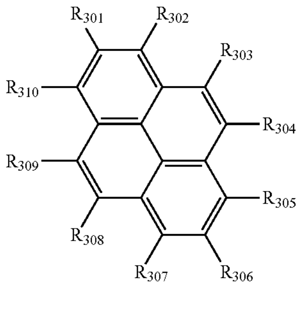

In the formula (3):

at least one combination of adjacent two or more of $R_{301}$ to $R_{310}$ are mutually bonded to form a substituted or unsubstituted monocyclic ring, mutually bonded to form a substituted or unsubstituted fused ring, or not mutually bonded;

at least one of $R_{301}$ to $R_{310}$ is a monovalent group represented by a formula (31) below; and $R_{301}$ to $R_{310}$ forming neither the monocyclic ring nor the fused ring and not being the monovalent group represented by the formula (31) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 283]

(31)

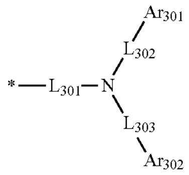

In the formula (31):

$Ar_{301}$ and $Ar_{302}$ are each independently a substituted or unsubstituted aryl group having 6 to 50 ring carbon atoms, or a substituted or unsubstituted heterocyclic group having 5 to 50 ring atoms;

$L_{301}$ to $L_{303}$ are each independently a single bond, a substituted or unsubstituted arylene group having 6 to 30 ring carbon atoms, or a substituted or unsubstituted divalent heterocyclic group having 5 to 30 ring atoms; and

* represents a bonding position to a pyrene ring in the formula (3).

In the third and fourth compounds: $R_{901}$, $R_{902}$, $R_{903}$, $R_{904}$, $R_{905}$, $R_{906}$, and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

In the formula (3), two of $R_{301}$ to $R_{310}$ are preferably groups represented by the formula (31).

In an exemplary embodiment, the compound represented by the formula (3) is a compound represented by a formula (33) below.

[Formula 284]

(33)

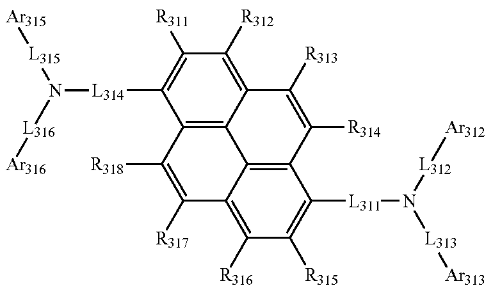

In the formula (33):

$R_{311}$ to $R_{318}$ each independently represent the same as $R_{301}$ to $R_{310}$ in the formula (3) that are not the monovalent group represented by the formula (31);

$L_{311}$ to $L_{316}$ are each independently a single bond, a substituted or unsubstituted arylene group having 6 to 30 ring carbon atoms, or a substituted or unsubstituted divalent heterocyclic group having 5 to 30 ring atoms; and $Ar_{312}$, $Ar_{313}$, $Ar_{315}$, and $Ar_{316}$ are each independently a substituted or unsubstituted aryl group having 6 to 50 ring carbon atoms, or a substituted or unsubstituted heterocyclic group having 5 to 50 ring atoms.

In the formula (31), $L_{301}$ is preferably a single bond, and $L_{302}$ and $L_{303}$ are each preferably a single bond.

In an exemplary embodiment, the compound represented by the formula (3) is represented by a formula (34) or (35) below.

[Formula 285]

(34)

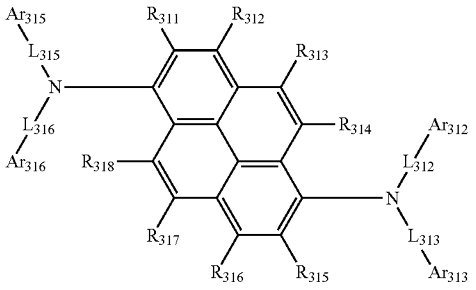

In the formula (34):

$R_{311}$ to $R_{318}$ each independently represent the same as $R_{301}$ to $R_{310}$ in the formula (3) that are not the monovalent group represented by the formula (31);

$L_{312}$, $L_{313}$, $L_{315}$ and $L_{316}$ each independently represent the same as $L_{312}$, $L_{313}$, $L_{315}$ and $L_{316}$ in the formula (33); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

[Formula 286]

(35)

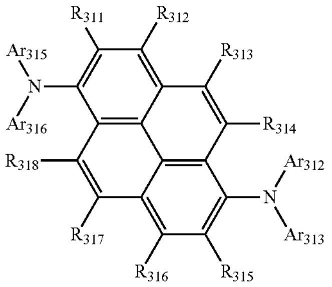

In the formula (35):

$R_{311}$ to $R_{318}$ each independently represent the same as $R_{301}$ to $R_{310}$ in the formula (3) that are not the monovalent group represented by the formula (31); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

In the formula (31), at least one of $Ar_{301}$ or $Ar_{302}$ is preferably a group represented by a formula (36) below.

In the formulae (33) to (35), at least one of $Ar_{312}$ or $Ar_{313}$ is preferably a group represented by the formula (36) below.

In the formulae (33) to (35), at least one of $Ar_{315}$ or $Ar_{316}$ is preferably a group represented by the formula (36) below.

[Formula 287]

(36)

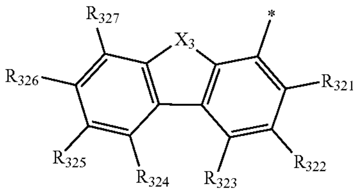

In the formula (36):

$X_3$ represents an oxygen atom or a sulfur atom;

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

$R_{321}$ to $R_{327}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position to $L_{302}$, $L_{303}$, $L_{312}$, $L_{313}$, $L_{315}$ or $L_{316}$.

$X_3$ is preferably an oxygen atom.

At least one of $R_{321}$ to $R_{327}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formula (31), it is preferable that $Ar_{301}$ is a group represented by the formula (36) and $Ar_{302}$ is a substituted or unsubstituted aryl group having 6 to 50 ring carbon atoms.

In the formulae (33) to (35), it is preferable that $Ar_{312}$ is a group represented by the formula (36) and $Ar_{313}$ is a substituted or unsubstituted aryl group having 6 to 50 ring carbon atoms.

In the formulae (33) to (35), it is preferable that $Ar_{315}$ is a group represented by the formula (36) and $Ar_{316}$ is a substituted or unsubstituted aryl group having 6 to 50 ring carbon atoms.

In an exemplary embodiment, the compound represented by the formula (3) is represented by a formula (37) below.

[Formula 288]

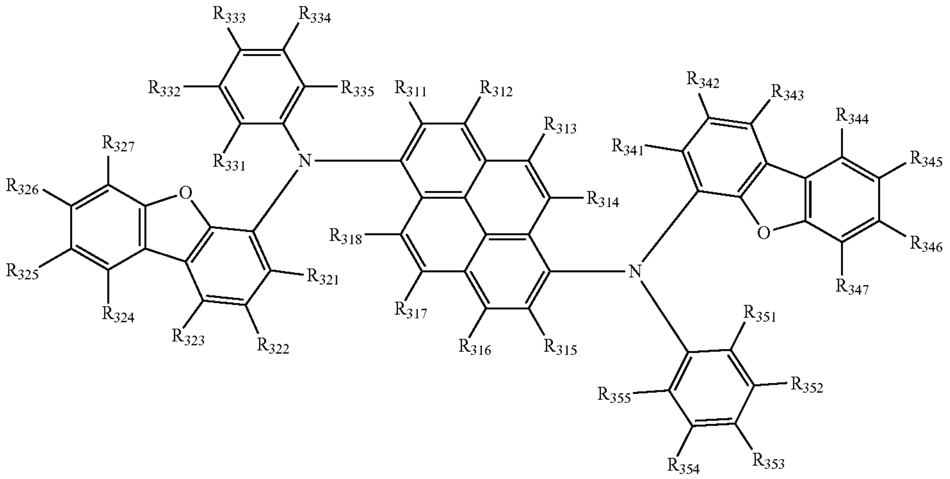

(37)

In the formula (37):

$R_{311}$ to $R_{318}$ each independently represent the same as $R_{301}$ to $R_{310}$ in the formula (3) that are not the monovalent group represented by the formula (31);

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

at least one combination of adjacent two or more of $R_{341}$ to $R_{347}$ are mutually bonded to form a substituted or unsubstituted monocyclic ring, mutually bonded to form a substituted or unsubstituted fused ring, or not mutually bonded;

$R_{321}$ to $R_{327}$ and $R_{341}$ to $R_{347}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{331}$ to $R_{335}$, and $R_{351}$ to $R_{335}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (3) include compounds shown below.

[Formula 289]
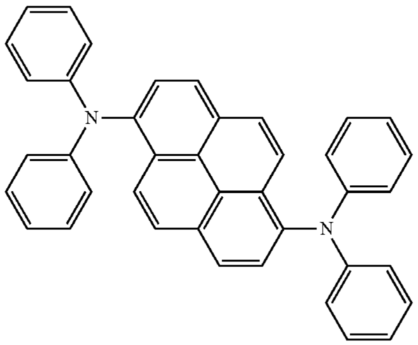
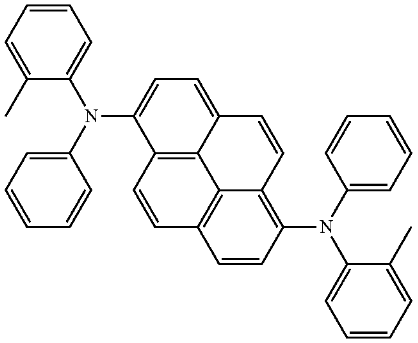
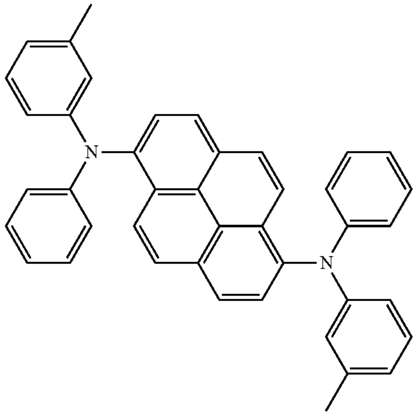
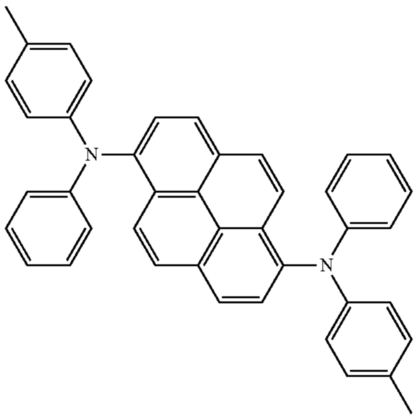
-continued
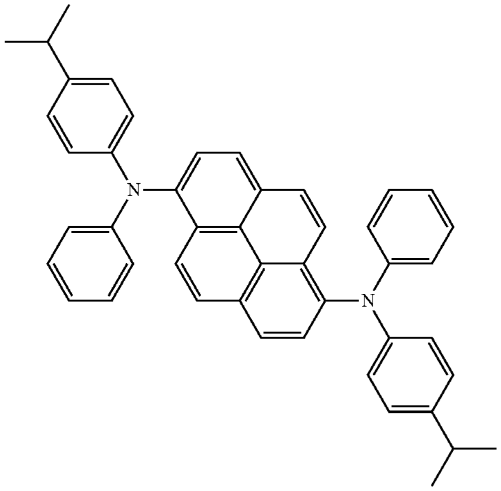
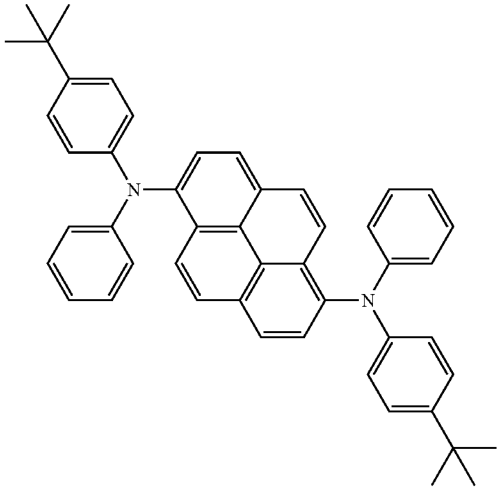
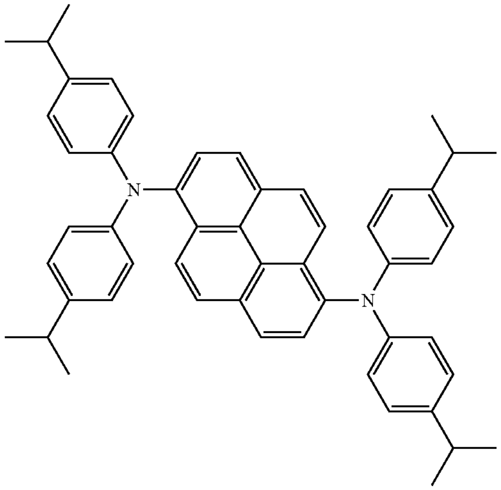

-continued
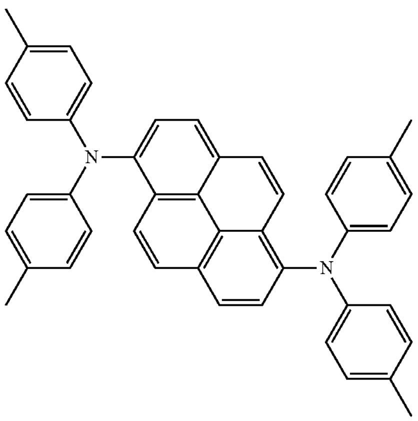
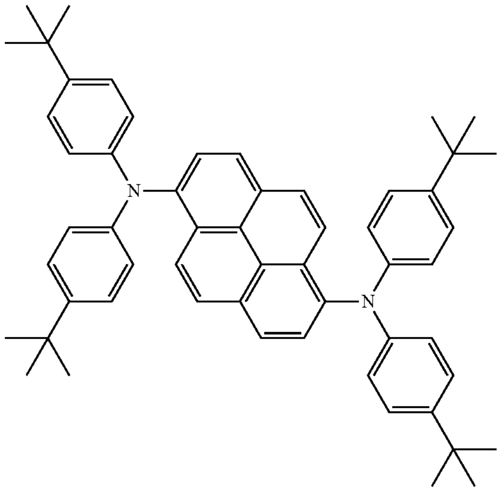
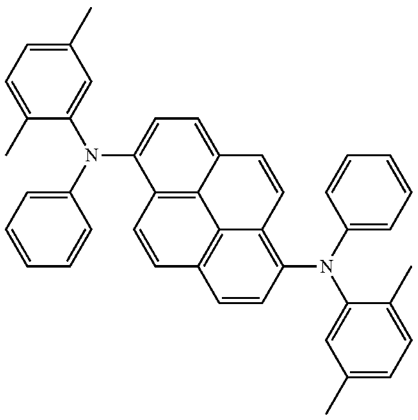
-continued
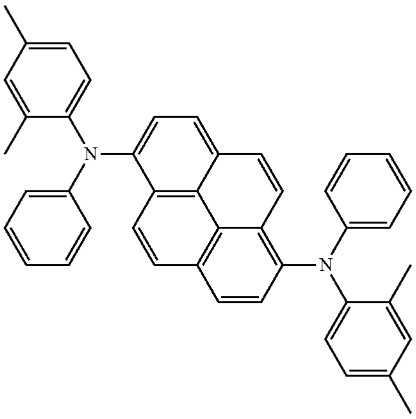
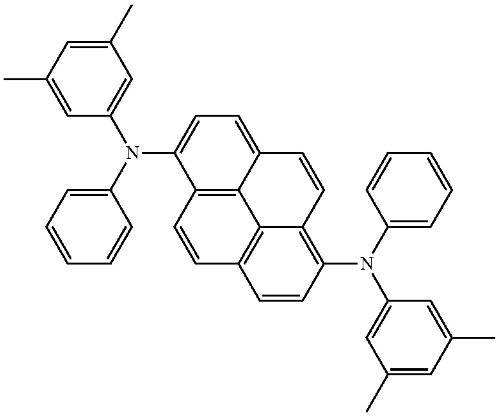
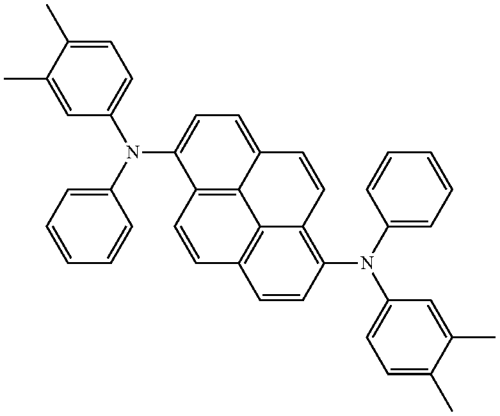
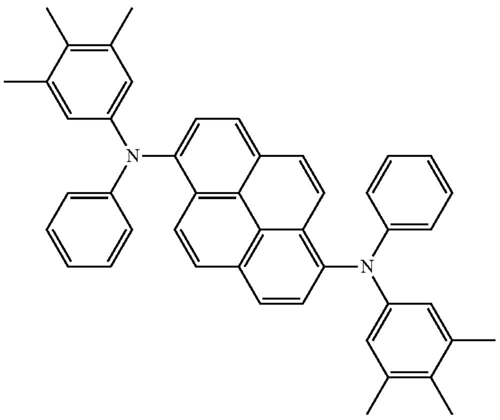

-continued
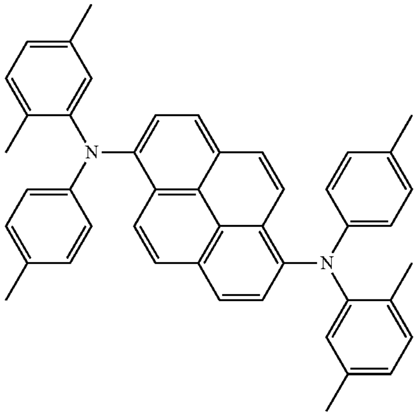
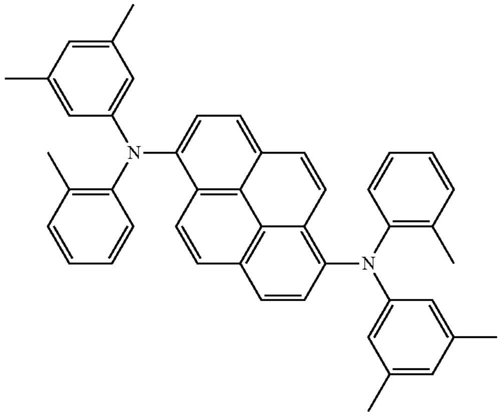
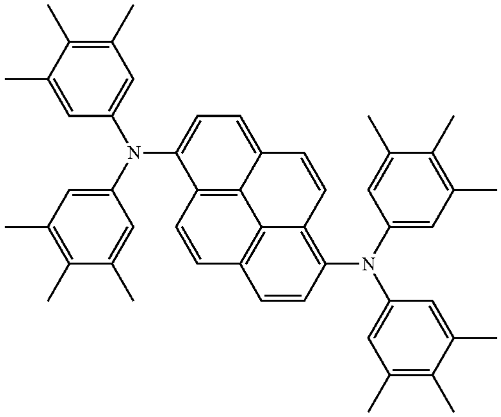
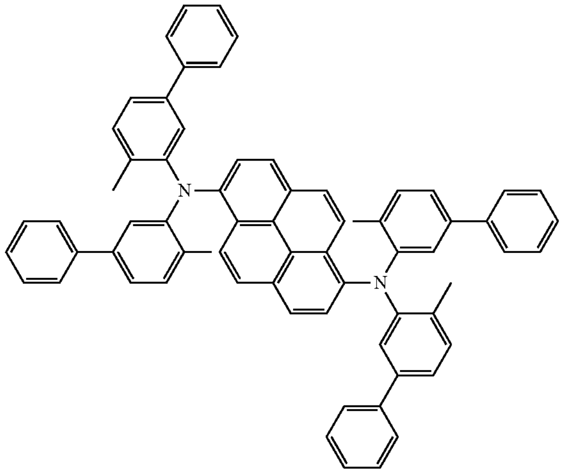
-continued
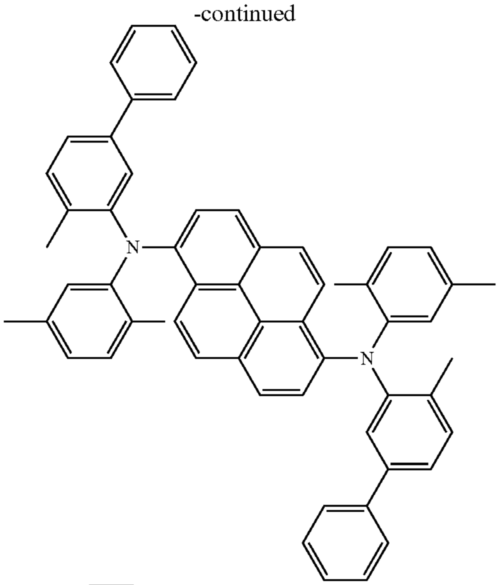
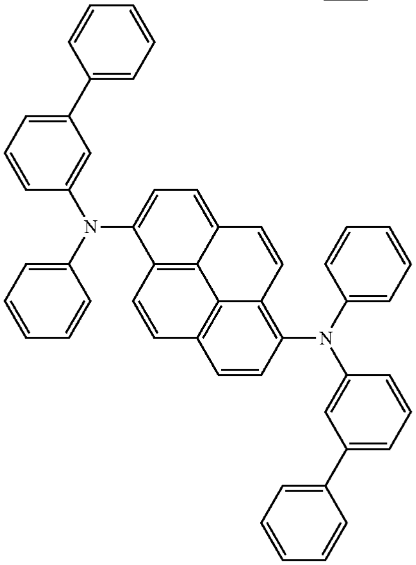
[Formula 290]
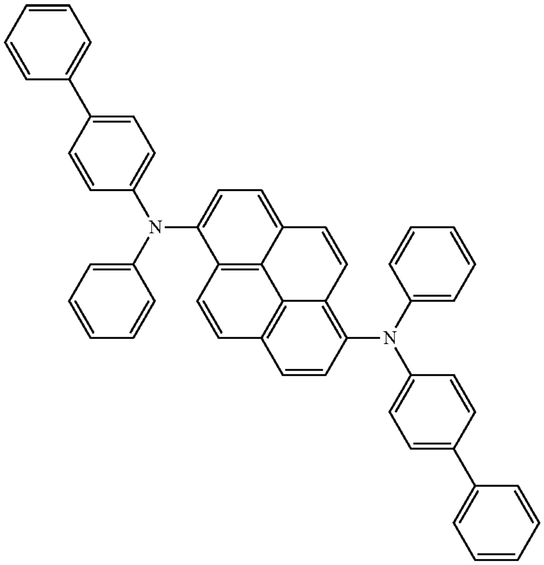

-continued
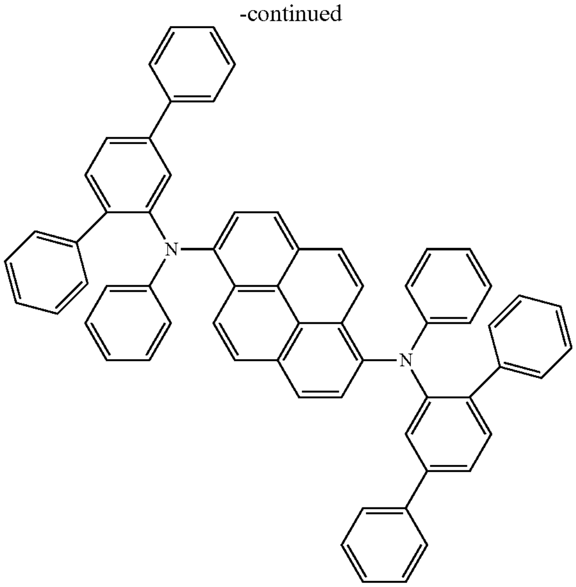
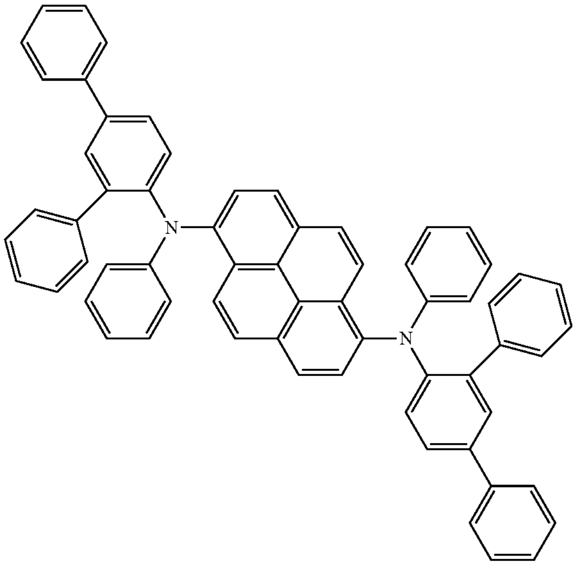
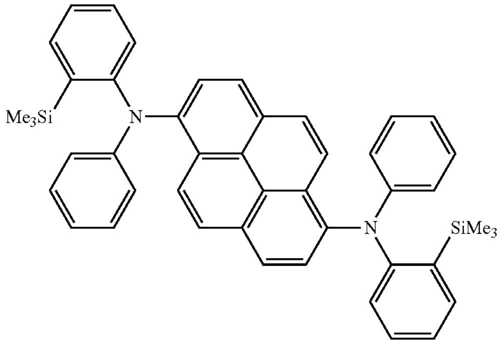
-continued
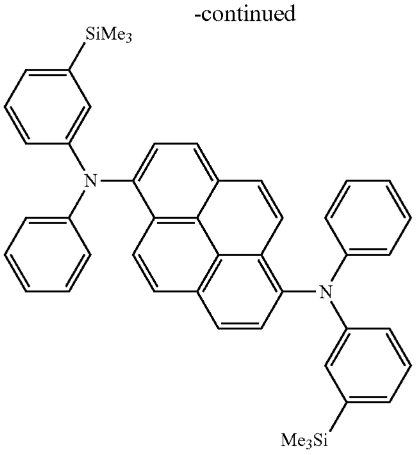
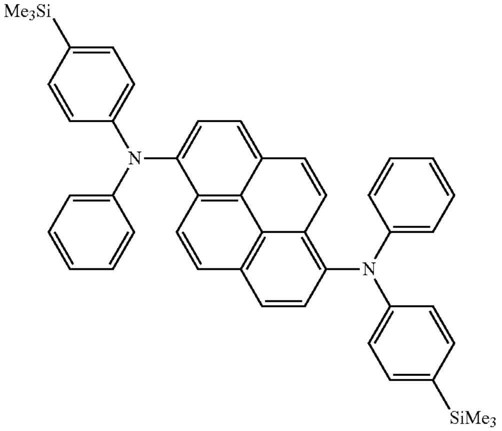
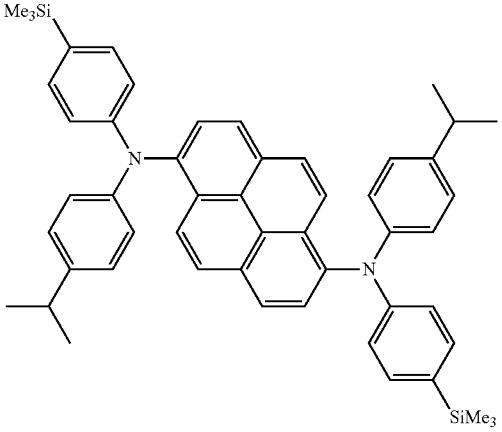
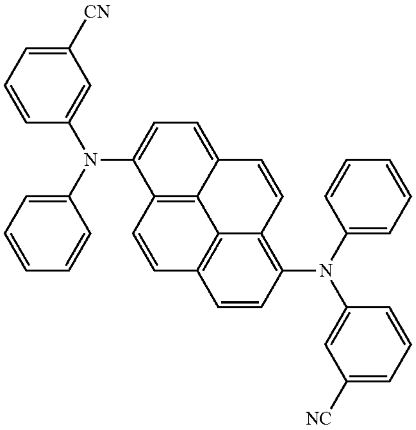

-continued
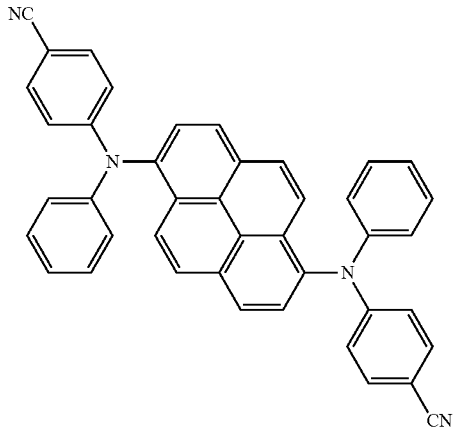
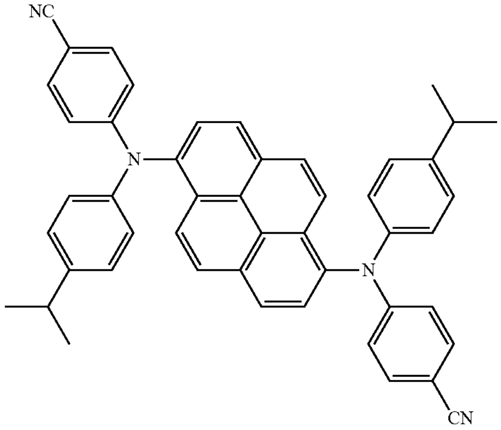
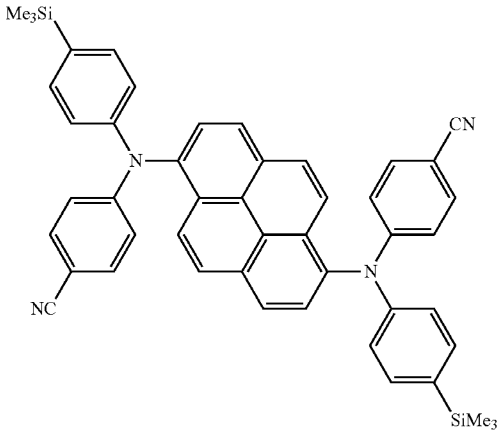
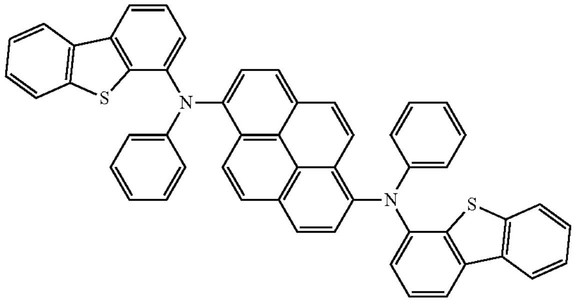
-continued
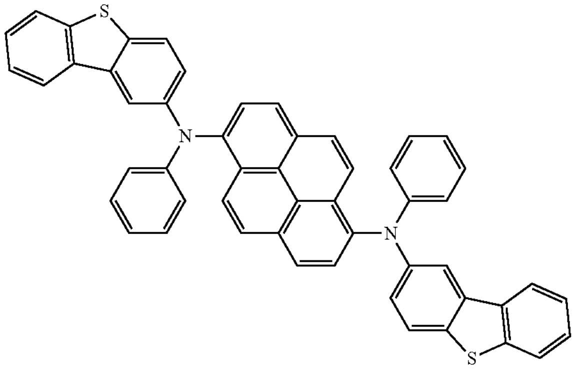
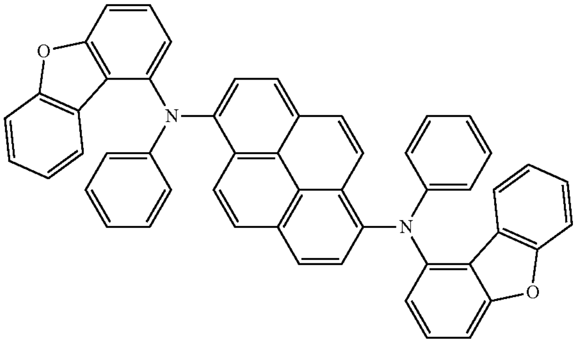
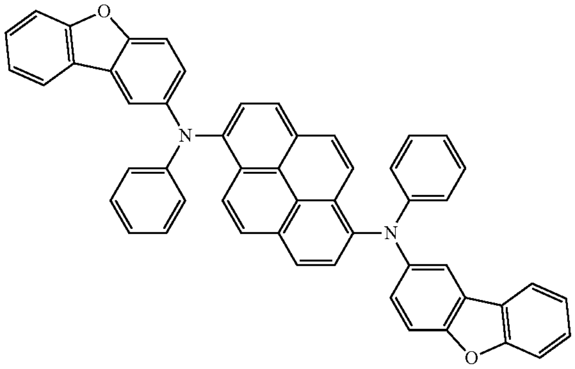
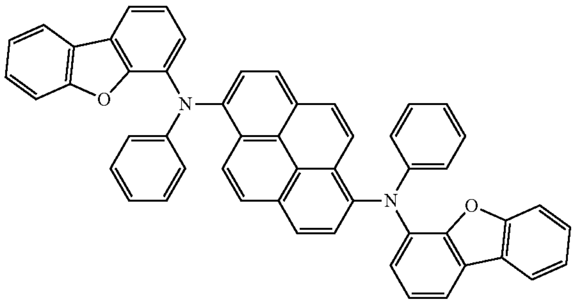

[Formula 291]
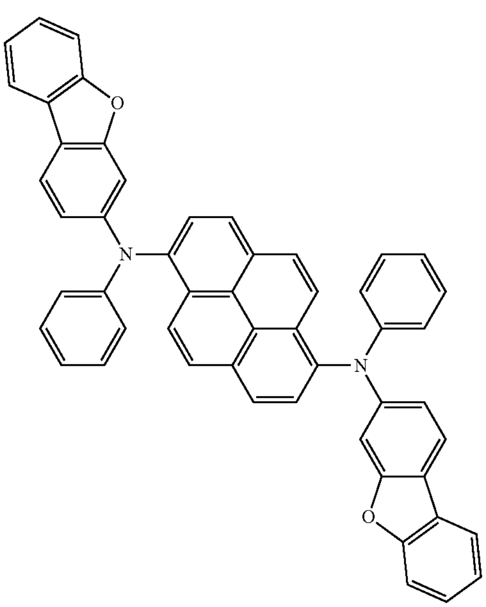
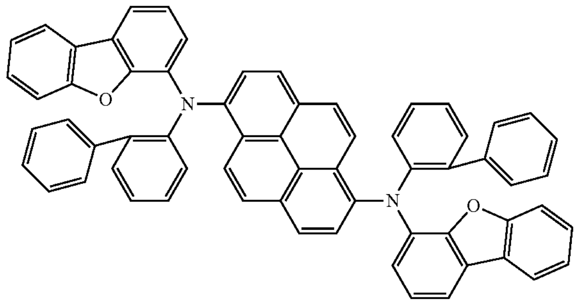
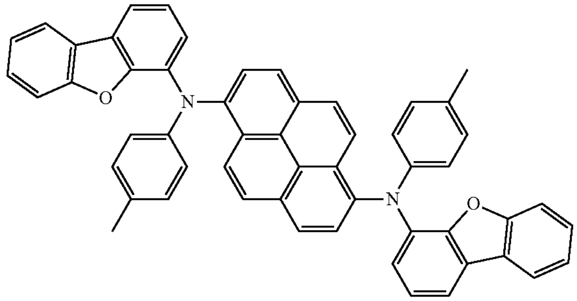
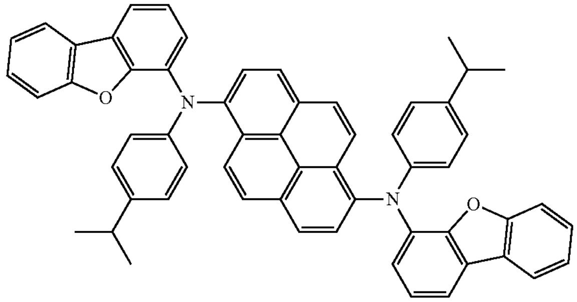
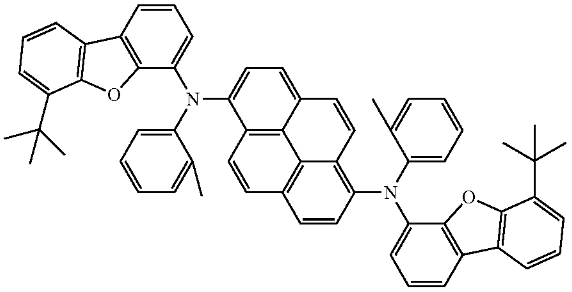
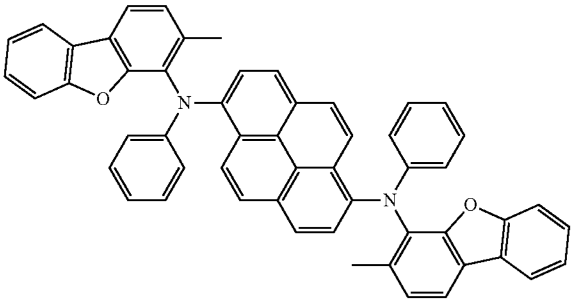
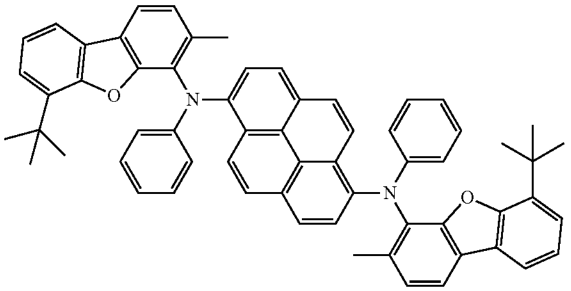
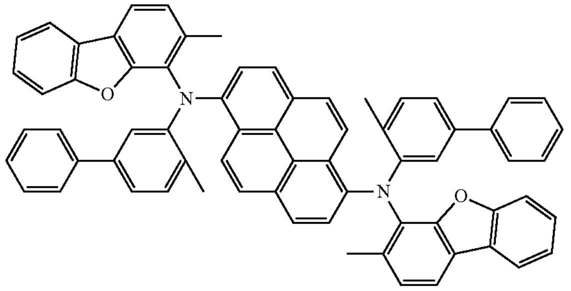
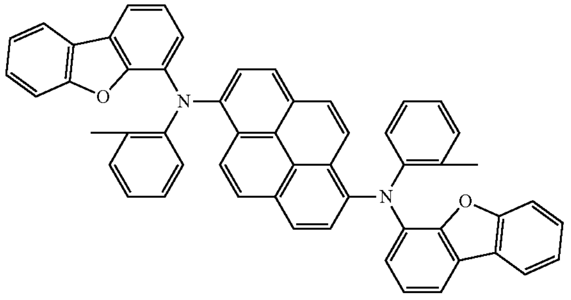

-continued
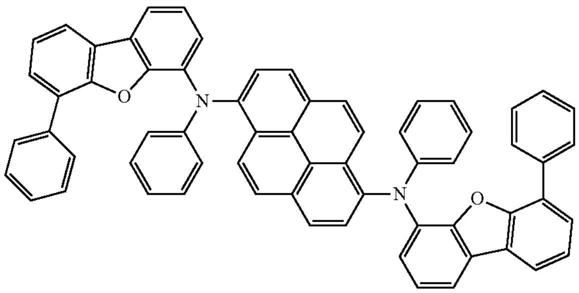
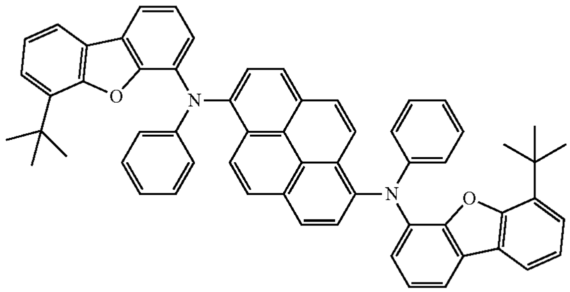
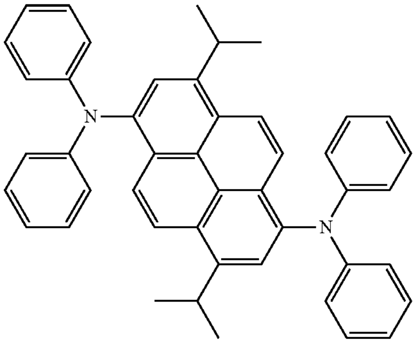
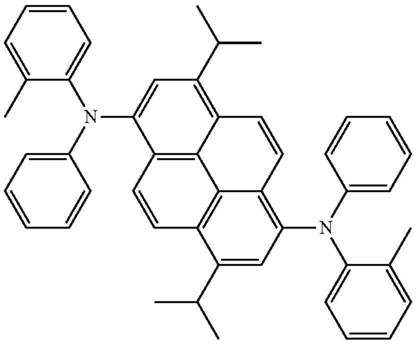
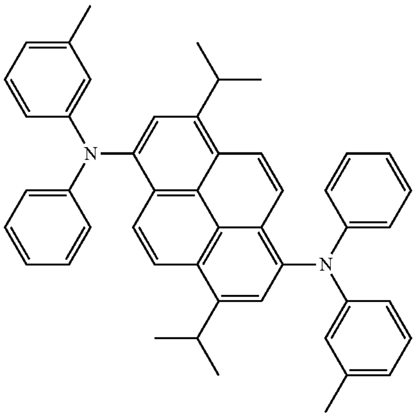
-continued
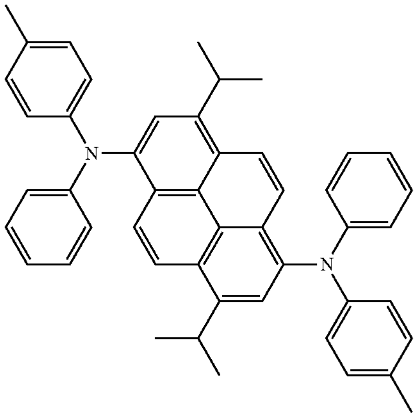
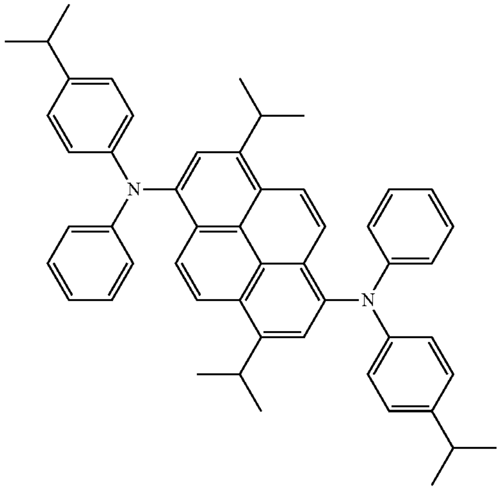
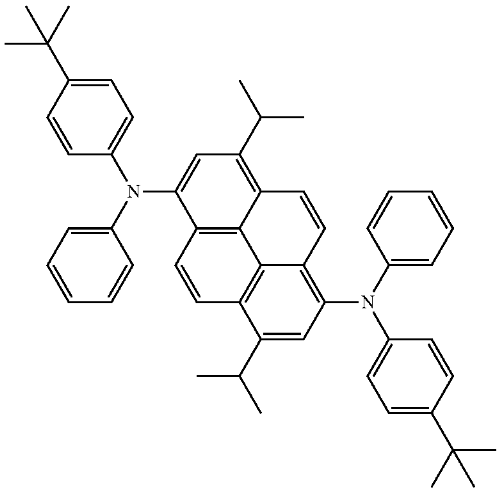

-continued
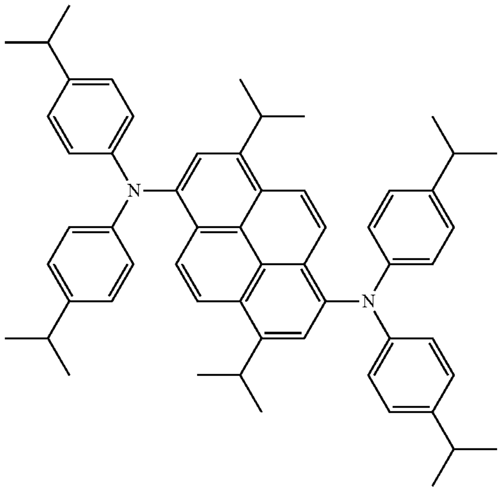
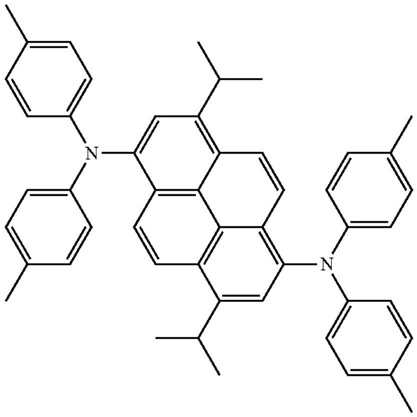
[Formula 292]
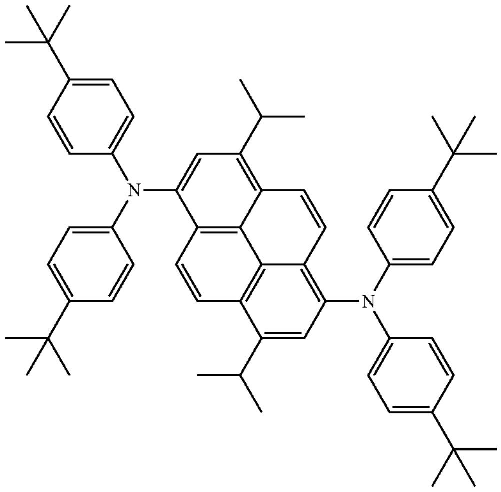
-continued
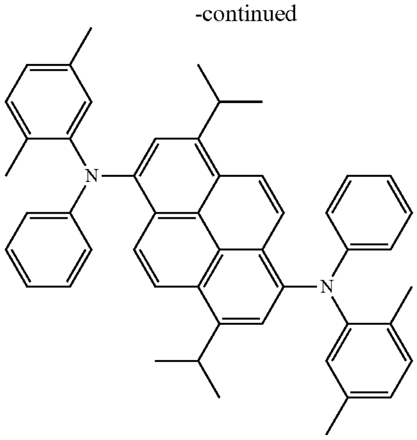
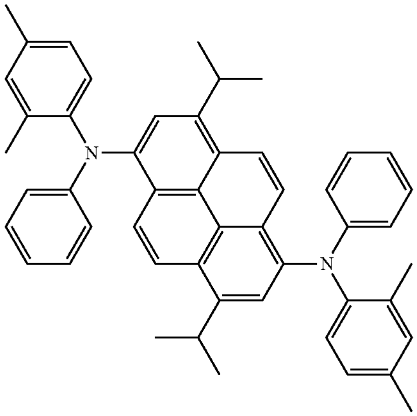
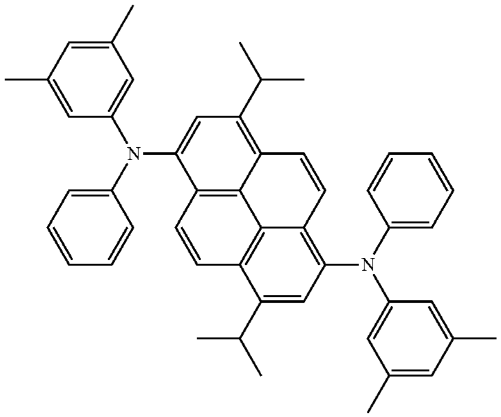
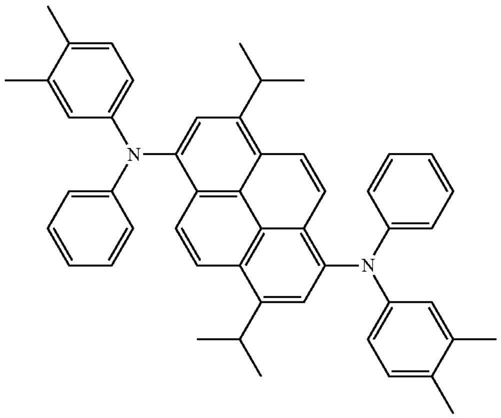

-continued
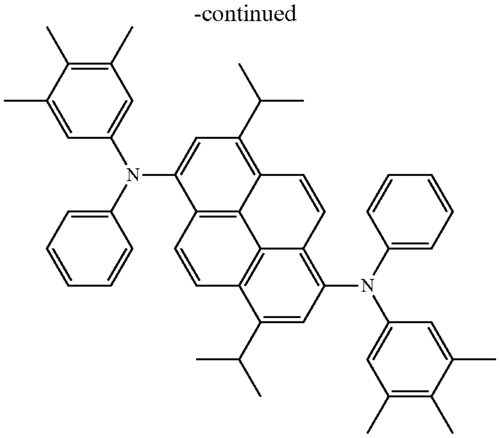
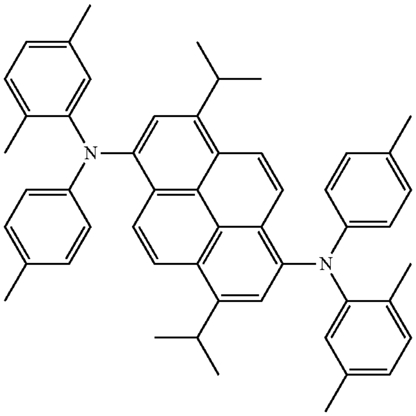
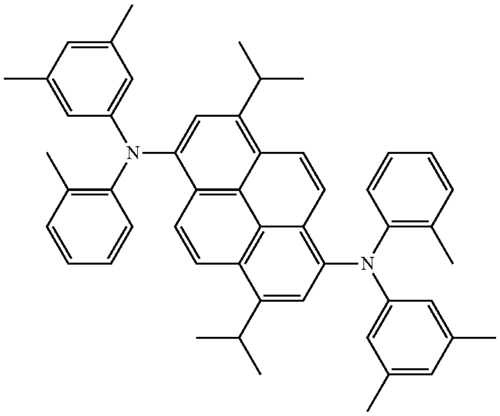
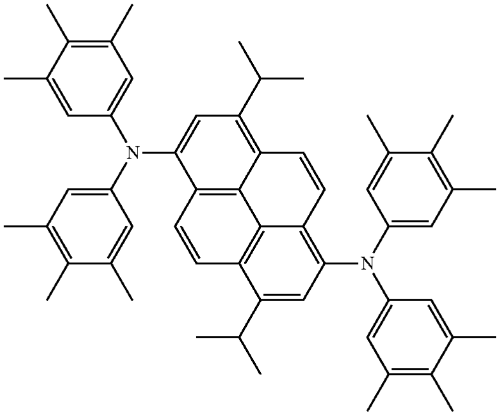
-continued
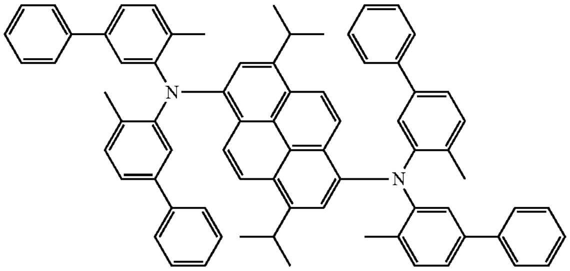
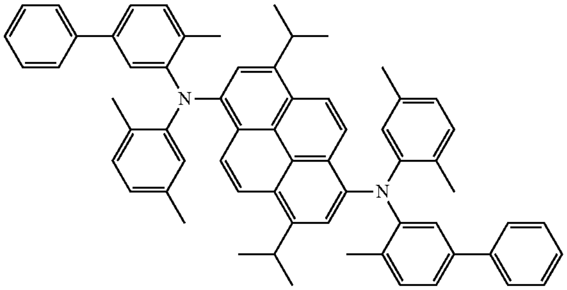
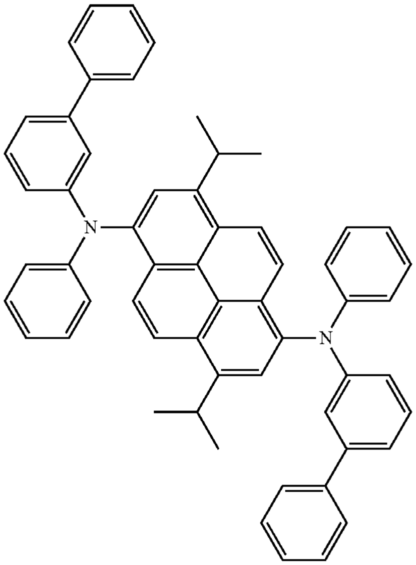
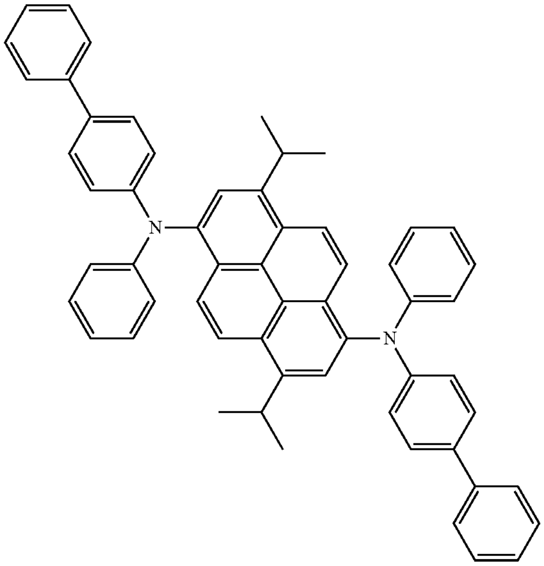

-continued
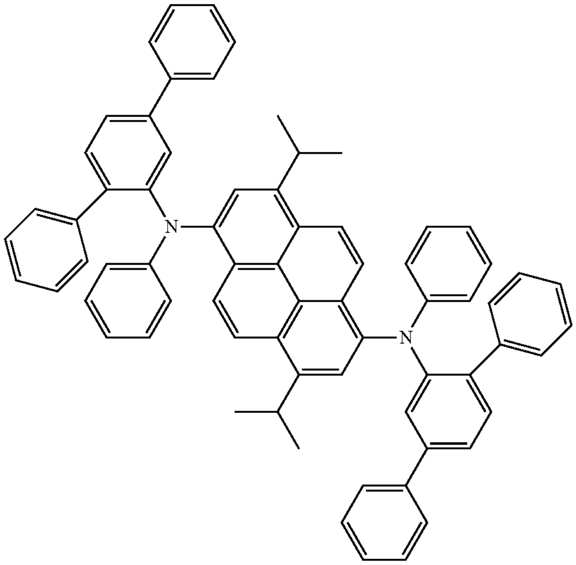
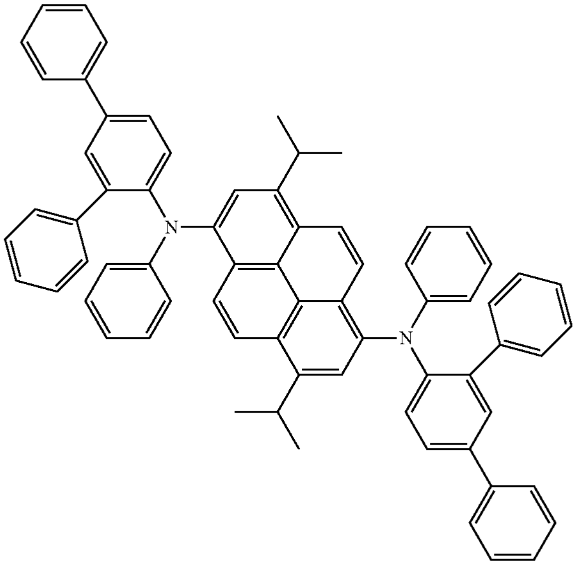
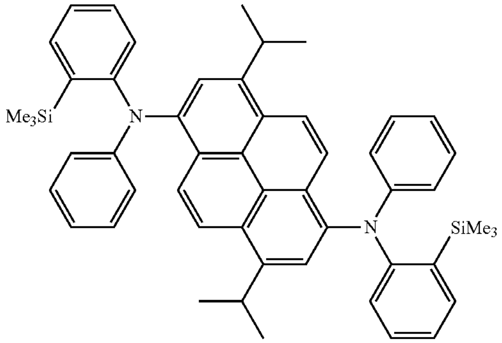
-continued
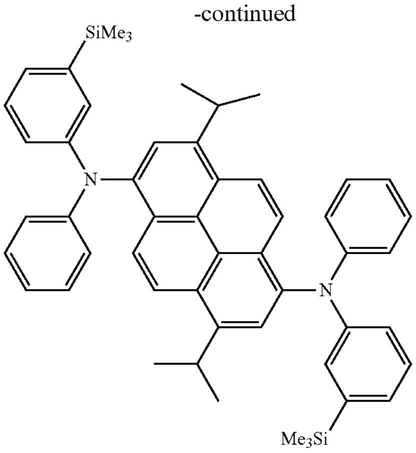
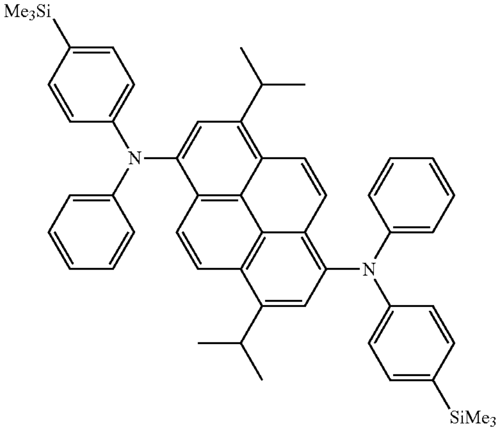
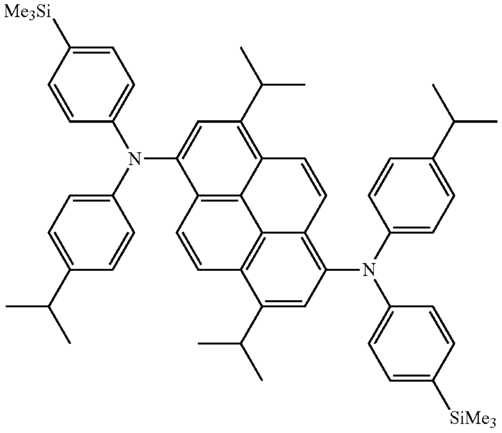
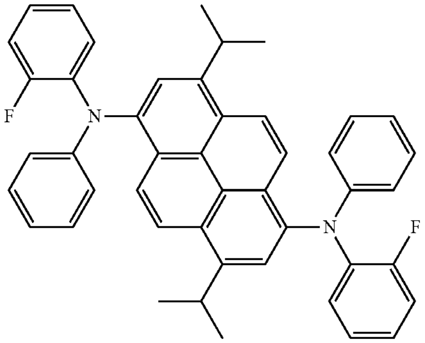

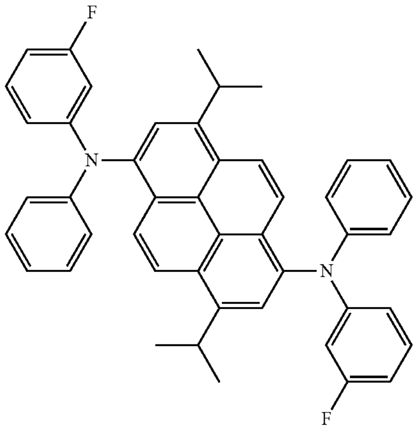
[Formula 293]
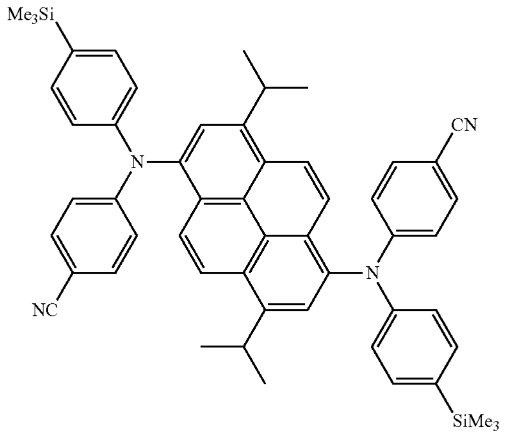
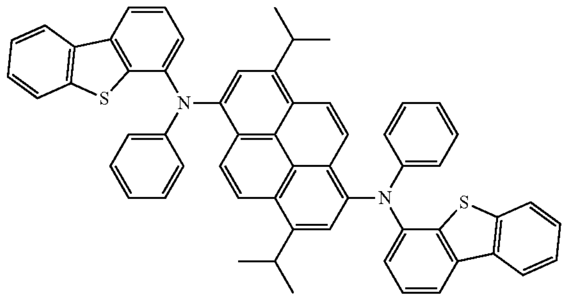
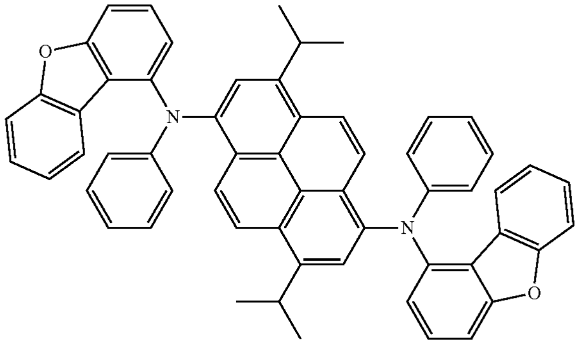
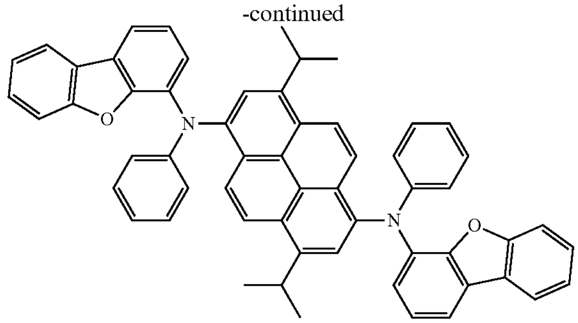
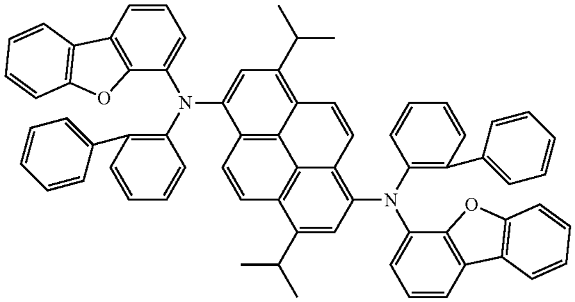
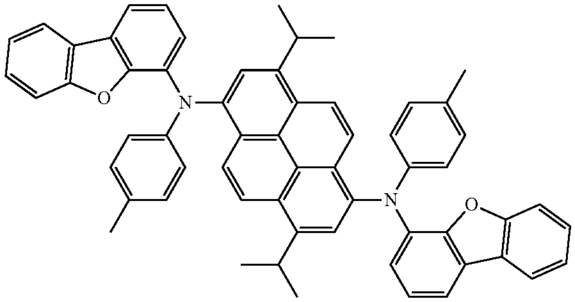
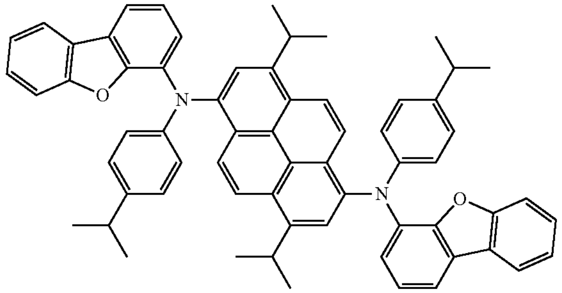
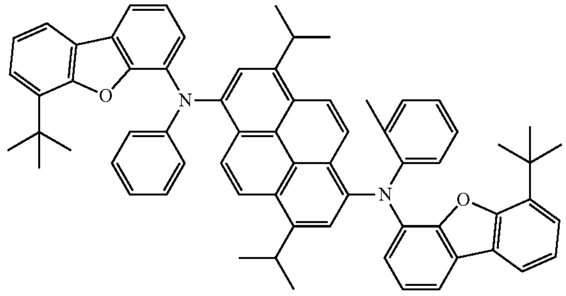

-continued

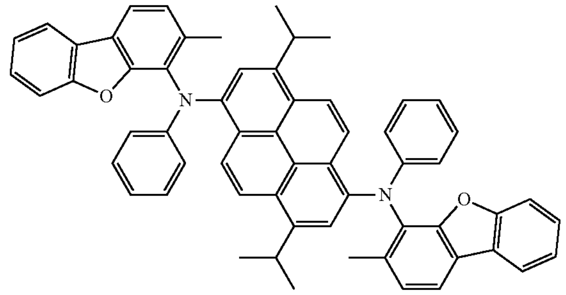

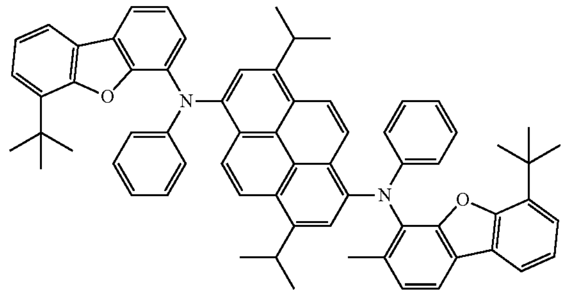

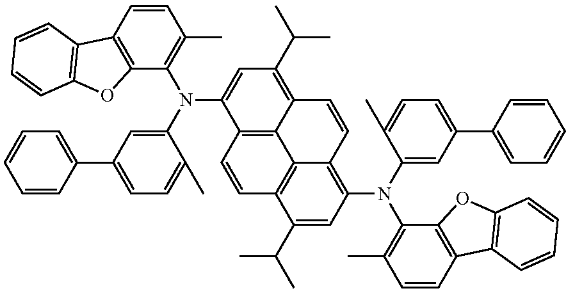

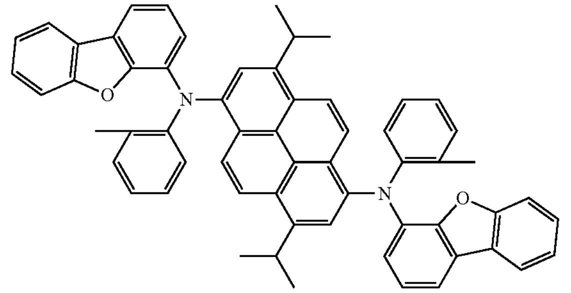

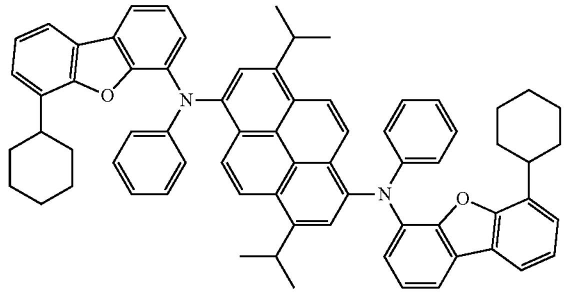

-continued

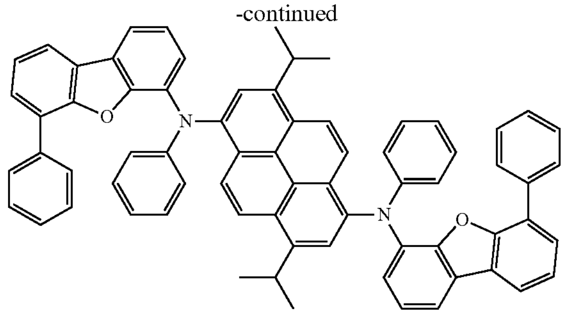

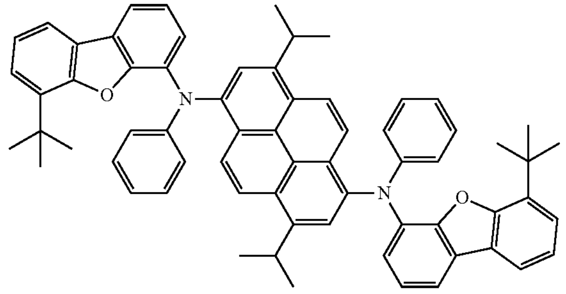

Compound Represented by Formula (4)

The compound represented by the formula (4) will be described below.

[Formula 294]

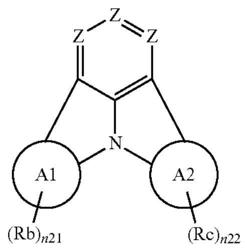

(4)

In the formula (4):

Z are each independently CRa or a nitrogen atom;

A1 ring and A2 ring are each independently a substituted or unsubstituted aromatic hydrocarbon ring having 6 to 50 ring carbon atoms, or a substituted or unsubstituted heterocycle having 5 to 50 ring atoms;

when a plurality of Ra are present, at least one combination of adjacent two or more of the plurality of Ra are mutually bonded to form a substituted or unsubstituted monocyclic ring, mutually bonded to form a substituted or unsubstituted fused ring, or not mutually bonded;

n21 and n22 are each independently 0, 1, 2, 3, or 4;

when a plurality of Rb are present, at least one combination of adjacent two or more of the plurality of Rb are mutually bonded to form a substituted or unsubstituted monocyclic ring, mutually bonded to form a substituted or unsubstituted fused ring, or not mutually bonded;

when a plurality of Rc are present, at least one combination of adjacent two or more of the plurality of Rc are mutually bonded to form a substituted or unsubstituted monocyclic ring, mutually bonded to form a substituted or unsubstituted fused ring, or not mutually bonded; and Ra, Rb, and Rc not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

The "aromatic hydrocarbon ring" for the A1 ring and A2 ring has the same structure as the compound formed by introducing a hydrogen atom to the "aryl group" described above.

Ring atoms of the "aromatic hydrocarbon ring" for the A1 ring and the A2 ring include two carbon atoms on a fused bicyclic structure at the center of the formula (4).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 ring and A2 ring has the same structure as the compound formed by introducing a hydrogen atom to the "heterocyclic group" described above.

Ring atoms of the "heterocycle" for the A1 ring and the A2 ring include two carbon atoms on a fused bicyclic structure at the center of the formula (4).

Specific examples of the "substituted or unsubstituted heterocycle having 5 to 50 ring atoms" include a compound formed by introducing a hydrogen atom to the "heterocyclic group" described in the specific example group G2.

Rb is bonded to any one of carbon atoms forming the aromatic hydrocarbon ring for the A1 ring or any one of the atoms forming the heterocycle for the A1 ring.

Rc is bonded to any one of carbon atoms forming the aromatic hydrocarbon ring for the A2 ring or any one of the atoms forming the heterocycle for the A2 ring.

At least one of Ra, Rb, or Rc is preferably a group represented by the formula (4a) below. More preferably, at least two of Ra, Rb, and Rc are groups represented by the formula (4a).

[Formula 295]

$$*\text{-}L_{401}\text{-}Ar_{401} \quad (4a)$$

In the formula (4a):

$L_{401}$ is a single bond, a substituted or unsubstituted arylene group having 6 to 30 ring carbon atoms, or a substituted or unsubstituted divalent heterocyclic group having 5 to 30 ring atoms; and $Ar_{401}$ is a substituted or unsubstituted aryl group having 6 to 50 ring carbon atoms, a substituted or unsubstituted heterocyclic group having 5 to 50 ring atoms, or a group represented by a formula (4b) below.

[Formula 296]

(4b)

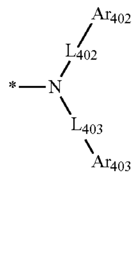

In the formula (4b):

$L_{402}$ and $L_{403}$ are each independently a single bond, a substituted or unsubstituted arylene group having 6 to 30 ring carbon atoms, or a substituted or unsubstituted divalent heterocyclic group having 5 to 30 ring atoms;

a combination of $Ar_{402}$ and $Ar_{403}$ are mutually bonded to form a substituted or unsubstituted monocyclic ring, mutually bonded to form a substituted or unsubstituted fused ring, or not mutually bonded; and $Ar_{402}$ and $Ar_{403}$ not forming the monocyclic ring and not forming the fused ring are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is represented by a formula (42) below.

[Formula 297]

(42)

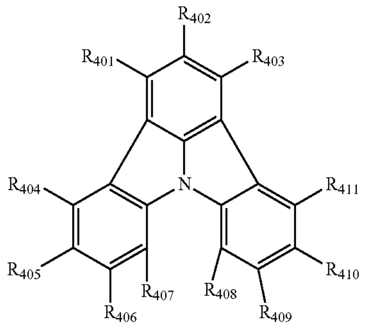

In the formula (42):

at least one combination of adjacent two or more of $R_{401}$ to $R_{411}$ are mutually bonded to form a substituted or unsubstituted monocyclic ring, mutually bonded to form a substituted or unsubstituted fused ring, or not mutually bonded; and $R_{401}$ to $R_{411}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

At least one of $R_{401}$ to $R_{411}$ is preferably a group represented by the formula (4a). More preferably, at least two of $R_{401}$ to $R_{411}$ are groups represented by the formula (21a).

$R_{404}$ and $R_{411}$ are preferably groups represented by the formula (4a).

In an exemplary embodiment, the compound represented by the formula (4) is a compound formed by bonding a structure represented by a formula (4-1) or (4-2) below to the A1 ring.

Further, in an exemplary embodiment, the compound represented by the formula (42) is a compound formed by bonding the structure represented by the formula (4-1) or (4-2) to the ring bonded with $R_{404}$ to $R_{407}$.

[Formula 298]

(4-1)

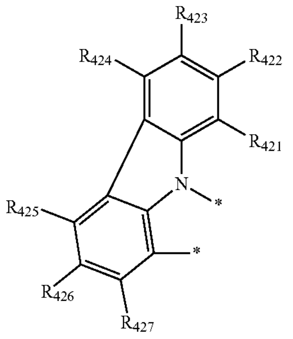

(4-2)

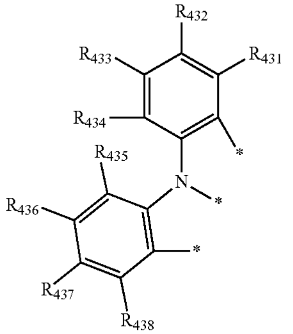

In the formula (4-1), two bonds * are each independently bonded to the ring-forming carbon atom of the aromatic hydrocarbon ring or the ring atom of the heterocycle for the A1 ring in the formula (4) or bonded to one of $R_{404}$ to $R_{407}$ in the formula (42);

in the formula (4-2), three bonds * are each independently bonded to the ring-forming carbon atom of the aromatic hydrocarbon ring or the ring atom of the heterocycle for the A1 ring in the formula (4) or bonded to one of $R_{404}$ to $R_{407}$ in the formula (42);

at least one combination of adjacent two or more of $R_{421}$ to $R_{427}$ are mutually bonded to form a substituted or unsubstituted monocyclic ring, mutually bonded to form a substituted or unsubstituted fused ring, or not mutually bonded;

at least one combination of adjacent two or more of $R_{431}$ to $R_{438}$ are mutually bonded to form a substituted or unsubstituted monocyclic ring, mutually bonded to form a substituted or unsubstituted fused ring, or not mutually bonded; and $R_{421}$ to $R_{427}$ and $R_{431}$ to $R_{438}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by a formula (41-3), (41-4) or (41-5) below.

[Formula 299]

(41-3)

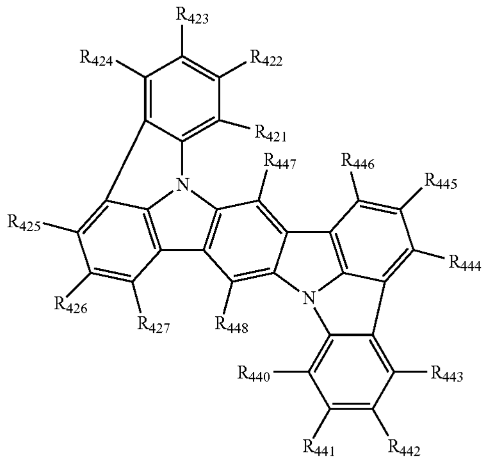

[Formula 300]

(41-4)

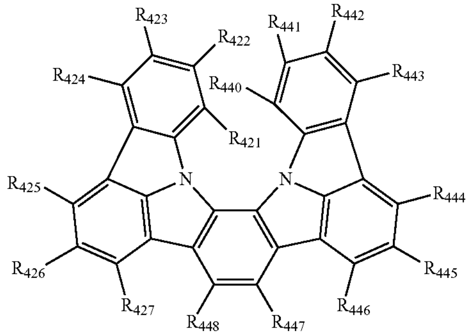

[Formula 301]

(41-5)

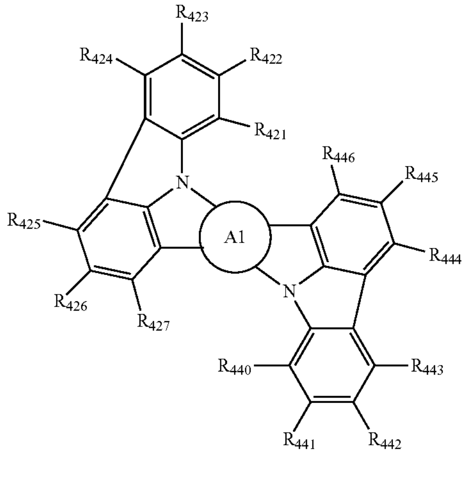

In the formulae (41-3), (41-4), and (41-5):

A1 ring is as defined for the formula (4);

$R_{421}$ to $R_{427}$ each independently represent the same as $R_{421}$ to $R_{427}$ in the formula (4-1); and $R_{440}$ to $R_{448}$ each independently represent the same as $R_{401}$ to $R_{411}$ in the formula (42).

In an exemplary embodiment, a substituted or unsubstituted aromatic hydrocarbon ring having 6 to 50 ring carbon atoms for the A1 ring in the formula (41-5) is a substituted or unsubstituted naphthalene ring, or a substituted or unsubstituted fluorene ring.

In an exemplary embodiment, a substituted or unsubstituted heterocycle having 5 to 50 ring atoms for the A1 ring in the formula (41-5) is a substituted or unsubstituted dibenzofuran ring, a substituted or unsubstituted carbazole ring, or a substituted or unsubstituted dibenzothiophene ring.

In an exemplary embodiment, the compound represented by the formula (4) or (42) is a compound selected from the group consisting of compounds represented by formulae (461) to (467) below.

[Formula 302]

(461)

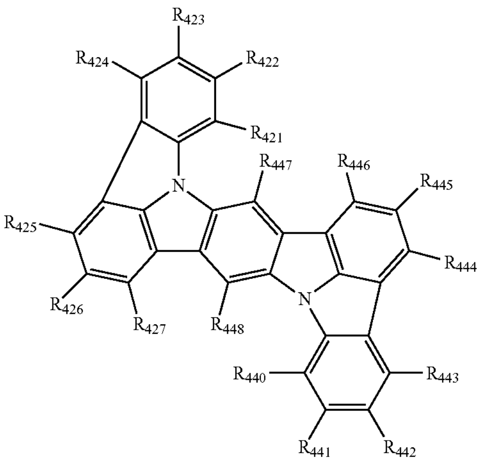

(462)

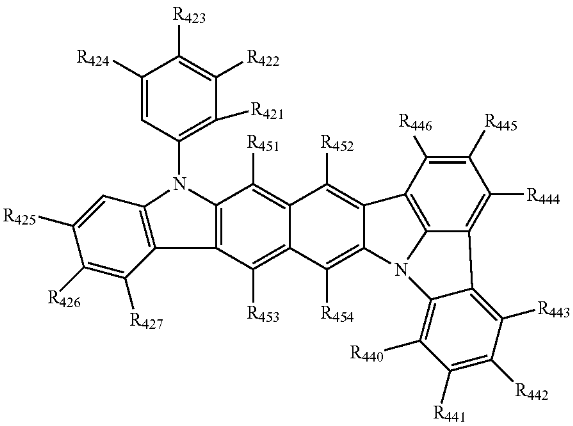

-continued

[Formula 303]

(463)

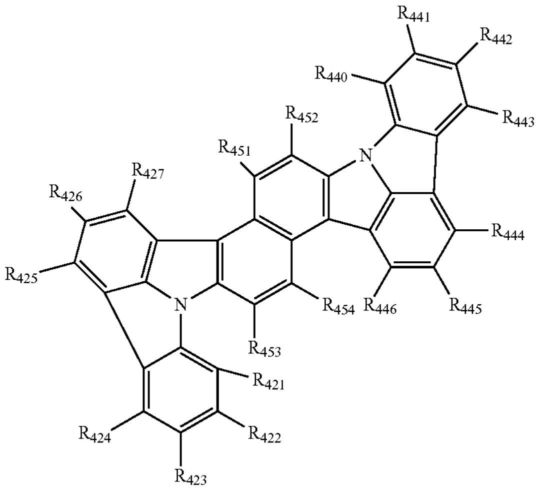

(464)

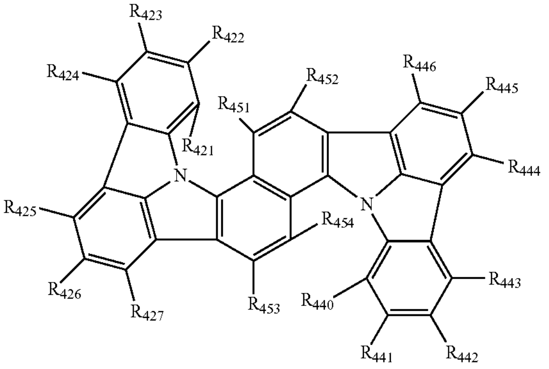

[Formula 304]

(465)

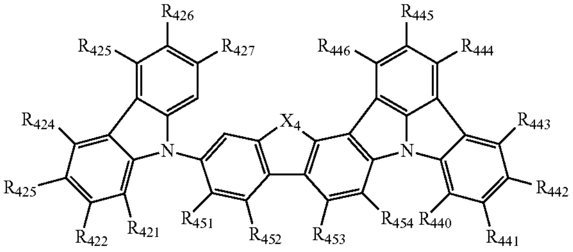

[Formula 305]

(466)

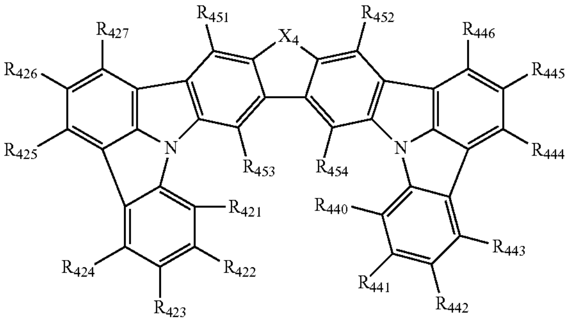

-continued

[Formula 306]

(467)

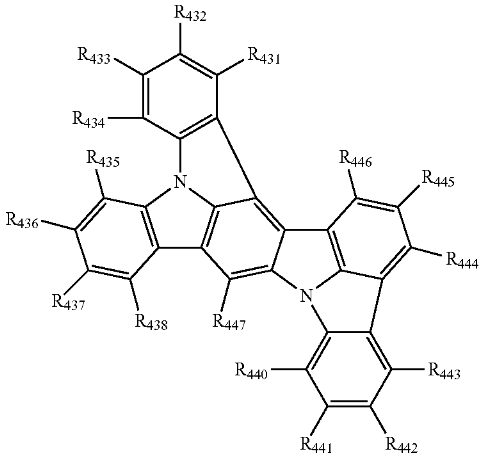

In the formulae (461), (462), (463), (464), (465), (466), and (467):

$R_{421}$ to $R_{427}$ each independently represent the same as $R_{421}$ to $R_{427}$ in the formula (4-1);

$R_{431}$ to $R_{438}$ each independently represent the same as $R_{431}$ to $R_{438}$ in the formula (4-2);

$R_{440}$ to $R_{448}$ and $R_{451}$ to $R_{454}$ each independently represent the same as $R_{401}$ to $R_{411}$ in the formula (42);

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, in the compound represented by the formula (42), at least one combination of adjacent two or more of $R_{401}$ to $R_{411}$ are mutually bonded to form a substituted or unsubstituted monocyclic ring or a substituted or unsubstituted fused ring. The compound represented by the formula (42) in the exemplary embodiment is described in detail as a compound represented by a formula (45).

Compound Represented by Formula (45)

The compound represented by the formula (45) will be described below.

[Formula 307]

(45)

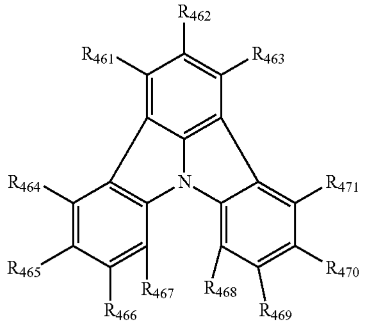

In the formula (45):

two or more of combinations selected from the group consisting of a combination of $R_{461}$ and $R_{462}$, a combination of $R_{462}$ and $R_{463}$, a combination of $R_{464}$ and $R_{465}$, a combination of $R_{465}$ and $R_{466}$, a combination of $R_{466}$ and $R_{467}$, a combination of $R_{468}$ and $R_{469}$, a combination of $R_{469}$ and $R_{470}$, and a combination of $R_{470}$ and $R_{471}$ are mutually bonded to form a substituted or unsubstituted monocyclic ring or mutually bonded to form a substituted or unsubstituted fused ring, the combination of $R_{461}$ and $R_{462}$ and the combination of $R_{462}$ and $R_{463}$, the combination of $R_{464}$ and $R_{465}$ and the combination of $R_{465}$ and $R_{466}$, the combination of $R_{465}$ and $R_{466}$ and the combination of $R_{466}$ and $R_{467}$, the combination of $R_{468}$ and $R_{469}$ and the combination of $R_{469}$ and $R_{470}$, and the combination of $R_{469}$ and $R_{470}$ and the combination of $R_{470}$ and $R_{471}$ do not simultaneously form a ring;

at least two rings formed by $R_{461}$ to $R_{471}$ are mutually the same or different; and $R_{461}$ to $R_{471}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (45), $R_n$ and $R_{n+1}$ (n being an integer selected from 461, 462, 464 to 466, and 468 to 470) are mutually bonded to form a substituted or unsubstituted monocyclic ring or fused ring together with two ring-forming carbon atoms bonded with $R_n$ and $R_{n+1}$. The ring is preferably formed of atoms selected from the group consisting of a carbon atom, an oxygen atom, a sulfur atom, and a nitrogen atom, and is preferably made of 3 to 7, more preferably 5 or 6 atoms.

The number of the above cyclic structures in the compound represented by the formula (45) is, for instance, 2, 3, or 4. The two or more of the cyclic structures may be present on the same benzene ring on the basic skeleton represented by the formula (45) or may be present on different benzene rings. For instance, when three cyclic structures are present, each of the cyclic structures may be present on corresponding one of the three benzene rings of the formula (45).

Examples of the above cyclic structures in the compound represented by the formula (45) include structures represented by formulae (451) to (460) below.

[Formula 308]

(451)

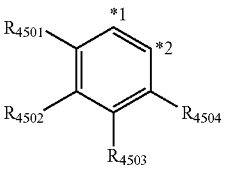

(452)

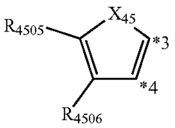

(453)

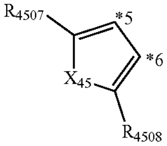

(454)

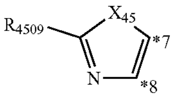

(455)

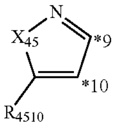

(456)

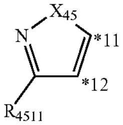

(457)

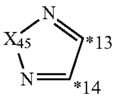

In the formulae (451) to (457):

each combination of *1 and *2, *3 and *4, *5 and *6, *7 and *8, *9 and *10, *11 and *12, and *13 and *14 represent the two ring-forming carbon atoms respectively bonded with $R_n$ and $R_{n+1}$;

the ring-forming carbon atom bonded with $R_n$ may be any one of the two ring-forming carbon atoms represented by *1 and *2, *3 and *4, *5 and *6, *7 and *8, *9 and *10, *11 and *12, and *13 and *14;

$X_{45}$ is $C(R_{4512})(R_{4513})$, $NR_{4514}$, an oxygen atom, or a sulfur atom;

at least one combination of adjacent two or more of $R_{4501}$ to $R_{4506}$ and $R_{4512}$ to $R_{4513}$ are mutually bonded to form a substituted or unsubstituted monocyclic ring, mutually bonded to form a substituted or unsubstituted fused ring, or not mutually bonded; and $R_{4501}$ to $R_{4514}$ not forming the monocyclic ring and not forming the fused ring each independently represent the same as $R_{461}$ to $R_{471}$ in the formula (45).

[Formula 309]

(458)

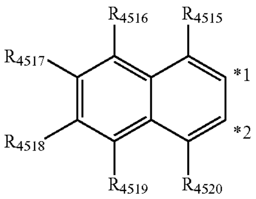

(459)

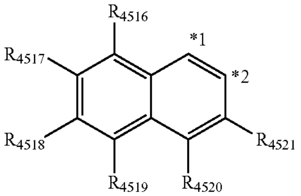

(460)

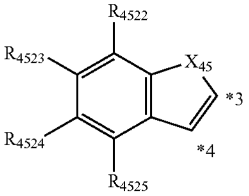

In the formulae (458) to (460):

each combination of *1 and *2, and *3 and *4 represent the two ring-forming carbon atoms each bonded with $R_n$ and $R_{n+1}$;

the ring-forming carbon atom bonded with $R_n$ may be any one of the two ring-forming carbon atoms represented by *1 and *2, or *3 and *4;

$X_{45}$ is $C(R_{4512})(R_{4513})$, $NR_{4514}$, an oxygen atom, or a sulfur atom;

at least one combination of adjacent two or more of $R_{4512}$ to $R_{4513}$ and $R_{4515}$ to $R_{4525}$ are mutually bonded to form a substituted or unsubstituted monocyclic ring, mutually bonded to form a substituted or unsubstituted fused ring, or not mutually bonded; and $R_{4512}$ to $R_{4513}$, $R_{4515}$ to $R_{4521}$ and $R_{4522}$ to $R_{4525}$ not forming the monocyclic ring and not forming the fused ring, and $R_{4514}$ each independently represent the same as $R_{461}$ to $R_{471}$ in the formula (45).

In the formula (45), it is preferable that at least one of $R_{462}$, $R_{464}$, $R_{465}$, $R_{470}$ or $R_{471}$ (preferably, at least one of $R_{462}$, $R_{465}$ or $R_{470}$, more preferably $R_{462}$) is a group not forming the cyclic structure.

(i) A substituent, if present, of the cyclic structure formed by $R_n$ and $R_{n+1}$ in the formula (45), (ii) $R_{461}$ to $R_{471}$ not forming the cyclic structure in the formula (45), and (iii) $R_{4501}$ to $R_{4514}$, $R_{4515}$ to $R_{4525}$ in the formulae (451) to (460) are preferably each independently any one of groups selected from the group consisting of a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-N(R_{906})(R_{907})$, a substituted or unsubstituted aryl group having 6 to 50 ring carbon atoms, a substituted or unsubstituted heterocyclic group having 5 to 50 ring atoms, and groups represented by formulae (461) to (464).

[Formula 310]

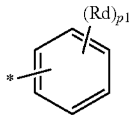
(461)

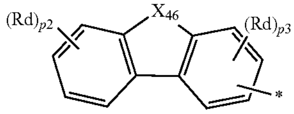
(462)

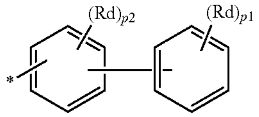
(463)

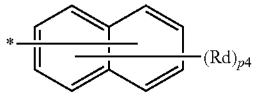
(464)

In the formulae (461) to (464):

$R_d$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_{46}$ is C($R_{801}$)($R_{802}$), $NR_{803}$, an oxygen atom, or a sulfur atom;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different;

when a plurality of $R_{803}$ are present, the plurality of $R_{803}$ are mutually the same or different;

p1 is 5;

p2 is 4;

p3 is 3;

p4 is 7; and

* in the formulae (461) to (464) each independently represent a bonding position to a cyclic structure.

In the third and fourth compounds, $R_{901}$ to $R_{907}$ represent the same as those as described above.

In an exemplary embodiment, the compound represented by the formula (45) is represented by one of formulae (45-1) to (45-6) below.

[Formula 311]

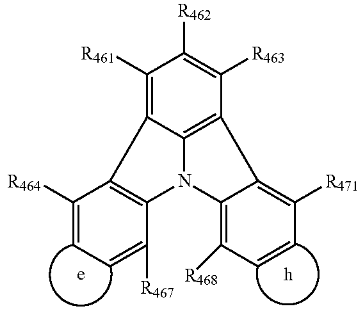
(45-1)

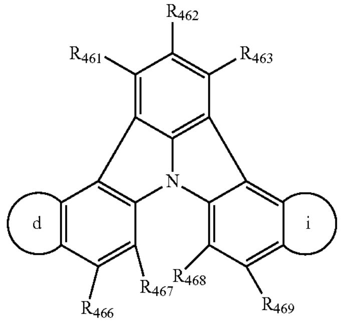
(45-2)

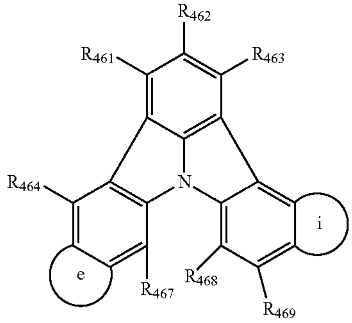
(45-3)

[Formula 312]

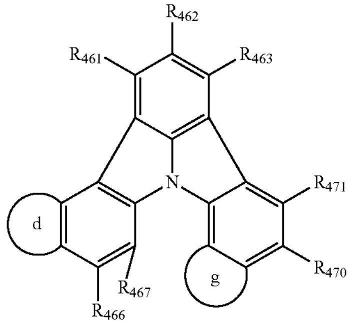
(45-4)

-continued (45-5)

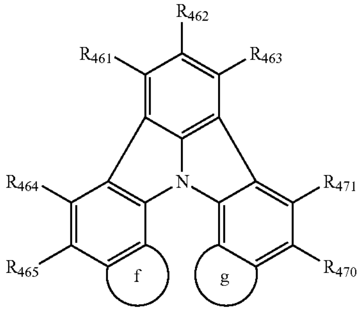

(45-6)

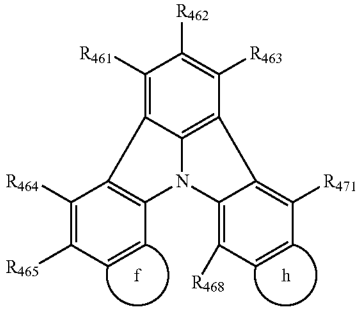

In the formulae (45-1) to (45-6):

rings d to i are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-7) to (45-12) below.

[Formula 313]

(45-7)

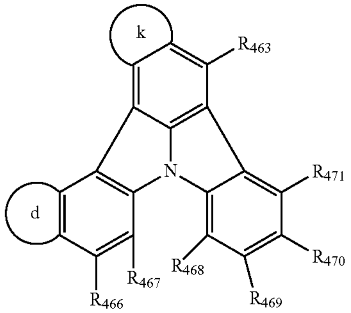

(45-8)

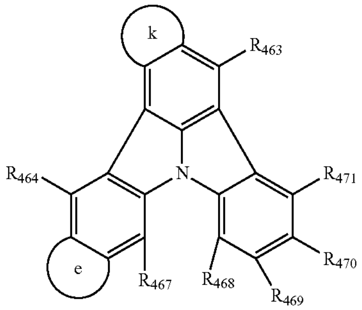

-continued (45-9)

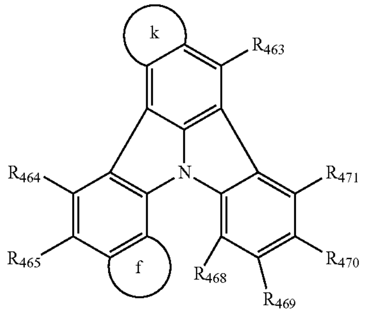

[Formula 314]

(45-10)

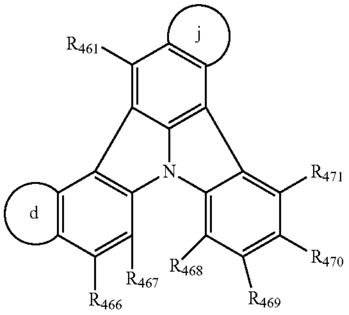

(45-11)

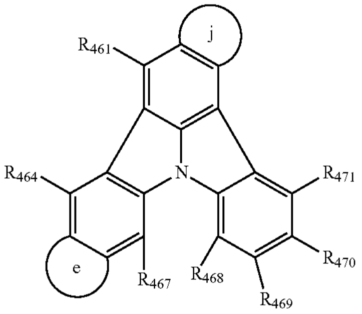

(45-12)

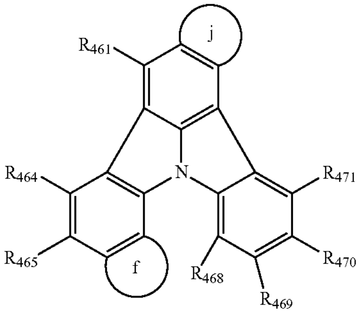

In the formulae (45-7) to (45-12):

rings d to f, k and j are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-13) to (45-21) below.

[Formula 315]
(45-13)
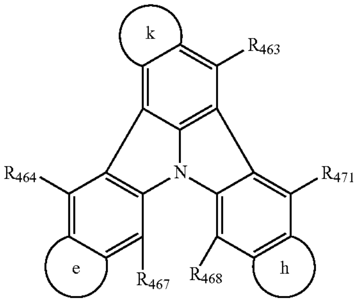
(45-14)
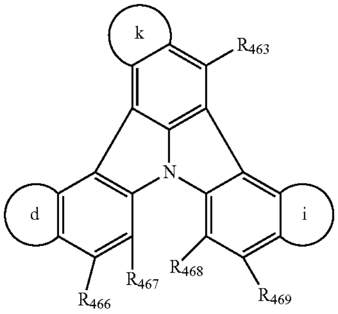
(45-15)
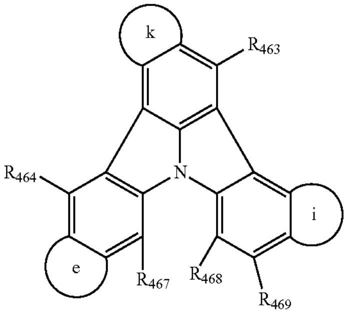
[Formula 316]
(45-16)
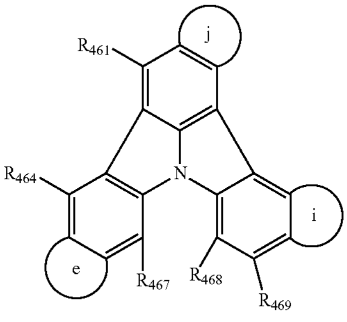
-continued
(45-17)
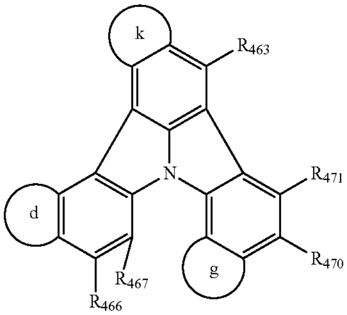
(45-18)
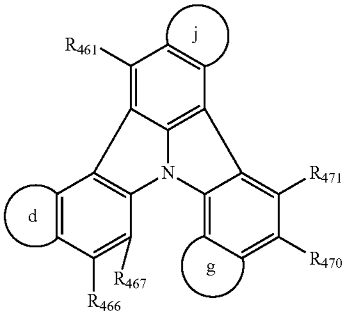
[Formula 317]
(45-19)
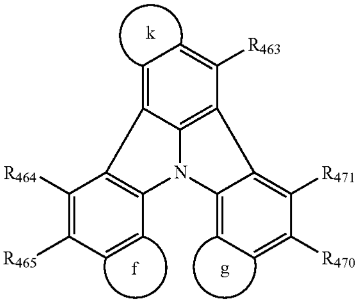
(45-20)
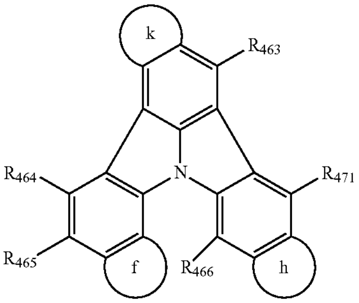
(45-21)
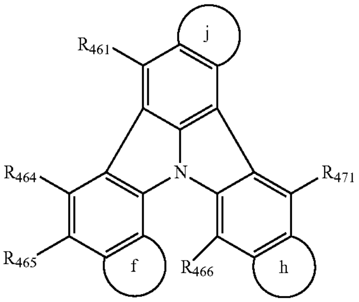

In the formulae (45-13) to (45-21):

rings d to k are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, a group represented by the formula (461), a group represented by the formula (463), and a group represented by the formula (464).

In an exemplary embodiment, the compound represented by the formula (45) is represented by one of formulae (45-22) to (45-25) below.

[Formula 318]

(45-22)

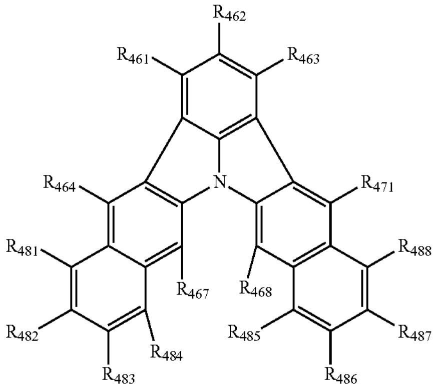

(45-23)

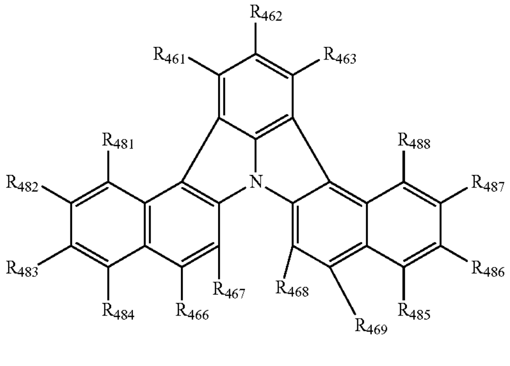

-continued (45-24)

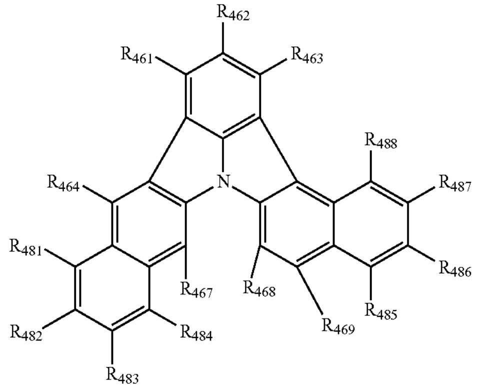

(45-25)

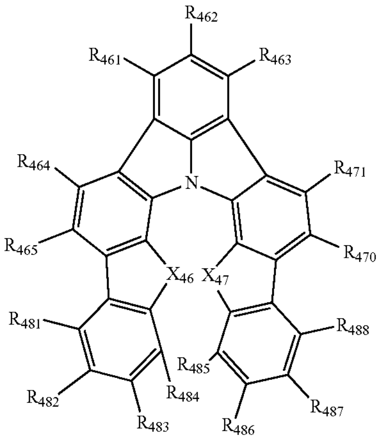

In the formulae (45-22) to (45-25):

$X_{46}$ and $X_{47}$ are each independently $C(R_{801})(R_{802})$, $NR_{803}$, an oxygen atom, or a sulfur atom;

$R_{461}$ to $R_{471}$ and $R_{481}$ to $R_{488}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, the compound represented by the formula (45) is represented by a formula (45-26) below.

[Formula 319]

(45-26)

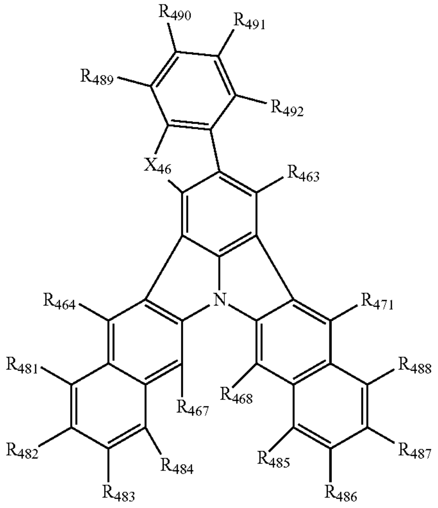

In the formula (45-26):

$X_{46}$ is $C(R_{801})(R_{802})$, $NR_{803}$, an oxygen atom, or a sulfur atom;

$R_{463}$, $R_{464}$, $R_{467}$, $R_{468}$, $R_{471}$, and $R_{481}$ to $R_{492}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms; a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

Specific examples of the compound represented by the formula (4) include compounds shown below. In the specific examples below, Ph represents a phenyl group, and D represents a deutrium atom.

[Formula 320]

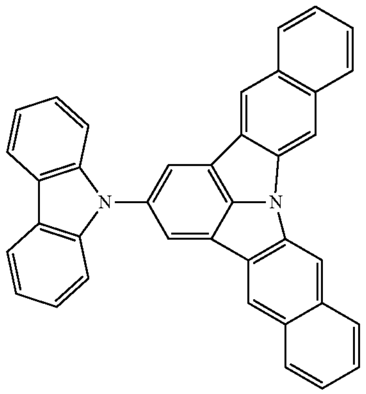

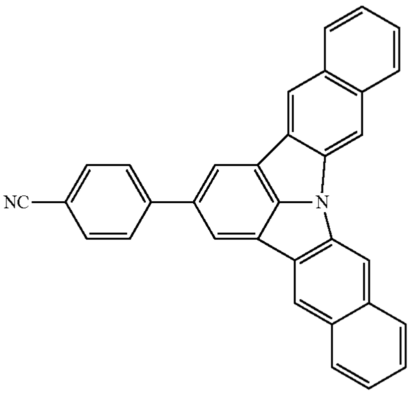

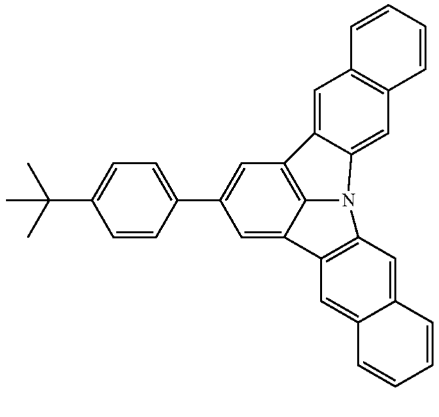

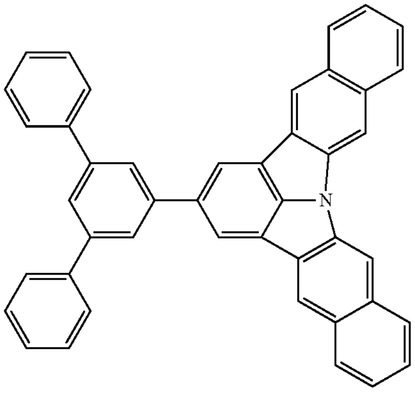

-continued
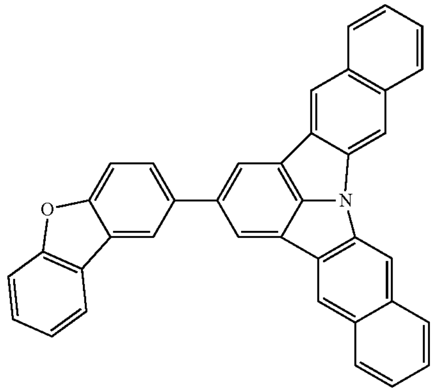
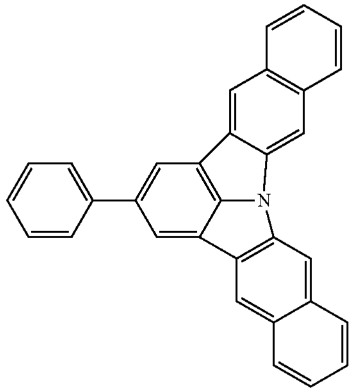
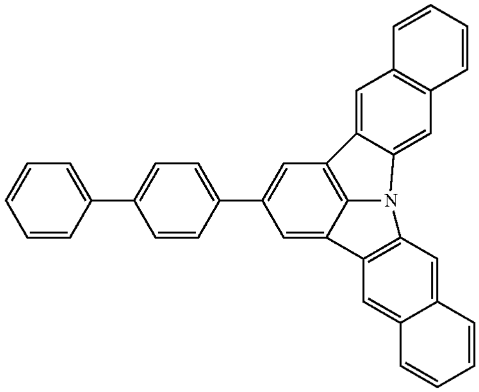
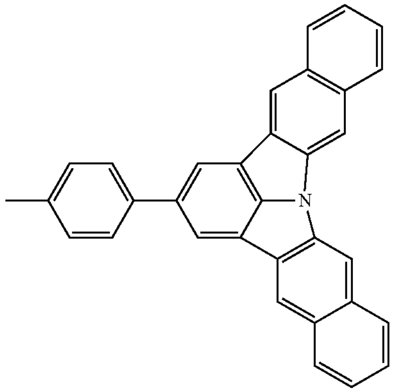
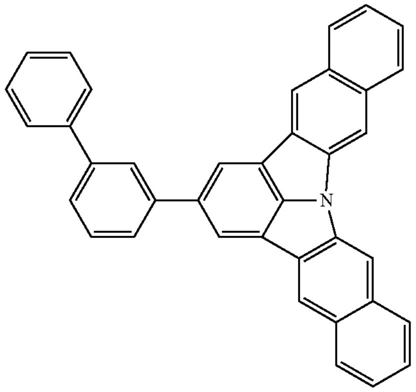
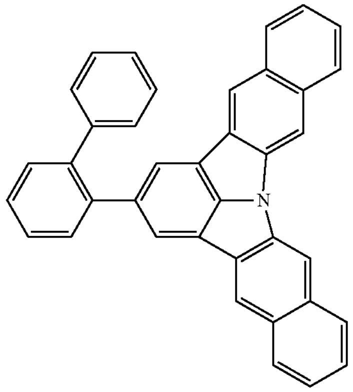
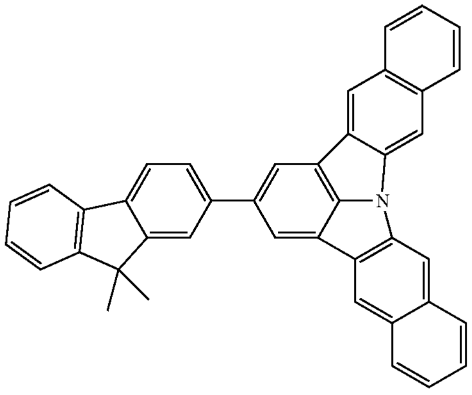
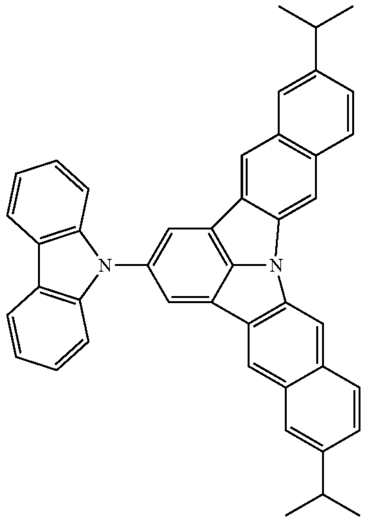

-continued
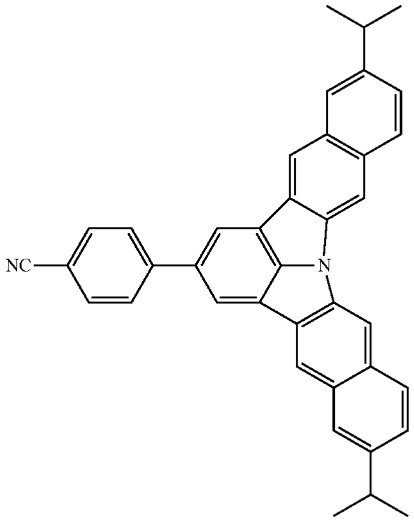
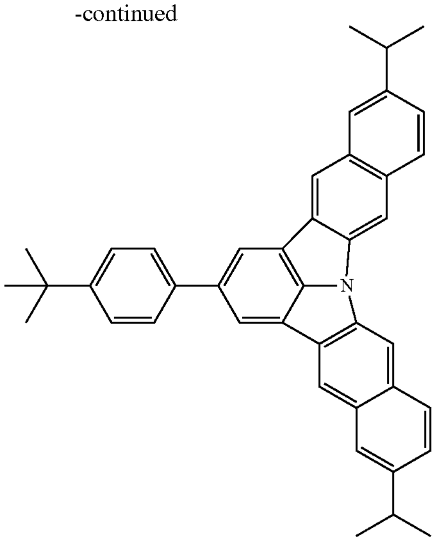
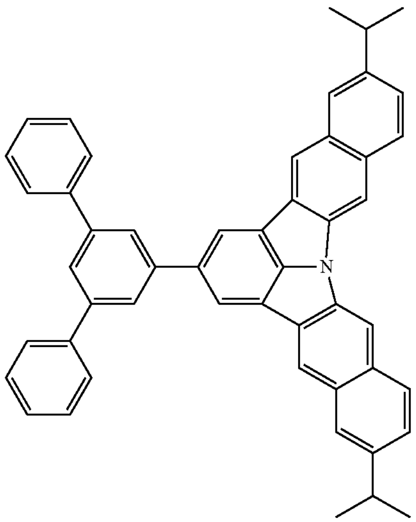
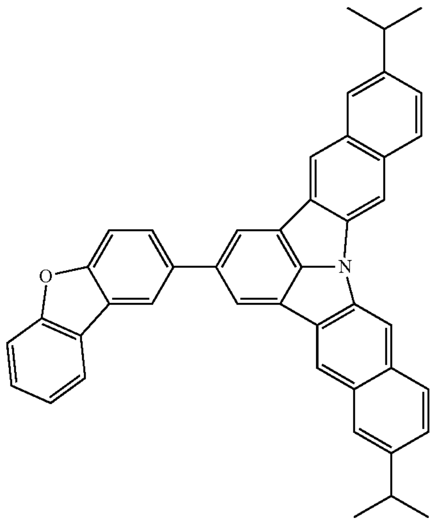
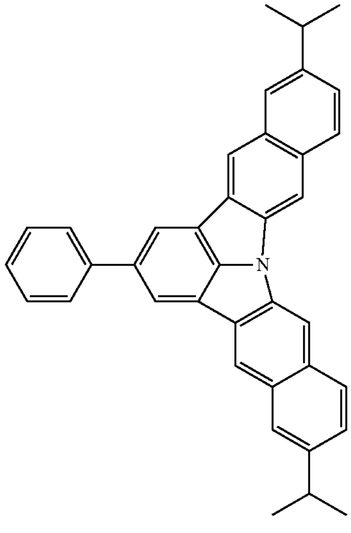
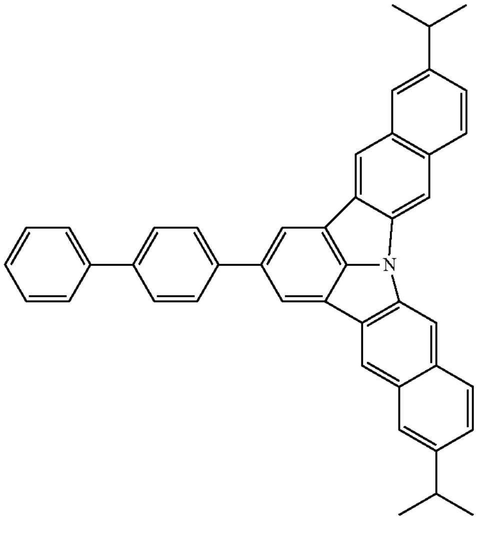

-continued
[Formula 321]
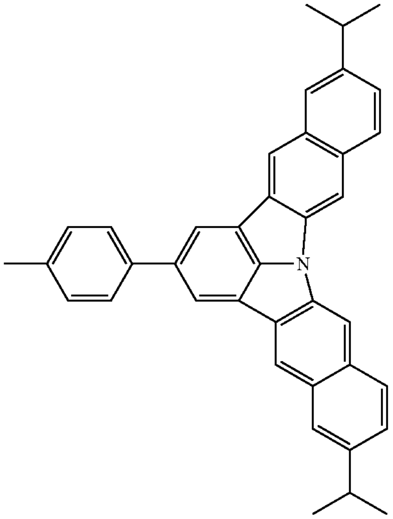
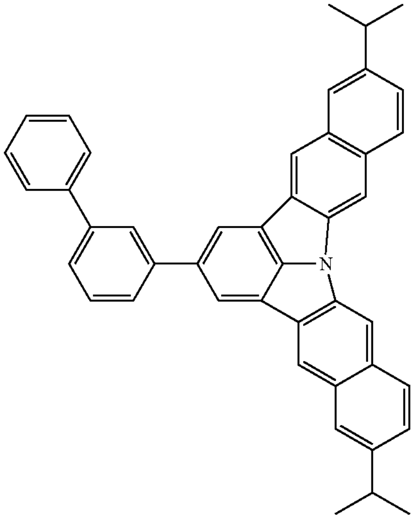
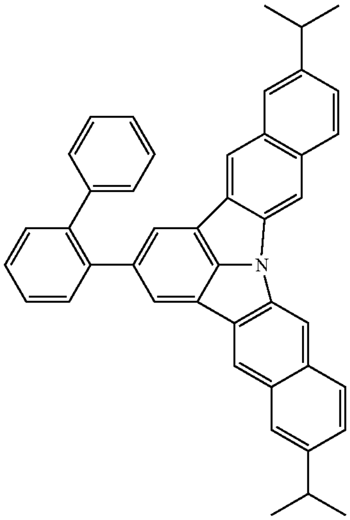
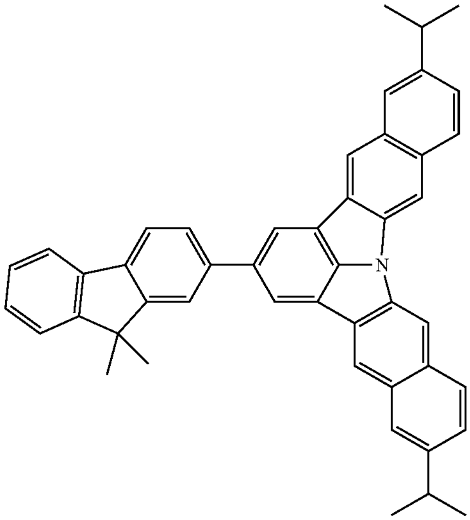
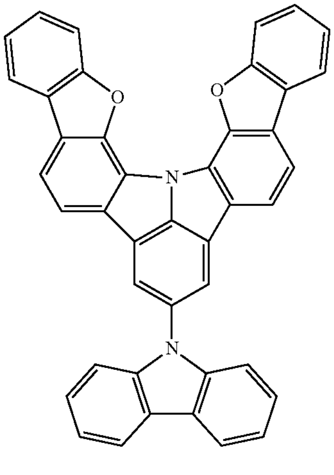
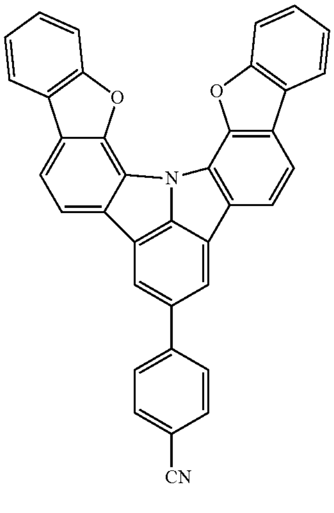
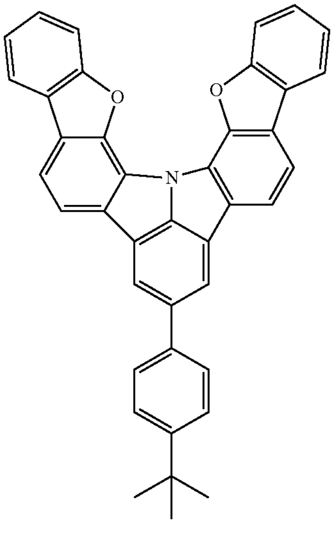

-continued
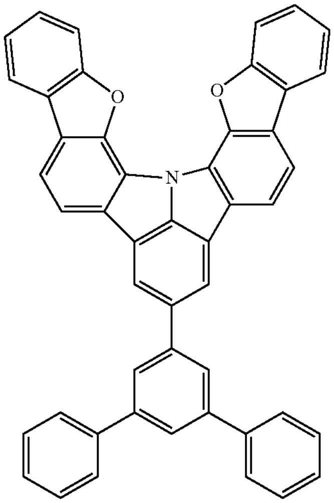
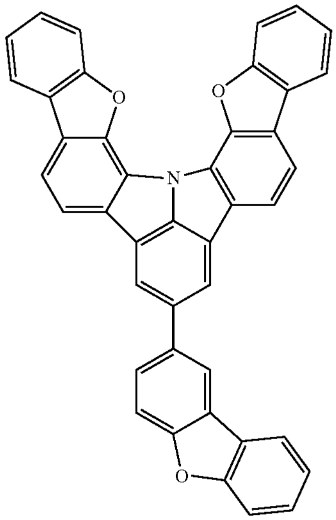
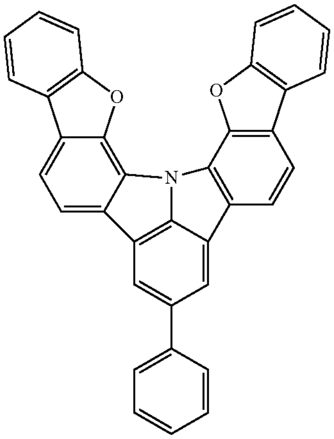
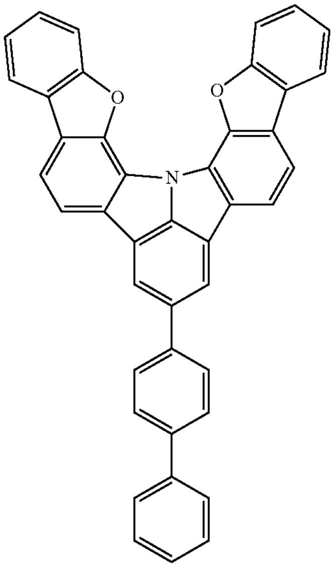
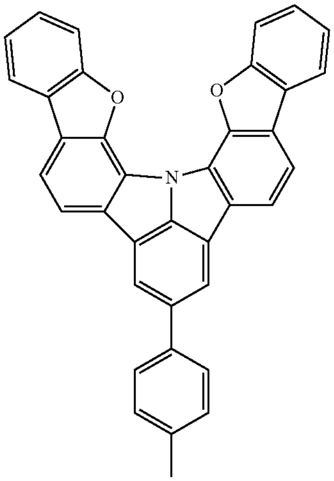
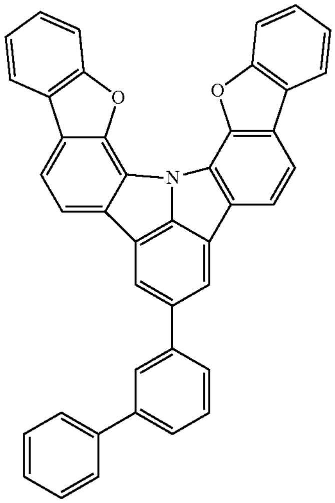
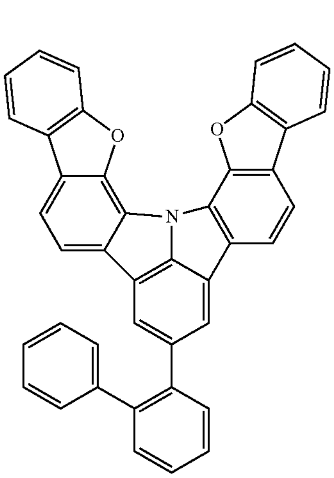
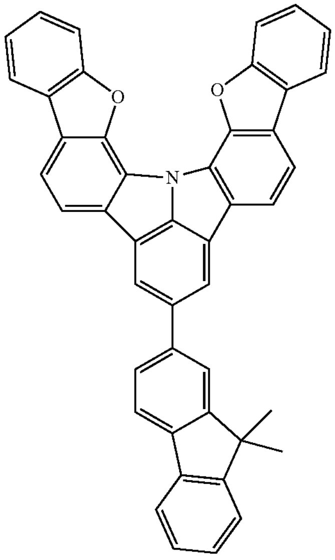

-continued
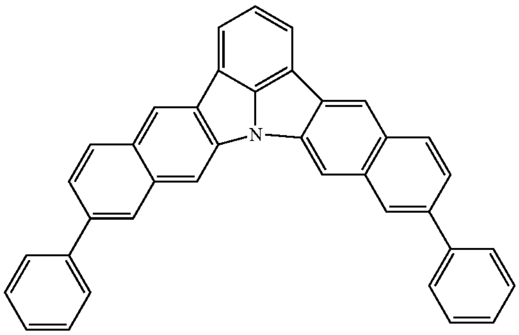
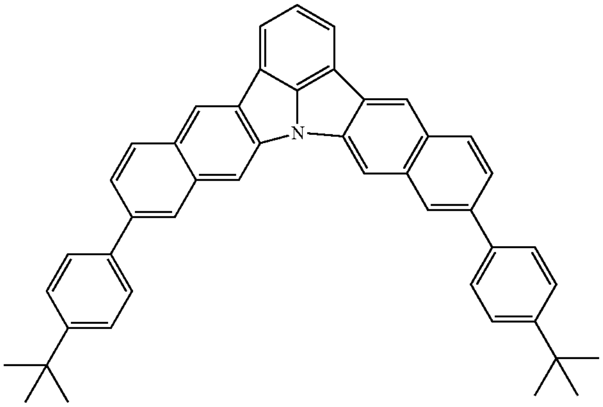
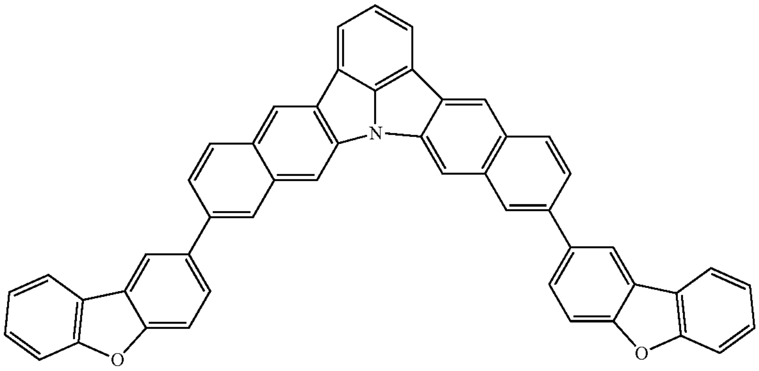
[Formula 322]
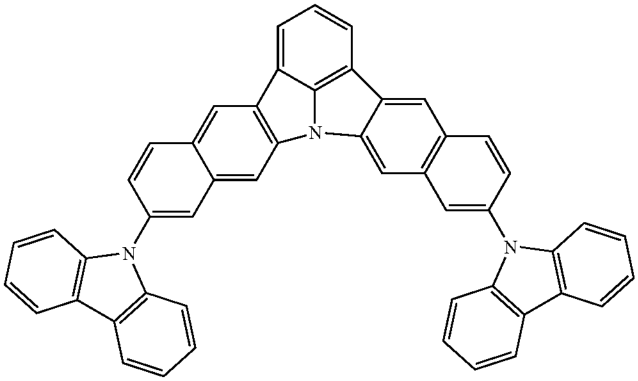
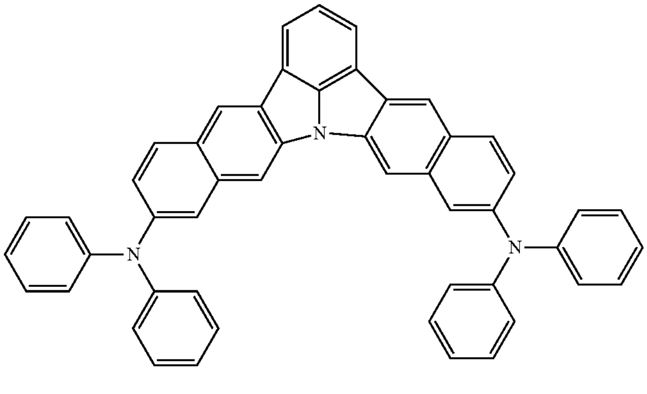

-continued
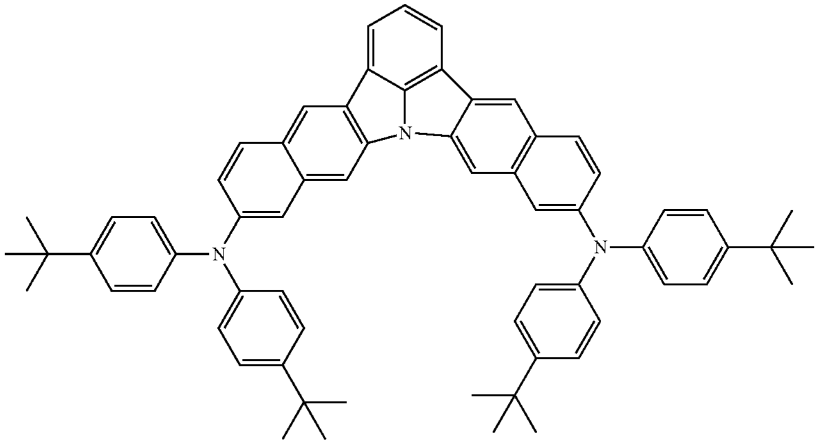
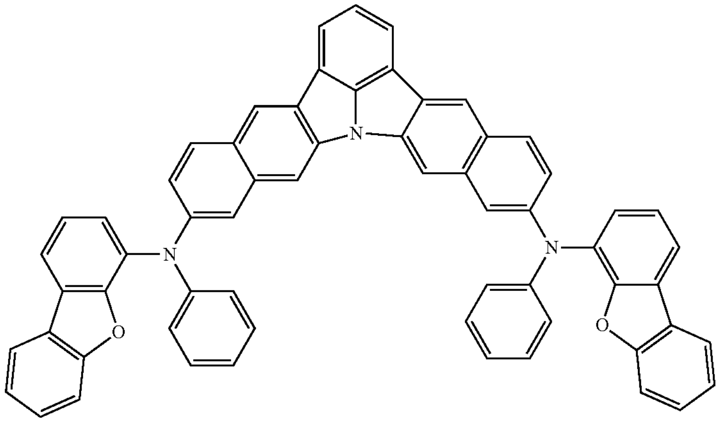
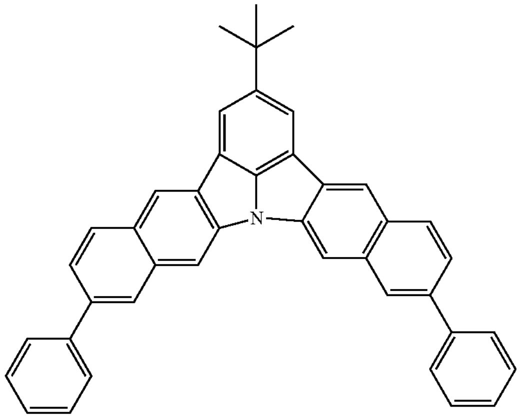
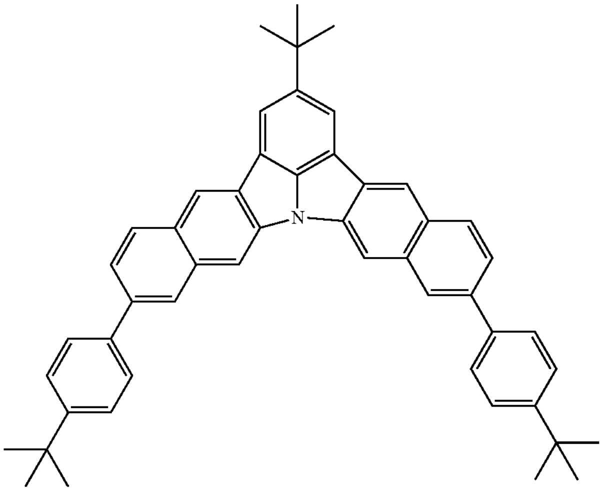

-continued
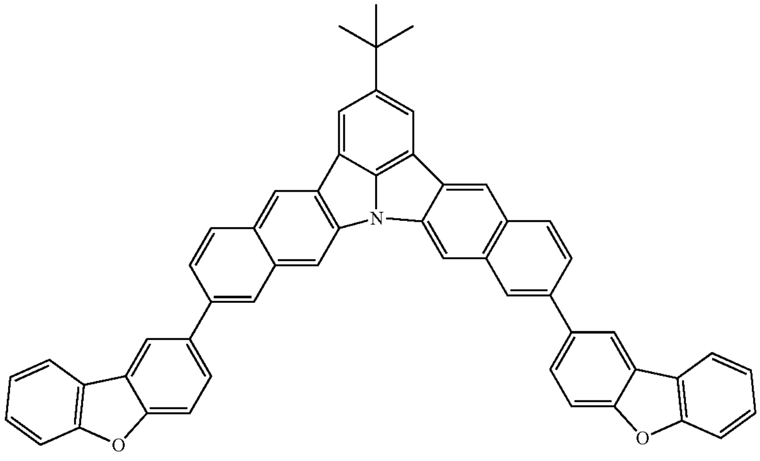
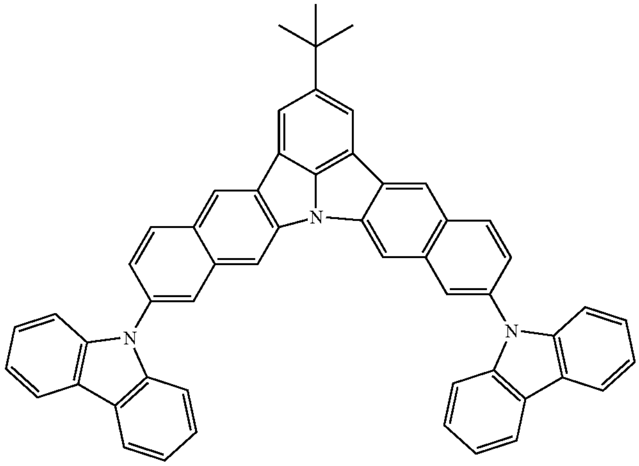
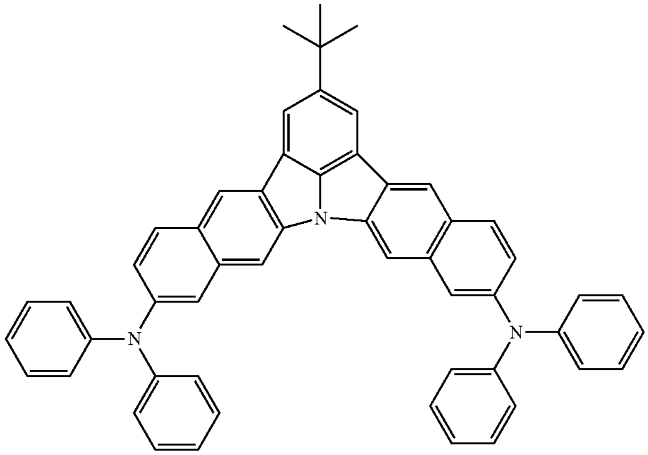

-continued
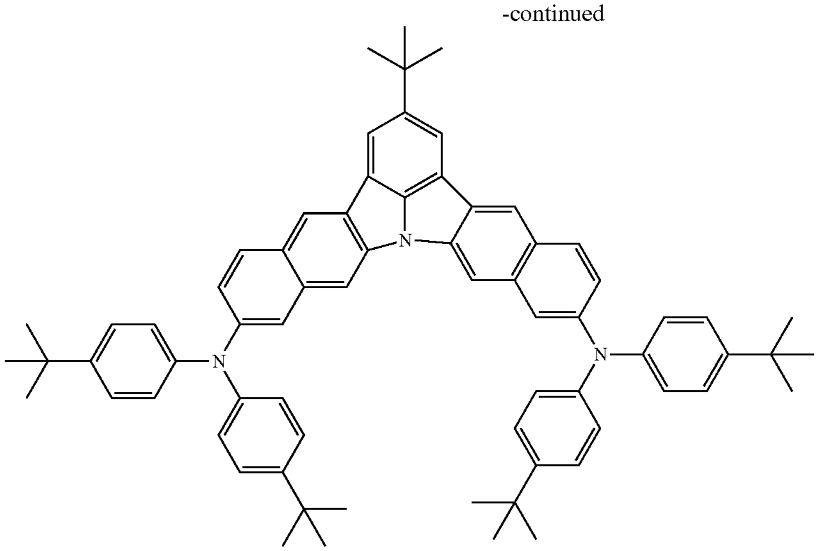
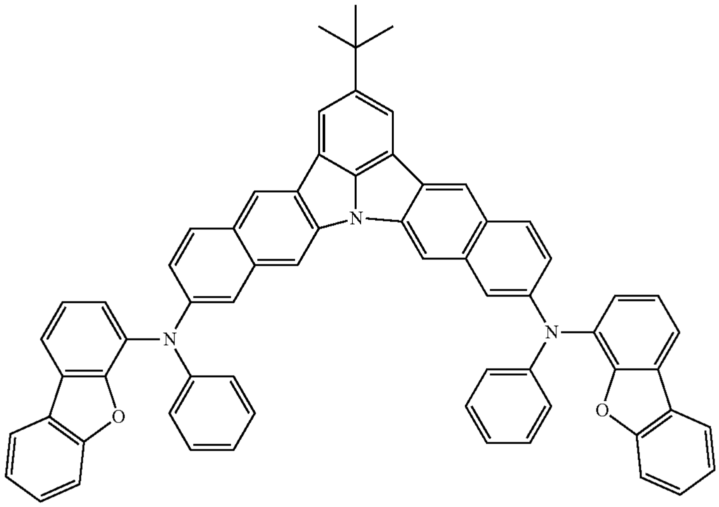
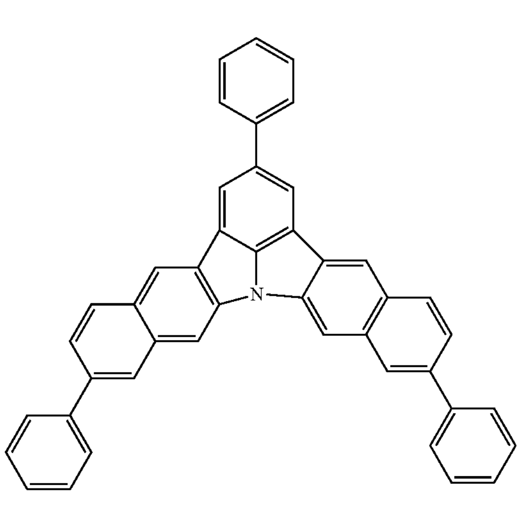
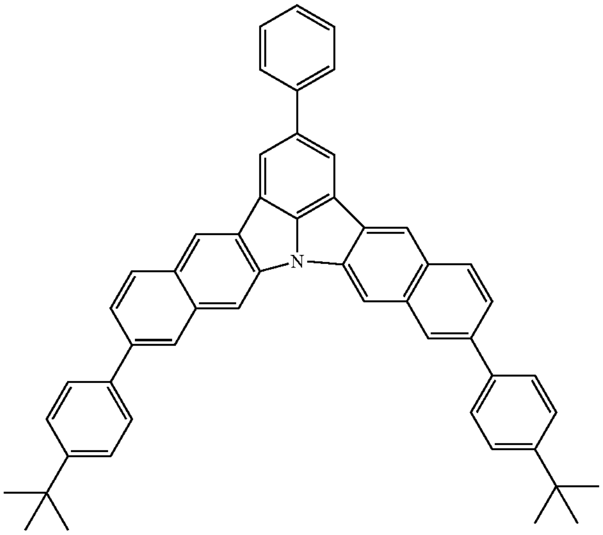

-continued
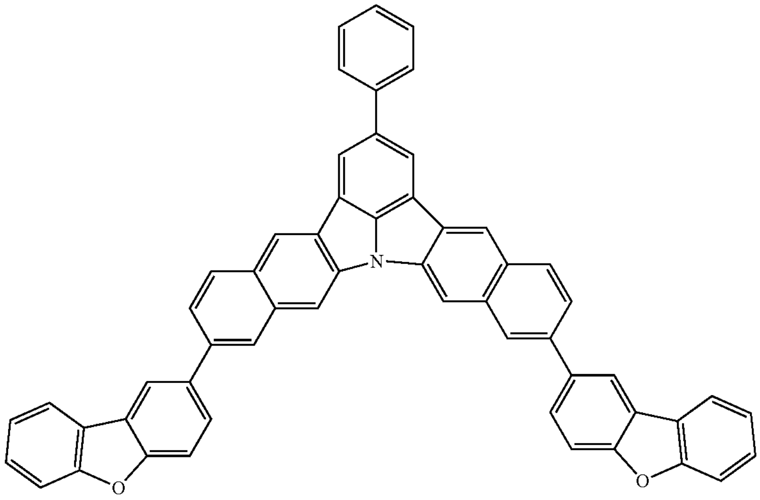
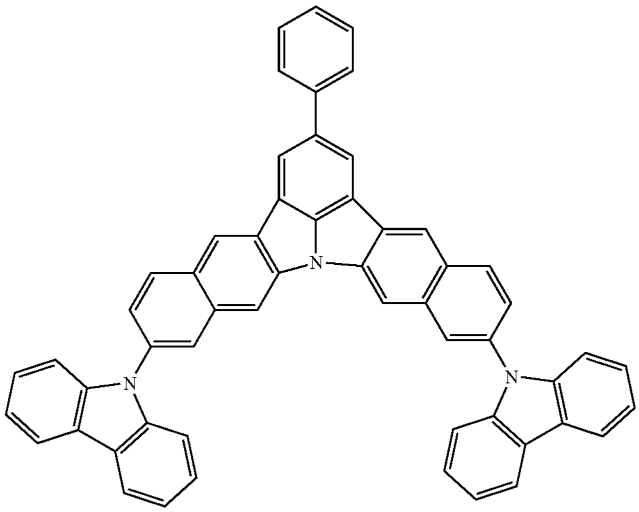
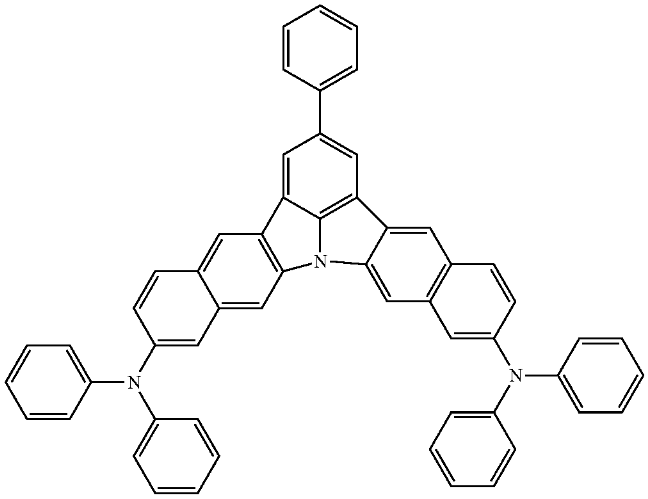

-continued
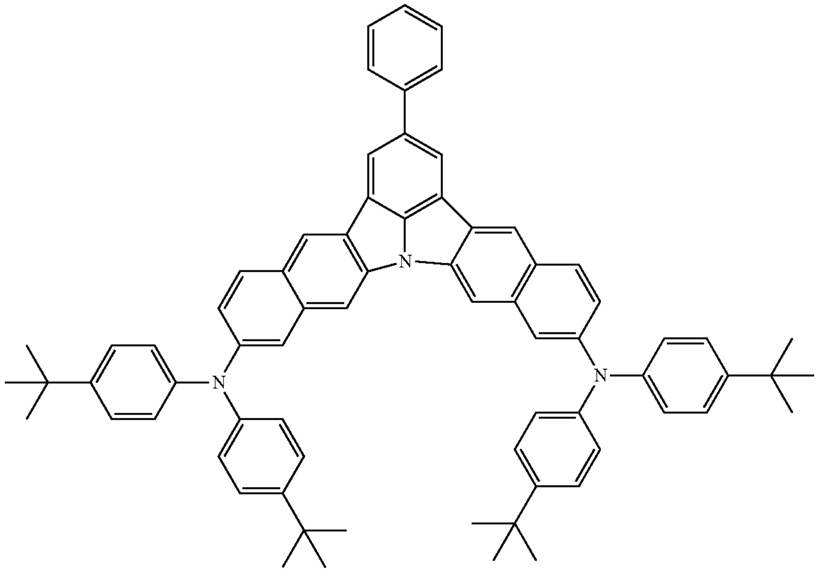
[Formula 323]
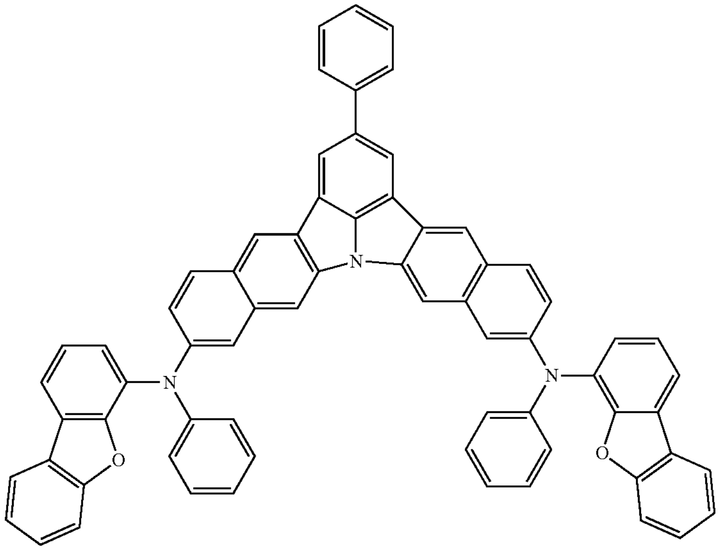

-continued
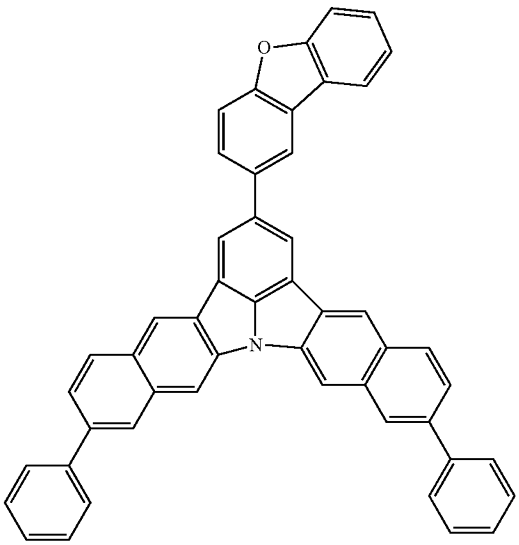
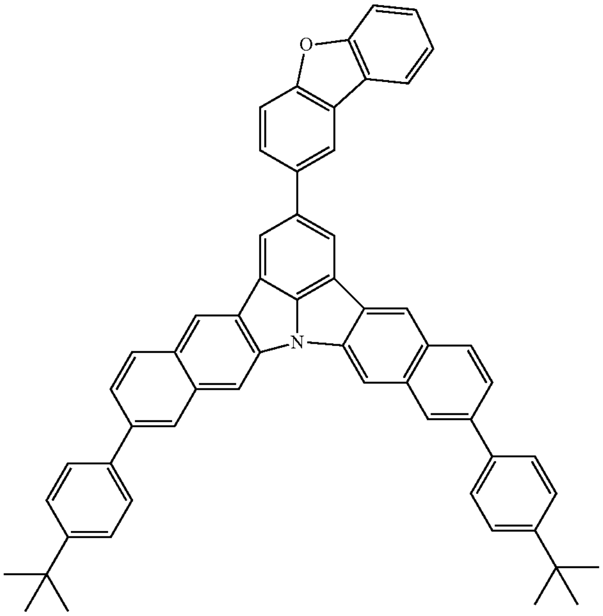
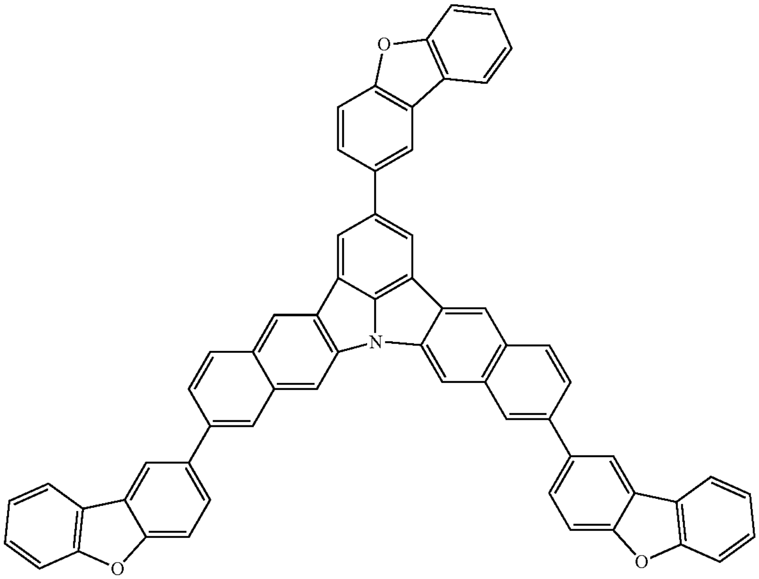

-continued
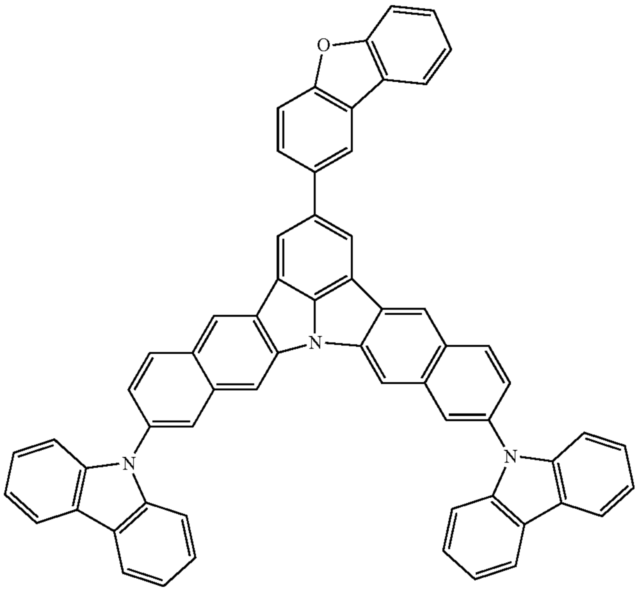
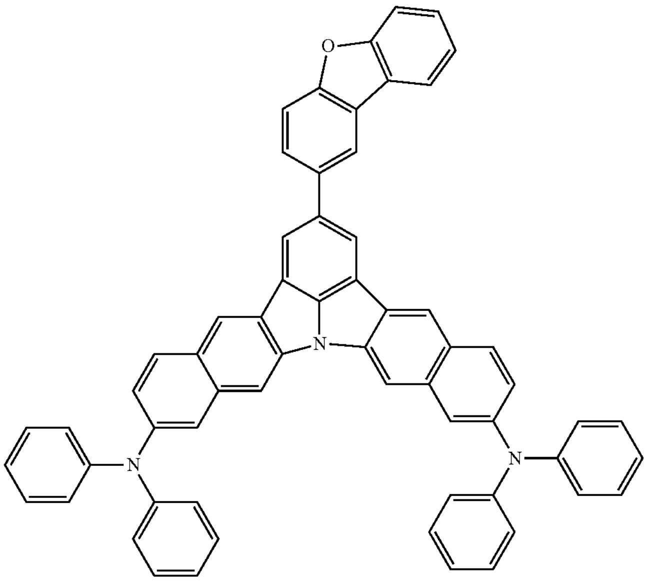

-continued
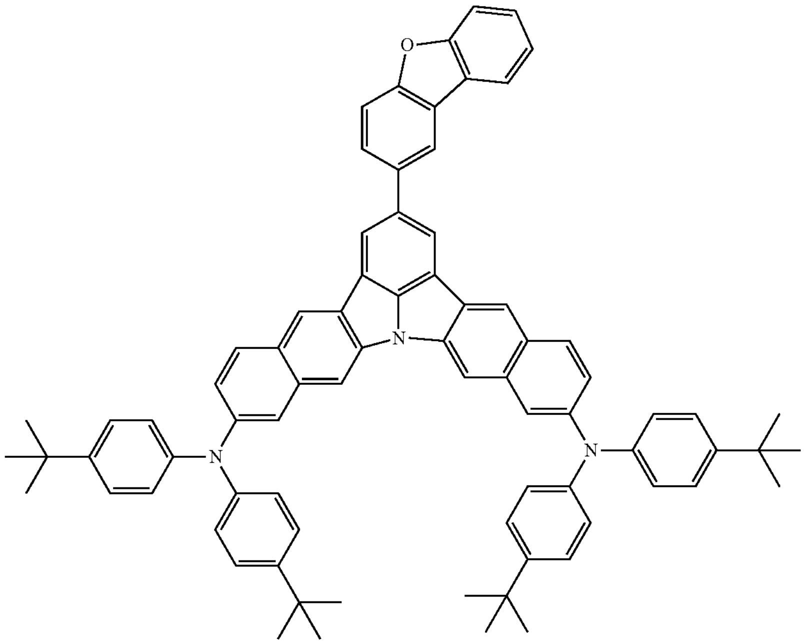
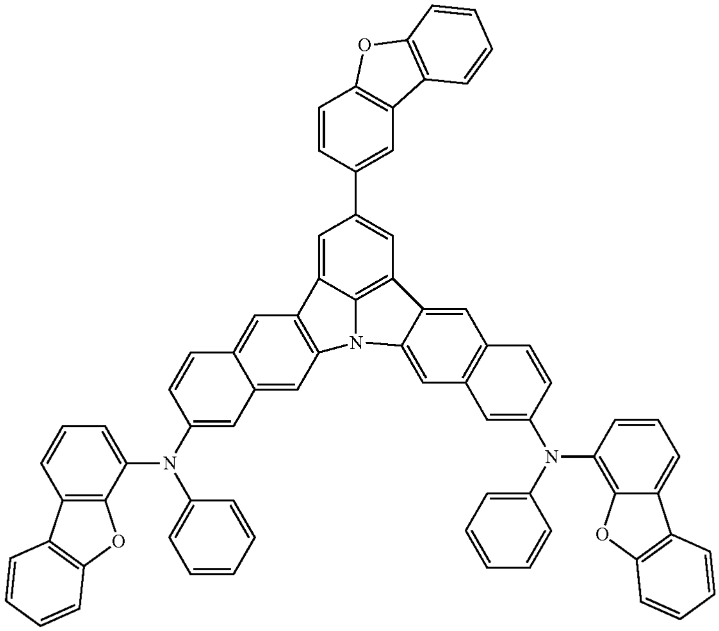

-continued
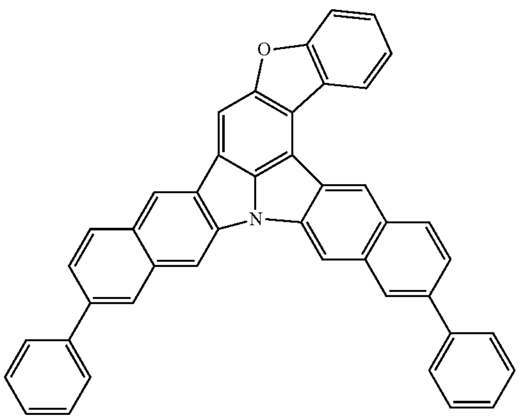
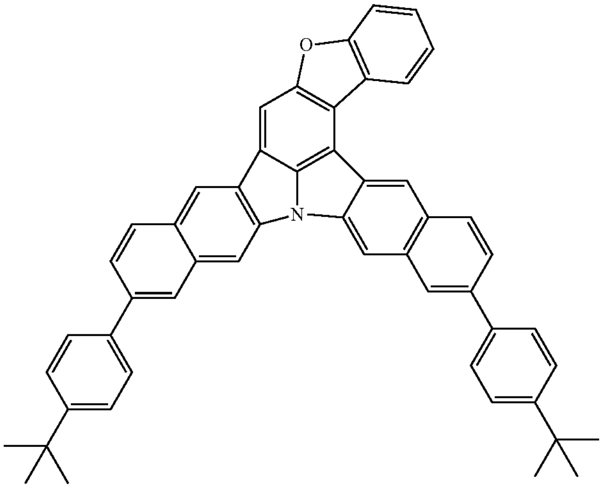
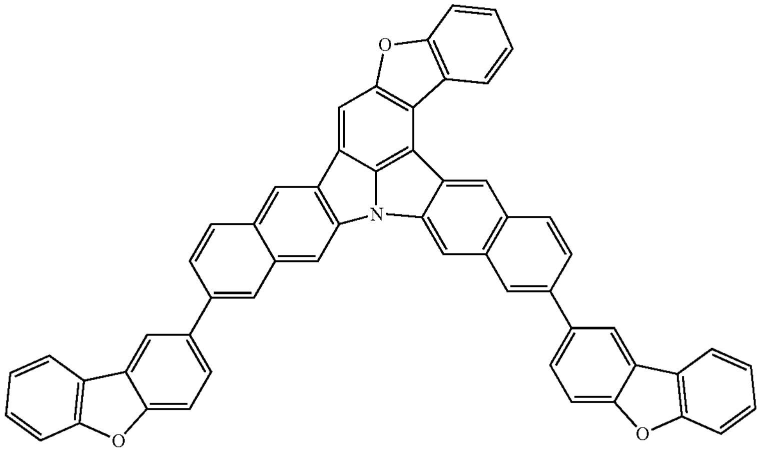
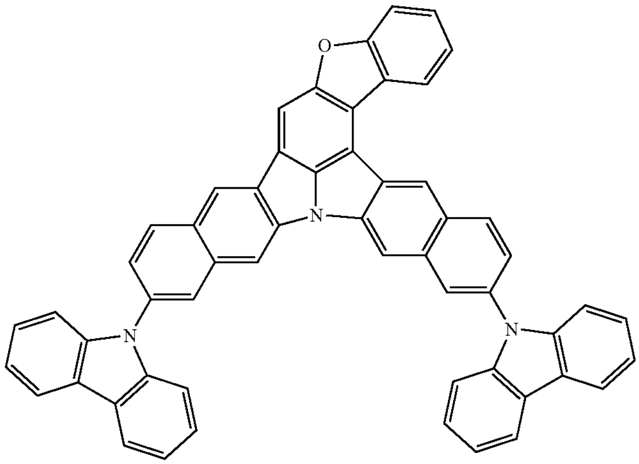

-continued
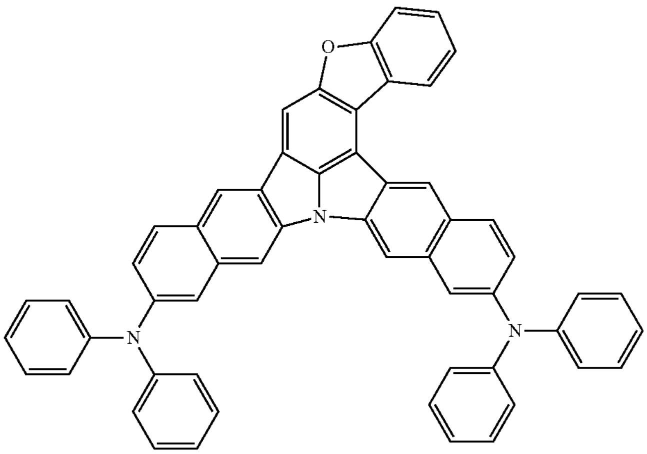
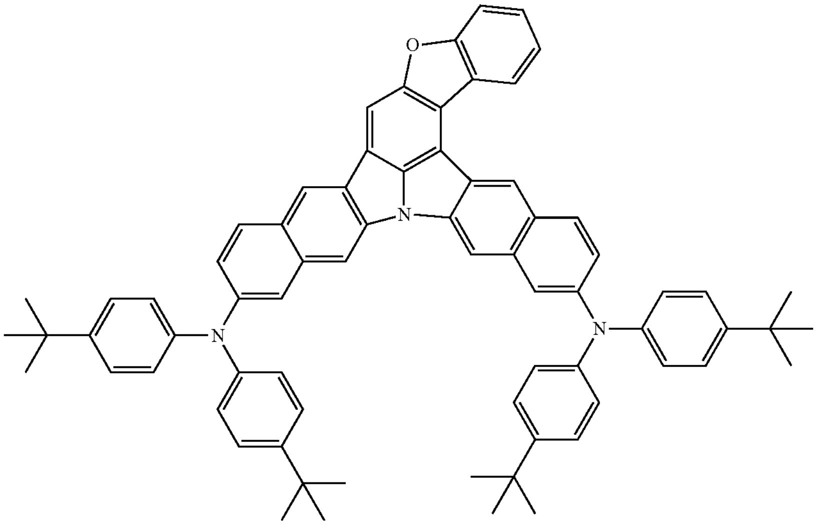
[Formula 324]
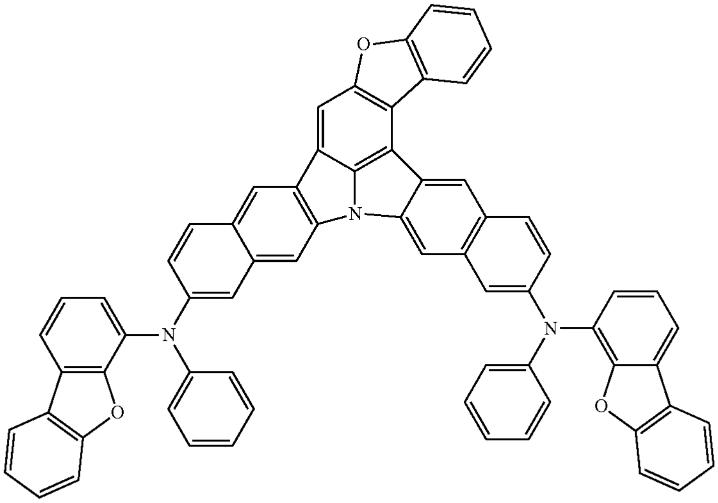

-continued
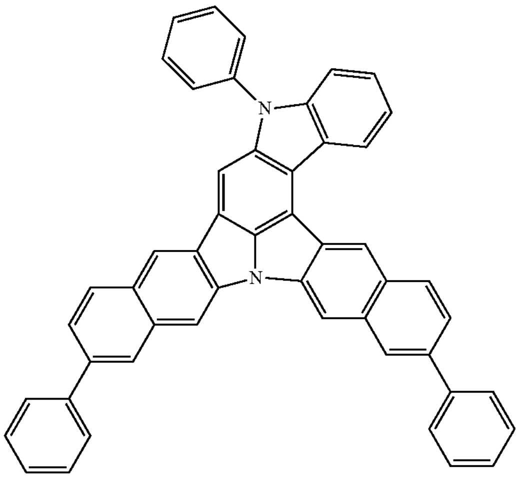
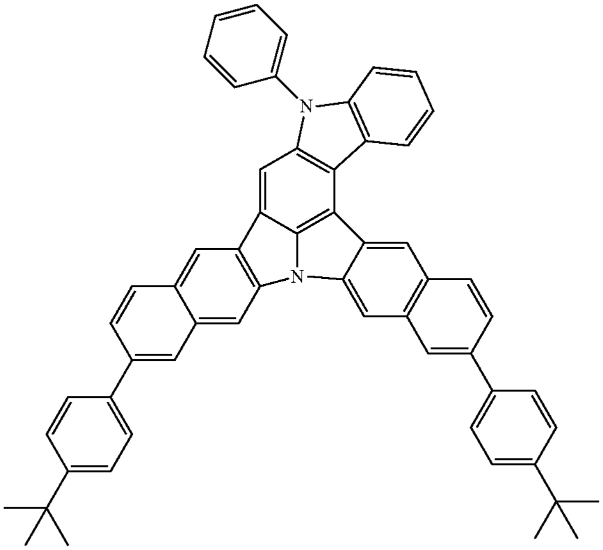
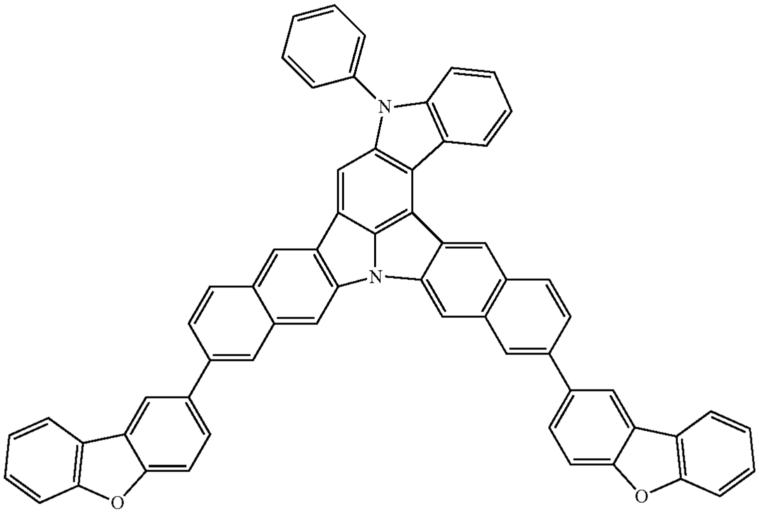
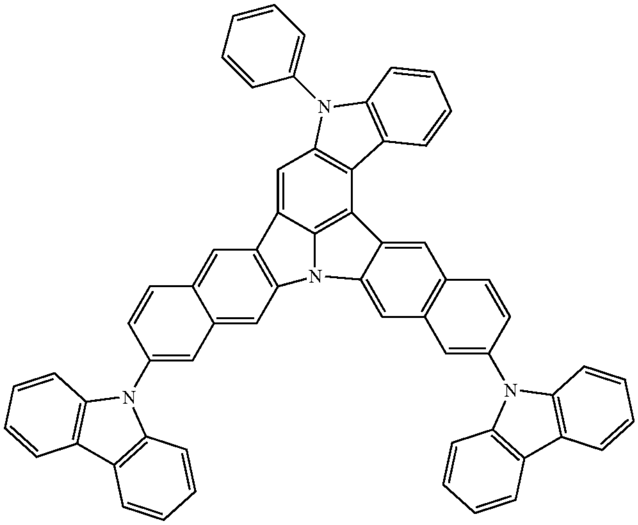

-continued
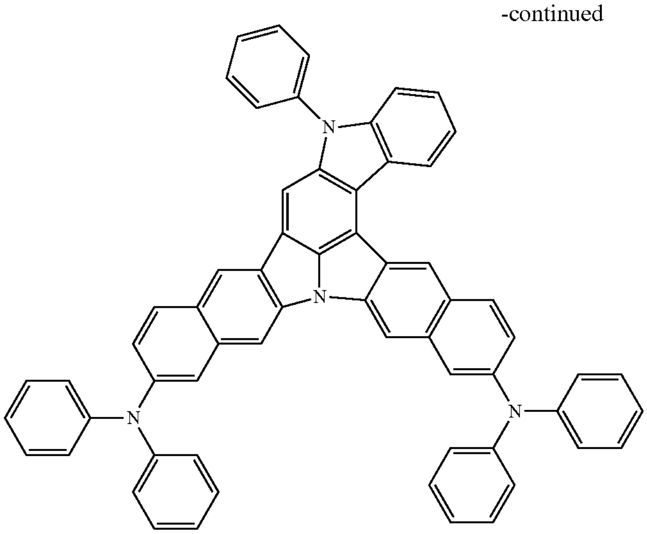
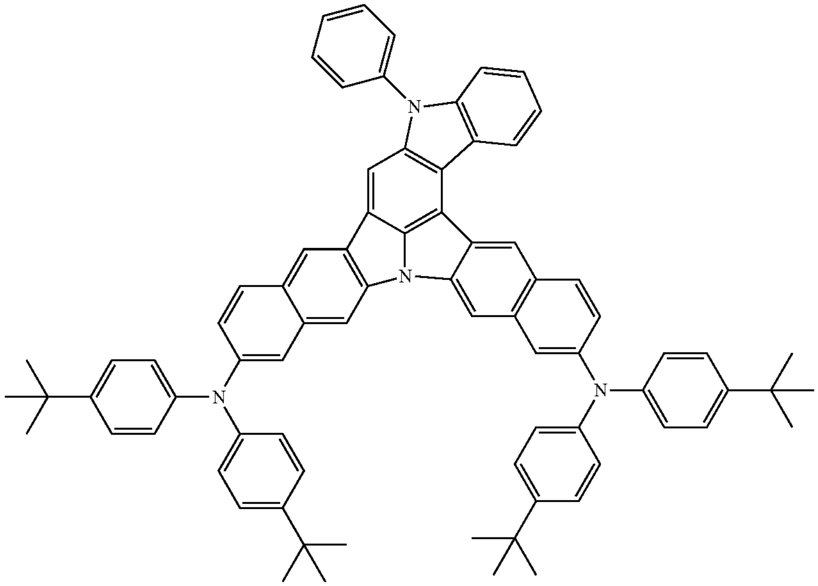
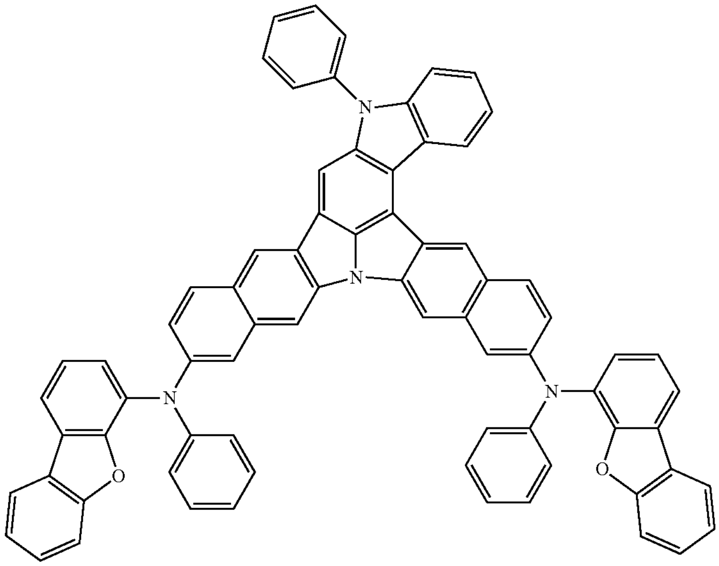

-continued
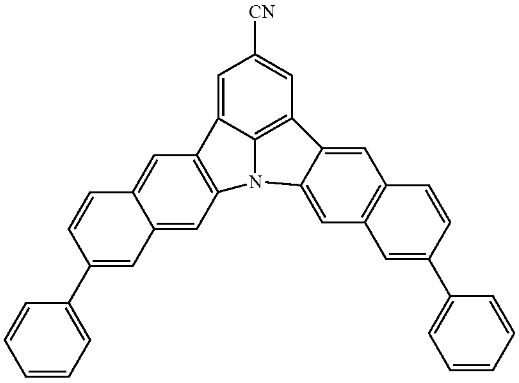
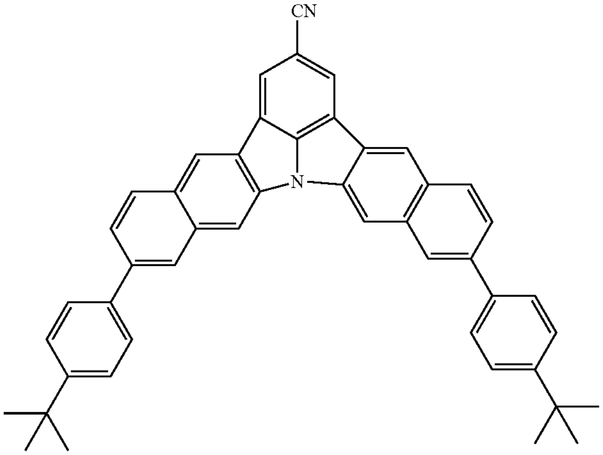
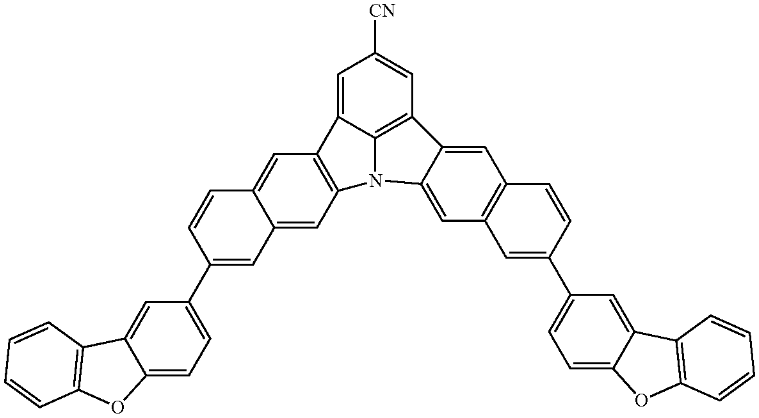
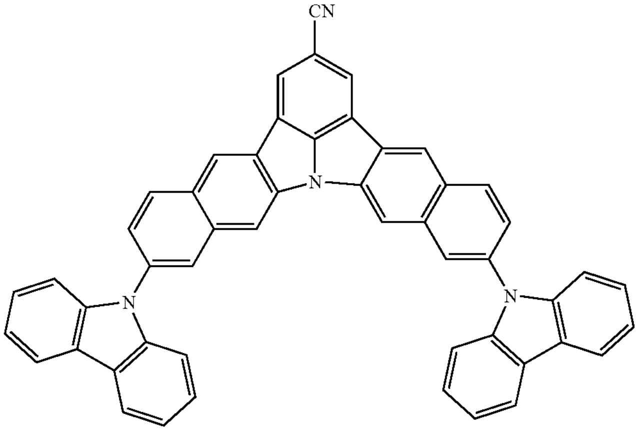
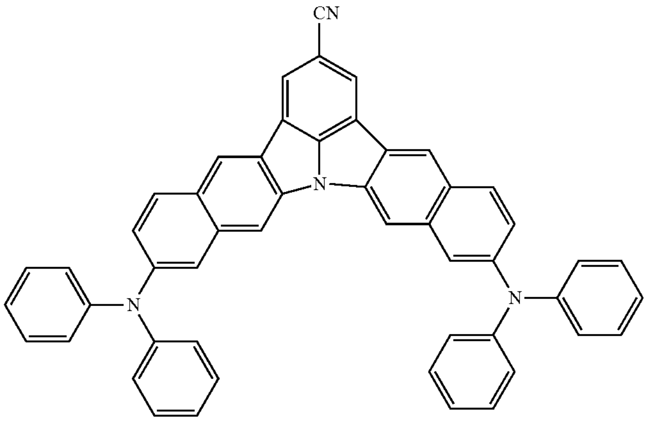

-continued
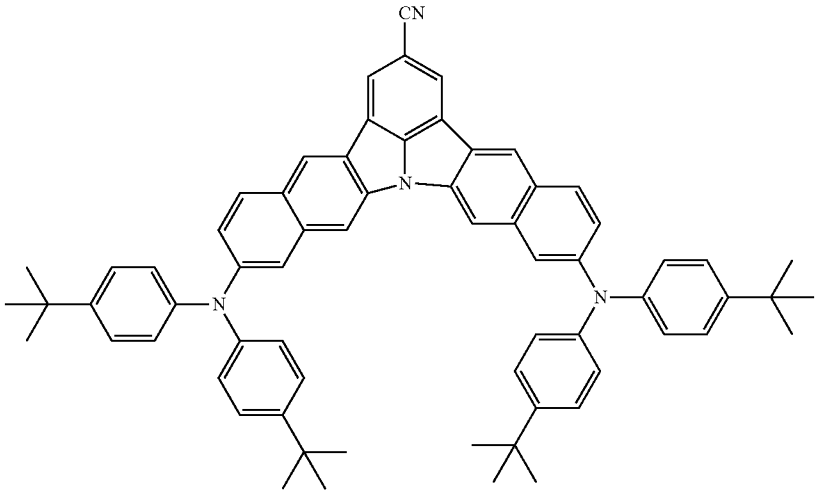
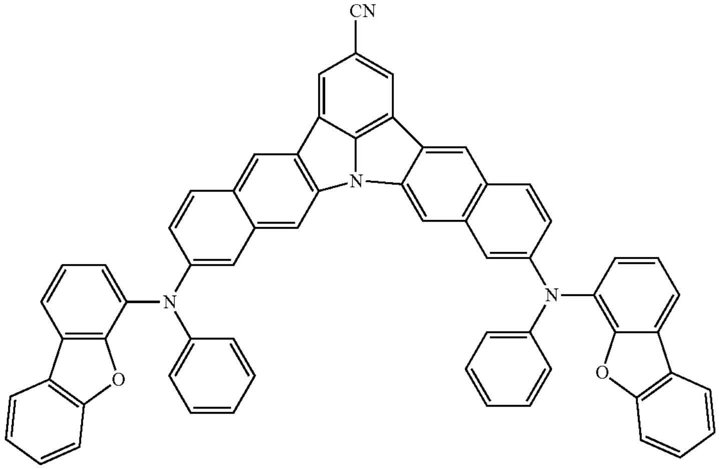
[Formula 325]
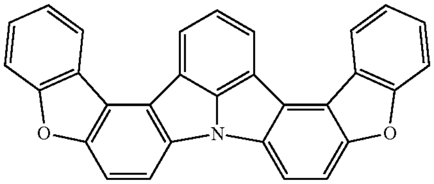
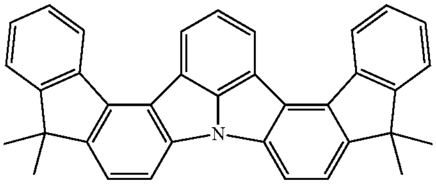
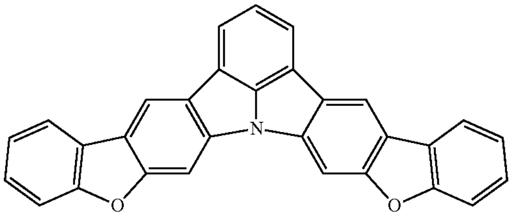
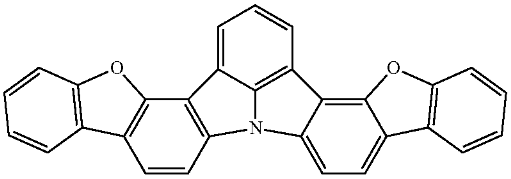
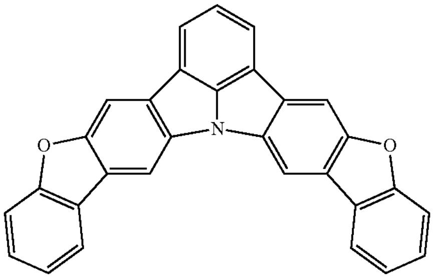
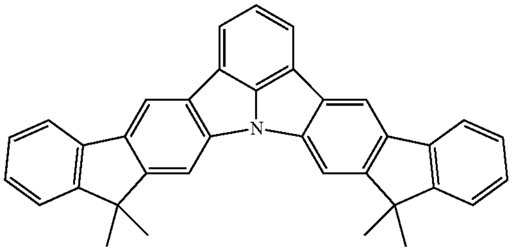

-continued
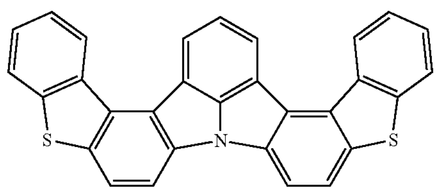
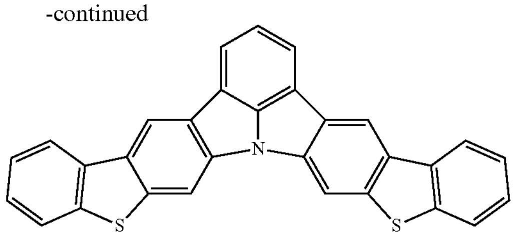
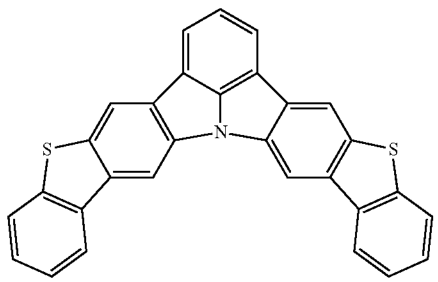
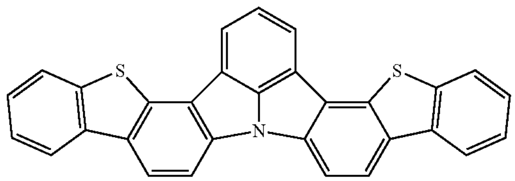
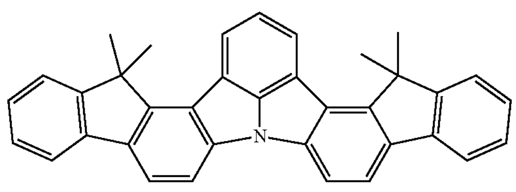
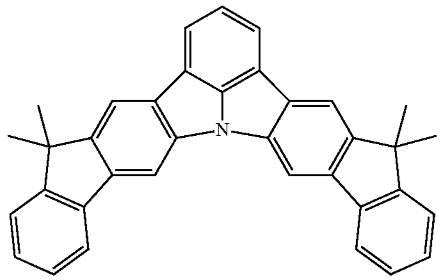
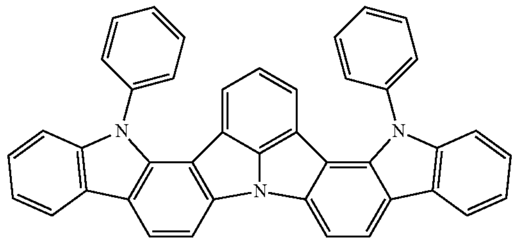
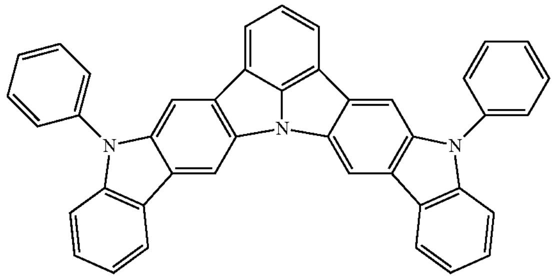
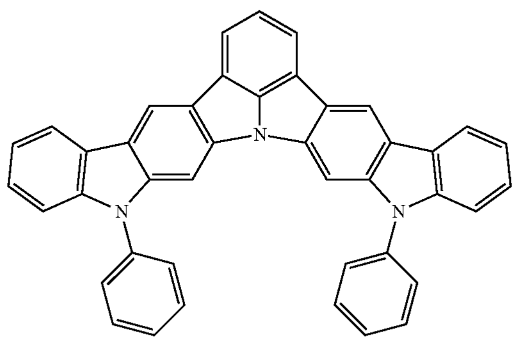
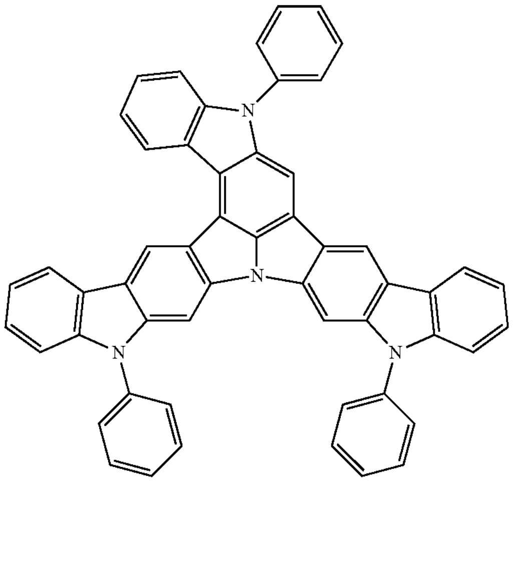

-continued
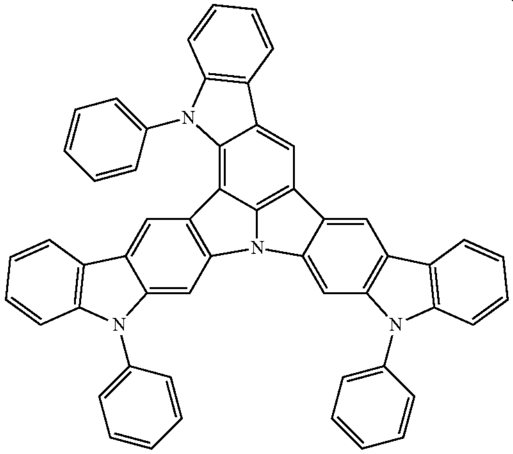
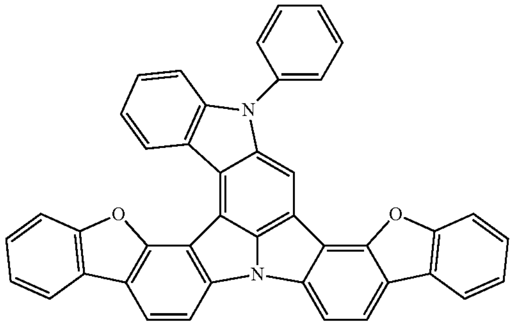
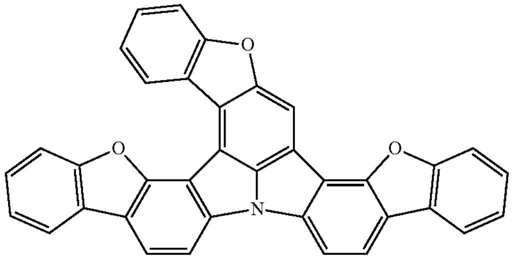
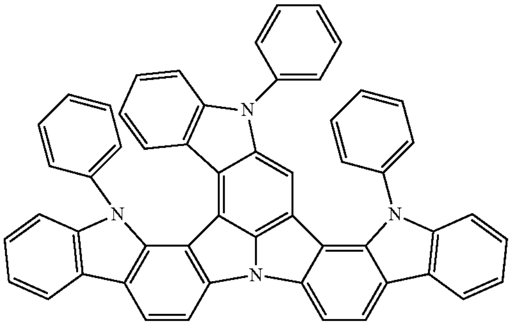
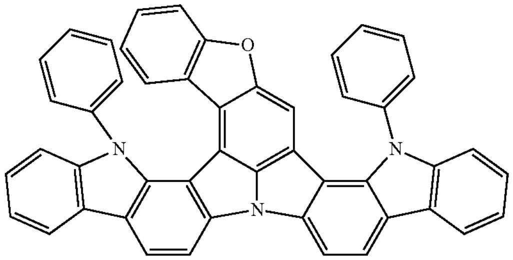
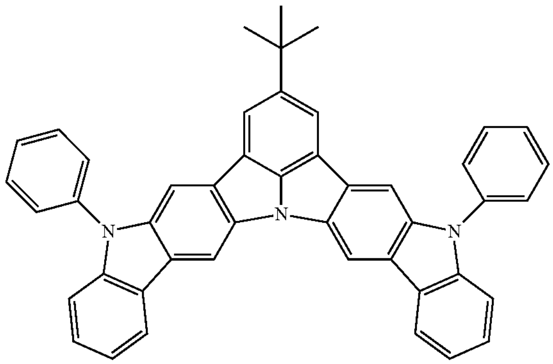
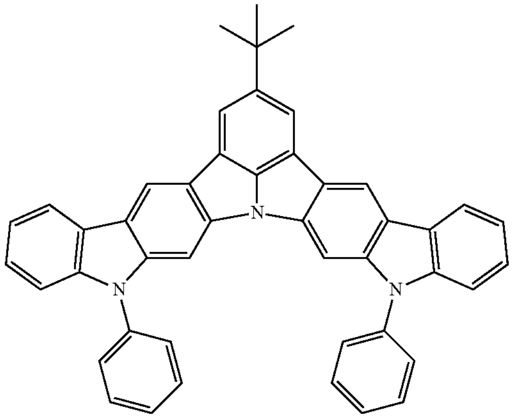

-continued
[Formula 326]
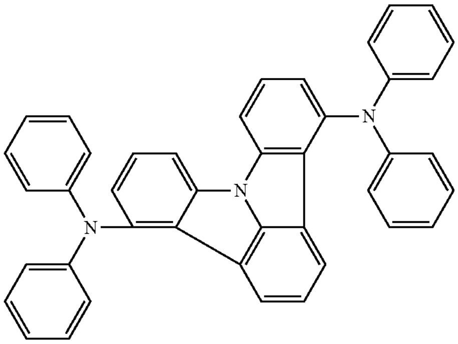
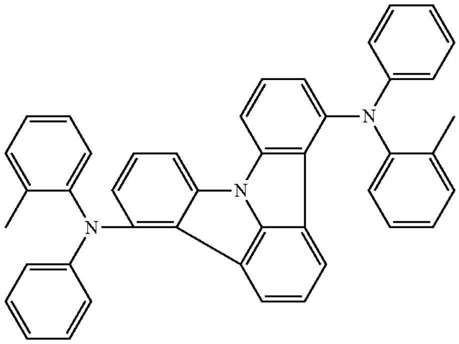
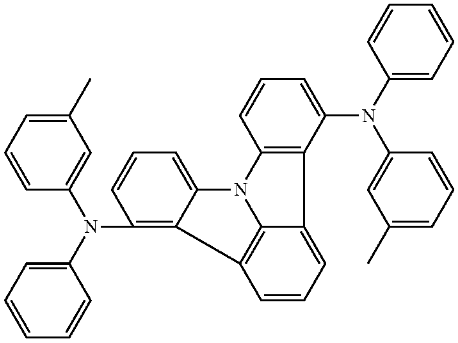
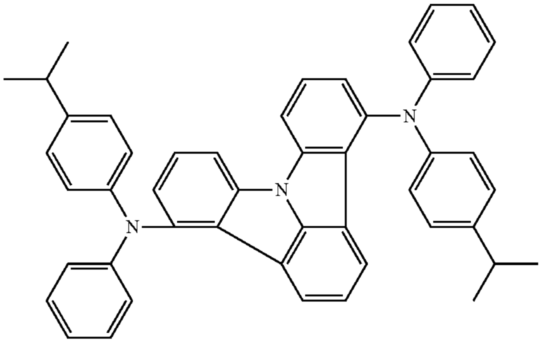
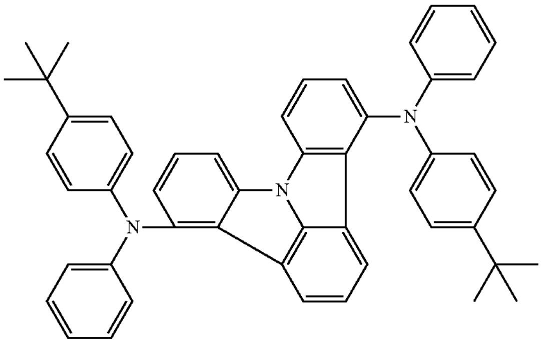
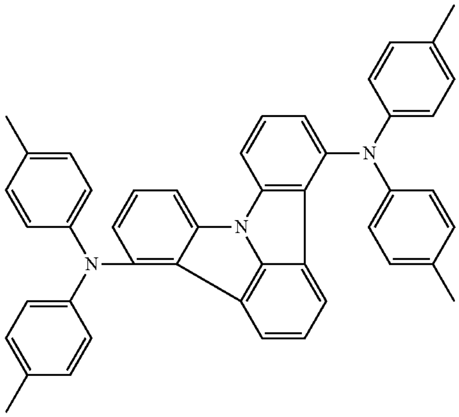
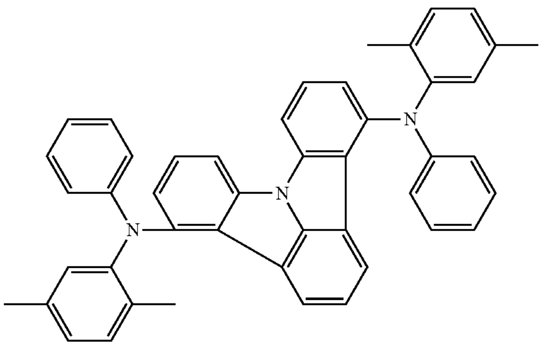
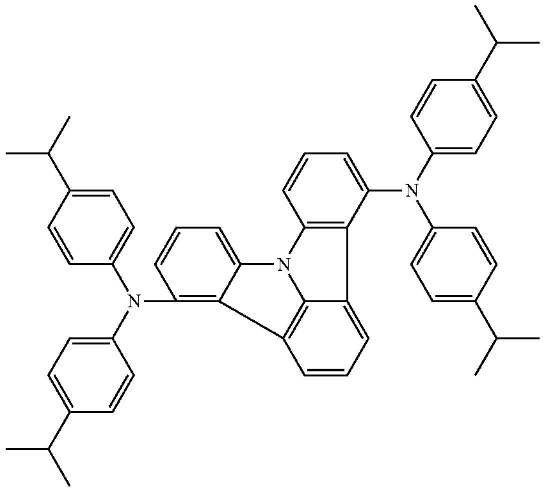

-continued
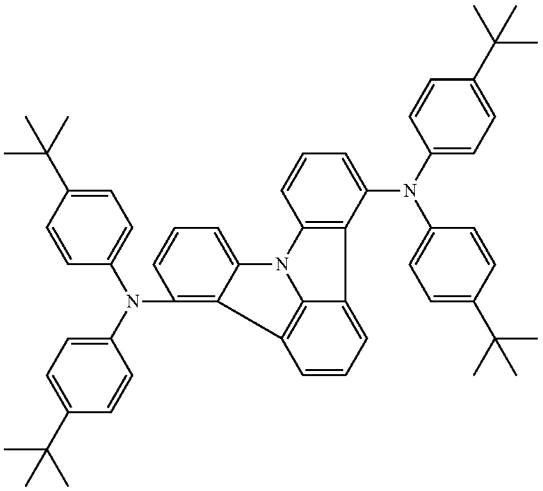
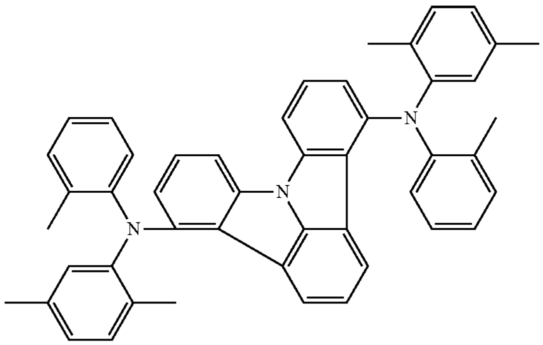
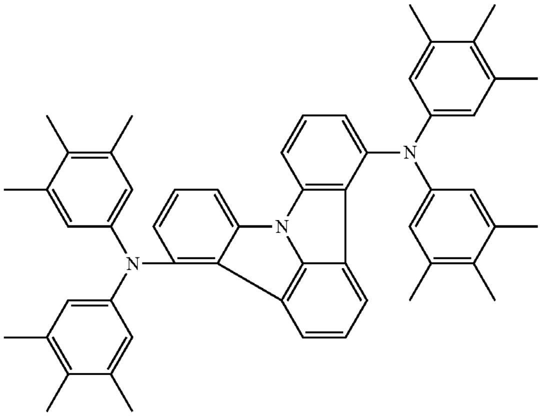
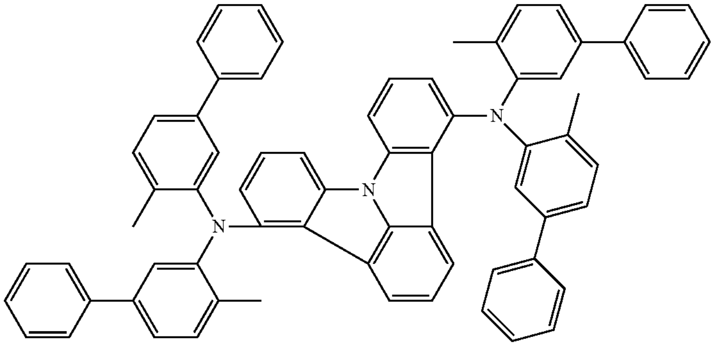
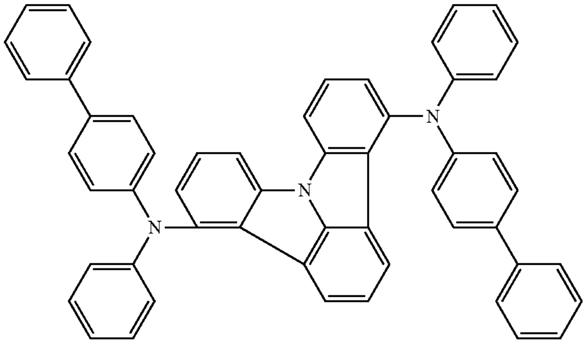
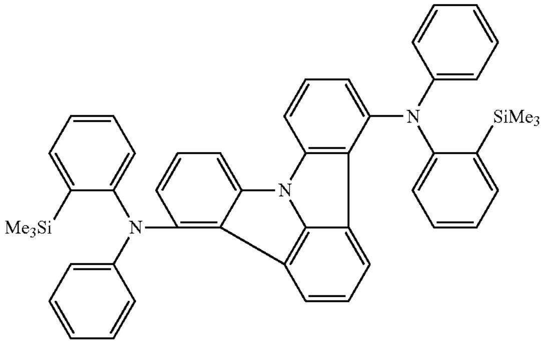

-continued
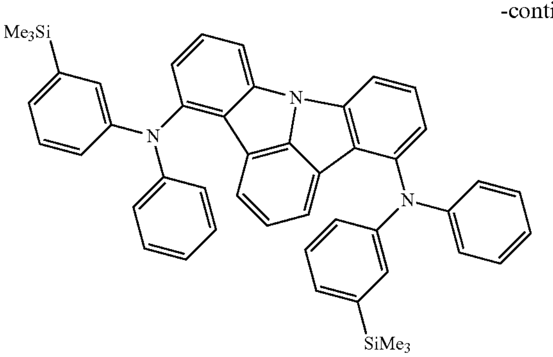
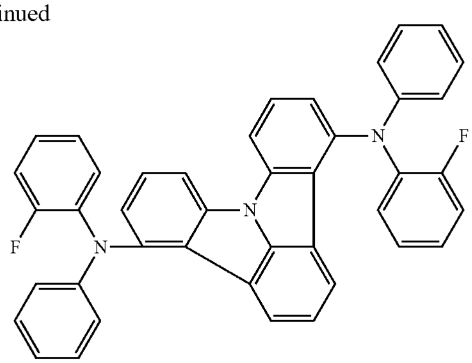
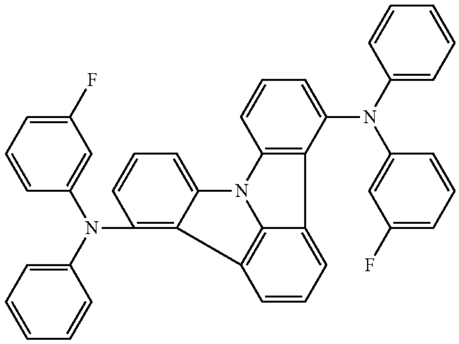
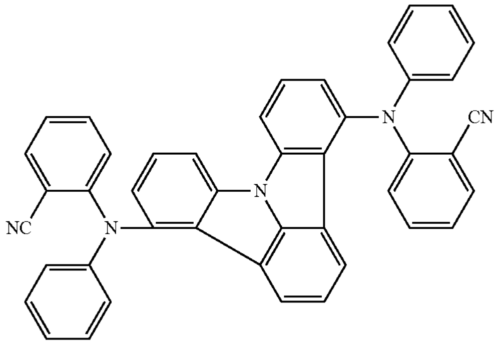
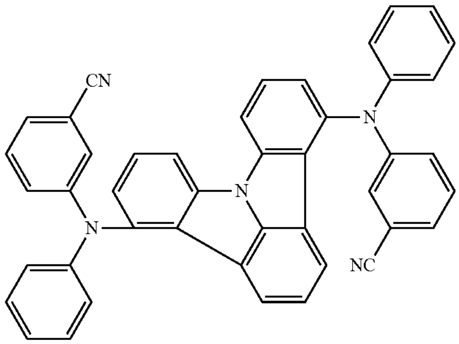
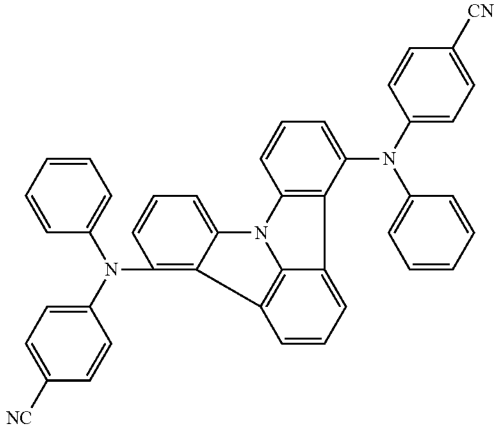
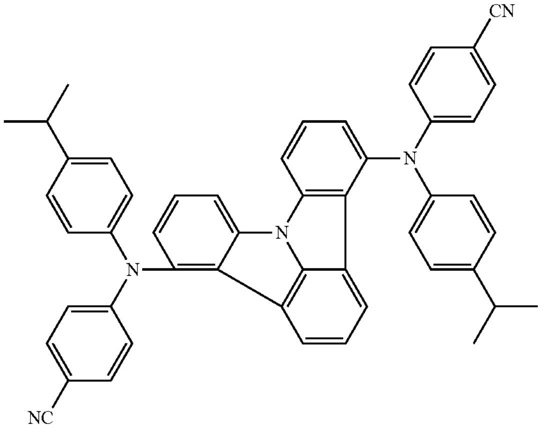

-continued
[Formula 327]
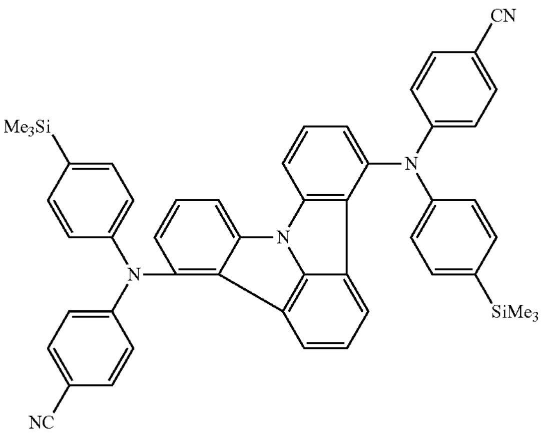
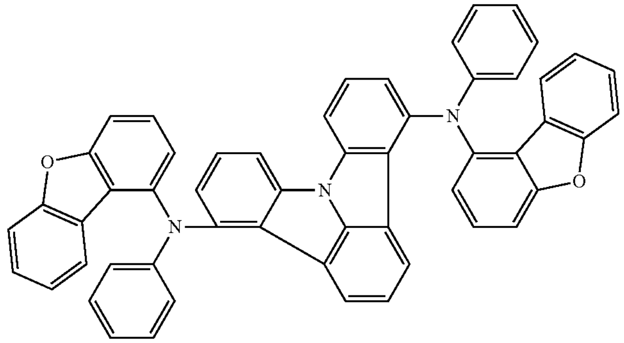
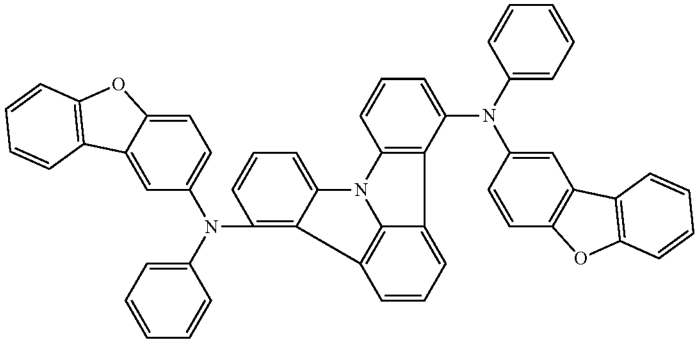
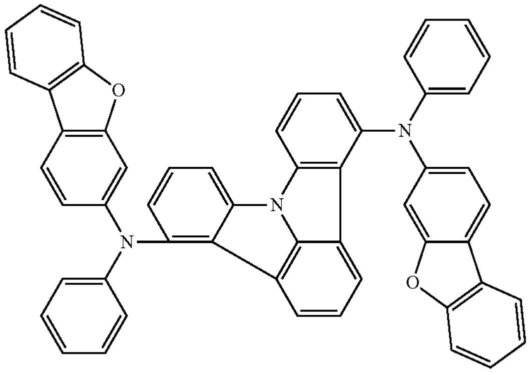

-continued
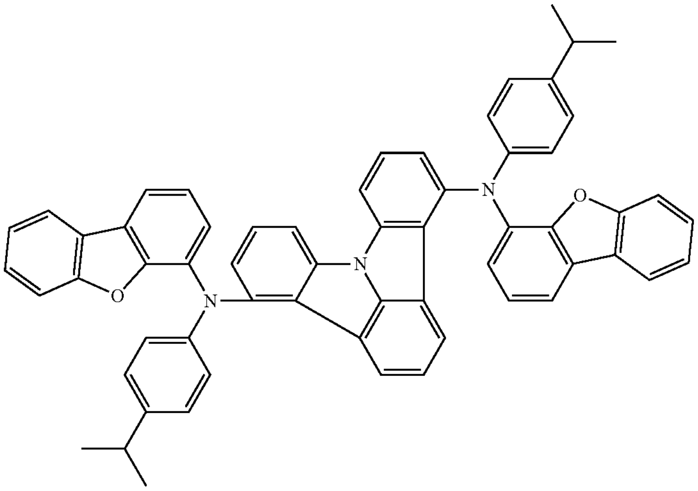
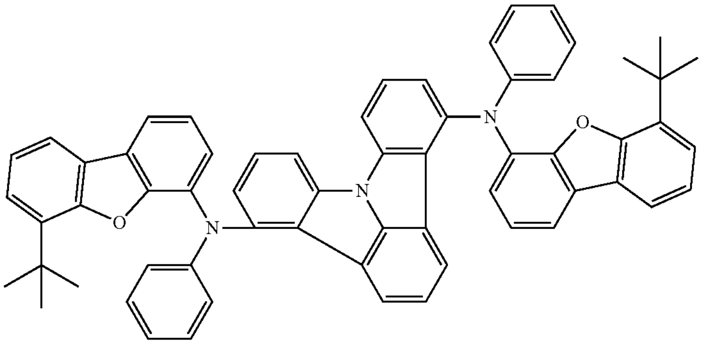
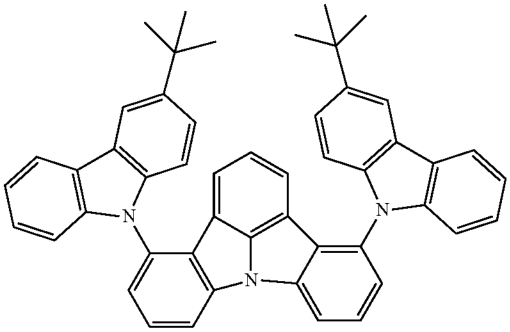
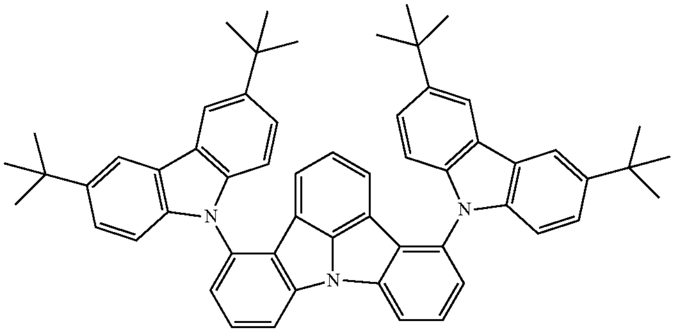

-continued
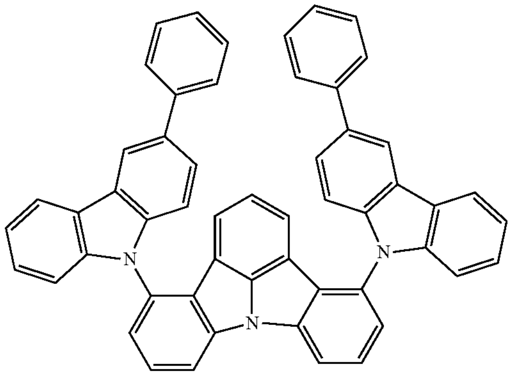
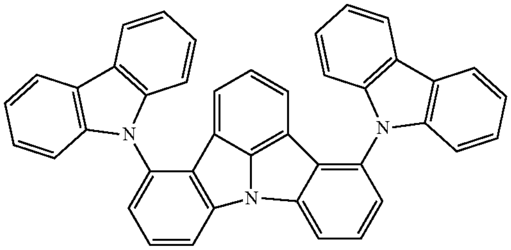
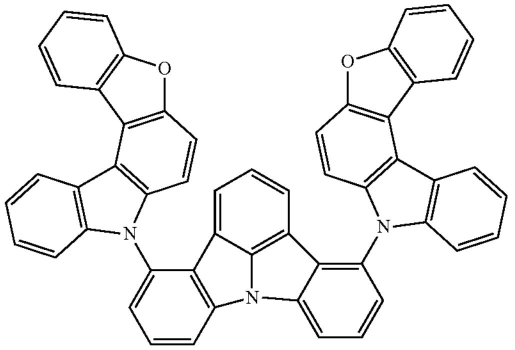
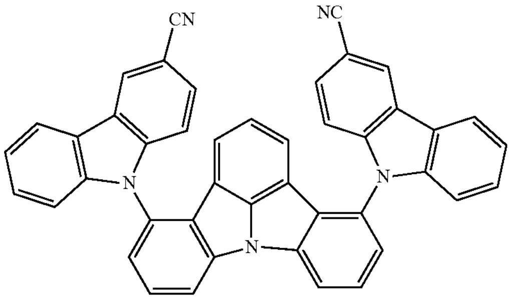
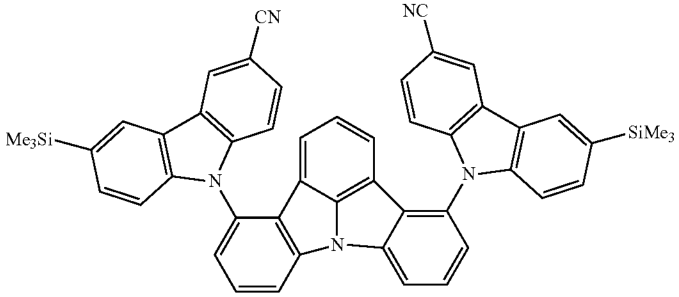
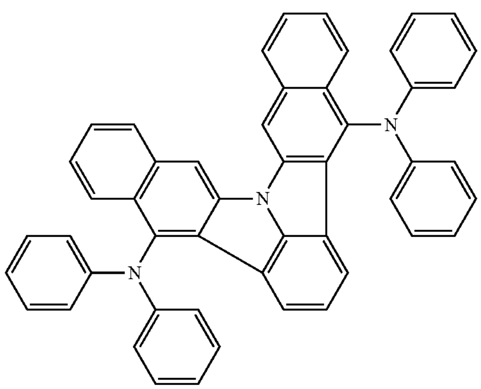
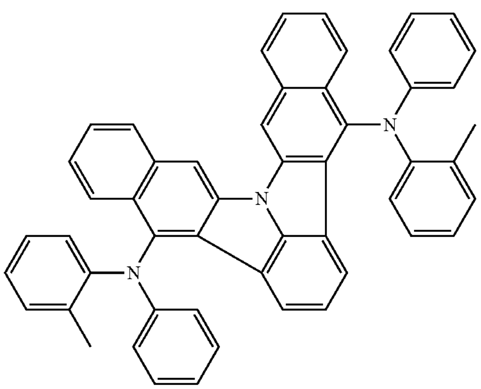

-continued
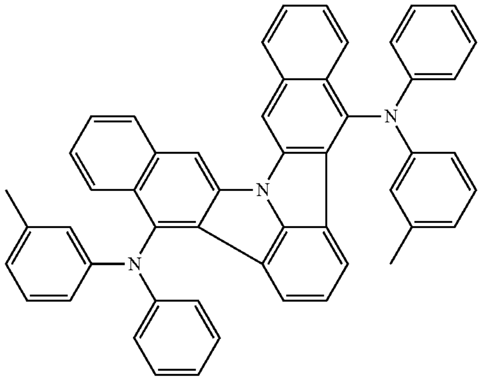
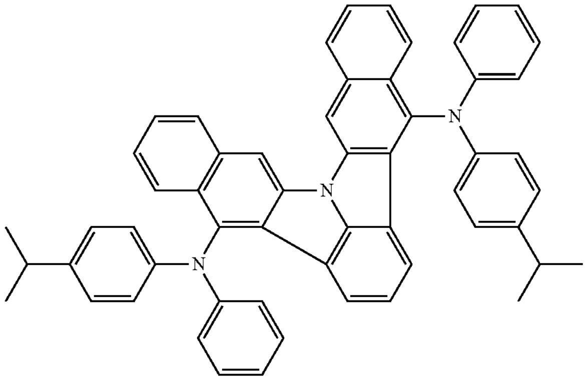
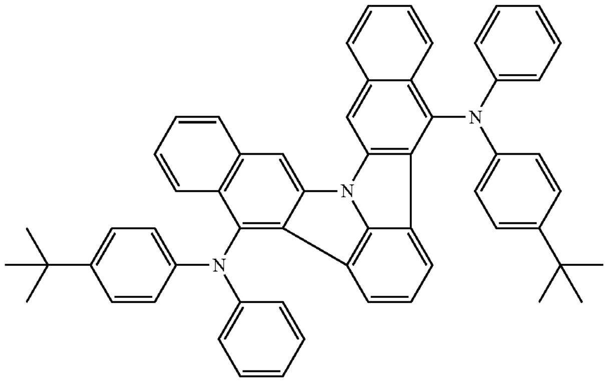
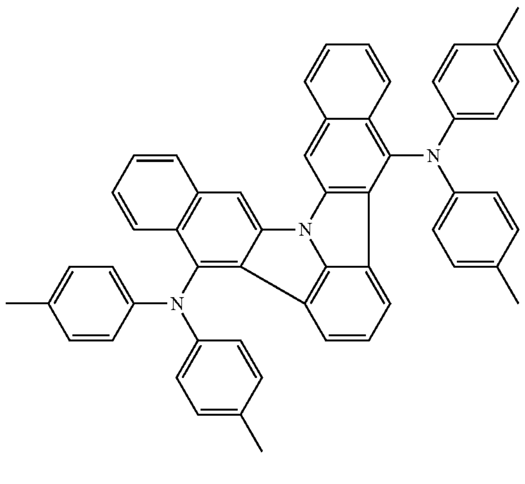
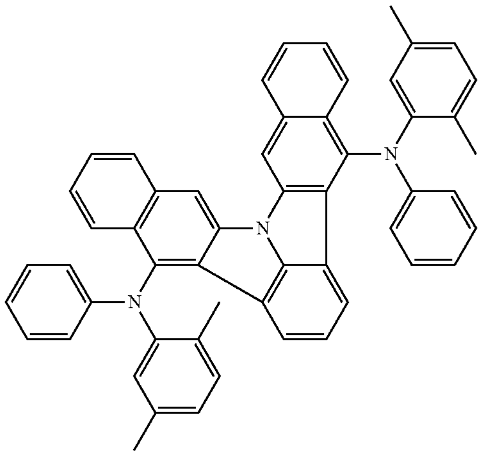

-continued
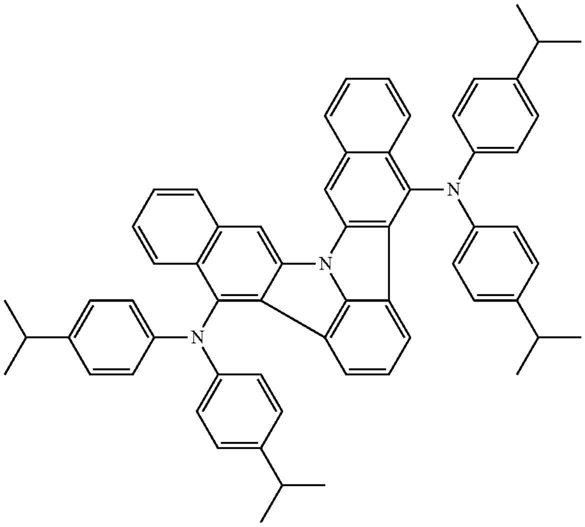
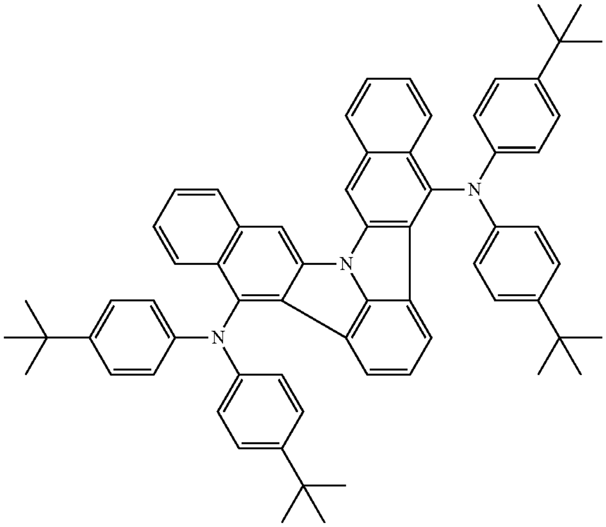
[Formula 328]
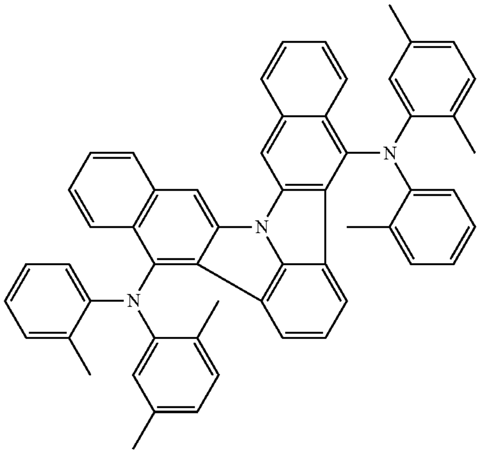
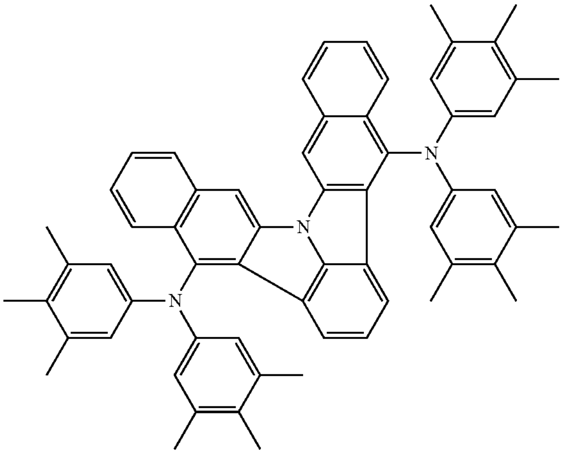

-continued
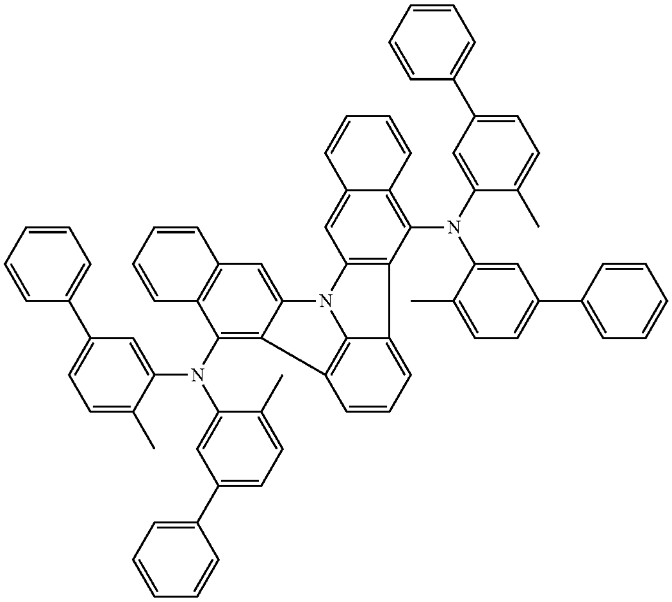
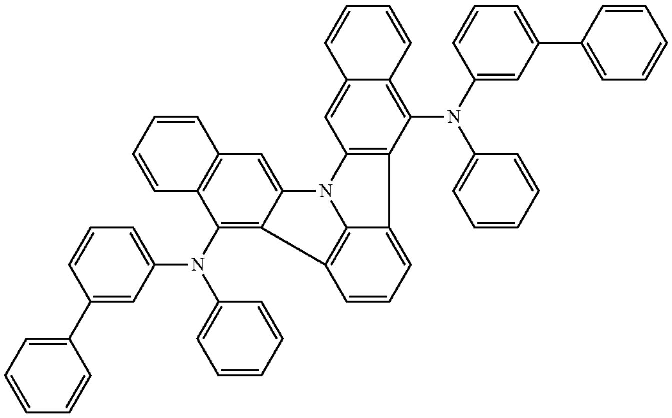
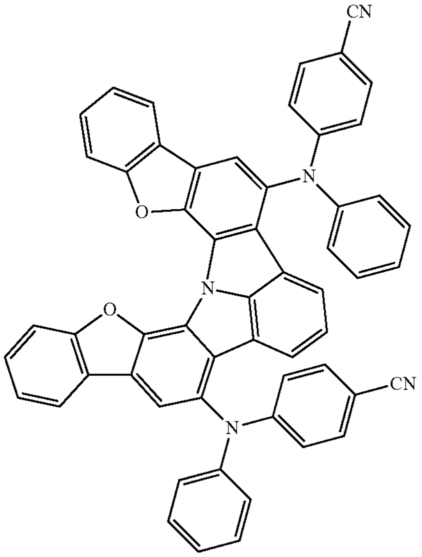

-continued
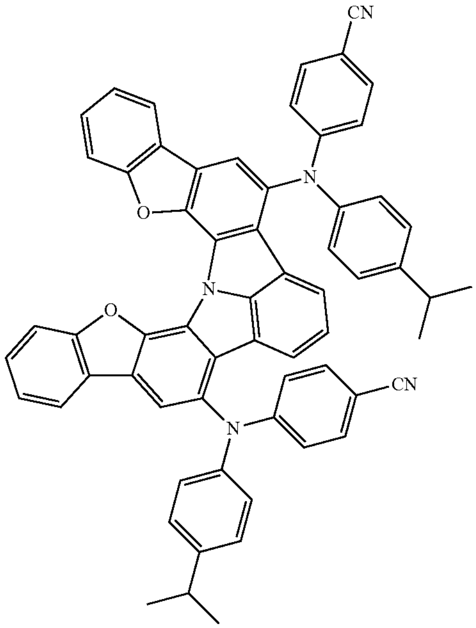
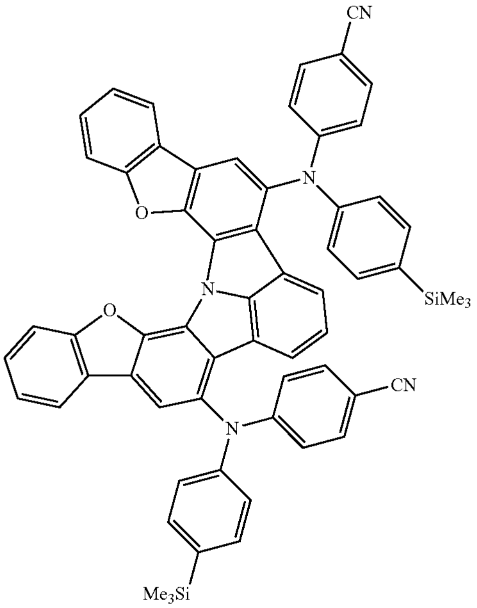
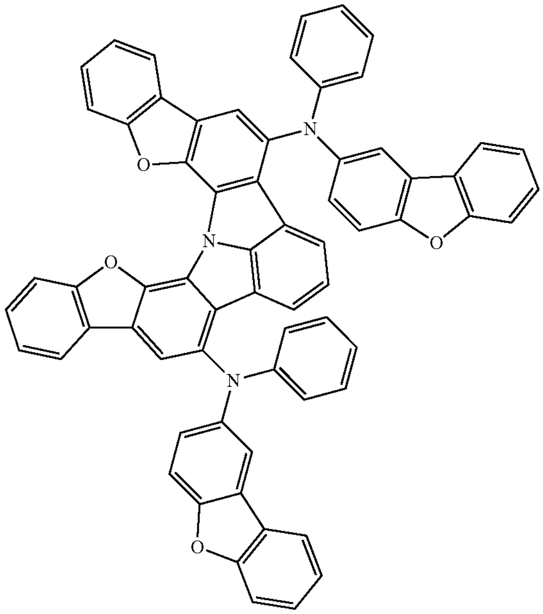
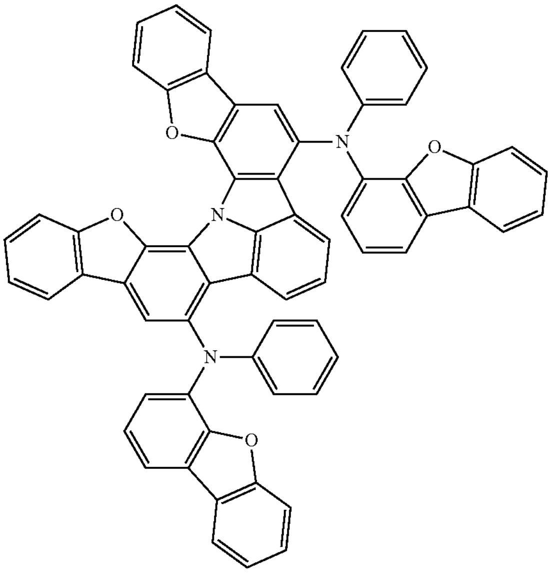

-continued
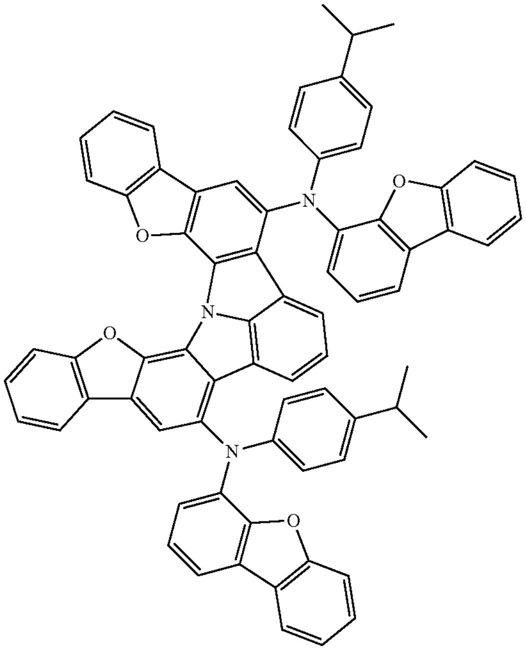
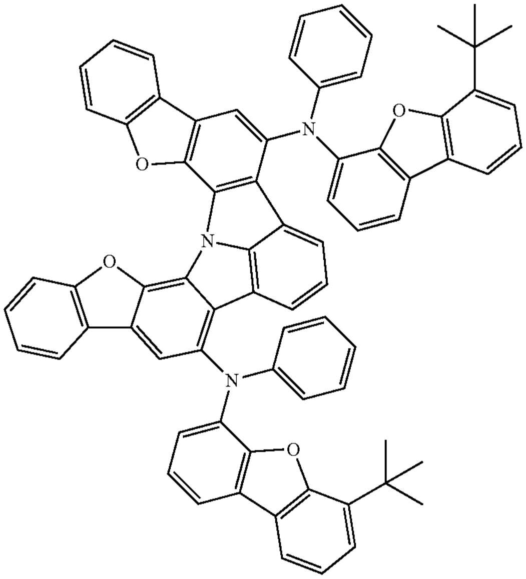
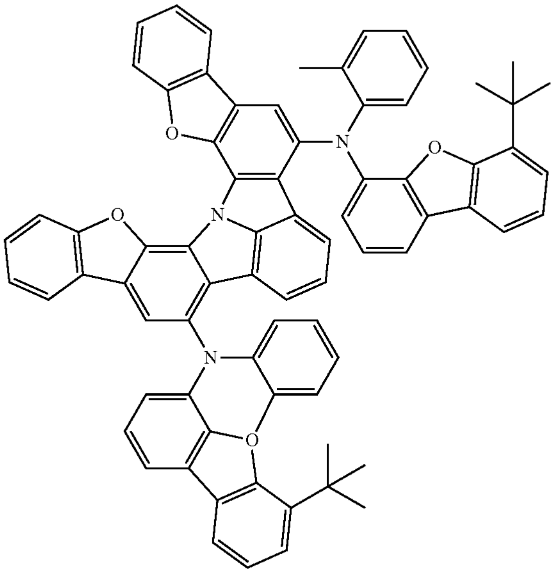
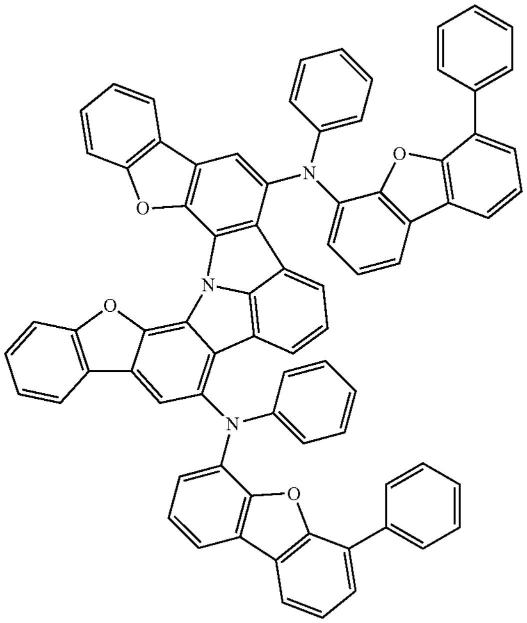

-continued
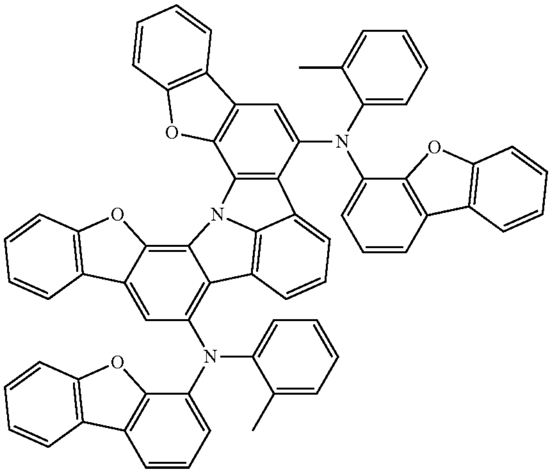
[Formula 329]
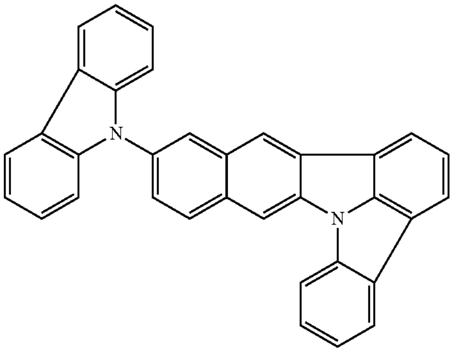
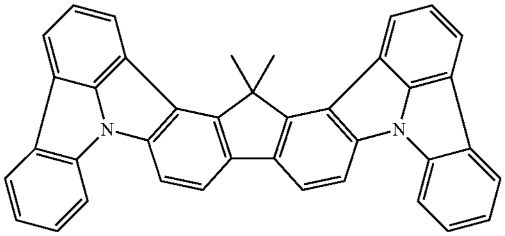
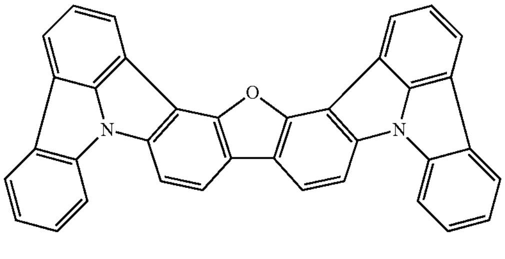
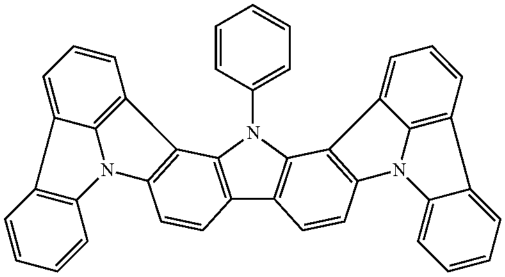
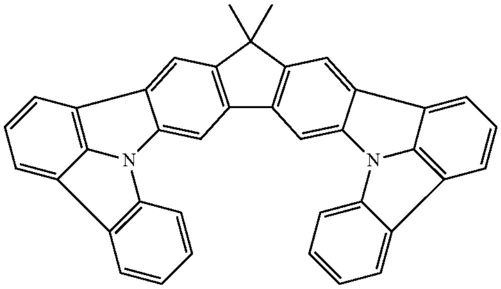
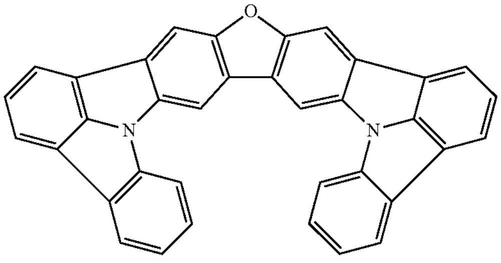

-continued
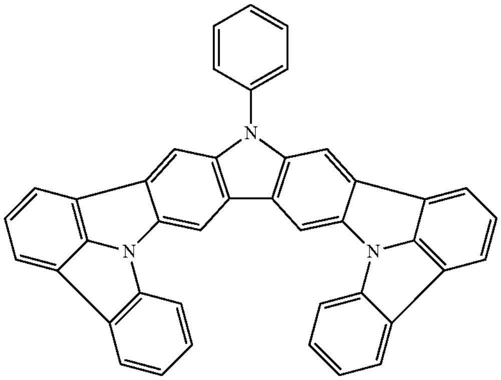
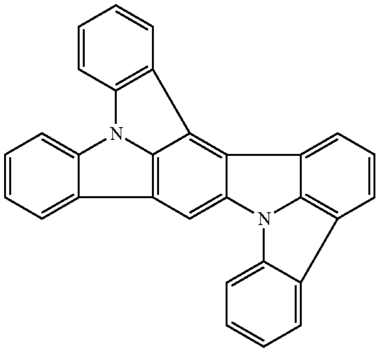
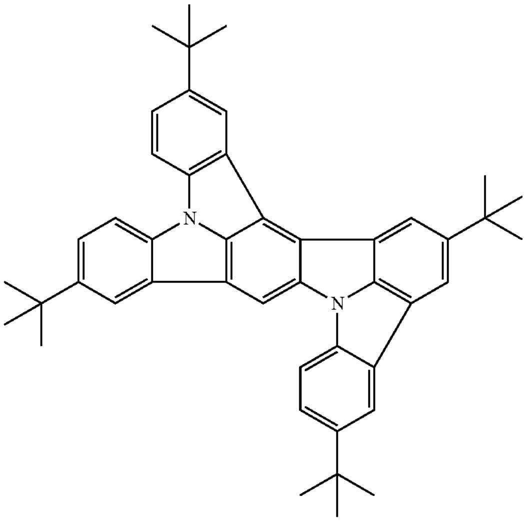
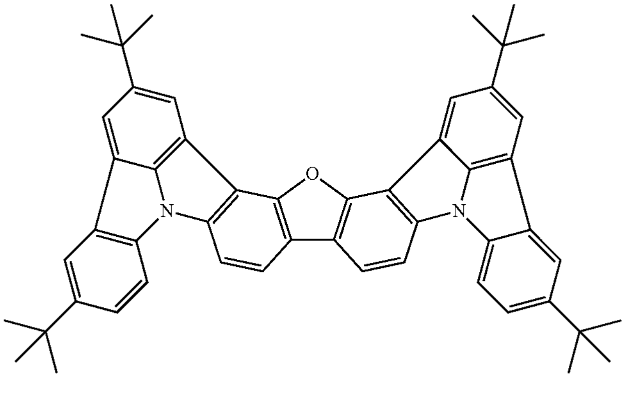 [SMILES: CC(C)(C)c1ccc2c(c1)c1cc(C(C)(C)C)cc3c4c5oc6c(ccc7c6c6cc(C(C)(C)C)cc8c9cc(C(C)(C)C)ccc9n7c86)c5ccc4n2c13]

Compound Represented by Formula (5)

The compound represented by the formula (5) will be described below. The compound represented by the formula (5) corresponds to the compound represented by the above-described formula (41-3).

[Formula 330]

(5)

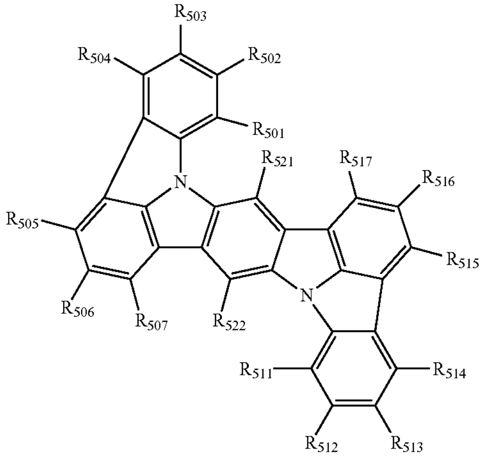

In the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$, and $R_{503}$.

In an exemplary embodiment, at least one, preferably two of $R_{501}$ to $R_{507}$ and $R_{511}$ to $R_{517}$ are groups represented by —N($R_{906}$)($R_{907}$).

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (52) below.

[Formula 331]

(52)

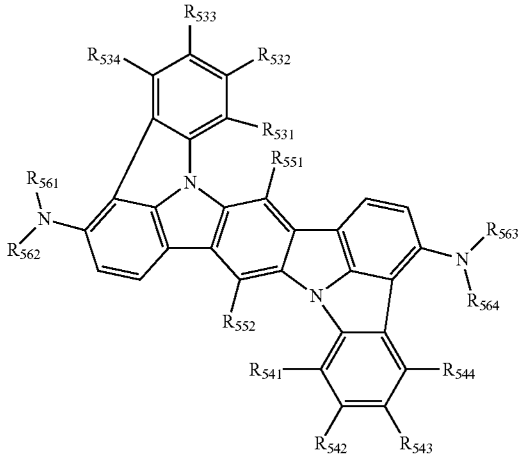

In the formula (52):

at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$ and $R_{541}$ to $R_{544}$ not forming the monocyclic ring and not forming the fused ring, and $R_{551}$ to $R_{552}$ are each independently a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (53) below.

[Formula 332]

(53)

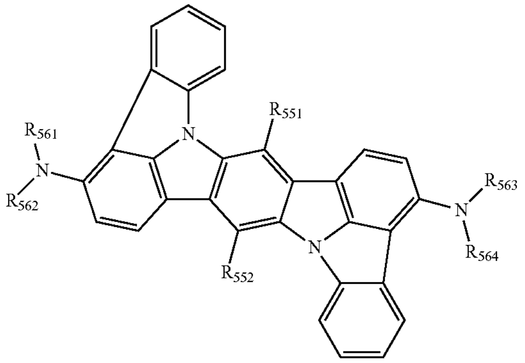

In the formula (53), $R_{551}$, $R_{552}$ and $R_{561}$ to $R_{564}$ each independently represent the same as $R_{551}$, $R_{552}$ and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5), and $R_{551}$ and $R_{552}$ in the formulae (52) and (53) are each a hydrogen atom.

In an exemplary embodiment, a substituent for the "substituted or unsubstituted" group in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

Specific examples of the compound represented by the formula (5) include compounds shown below.

[Formula 333]

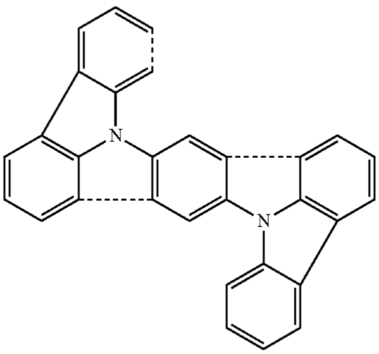

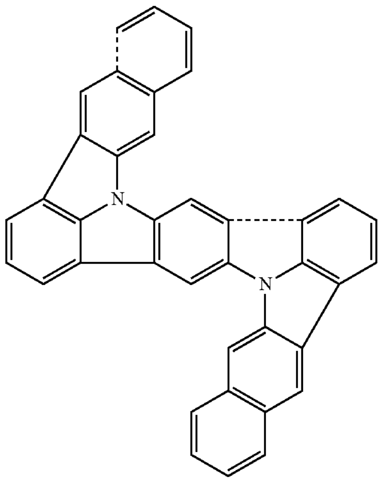

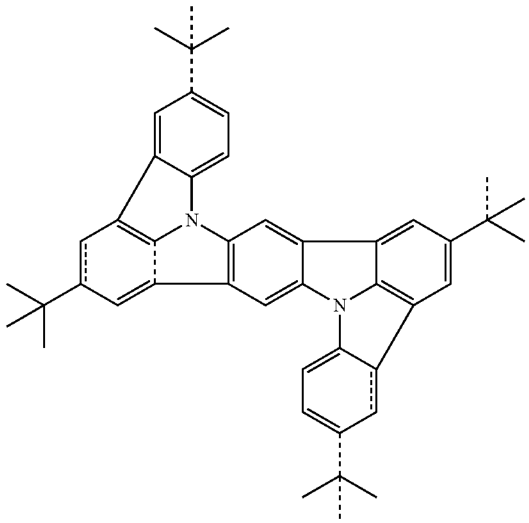

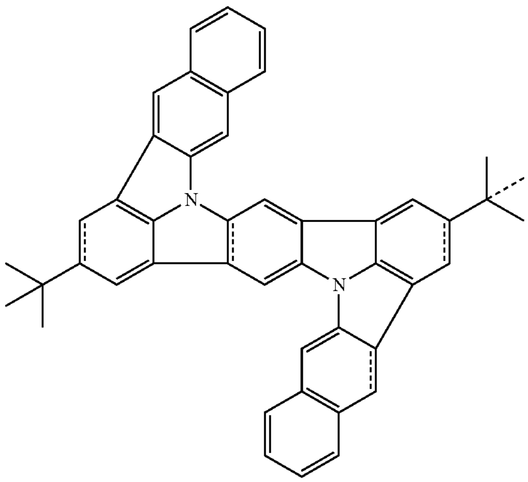

-continued
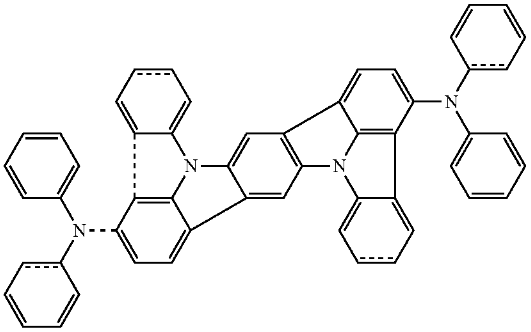
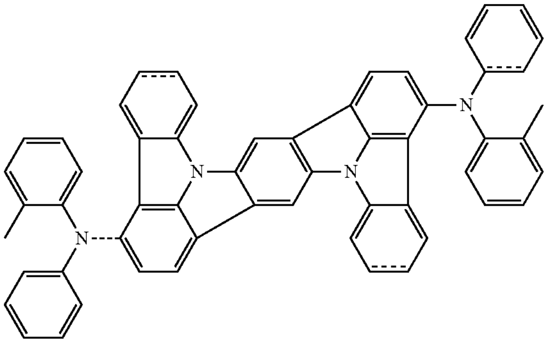
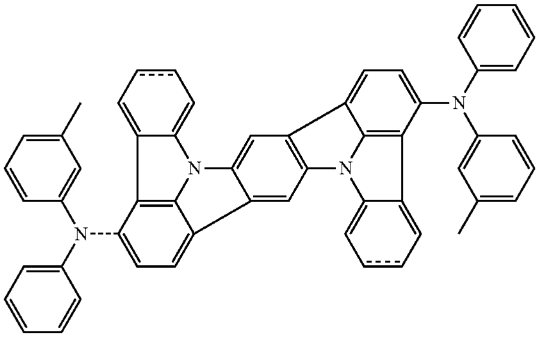
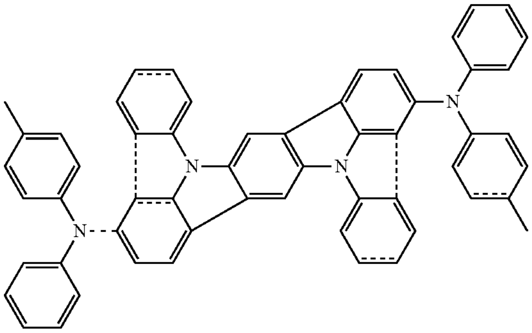
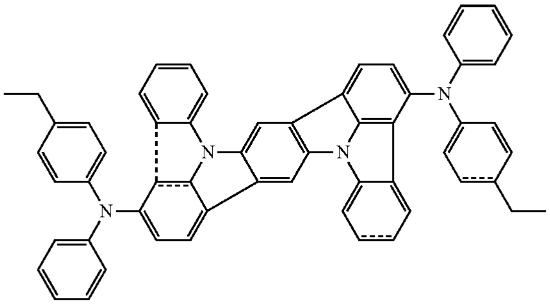
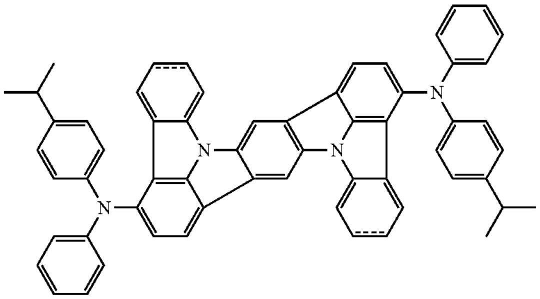
[Formula 334]
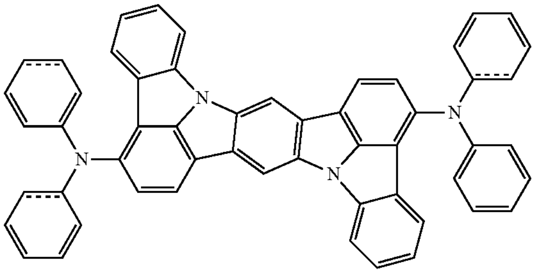
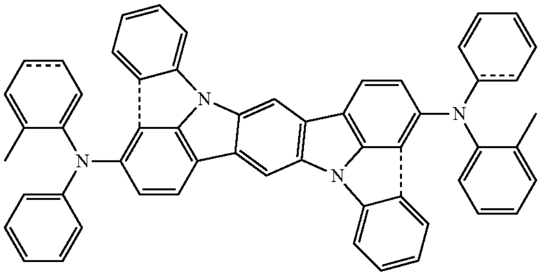
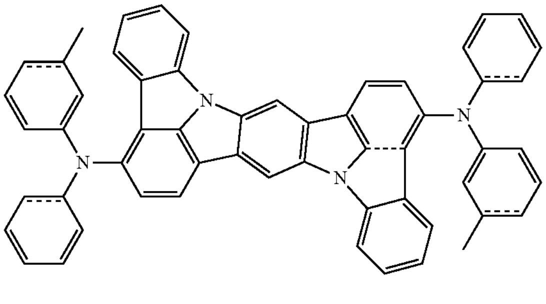
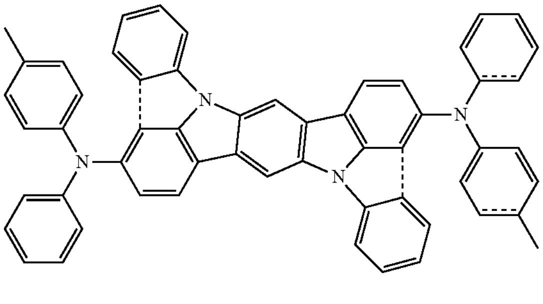

-continued
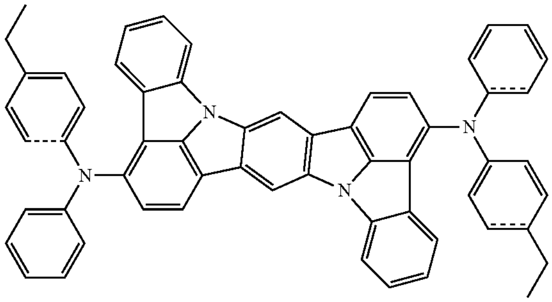
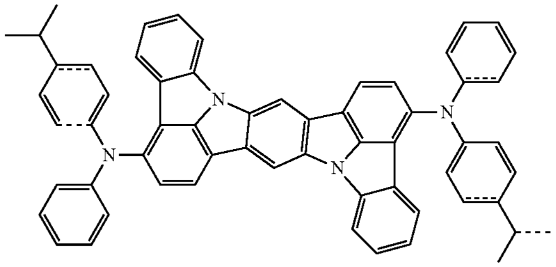
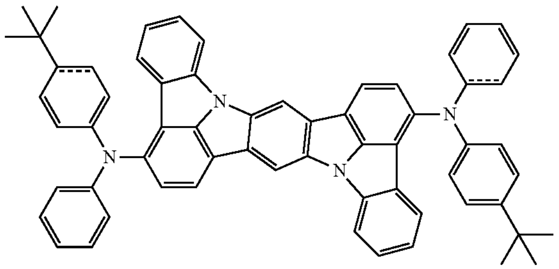
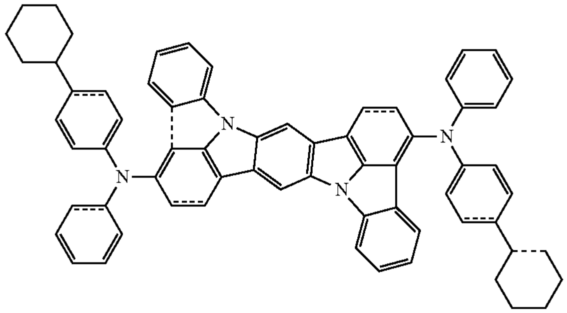
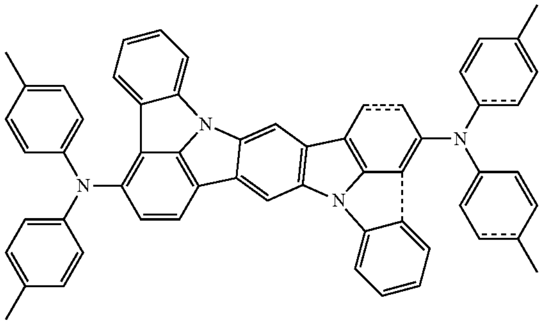
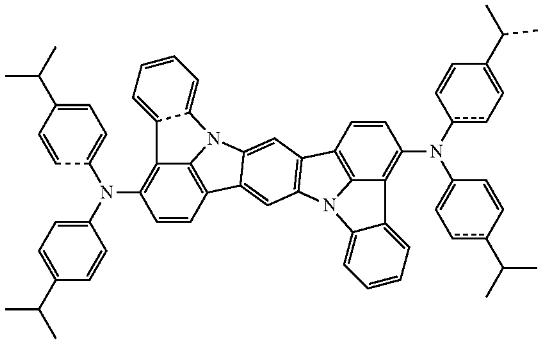
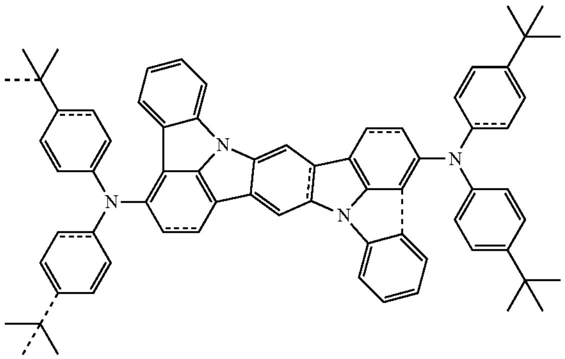
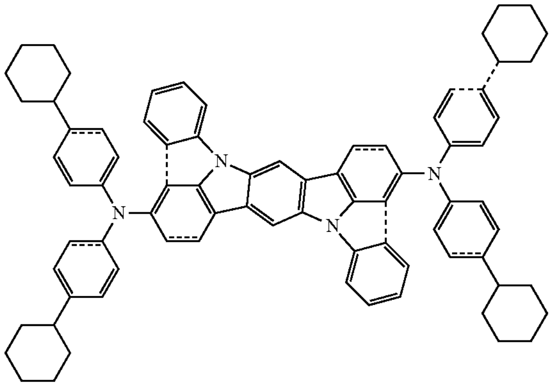
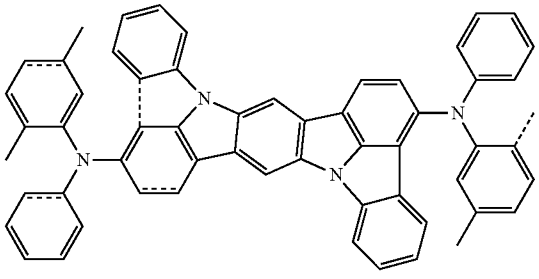
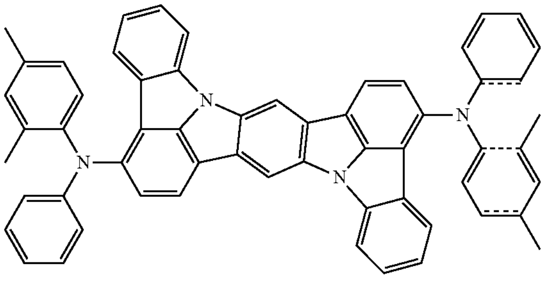

-continued
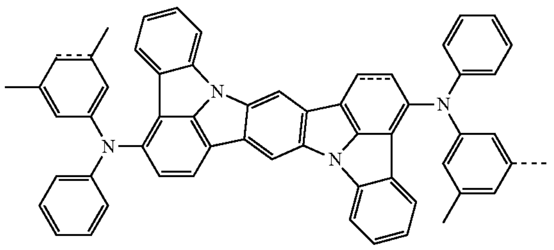
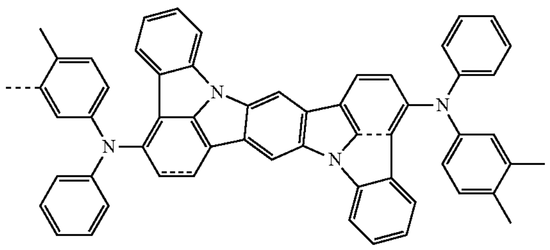
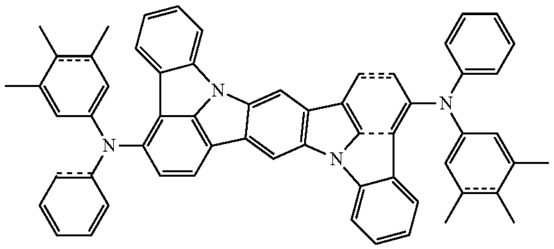
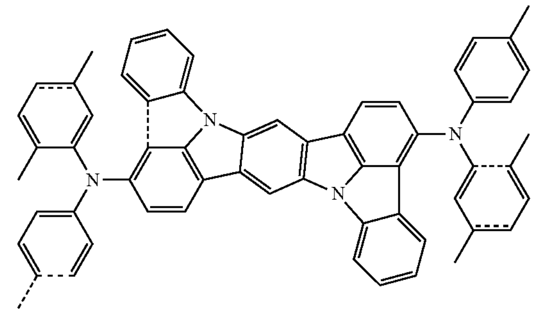
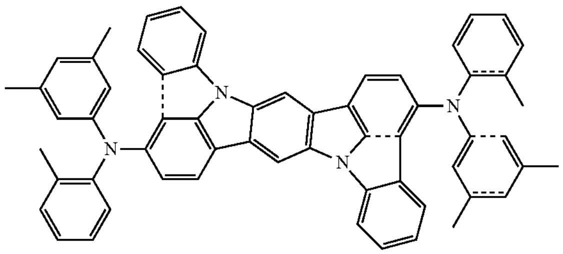
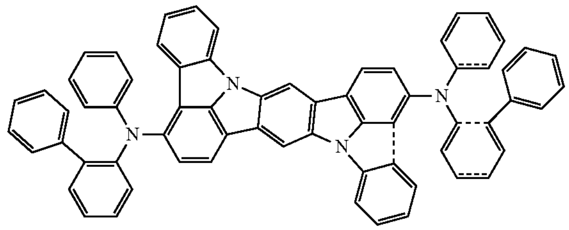
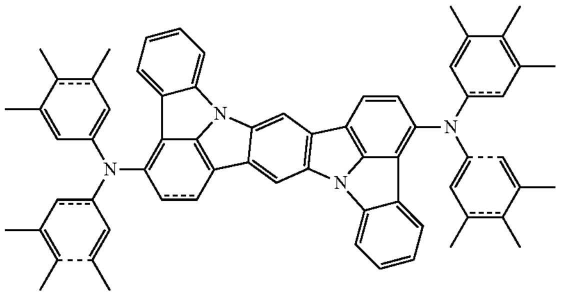
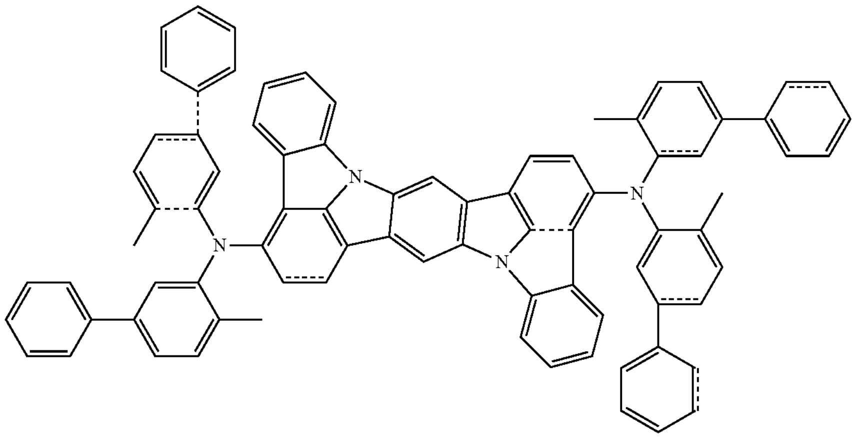

-continued
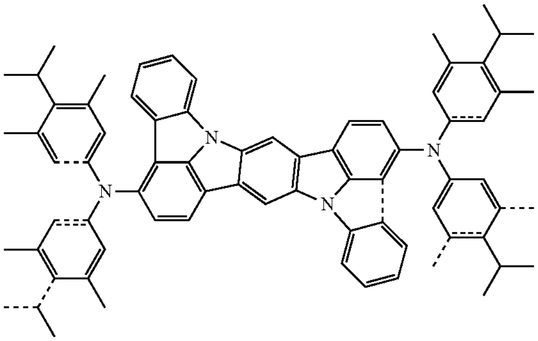
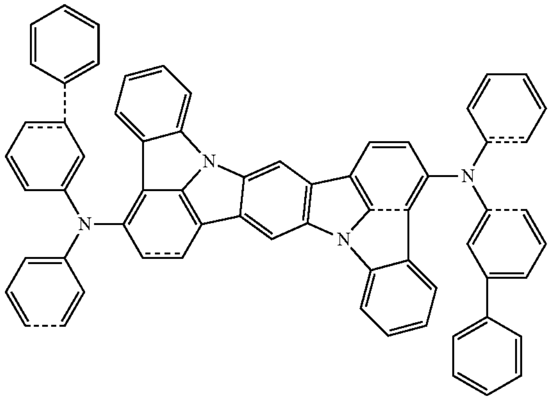
[Formula 335]
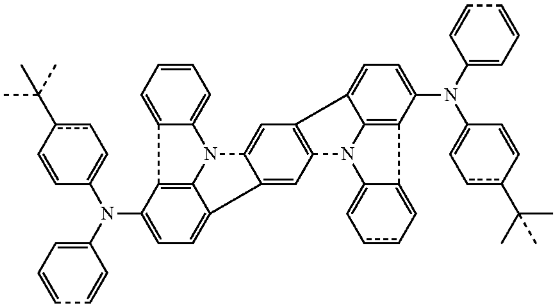
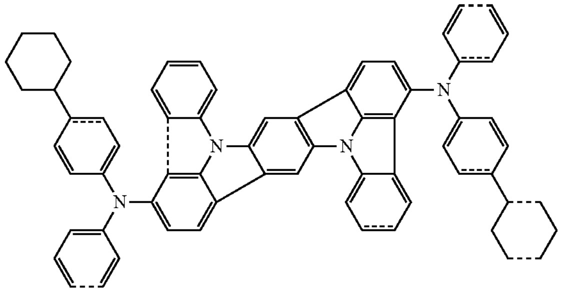
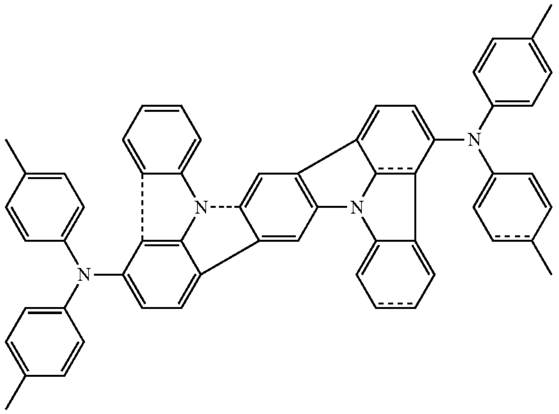
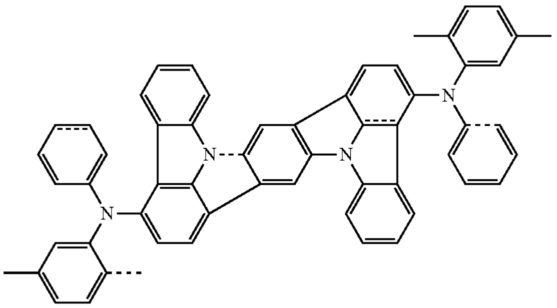
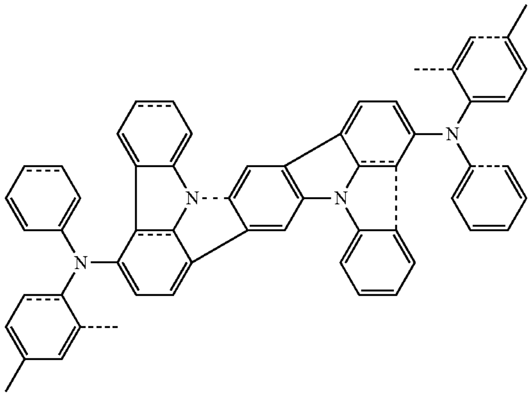
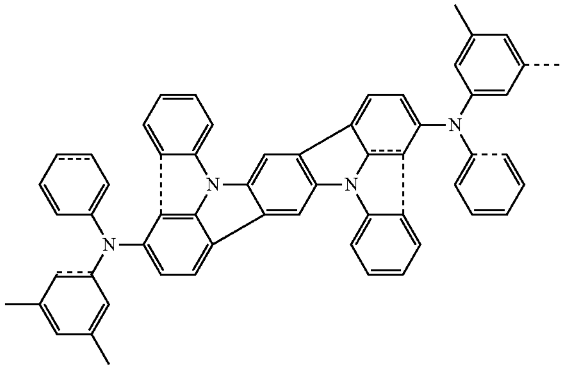

-continued
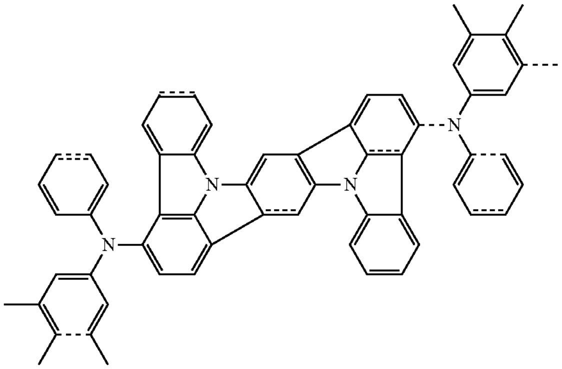
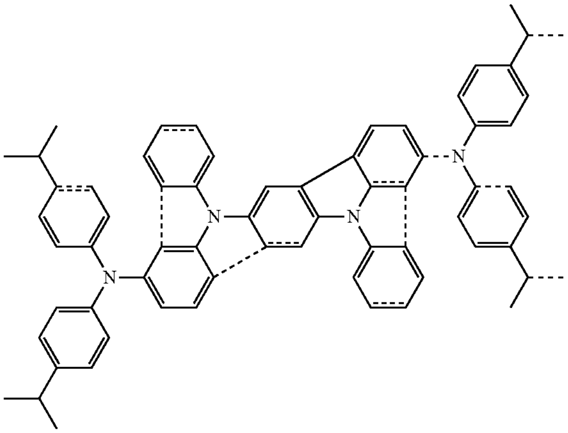
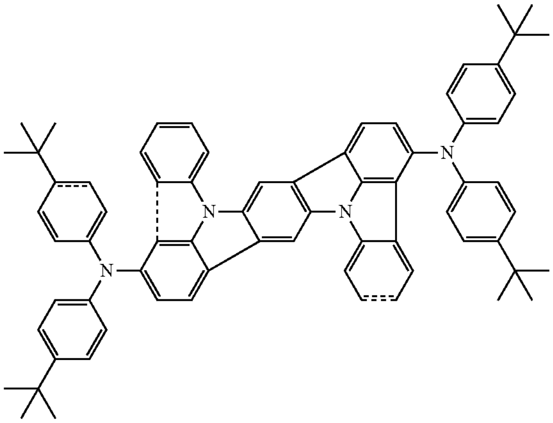
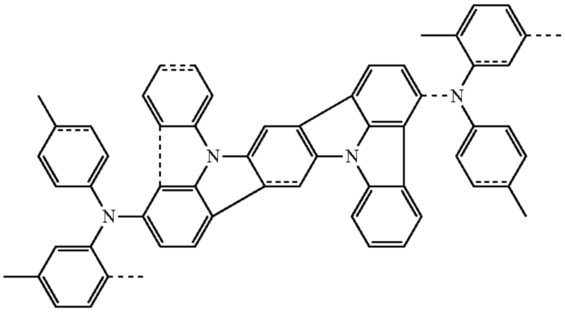
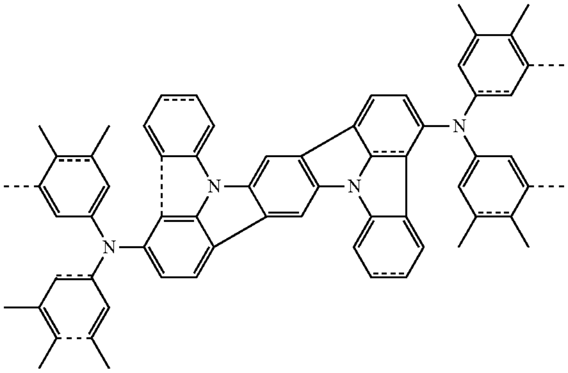
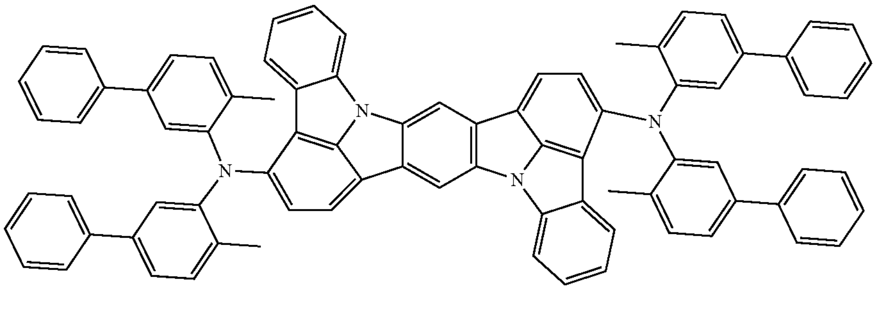

-continued
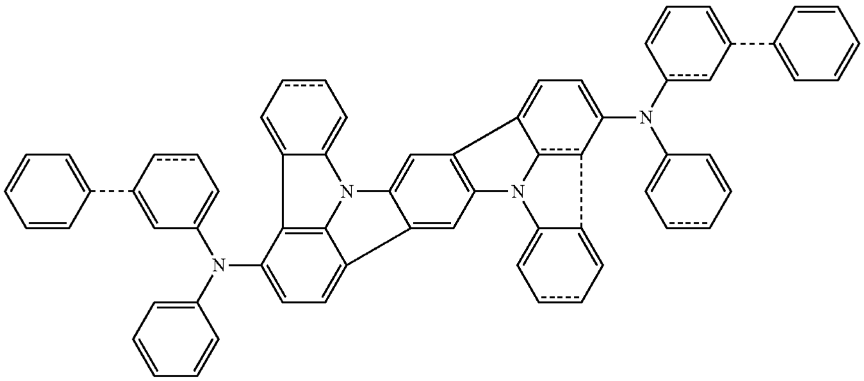
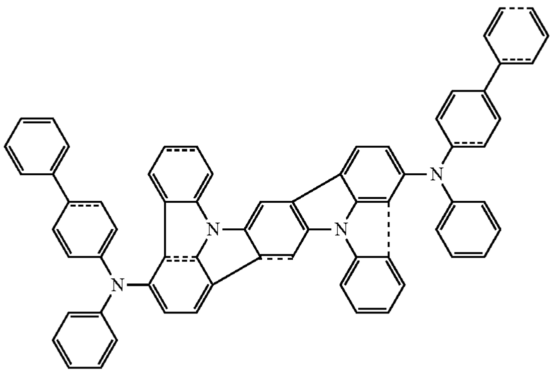
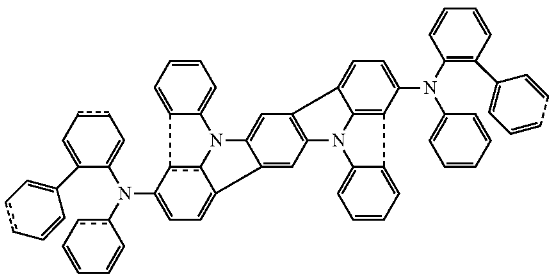
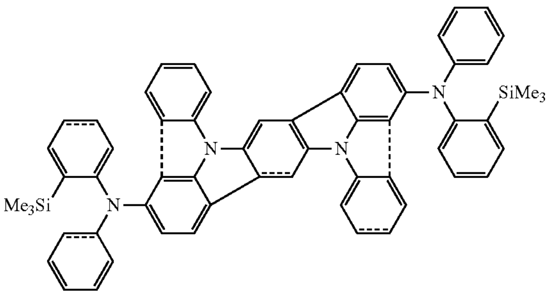
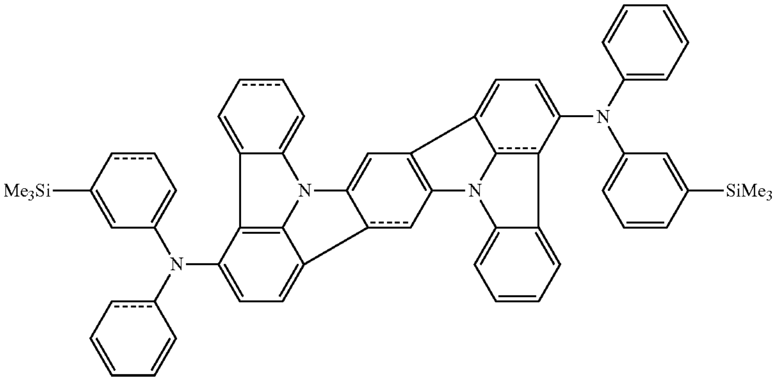

-continued
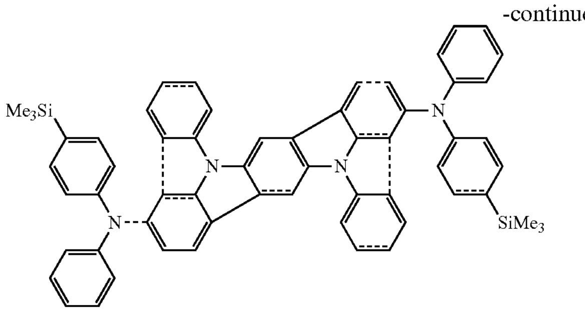
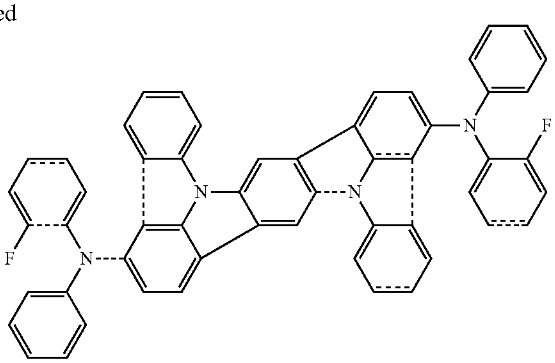
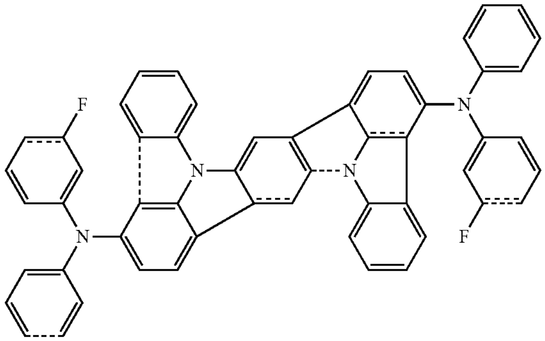
[Formula 336]
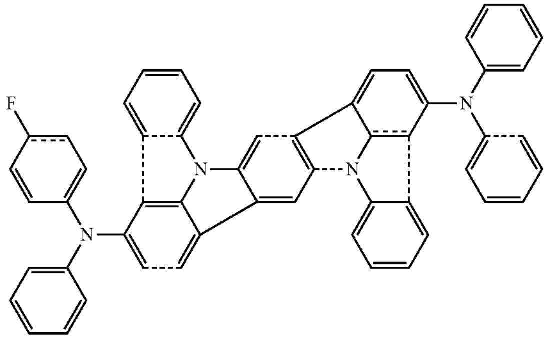
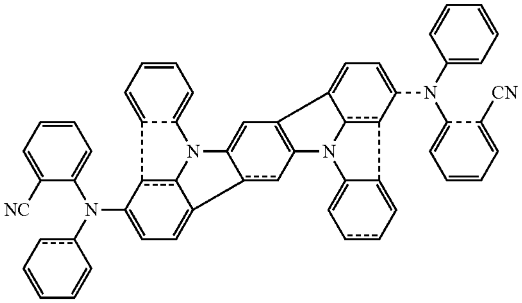
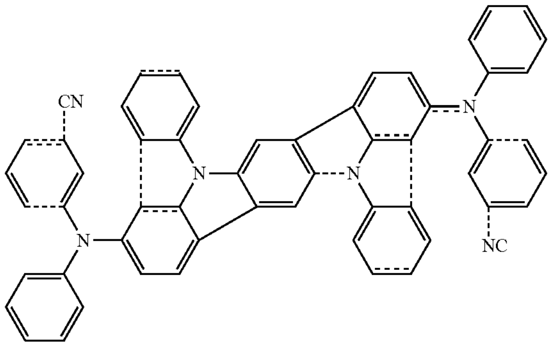
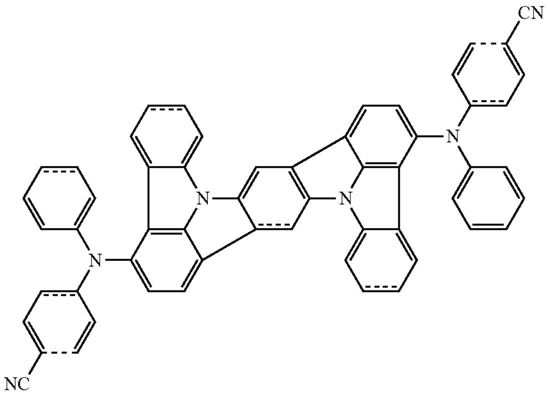

-continued
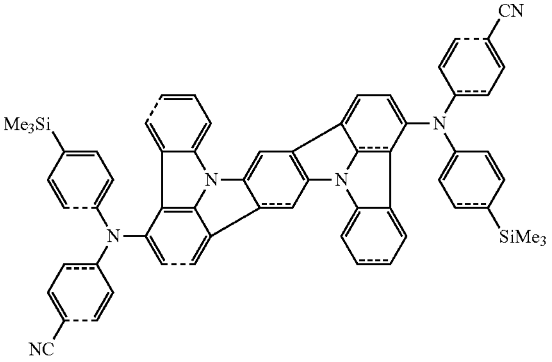
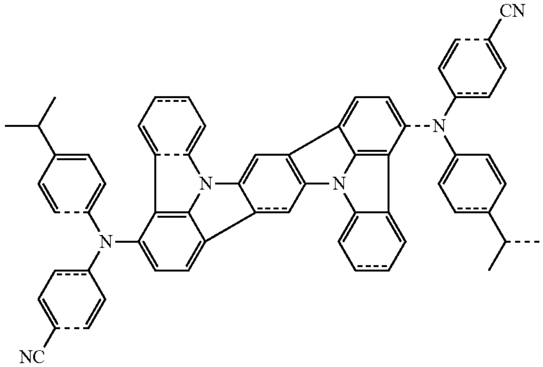
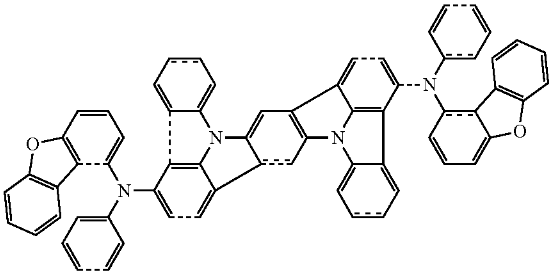
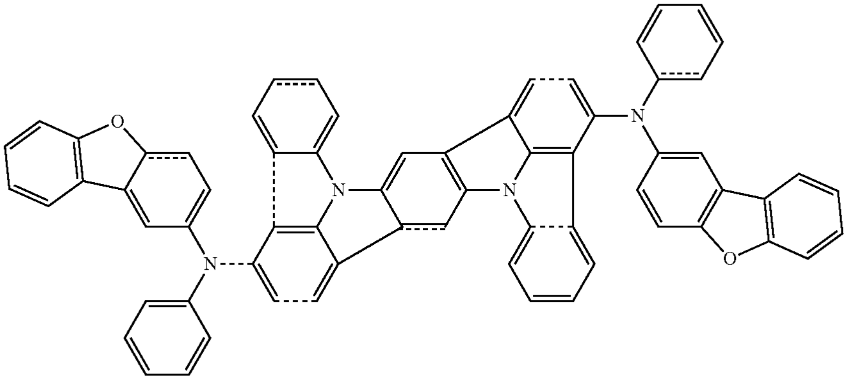
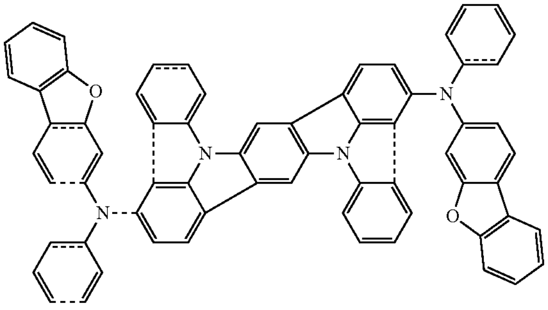
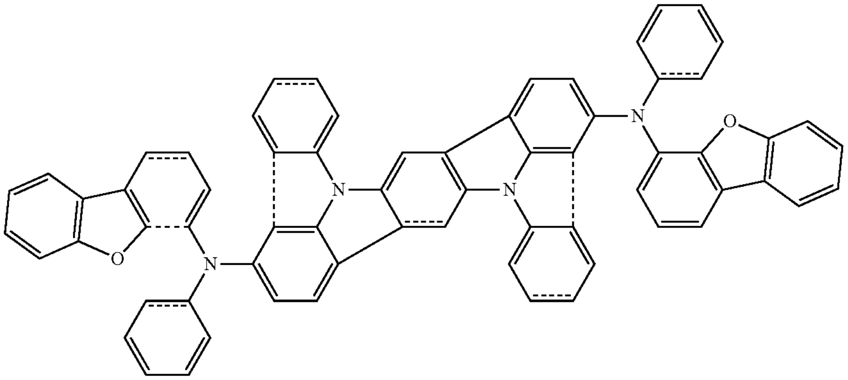

-continued
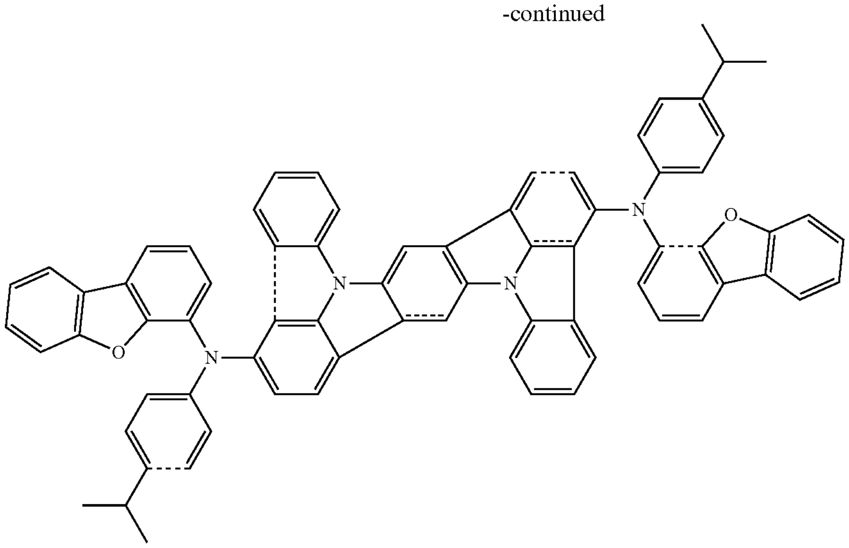
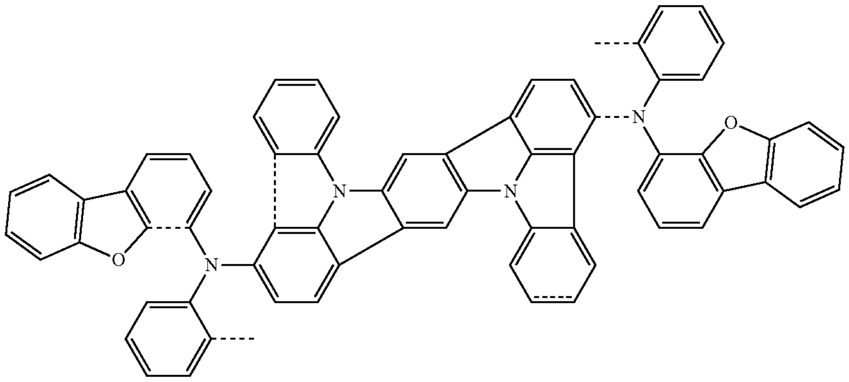
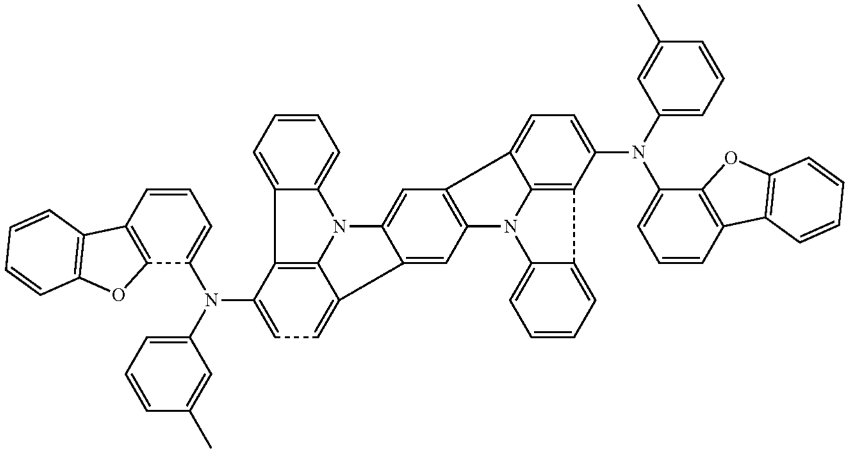

-continued
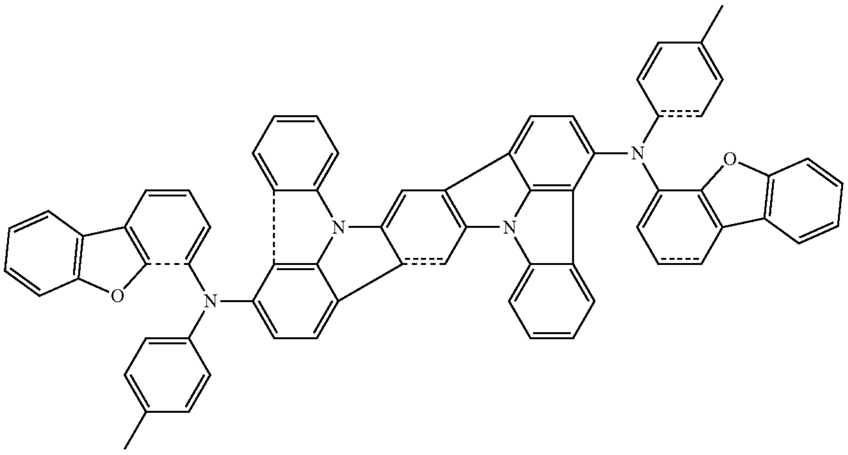
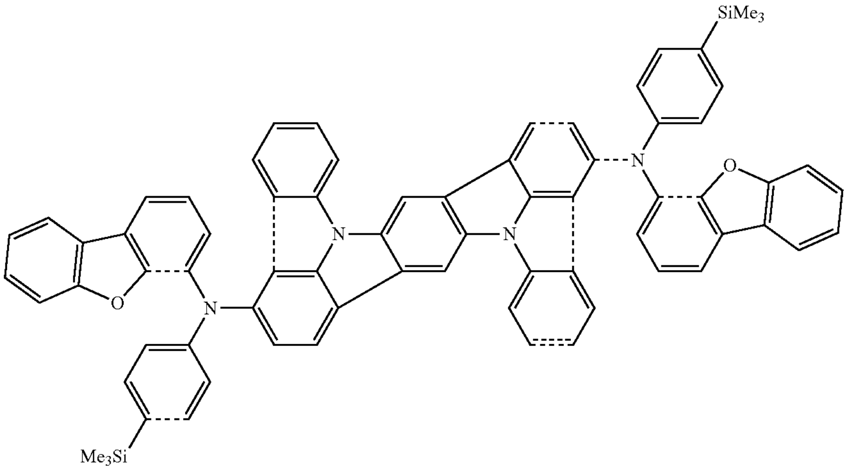
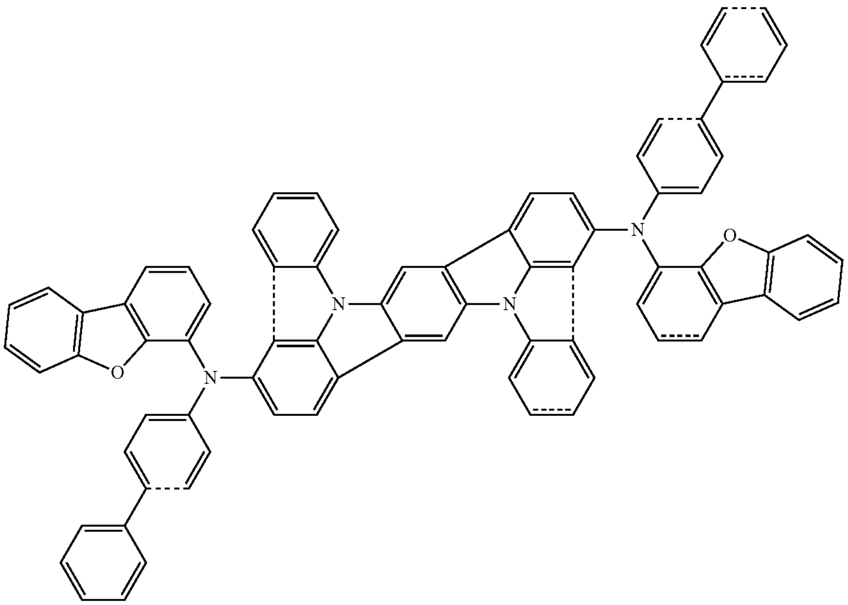

-continued
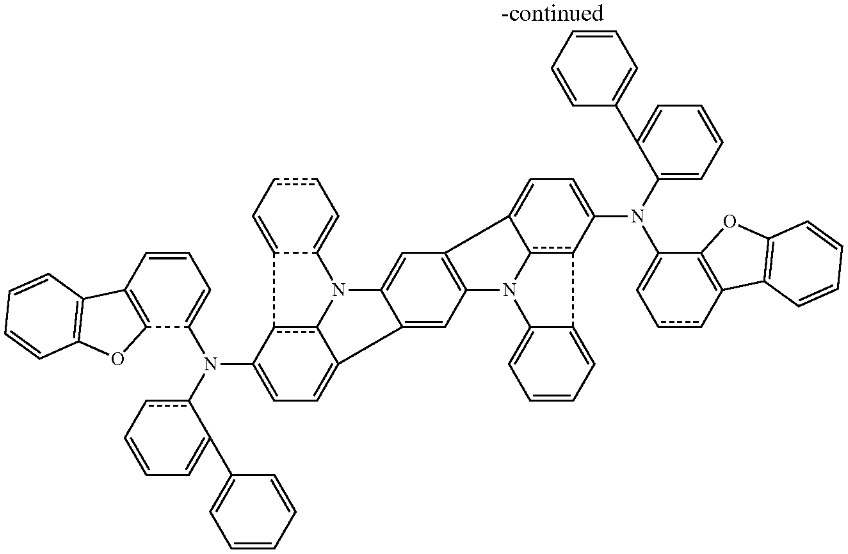
[Formula 337]
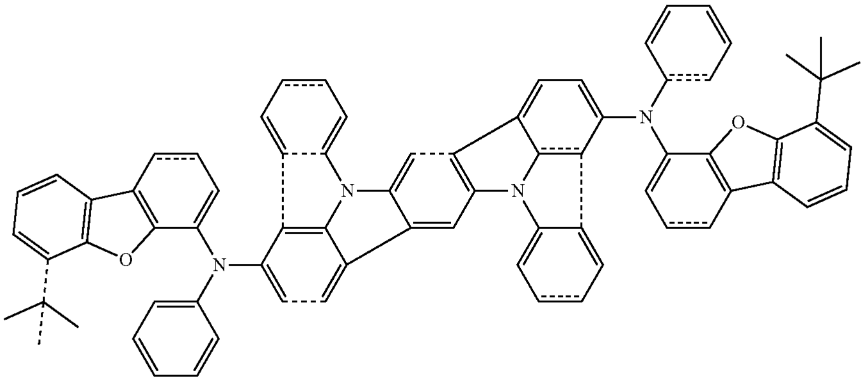
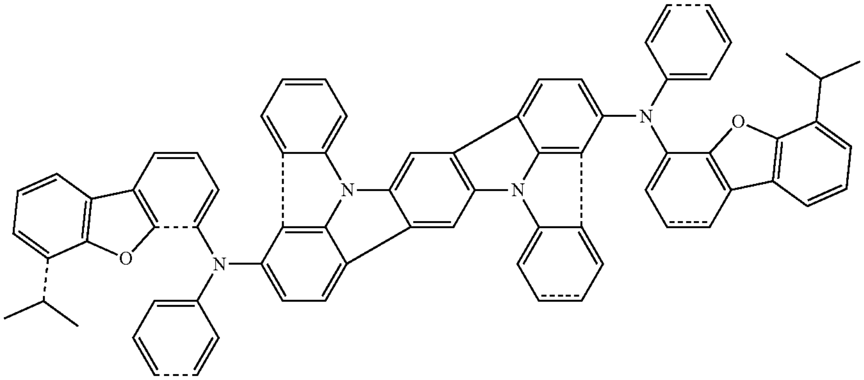
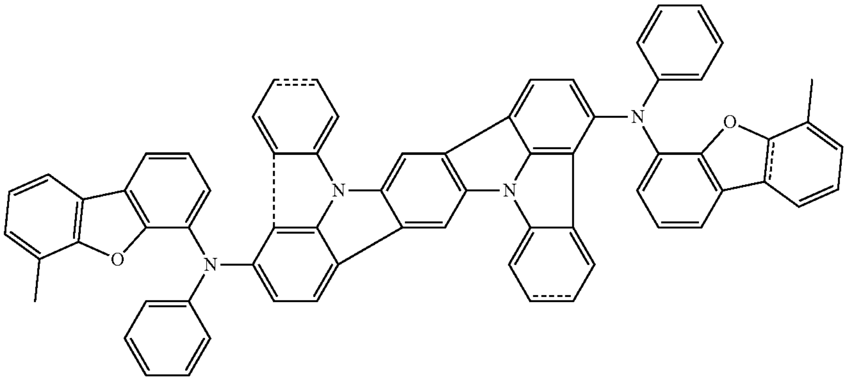

-continued
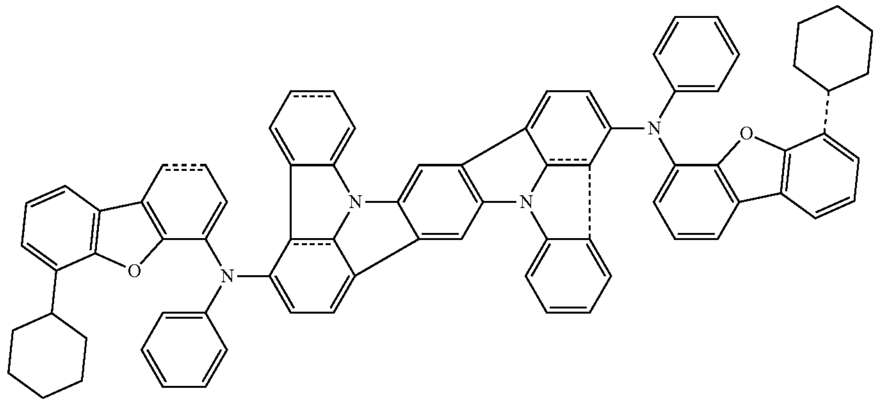
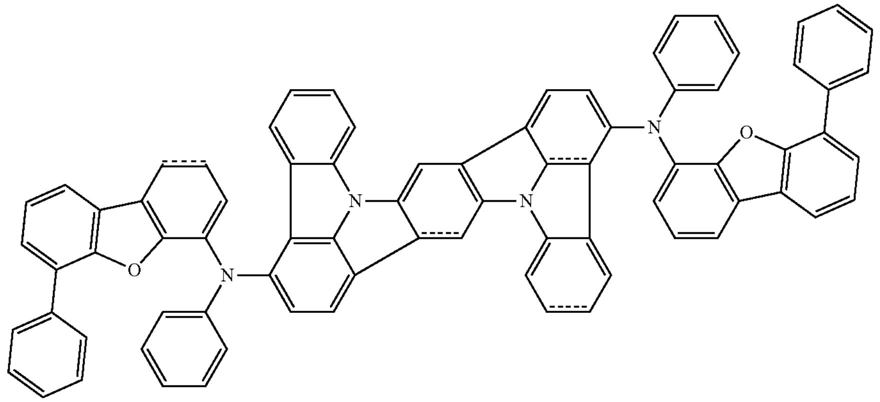
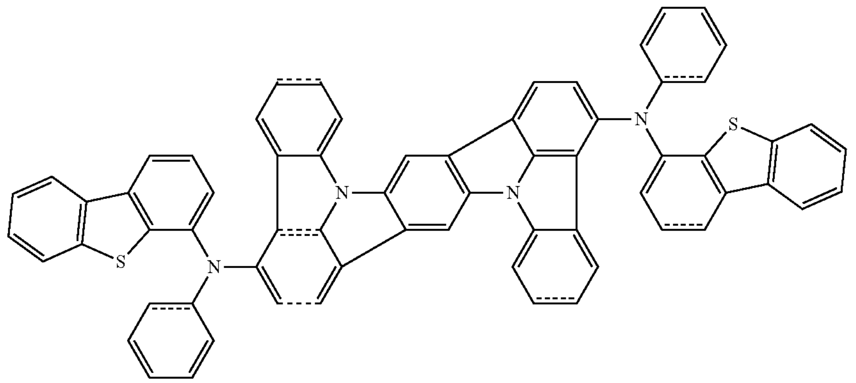

-continued
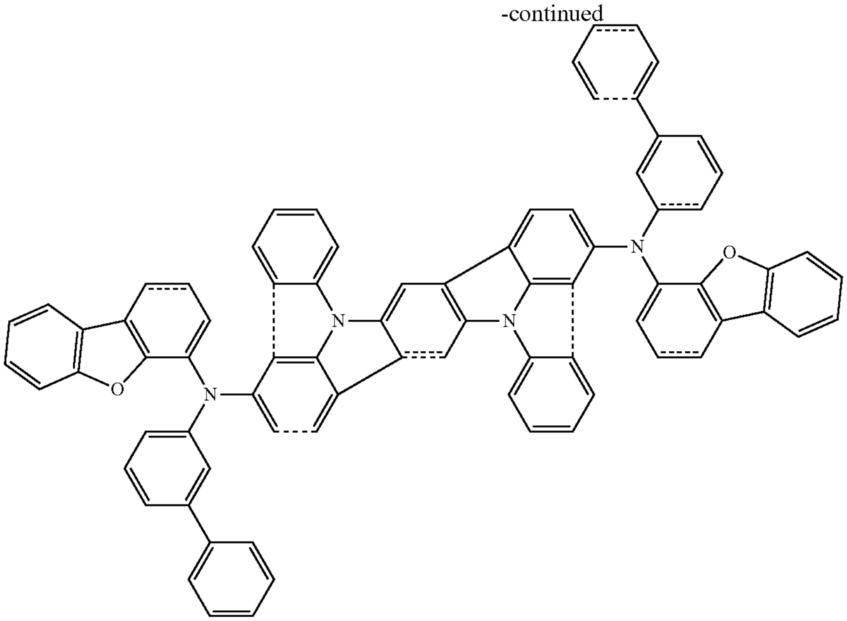
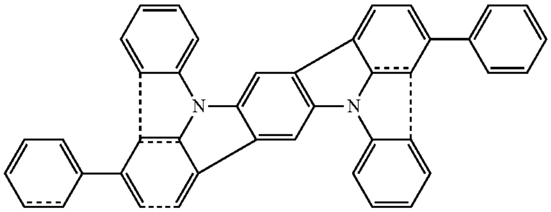
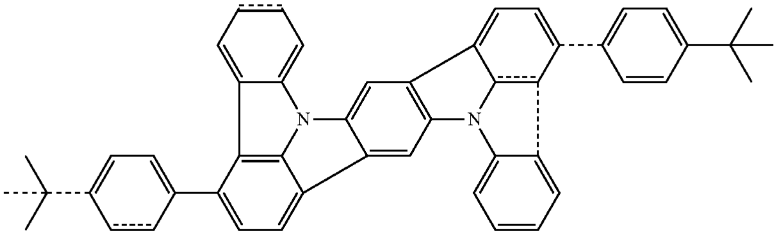
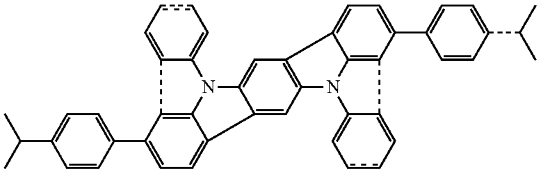
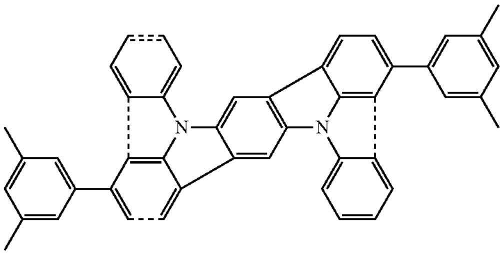
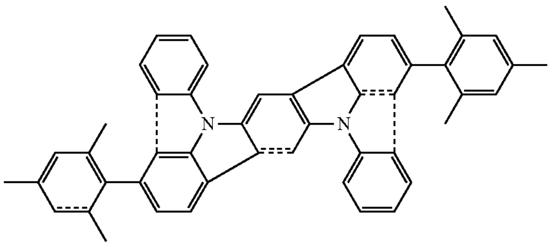

-continued
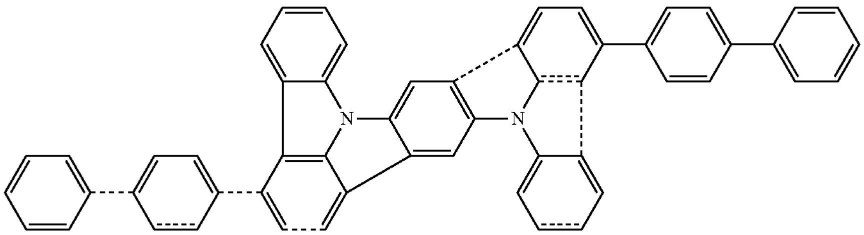
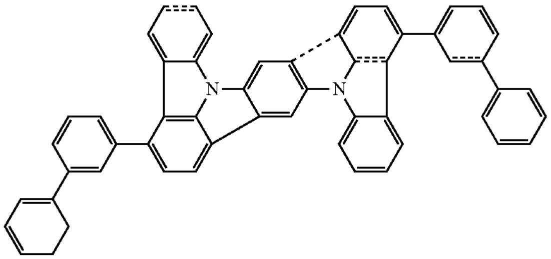
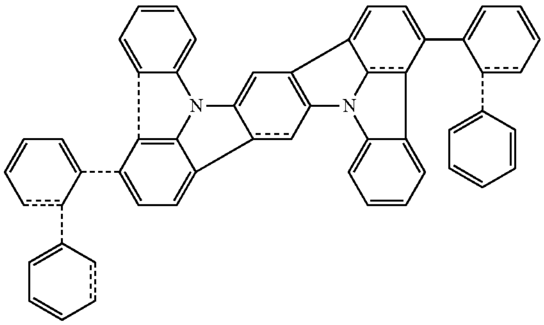
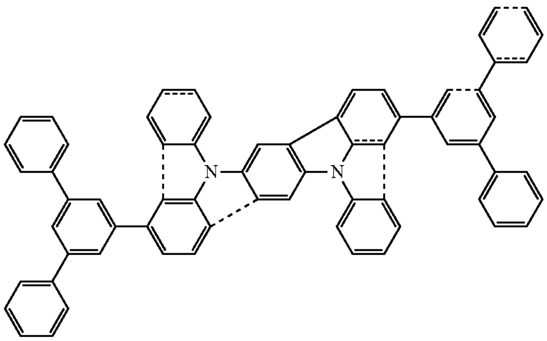
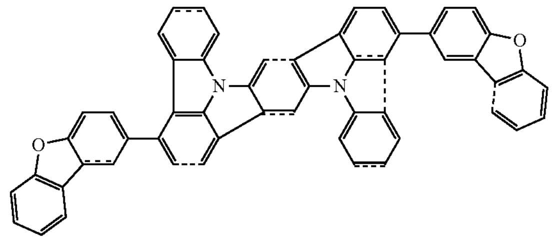
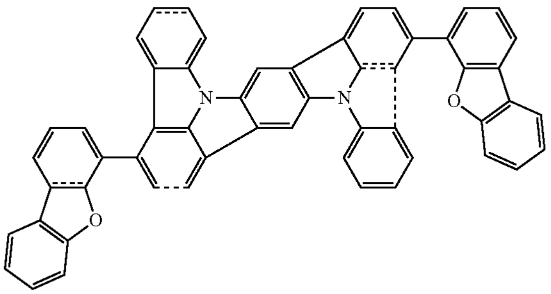
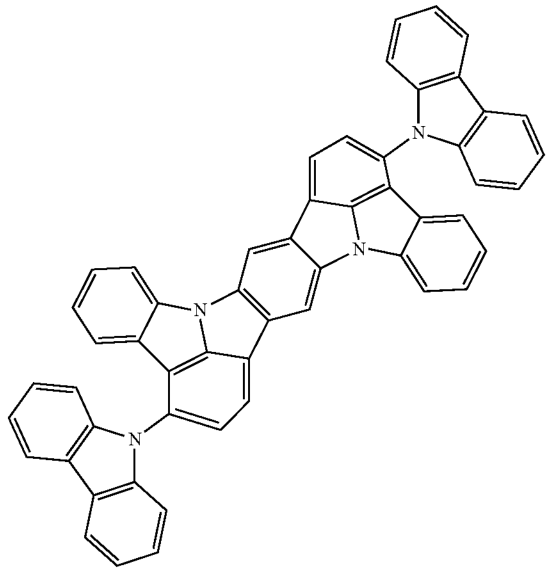

-continued
[Formula 338]
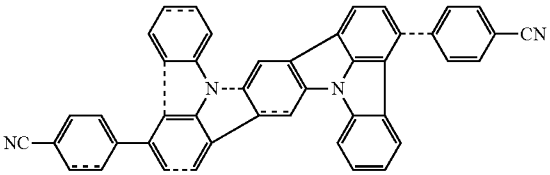
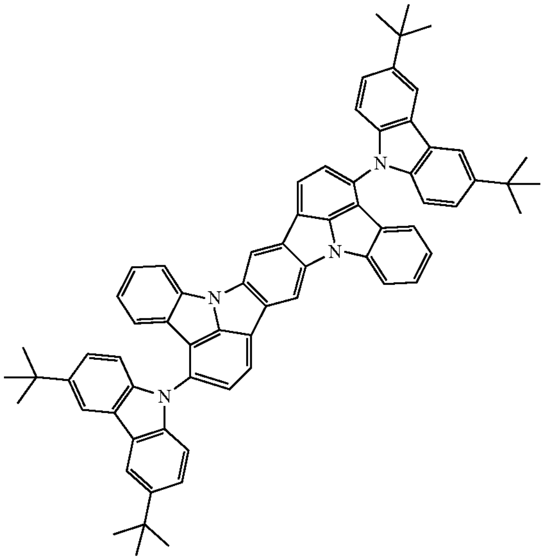
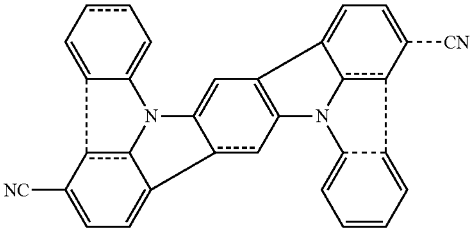
[Formula 339]
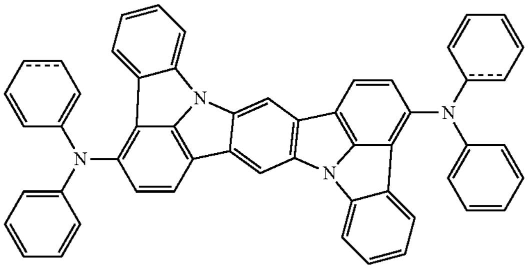
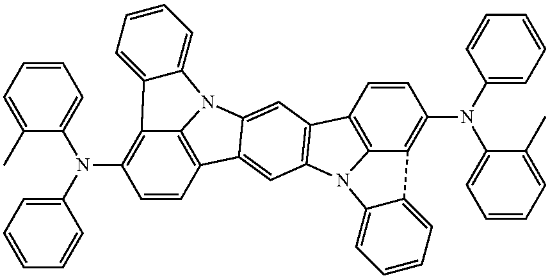
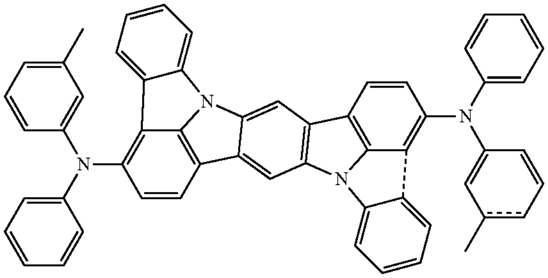
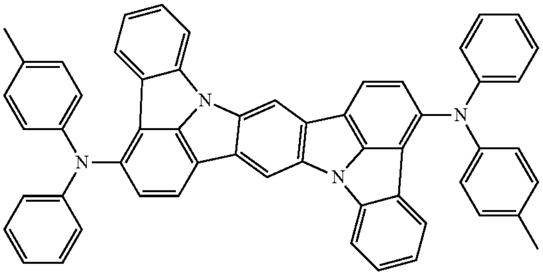
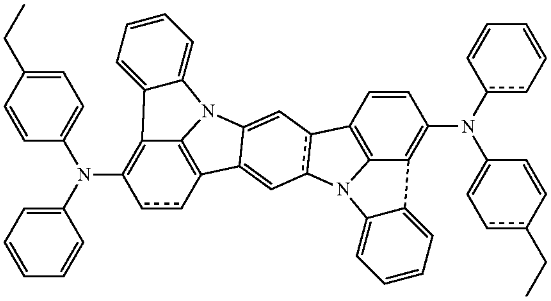
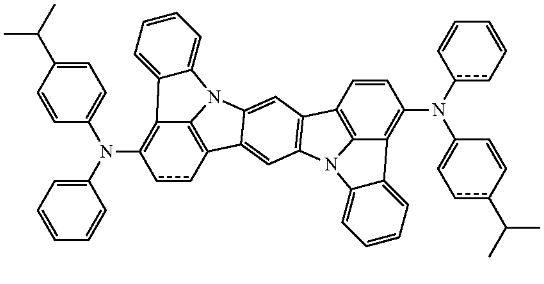

-continued
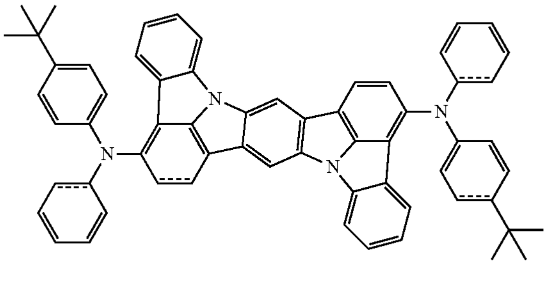
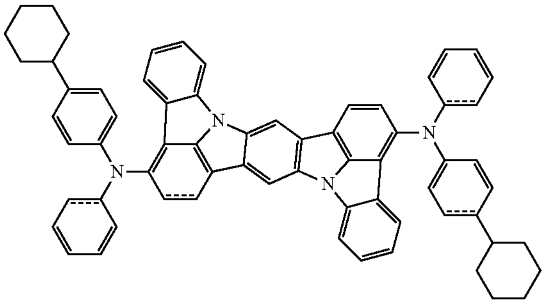
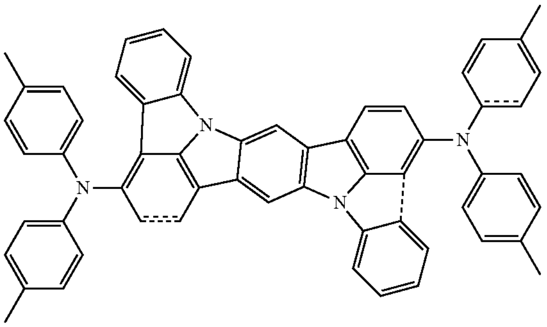
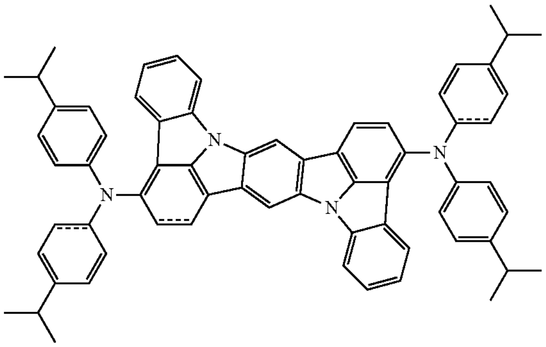
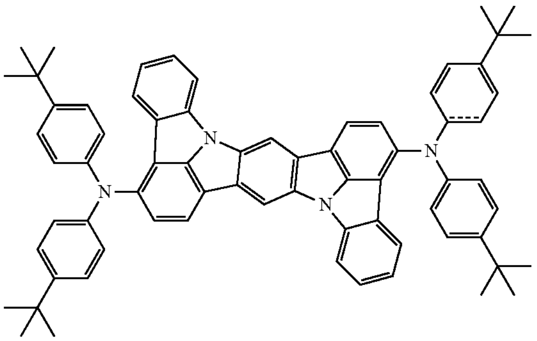
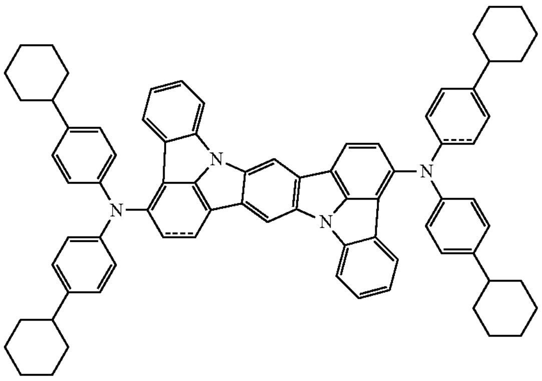
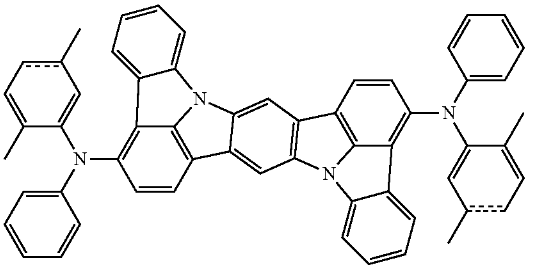
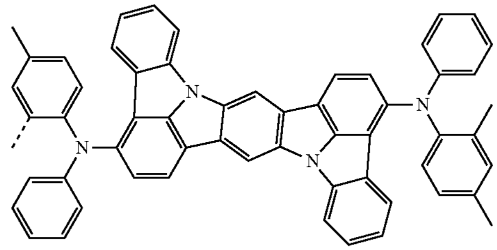
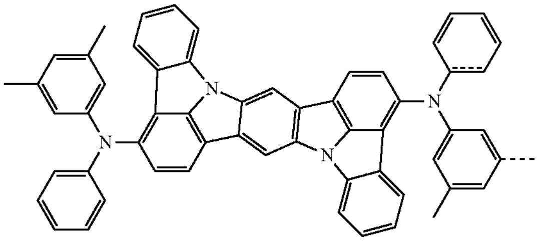
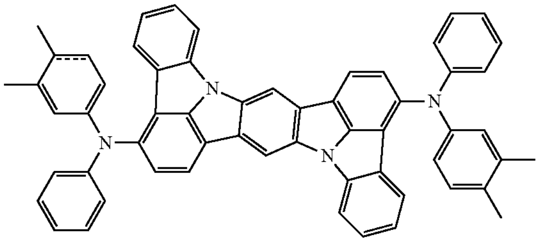

-continued
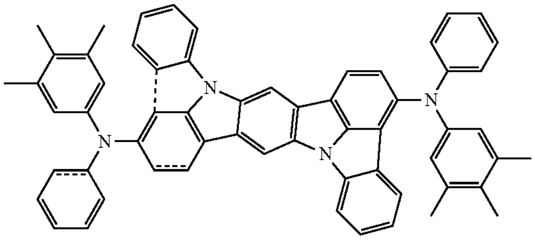
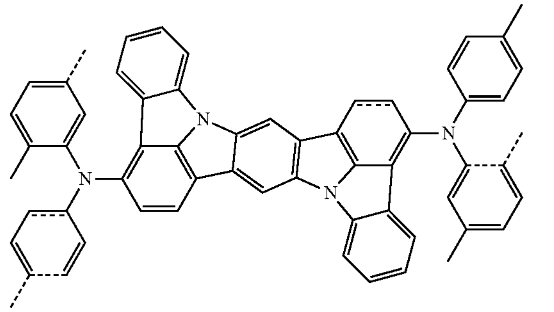
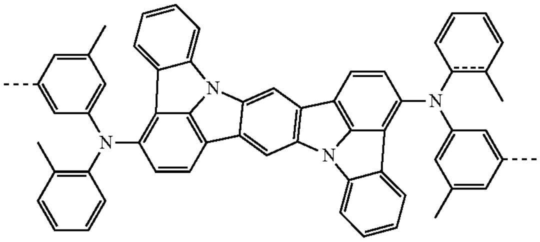
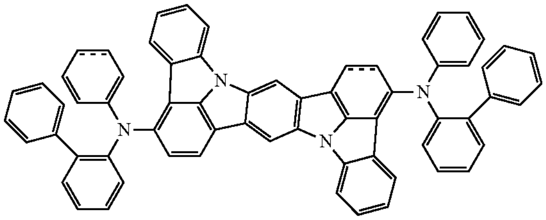
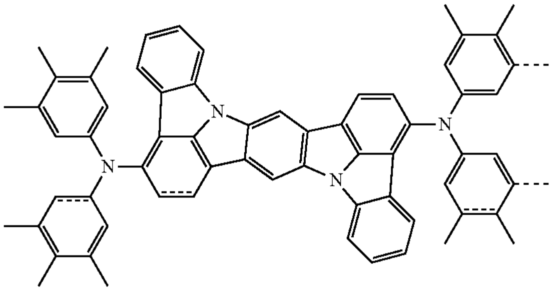
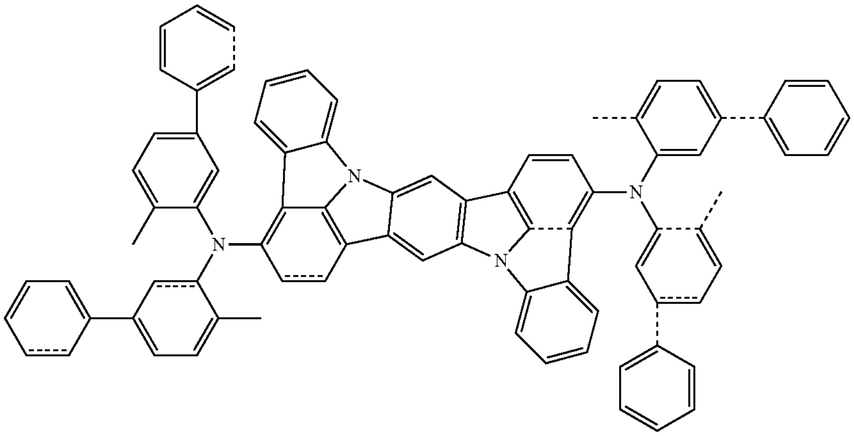
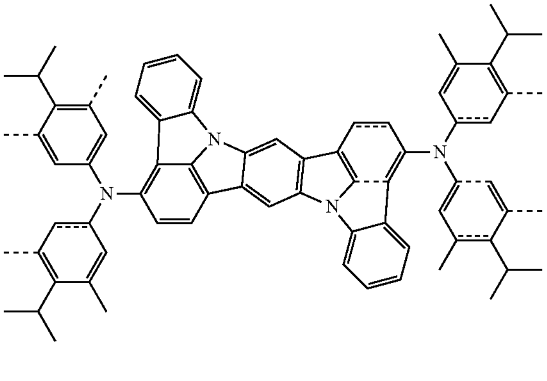
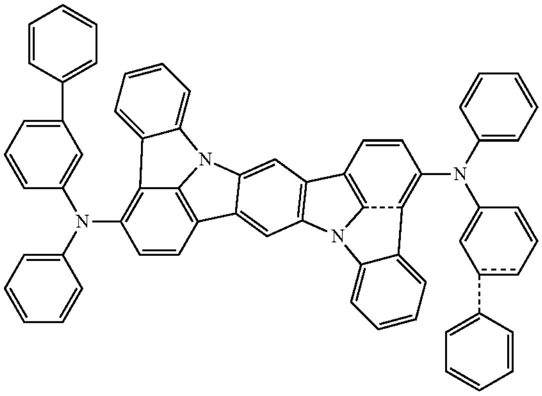

[fORMULA 340]
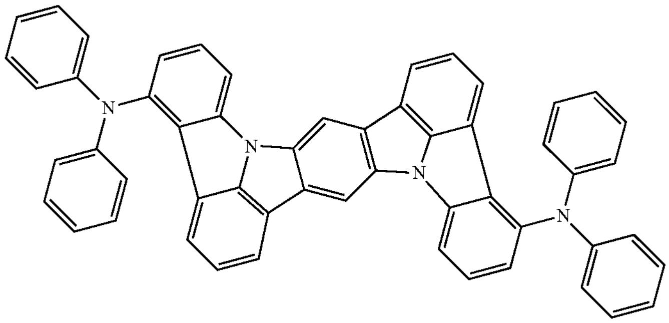
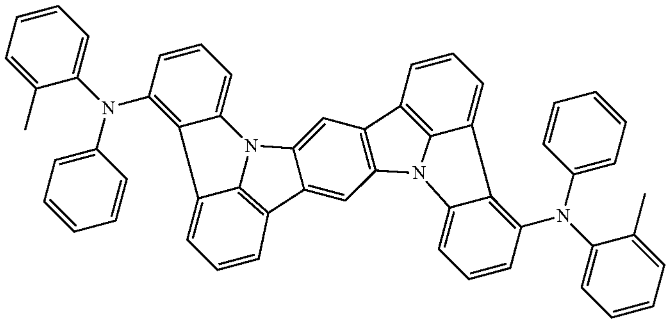
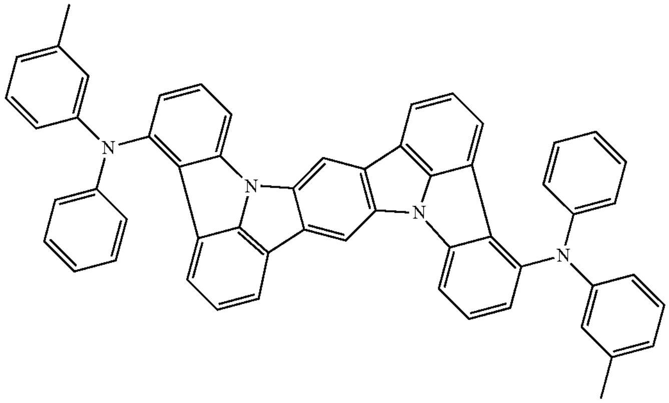
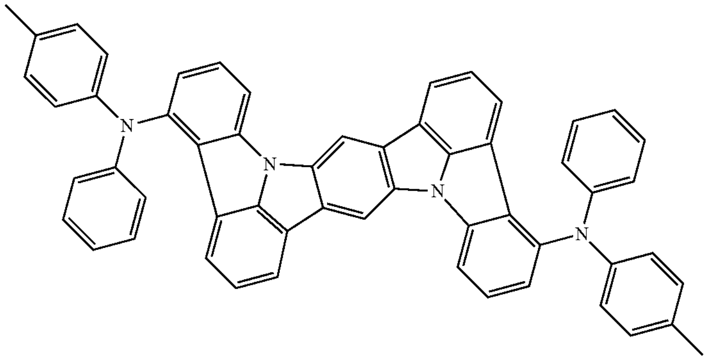

-continued
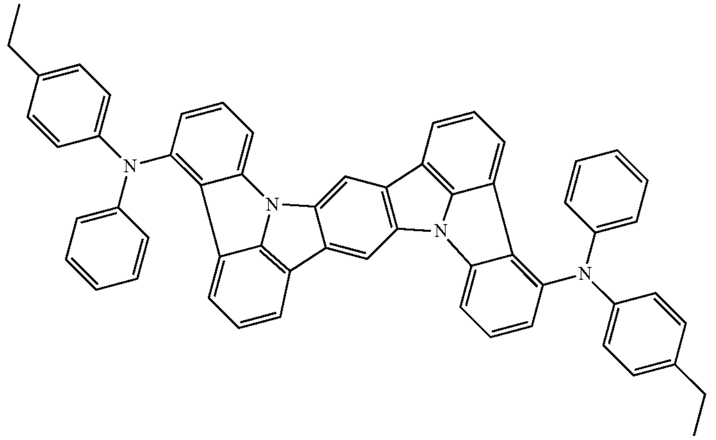
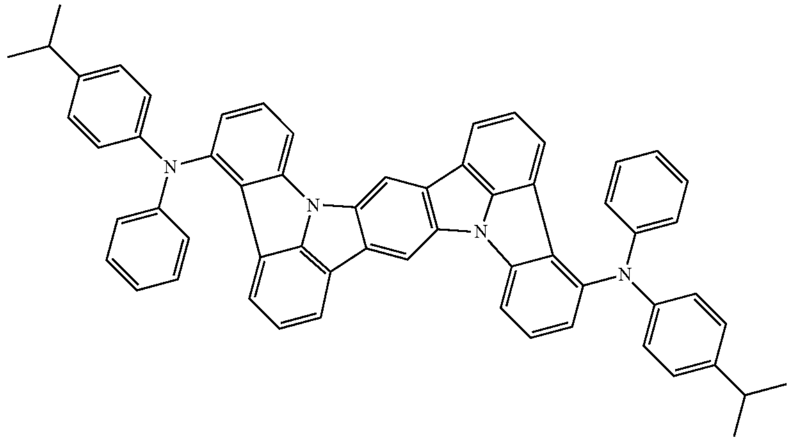
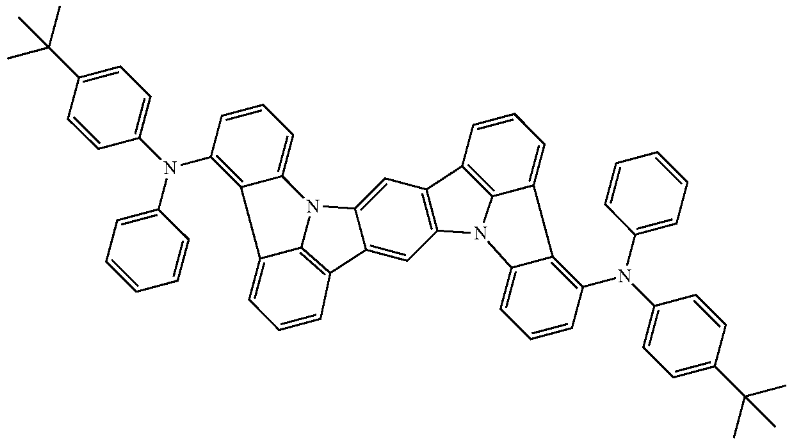

-continued
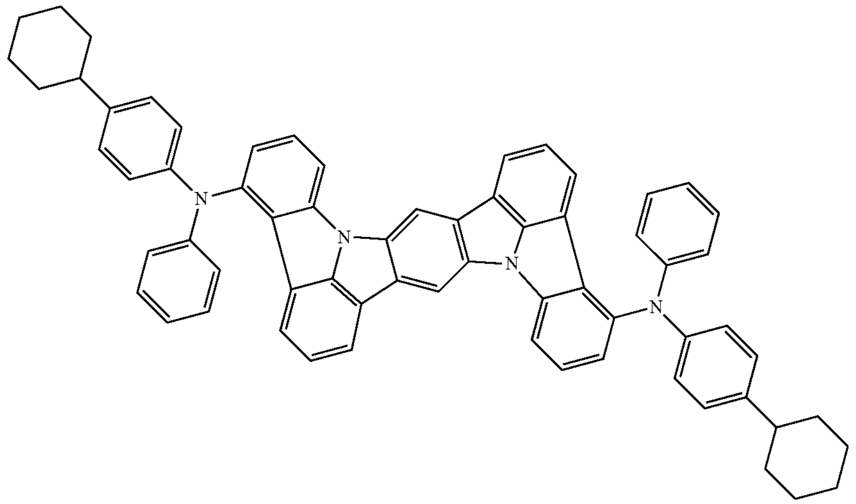
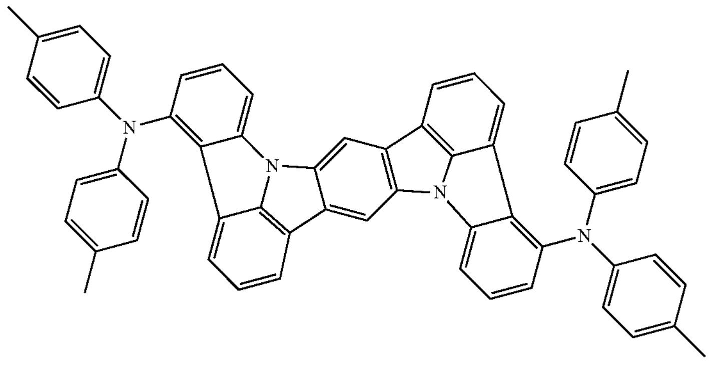
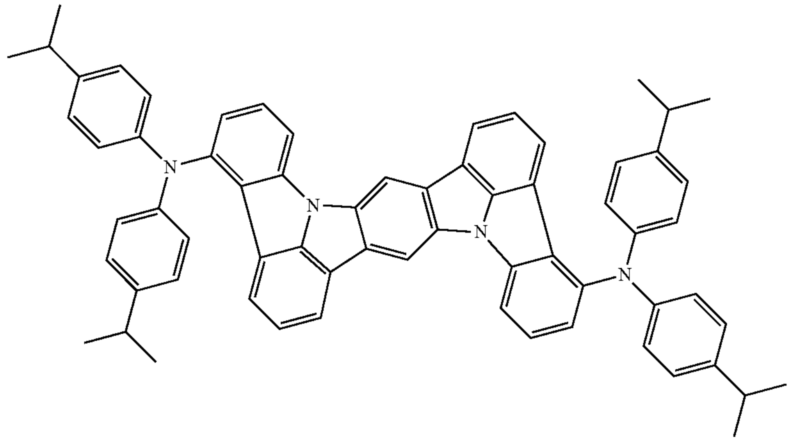

-continued
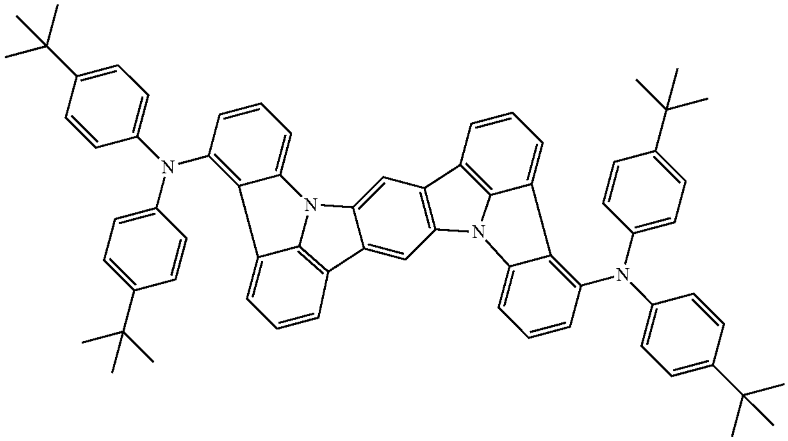
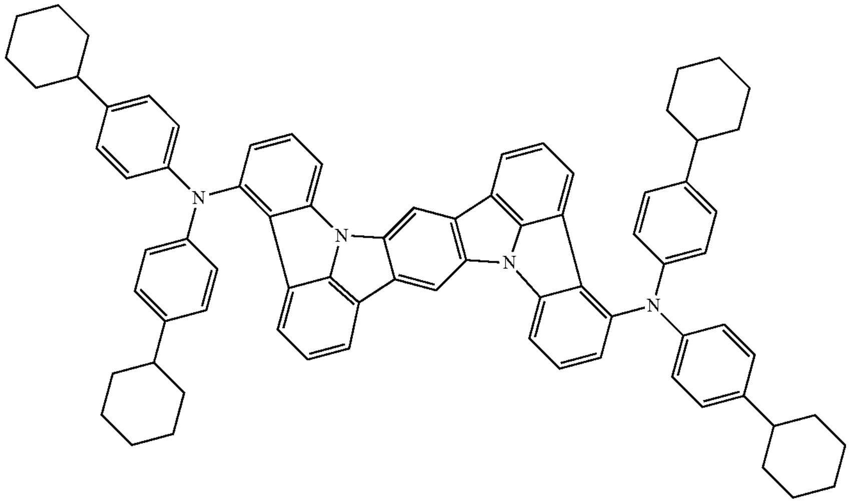
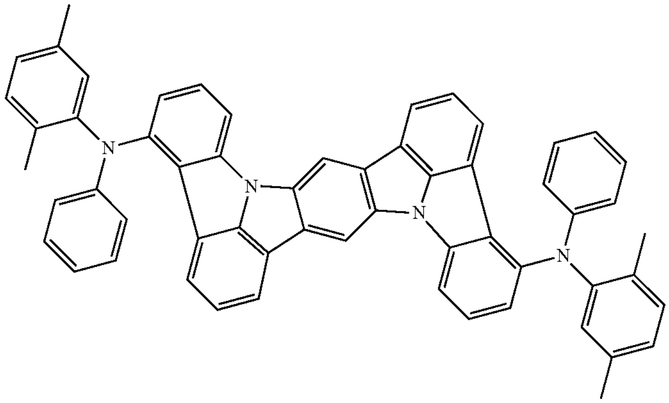
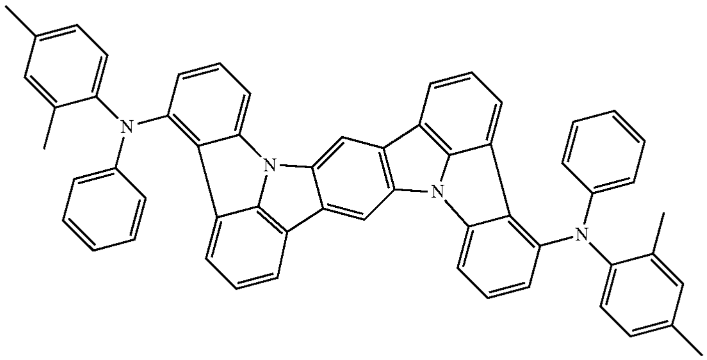

-continued
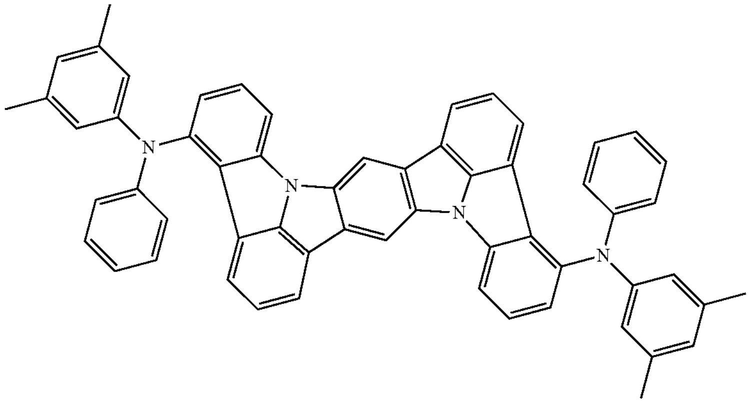
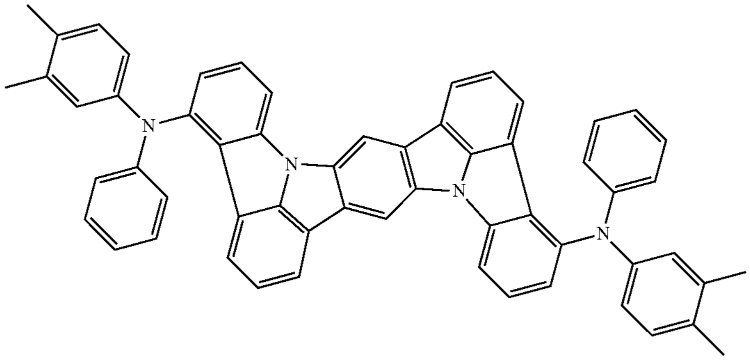
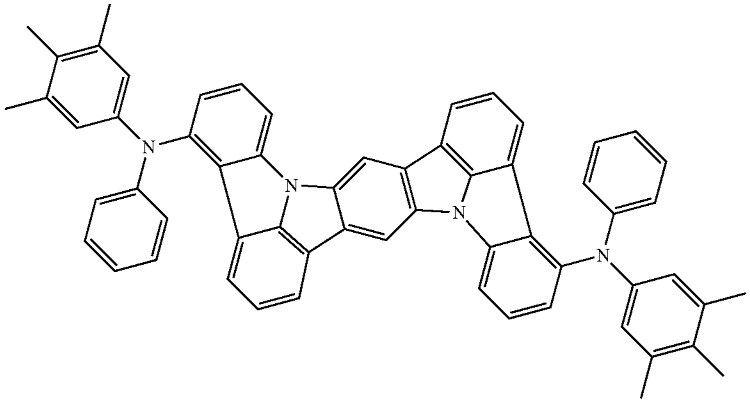
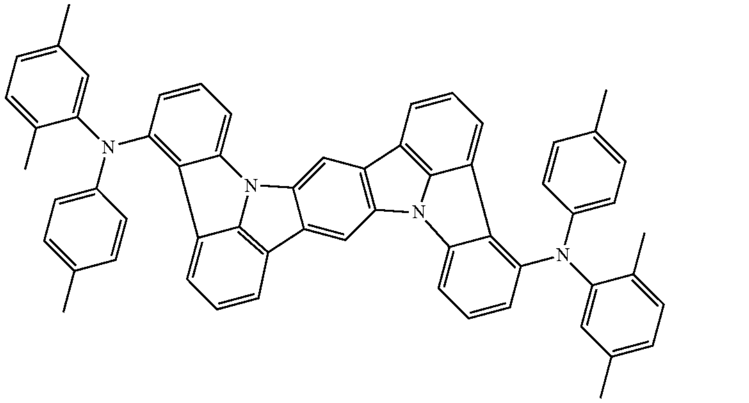

-continued
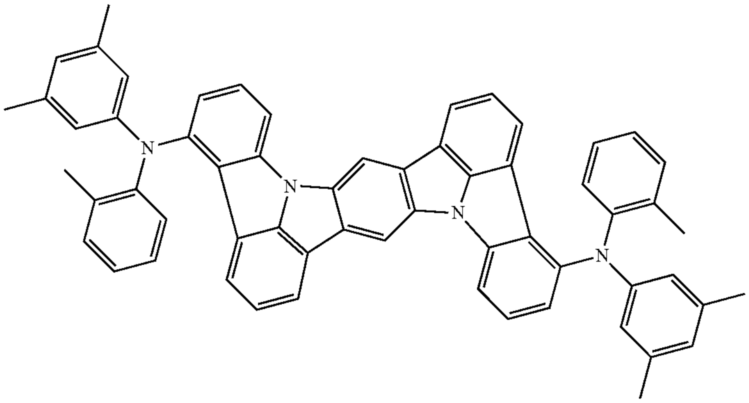
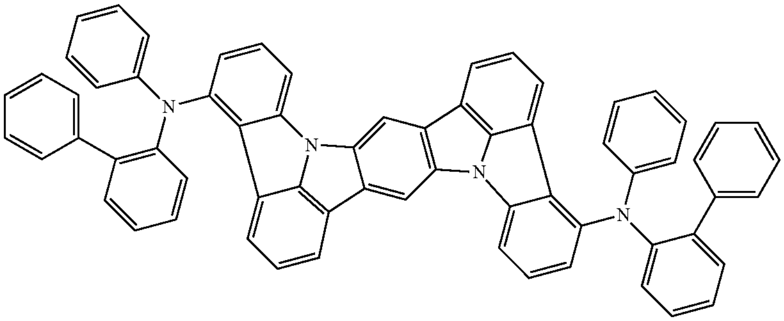
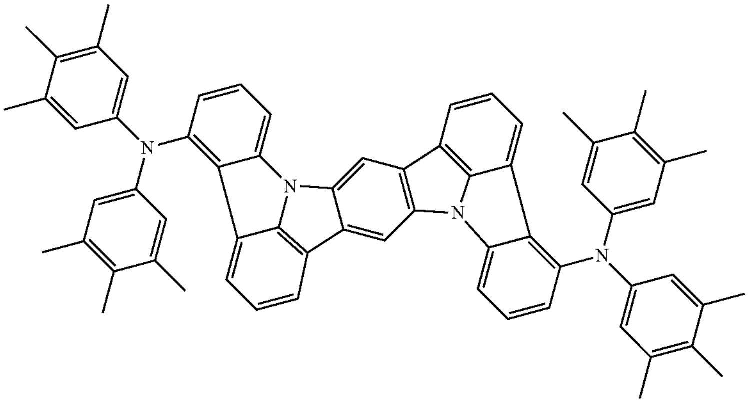
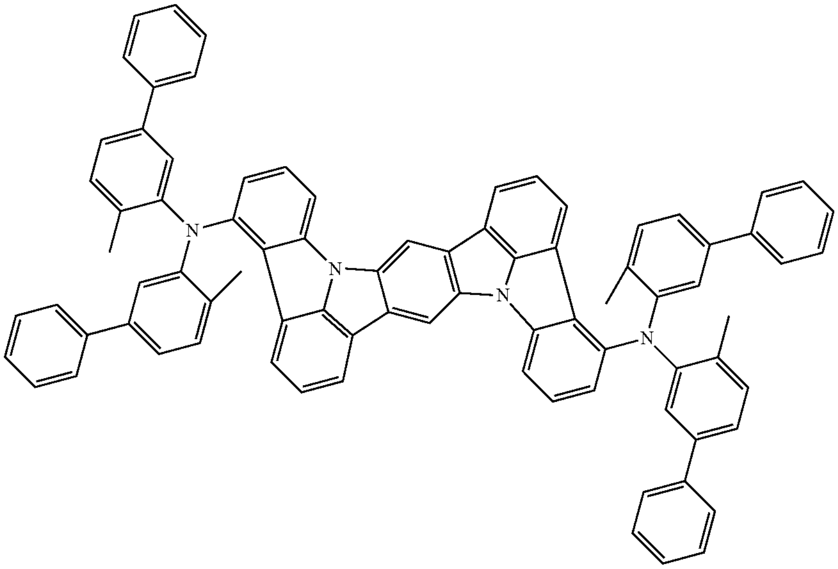

-continued
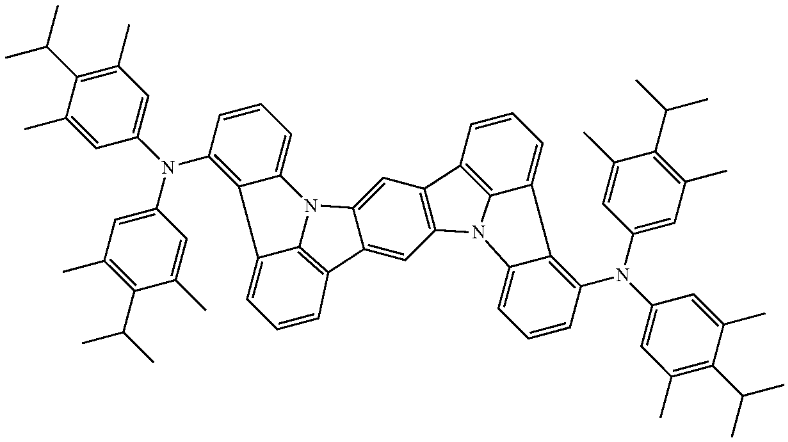
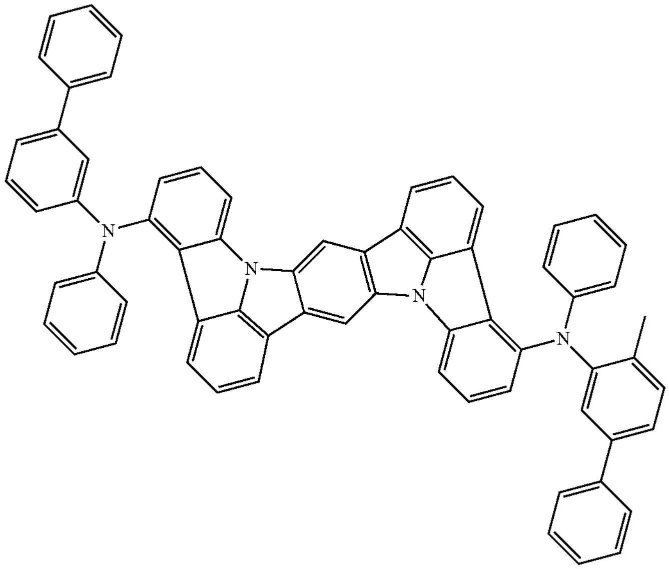
[fORMULA 341]
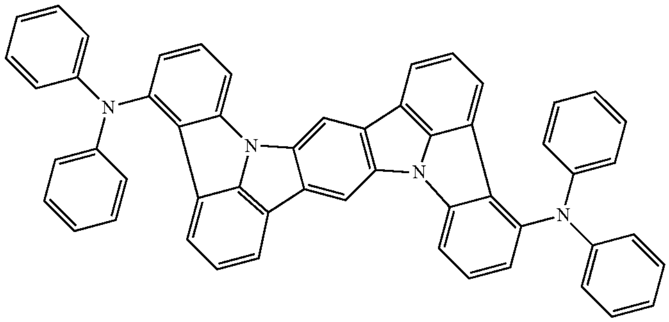
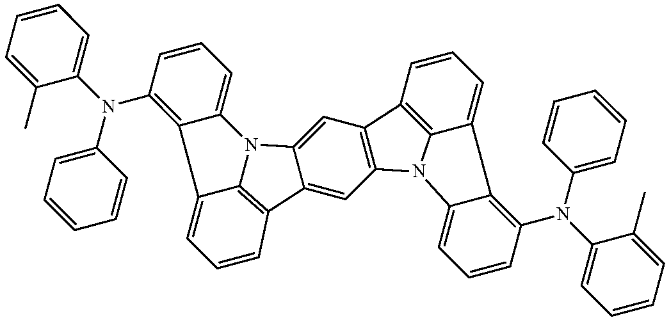

-continued
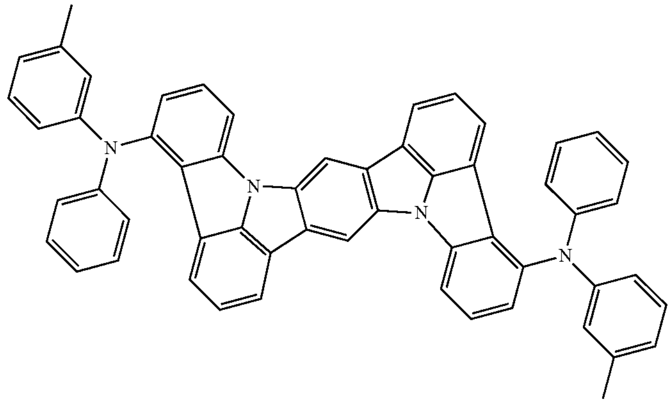
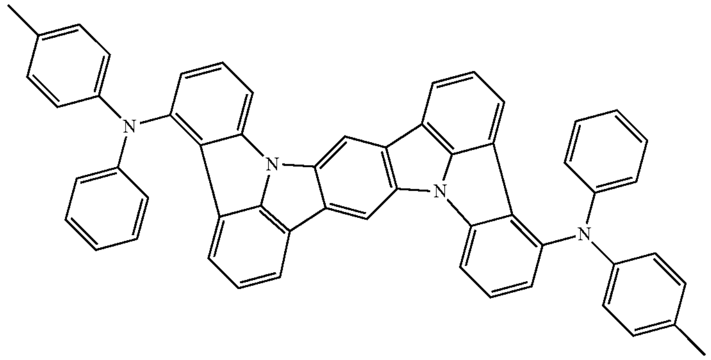
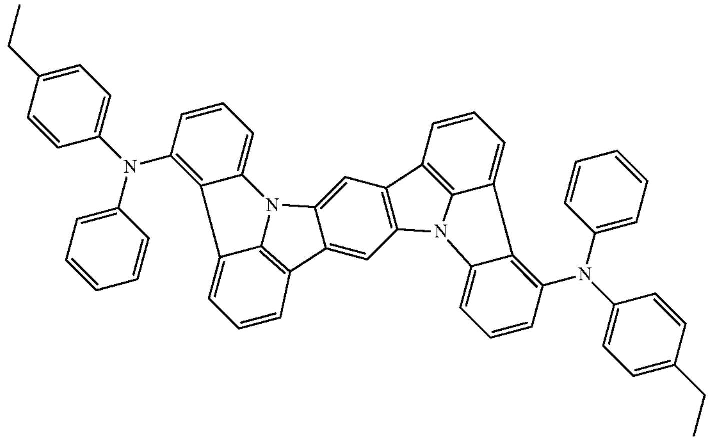
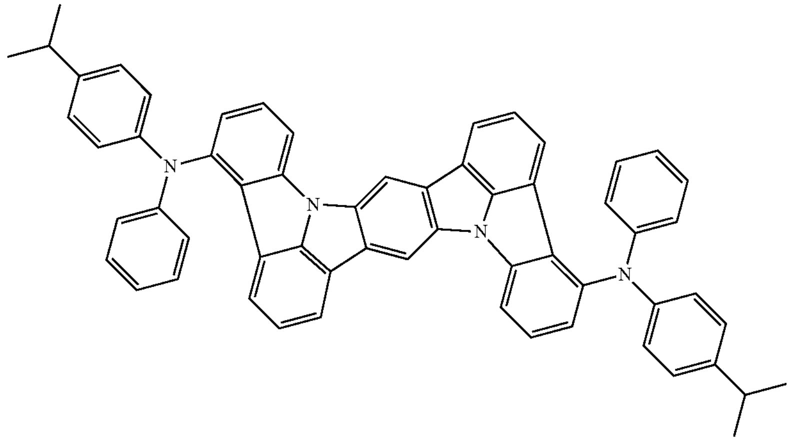

-continued
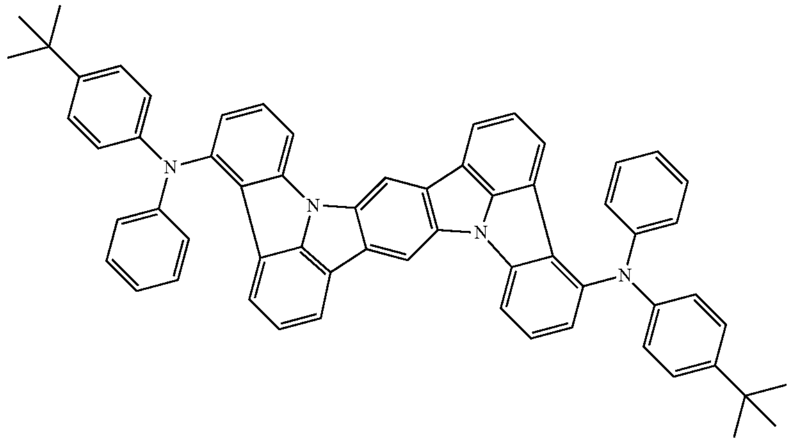
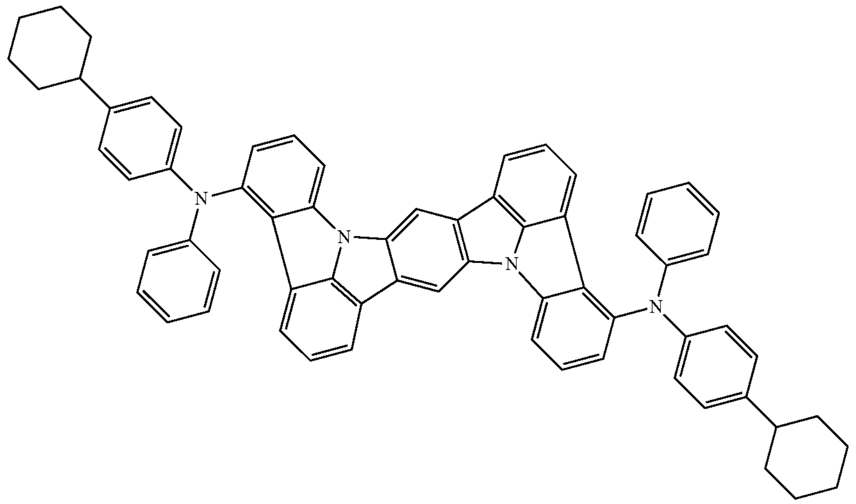
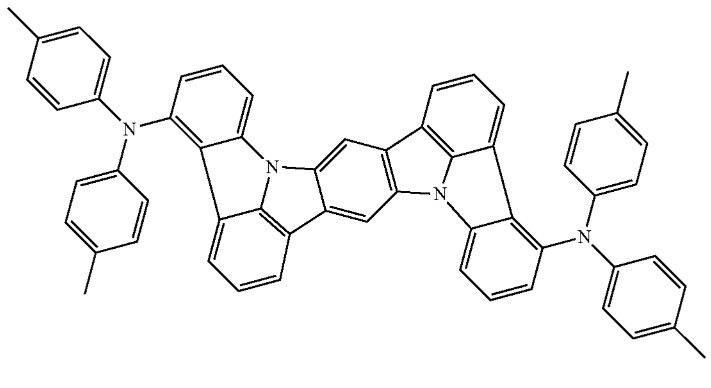

-continued
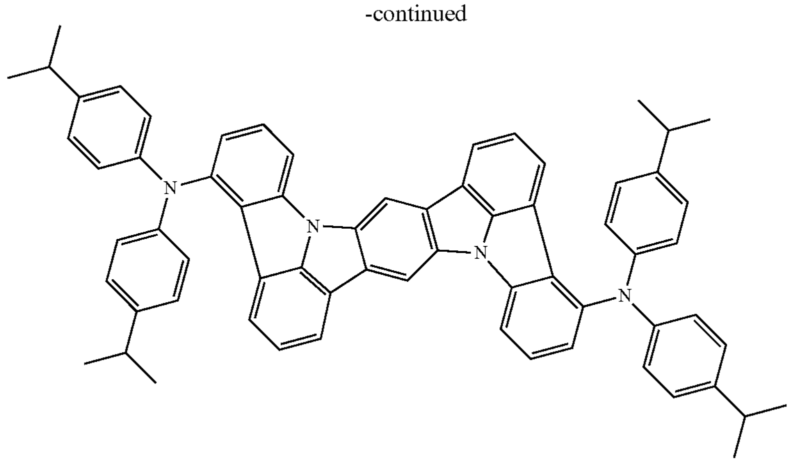
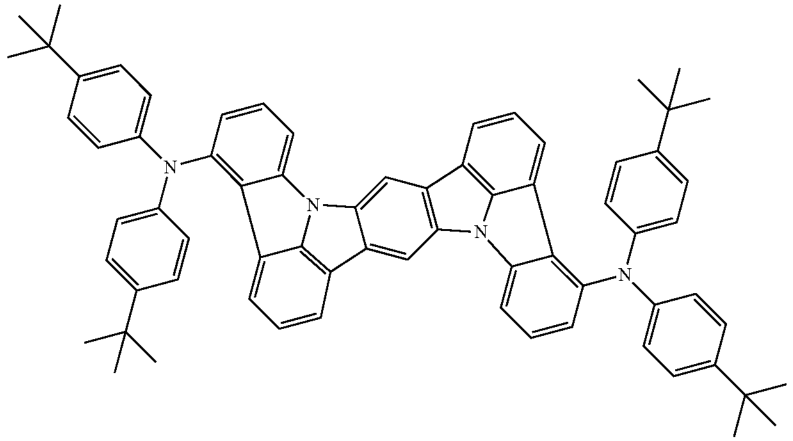
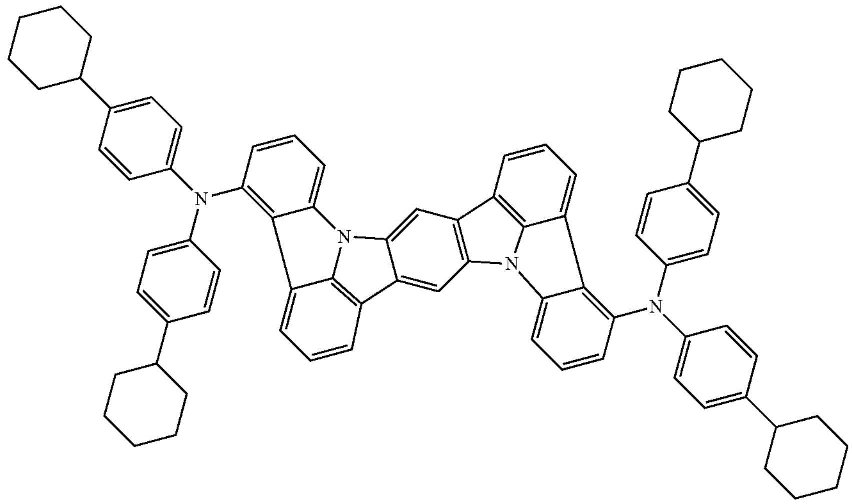

-continued
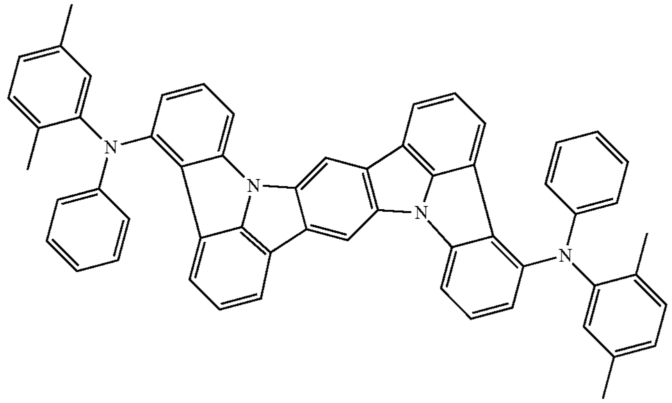
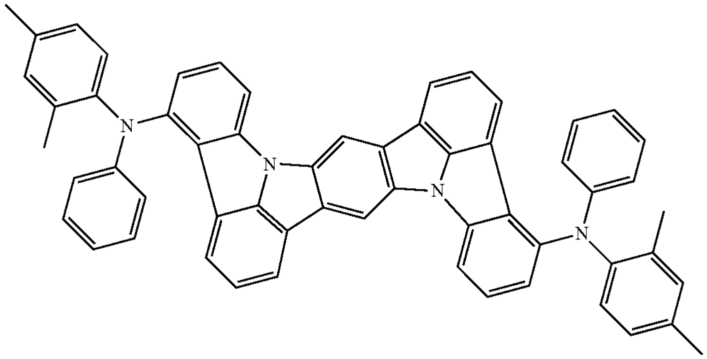
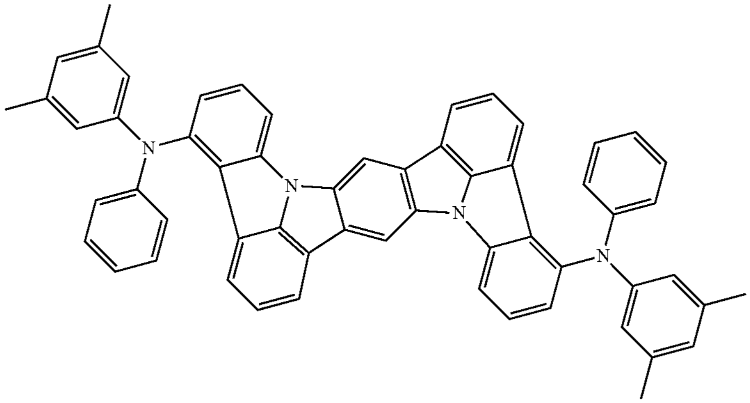
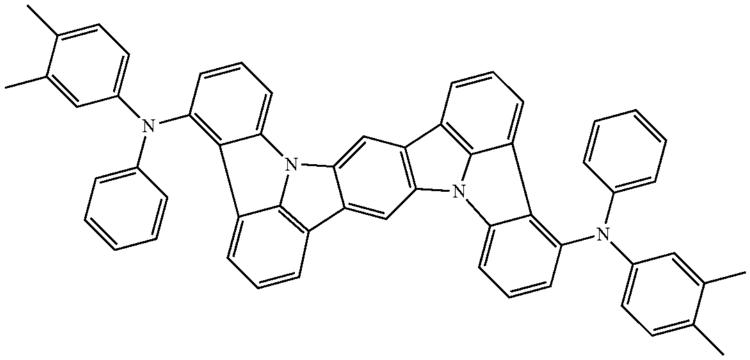

-continued
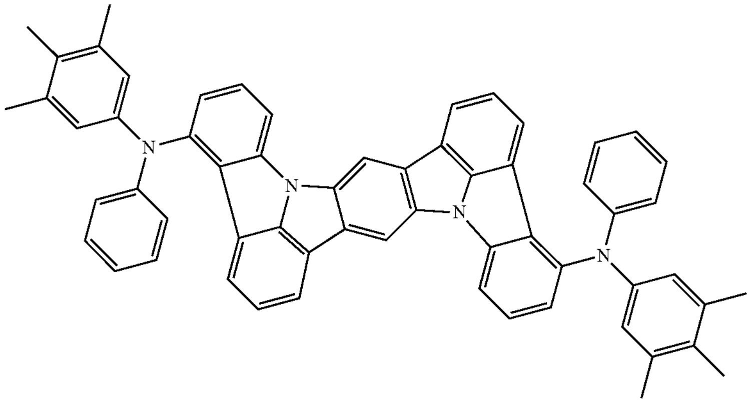
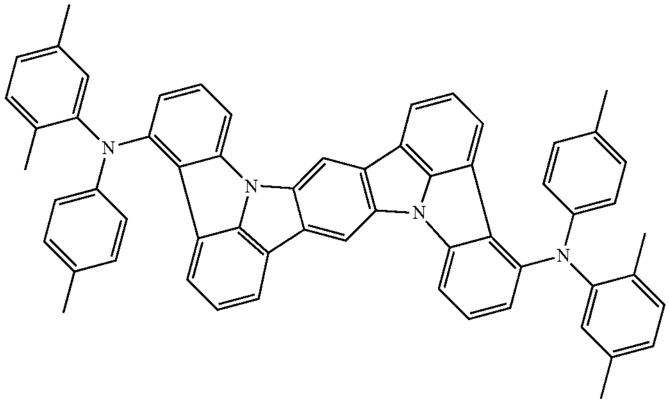
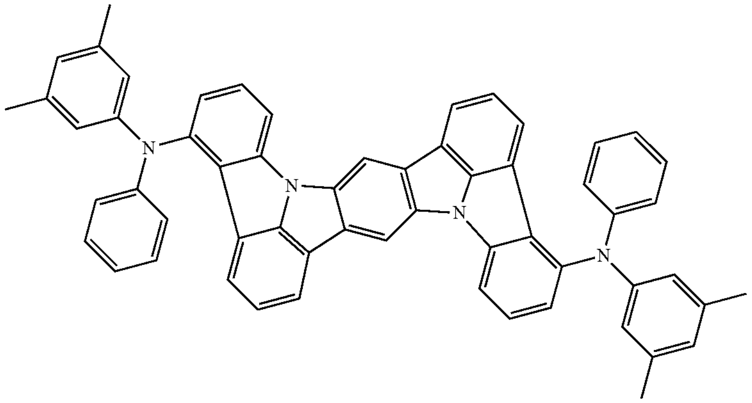
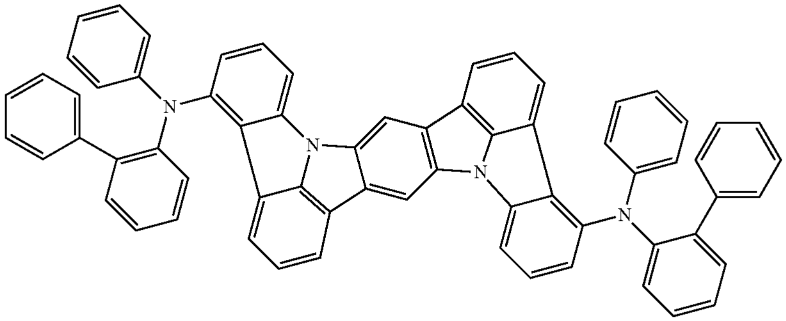

-continued
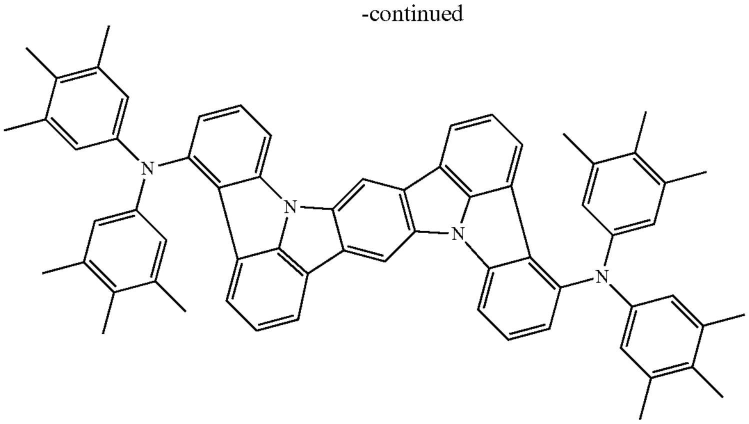
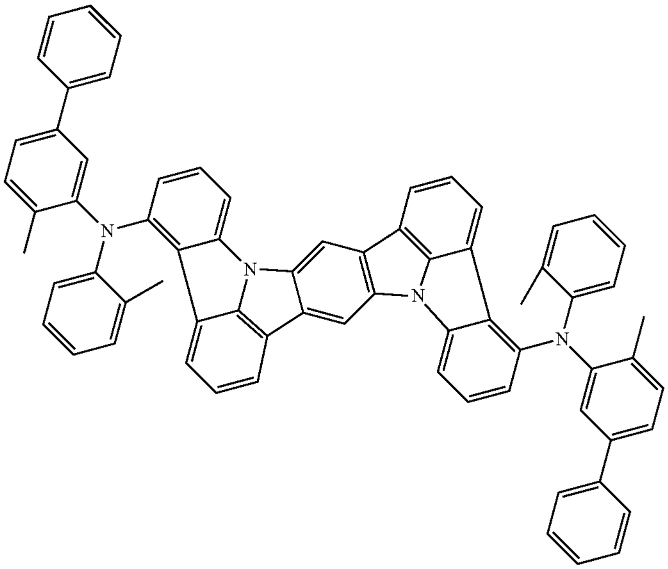
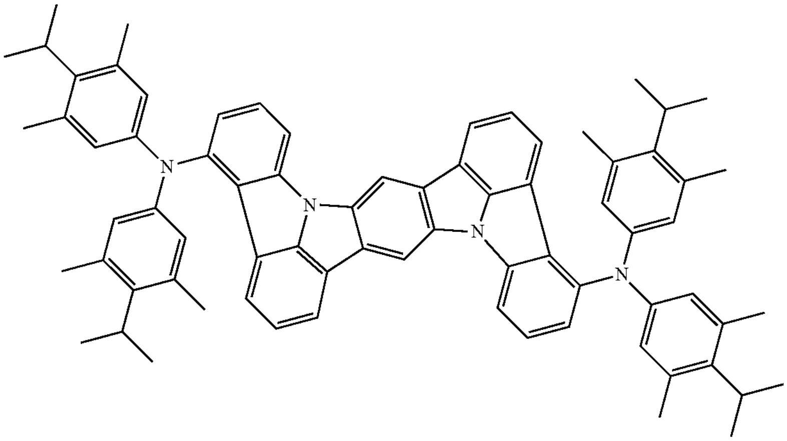

-continued
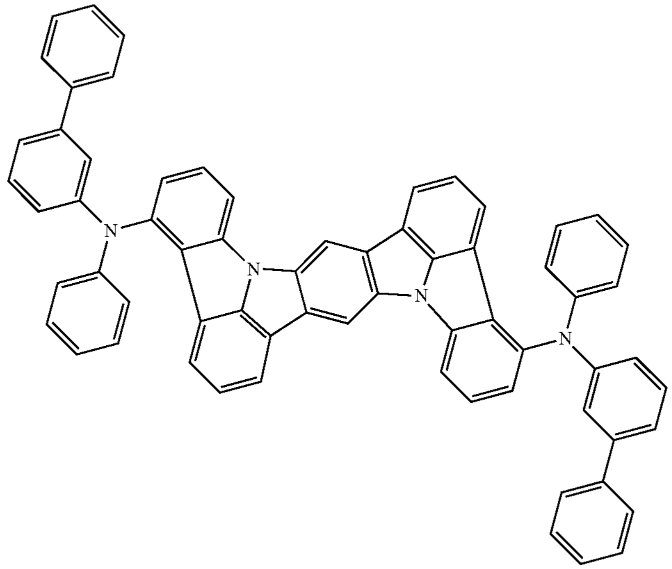
[fORMULA 342]
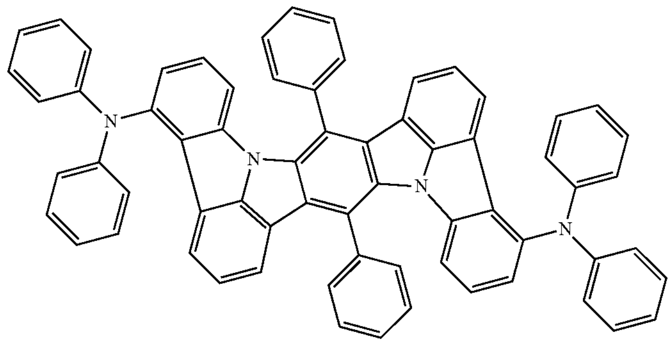
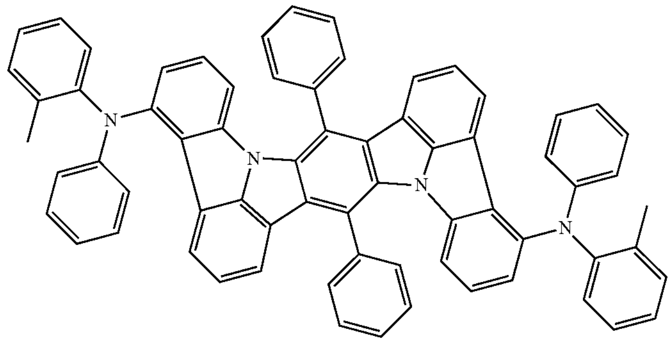
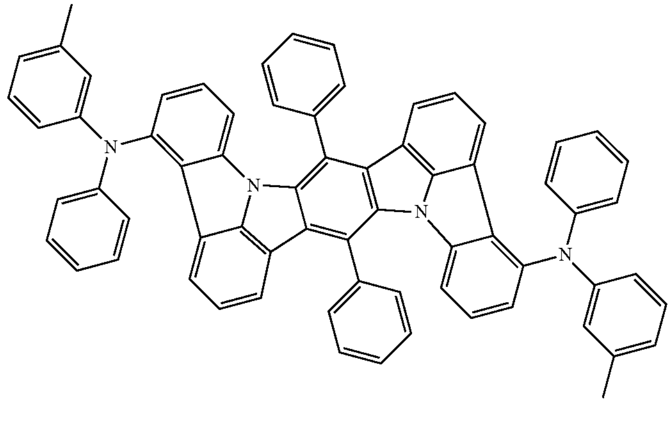

-continued
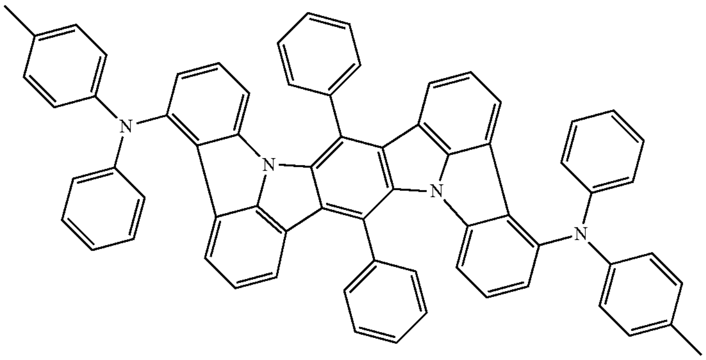
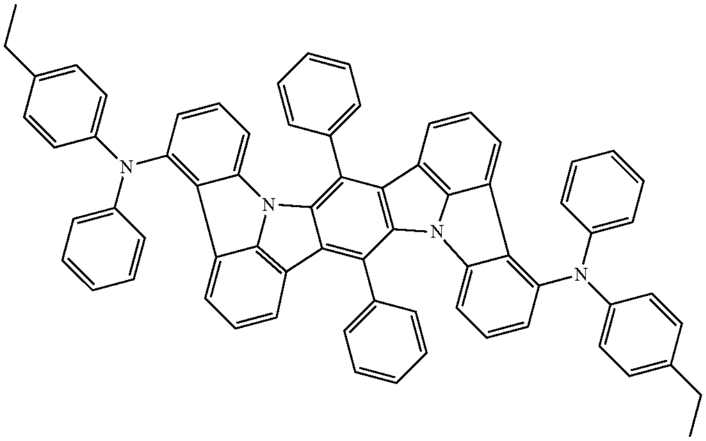
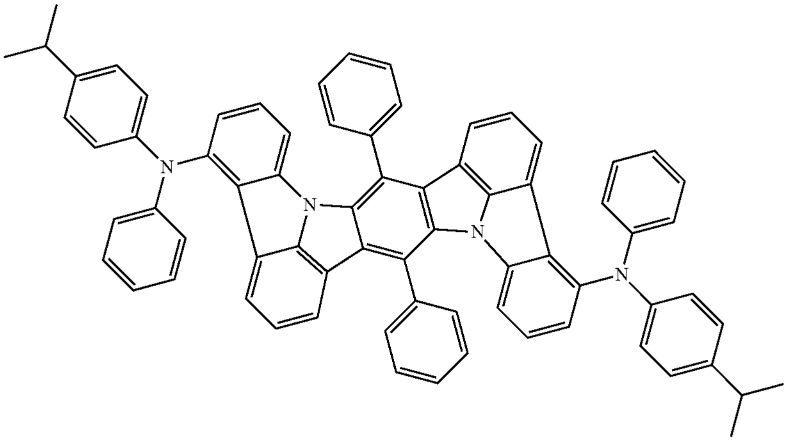
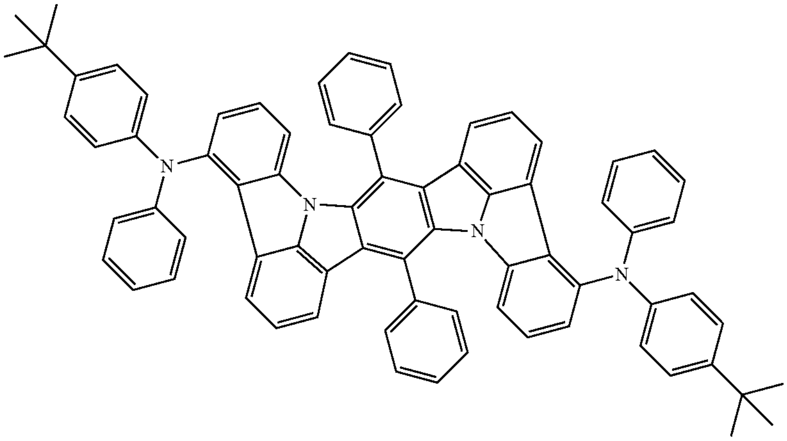

-continued
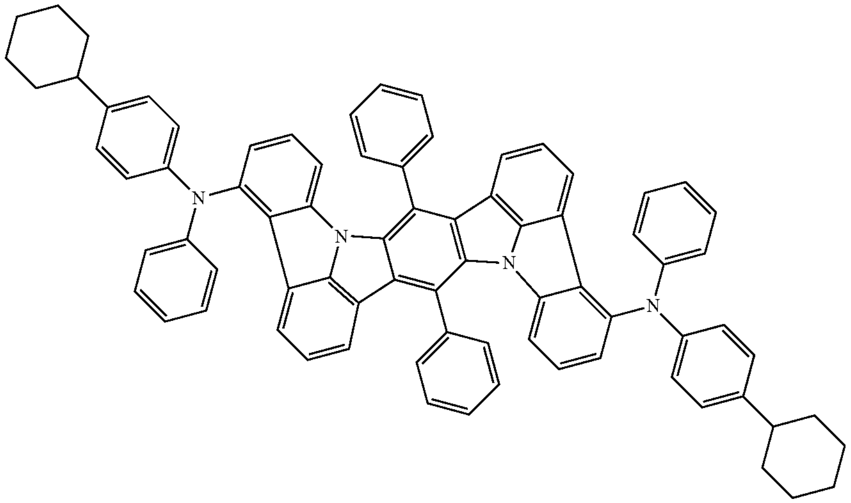
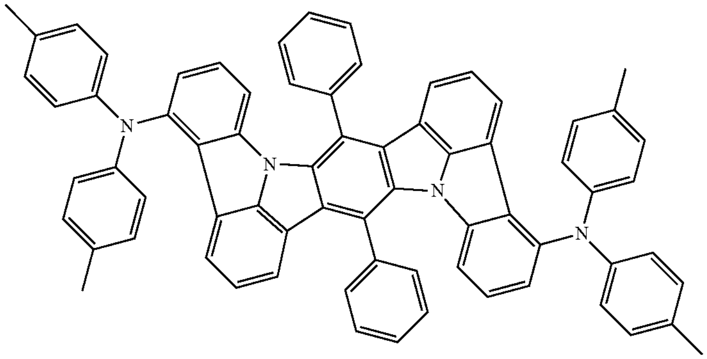
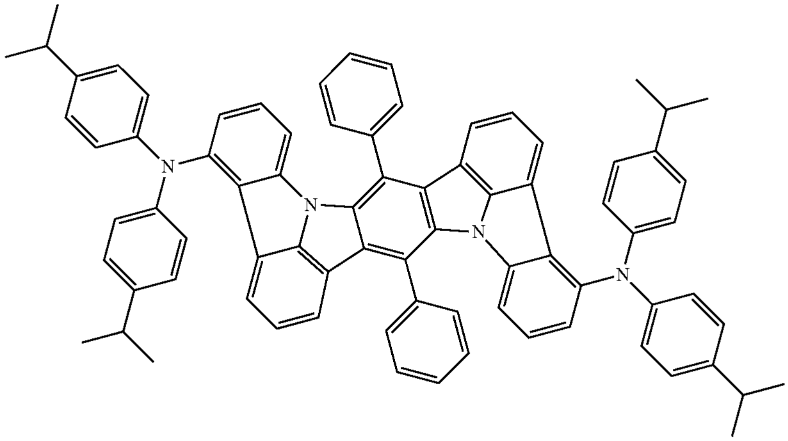

-continued
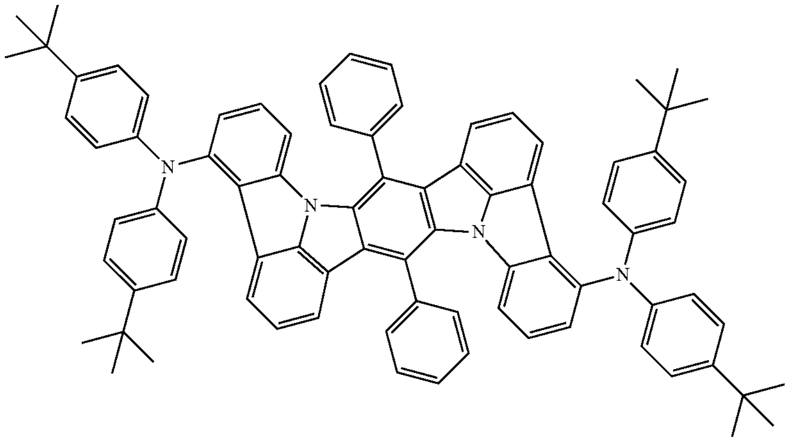
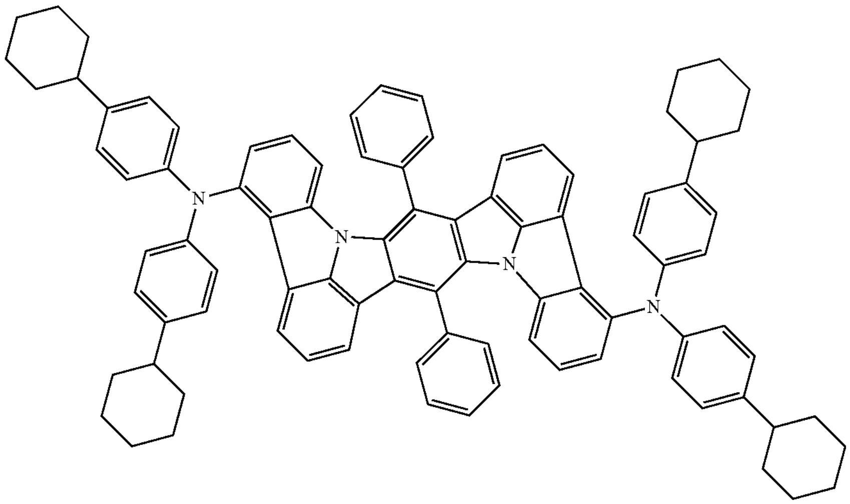
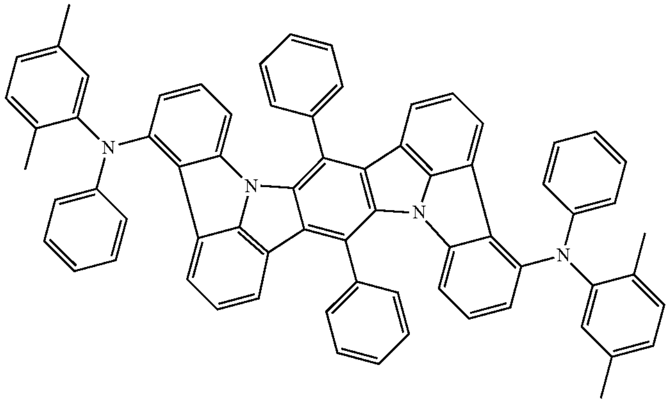
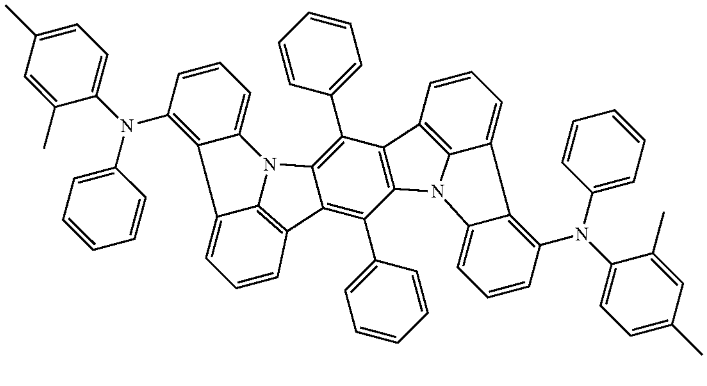

-continued
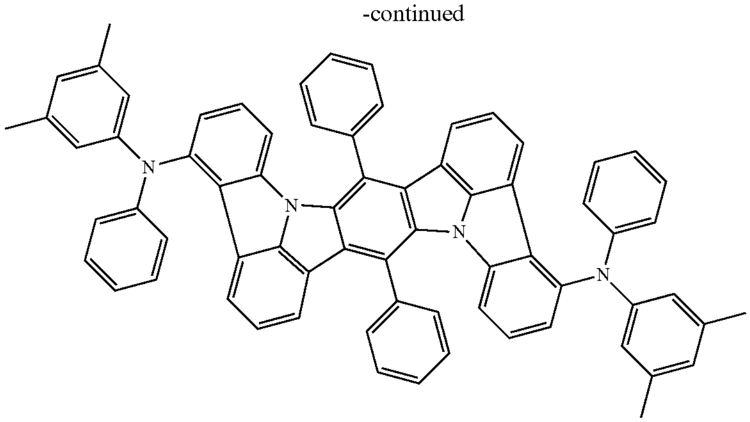
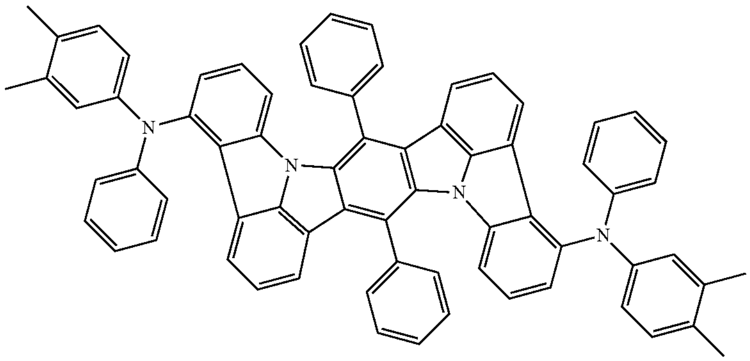
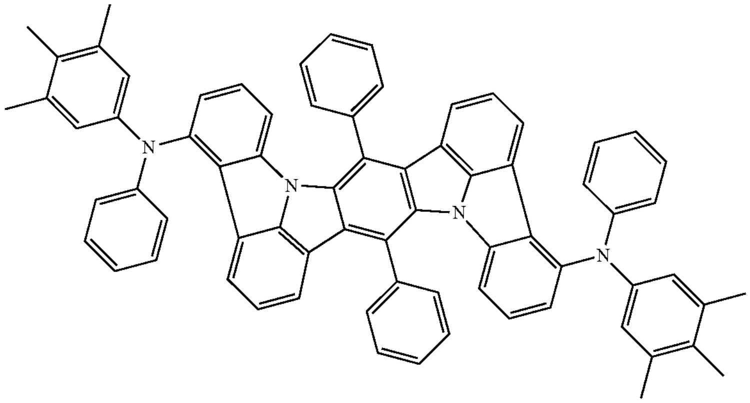
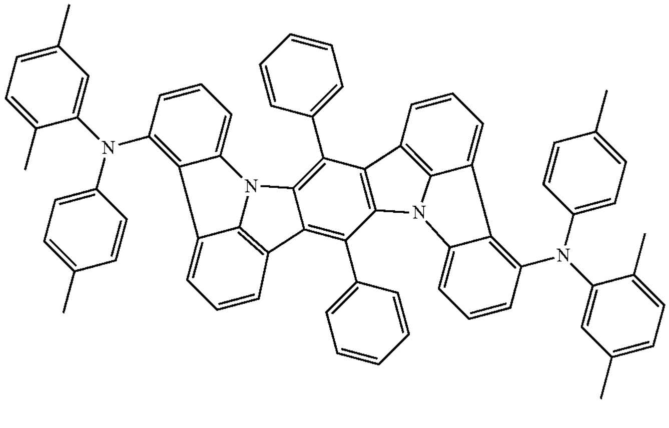

-continued
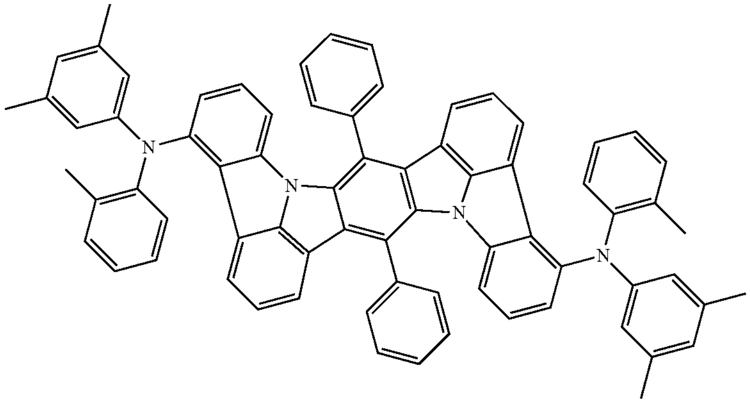
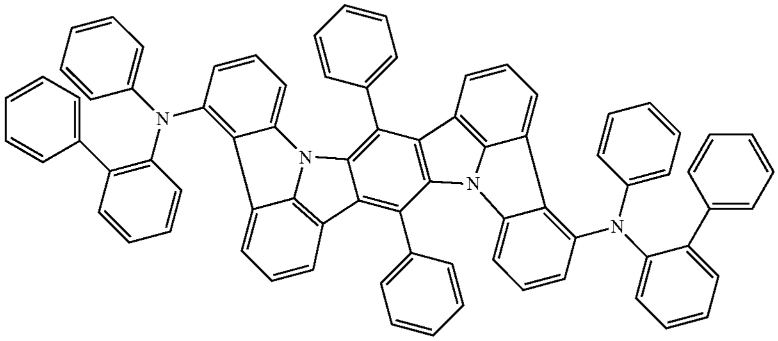
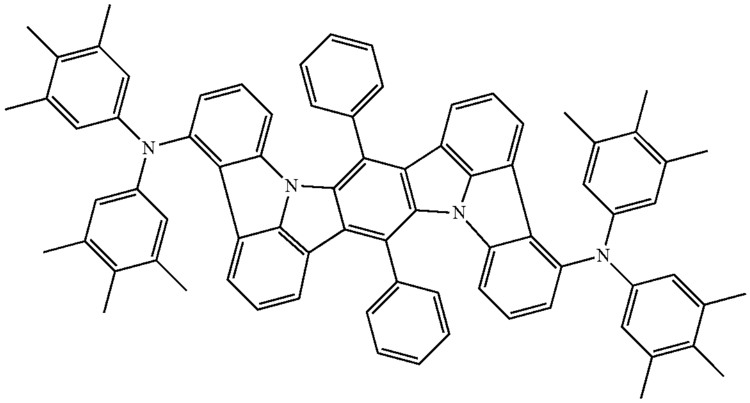
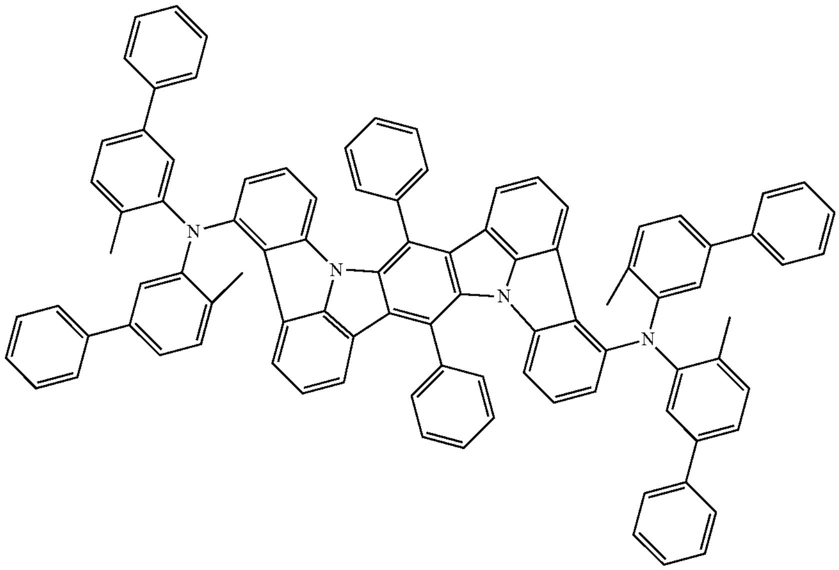

-continued
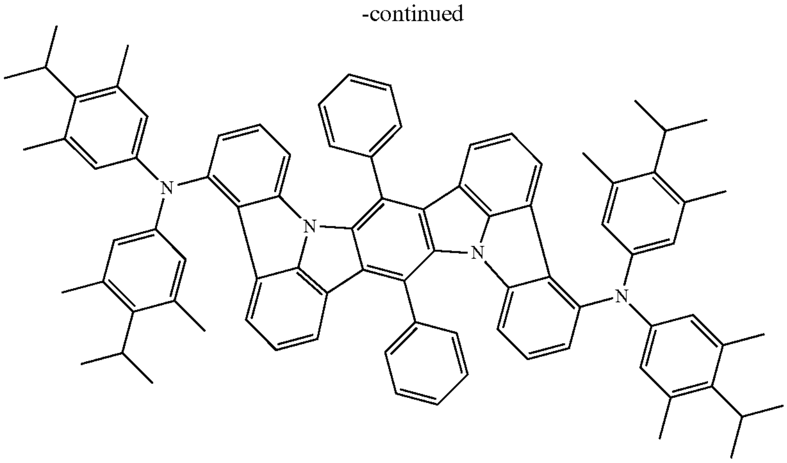
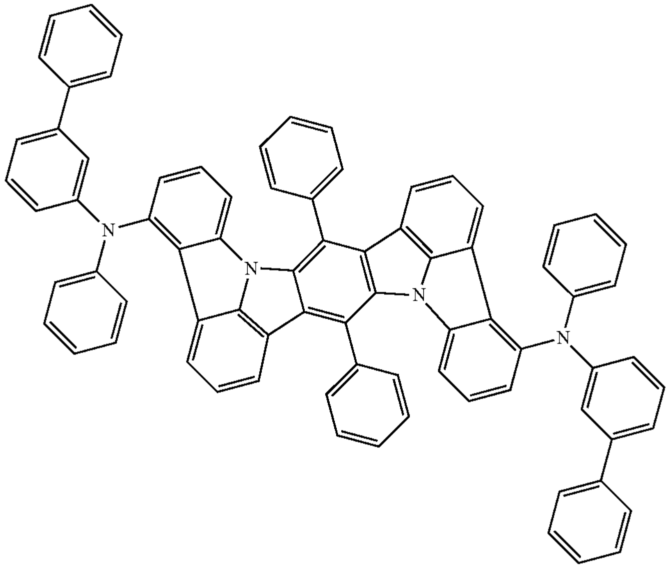
[Formula 343]
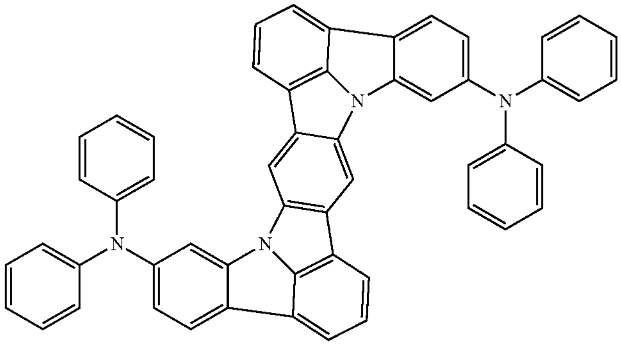

-continued
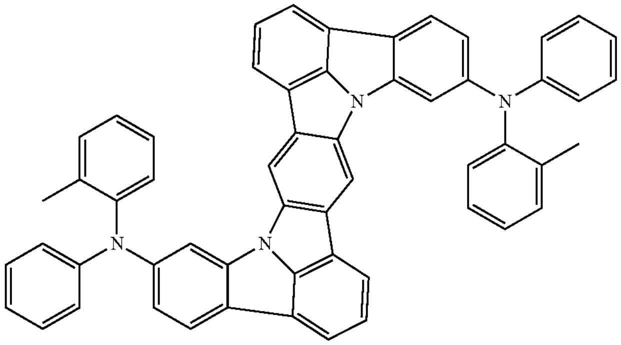
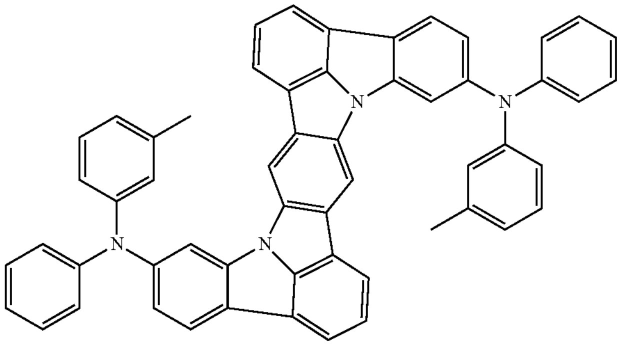
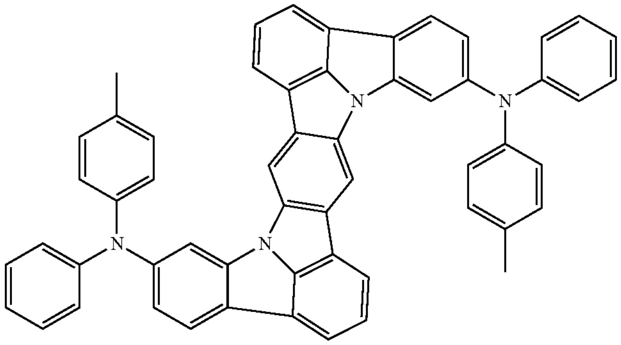
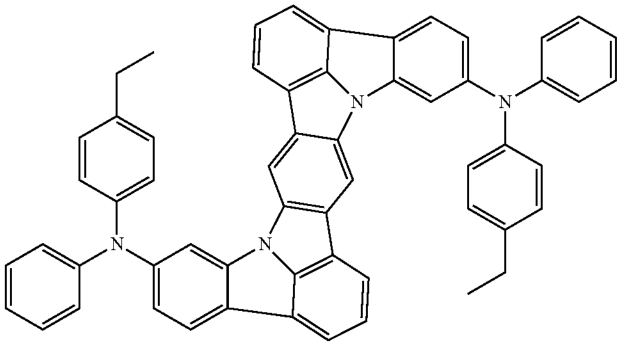
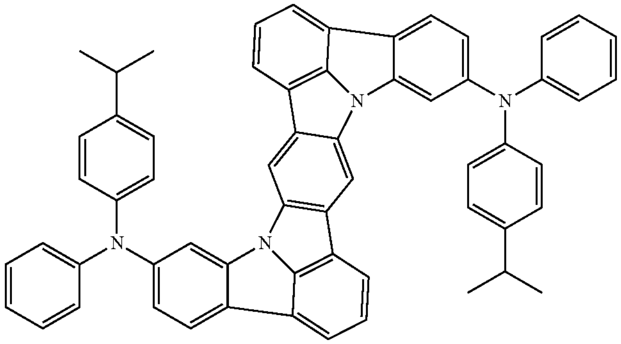

-continued
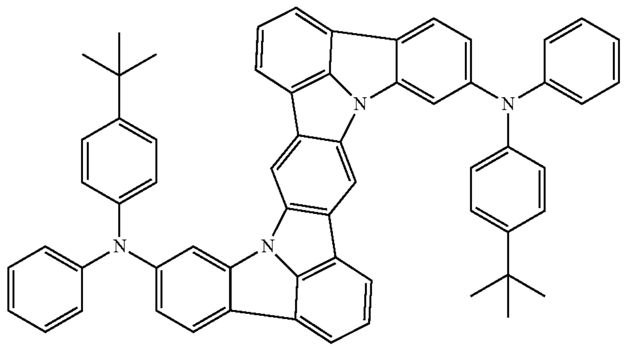
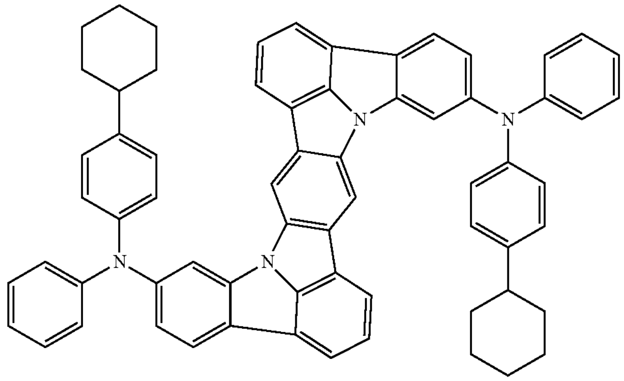
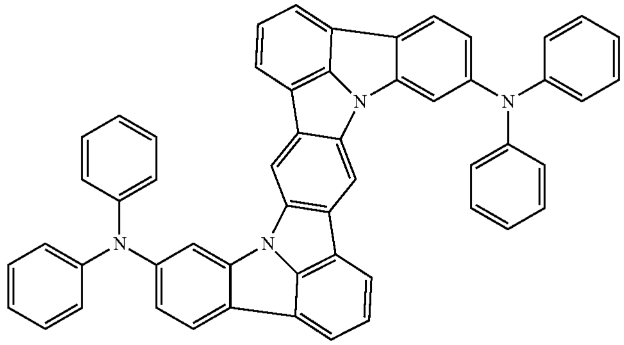
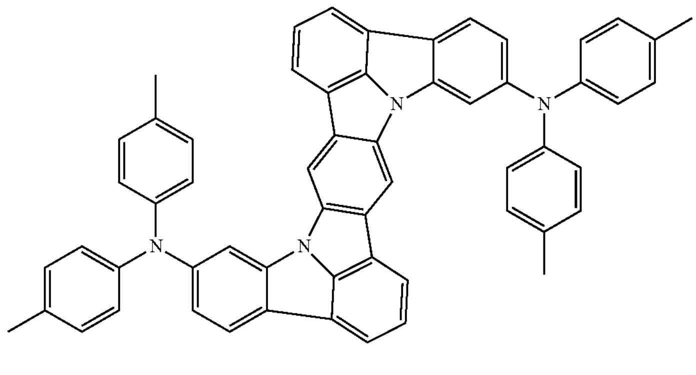

-continued
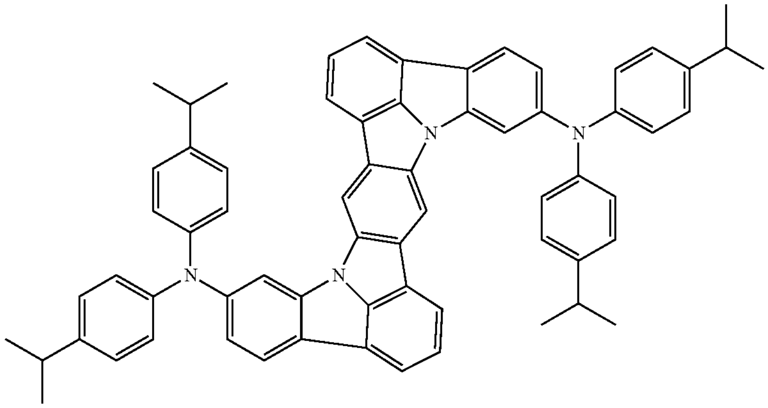
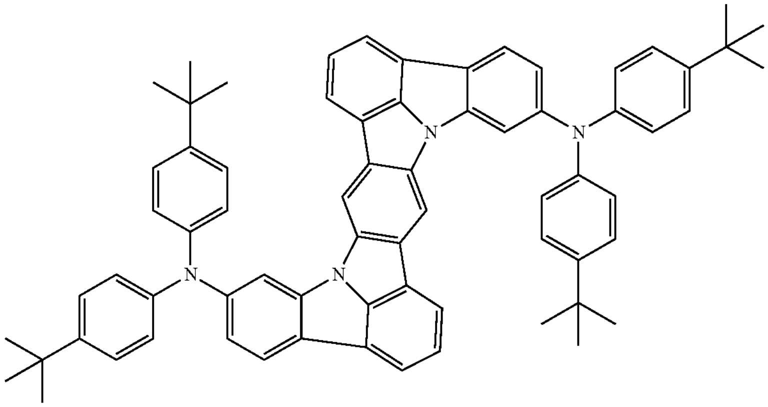
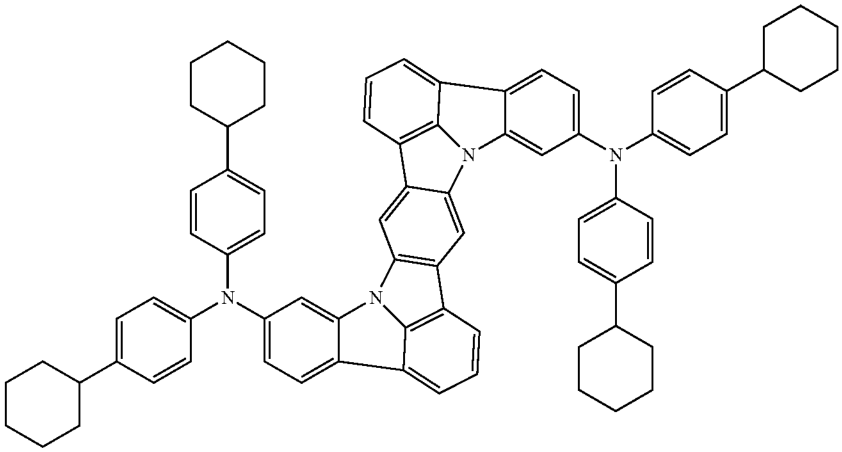
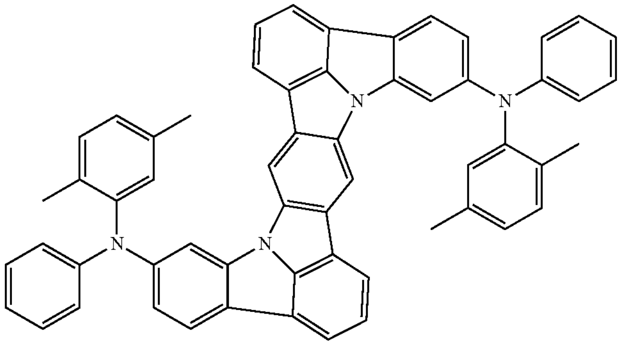

-continued
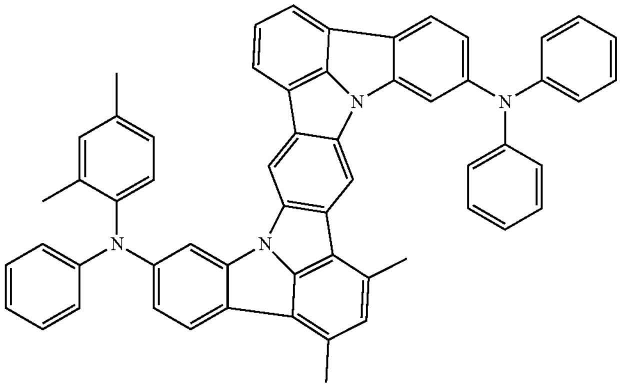
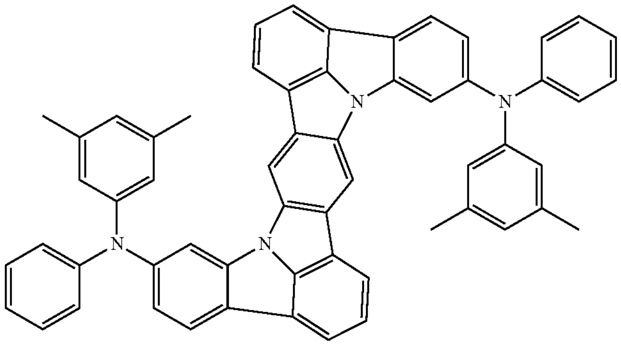
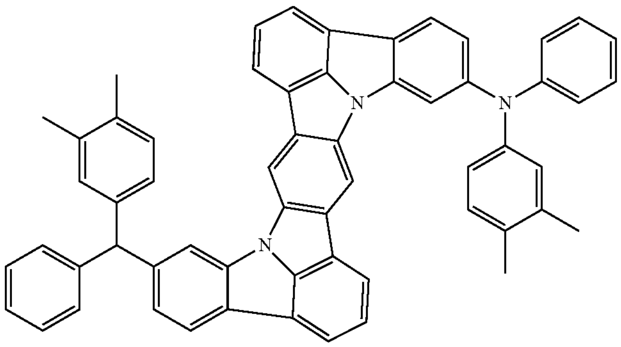
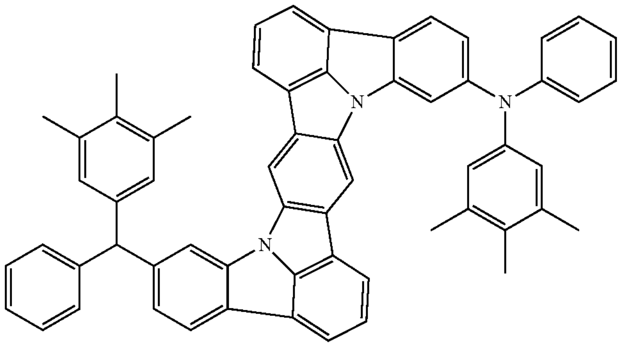

-continued
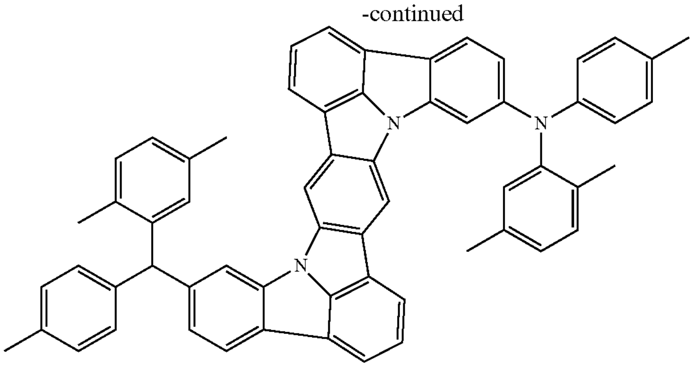
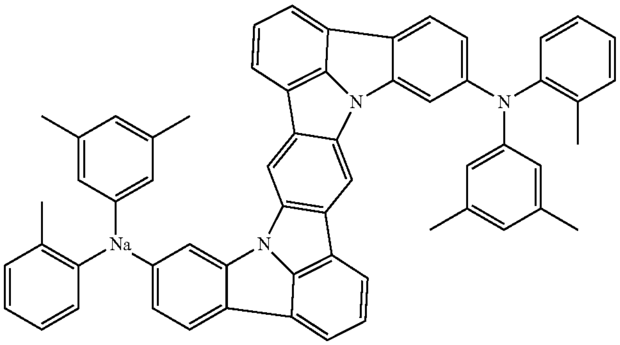
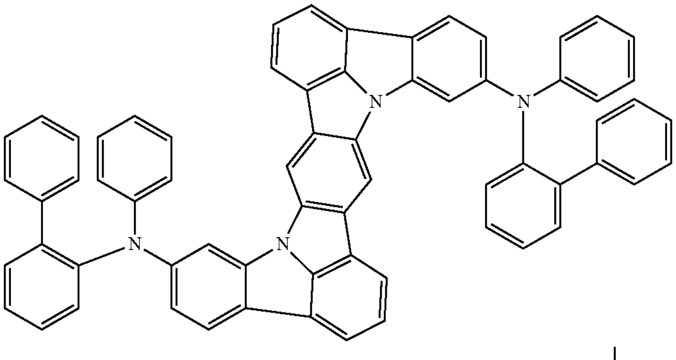
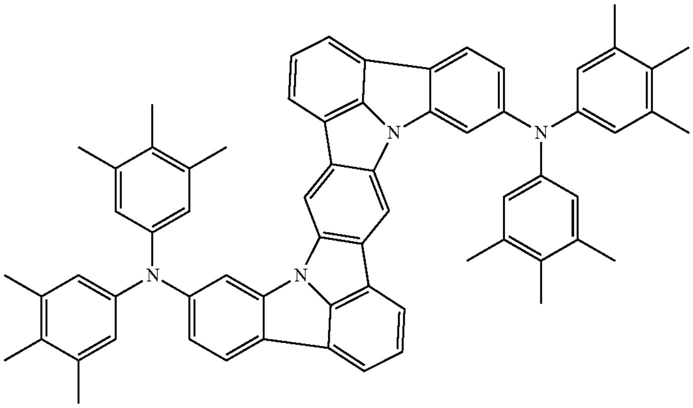

-continued
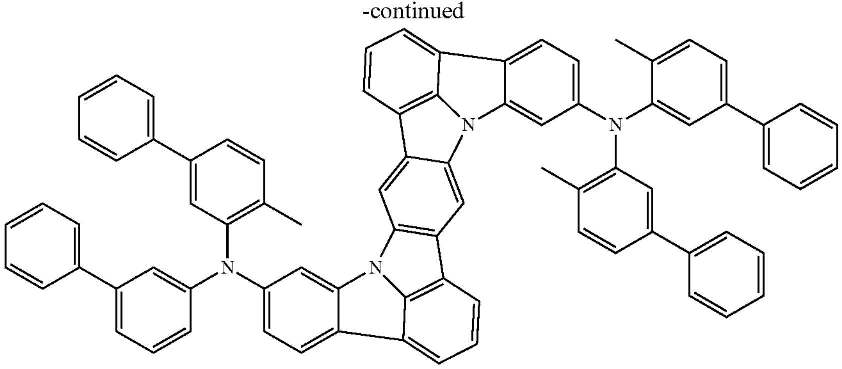
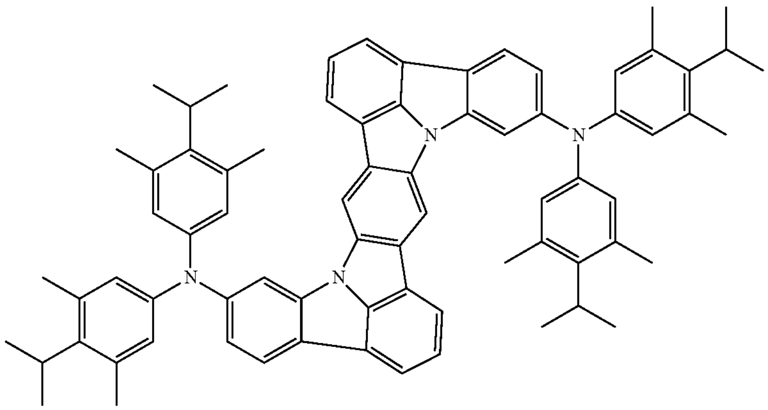
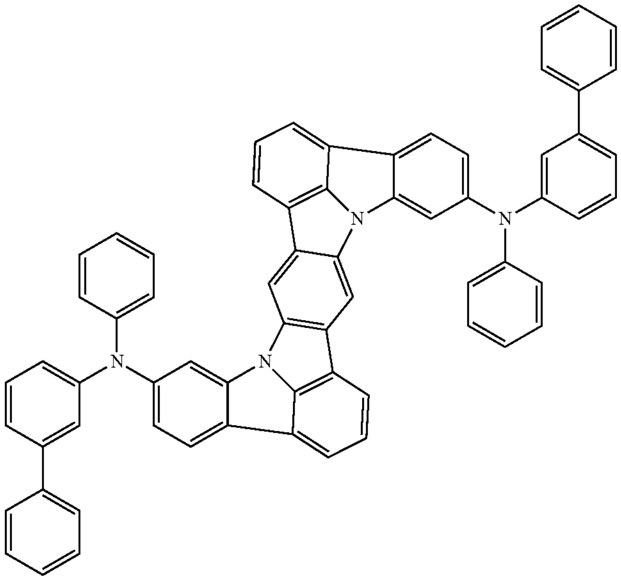

-continued
[Formula 344]
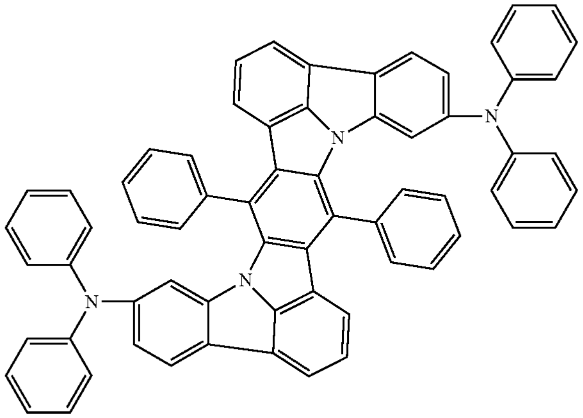
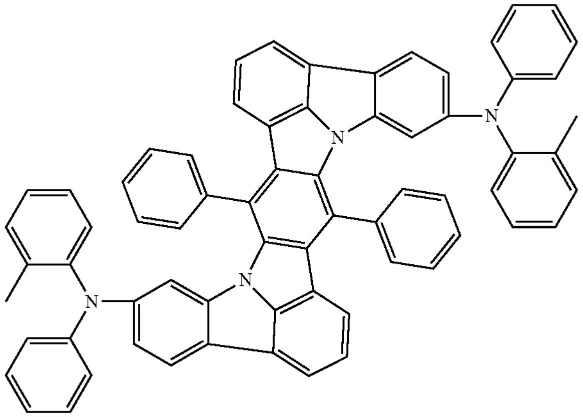
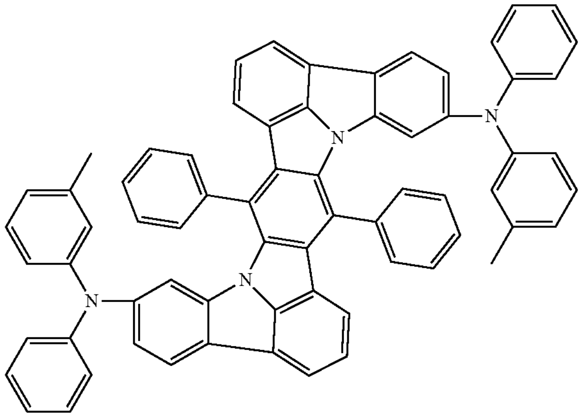
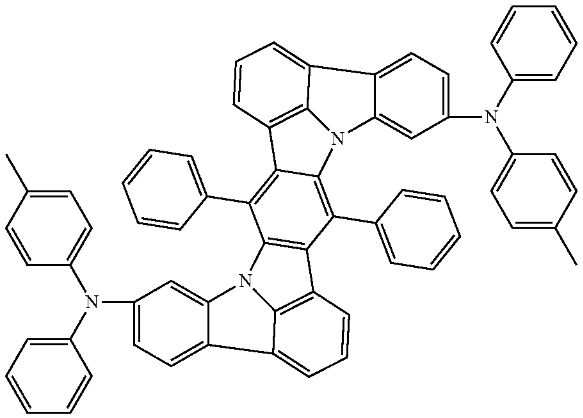

-continued
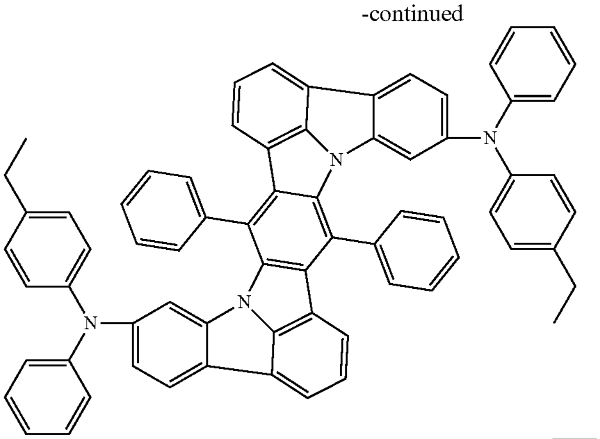
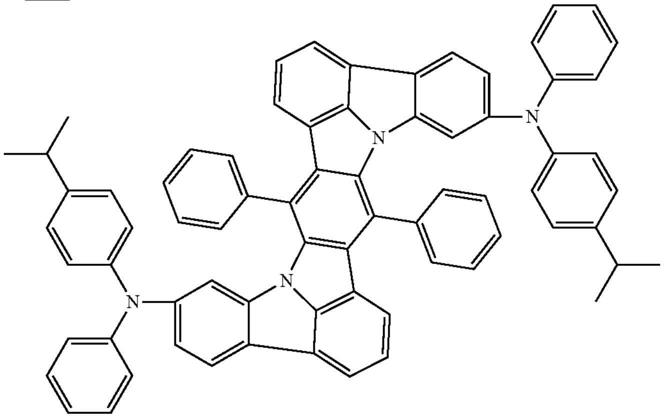
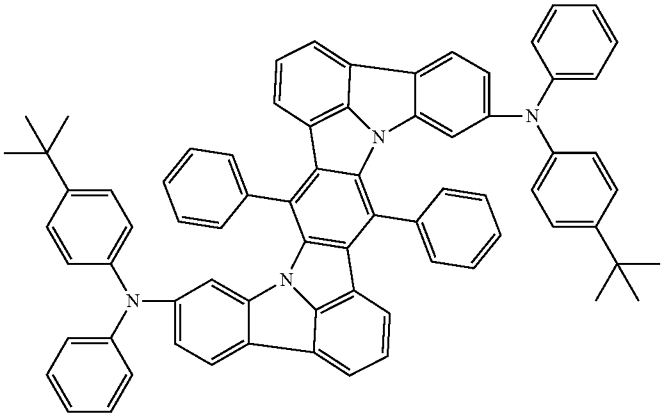
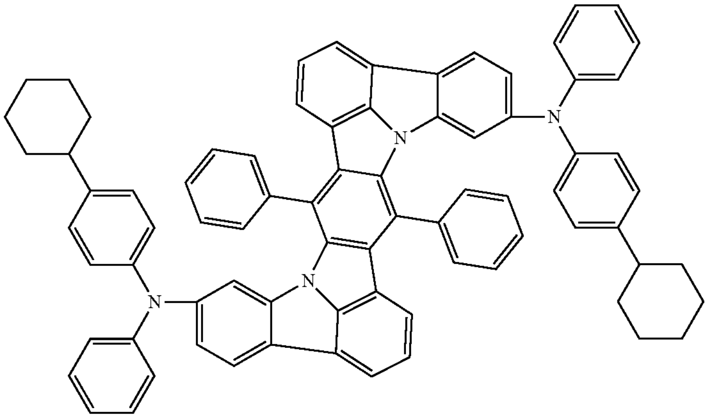

-continued
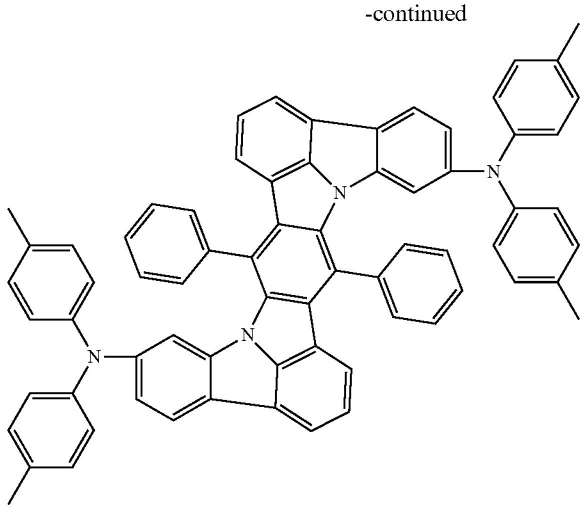
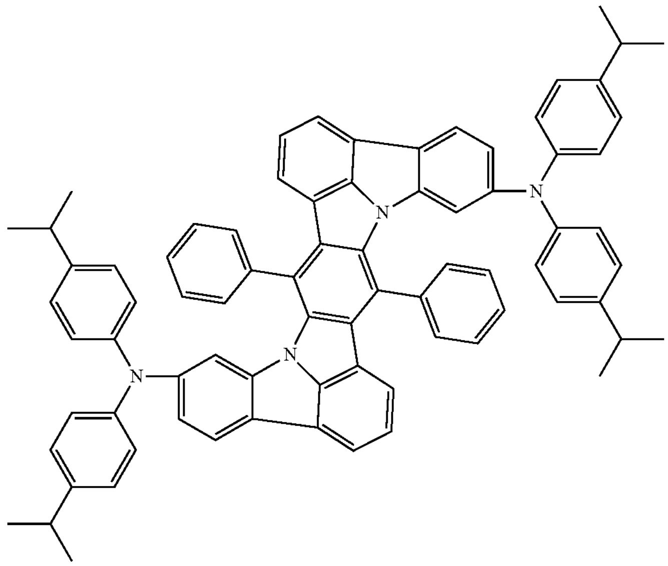
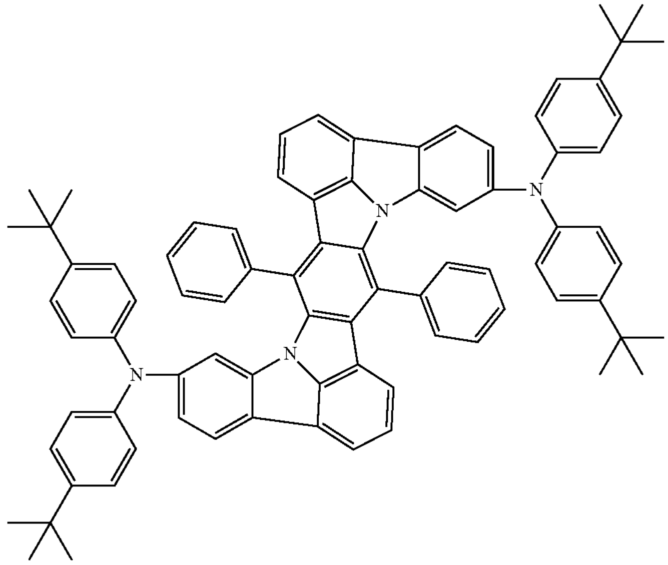

-continued
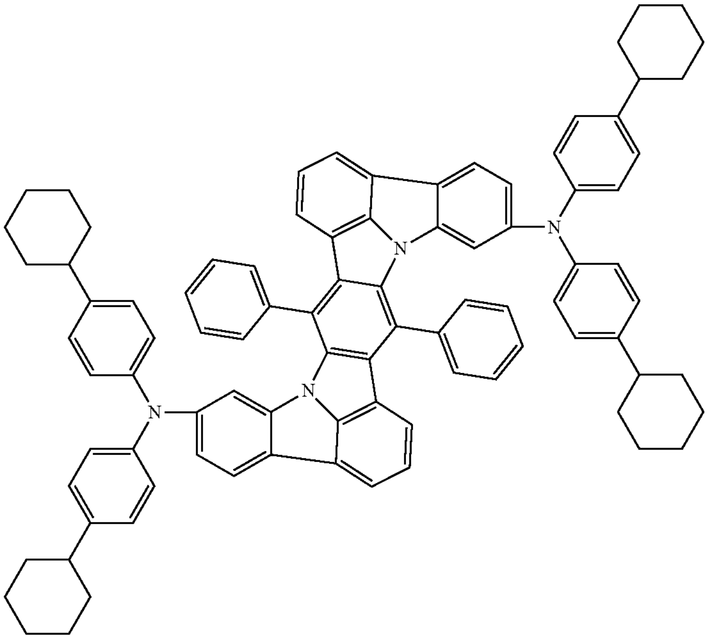
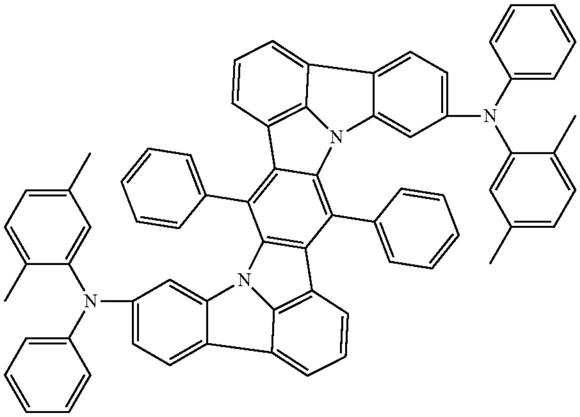
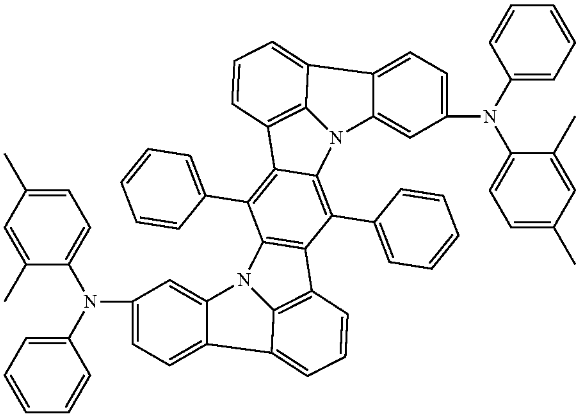

-continued
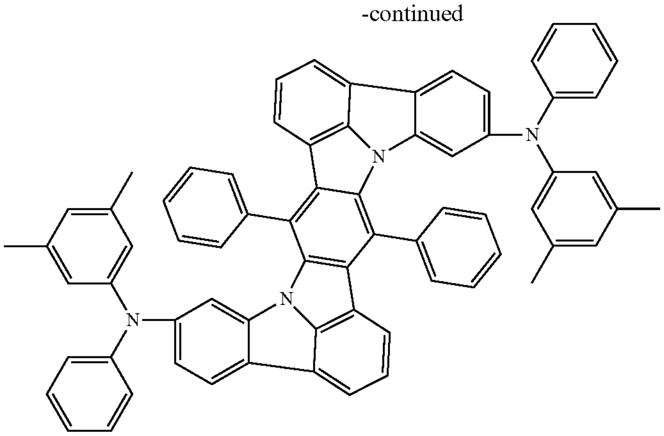
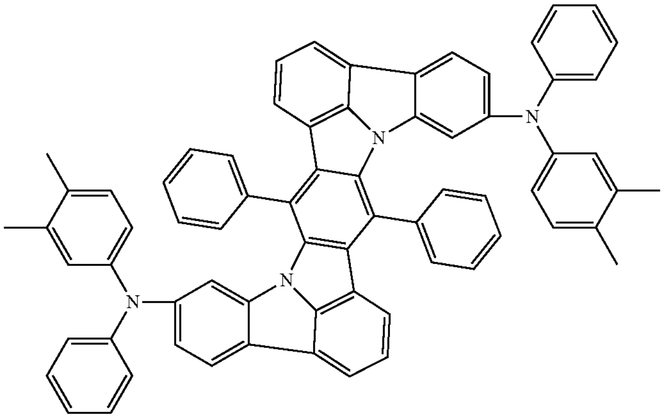
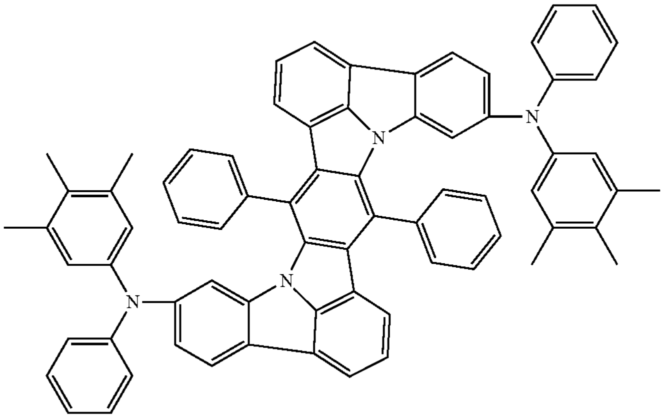

-continued
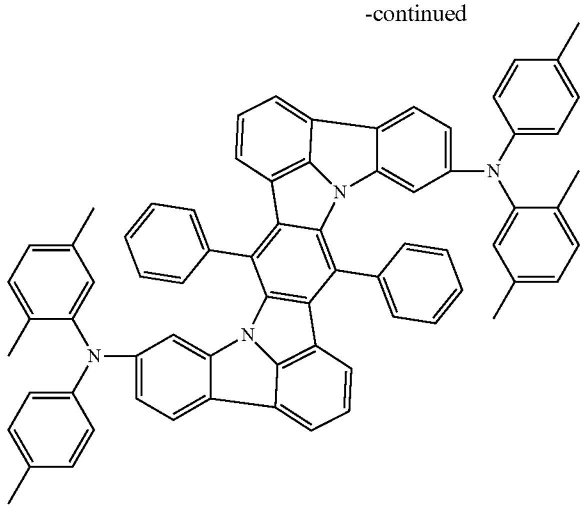
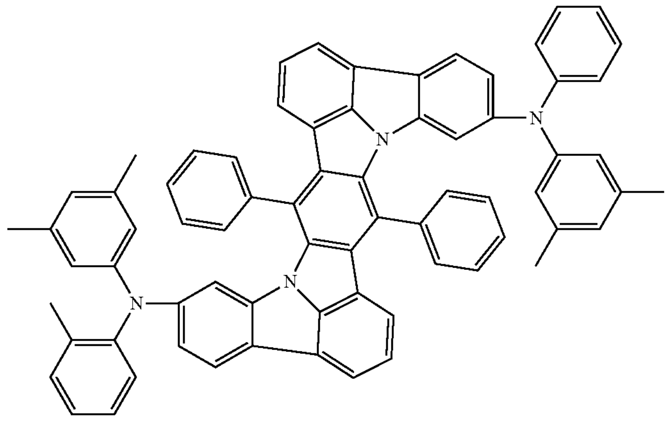
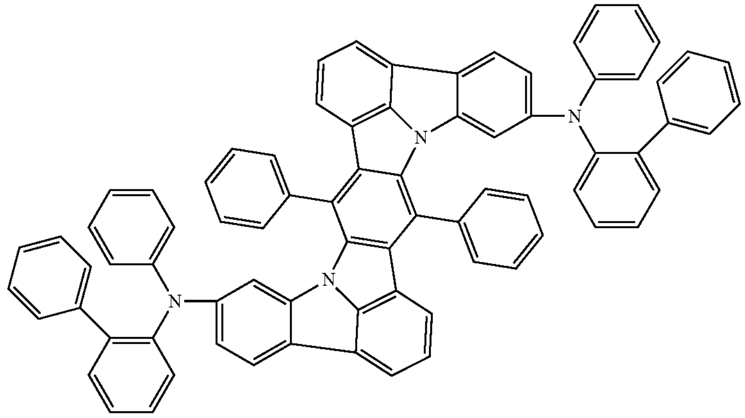

-continued
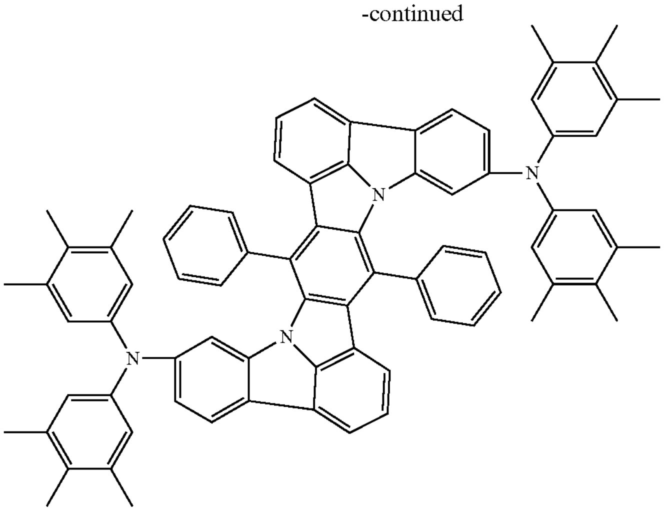
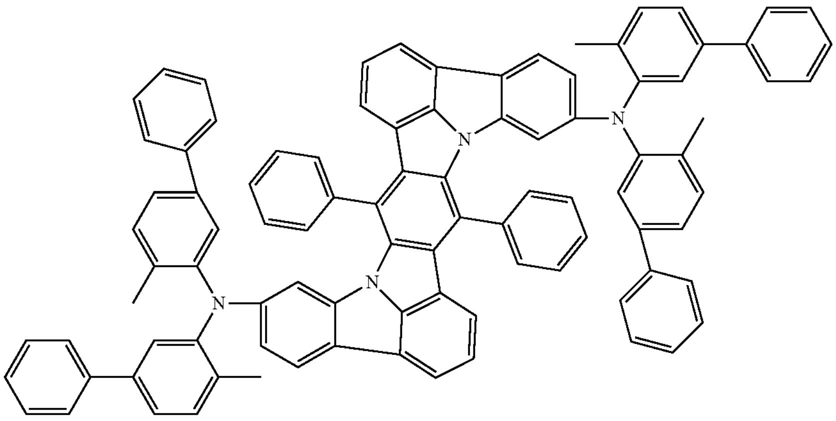
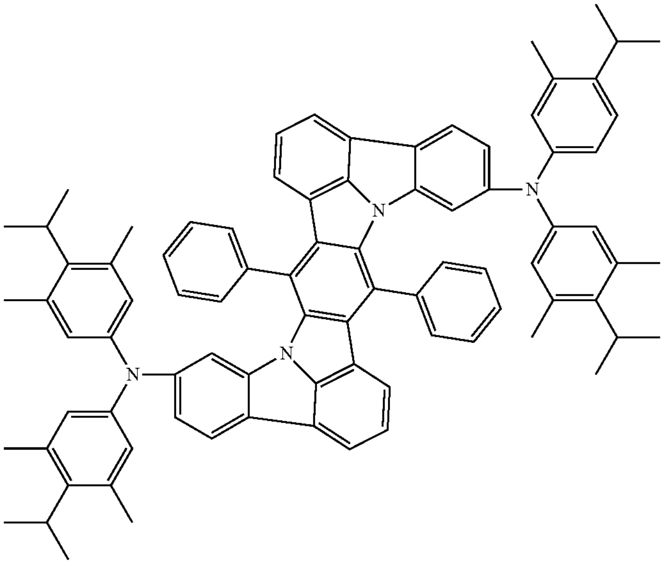

-continued
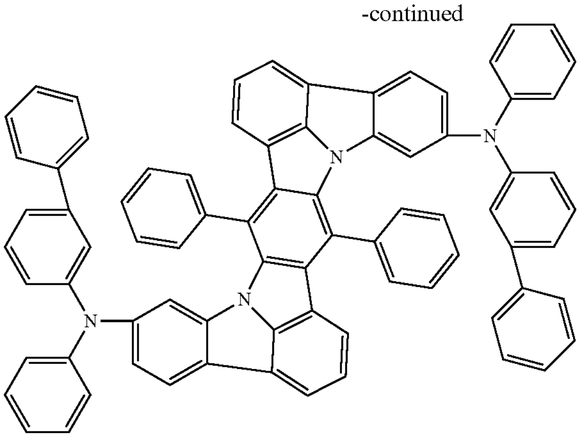
[Formula 345]
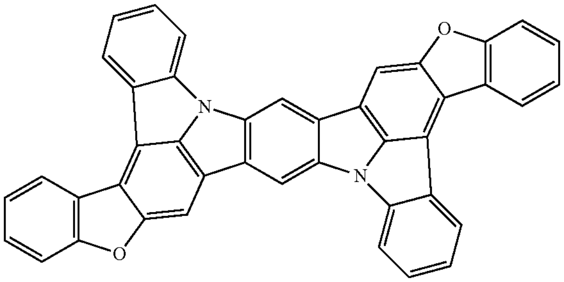
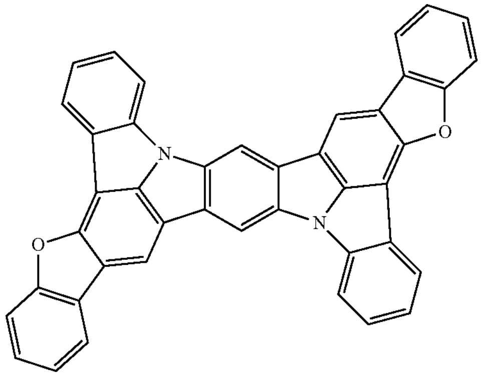
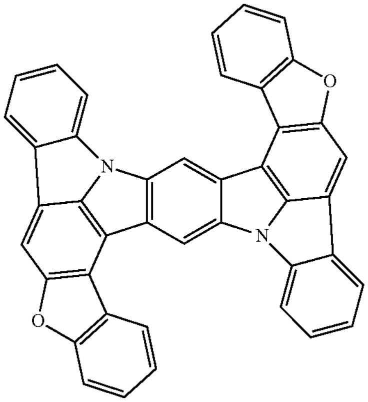
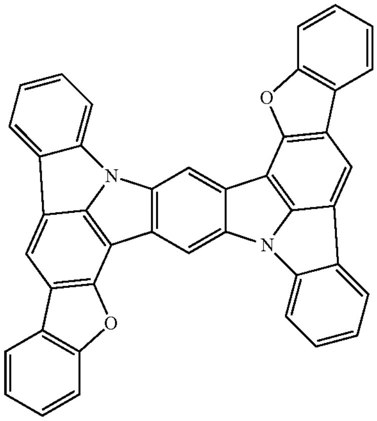
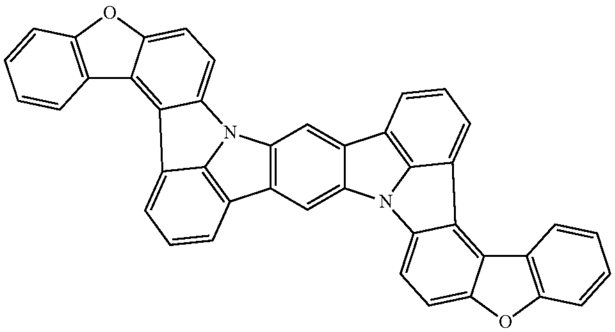

-continued
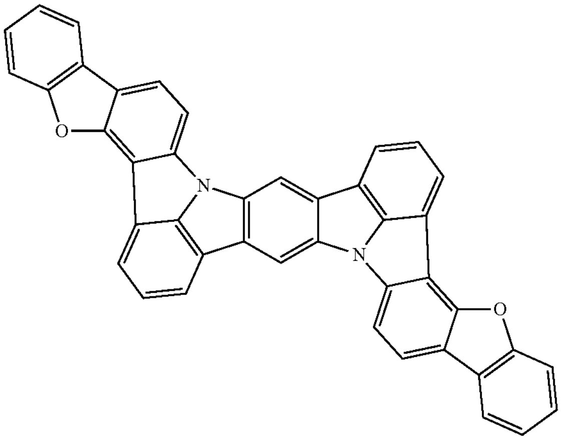
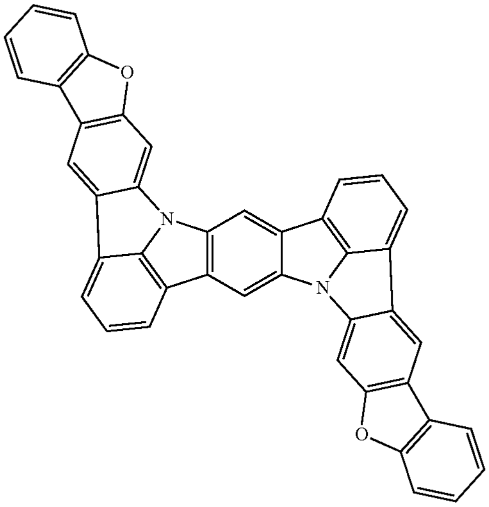
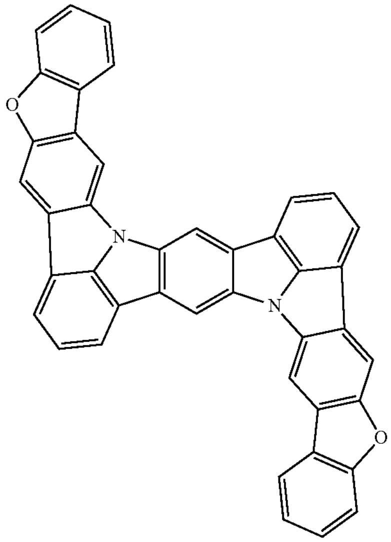
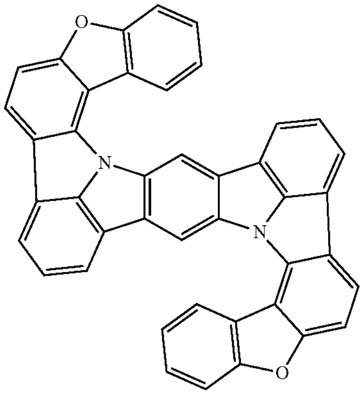
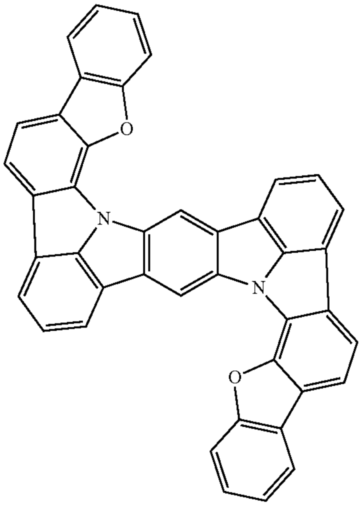
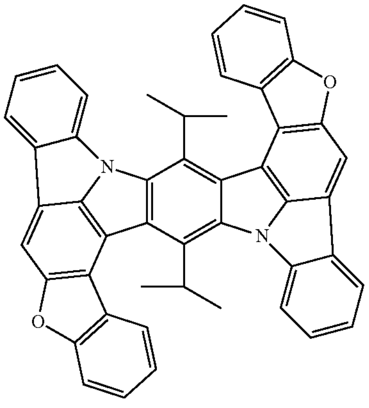
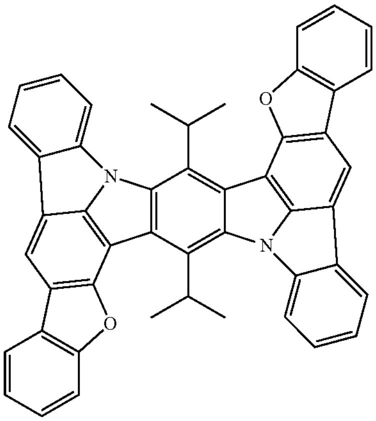

-continued
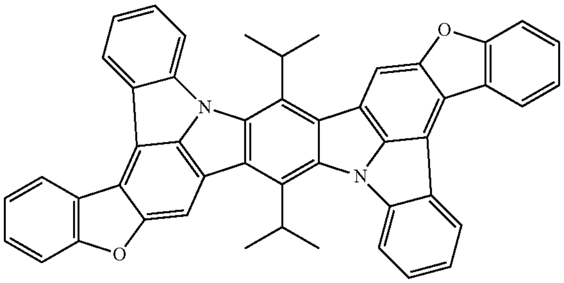
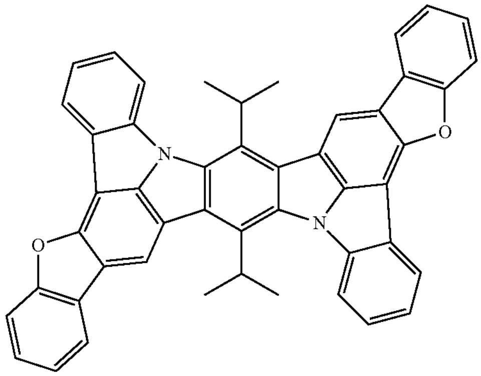
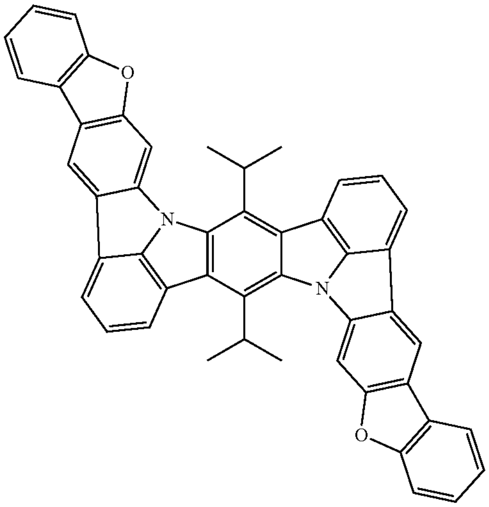
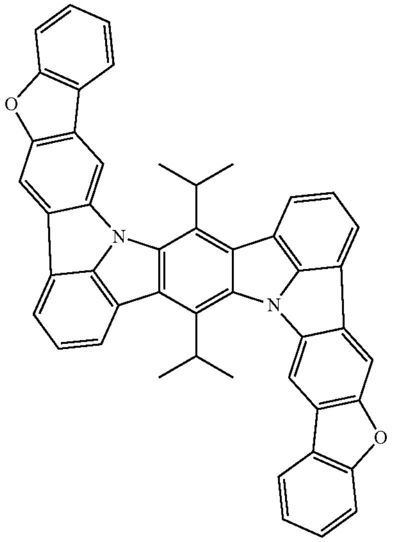
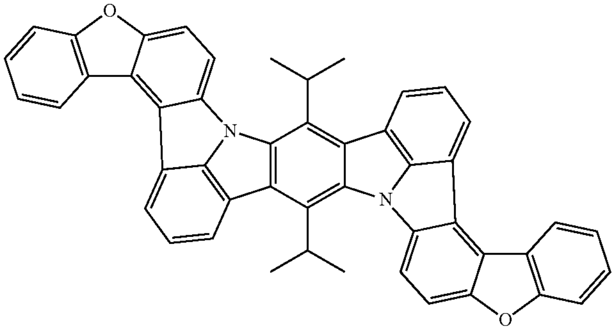
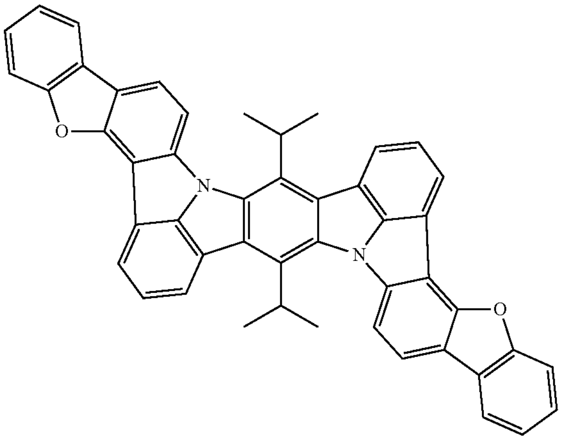
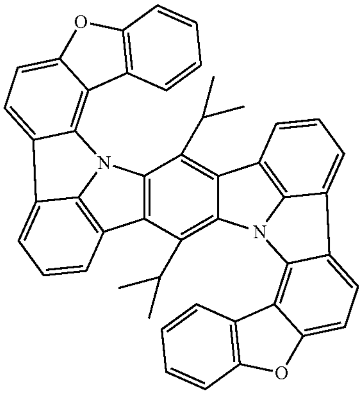

-continued
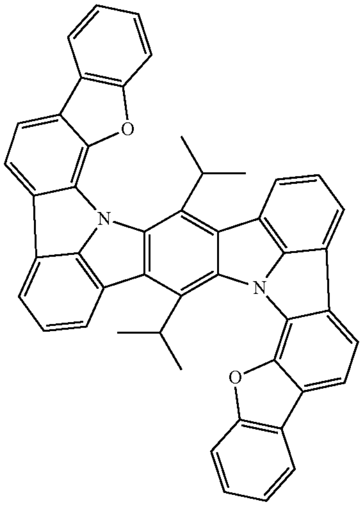
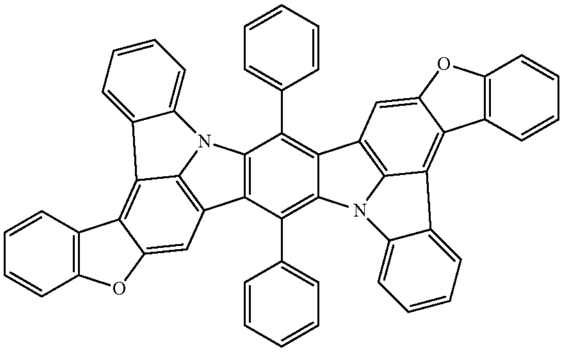
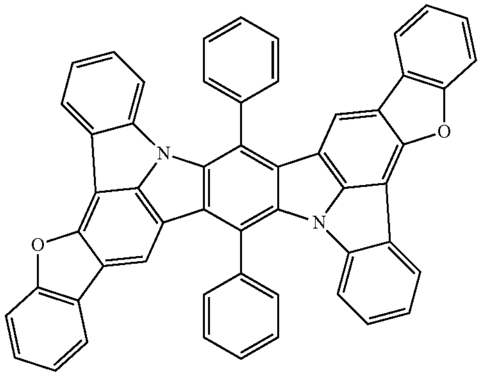
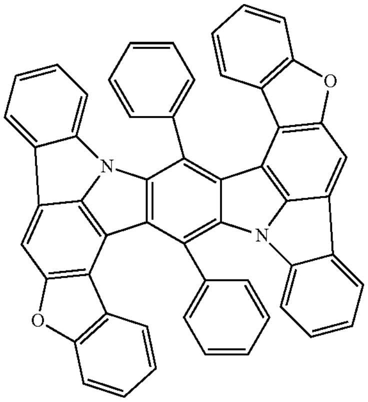
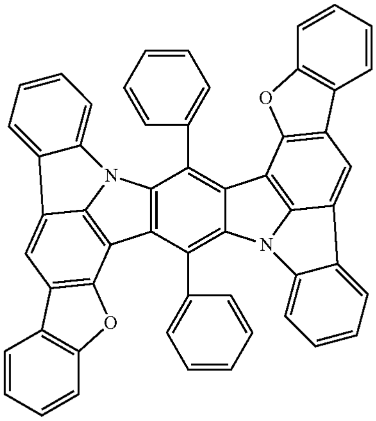
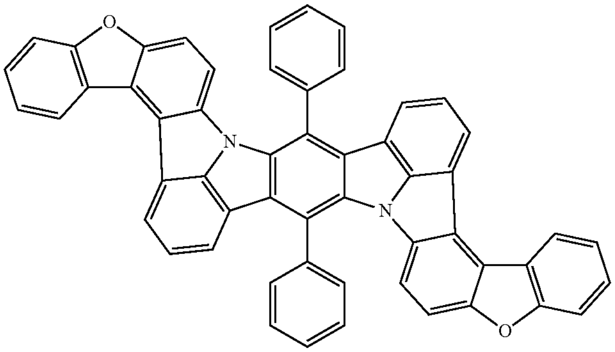

-continued
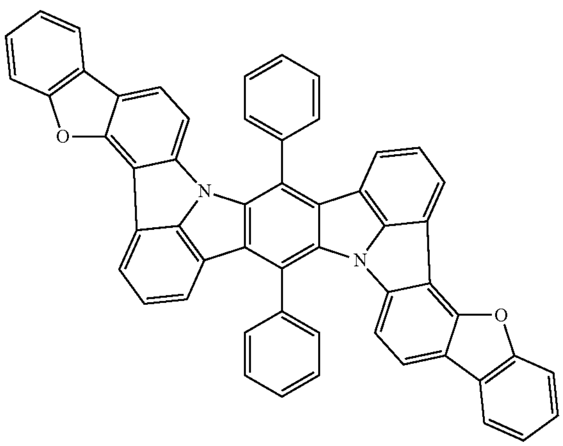
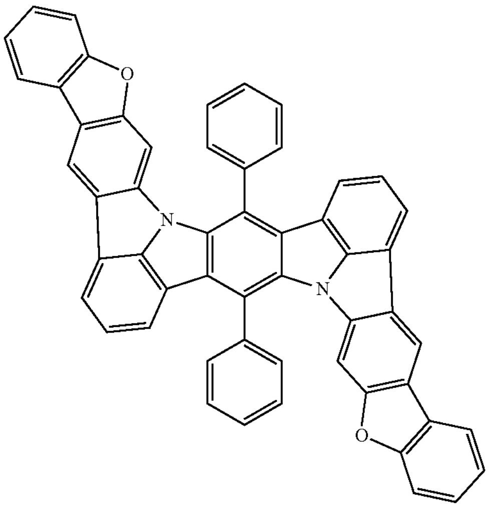
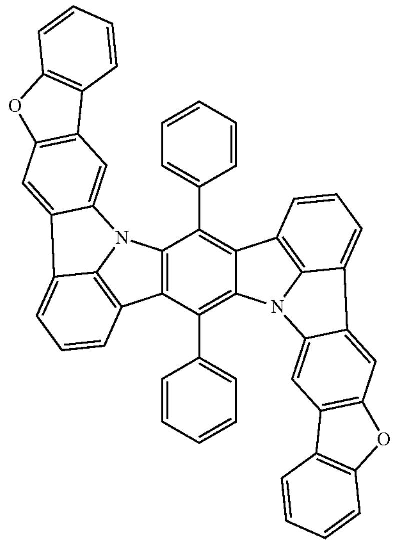
[Formula 346]
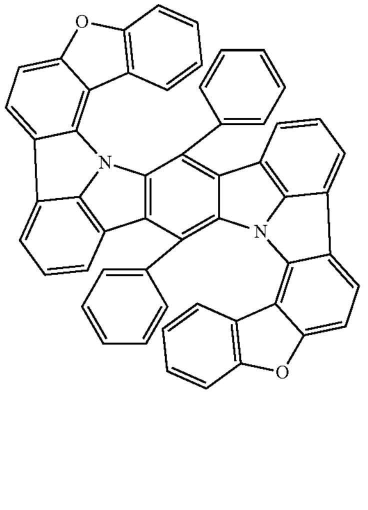
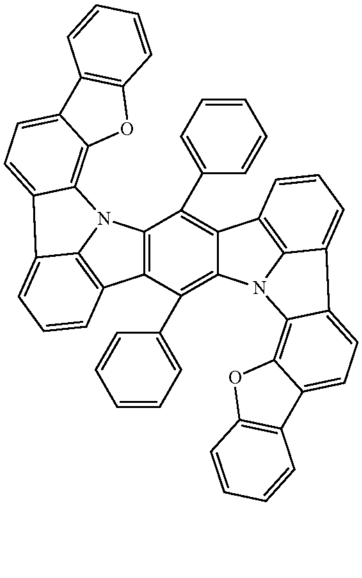

-continued
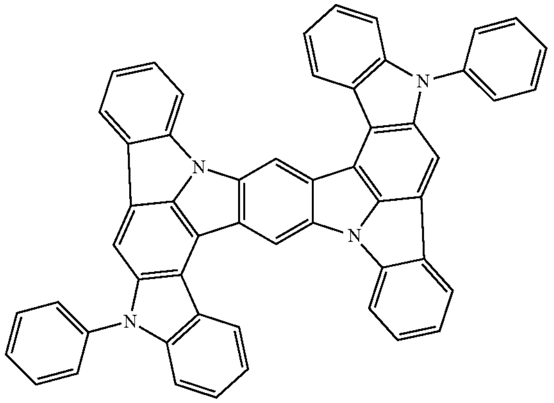
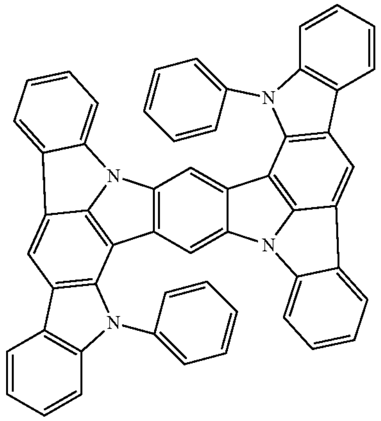
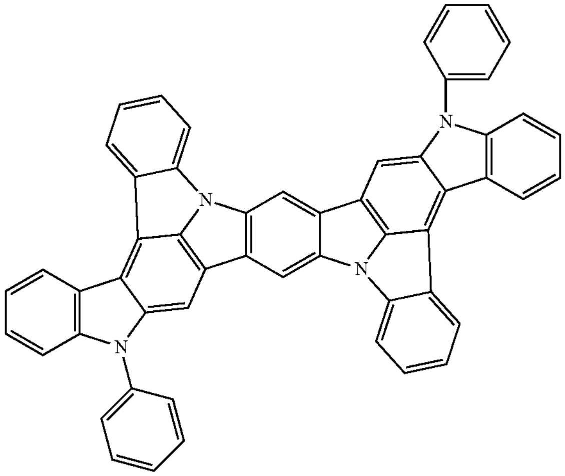
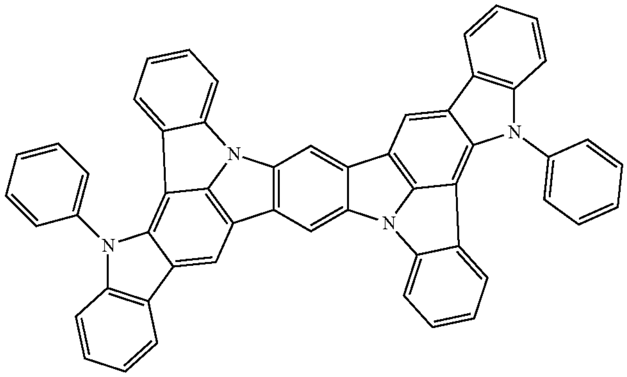
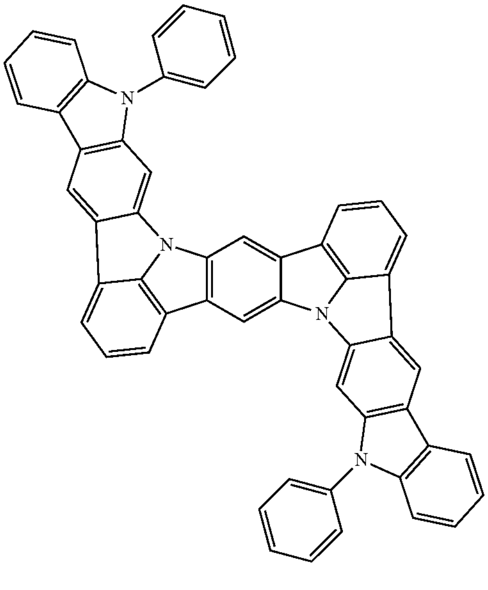

-continued
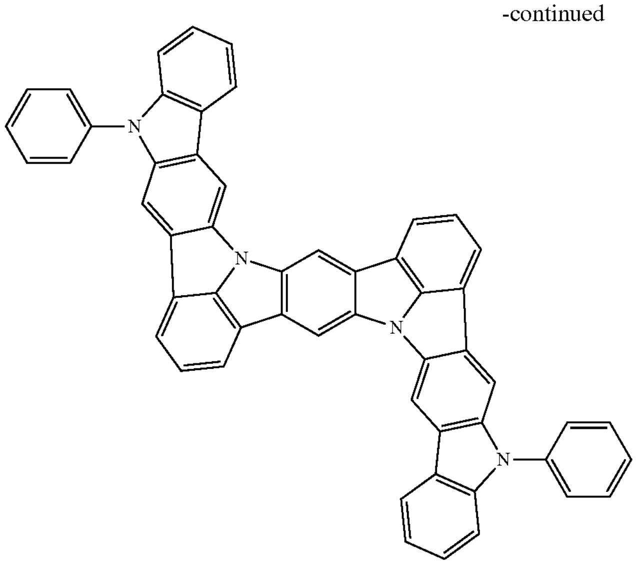
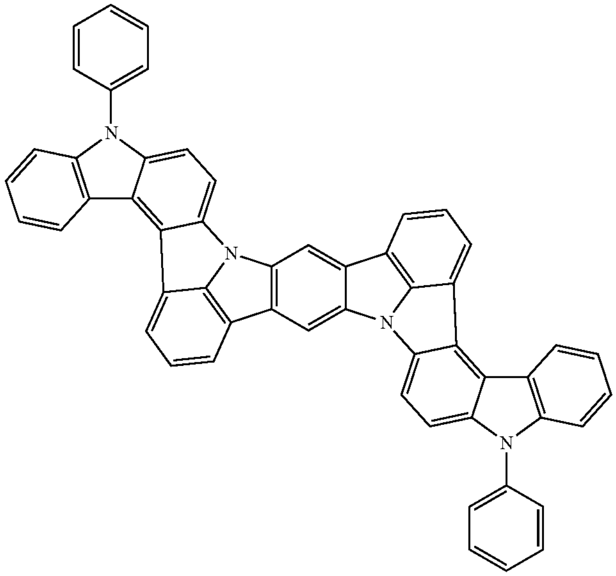
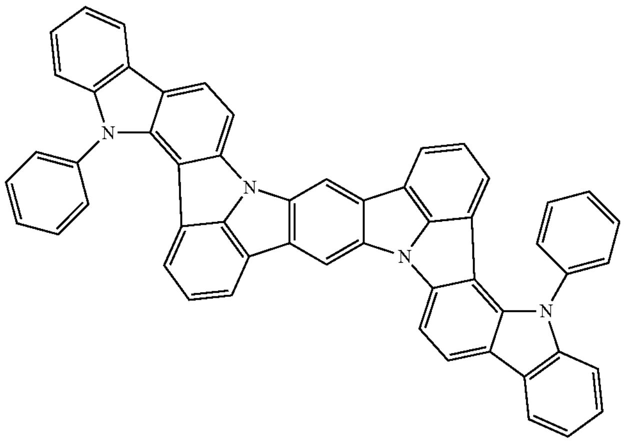
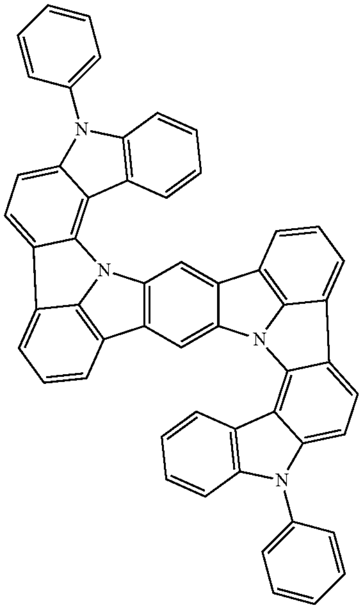

-continued
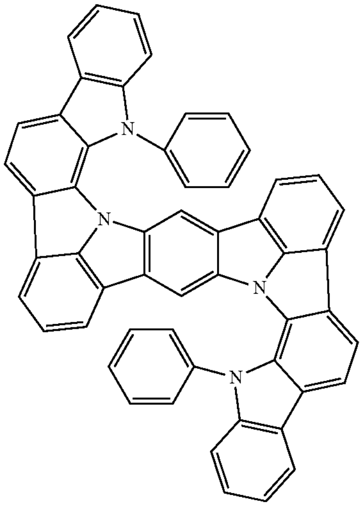
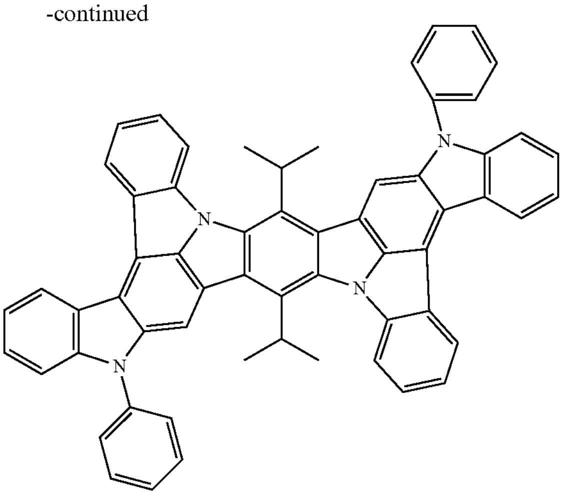
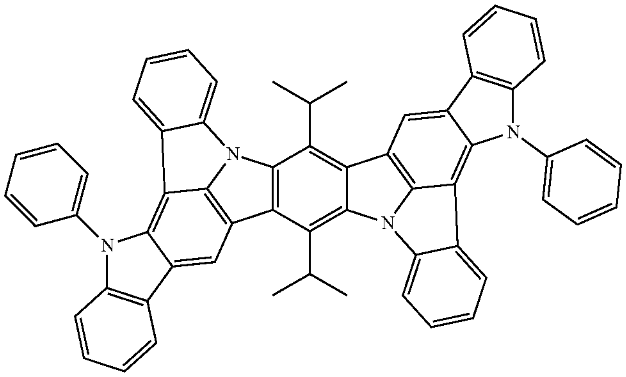
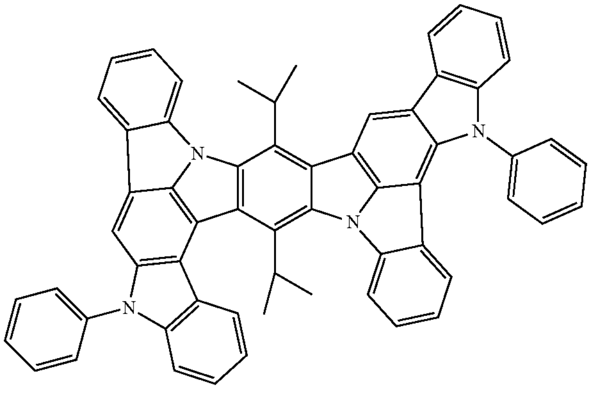
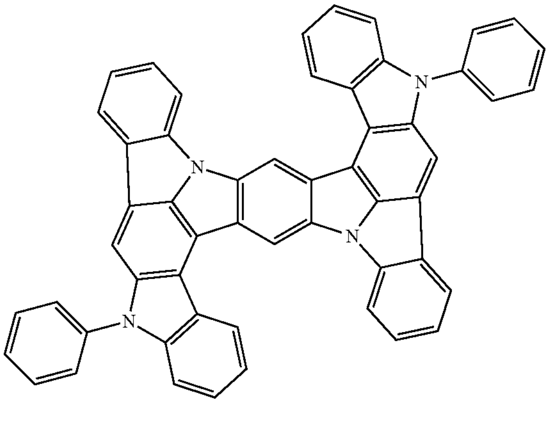

-continued
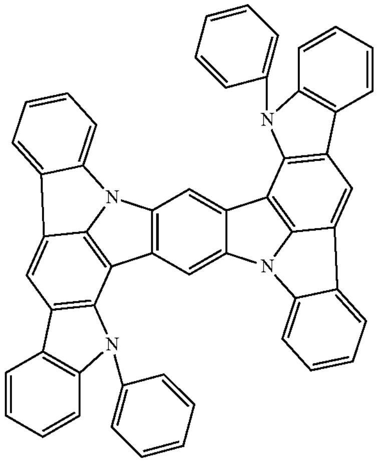
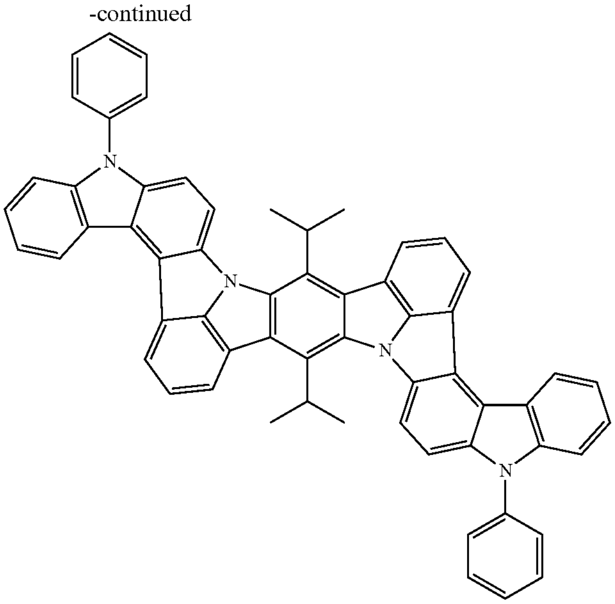
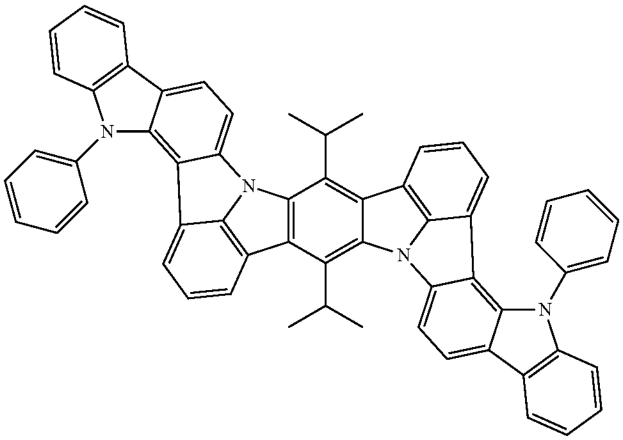
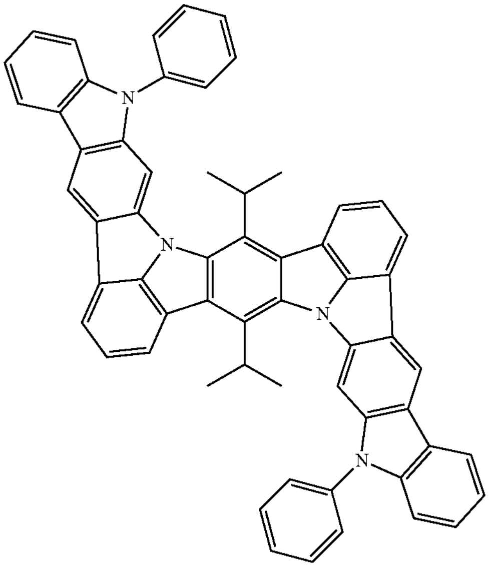

-continued
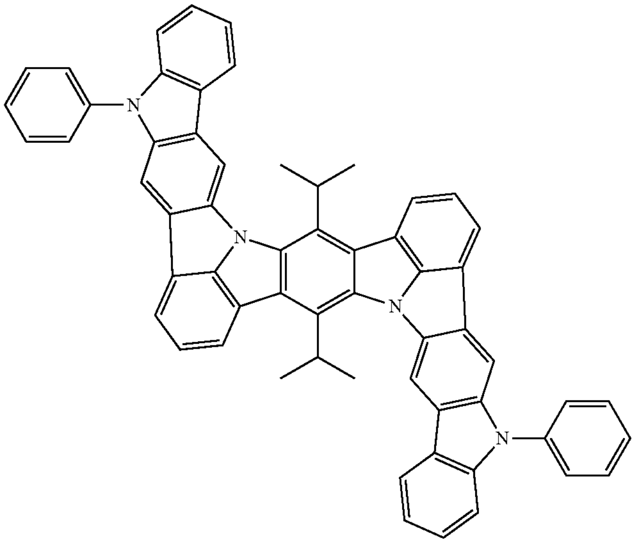
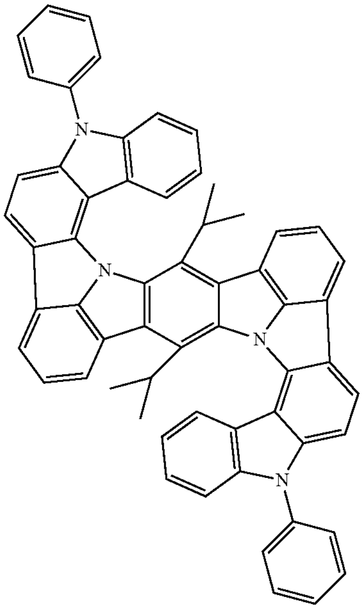
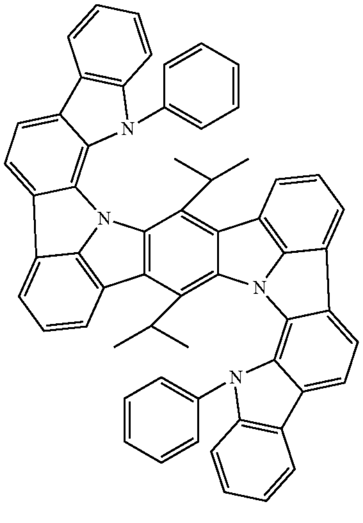
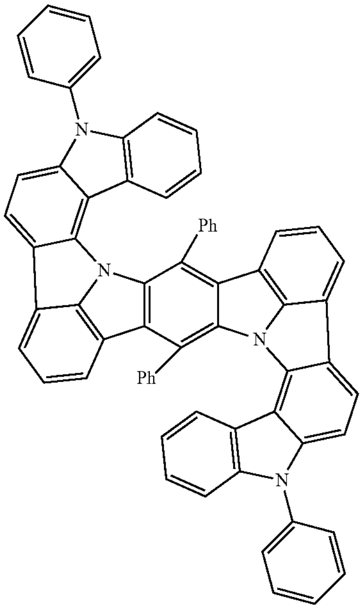
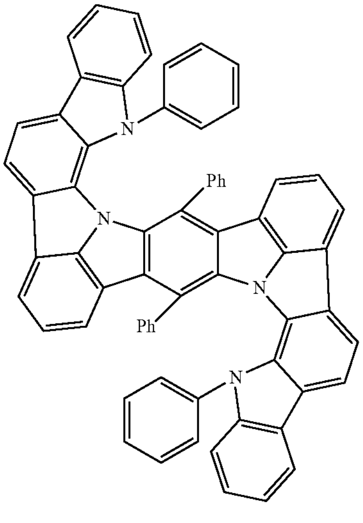
(In the formulae, Ph is a phenyl group.)

-continued
[Formula 347]
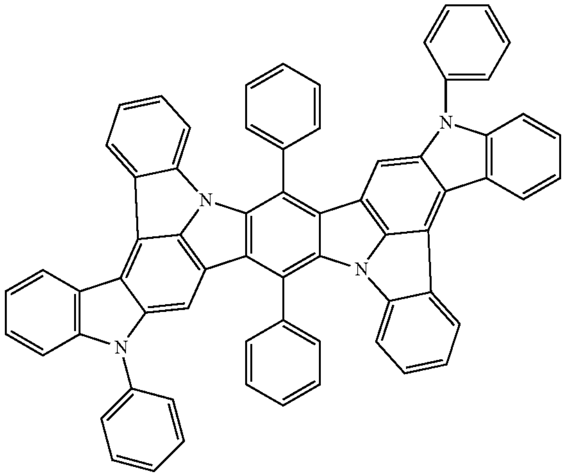
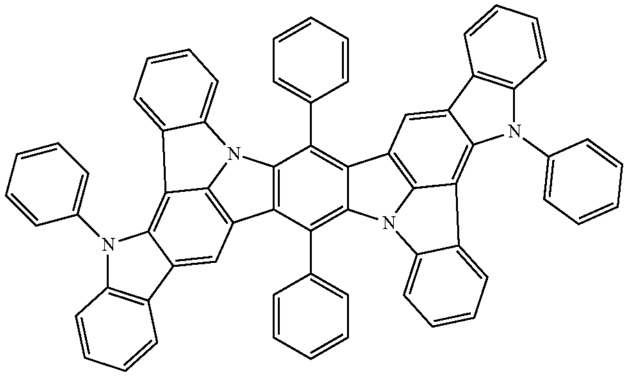
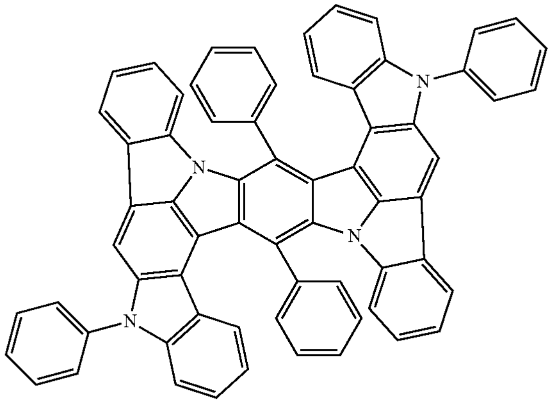
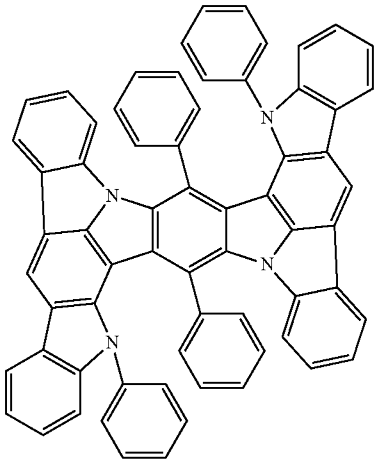

-continued
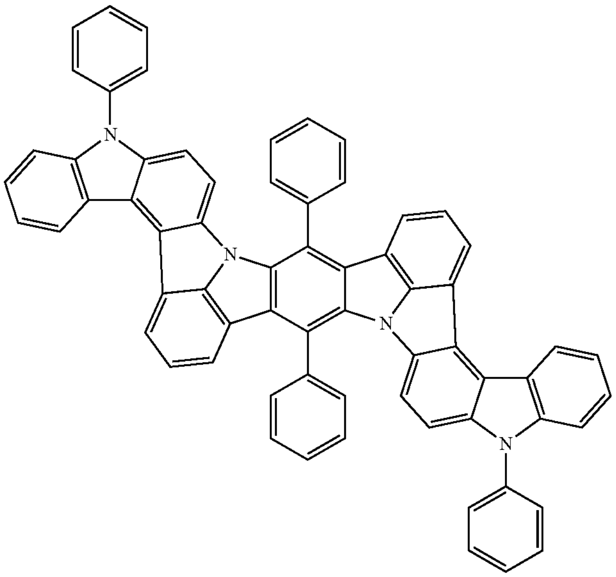
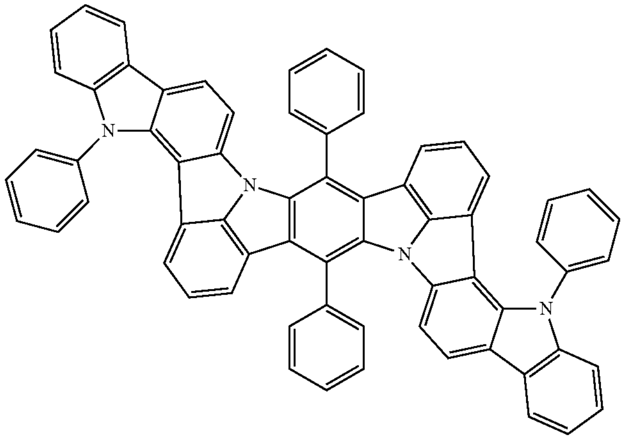
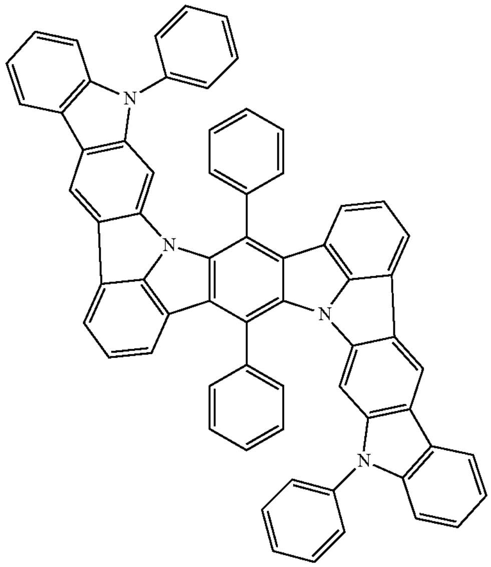
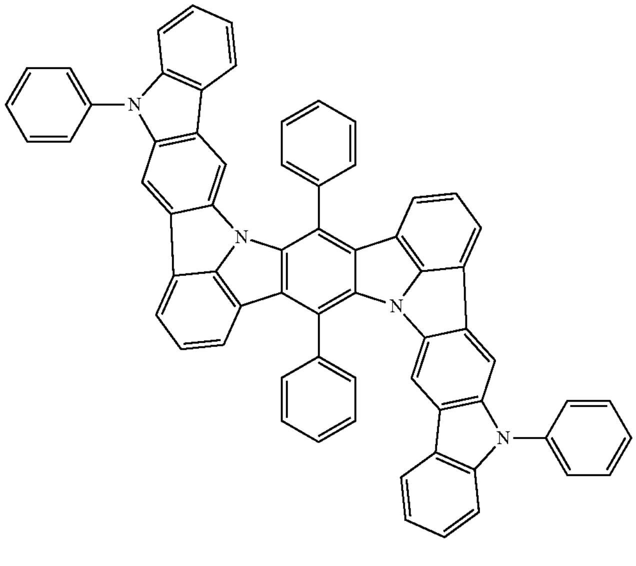

-continued
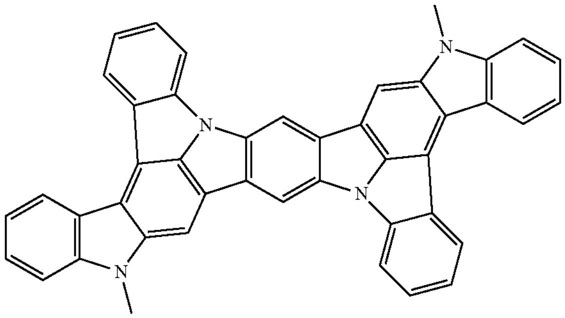
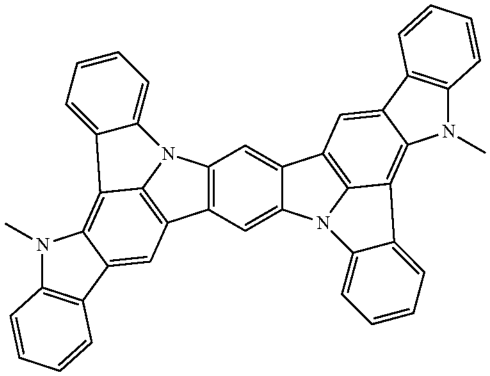
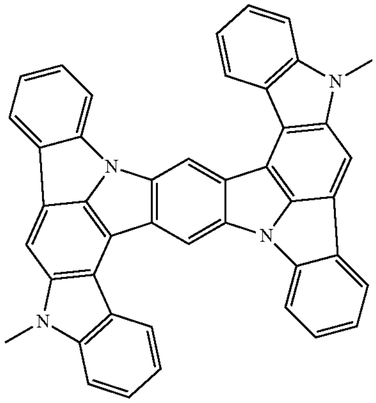
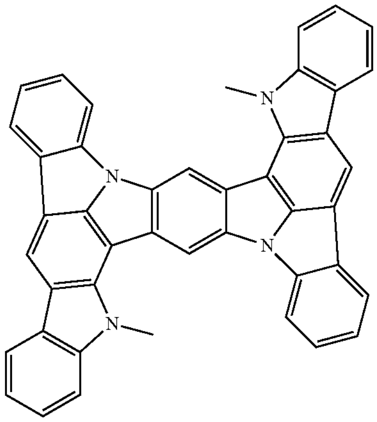
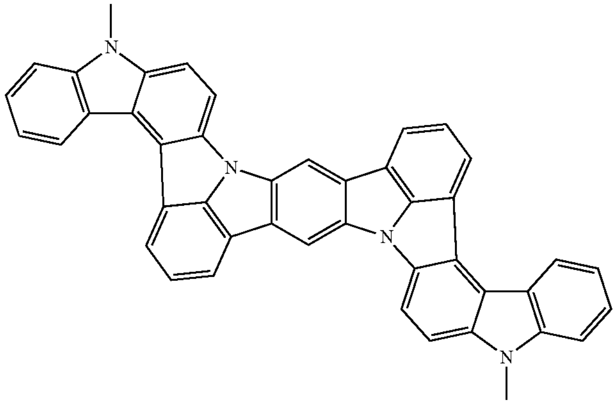
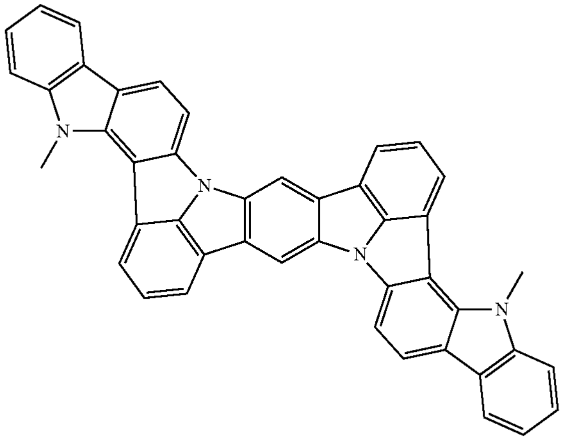
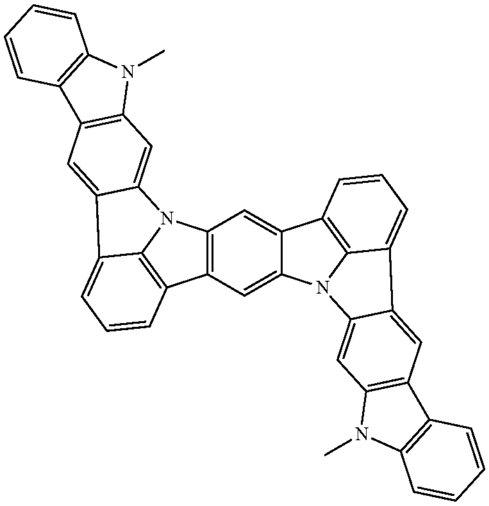

-continued
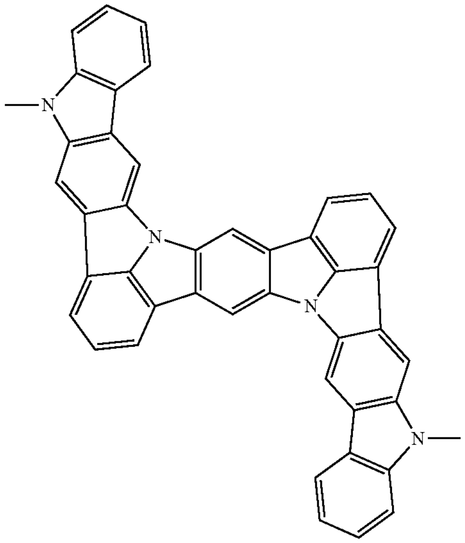
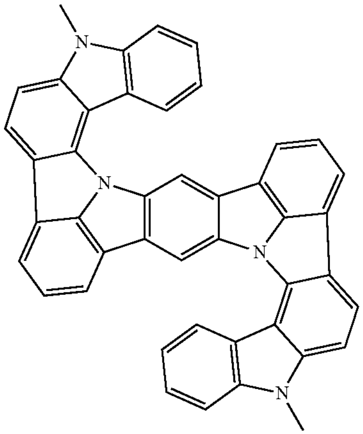
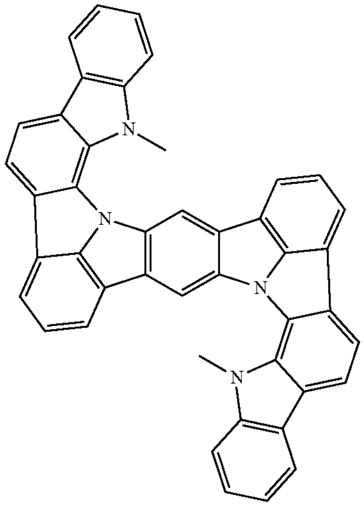
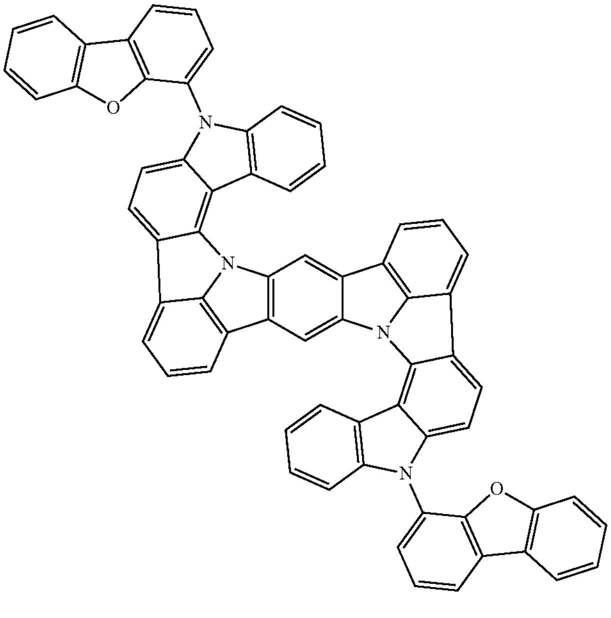

-continued
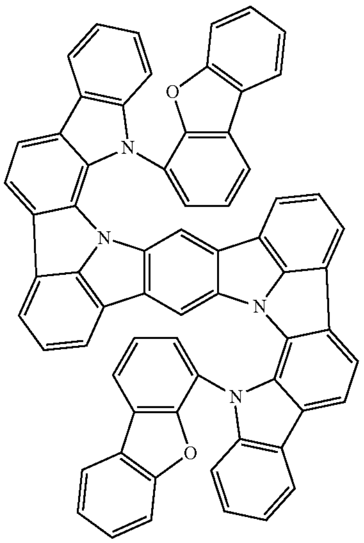
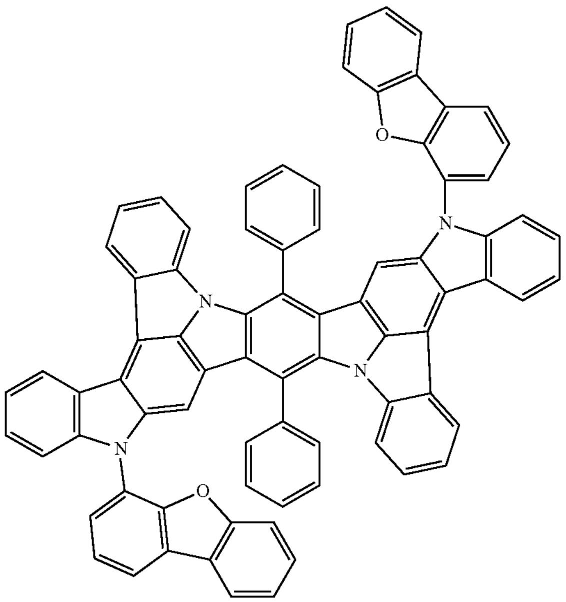
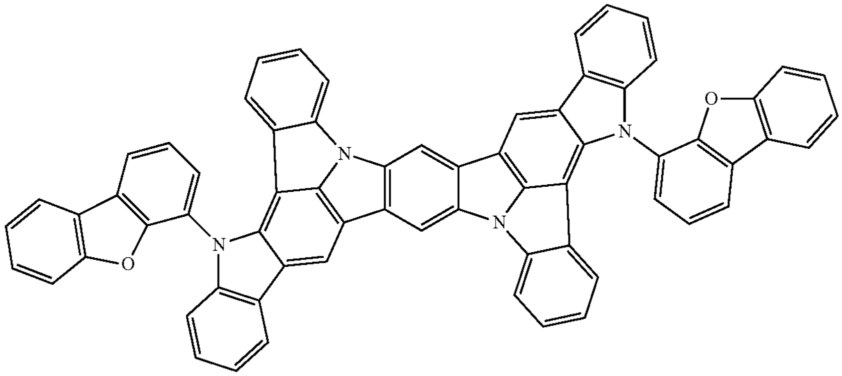
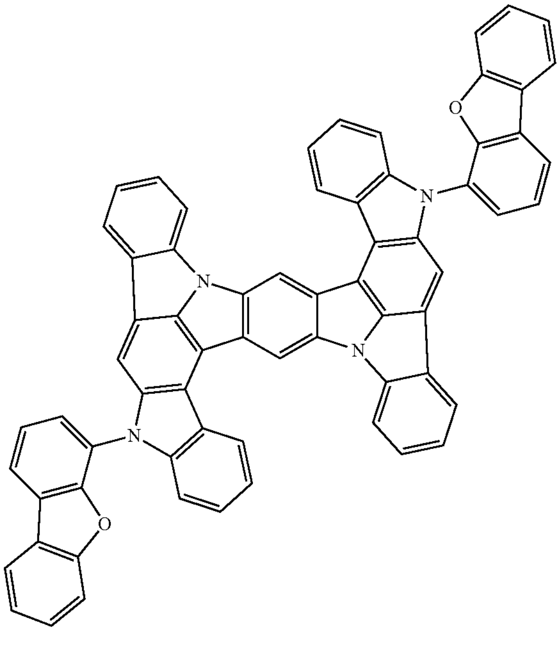
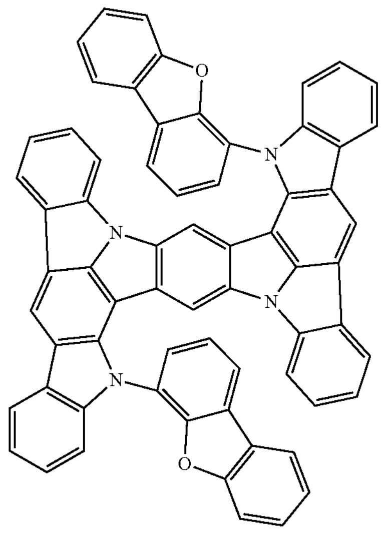

-continued
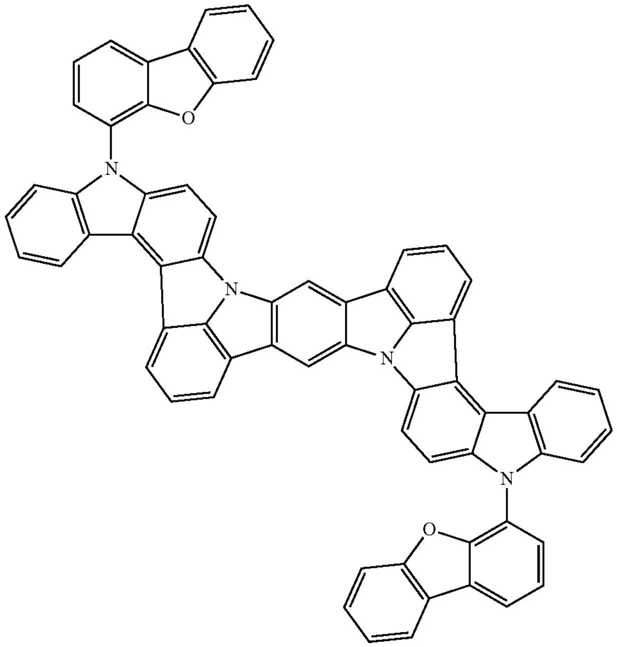
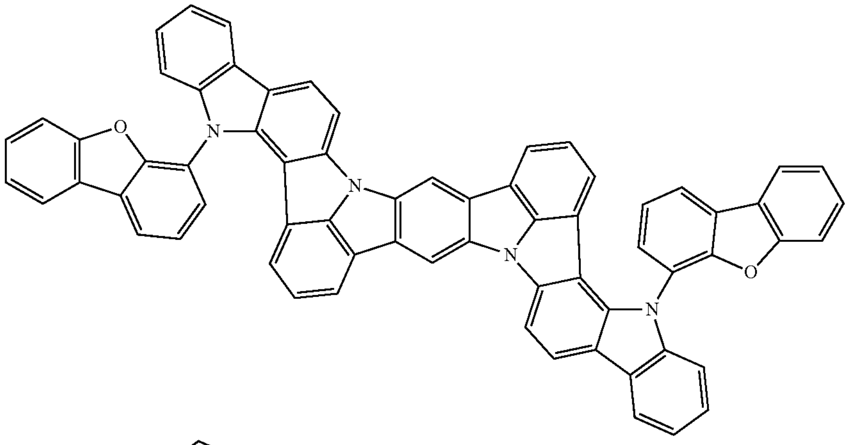
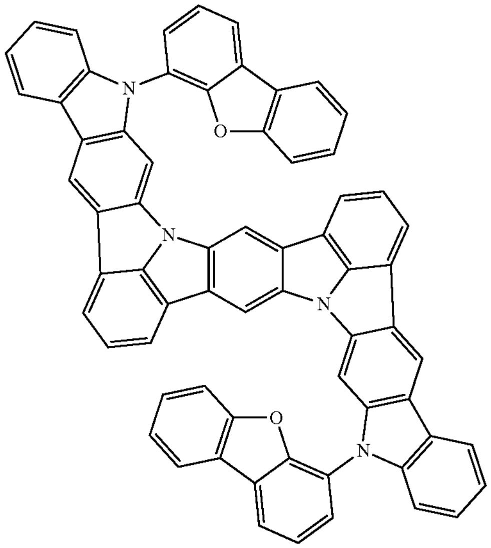

-continued
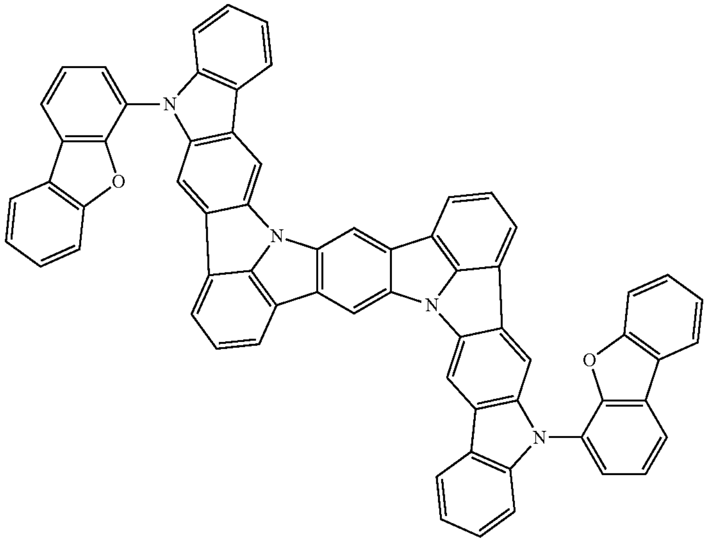
[Formula 348]
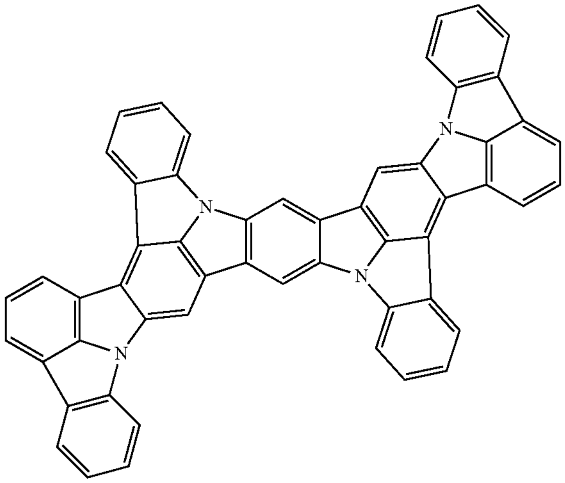
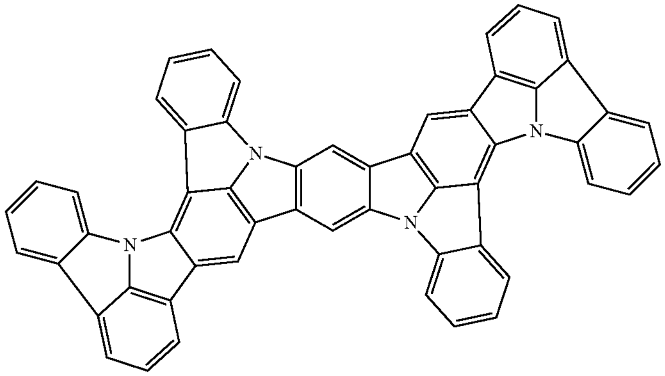

-continued
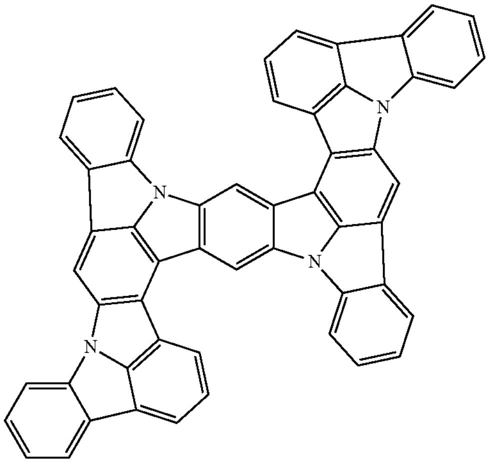
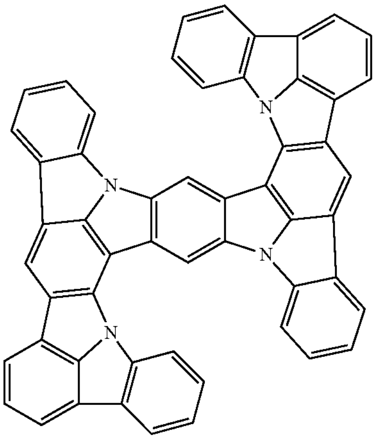
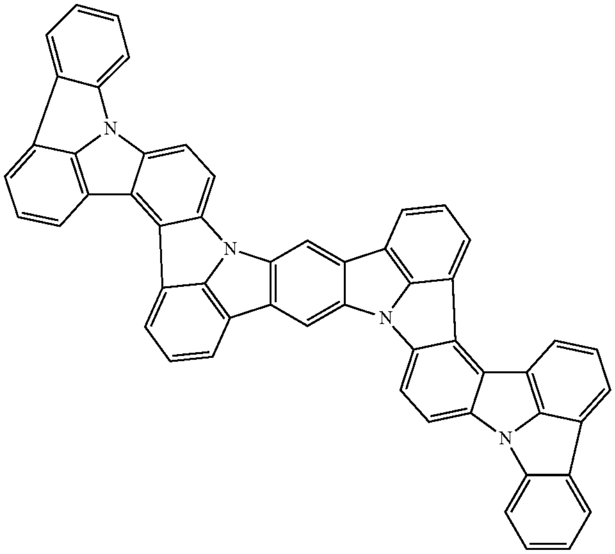
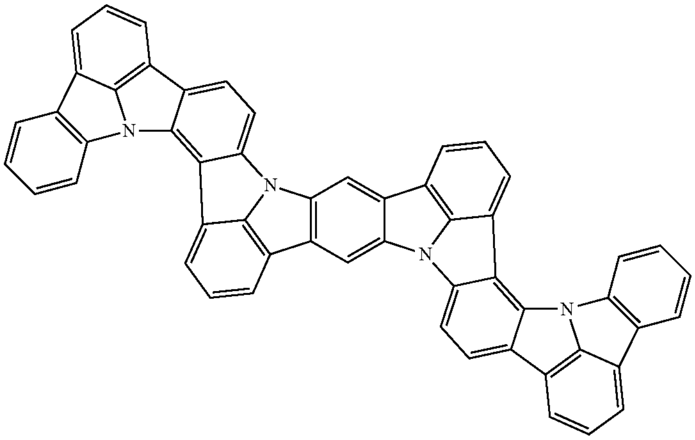

-continued
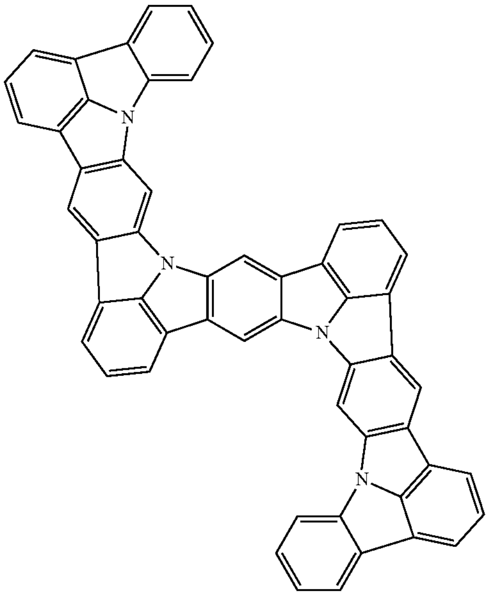
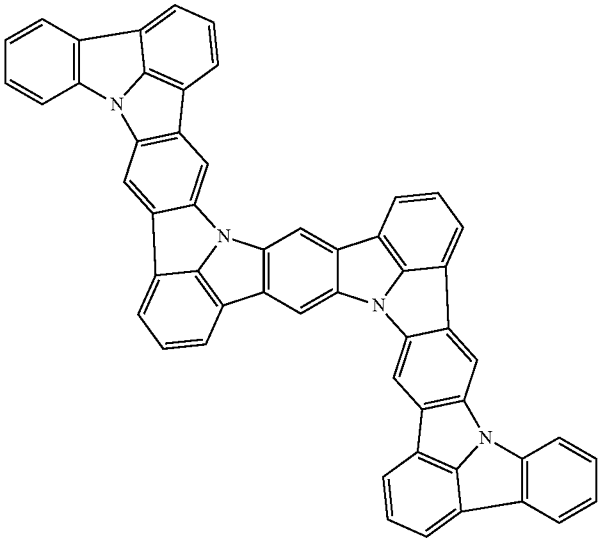
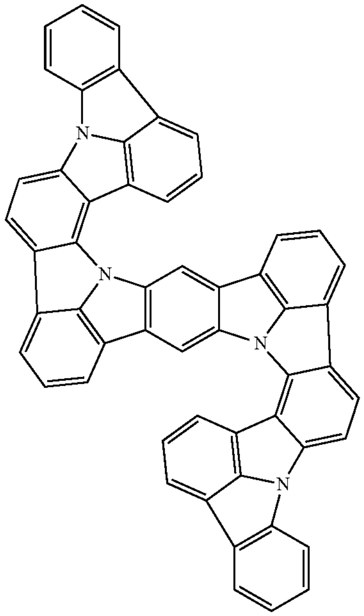
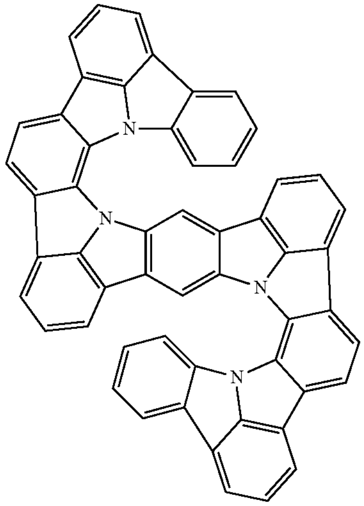
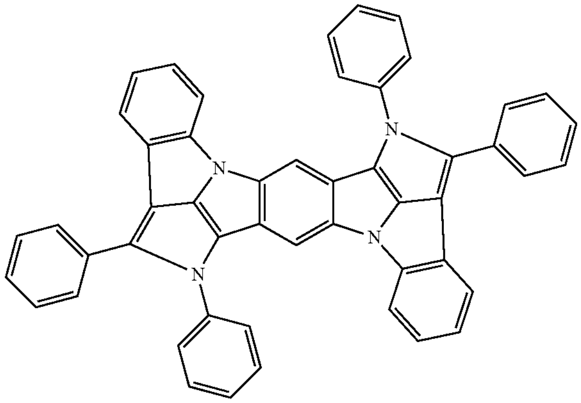
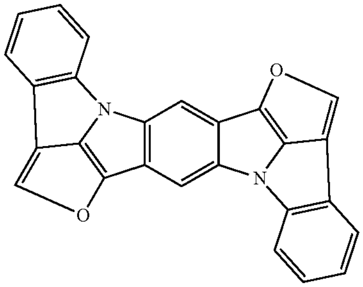

-continued
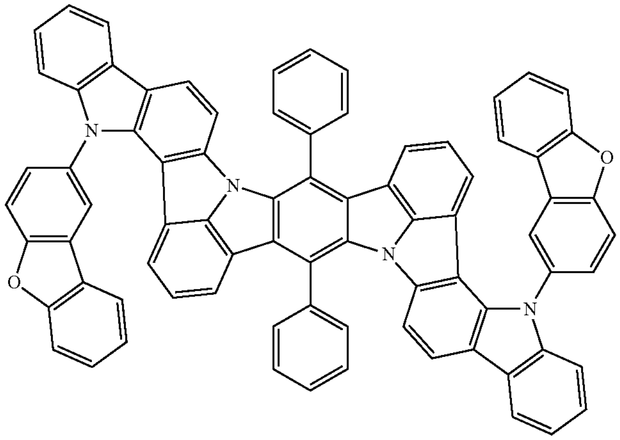
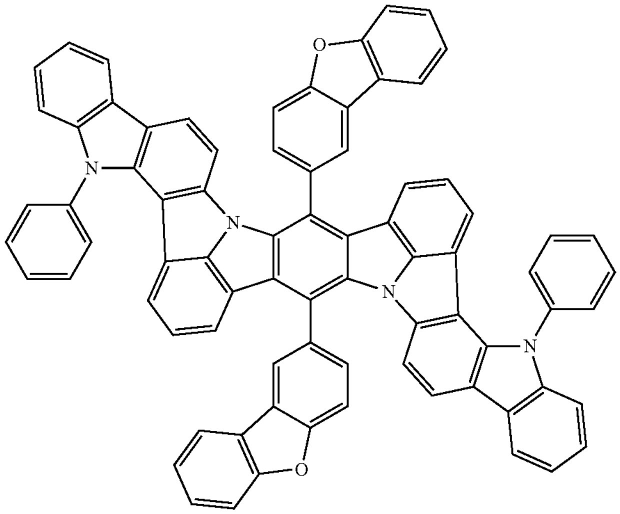
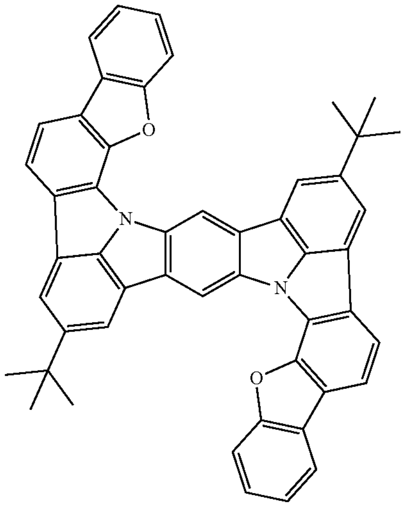
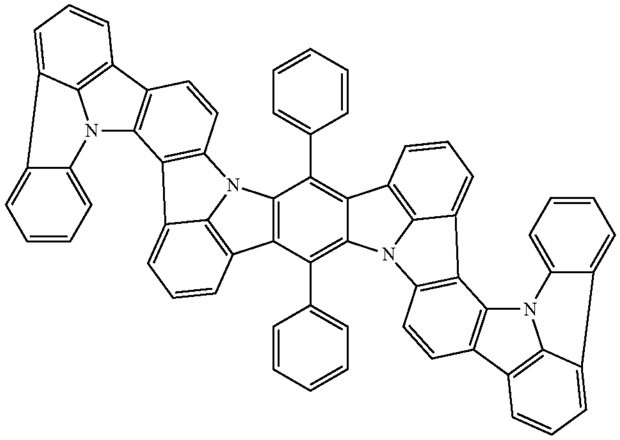

-continued
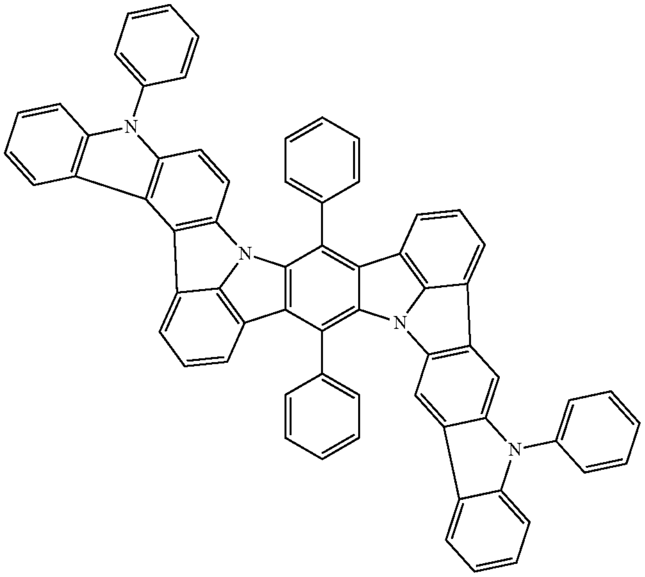
[Formula 349]
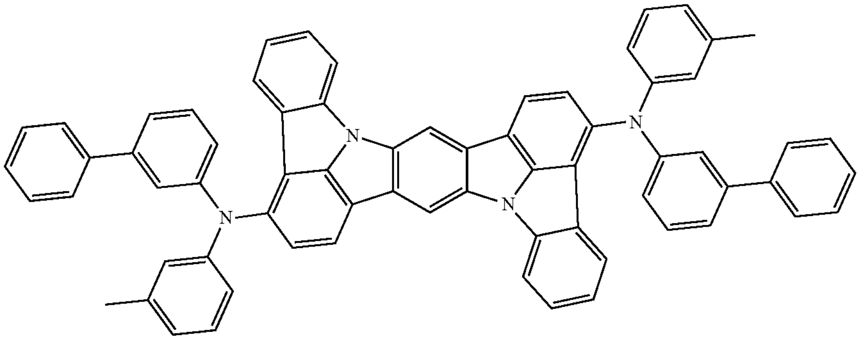
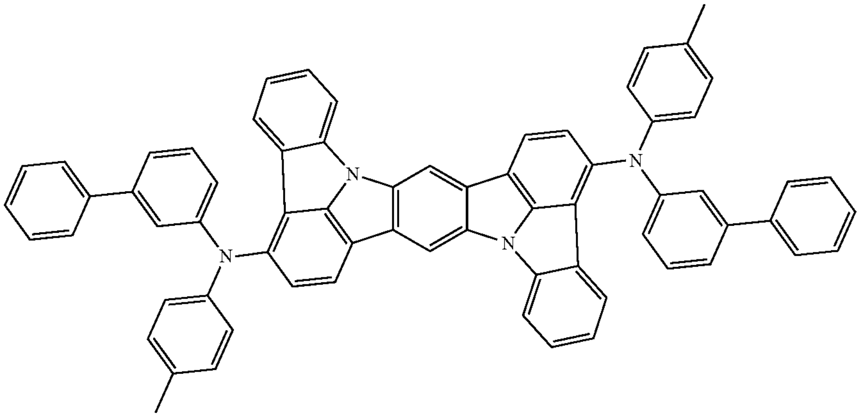
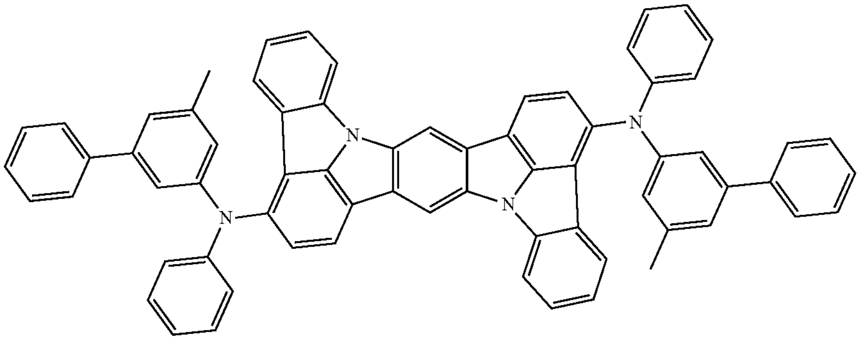

-continued
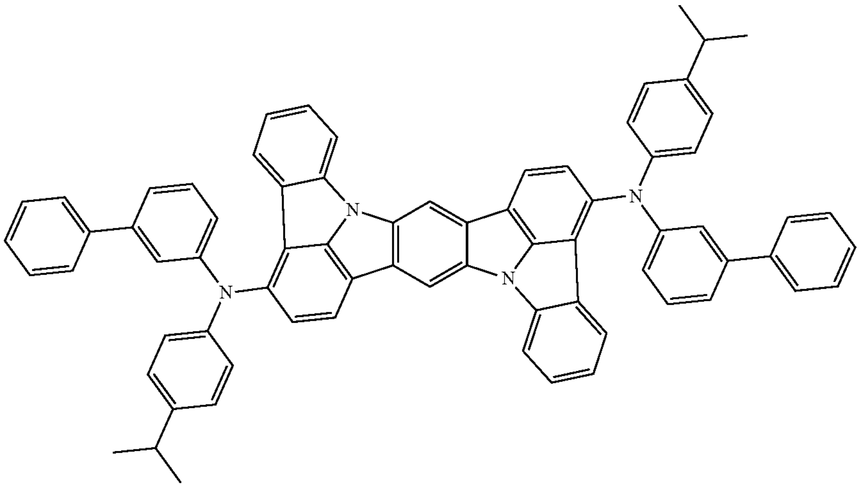
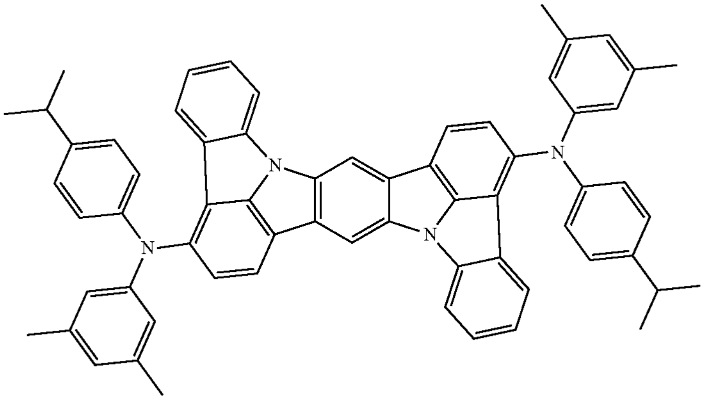
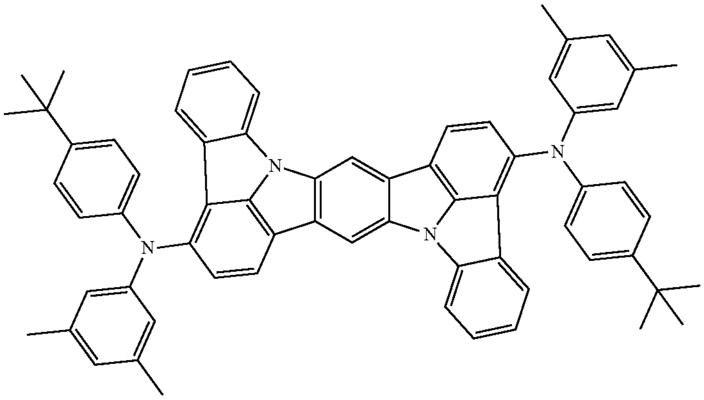

Compound Represented by Formula (6)

The compound represented by the formula (6) will be described below.

[Formula 350]

(6)

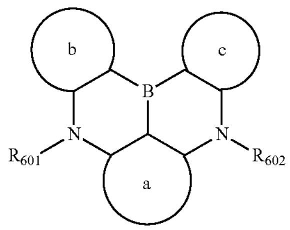

In the formula (6):

a ring, b ring and c ring are each independently a substituted or unsubstituted aromatic hydrocarbon ring having 6 to 50 ring carbon atoms, or a substituted or unsubstituted heterocycle having 5 to 50 ring atoms;

$R_{601}$ and $R_{602}$ are each independently bonded to the a ring, b ring or c ring to form a substituted or unsubstituted heterocycle, or not bonded to form no substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bycyclic structure formed of a boron atom and two nitrogen atoms at the center of the formula (6).

The "aromatic hydrocarbon ring" for the a, b, and c rings has the same structure as the compound formed by introducing a hydrogen atom to the "aryl group" described above.

Ring atoms of the "aromatic hydrocarbon ring" for the a ring include three carbon atoms on the fused bicyclic structure at the center of the formula (6). Ring atoms of the "aromatic hydrocarbon ring" for the b ring and the c ring include two carbon atoms on a fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as the compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and the c ring include two carbon atoms on a fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded with the a ring, b ring, or c ring to form a substituted or unsubstituted heterocycle. The "heterocycle" in this arrangement includes the nitrogen atom on the fused bicyclic structure at the center of the formula (6). The heterocycle in the above arrangement optionally include a hetero atom other than the nitrogen atom. $R_{601}$ and $R_{602}$ bonded with the a ring, b ring, or c ring specifically means that atoms forming $R_{601}$ and $R_{602}$ are bonded with atoms forming the a ring, b ring, or c ring. For instance, $R_{601}$ may be bonded to the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic fused heterocyclic group in the specific example group G2.

The same applies to $R_{601}$ bonded with the b ring, $R_{602}$ bonded with the a ring, and $R_{602}$ bonded with the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is a compound represented by a formula (62) below.

[Formula 351]

(62)

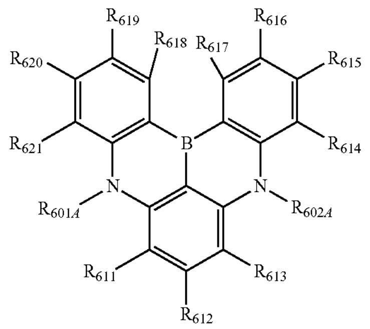

In the formula (62):

$R_{601A}$ is bonded with at least one of $R_{611}$ or $R_{621}$ to form a substituted or unsubstituted heterocycle, or not bonded to form no substituted or unsubstituted heterocycle;

$R_{602A}$ is bonded with at least one of $R_{613}$ or $R_{614}$ to form a substituted or unsubstituted heterocycle, or not bonded to form no substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ are mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded with each other to form a bicyclic (or tri-or-more cyclic) fused nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{601A}$ bonded with $R_{621}$, $R_{602A}$ bonded with $R_{613}$, and $R_{602A}$ bonded with $R_{614}$.

At least one combination of adjacent two or more of $R_{611}$ to $R_{621}$ may be mutually bonded to form a substituted or unsubstituted monocyclic ring, or mutually bonded to form a substituted or unsubstituted fused ring.

For instance, $R_{611}$ and $R_{612}$ are optionally mutually bonded to form a structure in which a benzene ring, indole ring, pyrrole ring, benzofuran ring, benzothiophene ring or the like is fused to the six-membered ring bonded with $R_{611}$ and $R_{612}$, the resultant fused ring forming a naphthalene ring, carbazole ring, indole ring, dibenzofuran ring, or dibenzothiophene ring, respectively.

In an exemplary embodiment, $R_{611}$ to $R_{621}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, or a substituted or unsubstituted alkyl group having 1 to 50 carbon atoms.

In an exemplary embodiment, $R_{611}$ to $R_{621}$ not contributing to ring formation are each independently a hydrogen atom, or a substituted or unsubstituted alkyl group having 1 to 50 carbon atoms, and at least one of $R_{611}$ to $R_{621}$ is a substituted or unsubstituted alkyl group having 1 to 50 carbon atoms.

In an exemplary embodiment, the compound represented by the formula (62) is a compound represented by a formula (63) below.

[Formula 352]

(63)

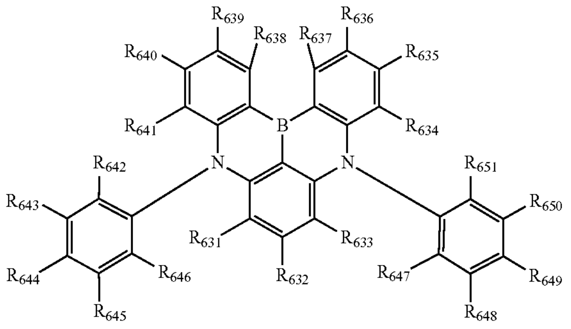

In the formula (63):

$R_{631}$ is bonded with $R_{646}$ to form a substituted or unsubstituted heterocycle, or not bonded to form no substituted or unsubstituted heterocycle, $R_{633}$ is bonded with $R_{647}$ to form a substituted or unsubstituted heterocycle, or not bonded to form no substituted or unsubstituted heterocycle;

$R_{634}$ is bonded with $R_{651}$ to form a substituted or unsubstituted heterocycle, or not bonded to form no substituted or unsubstituted heterocycle;

$R_{641}$ is bonded with $R_{642}$ to form a substituted or unsubstituted heterocycle, or not bonded to form no substituted or unsubstituted heterocycle; at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally mutually bonded with $R_{646}$ to form a substituted or unsubstituted heterocycle. For instance, $R_{631}$ and $R_{646}$ are optionally bonded with each other to form a tri-or-more cyclic fused nitrogen-containing heterocycle, in which a benzene ring bonded with $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies to $R_{633}$ bonded with $R_{647}$, $R_{634}$ bonded with $R_{651}$, and $R_{641}$ bonded with $R_{642}$.

In an exemplary embodiment, $R_{631}$ to $R_{651}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, or a substituted or unsubstituted alkyl group having 1 to 50 carbon atoms.

In an exemplary embodiment, $R_{631}$ to $R_{651}$ not contributing to ring formation are each independently a hydrogen atom, or a substituted or unsubstituted alkyl group having 1 to 50 carbon atoms, and at least one of $R_{631}$ to $R_{651}$ is a substituted or unsubstituted alkyl group having 1 to 50 carbon atoms.

In an exemplary embodiment, the compound represented by the formula (63) is a compound represented by a formula (63A) below.

[Formula 353]

(63A)

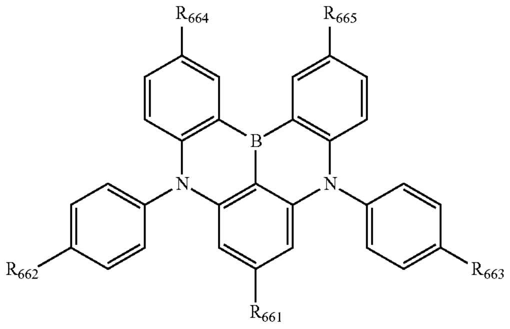

In the formula (63A):

$R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms, and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is a compound represented by a formula (63B) below.

[Formula 354]

(63B)

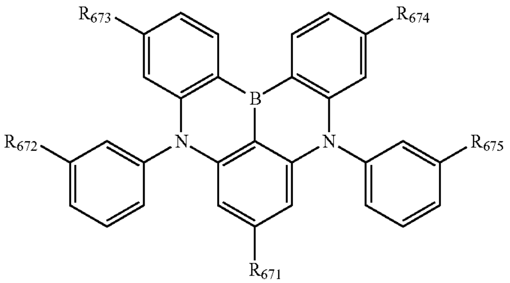

In the formula (63B):

$R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63B') below.

[Formula 355]

(63B')

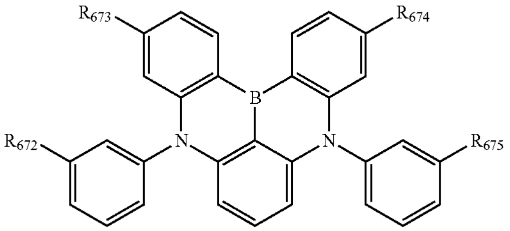

In the formula (63B'), $R_{672}$ to $R_{675}$ each independently represent the same as $R_{672}$ to $R_{675}$ in the formula (63B).

In an exemplary embodiment, at least one of $R_{671}$ to $R_{675}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment: $R_{672}$ is a hydrogen atom, a substituted or unsubstituted alkyl group having 1 to 50 carbon atoms, a group represented by —N($R_{906}$)($R_{907}$), or a substituted or unsubstituted aryl group having 6 to 50 ring carbon atoms; and $R_{671}$, and $R_{673}$ to $R_{675}$ are each independently a substituted or unsubstituted alkyl group having 1 to 50 carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63C) below.

[Formula 356]

(63C)

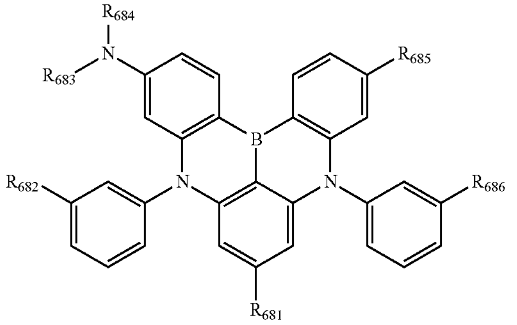

In the formula (63C):

$R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is a compound represented by a formula (63C') below.

[Formula 357]

(63C')

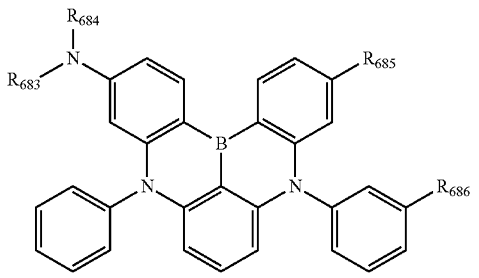

In the formula (63C'), $R_{683}$ to $R_{686}$ each independently represent the same as $R_{683}$ to $R_{686}$ in the formula (63C).

In an exemplary embodiment, $R_{681}$ to $R_{686}$ are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific examples of the compound represented by the formula (6) are shown below. It should however be noted that these specific examples are merely exemplary and do not limit the compound represented by the formula (6).

[Formula 358]

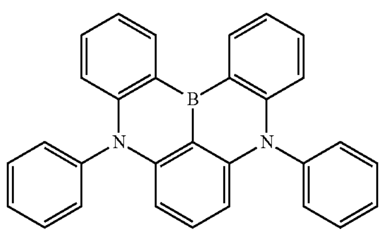

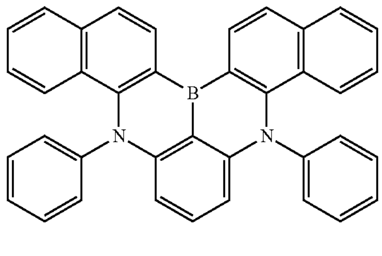

-continued
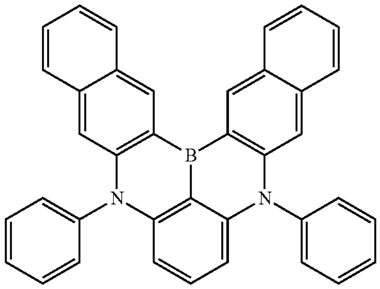
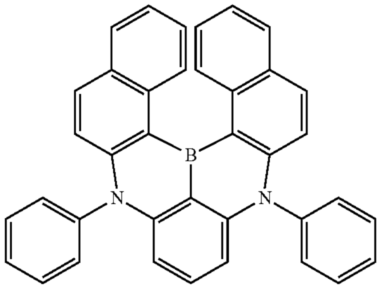
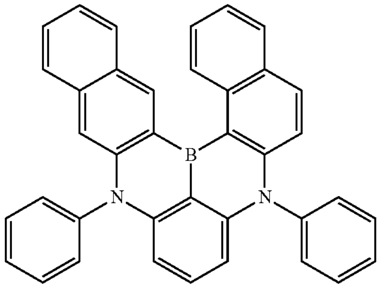
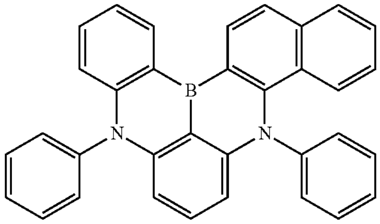
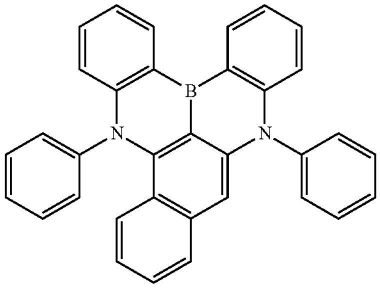
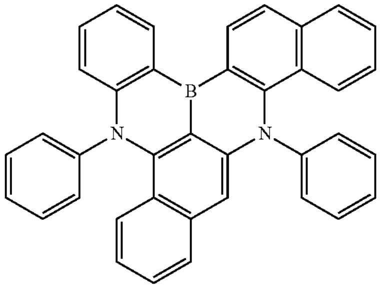
-continued
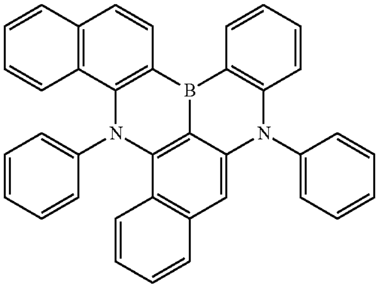
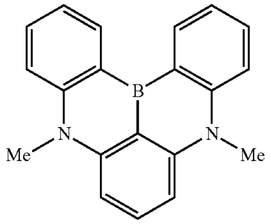
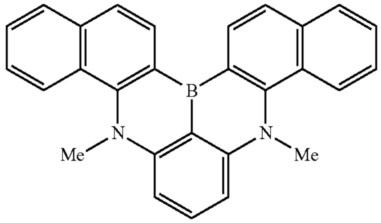
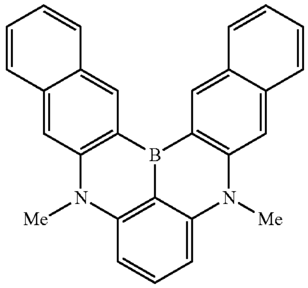
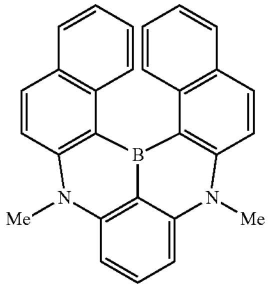
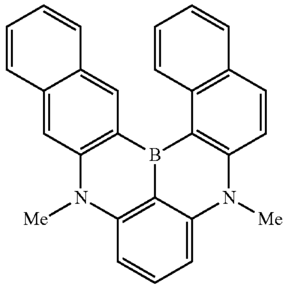

-continued
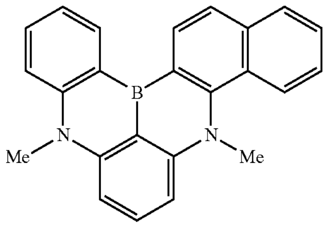
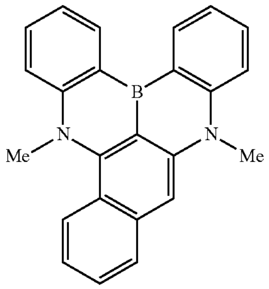
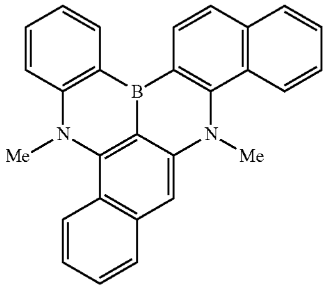
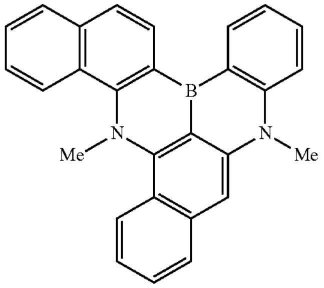
[Formula 359]
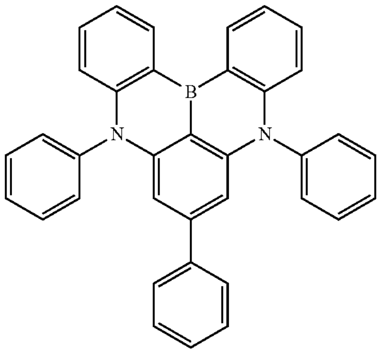
-continued
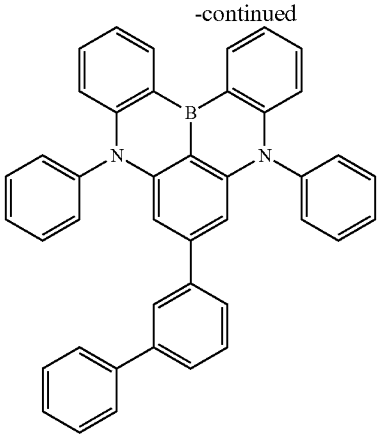
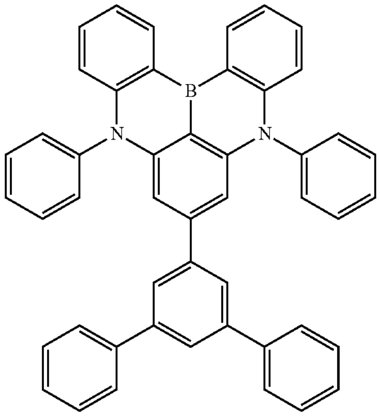
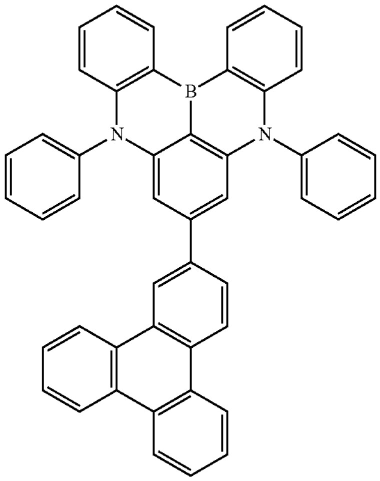

-continued
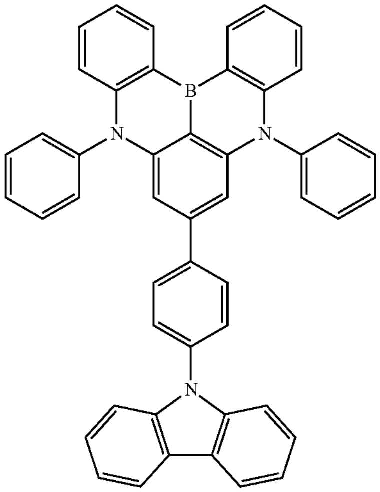
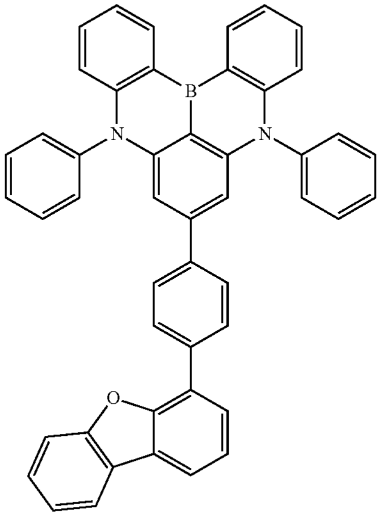
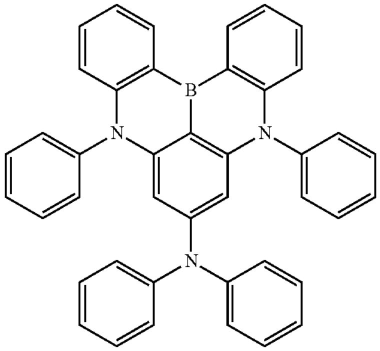
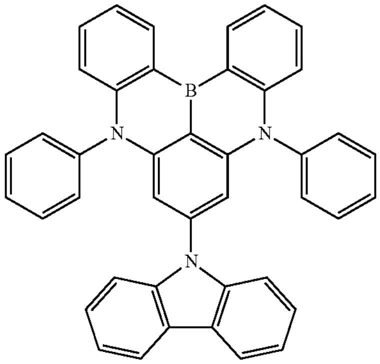
-continued
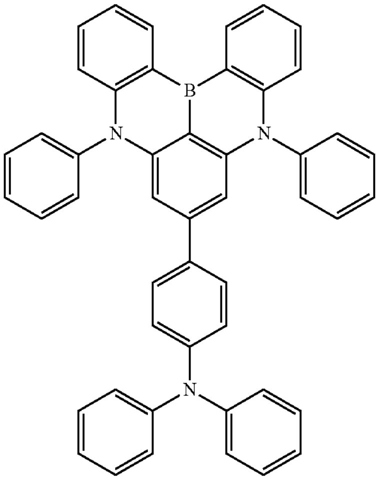
[Formula 360]
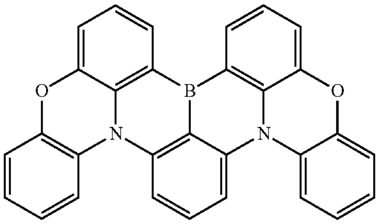
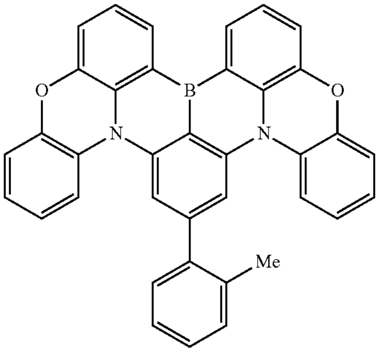
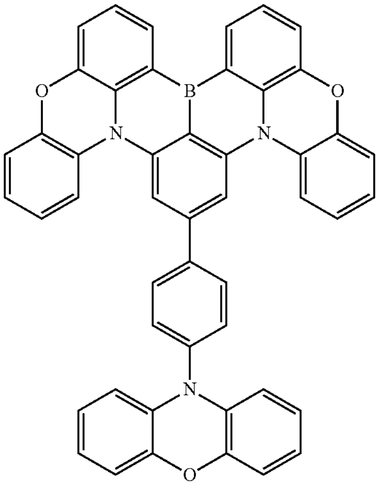

-continued
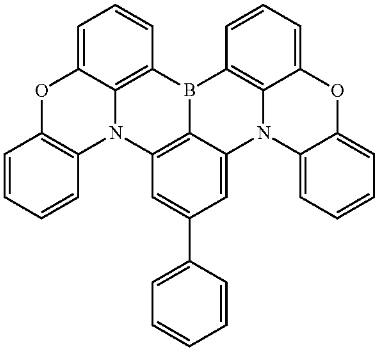
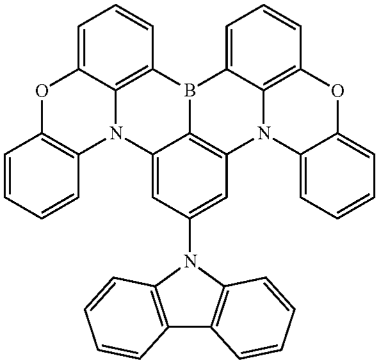
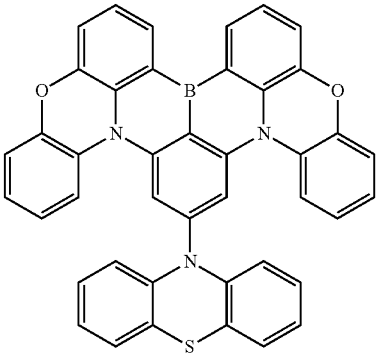
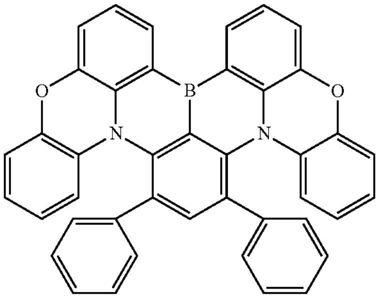
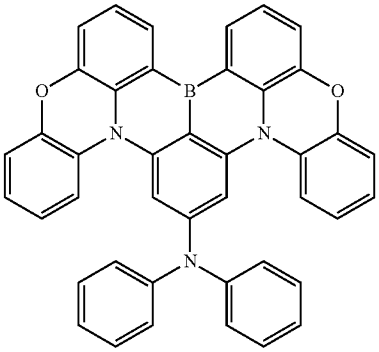
-continued
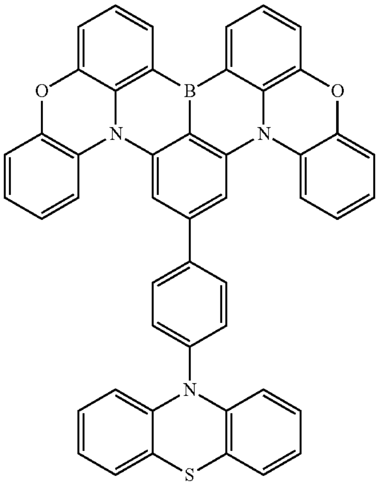
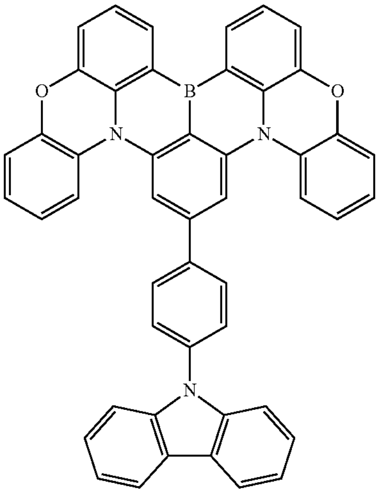
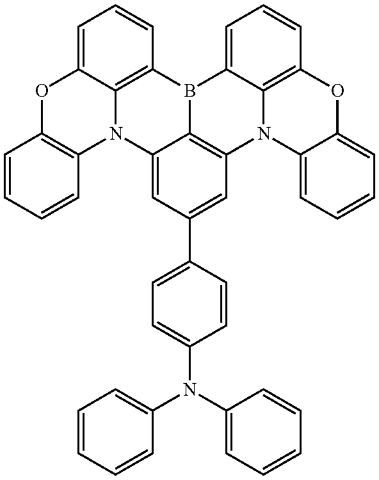

-continued
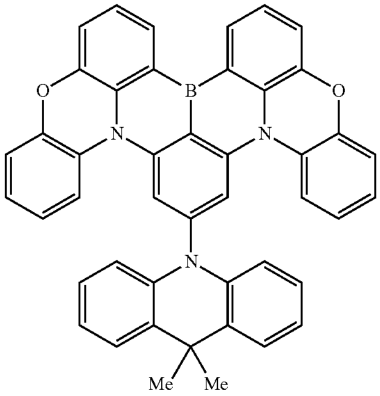
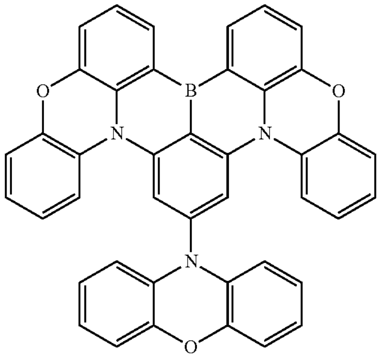
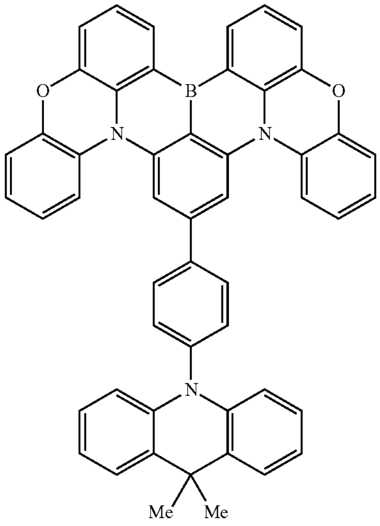
[Formula 361]
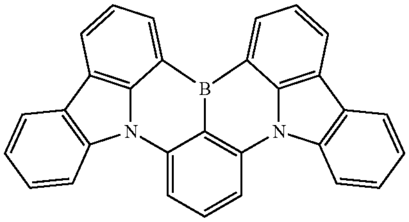
-continued
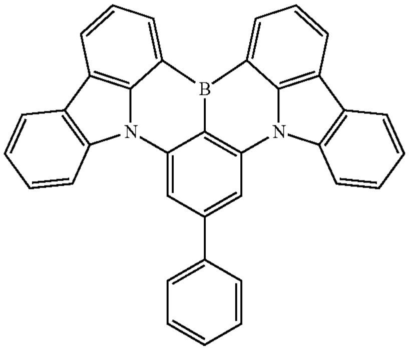
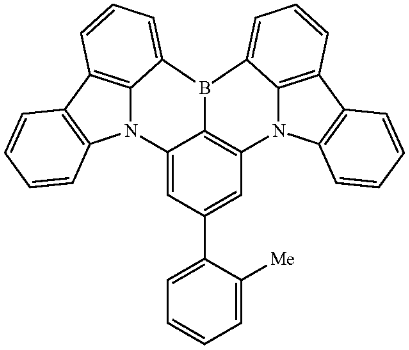
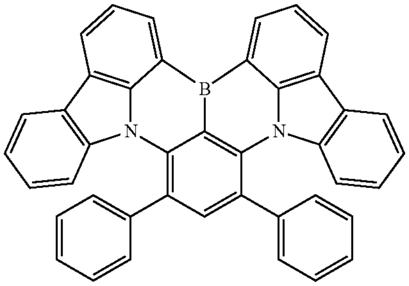
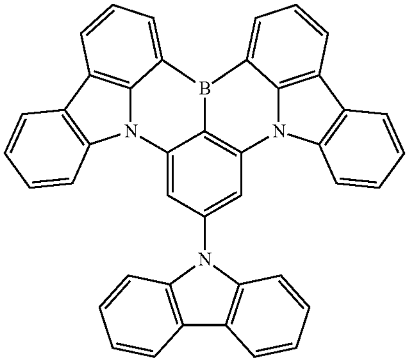
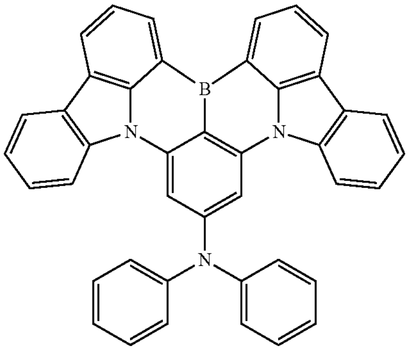

-continued
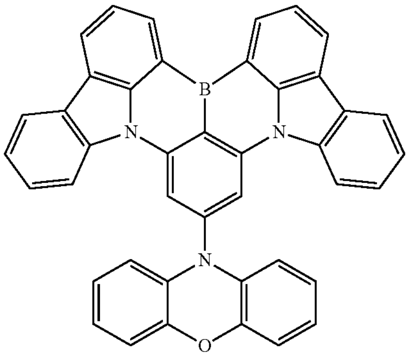
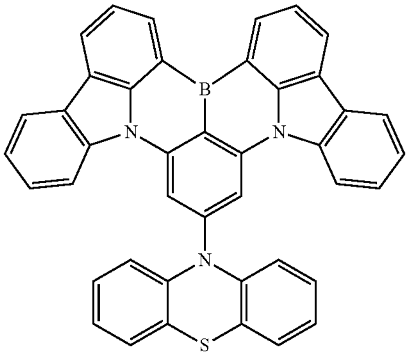
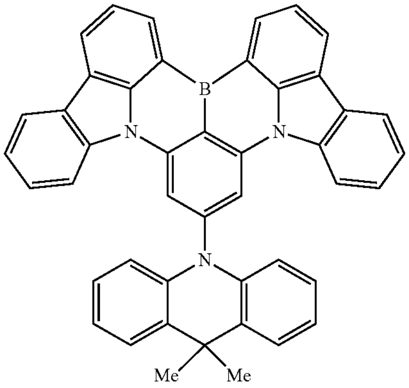
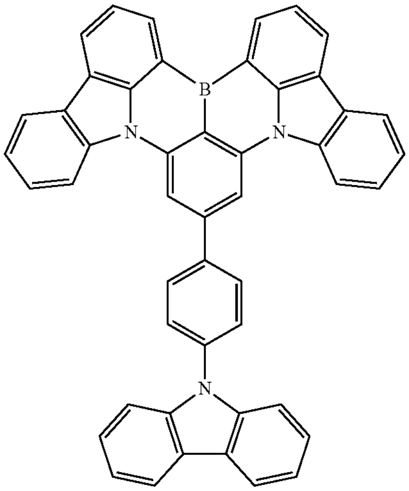
-continued
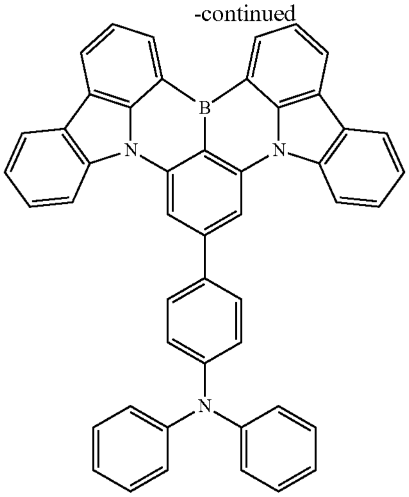
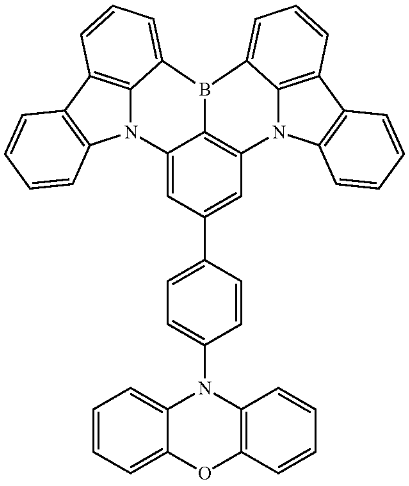
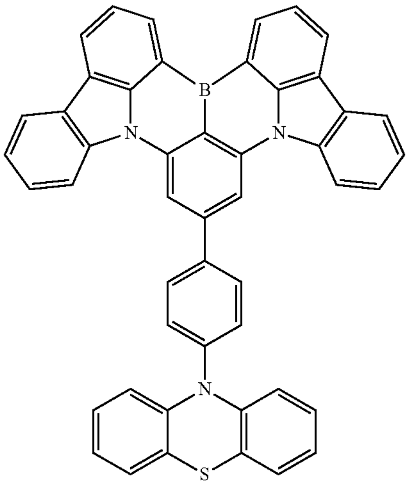

-continued
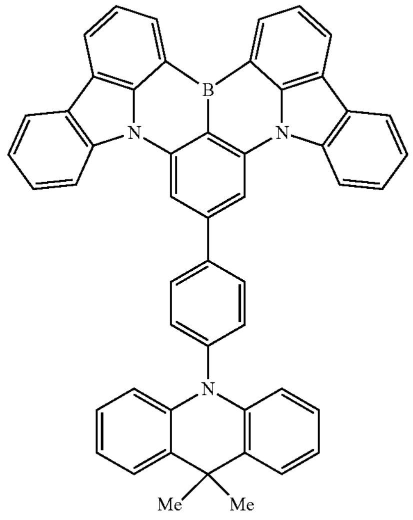
[Formula 362]
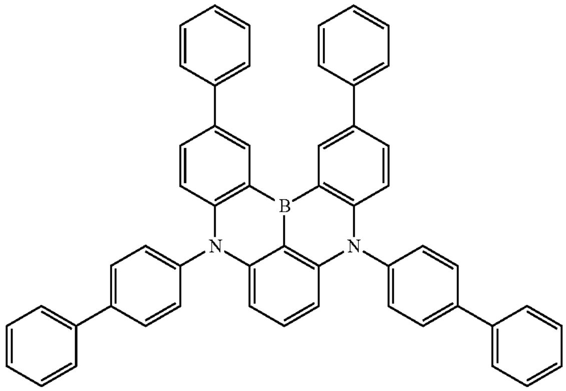
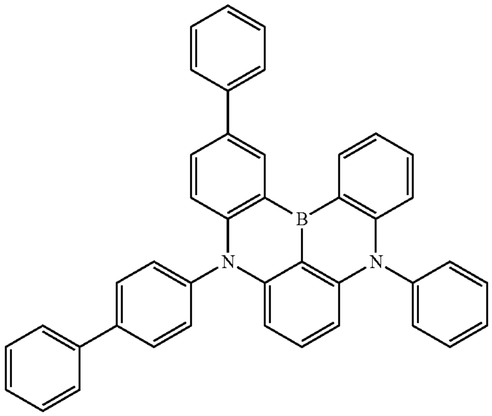
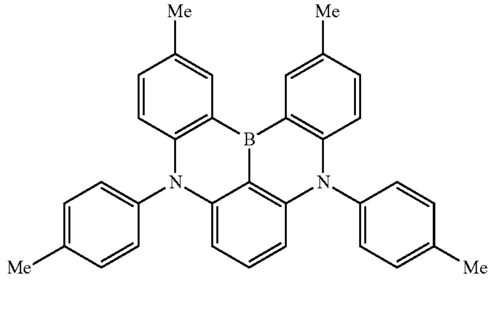
-continued
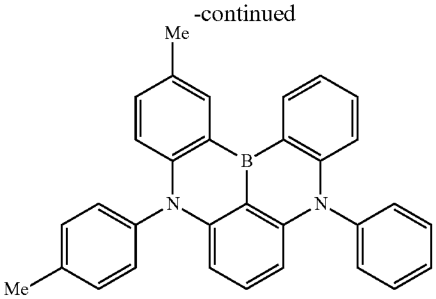
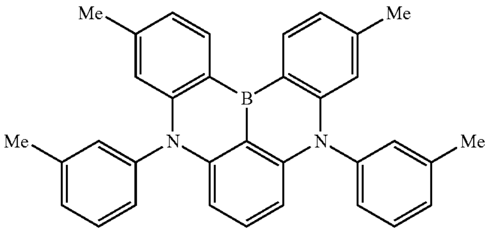
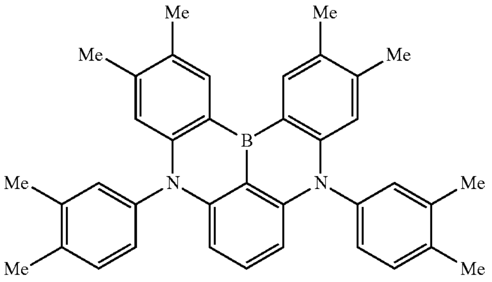
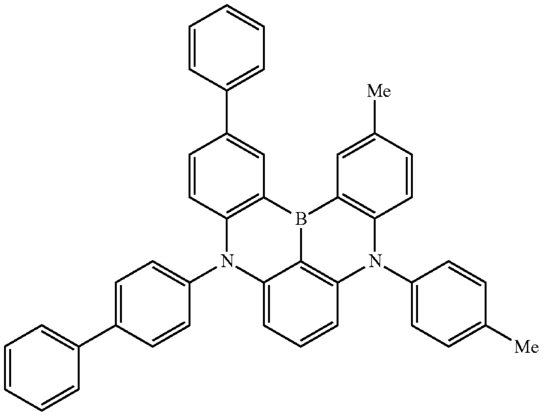
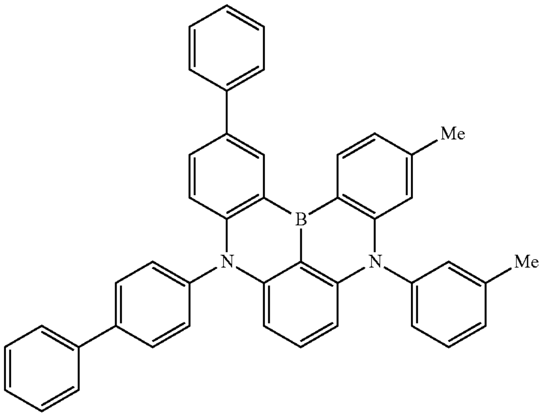

-continued
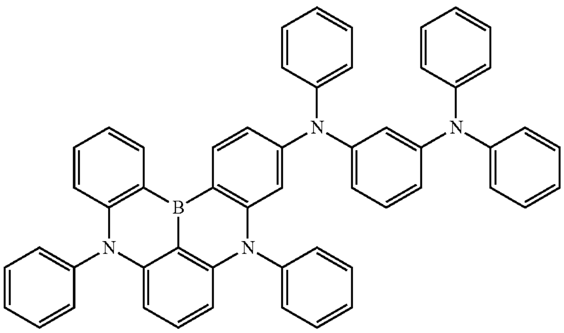
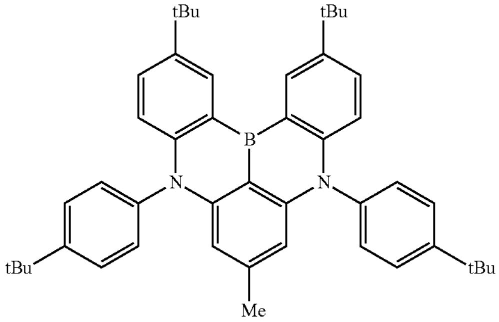
[Formula 363]
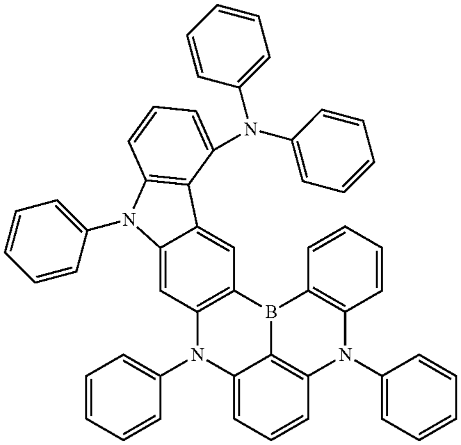
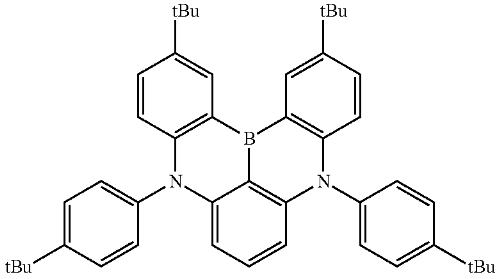
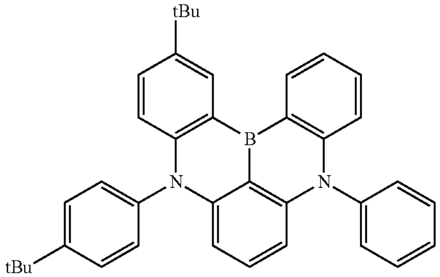
-continued
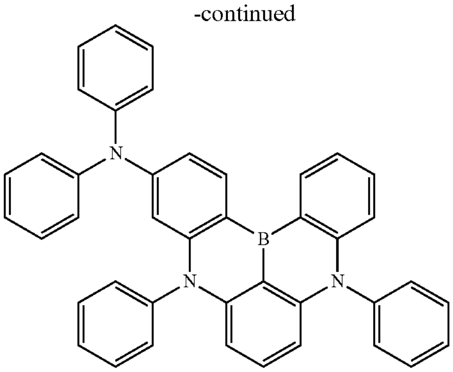
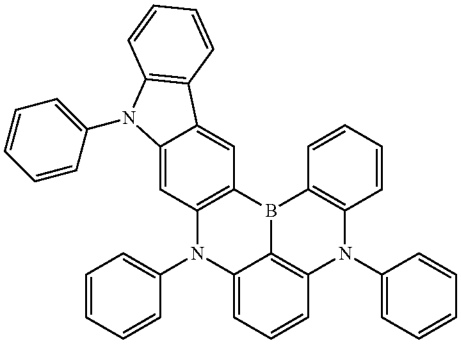
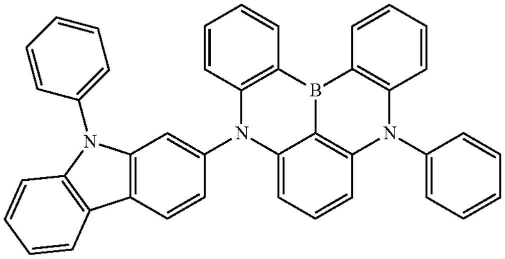
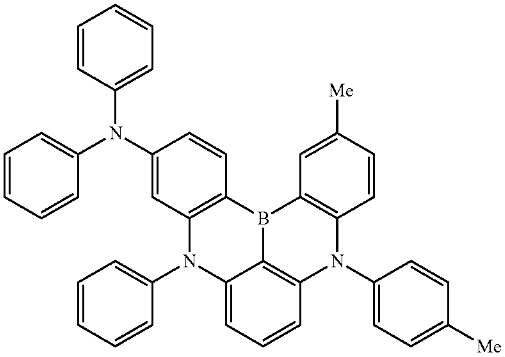
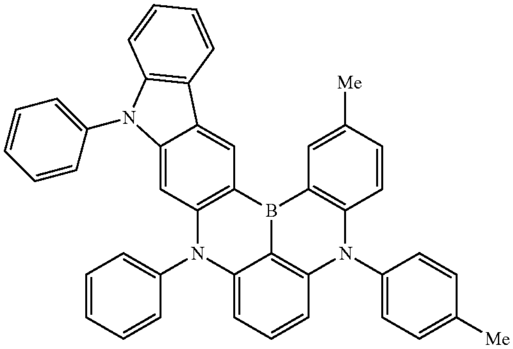

-continued
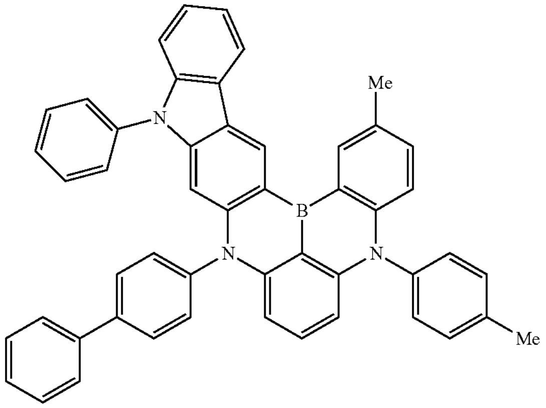
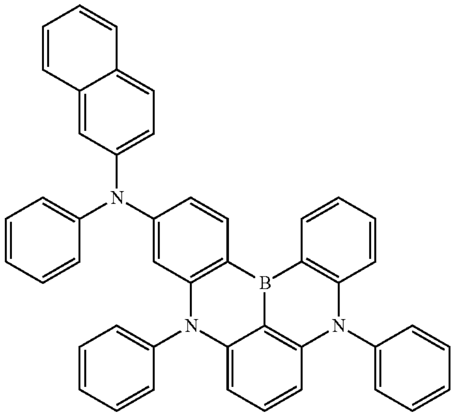
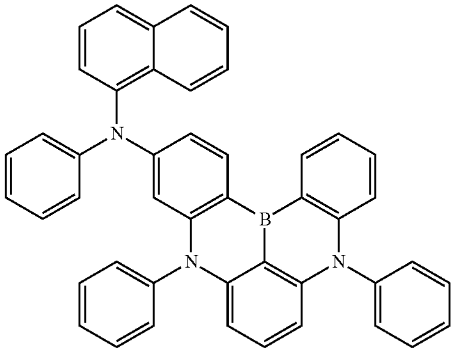
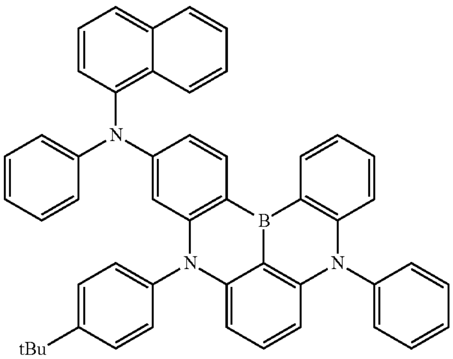
-continued
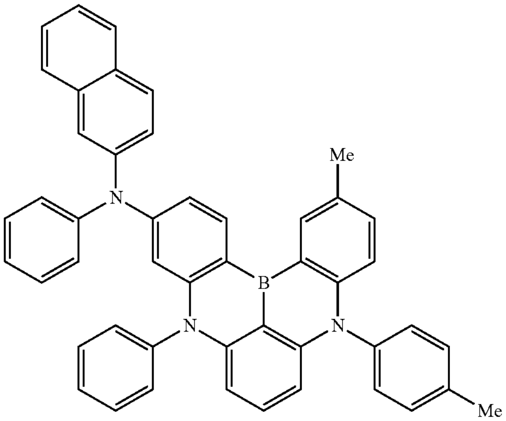
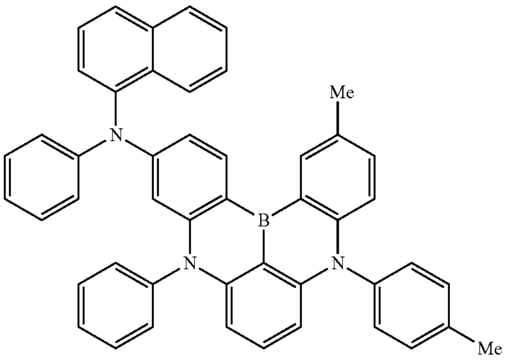
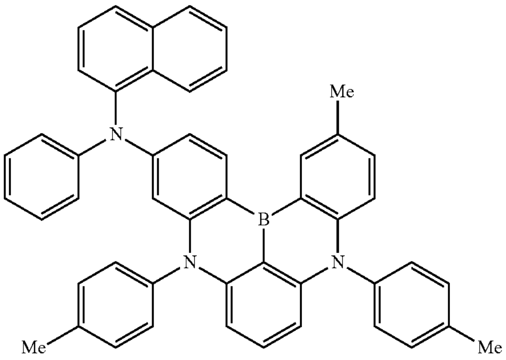
[Formula 364]
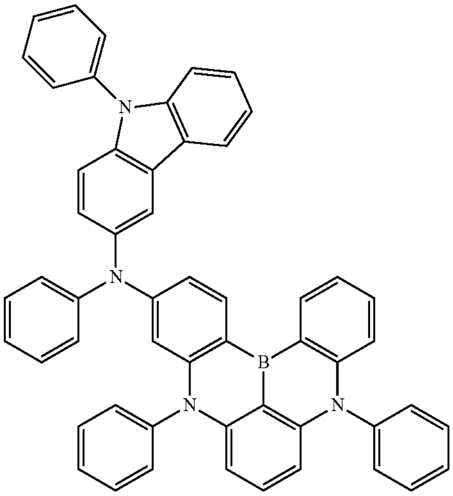

-continued
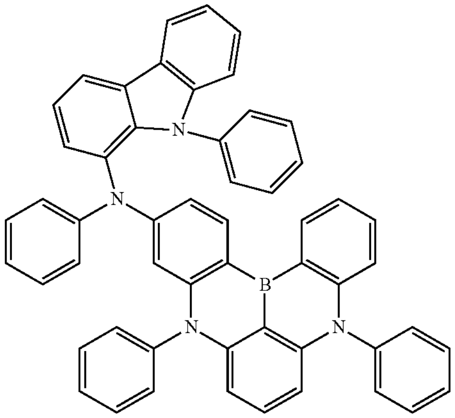
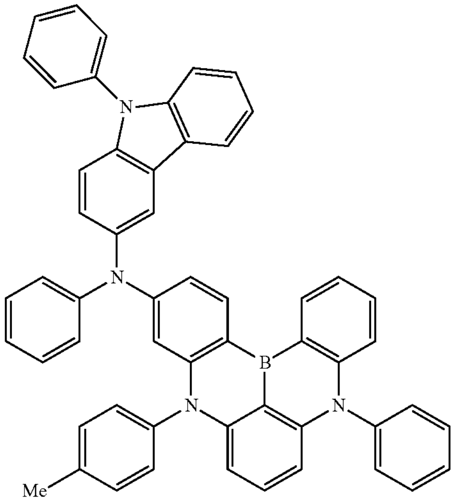
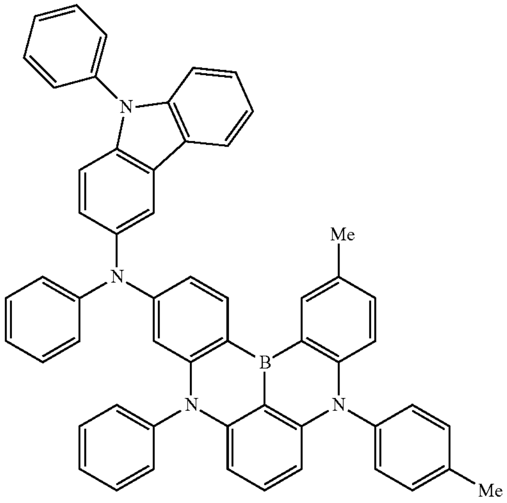
-continued
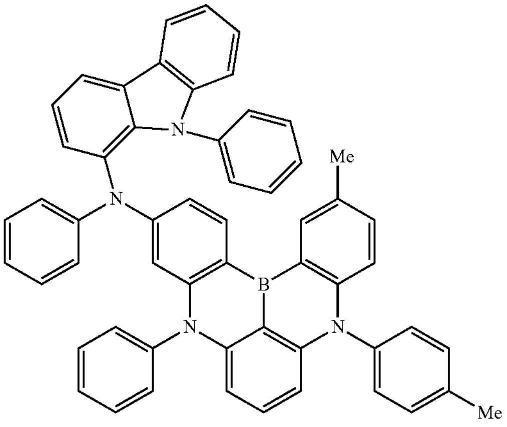
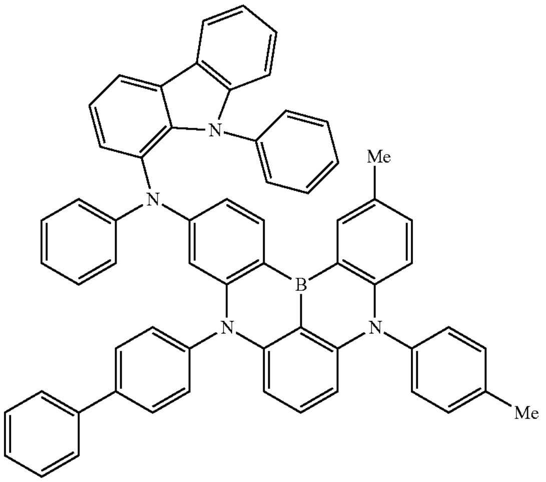
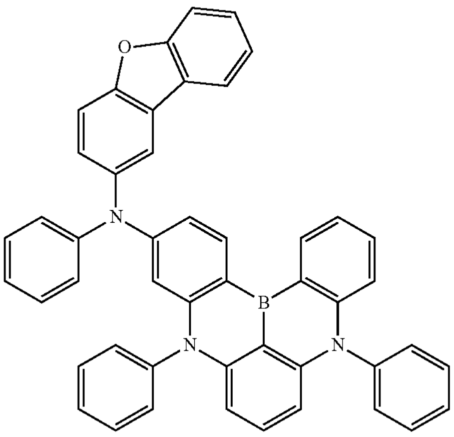

-continued
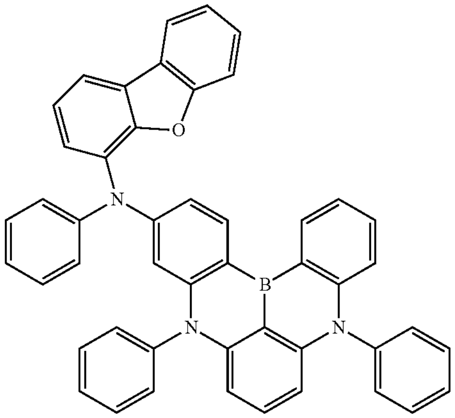
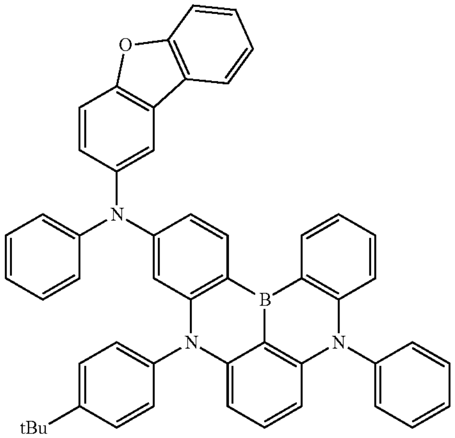
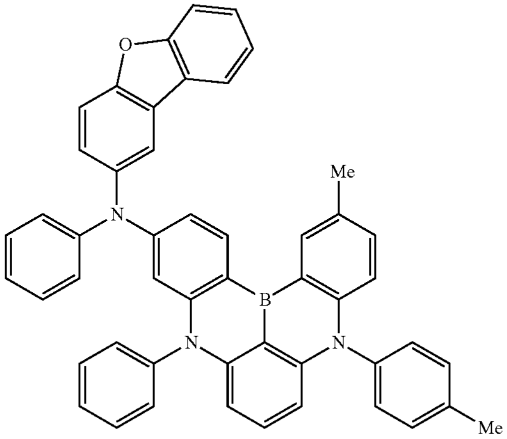
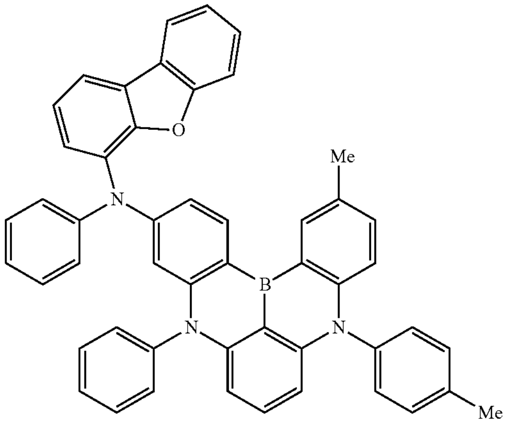
-continued
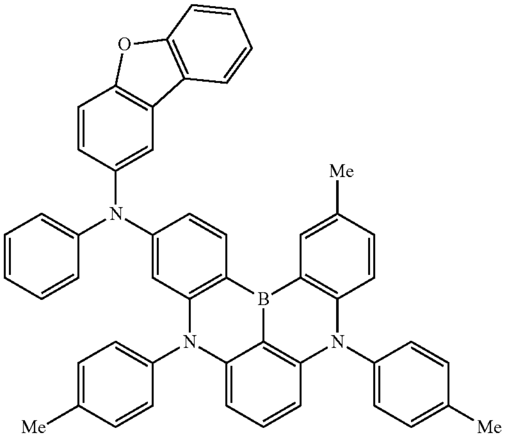
[Formula 365]
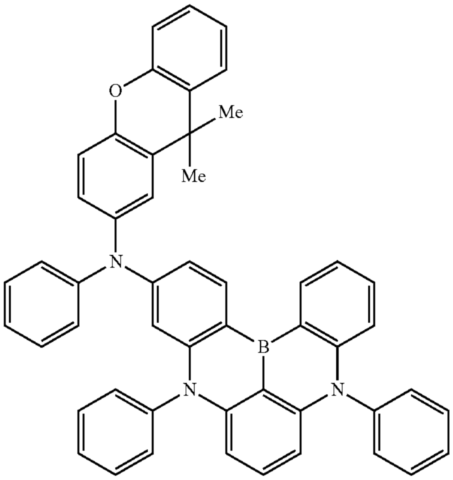
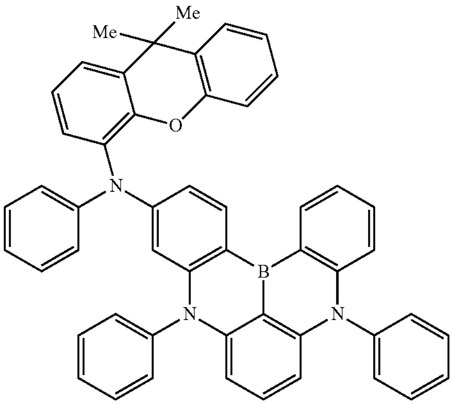

-continued
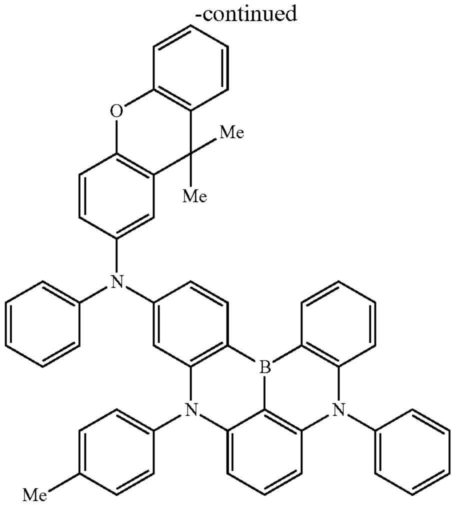
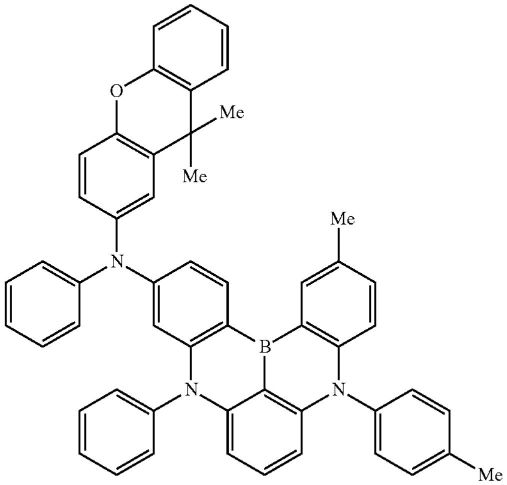
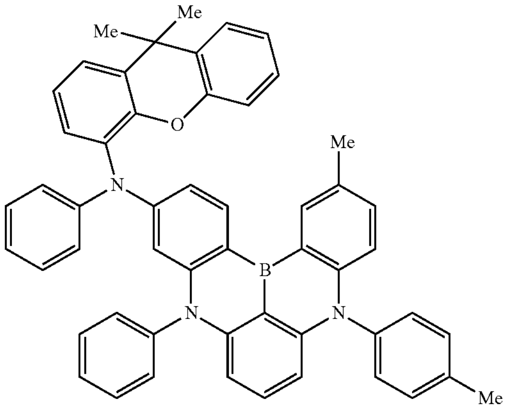
-continued
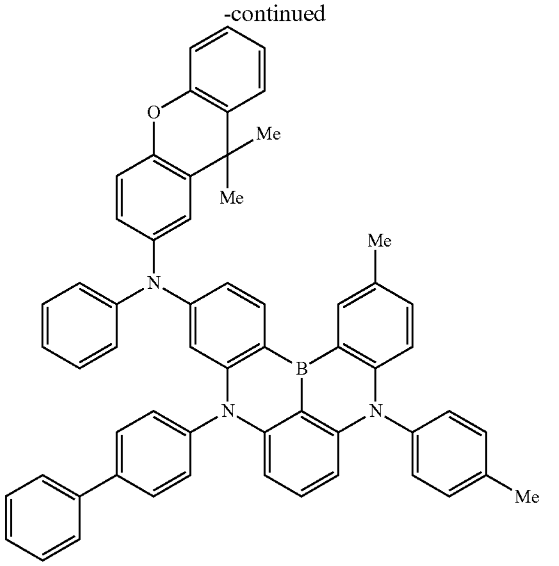
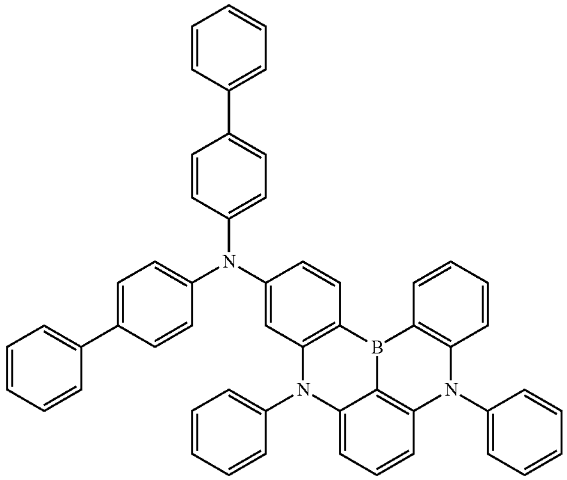
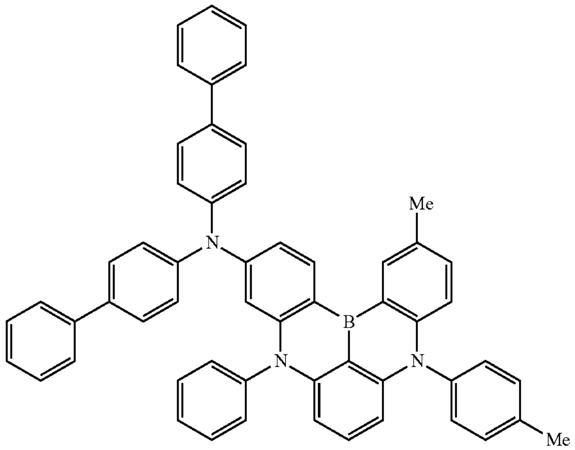

-continued
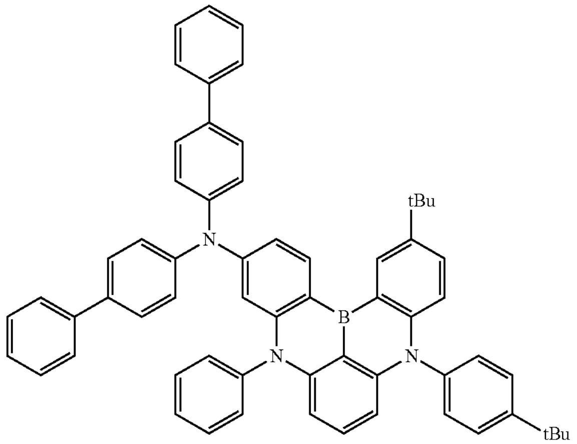
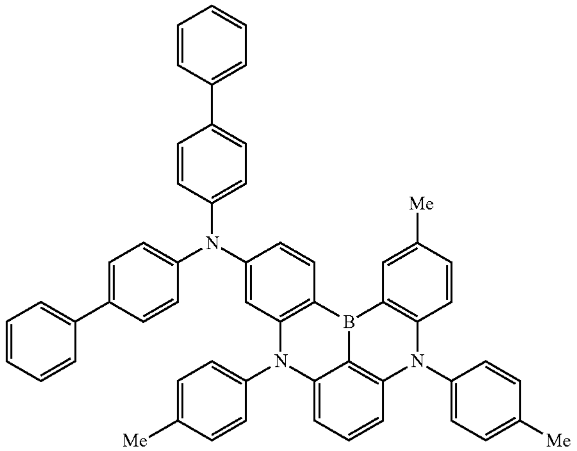
[Formula 366]
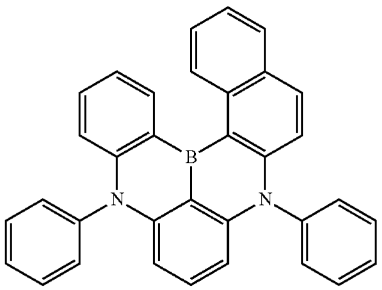
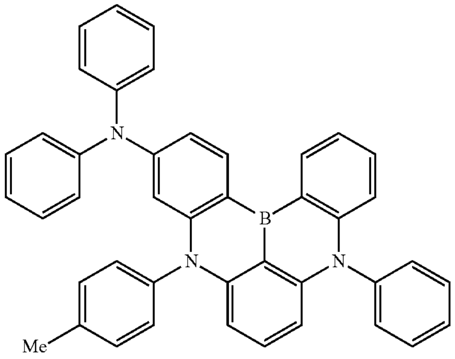
-continued
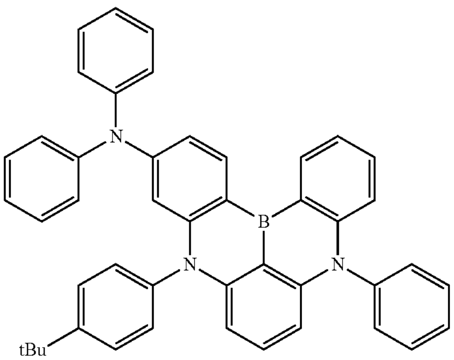
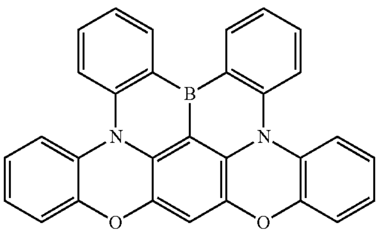
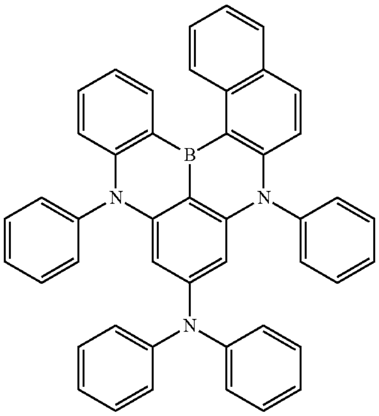
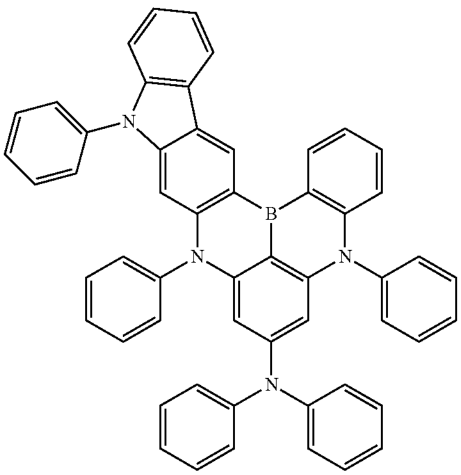

-continued
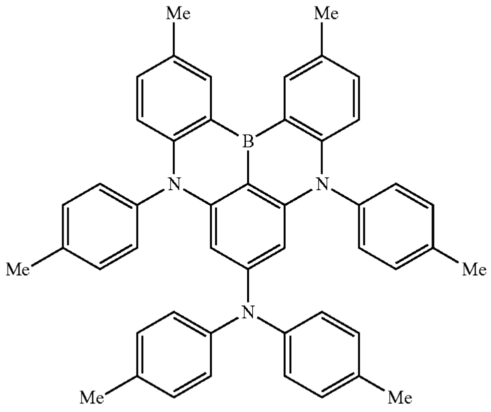
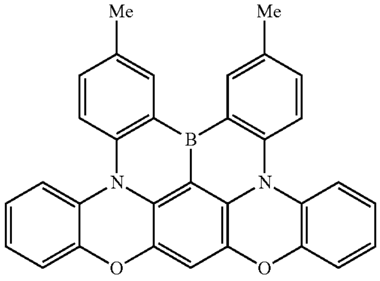
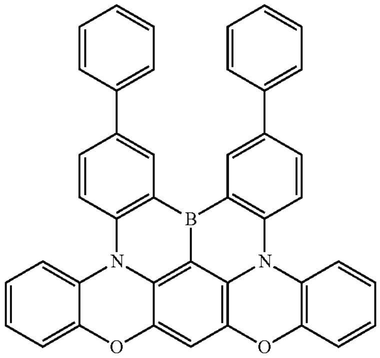
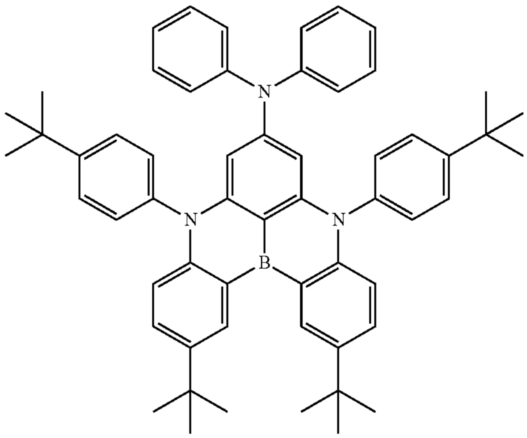
-continued
[Formula 367]
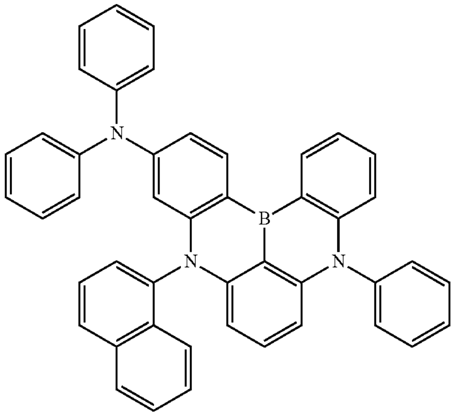
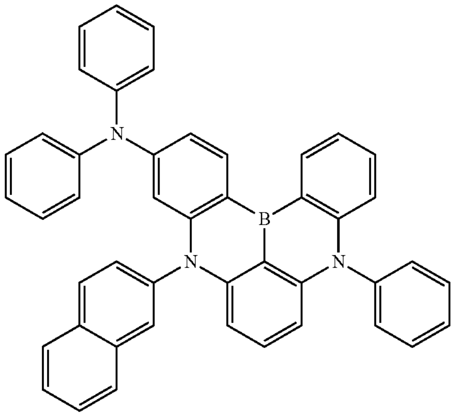
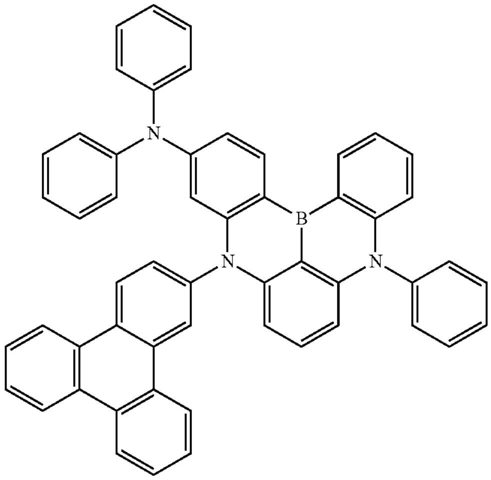

-continued
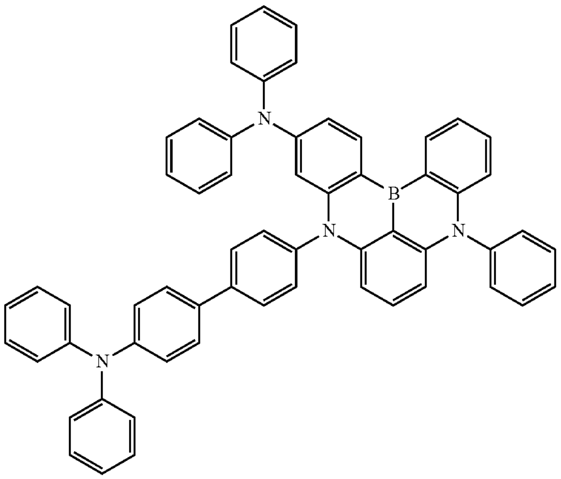
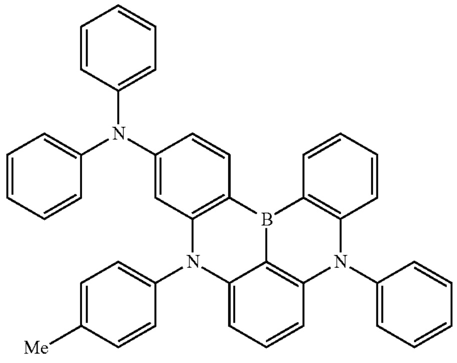
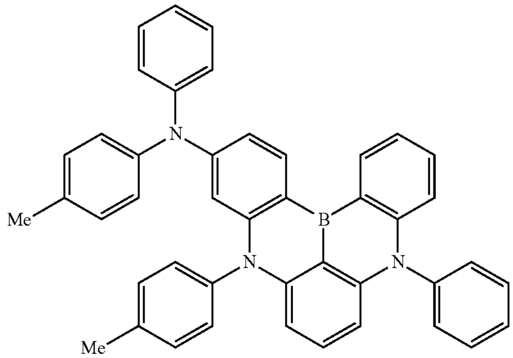
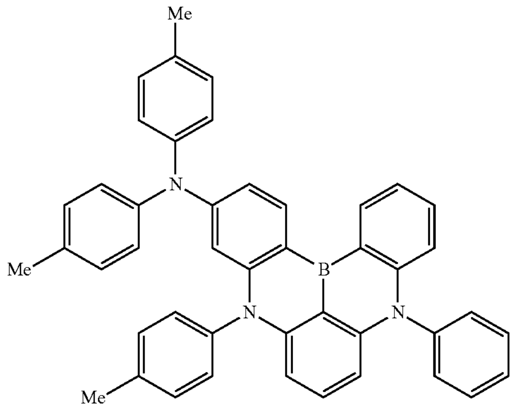
-continued
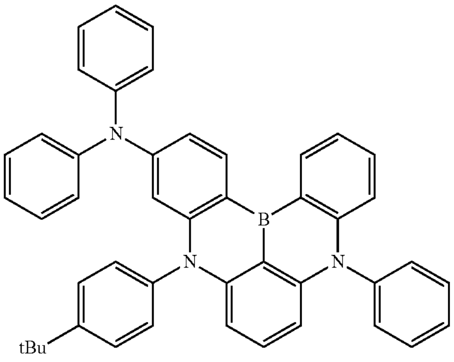
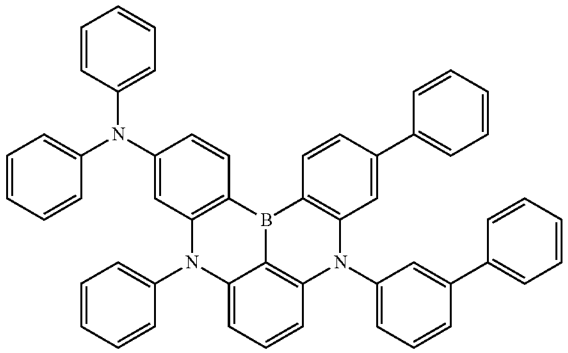
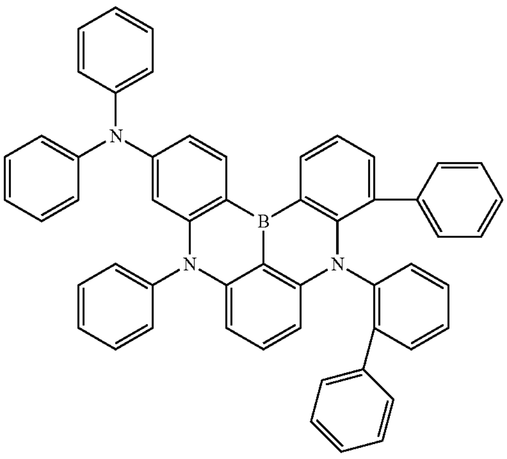
[Formula 368]
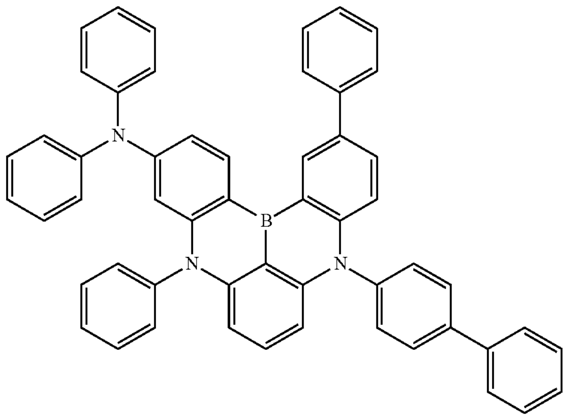

-continued
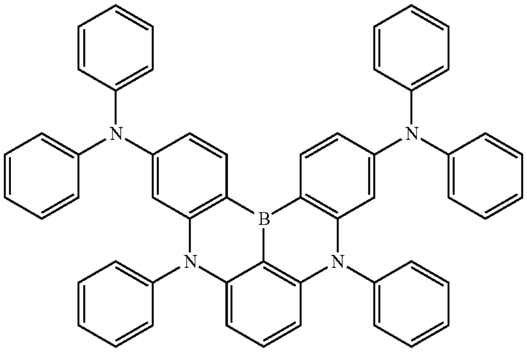
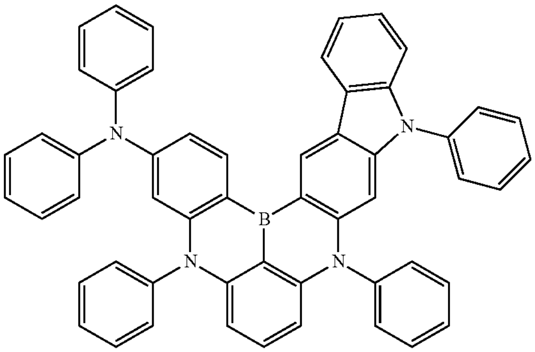
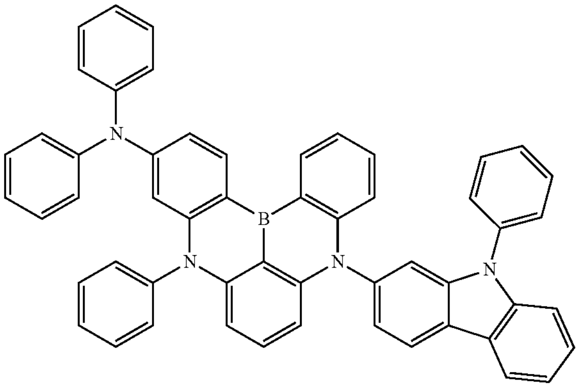
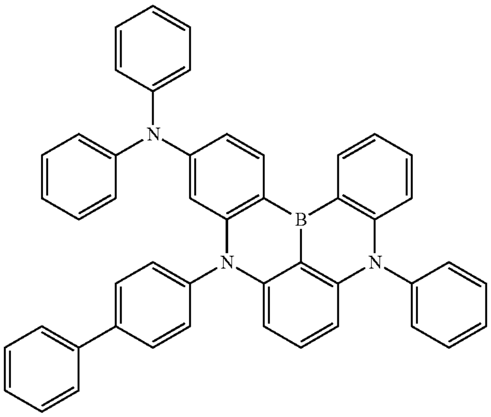
-continued
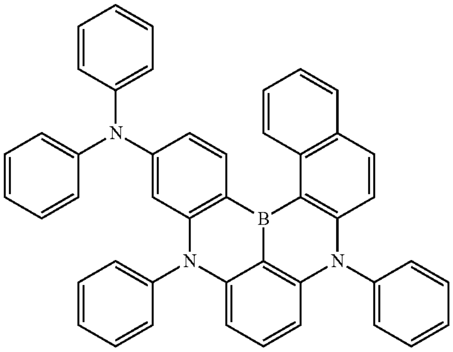
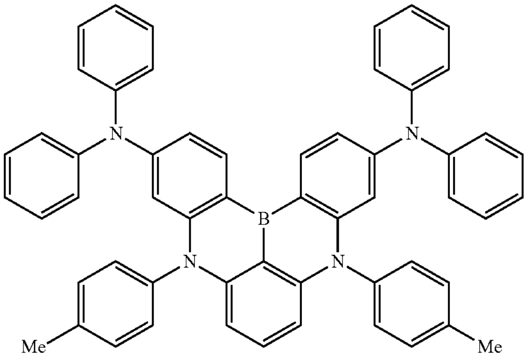
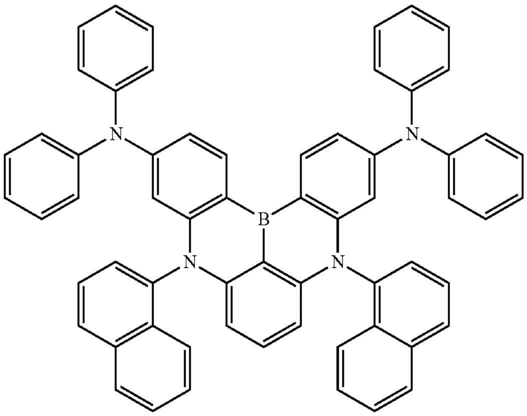
[Formula 369]
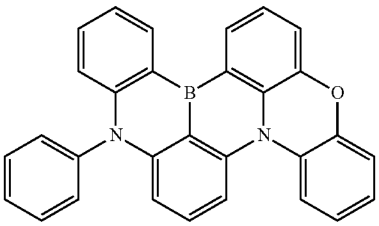

-continued
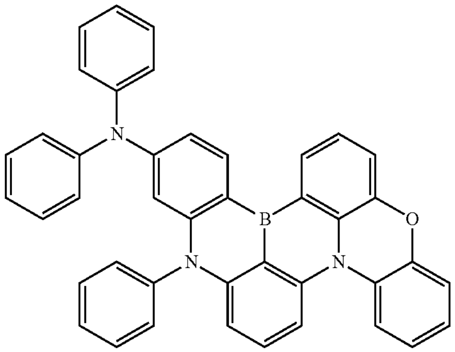
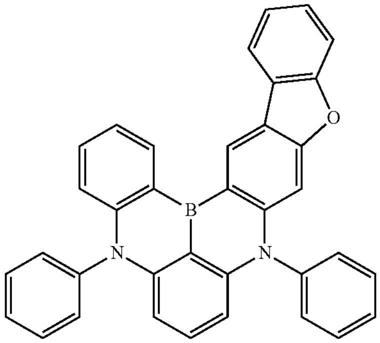
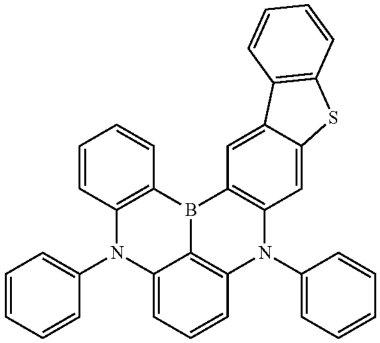
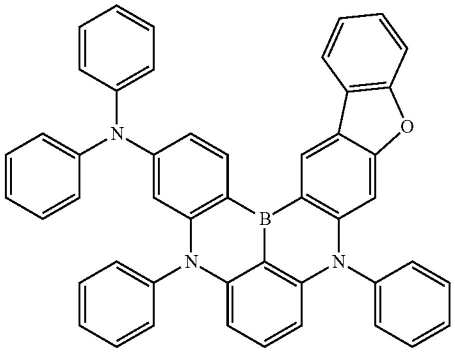
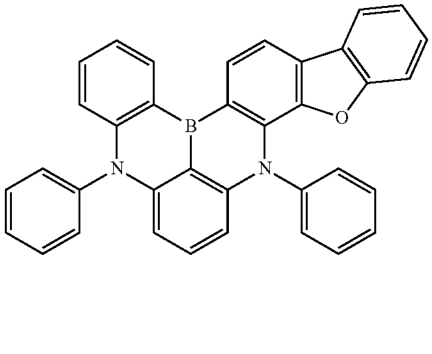
-continued
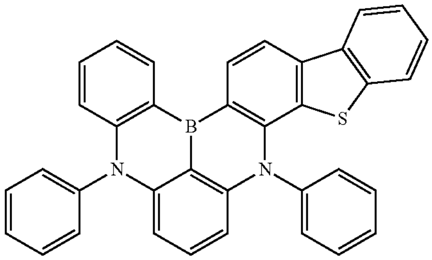
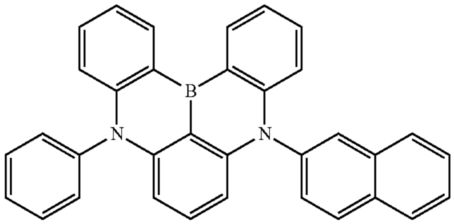
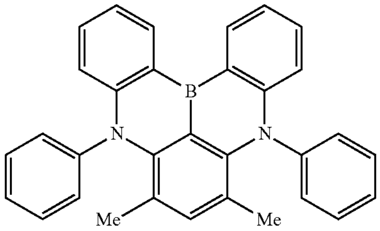
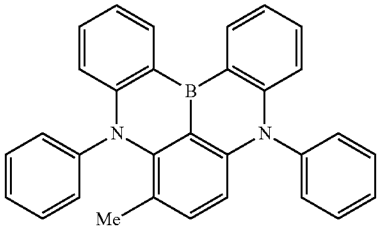
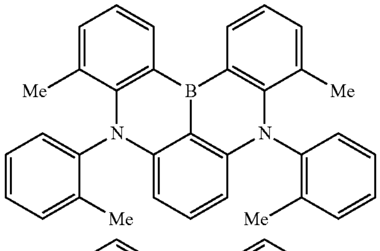
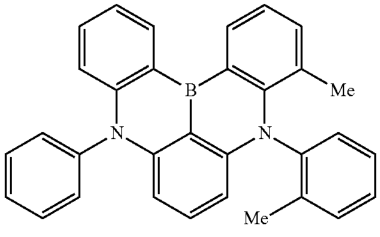
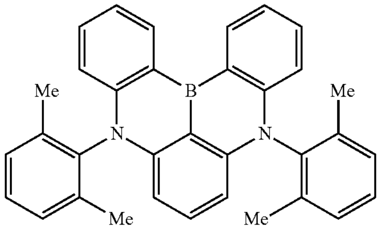

-continued

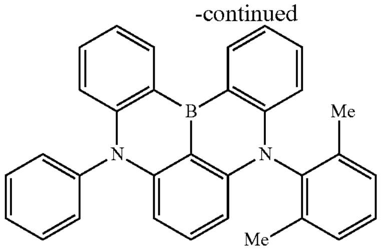

Compound Represented by Formula (7)

The compound represented by the formula (7) will be described below.

[Formula 370]

(7)

p-q-r-s-t

[Formula 371]

(72)

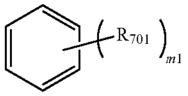

(73)

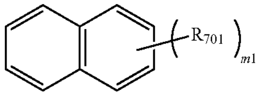

(74)

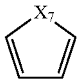

(75)

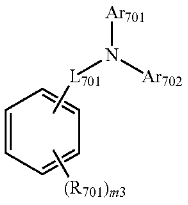

(76)

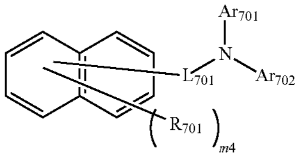

In the formula (7):

r ring is a ring represented by the formula (72) or (73), q ring and s ring are each independently a ring represented by the formula (74) and fused with any position(s) of adjacent ring(s);

p ring and t ring are each independently a structure represented by the formula (75) or (76) and fused with adjacent ring(s) at any position(s);

$X_7$ is an oxygen atom, a sulfur atom, or $NR_{702}$;

when a plurality of $R_{701}$ are present, adjacent ones of the plurality of $R_{701}$ are mutually bonded to form a substituted or unsubstituted monocyclic ring, mutually bonded to form a substituted or unsubstituted fused ring, or not mutually bonded;

$R_{701}$ and $R_{702}$ not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—($R_{904}$), a group represented by —S—($R_{905}$), a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$Ar_{701}$ and $Ar_{702}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{701}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is 0, 1, or 2;

m2 is 0, 1, 2, 3, or 4;

m3 is each independently 0, 1, 2, or 3;

m4 is each independently 0, 1, 2, 3, 4, or 5;

when a plurality of $R_{701}$ are present, the plurality of $R_{701}$ are mutually the same or different;

when a plurality of $X_7$ are present, the plurality of $X_7$ are mutually the same or different;

when a plurality of $R_{702}$ are present, the plurality of $R_{702}$ are mutually the same or different;

when a plurality of $Ar_{701}$ are present, the plurality of $Ar_{701}$ are mutually the same or different;

when a plurality of $Ar_{702}$ are present, the plurality of $Ar_{702}$ are mutually the same or different; and when a plurality of $L_{701}$ are present, the plurality of $L_{701}$ are mutually the same or different.

In the formula (7), each of the p ring, q ring, r ring, s ring, and t ring is fused with an adjacent ring(s) sharing two carbon atoms. The fused position and orientation are not limited but may be defined as required.

In an exemplary embodiment, in the formula (72) or (73) representing the r ring, m1=0 or m2=0 is satisfied.

In an exemplary embodiment, the compound represented by the formula (7) is represented by any one of formulae (71-1) to (71-6) below.

[Formula 372]

(71-1)

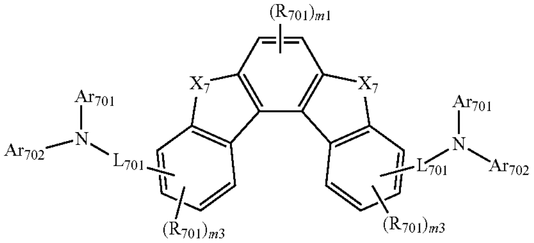

-continued

[Formula 373]

(71-2)

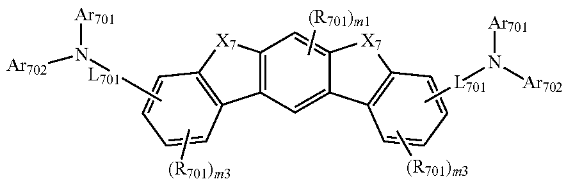

[Formula 374]

(71-3)

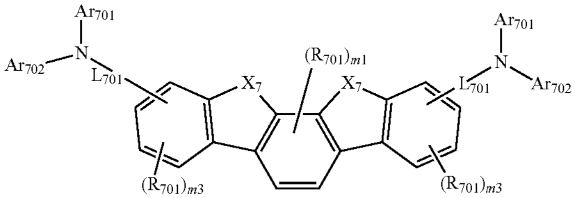

[Formula 375]

(71-4)

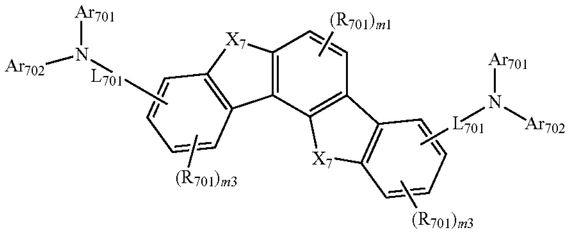

[Formula 376]

(71-5)

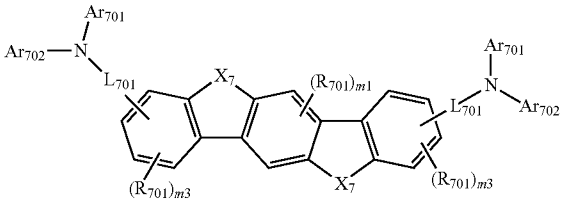

[Formula 377]

(71-6)

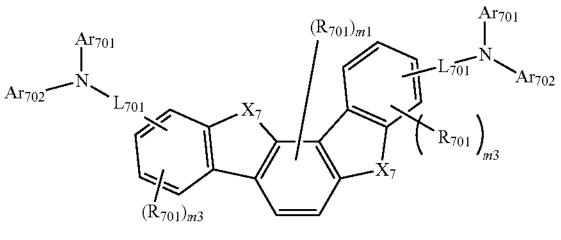

In the formulae (71-1) to (71-6), $R_{701}$, $X_7$, $Ar_{701}$, $Ar_{702}$, $L_{701}$, m1 and m3 respectively represent the same as $R_{701}$, $X_7$, $Ar_{701}$, $Ar_{702}$, $L_{701}$, m1 and m3 in the formula (7).

In an exemplary embodiment, the compound represented by the formula (7) is represented by any one of formulae (71-11) to (71-13) below.

[Formula 378]

(71-11)

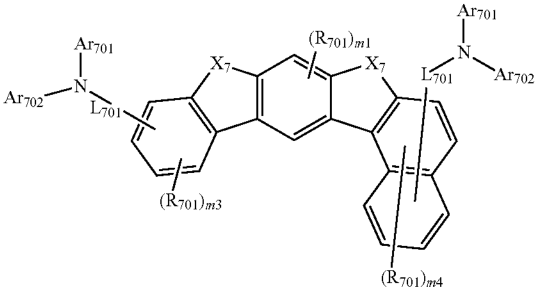

[Formula 379]

(71-12)

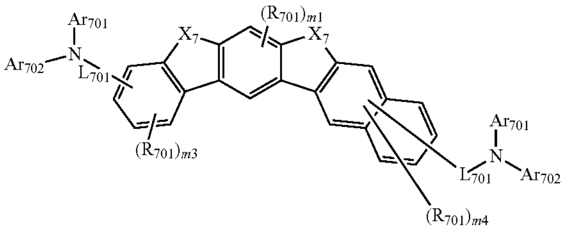

[Formula 380]

(71-13)

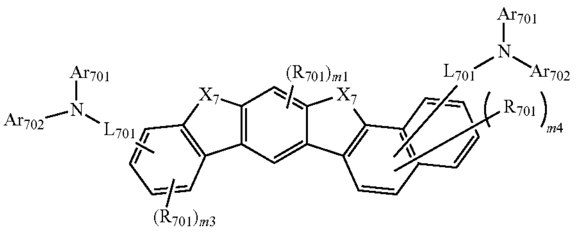

In the formulae (71-11) to (71-13), $R_{701}$, $X_7$, $Ar_{701}$, $Ar_{702}$, $L_{701}$, m1, m3 and m4 respectively represent the same as $R_{701}$, $X_7$, $Ar_{701}$, $Ar_{702}$, $L_{701}$, m1, m3 and m4 in the formula (7).

In an exemplary embodiment, the compound represented by the formula (7) is represented by any one of formulae (71-21) to (71-25) below.

[Formula 381]
(71-21)
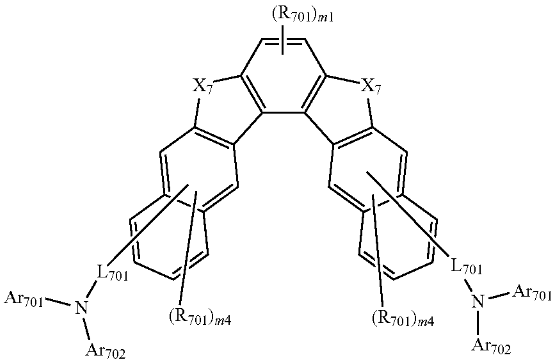
[Formula 382]
(71-22)
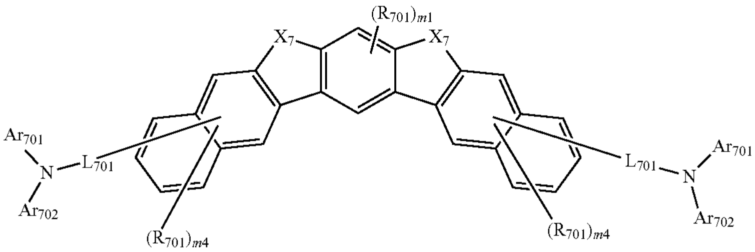
[Formula 383]
(71-23)
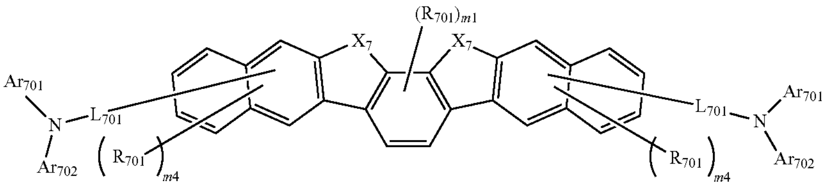
[Formula 384]
(71-24)
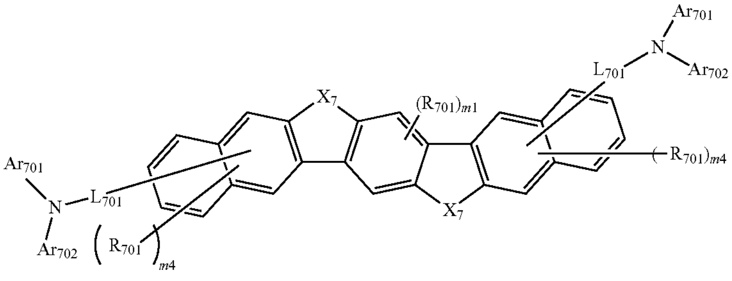

-continued
[Formula 385]
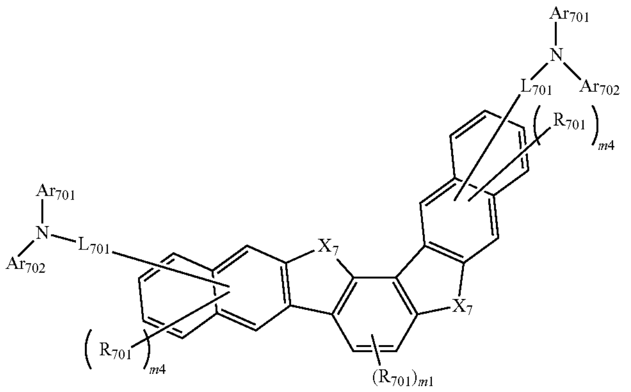
(71-25)
In the formulae (71-21) to (71-25), $R_{701}$, $X_7$, $Ar_{701}$, $Ar_{702}$, $L_{701}$, m1 and m4 respectively represent the same as $R_{701}$, $X_7$, $Ar_{701}$, $Ar_{702}$, $L_{701}$, m1 and m4 in the formula (7).
In an exemplary embodiment, the compound represented by the formula (7) is represented by any one of formulae (71-31) to (71-33) below.
[Formula 386]
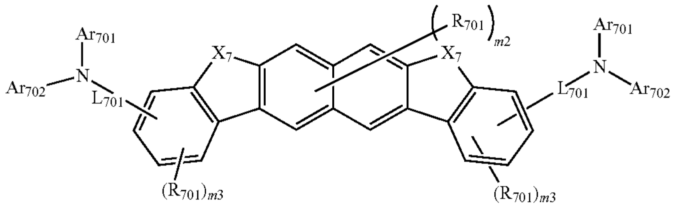
(71-31)
[Formula 387]
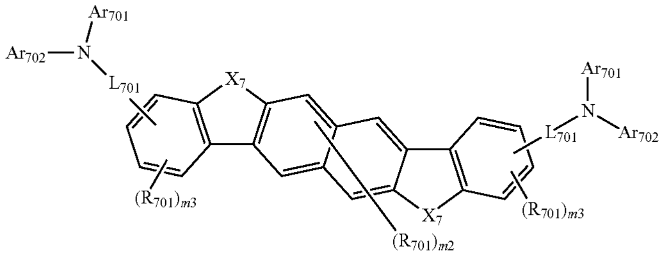
(71-32)
[Formula 388]
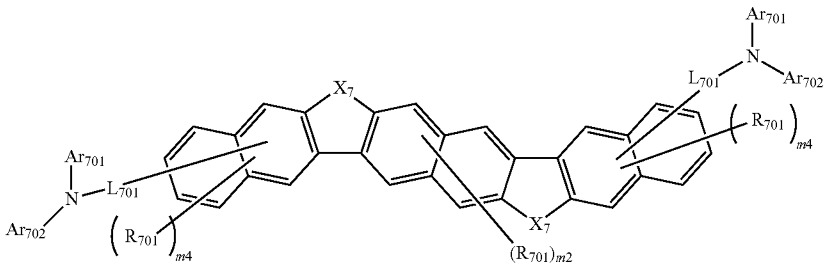
(71-33)

In the formulae (71-31) to (71-33), $R_{701}$, $X_7$, $Ar_{701}$, $Ar_{702}$, $L_{701}$, and m2 to m4 respectively represent the same as $R_{701}$, $X_7$, $Ar_{701}$, $Ar_{702}$, $L_{701}$, and m2 to m4 in the formula (7).

In an exemplary embodiment, $Ar_{701}$ and $Ar_{702}$ are each independently a substituted or unsubstituted aryl group having 6 to 50 ring carbon atoms.

In an exemplary embodiment, one of $Ar_{701}$ and $Ar_{702}$ is a substituted or unsubstituted aryl group having 6 to 50 ring carbon atoms, and the other of $Ar_{701}$ and $Ar_{702}$ is a substituted or unsubstituted heterocyclic group having 5 to 50 ring atoms.

Specific examples of the compound represented by the formula (7) include compounds shown below.

[Formula 389]

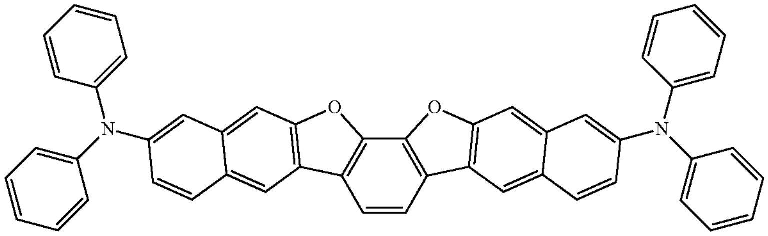

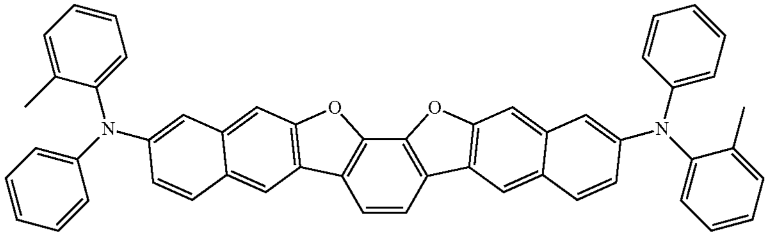

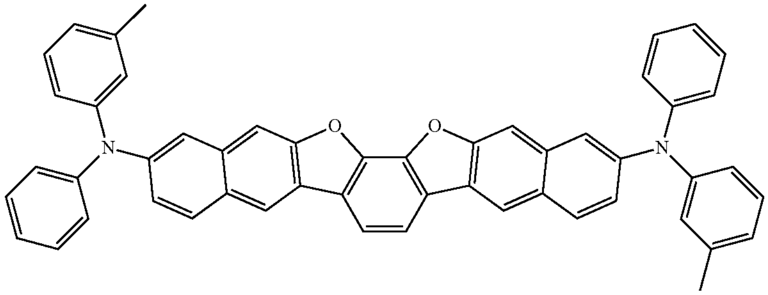

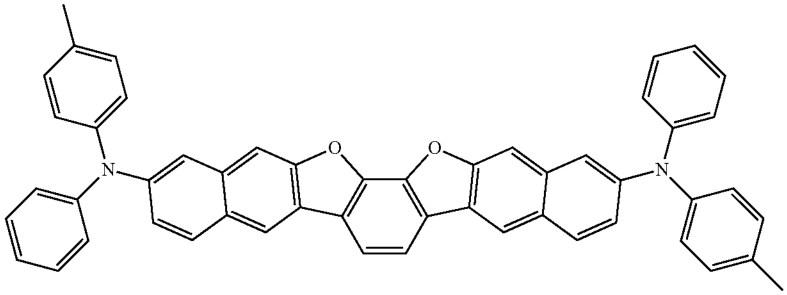

-continued
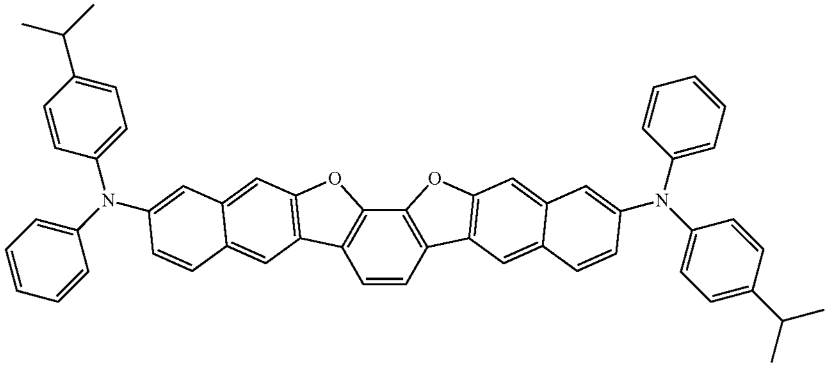
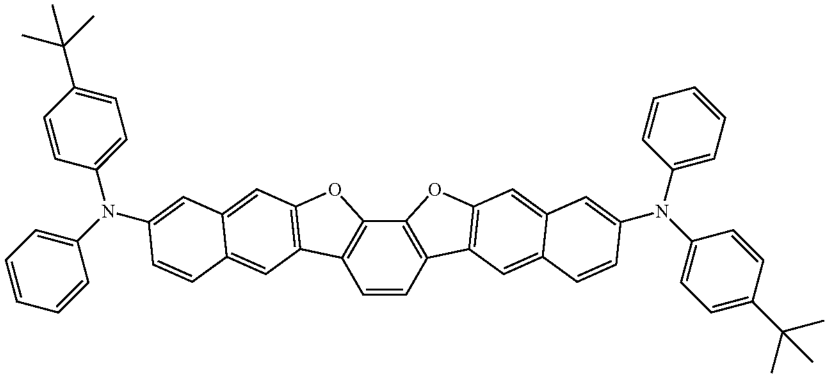
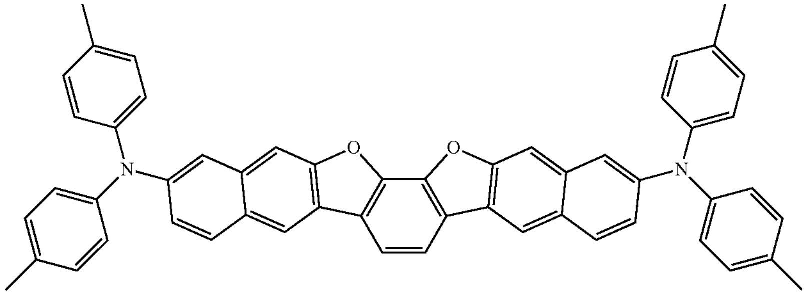
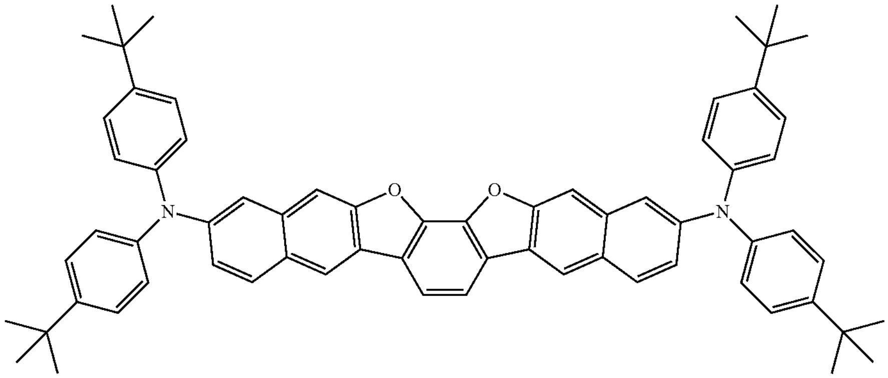
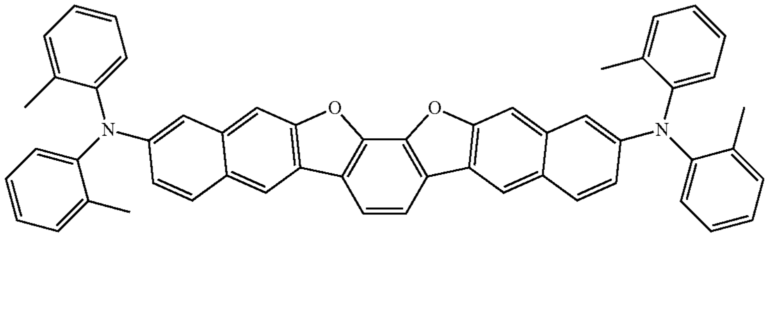

-continued
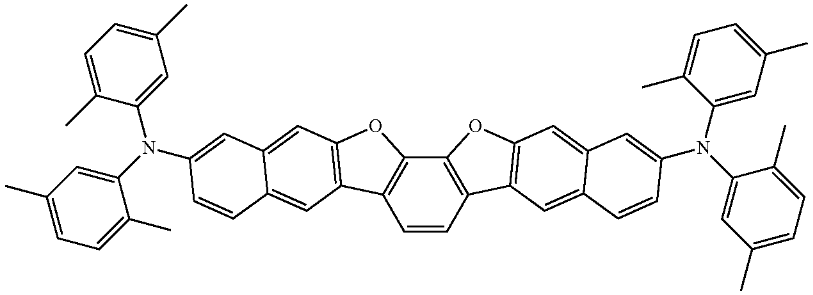
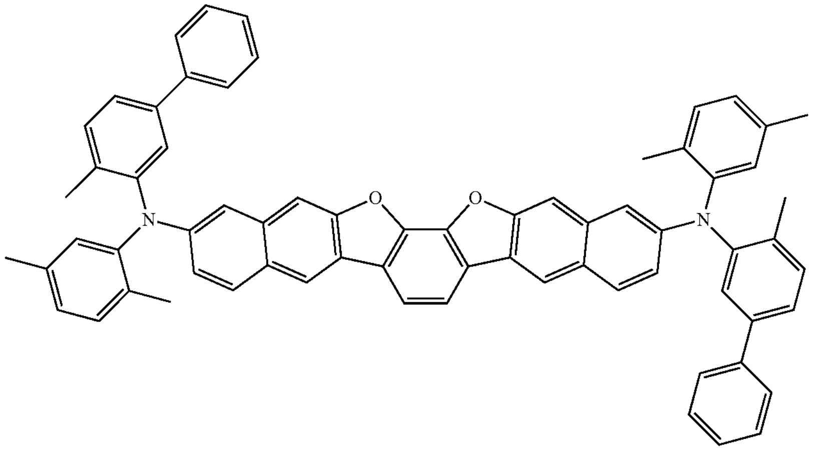
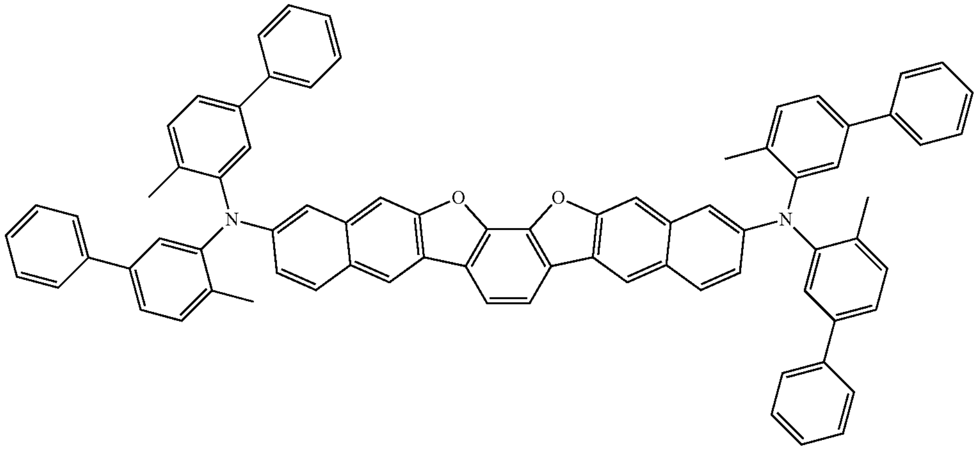
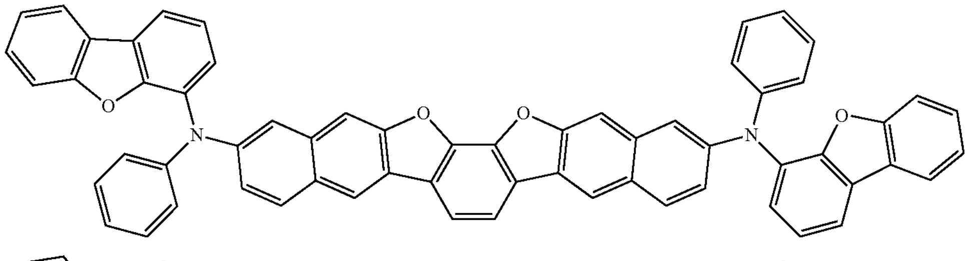
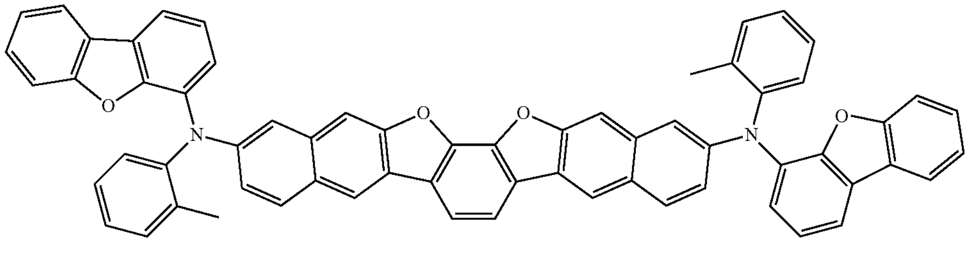

-continued
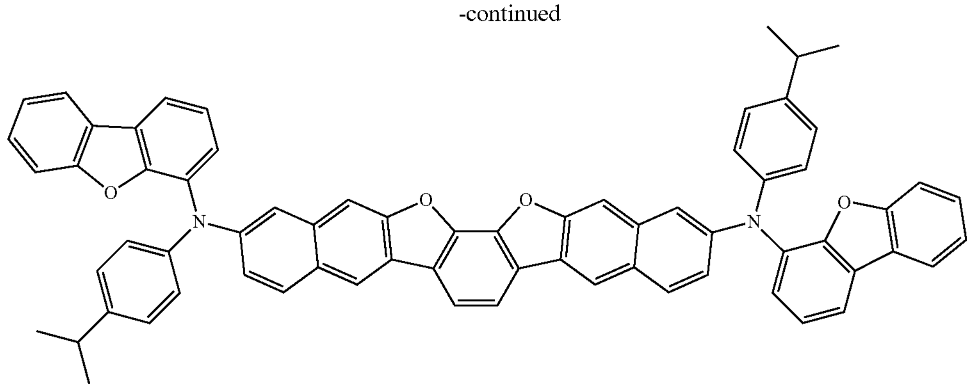
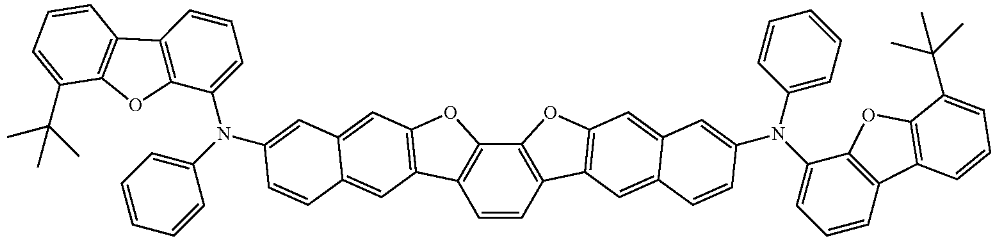
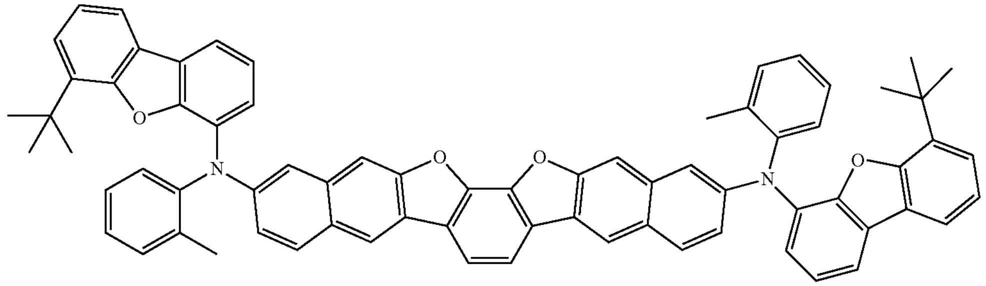
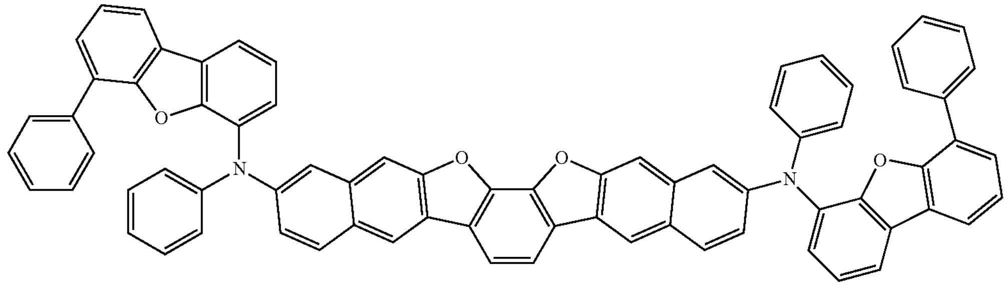
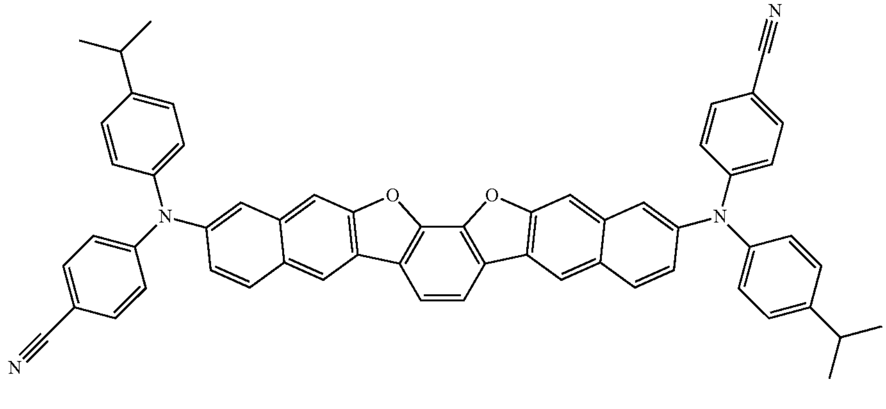

-continued
[Formula 390]
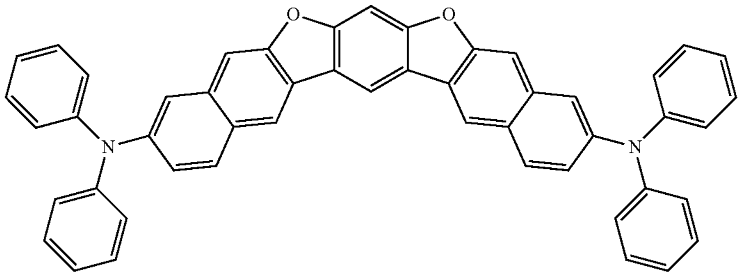
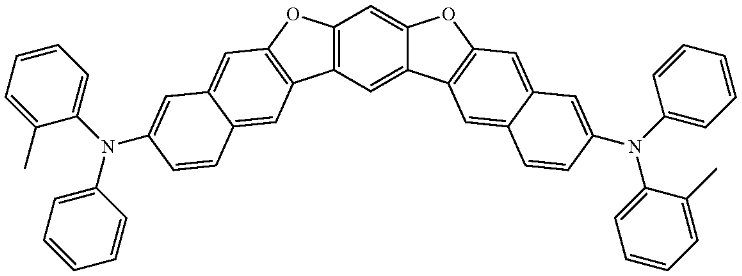
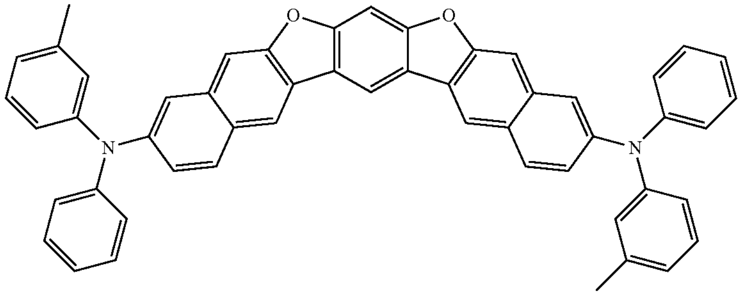
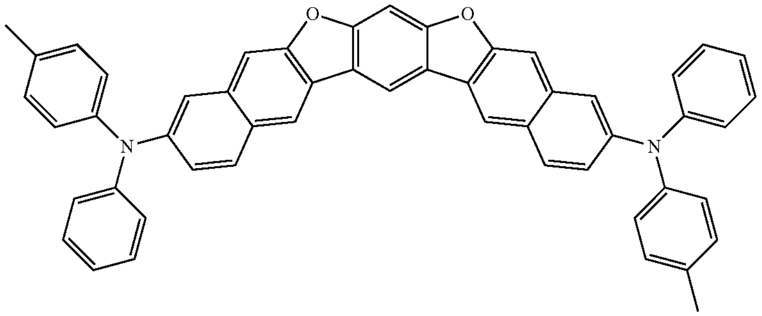
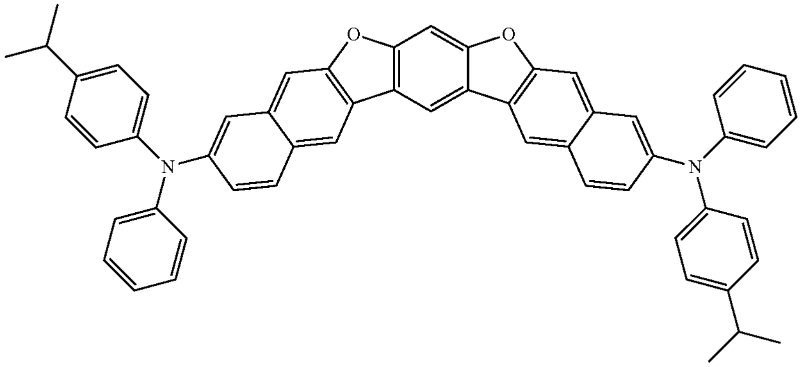

-continued
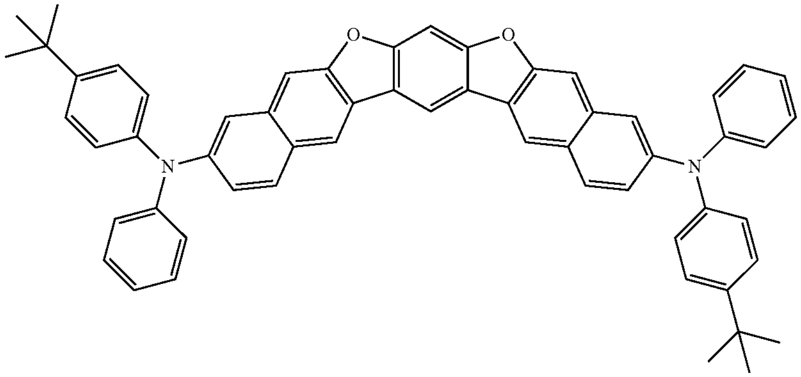
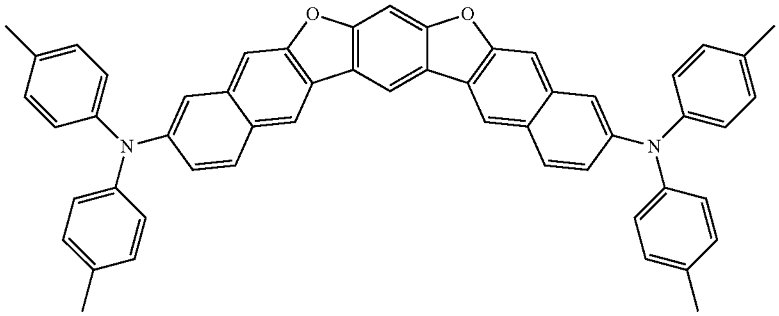
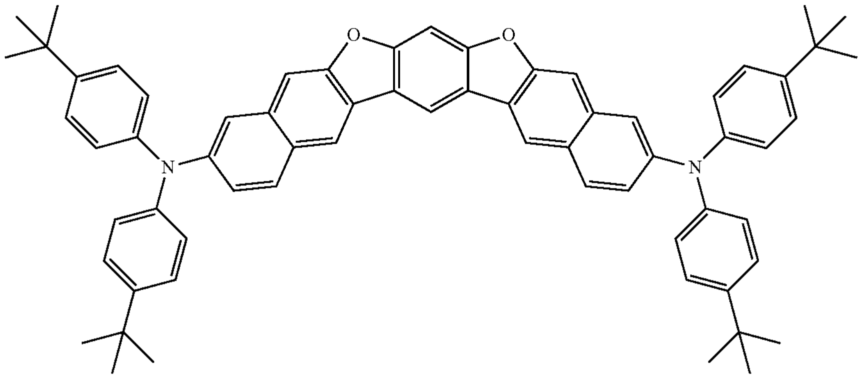
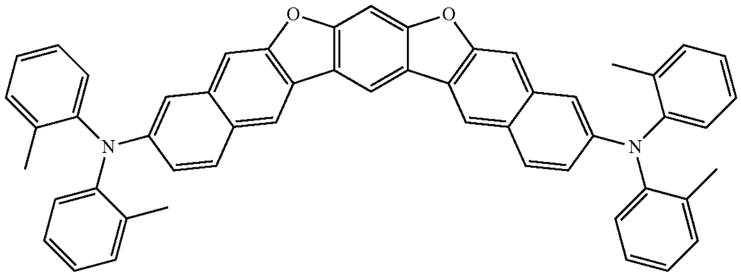
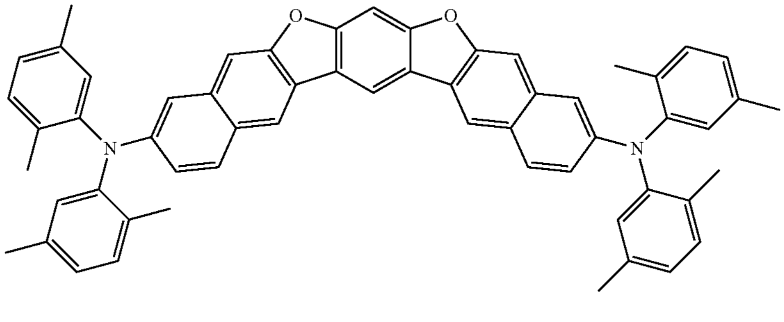

-continued
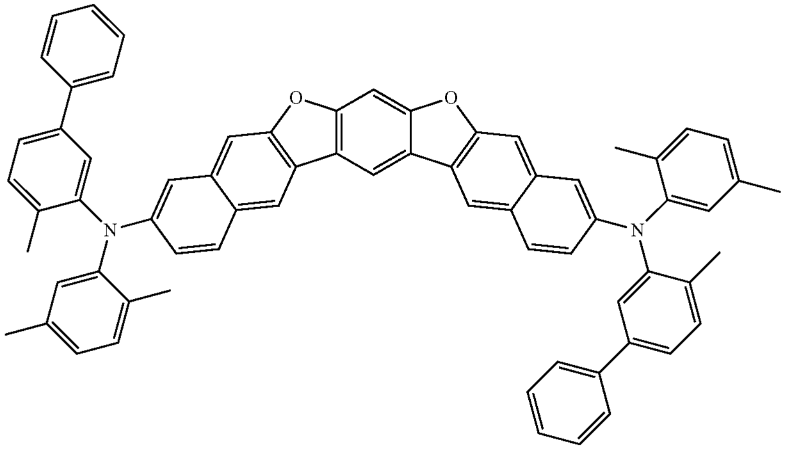
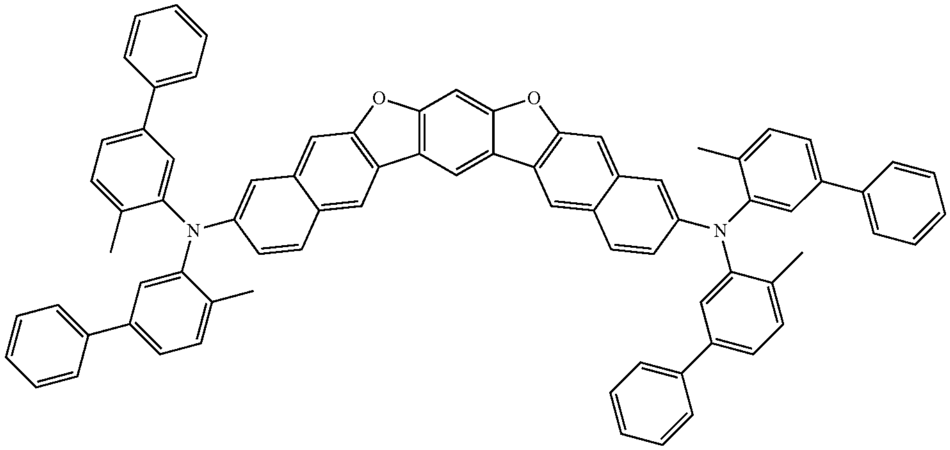
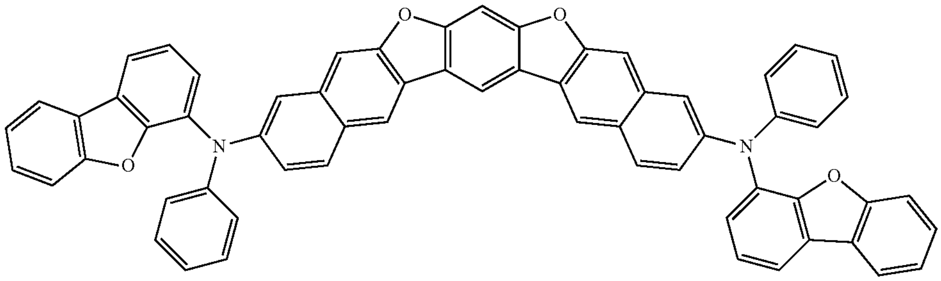
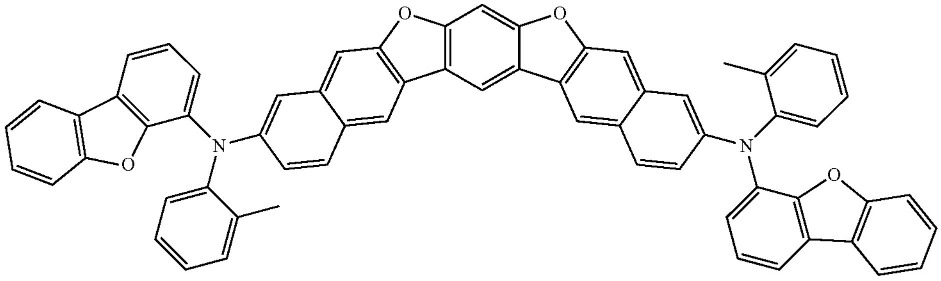

-continued
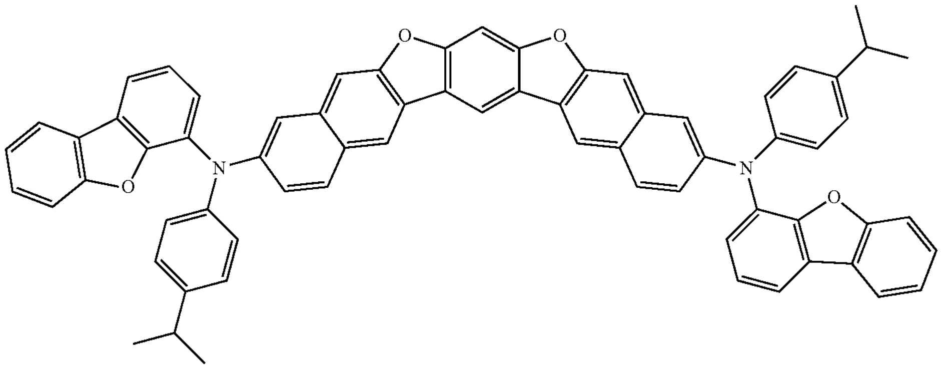
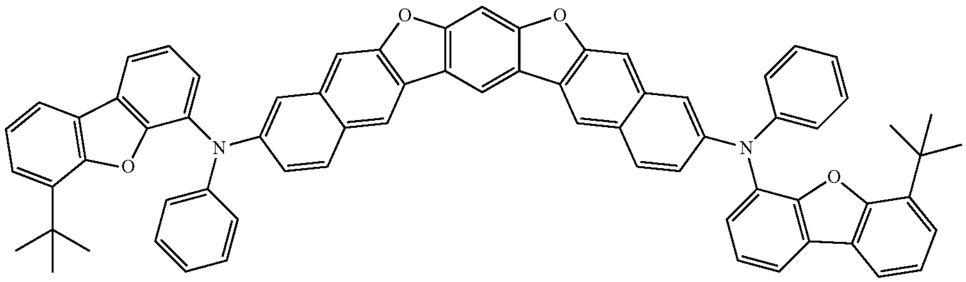
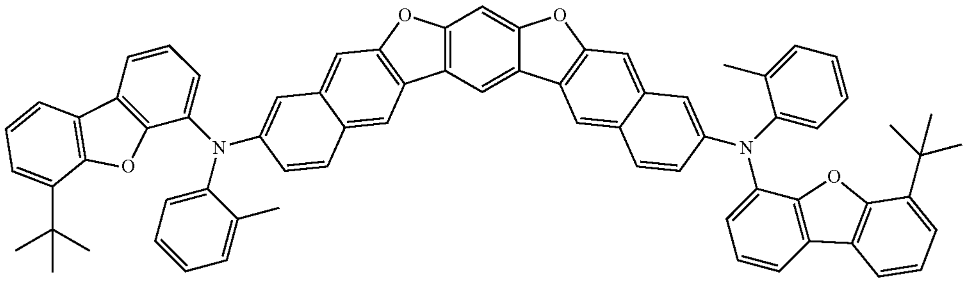
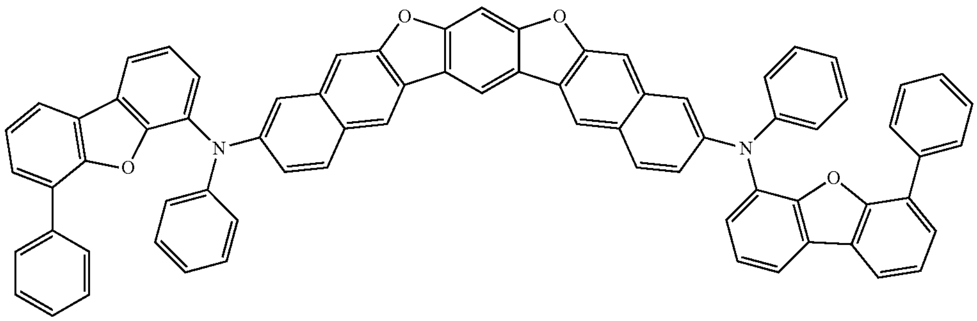
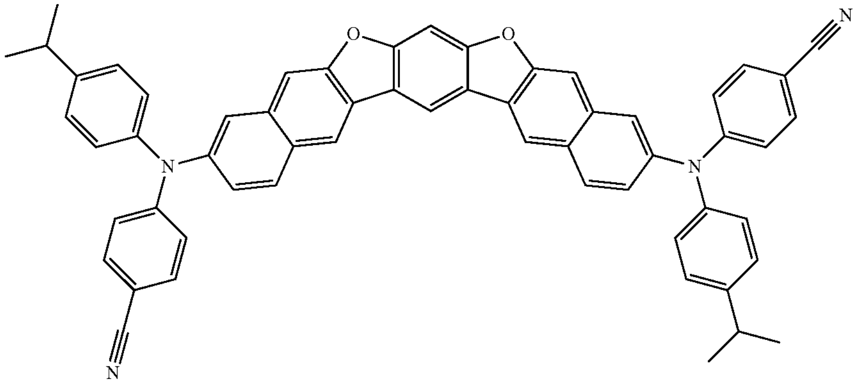

-continued
[Formula 391]
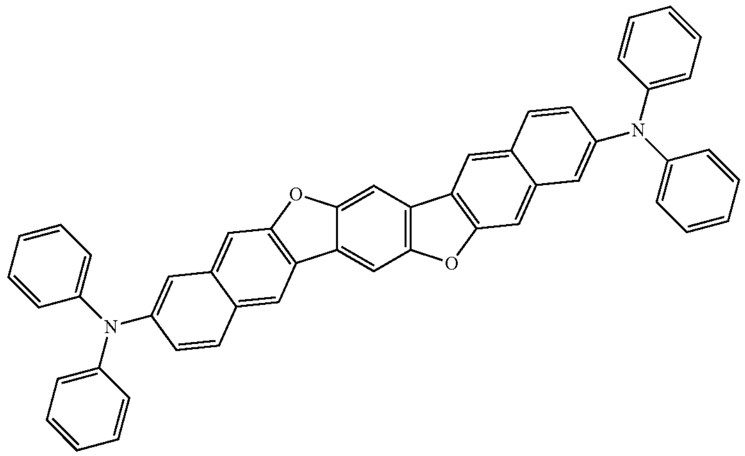
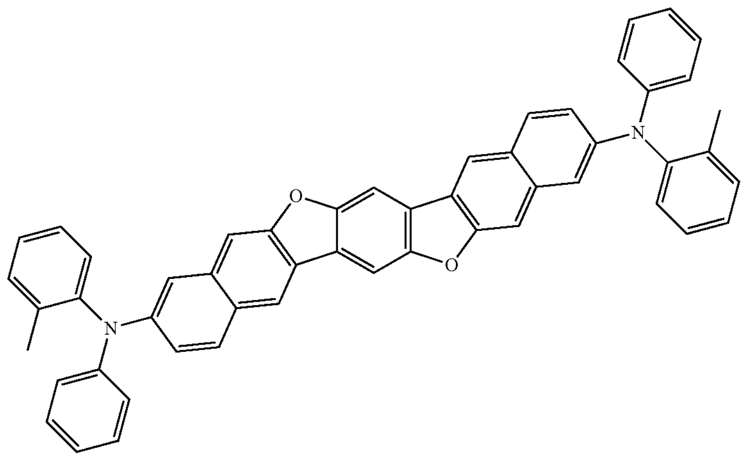
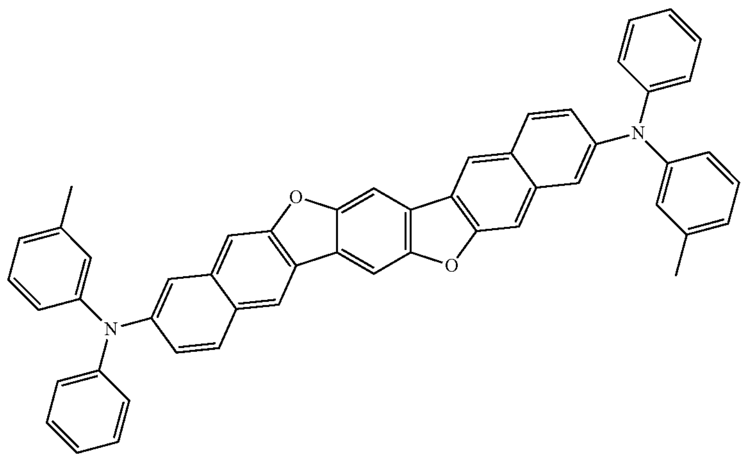

-continued
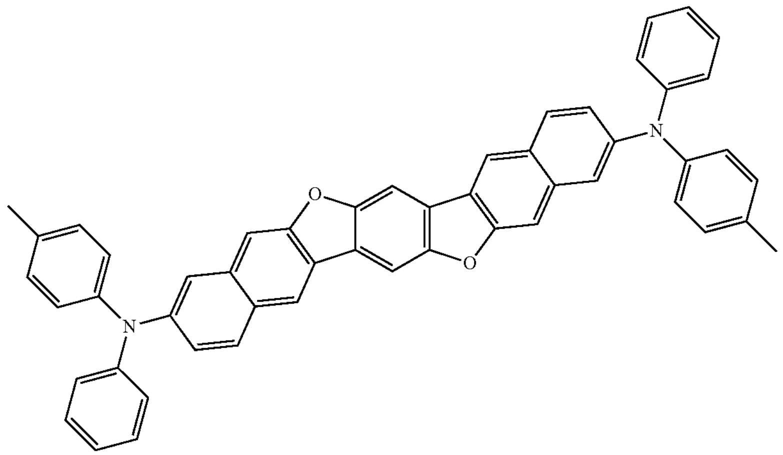
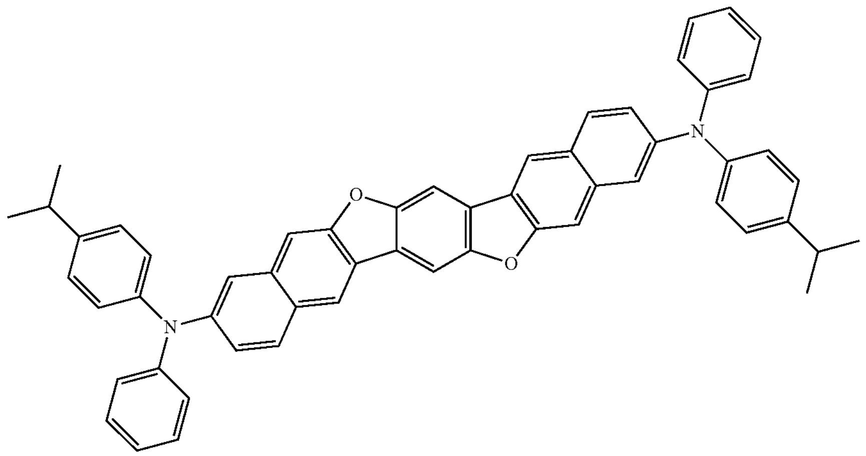
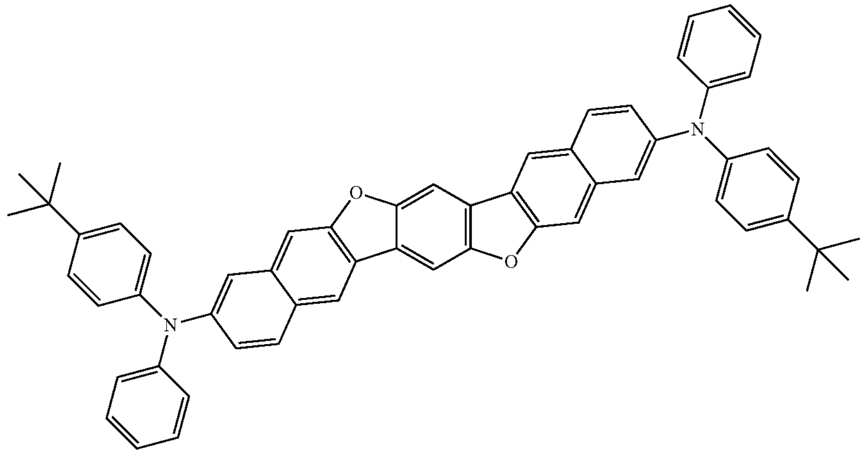

-continued
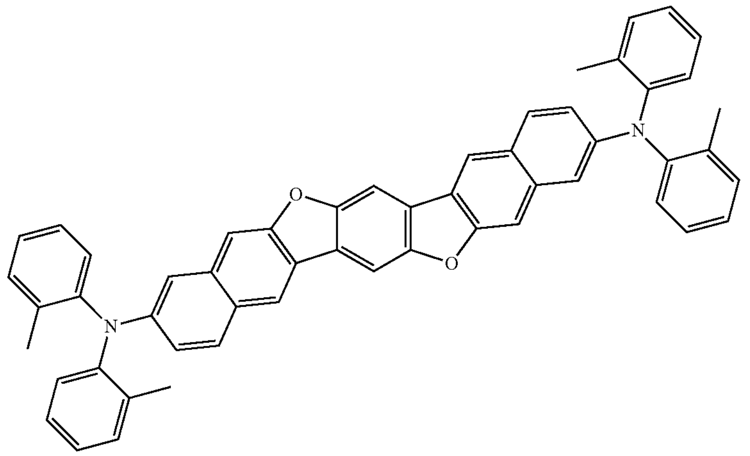
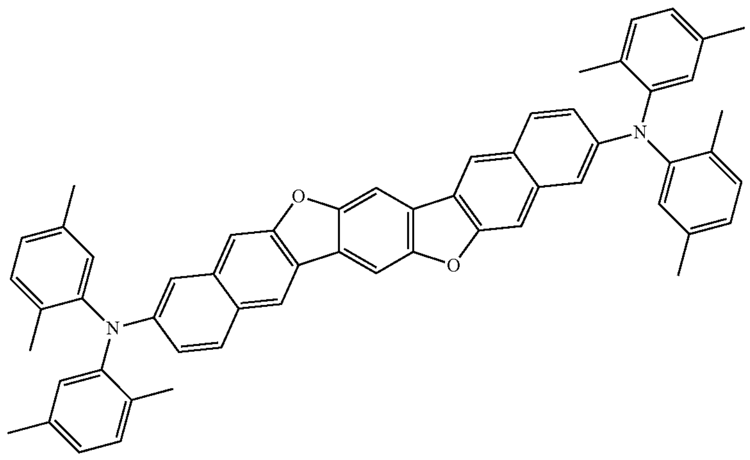
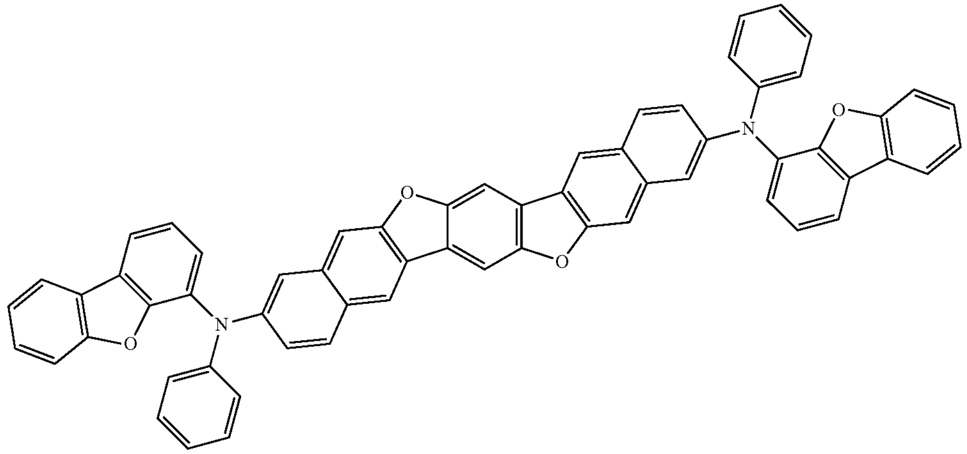

-continued
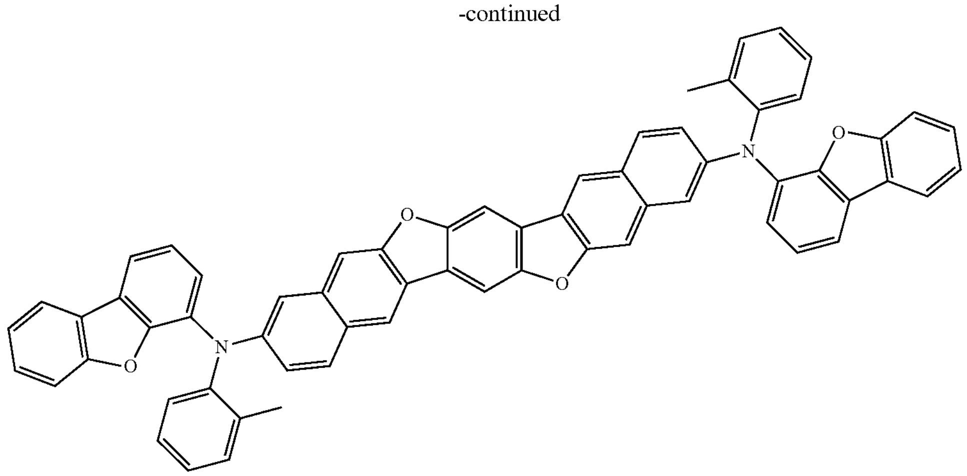
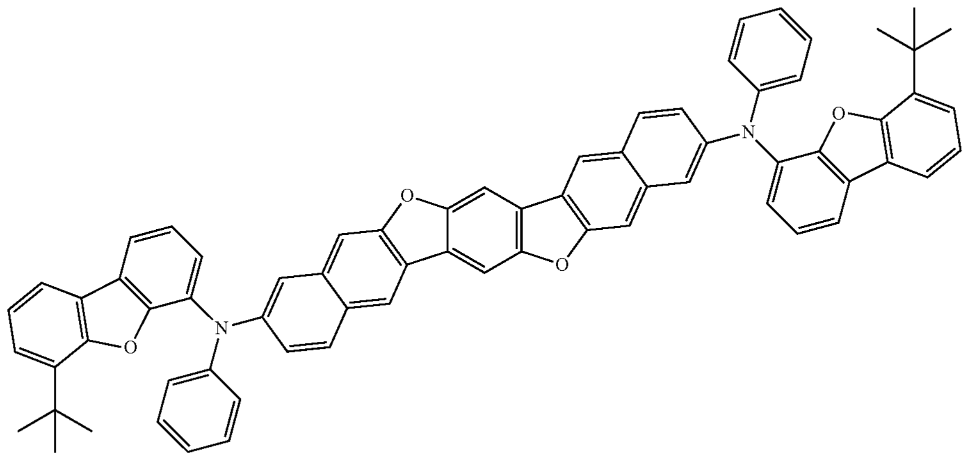
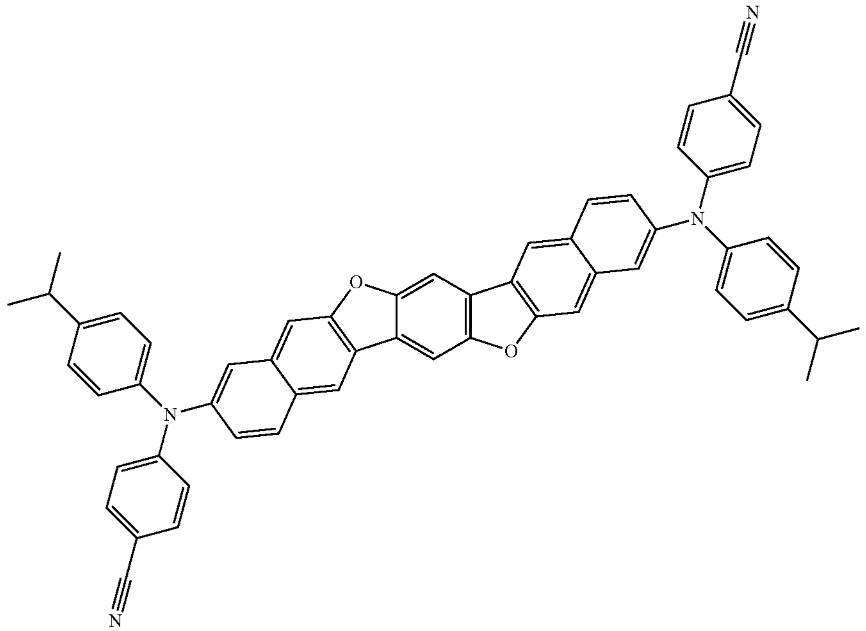

-continued
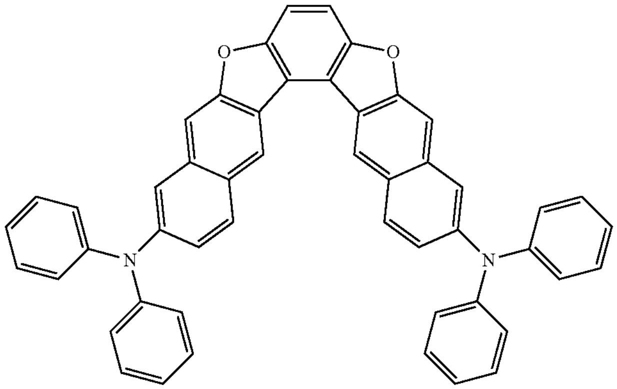
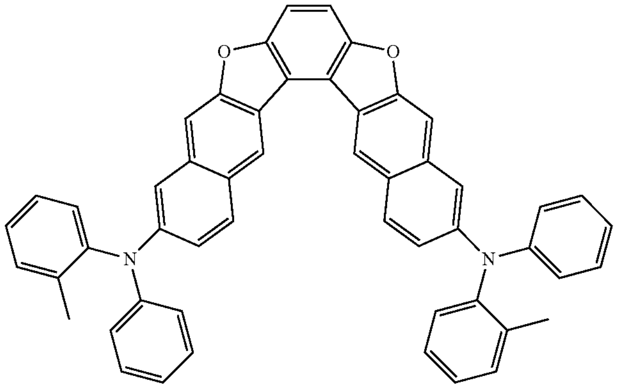
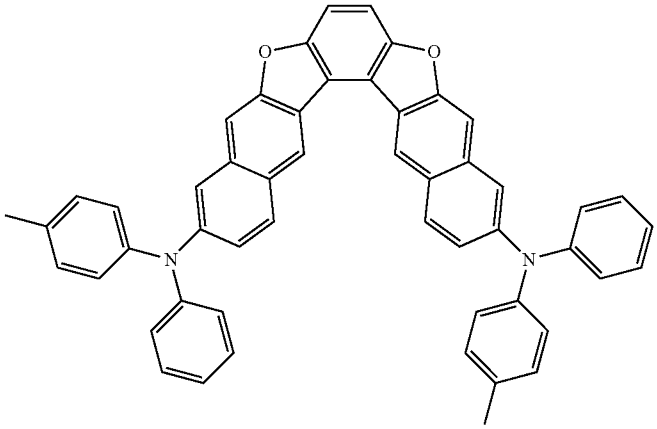
[Formula 392]
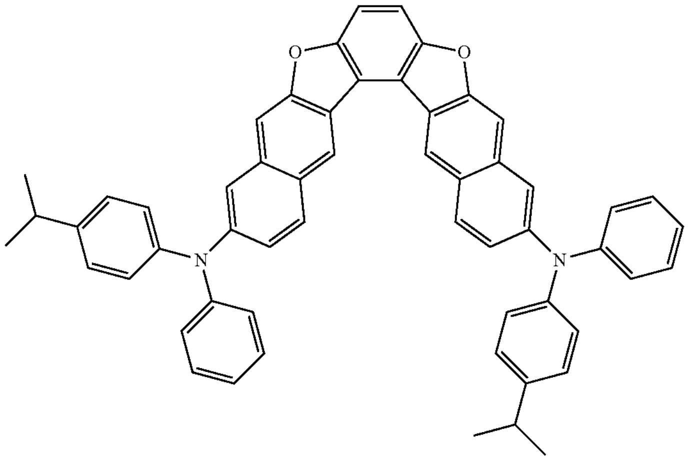

-continued
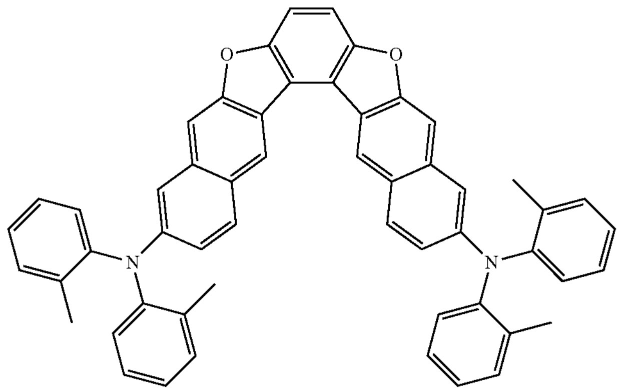
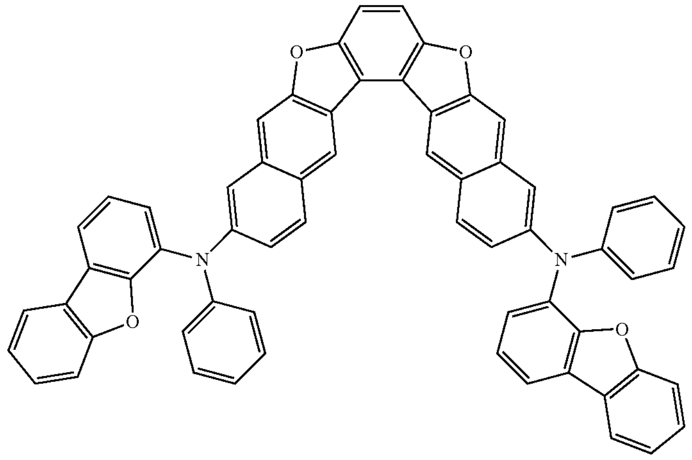
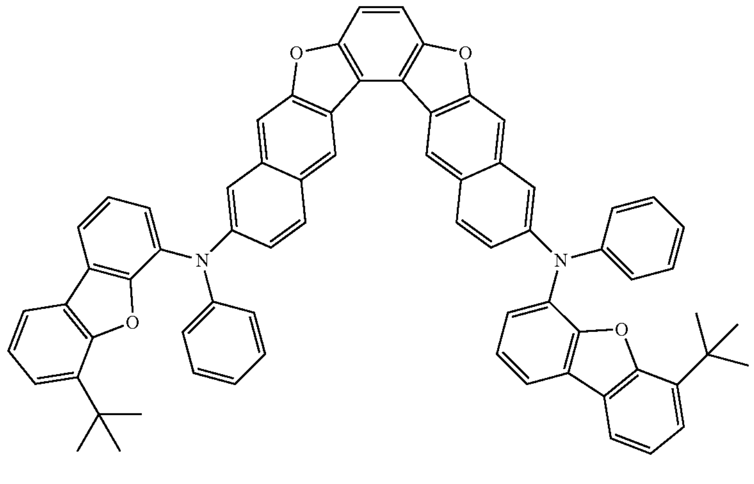

-continued
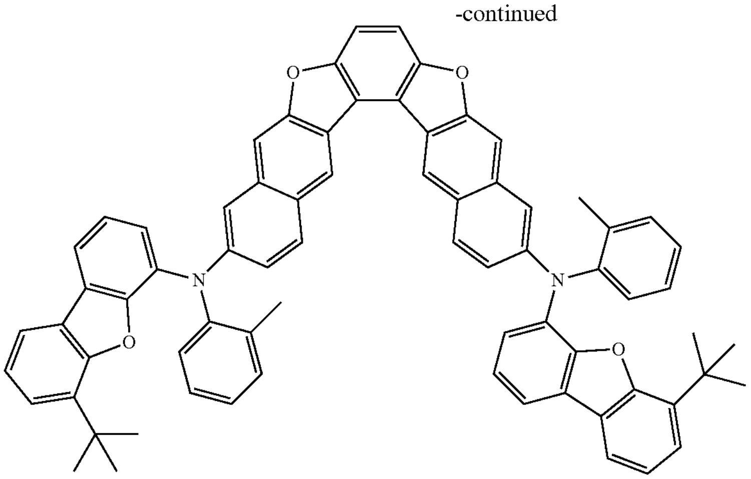
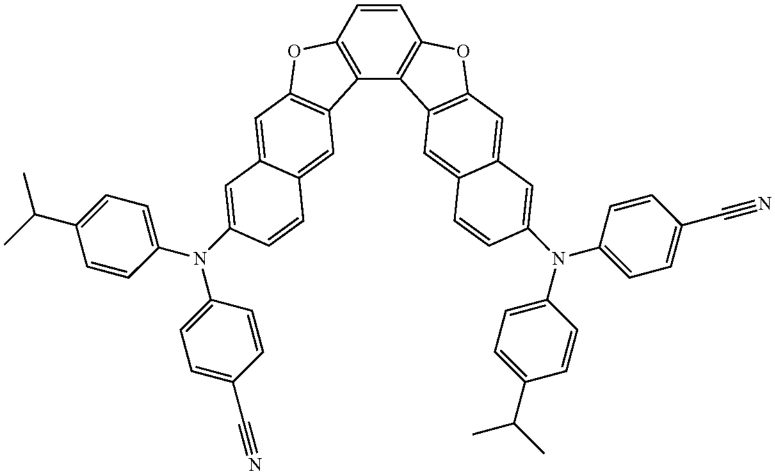
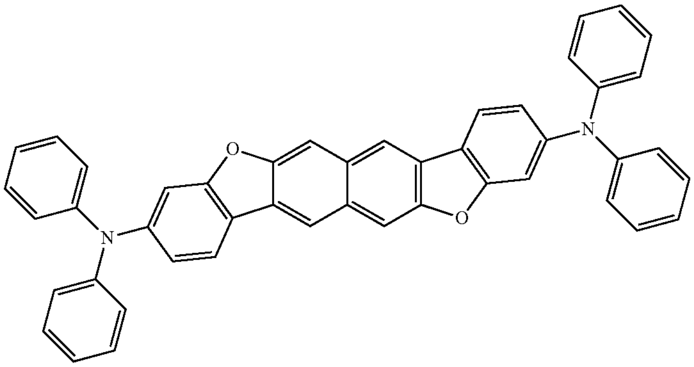
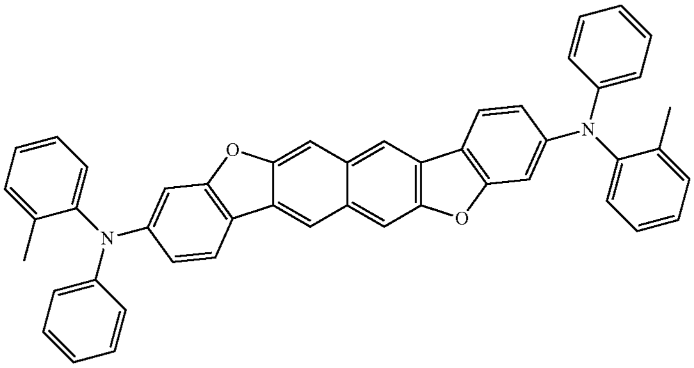

-continued
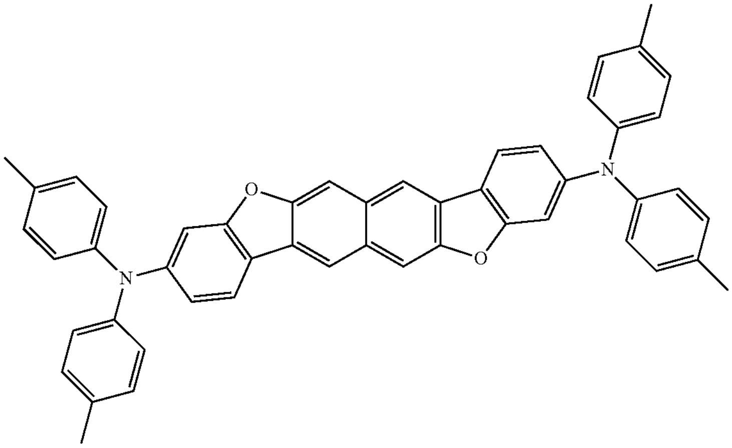
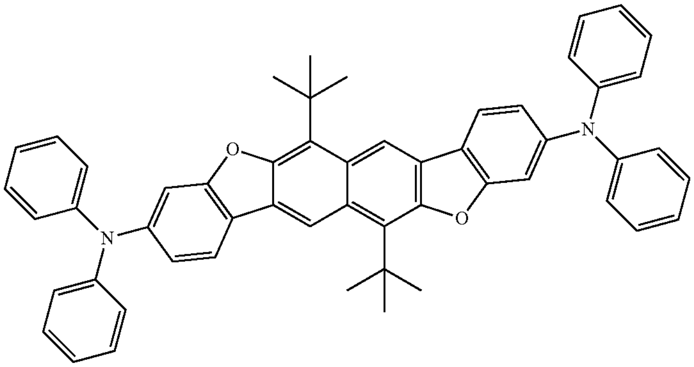
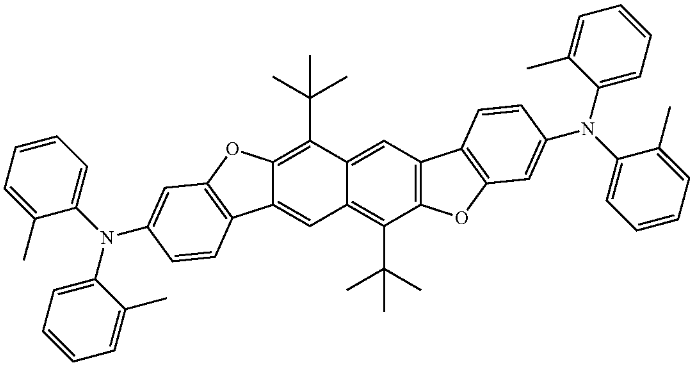
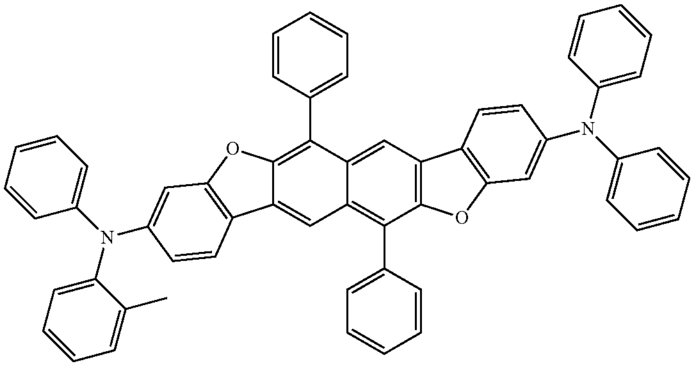

-continued
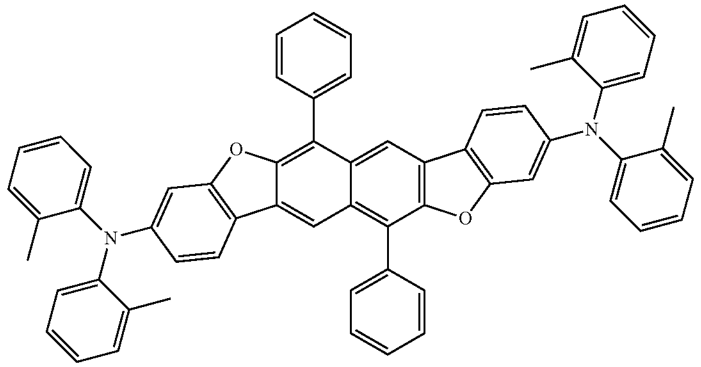
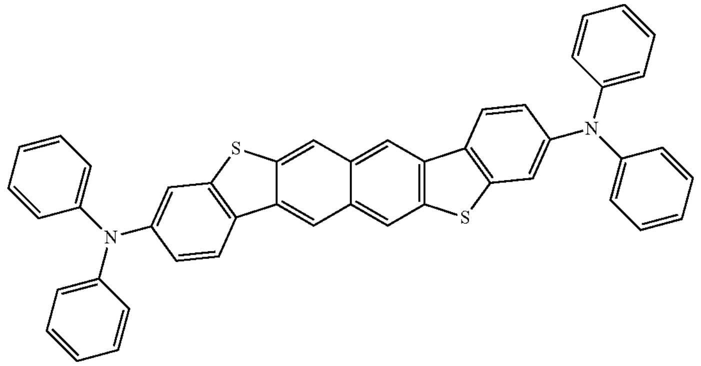
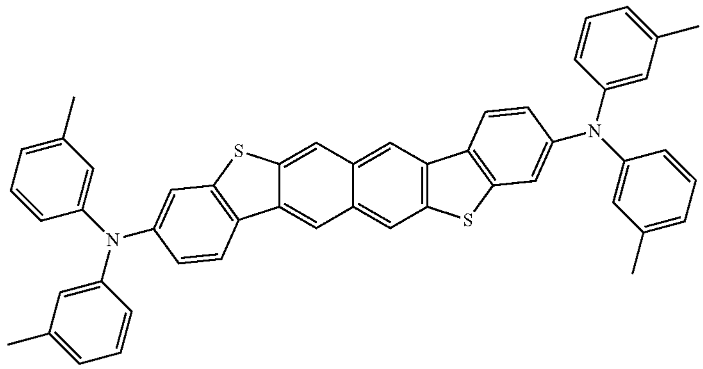
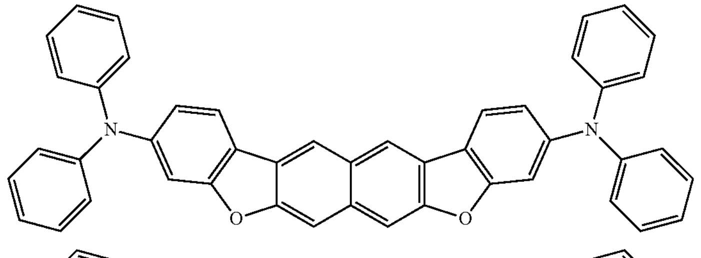
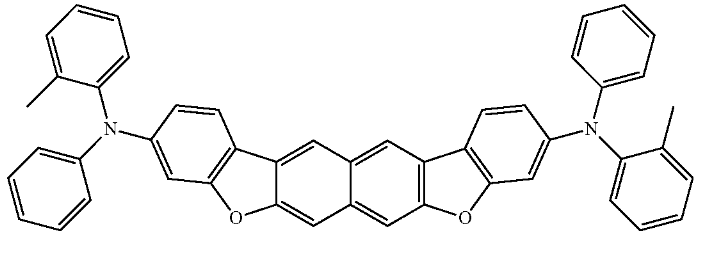

-continued
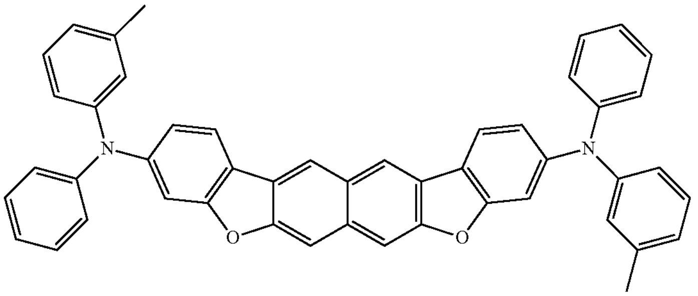
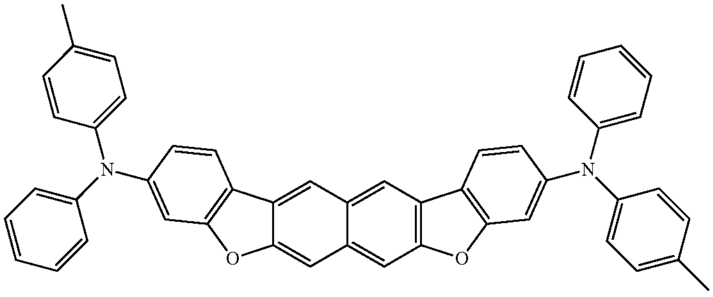
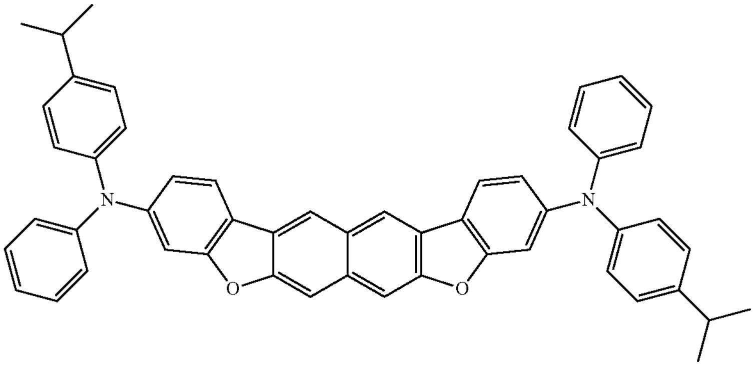
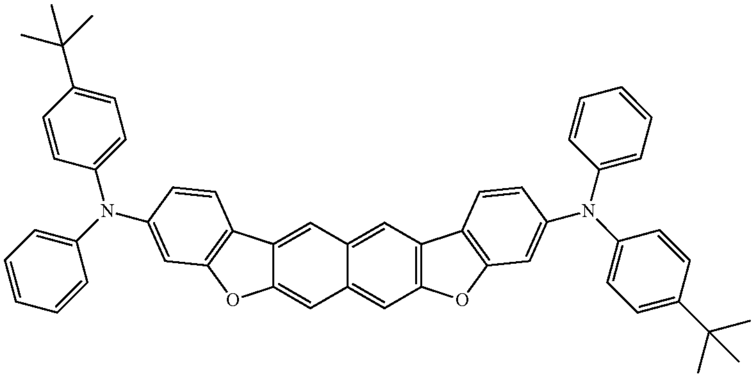
[Formula 393]
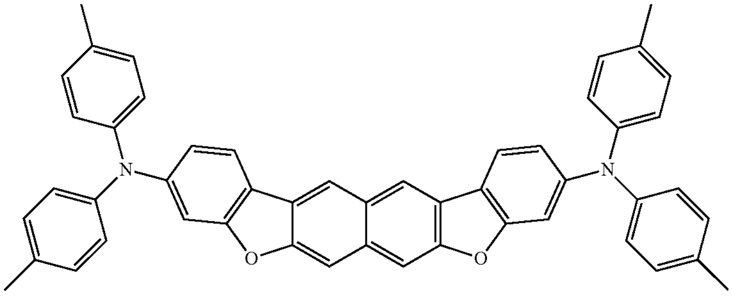

-continued
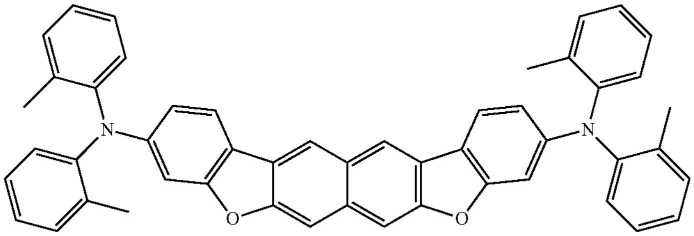
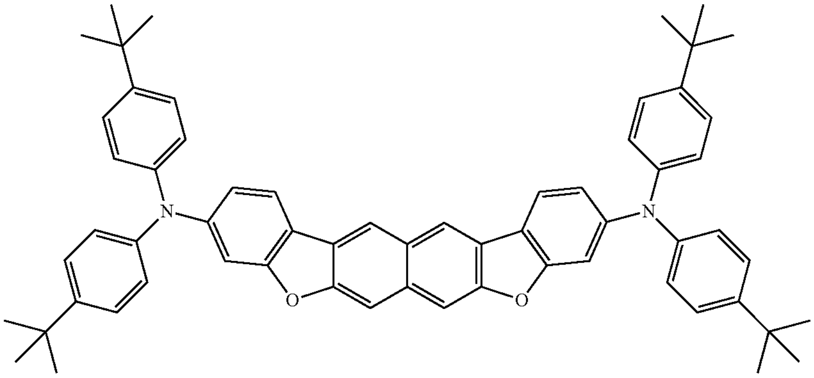
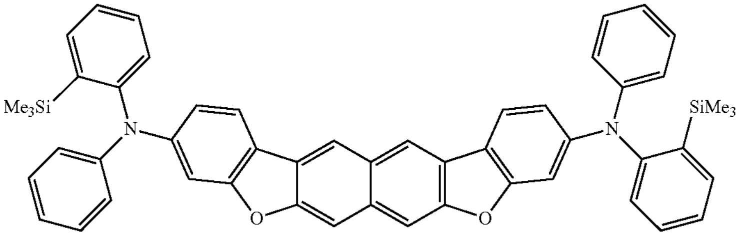
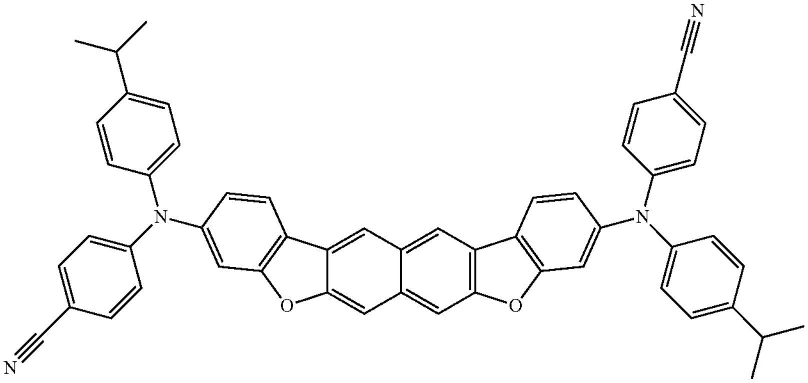
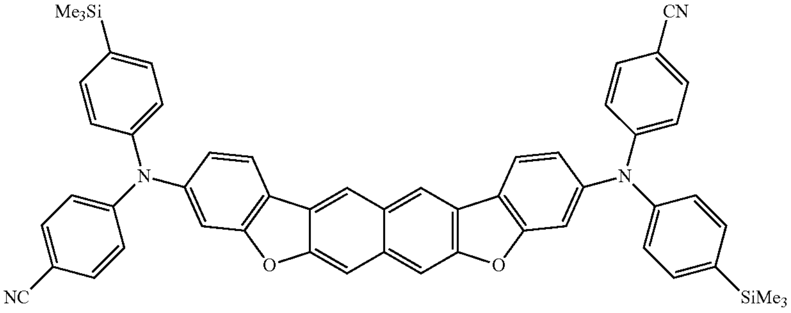

-continued
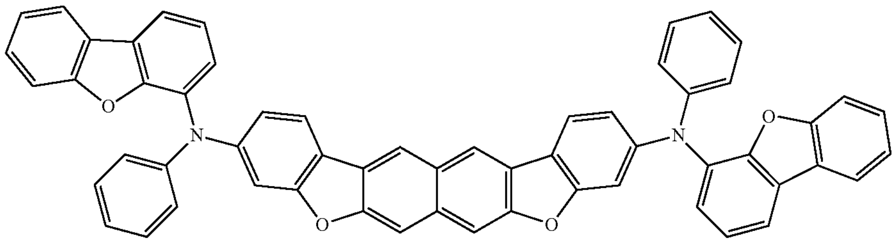
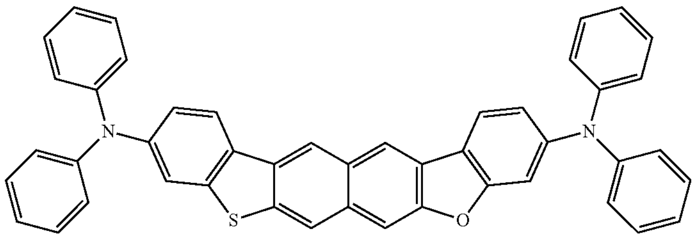
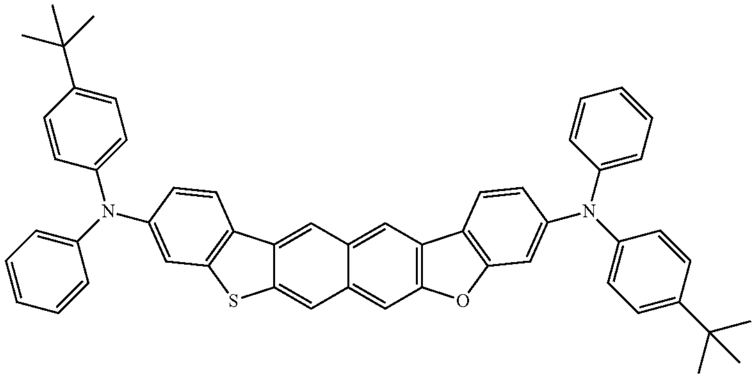
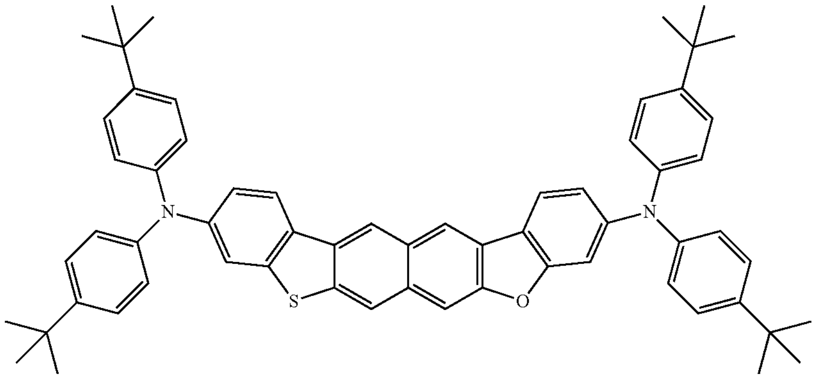
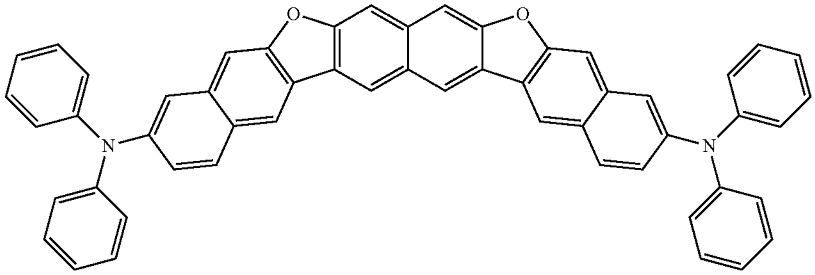

-continued
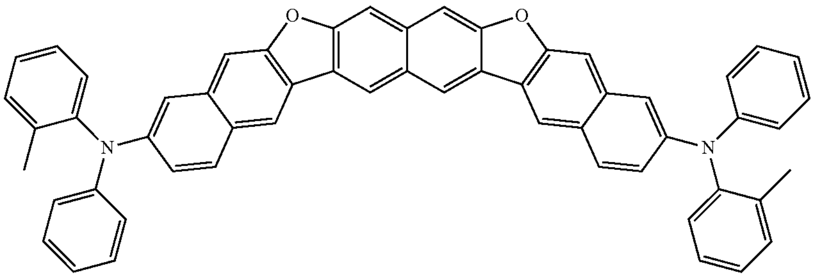
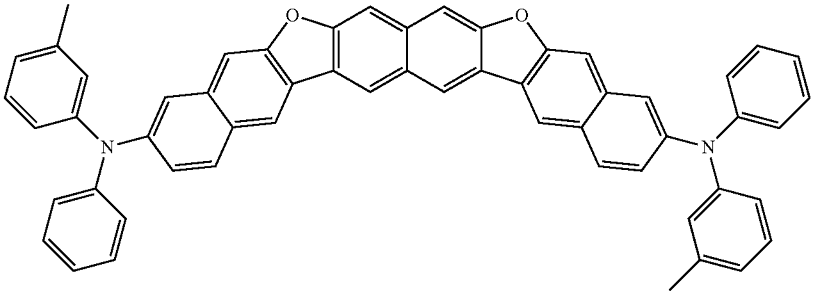
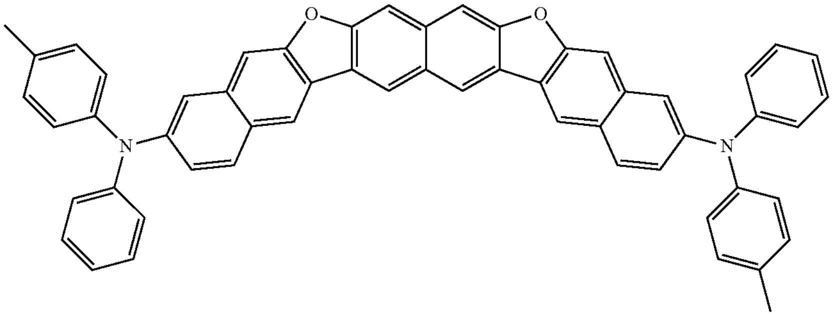
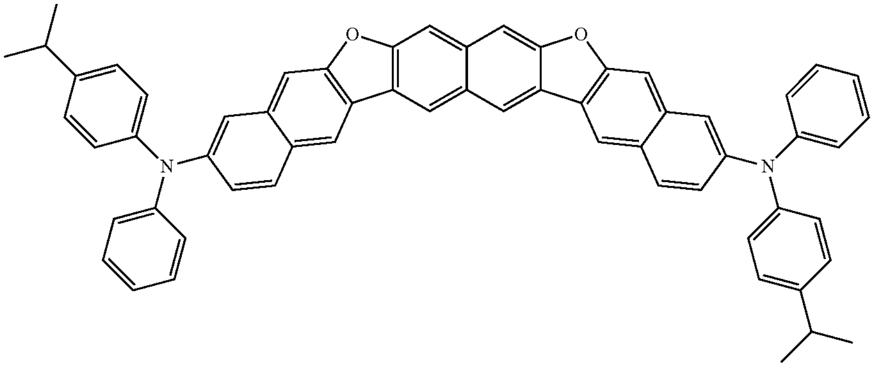
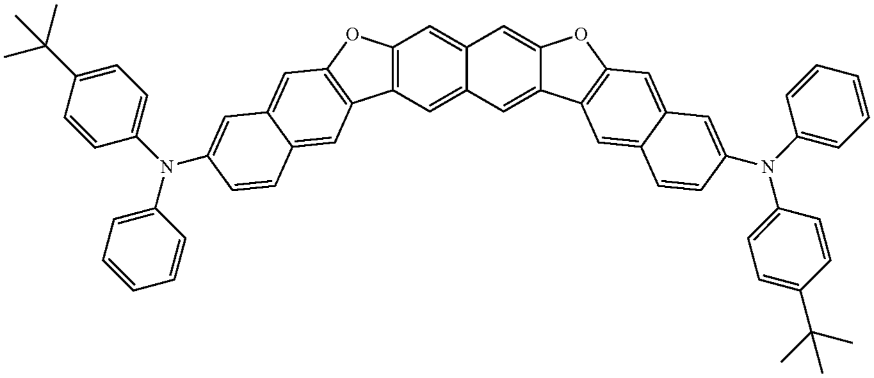

-continued
[Formula 394]
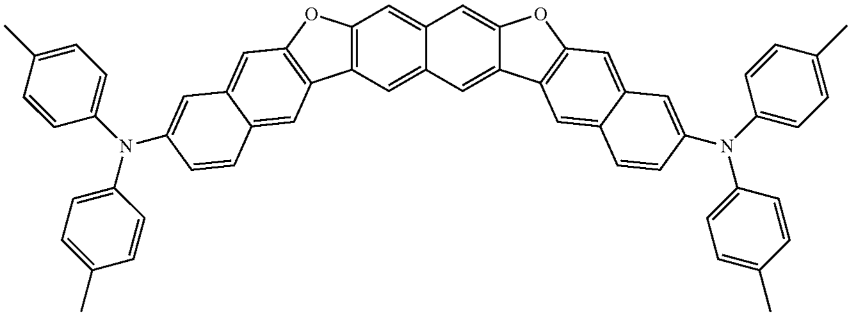
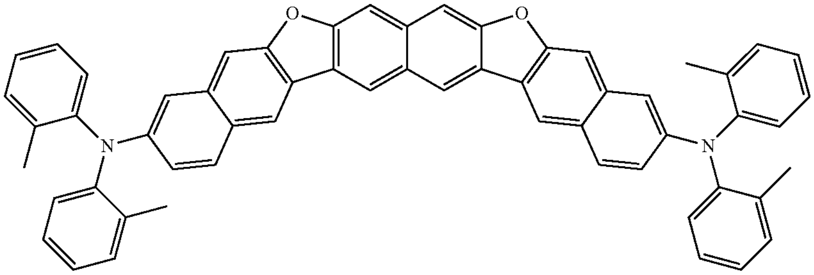
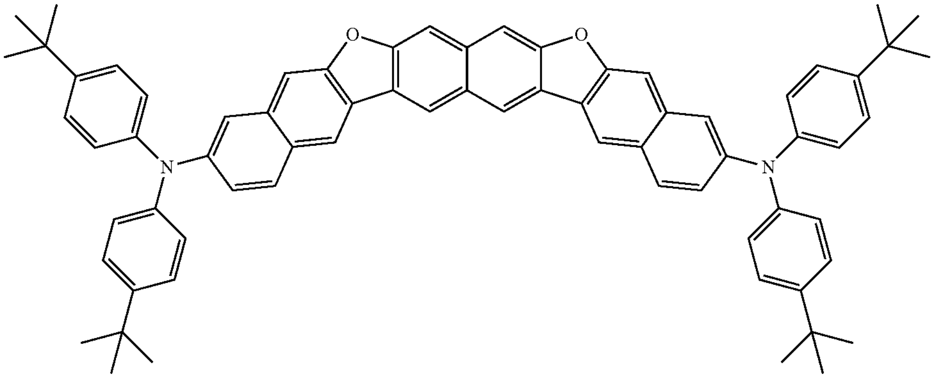
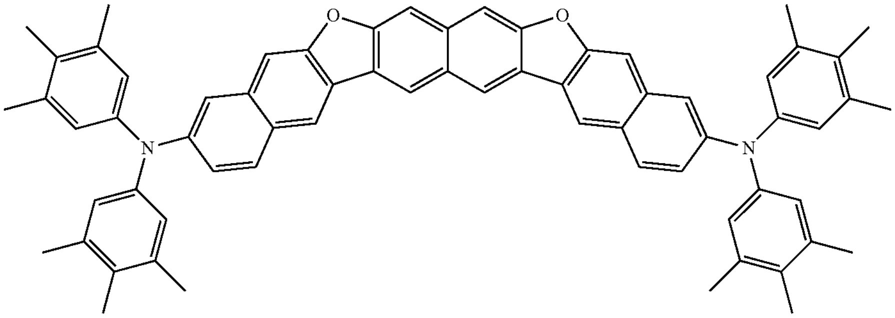
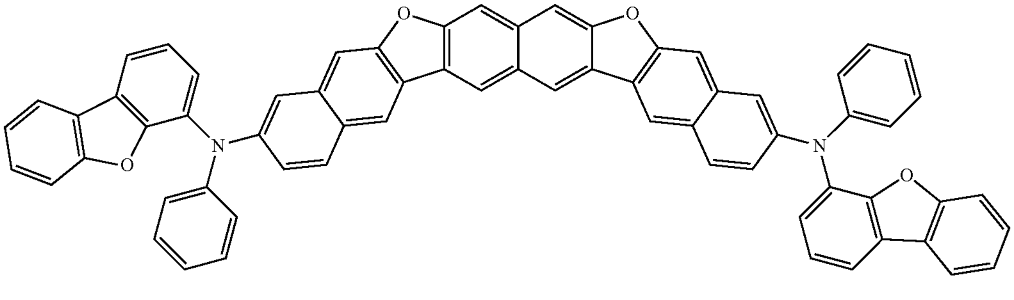

-continued

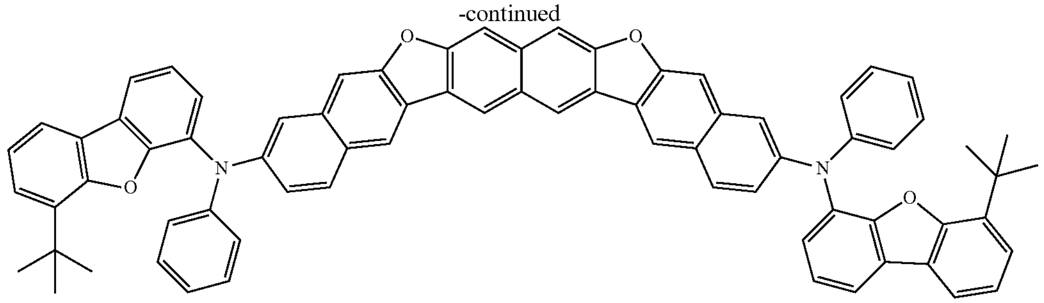

Compound Represented by Formula (8)

The compound represented by the formula (8) will be described below.

[Formula 395]

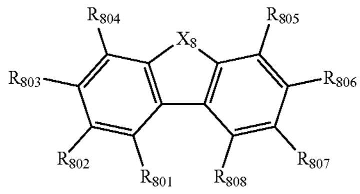

(8)

In the formula (8):

at least one combination of $R_{801}$ and $R_{802}$, $R_{802}$ and $R_{803}$, or $R_{803}$ and $R_{804}$ are mutually bonded to form a divalent group represented by a formula (82) below; and at least one combination of $R_{805}$ and $R_{806}$, $R_{806}$ and $R_{807}$, or $R_{807}$ and $R_{808}$ are mutually bonded to form a divalent group represented by a formula (83) below.

[Formula 396]

(82)

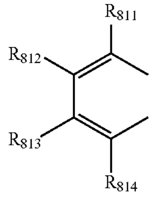

(83)

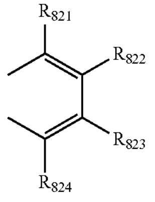

At least one of $R_{801}$ to $R_{804}$ not forming the divalent group represented by the formula (82) or $R_{811}$ to $R_{814}$ is a monovalent group represented by a formula (84) below;

at least one of $R_{805}$ to $R_{808}$ not forming the divalent group represented by the formula (83) or $R_{821}$ to $R_{824}$ is a monovalent group represented by a formula (84) below;

$X_8$ is an oxygen atom, a sulfur atom, or $NR_{809}$; and $R_{801}$ to $R_{808}$ not forming the divalent group represented by the formula (82) or (83) and not being the monovalent group represented by the formula (84), $R_{811}$ to $R_{814}$ and $R_{821}$ to $R_{824}$ not being the monovalent group represented by the formula (84), and $R_{809}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 397]

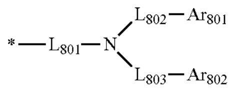

(84)

In the formula (84):

$Ar_{801}$ and $Ar_{802}$ are each independently a substituted or unsubstituted aryl group having 6 to 50 ring carbon atoms, or a substituted or unsubstituted heterocyclic group having 5 to 50 ring atoms;

$L_{801}$ to $L_{803}$ are each independently a single bond, a substituted or unsubstituted arylene group having 6 to 30 ring carbon atoms, a substituted or unsubstituted divalent divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (84) represents a bonding position to a cyclic structure represented by the formula (8) or a bonding position to a group represented by the formula (82) or (83).

In the formula (8), the positions for the divalent group represented by the formula (82) and the divalent group represented by the formula (83) to be formed are not specifically limited but the divalent groups may be formed at any possible positions on $R_{801}$ to $R_{808}$.

In an exemplary embodiment, the compound represented by the formula (8) is represented by any one of formulae (81-1) to (81-6) below.

[Formula 398]

(81-1)

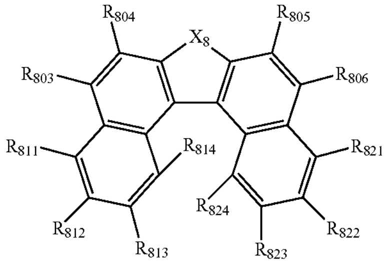

(81-2)

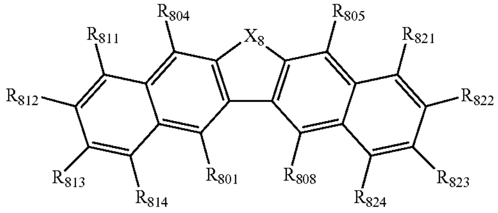

[Formula 399]

(81-3)

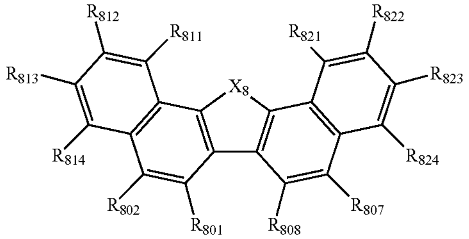

(81-4)

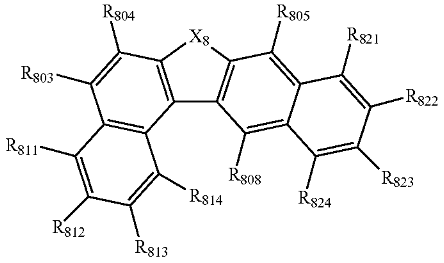

[Formula 400]

(81-5)

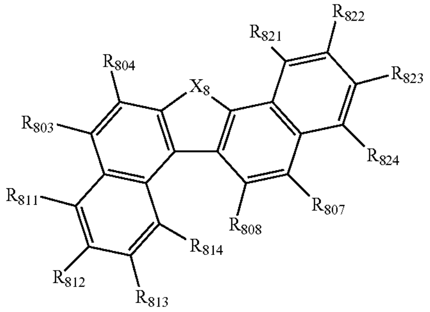

-continued (81-6)

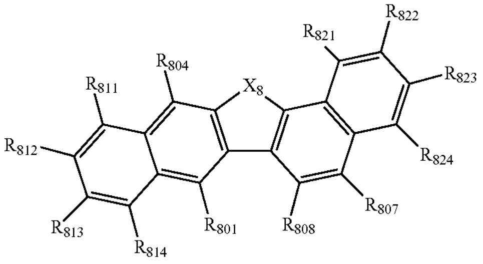

In the formulae (81-1) to (81-6):

$X_8$ represents the same as $X_8$ in the formula (8);

at least two of $R_{801}$ to $R_{824}$ are each a monovalent group represented by the formula (84); and $R_{801}$ to $R_{824}$ not being the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (8) is represented by any one of formulae (81-7) to (81-18) below.

[Formula 401]

(81-7)

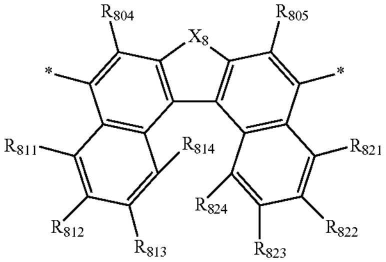

(81-8)

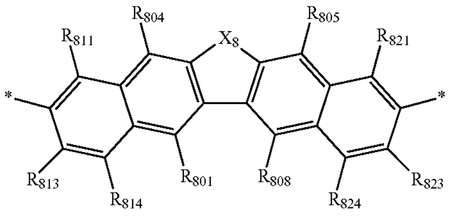

-continued

[Formula 402]

(81-9)

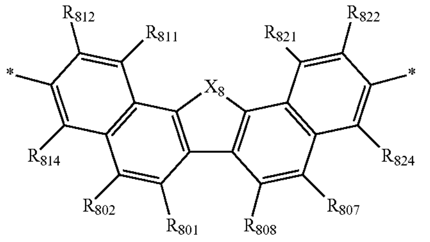

(81-10)

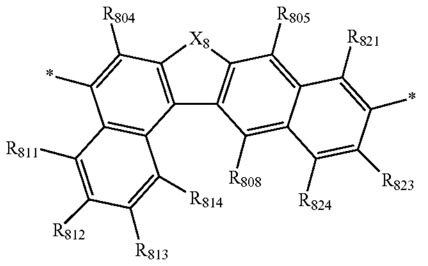

[Formula 403]

(81-11)

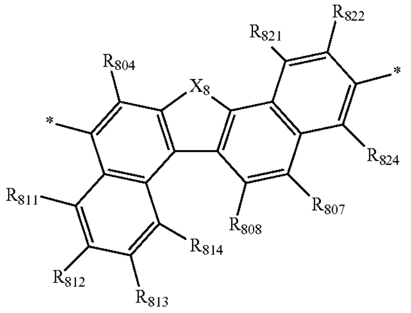

(81-12)

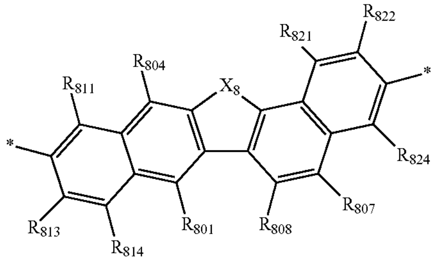

[Formula 404]

(81-13)

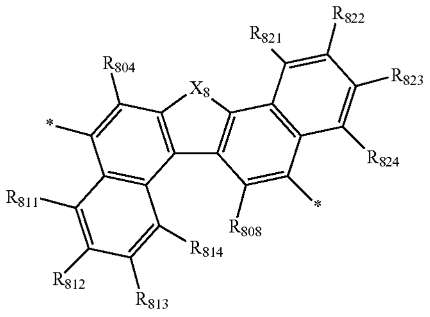

-continued (81-14)

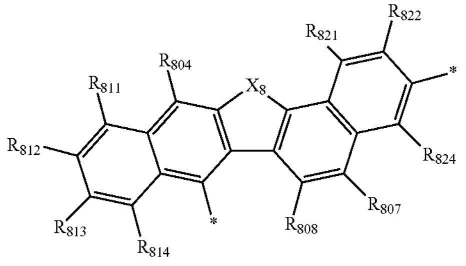

[Formula 405]

(81-15)

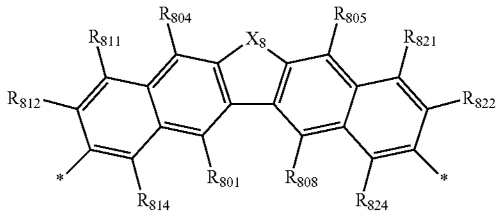

(81-16)

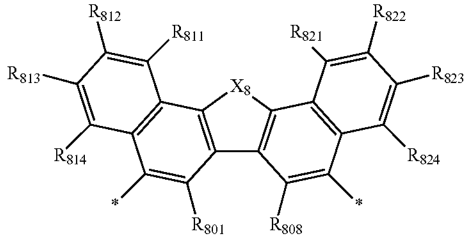

[Formula 406]

(81-17)

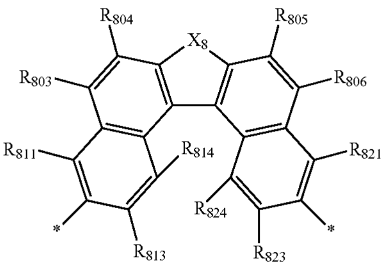

(81-18)

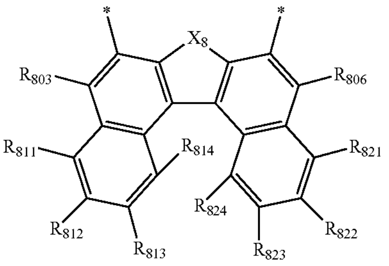

In the formulae (81-7) to (81-18):

$X_8$ represents the same as $X_8$ in the formula (8);

* is a single bond to be bonded with the monovalent group represented by the formula (84); and $R_{801}$ to $R_{824}$ each independently represent the same as $R_{801}$ to $R_{824}$ in the formulae (81-1) to (81-6) that are not the monovalent group represented by the formula (84).

$R_{801}$ to $R_{808}$ not forming the divalent group represented by the formula (82) or (83) and not being the monovalent group represented by the formula (84), and $R_{811}$ to $R_{814}$ and $R_{821}$ to $R_{824}$ not being the monovalent group represented by the formula (84) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The monovalent group represented by the formula (84) is preferably represented by a formula (85) or (86) below.

[Formula 407]

(85)

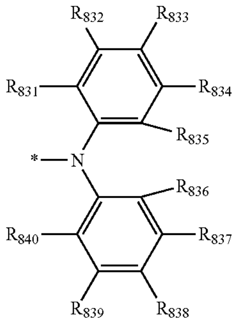

In the formula (85):

$R_{831}$ to $R_{840}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formula (85) represents the same as * in the formula (84).

[Formula 408]

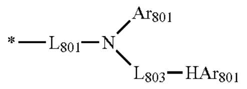

(86)

In the formula (86):

$Ar_{801}$, $L_{801}$, and $L_{803}$ represent the same as $Ar_{801}$, $L_{801}$, and $L_{803}$ in the formula (84); and $HAr_{801}$ is a structure represented by a formula (87) below.

[Formula 409]

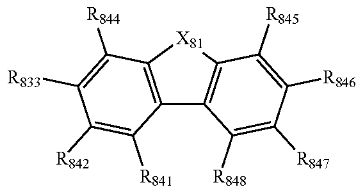

(87)

In the formula (87):

$X_{81}$ represents an oxygen atom or a sulfur atom;

one of $R_{841}$ to $R_{848}$ is a single bond with $L_{803}$; and $R_{841}$ to $R_{848}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (8) include compounds shown below as well as the compounds disclosed in WO 2014/104144.

[Formula 410]

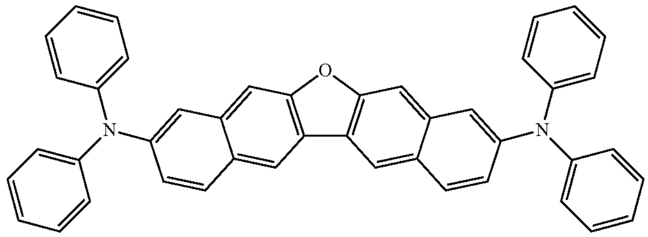

-continued
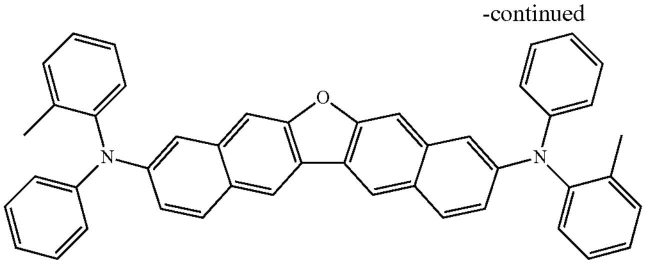
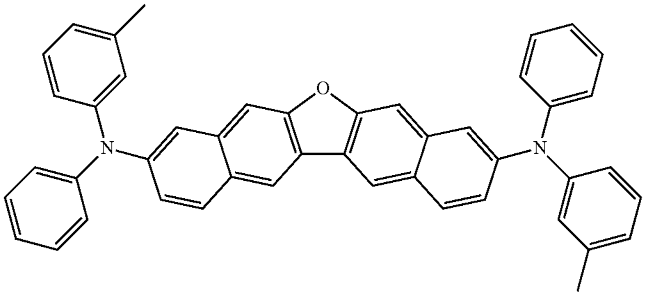
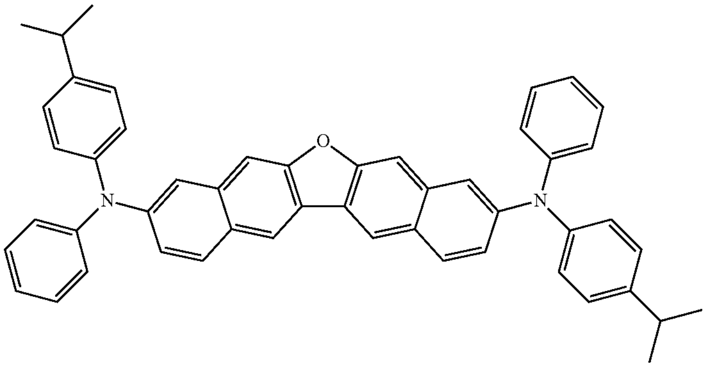
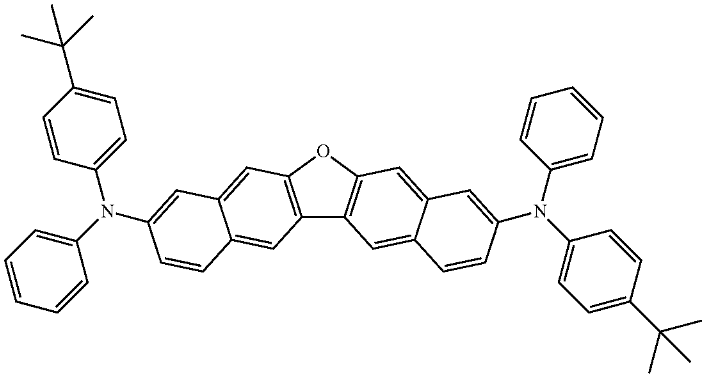
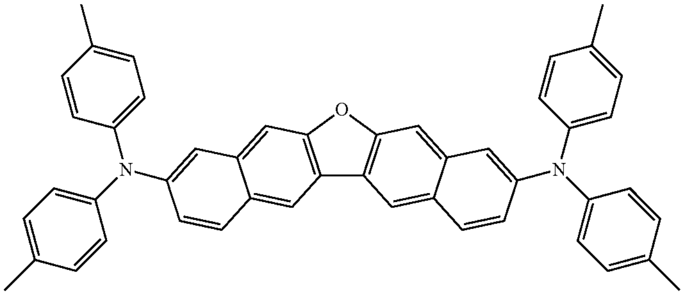

-continued
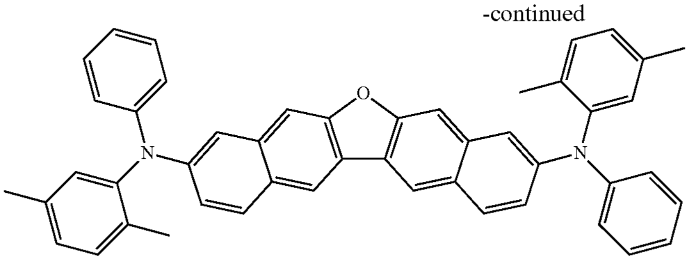
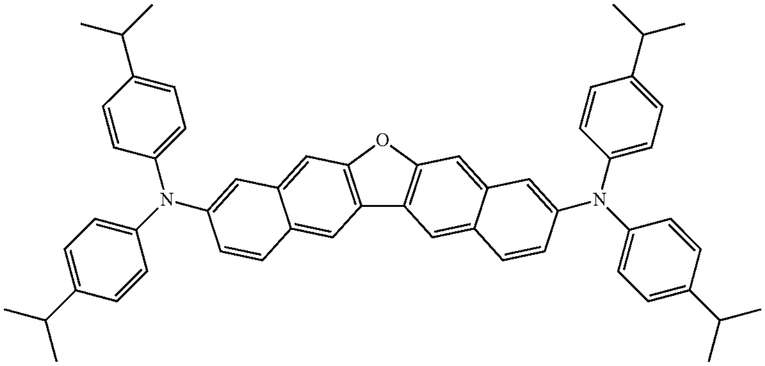
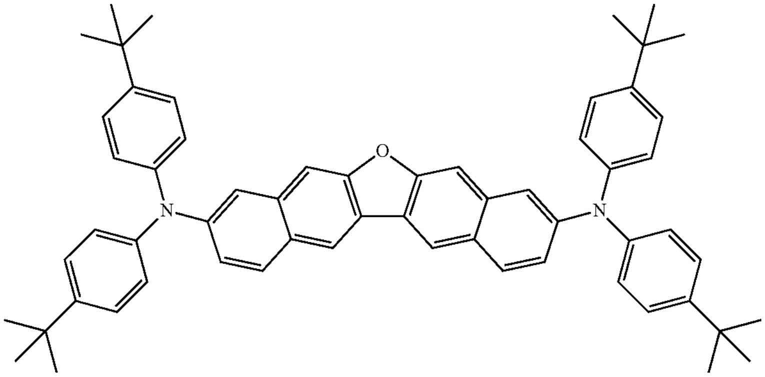
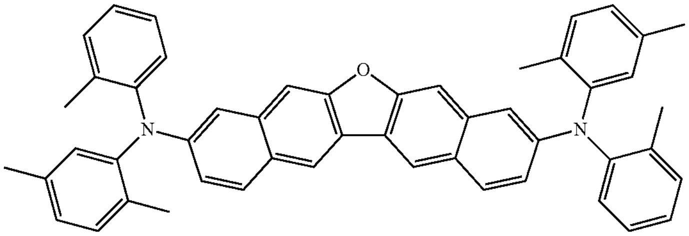
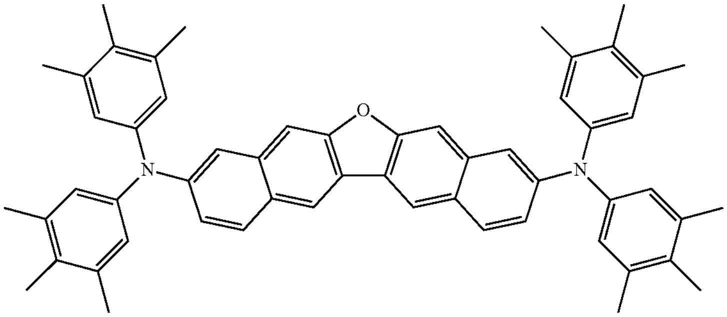

-continued
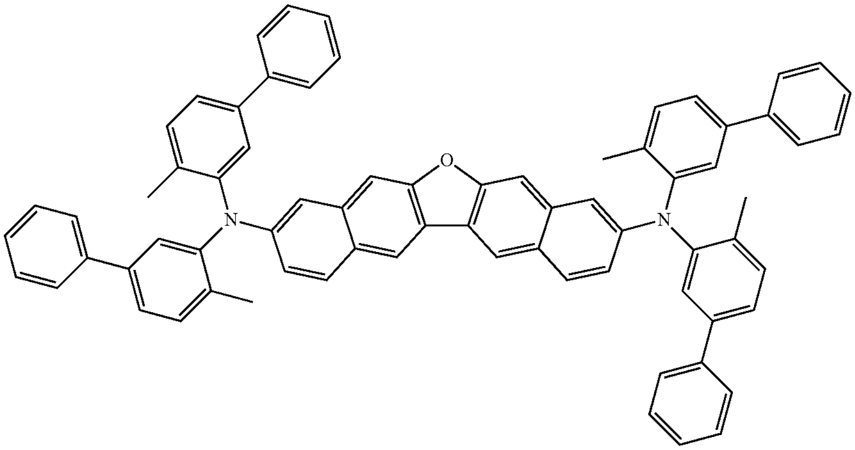
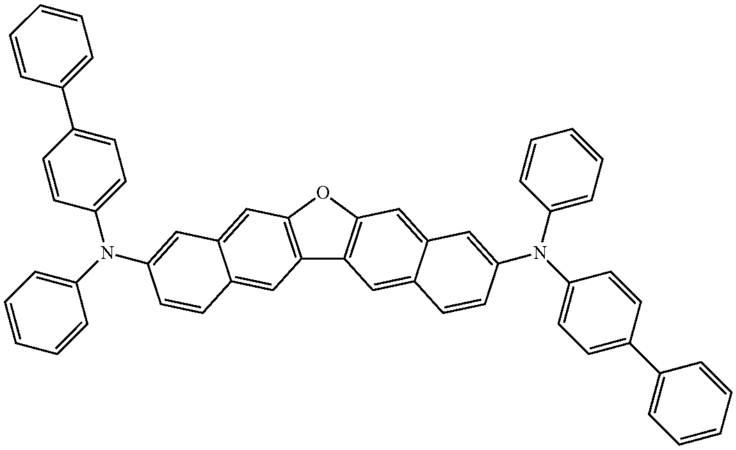
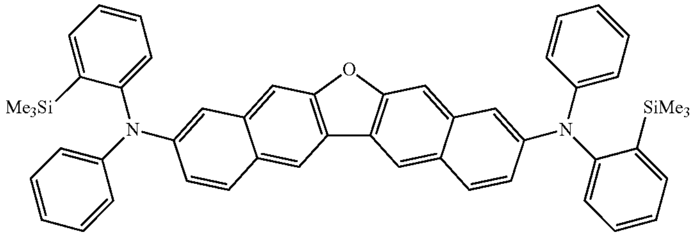
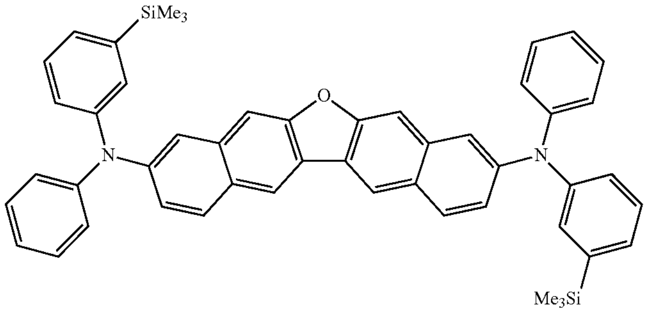
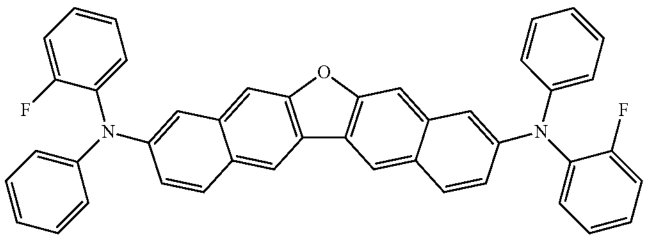

-continued
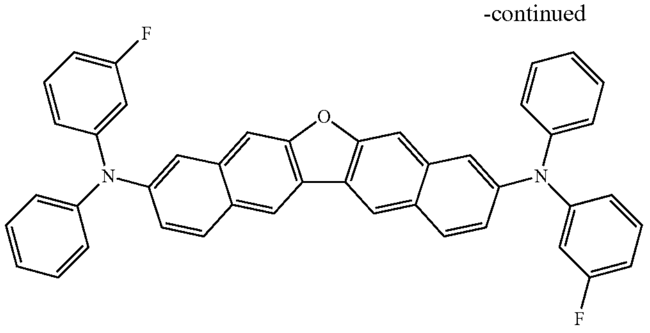
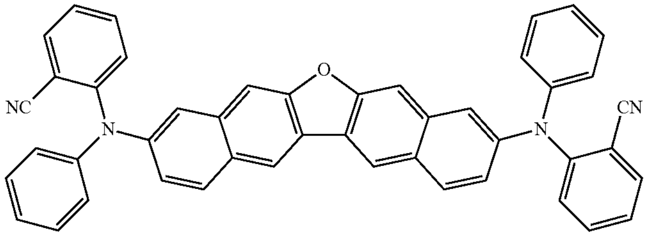
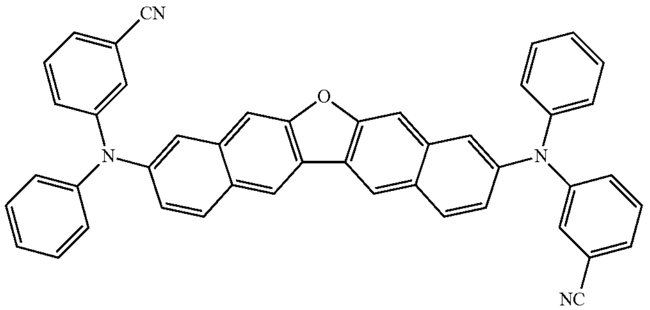
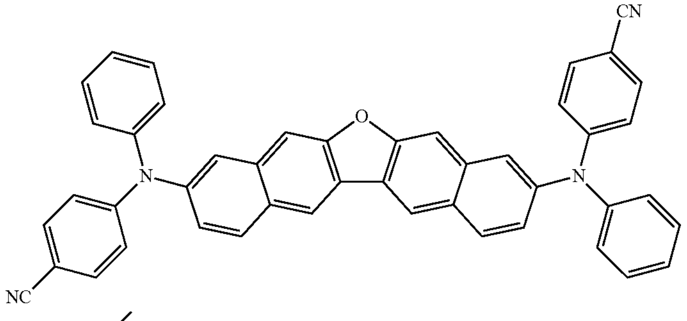
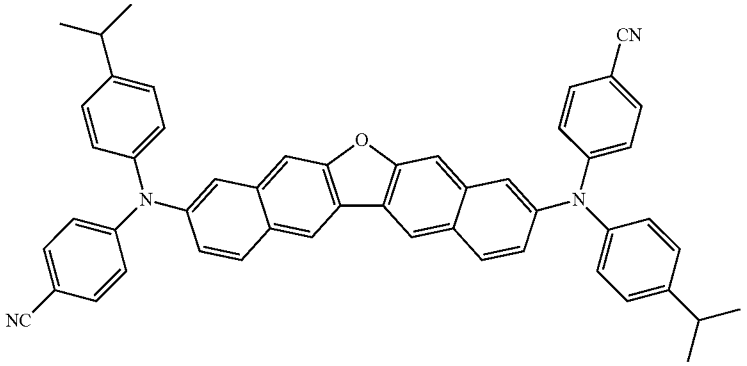

-continued
[Formula 411]
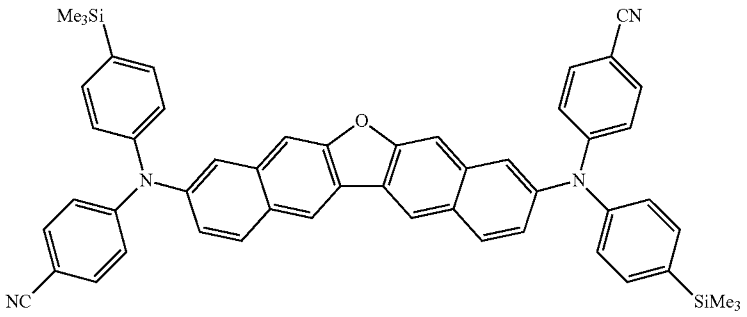
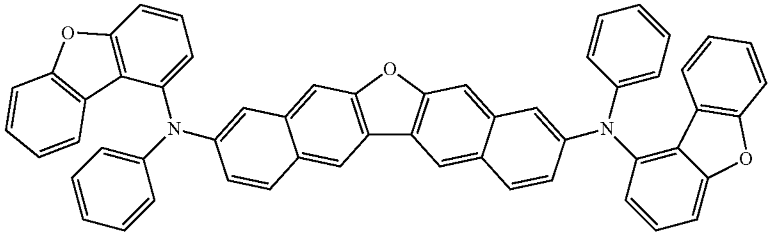
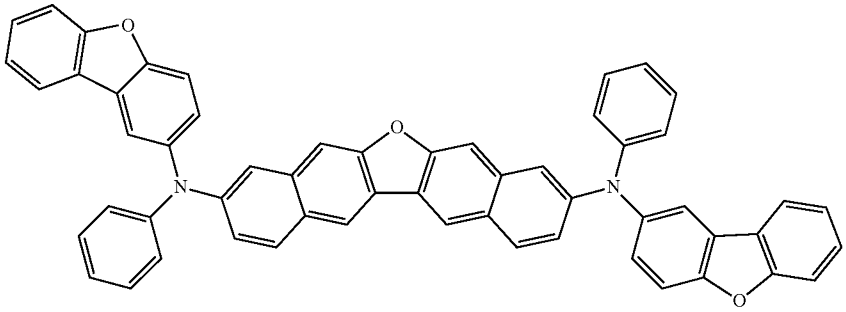
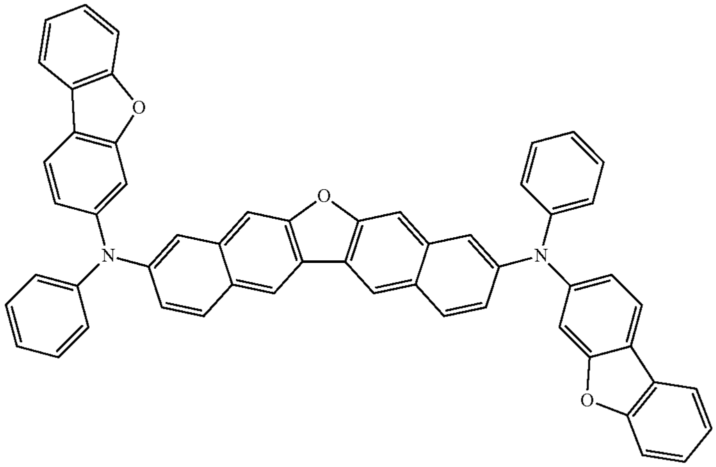
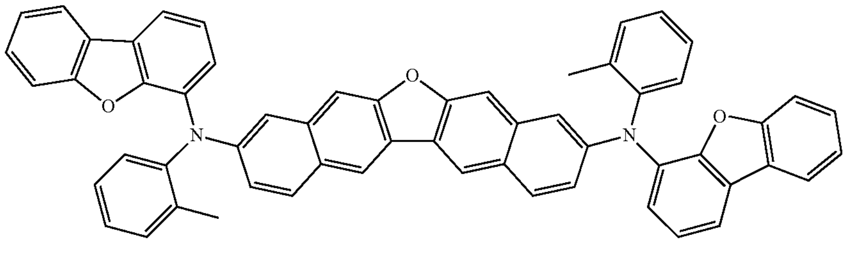

-continued
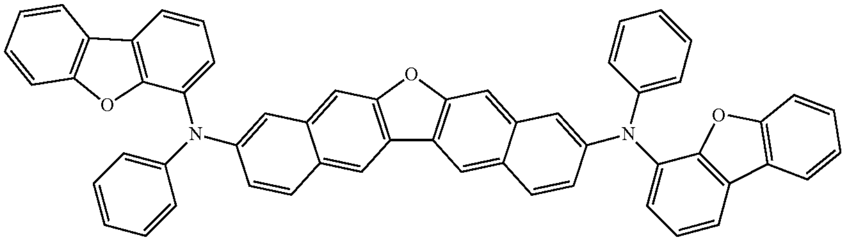
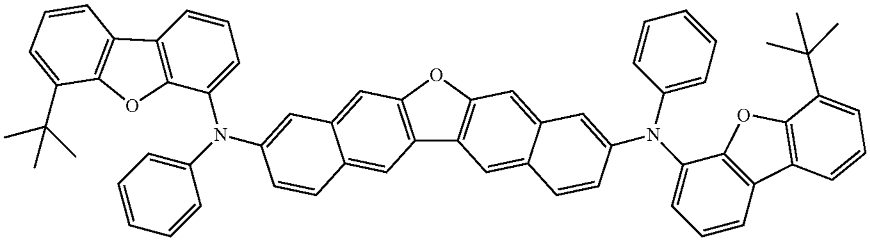
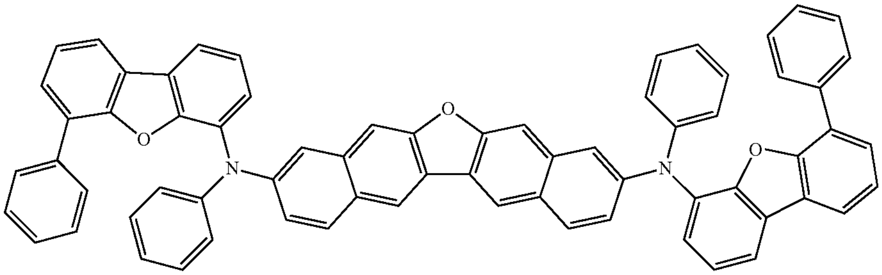
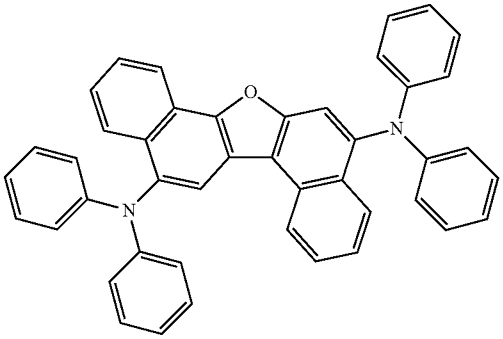
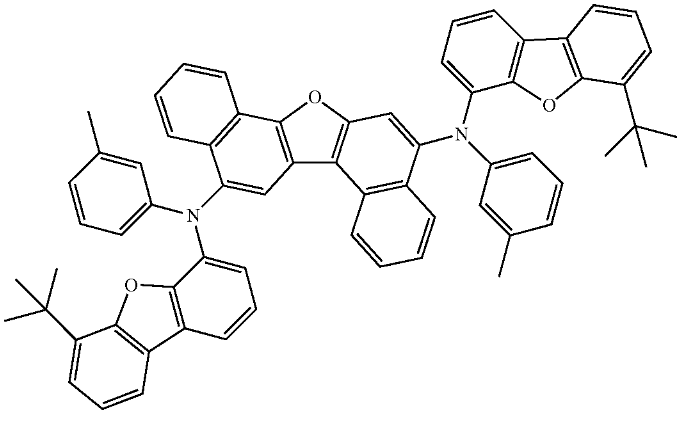

-continued
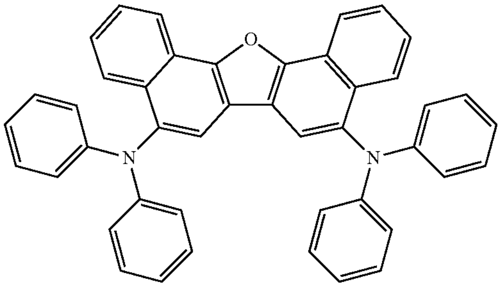
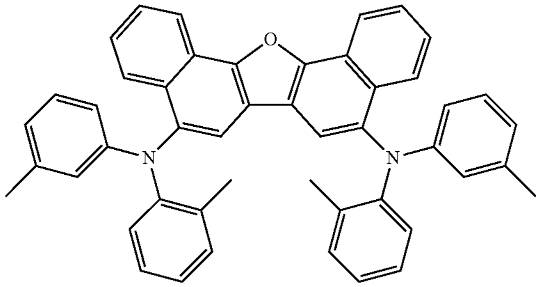
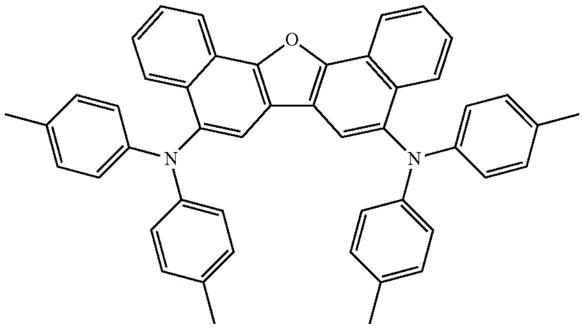
[Formula 412]
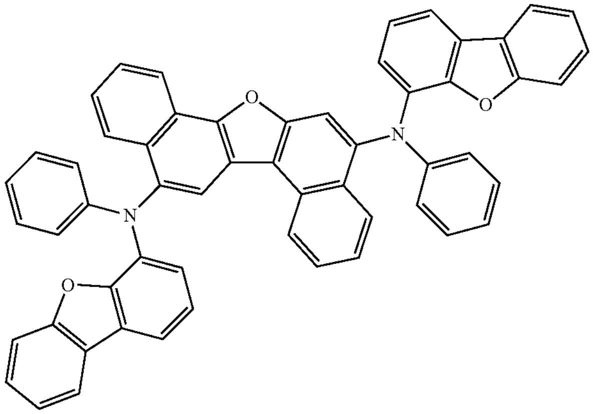
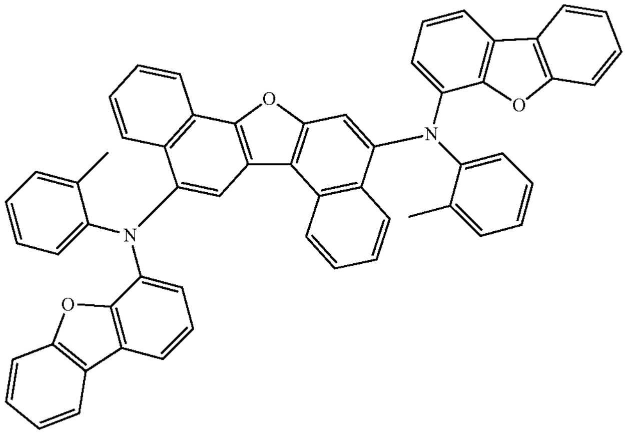

-continued
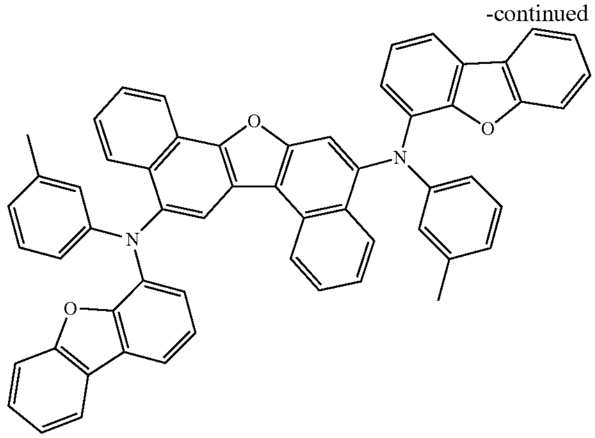
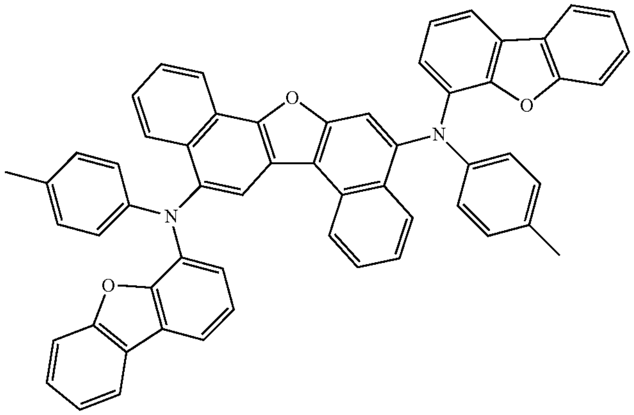
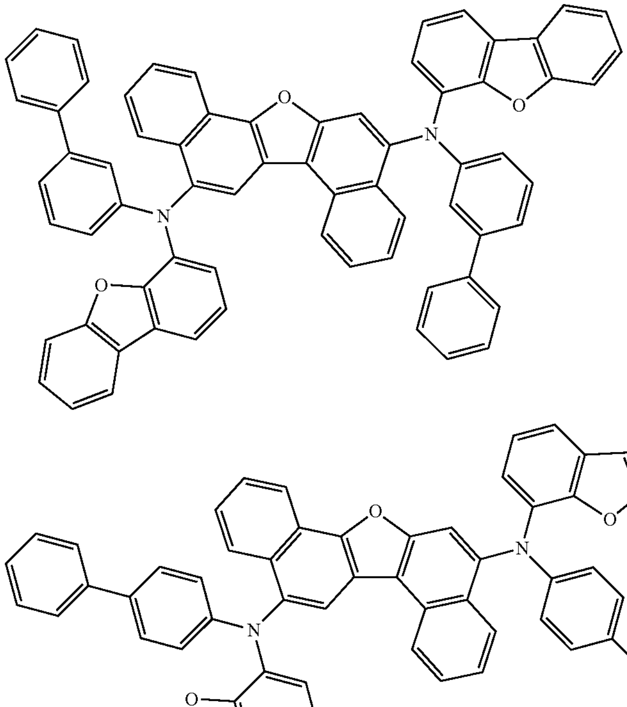
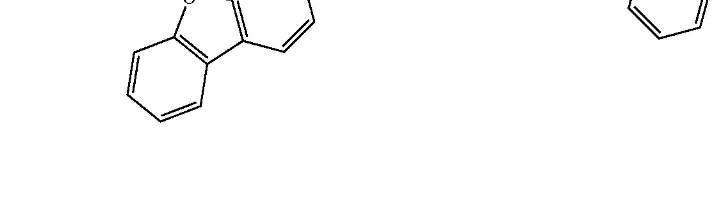

-continued
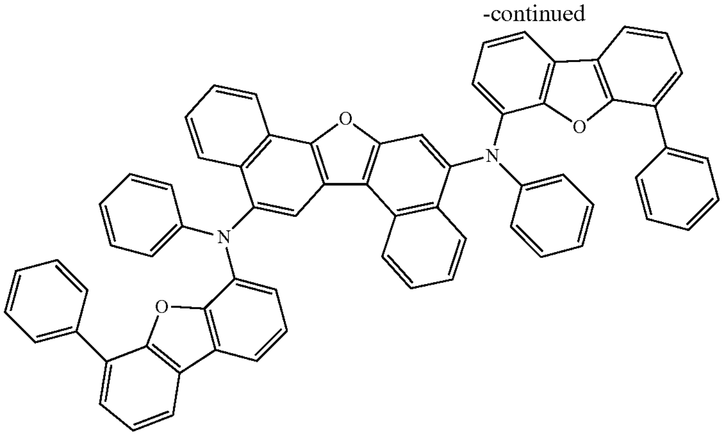
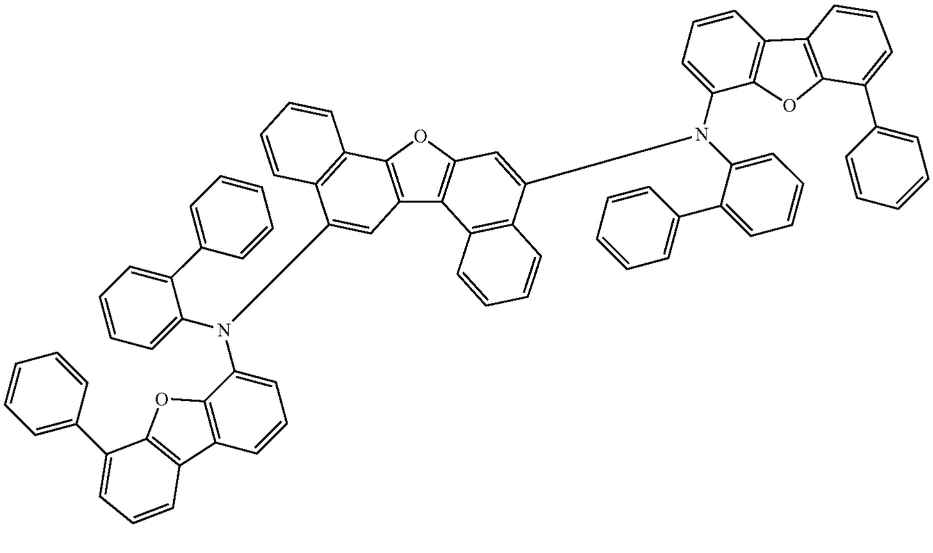
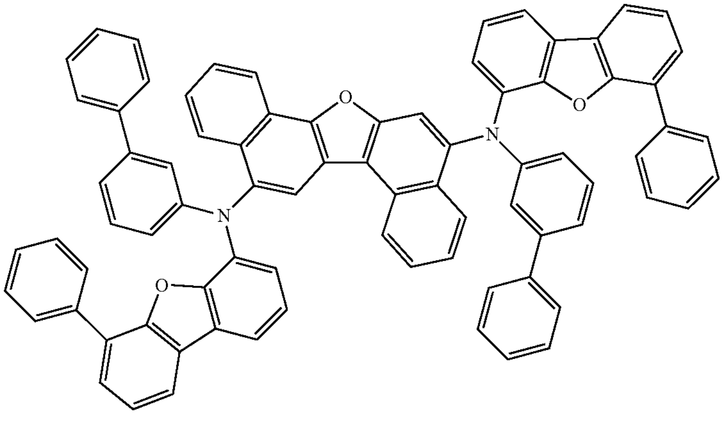

-continued
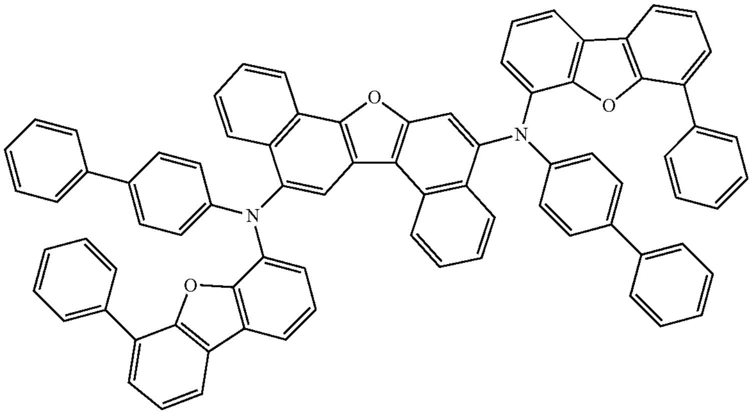
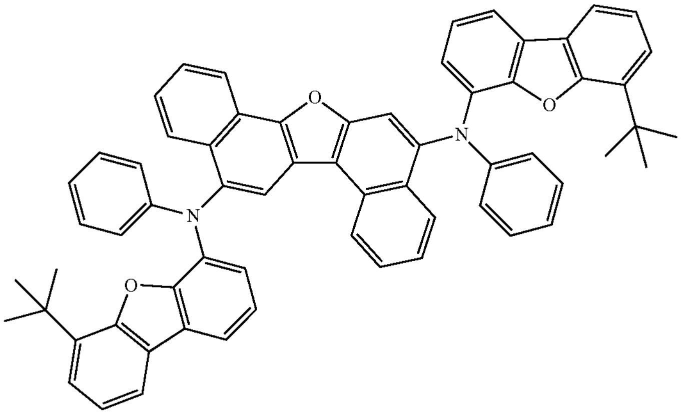
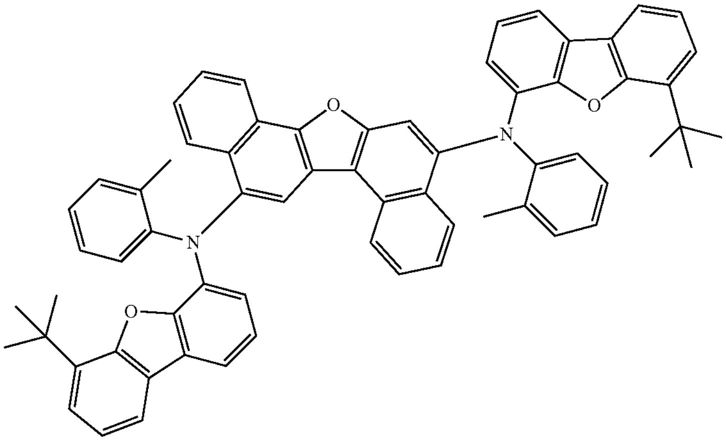
[Formula 413]
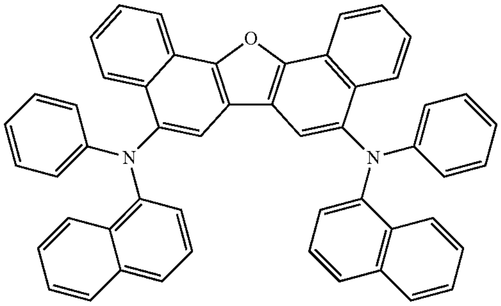
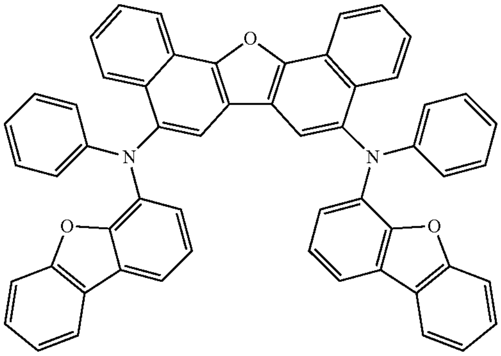

-continued
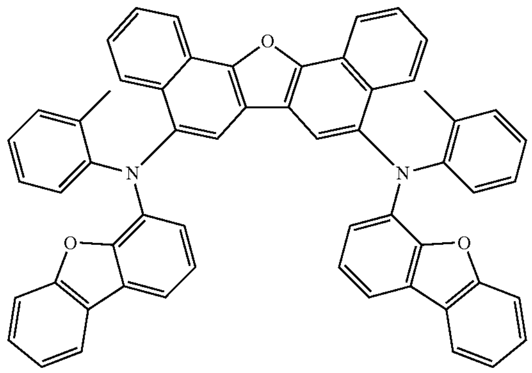
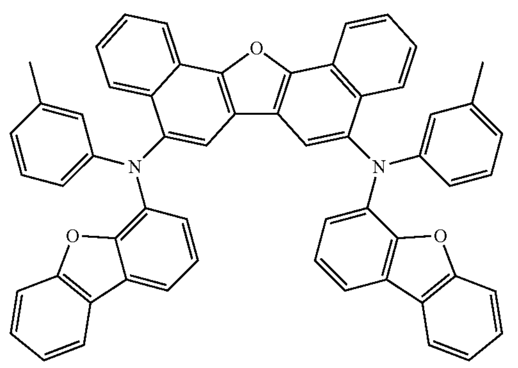
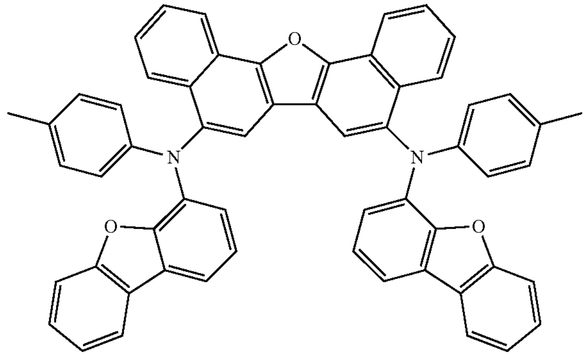
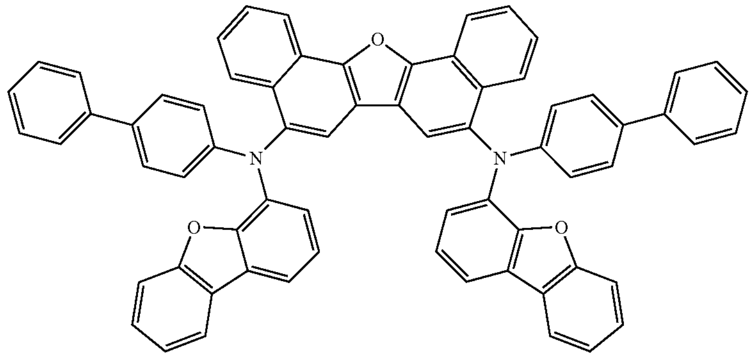
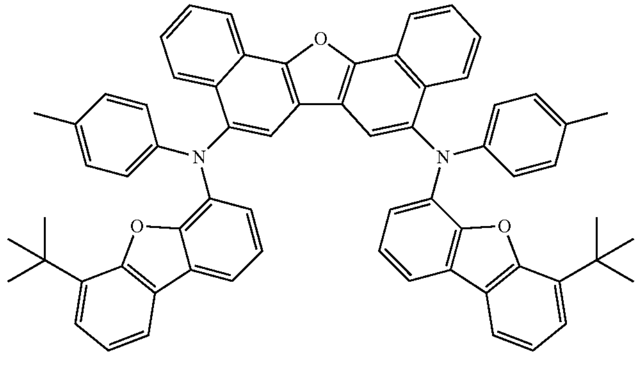

-continued
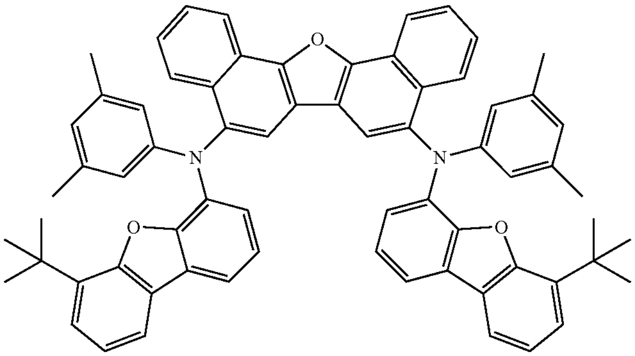
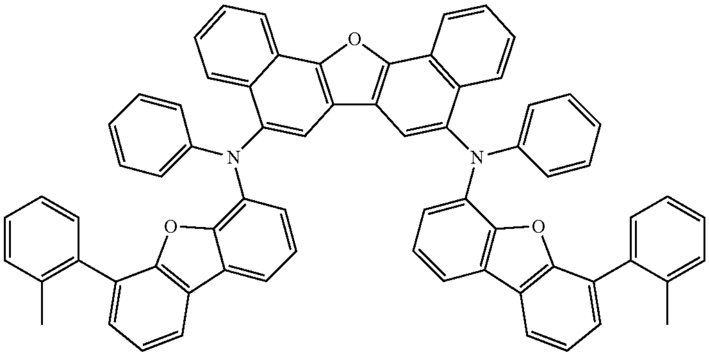
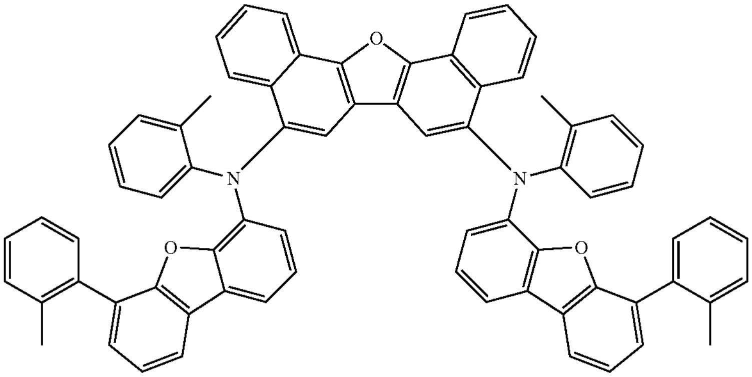
[Formula 414]
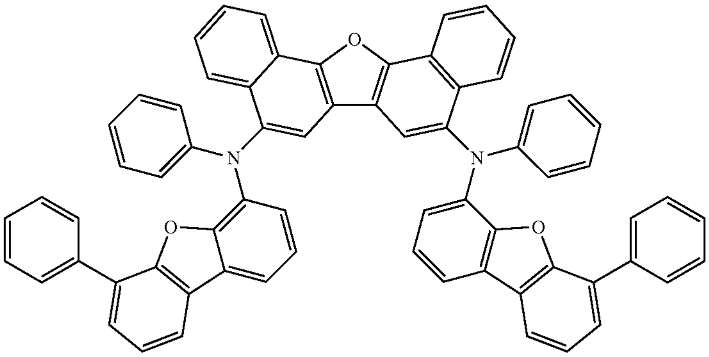

-continued
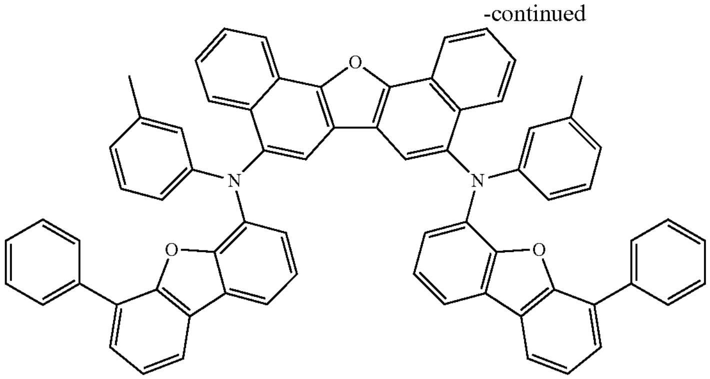
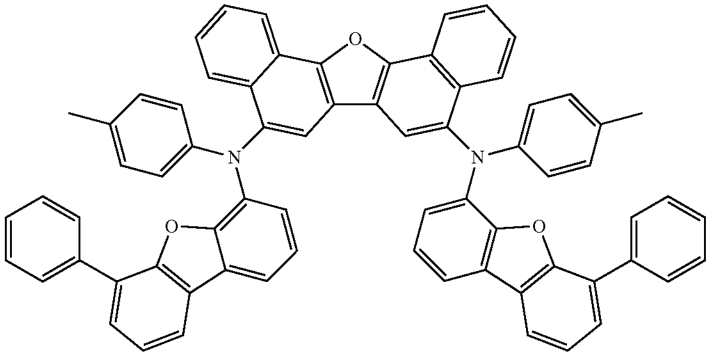
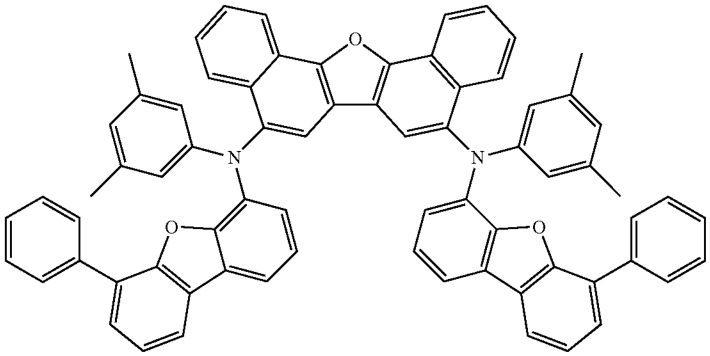
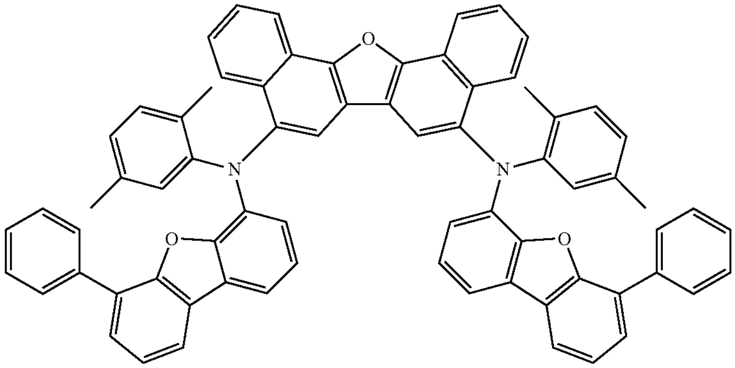

-continued
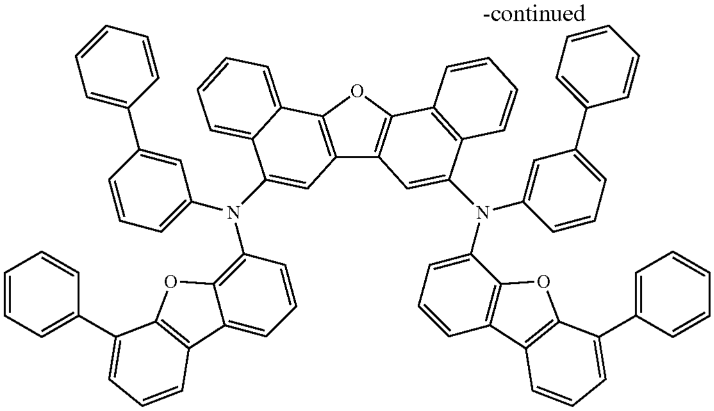
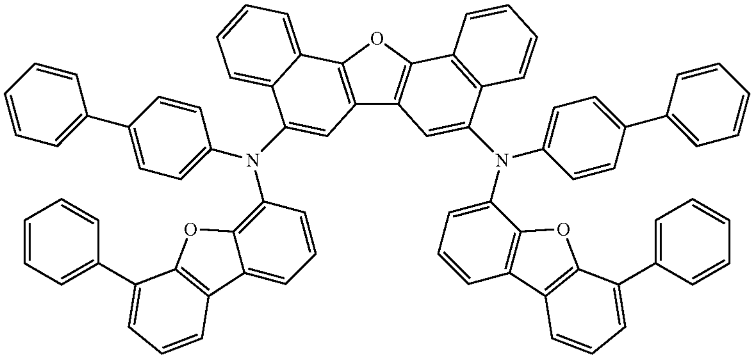
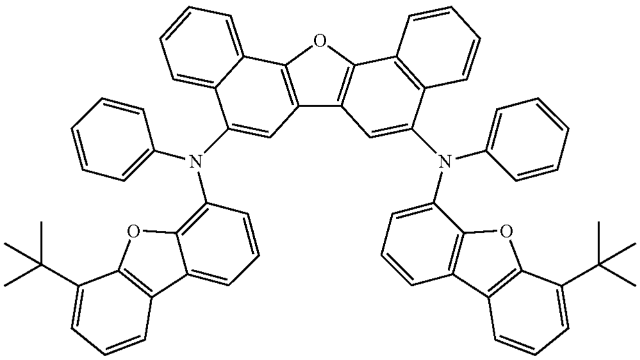
[Formula 415]
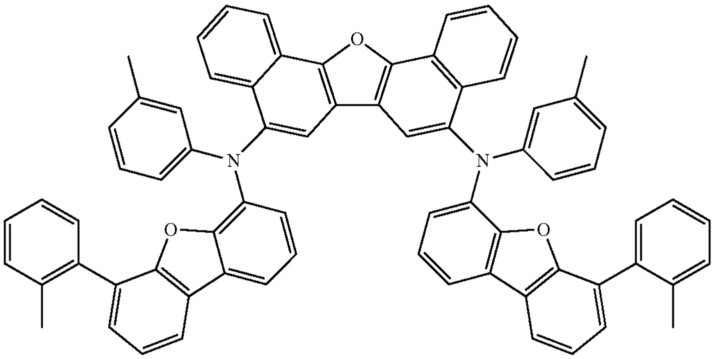

-continued
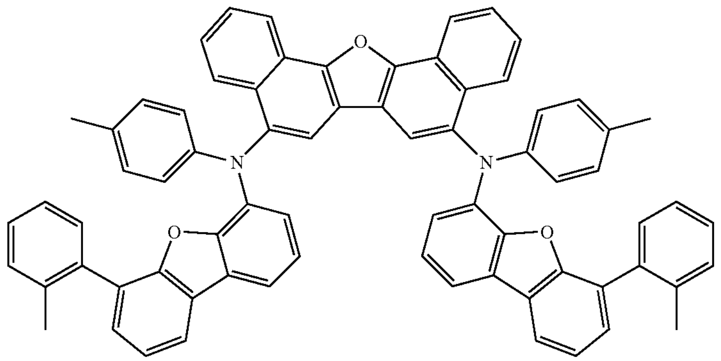
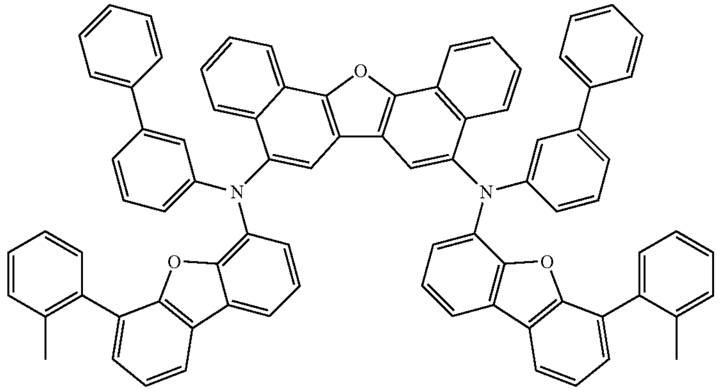
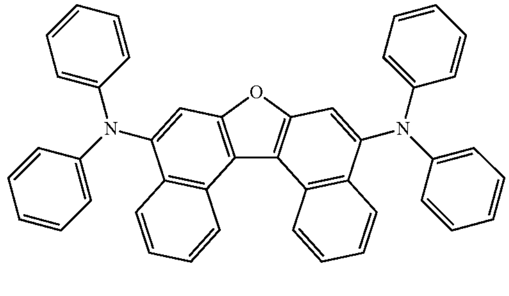
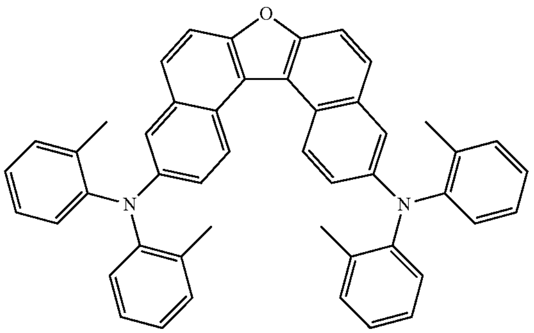
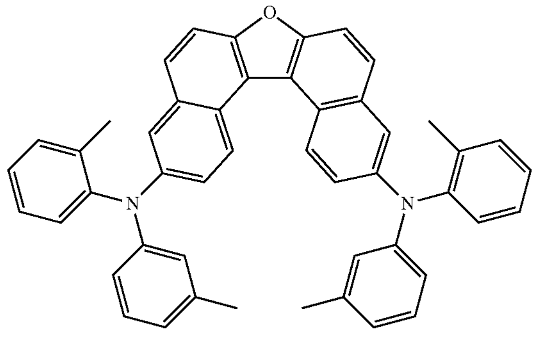
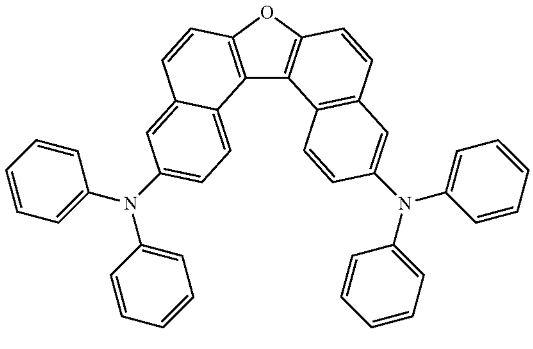

-continued
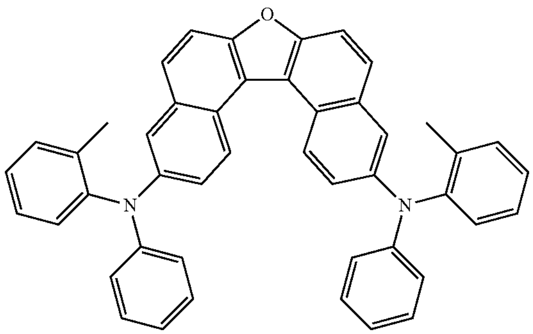
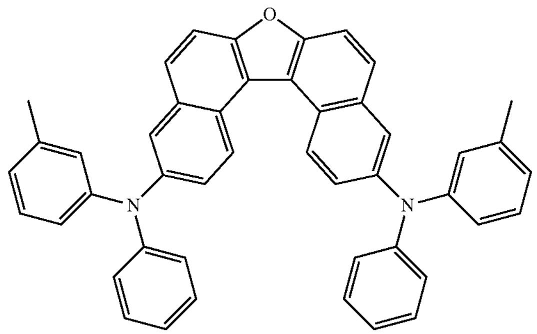
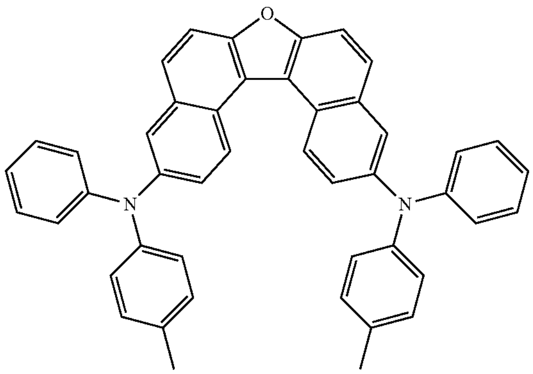
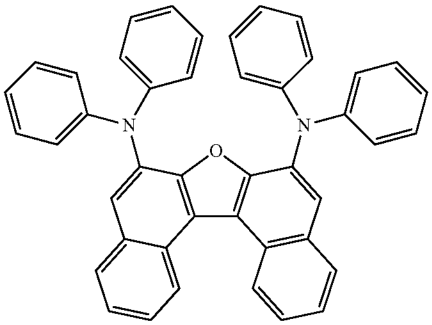
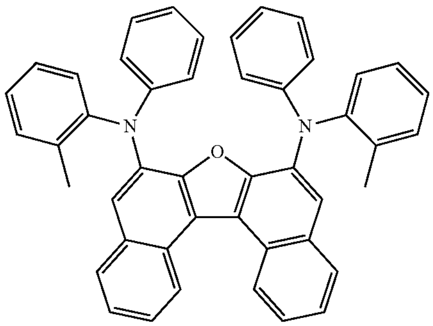
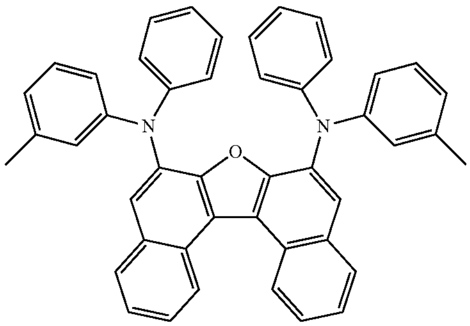
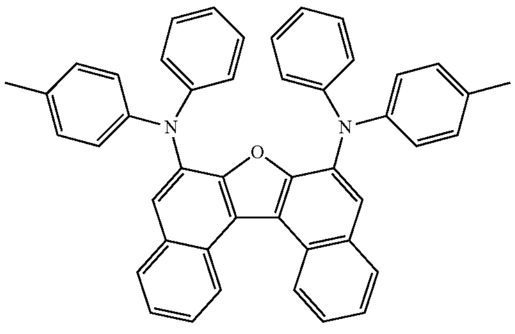
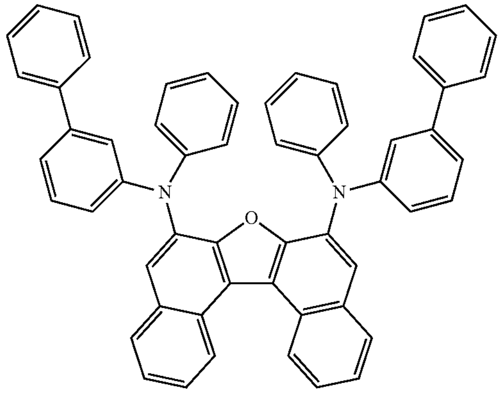

-continued

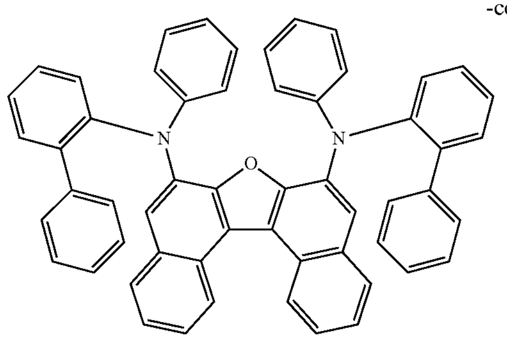

Compound Represented by Formula (9)

The compound represented by the formula (9) will be described below.

[Formula 416]

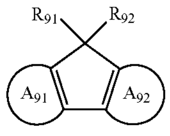

(9)

In the formula (9):

$A_{91}$ ring and $A_{92}$ ring are each independently a substituted or unsubstituted aromatic hydrocarbon ring having 6 to 50 ring carbon atoms, or a substituted or unsubstituted heterocycle having 5 to 50 ring atoms; and at least one of $A_{91}$ ring or $A_{92}$ ring is bonded with * in a structure represented by a formula (92) below.

[Formula 417]

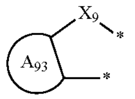

(92)

In the formula (92):

$A_{93}$ ring is a substituted or unsubstituted aromatic hydrocarbon ring having 6 to 50 ring carbon atoms, or a substituted or unsubstituted heterocycle having 5 to 50 ring atoms;

$X_9$ is $NR_{93}$, $C(R_{94})(R_{95})$, $Si(R_{96})(R_{97})$, $Ge(R_{98})(R_{99})$, an oxygen atom, a sulfur atom, or a selenium atom;

$R_{91}$ and $R_{92}$ are mutually bonded to form a substituted or unsubstituted monocyclic ring, mutually bonded to form a substituted or unsubstituted fused ring, or not mutually bonded; and $R_{91}$ and $R_{92}$ not forming the monocyclic ring and not forming the fused ring, and $R_{93}$ to $R_{99}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

At least one ring selected from the group consisting of $A_{91}$ ring and $A_{92}$ ring is bonded to a bond * of the structure represented by the formula (92). In other words, the ring-forming carbon atoms of the aromatic hydrocarbon ring or the ring atoms of the heterocycle of the $A_{91}$ ring in an exemplary embodiment are bonded to the bonds * in the structure represented by the formula (92). Further, the ring-forming carbon atoms of the aromatic hydrocarbon ring or the ring atoms of the heterocycle of the $A_{92}$ ring in an exemplary embodiment are bonded to the bonds * in the structure represented by the formula (92).

In an exemplary embodiment, the group represented by a formula (93) below is bonded to one or both of the $A_{91}$ ring and $A_{92}$ ring.

[Formula 418]

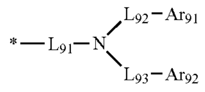

(93)

In the formula (93):

$Ar_{91}$ and $Ar_{92}$ are each independently a substituted or unsubstituted aryl group having 6 to 50 ring carbon atoms, or a substituted or unsubstituted heterocyclic group having 5 to 50 ring atoms;

$L_{91}$ to $L_{93}$ are each independently a single bond, a substituted or unsubstituted arylene group having 6 to 30 ring carbon atoms, a substituted or unsubstituted divalent divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (93) represents a bonding position to one of $A_{91}$ ring and $A_{92}$ ring.

In an exemplary embodiment, in addition to the $A_{91}$ ring, the ring-forming carbon atoms of the aromatic hydrocarbon ring or the ring atoms of the heterocycle of the $A_{92}$ ring are bonded to * in the structure represented by the formula (92). In this case, the structures represented by the formula (92) are mutually the same or different.

In an exemplary embodiment, $R_{91}$ and $R_{92}$ are each independently a substituted or unsubstituted aryl group having 6 to 50 ring carbon atoms.

In an exemplary embodiment, $R_{91}$ and $R_{92}$ are mutually bonded to form a fluorene structure.

In an exemplary embodiment, the rings $A_{91}$ and $A_{92}$ are each independently a substituted or unsubstituted aromatic hydrocarbon ring having 6 to 50 ring carbon atoms, example of which is a substituted or unsubstituted benzene ring.

In an exemplary embodiment, the ring $A_{93}$ is a substituted or unsubstituted aromatic hydrocarbon ring having 6 to 50 ring carbon atoms, example of which is a substituted or unsubstituted benzene ring.

In an exemplary embodiment, $X_9$ is an oxygen atom or a sulfur atom.

Specific examples of the compound represented by the formula (9) include compounds shown below.

[Formula 419]

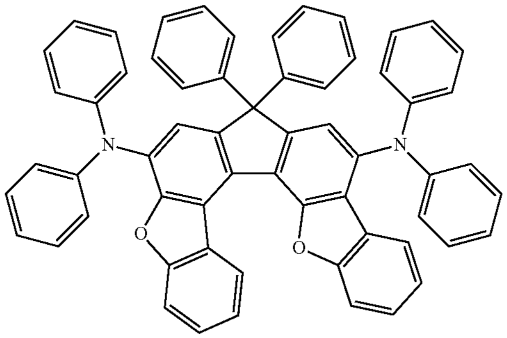

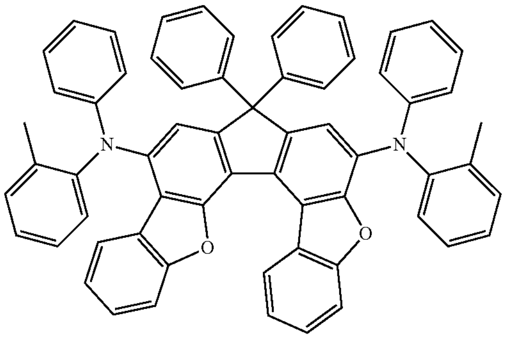

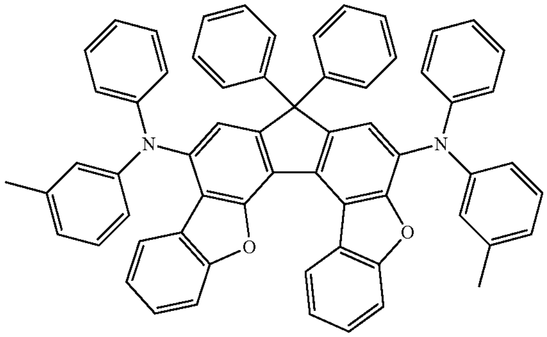

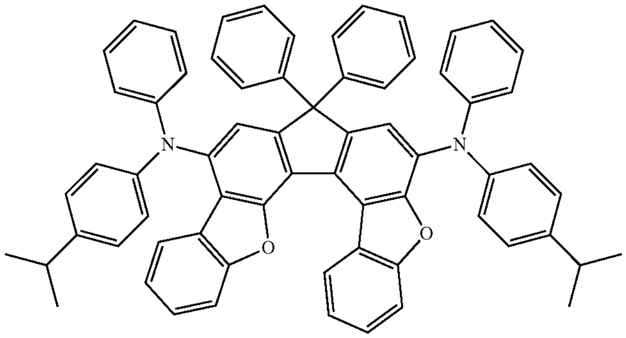

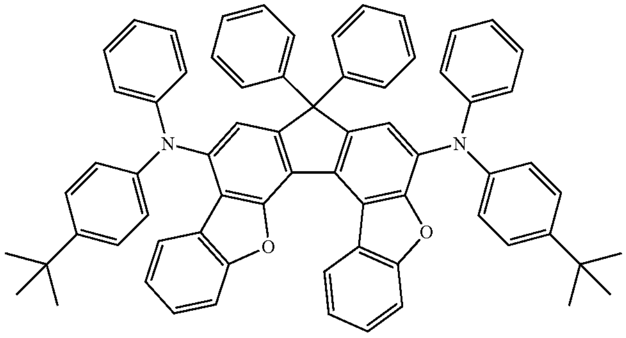

-continued
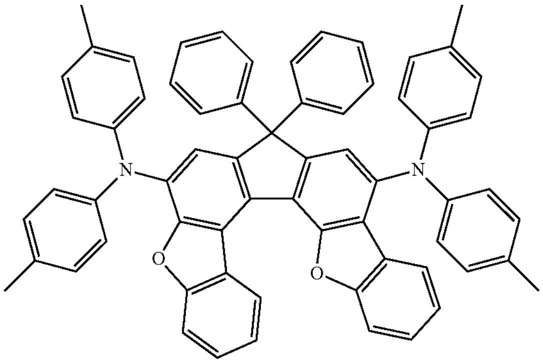
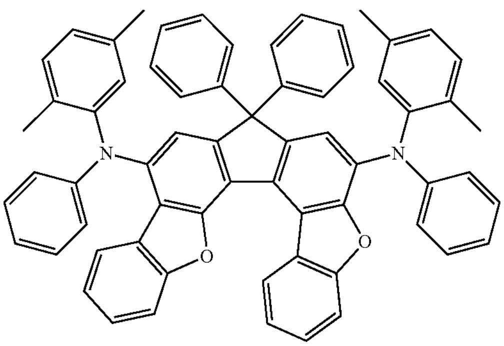
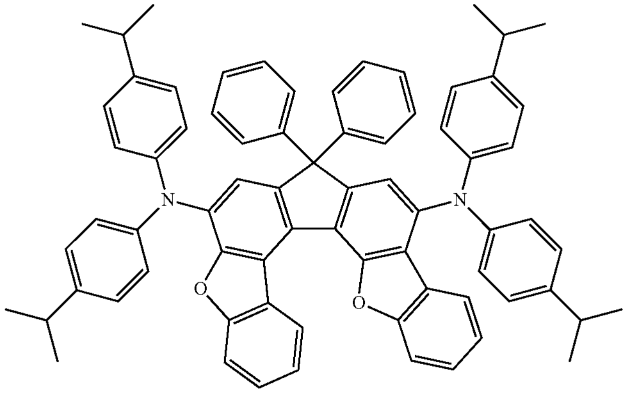
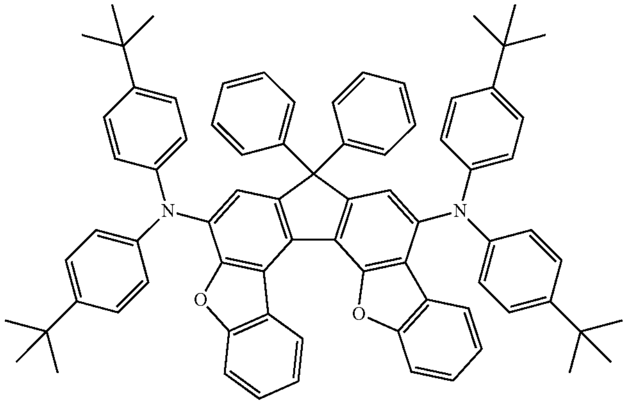
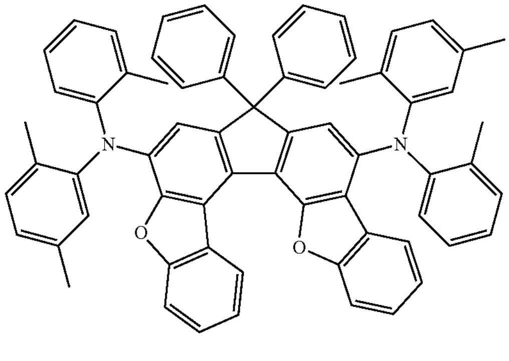
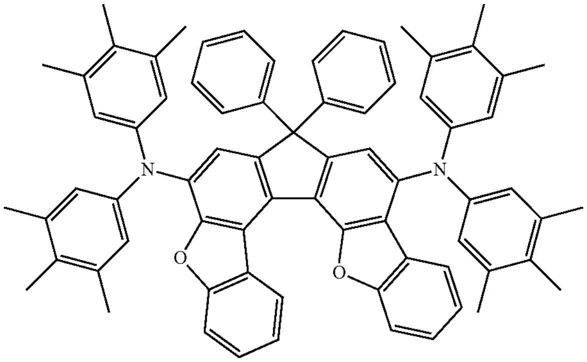

-continued
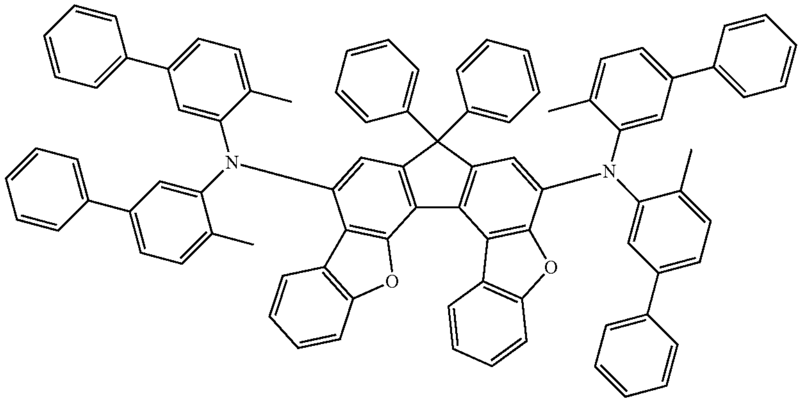
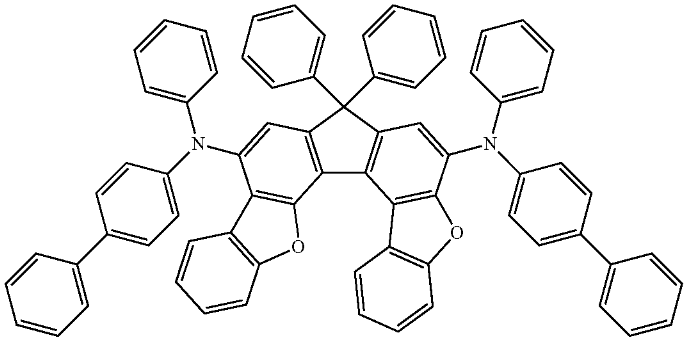
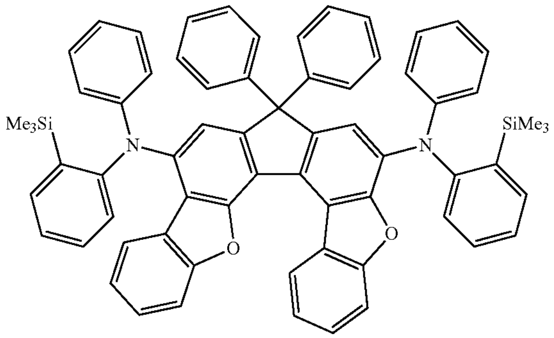
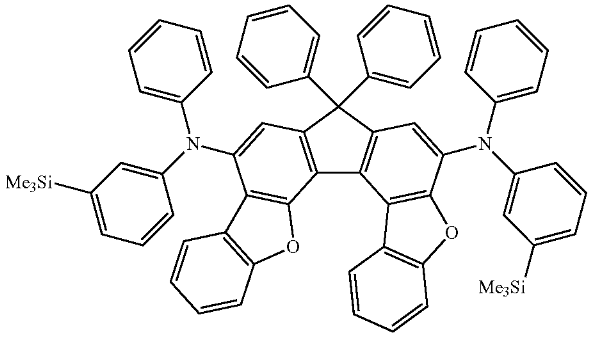
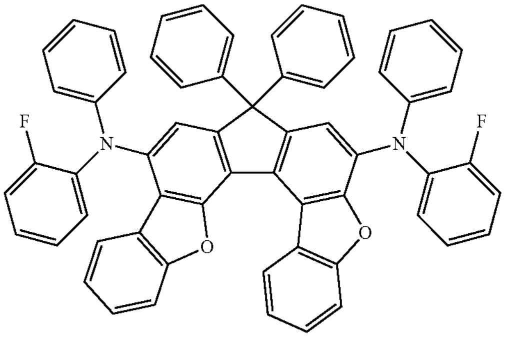

-continued
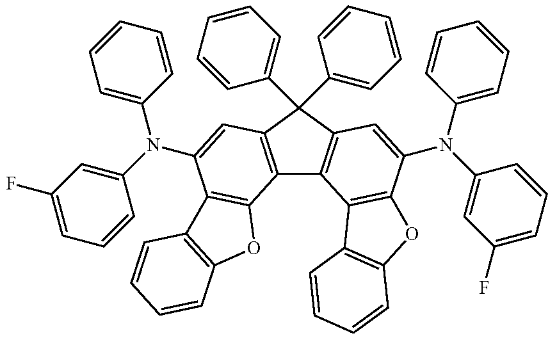
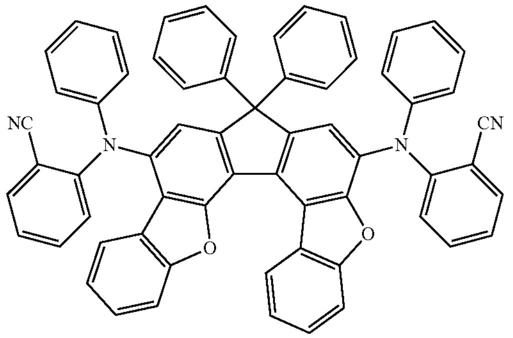
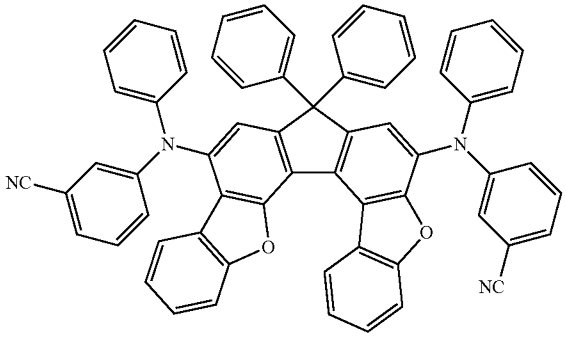
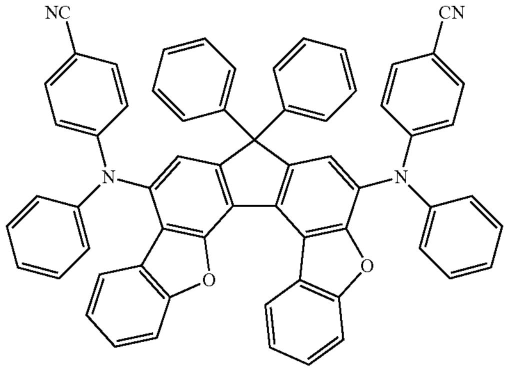
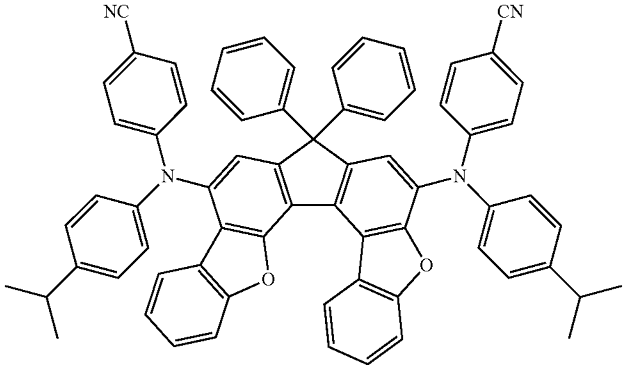
[Formula 420]
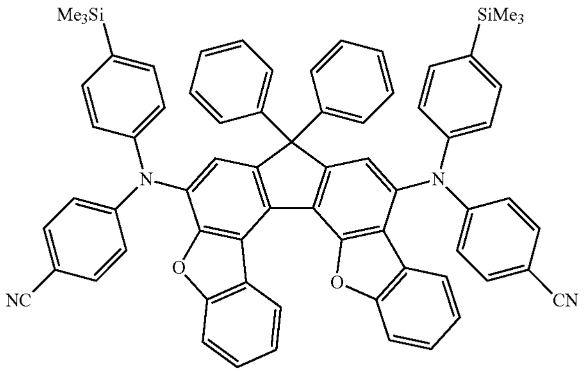

-continued
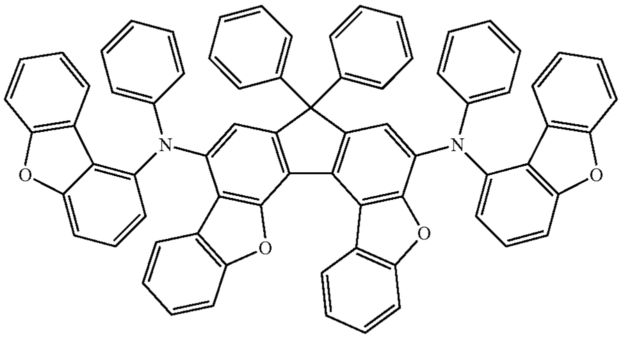
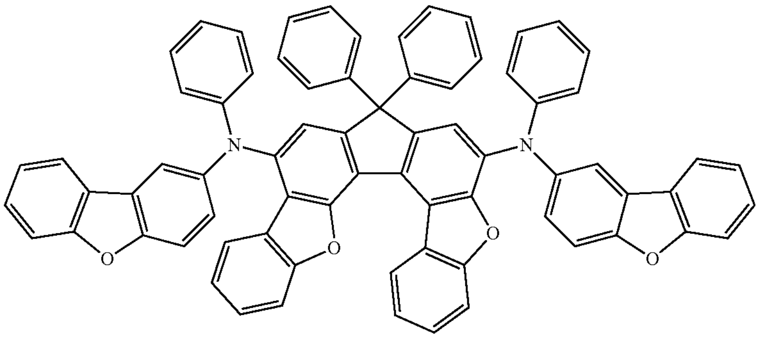
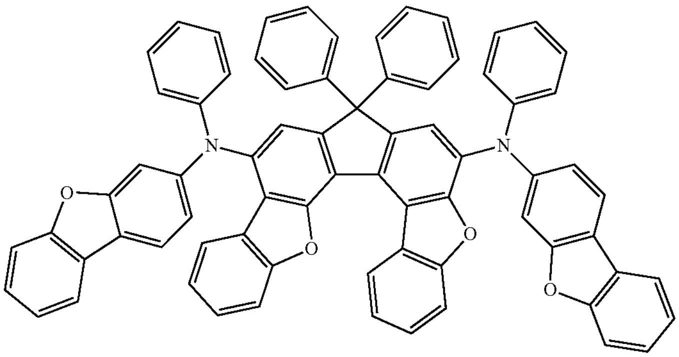
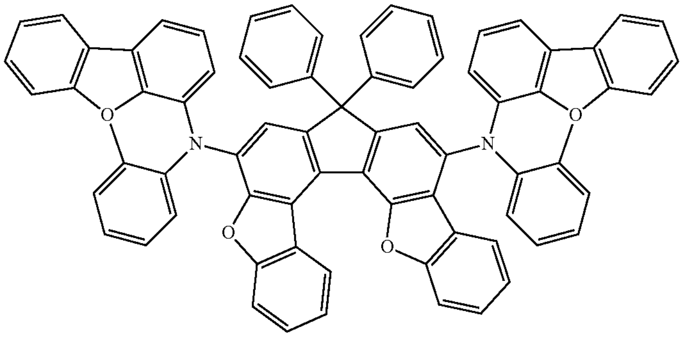
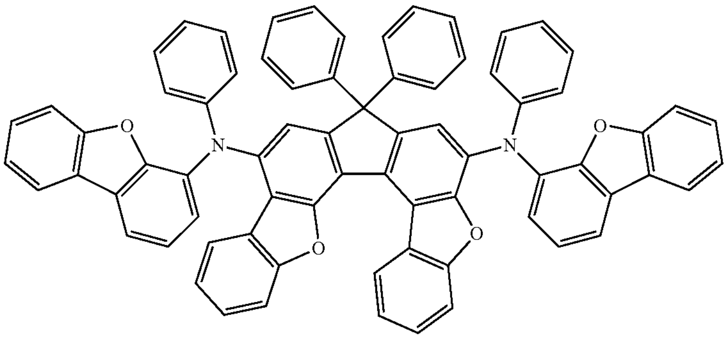

-continued
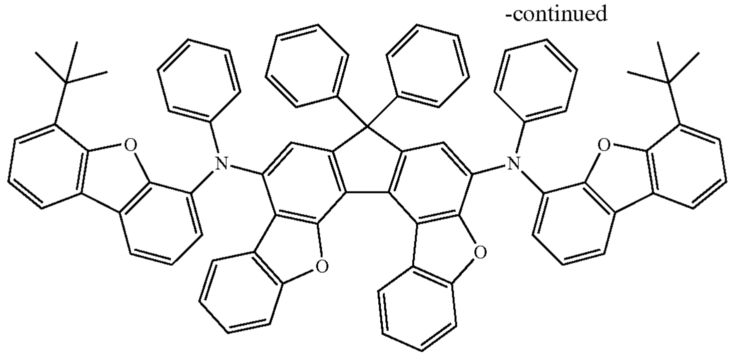
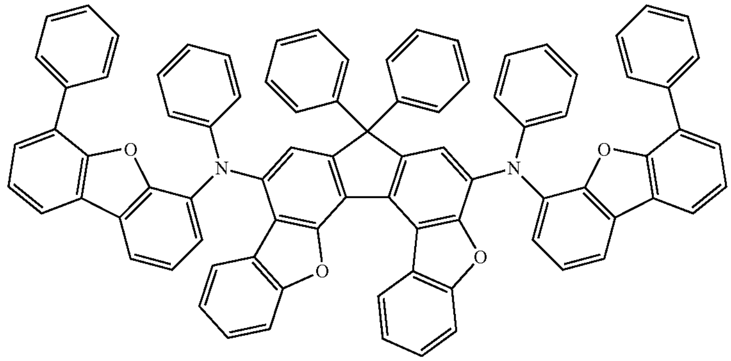
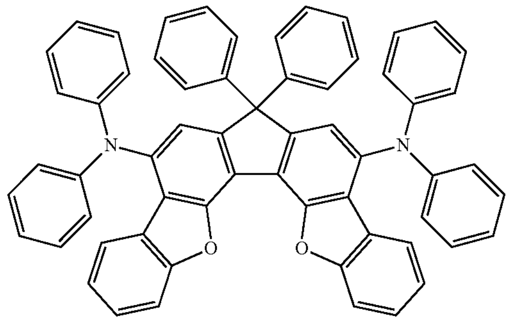
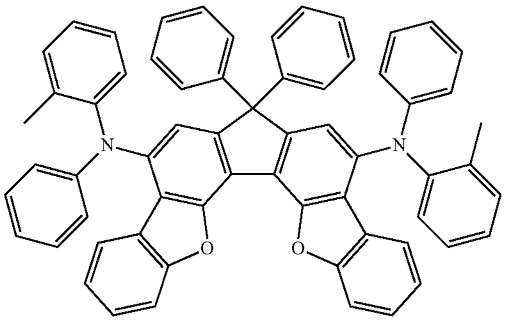
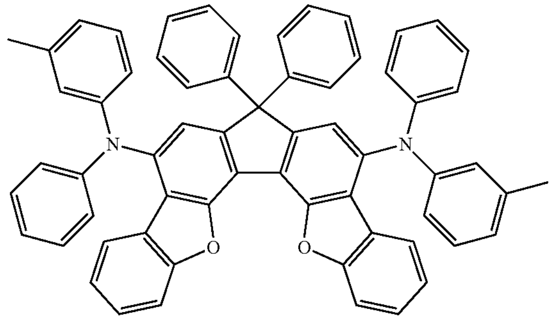
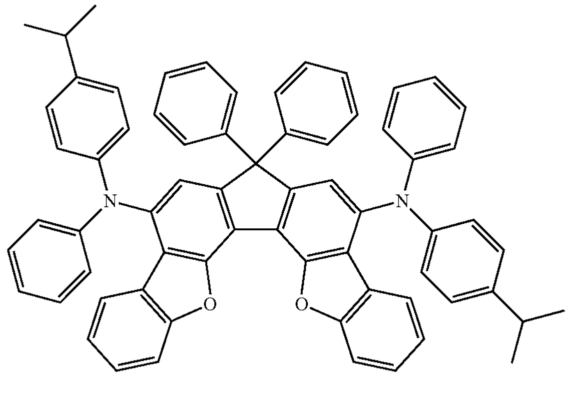

-continued
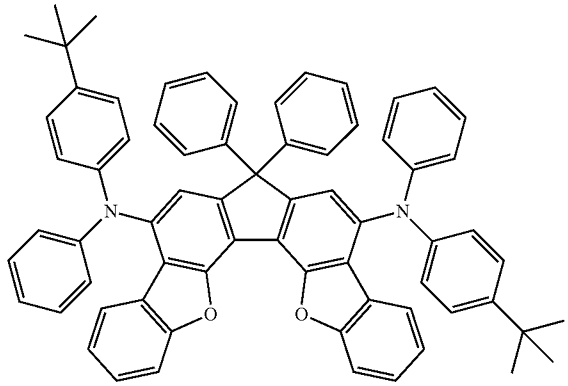
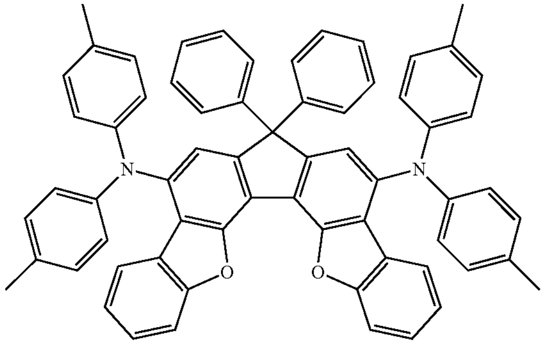
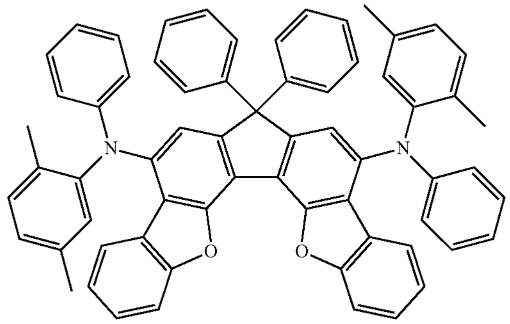
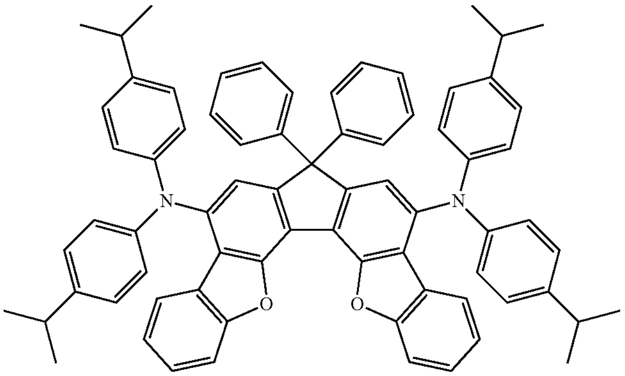
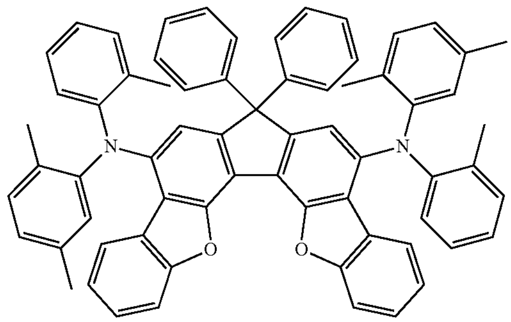
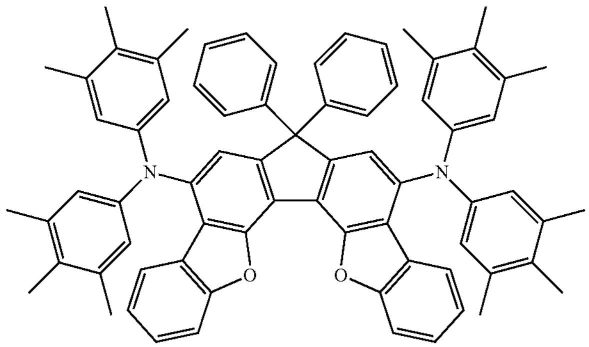
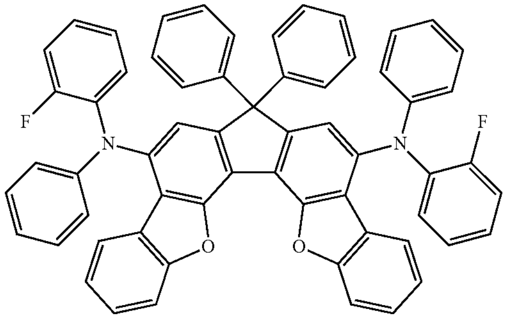
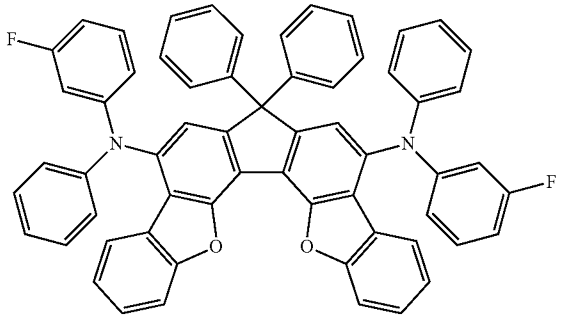

-continued
[Formula 421]
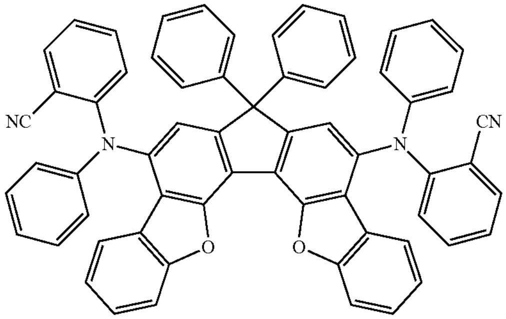
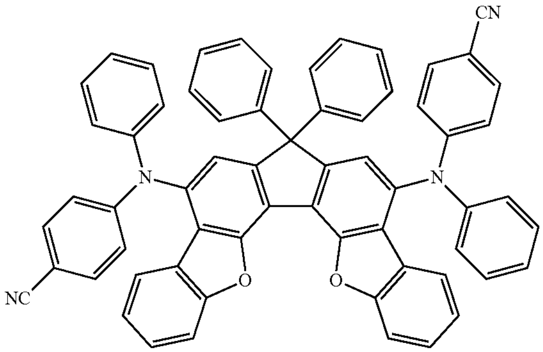
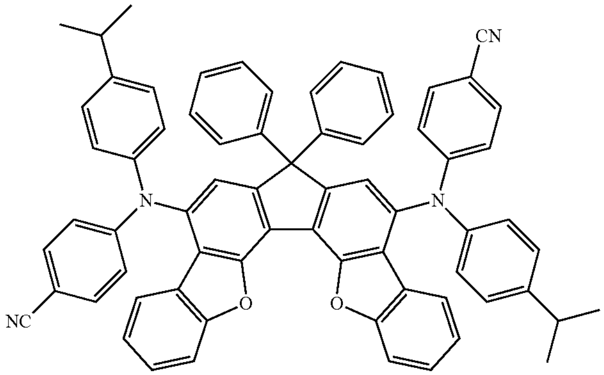
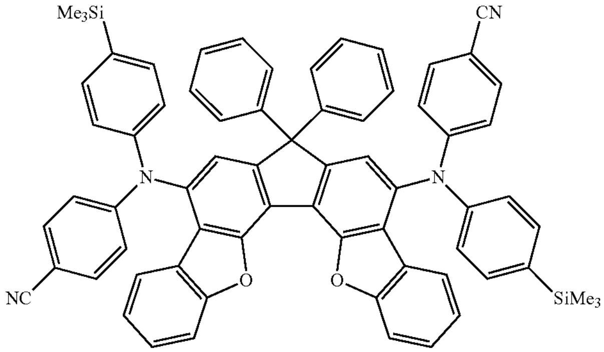
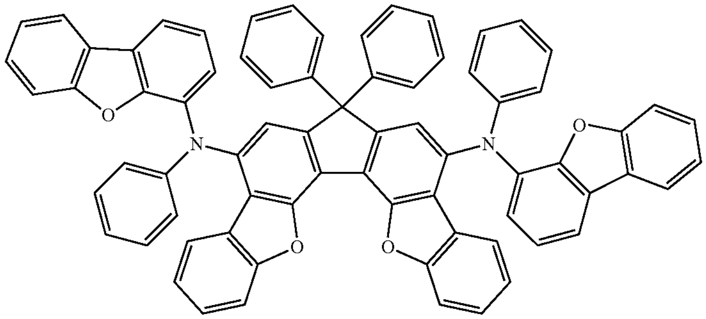

-continued
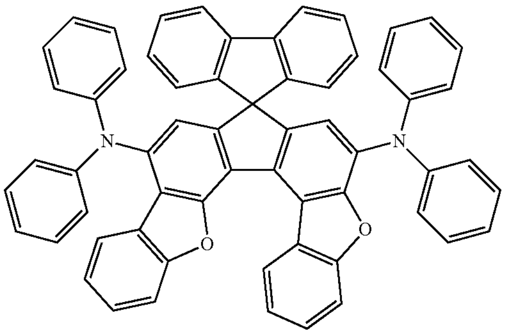
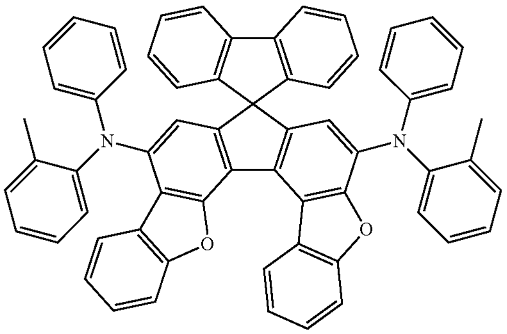
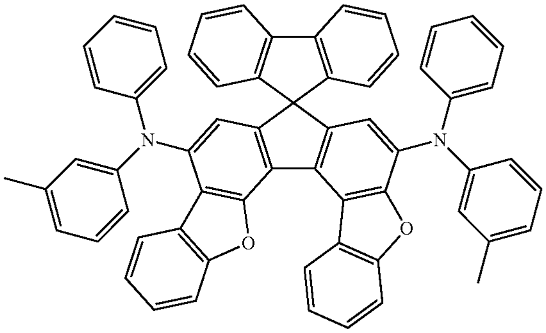
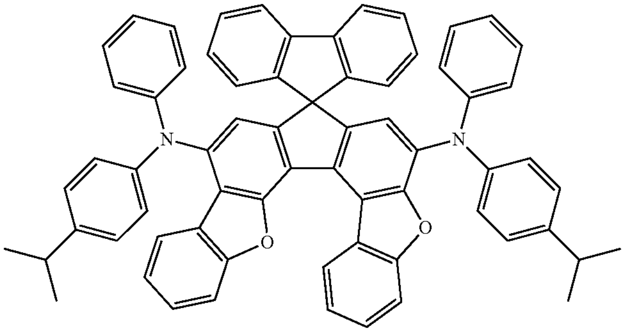
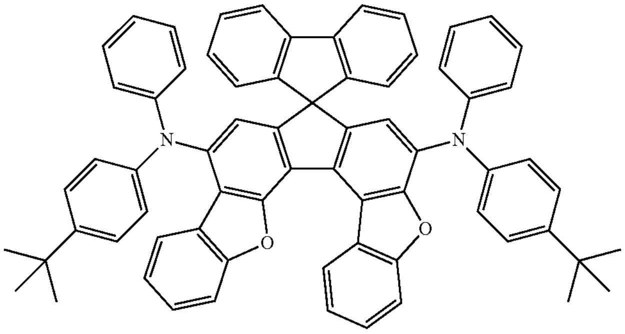
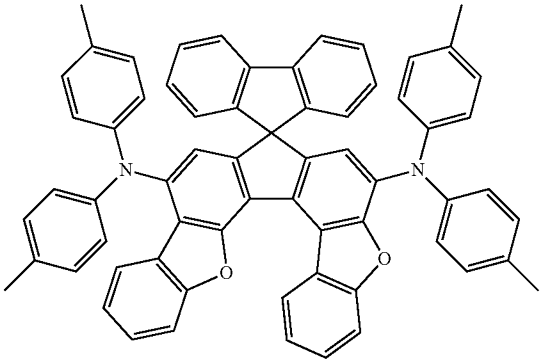
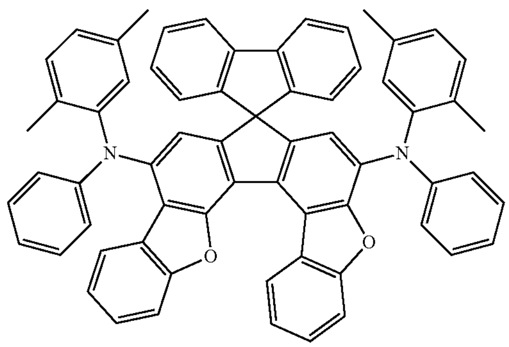

-continued
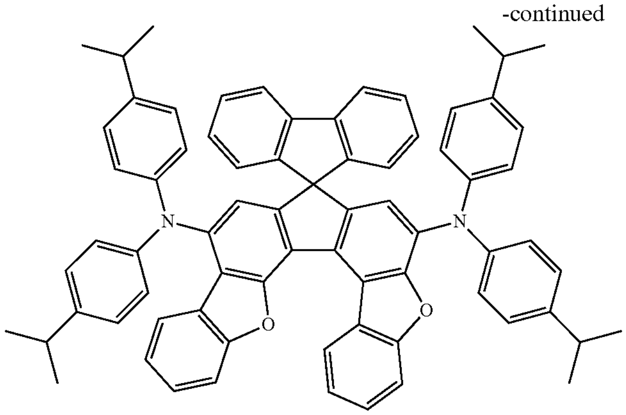
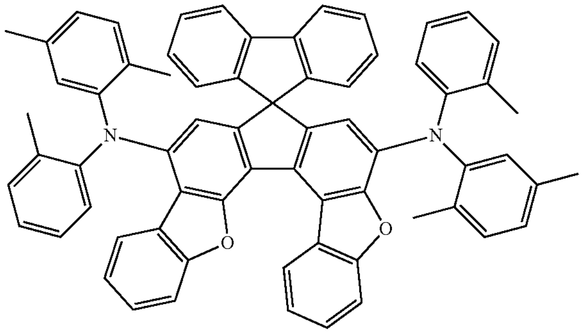
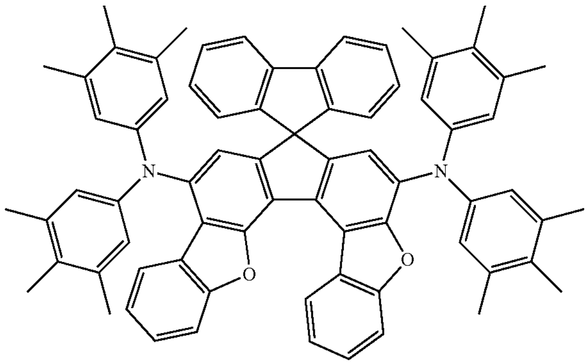
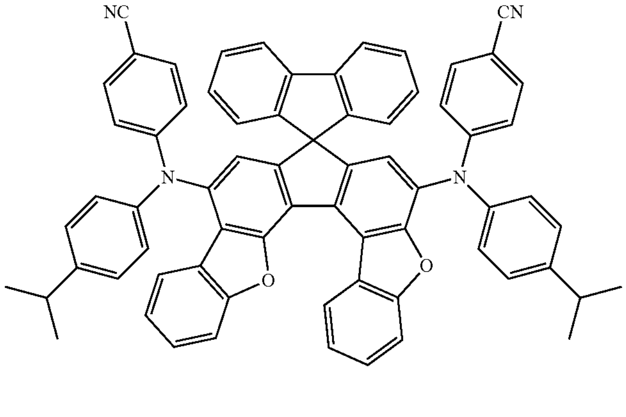

-continued
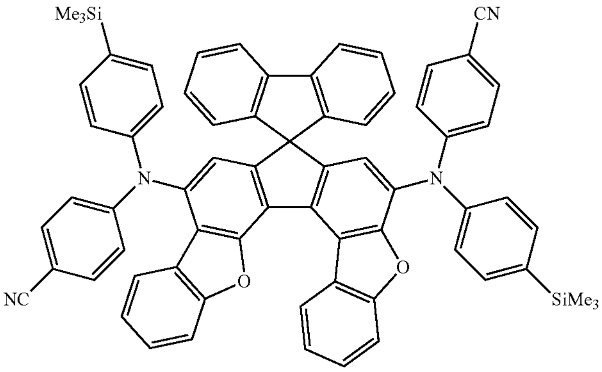
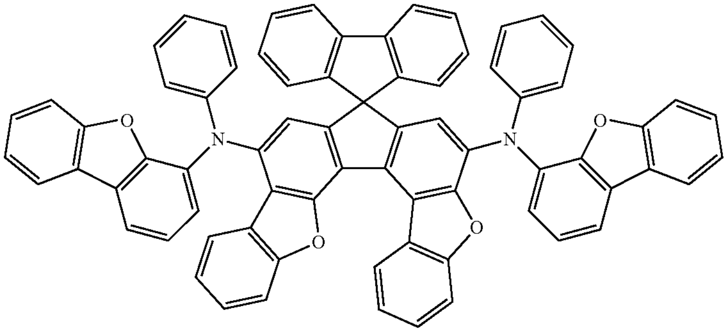
[Formula 422]
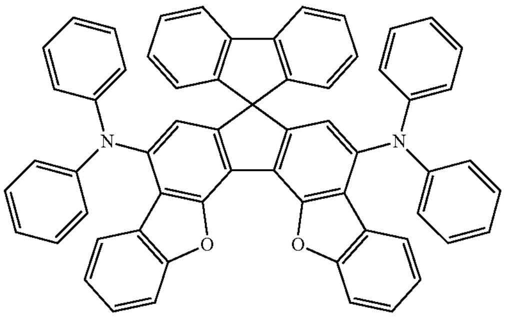
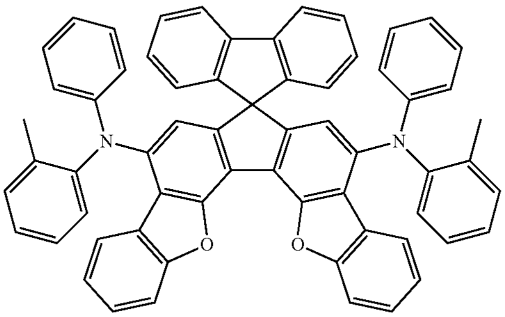
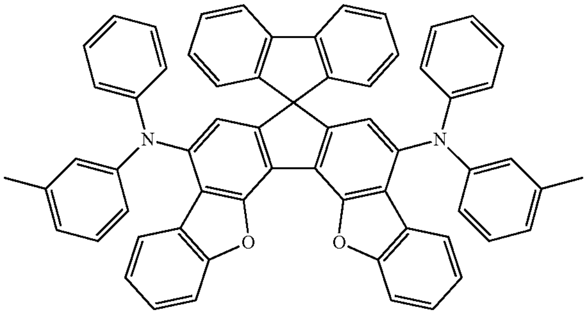
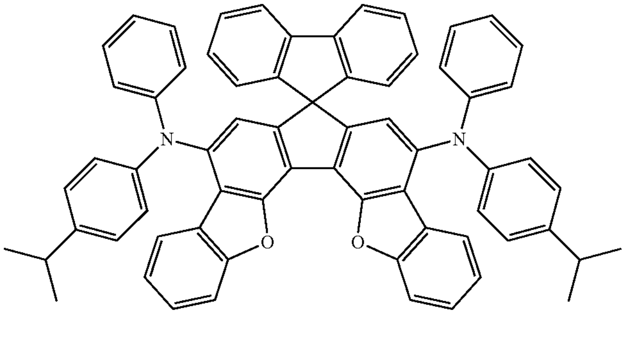

-continued
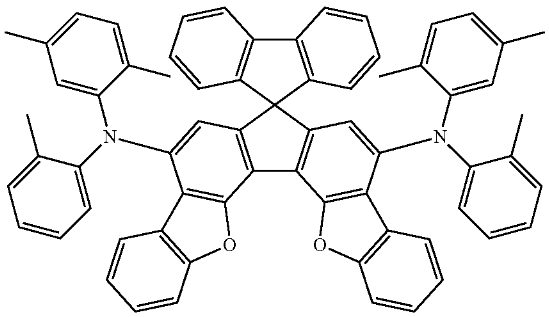
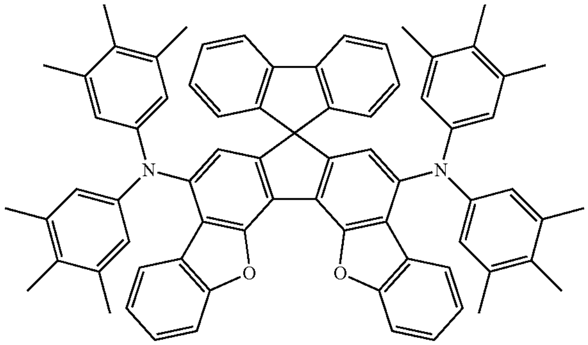
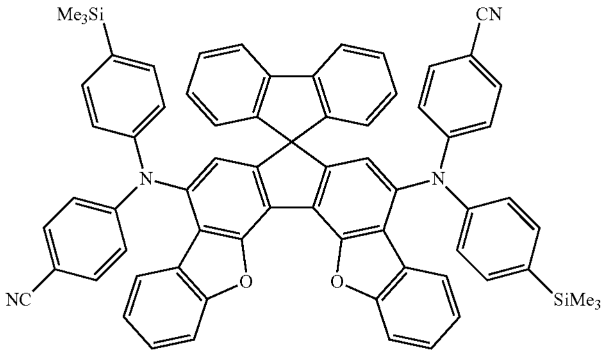
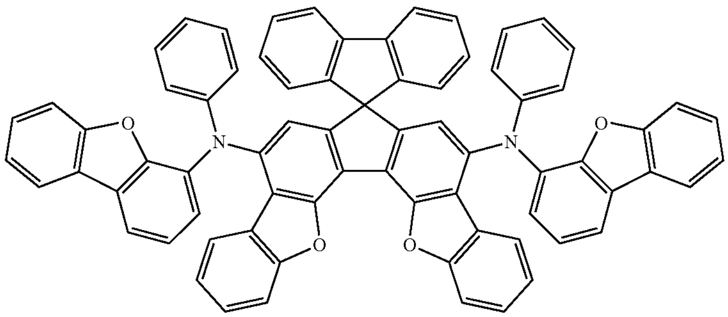

Compound Represented by Formula (10)

The compound represented by the formula (10) will be described below.

[Formula 423]

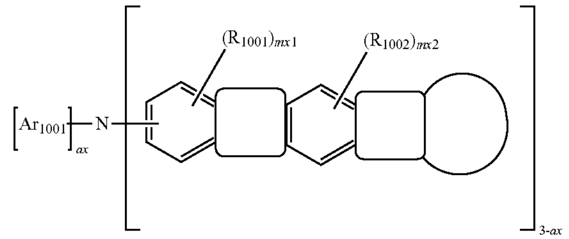

[Formula 424]

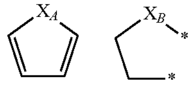

(10a) (10b)

In the formula (10):

$Ax_1$ ring is a ring represented by the formula (10a) and fused with adjacent ring(s) at any position(s);

$Ax_2$ ring is a ring represented by the formula (10b) and fused with adjacent ring(s) at any position(s);

two * in the formula (10b) are bonded to any position of $Ax_3$ ring;

$X_A$ and $X_B$ are each independently $C(R_{1003})(R_{1004})$, $Si(R_{1005})(R_{1006})$, an oxygen atom, or a sulfur atom;

$Ax_3$ ring is a substituted or unsubstituted aromatic hydrocarbon ring having 6 to 50 ring carbon atoms or a substituted or unsubstituted heterocycle having 5 to 50 ring atoms;

$Ar_{1001}$ is a substituted or unsubstituted aryl group having 6 to 50 ring carbon atoms, or a substituted or unsubstituted heterocyclic group having 5 to 50 ring atoms;

$R_{1001}$ to $R_{1006}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

mx1 is 3, mx2 is 2;

a plurality of $R_{1001}$ are mutually the same or different;

a plurality of $R_{1002}$ are mutually the same or different;

ax is 0, 1, or 2;

when ax is 0 or 1, the structures enclosed by brackets indicated by "3-ax" are mutually the same or different; and when ax is 2, a plurality of $Ar_{1001}$ are mutually the same or different.

In an exemplary embodiment, $Ar_{1001}$ is a substituted or unsubstituted aryl group having 6 to 50 ring carbon atoms.

In an exemplary embodiment, $Ax_3$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, $R_{1003}$ and $R_{1004}$ are each independently a substituted or unsubstituted alkyl group having 1 to 50 carbon atoms.

In an exemplary embodiment, ax is 1.

Specific examples of the compound represented by the formula (10) include compounds shown below.

[Formula 425]

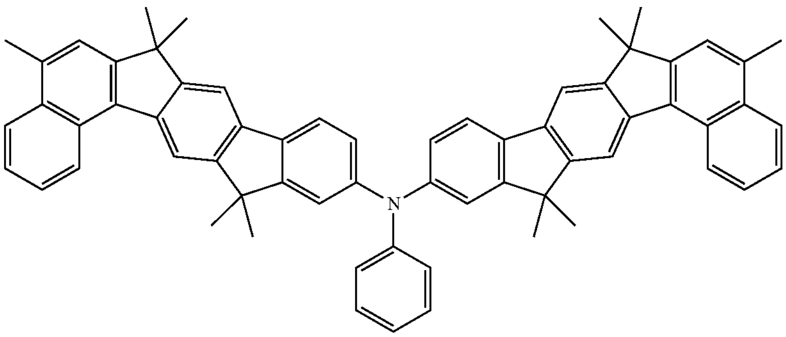

-continued
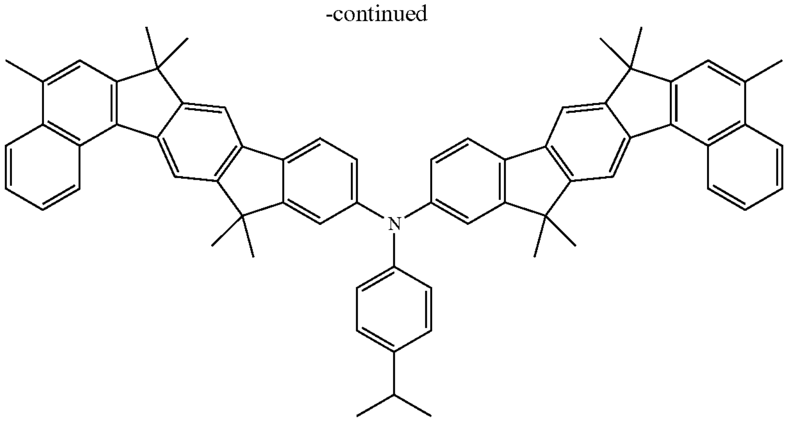
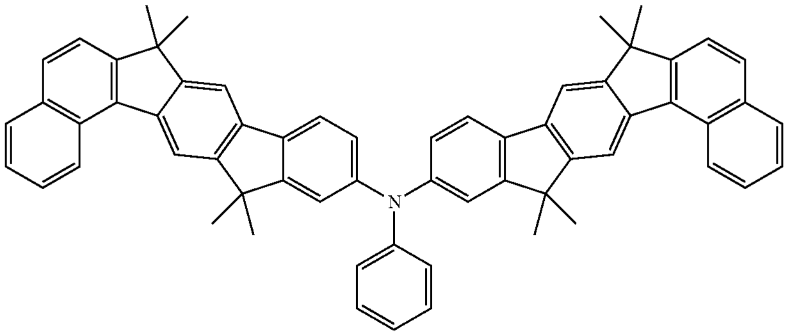
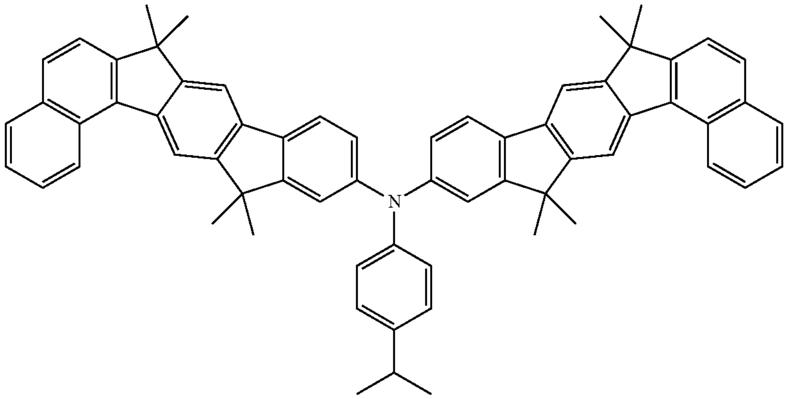
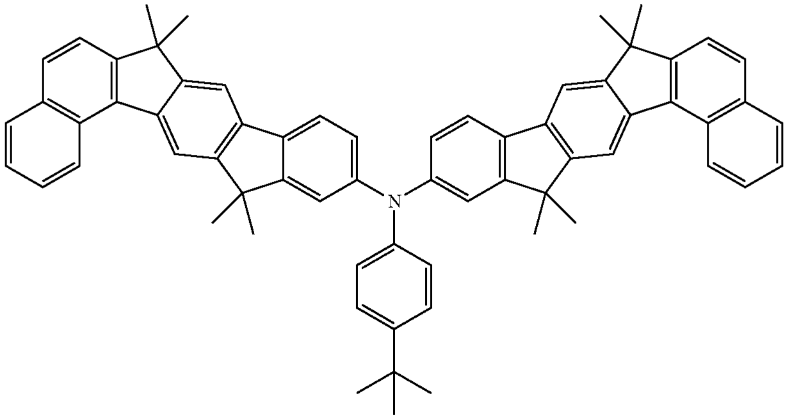

-continued
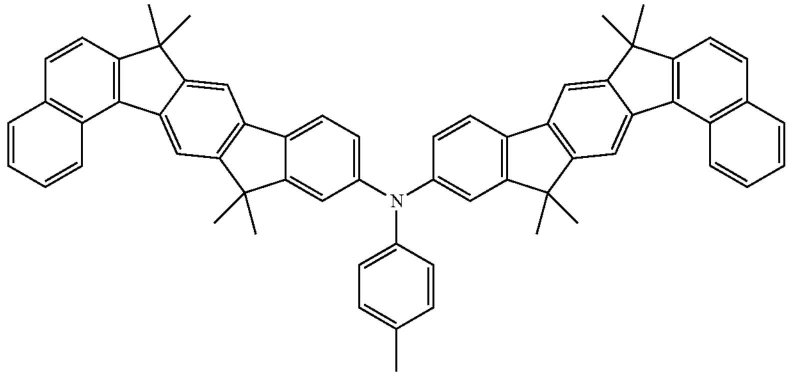
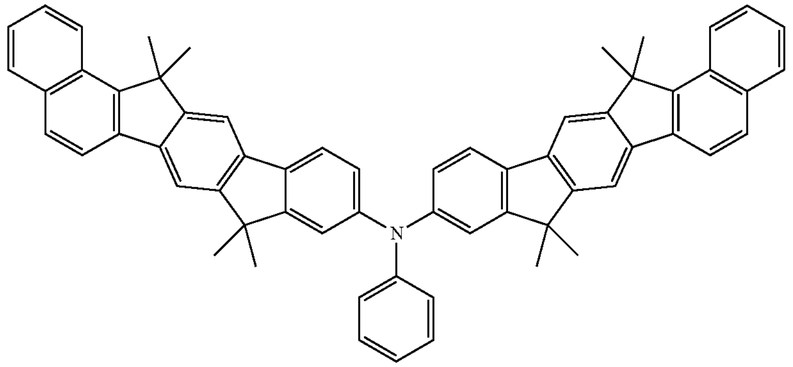
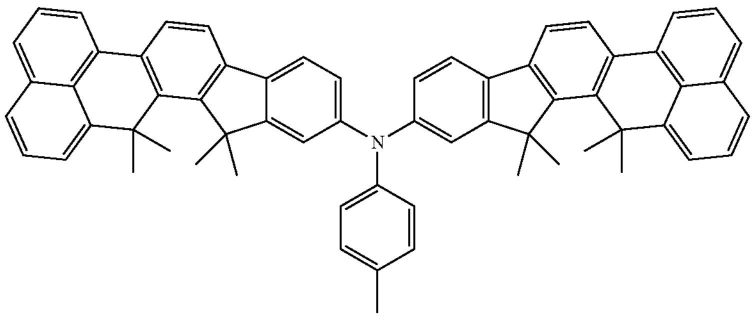
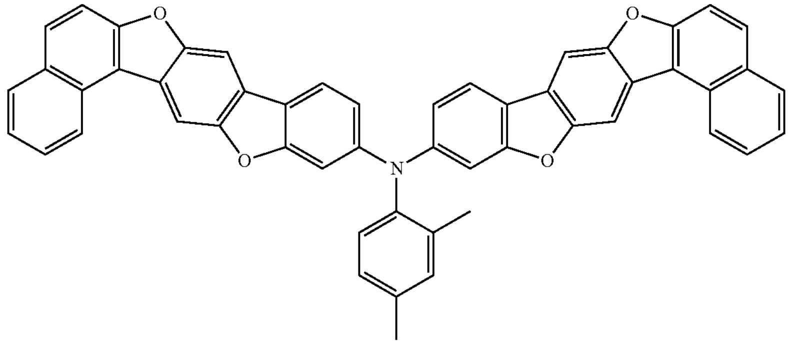

-continued

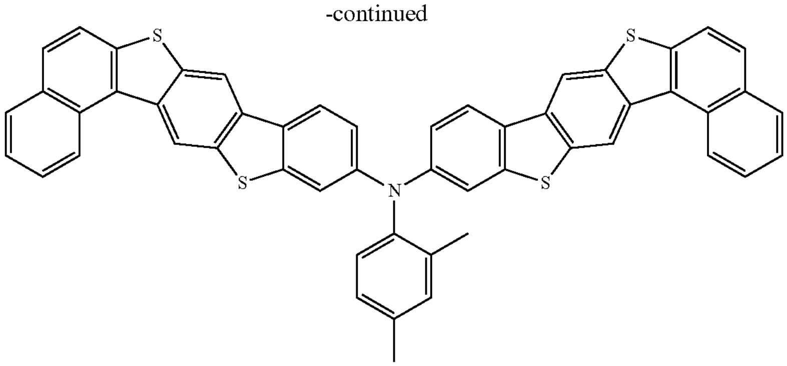

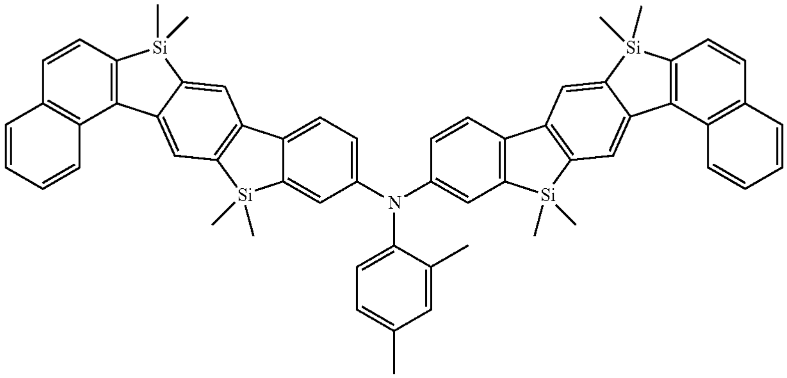

In an exemplary embodiment, the emitting layer contains, as at least one of the third compound or the fourth compound, at least one compound selected from the group consisting of the compound represented by the formula (4), the compound represented by the formula (5), the compound represented by the formula (7), the compound represented by the formula (8), the compound represented by the formula (9), and a compound represented by a formula (63a) below.

[Formula 426]

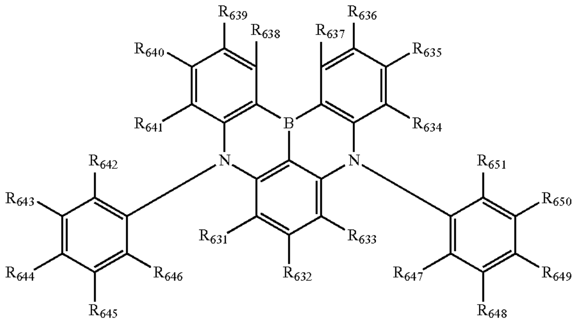

(63a)

In the formula (63A):

$R_{631}$ is bonded with $R_{646}$ to form a substituted or unsubstituted heterocycle or not bonded to form no substituted or unsubstituted heterocycle;

$R_{633}$ is bonded with $R_{647}$ to form a substituted or unsubstituted heterocycle or not bonded to form no substituted or unsubstituted heterocycle;

$R_{634}$ is bonded with $R_{651}$ to form a substituted or unsubstituted heterocycle or not bonded to form no substituted or unsubstituted heterocycle;

$R_{641}$ is bonded with $R_{642}$ to form a substituted or unsubstituted heterocycle or not bonded to form no substituted or unsubstituted heterocycle; at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded;

$R_{631}$ to $R_{651}$ not forming the substituted or unsubstituted heterocycle, not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, or a substituted or unsubstituted heterocyclic group having 5 to 50 ring atoms; and at least one of $R_{631}$ to $R_{651}$ not forming the substituted or unsubstituted heterocycle, not forming the monocyclic ring and not forming the fused ring are a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is the compound represented by the formula (41-3), (41-4) or (41-5), the A1 ring in the formula (41-5) being a substituted or unsubstituted fused aromatic hydrocarbon ring having 10 to 50 ring carbon atoms, or a substituted or unsubstituted fused heterocycle having 8 to 50 ring atoms.

In an exemplary embodiment, the substituted or unsubstituted fused aromatic hydrocarbon ring having 10 to 50 ring carbon atoms in the formulae (41-3), (41-4) and (41-5) is a substituted or unsubstituted naphthalene ring, a substituted or unsubstituted anthracene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the substituted or unsubstituted fused aromatic hydrocarbon ring having 10 to 50 ring carbon atoms in the formula (41-3), (41-4) or (41-5) is a substituted or unsubstituted naphthalene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the compound represented by the formula (4) is selected from the group consisting of a compound represented by a formula (461) below, a compound represented by a formula (462) below, a compound represented by a formula (463) below, a compound represented by a formula (464) below, a compound represented by a formula (465) below, a compound represented by a formula (466) below, and a compound represented by a formula (467) below.

[Formula 427]

(461)

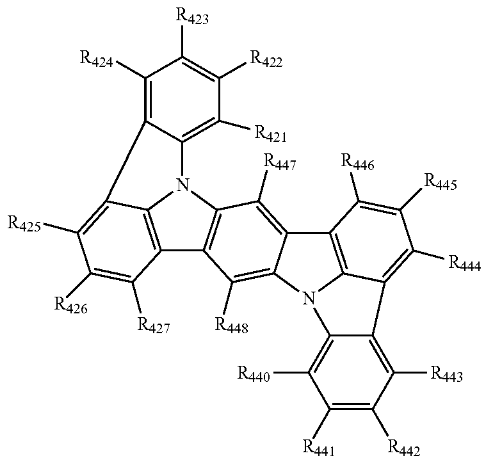

(462)

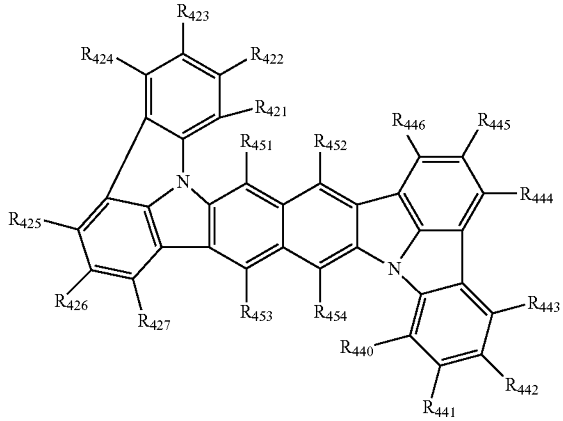

[Formula 428]

(463)

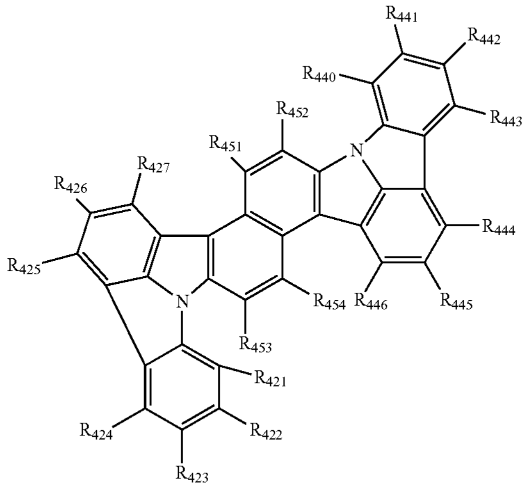

-continued (464)

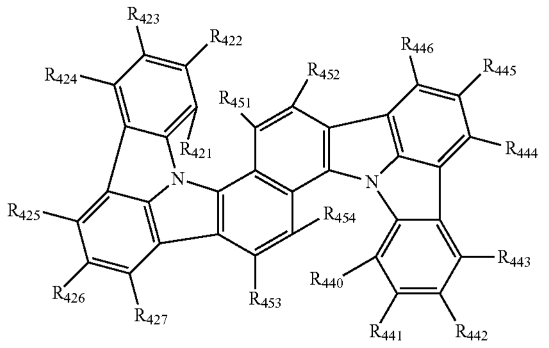

[Formula 429]

(465)

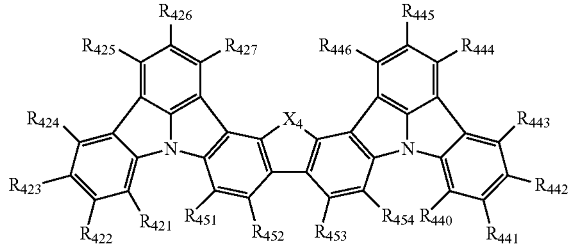

[Formula 430]

(466)

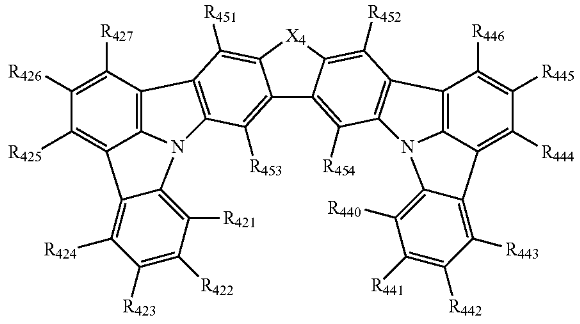

[Formula 431]

(467)

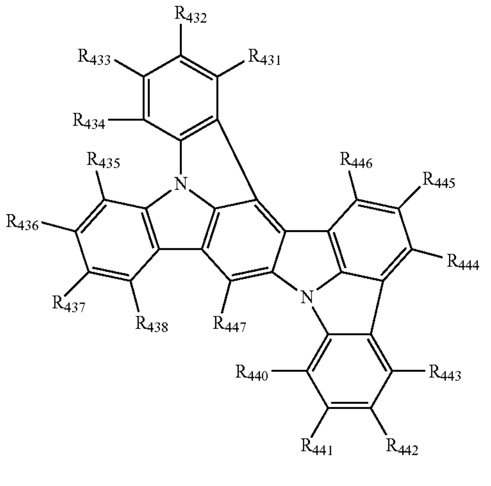

In the formulae (461) to (467):

at least one combination of adjacent two or more of $R_{421}$ to $R_{427}$, $R_{431}$ to $R_{436}$, $R_{440}$ to $R_{448}$, and $R_{451}$ to $R_{454}$ are mutually bonded to form a substituted or unsubstituted monocyclic ring, mutually bonded to form a substituted or unsubstituted fused ring, or not mutually bonded;

$R_{437}$, $R_{438}$, and $R_{421}$ to $R_{427}$, $R_{431}$ to $R_{436}$, $R_{440}$ to $R_{448}$, and $R_{451}$ to $R_{454}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_4$ is an oxygen atom, $NR_{801}$, or C($R_{802}$)($R_{803}$);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, $R_{421}$ to $R_{427}$ and $R_{440}$ to $R_{448}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{421}$ to $R_{427}$ and $R_{440}$ to $R_{447}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (41-3) is a compound represented by a formula (41-3-1) below.

[Formula 432]

(41-3-1)

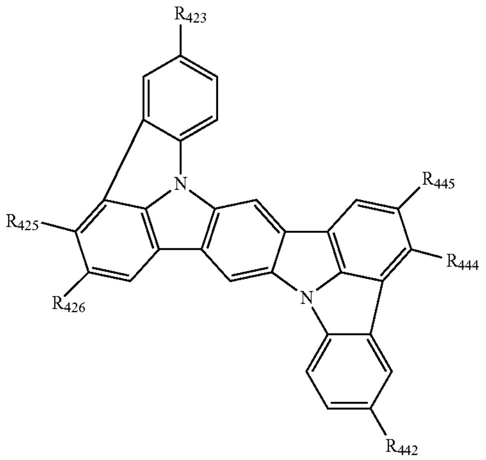

In the formula (41-3-1), $R_{423}$, $R_{425}$, $R_{426}$, $R_{442}$, $R_{444}$, and $R_{445}$ each independently represent the same as $R_{423}$, $R_{425}$, $R_{426}$, $R_{442}$, $R_{444}$, and $R_{445}$ in the formula (41-3).

In an exemplary embodiment, the compound represented by the formula (41-3) is a compound represented by a formula (41-3-2) below.

[Formula 433]

(41-3-2)

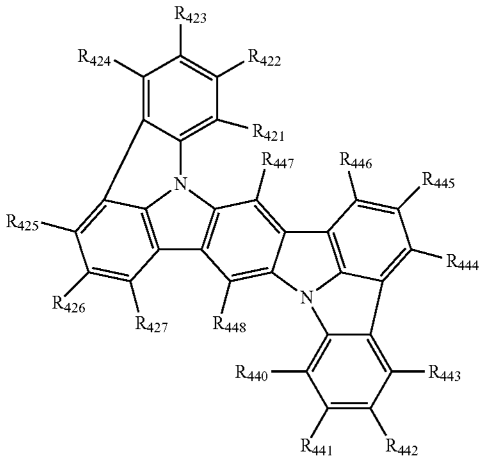

In the formula (41-3-2), $R_{421}$ to $R_{427}$ and $R_{440}$ to $R_{448}$ each independently represent the same as $R_{421}$ to $R_{427}$ and $R_{440}$ to $R_{448}$ in the formula (41-3); and at least one of $R_{421}$ to $R_{427}$ or $R_{440}$ to $R_{446}$ being a group represented by —$N(R_{906})(R_{907})$.

In an exemplary embodiment, two of $R_{421}$ to $R_{427}$ and $R_{440}$ to $R_{446}$ in the formula (41-3-2) are groups represented by —$N(R_{906})(R_{907})$.

In an exemplary embodiment, the compound represented by the formula (41-3-2) is a compound represented by a formula (41-3-3) below.

[Formula 434]

(41-3-3)

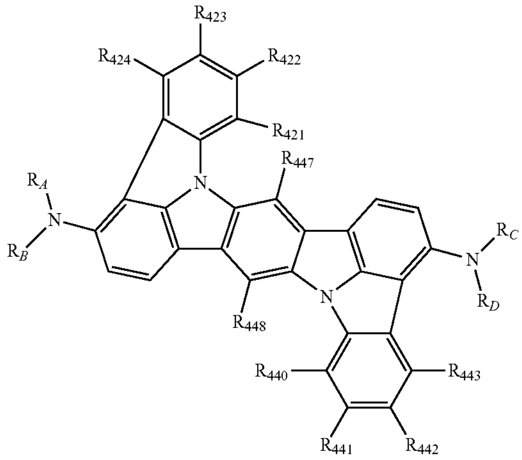

In the formula (41-3-3), $R_{421}$ to $R_{424}$, $R_{440}$ to $R_{443}$, $R_{447}$, and $R_{448}$ each independently represent the same as $R_{421}$ to $R_{424}$, $R_{440}$ to $R_{443}$, $R_{447}$, and $R_{448}$ in the formula (41-3); and $R_A$, $R_B$, $R_C$, and $R_D$ are each independently a substituted or unsubstituted aryl group having 6 to 18 ring carbon atoms, or a substituted or unsubstituted heterocyclic group having 5 to 18 ring atoms.

In an exemplary embodiment, the compound represented by the formula (41-3-3) is a compound represented by a formula (41-3-4) below.

[Formula 435]

(41-3-4)

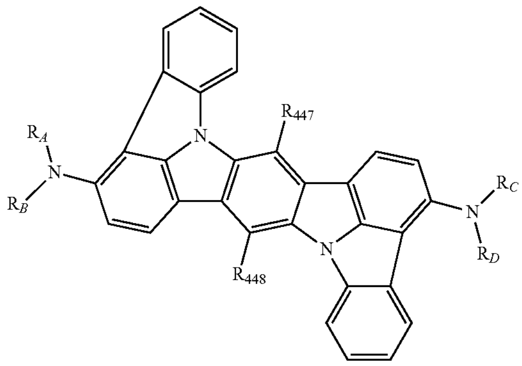

In the formula (41-3-4), $R_{447}$, $R_{448}$, $R_A$, $R_B$, $R_C$, and $R_D$ each independently represent the same as $R_{447}$, $R_{448}$, $R_A$, $R_B$, $R_C$, and $R_D$ in the formula (41-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, $R_{447}$ and $R_{448}$ are each a hydrogen atom.

In an exemplary embodiment, a substituent for "the substituted or unsubstituted" group in each of the formulae is an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901a}$)($R_{902a}$)($R_{903a}$), —O—($R_{904a}$), —S—($R_{905a}$), —N($R_{906a}$)($R_{907a}$), a halogen atom, a cyano group, a nitro group, an unsubstituted aryl group having 6 to 50 ring carbon atoms, or an unsubstituted heterocyclic group having 5 to 50 ring atoms;

$R_{901a}$ to $R_{907a}$ are each independently a hydrogen atom, an unsubstituted alkyl group having 1 to 50 carbon atoms, an unsubstituted aryl group having 6 to 50 ring carbon atoms, or an unsubstituted heterocyclic group having 5 to 50 ring atoms;

when two or more $R_{901a}$ are present, the two or more $R_{901a}$ are mutually the same or different;

when two or more $R_{902a}$ are present, the two or more $R_{902a}$ are mutually the same or different;

when two or more $R_{903a}$ are present, the two or more $R_{903a}$ are mutually the same or different;

when two or more $R_{904a}$ are present, the two or more $R_{904a}$ are mutually the same or different;

when two or more $R_{905a}$ are present, the two or more $R_{905a}$ are mutually the same or different;

when two or more $R_{906a}$ are present, the two or more $R_{906a}$ are mutually the same or different; and when two or more $R_{907a}$ are present, the two or more $R_{907a}$ are mutually the same or different.

In an exemplary embodiment, a substituent for "the substituted or unsubstituted" group in each of the formulae is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, a substituent for "the substituted or unsubstituted" group in each of the formulae is an unsubstituted alkyl group having 1 to 18 carbon atoms, an unsubstituted aryl group having 6 to 18 ring carbon atoms, or an unsubstituted heterocyclic group having 5 to 18 ring atoms.

In the organic EL device according to the exemplary embodiment, it is preferable that the second emitting layer further contains a fourth compound that fluoresces, and the fourth compound is a compound that emits light having a main peak wavelength in a range from 430 nm to 480 nm.

In the organic EL device according to the exemplary embodiment, it is preferable that the first emitting layer further contains a third compound that fluoresces, and the third compound is a compound that emits light having a main peak wavelength in a range from 430 nm to 480 nm.

The measurement method of the main peak wavelength of the compound is as follows. A toluene solution of a measurement target compound at a concentration ranging from $10^{-6}$ mol/L to $10^{-5}$ mol/L is prepared and put in a quartz cell. An emission spectrum (ordinate axis: luminous intensity, abscissa axis: wavelength) of the thus-obtained sample is measured at a normal temperature (300K). The emission spectrum is measurable using a spectrophotometer (machine name: F-7000) manufactured by Hitachi High-Tech Science Corporation. It should be noted that the machine for measuring the emission spectrum is not limited to the machine used herein.

A peak wavelength of the emission spectrum, at which the luminous intensity of the emission spectrum is at the maximum, is defined as the main peak wavelength. It should be noted that the main peak wavelength is sometimes referred to as a fluorescence main peak wavelength (FL-peak) herein.

When the first emitting layer of the organic EL device according to the exemplary embodiment contains the first compound and the third compound, the first compound is preferably a host material (sometimes referred to as a matrix material) and the third compound is preferably a dopant material (sometimes referred to as a guest material, emitter, or luminescent material).

When the first emitting layer of the organic EL device according to the exemplary embodiment contains the first and third compounds, a singlet energy $S_1(H1)$ of the first compound and a singlet energy $S_1(D3)$ of the third compound preferably satisfy a relationship of a numerical formula (Numerical Formula 1) below.

$$S_1(H1)>S_1(D3) \quad \text{(Numerical Formula 1)}$$

When the second emitting layer of the organic EL device according to the exemplary embodiment contains the second and fourth compounds, the second compound is preferably a host material (occasionally also referred to as a matrix material) and the fourth compound is preferably a dopant material (occasionally also referred to as a guest material, emitter or luminescent material).

When the second emitting layer of the organic EL device according to the exemplary embodiment contains the second and fourth compounds, a singlet energy $S_1(H2)$ of the second compound and a singlet energy $S_1(D4)$ of the fourth compound preferably satisfy a relationship of a numerical formula (Numerical Formula 2) below.

$$S_1(H2)>S_1(D4) \quad \text{(Numerical Formula 2)}$$

Singlet Energy S1

A method of measuring a singlet energy $S_1$ with use of a solution (occasionally referred to as a solution method) is exemplified by a method below. A toluene solution of a measurement target compound at a concentration ranging from $10^{-5}$ mol/L to $10^{-4}$ mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate the singlet energy.

$$S_1[\text{eV}]=1239.85/\lambda\text{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve fell (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region. The local maximum absorbance of 0.2 or less is not counted as the above-mentioned local maximum absorbance closest to the long-wavelength region.

In the organic EL device according to the exemplary embodiment, an electron mobility μH1 of the first compound and an electron mobility μH2 of the second compound also preferably satisfy a relationship of a numerical formula (Numerical Formula 3) below.

$$\mu H2>\mu H1 \quad \text{(Numerical Formula 3)}$$

When the first compound and the second compound satisfy the relationship of the numerical formula (Numerical Formula 3), a recombination ability of holes and electrons in the first emitting layer is improved.

The electron mobility can be measured according to impedance spectroscopy.

A measurement target layer having a thickness in a range from 100 nm to 200 nm is held between the anode and the cathode, and a small alternating voltage of 100 mV or less is applied thereto while a bias DC voltage is applied. The value of an alternating current (the absolute value and the phase) which flows at this time is measured. This measurement is performed while changing a frequency of the alternating voltage, and complex impedance (Z) is calculated from the current value and the voltage value. A frequency dependency of the imaginary part (ImM) of the modulus M=iωZ (i: imaginary unit, ω: angular frequency) is obtained. The reciprocal number of a frequency ω at which the ImM becomes the maximum is defined as a response time of electrons carried in the measurement target layer. The electron mobility is calculated by the following equation.

$$\text{Electron Mobility}=(\text{Film Thickness of Measurement Target Layer})^2/(\text{Response Time}\cdot\text{Voltage})$$

It is preferable that the first emitting layer and the second emitting layer do not contain a phosphorescent material (dopant material).

Further, it is preferable that the first emitting layer and the second emitting layer do not contain a heavy-metal complex and a phosphorescent rare-earth metal complex. Examples of the heavy-metal complex herein include iridium complex, osmium complex, and platinum complex.

Further, it is also preferable that the first emitting layer and the second emitting layer do not contain a metal complex.

Film Thickness of Emitting Layer

A film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, the emitting layer is easily formable and chromaticity is easily adjustable. When the film thickness of the emitting layer is 50 nm or less, an increase in the drive voltage is likely to be reducible.

Content Ratio of Compound in Emitting Layer

When the first emitting layer contains the first compound and the third compound, a content ratio of each of the first compound and the third compound in the first emitting layer preferably falls, for instance, within a range below.

The content ratio of the first compound is preferably in a range from 80 mass % to 99 mass %, more preferably in a range from 90 mass % to 99 mass %, further preferably in a range from 95 mass % to 99 mass %.

The content ratio of the third compound is preferably in a range from 1 mass % to 10 mass %, more preferably in a range from 1 mass % to 7 mass %, further preferably in a range from 1 mass % to 5 mass %.

The upper limit of the total of the content ratios of the first compound and the third compound in the first emitting layer is 100 mass %.

It is not excluded that the first emitting layer of the exemplary embodiment further contains a material(s) other than the first and third compounds.

The first emitting layer may include a single type of the first compound or may include two or more types of the first compound. The first emitting layer may include a single type of the third compound or may include two or more types of the third compound.

An example of the organic EL device whose first emitting layer contains two or more different types of the first compound is as follows.

An organic EL device includes: an anode; a cathode; a first emitting layer provided between the anode and the cathode; and a second emitting layer provided between the first emitting layer and the cathode, in which the first emitting layer contains a first compound represented by the formula (1) as a first host material, the first compound containing at least one group represented by the formula (11), the first emitting layer contains two or more different types of the first compound, the second emitting layer contains a second compound represented by the formula (2) as a second host material, and the first emitting layer is in direct contact with the second emitting layer.

When the second emitting layer contains the second compound and the fourth compound, a content ratio of each of the second compound and the fourth compound in the second emitting layer preferably falls, for instance, within a range below.

The content ratio of the second compound is preferably in a range from 80 mass % to 99 mass %, more preferably in a range from 90 mass % to 99 mass %, further preferably in a range from 95 mass % to 99 mass %.

The content ratio of the fourth compound is preferably in a range from 1 mass % to 10 mass %, more preferably in a range from 1 mass % to 7 mass %, further preferably in a range from 1 mass % to 5 mass %.

The upper limit of the total of the content ratios of the second compound and the fourth compound in the second emitting layer is 100 mass %.

It is not excluded that the second emitting layer of the exemplary embodiment further contains a material(s) other than the second and fourth compounds.

The second emitting layer may include a single type of the second compound or may include two or more types of the second compound. The second emitting layer may include a single type of the fourth compound or may include two or more types of the fourth compound.

An example of the organic EL device whose second emitting layer contains two or more different types of the second compound is as follows.

An organic EL device includes: an anode; a cathode; a first emitting layer provided between the anode and the cathode; and a second emitting layer provided between the first emitting layer and the cathode, in which the first emitting layer contains a first compound represented by the formula (1) as a first host material, the first compound containing at least one group represented by the formula (11), the second emitting layer contains a second compound represented by the formula (2) as a second host material, the second emitting layer contains two or more different types of the second compound, and the first emitting layer is in direct contact with the second emitting layer.

Arrangement(s) of an organic EL device 1 will be further described below. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate refers to a bendable substrate, example of which is a plastic substrate or the like. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid)(PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ $cm^2/(Vs)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinolato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ $cm^2/(Vs)$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Specific examples of the compound usable for the electron transporting layer is exemplified by compounds below. It should however be noted that the invention is not limited by the specific examples of the compound.

[Formula 436]

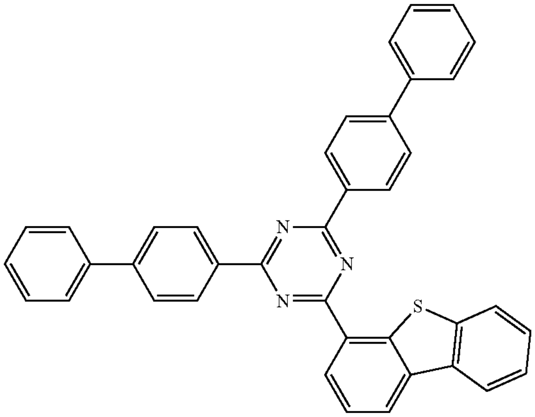

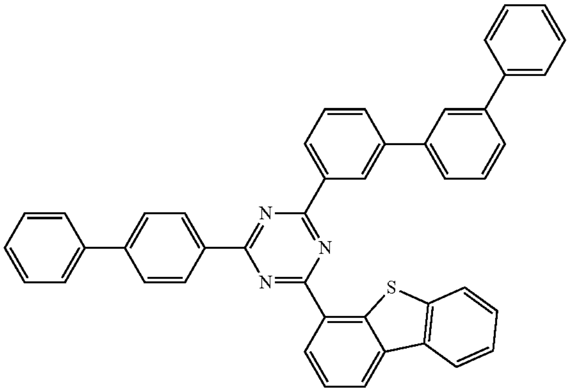

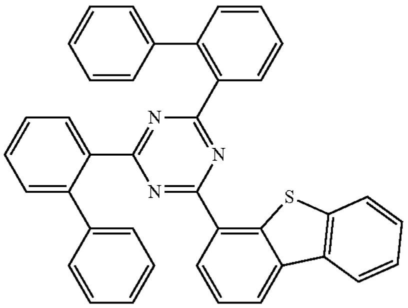

-continued
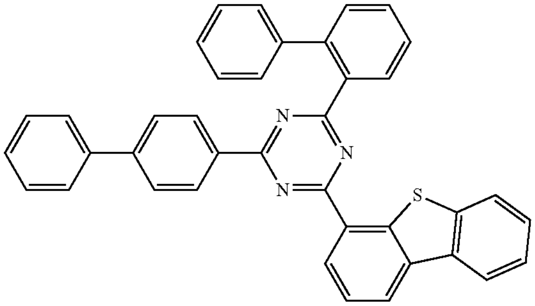
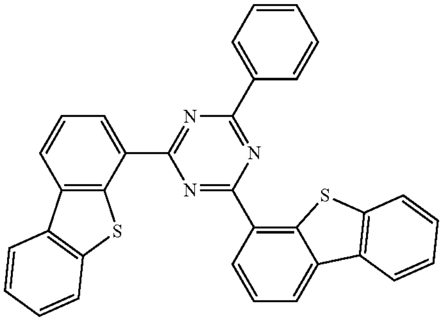
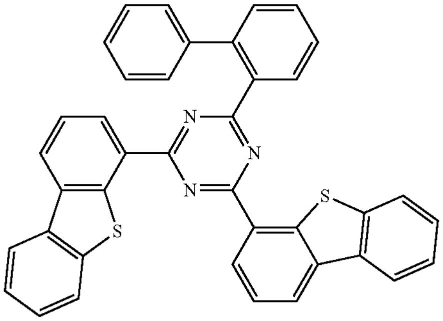
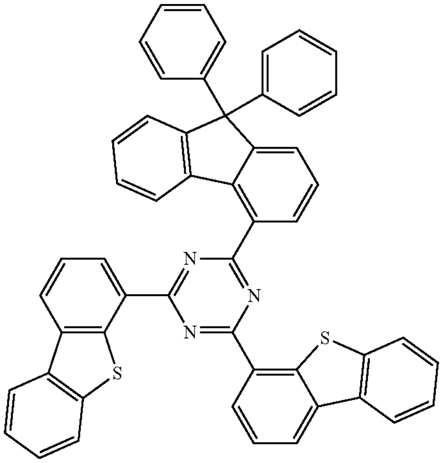
-continued
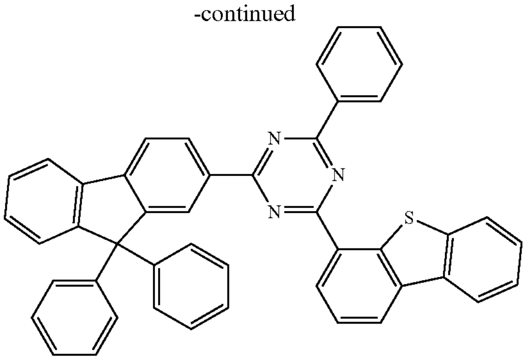
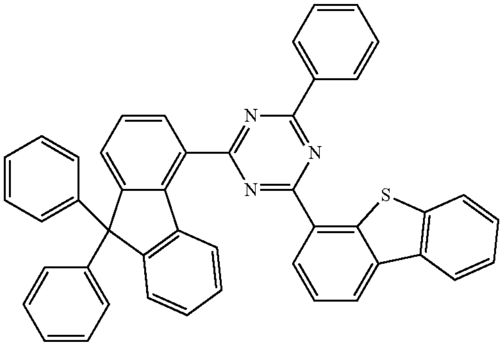
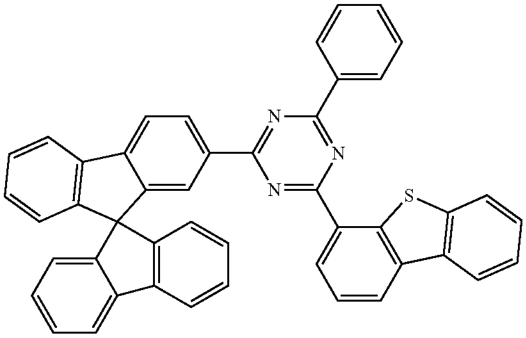
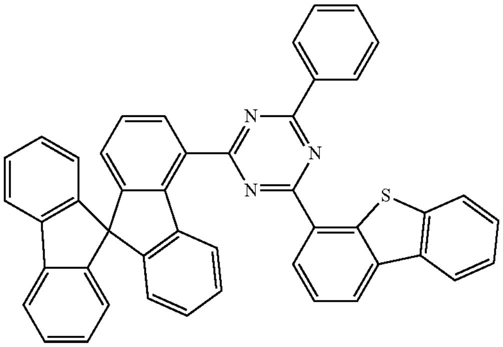
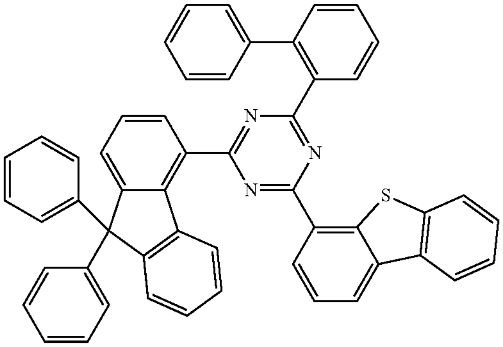

-continued

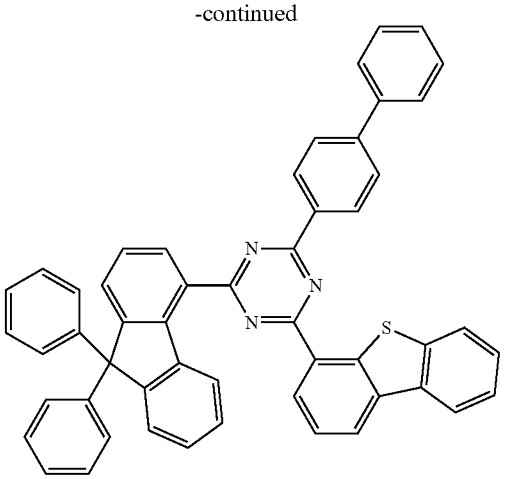

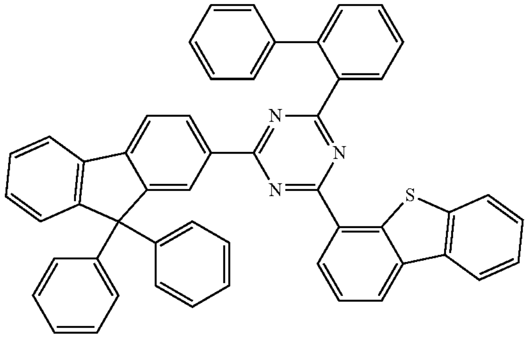

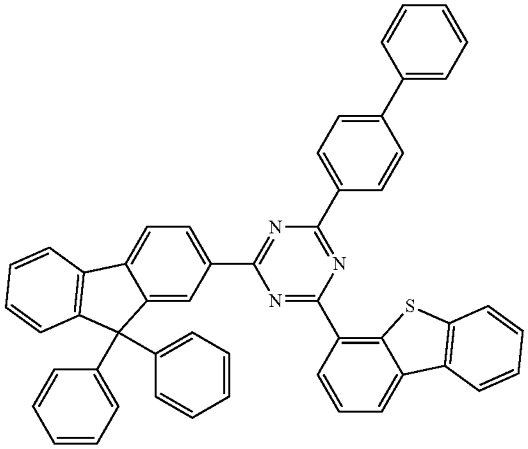

Moreover, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the anode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method(s)

A method for forming each layer of the organic EL device in the third exemplary embodiment is subject to no limitation except for the above particular description. However, known methods of dry film-forming such as vacuum deposition, sputtering, plasma or ion plating and wet film-forming such as spin coating, dipping, flow coating or inkjet printing are applicable.

Film Thickness

The film thickness of the organic layers of the organic EL device according to the exemplary embodiment is not limited unless otherwise specified in the above. In general, since excessively small film thickness is likely to cause defects (e.g. pin holes) and excessively large thickness leads to the necessity of applying high voltage and consequent reduction in efficiency, the thickness of the organic layer of the organic EL device usually preferably ranges from several nanometers to 1 μm.

According to the exemplary embodiment, an organic electroluminescence device with enhanced luminous efficiency can be provided.

In the organic EL device according to the exemplary embodiment, the first emitting layer containing the first host material in a form of the first compound represented by the formula (1) or the like and the second emitting layer containing the second host material in a form of the second compound represented by the formula (2) or the like are in direct contact with each other. By thus layering the first emitting layer and the second emitting layer, the generated singlet exitons and the triplet exitons can be efficiently used and, consequently, the luminous efficiency of the organic EL device can be improved.

Second Exemplary Embodiment

Electronic Device

An electronic device according to a second exemplary embodiment is installed with any one of the organic EL devices according to the above exemplary embodiment. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

The scope of the invention is not limited by the above-described exemplary embodiments but includes any modification and improvement as long as such modification and improvement are compatible with the invention.

For instance, only two emitting layers are not necessarily provided, and more than two emitting layers may be provided and laminated with each other. When the organic EL device includes more than two emitting layers, it is only necessary that at least two of the emitting layers should satisfy the requirements mentioned in the above exemplary embodiments. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

An example of the organic EL device including three or more emitting layers is as follows.

An organic EL device includes: an anode; a cathode; a first emitting layer provided between the anode and the cathode; a second emitting layer provided between the first emitting layer and the cathode; and a third emitting layer provided between the anode and the cathode, the third emitting layer not being in direct contact with both of the first emitting layer and the second emitting layer, in which the first emitting layer contains a first compound represented by the formula (1) as a first host material, the first compound containing at least one group represented by the formula (11), the second emitting layer contains a second compound represented by the formula (2) as a second host material, and the first emitting layer is in direct contact with the second emitting layer.

It is also preferable that the third emitting layer contains the first compound.

It is also preferable that the third emitting layer contains the second compound.

The organic electroluminescence device preferably includes an intermediate layer between the third emitting layer and the first emitting layer or the second emitting layer.

The intermediate layer is generally also referred to as an intermediate electrode, intermediate conductive layer, charge generating layer, electron drawing layer, connection layer or intermediate insulative layer.

The intermediate layer is a layer configured to supply electrons to a layer located close to the anode with respect to the intermediate layer and supply holes to a layer located close to the cathode with respect to the intermediate layer. The intermediate layer can be made of a known material. The intermediate layer is may be a single layer, or may be provided by two or more layers. A unit made of two or more intermediate layers is sometimes referred to as an intermediate unit. The compositions of the plurality of intermediate layers of the intermediate unit are mutually the same or different.

Further, a plurality of layers including the emitting layer, which are disposed between the intermediate layer/intermediate unit and the anode/cathode, are sometimes collectively referred to as an emitting unit. Examples of the device arrangement of the organic EL device including a plurality of emitting units include (TND1) to (TND4) below.

(TND1) anode/first emitting unit/intermediate layer/second emitting unit/cathode (TND2) anode/first emitting unit/intermediate unit/second emitting unit/cathode (TND3) anode/first emitting unit/first intermediate layer/second emitting unit/second intermediate layer/third emitting unit/cathode (TND4) anode/first emitting unit/first intermediate unit/second emitting unit/second intermediate unit/third emitting unit/cathode The number of the emitting units and the intermediate layers (or intermediate units) is not limited to the examples shown above.

It is preferable that the first emitting layer and the second emitting layer are included in at least one of the first emitting unit, second emitting unit, or the third emitting unit.

It is also preferable that the first emitting layer and the second emitting layer are included in all of the emitting units of the organic EL device.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, or excitons.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

The invention will be described in further detail with reference to Examples. It should be noted that the scope of the invention is by no means limited by Examples.

Compounds

Structures of compounds represented by the formula (1) in Examples and Reference Examples are as shown below.

[Formula 437]
BH1
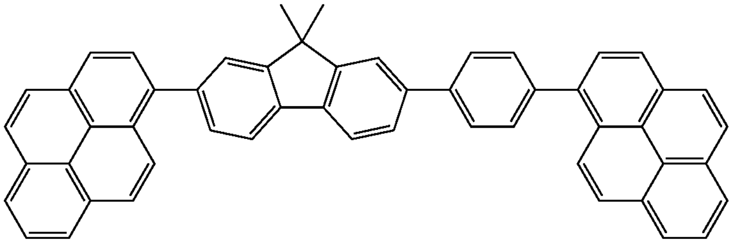
[Formula 438]
BH1-2
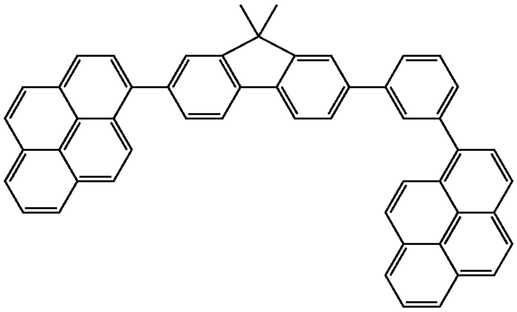
BH1-3
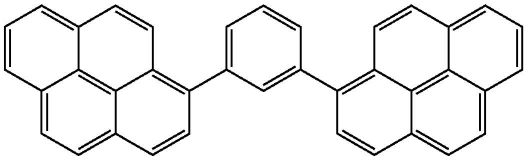
[Formula 439]
BH1-4
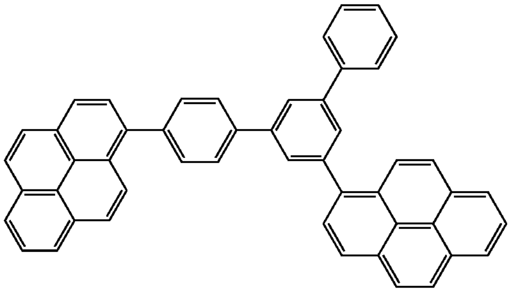
BH1-5
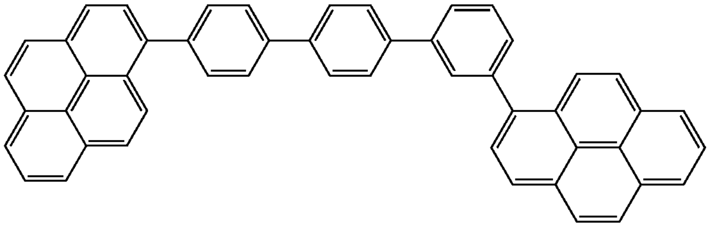
[Formula 440]
BH1-6
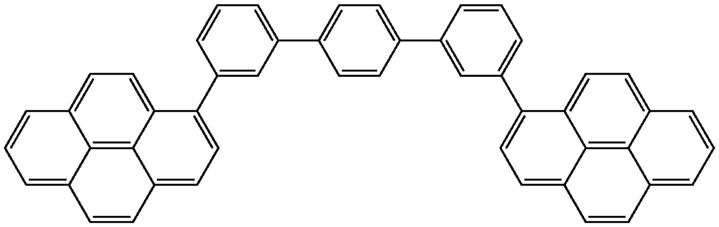

-continued
BH1-7
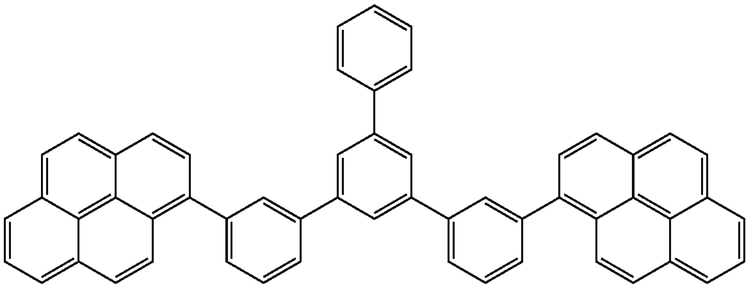
[Formula 441]
BH1-8
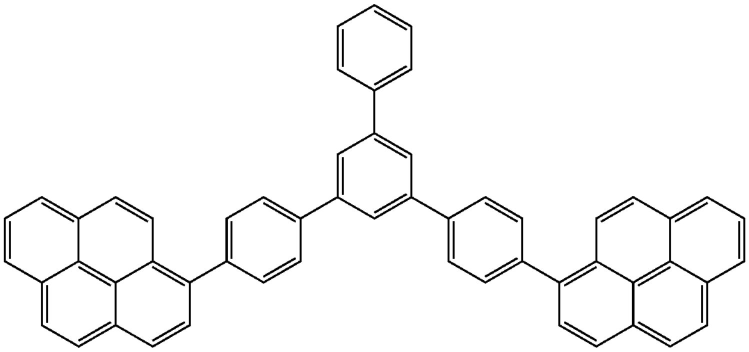
BH1-9
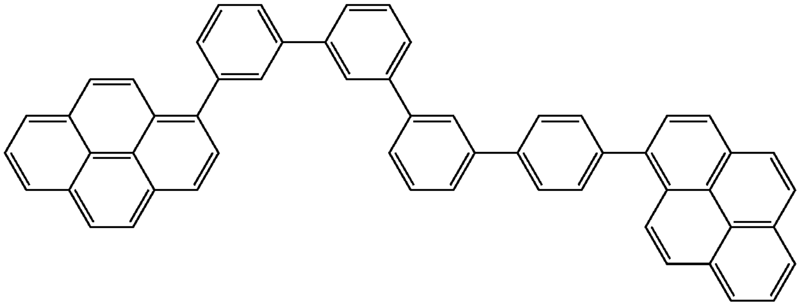
[Formula 442]
BH1-10
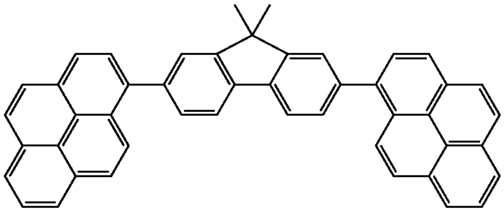
BH1-11
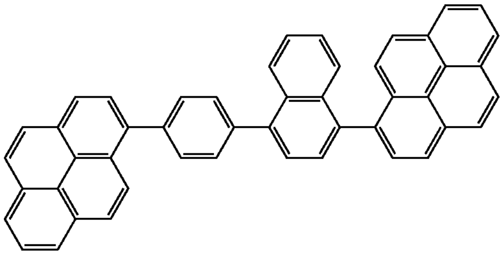

-continued
[Formula 443]
BH1-12
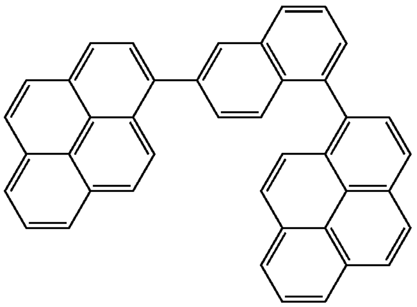
BH1-13
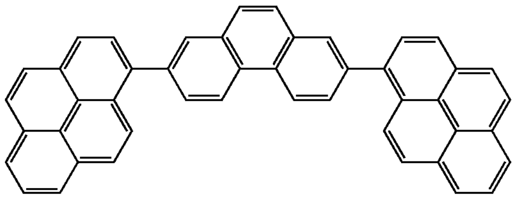
[Formula 444]
BH1-14
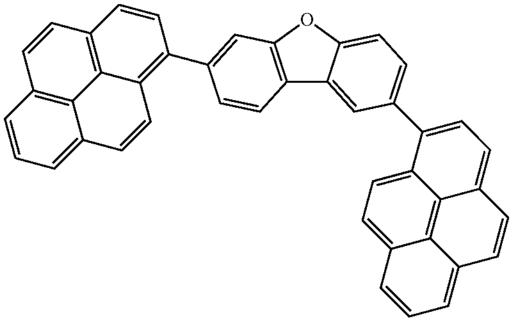
BH1-15
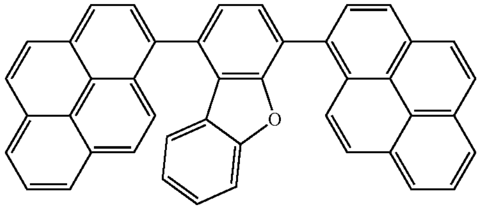
[Formula 445]
BH1-16
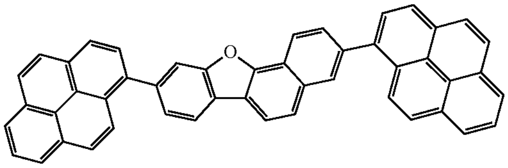
BH1-17
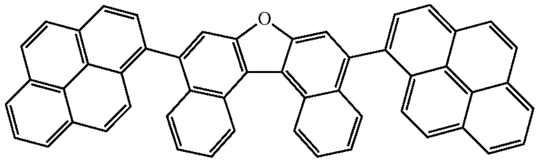
[Formula 446]
BH1-18
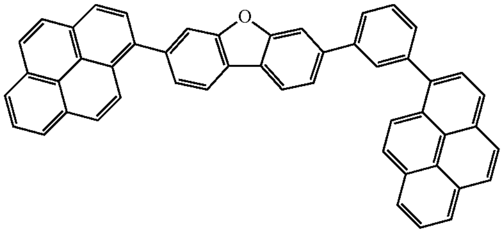
BH1-19
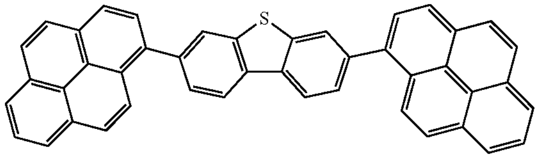
[Formula 447]
BH1-20
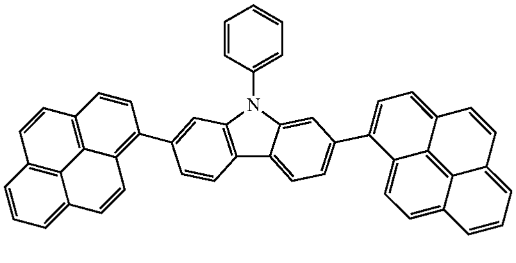

-continued
[Formula 448]
BH1-21
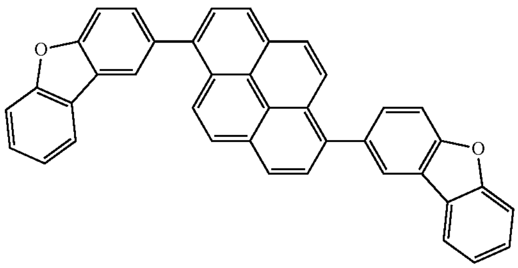
BH1-22
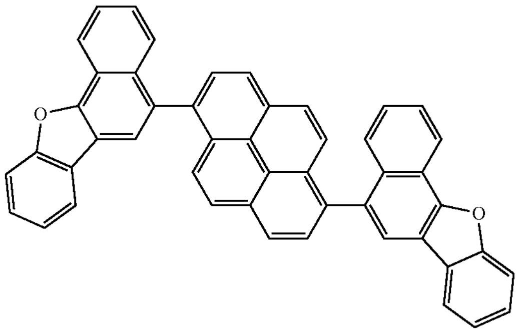
[Formula 449]
BH1-23
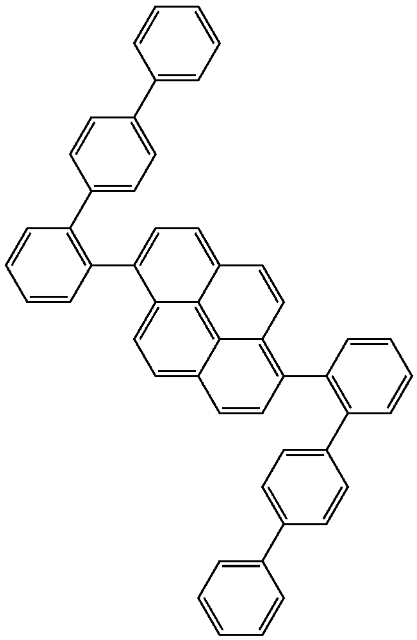
BH1-24
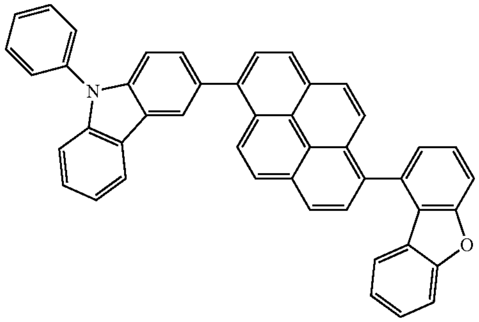
BH1-25
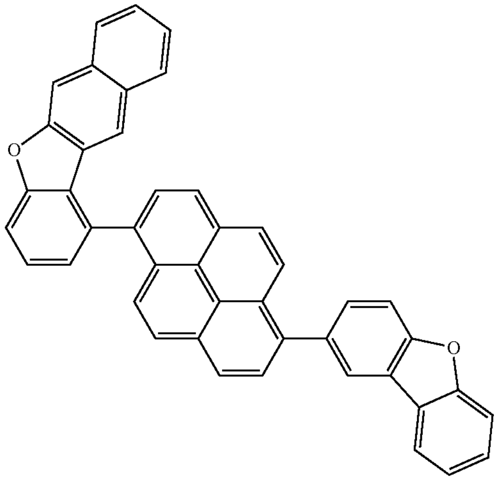

-continued
[Formula 450]
BH1-26
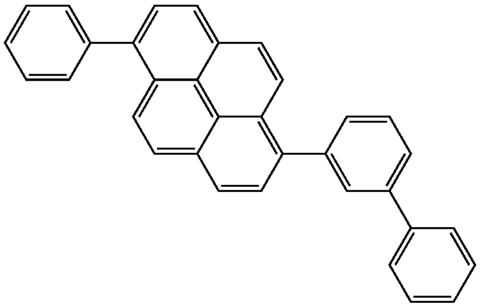
BH1-27
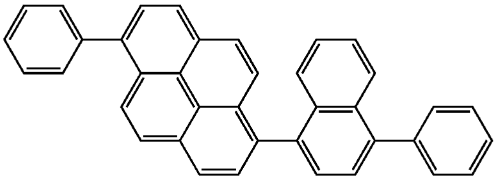
[Formula 451]
BH1-28
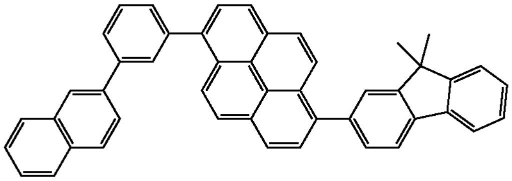
BH1-29
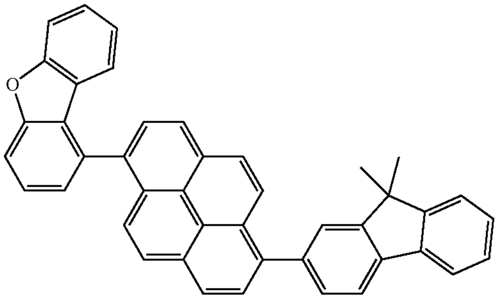
[Formula 452]
BH1-30
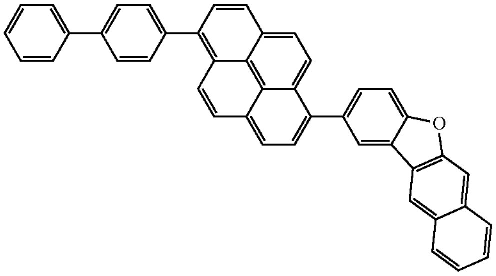
BH1-31
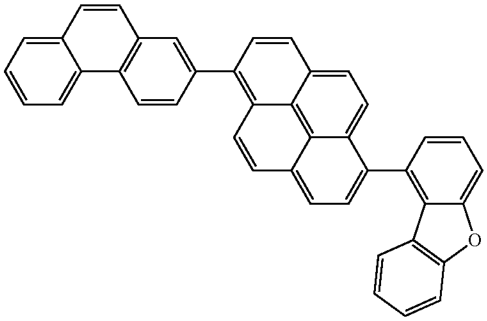

-continued
[Formula 453]
BH1-32
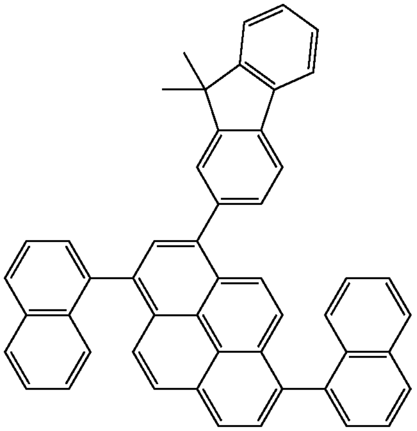
BH1-33
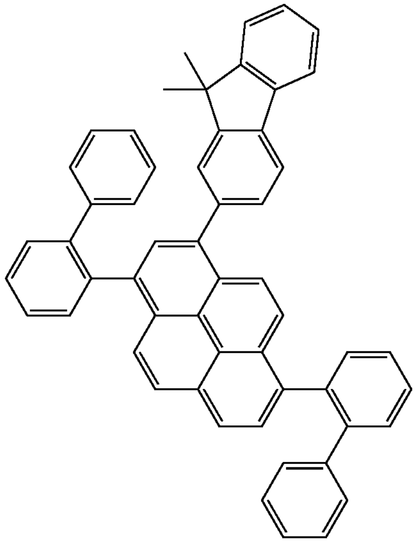
BH1-34
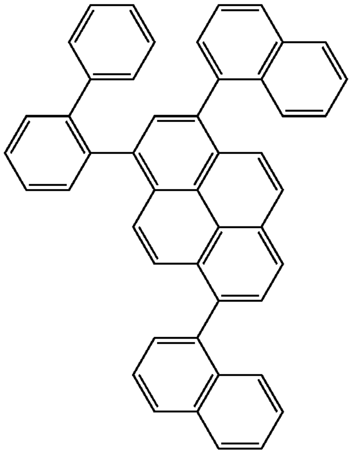
[Formula 454]
BH1-35
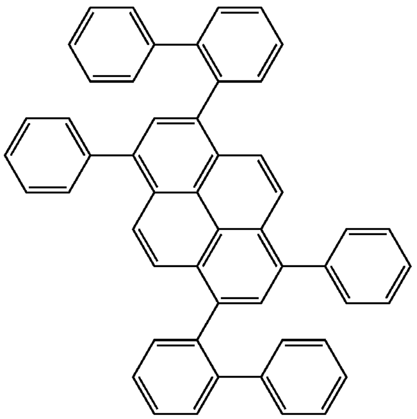
BH1-36
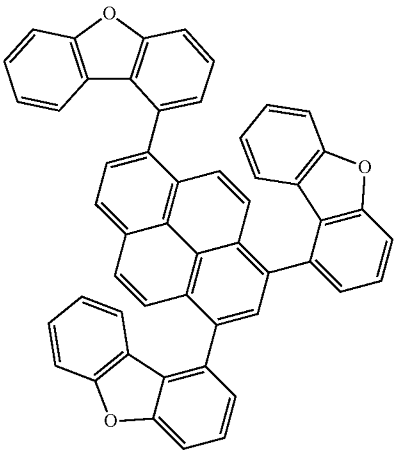

-continued
BH1-37
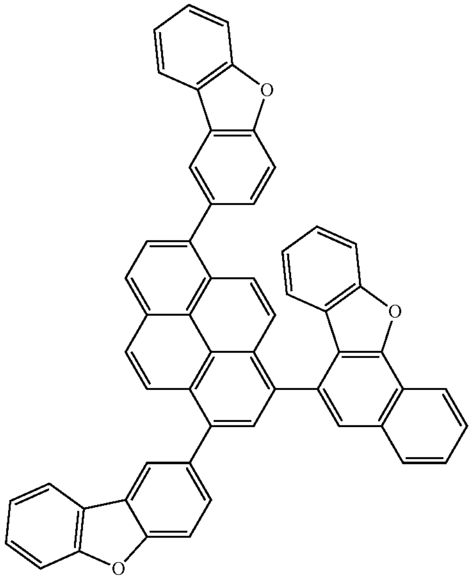
[Formula 455]
BH1-38
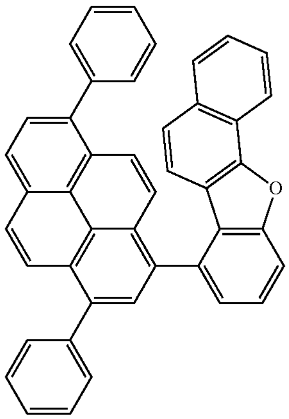
BH1-39
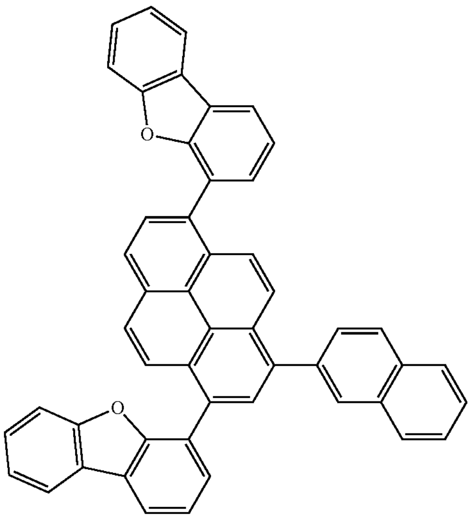
BH1-40
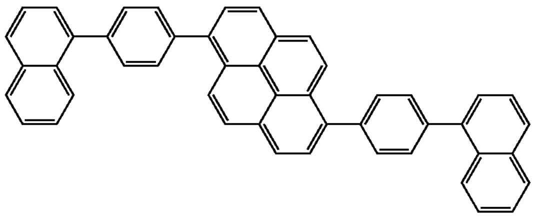

-continued
[Formula 456]
BH1-41
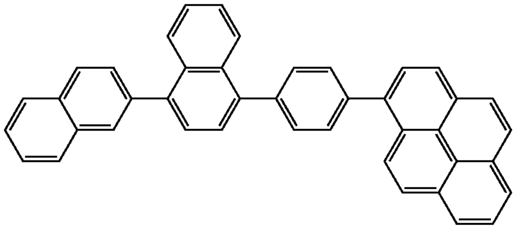
BH1-42
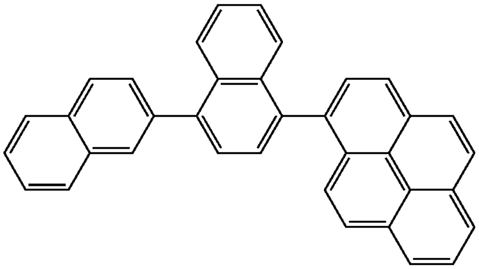
[Formula 457]
BH1-43
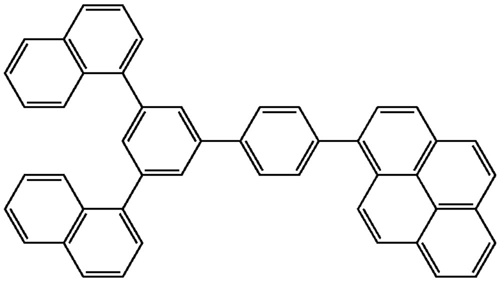
BH1-44
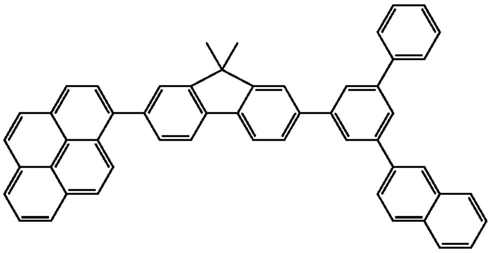
[Formula 458]
BH1-45
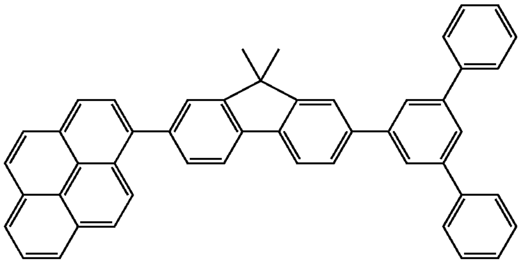
BH1-46
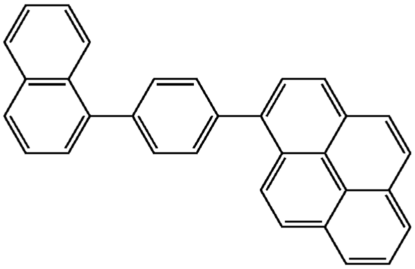
[Formula 459]
BH1-47
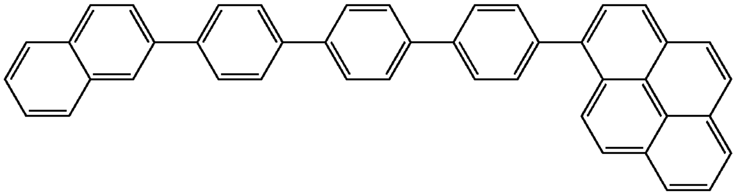
BH1-48
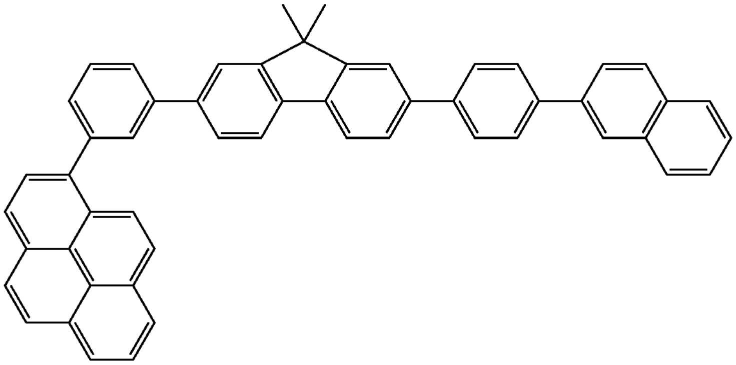

-continued
[Formula 460]
BH1-49
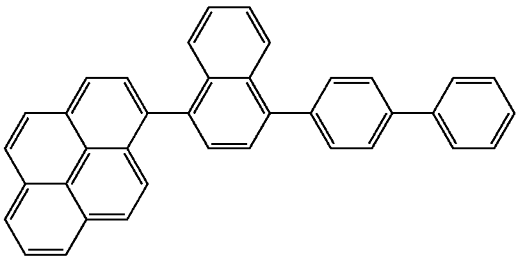
BH1-50
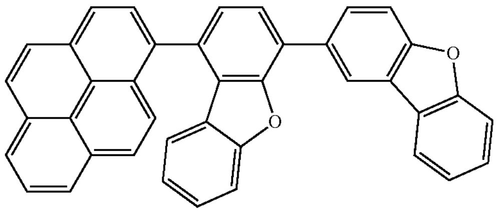
[Formula 461]
BH1-51
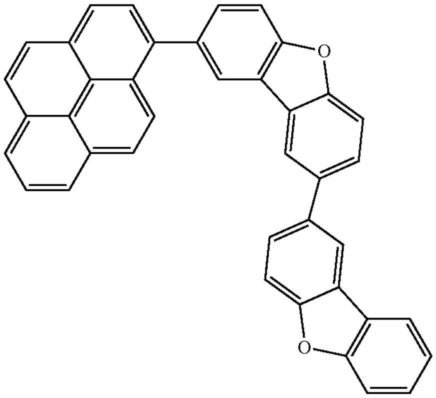
BH1-52
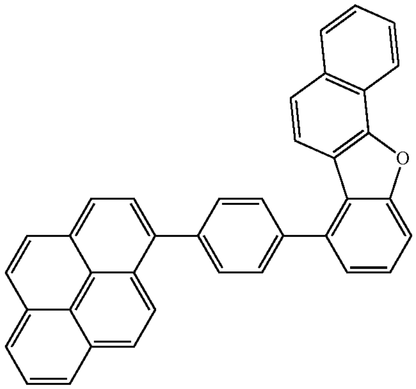
[Formula 462]
BH1-53
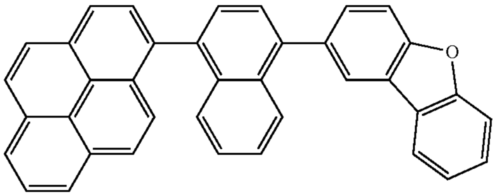
BH1-54
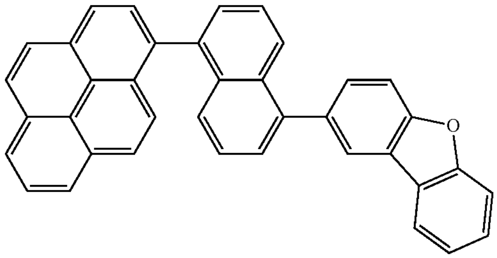
[Formula 463]
BH1-55
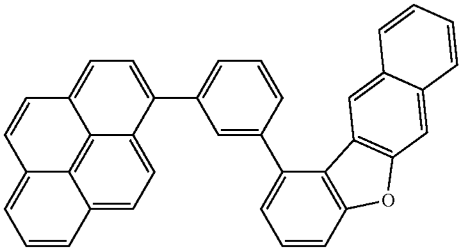
BH1-56
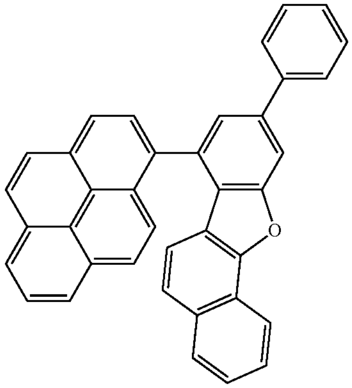

-continued
BH1-57
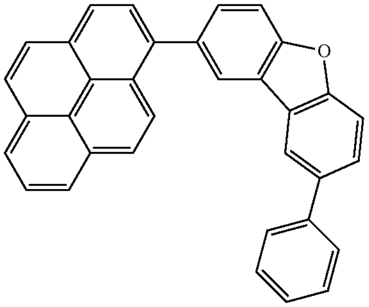
[Formula 464]
R-BH3
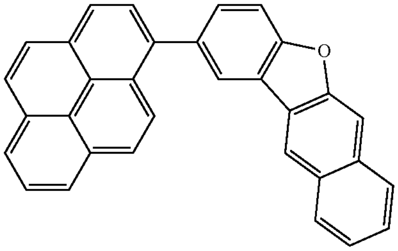
[Formula 465]
BH1-61
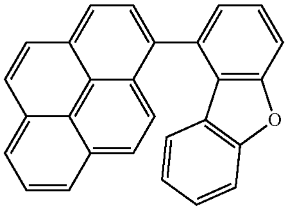
BH1-62
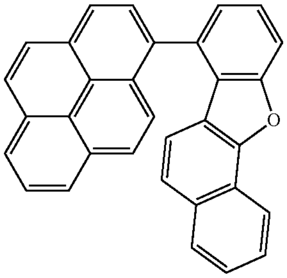
BH1-63
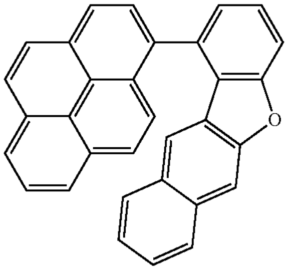
[Formula 466]
BH1-64
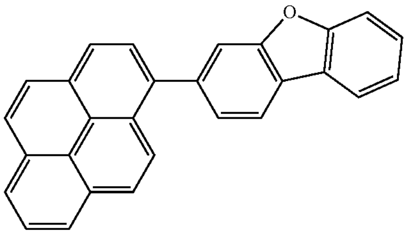
BH1-65
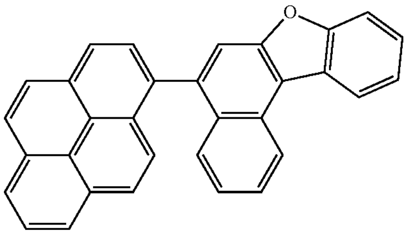

-continued
BH1-66
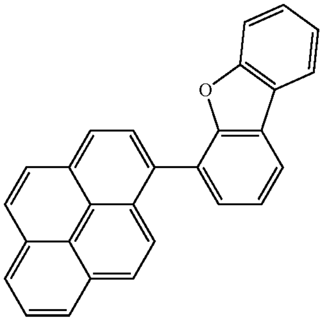
[Formula 467]
BH1-67
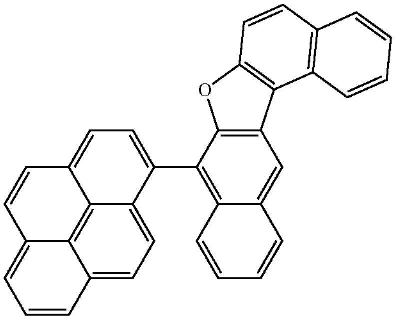
BH1-68
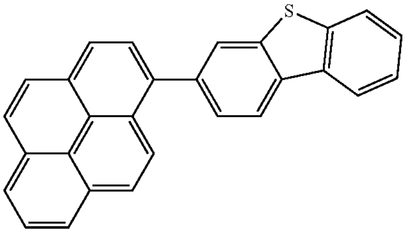
BH1-69
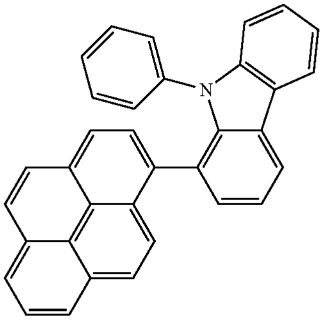
[Formula 468]
BH1-70
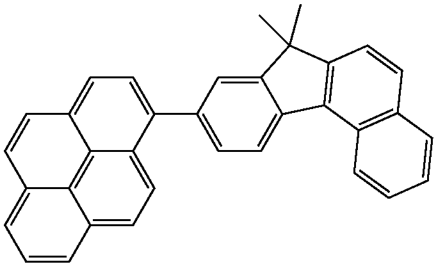
BH1-71
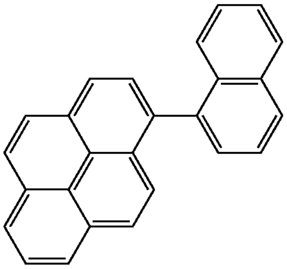
BH1-72
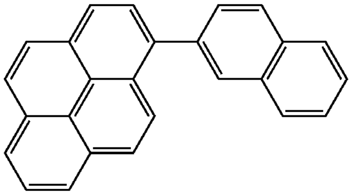

-continued
[Formula 469]
BH1-73
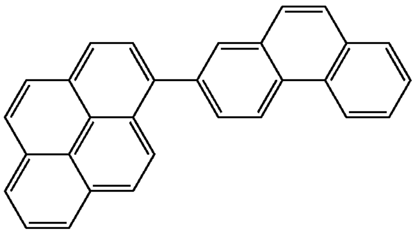
BH1-74
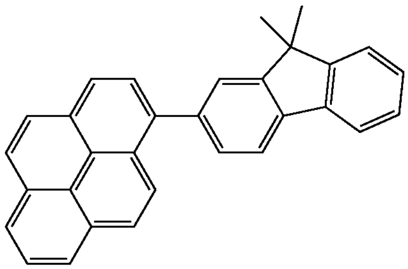
BH1-75
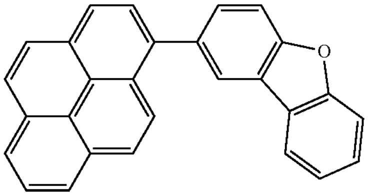
[Formula 470]
BH1-81
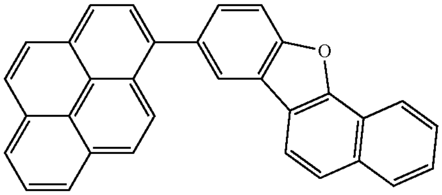
BH1-82
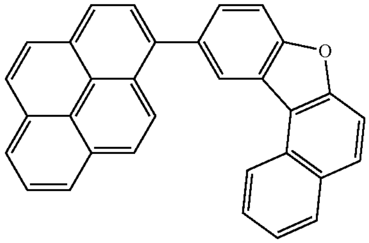
BH1-83
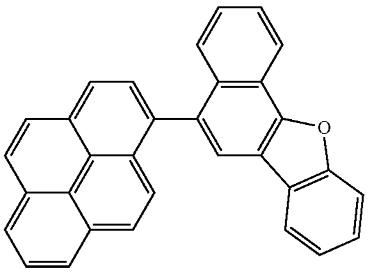
[Formula 471]
BH1-84
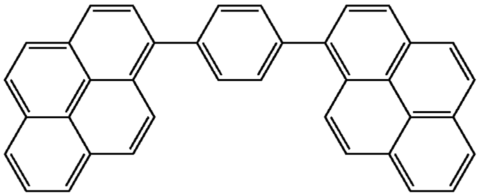
BH1-85
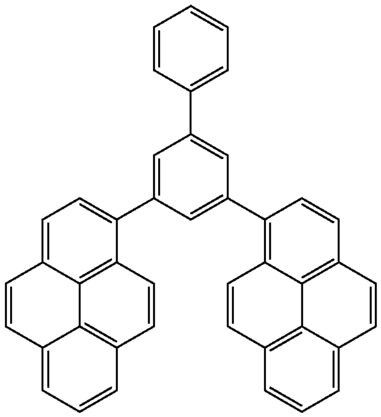

-continued
[Formula 472]
BH1-86
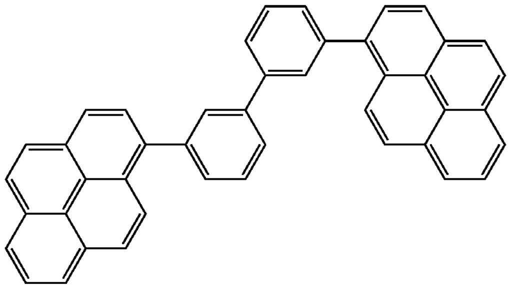
BH1-87
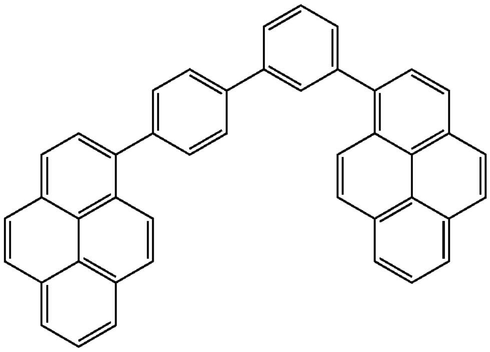
[Formula 473]
BH1-88
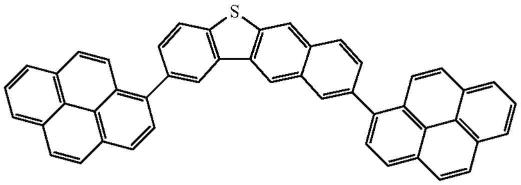
BH1-89
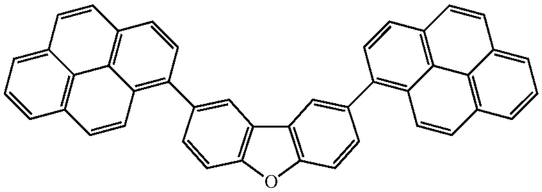
Structures of compounds represented by the formula (2) in Examples or Reference Examples are as shown below.
[Formula 474]
BH2
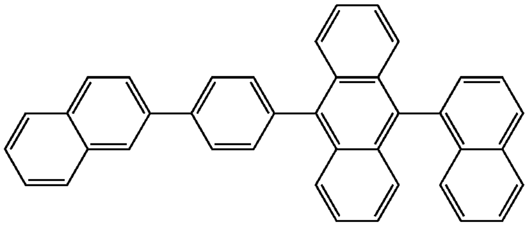
[Formula 475]
BH2-2
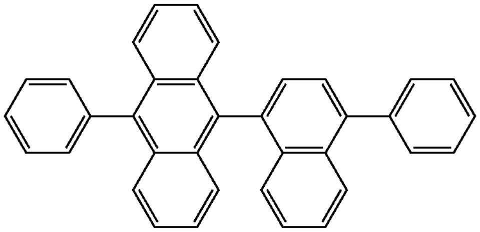
BH2-3
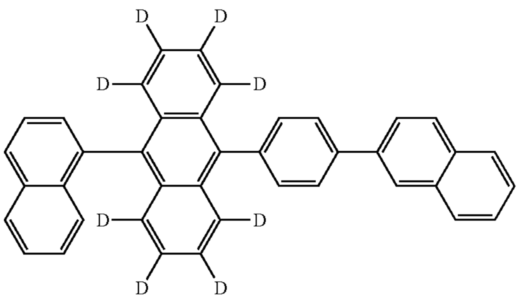

-continued
[Formula 476]
BH2-4
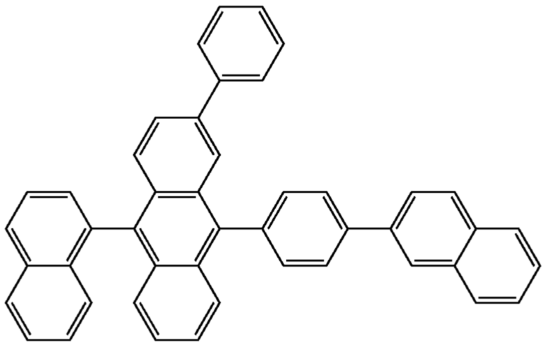
BH2-5
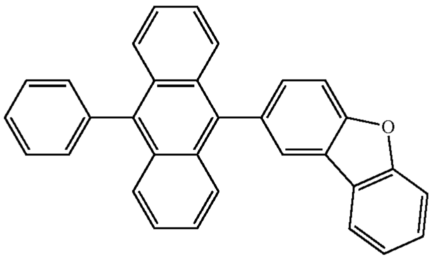
BH2-6
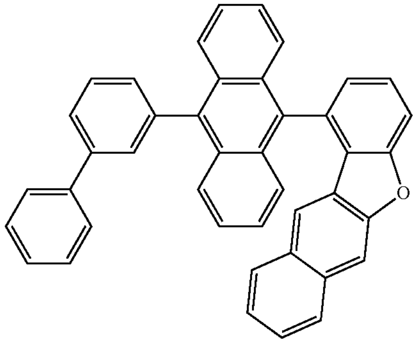
[Formula 477]
BH2-7
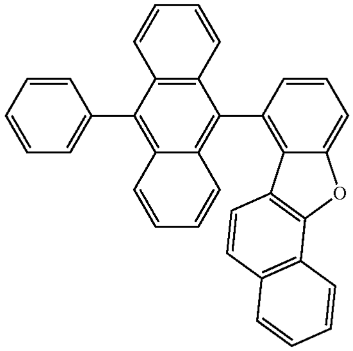
BH2-8
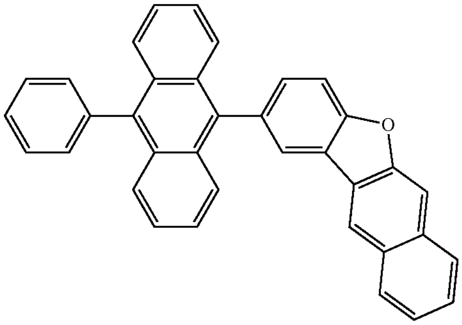
[Formula 478]
BH2-9
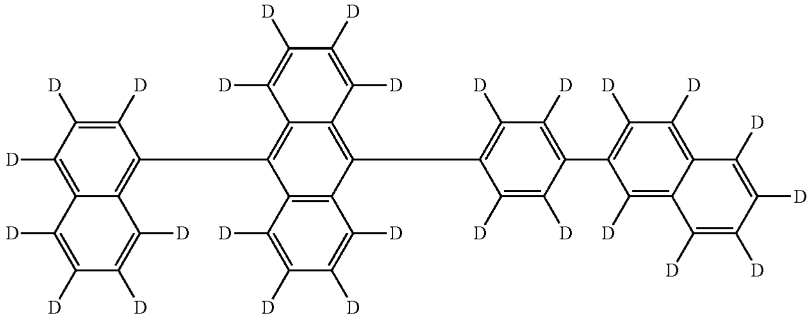

-continued
BH2-10
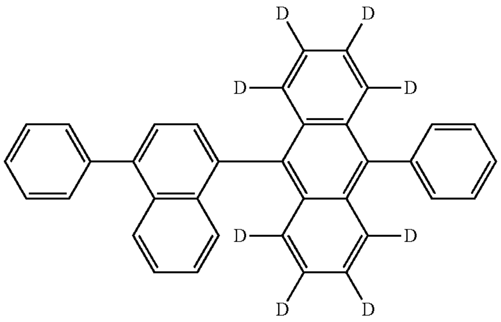
[Formula 479]
BH2-11
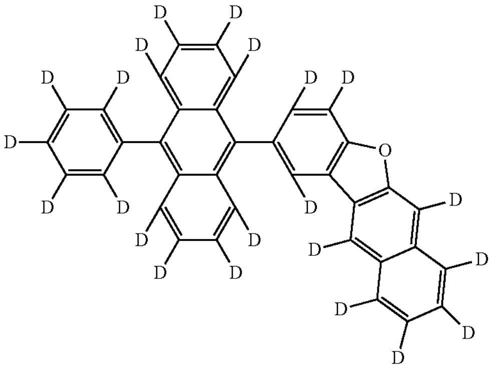
BH2-12
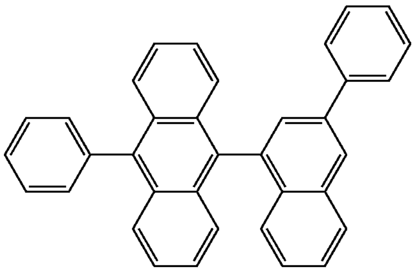
[Formula 480]
BH2-13
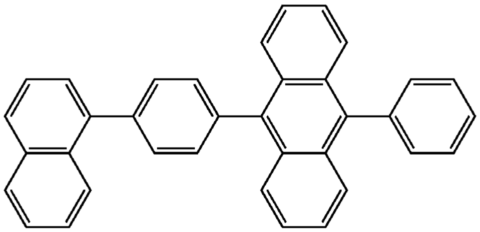
BH2-14
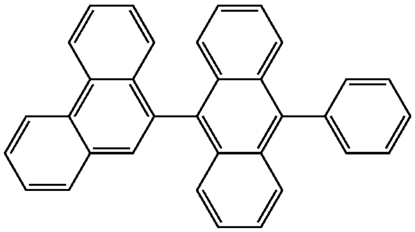
[Formula 481]
BH2-15
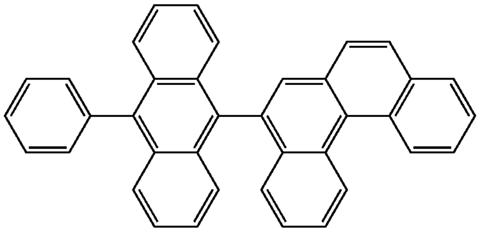
BH2-16
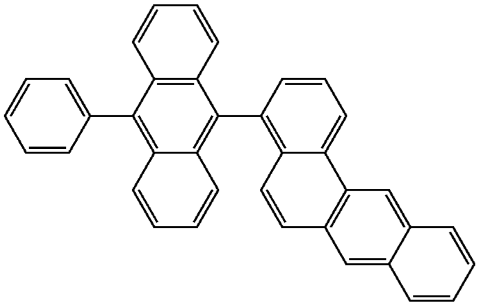

-continued
[Formula 482]
BH2-17
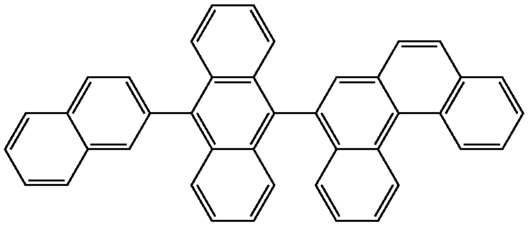
BH2-18
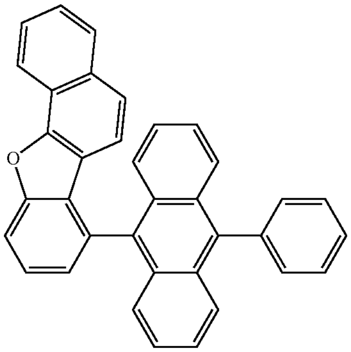
[Formula 483]
BH2-19
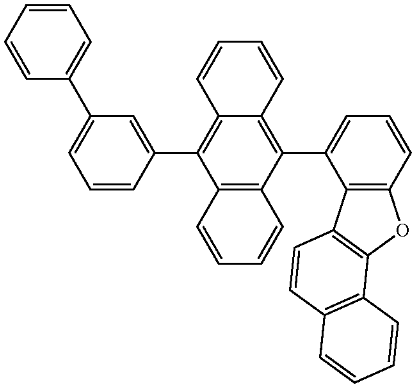
BH2-20
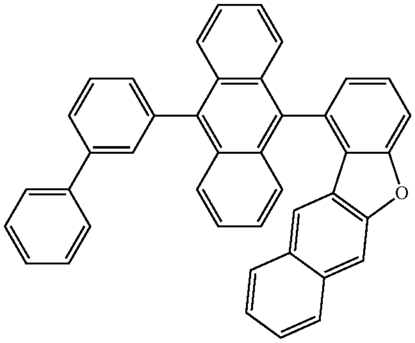
[Formula 484]
BH2-21
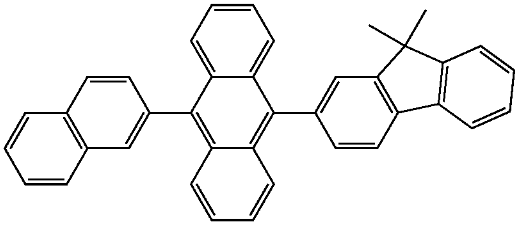
BH2-22
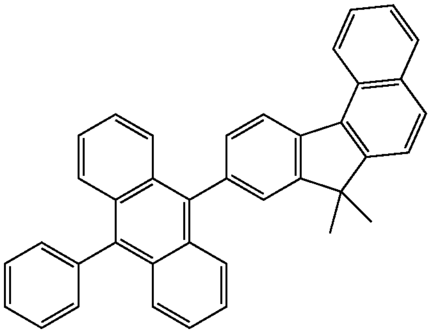
[Formula 485]
BH2-23
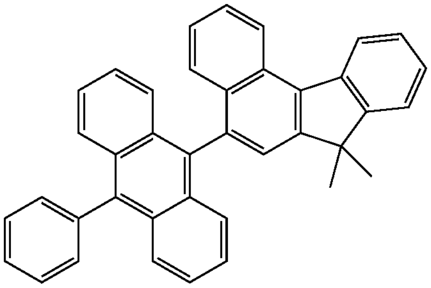
BH2-24
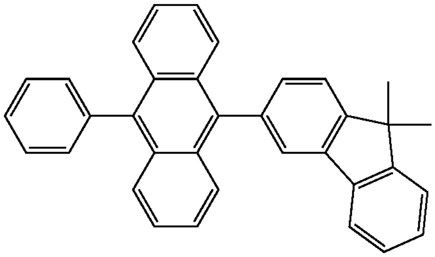

-continued
[Formula 486]
BH2-25
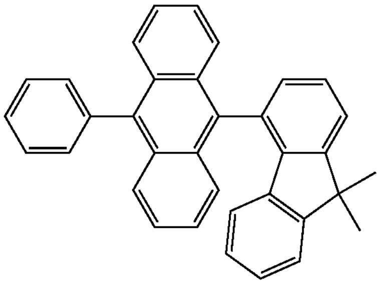
BH2-26
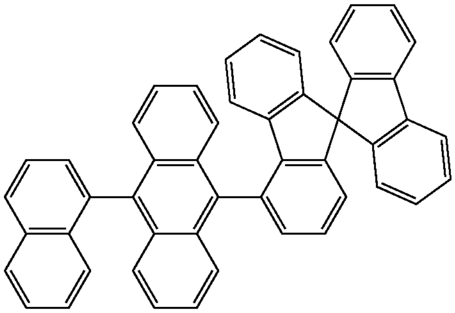
BH2-27
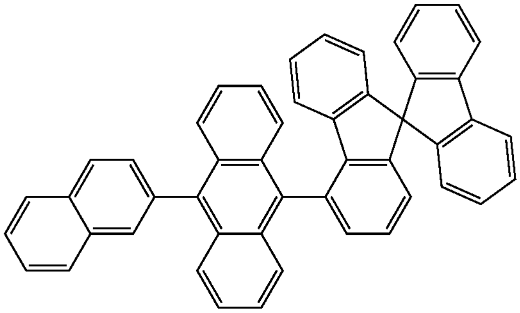
[Formula 487]
BH2-28
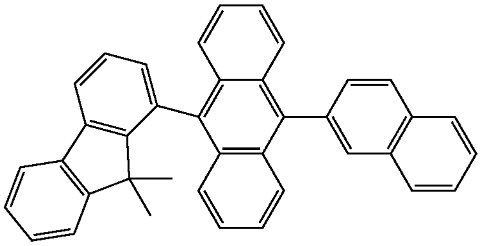
BH2-29
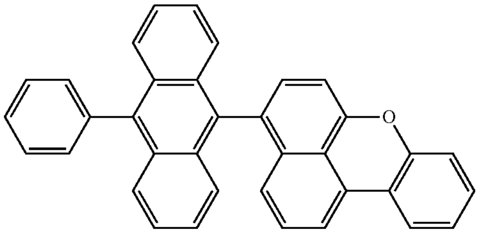
[Formula 488]
BH2-30
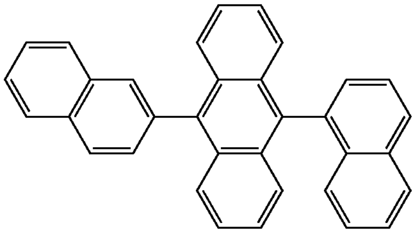
BH2-31
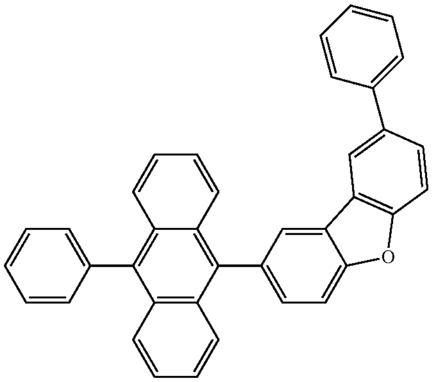

-continued
[Formula 489]
BH2-32
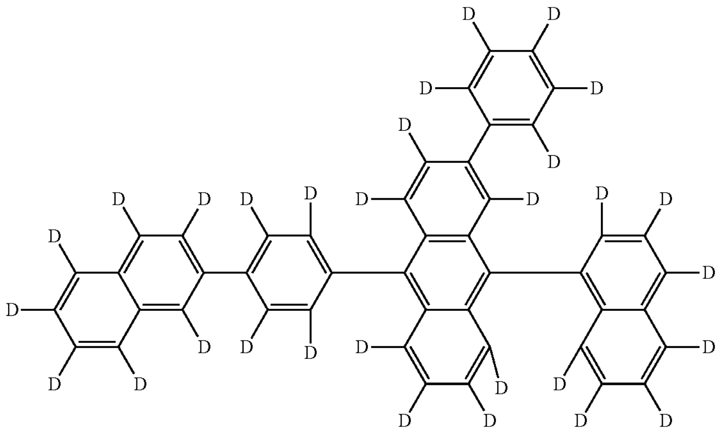
BH2-33
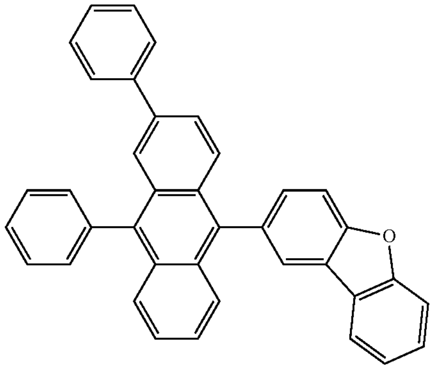
[Formula 490]
BH2-34
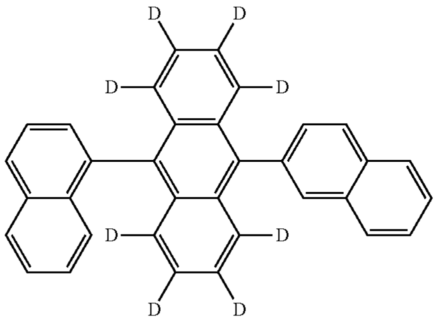
BH2-35
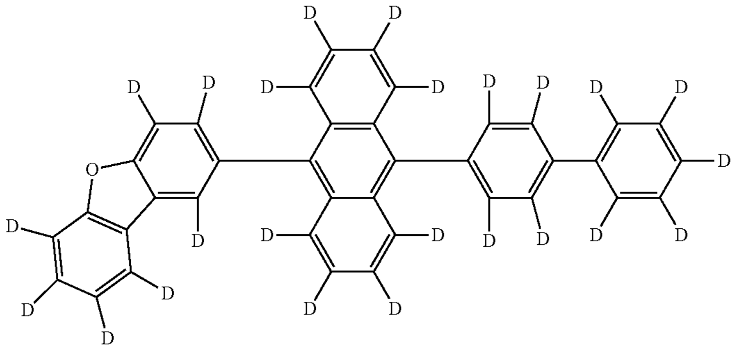

-continued
[Formula 491]
BH2-36
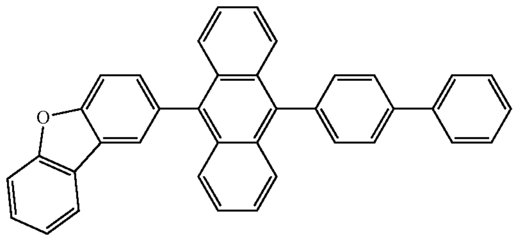
BH2-37
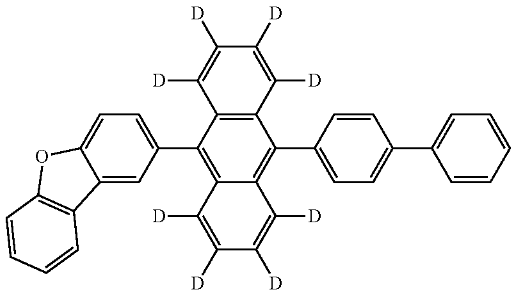
[Formula 492]
BH2-38
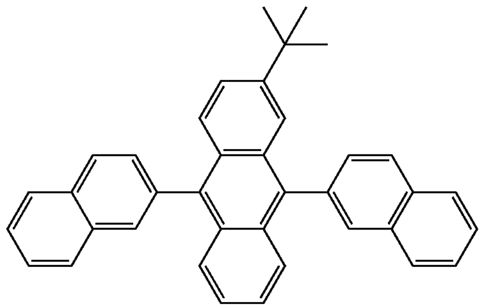
Structures of compounds used for manufacturing organic EL devices according to Comparatives are shown below.
[Formula 493]
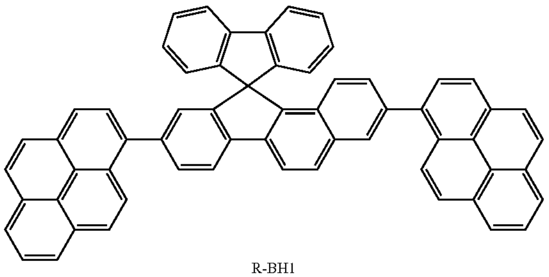
R-BH1
[Formula 493]
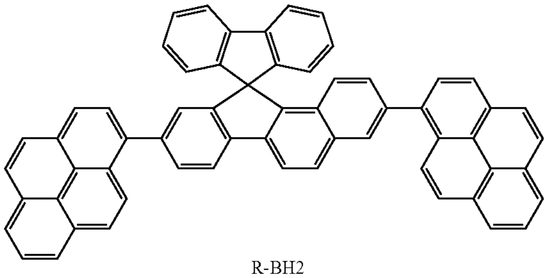
R-BH2
Structures of other compounds used for manufacturing organic EL devices according to Examples, Reference Examples, and Comparatives are shown below.
[Formula 494]
HA1
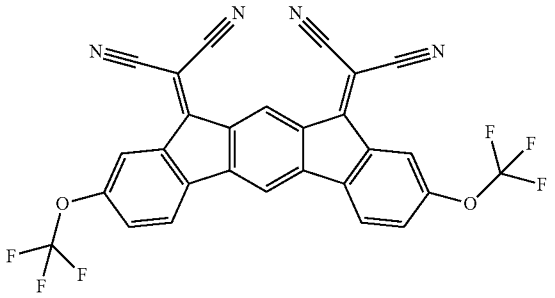
HT1
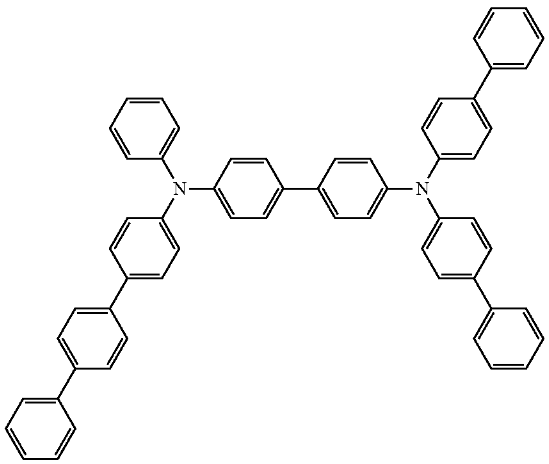

-continued
[Formula 495]
HT2
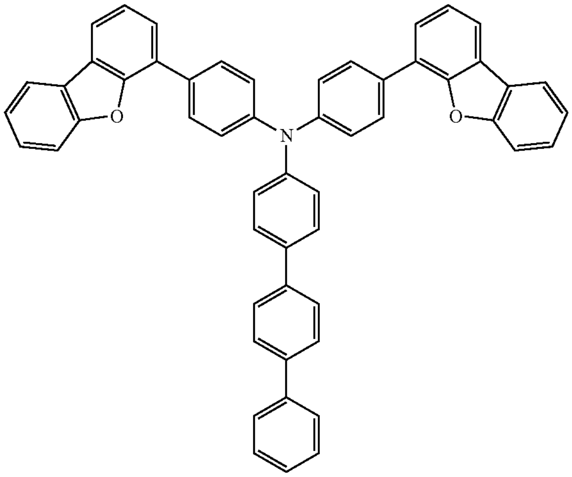
BD1
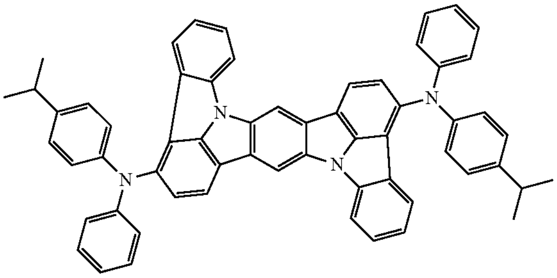
[Formula 496]
HT3
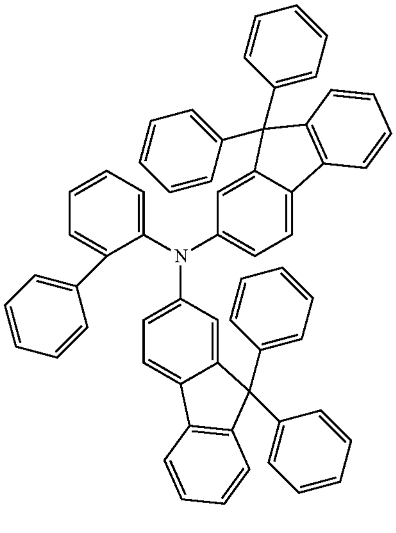
-continued
HT4
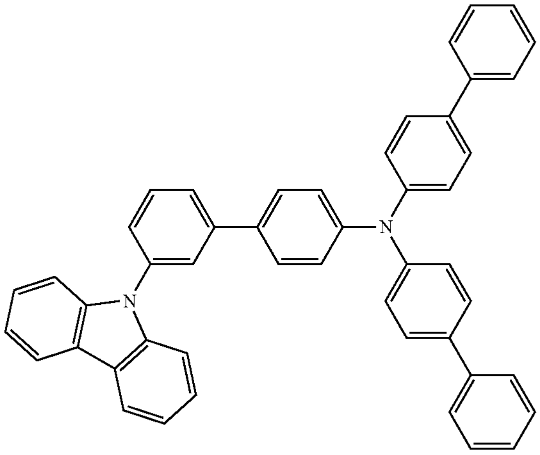
[Formula 497]
HT5
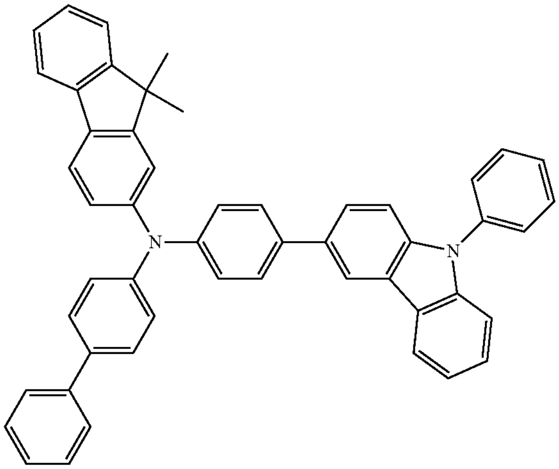
HA2
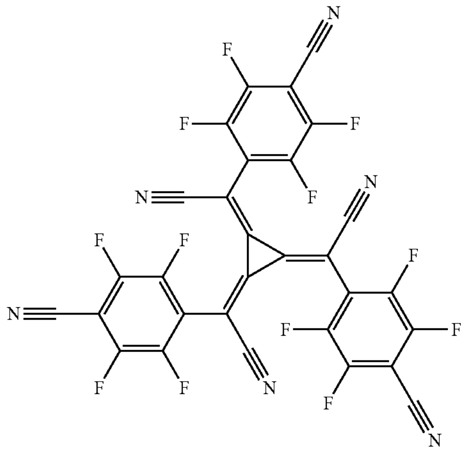

[Formula 498]
HT6
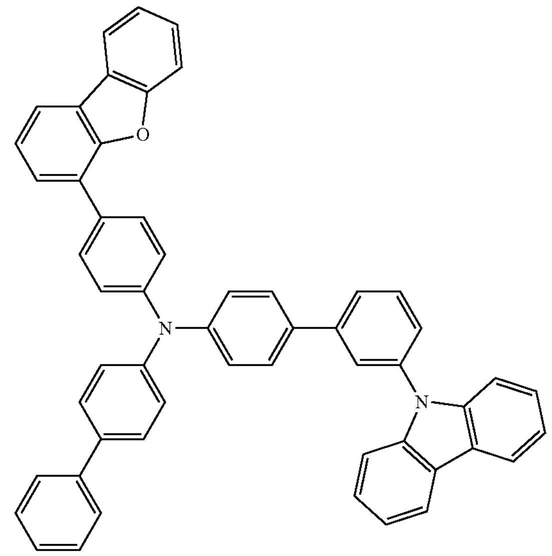
HT7
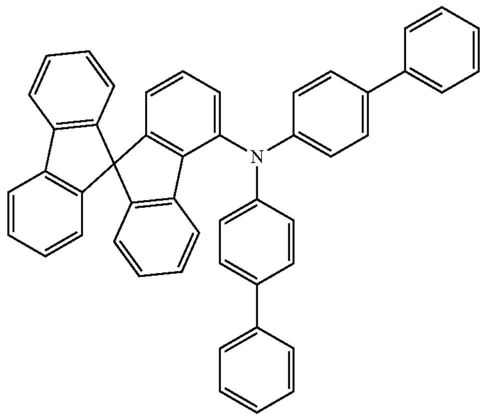
[Formula 499]
HT8
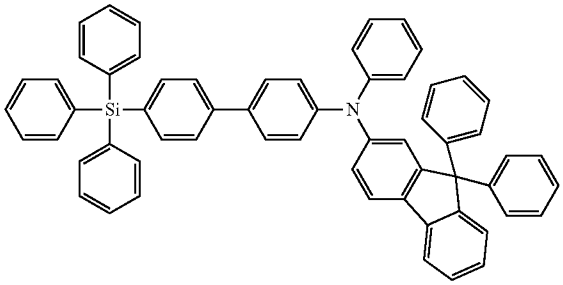
[Formula 500]
HT9
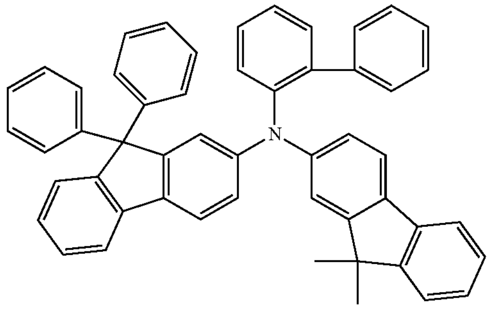
HT10
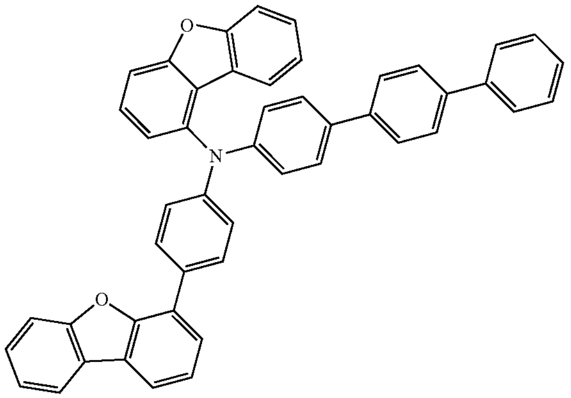
[Formula 501]
HT11
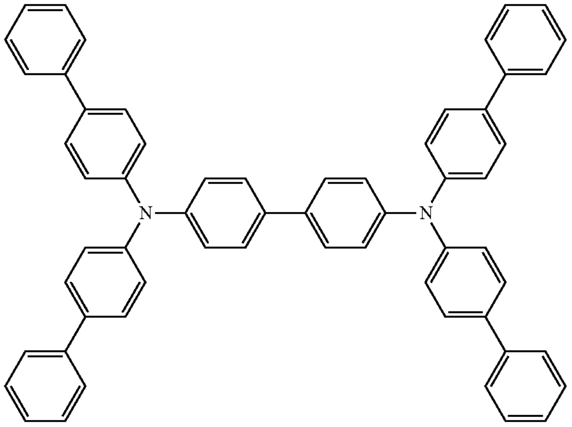

-continued
HT12
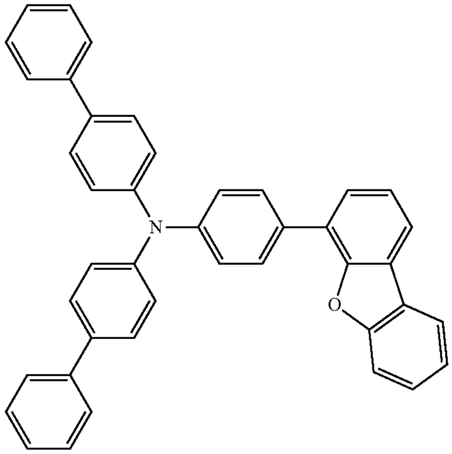
[Formula 502]
HA3
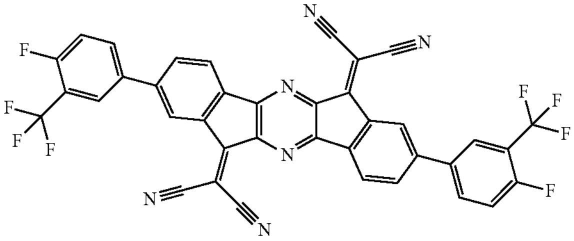
[Formula 503]
BD2
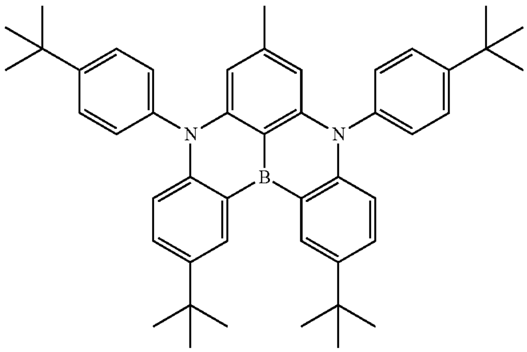
BD3
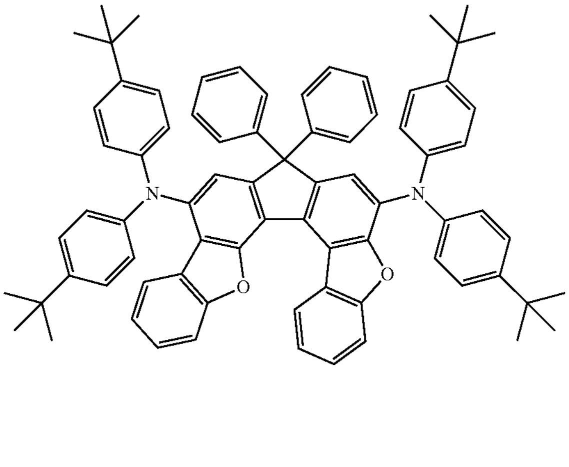
-continued
[Formula 504]
ET1
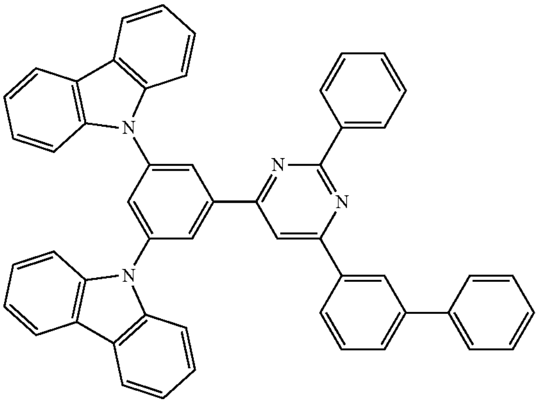
ET2
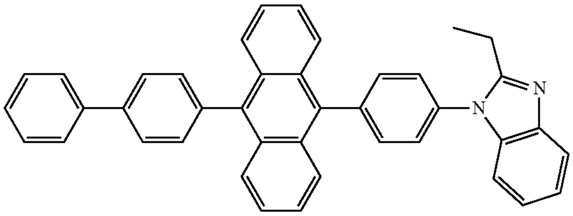
[Formula 505]
ET3
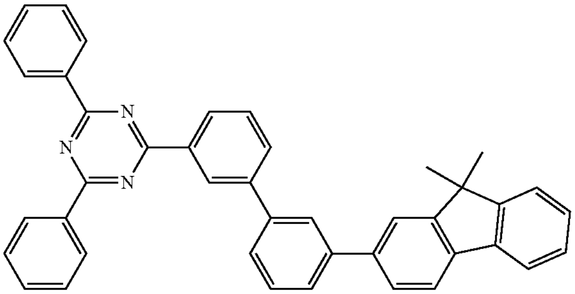
ET4
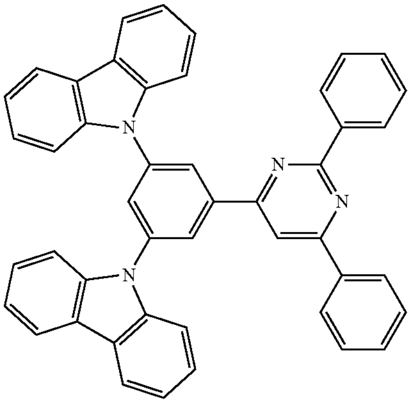

-continued

[Formula 506]

ET5

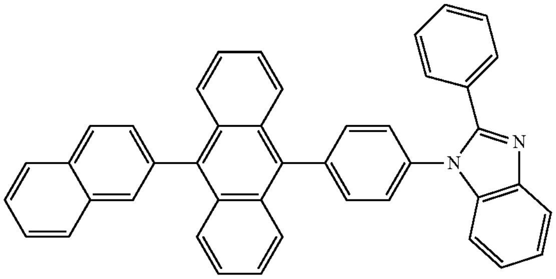

ET6

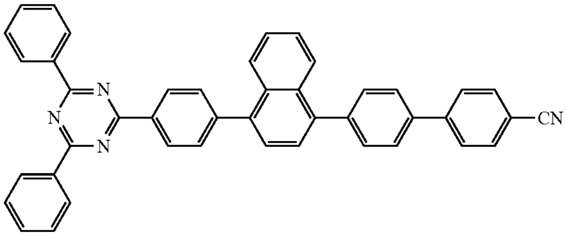

[Formula 507]

ET7

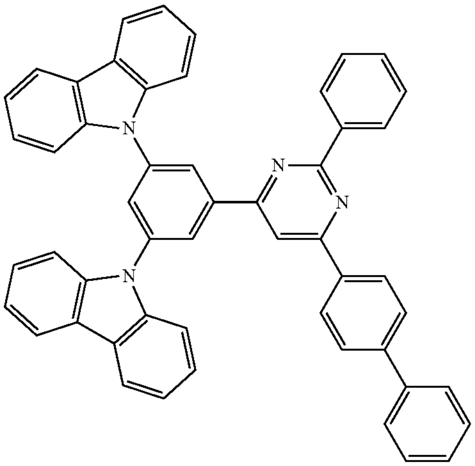

ET8

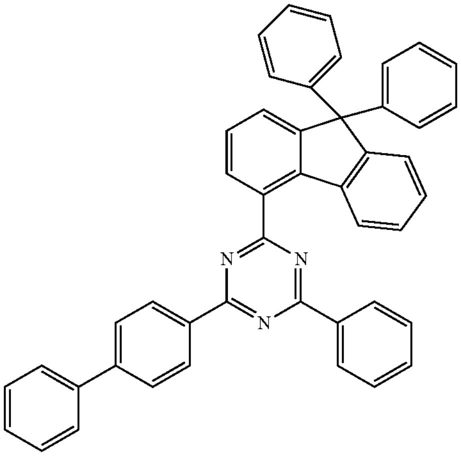

-continued

[Formula 508]

ET9

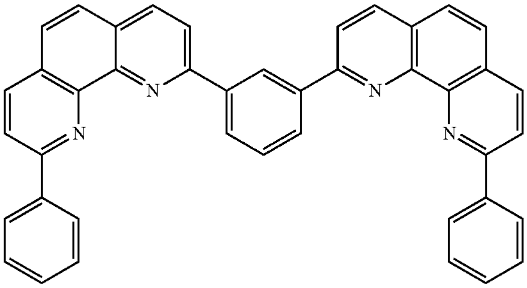

ET10

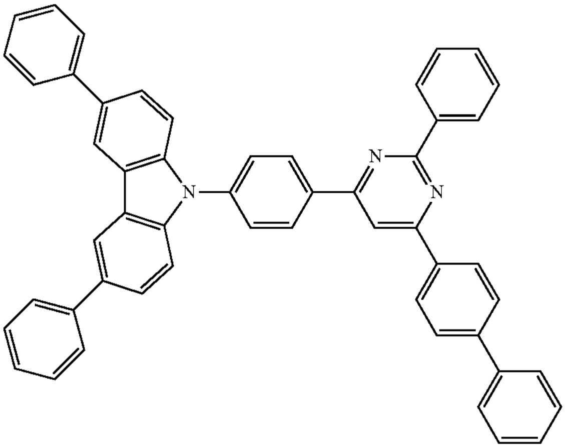

[Formula 509]

Liq

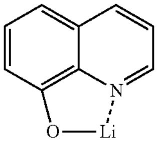

Cap1

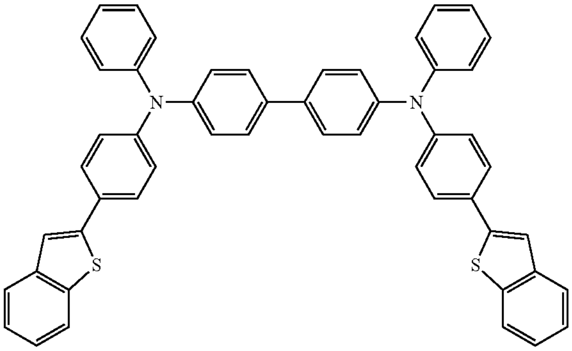

Preparation 1 of Organic EL Device

An organic EL device was prepared and evaluated as follows.

Example 1

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA1 was vapor-deposited on a surface provided with the transparent electrode line to cover the transparent electrode, thereby forming a 5-nm-thick hole injecting layer (HI).

After the formation of the hole injecting layer, a compound HT1 was vapor-deposited to form an 80-nm-thick first hole transporting layer (HT).

After the formation of the first hole transporting layer, a compound HT2 was vapor-deposited to form a 10-nm-thick second hole transporting layer (also referred to as an electron blocking layer (EBL)).

A compound BH1 (first host material (BH)) and a compound BD1 (dopant material (BD)) were co-deposited on the second hole transporting layer such that the ratio of the compound BD1 accounted for 2 mass %, thereby forming a 5-nm-thick first emitting layer.

A compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET1 was vapor-deposited on the second emitting layer to form a 10-nm-thick first electron transporting layer (also referred to as a hole blocking layer (HBL)).

A compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 1 is roughly shown as follows.

ITO(130)/HA1(5)/HT1(80)/HT2(10)/BH1:BD1(5,98%: 2%)/BH2:BD1(20,98%: 2%)/ET1(10)/ET2(15)/LiF(1)/Al (80)

The numerals in parentheses represent film thickness (unit: nm).

The numerals (98%:2%) represented by percentage in the same parentheses indicate a ratio (mass %) between the host material (the compound BH1 or the compound BH2) and the compound BD1 in the first emitting layer or the second emitting layer. Similar notations apply to the description below.

Comparative 1

As shown in Table 1, the organic EL device of Comparative 1 was prepared in the same manner as in Example 1 except that a 25-nm-thick first emitting layer was formed as the emitting layer and the first electron transporting layer was formed on the first emitting layer without forming the second emitting layer.

Comparative 2

As shown in Table 1, the organic EL device of Comparative 2 was prepared in the same manner as in Example 1 except that a 25-nm-thick second emitting layer was formed as the emitting layer on the second hole transporting layer without forming the first emitting layer.

Evaluation of Organic EL Device

The organic EL devices prepared in Examples, Reference Examples, and Comparatives were evaluated as follows. Tables 1 to 55 show the evaluation results.

It should be noted that evaluation results of some Examples and some Comparatives are shown in a plurality of Tables.

External Quantum Efficiency EQE

Voltage was applied on the organic EL devices such that a current density was 10 mA/cm$^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Lifetime LT90

Voltage was applied on the resultant organic EL devices such that a current density was 50 mA/cm$^2$, where a time (LT90 (unit: hr)) elapsed before a luminance intensity was reduced to 90% of the initial luminance intensity was measured.

Lifetime LT95

Voltage was applied on the resultant devices such that a current density was 50 mA/cm$^2$, where a time (LT95 (unit: hr)) elapsed before a luminance intensity was reduced to 95% of the initial luminance intensity was measured.

It should be noted that the lifetime LT95 of the organic EL devices according to Example 155 and Comparative 124 was measured as a time (LT95 (unit: hr)) elapsed before a luminance intensity was reduced to 95% of the initial luminance intensity after applying voltage on the devices such that a current density was 15 mA/cm$^2$.

Main Peak Wavelength λp when the Device is Driven

Voltage was applied on the organic EL devices such that a current density of the organic EL device was 10 mA/cm$^2$, where spectral radiance spectrum was measured by a spectroradiometer (CS-2000 manufactured by Konica Minolta, Inc.). The main peak wavelength λp (unit: nm) was calculated based on the obtained spectral radiance spectrum.

Drive Voltage

The voltage (unit: V) when electric current was applied between the anode and the cathode such that the current density was 10 mA/cm$^2$ was measured.

TABLE 1

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | EQE [%] | LT90 [hr] | λp [nm] |
| Ex. 1 | BH1 | BD1 | 5 | BH2 | BD1 | 20 | 10.6 | 600 | 461 |
| Comp. 1 | BH1 | BD1 | 25 | — | — | — | 7.6 | 360 | 462 |
| Comp. 2 | — | — | — | BH2 | BD1 | 25 | 9.9 | 363 | 460 |

As shown in Table 1, the organic EL device according to Example 1, in which the first emitting layer containing the first host material in a form of the first compound and the second emitting layer containing the second host material in a form of the second compound were in direct contact with each other, emitted at a higher luminous efficiency than the organic EL devices according to Comparatives 1 to 2 including only one of the emitting layers. Further, the organic EL device according to Example 1 exhibited longer lifetime than that of organic EL devices according to Comparatives 1 to 2.

Examples 2 to 19

The organic EL devices according to Examples 2 to 19 were prepared in the same manner as in Example 1 except that the compound BH1 (first host material) in the first emitting layer was replaced with the first compounds listed in Table 1.

Comparatives C20, 3 to 21

The organic EL devices according to Comparatives C20 and 3 to 21 were prepared in the same manner as in Comparative 1 except that the compound BH1 (first host material) in the first emitting layer was replaced with the first compounds listed in Table 3.

TABLE 2

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | voltage [V] | EQE [%] | LT95 [hr] |
| Ex. 1 | BH1 | BD1 | 5 | BH2 | BD1 | 20 | 3.47 | 10.6 | 255 |
| Ex. 2 | BH1-2 | BD1 | 5 | BH2 | BD1 | 20 | 3.47 | 10.2 | 205 |
| Ex. 3 | BH1-3 | BD1 | 5 | BH2 | BD1 | 20 | 3.56 | 10.5 | 268 |
| Ex. 4 | BH1-4 | BD1 | 5 | BH2 | BD1 | 20 | 3.56 | 10.7 | 222 |
| Ex. 5 | BH1-5 | BD1 | 5 | BH2 | BD1 | 20 | 3.64 | 10.7 | 251 |
| Ex. 6 | BH1-6 | BD1 | 5 | BH2 | BD1 | 20 | 3.65 | 10.6 | 224 |
| Ex. 7 | BH1-7 | BD1 | 5 | BH2 | BD1 | 20 | 3.63 | 10.4 | 239 |
| Ex. 8 | BH1-8 | BD1 | 5 | BH2 | BD1 | 20 | 3.62 | 10.4 | 224 |
| Ex. 9 | BH1-9 | BD1 | 5 | BH2 | BD1 | 20 | 3.70 | 10.8 | 249 |
| Ex. 10 | BH1-10 | BD1 | 5 | BH2 | BD1 | 20 | 3.34 | 10.4 | 216 |
| Ex. 11 | BH1-11 | BD1 | 5 | BH2 | BD1 | 20 | 3.48 | 10.8 | 275 |
| Ex. 12 | BH1-12 | BD1 | 5 | BH2 | BD1 | 20 | 3.39 | 10.6 | 212 |
| Ex. 13 | BH1-13 | BD1 | 5 | BH2 | BD1 | 20 | 3.51 | 10.6 | 231 |
| Ex. 14 | BH1-14 | BD1 | 5 | BH2 | BD1 | 20 | 3.36 | 10.4 | 198 |
| Ex. 15 | BH1-15 | BD1 | 5 | BH2 | BD1 | 20 | 3.43 | 10.5 | 190 |
| Ex. 16 | BH1-16 | BD1 | 5 | BH2 | BD1 | 20 | 3.30 | 10.5 | 192 |
| Ex. 17 | BH1-17 | BD1 | 5 | BH2 | BD1 | 20 | 3.38 | 10.2 | 185 |
| Ex. 18 | BH1-18 | BD1 | 5 | BH2 | BD1 | 20 | 3.41 | 10.6 | 204 |
| Ex. 19 | BH1-19 | BD1 | 5 | BH2 | BD1 | 20 | 3.39 | 10.3 | 191 |
| Comp. C20 | R-BH1 | BD1 | 5 | BH2 | BD1 | 20 | 3.91 | 10.1 | — |

TABLE 3

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Comp. 1 | BH1 | BD1 | 25 | — | — | — | — | 7.6 | 65 |
| Comp. 2 | — | — | — | BH2 | BD1 | 25 | — | 9.9 | 167 |
| Comp. 3 | BH1-2 | BD1 | 25 | — | — | — | — | 7.2 | 59 |
| Comp. 4 | BH1-3 | BD1 | 25 | — | — | — | — | 7.4 | 71 |
| Comp. 5 | BH1-4 | BD1 | 25 | — | — | — | — | 7.8 | 70 |
| Comp. 6 | BH1-5 | BD1 | 25 | — | — | — | — | 7.5 | 62 |
| Comp. 7 | BH1-6 | BD1 | 25 | — | — | — | — | 7.4 | 60 |
| Comp. 8 | BH1-7 | BD1 | 25 | — | — | — | — | 7.3 | 53 |
| Comp. 9 | BH1-8 | BD1 | 25 | — | — | — | — | 7.4 | 55 |
| Comp. 10 | BH1-9 | BD1 | 25 | — | — | — | — | 7.5 | 67 |
| Comp. 11 | BH1-10 | BD1 | 25 | — | — | — | — | 7.1 | 51 |
| Comp. 12 | BH1-11 | BD1 | 25 | — | — | — | — | 7.8 | 81 |
| Comp. 13 | BH1-12 | BD1 | 25 | — | — | — | — | 7.0 | 48 |
| Comp. 14 | BH1-13 | BD1 | 25 | — | — | — | — | 7.1 | 53 |
| Comp. 15 | BH1-14 | BD1 | 25 | — | — | — | — | 6.9 | 56 |
| Comp. 16 | BH1-15 | BD1 | 25 | — | — | — | — | 7.1 | 59 |
| Comp. 17 | BH1-16 | BD1 | 25 | — | — | — | — | 7.0 | 62 |
| Comp. 18 | BH1-17 | BD1 | 25 | — | — | — | — | 6.7 | 53 |

TABLE 3-continued

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Comp. 19 | BH1-18 | BD1 | 25 | — | — | — | — | 7.1 | 62 |
| Comp. 20 | BH1-19 | BD1 | 25 | — | — | — | — | 6.9 | 43 |
| Comp. 21 | BH1-20 | BD1 | 25 | — | — | — | — | 6.5 | 21 |

Example 21

The organic EL device according to Example 21 was prepared in the same manner as in Example 1 except that the compound BH2 (second host material) in the second emitting layer was replaced with the compound listed in Table 4.

Comparatives C22 to 23

The organic EL devices according to Comparatives C22 to 23 were prepared in the same manner as in Example 1 except that the compound BH1 (first host material) in the first emitting layer and the compound BH2 (second host material) in the second emitting layer were replaced with the compounds listed in Table 4.

Comparative 22

The organic EL device according to Comparative 22 was prepared in the same manner as in Comparative 2 except that the compound BH2 (second host material) in the second emitting layer was replaced with the compound listed in Table 4.

TABLE 4

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 21 | BH1 | BD1 | 5 | BH2-2 | BD1 | 20 | 3.96 | 9.8 | 192 |
| Comp. C22 | R-BH1 | BD1 | 5 | BH2-2 | BD1 | 20 | 4.40 | 9.4 | — |
| Comp. C23 | R-BH2 | BD1 | 5 | BH2-2 | BD1 | 20 | 4.68 | 9.5 | — |
| Comp. 1 | BH1 | BD1 | 25 | — | — | — | — | 7.6 | 65 |
| Comp. 22 | — | — | — | BH2-2 | BD1 | 25 | — | 9.2 | 115 |

Example 24

The organic EL device according to Example 24 was prepared in the same manner as in Example 1 except that the compound BH2 (second host material) in the second emitting layer was replaced with the compound listed in Table 5.

Comparatives C25 to 26

The organic EL devices according to Comparatives C25 to 26 were prepared in the same manner as in Example 1 except that the compound BH1 (first host material) in the first emitting layer and the compound BH2 (second host material) in the second emitting layer were replaced with the compounds listed in Table 5.

Comparative 23

The organic EL device according to Comparative 23 was prepared in the same manner as in Comparative 2 except that the compound BH2 (second host material) in the second emitting layer was replaced with the compound listed in Table 5.

TABLE 5

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 24 | BH1 | BD1 | 5 | BH2-3 | BD1 | 20 | 3.54 | 10.6 | 278 |
| Comp. C25 | R-BH1 | BD1 | 5 | BH2-3 | BD1 | 20 | 3.98 | 10.1 | — |
| Comp. C26 | R-BH2 | BD1 | 5 | BH2-3 | BD1 | 20 | 4.26 | 10.2 | — |
| Comp. 1 | BH1 | BD1 | 25 | — | — | — | — | 7.6 | 65 |
| Comp. 23 | — | — | — | BH2-3 | BD1 | 25 | — | 9.9 | 182 |

Example 27

The organic EL device according to Example 27 was prepared in the same manner as in Example 1 except that the compound BH2 (second host material) in the second emitting layer was replaced with the compound listed in Table 6.

Comparatives C28 to 29

The organic EL devices according to Comparatives C28 to 29 were prepared in the same manner as in Example 1 except that the compound BH1 (first host material) in the first emitting layer and the compound BH2 (second host material) in the second emitting layer were replaced with the compounds listed in Table 6.

Comparative 24

The organic EL device according to Comparative 24 was prepared in the same manner as in Comparative 2 except that the compound BH2 (second host material) in the second emitting layer was replaced with the compound listed in Table 6.

TABLE 6

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 27 | BH1 | BD1 | 5 | BH2-4 | BD1 | 20 | 3.26 | 8.1 | 272 |
| Comp. C28 | R-BH1 | BD1 | 5 | BH2-4 | BD1 | 20 | 3.70 | 7.9 | — |
| Comp. C29 | R-BH2 | BD1 | 5 | BH2-4 | BD1 | 20 | 3.98 | 7.9 | — |
| Comp. 1 | BH1 | BD1 | 25 | — | — | — | — | 7.6 | 65 |
| Comp. 24 | — | — | — | BH2-4 | BD1 | 25 | — | 7.7 | 114 |

Example 30

The organic EL device according to Example 30 was prepared in the same manner as in Example 1 except that the compound BH2 (second host material) in the second emitting layer was replaced with the compound listed in Table 7.

Comparatives C31 to 32

The organic EL devices according to Comparatives C31 to 32 were prepared in the same manner as in Example 1 except that the compound BH1 (first host material) in the first emitting layer and the compound BH2 (second host material) in the second emitting layer were replaced with the compounds listed in Table 7.

Comparative 25

The organic EL device according to Comparative 25 was prepared in the same manner as in Comparative 2 except that the compound BH2 (second host material) in the second emitting layer was replaced with the compound listed in Table 7.

TABLE 7

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 30 | BH1 | BD1 | 5 | BH2-5 | BD1 | 20 | 3.76 | 8.0 | 196 |
| Comp. C31 | R-BH1 | BD1 | 5 | BH2-5 | BD1 | 20 | 4.20 | 7.8 | — |
| Comp. C32 | R-BH2 | BD1 | 5 | BH2-5 | BD1 | 20 | 4.48 | 7.8 | — |
| Comp. 1 | BH1 | BD1 | 25 | — | — | — | — | 7.6 | 65 |
| Comp. 25 | — | — | — | BH2-5 | BD1 | 25 | — | 7.6 | 92 |

Example 33

The organic EL device according to Example 33 was prepared in the same manner as in Example 1 except that the compound BH2 (second host material) in the second emitting layer was replaced with the compound listed in Table 8.

Comparatives C34 to 35

The organic EL devices according to Comparatives C34 to 35 were prepared in the same manner as in Example 1 except that the compound BH1 (first host material) in the first emitting layer and the compound BH2 (second host material) in the second emitting layer were replaced with the compounds listed in Table 8.

Comparative 26

The organic EL device according to Comparative 26 was prepared in the same manner as in Comparative 2 except that the compound BH2 (second host material) in the second emitting layer was replaced with the compound listed in Table 8.

TABLE 8

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 33 | BH1 | BD1 | 5 | BH2-6 | BD1 | 20 | 3.14 | 10.5 | 198 |
| Comp. C34 | R-BH1 | BD1 | 5 | BH2-6 | BD1 | 20 | 3.58 | 8.2 | — |
| Comp. C35 | R-BH2 | BD1 | 5 | BH2-6 | BD1 | 20 | 3.86 | 8.2 | — |
| Comp. 1 | BH1 | BD1 | 25 | — | — | — | — | 7.6 | 65 |
| Comp. 26 | — | — | — | BH2-6 | BD1 | 25 | — | 8.0 | 71 |

Example 36

The organic EL device according to Example 36 was prepared in the same manner as in Example 1 except that the compound BH2 (second host material) in the second emitting layer was replaced with the compound listed in Table 9.

Comparatives C37 to 38

The organic EL devices according to Comparatives C37 to 38 were prepared in the same manner as in Example 1 except that the compound BH1 (first host material) in the first emitting layer and the compound BH2 (second host material) in the second emitting layer were replaced with the compounds listed in Table 9.

Comparative 27

The organic EL device according to Comparative 27 was prepared in the same manner as in Comparative 2 except that the compound BH2 (second host material) in the second emitting layer was replaced with the compound listed in Table 9.

TABLE 9

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 36 | BH1 | BD1 | 5 | BH2-7 | BD1 | 20 | 3.21 | 10.7 | 217 |
| Comp. C37 | R-BH1 | BD1 | 5 | BH2-7 | BD1 | 20 | 3.65 | 8.0 | — |
| Comp. C38 | R-BH2 | BD1 | 5 | BH2-7 | BD1 | 20 | 3.93 | 8.0 | — |
| Comp. 1 | BH1 | BD1 | 25 | — | — | — | — | 7.6 | 65 |
| Comp. 27 | — | — | — | BH2-7 | BD1 | 25 | — | 7.8 | 106 |

Example 39

The organic EL device according to Example 39 was prepared in the same manner as in Example 1 except that the compound BH2 (second host material) in the second emitting layer was replaced with the compound listed in Table 10.

Comparatives C40 to 41

The organic EL devices according to Comparatives C40 to 41 were prepared in the same manner as in Example 1 except that the compound BH1 (first host material) in the first emitting layer and the compound BH2 (second host material) in the second emitting layer were replaced with the compounds listed in Table 10.

Comparative 28

The organic EL device according to Comparative 28 was prepared in the same manner as in Comparative 2 except that the compound BH2 (second host material) in the second emitting layer was replaced with the compound listed in Table 10.

TABLE 10

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 39 | BH1 | BD1 | 5 | BH2-8 | BD1 | 20 | 3.39 | 9.2 | 192 |
| Comp. C40 | R-BH1 | BD1 | 5 | BH2-8 | BD1 | 20 | 3.83 | 8.0 | — |
| Comp. C41 | R-BH2 | BD1 | 5 | BH2-8 | BD1 | 20 | 4.11 | 8.0 | — |
| Comp. 1 | BH1 | BD1 | 25 | — | — | — | — | 7.6 | 65 |
| Comp. 28 | — | — | — | BH2-8 | BD1 | 25 | — | 7.8 | 74 |

Example 42

The organic EL device according to Example 42 was prepared in the same manner as in Example 1 except that the compound BH2 (second host material) in the second emitting layer was replaced with the compound listed in Table 11.

Comparatives C43 to 44

The organic EL devices according to Comparatives C43 to 44 were prepared in the same manner as in Example 1 except that the compound BH1 (first host material) in the first emitting layer and the compound BH2 (second host material) in the second emitting layer were replaced with the compounds listed in Table 11.

Comparative 29

The organic EL device according to Comparative 29 was prepared in the same manner as in Comparative 2 except that the compound BH2 (second host material) in the second emitting layer was replaced with the compound listed in Table 11.

TABLE 11

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 42 | BH1 | BD1 | 5 | BH2-9 | BD1 | 20 | 3.56 | 10.5 | 300 |
| Comp. C43 | R-BH1 | BD1 | 5 | BH2-9 | BD1 | 20 | 4.00 | 10.0 | — |
| Comp. C44 | R-BH2 | BD1 | 5 | BH2-9 | BD1 | 20 | 4.28 | 10.1 | — |
| Comp. 1 | BH1 | BD1 | 25 | — | — | — | — | 7.6 | 65 |
| Comp. 29 | — | — | — | BH2-9 | BD1 | 25 | — | 9.8 | 195 |

Example 45

The organic EL device according to Example 45 was prepared in the same manner as in Example 1 except that the compound BD1 in the first emitting layer and the compound BD1 in the second emitting layer were replaced with the compounds listed in Table 12.

Comparatives C46 to 47

The organic EL devices according to Comparatives C46 to 47 were prepared in the same manner as in Example 1 except that the compound BH1 (first host material) in the first emitting layer and the compound BD1 in the second emitting layer were replaced with the compounds listed in Table 12.

Comparative 30

The organic EL device according to Comparative 30 was prepared in the same manner as in Comparative 1 except that the compound BD1 in the first emitting layer was replaced with the compound listed in Table 12.

Comparative 31

The organic EL device according to Comparative 31 was prepared in the same manner as in Comparative 2 except that the compound BD1 in the second emitting layer was replaced with the compound listed in Table 12.

TABLE 12

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 45 | BH1 | BD2 | 5 | BH2 | BD2 | 20 | 3.57 | 9.7 | 203 |
| Comp. C46 | R-BH1 | BD2 | 5 | BH2 | BD2 | 20 | 4.01 | 9.3 | — |
| Comp. C47 | R-BH2 | BD2 | 5 | BH2 | BD2 | 20 | 4.29 | 9.4 | — |
| Comp. 30 | BH1 | BD2 | 25 | — | — | — | — | 7.0 | 51 |
| Comp. 31 | — | — | — | BH2 | BD2 | 25 | — | 9.1 | 120 |

Example 48

The organic EL device according to Example 48 was prepared in the same manner as in Example 1 except that the compound BD1 in the first emitting layer and the compound BD1 in the second emitting layer were replaced with the compounds listed in Table 13.

Comparatives C49 to 50

The organic EL devices according to Comparatives C49 to 50 were prepared in the same manner as in Example 1 except that the compound BH1 (first host material) in the first emitting layer and the compound BD1 in the second emitting layer were replaced with the compounds listed in Table 13.

Comparative 32

The organic EL device according to Comparative 32 was prepared in the same manner as in Comparative 1 except that the compound BD1 in the first emitting layer was replaced with the compound listed in Table 13.

Comparative 33

The organic EL device according to Comparative 33 was prepared in the same manner as in Comparative 2 except that the compound BD1 in the second emitting layer was replaced with the compound listed in Table 13.

TABLE 13

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 48 | BH1 | BD3 | 5 | BH2 | BD3 | 20 | 3.51 | 10.2 | 167 |
| Comp. C49 | R-BH1 | BD3 | 5 | BH2 | BD3 | 20 | 3.95 | 9.7 | — |
| Comp. C50 | R-BH2 | BD3 | 5 | BH2 | BD3 | 20 | 4.23 | 9.8 | — |
| Comp. 32 | BH1 | BD3 | 25 | — | — | — | — | 7.4 | 46 |
| Comp. 33 | — | — | — | BH2 | BD3 | 25 | — | 9.5 | 103 |

Reference Examples 51 to 69

The organic EL devices according to Reference Examples 51 to 69 were prepared in the same manner as in Example 1 except that the compound BH1 (first host material) in the first emitting layer was replaced with the compounds listed in Table 14.

TABLE 14

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 51 | BH1-23 | BD1 | 5 | BH2 | BD1 | 20 | 10.2 | 198 |
| Ref. 52 | BH1-26 | BD1 | 5 | BH2 | BD1 | 20 | 10.3 | 214 |
| Ref. 53 | BH1-27 | BD1 | 5 | BH2 | BD1 | 20 | 10.6 | 239 |
| Ref. 54 | BH1-28 | BD1 | 5 | BH2 | BD1 | 20 | 10.5 | 222 |
| Ref. 55 | BH1-32 | BD1 | 5 | BH2 | BD1 | 20 | 10.4 | 207 |
| Ref. 56 | BH1-33 | BD1 | 5 | BH2 | BD1 | 20 | 10.3 | 205 |
| Ref. 57 | BH1-34 | BD1 | 5 | BH2 | BD1 | 20 | 10.5 | 213 |
| Ref. 58 | BH1-35 | BD1 | 5 | BH2 | BD1 | 20 | 10.4 | 198 |
| Ref. 59 | BH1-40 | BD1 | 5 | BH2 | BD1 | 20 | 10.4 | 221 |
| Ref. 60 | BH1-41 | BD1 | 5 | BH2 | BD1 | 20 | 10.7 | 248 |
| Ref. 61 | BH1-42 | BD1 | 5 | BH2 | BD1 | 20 | 10.5 | 232 |
| Ref. 62 | BH1-43 | BD1 | 5 | BH2 | BD1 | 20 | 10.6 | 211 |
| Ref. 63 | BH1-44 | BD1 | 5 | BH2 | BD1 | 20 | 10.5 | 205 |
| Ref. 64 | BH1-45 | BD1 | 5 | BH2 | BD1 | 20 | 10.4 | 230 |
| Ref. 65 | BH1-46 | BD1 | 5 | BH2 | BD1 | 20 | 10.8 | 249 |
| Ref. 66 | BH1-47 | BD1 | 5 | BH2 | BD1 | 20 | 10.6 | 217 |
| Ref. 67 | BH1-48 | BD1 | 5 | BH2 | BD1 | 20 | 10.6 | 243 |
| Ref. 68 | BH1-49 | BD1 | 5 | BH2 | BD1 | 20 | 10.7 | 268 |
| Ref. 69 | R-BH3 | BD1 | 5 | BH2 | BD1 | 20 | 10.1 | 183 |

Comparatives 34 to 51

The organic EL devices according to Comparatives 34 to 51 were prepared in the same manner as in Comparative 1 except that the compound BH1 (first host material) in the first emitting layer was replaced with the compounds listed in Table 15.

TABLE 15

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comp. 34 | BH1-23 | BD1 | 25 | — | — | — | 6.3 | 50 |
| Comp. 35 | BH1-26 | BD1 | 25 | — | — | — | 6.6 | 78 |
| Comp. 36 | BH1-27 | BD1 | 25 | — | — | — | 6.7 | 81 |
| Comp. 37 | BH1-28 | BD1 | 25 | — | — | — | 6.5 | 72 |
| Comp. 38 | BH1-32 | BD1 | 25 | — | — | — | 6.1 | 49 |
| Comp. 39 | BH1-33 | BD1 | 25 | — | — | — | 6.2 | 55 |
| Comp. 40 | BH1-34 | BD1 | 25 | — | — | — | 6.2 | 57 |
| Comp. 41 | BH1-35 | BD1 | 25 | — | — | — | 6.0 | 49 |
| Comp. 42 | BH1-40 | BD1 | 25 | — | — | — | 6.2 | 68 |
| Comp. 43 | BH1-41 | BD1 | 25 | — | — | — | 6.6 | 91 |
| Comp. 44 | BH1-42 | BD1 | 25 | — | — | — | 6.4 | 85 |
| Comp. 45 | BH1-43 | BD1 | 25 | — | — | — | 6.4 | 72 |
| Comp. 46 | BH1-44 | BD1 | 25 | — | — | — | 6.4 | 77 |
| Comp. 47 | BH1-45 | BD1 | 25 | — | — | — | 6.2 | 81 |
| Comp. 48 | BH1-46 | BD1 | 25 | — | — | — | 6.3 | 94 |
| Comp. 49 | BH1-47 | BD1 | 25 | — | — | — | 6.2 | 67 |
| Comp. 50 | BH1-48 | BD1 | 25 | — | — | — | 6.1 | 64 |
| Comp. 51 | BH1-49 | BD1 | 25 | — | — | — | 6.8 | 97 |
| Comp. 2 | — | — | — | BH2 | BD1 | 25 | 9.9 | 167 |

Preparation 2 of Organic EL Device

An organic EL device was prepared and evaluated as follows.

Reference Example 70

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, a compound HT3 was vapor-deposited to form an 80-nm-thick first hole transporting layer (HT).

After the formation of the first hole transporting layer, a compound HT4 was vapor-deposited to form a 10-nm-thick second hole transporting layer (also referred to as an electron blocking layer (EBL)).

A compound BH1-21 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 70 is roughly shown as follows.

ITO(130)/HA1(5)/HT3(80)/HT4(10)/BH1-21:BD1(5, 98%:2%)/BH2:BD1(20,98%:2%)/ET4(10)/ET2(15)/LiF(1)/Al(80)

The numerals in parentheses represent film thickness (unit: nm).

The numerals (98%:2%) represented by percentage in the same parentheses indicate a ratio (mass %) between the host material (the compound BH1-21 or the compound BH2) and the compound BD1 in the first emitting layer or the second emitting layer. Similar notations apply to the description below.

Reference Examples 71 to 78

The organic EL devices according to Reference Examples 71 to 78 were prepared in the same manner as in Reference Example 70 except that the compound BH1-21 (first host material) in the first emitting layer was replaced with the first compounds listed in Table 16.

Comparatives 52 to 59

The organic EL devices of Comparatives 52 to 59 were prepared in the same manner as in Reference Example 70 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 16.

Comparative 60

As shown in Table 16, the organic EL device of Comparative 60 was prepared in the same manner as in Reference Example 70 except that a 25-nm-thick second emitting layer was formed on the second hole transporting layer without forming the first emitting layer.

TABLE 16

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ref. 70 | BH1-21 | BD1 | 5 | BH2 | BD1 | 20 | 3.40 | 8.7 | 160 |
| Ref. 71 | BH1-22 | BD1 | 5 | BH2 | BD1 | 20 | 3.46 | 9.0 | 225 |
| Ref. 72 | BH1-24 | BD1 | 5 | BH2 | BD1 | 20 | 3.27 | 8.4 | 79 |
| Ref. 73 | BH1-25 | BD1 | 5 | BH2 | BD1 | 20 | 3.35 | 8.7 | 174 |
| Ref. 74 | BH1-36 | BD1 | 5 | BH2 | BD1 | 20 | 3.39 | 8.5 | 125 |
| Ref. 75 | BH1-37 | BD1 | 5 | BH2 | BD1 | 20 | 3.44 | 8.8 | 135 |
| Ref. 76 | BH1-50 | BD1 | 5 | BH2 | BD1 | 20 | 3.42 | 8.5 | 111 |
| Ref. 77 | BH1-51 | BD1 | 5 | BH2 | BD1 | 20 | 3.31 | 8.4 | 105 |
| Ref. 78 | R-BH3 | BD1 | 5 | BH2 | BD1 | 20 | 3.53 | 7.9 | 36 |
| Comp. 52 | BH1-21 | BD1 | 25 | — | — | — | — | 6.2 | 32 |
| Comp. 53 | BH1-22 | BD1 | 25 | — | — | — | — | 6.4 | 45 |
| Comp. 54 | BH1-24 | BD1 | 25 | — | — | — | — | 6.0 | 13 |
| Comp. 55 | BH1-25 | BD1 | 25 | — | — | — | — | 6.2 | 25 |
| Comp. 56 | BH1-36 | BD1 | 25 | — | — | — | — | 6.1 | 25 |
| Comp. 57 | BH1-37 | BD1 | 25 | — | — | — | — | 6.3 | 27 |
| Comp. 58 | BH1-50 | BD1 | 25 | — | — | — | — | 6.1 | 21 |
| Comp. 59 | BH1-51 | BD1 | 25 | — | — | — | — | 6.0 | 19 |
| Comp. 60 | — | — | — | BH2 | BD1 | 25 | — | 7.7 | 56 |

Preparation 3 of Organic EL Device

An organic EL device was prepared and evaluated as follows.

Reference Example 79

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

A compound BH1-29 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET3 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 79 is roughly shown as follows.

ITO(130)/HA1(5)/HT3(80)/HT4(10)/BH1-29:BD1(5, 98%:2%)/BH2:BD1(20,98%:2%)/ET3(10)/ET2(15)/LiF(1)/Al(80)

The numerals in parentheses represent film thickness (unit: nm).

The numerals (98%:2%) represented by percentage in the same parentheses indicate a ratio (mass %) between the host material (the compound BH1-29 or the compound BH2) and the compound BD1 in the first emitting layer or the second emitting layer. Similar notations apply to the description below.

Reference Examples 80 to 90

The organic EL devices according to Reference Examples 80 to 90 were prepared in the same manner as in Reference Example 79 except that the compound BH1-29 (first host material) in the first emitting layer was replaced with the first compounds listed in Table 17.

Comparatives 61 to 71

The organic EL devices of Comparatives 61 to 71 were prepared in the same manner as in Reference Example 79 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 17.

Comparative 72

As shown in Table 17, the organic EL device of Comparative 72 was prepared in the same manner as in Reference Example 79 except that a 25-nm-thick second emitting layer was formed on the second hole transporting layer without forming the first emitting layer.

TABLE 17

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 79 | BH1-29 | BD1 | 5 | BH2 | BD1 | 20 | 9.3 | 125 |
| Ref. 80 | BH1-30 | BD1 | 5 | BH2 | BD1 | 20 | 9.3 | 103 |
| Ref. 81 | BH1-31 | BD1 | 5 | BH2 | BD1 | 20 | 9.6 | 119 |
| Ref. 82 | BH1-38 | BD1 | 5 | BH2 | BD1 | 20 | 9.8 | 138 |
| Ref. 83 | BH1-39 | BD1 | 5 | BH2 | BD1 | 20 | 9.7 | 122 |
| Ref. 84 | BH1-52 | BD1 | 5 | BH2 | BD1 | 20 | 9.5 | 151 |
| Ref. 85 | BH1-53 | BD1 | 5 | BH2 | BD1 | 20 | 9.3 | 132 |
| Ref. 86 | BH1-54 | BD1 | 5 | BH2 | BD1 | 20 | 9.1 | 110 |
| Ref. 87 | BH1-55 | BD1 | 5 | BH2 | BD1 | 20 | 9.4 | 109 |
| Ref. 88 | BH1-56 | BD1 | 5 | BH2 | BD1 | 20 | 9.2 | 111 |
| Ref. 89 | BH1-57 | BD1 | 5 | BH2 | BD1 | 20 | 9.2 | 121 |
| Ref. 90 | R-BH3 | BD1 | 5 | BH2 | BD1 | 20 | 8.3 | 97 |
| Comp. 61 | BH1-29 | BD1 | 25 | — | — | — | 6.7 | 61 |
| Comp. 62 | BH1-30 | BD1 | 25 | — | — | — | 6.9 | 53 |
| Comp. 63 | BH1-31 | BD1 | 25 | — | — | — | 6.4 | 51 |
| Comp. 64 | BH1-38 | BD1 | 25 | — | — | — | 6.1 | 48 |
| Comp. 65 | BH1-39 | BD1 | 25 | — | — | — | 6.1 | 45 |
| Comp. 66 | BH1-52 | BD1 | 25 | — | — | — | 6.8 | 62 |
| Comp. 67 | BH1-53 | BD1 | 25 | — | — | — | 6.8 | 54 |
| Comp. 68 | BH1-54 | BD1 | 25 | — | — | — | 6.7 | 42 |

TABLE 17-continued

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comp. 69 | BH1-55 | BD1 | 25 | — | — | — | 6.7 | 59 |
| Comp. 70 | BH1-56 | BD1 | 25 | — | — | — | 6.5 | 40 |
| Comp. 71 | BH1-57 | BD1 | 25 | — | — | — | 6.2 | 34 |
| Comp. 72 | — | — | — | BH2 | BD1 | 25 | 8.1 | 89 |

Preparation 4 of Organic EL Device

An organic EL device was prepared and evaluated as follows.

Reference Example 91

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HT5 and a compound HA2 were co-deposited on a surface provided with the transparent electrode line to cover the transparent electrode, thereby forming a 10-nm-thick hole injecting layer (HI). The ratio of the compound HT5 in the hole injecting layer was 97 mass %, and the ratio of the compound HA2 was 3 mass %.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-61 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

A compound ET6 and the compound Liq were co-deposited on the first electron transporting layer (HBL) to form a 25-nm-thick electron transporting layer (ET). The ratios of the compound ET6 and the compound Liq in the electron transporting layer (ET) were both 50 mass %. It should be noted that Liq is an abbreviation for (8-quinolinolato) lithium.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 91 is roughly shown as follows.

ITO(130)/HT5:HA2(10,97%:3%)/HT5(85)/HT4(5)/BH1-61:BD1(5,98%:2%)/BH2:BD1(20,98%:2%)/ET3(5)/ET6:Liq(25, 50%:50%)/Liq(1)/Al(80)

The numerals in parentheses represent film thickness (unit: nm).

The numerals (97%:3%) represented by percentage in the same parentheses indicate a ratio (mass %) between the compound HT5 and the compound HA2 in the hole injecting layer. The numerals (98%:2%) represented by percentage in the same parentheses indicate a ratio (mass %) between the host material (the compound BH1-61 or the compound BH2) and the dopant material (the compound BD1) in the first emitting layer or the second emitting layer. The numerals (50%:50%) represented by percentage in the same parentheses indicate a ratio (mass %) between the compound ET6 and the compound Liq in the electron transporting layer (ET). Similar notations apply to the description below.

Reference Examples 92 to 95

The organic EL devices according to Reference Examples 92 to 95 were prepared in the same manner as in Reference Example 91 except that the compound BH1-61 (first host material) in the first emitting layer was replaced with the first compounds listed in Table 18.

Comparatives 73 to 76

The organic EL devices of Comparatives 73 to 76 were prepared in the same manner as in Reference Example 91 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 18.

Comparative 77

As shown in Table 18, the organic EL device of Comparative 77 was prepared in the same manner as in Reference Example 91 except that a 25-nm-thick second emitting layer was formed on the second hole transporting layer without forming the first emitting layer.

TABLE 18

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 91 | BH1-61 | BD1 | 5 | BH2 | BD1 | 20 | 9.2 | 128 |
| Ref. 92 | BH1-62 | BD1 | 5 | BH2 | BD1 | 20 | 9.7 | 153 |
| Ref. 93 | BH1-63 | BD1 | 5 | BH2 | BD1 | 20 | 9.5 | 144 |
| Ref. 94 | BH1-69 | BD1 | 5 | BH2 | BD1 | 20 | 9.0 | 110 |
| Ref. 95 | R-BH3 | BD1 | 5 | BH2 | BD1 | 20 | 8.8 | 101 |
| Comp. 73 | BH1-61 | BD1 | 25 | — | — | — | 6.1 | 47 |
| Comp. 74 | BH1-62 | BD1 | 25 | — | — | — | 6.4 | 64 |
| Comp. 75 | BH1-63 | BD1 | 25 | — | — | — | 6.3 | 60 |
| Comp. 76 | BH1-69 | BD1 | 25 | — | — | — | 5.9 | 19 |
| Comp. 77 | — | — | — | BH2 | BD1 | 25 | 8.4 | 72 |

Preparation 5 of Organic EL Device

An organic EL device was prepared and evaluated as follows.

Reference Example 96

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT3 and the compound HA2 were co-deposited on a surface provided with the transparent electrode line to cover the transparent electrode, thereby forming a 10-nm-thick hole injecting layer (HI). The ratios of the compound HT3 and the compound HA2 in the hole injecting layer were 97 mass % and 3 mass %, respectively.

After the formation of the hole injecting layer, the compound HT3 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-75 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

A compound ET8 and the compound Liq were co-deposited on the first electron transporting layer (HBL) to form a 25-nm-thick electron transporting layer (ET). The ratios of the compound HT5 and the compound Liq in the electron transporting layer (ET) were both 50 mass %. It should be noted that Liq is an abbreviation for (8-quinolinolato) lithium.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 96 is roughly shown as follows.

ITO(130)/HT3:HA2(10,97%:3%)/HT3(85)/HT4(5)/BH1-75:BD1(5,98%:2%)/BH2:BD1(20,98%:2%)/ET3(5)/ET8:Liq(25, 50%:50%)/Liq(1)/Al(80)

The numerals in parentheses represent film thickness (unit: nm).

The numerals represented by percentage in the same parentheses (97%:3%) respectively indicate a ratio (mass %) between the compound HT3 and the compound HA2 in the hole injecting layer. The numerals represented by percentage in the same parentheses (98%:2%) respectively indicate a ratio (mass %) between the host material (the compound BH1-75 or the compound BH2) and the dopant material (the compound BD1) in the first emitting layer or the second emitting layer. The numerals represented by percentage in the same parentheses (50%:50%) respectively indicate a ratio (mass %) between the compound ET8 and the compound Liq in the electron transporting layer (ET). Similar notations apply to the description below.

Reference Example 97

The organic EL device according to Reference Example 97 was prepared in the same manner as in Reference Example 96 except that the compound BH1-75 (first host material) in the first emitting layer was replaced with the first compound listed in Table 19.

Comparative 78

The organic EL device of Comparative 78 was prepared in the same manner as in Reference Example 96 except that a 25-nm-thick first emitting layer was formed as the emitting layer, the first electron transporting layer was formed on the first emitting layer without forming the second emitting layer, and the first compound (first host material) in the first emitting layer was replaced with the first compound listed in Table 19.

Comparative 79

As shown in Table 19, the organic EL device of Comparative 79 was prepared in the same manner as in Reference Example 96 except that a 25-nm-thick second emitting layer was formed on the second hole transporting layer without forming the first emitting layer.

TABLE 19

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 96 | BH1-75 | BD1 | 5 | BH2 | BD1 | 20 | 9.2 | 169 |
| Ref. 97 | R-BH3 | BD1 | 5 | BH2 | BD1 | 20 | — | 118 |
| Comp. 78 | BH1-75 | BD1 | 25 | — | — | — | 6.0 | 63 |
| Comp. 79 | — | — | — | BH2 | BD1 | 25 | 8.1 | 91 |

Preparation 6 of Organic EL Device

An organic EL device was prepared and evaluated as follows.

Reference Example 98

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratio of the compound HT5 in the hole injecting layer was 97 mass %, and the ratio of the compound HA2 was 3 mass %.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-64 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET8 and the compound Liq in the electron transporting layer (ET) were both 50 mass %.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 98 is roughly shown as follows.

ITO(130)/HT5:HA2(10,97%:3%)/HT5(85)/HT4(5)/BH1-64:BD1(5,98%:2%)/BH2:BD1(20,98%:2%)/ET3(5)/ET8:Liq(25, 50%:50%)/Liq(1)/Al(80)

The numerals in parentheses represent film thickness (unit: nm). The numerals (97%:3%) represented by percentage in the same parentheses indicate a ratio (mass %) between the compound HT5 and the compound HA2 in the hole injecting layer. The numerals (98%:2%) represented by percentage in the same parentheses indicate a ratio (mass %) between the host material (the compound BH1-64 or the compound BH2) and the dopant material (the compound BD1) in the first emitting layer or the second emitting layer. The numerals (50%:50%) represented by percentage in the same parentheses indicate a ratio (mass %) between the compound ET8 and the compound Liq in the electron transporting layer (ET). Similar notations apply to the description below.

Reference Examples 99 to 103

The organic EL devices according to Reference Examples 99 to 103 were prepared in the same manner as in Reference Example 98 except that the compound BH1-64 (first host material) in the first emitting layer was replaced with the first compounds listed in Table 20.

Comparatives 80 to 84

The organic EL devices of Comparatives 80 to 84 were prepared in the same manner as in Reference Example 98 except that a 25-nm-thick first emitting layer was formed as the emitting layer, the first electron transporting layer was formed on the first emitting layer without forming the second emitting layer, and the first compound (first host material) in the first emitting layer was replaced with the first compound listed in Table 20.

Comparative 85

As shown in Table 20, the organic EL device of Comparative 85 was prepared in the same manner as in Reference Example 98 except that a 25-nm-thick second emitting layer was formed on the second hole transporting layer without forming the first emitting layer.

TABLE 20

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 98 | BH1-64 | BD1 | 5 | BH2 | BD1 | 20 | 9.6 | 106 |
| Ref. 99 | BH1-65 | BD1 | 5 | BH2 | BD1 | 20 | 9.7 | 112 |
| Ref. 100 | BH1-66 | BD1 | 5 | BH2 | BD1 | 20 | 9.5 | 83 |
| Ref. 101 | BH1-67 | BD1 | 5 | BH2 | BD1 | 20 | 9.4 | 93 |
| Ref. 102 | BH1-68 | BD1 | 5 | BH2 | BD1 | 20 | 9.5 | 101 |
| Ref. 103 | R-BH3 | BD1 | 5 | BH2 | BD1 | 20 | 9.1 | — |
| Comp. 80 | BH1-64 | BD1 | 25 | — | — | — | 6.1 | 31 |
| Comp. 81 | BH1-65 | BD1 | 25 | — | — | — | 6.3 | 48 |
| Comp. 82 | BH1-66 | BD1 | 25 | — | — | — | 6.1 | 31 |
| Comp. 83 | BH1-67 | BD1 | 25 | — | — | — | 6.3 | 55 |
| Comp. 84 | BH1-68 | BD1 | 25 | — | — | — | 6.0 | 28 |
| Comp. 85 | — | — | — | BH2 | BD1 | 25 | 8.6 | 61 |

Preparation 7 of Organic EL Device

An organic EL device was prepared and evaluated as follows.

Reference Example 104

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratio of the compound HT5 in the hole injecting layer was 97 mass %, and the ratio of the compound HA2 was 3 mass %.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-70 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 5-nm-thick first electron transporting layer (also referred to as a hole blocking layer (HBL)).

The compound ET6 and the compound Liq were co-deposited on the first electron transporting layer (HBL) to form a 25-nm-thick electron transporting layer (ET). The ratios of the compound ET6 and the compound Liq in the electron transporting layer (ET) were both 50 mass %.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 104 is roughly shown as follows.

ITO(130)/HT5:HA2(10,97%:3%)/HT5(85)/HT4(5)/BH1-70:BD1(5,98%:2%)/BH2:BD1(20,98%:2%)/ET1(5)/ET6:Liq(25, 50%:50%)/Liq(1)/Al(80)

The numerals in parentheses represent film thickness (unit: nm).

The numerals (97%:3%) represented by percentage in the same parentheses indicate a ratio (mass %) between the compound HT5 and the compound HA2 in the hole injecting layer. The numerals (98%:2%) represented by percentage in the same parentheses indicate a ratio (mass %) between the host material (the compound BH1-70 or the compound BH2) and the dopant material (the compound BD1) in the first emitting layer or the second emitting layer. The numerals (50%:50%) represented by percentage in the same parentheses indicate a ratio (mass %) between the compound ET6 and the compound Liq in the electron transporting layer (ET). Similar notations apply to the description below.

Reference Examples 105 to 109

The organic EL devices according to Reference Examples 105 to 109 were prepared in the same manner as in Reference Example 104 except that the compound BH1-70 (first host material) in the first emitting layer was replaced with the first compounds listed in Table 21.

Comparatives 86 to 90

The organic EL devices of Comparatives 86 to 90 were prepared in the same manner as in Reference Example 104 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 21.

Comparative 91

As shown in Table 21, the organic EL device of Comparative 91 was prepared in the same manner as in Reference Example 104 except that a 25-nm-thick second emitting layer was formed on the second hole transporting layer without forming the first emitting layer.

TABLE 21

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 104 | BH1-70 | BD1 | 5 | BH2 | BD1 | 20 | 10.2 | 185 |
| Ref. 105 | BH1-71 | BD1 | 5 | BH2 | BD1 | 20 | 10.7 | 223 |
| Ref. 106 | BH1-72 | BD1 | 5 | BH2 | BD1 | 20 | 10.4 | 212 |
| Ref. 107 | BH1-73 | BD1 | 5 | BH2 | BD1 | 20 | 10.6 | 220 |
| Ref. 108 | BH1-74 | BD1 | 5 | BH2 | BD1 | 20 | 10.3 | 218 |
| Ref. 109 | R-BH3 | BD1 | 5 | BH2 | BD1 | 20 | 8.7 | 101 |
| Comp. 86 | BH1-70 | BD1 | 25 | — | — | — | 6.2 | 59 |
| Comp. 87 | BH1-71 | BD1 | 25 | — | — | — | 6.6 | 63 |
| Comp. 88 | BH1-72 | BD1 | 25 | — | — | — | 6.5 | 51 |
| Comp. 89 | BH1-73 | BD1 | 25 | — | — | — | 6.5 | 62 |
| Comp. 90 | BH1-74 | BD1 | 25 | — | — | — | 6.4 | 60 |
| Comp. 91 | — | — | — | BH2 | BD1 | 25 | 8.3 | 76 |

Preparation 8 of Organic EL Device

Reference Example 110

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, a compound HT8 was vapor-deposited to form a 10-nm-thick second hole transporting layer (also referred to as an electron blocking layer (EBL)).

A compound BH1-81 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 110 is roughly shown as follows.

ITO(130)/HA1(5)/HT1(80)/HT8(10)/BH1-81:BD1(5, 98%:2%)/BH2:BD1(20,98%:2%)/ET1(10)/ET2(15)/LiF(1)/Al(80)

The numerals in parentheses represent film thickness (unit: nm).

The numerals (98%:2%) represented by percentage in the same parentheses indicate a ratio (mass %) between the host material (the compound BH1-81 or the compound BH2) and the compound BD1 in the first emitting layer or the second emitting layer. Similar notations apply to the description below.

Reference Example 111

The organic EL device according to Reference Example 111 was prepared in the same manner as in Reference Example 110 except that the compound BH1-81 (first host material) in the first emitting layer was replaced with the first compound listed in Table 22.

Comparative 92

The organic EL device of Comparative 92 was prepared in the same manner as in Example 110 except that a 25-nm-thick first emitting layer was formed as the emitting layer and the first electron transporting layer was formed on the first emitting layer without forming the second emitting layer.

Comparative 93

As shown in Table 22, the organic EL device of Comparative 93 was prepared in the same manner as in Reference Example 110 except that a 25-nm-thick second emitting layer was formed on the second hole transporting layer without forming the first emitting layer.

TABLE 22

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 110 | BH1-81 | BD1 | 5 | BH2 | BD1 | 20 | 10.7 | 134 |
| Ref. 111 | R-BH3 | BD1 | 5 | BH2 | BD1 | 20 | 10.4 | — |

TABLE 22-continued

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comp. 92 | BH1-81 | BD1 | 25 | — | — | — | 6.4 | 35 |
| Comp. 93 | — | — | — | BH2 | BD1 | 25 | 10.2 | 102 |

Preparation 9 of Organic EL Device

Reference Examples 112 to 113

The organic EL devices according to Reference Examples 112 to 113 were prepared in the same manner as in Example 1 except that the compound BH1 (first host material) in the first emitting layer was replaced with the compounds listed in Table 23.

Comparative 94

The organic EL device according to Comparative 94 was prepared in the same manner as in Comparative 1 except that the compound BH1 (first host material) in the first emitting layer was replaced with the compound listed in Table 23.

TABLE 23

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 112 | BH1-82 | BD1 | 5 | BH2 | BD1 | 20 | 10.4 | 219 |
| Ref. 113 | R-BH3 | BD1 | 5 | BH2 | BD1 | 20 | 10.1 | 183 |
| Comp. 94 | BH1-82 | BD1 | 25 | — | — | — | 6.2 | 71 |
| Comp. 2 | — | — | — | BH2 | BD1 | 25 | 9.9 | 167 |

Preparation 10 of Organic EL Device

Reference Example 114

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound BH1-83 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Reference Example 114 is roughly shown as follows.

ITO(130)/HA1(5)/HT1(80)/HT2(10)/BH1-83:BD1(5, 98%:2%)/BH2:BD1(20,98%:2%)/ET7(10)/ET2(15)/LiF(1)/Al(80)

The numerals in parentheses represent film thickness (unit: nm).

The numerals (98%:2%) represented by percentage in the same parentheses indicate a ratio (mass %) between the host material (the compound BH1-83 or the compound BH2) and the compound BD1 in the first emitting layer or the second emitting layer. Similar notations apply to the description below.

Reference Example 115

The organic EL device according to Reference Example 115 was prepared in the same manner as in Reference Example 114 except that the compound BH1-83 (first host material) in the first emitting layer was replaced with the first compound listed in Table 24.

Comparative 95

The organic EL device of Comparative 95 was prepared in the same manner as in Example 114 except that a 25-nm-thick first emitting layer was formed as the emitting layer and the first electron transporting layer was formed on the first emitting layer without forming the second emitting layer.

Comparative 96

As shown in Table 24, the organic EL device of Comparative 96 was prepared in the same manner as in Reference Example 114 except that a 25-nm-thick second emitting layer was formed on the second hole transporting layer without forming the first emitting layer.

TABLE 24

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Ref. 114 | BH1-83 | BD1 | 5 | BH2 | BD1 | 20 | 9.7 | 247 |
| Ref. 115 | R-BH3 | BD1 | 5 | BH2 | BD1 | 20 | 8.5 | — |
| Comp. 95 | BH1-83 | BD1 | 25 | — | — | — | 6.0 | 76 |
| Comp. 96 | — | — | — | BH2 | BD1 | 25 | 9.1 | 183 |

Preparation 11 of Organic EL Device

Example 116

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

A compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 116 is roughly shown as follows.

ITO(130)/HA1(5)/HT1(80)/HT4(10)/BH1:BD1(5,98%:2%)/BH2-8:BD1(20,98%:2%)/ET1(10)/ET2(20)/LiF(1)/Al (80)

The numerals in parentheses represent film thickness (unit: nm).

The numerals (98%:2%) represented by percentage in the same parentheses indicate a ratio (mass %) between the host material (the compound BH1) and the compound BD1 in the first emitting layer, and numerals (98%:2%) represented by percentage in the same parentheses indicate a ratio (mass %) between the host material (the compound BH2-8) and the compound BD1 in the second emitting layer. Similar notations apply to the description below.

Example 117

The organic EL device according to Example 117 was prepared in the same manner as in Example 116 except that the compound BH2-8 (second host material) in the second emitting layer was replaced with the second compound listed in Table 25.

Comparative 97

As shown in Table 25, the organic EL device of Comparative 97 was prepared in the same manner as in Example 116 except that a 25-nm-thick second emitting layer was formed on the second hole transporting layer without forming the first emitting layer, and the second compound (second host material) in the second emitting layer was replaced with the second compound listed in Table 25.

TABLE 25

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 116 | BH1 | BD1 | 5 | BH2-8 | BD1 | 20 | 3.4 | 9.8 | 120 |
| Ex. 117 | BH1 | BD1 | 5 | BH2-5 | BD1 | 20 | 3.6 | 10.1 | 160 |
| Comp. 97 | — | — | — | BH2-5 | BD1 | 25 | 3.8 | 8.9 | 110 |

Preparation 12 of Organic EL Device

Examples 118 to 119

The organic EL devices according to Examples 118 to 119 were prepared in the same manner as in Example 116 except that the compound BH2-8 (second host material) in the second emitting layer was replaced with the second compound listed in Table 26.

Comparative 98

As shown in Table 26, the organic EL device of Comparative 98 was prepared in the same manner as in Example 116 except that a 25-nm-thick second emitting layer was formed on the second hole transporting layer without forming the first emitting layer, and the second compound (second host material) in the second emitting layer was replaced with the second compound listed in Table 26.

TABLE 26

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 118 | BH1 | BD1 | 5 | BH2-2 | BD1 | 20 | 3.8 | 10.5 | 200 |
| Ex. 119 | BH1 | BD1 | 5 | BH2-10 | BD1 | 20 | 3.8 | 10.5 | 240 |
| Comp. 98 | — | — | — | BH2-10 | BD1 | 25 | 4.0 | 9.8 | 140 |

Example 120

The organic EL device according to Example 120 was prepared in the same manner as in Example 116 except that the compound BH2-8 (second host material) in the second emitting layer was replaced with the second compound listed in Table 27.

Comparative 99

As shown in Table 27, the organic EL device of Comparative 99 was prepared in the same manner as in Example 116 except that a 25-nm-thick second emitting layer was formed on the second hole transporting layer without forming the first emitting layer, and the second compound (second host material) in the second emitting layer was replaced with the second compound listed in Table 27.

TABLE 27

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 116 | BH1 | BD1 | 5 | BH2-8 | BD1 | 20 | 3.4 | 9.8 | 120 |
| Ex. 120 | BH1 | BD1 | 5 | BH2-11 | BD1 | 20 | 3.4 | 9.8 | 150 |
| Comp. 99 | — | — | — | BH2-11 | BD1 | 25 | 3.6 | 7.5 | 100 |

Preparation 13 of Organic EL Device

Example 121

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 121 is roughly shown as follows.

ITO(130)/HA1(5)/HT3(80)/HT4(10)/BH1:BD2(5,98%:2%)/BH2-2:BD2(20,98%:2%)/ET7(10)/ET2(20)/LiF(1)/Al(80)

The numerals in parentheses represent film thickness (unit: nm).

The numerals (98%:2%) represented by percentage in the same parentheses indicate a ratio (mass %) between the host material (the compound BH1) and the compound BD2 in the first emitting layer, and numerals (98%:2%) represented by percentage in the same parentheses indicate a ratio (mass %) between the host material (the compound BH2-2) and the compound BD2 in the second emitting layer. Similar notations apply to the description below.

Example 122

The organic EL device according to Example 122 was prepared in the same manner as in Example 121 except that the compound BH2-2 (second host material) in the second emitting layer was replaced with the second compound listed in Table 28.

Comparative 100

As shown in Table 28, the organic EL device of Comparative 100 was prepared in the same manner as in Example 121 except that a 25-nm-thick second emitting layer was formed on the second hole transporting layer without forming the first emitting layer, and the second compound (second host material) in the second emitting layer was replaced with the second compound listed in Table 28.

TABLE 28

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex 121 | BH1 | BD2 | 5 | BH2-2 | BD2 | 20 | 3.8 | 10.1 | 180 |
| Ex. 122 | BH1 | BD2 | 5 | BH2-12 | BD2 | 20 | 4.0 | 10.3 | 200 |
| Comp. 100 | — | — | — | BH2-12 | BD2 | 25 | 4.2 | 8.8 | 110 |

Preparation 14 of Organic EL Device

Example 123

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT5 was vapor-deposited to form an 80-nm-thick first hole transporting layer (HT).

After the formation of the first hole transporting layer, a compound HT6 was vapor-deposited to form a 10-nm-thick second hole transporting layer (also referred to as an electron blocking layer (EBL)).

A compound BH1-10 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

The compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 123 is roughly shown as follows.

ITO(130)/HA1(5)/HT5(80)/HT6(10)/BH1-10:BD2(5, 98%:2%)/BH2-2:BD2(20,98%:2%)/ET7(10)/ET2(20)/LiF (1)/Al(80)

The numerals in parentheses represent film thickness (unit: nm).

The numerals (98%:2%) represented by percentage in the same parentheses indicate a ratio (mass %) between the host material (the compound BH1-10) and the compound BD2 in the first emitting layer, and numerals (98%:2%) represented by percentage in the same parentheses indicate a ratio (mass %) between the host material (the compound BH2-2) and the compound BD2 in the second emitting layer. Similar notations apply to the description below.

Example 124

The organic EL device according to Example 124 was prepared in the same manner as in Example 123 except that the compound BH2-2 (second host material) in the second emitting layer was replaced with the second compound listed in Table 29.

Comparative 101

As shown in Table 29, the organic EL device of Comparative 101 was prepared in the same manner as in Example 123 except that a 25-nm-thick second emitting layer was formed on the second hole transporting layer without forming the first emitting layer, and the second compound (second host material) in the second emitting layer was replaced with the second compound listed in Table 29.

TABLE 29

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 123 | BH1-10 | BD2 | 5 | BH2-2 | BD2 | 20 | 3.9 | 10.0 | 210 |
| Ex. 124 | BH1-10 | BD2 | 5 | BH2-13 | BD2 | 20 | 3.8 | 10.3 | 190 |
| Comp. 101 | — | — | — | BH2-13 | BD2 | 25 | 4.1 | 9.2 | 110 |

Preparation 15 of Organic EL Device

Example 125

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, a compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 125 is roughly shown as follows.

ITO(130)/HA1(5)/HT3(80)/HT7(10)/BH1-10:BD1(5, 98%:2%)/BH2-2:BD1(20,98%:2%)/ET7(10)/ET2(20)/LiF (1)/Al(80)

The numerals in parentheses represent film thickness (unit: nm).

The numerals (98%:2%) represented by percentage in the same parentheses indicate a ratio (mass %) between the host material (the compound BH1-10) and the compound BD1 in the first emitting layer, and numerals (98%:2%) represented by percentage in the same parentheses indicate a ratio (mass %) between the host material (the compound BH2-2) and the compound BD1 in the second emitting layer. Similar notations apply to the description below.

Example 126

The organic EL device according to Example 126 was prepared in the same manner as in Example 125 except that the compound BH2-2 (second host material) in the second emitting layer was replaced with the second compound listed in Table 30.

Comparative 102

As shown in Table 30, the organic EL device of Comparative 102 was prepared in the same manner as in Example 125 except that a 25-nm-thick second emitting layer was formed on the second hole transporting layer without forming the first emitting layer, and the second compound (second host material) in the second emitting layer was replaced with the second compound listed in Table 30.

TABLE 30

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 125 | BH1-10 | BD1 | 5 | BH2-2 | BD1 | 20 | 4.0 | 10.5 | 150 |
| Ex. 126 | BH1-10 | BD1 | 5 | BH2-14 | BD1 | 20 | 4.0 | 10.8 | 160 |
| Comp. 102 | — | — | — | BH2-14 | BD1 | 25 | 4.2 | 9.5 | 100 |

Example 127

The organic EL device according to Example 127 was prepared in the same manner as in Example 125 except that the compound BH2-2 (second host material) in the second emitting layer was replaced with the second compound listed in Table 31.

Comparative 103

As shown in Table 31, the organic EL device of Comparative 103 was prepared in the same manner as in Example 125 except that a 25-nm-thick second emitting layer was formed on the second hole transporting layer without forming the first emitting layer, and the second compound (second host material) in the second emitting layer was replaced with the second compound listed in Table 31.

TABLE 31

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 125 | BH1-10 | BD1 | 5 | BH2-2 | BD1 | 20 | 4.0 | 10.5 | 150 |
| Ex. 127 | BH1-10 | BD1 | 5 | BH2-15 | BD1 | 20 | 3.9 | 10.3 | 180 |
| Comp. 103 | — | — | — | BH2-15 | BD1 | 25 | 4.0 | 9.2 | 80 |

Example 128

The organic EL device according to Example 128 was prepared in the same manner as in Example 125 except that the compound BH2-2 (second host material) in the second emitting layer was replaced with the second compound listed in Table 32.

Comparative 104

As shown in Table 32, the organic EL device of Comparative 104 was prepared in the same manner as in Example 125 except that a 25-nm-thick second emitting layer was formed on the second hole transporting layer without forming the first emitting layer, and the second compound (second host material) in the second emitting layer was replaced with the second compound listed in Table 32.

TABLE 32

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 125 | BH1-10 | BD1 | 5 | BH2-2 | BD1 | 20 | 4.0 | 10.5 | 150 |
| Ex. 128 | BH1-10 | BD1 | 5 | BH2-16 | BD1 | 20 | 3.8 | 10.5 | 170 |
| Comp. 104 | — | — | — | BH2-16 | BD1 | 25 | 4.1 | 9.5 | 70 |

Example 129

The organic EL device according to Example 129 was prepared in the same manner as in Example 125 except that the compound BH2-2 (second host material) in the second emitting layer was replaced with the second compound listed in Table 33.

Comparative 105

As shown in Table 33, the organic EL device of Comparative 105 was prepared in the same manner as in Example 125 except that a 25-nm-thick second emitting layer was formed on the second hole transporting layer without forming the first emitting layer, and the second compound (second host material) in the second emitting layer was replaced with the second compound listed in Table 33.

TABLE 33

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 125 | BH1-10 | BD1 | 5 | BH2-2 | BD1 | 20 | 4.0 | 10.5 | 150 |
| Ex. 129 | BH1-10 | BD1 | 5 | BH2-17 | BD1 | 20 | 3.7 | 10.6 | 170 |
| Comp. 105 | — | — | — | BH2-17 | BD1 | 25 | 4.0 | 9.1 | 60 |

Preparation 16 of Organic EL Device

Example 130

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

A compound ET5 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 130 is roughly shown as follows.

ITO(130)/HA1(5)/HT3(80)/HT7(10)/BH1-10:BD1(5, 98%:2%)/BH2-8:BD1(20,98%:2%)/ET1(10)/ET5(20)/LiF (1)/Al(80)

The numerals in parentheses represent film thickness (unit: nm).

The numerals (98%:2%) represented by percentage in the same parentheses indicate a ratio (mass %) between the host material (the compound BH1-10) and the compound BD1 in the first emitting layer, and numerals (98%:2%) represented by percentage in the same parentheses indicate a ratio (mass %) between the host material (the compound BH2-8) and the compound BD1 in the second emitting layer. Similar notations apply to the description below.

Example 131

The organic EL device according to Example 131 was prepared in the same manner as in Example 130 except that the compound BH2-8 (second host material) in the second emitting layer was replaced with the second compound listed in Table 34.

Comparative 106

As shown in Table 34, the organic EL device of Comparative 106 was prepared in the same manner as in Example 130 except that a 25-nm-thick second emitting layer was formed on the second hole transporting layer without forming the first emitting layer, and the second compound (second host material) in the second emitting layer was replaced with the second compound listed in Table 34.

TABLE 34

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 130 | BH1-10 | BD1 | 5 | BH2-8 | BD1 | 20 | 3.4 | 9.5 | 140 |
| Ex. 131 | BH1-10 | BD1 | 5 | BH2-18 | BD1 | 20 | 3.4 | 10.0 | 150 |
| Comp. 106 | — | — | — | BH2-18 | BD1 | 25 | 3.6 | 9.0 | 100 |

Example 132

The organic EL device according to Example 132 was prepared in the same manner as in Example 130 except that the compound BH2-8 (second host material) in the second emitting layer was replaced with the second compound listed in Table 35.

Comparative 107

As shown in Table 35, the organic EL device of Comparative 107 was prepared in the same manner as in Example 130 except that a 25-nm-thick second emitting layer was formed on the second hole transporting layer without forming the first emitting layer, and the second compound (second host material) in the second emitting layer was replaced with the second compound listed in Table 35.

TABLE 35

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 130 | BH1-10 | BD1 | 5 | BH2-8 | BD1 | 20 | 3.4 | 9.5 | 140 |
| Ex. 132 | BH1-10 | BD1 | 5 | BH2-19 | BD1 | 20 | 3.5 | 10.3 | 140 |
| Comp. 107 | — | — | — | BH2-19 | BD1 | 25 | 3.6 | 9.2 | 80 |

Example 133

The organic EL device according to Example 133 was prepared in the same manner as in Example 130 except that the compound BH2-8 (second host material) in the second emitting layer was replaced with the second compound listed in Table 36.

Comparative 108

As shown in Table 36, the organic EL device of Comparative 108 was prepared in the same manner as in Example 130 except that a 25-nm-thick second emitting layer was formed on the second hole transporting layer without forming the first emitting layer, and the second compound (second host material) in the second emitting layer was replaced with the second compound listed in Table 36.

TABLE 36

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 130 | BH1-10 | BD1 | 5 | BH2-8 | BD1 | 20 | 3.4 | 9.5 | 140 |
| Ex. 133 | BH1-10 | BD1 | 5 | BH2-20 | BD1 | 20 | 3.4 | 9.9 | 160 |
| Comp. 108 | — | — | — | BH2-20 | BD1 | 25 | 3.7 | 8.8 | 120 |

Preparation 17 of Organic EL Device

Example 134

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 134 is roughly shown as follows.

ITO(130)/HA1(5)/HT1(80)/HT2(10)/BH1:BD1(5,98%:2%)/BH2-8:BD1(20,98%:2%)/ET4(10)/ET2(20)/LiF(1)/Al(80)

The numerals in parentheses represent film thickness (unit: nm).

The numerals (98%:2%) represented by percentage in the same parentheses indicate a ratio (mass %) between the host material (the compound BH1) and the compound BD1 in the first emitting layer, and numerals (98%:2%) represented by percentage in the same parentheses indicate a ratio (mass %) between the host material (the compound BH2-8) and the compound BD1 in the second emitting layer. Similar notations apply to the description below.

Example 135

The organic EL device according to Example 135 was prepared in the same manner as in Example 134 except that the compound BH2-8 (second host material) in the second emitting layer was replaced with the second compound listed in Table 37.

Comparative 109

As shown in Table 37, the organic EL device of Comparative 109 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 37.

TABLE 37

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 135 | BH1 | BD1 | 5 | BH2-21 | BD1 | 20 | 3.3 | 9.6 | 130 |
| Comp. 109 | — | — | — | BH2-21 | BD1 | 25 | 3.5 | 8.5 | 80 |

Example 136

The organic EL device according to Example 136 was prepared in the same manner as in Example 134 except that the compound BH2-8 (second host material) in the second emitting layer was replaced with the second compound listed in Table 38.

Comparative 110

As shown in Table 38, the organic EL device of Comparative 110 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 38.

TABLE 38

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 136 | BH1 | BD1 | 5 | BH2-22 | BD1 | 20 | 3.4 | 8.3 | 140 |
| Comp. 110 | — | — | — | BH2-22 | BD1 | 25 | 3.5 | 7.3 | 80 |

Example 137

The organic EL device according to Example 137 was prepared in the same manner as in Example 134 except that the compound BH2-8 (second host material) in the second emitting layer was replaced with the second compound listed in Table 39.

Comparative 111

As shown in Table 39, the organic EL device of Comparative 111 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 39.

TABLE 39

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 137 | BH1 | BD1 | 5 | BH2-23 | BD1 | 20 | 3.3 | 8.8 | 130 |
| Comp. 111 | — | — | — | BH2-23 | BD1 | 25 | 3.4 | 8.0 | 80 |

Example 138

The organic EL device according to Example 138 was prepared in the same manner as in Example 134 except that the compound BH2-8 (second host material) in the second emitting layer was replaced with the second compound listed in Table 40.

Comparative 112

As shown in Table 40, the organic EL device of Comparative 112 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 40.

TABLE 40

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 138 | BH1 | BD1 | 5 | BH2-24 | BD1 | 20 | 3.5 | 9.1 | 120 |
| Comp. 112 | — | — | — | BH2-24 | BD1 | 25 | 3.7 | 7.8 | 90 |

Example 139

The organic EL device according to Example 139 was prepared in the same manner as in Example 134 except that the compound BH2-8 (second host material) in the second emitting layer was replaced with the second compound listed in Table 41.

Comparative 113

As shown in Table 41, the organic EL device of Comparative 113 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 41.

TABLE 41

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 139 | BH1 | BD1 | 5 | BH2-25 | BD1 | 20 | 3.4 | 9.4 | 130 |
| Comp. 113 | — | — | — | BH2-25 | BD1 | 25 | 3.4 | 7.1 | 70 |

Example 140

The organic EL device according to Example 140 was prepared in the same manner as in Example 134 except that the compound BH2-8 (second host material) in the second emitting layer was replaced with the second compound listed in Table 42.

Comparative 114

As shown in Table 42, the organic EL device of Comparative 114 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 42.

TABLE 42

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 140 | BH1 | BD1 | 5 | BH2-26 | BD1 | 20 | 3.5 | 9.2 | 130 |
| Comp. 114 | — | — | — | BH2-26 | BD1 | 25 | 3.4 | 7.5 | 75 |

Example 141

The organic EL device according to Example 141 was prepared in the same manner as in Example 134 except that the compound BH2-8 (second host material) in the second emitting layer was replaced with the second compound listed in Table 43.

Comparative 115

As shown in Table 43, the organic EL device of Comparative 115 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 43.

TABLE 43

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 141 | BH1 | BD1 | 5 | BH2-27 | BD1 | 20 | 3.2 | 9.1 | 130 |
| Comp. 115 | — | — | — | BH2-27 | BD1 | 25 | 3.5 | 7.2 | 80 |

Example 142

The organic EL device according to Example 142 was prepared in the same manner as in Example 134 except that the compound BH2-8 (second host material) in the second emitting layer was replaced with the second compound listed in Table 44.

Comparative 116

As shown in Table 44, the organic EL device of Comparative 116 was prepared in the same manner as in Example 134 except that a 25-nm-thick second emitting layer was formed on the second hole transporting layer without forming the first emitting layer, and the second compound (second host material) in the second emitting layer was replaced with the second compound listed in Table 44.

TABLE 44

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 134 | BH1 | BD1 | 5 | BH2-8 | BD1 | 20 | 3.3 | 9.8 | 90 |
| Ex. 143 | BH1 | BD1 | 5 | BH2-28 | BD1 | 20 | 3.3 | 9.0 | 140 |
| Comp. 116 | — | — | — | BH2-28 | BD1 | 25 | 3.4 | 7.4 | 65 |

Preparation 18 of Organic EL Device

Example 143

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 143 is roughly shown as follows.

ITO(130)/HA1(5)/HT1(80)/HT2(10)/BH1:BD1(5,98%:2%)/BH2-8:BD1(20,98%:2%)/ET7(10)/ET2(20)/LiF(1)/Al(80)

The numerals in parentheses represent film thickness (unit: nm).

The numerals (98%:2%) represented by percentage in the same parentheses indicate a ratio (mass %) between the host material (the compound BH1) and the compound BD1 in the first emitting layer, and numerals (98%:2%) represented by percentage in the same parentheses indicate a ratio (mass %) between the host material (the compound BH2-8) and the compound BD1 in the second emitting layer. Similar notations apply to the description below.

Example 144

The organic EL device according to Example 144 was prepared in the same manner as in Example 143 except that the compound BH2-8 (second host material) in the second emitting layer was replaced with the second compound listed in Table 45.

Comparative 117

As shown in Table 45, the organic EL device of Comparative 117 was prepared in the same manner as in Example 143 except that a 25-nm-thick second emitting layer was formed on the second hole transporting layer without forming the first emitting layer, and the second compound (second host material) in the second emitting layer was replaced with the second compound listed in Table 45.

TABLE 45

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Ex. 143 | BH1 | BD1 | 5 | BH2-8 | BD1 | 20 | 3.5 | 9.0 | 120 |
| Ex. 144 | BH1 | BD1 | 5 | BH2-29 | BD1 | 20 | 4.0 | 10.1 | 80 |
| Comp. 117 | — | — | — | BH2-29 | BD1 | 25 | 4.5 | 8.2 | 40 |

Preparation 19 of Organic EL Device

Example 145

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HT9 and the compound HA2 were co-deposited on a surface provided with the transparent electrode line to cover the transparent electrode, thereby forming a 10-nm-thick hole injecting layer (HI). The ratios of the compound HT9 and the compound HA2 in the hole injecting layer were 90 mass % and 10 mass %, respectively.

After the formation of the hole injecting layer, the compound HT9 was vapor-deposited to form an 85-nm-thick first hole transporting layer (HT).

After the formation of the first hole transporting layer, the compound HT8 was vapor-deposited to form a 5-nm-thick second hole transporting layer (also referred to as an electron blocking layer (EBL)).

The compound BH1 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-7 (second host material (BH)) and the compound BD2 (dopant material (BD)) were co-deposited on the first emitting layer such that the ratio of the compound BD2 accounted for 2 mass %, thereby forming a 15-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET8 and the compound Liq in the electron transporting layer (ET) were both 50 mass %. It should be noted that Liq is an abbreviation for (8-quinolinolato)lithium.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 145 is roughly shown as follows.

ITO(130)/HT9: HA2(10,90%:10%)/HT9(85)/HT8(5)/BH1: BD2(5,98%:2%)/BH 2-7:BD2(15,98%:2%)/ET3(5)/ET8:Liq(25,50%:50%)/Liq(1)/Al(80)

The numerals in parentheses represent film thickness (unit: nm).

The numerals (90%:10%) represented by percentage in the same parentheses indicate a ratio (mass %) between the compound HT9 and the compound HA2 in the hole injecting layer. The numerals (98%:2%) represented by percentage in the same parentheses indicate a ratio (mass %) between the host material (the compound BH1 or the compound BH2-7) and the dopant material (the compound BD2) in the first emitting layer or the second emitting layer. The numerals (50%:50%) represented by percentage in the same parentheses indicate a ratio (mass %) between the compound ET8 and the compound Liq in the electron transporting layer (ET). Similar notations apply to the description below.

Comparative 118

As shown in Table 46, the organic EL device of Comparative 118 was prepared in the same manner as in Example 145 except that a 20-nm-thick second emitting layer was formed on the second hole transporting layer without forming the first emitting layer.

Comparative 119

As shown in Table 46, the organic EL device of Comparative 119 was prepared in the same manner as in Example 145 except that a 20-nm-thick first emitting layer was formed as the emitting layer and the first electron transporting layer was formed on the first emitting layer without forming the second emitting layer.

TABLE 46

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 145 | BH1 | BD2 | 5 | BH2-7 | BD2 | 15 | 3.15 | 10.2 | 133 |
| Comp. 118 | — | — | — | BH2-7 | BD2 | 20 | 3.19 | 9.6 | 79 |
| Comp. 119 | BH1 | BD2 | 20 | — | — | — | 3.06 | 7.9 | 23 |

Preparation 20 of Organic EL Device

Examples 146 to 147

The organic EL devices according to Examples 146 to 147 were prepared in the same manner as in Example 1 except that the compound BH1 (first host material) in the first emitting layer was replaced with the compounds listed in Table 47.

TABLE 47

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 146 | BH1-84 | BD1 | 5 | BH2 | BD1 | 20 | 3.59 | 10.6 | 250 |
| Ex. 147 | BH1-85 | BD1 | 5 | BH2 | BD1 | 20 | 3.57 | 10.9 | 180 |
| Comp. 2 | — | — | — | BH2 | BD1 | 25 | 3.65 | 9.9 | 167 |

Preparation 21 of Organic EL Device

Example 148

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT9 and the compound HA2 were co-deposited on a surface provided with the transparent electrode line to cover the transparent electrode, thereby forming a 10-nm-thick hole injecting layer (HI). The ratios of the compound HT9 and the compound HA2 in the hole injecting layer were 97 mass % and 3 mass %, respectively.

After the formation of the hole injecting layer, the compound HT9 was vapor-deposited to form a 75-nm-thick first hole transporting layer (HT).

After the formation of the first hole transporting layer, a compound HT10 was vapor-deposited to form a 15-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 3-nm-thick first emitting layer.

A compound BH2-30 (second host material (BH)) and the compound BD1 (dopant material (BD)) were co-deposited on the first emitting layer such that the ratio of the compound BD1 accounted for 2 mass %, thereby forming a 17-nm-thick second emitting layer.

The compound ET1 was vapor-deposited on the second emitting layer to form a 3-nm-thick first electron transporting layer (also referred to as a hole blocking layer (HBL)).

The compound ET2 and the compound Liq were co-deposited on the first electron transporting layer (HBL) to form a 30-nm-thick second electron transporting layer (ET). The ratios of the compound ET2 and the compound Liq in the second electron transporting layer (ET) were 67 mass % and 33 mass %, respectively. It should be noted that Liq is an abbreviation for (8-quinolinolato)lithium.

LiF and Yb (ytterbium) were co-deposited on the second electron transporting layer to form a 1-nm-thick electron injecting layer. The ratios of LiF and Yb in the electron injecting layer were both 50 mass %.

Metal Al was vapor-deposited on the electron injecting layer to form an 50-nm-thick cathode.

The device arrangement of the organic EL device in Example 148 is roughly shown as follows.

ITO(130)/HT9:HA2(10,97%:3%)/HT9(75)/HT10(15)/BH1:BD1(3.98%:2%)/B H2-30:BD1(17,98%:2%)/ET1(3)/ET2:Liq(30, 67%:33%)/LiF:Yb(1, 50%:50%)/Al(50)

The numerals in parentheses represent film thickness (unit: nm).

The numerals (97%:3%) represented by percentage in the same parentheses indicate a ratio (mass %) between the compound HT9 and the compound HA2 in the hole injecting layer. The numerals (98%:2%) represented by percentage in the same parentheses indicate a ratio (mass %) between the host material (the compound BH1 or the compound BH2-30) and the dopant material (the compound BD1) in the first emitting layer or the second emitting layer. The numerals (67%:33%) represented by percentage in the same parentheses indicate a ratio (mass %) between the compound ET2 and the compound Liq in the electron transporting layer (ET). The numerals (50%:50%) represented by percentage in the same parentheses indicate a ratio (mass %) between LiF and Yb in the electron injecting layer. Similar notations apply to the description below.

Comparative 120

As shown in Table 48, the organic EL device of Comparative 120 was prepared in the same manner as in Example 148 except that a 20-nm-thick second emitting layer was formed as the emitting layer on the second hole transporting layer without forming the first emitting layer.

TABLE 48

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 148 | BH1 | BD1 | 3 | BH2-30 | BD1 | 17 | 3.88 | 10.9 | 191 |
| Comp. 120 | — | — | — | BH2-30 | BD1 | 20 | 3.96 | 10.2 | 170 |

Preparation 23 of Organic EL Device

Example 149

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT9 and the compound HA2 were co-deposited on a surface provided with the transparent electrode line to cover the transparent electrode, thereby forming a 10-nm-thick hole injecting layer (HI). The ratios of the compound HT9 and the compound HA2 in the hole injecting layer were 90 mass % and 10 mass %, respectively.

After the formation of the hole injecting layer, the compound HT9 was vapor-deposited to form an 85-nm-thick first hole transporting layer (HT).

After the formation of the first hole transporting layer, the compound HT8 was vapor-deposited to form a 5-nm-thick second hole transporting layer (also referred to as an electron blocking layer (EBL)).

A compound BH1-85 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-19 (second host material (BH)) and the compound BD2 (dopant material (BD)) were co-deposited on the first emitting layer such that the ratio of the compound BD2 accounted for 2 mass %, thereby forming a 15-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET8 and the compound Liq in the electron transporting layer (ET) were both 50 mass %. It should be noted that Liq is an abbreviation for (8-quinolinolato)lithium.

Liq was vapor-deposited on the second electron transporting layer to form a 1-nm-thick electron injecting layer.

Metal Al was vapor-deposited on the electron injecting layer to form an 80-nm-thick cathode.

The device arrangement of the organic EL device in Example 149 is roughly shown as follows.

ITO(130)/HT9: HA2(10,90%:10%)/HT9(85)/HT8(5)/BH1-85:BD2(5,98%:2%)/BH2-19:BD2(15,98%:2%)/ET3(5)/ET8:Liq(25, 50%:50%)/Liq(1)/Al(80)

The numerals in parentheses represent film thickness (unit: nm).

The numerals (90%:10%) represented by percentage in the same parentheses indicate a ratio (mass %) between the compound HT9 and the compound HA2 in the hole injecting layer. The numerals (98%:2%) represented by percentage in the same parentheses indicate a ratio (mass %) between the host material (the compound BH1-85 or the compound BH2-19) and the dopant material (the compound BD2) in the first emitting layer or the second emitting layer. The numerals (50%:50%) represented by percentage in the same parentheses indicate a ratio (mass %) between the compound ET8 and the compound Liq in the electron transporting layer (ET). Similar notations apply to the description below.

Example 150

The organic EL device according to Example 150 was prepared in the same manner as in Example 149 except that the compound BH2-19 (second host material) in the second emitting layer was replaced with the second compound listed in Table 49.

Comparative 121

As shown in Table 49, the organic EL device of Comparative 121 was prepared in the same manner as in Example 149 except that a 20-nm-thick first emitting layer was formed as the emitting layer and the first electron transporting layer was formed on the first emitting layer without forming the second emitting layer.

TABLE 49

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 149 | BH1-85 | BD2 | 5 | BH2-19 | BD2 | 15 | 3.22 | 10.3 | 104 |
| Ex. 150 | BH1-85 | BD2 | 5 | BH2-7 | BD2 | 15 | 3.23 | 10.3 | 129 |
| Comp. 118 | — | — | — | BH2-7 | BD2 | 20 | 3.19 | 9.6 | 79 |
| Comp. 121 | BH1-85 | BD2 | 20 | — | — | — | 3.51 | 7.1 | 134 |

Examples 151 to 152

The organic EL devices according to Examples 151 to 152 were prepared in the same manner as in Example 150 except that the compound BH1-85 (first host material) in the first emitting layer was replaced with the compounds listed in Table 50.

TABLE 50

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Ex. 151 | BH1-86 | BD2 | 5 | BH2-7 | BD2 | 15 | 3.24 | 10.1 | 130 |
| Ex. 152 | BH1-87 | BD2 | 5 | BH2-7 | BD2 | 15 | 3.22 | 10.4 | 142 |
| Comp. 118 | — | — | — | BH2-7 | BD2 | 20 | 3.19 | 9.6 | 79 |

Preparation 24 of Organic EL Device

Example 153

An APC (Ag—Pd—Cu) layer (reflective layer) having a film thickness of 100 nm, which was silver alloy layer, and an indium zinc oxide (IZO: registered trademark) film (transparent conductive layer) having a thickness of 10 nm were sequentially formed by sputtering on a glass substrate (25 mm×75 mm×0.7 mm thickness) to be a substrate for preparing a device. Thus, a conductive material layer formed of the APC layer and the IZO film was obtained. .

Subsequently, the conductive material layer was patterned by etching using a resist pattern as a mask using a normal lithography technique to form a lower electrode (anode).

Formation of First Emitting Unit

Next, the compound HT9 and the compound HA2 were co-deposited on the lower electrode by vacuum deposition to form a hole injecting layer having a film thickness of 10 nm. The concentrations of the compound HT9 and the compound HA2 in the hole injecting layer were 90 mass % and 10 mass %, respectively.

Next, the compound HT9 was vapor-deposited on the hole injecting layer to form a first hole transporting layer having a thickness of 22 nm.

Next, the compound HT8 was vapor-deposited on the first hole injecting layer to form a second hole transporting layer having a thickness of 5 nm.

The compound BH1 (first host material (BH)) and the compound BD2 (dopant material (BD)) were co-deposited on the second hole transporting layer to form a 3.5-nm-thick first emitting layer (UT1-EM1) of a first emitting unit. The concentrations of the compound BH1 and the compound BD2 in the first emitting layer (UT1-EM1) were 99 mass % and 1 mass %, respectively.

The compound BH2-19 (second host material (BH)) and the compound BD2 (dopant material (BD)) were co-deposited on the first emitting layer (UT1-EM1) to form a 13.5-nm-thick second emitting layer (UT1-EM2) of the first emitting unit. The concentrations of the compound BH2-19 and the compound BD2 in the second emitting layer (UT1-EM2) were 99 mass % and 1 mass %, respectively.

The compound ET1 was vapor-deposited on the second emitting layer (UT1-EM2) to form a 5-nm-thick first electron transporting layer (also referred to as a hole blocking layer (HBL)).

Formation of First Charge Generating Layer

Subsequently, the compound ET8 and Liq were co-deposited on the first electron transporting layer of the first emitting unit to form a 25-nm-thick first N layer. The concentrations of the compound ET8 and Liq in the first N layer were both 50 mass %.

Then, a compound ET9 and lithium (Li) were co-deposited on the first N layer to form a 15-nm-thick second N layer. The concentrations of the compound ET9 and Li in the second N layer were 96 mass % and 4 mass %, respectively.

Thereafter, the compound HT9 and the compound HA2 were co-deposited on the second N layer to form a 10-nm-thick first P layer. The concentrations of the compound HT9 and the compound HA2 in the first P layer were 90 mass % and 10 mass %, respectively.

Formation of Second Emitting Unit

Next, the compound HT9 was vapor-deposited on the first P layer to form a 45-nm-thick first hole transporting layer.

Next, the compound HT8 was vapor-deposited on the first hole injecting layer to form a second hole transporting layer having a thickness of 5 nm.

The compound BH1 and the compound BD2 were then co-deposited on the second hole transporting layer to form a 3.5-nm-thick first emitting layer (UT2-EM1) of a second emitting unit. The concentrations of the compound BH1 and the compound BD2 in the first emitting layer (UT2-EM1) were 99 mass % and 1 mass %, respectively.

Subsequently, the compound BH2-19 (second host material (BH)) and the compound BD2 (dopant material (BD)) were co-deposited on the first emitting layer (UT2-EM1) to form a 13.5-nm-thick second emitting layer (UT2-EM2) of the second emitting unit. The concentrations of the compound BH2-19 and the compound BD2 in the second emitting layer (UT2-EM2) were 99 mass % and 1 mass %, respectively.

Thereafter, the compound ET1 was vapor-deposited on the second emitting layer (UT2-EM2) to form a 5-nm-thick first electron transporting layer (also referred to as a hole blocking layer (HBL)).

Formation of Second Charge Generating Layer

Subsequently, the compound ET8 and Liq were co-deposited on the first electron transporting layer of the second emitting unit to form a 25-nm-thick third N layer. The concentrations of the compound ET8 and Liq in the third N layer were both 50 mass %.

Then, the compound ET9 and lithium (Li) were co-deposited on the third N layer to form a 15-nm-thick fourth N layer. The concentrations of the compound ET9 and Li in the fourth N layer were 96 mass % and 4 mass %, respectively.

Thereafter, the compound HT9 and the compound HA2 were co-deposited on the fourth N layer to form a 10-nm-thick second P layer. The concentrations of the compound HT9 and the compound HA2 in the second P layer were 90 mass % and 10 mass %, respectively.

Formation of Third Emitting Unit

Subsequently, the compound HT9 was vapor-deposited on the second P layer to form a 35-nm-thick first hole transporting layer on the second P layer.

Next, the compound HT8 was vapor-deposited on the first hole injecting layer to form a second hole transporting layer having a thickness of 5 nm.

The compound BH1 and the compound BD2 were then co-deposited on the second hole transporting layer to form a 3.5-nm-thick first emitting layer (UT3-EM1) of a third emitting unit. The concentrations of the compound BH1 and the compound BD2 in the first emitting layer (UT3-EM1) were 99 mass % and 1 mass %, respectively.

Subsequently, the compound BH2-19 (second host material (BH)) and the compound BD2 (dopant material (BD)) were co-deposited on the first emitting layer (UT3-EM1) to form a 13.5-nm-thick second emitting layer (UT3-EM2) of the second emitting unit. The concentrations of the compound BH2-19 and the compound BD2 in the second emitting layer (UT3-EM2) were 99 mass % and 1 mass %, respectively.

Thereafter, the compound ET1 was vapor-deposited on the second emitting layer (UT3-EM2) to form a 5-nm-thick first electron transporting layer (also referred to as a hole blocking layer (HBL)).

Subsequently, the compound ET8 and Liq were co-deposited on the first electron transporting layer of the third emitting unit to form a 38-nm-thick second electron transporting layer. The concentrations of the compound ET8 and Liq in the second electron transporting layer were both 50 mass %.

Thereafter, ytterbium (Yb) was vapor-deposited on the second electron transporting layer of the third emitting unit to form a 1.5-nm-thick electron injecting layer.

Then, Mg and Ag were co-deposited on the electron injecting layer of the third emitting unit so as to have a mixing ratio (mass % ratio) of 15%:85%, so that an upper electrode (cathode) made of a semi-transparent MgAg alloy (total film thickness 12 nm) was formed.

Next, the compound Cap1 was deposited on the entire surface of the upper electrode to form a capping layer having a thickness of 50 nm.

A top emission organic EL device according to Example 153 was prepared as described above.

The device arrangement of the organic EL device in Example 153 is roughly shown as follows.

APC(100)/IZO(10)/HT9: HA2(10,90%:10%)/HT9(22)/HT8(5)/BH1:BD2(3.5,99%:1%)/BH2-19:BD2(13.5,99%:1%)/ET1(5)/ET8:Liq(25.50%:50%)/ET9:Li(15,96%:4%)/HT9:HA2(10,90%:10%)/HT9(45)/HT8(5)/BH1:BD2(3.5,99%:1%)/BH2-19:BD2(13.5,99%:1%)/ET1(5)/ET8:Liq(25,50%:50%)/ET9:Li(15,96%:4%)/HT9:HA2(10,90%:10%)/HT9(35)/HT8(5)/BH1:BD2(3.5,99%:1%)/BH2-19:BD2(13.5,99%:1%)/ET1(5)/ET8:Liq(38,50%:50%)/Yb(1.5)/Mg:Ag(12,15%:85%)/Cap1(50)

Comparative 122

As shown in Table 51, the top emission organic EL device of Comparative 122 was prepared in the same manner as in Example 153 except that a 17-nm-thick second emitting layer was formed on the second hole transporting layer without forming the first emitting layer in the first, second and third emitting units.

TABLE 51

| | | First Emitting Layer | | | Second Emitting Layer | | | | | | |
|---|---|---|---|---|---|---|---|---|---|---|---|
| | Emitting Unit | First Compound | Third Compound | Film Thickness [nm] | Second Compound | Fourth Compound | Film Thickness [nm] | First Electron Transporting Layer | Voltage [V] | EQE [%] | LT95 [hr] |
| Ex. 153 | First | BH1 | BD2 | 3.5 | BH2-19 | BD2 | 13.5 | ET1 | 9.67 | 29.6 | 102 |
| | Second | BH1 | BD2 | 3.5 | BH2-19 | BD2 | 13.5 | ET1 | | | |
| | Third | BH1 | BD2 | 3.5 | BH2-19 | BD2 | 13.5 | ET1 | | | |
| Comp. 122 | First | — | — | — | BH2-19 | BD2 | 17.0 | ET1 | 10.09 | 24.7 | 42 |
| | Second | — | — | — | BH2-19 | BD2 | 17.0 | ET1 | | | |
| | Third | — | — | — | BH2-19 | BD2 | 17.0 | ET1 | | | |

Example 154

The top emission organic EL device according to Example 154 was prepared in the same manner as Example 153 except that the compound BH2-19 (second host material) in the second emitting layer of the first, second, and third emitting units was replaced with the second compound listed in Table 52 and the compound ET1 in the first electron transporting layer was replaced with the compound listed in Table 52.

Comparative 123

As shown in Table 52, the top emission organic EL device of Comparative 123 was prepared in the same manner as in Example 154 except that a 17-nm-thick second emitting layer was formed on the second hole transporting layer without forming the first emitting layer in the first, second and third emitting units.

TABLE 52

| | | First Emitting Layer | | | Second Emitting Layer | | | | | | |
|---|---|---|---|---|---|---|---|---|---|---|---|
| | Emitting Unit | First Compound | Third Compound | Film Thickness [nm] | Second Compound | Fourth Compound | Film Thickness [nm] | First Electron Transporting Layer | Voltage [V] | EQE [%] | LT95 [hr] |
| Ex. 154 | First | BH1 | BD2 | 3.5 | BH2-8 | BD2 | 13.5 | ET3 | 9.33 | 29.8 | 85 |
| | Second | BH1 | BD2 | 3.5 | BH2-8 | BD2 | 13.5 | ET3 | | | |
| | Third | BH1 | BD2 | 3.5 | BH2-8 | BD2 | 13.5 | ET3 | | | |
| Comp. 123 | First | — | — | — | BH2-8 | BD2 | 17.0 | ET3 | 9.43 | 26.2 | 49 |
| | Second | — | — | — | BH2-8 | BD2 | 17.0 | ET3 | | | |
| | Third | — | — | — | BH2-8 | BD2 | 17.0 | ET3 | | | |

It should be noted that the values of voltage, EQE and LT95 shown in Tables 51 and 52 are not measured for each of the emitting units but for the entire organic EL device including the first, second, and third emitting units.

Preparation 25 of Organic EL Device

Example 155

An APC (Ag—Pd—Cu) layer (reflective layer) having a film thickness of 100 nm, which was silver alloy layer, and an indium zinc oxide (IZO: registered trademark) film (transparent conductive layer) having a thickness of 10 nm were sequentially formed by sputtering on a glass substrate (25 mm×75 mm×0.7 mm thickness) to be a substrate for preparing a device. Thus, a conductive material layer formed of the APC layer and the IZO film was obtained. .

Subsequently, the conductive material layer was patterned by etching using a resist pattern as a mask using a normal lithography technique to form a lower electrode (anode).

Next, the compound HT5 and the compound HA2 were co-deposited on the lower electrode by vacuum deposition to form 10-nm-thick hole injecting layer. The concentrations of the compound HT5 and the compound HA2 in the hole injecting layer were 97 mass % and 3 mass %, respectively.

Next, the compound HT5 was vapor-deposited on the hole injecting layer to form a 114-nm-thick first hole transporting layer on the hole injecting layer.

Subsequently, the compound HT4 was vapor-deposited on the first hole injecting layer to form a 5-nm-thick second hole transporting layer.

The compound BH1-85 (first host material (BH)) and the compound BD2 (dopant material (BD)) were then co-deposited on the second hole transporting layer to form a 5-nm-thick first emitting layer. The concentrations of the compound BH1-85 and the compound BD2 in the first emitting layer were 99 mass % and 1 mass %, respectively.

A compound BH2-5 (second host material (BH)) and the compound BD2 (dopant material (BD)) were then co-deposited on the first emitting layer to form a 15-nm-thick second emitting layer. The concentrations of the compound BH2-5 and the compound BD2 in the second emitting layer were 99 mass % and 1 mass %, respectively.

The compound ET3 was then vapor-deposited on the second emitting layer to form a 5-nm-thick first electron transporting layer (also referred to as a hole blocking layer (HBL)).

Subsequently, the compound ET8 and Liq were co-deposited on the first electron transporting layer to form a 25-nm-thick second electron transporting layer. The concentrations of the compound ET8 and Liq in the second electron transporting layer were both 50 mass %.

Then, ytterbium (Yb) was vapor-deposited on the second electron transporting layer to form a 1-nm-thick electron injecting layer.

Next, Mg and Ag were co-deposited on the electron injecting layer so as to have a mixing ratio (mass % ratio) of 10%:90%, so that an upper electrode (cathode) made of a semi-transparent MgAg alloy (total film thickness 12 nm) was formed.

Next, the compound Cap1 was deposited on the entire surface of the upper electrode to form a capping layer having a thickness of 65 nm.

A top emission organic EL device according to Example 156 was prepared as described above.

The device arrangement of the organic EL device in Example 155 is roughly shown as follows.

APC(100)/IZO(10)/HT5:HA2(10,97%:3%)/HT5(114)/HT4(5)/BH1-85:BD2(5,99%:1%)/BH2-5:BD2(15,99%:1%)/ET3(5)/ET8:Liq(25,50%:50%)/Yb(1)/Mg:Ag(12,10%:90%)/Cap1 (65)

Comparative 124

As shown in Table 53, the organic EL device of Comparative 124 was prepared in the same manner as in Example 155 except that the thickness of the first hole transporting layer was changed and a 20-nm-thick second emitting layer was formed on the second hole transporting layer without forming the first emitting layer.

TABLE 53

| | First Hole Transporting Layer | | First Emitting Layer | | | Second Emitting Layer | | | | | |
|---|---|---|---|---|---|---|---|---|---|---|---|
| | Compound | Film Thickness [nm] | First Compound | Third Compound | Film Thickness [nm] | Second Compound | Fourth Compound | Film Thickness [nm] | Voltage [V] | EQE [%] | LT95 [hr] |
| Ex. 155 | HT5 | 114 | BH1-85 | BD2 | 5 | BH2-5 | BD2 | 15 | 3.61 | 16.5 | 500 |
| Comp. 124 | HT5 | 117 | — | — | — | BH2-5 | BD2 | 20 | 3.61 | 16.1 | 500 |

Preparation 26 of Organic EL Device

Example 156

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA3 was vapor-deposited on a surface provided with the transparent electrode line to cover the transparent electrode, thereby forming a 10-nm-thick hole injecting layer (HI).

After the formation of the hole injecting layer, a compound HT11 was vapor-deposited to form a 90-nm-thick first hole transporting layer (HT).

After the formation of the first hole transporting layer, a compound HT12 was vapor-deposited to form a 5-nm-thick second hole transporting layer (also referred to as an electron blocking layer (EBL)).

The compound BH1 (first host material (BH)) and the compound BD2 (dopant material (BD)) were co-deposited on the second hole transporting layer such that the ratio of the compound BD2 accounted for 2 mass %, thereby forming a 5-nm-thick first emitting layer. It should be noted that the first emitting layer was formed by setting a vapor deposition rate of the compound BH1 at 1 □/s (angstrom/second).

The compound BH2-30 (second host material (BH)) and the compound BD2 (dopant material (BD)) were co-deposited on the first emitting layer such that the ratio of the compound BD2 accounted for 2 mass %, thereby forming a 15-nm-thick second emitting layer.

A compound ET10 was vapor-deposited on the second emitting layer to form a 5-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 50-nm-thick cathode.

The device arrangement of the organic EL device in Example 156 is roughly shown as follows.

ITO(130)/HA3(10)/HT11(90)/HT12(5)/BH1:BD2(5, 98%:2%)/BH2-30:BD2(15,98%:2%)/ET10(5)/ET2(20)/LiF (1)/Al(50)

The numerals in parentheses represent film thickness (unit: nm).

The numerals (98%:2%) represented by percentage in the same parentheses indicate a ratio (mass %) between the host material (the compound BH1) and the compound BD2 in the first emitting layer, and numerals (98%:2%) represented by percentage in the same parentheses indicate a ratio (mass %) between the host material (the compound BH2-30) and the compound BD2 in the second emitting layer.

Example 157

As shown in Table 54, the organic EL device according to Example 157 was prepared in the same manner as in Example 156 except that the first emitting layer was formed by changing the vapor deposition rate of the first compound to 20 □/s Example 158

The organic EL device according to Example 158 was prepared in the same manner as in Example 156 except that the first emitting layer was formed by replacing the first compound with the compound listed in Table 54.

Example 159

As shown in Table 54, the organic EL device according to Example 159 was prepared in the same manner as in Example 158 except that the first emitting layer was formed by changing the vapor deposition rate of the first compound to 20 A/s.

Example 160

The organic EL device according to Example 160 was prepared in the same manner as in Example 156 except that the first emitting layer was formed by replacing the first compound with the compound listed in Table 54.

Example 161

As shown in Table 54, the organic EL device according to Example 161 was prepared in the same manner as in Example 160 except that the first emitting layer was formed by changing the vapor deposition rate of the first compound to 20 A/s.

Example 162

The organic EL device according to Example 162 was prepared in the same manner as in Example 156 except that the first emitting layer was formed by replacing the first compound with the compound listed in Table 54.

Example 163

As shown in Table 54, the organic EL device according to Example 163 was prepared in the same manner as in Example 162 except that the first emitting layer was formed by changing the vapor deposition rate of the first compound to 20 A/s.

Example 164

The organic EL device according to Example 164 was prepared in the same manner as in Example 156 except that the first emitting layer was formed by replacing the first compound with the compound listed in Table 54.

Example 165

As shown in Table 54, the organic EL device according to Example 165 was prepared in the same manner as in Example 164 except that the first emitting layer was formed by changing the vapor deposition rate of the first compound to 20 A/s.

Comparative 125

As shown in Table 54, the organic EL device of Comparative 125 was prepared in the same manner as in Example 156 except that a 20-nm-thick second emitting layer was formed as the emitting layer on the second hole transporting layer without forming the first emitting layer.

Comparative 126

The organic EL device according to Comparative 126 was prepared in the same manner as in Example 156 except that the first emitting layer was formed by replacing the first compound with the compound listed in Table 54.

Comparative 127

As shown in Table 54, the organic EL device according to Comparative 127 was prepared in the same manner as in Comparative 126 except that the first emitting layer was formed by changing the vapor deposition rate of the first compound to 20 Å/s.

Table 54 also shows EQEs (relative values). An EQE (relative value) is a ratio in EQE between organic EL devices having the same device arrangement, the ratio representing a ratio of EQE1 obtained at a vapor deposition rate of 1 Å/s or EQE20 obtained at a vapor deposition rate of 20 Å/s to EQE1 obtained at a vapor deposition rate of 1 Å/s. For instance, an EQE (relative value) of Example 156 is 1.00, which is a ratio of EQE1 obtained at a vapor deposition rate of 1 Å/s to EQE1 obtained at a vapor deposition rate of 1 Å/s. An EQE (relative value) of Example 157 is 0.95, which is a ratio (EQE20/EQE1) of EQE20 obtained at a vapor deposition rate of 20 Å/s to EQE1 obtained at a vapor deposition rate of 1 Å/s. EQEs (relative values) are similarly shown for the following pairs: Example 158 and Example 159, Example 160 and Example 161, Example 162 and Example 163, Example 164 and Example 165, and Comparative 126 and Comparative 127.

TABLE 54

| | First Emitting Layer | | | | Second Emitting Layer | | | | EQE | |
|---|---|---|---|---|---|---|---|---|---|---|
| | First Compound | Third Compound | Vapor Deposition Rate [Å/s] | Film Thickness [nm] | Second Compound | Fourth Compound | Film Thickness [nm] | EQE [%] | EQE (Relative Value) [—] | LT90 [hr] |
| Ex. 156 | BH1 | BD2 | 1 | 5 | BH2-30 | BD2 | 15 | 10.7 | 1.00 | 200 |
| Ex. 157 | BH1 | BD2 | 20 | 5 | BH2-30 | BD2 | 15 | 10.2 | 0.95 | 190 |
| Ex. 158 | BH1-88 | BD2 | 1 | 5 | BH2-30 | BD2 | 15 | 10.6 | 1.00 | 203 |
| Ex. 159 | BH1-88 | BD2 | 20 | 5 | BH2-30 | BD2 | 15 | 10.1 | 0.95 | 193 |
| Ex. 160 | BH1-10 | BD2 | 1 | 5 | BH2-30 | BD2 | 15 | 10.5 | 1.00 | 214 |
| Ex. 161 | BH1-10 | BD2 | 20 | 5 | BH2-30 | BD2 | 15 | 10.1 | 0.96 | 205 |
| Ex. 162 | BH1-89 | BD2 | 1 | 5 | BH2-30 | BD2 | 15 | 10.5 | 1.00 | 210 |
| Ex. 163 | BH1-89 | BD2 | 20 | 5 | BH2-30 | BD2 | 15 | 10.2 | 0.97 | 204 |
| Ex. 164 | BH1-85 | BD2 | 1 | 5 | BH2-30 | BD2 | 15 | 10.7 | 1.00 | 215 |
| Ex. 165 | BH1-85 | BD2 | 20 | 5 | BH2-30 | BD2 | 15 | 10.8 | 1.01 | 214 |
| Comp. 125 | — | — | — | — | BH2-30 | BD2 | 20 | 8.8 | — | 173 |
| Comp. 126 | R-BH2 | BD2 | 1 | 5 | BH2-30 | BD2 | 15 | 10.6 | 1.00 | 180 |
| Comp. 127 | R-BH2 | BD2 | 20 | 5 | BH2-30 | BD2 | 15 | 8.5 | 0.80 | 140 |

As shown in Comparatives 126 and 127 of Table 54, it has been found that in an organic EL device in which a compound that has a linking group having many ring carbon atoms (i.e., having a large molecular weight) and provided between two pyrene rings (e.g., a compound R—BH2) is used as a host material, increasing the vapor deposition rate results in a decrease in EQE by about 20%.

In contrast, the first emitting layer of the organic EL devices of Examples 156 to 165 was formed by using a compound that had, between two pyrene rings, a linking group having less ring carbon atoms (i.e., having a smaller molecular weight) than that of the compound R—BH2; and thus even when the vapor deposition rate was increased, a decrease in EQE was inhibited to about 5%.

Example 166

The organic EL device according to Example 166 was prepared in the same manner as in Example 156 except that the emitting layers were formed by replacing the first compound in the first emitting layer and the second compound in the second emitting layer with the respective compounds listed in Table 55.

TABLE 55

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT90 [hr] |
| Ex. 166 | BH1-10 | BD2 | 5 | BH2-38 | BD2 | 15 | 9.5 | 145 |

An organic EL device containing a compound BH2-38 in the second emitting layer, although having the device arrangement of the invention that improves luminous efficiency, may have a limited degree of increase in luminous efficiency because the compound BH2-38 has a bulky tert-butyl group and thus has inhibited intermolecular interaction.

Evaluation of Compounds

Preparation of Toluene Solution

The compound BD1 was dissolved in toluene at a concentration of $4.9\times10^{-6}$ mol/L to prepare a toluene solution of the compound BD1. Toluene solutions of the compound BD2 and compound BD3 were prepared in the same manner.

Measurement of Fluorescence Main Peak Wavelength (FL-Peak)

Fluorescence main peak wavelength of the toluene solution of the compound BD1 excited at 390 nm was measured using a fluorescence spectrometer (spectrophotofluorometer F-7000 (manufactured by Hitachi High-Tech Science Corporation). The fluorescence main peak wavelengths of the toluene solutions of the compound BD2 and the compound BD3 were measured in the same manner as the compound BD1.

The fluorescence main peak wavelength of the compound BD1 was 453 nm.

The fluorescence main peak wavelength of the compound BD2 was 455 nm.

The fluorescence main peak wavelength of the compound BD3 was 451 nm.

The invention claimed is:

1. An organic electroluminescence device comprising:
an anode;
a cathode;
a first emitting layer provided between the anode and the cathode; and
a second emitting layer provided between the first emitting layer and the cathode, wherein
the first emitting layer comprises a first host material in a form of a first compound represented by a formula (101) below,
the second emitting layer comprises a second host material in a form of a second compound, (101)

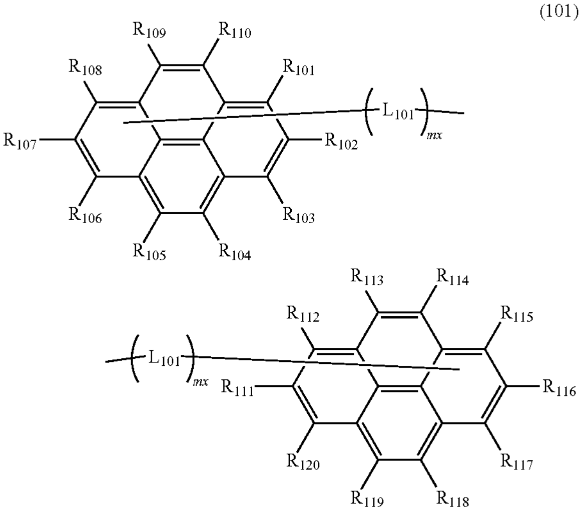

where, in the formula (101):

$R_{101}$ to $R_{110}$ and $R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$) ($R_{902}$) ($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 24 ring carbon atoms, or a substituted or unsubstituted divalent heterocyclic group having 5 to 24 ring atoms;

mx is 1, 2, 3, 4, or 5; and when two or more $L_{101}$ are present, the two or more $L_{101}$ are mutually the same or different, and in the first compound represented by the formula (101):

$R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different, and wherein an electron mobility μH1 of the first compound and an electron mobility μH2 of the second compound satisfy a relationship of a numerical formula (Numerical Formula 3) below, $$\mu H2 > \mu H1 \quad \text{(Numerical Formula 3).}$$

2. The organic electroluminescence device according to claim 1, wherein the first compound is represented by a formula (1010) below, (1010)

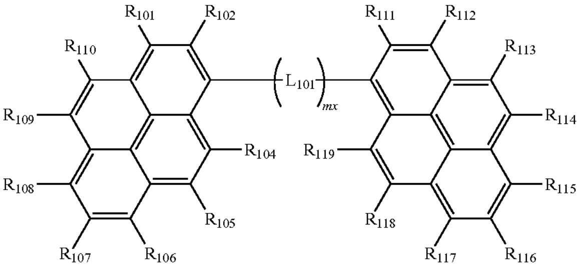

where, in the formula (1010):

$R_{101}$, $R_{102}$, $R_{104}$ to $R_{110}$ and $R_{111}$ to $R_{119}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$) ($R_{902}$) ($R_{903}$), a group represented by —O—($R_{904}$), a group represented by —S—($R_{905}$), a substituted or unsubstituted aralkyl group having 7 to 50 carbon atoms, a group represented by —C(═O) $R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

mx is 1, 2, 3, 4, or 5; and when two or more $L_{101}$ are present, the two or more $L_{101}$ are mutually the same or different.

3. The organic electroluminescence device according to claim 1, wherein $L_{101}$ is a single bond, a substituted or unsubstituted arylene group having 6 to 18 ring carbon atoms, or a substituted or unsubstituted divalent heterocyclic group having 5 to 18 ring atoms.

4. The organic electroluminescence device according to claim 1, wherein $L_{101}$ is a single bond, a substituted or unsubstituted arylene group having 6 to 13 ring carbon atoms, or a substituted or unsubstituted divalent heterocyclic group having 5 to 13 ring atoms.

5. The organic electroluminescence device according to claim 1, wherein the total number of carbon atoms comprised in a group represented by a formula (11X) below in the first compound is 21 or less, (11X)

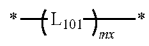

where, in the formula (11X): $L_{101}$ and mx respectively represent the same as $L_{101}$ and mx in the formula (1010).

6. The organic electroluminescence device according to claim 1, wherein the total number of carbon atoms comprised in $R_{101}$ to $R_{110}$ and $R_{111}$ to $R_{120}$ not being a bonding position to $L_{101}$ is 21 or less.

7. The organic electroluminescence device according to claim 1, wherein the total number of carbon atoms comprised in $R_{101}$ to $R_{110}$ and $R_{111}$ to $R_{120}$ not being a bonding position to $L_{101}$ and in a group represented by a formula (11X) below is 21 or less,

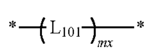

(11X)

where, in the formula (11X): $L_{101}$ and mx respectively represent the same as $L_{101}$ and mx in the formula (1010).

8. The organic electroluminescence device according to claim 1, wherein $R_{101}$ to $R_{110}$ not being a bonding position to $L_{101}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

9. The organic electroluminescence device according to claim 1, wherein $R_{101}$ to $R_{110}$ not being a bonding position to $L_{101}$ are each independently a hydrogen atom, a substituted or unsubstituted alkyl group having 1 to 50 carbon atoms, or a substituted or unsubstituted cycloalkyl group having 3 to 50 ring carbon atoms.

10. The organic electroluminescence device according to claim 1, wherein $R_{101}$ to $R_{110}$ not being a bonding position to $L_{101}$ are each a hydrogen atom.

11. The organic electroluminescence device according to claim 1, wherein $R_{111}$ to $R_{120}$ not being a bonding position to $L_{101}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

12. The organic electroluminescence device according to claim 1, wherein $R_{111}$ to $R_{120}$ not being a bonding position to $L_{101}$ are each independently a hydrogen atom, a substituted or unsubstituted alkyl group having 1 to 50 carbon atoms, or a substituted or unsubstituted cycloalkyl group having 3 to 50 ring carbon atoms.

13. The organic electroluminescence device according to claim 1, wherein $R_{111}$ to $R_{120}$ not being a bonding position to $L_{101}$ are each a hydrogen atom.

14. The organic electroluminescence device according to claim 1, wherein the first compound is represented by a formula (102) below, (102)

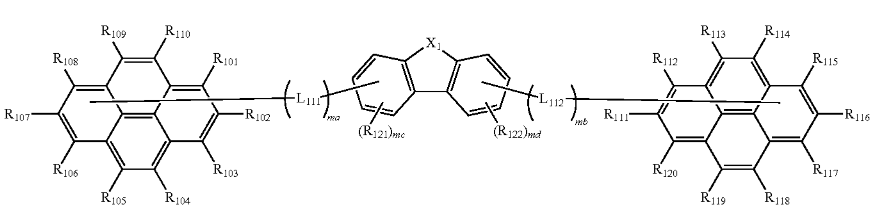

where, in the formula (102):

$R_{101}$ to $R_{120}$ each independently represent the same as $R_{101}$ to $R_{120}$ in the formula (101);

one of $R_{101}$ to $R_{110}$ represents a bonding position to $L_{111}$, and one of $R_{111}$ to $R_{120}$ represents a bonding position to $L_{112}$;

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 24 ring carbon atoms, or a substituted or unsubstituted divalent heterocyclic group having 5 to 24 ring atoms;

ma is 1, 2, or 3;

mb is 1, 2, or 3;

ma+mb is 2, 3, or 4;

$R_{121}$, $R_{122}$, $R_{123}$, $R_{124}$ and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

15. The organic electroluminescence device according to claim 14, wherein ma is 1 or 2, and mb is 1 or 2.

16. The organic electroluminescence device according to claim 14, wherein ma is 1, and mb is 1.

17. The organic electroluminescence device according to claim 14, wherein $R_{101}$ to $R_{110}$ not being a bonding position to $L_{111}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

18. The organic electroluminescence device according to claim 14, wherein $R_{101}$ to $R_{110}$ not being a bonding position to $L_{111}$ are each independently a hydrogen atom, a substituted or unsubstituted alkyl group having 1 to 50 carbon atoms, or a substituted or unsubstituted cycloalkyl group having 3 to 50 ring carbon atoms.

19. The organic electroluminescence device according to claim 14, wherein $R_{101}$ to $R_{110}$ not being a bonding position to $L_{111}$ are each a hydrogen atom.

20. The organic electroluminescence device according to claim 14, wherein $R_{111}$ to $R_{120}$ not being a bonding position to $L_{112}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

21. The organic electroluminescence device according to claim 14, wherein $R_{111}$ to $R_{120}$ not being a bonding position to $L_{112}$ are each independently a hydrogen atom, a substituted or unsubstituted alkyl group having 1 to 50 carbon atoms, or a substituted or unsubstituted cycloalkyl group having 3 to 50 ring carbon atoms.

22. The organic electroluminescence device according to claim 14, wherein $R_{111}$ to $R_{120}$ not being a bonding position to $L_{112}$ are each a hydrogen atom.

23. The organic electroluminescence device according to claim 1, wherein in the first compound, all groups described as "substituted or unsubstituted" groups are "unsubstituted" groups.

24. The organic electroluminescence device according to claim 1, wherein the first emitting layer is in direct contact with the second emitting layer.

25. The organic electroluminescence device according to claim 1, wherein $L_{101}$ is a divalent group derived by removing one hydrogen atom from an aryl ring of a substituted or unsubstituted phenyl group, a substituted or unsubstituted p-biphenyl group, a substituted or unsubstituted m-biphenyl group, a substituted or unsubstituted o-biphenyl group, a substituted or unsubstituted 1-naphthyl group, a substituted or unsubstituted 2-naphthyl group, a substituted or unsubstituted anthryl group, a substituted or unsubstituted phenanthryl group or a substituted or unsubstituted fluorenyl group.

26. The organic electroluminescence device according to claim 1, wherein $L_{101}$ is a divalent group derived by removing one hydrogen atom from an aryl ring of a substituted or unsubstituted phenyl group, a substituted or unsubstituted p-biphenyl group, a substituted or unsubstituted m-biphenyl group, a substituted or unsubstituted o-biphenyl group, a substituted or unsubstituted 1-naphthyl group, a substituted or unsubstituted 2-naphthyl group or a substituted or unsubstituted phenanthryl group.

27. The organic electroluminescence device according to claim 1, wherein $L_{101}$ is a divalent group derived by removing one hydrogen atom from an aryl ring of a substituted or unsubstituted phenyl group.

28. The organic electroluminescence device according to claim 1, wherein $L_{101}$ is a substituted or unsubstituted divalent heterocyclic group having 5 to 24 ring atoms.

29. The organic electroluminescence device according to claim 1, wherein the group represented by a formula (11X) below in the first compound does not contain a fused ring, (11X)

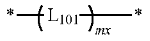

where, in the formula (11X): $L_{101}$ and mx respectively represent the same as $L_{101}$ and mx in the formula (101).

30. The organic electroluminescence device according to claim 1, wherein the group represented by a formula (11X) below in the first compound is a group represented by any one of formulae (113), (114), (115), (119), (120) and (121) below, (11X)

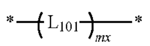

(113)

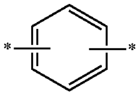

(114)

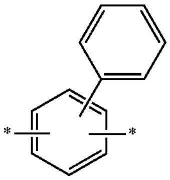

(115)

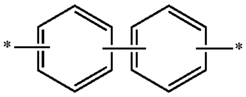

(119)

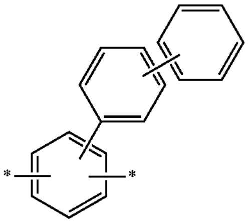

(120)

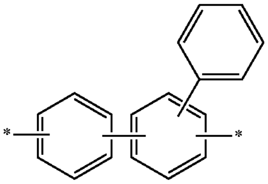

(121)

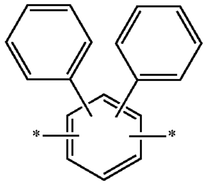

where, $L_{101}$ and mx in the formula (11X) respectively represent the same as $L_{101}$ and mx in the formula (101), and

* in the formulae (11X), (113), (114), (115), (119), (120) and (121) represents a bonding position.

31. The organic electroluminescence device according to claim 1, wherein mx is 0.

32. The organic electroluminescence device according to claim 1, wherein at least one hydrogen atom included in the first compound is deuterium atom.

33. The organic electroluminescence device according to claim 1, wherein the first emitting layer includes two or more types of the first compound.

34. The organic electroluminescence device according to claim 1, wherein the second compound is a compound represented by a formula (2) below, at least one hydrogen atom included in the second compound is deuterium atom, (2)

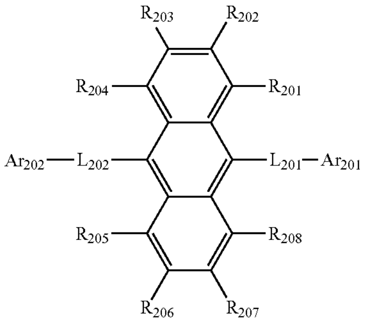

where, in the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms;

$Ar_{201}$ and $Ar_{202}$ are each independently a substituted or unsubstituted aryl group having 6 to 50 ring carbon atoms, or a substituted or unsubstituted heterocyclic group having 5 to 50 ring atoms, and in the second compound: $R_{901}$, $R_{902}$, $R_{903}$, $R_{904}$, $R_{905}$, $R_{906}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

* * * * *